US012766150B2

(12) United States Patent
Barsanti et al.

(10) Patent No.: US 12,766,150 B2
(45) Date of Patent: Oct. 20, 2026

(54) SUBSTITUTED THIADIAZOLYL DERIVATIVES AS DNA POLYMERASE THETA INHIBITORS

(71) Applicants: IDEAYA Biosciences, Inc., South San Francisco, CA (US); GLAXOSMITHKLINE INTELLECTUAL PROPERTY (No. 4) LIMITED, Stevenage (GB)

(72) Inventors: Paul A. Barsanti, South San Francisco, CA (US); Hilary Plake Beck, South San Francisco, CA (US); Melissa Fleury, South San Francisco, CA (US); Brian Thomas Jones, South San Francisco, CA (US); Ethan DeNardo McSpadden, South San Francisco, CA (US); Zhonghua Pei, South San Francisco, CA (US); Chenbo Wang, South San Francisco, CA (US); Firoz Ali Jaipuri, South San Francisco, CA (US); Daniel Lee Severance, South San Francisco, CA (US); Kevin J. Duffy, Collegeville, PA (US); Brian Lawhorn, Collegeville, PA (US)

(73) Assignees: IDEAYA Biosciences, Inc., South San Francisco, CA (US); GLAXOSMITHKLINE INTELLECTUAL PROPERTY (NO.4) LIMITED, Stevenage (GB)

( * ) Notice: Subject to any disclaimer, the term of this patent is extended or adjusted under 35 U.S.C. 154(b) by 387 days.

(21) Appl. No.: 18/255,306

(22) PCT Filed: Dec. 1, 2021

(86) PCT No.: PCT/IB2021/061173
§ 371 (c)(1),
(2) Date: May 31, 2023

(87) PCT Pub. No.: WO2022/118210
PCT Pub. Date: Jun. 9, 2022

(65) Prior Publication Data

US 2025/0325552 A1 Oct. 23, 2025

Related U.S. Application Data

(60) Provisional application No. 63/232,749, filed on Aug. 13, 2021, provisional application No. 63/120,410, filed on Dec. 2, 2020.

(51) Int. Cl.

| | |
|---|---|
| ***A61K 31/5377*** | (2006.01) |
| ***A61K 31/433*** | (2006.01) |

(Continued)

(52) U.S. Cl.
CPC ........ *A61K 31/5377* (2013.01); *A61K 31/433* (2013.01); *A61K 31/437* (2013.01);
(Continued)

(58) Field of Classification Search
CPC .. C07D 417/12; C07D 417/14; C07D 471/04; C07D 471/08; C07D 491/052;
(Continued)

(56) References Cited

U.S. PATENT DOCUMENTS

| | | | | |
|---|---|---|---|---|
| 10,130,619 B2 * | 11/2018 | Machin | ................ | C07D 417/04 |
| 2021/0387968 A1 * | 12/2021 | Beck | .................... | C07D 401/14 |
| 2023/0078112 A1 * | 3/2023 | Barsanti | .................. | A61P 35/00 548/136 |

FOREIGN PATENT DOCUMENTS

| | | | | |
|---|---|---|---|---|
| WO | WO-2008075068 A2 * | 6/2008 | .............. | A61P 35/00 |
| WO | 3 034 500 A1 | 6/2016 | | |

(Continued)

OTHER PUBLICATIONS

International Search Report and Written Opinion for International Application No. PCT/IB2021/061173, mailed Feb. 22, 2022, 6 Pages.

*Primary Examiner* — James H Alstrum-Acevedo
*Assistant Examiner* — Carolyn L. Ladd
(74) *Attorney, Agent, or Firm* — Bryan Cave Leighton Paisner LLP

(57) ABSTRACT

Disclosed herein are certain thiadiazolyl derivatives of Formula (I), (II), (III), or (IV):

(I)

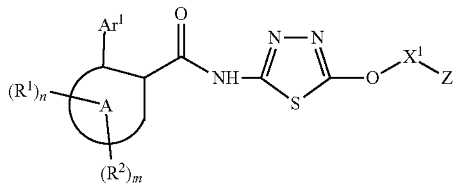

(II)

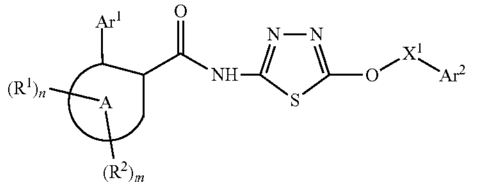

(III)

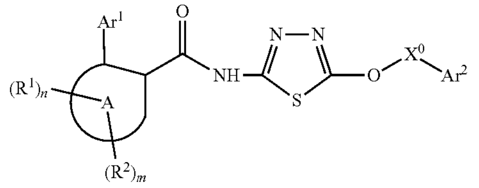

(Continued)

-continued (IV)

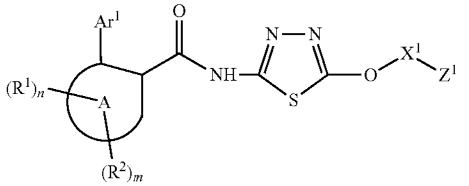

that inhibit DNA Polymerase Theta (Polθ) activity, in particular inhibit Polθ activity by inhibiting ATP dependent helicase domain activity of Polθ. Also, disclosed are pharmaceutical compositions comprising such compounds and methods of treating and/or preventing diseases treatable by inhibition of Polθ such as cancer, including homologous recombination (HR) deficient cancers.

18 Claims, No Drawings

(51) Int. Cl.

| | |
|---|---|
| ***A61K 31/437*** | (2006.01) |
| ***A61K 31/4439*** | (2006.01) |
| ***A61K 31/444*** | (2006.01) |
| ***A61K 31/4709*** | (2006.01) |
| ***A61K 31/497*** | (2006.01) |
| ***A61K 31/501*** | (2006.01) |
| ***A61K 31/506*** | (2006.01) |
| ***C07D 417/12*** | (2006.01) |
| ***C07D 417/14*** | (2006.01) |
| ***C07D 471/04*** | (2006.01) |
| ***C07D 471/08*** | (2006.01) |
| ***C07D 491/052*** | (2006.01) |
| ***C07D 491/056*** | (2006.01) |
| ***C07D 493/10*** | (2006.01) |

(52) U.S. Cl.

CPC ........ *A61K 31/4439* (2013.01); *A61K 31/444* (2013.01); *A61K 31/4709* (2013.01); *A61K 31/497* (2013.01); *A61K 31/501* (2013.01); *A61K 31/506* (2013.01); *C07D 417/12* (2013.01); *C07D 417/14* (2013.01); *C07D 471/04* (2013.01); *C07D 471/08* (2013.01); *C07D 491/052* (2013.01); *C07D 491/056* (2013.01); *C07D 493/10* (2013.01)

(58) Field of Classification Search

CPC .............. C07D 491/056; C07D 493/10; A61K 31/5377; A61K 31/433; A61K 31/437; A61K 31/4439; A61K 31/444; A61K 31/4709; A61K 31/497; A61K 31/501; A61K 31/506

See application file for complete search history.

(56) References Cited

FOREIGN PATENT DOCUMENTS

| | | | |
|---|---|---|---|
| WO | 2019028104 | A1 | 2/2019 |
| WO | WO 2020/160134 | A1 | 8/2020 |
| WO | WO 2020/160213 | A1 | 8/2020 |
| WO | WO 2020/243459 | A1 | 12/2020 |

* cited by examiner

SUBSTITUTED THIADIAZOLYL DERIVATIVES AS DNA POLYMERASE THETA INHIBITORS

CROSS-REFERENCES TO RELATED APPLICATIONS

This application claims the benefit under 35 U.S.C. 119(e) of U.S. Provisional Application No. 63/120,410, filed on Dec. 2, 2020 and U.S. Provisional Application No. 63/232,749, filed on Aug. 13, 2021, the contents of each is hereby incorporated by reference in their entirety for all purposes.

BACKGROUND OF THE INVENTION

Targeting DNA repair deficiencies has become a proven and effective strategy in cancer treatment. However, DNA repair deficient cancers often become dependent on backup DNA repair pathways, which present an "Achilles heel" that can be targeted to eliminate cancer cells, and is the basis of synthetic lethality. Synthetic lethality is exemplified by the success of poly (ADP-ribose) polymerase (PARP) inhibitors in treating BRCA-deficient breast and ovarian cancers (Audeh M. W., et al., Lancet (2010); 376 (9737): 245-51).

DNA damage repair processes are critical for genome maintenance and stability, among which, double strand breaks (DSBs) are predominantly repaired by the nonhomologous end joining (NHEJ) pathway in G1 phase of the cell cycle and by homologous recombination (HR) in S-G2 phases. A less addressed alternative end-joining (alt-EJ), also known as microhomology-mediated end-joining (MMEJ) pathway, is commonly considered as a "backup" DSB repair pathway when NHEJ or HR are compromised. Numerous genetic studies have highlighted a role for DNA polymerase theta (Polθ, encoded by POLQ) in stimulating MMEJ in higher organisms (Chan S. H., et al., PLoS Genet. (2010); 6: e1001005; Roerink S. F., et al., Genome research. (2014); 24: 954-962; Ceccaldi R., et. al., Nature (2015); 518: 258-62; and Mateos-Gomez P. A., et al., Nature (2015); 518: 254-57).

Polθ is distinct among human DNA polymerases, exhibiting not only a C-terminal DNA polymerase domain but also an N-terminal helicase domain separated by a long and lesser-conserved central domain of unknown function beyond Rad51 binding (Seki eta. Al, 2003, Shima et al 2003; Yousefzadeh and Wood 2013). The N-terminal ATPase/helicase domain belongs to the HELQ class of SF2 helicase super family. In homologous recombination deficient (HRD) cells, Polθ can carry out error-prone DNA synthesis at DNA damage sites through alt-EJ pathway. It has been shown that the helicase domain of Polθ causes suppression of HR pathway through disruption of Rad51 nucleoprotein complex formation involved in initiation of the HR-dependent DNA repair reactions following ionizing radiation. This anti-recombinase activity of Polθ promotes the alt-EJ pathway. In addition, the helicase domain of Polθ contributes to microhomology-mediated strand annealing (Chan S H et al., PLoS Genet. (2010); 6: e1001005; and Kawamura K et al., Int. J. Cancer (2004); 109: 9-16). Polθ efficiently promotes end-joining in alt-EJ pathway by employing this annealing activity when ssDNA overhangs contain >2 bp of microhomology (Kent T., et al., Elife (2016); 5: e13740), and Kent T., et al., Nat. Struct. Mol. Biol. (2015); 22: 230-237). This reannealing activity is achieved through coupled actions of Rad51 interaction followed by ATPase-mediated displacement of Rad51 from DSB damage sites. Once annealed, the primer strand of DNA can be extended by the polymerase domain of Polθ.

The expression of Polθ is largely absent in normal cells but upregulated in breast, lung, and ovarian cancers (Ceccaldi R., et al., Nature (2015); 518, 258-62). Additionally, the increase of Polθ expression correlates with poor prognosis in breast cancer (Lemee F et al., Proc Natl Acad Sci USA. (2010); 107: 13390-5). It has been shown that cancer cells with deficiency in HR, NHEJ or ATM are highly dependent on Polθ expression (Ceccaldi R., et al., Nature (2015); 518: 258-62, Mateos-Gomez P A et al., Nature (2015); 518: 254-57, and Wyatt D. W., et al., Mol. Cell (2016); 63: 662-73). Therefore, Polθ is an attractive target for novel synthetic lethal therapy in cancers containing DNA repair defects.

SUMMARY OF THE INVENTION

Disclosed herein are certain thiadiazolyl derivatives that inhibit Polθ activity, in particular inhibit Polθ activity by inhibiting the ATP dependent helicase domain activity of Polθ. Also, disclosed are pharmaceutical compositions comprising such compounds and methods of treating and/or preventing diseases treatable by inhibition of Polθ such as cancer, including homologous recombination (HR) deficient cancers.

In one aspect, provided is a compound of Formula (I), or a pharmaceutically acceptable salt thereof:

(I)

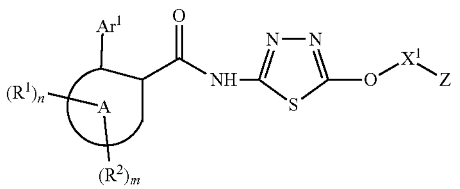

wherein ring A, $Ar^1$, $R^1$, $R^2$, $X^1$, Z, and subscripts n and m having the meanings provided hereinbelow.

In another aspect, provided is a compound of Formula (II), or a pharmaceutically acceptable salt thereof:

(II)

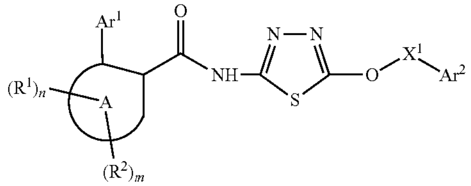

wherein ring A, $Ar^1$, $Ar^2$, $R^1$, $R^2$, $X^1$, and subscripts n and m having the meanings provided hereinbelow.

In another aspect, provided is a compound of Formula (III), or a pharmaceutically acceptable salt thereof:

(III)

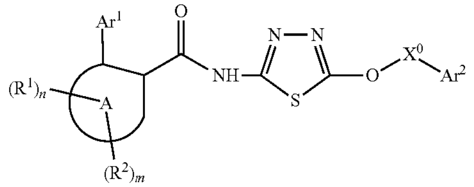

wherein ring A, $Ar^1$, $Ar^2$, $R^1$, $R^2$, $X^0$, and subscripts n and m having the meanings provided hereinbelow.

In one aspect, provided is a compound of Formula (IV), or a pharmaceutically acceptable salt thereof (IV)

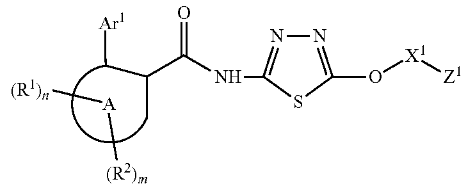

wherein ring A, $Ar^1$, $R^1$, $R^2$, $X^1$, $Z^1$, and subscripts n and m having the meanings provided hereinbelow.

In related aspects, provided are pharmaceutical compositions comprising a compound of Formula (I), (II), (III), (IV), or Table 1, or a pharmaceutically acceptable salt thereof and at least one pharmaceutically acceptable excipient.

In another aspect, provided is a method for treating and/or preventing a disease characterized by overexpression of Polθ in a patient comprising administering to the patient a therapeutically effective amount of a compound of Formula (I), (II), (III), (IV), or Table 1, or a pharmaceutically acceptable salt thereof (or an embodiment thereof disclosed herein). In one embodiment, the patient is in recognized need of such treatment. In another embodiment, the compound of Formula (I), (II), (III), (IV), or Table 1 (or an embodiment thereof disclosed herein), or a pharmaceutically acceptable salt thereof is administered in a pharmaceutical composition. In yet another embodiment, the disease is a cancer.

In still another aspect, provided is a method for treating and/or preventing a homologous recombinant (HR) deficient cancer in a patient comprising administering to the patient a therapeutically effective amount of a compound of Formula (I), (II), (III), (IV), or Table 1, or a pharmaceutically acceptable salt thereof (or an embodiment thereof disclosed herein). In one embodiment, the patient is in recognized need of such treatment. In another embodiment, the compound of Formula (I), (II), (III), (IV), or Table 1 (or an embodiment thereof disclosed herein), or a pharmaceutically acceptable salt thereof is administered in a pharmaceutical composition.

In another aspect, provided is a method for inhibiting DNA repair by Polθ in a cancer cell comprising contacting the cell with an effective amount of a compound of Formula (I), (II), (III), (IV), or Table 1 (or an embodiment thereof disclosed herein), or a pharmaceutically acceptable salt thereof. In one embodiment, the cancer is HR deficient cancer.

In yet another aspect, provided is a method for treating and/or preventing a cancer in a patient, wherein the cancer is characterized by a reduction or absence of BRCA gene expression, the absence or mutation of the BRAC gene, or reduced function of BRCA protein, comprising administering to the subject a therapeutically effective amount of a compound of Formula (I), (II), (III), (IV), or Table 1 (or an embodiment thereof disclosed herein), or a pharmaceutically acceptable salt thereof, optionally in a pharmaceutical composition.

In still another aspect, provided is a compound of Formula (I), (II), (III), (IV), or Table 1 (or an embodiment thereof disclosed herein), or a pharmaceutically acceptable salt thereof for inhibiting DNA repair by Polθ in a cell. In one embodiment, the cell is HR deficient cell.

In another aspect, provided is a compound of Formula (I), (II), (III), (IV), or Table 1 (or an embodiment thereof disclosed herein), or a pharmaceutically acceptable salt thereof for use in the treatment and/or prevention of a disease in a patient, wherein the disease is characterized by overexpression of Polθ.

In yet another aspect, provided is a compound of Formula (I), (II), (III), (IV), or Table 1 (or an embodiment thereof disclosed herein), or a pharmaceutically acceptable salt thereof for use in the treatment and/or prevention of a cancer in a patient, wherein the cancer is characterized by a reduction or absence of BRAC gene expression, the absence or mutation of the BRAC gene, or reduced function of BRAC protein.

In still another aspect, provided is a compound of Formula (I), (II), (III), (IV), or Table 1 (or an embodiment thereof disclosed herein), or a pharmaceutically acceptable salt thereof for use in the treatment and/or prevention of a HR deficient cancer in a patient.

In another aspect, provided is a compound of Formula (I), (II), (III), (IV), or Table 1 (or an embodiment thereof disclosed herein), or a pharmaceutically acceptable salt thereof for use in the treatment and/or prevention of a cancer that is resistant to poly(ADP-ribose) polymerase (PARP) inhibitor therapy in a patient. Examples of cancers resistant to PARP-inhibitors include, but are not limited to, breast cancer, ovarian cancer, lung cancer, bladder cancer, liver cancer, head and neck cancer, pancreatic cancer, gastrointestinal cancer, prostate cancer and colorectal cancer. In an embodiments, the cancers resistant to PARP-inhibitors include breast cancer, ovarian cancer, prostate cancer and colorectal cancer.

In related aspects for the methods, uses and compositions above, the cancer is lymphoma, rhabdoid tumor, multiple myeloma, uterine cancer, gastric cancer, peripheral nervous system cancer, rhabdomyosarcoma, bone cancer, colorectal cancer, mesothelioma, breast cancer, ovarian cancer, lung cancer, fibroblast cancer, central nervous system cancer, urinary tract cancer, upper aerodigestive cancer, leukemia, kidney cancer, skin cancer, esophageal cancer, prostate cancer, and pancreatic cancer (data from large scale drop out screens in cancer cell lines indicate that some cell lines from the above cancers are dependent on polymerase theta for proliferation https://depmap.org/portal/).

In some embodiments, a HR-deficient cancer is breast cancer. Breast cancer includes, but is not limited to, lobular carcinoma in situ (LCIS), a ductal carcinoma in situ (DCIS), an invasive ductal carcinoma (IDC), inflammatory breast cancer, Paget disease of the nipple, Phyllodes tumor, Angiosarcoma, adenoid cystic carcinoma, low-grade adenosquamous carcinoma, medullary carcinoma, mucinous carcinoma, papillary carcinoma, tubular carcinoma, metaplastic carcinoma, micropapillary carcinoma, mixed carcinoma, or another breast cancer, including but not limited to triple negative, HER positive, estrogen receptor positive, progesterone receptor positive, HER and estrogen receptor positive, HER and progesterone receptor positive, estrogen and progesterone receptor positive, and HER and estrogen and progesterone receptor positive. In other embodiments, HR-deficient cancer is ovarian cancer. Ovarian cancer includes, but is not limited to, epithelial ovarian carcinomas (EOC), maturing teratomas, dysgerminomas, endodermal sinus tumors, granulosa-theca tumors, Sertoli-Leydig cell tumors, and primary peritoneal arcinoma.

DETAILED DESCRIPTION

Before the present invention is further described, it is to be understood that the invention is not limited to the particular embodiments set forth herein, and it is also to be understood that the terminology used herein is for the purpose of describing particular embodiments only, and is not intended to be limiting.

The singular forms "a," "an," and "the" as used herein and in the appended claims include plural referents unless the context clearly dictates otherwise. It is further noted that the claims may be drafted to exclude any optional element. As such, this statement is intended to serve as antecedent basis for use of such exclusive terminology such as "solely," "only" and the like in connection with the recitation of claim elements, or use of a "negative" limitation.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention. Unless defined otherwise, all technical and scientific terms used herein have the same meaning as commonly understood by one of ordinary skill in the art to which this invention belongs.

When needed, any definition herein may be used in combination with any other definition to describe a composite structural group. By convention, the trailing element of any such definition is that which attaches to the parent moiety. For example, the composite group alkoxyalkyl means that an alkoxy group is attached to the parent molecule through an alkyl group.

The publications discussed herein are provided solely for their disclosure prior to the filing date of the present application. Further, the dates of publication provided may be different from the actual publication dates, which may need to be independently confirmed.

Definitions

Unless otherwise stated, the following terms used in the specification and claims are defined for the purposes of this Application and have the following meaning: The term "alkyl", by itself or as part of another substituent, means, unless otherwise stated, a saturated straight or branched chain hydrocarbon radical, having the number of carbon atoms designated (i.e. $C_{1-8}$ means one to eight carbons). Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. Examples of alkyl groups include methyl, ethyl, n-propyl, isopropyl, n-butyl, t-butyl, isobutyl, sec-butyl, n-pentyl, n-hexyl, n-heptyl, n-octyl, and the like.

The term "alkylene" refers to a straight or branched, saturated, aliphatic radical having the number of carbon atoms indicated, and linking at least two other groups, i.e., a divalent hydrocarbon radical. The two moieties linked to the alkylene can be linked to the same atom or different atoms of the alkylene group. For instance, a straight chain alkylene can be the bivalent radical of $-(CH_2)_n-$, where n is 1, 2, 3, 4, 5 or 6. Representative alkylene groups include, but are not limited to, methylene, ethylene, propylene, isopropylene, butylene, isobutylene, sec-butylene, pentylene, hexylene, and the like.

The term "alkoxy" refers to an alkyl group having an oxygen atom that connects the alkyl group to the point of attachment: alkyl-O—. As for an alkyl group, alkoxy groups can have any suitable number of carbon atoms, such as $C_{1-6}$, and can be straight or branced. Alkoxy groups include, for example, methoxy, ethoxy, propoxy, iso-propoxy, butoxy, 2-butoxy, iso-butoxy, sec-butoxy, tert-butoxy, pentoxy, hexoxy, etc.

As used herein, the term "cyano," by itself or as part of another substituent, refers to a moiety having the formula —CN, i.e., a carbon atom triple-bonded to nitrogen atom.

The term "cycloalkyl" refers to a saturated or partially unsaturated hydrocarbon ring having the indicated number of ring atoms (e.g., $C_{3-6}$ cycloalkyl). Cycloalkyl can include any number of carbons, such as $C_{3-6}$, $C_{4-6}$, $C_{5-6}$, $C_{3-8}$, $C_{4-8}$, $C_{5-8}$, $C_{6-8}$, $C_{3-9}$, and $C_{3-10}$. Partially unsaturated cycloalkyl groups have one or more double or triple bonds in the ring, but cycloalkyl groups are not aromatic. Saturated monocyclic cycloalkyl rings include, for example, cyclopropyl, cyclobutyl, cyclopentyl, cyclohexyl, and cyclooctyl.

The term "cycloalkyloxy" refers to a cycloalkyl group having an oxygen atom that connects the cycloalkyl group to the point of attachment: cycloalkyl-O—. The cycloalkyl group is as defined herein.

The terms "bridged cyclyl" or "bridged cycloalkyl" refer to a cycloalkyl ring (having 4 to 8 ring vertices) in which two non-adjacent ring atoms are linked by a $(CRR')_n$ group where n is 1 to 3 and each R is independently H or methyl (also may be referred to herein as "bridging" group). Bridged cycloalkyl groups do not have any heteroatoms as ring vertices. Additionally, $C_{5-8}$ refers to a bridged cycloalkyl group having 5-8 ring members. Examples include, but are not limited to, bicyclo[1.1.1]pentane, bicyclo[2.2.2]octane, bicyclo[2.2.1]heptane, and the like.

The terms "spirocyclyl" or "spirocycloalkyl" refer to a saturated or partially unsaturated bicyclic ring having 6 to 12 ring atoms, where the two rings are connected via a single carbon atom (also called the spiroatom). Partially unsaturated spirocycloalkyl groups have one or more double or triple bonds in the ring, but spirocycloalkyl groups are not aromatic. Representative examples include, but are not limited to, spiro[3.3]heptane, spiro[4.4]nonane, spiro[3.4]octane, and the like.

The term "heterocycloalkyl" refers to a saturated or partially unsatured monocyclic ring having the indicated number of ring vertices (e.g., a 3- to 7-membered ring) and having from one to five heteroatoms selected from N, O, and S as ring vertices. Partially unsaturated heterocycloalkyl groups have one or more double or triple bonds in the ring, but heterocycloalkyl group are not aromatic. Heterocycloalkyl groups can include any number of ring atoms, such as, 3 to 6, 4 to 6, 5 to 6, 3 to 7, 4 to 7, or 5 to 7 ring members. Any suitable number of heteroatoms can be included in the heterocycloalkyl groups, such as 1, 2, 3, or 4, or 1 to 2, 1 to 3, 1 to 4, 2 to 3, 2 to 4, or 3 to 4. Non-limiting examples of heterocycloalkyl groups include pyrrolidine, imidazolidine, pyrazolidine, butyrolactam, valerolactam, imidazolidinone, hydantoin, dioxolane, phthalimide, piperidine, 1,4-dioxane, morpholine, thiomorpholine, thiomorpholine-S-oxide, thiomorpholine-S,S-oxide, piperazine, pyran, pyridone, 3-pyrroline, thiopyran, pyrone, tetrahydrofuran, tetrahydrothiophene, quinuclidine, and the like. A heterocycloalkyl group can be attached to the remainder of the molecule through a ring carbon or a heteroatom.

The term "bicyclic heterocycloalkyl" or "bicyclic heterocyclyl" refers to a saturated or partially unsaturated fused bicyclic ring having the indicated number of ring vertices (e.g., a 6- to 12-membered ring) and having from one to five heteroatoms selected from N, O, and S as ring vertices. Partially unsaturated bicyclic heterocycloalkyl groups have one or more double or triple bonds in the ring, but bicyclic heterocycloalkyl groups are not aromatic. Bicyclic heterocycloalkyl groups can include any number of ring atoms, such as, 6 to 8, 6 to 9, 6 to 10, 6 to 11, or 6 to 12 ring members. Any suitable number of heteroatoms can be included in the heterocycloalkyl groups, such as 1, 2, 3, or 4, or 1 to 2, 1 to 3, 1 to 4, 2 to 3, 2 to 4, or 3 to 4. Non-limiting examples of bicyclic heterocycloalkyl groups include 3-oxabicyclo[3.1.0]hexane, decahydro-1,5-naphthyridine, octahydropyrrolo[1,2-a]pyrazine, and the like.

The terms "bridged heterocyclyl" or "bridged heterocycloalkyl" refers to a heterocycloalkyl ring (having 5 to 7 ring vertices) in which two non-adjacent ring atoms are linked by a $(CRR')_n$ group where n is 1 to 3 and each R is independently H or methyl (also may be referred to herein as "bridging" group). Bridged heterocyclyl groups have one to five heteroatoms selected from N, O, and S as ring vertices. The heteroatom ring vertices can be in both the heterocycloalkyl ring portion as well as the bridging group. When in the bridging group, the heteroatom replaces a CRR' group. Examples include, but are not limited to, 2-oxabicyclo[2.1.1]hexane, 2-azabicyclo[2.2.2]octane, quinuclidine, 7-oxabicyclo[2.2.1]heptane, and the like.

The terms "spiroheterocyclyl" or "spiroheterocycloalkyl" refer to a saturated or partially unsaturated bicyclic ring having 6 to 12 ring atoms, where the two rings are connected via a single carbon atom (also called the spiroatom). Spiroheterocyclyl groups have from one to five heteroatoms selected from N, O, and S as ring vertices, and the nitrogen atom(s) are optionally quaternized. Partially unsaturated spiroheterocycloalkyl groups have one or more double or triple bonds in the ring, but spiroheterocycloalkyl groups are not aromatic. Representative examples include, but are not limited to, 2,6-diazaspiro[3.3]heptane, 2,6-diazaspiro[3.4]octane, 2-azaspiro[3.4]octane, 5-oxaspiro[3.4]octane, 2,5-dioxaspiro[3.4]octane, 2-azaspiro[3.5]-nonane, 2,7-diazaspiro[4.4]nonane, and the like.

The term "5- to 6-membered saturated or partially unsaturated ring comprising 0 to 2 additional heteroatoms independently selected from the group consisting of N, O, and S" refers to a monocylic 5 or 6 membered cycloalkyl or heterocycloalkyl as defined herein.

The terms "halo" or "halogen," by themselves or as part of another substituent, mean, unless otherwise stated, a fluorine, chlorine, bromine, or iodine atom.

The term "haloalkyl" refers to alkyl, as defined above, where some or all of the hydrogen atoms are replaced with halogen atoms. As for alkyl group, haloalkyl groups can have any suitable number of carbon atoms, such as $C_{1-6}$. For example, the term "$C_{1-4}$ haloalkyl" is meant to include trifluoromethyl, 2,2,2-trifluoroethyl, 4-chlorobutyl, 3-bromopropyl, and the like.

The term "haloalkoxy" refers to an alkoxy group where some or all of the hydrogen atoms are substituted with halogen atoms. As for an alkyl group, haloalkoxy groups can have any suitable number of carbon atoms, such as $C_{1-6}$, and can be straight or branced, and are substituted with 1, 2, 3, or more halogens. When all the hydrogens are replaced with a halogen, for example by fluorine, the compounds are per-substituted, for example, perfluorinated. Haloalkoxy includes, but is not limited to, trifluoromethoxy, 2,2,2-trifluoroethoxy, perfluoroethoxy, etc.

The term "hydroxyalkyl" refers to an alkyl group where one of the hydrogen atoms is substituted with hydroxy (—OH) groups. As for an alkyl group, hydroxyalkyl groups can have any suitable number of carbon atoms, such as $C_{1-6}$, and can be straight or branced. Hydroxyalkyl groups include, for example, hydroxymethyl, 1-hydroxylethyl, 2-hydroxyethyl, 2-hydroxylpropan-2-yl, etc.

The term "aryl" means, unless otherwise stated, a polyunsaturated, typically aromatic, hydrocarbon group which can be a single ring or multiple rings (up to three rings) which are fused together or linked covalently. Non-limiting examples of aryl groups include phenyl, naphthyl and biphenyl.

The term "heteroaryl" refers to a 5- to 10-membered aromatic ring (or fused ring system) that contains from one to five heteroatoms selected from N, O, and S. Heteroaryl groups can include any number of ring atoms, such as, 5 to 6, 3 to 8, 4 to 8, 5 to 8, 6 to 8, 3 to 9, or 3 to 10 ring members. Any suitable number of heteroatoms can be included in the heteroaryl groups, such as 1, 2, 3, 4, or 5, or 1 to 2, 1 to 3, 1 to 4, 1 to 5, 2 to 3, 2 to 4, 2 to 5, 3 to 4, or 3 to 5. A heteroaryl group can be attached to the remainder of the molecule through a heteroatom. Non-limiting examples of heteroaryl groups include pyridyl, pyridazinyl, pyrazinyl, pyrimindinyl, triazinyl, quinolinyl, quinoxalinyl, quinazolinyl, cinnolinyl, phthalazinyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like.

As used herein, the term "heteroatom" is meant to include oxygen (O), nitrogen (N), sulfur (S).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylamino-ethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. When a stereochemical depiction is shown, it is meant to refer the compound in which one of the isomers is present and substantially free of the other isomer. 'Substantially free of' another isomer indicates at least an 80/20 ratio of the two isomers, more preferably 90/10, or 95/5 or more. In some embodiments, one of the isomers will be present in an amount of at least 99%.

The compounds of the present invention may also contain unnatural proportions of atomic isotopes at one or more of the atoms that constitute such compounds. Unnatural proportions of an isotope may be defined as ranging from the amount found in nature to an amount consisting of 100% of the atom in question. For example, the compounds may incorporate radioactive isotopes, such as for example tritium ($^{3}H$), iodine-125 ($^{125}I$) or carbon-14 ($^{14}C$), or non-radioactive isotopes, such as deuterium ($^{2}H$) or carbon-13 ($^{13}C$). Such isotopic variations can provide additional utilities to those described elsewhere within this application. For instance, isotopic variants of the compounds of the invention may find additional utility, including but not limited to, as diagnostic and/or imaging reagents, or as cytotoxic/radiotoxic therapeutic agents.

Additionally, isotopic variants of the compounds of the invention can have altered pharmacokinetic and pharmacodynamic characteristics which can contribute to enhanced safety, tolerability or efficacy during treatment. All isotopic variations of the compounds of the present invention, whether radioactive or not, are intended to be encompassed within the scope of the present invention.

The terms "patient" or "subject" are used interchangeably to refer to a human or a non-human animal (e.g., a mammal). In one embodiment, the patient is human.

The terms "administration," "administer" and the like, as they apply to, for example, a subject, cell, tissue, organ, or biological fluid, refer to contact of, for example, an Polθ modulator, a pharmaceutical composition comprising same, or a diagnostic agent to the subject, cell, tissue, organ, or biological fluid. In the context of a cell, administration includes contact (e.g., in vitro or ex vivo) of a reagent to the cell, as well as contact of a reagent to a fluid, where the fluid is in contact with the cell.

The terms "treat," "treating," "treatment" and the like refer to a course of action (such as administering an Polθ modulator or a pharmaceutical composition comprising same) initiated after a disease, disorder or condition, or a symptom thereof, has been diagnosed, observed, and the like so as to eliminate, reduce, suppress, mitigate, or ameliorate, either temporarily or permanently, at least one of the underlying causes of a disease, disorder, or condition afflicting a subject, or at least one of the symptoms associated with a disease, disorder, condition afflicting a subject. Thus, treatment includes inhibiting (e.g., arresting the development or further development of the disease, disorder or condition or clinical symptoms association therewith) an active disease.

The term "in need of treatment" as used herein refers to a judgment made by a physician or other caregiver that a subject requires or will benefit from treatment. This judgment is made based on a variety of factors that are in the realm of the physician's or caregiver's expertise. For example, the patient has been diagnosed as having a disease linked to overexpression of Polθ or a homologous recombination (HR)-deficient cancer.

The terms "prevent," "preventing," "prevention" and the like refer to a course of action (such as administering an Polθ modulator or a pharmaceutical composition comprising same) initiated in a manner (e.g., prior to the onset of a disease, disorder, condition or symptom thereof) so as to prevent, suppress, inhibit or reduce, either temporarily or permanently, a subject's risk of developing a disease, disorder, condition or the like (as determined by, for example, the absence of clinical symptoms) or delaying the onset thereof, generally in the context of a subject predisposed to having a particular disease, disorder or condition. In certain instances, the terms also refer to slowing the progression of the disease, disorder or condition or inhibiting progression thereof to a harmful or otherwise undesired state.

The term “in need of prevention” as used herein refers to a judgment made by a physician or other caregiver that a subject requires or will benefit from preventative care. This judgment is made based on a variety of factors that are in the realm of a physician’s or caregiver’s expertise.

The phrase “therapeutically effective amount” refers to the administration of an agent to a subject, either alone or as part of a pharmaceutical composition and either in a single dose or as part of a series of doses, in an amount capable of having any detectable, positive effect on any symptom, aspect, or characteristic of a disease, disorder or condition when administered to the subject. The therapeutically effective amount can be ascertained by measuring relevant physiological effects, and it can be adjusted in connection with the dosing regimen and diagnostic analysis of the subject’s condition, and the like. By way of example, measurement of the serum level of an Polθ modulator (or, e.g., a metabolite thereof) at a particular time post-administration may be indicative of whether a therapeutically effective amount has been used.

The phrase “in a sufficient amount to effect a change” means that there is a detectable difference between a level of an indicator measured before (e.g., a baseline level) and after administration of a particular therapy. Indicators include any objective parameter (e.g., serum concentration) or subjective parameter (e.g., a subject’s feeling of well-being).

The terms “inhibitors” and “antagonists,” or “activators” and “agonists” refer to inhibitory or activating molecules, respectively, for example, for the activation of, e.g., a ligand, receptor, cofactor, gene, cell, tissue, or organ. Inhibitors are molecules that decrease, block, prevent, delay activation, inactivate, desensitize, or down-regulate, e.g., a gene, protein, ligand, receptor, or cell. Activators are molecules that increase, activate, facilitate, enhance activation, sensitize, or up-regulate, e.g., a gene, protein, ligand, receptor, or cell. An inhibitor may also be defined as a molecule that reduces, blocks, or inactivates a constitutive activity. An “agonist” is a molecule that interacts with a target to cause or promote an increase in the activation of the target. An “antagonist” is a molecule that opposes the action(s) of an agonist. An antagonist prevents, reduces, inhibits, or neutralizes the activity of an agonist, and an antagonist can also prevent, inhibit, or reduce constitutive activity of a target, e.g., a target receptor, even where there is no identified agonist.

The terms “modulate,” “modulation” and the like refer to the ability of a molecule (e.g., an activator or an inhibitor) to increase or decrease the function or activity of Polθ, either directly or indirectly. A modulator may act alone, or it may use a cofactor, e.g., a protein, metal ion, or small molecule. Examples of modulators include small molecule compounds and other bioorganic molecules.

The “activity” of a molecule may describe or refer to the binding of the molecule to a ligand or to a receptor; to catalytic activity; to the ability to stimulate gene expression or cell signaling, differentiation, or maturation; to antigenic activity; to the modulation of activities of other molecules; and the like. The term “proliferative activity” encompasses an activity that promotes, that is necessary for, or that is specifically associated with, for example, normal cell division, as well as cancer, tumors, dysplasia, cell transformation, metastasis, and angiogenesis.

Certain compounds of the present disclosure can exist as tautomers and/or geometric isomers. All possible tautomers and cis and trans isomers, as individual forms and mixtures thereof are within the scope of this disclosure. For example, certain hydroxy substituted compounds may exist as tautomers as shown below

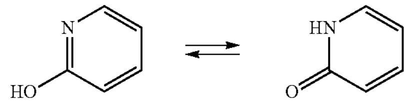 [SMILES: Oc1ccccn1 ; O=c1cccc[nH]1]

“Pharmaceutically acceptable carrier or excipient” means a carrier or an excipient that is useful in preparing a pharmaceutical composition that is generally safe, non-toxic and neither biologically nor otherwise undesirable, and includes a carrier or an excipient that is acceptable for veterinary use as well as human pharmaceutical use. “A pharmaceutically acceptable carrier/excipient” as used in the specification and claims includes both one and more than one such excipient.

As used herein, a wavy line, “∿”, that intersects a single, double or triple bond in any chemical structure depicted herein, represent the point attachment of the single, double, or triple bond to the remainder of the molecule. Additionally, a bond extending to the center of a ring (e.g., a phenyl ring) is meant to indicate attachment at any of the available ring vertices. One of skill in the art will understand that multiple substituents shown as being attached to a ring will occupy ring vertices that provide stable compounds and are otherwise sterically compatible.

“About,” as used herein, is intended to qualify the numerical values which it modifies, denoting such a value as variable within a margin of error. When no particular margin of error, such as a standard deviation to a mean value given in a chart or table of data, is recited, the term “about” should be understood to mean that range which would encompass±10%, preferably ±5%, the recited value and the range is included.

“Disease” as used herein is intended to be generally synonymous, and is used interchangeably with, the terms “disorder,” “syndrome,” and “condition” (as in medical condition), in that all reflect an abnormal condition of the human or animal body or of one of its parts that impairs normal functioning, is typically manifested by distinguishing signs and symptoms, and causes the human or animal to have a reduced duration or quality of life.

“Patient” is generally synonymous with the term “subject” and as used herein includes all mammals including humans. Examples of patients include humans, livestock such as cows, goats, sheep, pigs, and rabbits, and companion animals such as dogs, cats, rabbits, and horses. Preferably, the patient is a human.

“Inhibiting”, “reducing,” or any variation of these terms in relation of Polθ, includes any measurable decrease or complete inhibition to achieve a desired result. For example, there may be a decrease of about, at most about, or at least about 5%, 10%, 15%, 20%, 25%, 30%, 35%, 40%, 45%, 50%, 55%, 60%, 65%, 70%, 75%, 80%, 85%, 90%, 95%, 99%, or more, or any range derivable therein, reduction of Polθ activity compared to its normal activity.

The term “homologous recombination” refers to the cellular process of genetic recombination in which nucleotide sequences are exchanged between two similar or identical DNA.

The term “homologous recombination (HR) deficient cancer” refers to a cancer that is characterized by a reduction or absence of a functional HR repair pathway. HR deficiency may arise from absence of one or more HR-assocated genes or presence of one or more mutations in one or more HR-assocated genes. Examples of HR-assocated genes include BRCA1, BRCA2, RAD54, RAD51B, Ct1P (Choline Transporter-Like Protein), PALB2 (Partner and Localizer of BRCA2), XRCC2 (X-ray repair complementing defective repair in Chinese hamster cells 2), RECQL4 (RecQ Protein-Like 4), BLM (Bloom syndrome, RecQ helicase-like), WRN (Werner syndrome, one or more HR-assocated genes) Nbs 1 (Nibrin), and genes encoding Fanconi anemia (FA) proteins or FA-like genes e.g, FANCA, FANCB, FANCC, FANCD1 (BRCA2), FANCD2, FANCE, FANCF, FANCG, FANCI, FANJ (BRIP1), FANCL, FANCM, FANCN (RALB2), FANCP (SLX4), FANCS (BRCA1), RAD51C, and XPF.

The term "Polθ overexpression" refers to the increased expression or activity of Polθ in a diseases cell e.g., cancerous cell, relative to expression or activity of Polθ in a normal cell (e.g., non-diseased cell of the same kind). The amount of Polθ can be at least 2-fold, at least 3-fold, at least 4-fold, at least 5-fold, at least 10-fold, or more relative to the Polθ expression in a normal cell. Examples of Polθ cancers include, but are not limited to, breast, ovarian, cervical, lung, colorectal, gastric, bladder and prostate cancers.

Compounds

In some aspects, provided herein are compounds of Formula (I)

(I)

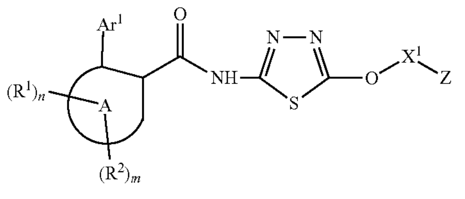

wherein:

$X^1$ is selected from the group consisting of $CH_2$ and $C_{2-4}$ alkylene substituted with from 0 to 1 —OH;

ring A is selected from the group consisting of phenyl and a 5- to 10-membered heteroaryl having 1 to 4 heteroatoms as ring vertices independently selected from N, O, and S;

the subscripts m and n are each independently 0 or 1;

$R^1$ and $R^2$, when present, are each independently selected from the group consisting of $C_{1-4}$ alkyl, $C_{1-4}$ alkoxy, halo, $C_{1-4}$ haloalkyl, $C_{1-4}$ haloalkoxy, $C_{1-4}$ hydroxyalkyl, —$X^a$—O—$C_{1-4}$ alkyl, —C(O)OH, and cyano, wherein $X^a$ is independently selected from a bond and $C_{1-4}$ alkylene;

$Ar^1$ is selected from the group consisting of phenyl, 5- to 6-membered heteroaryl having 1 to 4 heteroatoms as ring vertices independently selected from N, O, and S, 5- to 6-membered heterocycloalkyl having 1 to 3 heteroatoms as ring vertices independently selected from N, O, and S, 6- to 10-membered bicyclic heterocyclyl having 1 to 4 heteroatoms as ring vertices independently selected from N, O, and S, 6- to 10-membered bridged heterocyclyl having 1 to 3 heteroatoms as ring vertices independently selected from N, O, and S, and 6- to 12-membered spiroheterocyclyl having 1 to 3 heteroatoms as ring vertices independently selected from N, O, and S, wherein $Ar^1$ is substituted with 0 to 3 $R^3$;

each $R^3$ is independently selected from the group consisting of $C_{1-4}$ alkyl, halo, $C_{1-4}$ haloalkyl, $C_{1-4}$ haloalkoxy, $C_{3-6}$ cycloalkyl, $C_{3-6}$ cycloalkyloxy, —$X^2$—OH, —$X^2$—O—$C_{1-4}$ alkyl, —C(O)—$C_{1-4}$ alkyl, and —$X^2$-cyano; or two $R^3$ on adjacent ring vertices, combine to form a $C_{3-6}$ cycloalkyl, or two $R^3$ on the same ring vertex, combine to form oxo, wherein each $X^2$ is independently selected from a bond and $C_{1-4}$ alkylene;

Z is selected from the group consisting of:

(i) 4- to 6-membered heterocycloalkyl having 1 to 3 heteroatoms as ring vertices independently selected from N, O, and S, wherein ring vertices having S are optionally oxidized to S(O) or $S(O)_2$;

(ii) $C_{5-8}$ bridged cycloalkyl (iii) $C_{6-12}$ spirocyclyl;

(iv) $C_{5-7}$ cycloalkyl substituted at adjacent ring vertices with moieties that combine to form a 5- or 6-membered heteroaryl having 1 to 3 heteroatoms as ring vertices independently selected from N, O, and S, thereby forming a fused ring system;

(v) 5- to 7-membered heterocycloalkyl having 1 to 3 heteroatoms as ring vertices independently selected from N, O, and S substituted at adjacent ring vertices with moieties that combine to form a 5- or 6-membered heteroaryl having 0 to 2 additional heteroatoms as ring vertices independently selected from N, O, and S, thereby forming a fused ring system;

(vi) 5- or 6-membered heteroaryl having 1 to 3 heteroatoms as ring vertices independently selected from N, O, and S, and is substituted at adjacent ring vertices with two moieties that combine to form a 5- to 6-membered saturated or partially unsaturated ring comprising 0 to 2 additional heteroatoms as ring vertices independently selected from the group consisting of N, O, and S, thereby forming a fused ring system;

(vii) $C_{5-7}$ bridged heterocyclyl having 1 to 3 heteroatoms as ring vertices independently selected from N, O, and S;

(viii) 6- to 12-membered spiroheterocyclyl having 1 to 3 heteroatoms as ring vertices independently selected from N, O, and S; and (ix) 4- to 10-membered bicyclic heterocyclyl having 1 to 4 heteroatoms as ring vertices independently selected from N, O, and S, wherein each Z is substituted with 0 to 3 $R^4$ substituents, each of which is independently selected from $C_{1-4}$ alkyl, halo, $C_{1-4}$ haloalkyl, $C_{1-4}$ alkoxy, $C_{1-4}$ haloalkoxy, —$X^3$—OH, $C_{3-6}$cycloalkyl, $C_{3-6}$ cycloalkyloxy, —$X^3$-cyano, —$X^3$—O—$C_{1-4}$ alkyl, —$X^3$—C(O)OH, —S(O)(NH)—$C_{1-4}$ alkyl, —$S(O)_2$—$C_{1-4}$ alkyl, —C(O)—$C_{1-4}$ alkyl, and —$X^4$-heterocycloalkyl comprising 4- to 6-ring members and 1 to 3 heteroatoms as ring vertices independently selected from N, O, and S; or two $R^4$ substituents are combined to form an oxo moiety, wherein each cycloalkyl is independently substituted with from 0 to 3 substituents independently selected from the group consisting of $C_{1-4}$ alkyl, halo, $C_{1-4}$ haloalkyl, $C_{1-4}$ alkoxy, —$X^3$—O—$C_{1-4}$ alkyl, —$X^3$—C(O)OH and —$X^3$—OH;

each $X^3$ is independently selected from a bond and $C_{1-4}$ alkylene, and each $X^4$ is independently selected from a bond, —O—, and $C_{1-4}$ alkylene;

or a pharmaceutically acceptable salt thereof.

In some aspects, provided herein are compounds of Formula (I)

(I)

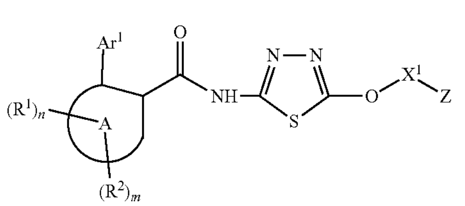

wherein:

$X^1$ is selected from the group consisting of $CH_2$ and $C_{2-4}$ alkylene substituted with from 0 to 1 —OH;

ring A is selected from the group consisting of phenyl and a 5- to 10-membered heteroaryl having 1 to 4 heteroatoms as ring vertices independently selected from N, O, and S; the subscripts m and n are each independently 0 or 1;

$R^1$ and $R^2$, when present, are each independently selected from the group consisting of $C_{1-4}$ alkyl, $C_{1-4}$ alkoxy, halo, $C_{1-4}$ haloalkyl, $C_{1-4}$ haloalkoxy, $C_{1-4}$ hydroxyalkyl, —C(O)OH, and cyano;

$Ar^1$ is selected from the group consisting of phenyl, 5- to 6-membered heteroaryl having 1 to 4 heteroatoms as ring vertices independently selected from N, O, and S, 5- to 6-membered heterocycloalkyl having 1 to 3 heteroatoms as ring vertices independently selected from N, O, and S, 6- to 10-membered bicyclic heterocyclyl having 1 to 4 heteroatoms as ring vertices independently selected from N, O, and S, 6- to 10-membered bridged heterocyclyl having 1 to 3 heteroatoms as ring vertices independently selected from N, O, and S, and 6- to 12-membered spiroheterocyclyl having 1 to 3 heteroatoms as ring vertices independently selected from N, O, and S, wherein $Ar^1$ is substituted with 0 to 3 $R^3$;

each $R^3$ is independently selected from the group consisting of $C_{1-4}$ alkyl, halo, $C_{1-4}$ haloalkyl, $C_{1-4}$haloalkoxy, $C_{3-6}$ cycloalkyl, $C_{3-6}$ cycloalkyloxy, —$X^2$—OH, —$X^2$—O—$C_{1-4}$ alkyl, —C(O)—$C_{1-4}$ alkyl, and —$X^2$-cyano; or two $R^3$ on adjacent ring vertices, combine to form a $C_{3-6}$ cycloalkyl, or two $R^3$ on the same ring vertex, combine to form oxo, wherein each $X^2$ is independently selected from a bond and $C_{1-4}$ alkylene;

Z is selected from the group consisting of:

(i) 4- to 6-membered heterocycloalkyl having 1 to 3 heteroatoms as ring vertices independently selected from N, O, and S, wherein ring vertices having S are optionally oxidized to S(O) or $S(O)_2$;

(ii) $C_{5-8}$ bridged cycloalkyl (iii) $C_{6-12}$ spirocyclyl;

(iv) $C_{5-7}$ cycloalkyl substituted at adjacent ring vertices with moieties that combine to form a 5- or 6-membered heteroaryl having 1 to 3 heteroatoms as ring vertices independently selected from N, O, and S, thereby forming a fused ring system;

(v) 5- to 7-membered heterocycloalkyl having 1 to 3 heteroatoms as ring vertices independently selected from N, O, and S substituted at adjacent ring vertices with moieties that combine to form a 5- or 6-membered heteroaryl having 0 to 2 additional heteroatoms as ring vertices independently selected from N, O, and S, thereby forming a fused ring system;

(vi) 5- or 6-membered heteroaryl having 1 to 3 heteroatoms as ring vertices independently selected from N, O, and S, and is substituted at adjacent ring vertices with two moieties that combine to form a 5- to 6-membered saturated or partially unsaturated ring comprising 0 to 2 additional heteroatoms as ring vertices independently selected from the group consisting of N, O, and S, thereby forming a fused ring system;

(vii) $C_{5-7}$ bridged heterocyclyl having 1 to 3 heteroatoms as ring vertices independently selected from N, O, and S; and (viii) 6- to 12-membered spiroheterocyclyl having 1 to 3 heteroatoms as ring vertices independently selected from N, O, and S, wherein each Z is substituted with 0 to 3 $R^4$ substituents, each of which is independently selected from $C_{1-4}$ alkyl, halo, $C_{1-4}$ haloalkyl, $C_{1-4}$ alkoxy, $C_{1-4}$ haloalkoxy, —$X^3$—OH, $C_{3-6}$ cycloalkyl, $C_{3-6}$ cycloalkyloxy, —$X^3$-cyano, —$X^3$—O—$C_{1-4}$ alkyl, —$X^3$—C(O)OH, —S(O)(NH)—$C_{1-4}$ alkyl, —$S(O)_2$—$C_{1-4}$ alkyl, —C(O)—$C_{1-4}$ alkyl, and —$X^4$-heterocycloalkyl comprising 4- to 6-ring members and 1 to 3 heteroatoms as ring vertices independently selected from N, O, and S, wherein each cycloalkyl is independently substituted with from 0 to 3 substituents independently selected from the group consisting of $C_{1-4}$ alkyl, halo, $C_{1-4}$ haloalkyl, $C_{1-4}$ alkoxy, —$X^3$—O—$C_{1-4}$ alkyl, —$X^3$—C(O)OH and —$X^3$—OH;

each $X^3$ is independently selected from a bond and $C_{1-4}$ alkylene, and each $X^4$ is independently selected from a bond, —O—, and $C_{1-4}$ alkylene;

or a pharmaceutically acceptable salt thereof.

In some aspects, provided herein are compounds of Formula (I)

(I)

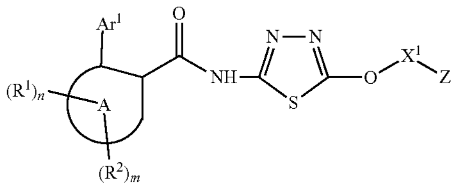

wherein:

$X^1$ is selected from the group consisting of $CH_2$ and $C_{2-4}$ alkylene substituted with from 0 to 1 —OH;

ring A is selected from the group consisting of phenyl and a 5- to 10-membered heteroaryl having 1 to 4 heteroatoms as ring vertices independently selected from N, O, and S; the subscripts m and n are each independently 0 or 1;

$R^1$ and $R^2$, when present, are each independently selected from the group consisting of $C_{1-4}$ alkyl, $C_{1-4}$ alkoxy, halo, $C_{1-4}$ haloalkyl, $C_{1-4}$ haloalkoxy, $C_{1-4}$ hydroxyalkyl, —C(O)OH, and cyano;

$Ar^1$ is selected from the group consisting of phenyl, 5- to 6-membered heteroaryl having 1 to 4 heteroatoms as ring vertices independently selected from N, O, and S, 5- to 6-membered heterocycloalkyl having 1 to 3 heteroatoms as ring vertices independently selected from N, O, and S, 6- to 10-membered bicyclic heterocyclyl having 1 to 4 heteroatoms as ring vertices independently selected from N, O, and S, 6- to 10-membered bridged heterocyclyl having 1 to 3 heteroatoms as ring vertices independently selected from N, O, and S, and 6- to 12-membered spiroheterocyclyl having 1 to 3 heteroatoms as ring vertices independently selected from N, O, and S, wherein $Ar^1$ is substituted with 0 to 3 $R^3$;

each $R^3$ is independently selected from the group consisting of $C_{1-4}$ alkyl, halo, $C_{1-4}$ haloalkyl, $C_{1-4}$haloalkoxy, $C_{3-6}$ cycloalkyl, $C_{3-6}$ cycloalkyloxy, —$X^2$—OH, —$X^2$—O—$C_{1-4}$ alkyl, —C(O)—$C_{1-4}$alkyl, and —$X^2$-cyano; or two $R^3$ on adjacent ring vertices, combine to form a $C_{3-6}$ cycloalkyl, or two $R^3$ on the same ring vertex, combine to form oxo, wherein each $X^2$ is independently selected from a bond and $C_{1-4}$ alkylene;

Z is selected from the group consisting of:

(i) 5- to 6-membered heterocycloalkyl;

(ii) $C_{5-8}$ bridged cycloalkyl (iii) $C_{6-12}$ spirocyclyl;

(iv) $C_{5-7}$ cycloalkyl substituted at adjacent ring vertices with moieties that combine to form a 5- or 6-membered heteroaryl having 1 to 3 heteroatoms as ring vertices independently selected from N, O, and S, thereby forming a fused ring system;

(v) 5- to 7-membered heterocycloalkyl having 1 to 3 heteroatoms as ring vertices independently selected from N, O, and S substituted at adjacent ring vertices with moieties that combine to form a 5- or 6-membered heteroaryl having 0 to 2 additional heteroatoms as ring vertices independently selected from N, O, and S, thereby forming a fused ring system;

(vi) 5- or 6-membered heteroaryl having 1 to 3 heteroatoms as ring vertices independently selected from N, O, and S, and is substituted at adjacent ring vertices with two moieties that combine to form a 5- to 6-membered saturated or partially unsaturated ring comprising 0 to 2 additional heteroatoms as ring vertices independently selected from the group consisting of N, O, and S, thereby forming a fused ring system; and (vii) $C_{5-7}$ bridged heterocyclyl having 1 to 3 heteroatoms as ring vertices independently selected from N, O, and S, wherein each Z is substituted with 0 to 3 $R^4$ substituents, each of which is independently selected from $C_{1-4}$ alkyl, halo, $C_{1-4}$ haloalkyl, $C_{1-4}$ alkoxy, $C_{1-4}$ haloalkoxy, —$X^3$—OH, $C_{3-6}$ cycloalkyl, $C_{3-6}$ cycloalkyloxy, —$X^3$-cyano, —$X^3$—O—$C_{1-4}$ alkyl, —$X^3$—C(O)OH, —S(O)(NH)—$C_{1-4}$ alkyl, —$S(O)_2$—$C_{1-4}$ alkyl, —C(O)—$C_{1-4}$ alkyl, and —$X^4$-heterocycloalkyl comprising 4- to 6-ring members and 1 to 3 heteroatoms as ring vertices independently selected from N, O, and S, wherein each cycloalkyl is independently substituted with from 0 to 3 substituents independently selected from the group consisting of $C_{1-4}$ alkyl, halo, $C_{1-4}$ haloalkyl, $C_{1-4}$ alkoxy, —$X^3$—O—$C_{1-4}$ alkyl, —$X^3$—C(O)OH and —$X^3$—OH;

each $X^3$ is independently selected from a bond and $C_{1-4}$ alkylene, and each $X^4$ is independently selected from a bond, —O—, and $C_{1-4}$ alkylene;

or a pharmaceutically acceptable salt thereof.

In some embodiments, compounds of Formula (I) have the structure of Formula (Ia)

(Ia)

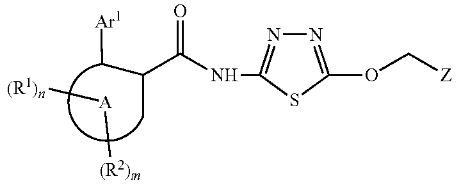

or a pharmaceutically acceptable salt thereof.

In some embodiments, Z in Formula (I) is

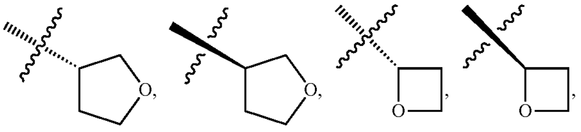

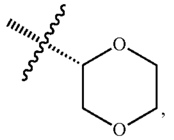

or

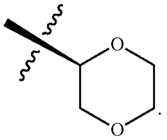

In some embodiments, Z in Formula (I) is

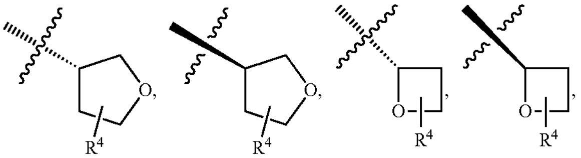

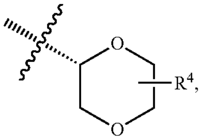

or

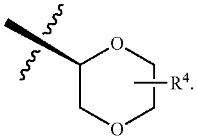

In some embodiments, Z in Formula (I) is

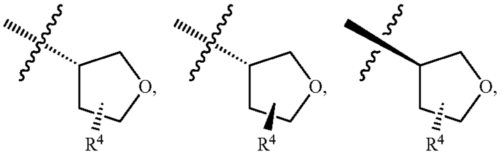

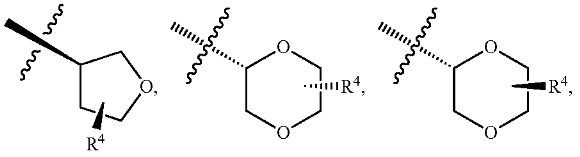

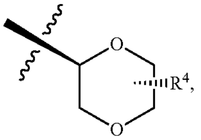

or

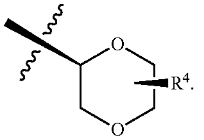

In some embodiments, Z in Formula (I) is a 4-membered heterocycloalkyl substituted with 0 to 3 $R^4$. In some embodiments, Z in Formula (I) is azetidinyl, substituted with 0 to 3 $R^4$. In some embodiments, Z in Formula (I) is azetidin-3-yl, substituted with 0 to 3 $R^4$. In some embodiments, Z in Formula (I) is thietanyl, substituted with 0 to 3 $R^4$, wherein the thio ring vertex is oxidized with two oxo groups. In some embodiments, Z in Formula (I) is thietan-3-yl, substituted with 0 to 3 $R^4$, wherein the thio ring vertex is oxidized with two oxo groups. In some embodiments, Z in Formula (I) is oxetanyl, substituted with 0 to 3 $R^4$. In some embodiments, Z in Formula (I) is oxetan-3-yl, substituted with 0 to 3 $R^4$. In some embodiments, Z in Formula (I) is oxetan-2-yl, substituted with 0 to 3 $R^4$. In some embodiments, the 4-membered heterocycloalkyl group is substituted with one $R^4$. In some embodiments, the 4-membered heterocycloalkyl group is substituted with two $R^4$. In some embodiments $R^4$ is —OH. In some embodiments $R^4$ is $C_{1-4}$ alkyl, halo, $C_{1-4}$ haloalkyl, —$X^3$—OH, cyano, or —C(O)—$C_{1-4}$ alkyl. In some embodiments $R^4$ is $C_{1-4}$ alkyl. In some embodiments $R^4$ is halo. In some embodiments $R^4$ is chloro or fluoro. In some embodiments $R^4$ is —OH. In some embodiments $R^4$ is cyano. In some embodiments —C(O)—$C_{1-4}$ alkyl.

In some embodiments, Z in Formula (I) is a 5-membered heterocycloalkyl substituted with 0 to 3 $R^4$. In some embodiments, Z in Formula (I) is tetrahydrofuranyl, substituted with 0 to 3 $R^4$. In some embodiments, Z in Formula (I) is tetrahydrofuran-3-yl, substituted with 0 to 3 $R^4$. In some embodiments, Z in Formula (I) is pyrrolidinyl, substituted with 0 to 3 $R^4$. In some embodiments, Z in Formula (I) is pyrrolidin-3-yl, substituted with 0 to 3 $R^4$. In some embodiments, Z in Formula (I) is imidazolyl, substituted with 0 to 3 $R^4$. In some embodiments, Z in Formula (I) is imidazol-1-yl, substituted with 0 to 3 $R^4$. In some embodiments, the 5-membered heterocycloalkyl group is substituted with one $R^4$. In some embodiments, the 5-membered heterocycloalkyl group is substituted with two $R^4$. In some embodiments, the 5-membered heterocycloalkyl group is substituted with two $R^4$. In some embodiments $R^4$ is —OH. In some embodiments $R^4$ is $C_{1-4}$ alkyl, halo, $C_{1-4}$ haloalkyl, —$X^3$—OH, cyano, or —C(O)—$C_{1-4}$ alkyl. In some embodiments $R^4$ is $C_{1-4}$ alkyl. In some embodiments $R^4$ is halo. In some embodiments $R^4$ is chloro or fluoro. In some embodiments $R^4$ is —OH. In some embodiments $R^4$ is cyano. In some embodiments —C(O)—$C_{1-4}$ alkyl.

In some embodiments, Z in Formula (I) is a 6-membered heterocycloalkyl substituted with 0 to 3 $R^4$. In some embodiments, Z in Formula (I) is tetrahydropyranyl, substituted with 0 to 3 $R^4$. In some embodiments, Z in Formula (I) is tetrahydropyran-4-yl, substituted with 0 to 3 $R^4$. In some embodiments, Z in Formula (I) is tetrahydropyran-2-yl, substituted with 0 to 3 $R^4$. In some embodiments, Z in Formula (I) is tetrahydrothiopyranyl, substituted with 0 to 3 $R^4$, wherein the thio ring vertex is oxidized with two oxo groups. In some embodiments, Z in Formula (I) is tetrahydrothiopyran-4-yl, substituted with 0 to 3 $R^4$, wherein the thio ring vertex is oxidized with two oxo groups. In some embodiments, Z in Formula (I) is piperidinyl, substituted with 0 to 3 $R^4$. In some embodiments, Z in Formula (I) is piperidin-4-yl, substituted with 0 to 3 $R^4$. In some embodiments, Z in Formula (I) is dioxanyl, substituted with 0 to 3 $R^4$. In some embodiments, Z in Formula (I) is dioxan-2-yl, substituted with 0 to 3 $R^4$. In some embodiments, the 6-membered heterocycloalkyl group is substituted with one $R^4$. In some embodiments, the 6-membered heterocycloalkyl group is substituted with two $R^4$. In some embodiments $R^4$ is —OH. In some embodiments $R^4$ is $C_{1-4}$ alkyl, halo, $C_{1-4}$ haloalkyl, —$X^3$—OH, cyano, or —C(O)—$C_{1-4}$ alkyl. In some embodiments $R^4$ is $C_{1-4}$ alkyl. In some embodiments $R^4$ is halo. In some embodiments $R^4$ is chloro or fluoro. In some embodiments $R^4$ is —OH. In some embodiments $R^4$ is cyano. In some embodiments —C(O)—$C_{1-4}$ alkyl.

In some embodiments, Z in Formula (I) is a $C_{5-8}$ bridged cycloalkyl, substituted with 0 to 3 $R^4$. In some embodiments, Z in Formula (I) is bicyclo[1.1.1]pentanyl, substituted with 0 to 3 $R^4$. In some embodiments, Z in Formula (I) is bicyclo[2.2.1]heptanyl, substituted with 0 to 3 $R^4$. In some embodiments, Z in Formula (I) is bicyclo[2.2.2]octanyl, substituted with 0 to 3 $R^4$. In some embodiments, the $C_{5-8}$ bridged cycloalkyl group is substituted with one $R^4$. In some embodiments, the $C_{5-8}$ bridged cycloalkyl group is substituted with two $R^4$. In some embodiments $R^4$ is —OH. In some embodiments $R^4$ is $C_{1-4}$ alkyl, halo, $C_{1-4}$ haloalkyl, —$X^3$—OH, cyano, or —C(O)—$C_{1-4}$ alkyl. In some embodiments $R^4$ is $C_{1-4}$ alkyl. In some embodiments $R^4$ is halo. In some embodiments $R^4$ is chloro or fluoro. In some embodiments $R^4$ is —OH. In some embodiments $R^4$ is cyano. In some embodiments —C(O)—$C_{1-4}$ alkyl.

In some embodiments, Z in Formula (I) is a $C_{6-12}$ spirocyclyl, substituted with 0 to 3 $R^4$. In some embodiments, Z in Formula (I) is spiro[3.3]heptanyl, substituted with 0 to 3 $R^4$. In some embodiments, the $C_{6-12}$ spirocyclyl group is substituted with one $R^4$. In some embodiments, the $C_{6-12}$ spirocyclyl group is substituted with two $R^4$. In some embodiments $R^4$ is —OH. In some embodiments $R^4$ is $C_{1-4}$ alkyl, halo, $C_{1-4}$ haloalkyl, —$X^3$—OH, cyano, or —C(O)—$C_{1-4}$ alkyl. In some embodiments $R^4$ is $C_{1-4}$ alkyl. In some embodiments $R^4$ is halo. In some embodiments $R^4$ is chloro or fluoro. In some embodiments $R^4$ is —OH. In some embodiments $R^4$ is cyano. In some embodiments —C(O)—$C_{1-4}$ alkyl.

In some embodiments, Z in Formula (I) is $C_{5-7}$ cycloalkyl substituted at adjacent ring vertices with two moieties that combine to form a 5- to 6-membered heteroaryl having 1 to 3 heteroatoms as ring vertices independently selected from N, O, and S, thereby forming a fused ring system, wherein the fused ring system is further substituted with 0 to 3 $R^4$. In some embodiments, the fused ring system is substituted with one $R^4$. In some embodiments, the fused ring system is substituted with two $R^4$. In some embodiments $R^4$ is —OH. In some embodiments $R^4$ is $C_{1-4}$ alkyl, halo, $C_{1-4}$ haloalkyl, —$X^3$—OH, cyano, or —C(O)—$C_{1-4}$ alkyl. In some embodiments $R^4$ is $C_{1-4}$ alkyl. In some embodiments $R^4$ is halo. In some embodiments $R^4$ is chloro or fluoro. In some embodiments $R^4$ is —OH. In some embodiments $R^4$ is cyano. In some embodiments —C(O)—$C_{1-4}$ alkyl.

In some embodiments, Z in Formula (I) is a 5- to 7-membered heterocycloalkyl having 1 to 3 heteroatoms as ring vertices independently selected from N, O, and S substituted at adjacent ring vertices with two moieties that combine to form a 5- to 6-membered heteroaryl having 0 to 2 additional heteroatoms as ring vertices independently selected from N, O, and S, thereby forming a fused ring system, wherein the fused ring system is further substituted with 0 to 3 $R^4$. In some embodiments, Z in Formula (I) is 4,5,6,7-tetrahydropyrazolo[1,5-a]pyridinyl, substituted with 0 to 3 $R^4$. In some embodiments, the fused ring system is substituted with one $R^4$.

In some embodiments, Z in Formula (I) a 5- or 6-membered heteroaryl having 1 to 3 heteroatoms as ring vertices independently selected from N, O, and S, and is substituted at adjacent ring vertices with two moieties that combine to form a 5- or 6-membered ring comprising 0 to 2 additional heteroatoms as ring vertices independently selected from the group consisting of N, O, and S, thereby forming a fused ring system, wherein the fused ring system is further substituted with 0 to 3 $R^4$. In some embodiments, Z in Formula (I) is pyridyl substituted at adjacent ring vertices with two moieties that combine to form a 5- or 6-membered ring comprising 0 to 2 additional heteroatoms as ring vertices independently selected from the group consisting of N and O, thereby forming a fused ring system, wherein the fused ring system is further substituted with 0 to 3 $R^4$. In some embodiments, Z in Formula (I) is 4,5,6,7-tetrahydro-1H-indazolyl, substituted with 0 to 3 $R^4$. In some embodiments, Z in Formula (I) is 5,6,7,8-tetrahydroquinolinyl, substituted with 0 to 3 $R^4$. In some embodiments, Z in Formula (I) is 2,3-dihydro-[1,4]dioxino[2,3-b]pyridinyl or 7,8-dihydro-5H-pyrano[4,3-b]pyridinyl, substituted with 0 to 3 $R^4$. In some embodiments, Z in Formula (I) is 5,6,7,8-tetrahydro-1,6-naphthyridinyl, substituted with 0 to 3 $R^4$. In some embodiments, the 5- or 6-membered heteroaryl group is substituted with one $R^4$. In some embodiments, the 45- or 6-membered heteroaryl group is substituted with two $R^4$. In some embodiments $R^4$ is —OH. In some embodiments $R^4$ is $C_{1-4}$ alkyl, halo, $C_{1-4}$ haloalkyl, —$X^3$—OH, cyano, or —C(O)—$C_{1-4}$ alkyl. In some embodiments $R^4$ is $C_{1-4}$ alkyl. In some embodiments $R^4$ is halo. In some embodiments $R^4$ is chloro or fluoro. In some embodiments $R^4$ is —OH. In some embodiments $R^4$ is cyano. In some embodiments —C(O)—$C_{1-4}$ alkyl.

In some embodiments, Z in Formula (I) is a $C_{5-7}$ bridged heterocyclyl having 1 to 3 heteroatoms as ring vertices independently selected from N, O, and S, substituted with 0 to 3 $R^4$. In some embodiments, Z is 2-azabicyclo[2.2.1]heptanyl, substituted with 0 to 3 $R^4$. In some embodiments, the $C_{5-7}$ bridged heterocyclyl group is substituted with one $R^4$. In some embodiments, the $C_{5-7}$ bridged heterocyclyl group is substituted with two $R^4$. In some embodiments $R^4$ is —OH. In some embodiments $R^4$ is $C_{1-4}$ alkyl, halo, $C_{1-4}$ haloalkyl, —$X^3$—OH, cyano, or —C(O)—$C_{1-4}$ alkyl. In some embodiments $R^4$ is $C_{1-4}$ alkyl. In some embodiments $R^4$ is halo. In some embodiments $R^4$ is chloro or fluoro. In some embodiments $R^4$ is —OH. In some embodiments $R^4$ is cyano. In some embodiments —C(O)—$C_{1-4}$ alkyl.

In some embodiments, Z in Formula (I) is 6- to 12-membered spiroheterocyclyl having 1 to 3 heteroatoms as ring vertices independently selected from N, O, and S, substituted with 0 to 3 $R^4$. In some embodiments, Z in Formula (I) is 2-oxaspiro[3.3]heptanyl, substituted with 0 to 3 $R^4$. In some embodiments, Z in Formula (I) is 2-oxaspiro[3.3]heptan-6-yl, substituted with 0 to 3 $R^4$. In some embodiments, the 6- to 12-membered spiroheterocyclyl group is substituted with one $R^4$. In some embodiments, the 6- to 12-membered spiroheterocyclyl group is substituted with two $R^4$. In some embodiments $R^4$ is —OH. In some embodiments $R^4$ is $C_{1-4}$ alkyl, halo, $C_{1-4}$ haloalkyl, —$X^3$—OH, cyano, or —C(O)—$C_{1-4}$ alkyl. In some embodiments $R^4$ is $C_{1-4}$ alkyl. In some embodiments $R^4$ is halo. In some embodiments $R^4$ is chloro or fluoro. In some embodiments $R^4$ is —OH. In some embodiments $R^4$ is cyano. In some embodiments —C(O)—$C_{1-4}$ alkyl.

In some embodiments, Z in Formula (I) is 4- to 10-membered bicyclic heterocyclyl having 1 to 4 heteroatoms as ring vertices independently selected from N, O, and S, substituted with 0 to 3 $R^4$. In some embodiments, Z in Formula (I) is oxabicyclo(3.1.0)hexanyl, substituted with 0 to 3 $R^4$. In some embodiments, the 4- to 10-membered bicyclic heterocyclyl group is substituted with one $R^4$. In some embodiments, the 4- to 10-membered bicyclic heterocyclyl group is substituted with two $R^4$. In some embodiments $R^4$ is —OH. In some embodiments $R^4$ is $C_{1-4}$ alkyl, halo, $C_{1-4}$ haloalkyl, —$X^3$—OH, cyano, or —C(O)—$C_{1-4}$ alkyl. In some embodiments $R^4$ is $C_{1-4}$ alkyl. In some embodiments $R^4$ is halo. In some embodiments $R^4$ is chloro or fluoro. In some embodiments $R^4$ is —OH. In some embodiments $R^4$ is cyano. In some embodiments —C(O)—$C_{1-4}$ alkyl.

In some embodiments, Z in Formula (I) is not substituted with $R^4$. In some embodiments, Z in Formula (I) is substituted with 1 $R^4$. In some embodiments, Z in Formula (I) is substituted with 2 $R^4$. In some embodiments $R^4$ is —OH. In some embodiments $R^4$ is $C_{1-4}$ alkyl, halo, $C_{1-4}$ haloalkyl, —$X^3$—OH, cyano, or —C(O)—$C_{1-4}$ alkyl. In some embodiments $R^4$ is $C_{14}$ alkyl. In some embodiments $R^4$ is halo. In some embodiments $R^4$ is chloro or fluoro. In some embodiments $R^4$ is —OH. In some embodiments $R^4$ is cyano. In some embodiments —C(O)—$C_{1-4}$ alkyl.

In some aspects, provided herein are compounds of Formula (II)

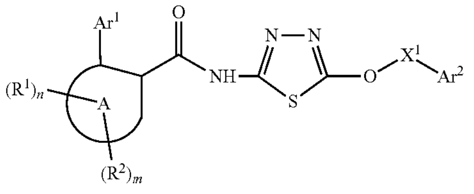

(II)

wherein:

$X^1$ is selected from the group consisting of $CH_2$ and $C_{2-4}$ alkylene substituted with from 0 to 1 —OH;

ring A is selected from the group consisting of phenyl and a 5- to 10-membered heteroaryl having 1 to 3 heteroatoms as ring vertices independently selected from N, O, and S; the subscripts m and n are each independently 0 or 1;

each $R^1$ and $R^2$, when present, are each independently selected from $C_{1-4}$ alkyl, $C_{1-4}$ alkoxy, halo, $C_{1-4}$ haloalkyl, $C_{1-4}$ haloalkoxy, $C_{1-4}$ hydroxyalkyl, —C(O)OH, and cyano;

$Ar^1$ is selected from the group consisting of phenyl, 5- to 6-membered heteroaryl having 1 to 3 heteroatoms as ring vertices independently selected from N, O, and S, 5- to 6-membered heterocycloalkyl having 1 to 3 heteroatoms as ring vertices independently selected from N, O, and S, 6- to 10-membered bicyclic heterocyclyl having 1 to 4 heteroatoms as ring vertices independently selected from N, O, and S, 6- to 10-membered bridged heterocyclyl having 1 to 3 heteroatoms as ring vertices independently selected from N, O, and S, and 6- to 12-membered spiroheterocyclyl having 1 to 3 heteroatoms as ring vertices independently selected from N, O, and S, wherein $Ar^1$ is substituted with 0 to 3 $R^3$;

each $R^3$ is independently selected from the group consisting of $C_{1-4}$ alkyl, halo, $C_{1-4}$ haloalkyl, $C_{1-4}$haloalkoxy, $C_{3-6}$ cycloalkyl, $C_{3-6}$ cycloalkyloxy, —$X^2$—OH, —$X^2$—O—$C_{1-4}$ alkyl, —C(O)—$C_{1-4}$ alkyl, and —$X^2$-cyano; or two $R^3$ on adjacent ring vertices, combine to form a $C_{3-6}$ cycloalkyl, or two $R^3$ on the same ring vertex, combine to form oxo, wherein each $X^2$ is independently selected from a bond and $C_{1-4}$ alkylene;

$Ar^2$ is selected from the group consisting of phenyl, 5- to 10-membered heteroaryl having 1 to 3 heteroatoms as ring vertices independently selected from N, O, and S, and $C_{3-6}$ cycloalkyl, wherein each $Ar^2$ is substituted with an $R^{4a}$ substituent selected from the group consisting of $-X^3-OH$, $-X^3-O-C_{1-4}$ alkyl, $C_{3-6}$ cycloalkyl, $-X^5-C(O)OH$, $-C_{2-4}$ alkylene-cyano, $-S(O)(NH)-C_{1-4}$ alkyl, $-S(O)_2-C_{1-4}$ alkyl, and $-X^4$-heterocycloalkyl comprising 4- to 6-ring members and 1 to 3 heteroatoms as ring vertices independently selected from N, O, and S wherein each cycloalkyl is independently substituted with from 1 to 2 substituents independently selected from $-X^3-O-C_{1-4}$ alkyl, $-X^5-C(O)OH$ and $-X^3-OH$;

and wherein each $Ar^2$ is also substituted with 0 to 2 $R^4$ substituents each of which is independently selected from the group consisting of $C_{1-4}$ alkyl, halo, $C_{1-4}$ haloalkyl, $C_{1-4}$ alkoxy, $C_{1-4}$ haloalkoxy, $-X^5-OH$, $C_{3-6}$ cycloalkyl, $-X^5$-cyano, and $C_{3-6}$ cycloalkyloxy;

each $X^3$ is independently $C_{1-4}$ alkylene;

each $X^4$ is selected from —O— and $C_{1-4}$ alkylene; and each $X^5$ is independently selected from a bond and $C_{1-4}$ alkylene;

or a pharmaceutically acceptable salt thereof.

In some embodiments $Ar^2$ and $R^{4a}$ combine to form

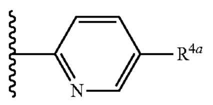

wherein the wavy line represents the point of attachment to the remainder of the molecule.

In some embodiments, $X^1$ in Formula (II) is $CH_2$.

In some embodiments, $R^{4a}$ in Formula (II) is $-X^3-OH$. In some embodiments, $R^{4a}$ in Formula (II) is selected from the group consisting of hydroxymethyl, 1-hydroxylethyl, 2-hydroxyethyl, and 2-hydroxylpropan-2-yl. In some embodiments, $Ar^2$ is pyridyl or piperazinyl and $R^{4a}$ is hydroxymethyl or 2-hydroxylpropan-2-yl.

In some embodiments, $R^{4a}$ in Formula (II) is $-X^3-O-C_{1-4}$ alkyl. In some embodiments, $R^{4a}$ in Formula (II) is selected from the group consisting of methoxymethyl, 2-methoxypropan-2-yl, and 1-methoxyethyl. In some embodiments, $Ar^2$ is pyridyl or piperazinyl and $R^{4a}$ is selected from the group consisting of methoxymethyl, 2-methoxypropan-2-yl, and 1-methoxyethyl.

In some embodiments, $R^{4a}$ in Formula (II) is $C_{3-6}$ cycloalkyl substituted with 1 to 2 substituents independently selected from the group consisting of —C(O)OH and hydroxymethyl. In some embodiments, $R^{4a}$ is cycloalkyl substituted with —C(O)OH or hydroxymethyl.

In some embodiments, $R^{4a}$ in Formula (II) is $-X^5-C(O)OH$. In some embodiments, $R^{4a}$ is —C(O)OH. In some embodiments, $Ar^2$ and $R^{4a}$ combine to form

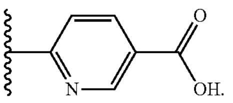 [SMILES: *c1ccc(C(=O)O)cn1]

In some embodiments, $R^{4a}$ in Formula (II) is $-C_{24}$ alkylene-cyano. In some embodiments $R^{4a}$ is selected from the group consisting of 1-cyanoethyl, 2-cyanoethyl, and 2-cyanopropan-2-yl. In some embodiments $R^{4a}$ is 2-cyano-propan-2-yl.

In some embodiments, $R^{4a}$ in Formula (II) is $-S(O)(NH)-C_{1-4}$ alkyl. In some embodiments $R^{4a}$ is —S(O)(NH)-methyl. In some embodiments, $Ar^2$ and $R^{4a}$ combine to form

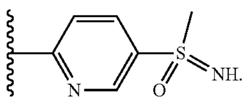

In some embodiments, $R^{4a}$ in Formula (II) is $-S(O)_2-C_{1-4}$ alkyl. In some embodiments $R^{4a}$ is $-S(O)_2$-methyl. In some embodiments, $Ar^2$ and $R^{4a}$ combine to form

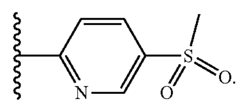

In some embodiments, $R^{4a}$ in Formula (II) is $-X^4$-heterocycloalkyl comprising 4- to 6-ring members and 1 to 3 heteroatoms as ring vertices independently selected from N, O, and S. In some embodiments, $R^{4a}$ is -methylene-heterocycloalkyl comprising 4- to 6-ring members and 1 to 3 heteroatoms as ring vertices independently selected from N, O, and S. In some embodiments, $R^{4a}$ is —O-heterocycloalkyl comprising 4- to 6-ring members and 1 to 3 heteroatoms as ring vertices independently selected from N, O, and S. In some embodiments, the heterocycloalkyl comprising 4- to 6-ring members and 1 to 3 heteroatoms as ring vertices independently selected from N, O, and S is selected from the group consisting of oxetanyl, azetidinyl, tetrahydropyran, tetrahydrofurane, pyrrolidine, pyrazolidine, piperidine, morpholine, and piperazine. In some embodiments, the heterocycloalkyl comprising 4- to 6-ring members and 1 to 3 heteroatoms as ring vertices independently selected from N, O, and S is oxetanyl.

In some aspects, provided herein are compounds of Formula (III)

(III)

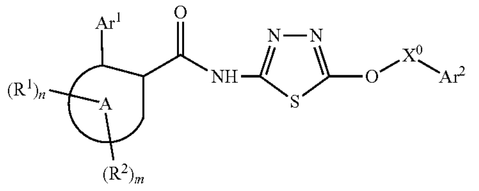

wherein:

$X^1$ is $C_{2-4}$ alkylene substituted with —OH;

ring A is selected from the group consisting of phenyl and a 5- to 10-membered heteroaryl having 1 to 3 heteroatoms as ring vertices independently selected from N, O, and S;

the subscripts m and n are each independently 0 or 1;

each $R^1$ and $R^2$, when present, are each independently selected from $C_{1-4}$ alkyl, $C_{1-4}$ alkoxy, halo, $C_{1-4}$ haloalkyl, $C_{1-4}$ haloalkoxy, $C_{1-4}$ hydroxyalkyl, —C(O)OH, and cyano;

$Ar^1$ is selected from the group consisting of phenyl and 5- to 6-membered heteroaryl having 1 to 3 heteroatoms as ring vertices independently selected from N, O, and S, wherein $Ar^1$ is substituted with 0 to 3 $R^3$;

each $R^3$ is independently selected from the group consisting of $C_{1-4}$ alkyl, halo, $C_{1-4}$ haloalkyl, $C_{1-4}$haloalkoxy, $C_{3-6}$ cycloalkyl, $C_{3-6}$ cycloalkyloxy, —$X^2$—OH, —$X^2$—O—$C_{1-4}$ alkyl, —C(O)—$C_{1-4}$ alkyl, and —$X^2$-cyano; or two $R^3$ on adjacent ring vertices, combine to form a $C_{5-6}$cycloalkyl, wherein each $X^2$ is independently selected from a bond and $C_{1-4}$ alkylene;

$Ar^2$ is selected from the group consisting of phenyl, 5- to 10-membered heteroaryl having 1 to 3 heteroatoms as ring vertices independently selected from N, O, and S, and $C_{3-6}$ cycloalkyl, wherein each $Ar^2$ is substituted with 0 to 3 $R^4$, and each $R^4$ is independently selected from the group consisting of $C_{1-4}$ alkyl, halo, $C_{1-4}$haloalkyl, $C_{1-4}$haloalkoxy, $C_{3-6}$ cycloalkyl, $C_{3-6}$ cycloalkyloxy, —$X^3$—OH, —$X^3$—O—$C_{1-4}$ alkyl, $C_{3-6}$ cycloalkyl, —$X^5$—C(O)OH, —$C_{2-4}$alkylene-cyano, —S(O)(NH)—$C_{1-4}$ alkyl, —$S(O)_2$—$C_{1-4}$ alkyl, and —$X^4$-heterocycloalkyl comprising 4- to 6-ring members and 1 to 3 heteroatoms as ring vertices independently selected from N, O, and S wherein each cycloalkyl is independently substituted with from 1 to 2 substituents independently selected from —$X^3$—O—$C_{1-4}$ alkyl, —$X^5$—C(O)OH and —$X^3$—OH;

each $X^3$ is independently $C_{1-4}$ alkylene;

each $X^4$ is independently selected from —O— and $C_{1-4}$ alkylene; and each $X^5$ is independently selected from a bond and $C_{1-4}$ alkylene;

or a pharmaceutically acceptable salt thereof.

In some aspects, provided herein are compounds of Formula (IV)

(IV)

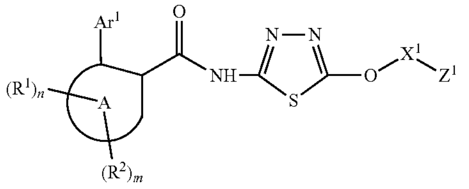

wherein:

$X^1$ is selected from the group consisting of $CH_2$ and $C_{2-4}$ alkylene substituted with from 0 to 1 —OH;

ring A is selected from the group consisting of phenyl and a 5- to 10-membered heteroaryl having 1 to 4 heteroatoms as ring vertices independently selected from N, O, and S; the subscripts m and n are each independently 0 or 1;

$R^1$ and $R^2$, when present, are each independently selected from the group consisting of $C_{1-4}$ alkyl, $C_{1-4}$ alkoxy, halo, $C_{1-4}$ haloalkyl, $C_{1-4}$ haloalkoxy, $C_{1-4}$ hydroxyalkyl, —$X^a$—O—$C_{3-6}$ cycaloalkyl, —C(O)OH, and cyano, wherein $X^a$ is independently selected from a bond and $C_{1-4}$ alkylene;

$Ar^1$ is selected from the group consisting of phenyl, 5- to 6-membered heteroaryl having 1 to 4 heteroatoms as ring vertices independently selected from N, O, and S, 5- to 6-membered heterocycloalkyl having 1 to 3 heteroatoms as ring vertices independently selected from N, O, and S, 6- to 10-membered bicyclic heterocyclyl having 1 to 4 heteroatoms as ring vertices independently selected from N, O, and S, 6- to 10-membered bridged heterocyclyl having 1 to 3 heteroatoms as ring vertices independently selected from N, O, and S, and 6- to 12-membered spiroheterocyclyl having 1 to 3 heteroatoms as ring vertices independently selected from N, O, and S, wherein $Ar^1$ is substituted with 0 to 3 $R^3$;

each $R^3$ is independently selected from the group consisting of $C_{1-4}$ alkyl, halo, $C_{1-4}$ haloalkyl, $C_{1-4}$haloalkoxy, $C_{3-6}$ cycloalkyl, $C_{3-6}$ cycloalkyloxy, —$X^2$—OH, —$X^2$—O—$C_{1-4}$ alkyl, —C(O)—$C_{1-4}$ alkyl, and —$X^2$-cyano; or two $R^3$ on adjacent ring vertices, combine to form a $C_{3-6}$ cycloalkyl, or two $R^3$ on the same ring vertex, combine to form oxo, wherein each $X^2$ is selected from a bond and $C_{1-4}$ alkylene; and $Z^1$ is $C_{3-6}$ cycloalkyl substituted with 1 to 3 $R^5$ substituents, wherein each $R^5$ is independently selected from —OH, cyano, $C_{1-4}$ alkyl, halo, $C_{1-4}$ haloalkyl, $C_{1-4}$alkoxy, and $C_{1-4}$ haloalkoxy;

or a pharmaceutically acceptable salt thereof.

In some aspects, provided herein are compounds of Formula (IV)

(IV)

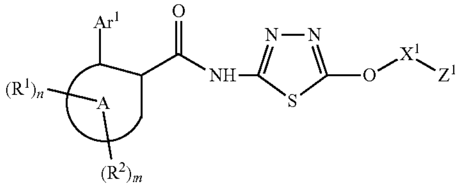

wherein:

$X^1$ is selected from the group consisting of $CH_2$ and $C_{2-4}$ alkylene substituted with from 0 to 1 —OH;

ring A is selected from the group consisting of phenyl and a 5- to 10-membered heteroaryl having 1 to 4 heteroatoms as ring vertices independently selected from N, O, and S;

the subscripts m and n are each independently 0 or 1;

$R^1$ and $R^2$, when present, are each independently selected from the group consisting of $C_{1-4}$ alkyl, $C_{1-4}$ alkoxy, halo, $C_{1-4}$ haloalkyl, $C_{1-4}$ haloalkoxy, $C_{1-4}$ hydroxyalkyl, —C(O)OH, and cyano;

$Ar^1$ is selected from the group consisting of phenyl, 5- to 6-membered heteroaryl having 1 to 4 heteroatoms as ring vertices independently selected from N, O, and S, 5- to 6-membered heterocycloalkyl having 1 to 3 heteroatoms as ring vertices independently selected from N, O, and S, 6- to 10-membered bicyclic heterocyclyl having 1 to 4 heteroatoms as ring vertices independently selected from N, O, and S, 6- to 10-membered bridged heterocyclyl having 1 to 3 heteroatoms as ring vertices independently selected from N, O, and S, and 6- to 12-membered spiroheterocyclyl having 1 to 3 heteroatoms as ring vertices independently selected from N, O, and S, wherein $Ar^1$ is substituted with 0 to 3 $R^3$;

each $R^3$ is independently selected from the group consisting of $C_{1-4}$ alkyl, halo, $C_{1-4}$ haloalkyl, $C_{1-4}$haloalkoxy, $C_{3-6}$ cycloalkyl, $C_{3-6}$ cycloalkyloxy, —$X^2$—OH, —$X^2$—O—$C_{1-4}$ alkyl, —C(O)—$C_{1-4}$ alkyl, and —$X^2$-cyano; or two $R^3$ on adjacent ring vertices, combine to form a $C_{3-6}$cycloalkyl, or two $R^3$ on the same ring vertex, combine to form oxo, wherein each $X^2$ is selected from a bond and $C_{1-4}$ alkylene; and $Z^1$ is $C_{3-6}$ cycloalkyl substituted with 1 to 3 $R^5$ substituents, wherein each $R^5$ is independently selected from —OH, cyano, $C_{1-4}$ alkyl, halo, $C_{1-4}$ haloalkyl, $C_{1-4}$alkoxy, and $C_{1-4}$ haloalkoxy;

or a pharmaceutically acceptable salt thereof.

In some embodiments, compounds of Formula (IV) have the structure of Formula (IVa)

(IVa)

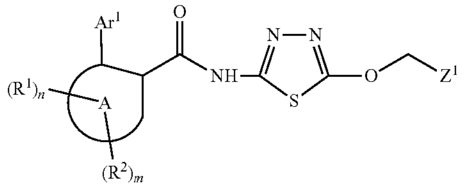

or a pharmaceutically acceptable salt thereof.

In some embodiments, compounds of Formula (IV) have the structure of Formula (IVb)

(IVb)

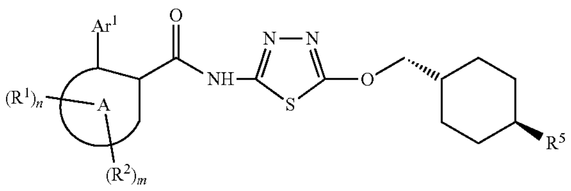

or a pharmaceutically acceptable salt thereof.

In some embodiments, compounds of Formula (IV) have the structure of Formula (IVc)

(IVc)

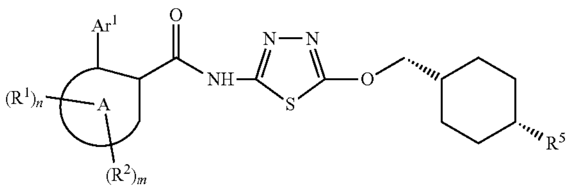

or a pharmaceutically acceptable salt thereof.

In some embodiments, $Z^1$ in formula (IV) is

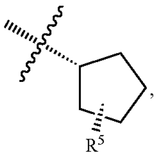,
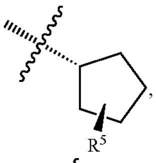,
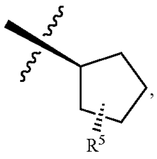, or
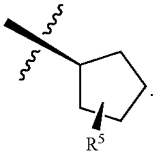.

In some embodiments, $Z^1$ in formula (IV) is

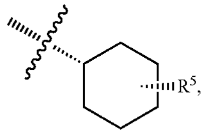
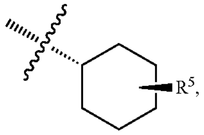
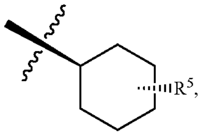 or
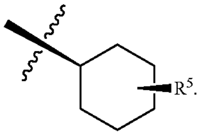

In some embodiments, $X^1$ in Formula (IV) is $CH_2$.

In some embodiments, $X^1$ in Formula (IV) is $CH_2CH_2$.

In some embodiments, $R^5$ in Formula (IV) is halo. In some embodiments, $R^5$ in Formula (IV) is cholo. In some embodiments, $R^5$ in Formula (IV) is fluoro.

In some embodiments, $R^5$ in Formula (IV) is $C_{1-4}$ alkoxy. In some embodiments, $R^5$ in Formula (IV) is methoxy. In some embodiments, $R^5$ in Formula (IV) is ethoxy.

In some embodiments, $R^5$ in Formula (IV) is —OH. In some embodiments, $R^5$ in Formula (IV) is cyano.

In some embodiments, $Z^1$ in Formula (IV) is substituted (i.e., $Z^1$ is substituted with 1 $R^5$ substituents). In some embodiments, $Z^1$ in Formula (IV) is substituted (i.e., $Z^1$ is substituted with 2 $R^5$ substituents). In some embodiments, $Z^1$ in Formula (IV) is substituted (i.e., $Z^1$ is substituted with 3 $R^5$ substituents).

In some embodiments, $Z^1$ in Formula (IV) is cyclopropyl, cyclobutyl, cyclocpentyl or cyclohexyl. In some embodiments, $Z^1$ in Formula (IV) is cyclopropyl. In some embodiments, $Z^1$ in Formula (IV) is cyclobutyl. In some embodiments, $Z^1$ in Formula (IV) is cyclopentyl. In some embodiments, $Z^1$ in Formula (IV) is cyclohexyl.

In some embodiments, $Z^1$ in Formula (IV) is cyclopropyl, cyclobutyl, cyclopentyl or cyclohexyl, wherein each $Z^1$ is independently substituted with one or two $R^5$ independently selected from cyano, hydroxy, and halo.

In some embodiments, $Z^1$ in Formula (IV) is cyclopropyl, cyclobutyl, cyclopentyl or cyclohexyl, wherein each $Z^1$ is independently substituted with one or two $R^5$ independently selected from cyano, hydroxy, and fluoro.

In some embodiments, $Z^1$ in Formula (IV) is cyclopropyl, cyclobutyl, cyclopentyl or cyclohexyl, wherein each $Z^1$ is independently substituted with one or two $R^5$ independently selected from hydroxy and fluoro.

In some embodiments, $Z^1$ in Formula (IV) is cyclopropyl, cyclobutyl, cyclopentyl or cyclohexyl, wherein each $Z^1$ is independently substituted with cyano.

In some embodiments, $Z^1$ in Formula (IV) is cyclopropyl, cyclobutyl, cyclopentyl or cyclohexyl, wherein each $Z^1$ is independently substituted with hydroxy.

In some embodiments, $Z^1$ in Formula (IV) is cyclopropyl, cyclobutyl, cyclopentyl or cyclohexyl, wherein each $Z^1$ is independently substituted with halo. In some embodiments, $Z^1$ in Formula (IV) is cyclopropyl, cyclobutyl, cyclopentyl or cyclohexyl, wherein each $Z^1$ is independently substituted with fluoro.

In some embodiments, $Z^1$ in Formula (IV) is cyclopropyl substituted with one or two $R^5$ independently selected from halo and cyano.

In some embodiments, $Z^1$ in Formula (IV) is cyclobutyl substituted with one or two $R^5$ independently selected from hydroxy and halo.

In some embodiments, $Z^1$ in Formula (IV) is cyclopentyl substituted with hydroxy.

In some embodiments, $Z^1$ in Formula (IV) is cyclohexyl substituted with one or two $R^5$ independently selected from hydroxy, and halo.

In some embodiments, $X^1$ in Formula (I) (II), or (IV) is $C_2$ alkylene substituted with —OH. In some embodiments, $X^0$ in Formula (III) is $C_2$ alkylene substituted with —OH.

In some embodiments, ring A in Formula (I), (II), (III) or (IV) is phenyl, pyridinyl, pyridazinyl, imidazolyl, pyrazolyl, triazolyl, imidazo[1,2-a]pyridinyl, [1,2,3]triazolo[1,5-a]pyridinyl, imidazo[1,5-a]pyridinyl, pyrrolo[2,3-b]pyridinyl, pyrrolo[3,2-b]pyridinyl, pyrazolo[1,5-a]pyridinyl, [1,2,4]triazolo[1,5-a]pyridinyl, 1,6-naphthyridinyl, or 1,7-naphthyridinyl.

In some embodiments, ring A in Formula (I), (II), (III) or (IV) is phenyl.

In some embodiments, ring A in Formula (I), (II), (III) or (IV) is a nine or ten membered heteroaryl ring.

In some embodiments, ring A in Formula (I), (II), (III) or (IV) is imidazo[1,2-a]pyridinyl, [1,2,3]triazolo[1,5-a]pyridinyl, imidazo[1,5-a]pyridinyl, pyrrolo[2,3-b]pyridinyl, pyrrolo[3,2-b]pyridinyl, pyrazolo[1,5-a]pyridinyl, [1,2,4]triazolo[1,5-a]pyridinyl, 1,6-naphthyridinyl, or 1,7-naphthyridinyl.

In some embodiments, ring A in Formula (I), (II), (III) or (IV) is a five or six membered heteroaryl ring.

In some embodiments, ring A in Formula (I), (II), (III) or (IV) is pyridinyl, pyridazinyl, pyrimidinyl, imidazolyl, pyrazolyl, or triazolyl.

In some embodiments, ring A in Formula (I), (II), (III) or (IV) is pyridyl.

In some embodiments, ring A in Formula (I), (II), (III) or (IV) is selected from the group consisting of

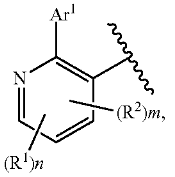 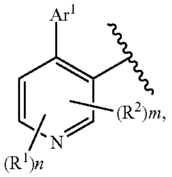 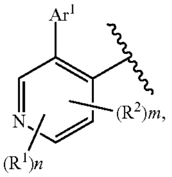

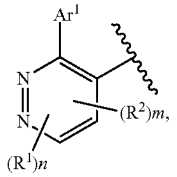 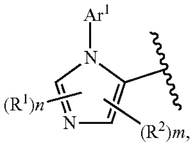 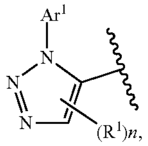

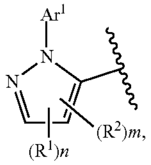 and 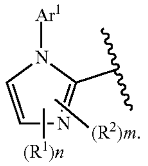

In some embodiments, ring A in Formula (I), (II), (III) or (IV) is selected from the group consisting of

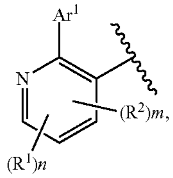 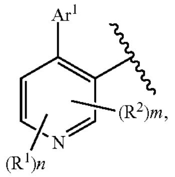

-continued

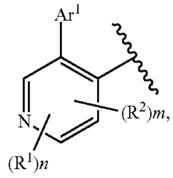 and 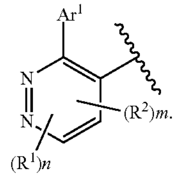

In some embodiments, ring A in Formula (I), (II), (III) or (IV) is selected from the group consisting of

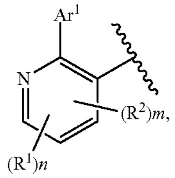 and 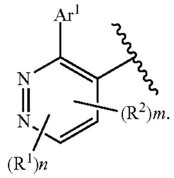

In some embodiments, ring A in Formula (I), (II), (III) or (IV) is selected from the group consisting of

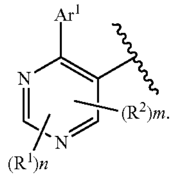

In some embodiments, ring A in Formula (I), (II), (III) or (IV) is

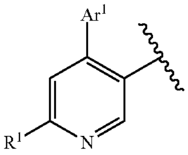

In some embodiments, ring A in Formula (I), (II), (III) or (IV) is

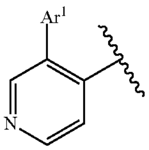

In some embodiments, ring A in Formula (I), (II), (III) or (IV) is

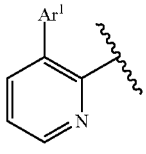

In some embodiments, ring A in Formula (I), (II), (III) or (IV) is

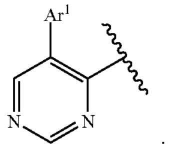

In some embodiments, ring A in Formula (I), (II), (III) or (IV) is

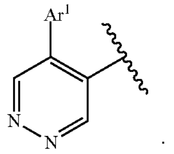

In some embodiments, ring A in Formula (I), (II), (III) or (IV) is not pyrimidine.

In some embodiments, $Ar^1$ in Formula (I), (II), (III) or (IV) is selected from the group consisting of 5- to 6-membered heterocycloalkyl having 1 to 3 heteroatoms as ring vertices independently selected from N, O, and S, wherein $Ar^1$ in Formula (I), (II), (III) or (IV) is substituted with 0 to 3 R. In some embodiments, $Ar^1$ in Formula (I), (II), (III) or (IV) is selected from the group consisting of piperidinyl, piperazinyl, morpholinyl, 2-oxopiperazinyl, 2-tetrahydropyranyl, 3,6-dihydro-2H-pyranyl, 2-oxo-1,2-dihydropyridinyl, thiomorpholinyl, and 1,1-dioxothiomorpholinyl, each $Ar^1$ is substituted with 0 to 3 $R^3$. In some embodiments, $Ar^1$ in Formula (I), (II), (III) or (IV) is selected from the group consisting of piperidin-1-yl, piperazin-1-yl, morpholin-4-yl, tetrahydropyran-4-yl, 3,6-dihydro-2H-pyran-4-yl, 6-oxo-1,6-dihydropyridin-3-yl, 6-oxo-1,6-dihydropyridin-4-yl, thiomorpholin-4-yl, and 1,1-dioxothiomorpholin-4-yl, each $Ar^1$ is substituted with 0 to 3 $R^3$. In some embodiments, $Ar^1$ in Formula (I), (II), (III) or (IV) is morpholin-4-yl substituted with 0 to 3 $R^3$. In some embodiments, $Ar^1$ in Formula (I), (II), (III) or (IV) is selected from the group consisting of morpholin-4-yl, 2-methylmorpholin-4-yl, 3-methylmorpholin-4-yl, 3R-methylmorpholin-4-yl, 3S-methylmorpholin-4-yl, 3-oxopiperazin-1-yl, 4-methyl-3-oxo-piperazin-1-yl, 2-methyl-3-oxopiperazin-1-yl, 6-methyl-3-oxopiperazin-1-yl, 5-methyl-3-oxopiperazin-1-yl, 4-dimethylaminocarbonylpiperazin-1-yl, tetrahydropyran-4-yl, 3,6-dihydro-2H-pyran-4-yl, 4-(2-hydroxyethyl)-3-oxopiperazin-1-yl, 6-oxo-1,6-dihydropyridin-4-yl, 6-oxo-1,6-dihydropyridin-3-yl, 1-methyl-6-oxo-1,6-dihydropyridin-3-yl, 4-(2-morpholin-4-ylethyl)-3-oxopiperazin-1-yl, 4-methylcarbonylpiperazin-1-yl, 4-methylsulfonylpiperazin-1-yl, 1,1-dioxothiomorpholin-4-yl, and 4,4-difluoropiperidin-1-yl.

In some embodiments, $Ar^1$ in Formula (I), (II), or (IV) is bicyclic heterocyclyl substituted with 0 to 3 $R^3$. In some embodiments, $Ar^1$ in Formula (I), (II) or (IV) is selected from the group consisting of 6-oxohexahydropyrrolo[1,2-a]pyrazin-2 (1H)-yl and 2,3-dihydro-4H-benzo[b][1,4]oxazin-4-yl, each ring substituted with 0 to 3 $R^3$. In some embodiments, $Ar^1$ in Formula (I), (II), or (IV) is selected from the group consisting of 6-oxohexahydropyrrolo[1,2-a]pyrazin-2 (1H)-yl, 3-oxo-3,4-dihydro-2H-benzo[b][1,4]oxazin-8-yl, benzo[d][1,3]dioxol-4-yl, (3,4-dihydro-2H-1,4-benzoxazin-8-yl), [5H,6H,7H-pyrazolo[1,5-a]pyrimidin-4-yl] and 2,3-dihydro-4H-benzo[b][1,4]oxazin-4-yl, each ring substituted with 0 to 3 $R^3$. In some embodiments, $Ar^1$ in Formula (I), (II) or (IV) is substituted with 0 to 3 $R^3$, each of which is independently selected from the group consisting of methyl, ethyl, fluoro, cyano, difluoromethyl, trifluoromethyl, trifluoroethyl, methoxy, ethoxy, difluoromethoxy, trifluoromethoxy, trifluoroethoxy, hydroxy, methylsulfonyl, 2-hydroxyethyl, and 2-methoxyethyl.

In some embodiments, $Ar^1$ in Formula (I), (II), (III) or (IV) is phenyl substituted with 0 to 3 $R^3$. In some embodiments, $Ar^1$ in Formula (I), (II), (III) or (IV) is phenyl, 2-methoxyphenyl, 3-methoxyphenyl, 4-methoxyphenyl, 2,4-dimethoxyphenyl, 2-chlorophenyl, 2-cyanophenyl, or 2-cyclopropyl-oxyphenyl. In some embodiments, $Ar^1$ in Formula (I), (II), (III) or (IV) is 2-methoxyphenyl. In some embodiments, $Ar^1$ in Formula (I), (II), (III) or (IV) is 3-methoxyphenyl. In some embodiments, $Ar^1$ in Formula (I), (II), (III) or (IV) is 2,4-dimethoxyphenyl. In some embodiments, $Ar^1$ in Formula (I), (II), (III) or (IV) is

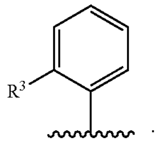

In some embodiments, $Ar^1$ in Formula (I), (II), (III) or (IV) is

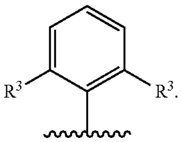

In some embodiments, $Ar^1$ in Formula (I), (II), (III) or (IV) is

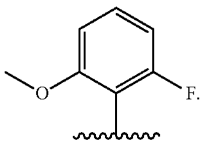 [SMILES: *c1c(F)cccc1OC]

In some embodiments, $Ar^1$ in Formula (I), (II), or (IV) is 6- to 10-membered bridged heterocyclyl having 1 to 3 heteroatoms as ring vertices independently selected from N, O, and S, or 6- to 12-membered spiroheterocyclyl, having 1 to 3 heteroatoms as ring vertices independently selected from N, O, and S, wherein $Ar^1$ is substituted with 0 to 3 $R^3$.

In some embodiments, $Ar^1$ in Formula (I), (II), (III) or (IV) is heteroaryl substituted with 0 to 3 R. In some embodiments, $Ar^1$ in Formula (I), (II), (III) or (IV) is pyridinyl, pyrimidinyl, pyrazolyl, pyrrolyl, imidazolyl, or triazolyl substituted with 0 to 3 $R^3$. In some embodiments, $Ar^1$ is substituted with 0 to 3 $R^3$, each of which is independently selected from the group consisting of methyl, ethyl, fluoro, difluoromethyl, trifluoromethyl, trifluoroethyl, methoxy, ethoxy, difluoromethoxy, trifluoromethoxy, trifluoroethoxy, hydroxy, 2-hydroxyethyl, and 2-methoxyethyl.

In some embodiments, $Ar^1$ in Formula (I) (II), (III) or (IV) is

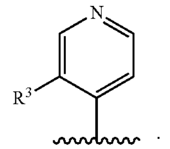

In some embodiments, $Ar^1$ in Formula (I), (II), (III) or (IV) is

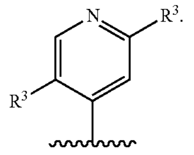

In some embodiments, $Ar^1$ in Formula (I), (II), (III) or (IV) is

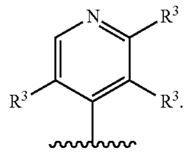

In some embodiments, $Ar^1$ in Formula (I), (II), (III) or (IV) is

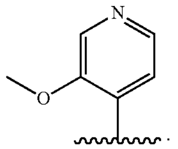 [SMILES: *c1ccncc1OC]

In some embodiments, $Ar^1$ in Formula (I), (II), (III) or (IV) is

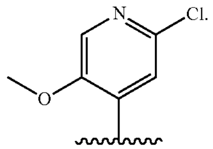 [SMILES: *c1cc(Cl)ncc1OC]

In some embodiments, $Ar^1$ in Formula (I), (II), (III) or (IV) is

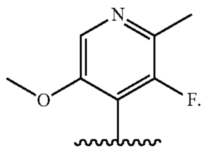 [SMILES: *c1c(OC)cnc(C)c1F]

In some embodiments, $R^1$ and $R^2$ in Formula (I), (II), (III) or (IV), when present, are each independently selected from the group consisting of $C_{1-4}$ alkyl, $C_{1-4}$ alkoxy, halo, and $C_{1-4}$ haloalkyl. In some embodiments, $R^1$ and $R^2$ in Formula (I), (II), (III) or (IV), when present are each independently $C_{1-4}$ alkyl. In some embodiments, $R^1$ and $R^2$ in Formula (I), (II), (III) or (IV), when present are each independently methyl. In some embodiments, $R^1$ and $R^2$ in Formula (I), (II), (III) or (IV), when present, can also include —$X^a$—O—$C_{1-4}$ alkyl and —$X^a$—O—$C_{3-6}$ cycaloalkyl, wherein $X^a$ is independently selected from a bond and $C_{1-4}$ alkylene. In some embodiments, $R^2$ in Formula (I), (II), (III) or (IV), when present, is —$X^a$—O—$C_{1-4}$ alkyl, wherein $X^a$ is independently selected from a bond and $C_{1-4}$ alkylene. In some embodiments, $R^2$ in Formula (I), (II), (III) or (IV), when present, is —$X^a$—O—$C_{3-6}$ cycaloalkyl, wherein $X^a$ is independently selected from a bond and $C_{1-4}$ alkylene.

In some embodiments, $Ar^1$ in Formula (I), (II), (III) or (IV) is substituted with 0 to 2 $R^3$. In some embodiments, $Ar^1$ in Formula (I), (II), (III) or (IV) is substituted with 0 to 1 $R^3$. In some embodiments, $Ar^1$ in Formula (I), (II), (III) or (IV) is not substituted with $R^3$. In some embodiments, $Ar^1$ in Formula (I), (II), (III) or (IV) is substituted with 1 $R^3$. In some embodiments, $Ar^1$ in Formula (I), (II), (III) or (IV) is substituted with 2 $R^3$. In some embodiments, $Ar^1$ in Formula (I), (II), (III) or (IV) is substituted with 3 $R^3$.

In some embodiments, each $R^3$ in Formula (I), (II), (III) or (IV) is independently selected from $C_{1-4}$ alkyl, halo, $C_{1-4}$ haloalkyl, $C_{1-4}$ alkoxy, $C_{1-4}$ haloalkoxy, $C_{3-6}$ cycloalkyl, and cyano. In some embodiments, each $R^3$ in Formula (I), (II), (III) or (IV) is independently selected from $C_{1-4}$ alkyl, halo, $C_{1-4}$ haloalkyl, $C_{1-4}$ alkoxy, and $C_{1-4}$ haloalkoxy. In some embodiments, each $R^3$ in Formula (I), (II), (III) or (IV) is independently selected from methoxy, methyl, ethyl, fluoro, chloro, difluoromethoxy, cyano, and cyclopropyl.

In some embodiments, each $R^3$ in Formula (I), (II), (III) or (IV) is independently selected from $C_{1-4}$ alkyl, halo, $C_{1-4}$ haloalkyl, $C_{1-4}$ alkoxy, $C_{1-4}$ haloalkoxy, and $C_{3-6}$ cycloalkyl, —$X^2$—OH, and —$X^2$-cyano. In some embodiments, each $R^3$ in Formula (I), (II), (III) or (IV) is independently selected from $C_{1-4}$ alkyl, halo, $C_{1-4}$ haloalkyl, $C_{1-4}$ alkoxy, $C_{1-4}$ haloalkoxy, $C_{3-6}$ cycloalkyl, and cyano. In some embodiments, each $R^3$ in Formula (I), (II), (III) or (IV) is independently selected from methoxy, methyl, ethyl, fluoro, chloro, difluoromethoxy, cyano, hydroxymethyl, and cyclopropyl. In some embodiments, each $R^3$ in Formula (I), (II), (III) or (IV) is selected from methyl, fluoro, chloro, and cyclopropyl. In some embodiments, each $R^3$ in Formula (I), (II), (III) or (IV) is difluoromethoxy, fluoro, chloro, and cyano. In some embodiments, each $R^3$ in Formula (I), (II), (III) or (IV) is methoxy, fluoro, and chloro.

In some embodiments, Z or $Ar^2$ in Formula (I) or (II) is substituted with 0 to 2 $R^4$ substituents, and each $R^4$ is independently selected from the group consisting of $C_{1-4}$ alkyl, halo, $C_{1-4}$ haloalkyl, $C_{1-4}$ alkoxy, $C_{1-4}$ haloalkoxy, —OH, cyano, and —C(O)—$C_{1-4}$ alkyl. In some embodiments, Z or $Ar^2$ in Formula (I) or (II) is substituted with 0 to 2 $R^4$ substituents, and each $R^4$ is independently selected from the group consisting of methyl, ethyl, chloro, fluoro, methoxy, ethoxy, —OH, cyano, —C(O)-methyl, —C(O)-ethyl, and —C(O)-2-propyl. In some embodiments, Z or $Ar^2$ in Formula (I) or (II) is substituted with 0 to 2 $R^4$ substituents, and each $R^4$ is independently selected from the group consisting of chloro, fluoro, —OH, cyano, and —C(O)-2-propyl.

In some embodiments, Z or $Ar^2$ in Formula (I) or (II) is substituted with 0 to 1 $R^4$ substituents, and each $R^4$ is independently selected from the group consisting of $C_{1-4}$ alkyl, halo, $C_{1-4}$ haloalkyl, —OH, and —C(O)—$C_{1-4}$ alkyl. In some embodiments, Z or $Ar^2$ in Formula (I) or (II) is substituted with 0 to 1 $R^4$ substituents, and each $R^4$ is independently selected from the group consisting of methyl, ethyl, chloro, fluoro, methoxy, ethoxy, —OH, —C(O)-methyl, —C(O)-ethyl, and —C(O)-2-propyl. In some embodiments, Z or $Ar^2$ in Formula (I) or (II) is substituted with 0 to 1 $R^4$ substituents, and each $R^4$ is independently selected from the group consisting of chloro, fluoro, —OH, and —C(O)-2-propyl. In some embodiments, Z or $Ar^2$ in Formula (I) or (II) is substituted with 0 to 2 $R^4$ substituents that combine to form an oxo moiety.

In some embodiments, $Ar^2$ in Formula (III) is substituted with 0 to 2 $R^4$ substituents, and each $R^4$ is independently selected from the group consisting of $C_{1-4}$ alkyl, halo, $C_{1-4}$haloalkyl, $C_{1-4}$ alkoxy, and $C_{1-4}$ haloalkoxy. In some embodiments, $Ar^2$ in Formula (III) is substituted with 0 to 2 $R^4$ substituents, and each $R^4$ is independently selected from the group consisting of methyl, ethyl, chloro, fluoro, methoxy, and ethoxy. In some embodiments, $Ar^2$ in Formula (III) is substituted with chloro.

In some embodiments, Z or $Ar^2$ in Formula (I), (II), or (III) is substituted with —$X^3$—OH wherein $X^3$ is $C_{1-4}$ alkylene. In some embodiments, Z or $Ar^2$ in Formula (I), (II), or (III) is substituted with hydroxymethyl. In some embodiments, Z or $Ar^2$ in Formula (I), (II), or (III) is substituted with 2-hydroxyethyl. In some embodiments, Z or $Ar^2$ in Formula (I), (II), or (III) is substituted with hydroxylpropan-2-yl.

In some embodiments, Z or $Ar^2$ in Formula (I), (II), or (III) is unsubstituted (i.e., Z or $Ar^2$ is substituted with 0 $R^4$ substituents). In some embodiments, Z or $Ar^2$ in Formula (I), (II), or (III) is substituted with 1 $R^4$ substituents. In some embodiments, Z or $Ar^2$ in Formula (I), (II), or (III) is substituted with 2 $R^4$ substituents.

In some embodiments, the subscripts m and n in Formula (I), (II), (III) or (IV) are both 0. In some embodiments, the subscripts m and n in Formula (I), (II), (III) or (IV) are 1 and 0, respectively. In some embodiments, the subscripts m and n in Formula (I), (II), (III) or (IV) are both 1.

Representative compounds of Formula (I), (II), (III) or (IV) are listed in Table 1 below

| Cpd # | Structure |
|---|---|
| 1 | 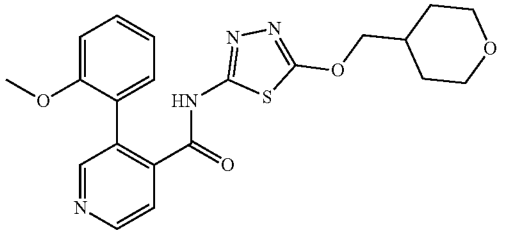 [SMILES: COc1ccccc1-c1cnccc1C(=O)Nc1nnc(OCC2CCOCC2)s1] |
| 2 | 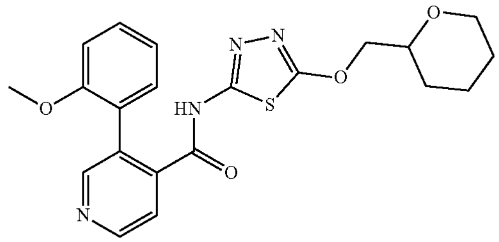 [SMILES: COc1ccccc1-c1cnccc1C(=O)Nc1nnc(OCC2CCCCO2)s1] |
| 3 | 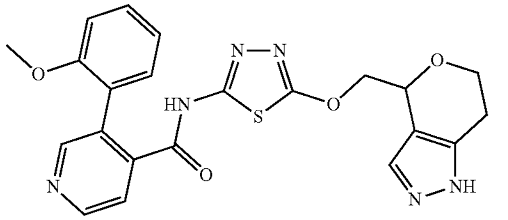 [SMILES: COc1ccccc1-c1cnccc1C(=O)Nc1nnc(OCC2OCCc3[nH]ncc32)s1] |
| 4 | 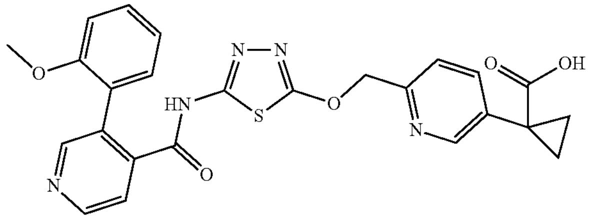 [SMILES: COc1ccccc1-c1cnccc1C(=O)Nc1nnc(OCc2ccc(C3(C(=O)O)CC3)cn2)s1] |

-continued
| Cpd # | Structure |
| --- | --- |
| 5 | 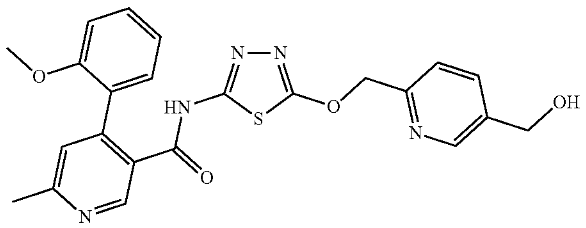 [SMILES: COc1ccccc1-c1cc(C)ncc1C(=O)Nc1nnc(OCc2ccc(CO)cn2)s1] |
| 6 | 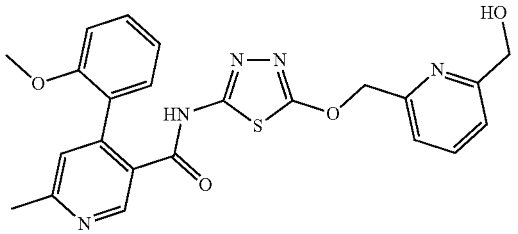 [SMILES: COc1ccccc1-c1cc(C)ncc1C(=O)Nc1nnc(OCc2cccc(CO)n2)s1] |
| 7 | 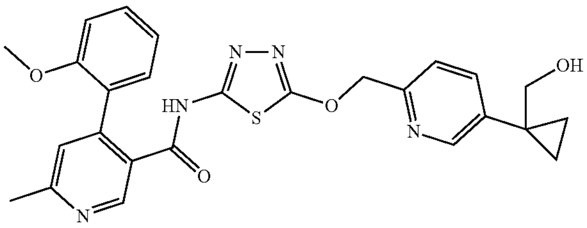 [SMILES: COc1ccccc1-c1cc(C)ncc1C(=O)Nc1nnc(OCc2ccc(C3(CO)CC3)cn2)s1] |
| 8 | 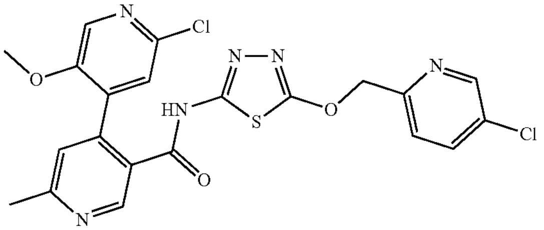 |
| 9 | 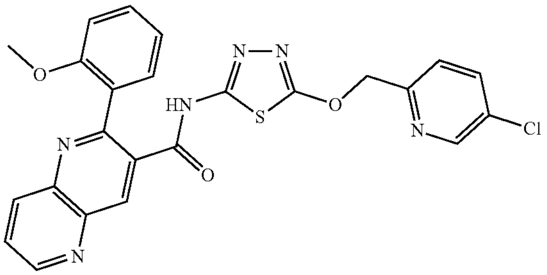 [SMILES: COc1ccccc1-c1nc2cccnc2cc1C(=O)Nc1nnc(OCc2ccc(Cl)cn2)s1] |
| 10 | 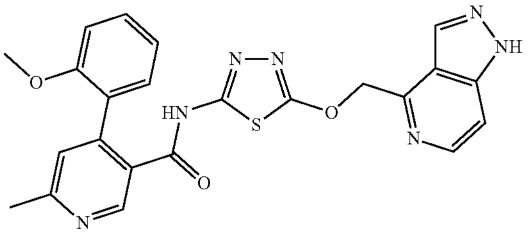 [SMILES: COc1ccccc1-c1cc(C)ncc1C(=O)Nc1nnc(OCc2nccc3[nH]ncc23)s1] |

-continued
| Cpd # | Structure |
|---|---|
| 11 | 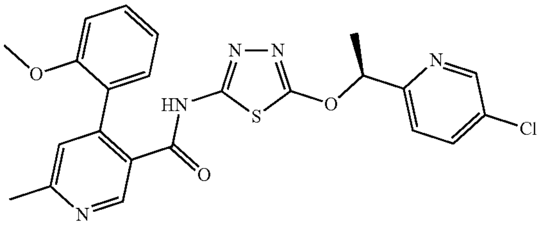 [SMILES: COc1ccccc1-c1cc(C)ncc1C(=O)Nc1nnc(O[C@@H](C)c2ccc(Cl)cn2)s1] |
| 12 | 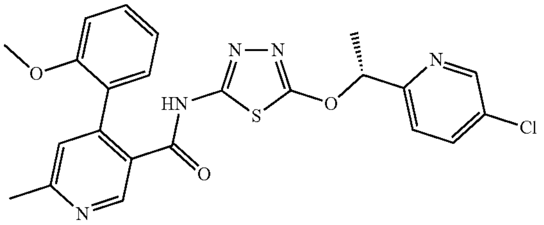 [SMILES: COc1ccccc1-c1cc(C)ncc1C(=O)Nc1nnc(O[C@H](C)c2ccc(Cl)cn2)s1] |
| 13 | 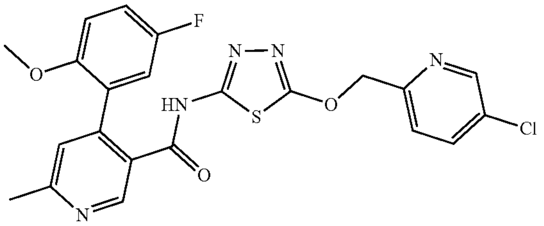 |
| 14 | 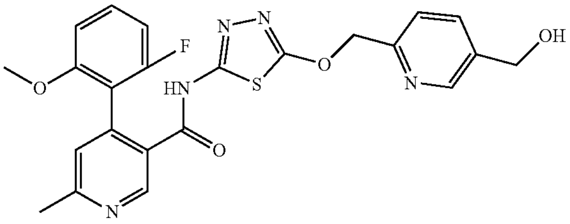 [SMILES: COc1cccc(F)c1-c1cc(C)ncc1C(=O)Nc1nnc(OCc2ccc(CO)cn2)s1] |
| 15 | 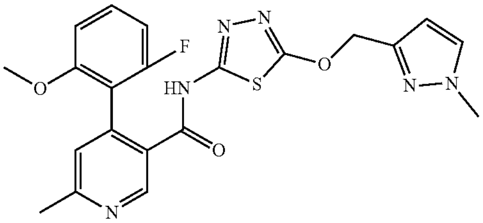 |
| 16 | 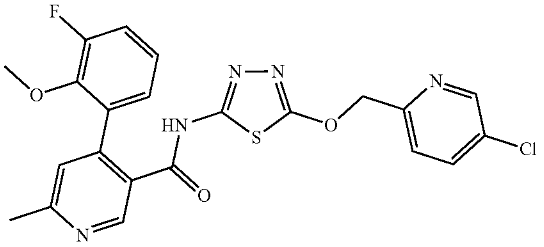 [SMILES: COc1c(F)cccc1-c1cc(C)ncc1C(=O)Nc1nnc(OCc2ccc(Cl)cn2)s1] |

-continued
| Cpd # | Structure |
| --- | --- |
| 17 | 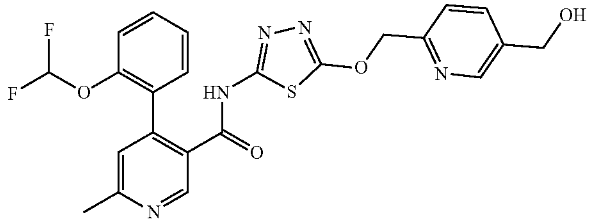 [SMILES: Cc1cc(-c2ccccc2OC(F)F)c(C(=O)Nc2nnc(OCc3ccc(CO)cn3)s2)cn1] |
| 18 | 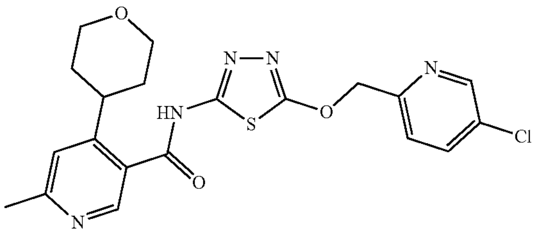 [SMILES: Cc1cc(C2CCOCC2)c(C(=O)Nc2nnc(OCc3ccc(Cl)cn3)s2)cn1] |
| 19 | 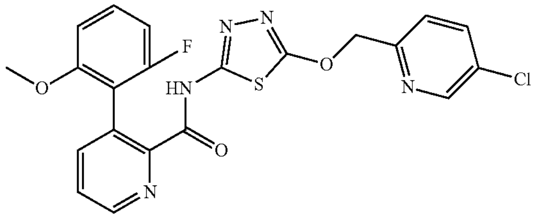 [SMILES: COc1cccc(F)c1-c1cccnc1C(=O)Nc1nnc(OCc2ccc(Cl)cn2)s1] |
| 20 | 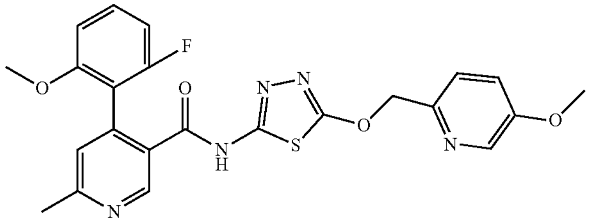 |
| 21 | 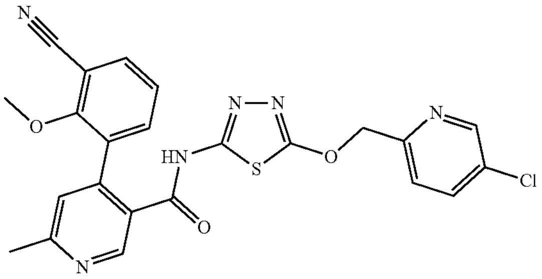 [SMILES: COc1c(C#N)cccc1-c1cc(C)ncc1C(=O)Nc1nnc(OCc2ccc(Cl)cn2)s1] |
| 22 | 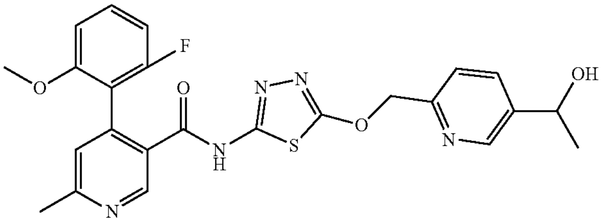 [SMILES: COc1cccc(F)c1-c1cc(C)ncc1C(=O)Nc1nnc(OCc2ccc(C(C)O)cn2)s1] |

-continued
| Cpd # | Structure |
|---|---|
| 23 | 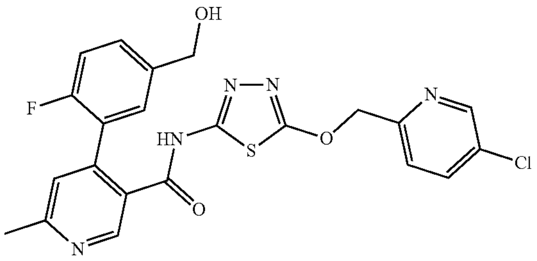 [SMILES: Cc1cc(-c2cc(CO)ccc2F)c(C(=O)Nc2nnc(OCc3ccc(Cl)cn3)s2)cn1] |
| 24 | 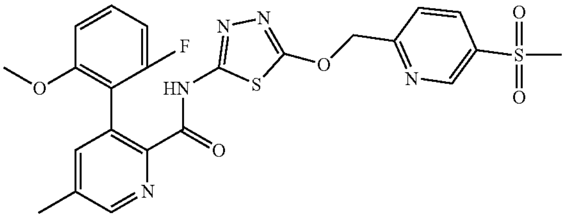 |
| 25 | 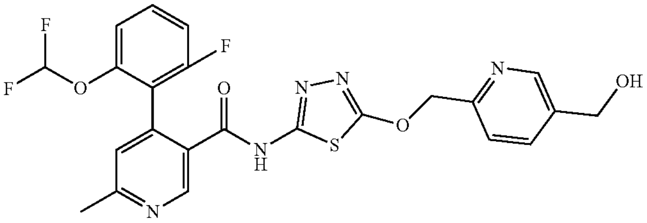 [SMILES: Cc1cc(-c2c(F)cccc2OC(F)F)c(C(=O)Nc2nnc(OCc3ccc(CO)cn3)s2)cn1] |
| 26 | 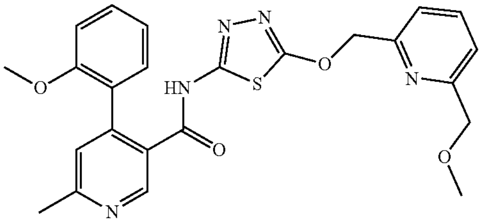 [SMILES: COCc1cccc(COc2nnc(NC(=O)c3cnc(C)cc3-c3ccccc3OC)s2)n1] |
| 27 | 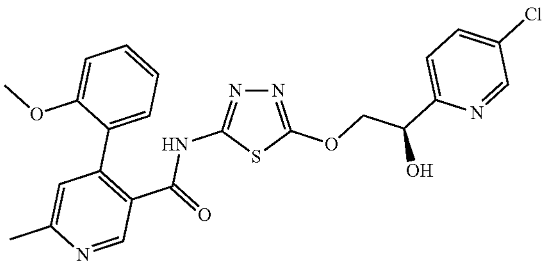 [SMILES: COc1ccccc1-c1cc(C)ncc1C(=O)Nc1nnc(OC[C@H](O)c2ccc(Cl)cn2)s1] |
| 28 | 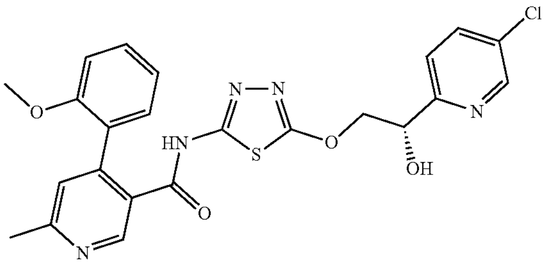 [SMILES: COc1ccccc1-c1cc(C)ncc1C(=O)Nc1nnc(OC[C@@H](O)c2ccc(Cl)cn2)s1] |

-continued
| Cpd # | Structure |
|---|---|
| 29 | 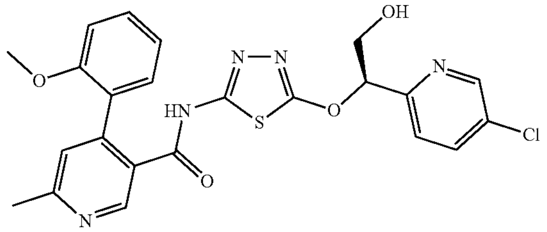 [SMILES: COc1ccccc1-c1cc(C)ncc1C(=O)Nc1nnc(O[C@@H](CO)c2ccc(Cl)cn2)s1] |
| 30 | 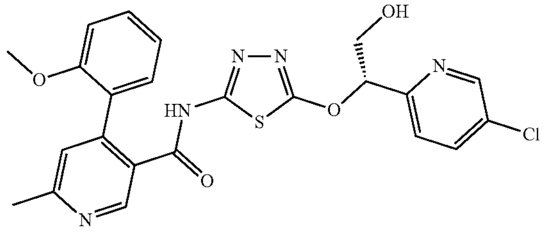 [SMILES: COc1ccccc1-c1cc(C)ncc1C(=O)Nc1nnc(O[C@H](CO)c2ccc(Cl)cn2)s1] |
| 31 | 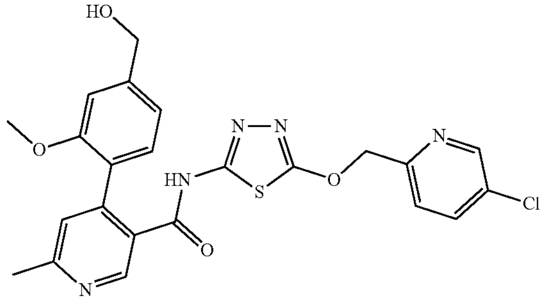 [SMILES: COc1cc(CO)ccc1-c1cc(C)ncc1C(=O)Nc1nnc(OCc2ccc(Cl)cn2)s1] |
| 32 | 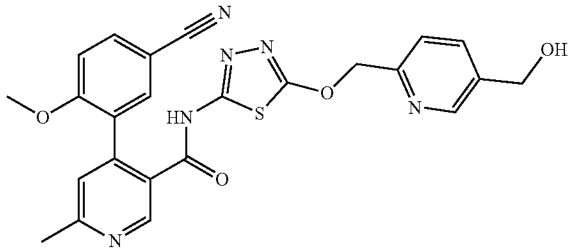 [SMILES: COc1ccc(C#N)cc1-c1cc(C)ncc1C(=O)Nc1nnc(OCc2ccc(CO)cn2)s1] |
| 33 | 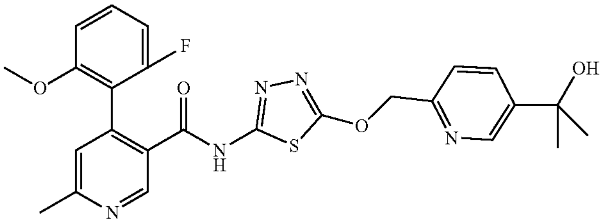 [SMILES: COc1cccc(F)c1-c1cc(C)ncc1C(=O)Nc1nnc(OCc2ccc(C(C)(C)O)cn2)s1] |
| 34 | 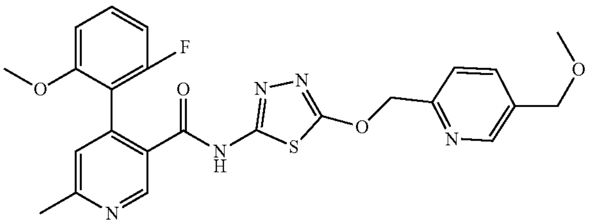 [SMILES: COCc1ccc(COc2nnc(NC(=O)c3cnc(C)cc3-c3c(F)cccc3OC)s2)nc1] |

-continued
| Cpd # | Structure |
|---|---|
| 35 | 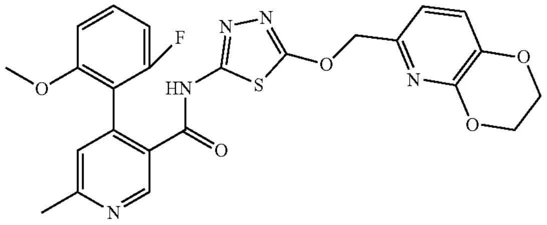 [SMILES: COc1cccc(F)c1-c1cc(C)ncc1C(=O)Nc1nnc(OCc2ccc3c(n2)OCCO3)s1] |
| 36 | 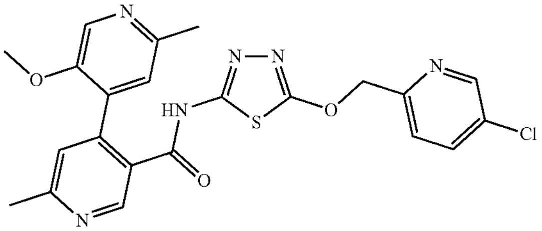 [SMILES: COc1cnc(C)cc1-c1cc(C)ncc1C(=O)Nc1nnc(OCc2ccc(Cl)cn2)s1] |
| 37 | 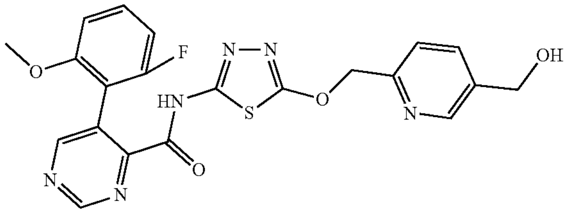 [SMILES: COc1cccc(F)c1-c1cncnc1C(=O)Nc1nnc(OCc2ccc(CO)cn2)s1] |
| 38 | 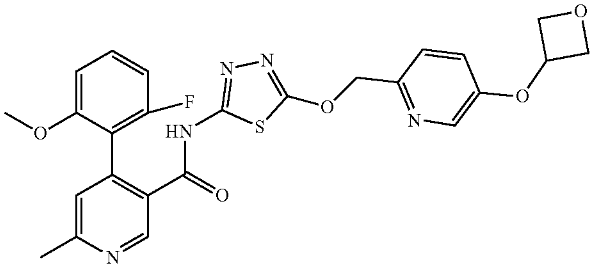 [SMILES: COc1cccc(F)c1-c1cc(C)ncc1C(=O)Nc1nnc(OCc2ccc(OC3COC3)cn2)s1] |
| 39 | 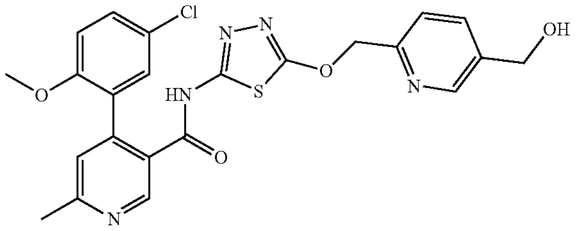 [SMILES: COc1ccc(Cl)cc1-c1cc(C)ncc1C(=O)Nc1nnc(OCc2ccc(CO)cn2)s1] |
| 40 | 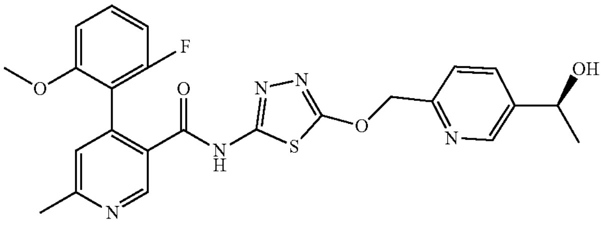 [SMILES: COc1cccc(F)c1-c1cc(C)ncc1C(=O)Nc1nnc(OCc2ccc([C@H](C)O)cn2)s1] |

-continued
| Cpd # | Structure |
|---|---|
| 41 | 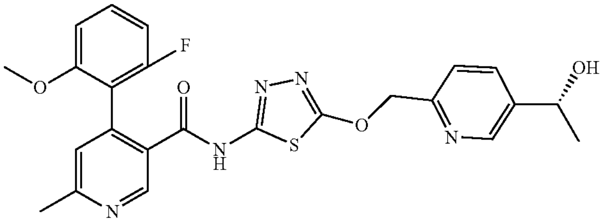 [SMILES: COc1cccc(F)c1-c1cc(C)ncc1C(=O)Nc1nnc(OCc2ccc([C@@H](C)O)cn2)s1] |
| 42 | 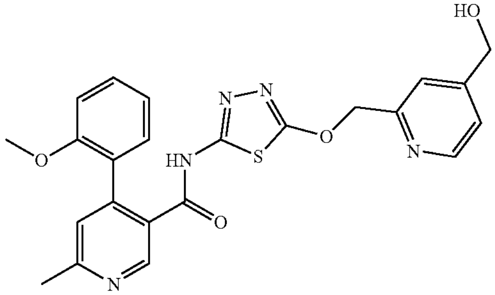 [SMILES: COc1ccccc1-c1cc(C)ncc1C(=O)Nc1nnc(OCc2cc(CO)ccn2)s1] |
| 43 | 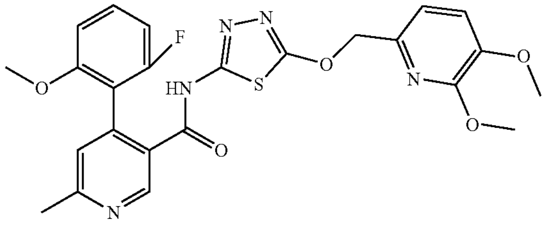 |
| 44 | 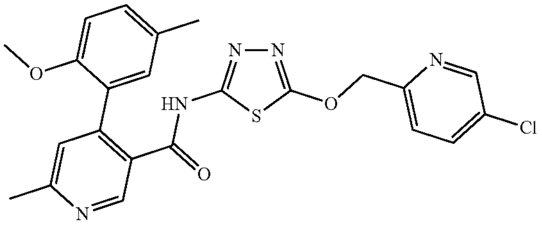 [SMILES: COc1ccc(C)cc1-c1cc(C)ncc1C(=O)Nc1nnc(OCc2ccc(Cl)cn2)s1] |
| 45 | 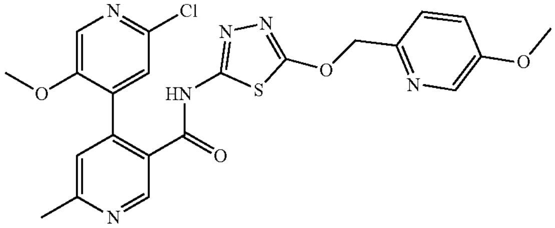 |
| 46 | 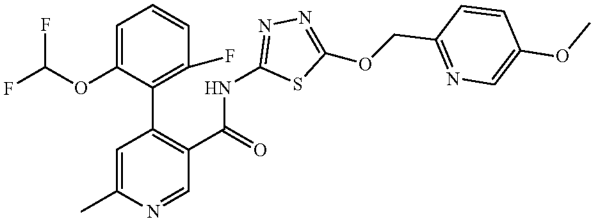 [SMILES: COc1ccc(COc2nnc(NC(=O)c3cnc(C)cc3-c3c(F)cccc3OC(F)F)s2)nc1] |

-continued
| Cpd # | Structure |
|---|---|
| 47 | 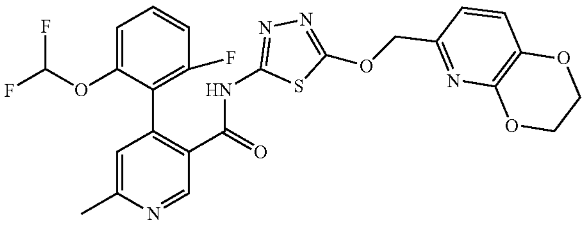 [SMILES: Cc1cc(-c2c(F)cccc2OC(F)F)c(C(=O)Nc2nnc(OCc3ccc4c(n3)OCCO4)s2)cn1] |
| 48 | 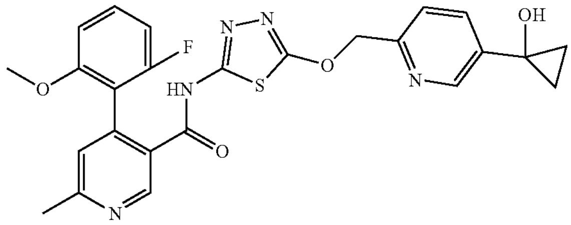 [SMILES: COc1cccc(F)c1-c1cc(C)ncc1C(=O)Nc1nnc(OCc2ccc(C3(O)CC3)cn2)s1] |
| 49 | 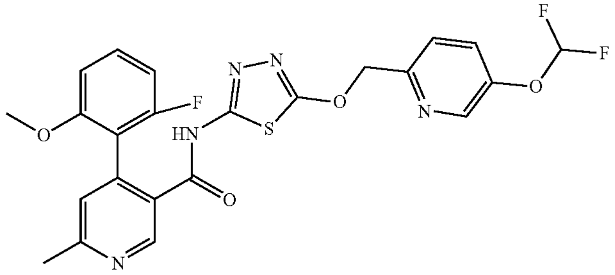 [SMILES: COc1cccc(F)c1-c1cc(C)ncc1C(=O)Nc1nnc(OCc2ccc(OC(F)F)cn2)s1] |
| 50 | 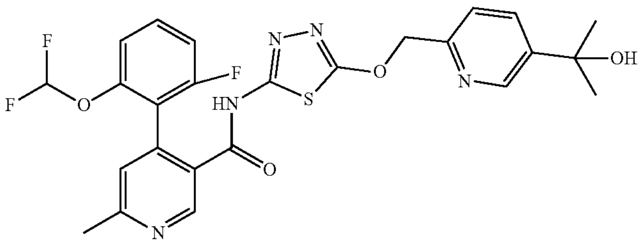 [SMILES: Cc1cc(-c2c(F)cccc2OC(F)F)c(C(=O)Nc2nnc(OCc3ccc(C(C)(C)O)cn3)s2)cn1] |
| 51 | 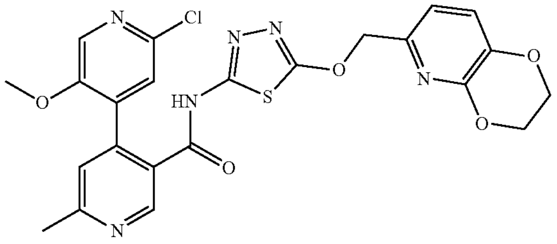 [SMILES: COc1cnc(Cl)cc1-c1cc(C)ncc1C(=O)Nc1nnc(OCc2ccc3c(n2)OCCO3)s1] |
| 52 | 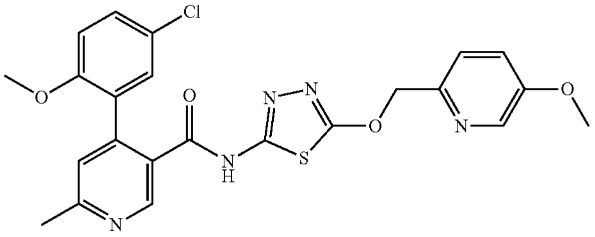 |

-continued
| Cpd # | Structure |
|---|---|
| 53 | 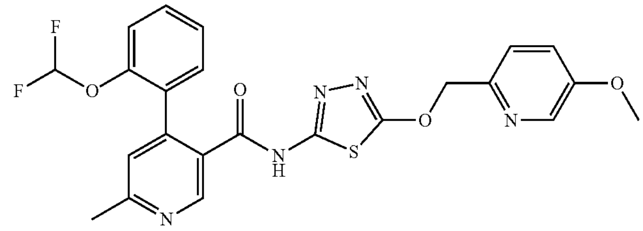 [SMILES: COc1ccc(COc2nnc(NC(=O)c3cnc(C)cc3-c3ccccc3OC(F)F)s2)nc1] |
| 54 | 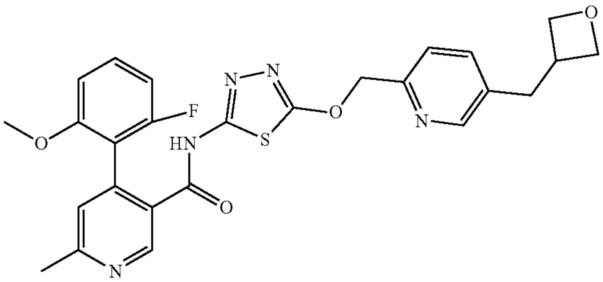 [SMILES: COc1cccc(F)c1-c1cc(C)ncc1C(=O)Nc1nnc(OCc2ccc(CC3COC3)cn2)s1] |
| 55 | 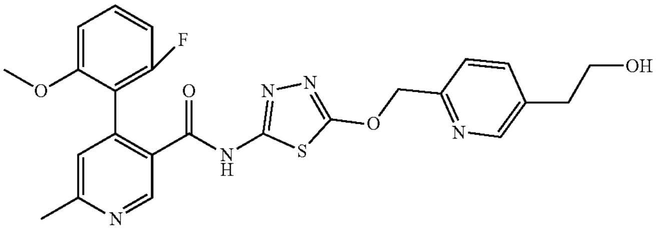 [SMILES: COc1cccc(F)c1-c1cc(C)ncc1C(=O)Nc1nnc(OCc2ccc(CCO)cn2)s1] |
| 56 | 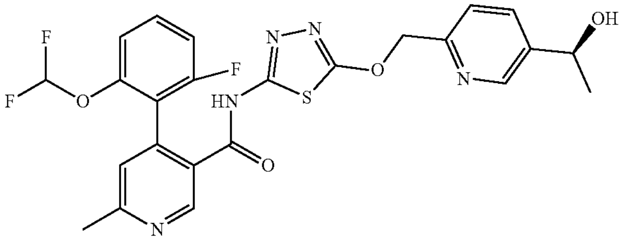 [SMILES: Cc1cc(-c2c(F)cccc2OC(F)F)c(C(=O)Nc2nnc(OCc3ccc([C@H](C)O)cn3)s2)cn1] |
| 57 | 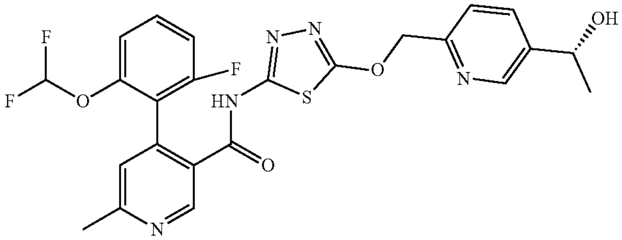 [SMILES: Cc1cc(-c2c(F)cccc2OC(F)F)c(C(=O)Nc2nnc(OCc3ccc([C@@H](C)O)cn3)s2)cn1] |
| 58 | 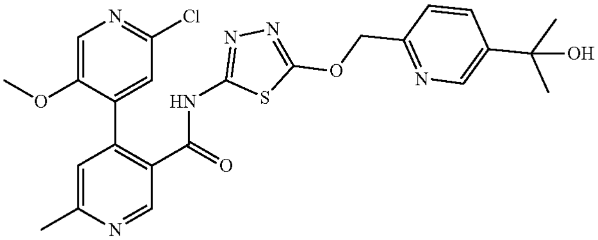 [SMILES: COc1cnc(Cl)cc1-c1cc(C)ncc1C(=O)Nc1nnc(OCc2ccc(C(C)(C)O)cn2)s1] |

-continued
| Cpd # | Structure |
|---|---|
| 59 | 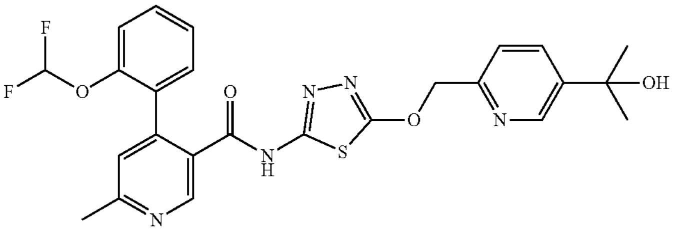 [SMILES: Cc1cc(-c2ccccc2OC(F)F)c(C(=O)Nc2nnc(OCc3ccc(C(C)(C)O)cn3)s2)cn1] |
| 60 | 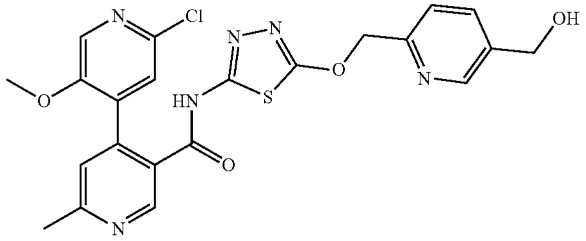 [SMILES: COc1cnc(Cl)cc1-c1cc(C)ncc1C(=O)Nc1nnc(OCc2ccc(CO)cn2)s1] |
| 61 | 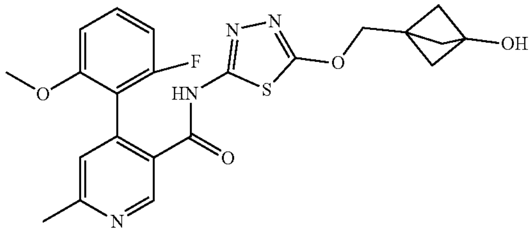 |
| 62 | 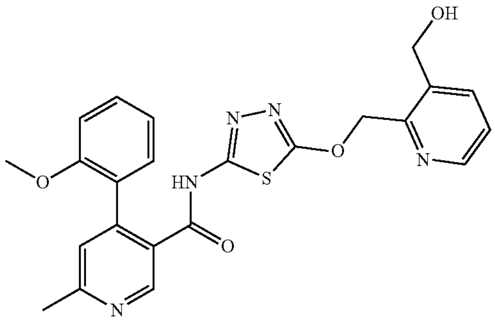 [SMILES: COc1ccccc1-c1cc(C)ncc1C(=O)Nc1nnc(OCc2ncccc2CO)s1] |
| 63 | 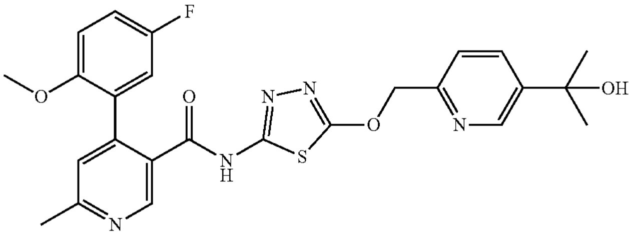 [SMILES: COc1ccc(F)cc1-c1cc(C)ncc1C(=O)Nc1nnc(OCc2ccc(C(C)(C)O)cn2)s1] |
| 64 | 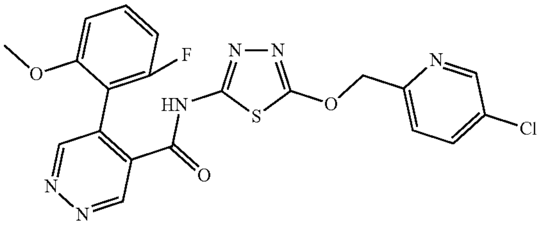 [SMILES: COc1cccc(F)c1-c1cnncc1C(=O)Nc1nnc(OCc2ccc(Cl)cn2)s1] |

-continued
| Cpd # | Structure |
|---|---|
| 65 | 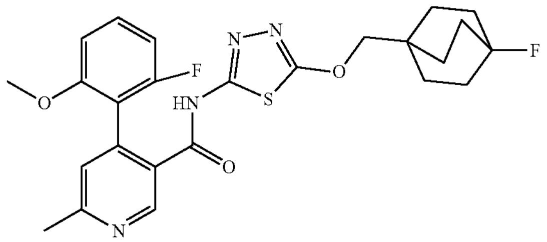 [SMILES: COc1cccc(F)c1-c1cc(C)ncc1C(=O)Nc1nnc(OCC23CCC(F)(CC2)CC3)s1] |
| 66 | 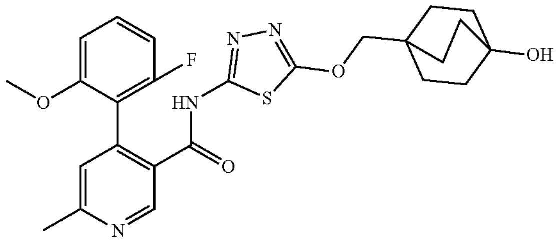 [SMILES: COc1cccc(F)c1-c1cc(C)ncc1C(=O)Nc1nnc(OCC23CCC(O)(CC2)CC3)s1] |
| 67 | 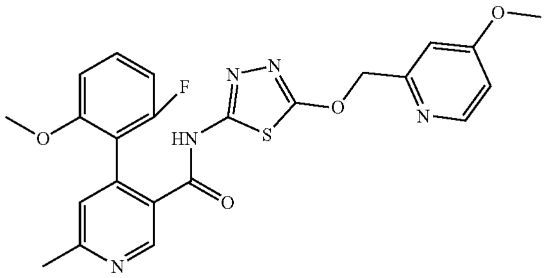 |
| 68 | 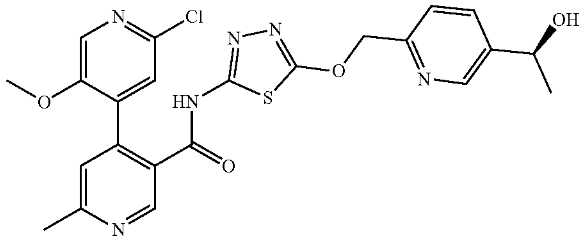 [SMILES: COc1cnc(Cl)cc1-c1cc(C)ncc1C(=O)Nc1nnc(OCc2ccc([C@H](C)O)cn2)s1] |
| 69 | 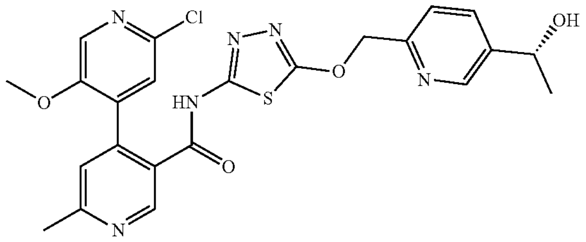 [SMILES: COc1cnc(Cl)cc1-c1cc(C)ncc1C(=O)Nc1nnc(OCc2ccc([C@@H](C)O)cn2)s1] |
| 70 | 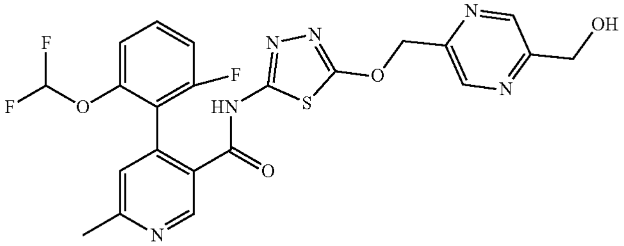 [SMILES: Cc1cc(-c2c(F)cccc2OC(F)F)c(C(=O)Nc2nnc(OCc3cnc(CO)cn3)s2)cn1] |

-continued
| Cpd # | Structure |
|---|---|
| 71 | 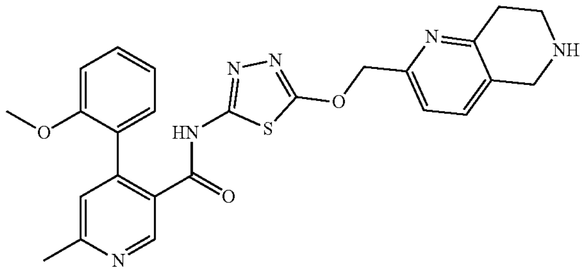 [SMILES: COc1ccccc1-c1cc(C)ncc1C(=O)Nc1nnc(OCc2ccc3c(n2)CCNC3)s1] |
| 72 | 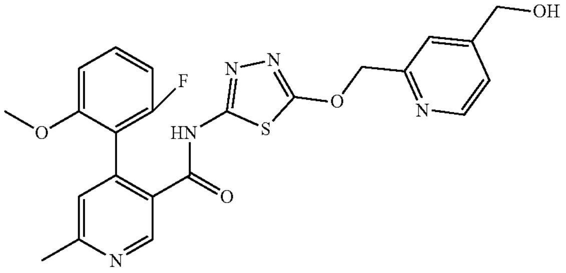 [SMILES: COc1cccc(F)c1-c1cc(C)ncc1C(=O)Nc1nnc(OCc2cc(CO)ccn2)s1] |
| 73 | 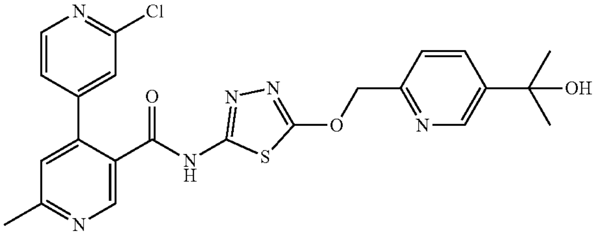 |
| 74 | 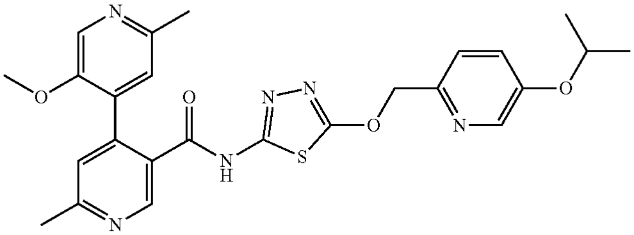 [SMILES: COc1cnc(C)cc1-c1cc(C)ncc1C(=O)Nc1nnc(OCc2ccc(OC(C)C)cn2)s1] |
| 75 | 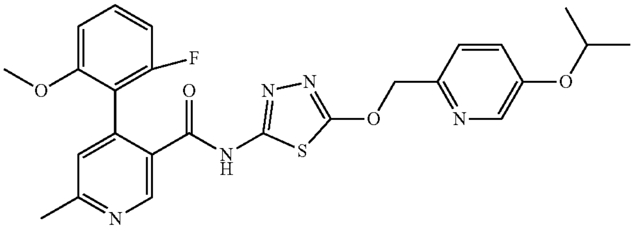 [SMILES: COc1cccc(F)c1-c1cc(C)ncc1C(=O)Nc1nnc(OCc2ccc(OC(C)C)cn2)s1] |
| 76 | 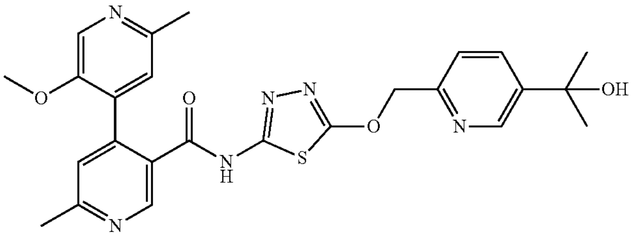 |

-continued
| Cpd # | Structure |
|---|---|
| 77 | 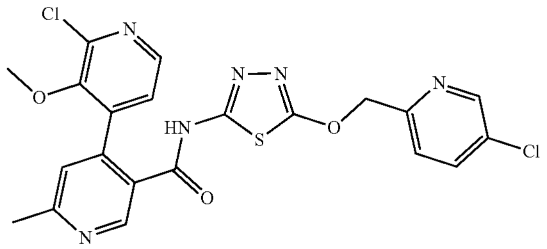 [SMILES: COc1c(-c2cc(C)ncc2C(=O)Nc2nnc(OCc3ccc(Cl)cn3)s2)ccnc1Cl] |
| 78 | 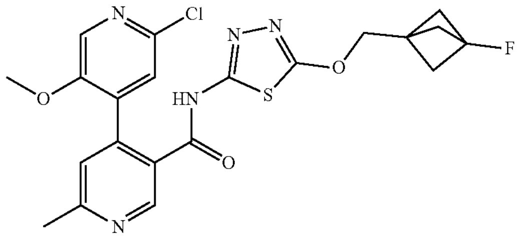 [SMILES: COc1cnc(Cl)cc1-c1cc(C)ncc1C(=O)Nc1nnc(OCC23CC(F)(C2)C3)s1] |
| 79 | 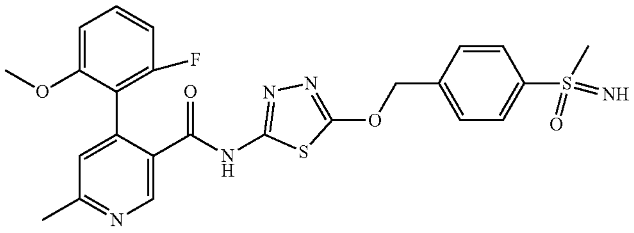 [SMILES: COc1cccc(F)c1-c1cc(C)ncc1C(=O)Nc1nnc(OCc2ccc(S(C)(=N)=O)cc2)s1] |
| 80 | 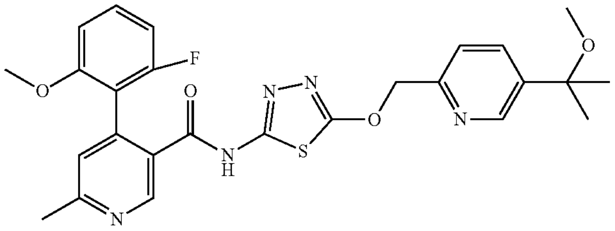 [SMILES: COc1cccc(F)c1-c1cc(C)ncc1C(=O)Nc1nnc(OCc2ccc(C(C)(C)OC)cn2)s1] |
| 81 | 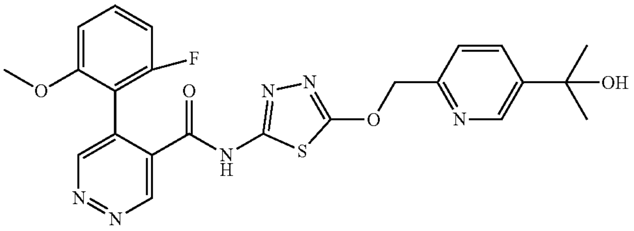 [SMILES: COc1cccc(F)c1-c1cnncc1C(=O)Nc1nnc(OCc2ccc(C(C)(C)O)cn2)s1] |
| 82 | 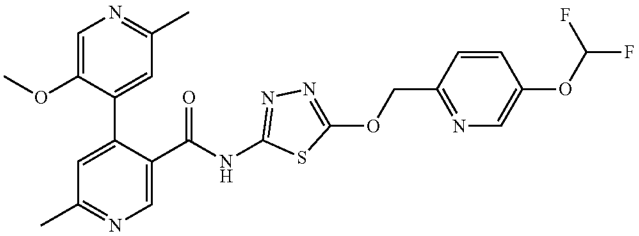 [SMILES: COc1cnc(C)cc1-c1cc(C)ncc1C(=O)Nc1nnc(OCc2ccc(OC(F)F)cn2)s1] |

-continued
| Cpd # | Structure |
|---|---|
| 83 | 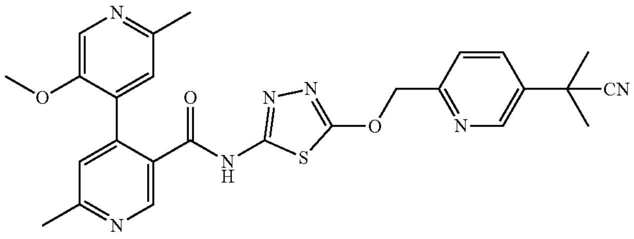 [SMILES: COc1cnc(C)cc1-c1cc(C)ncc1C(=O)Nc1nnc(OCc2ccc(C(C)(C)C#N)cn2)s1] |
| 84 | 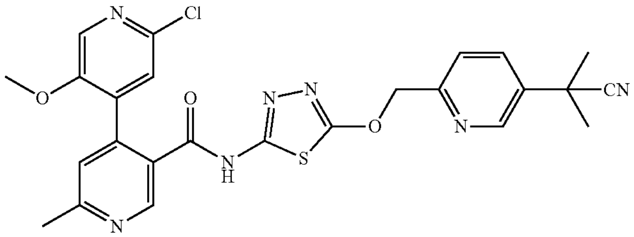 |
| 85 | 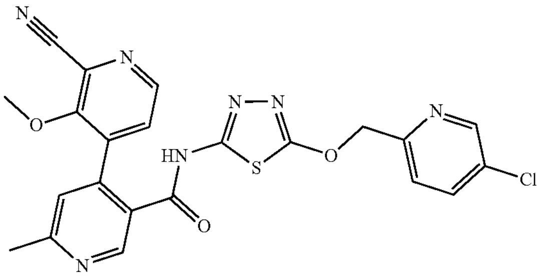 [SMILES: COc1c(-c2cc(C)ncc2C(=O)Nc2nnc(OCc3ccc(Cl)cn3)s2)ccnc1C#N] |
| 86 | 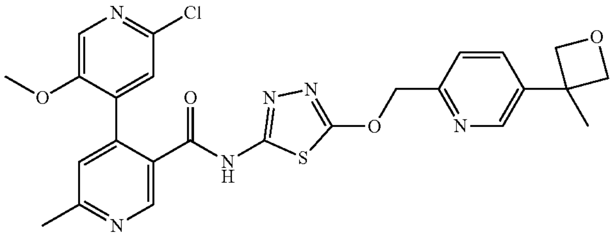 [SMILES: COc1cnc(Cl)cc1-c1cc(C)ncc1C(=O)Nc1nnc(OCc2ccc(C3(C)COC3)cn2)s1] |
| 87 | 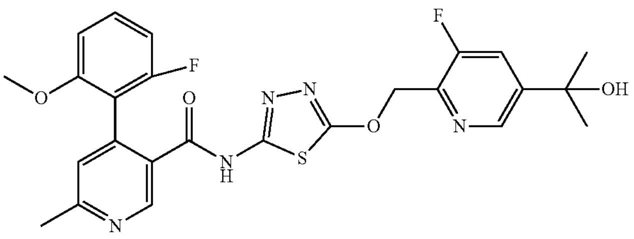 [SMILES: COc1cccc(F)c1-c1cc(C)ncc1C(=O)Nc1nnc(OCc2ncc(C(C)(C)O)cc2F)s1] |
| 88 | 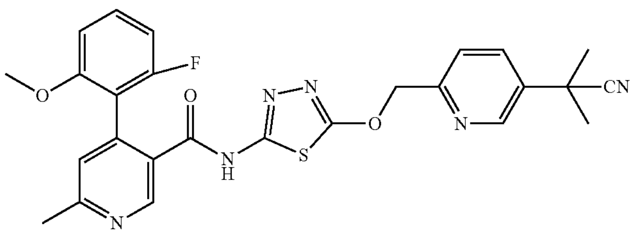 [SMILES: COc1cccc(F)c1-c1cc(C)ncc1C(=O)Nc1nnc(OCc2ccc(C(C)(C)C#N)cn2)s1] |

-continued
| Cpd # | Structure |
| --- | --- |
| 89 | 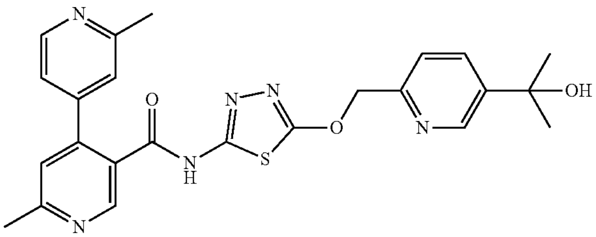 [SMILES: Cc1cc(-c2cc(C)ncc2C(=O)Nc2nnc(OCc3ccc(C(C)(C)O)cn3)s2)ccn1] |
| 90 | 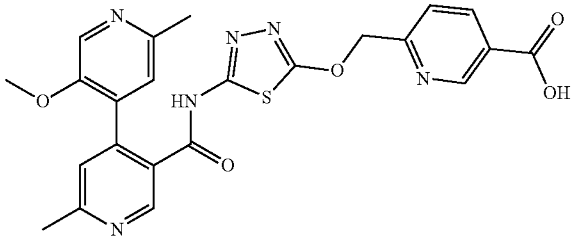 [SMILES: COc1cnc(C)cc1-c1cc(C)ncc1C(=O)Nc1nnc(OCc2ccc(C(=O)O)cn2)s1] |
| 91 | 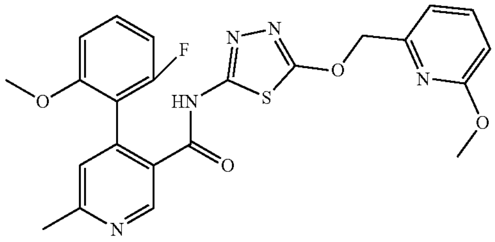 [SMILES: COc1cccc(COc2nnc(NC(=O)c3cnc(C)cc3-c3c(F)cccc3OC)s2)n1] |
| 92 | 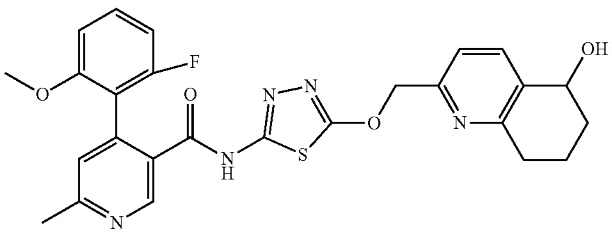 [SMILES: COc1cccc(F)c1-c1cc(C)ncc1C(=O)Nc1nnc(OCc2ccc3c(n2)CCCC3O)s1] |
| 93 | 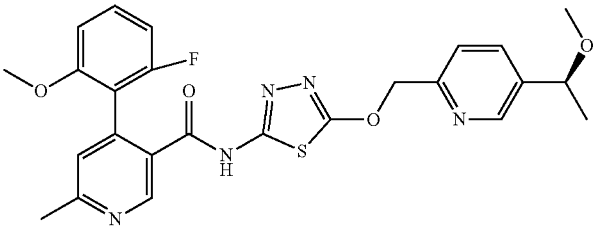 [SMILES: COc1cccc(F)c1-c1cc(C)ncc1C(=O)Nc1nnc(OCc2ccc([C@H](C)OC)cn2)s1] |
| 94 | 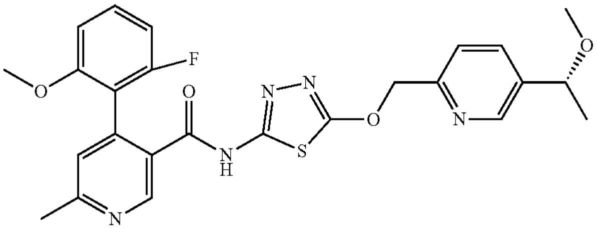 [SMILES: COc1cccc(F)c1-c1cc(C)ncc1C(=O)Nc1nnc(OCc2ccc([C@@H](C)OC)cn2)s1] |

-continued
| Cpd # | Structure |
| --- | --- |
| 95 | 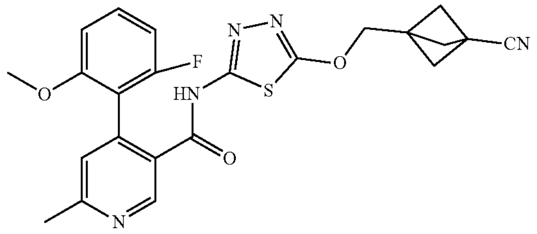 [SMILES: COc1cccc(F)c1-c1cc(C)ncc1C(=O)Nc1nnc(OCC23CC(C#N)(C2)C3)s1] |
| 96 | 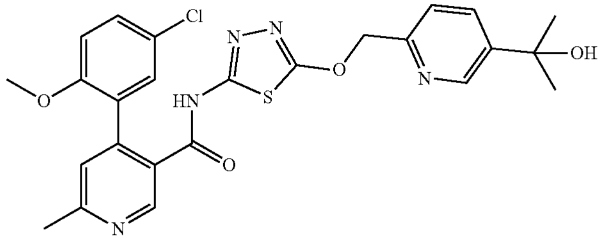 |
| 97 | 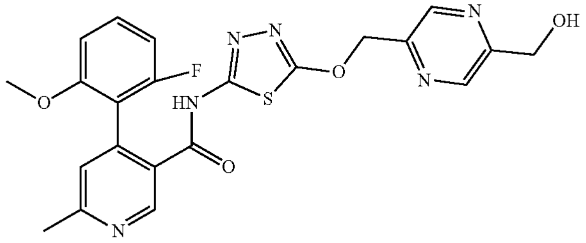 [SMILES: COc1cccc(F)c1-c1cc(C)ncc1C(=O)Nc1nnc(OCc2cnc(CO)cn2)s1] |
| 98 | 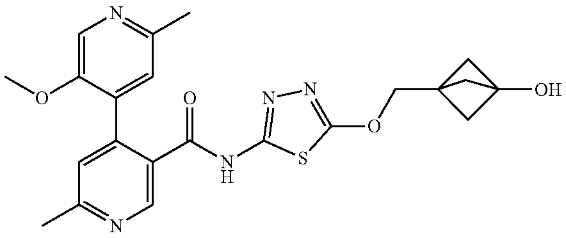 [SMILES: COc1cnc(C)cc1-c1cc(C)ncc1C(=O)Nc1nnc(OCC23CC(O)(C2)C3)s1] |
| 99 | 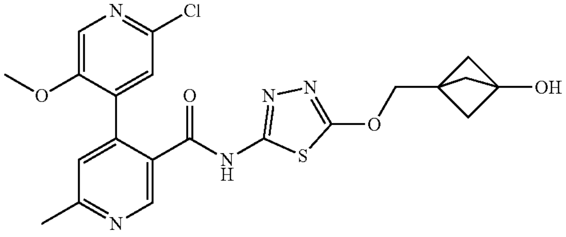 [SMILES: COc1cnc(Cl)cc1-c1cc(C)ncc1C(=O)Nc1nnc(OCC23CC(O)(C2)C3)s1] |
| 100 | 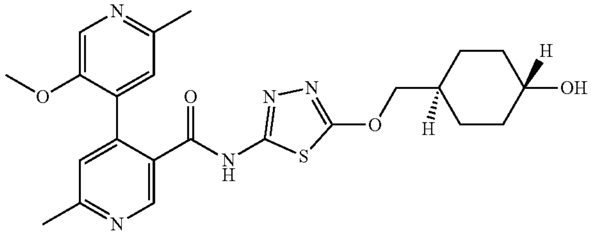 [SMILES: COc1cnc(C)cc1-c1cc(C)ncc1C(=O)Nc1nnc(OC[C@H]2CC[C@H](O)CC2)s1] |

-continued
| Cpd # | Structure |
| --- | --- |
| 101 | 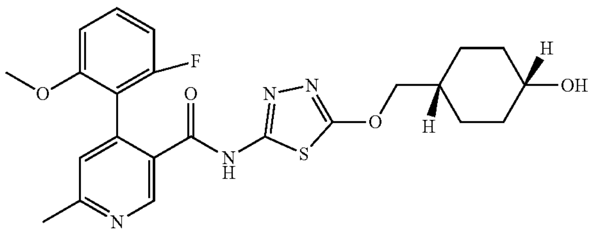 [SMILES: COc1cccc(F)c1-c1cc(C)ncc1C(=O)Nc1nnc(OC[C@H]2CC[C@@H](O)CC2)s1] |
| 102 | 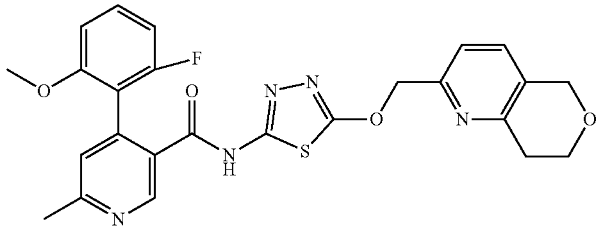 [SMILES: COc1cccc(F)c1-c1cc(C)ncc1C(=O)Nc1nnc(OCc2ccc3c(n2)CCOC3)s1] |
| 103 | 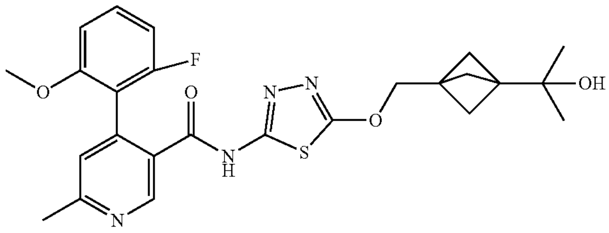 [SMILES: COc1cccc(F)c1-c1cc(C)ncc1C(=O)Nc1nnc(OCC23CC(C(C)(C)O)(C2)C3)s1] |
| 104 | 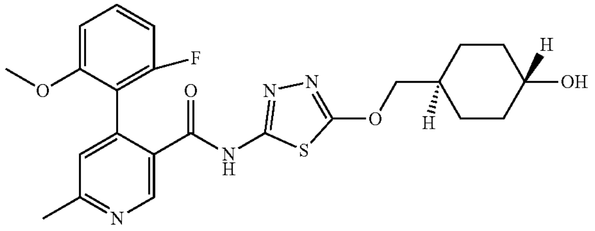 [SMILES: COc1cccc(F)c1-c1cc(C)ncc1C(=O)Nc1nnc(OC[C@H]2CC[C@H](O)CC2)s1] |
| 105 | 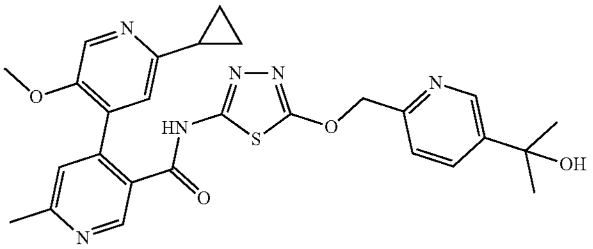 [SMILES: COc1cnc(C2CC2)cc1-c1cc(C)ncc1C(=O)Nc1nnc(OCc2ccc(C(C)(C)O)cn2)s1] |
| 106 | 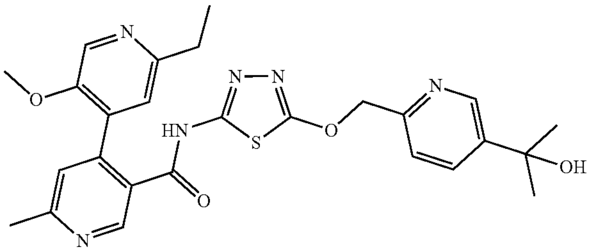 [SMILES: CCc1cc(-c2cc(C)ncc2C(=O)Nc2nnc(OCc3ccc(C(C)(C)O)cn3)s2)c(OC)cn1] |

-continued
| Cpd # | Structure |
|---|---|
| 107 | 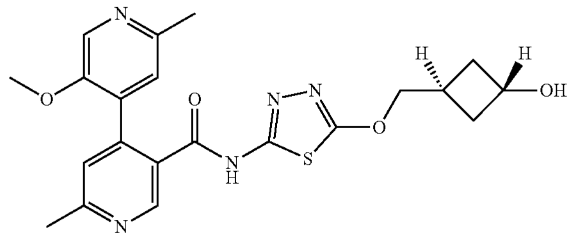 |
| 108 | 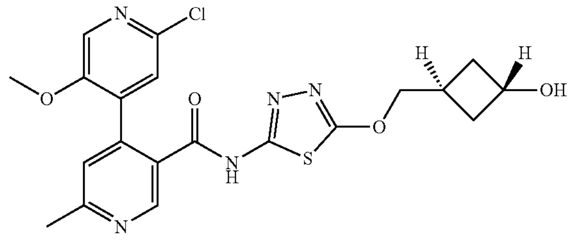 |
| 109 | 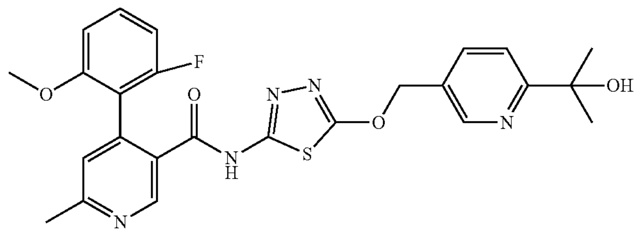 [SMILES: COc1cccc(F)c1-c1cc(C)ncc1C(=O)Nc1nnc(OCc2ccc(C(C)(C)O)nc2)s1] |
| 110 | 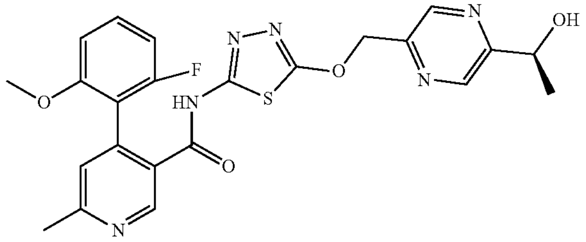 [SMILES: COc1cccc(F)c1-c1cc(C)ncc1C(=O)Nc1nnc(OCc2cnc([C@H](C)O)cn2)s1] |
| 111 | 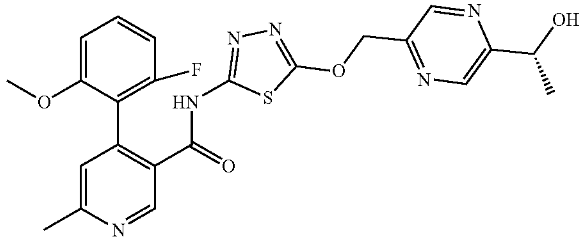 [SMILES: COc1cccc(F)c1-c1cc(C)ncc1C(=O)Nc1nnc(OCc2cnc([C@@H](C)O)cn2)s1] |
| 112 | 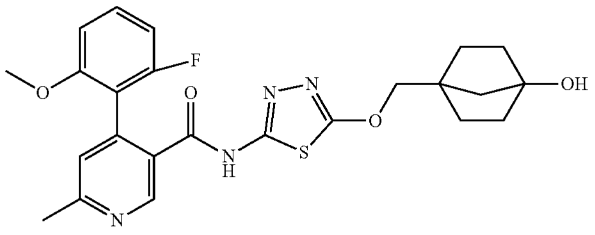 [SMILES: COc1cccc(F)c1-c1cc(C)ncc1C(=O)Nc1nnc(OCC23CCC(O)(CC2)C3)s1] |

-continued
| Cpd # | Structure |
|---|---|
| 113 | 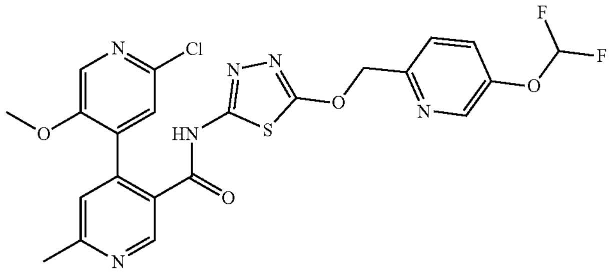 [SMILES: COc1cnc(Cl)cc1-c1cc(C)ncc1C(=O)Nc1nnc(OCc2ccc(OC(F)F)cn2)s1] |
| 114 | 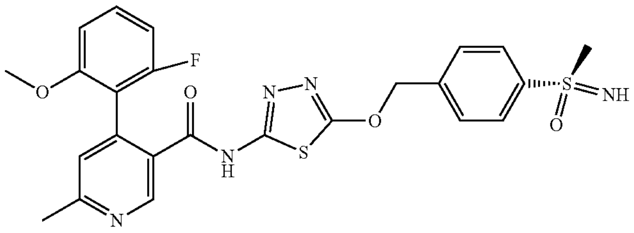 [SMILES: COc1cccc(F)c1-c1cc(C)ncc1C(=O)Nc1nnc(OCc2ccc([S@](C)(=N)=O)cc2)s1] |
| 115 | 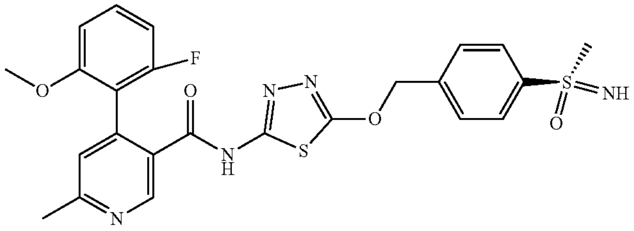 [SMILES: COc1cccc(F)c1-c1cc(C)ncc1C(=O)Nc1nnc(OCc2ccc([S@@](C)(=N)=O)cc2)s1] |
| 116 | 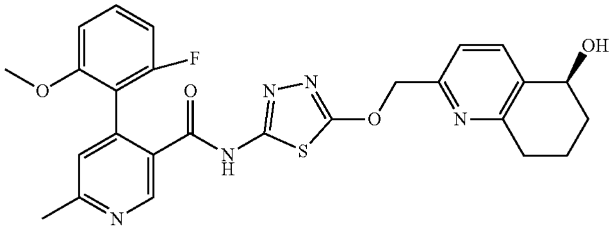 [SMILES: COc1cccc(F)c1-c1cc(C)ncc1C(=O)Nc1nnc(OCc2ccc3c(n2)CCC[C@@H]3O)s1] |
| 117 | 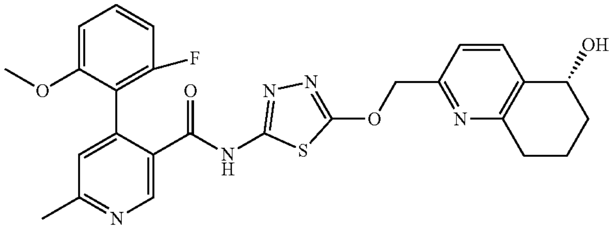 |
| 118 | 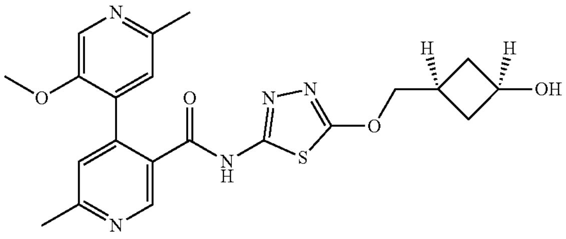 [SMILES: COc1cnc(C)cc1-c1cc(C)ncc1C(=O)Nc1nnc(OC[C@H]2C[C@@H](O)C2)s1] |

-continued
| Cpd # | Structure |
|---|---|
| 119 | 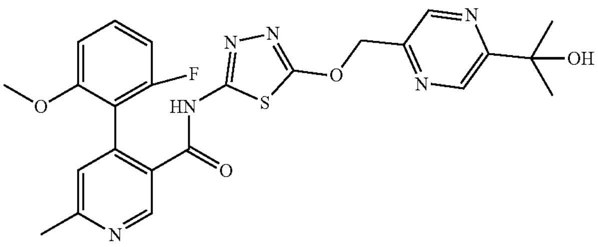 [SMILES: COc1cccc(F)c1-c1cc(C)ncc1C(=O)Nc1nnc(OCc2cnc(C(C)(C)O)cn2)s1] |
| 120 | 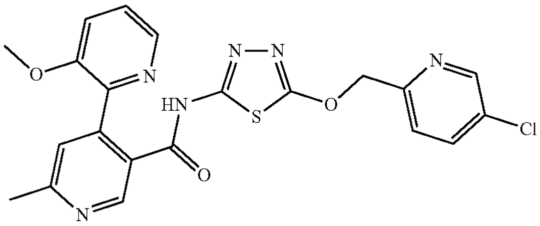 [SMILES: COc1cccnc1-c1cc(C)ncc1C(=O)Nc1nnc(OCc2ccc(Cl)cn2)s1] |
| 121 | 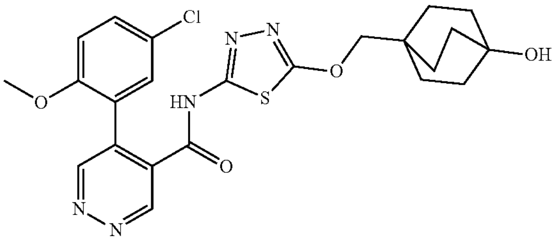 [SMILES: COc1ccc(Cl)cc1-c1cnncc1C(=O)Nc1nnc(OCC23CCC(O)(CC2)CC3)s1] |
| 122 | 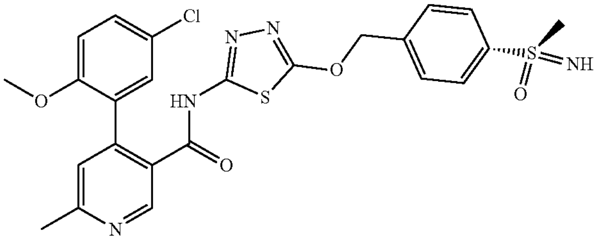 |
| 123 | 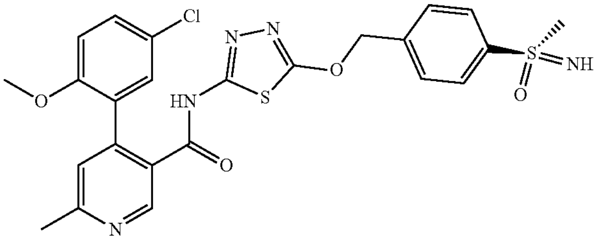 [SMILES: COc1ccc(Cl)cc1-c1cc(C)ncc1C(=O)Nc1nnc(OCc2ccc([S@@](C)(=N)=O)cc2)s1] |
| 124 | 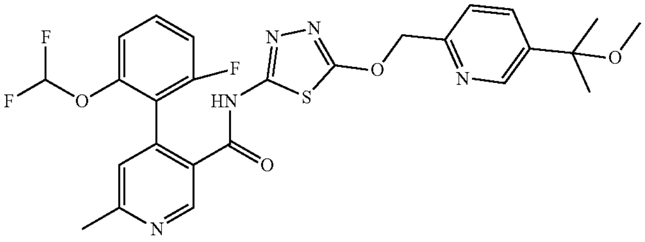 [SMILES: COC(C)(C)c1ccc(COc2nnc(NC(=O)c3cnc(C)cc3-c3c(F)cccc3OC(F)F)s2)nc1] |

-continued
| Cpd # | Structure |
| --- | --- |
| 125 | 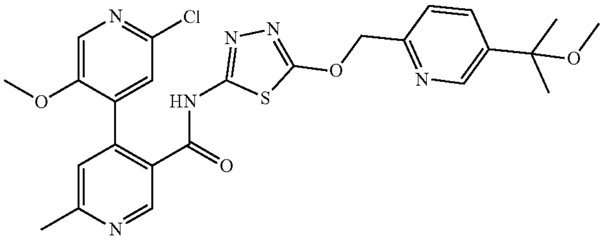 |
| 126 | 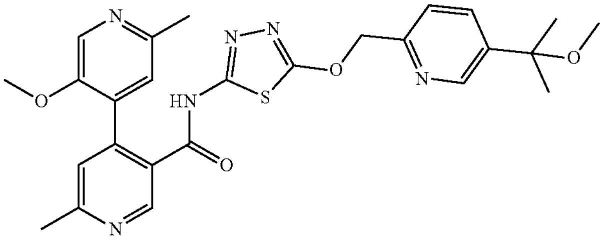 |
| 127 | 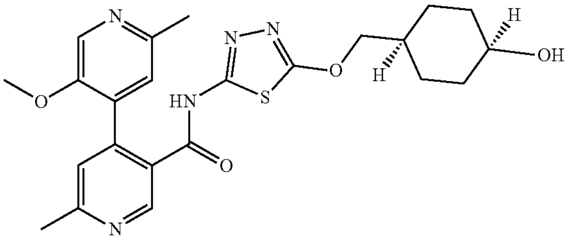 |
| 128 | 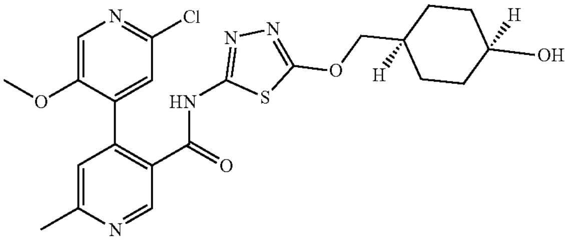 [SMILES: COc1cnc(Cl)cc1-c1cc(C)ncc1C(=O)Nc1nnc(OC[C@H]2CC[C@@H](O)CC2)s1] |
| 129 | 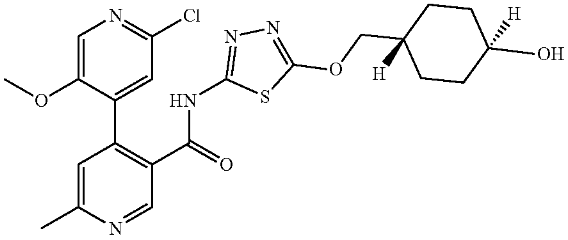 [SMILES: COc1cnc(Cl)cc1-c1cc(C)ncc1C(=O)Nc1nnc(OC[C@H]2CC[C@H](O)CC2)s1] |
| 130 | 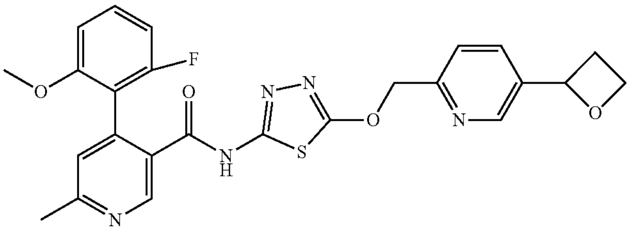 [SMILES: COc1cccc(F)c1-c1cc(C)ncc1C(=O)Nc1nnc(OCc2ccc(C3CCO3)cn2)s1] |

-continued
| Cpd # | Structure |
| --- | --- |
| 131 | 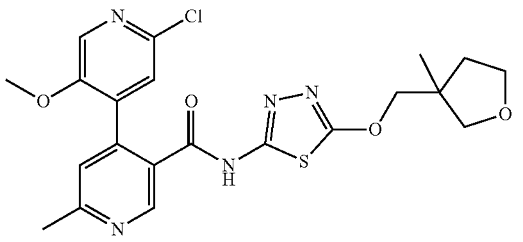 [SMILES: COc1cnc(Cl)cc1-c1cc(C)ncc1C(=O)Nc1nnc(OCC2(C)CCOC2)s1] |
| 132 | 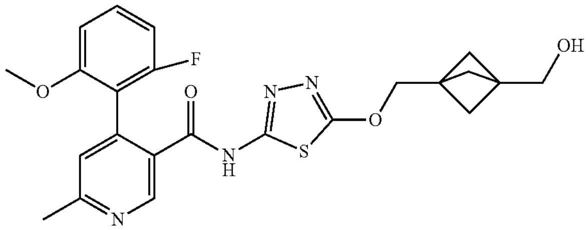 [SMILES: COc1cccc(F)c1-c1cc(C)ncc1C(=O)Nc1nnc(OCC23CC(CO)(C2)C3)s1] |
| 133 | 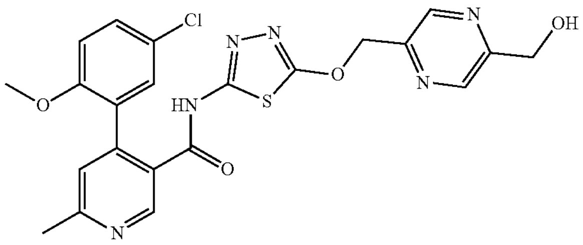 |
| 134 | 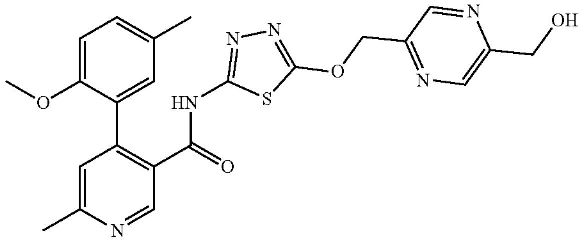 [SMILES: COc1ccc(C)cc1-c1cc(C)ncc1C(=O)Nc1nnc(OCc2cnc(CO)cn2)s1] |
| 135 | 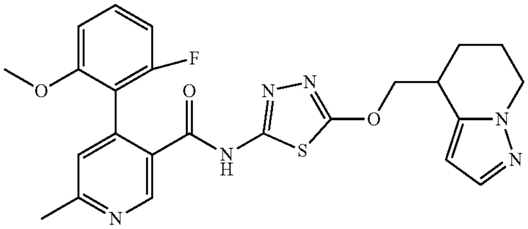 [SMILES: COc1cccc(F)c1-c1cc(C)ncc1C(=O)Nc1nnc(OCC2CCCn3nccc32)s1] |
| 136 | 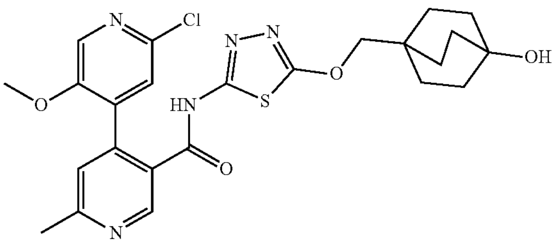 [SMILES: COc1cnc(Cl)cc1-c1cc(C)ncc1C(=O)Nc1nnc(OCC23CCC(O)(CC2)CC3)s1] |

-continued
| Cpd # | Structure |
|---|---|
| 137 | 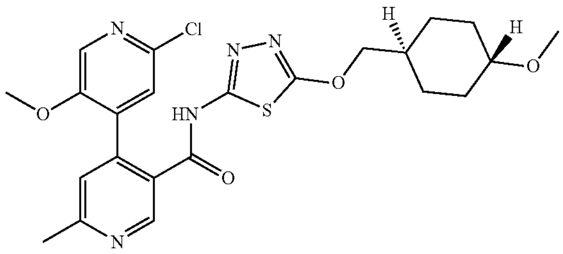 |
| 138 | 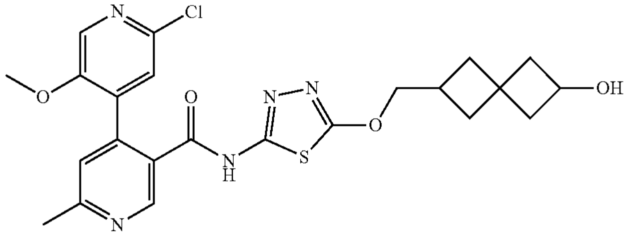 [SMILES: COc1cnc(Cl)cc1-c1cc(C)ncc1C(=O)Nc1nnc(OCC2CC3(CC(O)C3)C2)s1] |
| 139 | 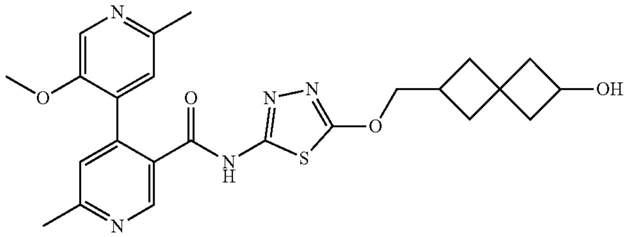 [SMILES: COc1cnc(C)cc1-c1cc(C)ncc1C(=O)Nc1nnc(OCC2CC3(CC(O)C3)C2)s1] |
| 140 | 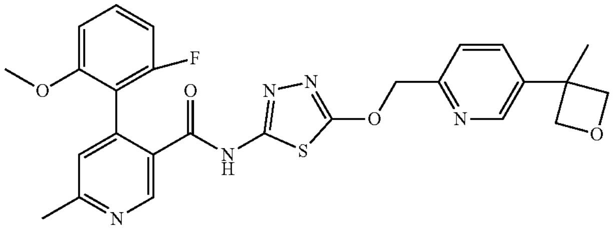 [SMILES: COc1cccc(F)c1-c1cc(C)ncc1C(=O)Nc1nnc(OCc2ccc(C3(C)COC3)cn2)s1] |
| 141 | 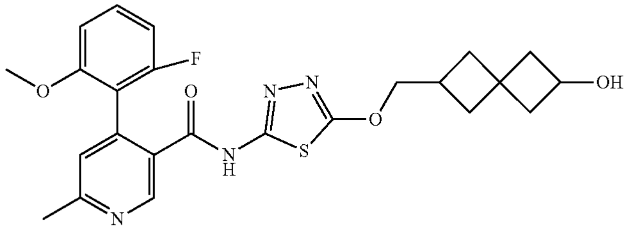 [SMILES: COc1cccc(F)c1-c1cc(C)ncc1C(=O)Nc1nnc(OCC2CC3(CC(O)C3)C2)s1] |
| 142 | 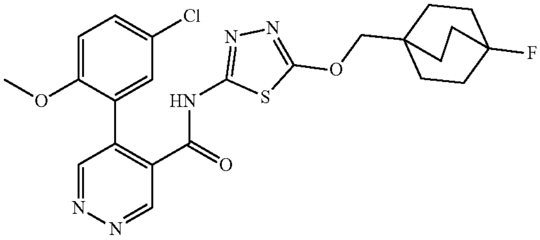 [SMILES: COc1ccc(Cl)cc1-c1cnncc1C(=O)Nc1nnc(OCC23CCC(F)(CC2)CC3)s1] |

-continued
| Cpd # | Structure |
| --- | --- |
| 143 | 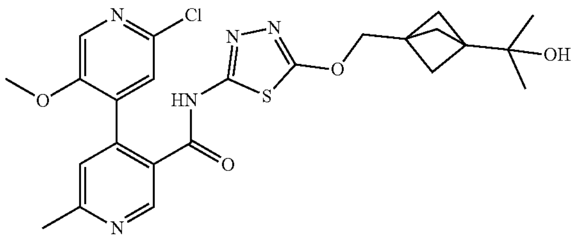 [SMILES: COc1cnc(Cl)cc1-c1cc(C)ncc1C(=O)Nc1nnc(OCC23CC(C(C)(C)O)(C2)C3)s1] |
| 144 | 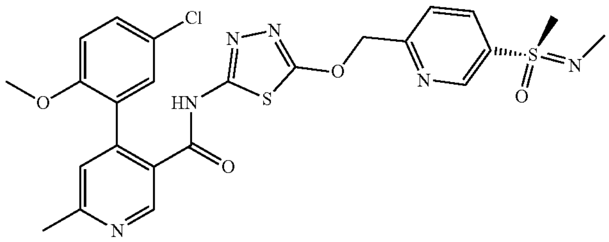 |
| 145 | 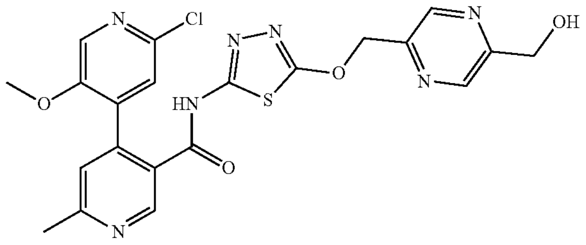 |
| 146 | 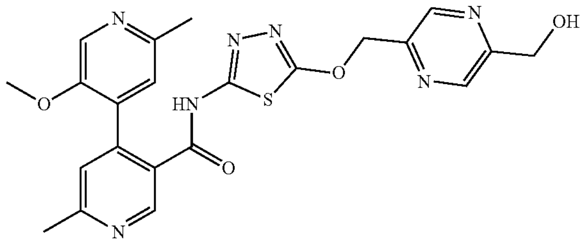 [SMILES: COc1cnc(C)cc1-c1cc(C)ncc1C(=O)Nc1nnc(OCc2cnc(CO)cn2)s1] |
| 147 | 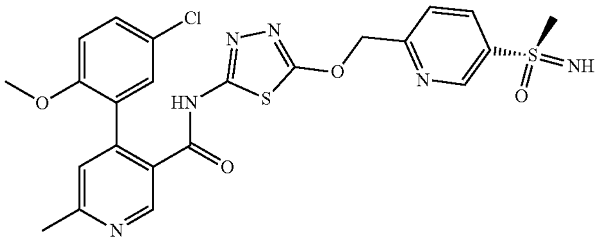 [SMILES: COc1ccc(Cl)cc1-c1cc(C)ncc1C(=O)Nc1nnc(OCc2ccc([S@](C)(=N)=O)cn2)s1] |
| 148 | 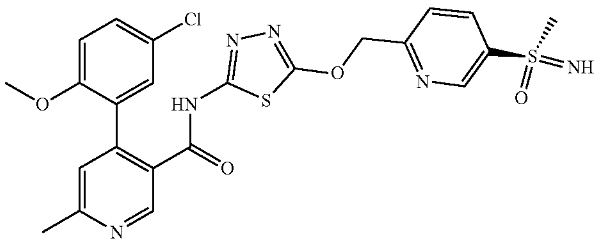 [SMILES: COc1ccc(Cl)cc1-c1cc(C)ncc1C(=O)Nc1nnc(OCc2ccc([S@@](C)(=N)=O)cn2)s1] |

-continued
| Cpd # | Structure |
|---|---|
| 149 | 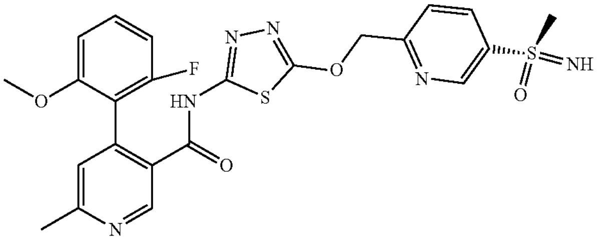 [SMILES: COc1cccc(F)c1-c1cc(C)ncc1C(=O)Nc1nnc(OCc2ccc([S@](C)(=N)=O)cn2)s1] |
| 150 | 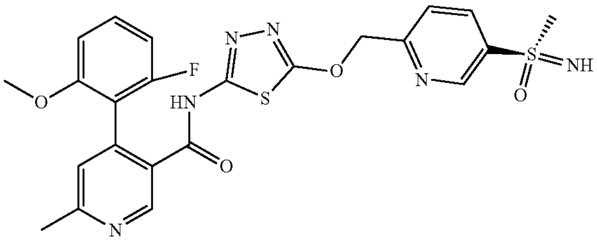 [SMILES: COc1cccc(F)c1-c1cc(C)ncc1C(=O)Nc1nnc(OCc2ccc([S@@](C)(=N)=O)cn2)s1] |
| 151 | 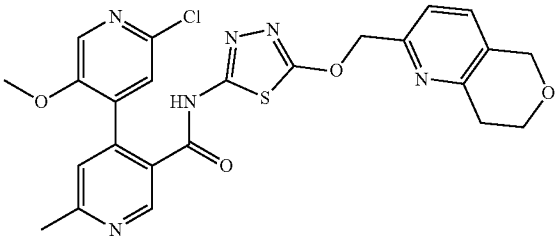 [SMILES: COc1cnc(Cl)cc1-c1cc(C)ncc1C(=O)Nc1nnc(OCc2ccc3c(n2)CCOC3)s1] |
| 152 | 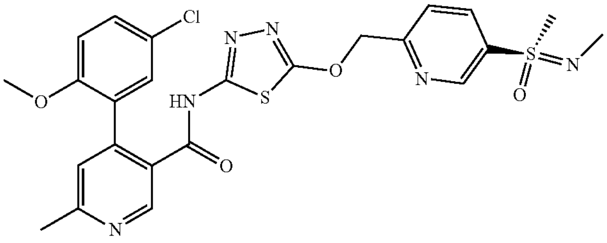 |
| 153 | 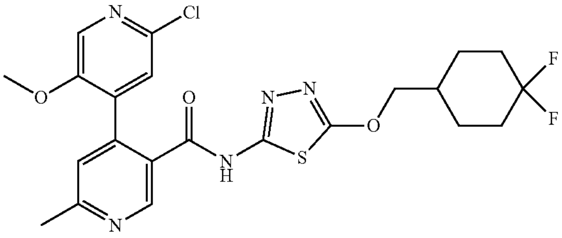 [SMILES: COc1cnc(Cl)cc1-c1cc(C)ncc1C(=O)Nc1nnc(OCC2CCC(F)(F)CC2)s1] |
| 154 | 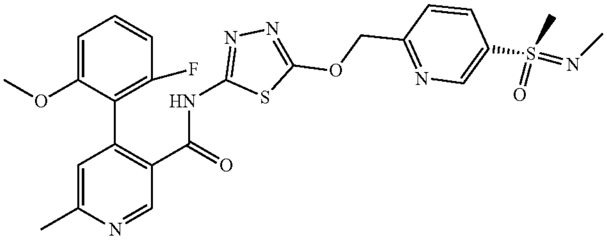 |

-continued
| Cpd # | Structure |
| --- | --- |
| 155 | 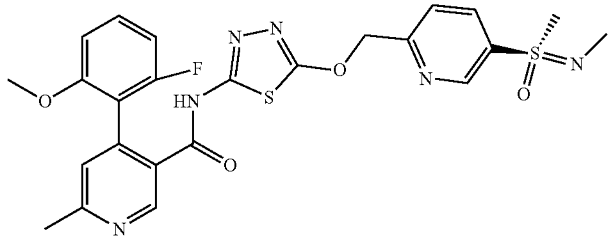 |
| 156 | 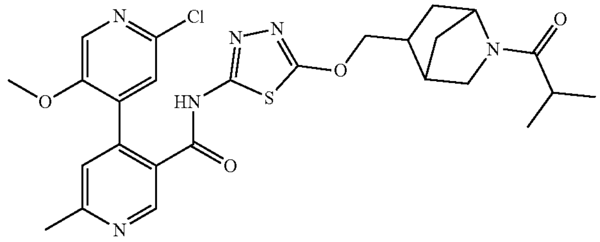 [SMILES: COc1cnc(Cl)cc1-c1cc(C)ncc1C(=O)Nc1nnc(OCC2CC3CC2CN3C(=O)C(C)C)s1] |
| 157 | 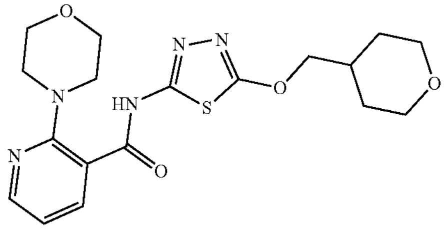 [SMILES: O=C(Nc1nnc(OCC2CCOCC2)s1)c1cccnc1N1CCOCC1] |
| 158 | 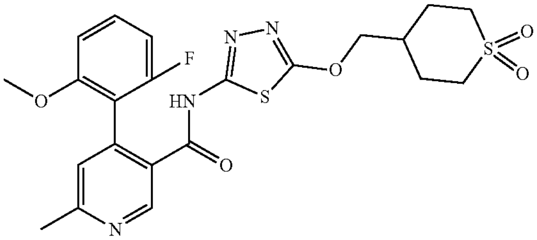 [SMILES: COc1cccc(F)c1-c1cc(C)ncc1C(=O)Nc1nnc(OCC2CCS(=O)(=O)CC2)s1] |
| 159 | 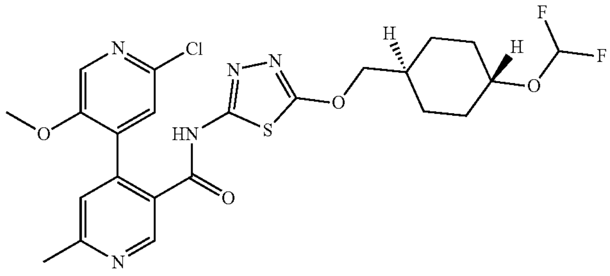 [SMILES: COc1cnc(Cl)cc1-c1cc(C)ncc1C(=O)Nc1nnc(OC[C@H]2CC[C@H](OC(F)F)CC2)s1] |
| 160 | 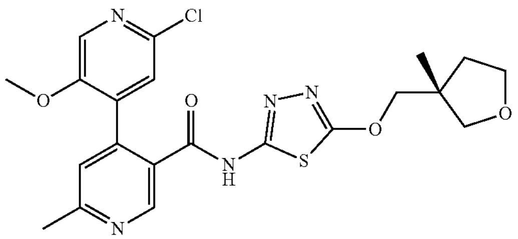 [SMILES: COc1cnc(Cl)cc1-c1cc(C)ncc1C(=O)Nc1nnc(OC[C@]2(C)CCOC2)s1] |

-continued
| Cpd # | Structure |
|---|---|
| 161 | 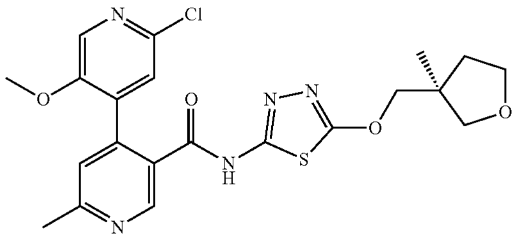 |
| 162 | 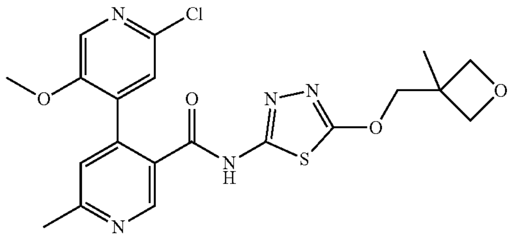 [SMILES: COc1cnc(Cl)cc1-c1cc(C)ncc1C(=O)Nc1nnc(OCC2(C)COC2)s1] |
| 163 | 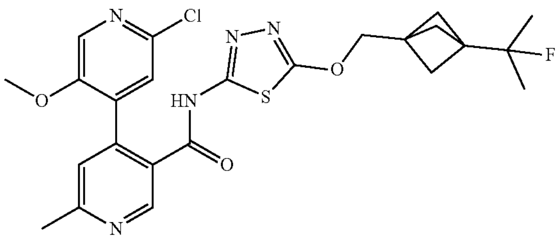 [SMILES: COc1cnc(Cl)cc1-c1cc(C)ncc1C(=O)Nc1nnc(OCC23CC(C(C)(C)F)(C2)C3)s1] |
| 164 | 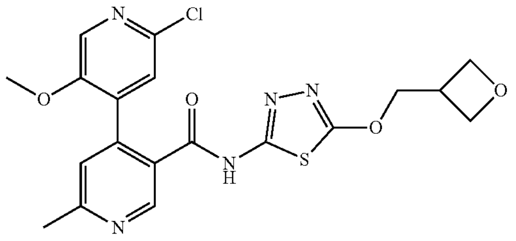 [SMILES: COc1cnc(Cl)cc1-c1cc(C)ncc1C(=O)Nc1nnc(OCC2COC2)s1] |
| 165 | 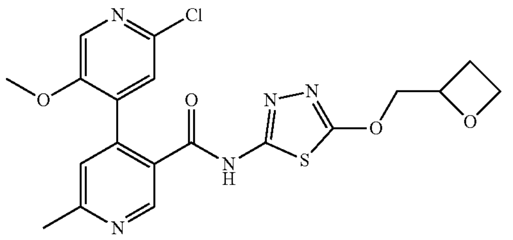 |
| 166 | 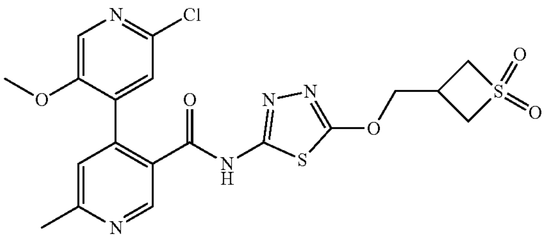 [SMILES: COc1cnc(Cl)cc1-c1cc(C)ncc1C(=O)Nc1nnc(OCC2CS(=O)(=O)C2)s1] |

-continued
| Cpd # | Structure |
| --- | --- |
| 167 | 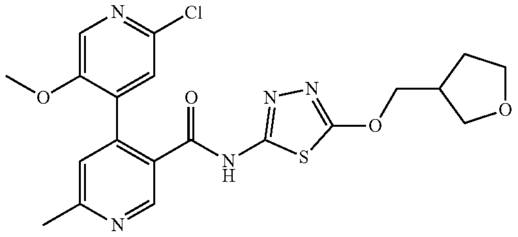 [SMILES: COc1cnc(Cl)cc1-c1cc(C)ncc1C(=O)Nc1nnc(OCC2CCOC2)s1] |
| 168 | 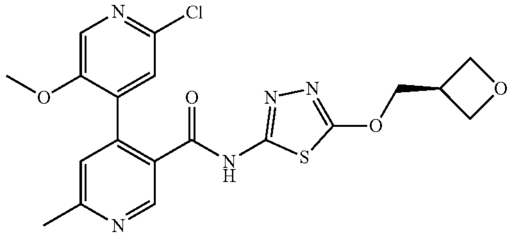 |
| 169 | 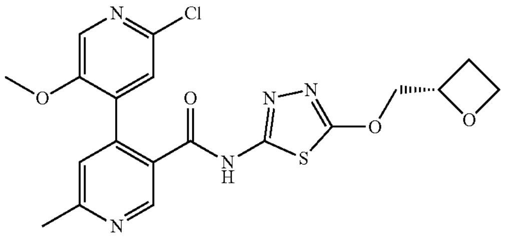 [SMILES: COc1cnc(Cl)cc1-c1cc(C)ncc1C(=O)Nc1nnc(OC[C@@H]2CCO2)s1] |
| 170 | 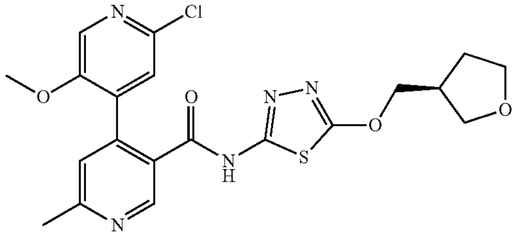 |
| 171 | 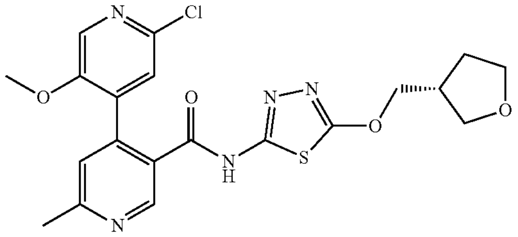 |
| 172 | 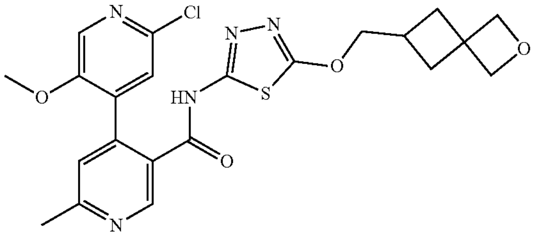 [SMILES: COc1cnc(Cl)cc1-c1cc(C)ncc1C(=O)Nc1nnc(OCC2CC3(COC3)C2)s1] |

-continued
| Cpd # | Structure |
|---|---|
| 173 | 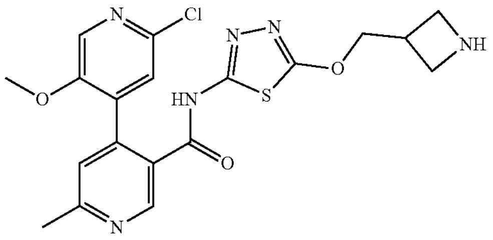 [SMILES: COc1cnc(Cl)cc1-c1cc(C)ncc1C(=O)Nc1nnc(OCC2CNC2)s1] |
| 174 | 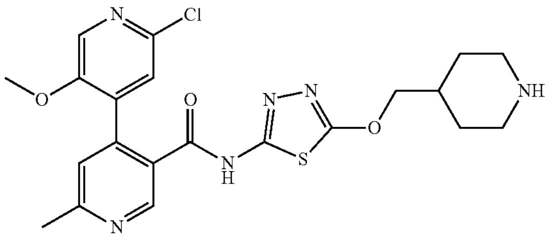 [SMILES: COc1cnc(Cl)cc1-c1cc(C)ncc1C(=O)Nc1nnc(OCC2CCNCC2)s1] |
| 175 | 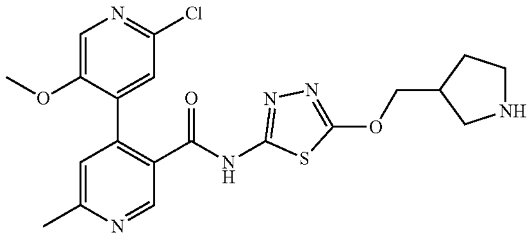 [SMILES: COc1cnc(Cl)cc1-c1cc(C)ncc1C(=O)Nc1nnc(OCC2CCNC2)s1] |
| 176 | 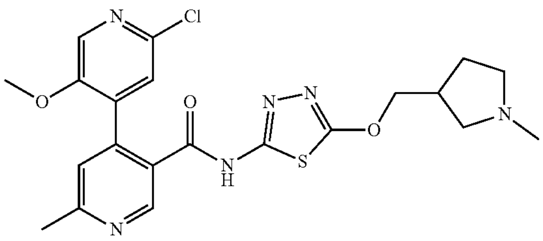 |
| 177 | 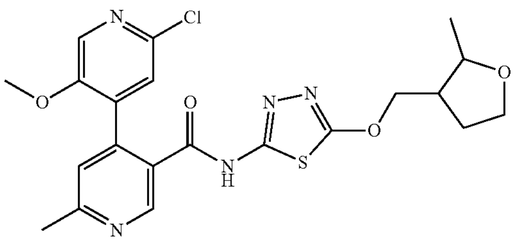 |
| 178 | 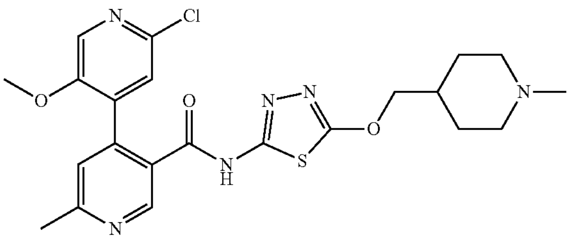 |

-continued
| Cpd # | Structure |
| --- | --- |
| 179 | 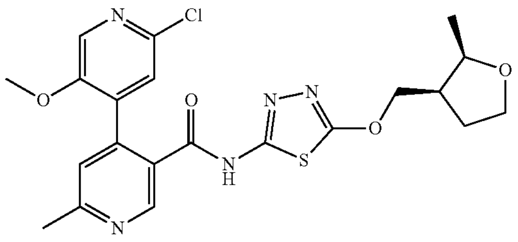 [SMILES: COc1cnc(Cl)cc1-c1cc(C)ncc1C(=O)Nc1nnc(OC[C@@H]2CCO[C@@H]2C)s1] |
| 180 | 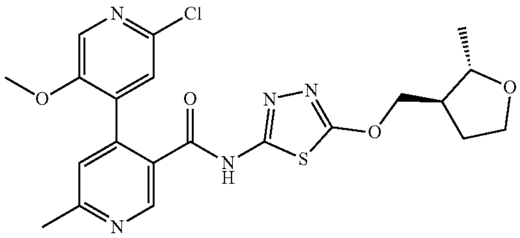 [SMILES: COc1cnc(Cl)cc1-c1cc(C)ncc1C(=O)Nc1nnc(OC[C@@H]2CCO[C@H]2C)s1] |
| 181 | 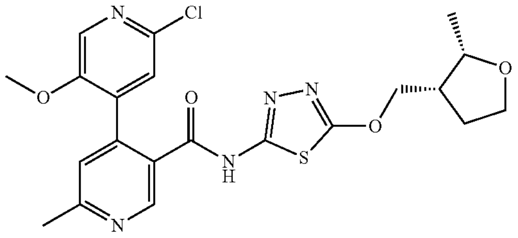 [SMILES: COc1cnc(Cl)cc1-c1cc(C)ncc1C(=O)Nc1nnc(OC[C@H]2CCO[C@H]2C)s1] |
| 182 | 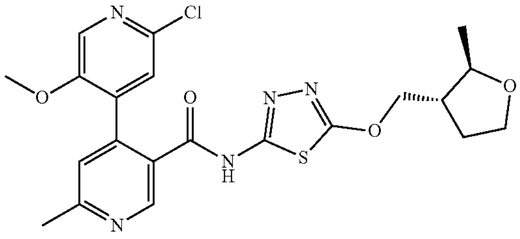 [SMILES: COc1cnc(Cl)cc1-c1cc(C)ncc1C(=O)Nc1nnc(OC[C@H]2CCO[C@@H]2C)s1] |
| 183 | 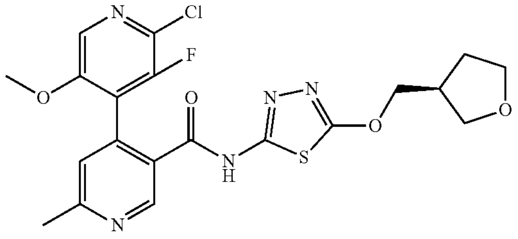 [SMILES: COc1cnc(Cl)c(F)c1-c1cc(C)ncc1C(=O)Nc1nnc(OC[C@H]2CCOC2)s1] |
| 184 | 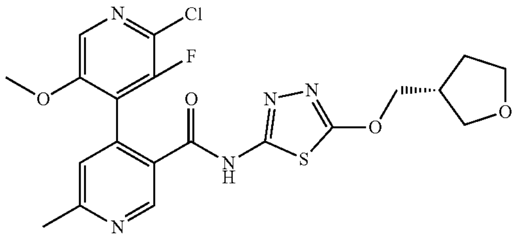 |

-continued
| Cpd # | Structure |
| --- | --- |
| 185 | 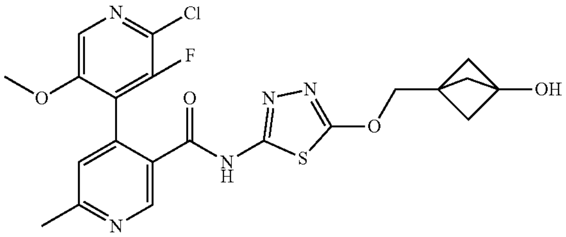 [SMILES: COc1cnc(Cl)c(F)c1-c1cc(C)ncc1C(=O)Nc1nnc(OCC23CC(O)(C2)C3)s1] |
| 186 | 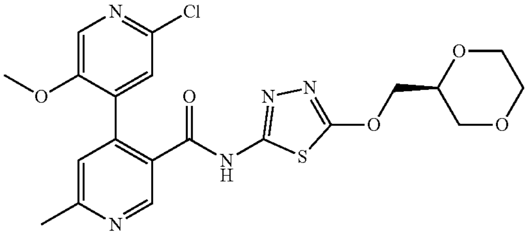 |
| 187 | 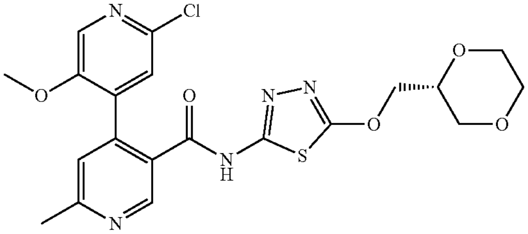 [SMILES: COc1cnc(Cl)cc1-c1cc(C)ncc1C(=O)Nc1nnc(OC[C@H]2COCCO2)s1] |
| 188 | 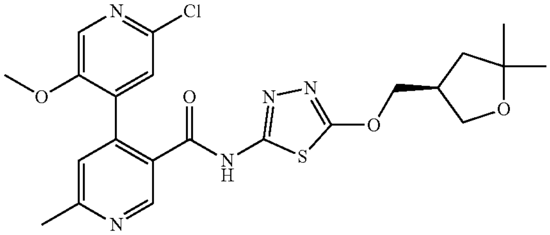 |
| 189 | 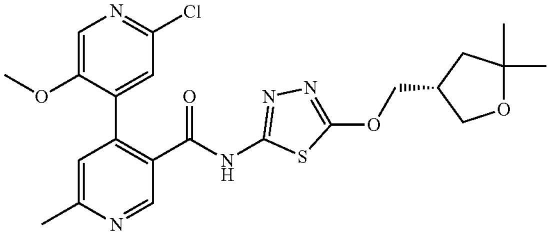 |
| 190 | 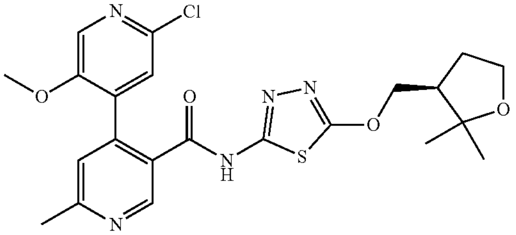 [SMILES: COc1cnc(Cl)cc1-c1cc(C)ncc1C(=O)Nc1nnc(OC[C@H]2CCOC2(C)C)s1] |

-continued
| Cpd # | Structure |
|---|---|
| 191 | 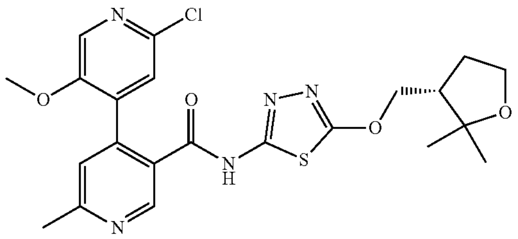 [SMILES: COc1cnc(Cl)cc1-c1cc(C)ncc1C(=O)Nc1nnc(OC[C@@H]2CCOC2(C)C)s1] |
| 192 | 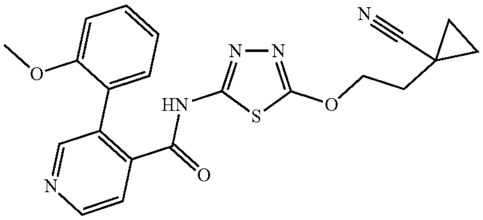 [SMILES: COc1ccccc1-c1cnccc1C(=O)Nc1nnc(OCCC2(C#N)CC2)s1] |
| 193 | 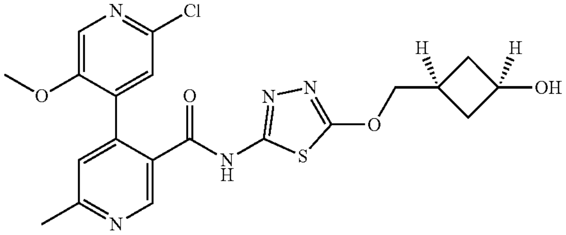 [SMILES: COc1cnc(Cl)cc1-c1cc(C)ncc1C(=O)Nc1nnc(OC[C@H]2C[C@@H](O)C2)s1] |
| 194 | 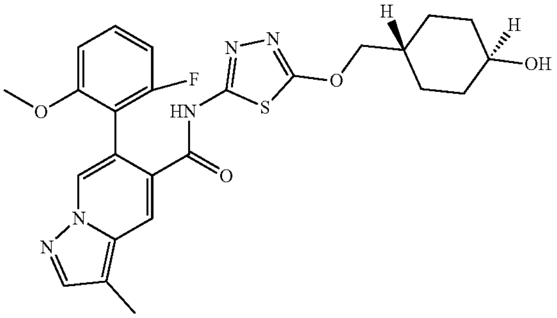 [SMILES: COc1cccc(F)c1-c1cn2ncc(C)c2cc1C(=O)Nc1nnc(OC[C@H]2CC[C@H](O)CC2)s1] |
| 195 | 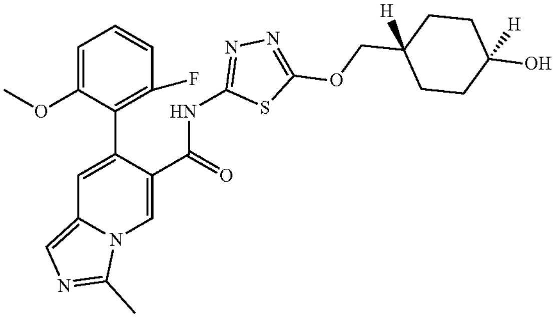 [SMILES: COc1cccc(F)c1-c1cc2cnc(C)n2cc1C(=O)Nc1nnc(OC[C@H]2CC[C@H](O)CC2)s1] |
| 196 | 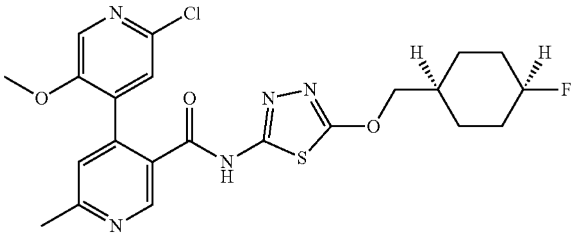 [SMILES: COc1cnc(Cl)cc1-c1cc(C)ncc1C(=O)Nc1nnc(OC[C@H]2CC[C@@H](F)CC2)s1] |

-continued
| Cpd # | Structure |
|---|---|
| 197 | 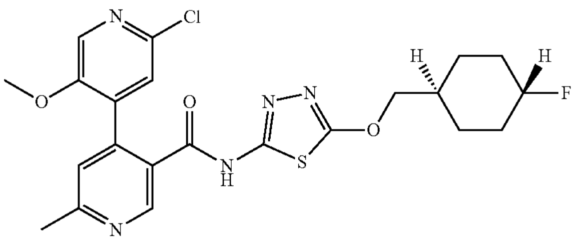 [SMILES: COc1cnc(Cl)cc1-c1cc(C)ncc1C(=O)Nc1nnc(OC[C@H]2CC[C@H](F)CC2)s1] |
| 198 | 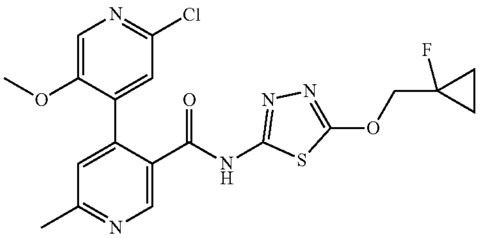 [SMILES: COc1cnc(Cl)cc1-c1cc(C)ncc1C(=O)Nc1nnc(OCC2(F)CC2)s1] |
| 199 | 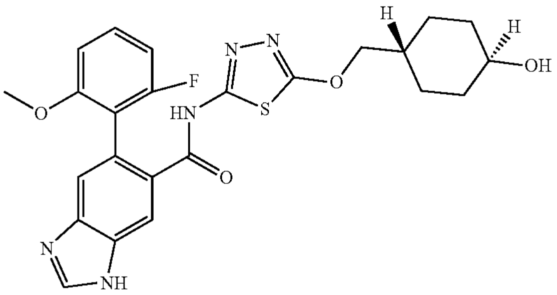 [SMILES: COc1cccc(F)c1-c1cc2nc[nH]c2cc1C(=O)Nc1nnc(OC[C@H]2CC[C@H](O)CC2)s1] |
| 200 | 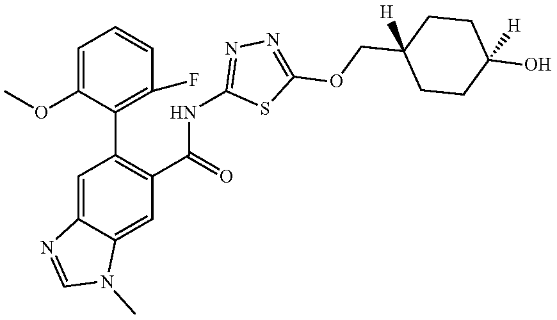 [SMILES: COc1cccc(F)c1-c1cc2ncn(C)c2cc1C(=O)Nc1nnc(OC[C@H]2CC[C@H](O)CC2)s1] |
| 201 | 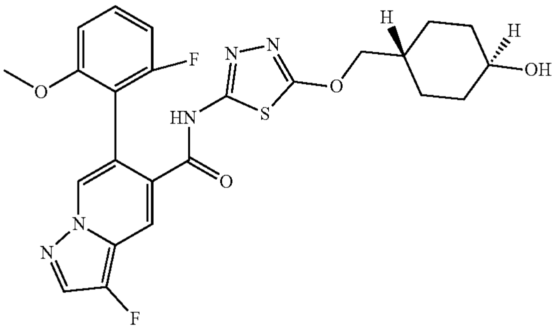 [SMILES: COc1cccc(F)c1-c1cn2ncc(F)c2cc1C(=O)Nc1nnc(OC[C@H]2CC[C@H](O)CC2)s1] |

-continued
| Cpd # | Structure |
| --- | --- |
| 202 | 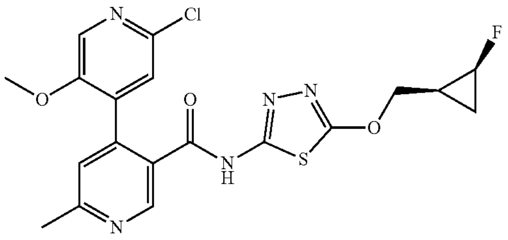 [SMILES: COc1cnc(Cl)cc1-c1cc(C)ncc1C(=O)Nc1nnc(OC[C@@H]2C[C@@H]2F)s1] |
| 203 | 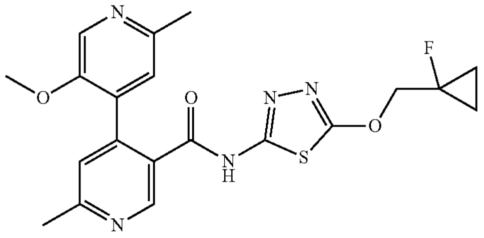 [SMILES: COc1cnc(C)cc1-c1cc(C)ncc1C(=O)Nc1nnc(OCC2(F)CC2)s1] |
| 204 | 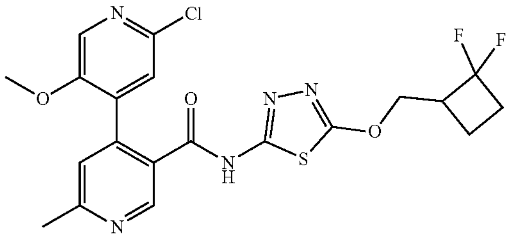 [SMILES: COc1cnc(Cl)cc1-c1cc(C)ncc1C(=O)Nc1nnc(OCC2CCC2(F)F)s1] |
| 205 | 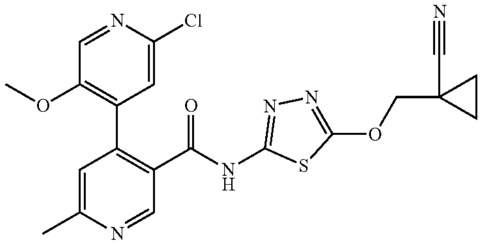 [SMILES: COc1cnc(Cl)cc1-c1cc(C)ncc1C(=O)Nc1nnc(OCC2(C#N)CC2)s1] |
| 206 | 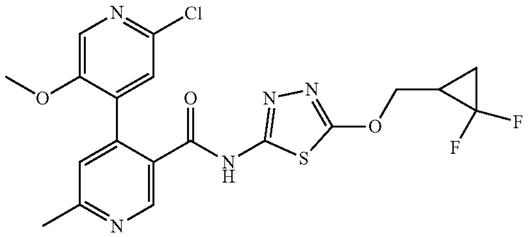 [SMILES: COc1cnc(Cl)cc1-c1cc(C)ncc1C(=O)Nc1nnc(OCC2CC2(F)F)s1] |
| 207 | 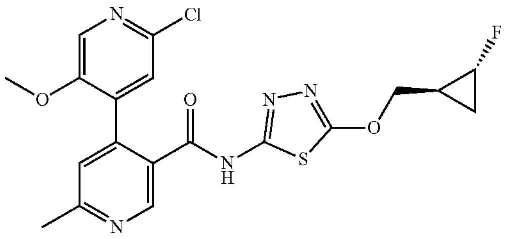 [SMILES: COc1cnc(Cl)cc1-c1cc(C)ncc1C(=O)Nc1nnc(OC[C@@H]2C[C@H]2F)s1] |

-continued
| Cpd # | Structure |
| --- | --- |
| 208 | 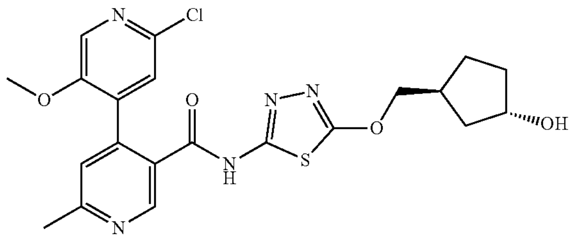 [SMILES: COc1cnc(Cl)cc1-c1cc(C)ncc1C(=O)Nc1nnc(OC[C@H]2CC[C@H](O)C2)s1] |
| 209 | 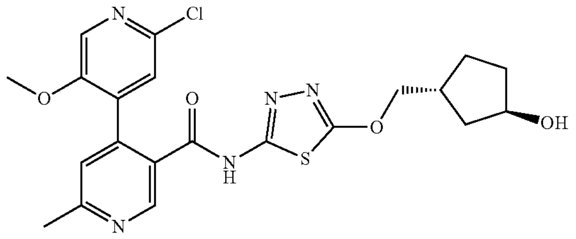 [SMILES: COc1cnc(Cl)cc1-c1cc(C)ncc1C(=O)Nc1nnc(OC[C@@H]2CC[C@@H](O)C2)s1] |
| 210 | 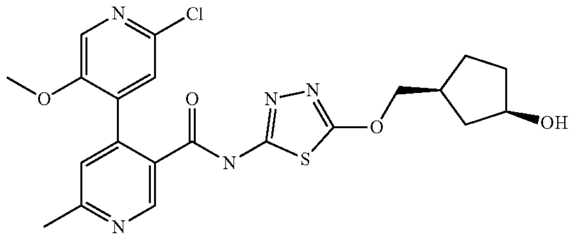 |
| 211 | 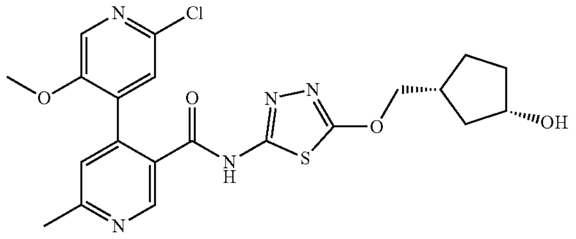 [SMILES: COc1cnc(Cl)cc1-c1cc(C)ncc1C(=O)Nc1nnc(OC[C@@H]2CC[C@H](O)C2)s1] |
| 212 | 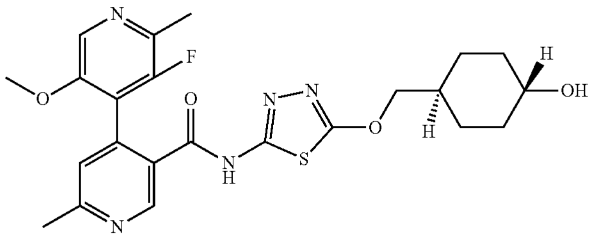 [SMILES: COc1cnc(C)c(F)c1-c1cc(C)ncc1C(=O)Nc1nnc(OC[C@H]2CC[C@H](O)CC2)s1] |
| 213 | 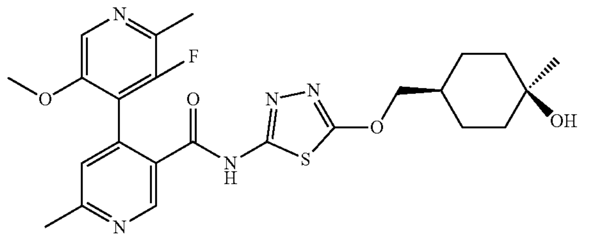 |

-continued
| Cpd # | Structure |
|---|---|
| 214 | 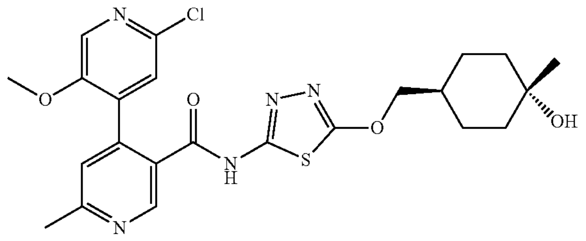 |
| 215 | 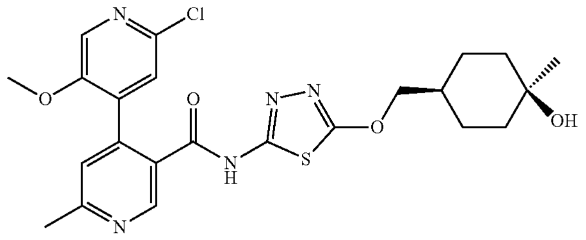 |
| 216 | 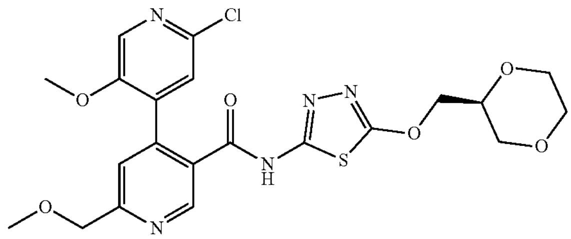 [SMILES: COCc1cc(-c2cc(Cl)ncc2OC)c(C(=O)Nc2nnc(OC[C@@H]3COCCO3)s2)cn1] |
| 217 | 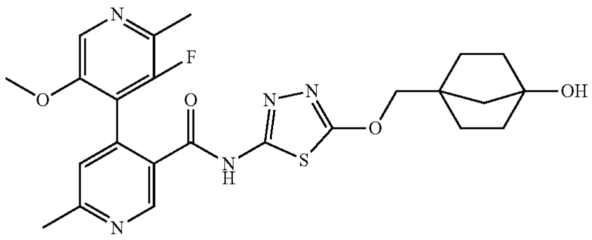 [SMILES: COc1cnc(C)c(F)c1-c1cc(C)ncc1C(=O)Nc1nnc(OCC23CCC(O)(CC2)C3)s1] |
| 218 | 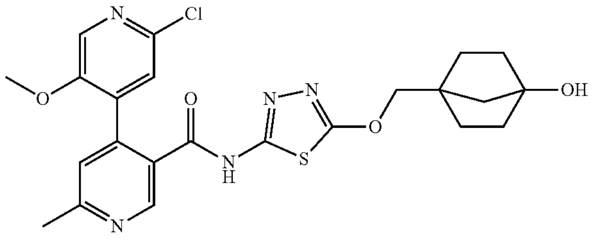 [SMILES: COc1cnc(Cl)cc1-c1cc(C)ncc1C(=O)Nc1nnc(OCC23CCC(O)(CC2)C3)s1] |
| 219 | 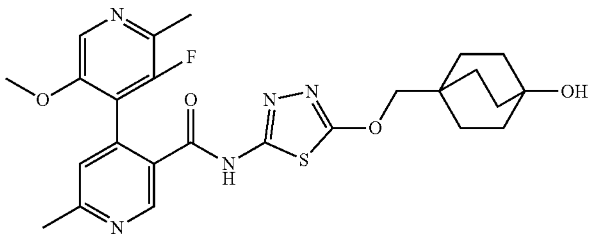 [SMILES: COc1cnc(C)c(F)c1-c1cc(C)ncc1C(=O)Nc1nnc(OCC23CCC(O)(CC2)CC3)s1] |

-continued
| Cpd # | Structure |
| --- | --- |
| 220 | 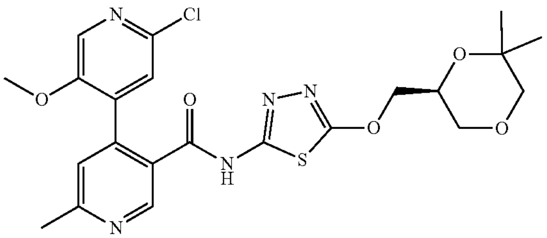 |
| 221 | 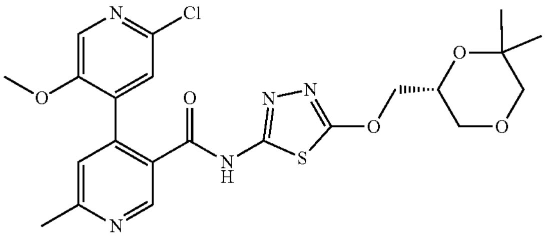 |
| 222 | 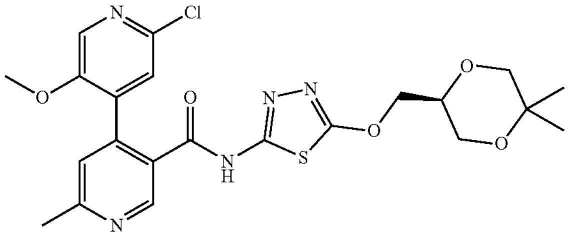 |
| 223 | 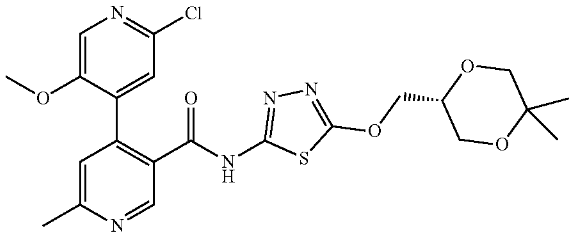 |
| 224 | 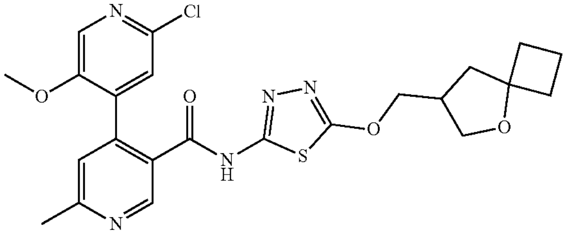 [SMILES: COc1cnc(Cl)cc1-c1cc(C)ncc1C(=O)Nc1nnc(OCC2COC3(CCC3)C2)s1] |
| 225 | 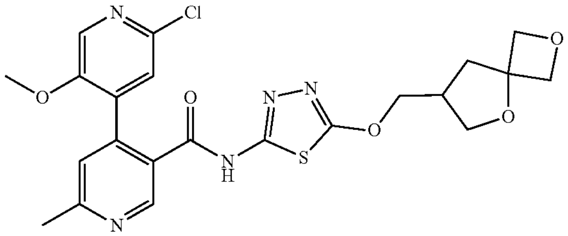 [SMILES: COc1cnc(Cl)cc1-c1cc(C)ncc1C(=O)Nc1nnc(OCC2COC3(COC3)C2)s1] |

-continued
| Cpd # | Structure |
|---|---|
| 226 | 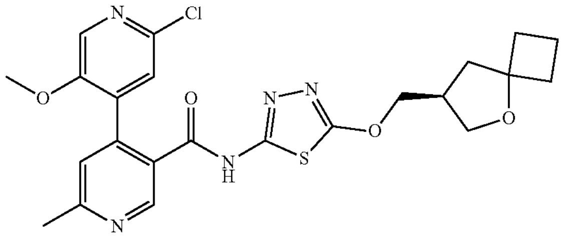 [SMILES: COc1cnc(Cl)cc1-c1cc(C)ncc1C(=O)Nc1nnc(OC[C@@H]2COC3(CCC3)C2)s1] |
| 227 | 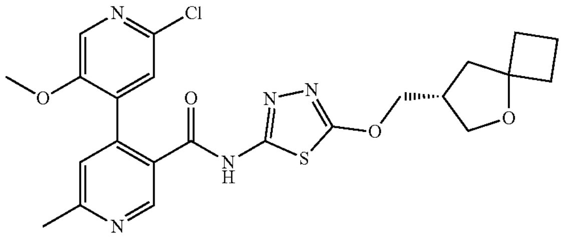 [SMILES: COc1cnc(Cl)cc1-c1cc(C)ncc1C(=O)Nc1nnc(OC[C@H]2COC3(CCC3)C2)s1] |
| 228 | 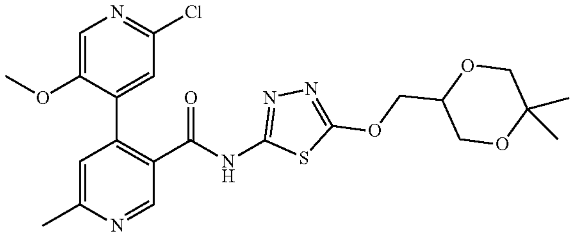 |
| 229 | 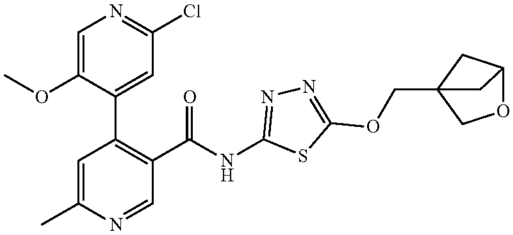 [SMILES: COc1cnc(Cl)cc1-c1cc(C)ncc1C(=O)Nc1nnc(OCC23COC(C2)C3)s1] |
| 230 | 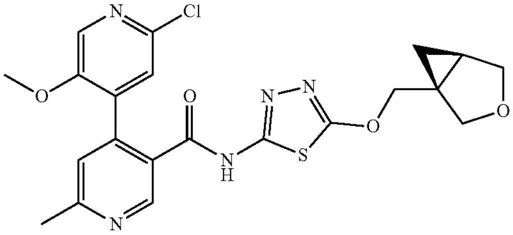 [SMILES: COc1cnc(Cl)cc1-c1cc(C)ncc1C(=O)Nc1nnc(OC[C@@]23COC[C@@H]2C3)s1] |
| 231 | 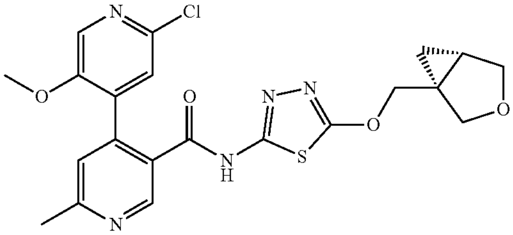 [SMILES: COc1cnc(Cl)cc1-c1cc(C)ncc1C(=O)Nc1nnc(OC[C@]23COC[C@H]2C3)s1] |

-continued
| Cpd # | Structure |
|---|---|
| 232 | 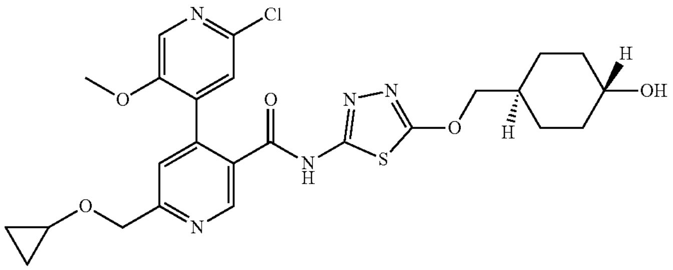 [SMILES: COc1cnc(Cl)cc1-c1cc(COC2CC2)ncc1C(=O)Nc1nnc(OC[C@H]2CC[C@H](O)CC2)s1] |
| 233 | 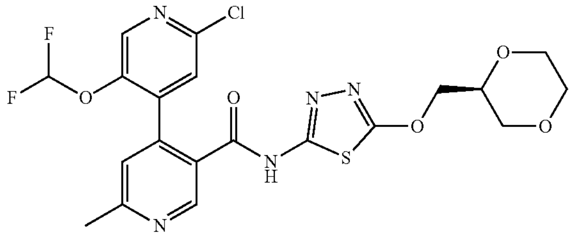 [SMILES: Cc1cc(-c2cc(Cl)ncc2OC(F)F)c(C(=O)Nc2nnc(OC[C@@H]3COCCO3)s2)cn1] |
| 234 | 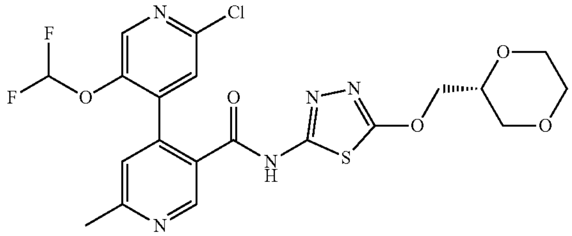 [SMILES: Cc1cc(-c2cc(Cl)ncc2OC(F)F)c(C(=O)Nc2nnc(OC[C@H]3COCCO3)s2)cn1] |
| 235 | 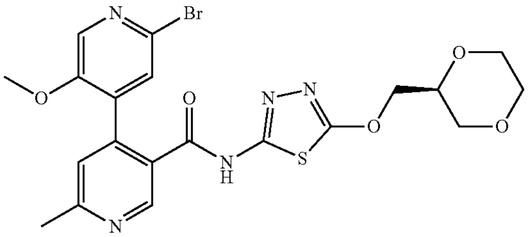 [SMILES: COc1cnc(Br)cc1-c1cc(C)ncc1C(=O)Nc1nnc(OC[C@@H]2COCCO2)s1] |
| 236 | 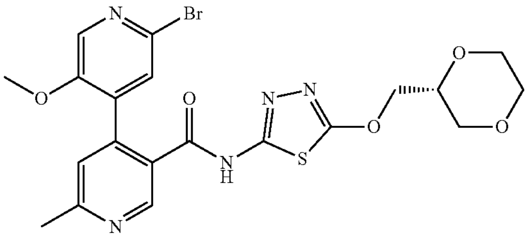 [SMILES: COc1cnc(Br)cc1-c1cc(C)ncc1C(=O)Nc1nnc(OC[C@H]2COCCO2)s1] |
| 237 | 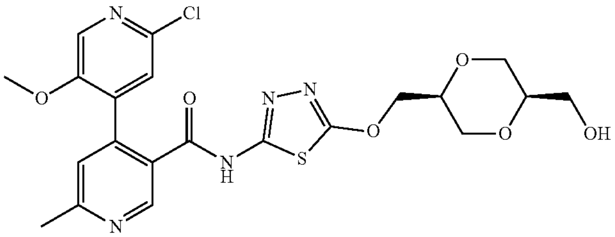 [SMILES: COc1cnc(Cl)cc1-c1cc(C)ncc1C(=O)Nc1nnc(OC[C@@H]2CO[C@H](CO)CO2)s1] |

-continued
| Cpd # | Structure |
| --- | --- |
| 238 | 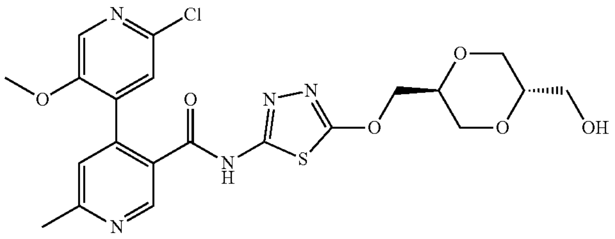 [SMILES: COc1cnc(Cl)cc1-c1cc(C)ncc1C(=O)Nc1nnc(OC[C@@H]2CO[C@@H](CO)CO2)s1] |
| 239 | 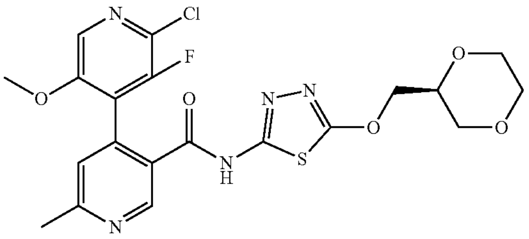 [SMILES: COc1cnc(Cl)c(F)c1-c1cc(C)ncc1C(=O)Nc1nnc(OC[C@@H]2COCCO2)s1] |
| 240 | 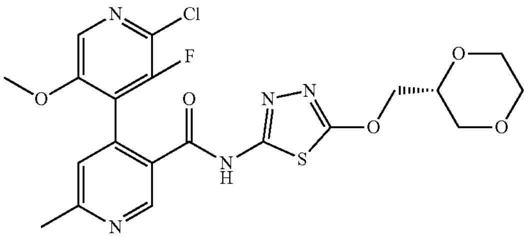 [SMILES: COc1cnc(Cl)c(F)c1-c1cc(C)ncc1C(=O)Nc1nnc(OC[C@H]2COCCO2)s1] |
| 241 | 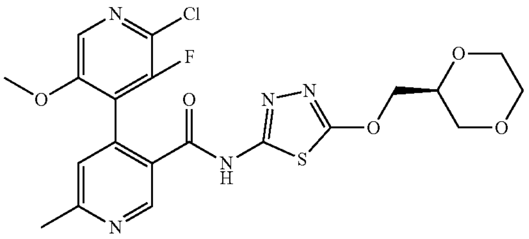 [SMILES: COc1cnc(Cl)c(F)c1-c1cc(C)ncc1C(=O)Nc1nnc(OC[C@@H]2COCCO2)s1] |
| 242 | 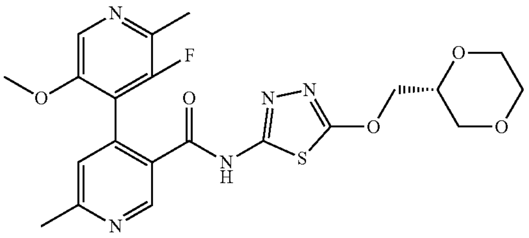 [SMILES: COc1cnc(C)c(F)c1-c1cc(C)ncc1C(=O)Nc1nnc(OC[C@H]2COCCO2)s1] |
| 243 | 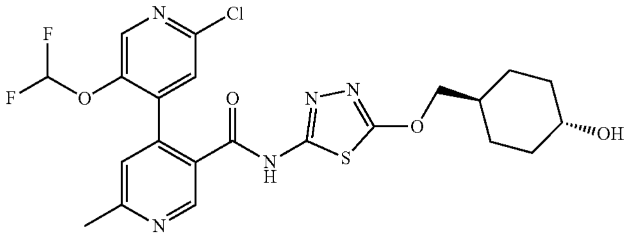 [SMILES: Cc1cc(-c2cc(Cl)ncc2OC(F)F)c(C(=O)Nc2nnc(OC[C@H]3CC[C@H](O)CC3)s2)cn1] |

-continued
| Cpd # | Structure |
| --- | --- |
| 244 | 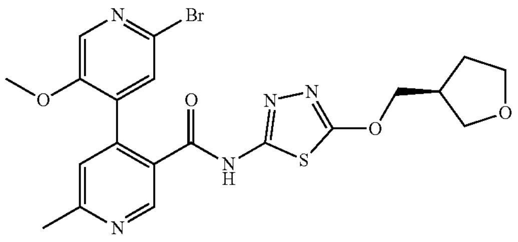 [SMILES: COc1cnc(Br)cc1-c1cc(C)ncc1C(=O)Nc1nnc(OC[C@H]2CCOC2)s1] |
| 245 | 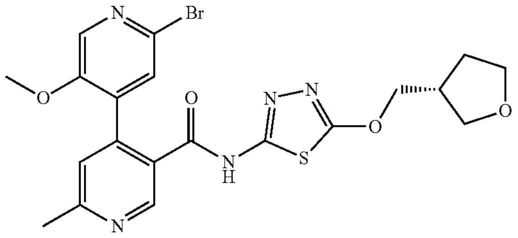 [SMILES: COc1cnc(Br)cc1-c1cc(C)ncc1C(=O)Nc1nnc(OC[C@@H]2CCOC2)s1] |
| 246 | 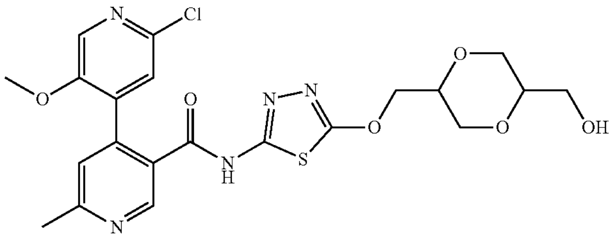 [SMILES: COc1cnc(Cl)cc1-c1cc(C)ncc1C(=O)Nc1nnc(OCC2COC(CO)CO2)s1] |
| 247 | 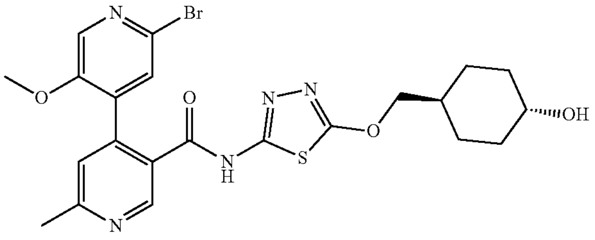 [SMILES: COc1cnc(Br)cc1-c1cc(C)ncc1C(=O)Nc1nnc(OC[C@H]2CC[C@H](O)CC2)s1] |
| 248 | 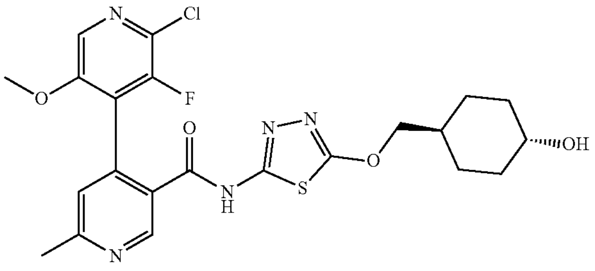 [SMILES: COc1cnc(Cl)c(F)c1-c1cc(C)ncc1C(=O)Nc1nnc(OC[C@H]2CC[C@H](O)CC2)s1] |
| 249 | 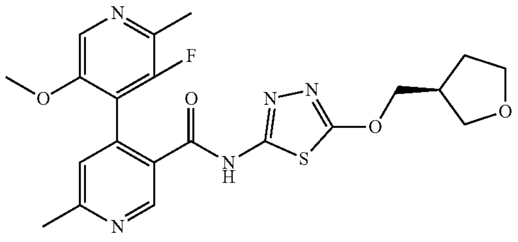 [SMILES: COc1cnc(C)c(F)c1-c1cc(C)ncc1C(=O)Nc1nnc(OC[C@H]2CCOC2)s1] |

-continued
| Cpd # | Structure |
|---|---|
| 250 | 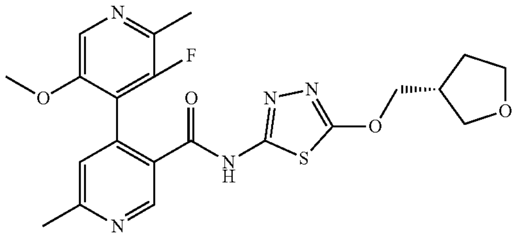 [SMILES: COc1cnc(C)c(F)c1-c1cc(C)ncc1C(=O)Nc1nnc(OC[C@@H]2CCOC2)s1] |
| 251 | 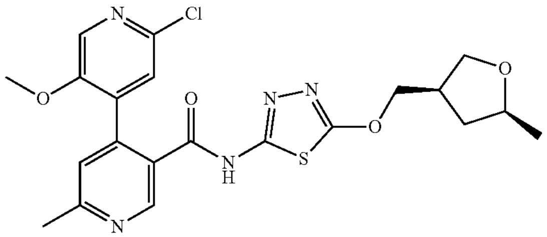 |
| 252 | 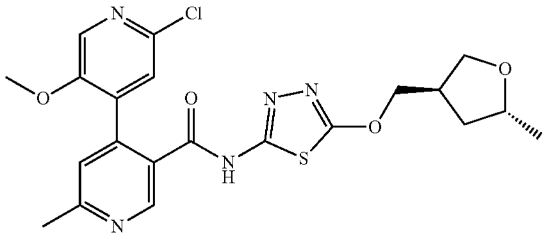 |
| 253 | 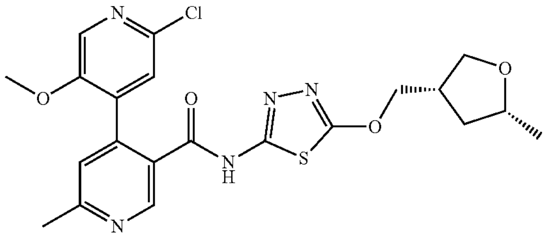 |
| 254 | 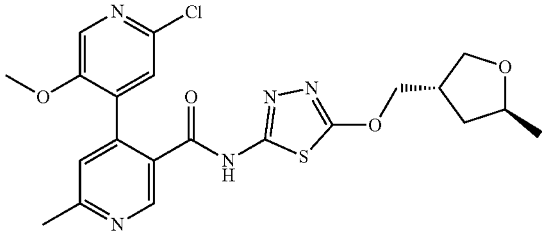 |
| 255 | 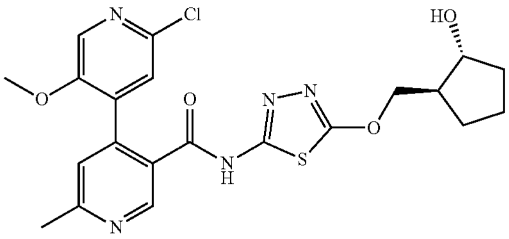 [SMILES: COc1cnc(Cl)cc1-c1cc(C)ncc1C(=O)Nc1nnc(OC[C@@H]2CCC[C@H]2O)s1] |

-continued
| Cpd # | Structure |
| --- | --- |
| 256 | 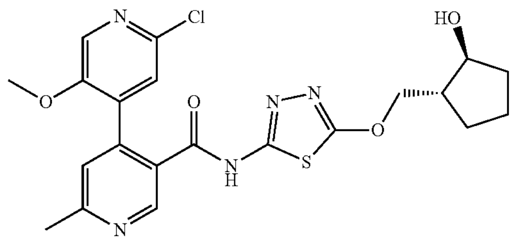 [SMILES: COc1cnc(Cl)cc1-c1cc(C)ncc1C(=O)Nc1nnc(OC[C@H]2CCC[C@@H]2O)s1] |
| 257 | 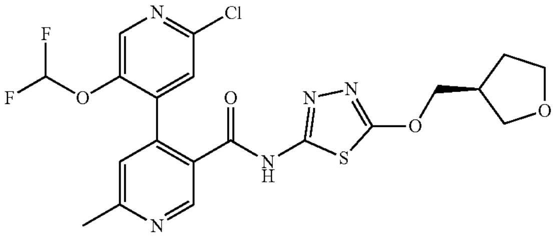 [SMILES: Cc1cc(-c2cc(Cl)ncc2OC(F)F)c(C(=O)Nc2nnc(OC[C@H]3CCOC3)s2)cn1] |
| 258 | 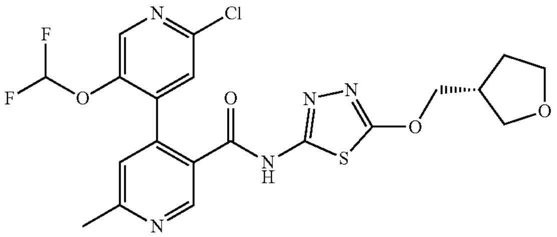 [SMILES: Cc1cc(-c2cc(Cl)ncc2OC(F)F)c(C(=O)Nc2nnc(OC[C@@H]3CCOC3)s2)cn1] |
| 259 | 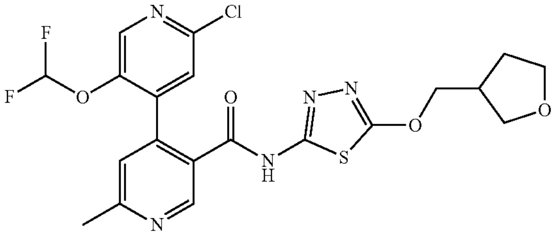 [SMILES: Cc1cc(-c2cc(Cl)ncc2OC(F)F)c(C(=O)Nc2nnc(OCC3CCOC3)s2)cn1] |
| 260 | 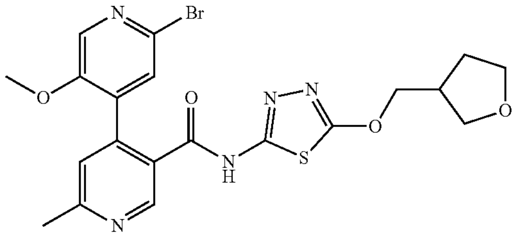 |
| 261 | 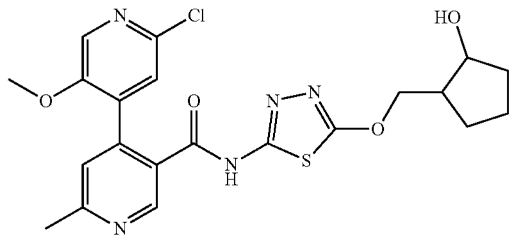 [SMILES: COc1cnc(Cl)cc1-c1cc(C)ncc1C(=O)Nc1nnc(OCC2CCCC2O)s1] |

-continued
| Cpd # | Structure |
| --- | --- |
| 262 | 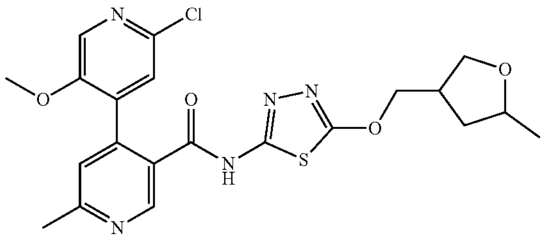 |
| 263 | 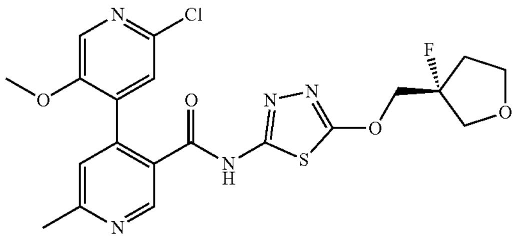 [SMILES: COc1cnc(Cl)cc1-c1cc(C)ncc1C(=O)Nc1nnc(OC[C@@]2(F)CCOC2)s1] |
| 264 | 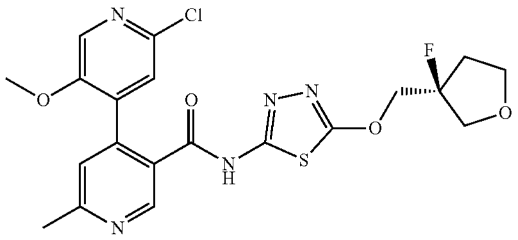 [SMILES: COc1cnc(Cl)cc1-c1cc(C)ncc1C(=O)Nc1nnc(OC[C@]2(F)CCOC2)s1] |
| 265 | 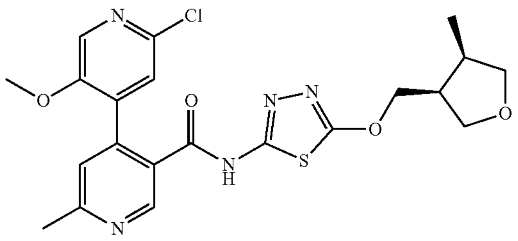 [SMILES: COc1cnc(Cl)cc1-c1cc(C)ncc1C(=O)Nc1nnc(OC[C@@H]2COC[C@@H]2C)s1] |
| 266 | 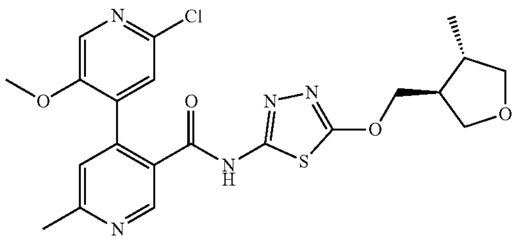 [SMILES: COc1cnc(Cl)cc1-c1cc(C)ncc1C(=O)Nc1nnc(OC[C@@H]2COC[C@H]2C)s1] |
| 267 | 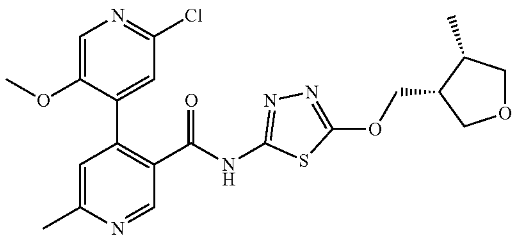 [SMILES: COc1cnc(Cl)cc1-c1cc(C)ncc1C(=O)Nc1nnc(OC[C@H]2COC[C@H]2C)s1] |

-continued
| Cpd # | Structure |
|---|---|
| 268 | 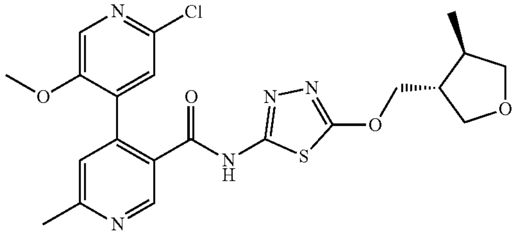 [SMILES: COc1cnc(Cl)cc1-c1cc(C)ncc1C(=O)Nc1nnc(OC[C@H]2COC[C@@H]2C)s1] |
| 269 | 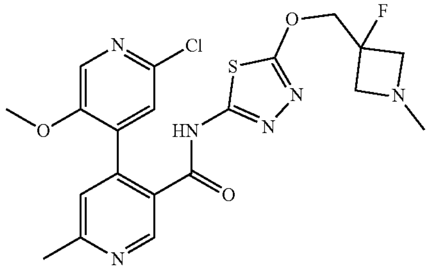 |
| 270 | 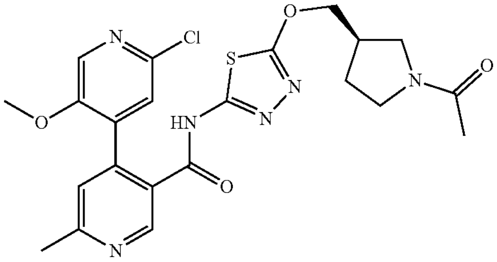 [SMILES: COc1cnc(Cl)cc1-c1cc(C)ncc1C(=O)Nc1nnc(OC[C@@H]2CCN(C(C)=O)C2)s1] |
| 271 | 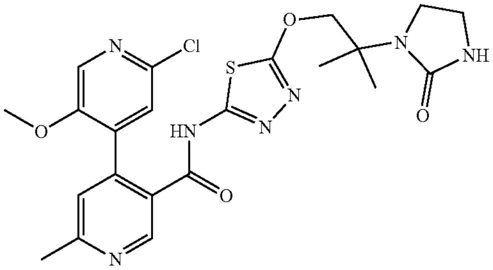 [SMILES: COc1cnc(Cl)cc1-c1cc(C)ncc1C(=O)Nc1nnc(OCC(C)(C)N2CCNC2=O)s1] |
| 272 | 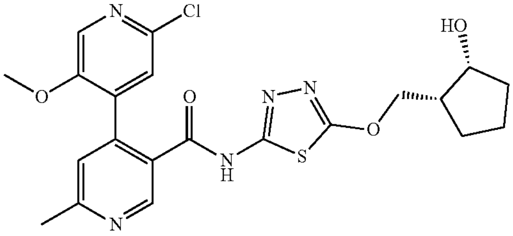 [SMILES: COc1cnc(Cl)cc1-c1cc(C)ncc1C(=O)Nc1nnc(OC[C@H]2CCC[C@H]2O)s1] |
| 273 | 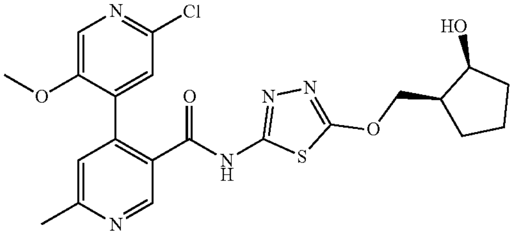 [SMILES: COc1cnc(Cl)cc1-c1cc(C)ncc1C(=O)Nc1nnc(OC[C@@H]2CCC[C@@H]2O)s1] |

In some embodiments, the compounds or pharmaceutically acceptable salts thereof is a compound from Table 1.

In some embodiment, the compounds or pharmaceutically acceptable salts thereof is a compound selected from the group consisting of compound number 8, 9, 10, 11, 12, 13, 15, 16, 18, 19, 20, 21, 23, 31, 36, 43, 44, 45, 46, 49, 52, 53, 64, 67, 74, 75, 77, 82, 85, 86, 91, 100, 101, 104, 113, 120, 127, 128, 129, 130, 140, and 153.

In some embodiments, the compounds or pharmaceutically acceptable salts thereof is a compound selected from the group consisting of compound number 1, 2, 3, 7, 35, 47, 51, 61, 65, 66, 71, 78, 92, 95, 98, 99, 102, 103, 112, 116, 117, 121, 131, 132, 135, 136, 138, 139, 141, 142, 143, 151, and 156.

In some embodiments, the compounds or pharmaceutically acceptable salts thereof is a compound selected from the group consisting of compound number 4, 5, 6, 14, 17, 22, 24, 25, 26, 32, 33, 34, 37, 38, 39, 40, 41, 42, 48, 50, 54, 55, 56, 57, 58, 59, 60, 62, 63, 68, 69, 70, 72, 73, 76, 79, 80, 81, 83, 84, 87, 88, 89, 90, 93, 94, 96, 97, 105, 106, 109, 110, 111, 114, 115, 119, 122, 123, 124, 125, 126, 133, 134, 144, 145, 146, 147, 148, 149, 150, 152, 154, and 155.

In some embodiments, the compounds or pharmaceutically acceptable salts thereof is a compound selected from the group consisting of compound number 27, 28, 29, and 30.

In some embodiments, the compounds or pharmaceutically acceptable salts thereof is a compound selected from the group consisting of compound number 100, 101, 104, 107, 108, 118, 127, 128, 129, 137, and 153.

In some embodiments, the compounds or pharmaceutically acceptable salts thereof is a compound selected from the group consisting of compound number 156, 157, 158, 159, 160, 161, 161, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 109, 210, 211, and 212.

In some embodiments, the compounds or pharmaceutically acceptable salts thereof is a compound selected from the group consisting of compound number 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, and 273.

Assay

The ability of compounds of the disclosure to inhibit Polθ can be measured as described in the biological assay below.

Pharmaceutical Composition

The compounds of Formula (I), (II), (III), (IV), or Table 1, or a pharmaceutically acceptable salt thereof, provided herein may be in the form of compositions suitable for administration to a subject. In general, such compositions are pharmaceutical compositions comprising a compound of Formula (I), (II), (III), (IV), or Table 1, or a pharmaceutically acceptable salt thereof and one or more pharmaceutically acceptable or physiologically acceptable excipients. In certain embodiments, the compound of Formula (I), (II), (III), (IV), or Table 1, or a pharmaceutically acceptable salt thereof is present in a therapeutically effective amount. The pharmaceutical compositions may be used in all the methods disclosed herein; thus, for example, the pharmaceutical compositions can be administered ex vivo or in vivo to a subject in order to practice the therapeutic methods and uses described herein.

The pharmaceutical compositions can be formulated to be compatible with the intended method or route of administration; exemplary routes of administration are set forth herein. Furthermore, the pharmaceutical compositions may be used in combination with other therapeutically active agents or compounds as described herein in order to treat the diseases, disorders and conditions contemplated by the present disclosure.

The pharmaceutical compositions containing the active ingredient (e.g., a compound of Formula (I), (II), (III), (IV), or Table 1, a pharmaceutically acceptable salt thereof) may be in a form suitable for oral use, for example, as tablets, capsules, troches, lozenges, aqueous or oily suspensions, dispersible powders or granules, emulsions, hard or soft capsules, or syrups, solutions, microbeads or elixirs. Pharmaceutical compositions intended for oral use may be prepared according to any method known to the art for the manufacture of pharmaceutical compositions, and such compositions may contain one or more agents such as, for example, sweetening agents, flavoring agents, coloring agents and preserving agents in order to provide pharmaceutically elegant and palatable preparations. Tablets, capsules and the like contain the active ingredient in admixture with non-toxic pharmaceutically acceptable excipients which are suitable for the manufacture of tablets, capsules, and the like. These excipients may be, for example, diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc.

The tablets, capsules and the like suitable for oral administration may be uncoated or coated by known techniques to delay disintegration and absorption in the gastrointestinal tract and thereby provide a sustained action. For example, a time-delay material such as glyceryl monostearate or glyceryl di-stearate may be employed. The tablets may also be coated by techniques known in the art to form osmotic therapeutic tablets for controlled release. Additional agents include biodegradable or biocompatible particles or a polymeric substance such as polyesters, polyamine acids, hydrogel, polyvinyl pyrrolidone, polyanhydrides, polyglycolic acid, ethylene-vinyl acetate, methylcellulose, carboxymethylcellulose, protamine sulfate, or lactide and glycolide copolymers, polylactide and glycolide copolymers, or ethylene vinyl acetate copolymers in order to control delivery of an administered composition. For example, the oral agent can be entrapped in microcapsules prepared by coacervation techniques or by interfacial polymerization, by the use of hydroxymethyl cellulose or gelatin-microcapsules or poly (methyl methacrylate) microcapsules, respectively, or in a colloid drug delivery system. Colloidal dispersion systems include macromolecule complexes, nanocapsules, microspheres, microbeads, and lipid-based systems, including oil-in-water emulsions, micelles, mixed micelles, and liposomes. Methods for the preparation of the above-mentioned formulations are known in the art.

Formulations for oral use may also be presented as hard gelatin capsules wherein the active ingredient is mixed with an inert solid diluent, for example, calcium carbonate, calcium phosphate, kaolin or microcrystalline cellulose, or as soft gelatin capsules wherein the active ingredient is mixed with water or an oil medium, for example peanut oil, liquid paraffin, or olive oil.

Aqueous suspensions contain the active materials in admixture with excipients suitable for the manufacture thereof. Such excipients can be suspending agents, for example sodium carboxymethylcellulose, methylcellulose, (hydroxypropyl)methyl cellulose, sodium alginate, polyvinyl-pyrrolidone, gum tragacanth and gum acacia; dispersing or wetting agents, for example a naturally-occurring phosphatide (e.g., lecithin), or condensation products of an alkylene oxide with fatty acids (e.g., poly-oxyethylene stearate), or condensation products of ethylene oxide with long chain aliphatic alcohols (e.g., for heptdecaethyleneoxycetanol), or condensation products of ethylene oxide with partial esters derived from fatty acids and a hexitol (e.g., polyoxyethylene sorbitol monooleate), or condensation products of ethylene oxide with partial esters derived from fatty acids and hexitol anhydrides (e.g., polyethylene sorbitan monooleate). The aqueous suspensions may also contain one or more preservatives.

Oily suspensions may be formulated by suspending the active ingredient in a vegetable oil, for example, arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified herein.

The pharmaceutical compositions may also be in the form of oil-in-water emulsions. The oily phase may be a vegetable oil, for example olive oil or arachis oil, or a mineral oil, for example, liquid paraffin, or mixtures of these. Suitable emulsifying agents may be naturally occurring gums, for example, gum acacia or gum tragacanth; naturally occurring phosphatides, for example, soy bean, lecithin, and esters or partial esters derived from fatty acids; hexitol anhydrides, for example, sorbitan monooleate; and condensation products of partial esters with ethylene oxide, for example, polyoxyethylene sorbitan monooleate.

The pharmaceutical compositions typically comprise a therapeutically effective amount of a compound of Formula (I), (II), (III), (IV), or Table 1, or a pharmaceutically acceptable salt thereof, and one or more pharmaceutically acceptable excipient. Suitable pharmaceutically acceptable excipients include, but are not limited to, antioxidants (e.g., ascorbic acid and sodium bisulfate), preservatives (e.g., benzyl alcohol, methyl parabens, ethyl or n-propyl, p-hydroxybenzoate), emulsifying agents, suspending agents, dispersing agents, solvents, fillers, bulking agents, detergents, buffers, vehicles, diluents, and/or adjuvants. For example, a suitable vehicle may be physiological saline solution or citrate buffered saline, possibly supplemented with other materials common in pharmaceutical compositions for parenteral administration. Neutral buffered saline or saline mixed with serum albumin are further exemplary vehicles. Those skilled in the art will readily recognize a variety of buffers that can be used in the pharmaceutical compositions and dosage forms contemplated herein. Typical buffers include, but are not limited to, pharmaceutically acceptable weak acids, weak bases, or mixtures thereof. As an example, the buffer components can be water soluble materials such as phosphoric acid, tartaric acids, lactic acid, succinic acid, citric acid, acetic acid, ascorbic acid, aspartic acid, glutamic acid, and salts thereof. Acceptable buffering agents include, for example, a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), and N-tris[Hydroxymethyl]methyl-3-aminopropanesulfonic acid (TAPS).

After a pharmaceutical composition has been formulated, it may be stored in sterile vials as a solution, suspension, gel, emulsion, solid, or dehydrated or lyophilized powder. Such formulations may be stored either in a ready-to-use form, a lyophilized form requiring reconstitution prior to use, a liquid form requiring dilution prior to use, or other acceptable form. In some embodiments, the pharmaceutical composition is provided in a single-use container (e.g., a single-use vial, ampoule, syringe, or autoinjector (similar to, e.g., an EpiPen®)), whereas a multi-use container (e.g., a multi-use vial) is provided in other embodiments.

Formulations can also include carriers to protect the composition against rapid degradation or elimination from the body, such as a controlled release formulation, including liposomes, hydrogels, prodrugs and microencapsulated delivery systems. For example, a time delay material such as glyceryl monostearate or glyceryl stearate alone, or in combination with a wax, may be employed. Any drug delivery apparatus may be used to deliver a compound of Formula (I), (II), (III), (IV), or Table 1, or a pharmaceutically acceptable salt thereof, including implants (e.g., implantable pumps) and catheter systems, slow injection pumps and devices, all of which are well known to the skilled artisan.

Depot injections, which are generally administered subcutaneously or intramuscularly, may also be utilized to release the compound of Formula (I), (II), (III), (IV), or Table 1, or a pharmaceutically acceptable salt thereof disclosed herein over a defined period of time. Depot injections are usually either solid- or oil-based and generally comprise at least one of the formulation components set forth herein. One of ordinary skill in the art is familiar with possible formulations and uses of depot injections.

The pharmaceutical compositions may be in the form of a sterile injectable aqueous or oleagenous suspension. The suspension may be formulated according to the known art using those suitable dispersing or wetting agents and suspending agents mentioned herein. The sterile injectable preparation may also be a sterile injectable solution or suspension in a non-toxic parenterally acceptable diluent or solvent, for example, as a solution in 1,3-butane diol. Acceptable diluents, solvents and dispersion media that may be employed include water, Ringer's solution, isotonic sodium chloride solution, Cremophor EL™ (BASF, Parsippany, NJ) or phosphate buffered saline (PBS), ethanol, polyol (e.g., glycerol, propylene glycol, and liquid polyethylene glycol), and suitable mixtures thereof. In addition, sterile, fixed oils are conventionally employed as a solvent or suspending medium. For this purpose, any bland fixed oil may be employed, including synthetic mono- or diglycerides. Moreover, fatty acids such as oleic acid, find use in the preparation of injectables. Prolonged absorption of particular injectable formulations can be achieved by including an agent that delays absorption (e.g., aluminum monostearate or gelatin).

A compound of Formula (I), (II), (III), (IV), or Table 1, or a pharmaceutically acceptable salt thereof may also be administered in the form of suppositories for rectal administration or sprays for nasal or inhalation use. The suppositories can be prepared by mixing the drug with a suitable non-irritating excipient which is solid at ordinary temperatures but liquid at the rectal temperature and will therefore melt in the rectum to release the drug. Such materials include, but are not limited to, cocoa butter and polyethylene glycols.

All the compounds and pharmaceutical compositions provided herein can be used in all the methods provided herein. For example, the compounds and pharmaceutical compositions provided herein can be used in all the methods for treatment and/or prevention of all diseases or disorders provided herein. Thus, the compounds and pharmaceutical compositions provided herein are for use as a medicament.

Routes of Administration

Compounds of Formula (I), (II), (III), (IV), or Table 1, or a pharmaceutically acceptable salt thereof and compositions containing the same may be administered in any appropriate manner. Suitable routes of administration include oral, parenteral (e.g., intramuscular, intravenous, subcutaneous (e.g., injection or implant), intraperitoneal, intracisternal, intraarticular, intraperitoneal, intracerebral (intraparenchymal) and intracerebroventricular), nasal, vaginal, sublingual, intraocular, rectal, topical (e.g., transdermal), buccal and inhalation. Depot injections, which are generally administered subcutaneously or intramuscularly, may also be utilized to administer the compounds of Formula (I), (II), (III), (IV), or Table 1, or a pharmaceutically acceptable salt thereof over a defined period of time. Particular embodiments of the present invention contemplate oral administration.

Combination Therapy

The present invention contemplates the use of compounds of Formula (I), (II), (III), (IV), or Table 1, or a pharmaceutically acceptable salt thereof in combination with one or more active therapeutic agents (e.g., chemotherapeutic agents) or other prophylactic or therapeutic modalities (e.g., radiation). In such combination therapy, the various active agents frequently have different, complementary mechanisms of action. Such combination therapy may be especially advantageous by allowing a dose reduction of one or more of the agents, thereby reducing or eliminating the adverse effects associated with one or more of the agents. Furthermore, such combination therapy may have a synergistic therapeutic or prophylactic effect on the underlying disease, disorder, or condition.

As used herein, "combination" is meant to include therapies that can be administered separately, for example, formulated separately for separate administration (e.g., as may be provided in a kit), and therapies that can be administered together in a single formulation (i.e., a "co-formulation").

In certain embodiments, the compounds of Formula (I), (II), (III), (IV), or Table 1, or a pharmaceutically acceptable salt thereof are administered or applied sequentially, e.g., where one agent is administered prior to one or more other agents. In other embodiments, the compounds of Formula (I), (II), (III), (IV), or Table 1, or a pharmaceutically acceptable salt thereof are administered simultaneously, e.g., where two or more agents are administered at or about the same time; the two or more agents may be present in two or more separate formulations or combined into a single formulation (i.e., a co-formulation). Regardless of whether the two or more agents are administered sequentially or simultaneously, they are considered to be administered in combination for purposes of the present disclosure.

The compounds of Formula (I), (II), (III), (IV), or Table 1, or a pharmaceutically acceptable salt thereof may be used in combination with at least one other (active) agent in any manner appropriate under the circumstances. In one embodiment, treatment with the at least one active agent and at least one compound of Formula (I), (II), (III), (IV), or Table 1, or a pharmaceutically acceptable salt thereof is maintained over a period of time. In another embodiment, treatment with the at least one active agent is reduced or discontinued (e.g., when the subject is stable), while treatment with the compound of Formula (I), (II), (III), (IV), or Table 1, or a pharmaceutically acceptable salt thereof is maintained at a constant dosing regimen. In a further embodiment, treatment with the at least one active agent is reduced or discontinued (e.g., when the subject is stable), while treatment with a compound of Formula (I), (II), (III), (IV), or Table 1, or a pharmaceutically acceptable salt thereof is reduced (e.g., lower dose, less frequent dosing or shorter treatment regimen). In yet another embodiment, treatment with the at least one active agent is reduced or discontinued (e.g., when the subject is stable), and treatment with the compound of Formula (I), (II), (III), (IV), or Table 1, or a pharmaceutically acceptable salt thereof is increased (e.g., higher dose, more frequent dosing or longer treatment regimen). In yet another embodiment, treatment with the at least one active agent is maintained and treatment with the compound of Formula (I), (II), (III), (IV), or Table 1, or a pharmaceutically acceptable salt thereof is reduced or discontinued (e.g., lower dose, less frequent dosing or shorter treatment regimen). In yet another embodiment, treatment with the at least one active agent and treatment with the compound of Formula (I), (II), (III), (IV), or Table 1, or a pharmaceutically acceptable salt thereof are reduced or discontinued (e.g., lower dose, less frequent dosing or shorter treatment regimen).

The present disclosure provides methods for treating cancer with a compound of Formula (I), (II), (III), (IV), or Table 1, or a pharmaceutically acceptable salt thereof and at least one additional therapeutic or diagnostic agent.

In some embodiments, the compound of Formula (I), (II), (III), (IV), or Table 1, or a pharmaceutically acceptable salt thereof is administered in combination with at least one additional therapeutic agent, selected from Temozolomide, Pemetrexed, Pegylated liposomal doxorubicin (Doxil), Eribulin (Halaven), Ixabepilone (Ixempra), Protein-bound paclitaxel (Abraxane), Oxaliplatin, Irinotecan, Venatoclax (bcl2 inhibitor), 5-azacytadine, Anti-CD20 therapeutics, such as Rituxan and obinutuzumab, Hormonal agents (anastrozole, exemestand, letrozole, zoladex, lupon eligard), CDK4/6 inhibitors, Palbociclib, Abemaciclib, CPI (Avelumab, Cemiplimab-rwlc, and Bevacizumab.

In certain embodiments, the present disclosure provides methods for treating cancer comprising administration of a compound of Formula (I), (II), (III), (IV), or Table 1, or a pharmaceutically acceptable salt thereof described herein in combination with a signal transduction inhibitor (STI) to achieve additive or synergistic suppression of tumor growth. As used herein, the term "signal transduction inhibitor" refers to an agent that selectively inhibits one or more steps in a signaling pathway. Examples of signal transduction inhibitors (STIs) useful in methods described herein include, but are not limited to: (i) bcr/abl kinase inhibitors (e.g., GLEEVEC); (ii) epidermal growth factor (EGF) receptor inhibitors, including kinase inhibitors and antibodies; (iii) her-2/neu receptor inhibitors (e.g., HERCEPTIN); (iv) inhibitors of Akt family kinases or the Akt pathway (e.g., rapamycin); (v) cell cycle kinase inhibitors (e.g., flavopiridol); and (vi) phosphatidyl inositol kinase inhibitors. Agents involved in immunomodulation can also be used in combination with one or more compounds of Formula (I), (II), (III), (IV), or Table 1, or a pharmaceutically acceptable salt thereof described herein for the suppression of tumor growth in cancer patients.

In certain embodiments, the present disclosure provides methods for treating cancer comprising administration of a compound of Formula (I), (II), (III), (IV), or Table 1, or a pharmaceutically acceptable salt thereof described herein in combination with a chemotherapeutic agents. Examples of chemotherapeutic agents include, but are not limited to, alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethio-phosphaoramide and trimethylolomelamime; nitrogen mustards such as chiorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside (Ara-C); cyclophosphamide; thiotepa; taxoids, e.g., paclitaxel and doxetaxel; chlorambucil; gemcitabine; 6-thioguanine; mercaptopurine; methotrexate; platinum and platinum coordination complexes such as cisplatin and carboplatin; vinblastine; etoposide (VP-16); ifosfamide; mitomycin C; mitoxantrone; vincristine; vinorelbine; navelbine; novantrone; teniposide; daunomycin; aminopterin; xeloda; ibandronate; CPT11; topoisomerase inhibitors; difluoromethylornithine (DMFO); retinoic acid; esperamicins; capecitabine; and pharmaceutically acceptable salts, acids or derivatives of any of the above. In a particular embodiment, compounds of the present disclosure are coadministered with a cytostatic compound selected from the group consisting of cisplatin, doxorubicin, taxol, taxotere and mitomycin C. In a particular embodiment, the cytostatic compound is doxorubicin.

Chemotherapeutic agents also include anti-hormonal agents that act to regulate or inhibit hormonal action on tumors such as anti-estrogens, including for example tamoxifen, raloxifene, aromatase inhibiting 4 (5)-imidazoles, 4-hydroxytamoxifen, trioxifene, keoxifene, onapristone, and toremifene; and antiandrogens such as flutamide, nilutamide, bicalutamide, enzalutamide, apalutamide, abiraterone acetate, leuprolide, and goserelin; and pharmaceutically acceptable salts, acids or derivatives of any of the above. In certain embodiments, combination therapy comprises administration of a hormone or related hormonal agent.

The present disclosure also contemplates the use of the compounds of Formula (I), (II), (III), (IV), or Table 1, or a pharmaceutically acceptable salt thereof described herein in combination with immune checkpoint inhibitors. The tremendous number of genetic and epigenetic alterations that are characteristic of all cancers provides a diverse set of antigens that the immune system can use to distinguish tumor cells from their normal counterparts. In the case of T cells, the ultimate amplitude (e.g., levels of cytokine production or proliferation) and quality (e.g., the type of immune response generated, such as the pattern of cytokine production) of the response, which is initiated through antigen recognition by the T-cell receptor (TCR), is regulated by a balance between co-stimulatory and inhibitory signals (immune checkpoints). Under normal physiological conditions, immune checkpoints are crucial for the prevention of autoimmunity (i.e., the maintenance of self-tolerance) and also for the protection of tissues from damage when the immune system is responding to pathogenic infection. The expression of immune checkpoint proteins can be dysregulated by tumors as an important immune resistance mechanism. Examples of immune checkpoint inhibitors include but are not limited to CTLA-4, PD-1, PD-L1, BTLA, TIM3, LAG3, OX40, 41BB, VISTA, CD96, TGFβ, CD73, CD39, A2AR, A2BR, IDO1, TDO2, Arginase, B7-H3, B7-H4. Cell-based modulators of anti-cancer immunity are also contemplated. Examples of such modulators include but are not limited to chimeric antigen receptor T-cells, tumor infiltrating T-cells and dendritic-cells.

The present disclosure contemplates the use of compounds of Formula (I), (II), (III), (IV), or Table 1, or a pharmaceutically acceptable salt thereof described herein in combination with inhibitors of the aforementioned immune-checkpoint receptors and ligands, for example ipilimumab, abatacept, nivolumab, pembrolizumab, atezolizumab, nivolumab, and durvalumab.

Additional treatment modalities that may be used in combination with a compound of Formula (I), (II), (III), (IV), or Table 1, or a pharmaceutically acceptable salt thereof disclosed herein include radiotherapy, a monoclonal antibody against a tumor antigen, a complex of a monoclonal antibody and toxin, a T-cell adjuvant, bone marrow transplant, or antigen presenting cells (e.g., dendritic cell therapy).

The present disclosure contemplates the use of compounds of Formula (I), (II), (III), (IV), or Table 1, or a pharmaceutically acceptable salt thereof described herein for the treatment of glioblastoma either alone or in combination with radiation and/or temozolomide (TMZ), avastin or lomustine.

The present disclosure encompasses pharmaceutically acceptable salts, acids or derivatives of any of the above.

Dosing

The compounds of Formula (I), (II), (III), (IV), or Table 1, or a pharmaceutically acceptable salt thereof provided herein may be administered to a subject in an amount that is dependent upon, for example, the goal of administration (e.g., the degree of resolution desired); the age, weight, sex, and health and physical condition of the subject to which the formulation is being administered; the route of administration; and the nature of the disease, disorder, condition or symptom thereof. The dosing regimen may also take into consideration the existence, nature, and extent of any adverse effects associated with the agent(s) being administered. Effective dosage amounts and dosage regimens can readily be determined from, for example, safety and dose-escalation trials, in vivo studies (e.g., animal models), and other methods known to the skilled artisan.

In general, dosing parameters dictate that the dosage amount be less than an amount that could be irreversibly toxic to the subject (the maximum tolerated dose (MTD)) and not less than an amount required to produce a measurable effect on the subject. Such amounts are determined by, for example, the pharmacokinetic and pharmacodynamic parameters associated with ADME, taking into consideration the route of administration and other factors.

An effective dose (ED) is the dose or amount of an agent that produces a therapeutic response or desired effect in some fraction of the subjects taking it. The "median effective dose" or $ED_{50}$ of an agent is the dose or amount of an agent that produces a therapeutic response or desired effect in 50% of the population to which it is administered. Although the $ED_{50}$ is commonly used as a measure of reasonable expectance of an agent's effect, it is not necessarily the dose that a clinician might deem appropriate taking into consideration all relevant factors. Thus, in some situations the effective amount is more than the calculated $ED_{50}$, in other situations the effective amount is less than the calculated $ED_{50}$, and in still other situations the effective amount is the same as the calculated $ED_{50}$.

In addition, an effective dose of a compound of Formula (I), (II), (III), (IV), or Table 1, or a salt thereof, as provided herein, may be an amount that, when administered in one or more doses to a subject, produces a desired result relative to a healthy subject. For example, for a subject experiencing a particular disorder, an effective dose may be one that improves a diagnostic parameter, measure, marker and the like of that disorder by at least about 5%, at least about 10%, at least about 20%, at least about 25%, at least about 30%, at least about 40%, at least about 50%, at least about 60%, at least about 70%, at least about 80%, at least about 90%, or more than 90%, where 100% is defined as the diagnostic parameter, measure, marker and the like exhibited by a normal subject.

In certain embodiments, the compounds of Formula (I), (II), (III), (IV), or Table 1, or a pharmaceutically acceptable salt thereof disclosed herein may be administered (e.g., orally) at dosage levels of about 0.01 mg/kg to about 50 mg/kg, or about 1 mg/kg to about 25 mg/kg, of subject body weight per day, one or more times a day, to obtain the desired therapeutic effect.

For administration of an oral agent, the compositions can be provided in the form of tablets, capsules and the like containing from 1.0 to 1000 milligrams of the active ingredient, particularly 1.0, 3.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient.

In certain embodiments, the dosage of the compound of Formula (I), (II), (III), (IV), or Table 1, or a pharmaceutically acceptable salt thereof is contained in a "unit dosage form". The phrase "unit dosage form" refers to physically discrete units, each unit containing a predetermined amount of the compound of Formula (I), (II), (III), (IV), or Table 1, or a pharmaceutically acceptable salt thereof, either alone or in combination with one or more additional agents, sufficient to produce the desired effect. It will be appreciated that the parameters of a unit dosage form will depend on the particular agent and the effect to be achieved.

Kits

The present invention also contemplates kits comprising a compound of Formula (I), (II), (III), (IV), or Table 1, or a pharmaceutically acceptable salt thereof, and pharmaceutical compositions thereof. The kits are generally in the form of a physical structure housing various components, as described below, and may be utilized, for example, in practicing the methods described above.

A kit can include one or more of the compound of Formula (I), (II), (III), (IV), or Table 1, or a pharmaceutically acceptable salt thereof disclosed herein (provided in, e.g., a sterile container), which may be in the form of a pharmaceutical composition suitable for administration to a subject. The compound of Formula (I), (II), (III), (IV), or Table 1, or a pharmaceutically acceptable salt thereof can be provided in a form that is ready for use (e.g., a tablet or capsule) or in a form requiring, for example, reconstitution or dilution (e.g., a powder) prior to administration. When the compounds of Formula (I), (II), (III), (IV), or Table 1, or a pharmaceutically acceptable salt thereof are in a form that needs to be reconstituted or diluted by a user, the kit may also include diluents (e.g., sterile water), buffers, pharmaceutically acceptable excipients, and the like, packaged with or separately from the compounds of Formula (I), (II), (III), (IV), or Table 1, or a pharmaceutically acceptable salt thereof. When combination therapy is contemplated, the kit may contain the several agents separately or they may already be combined in the kit. Each component of the kit may be enclosed within an individual container, and all of the various containers may be within a single package. A kit of the present invention may be designed for conditions necessary to properly maintain the components housed therein (e.g., refrigeration or freezing).

A kit may contain a label or packaging insert including identifying information for the components therein and instructions for their use (e.g., dosing parameters, clinical pharmacology of the active ingredient(s), including mechanism of action, pharmacokinetics and pharmacodynamics, adverse effects, contraindications, etc.). Labels or inserts can include manufacturer information such as lot numbers and expiration dates. The label or packaging insert may be, e.g., integrated into the physical structure housing the components, contained separately within the physical structure, or affixed to a component of the kit (e.g., an ampule, tube or vial).

Labels or inserts can additionally include, or be incorporated into, a computer readable medium, such as a disk (e.g., hard disk, card, memory disk), optical disk such as CD- or DVD-ROM/RAM, DVD, MP3, magnetic tape, or an electrical storage media such as RAM and ROM or hybrids of these such as magnetic/optical storage media, FLASH media or memory-type cards. In some embodiments, the actual instructions are not present in the kit, but means for obtaining the instructions from a remote source, e.g., via the internet, are provided.

EXAMPLES

The following examples and references (intermediates) are put forth so as to provide those of ordinary skill in the art with a complete disclosure and description of how to make and use the present invention, and are not intended to limit the scope of what the inventors regard as their invention, nor are they intended to represent that the experiments below were performed or that they are all of the experiments that may be performed. It is to be understood that exemplary descriptions written in the present tense were not necessarily performed, but rather that the descriptions can be performed to generate data and the like of a nature described therein. Efforts have been made to ensure accuracy with respect to numbers used (e.g., amounts, temperature, etc.), but some experimental errors and deviations should be accounted for.

The compounds of Formula (I), (II), (III), (IV), may be prepared by the methods described below, together with synthetic methods known in the art of organic chemistry, or modifications and transformations that are familiar to those of ordinary skill in the art. The starting materials used herein are commercially available or may be prepared by routine methods known in the art [such as those methods disclosed in standard reference books such as the Compendium of Organic Synthetic Methods, Vol. I-XII (published by Wiley-Interscience)].

Unless indicated otherwise, parts are parts by weight, molecular weight is weight average molecular weight, temperature is in degrees Celsius (° C.), and pressure is at or near atmospheric. Standard abbreviations are used, including the following: THF=tetrahydrofuran; DIEA=diisopropylethylamine; EtOAc=ethyl acetate; NMP=N-methylpyridine, TFA=trifluoroacetic acid; DCM=dichloromethane; $Cs_2CO_3$=cesium carbonate; XPhos Pd G3=2-dicyclohexylphosphino-2',4',6'-triisopropyl-1,1'-biphenyl)(2-(2'-amino-1,1'-biphenyl))palladium-(II) methanesulfonate; LiCl=lithium chloride; $POCl_3$=phosphoryl chloride; PE=petroleum ether; DMSO=dimethylsulfoxide; HCl=hydrochloric acid; $Na_2SO_4$=sodium sulfate; DMF=dimethylformamide; NaOH=sodium hydroxide; $K_2CO_3$=potassium carbonate; MeCN=acetonitrile; BOC=tert-butoxycarbonyl; MTBE=methyl tert-butyl ether; MeOH=methanol; $NaHCO_3$=sodium bicarbonate; $NaBH_3CN$=sodium cyanoborohydride; EtOH=ethanol; $PCl_5$=phosphorus pentachloride; $NH_4OAc$=ammonium acetate; $Et_2O$=ether; HOAc=acetic acid; $Ac_2O$=acetic anhydride; i-PrOH=isopropanol; NCS=N-chlorosuccinimide; $K_3PO_4$=potassium phosphate; $Pd(dtbpf)Cl_2$=1,1'-Bis(di-tert-butylphosphino)ferrocene)dichloro-palladium(II); $Zn(CN)_2$=Zinc cyanide; $Pd(PPh_3)_4$=tetrakis(triphenylphosphine)palladium(0); $Et_3N$=triethylamine; CuCN=copper cyanide; t-BuONO=tert-butyl nitrite; HATU=1-(bis(dimethylamino)methylene)-1H-1,2,3-triazolo(4,5-b)pyridinium 3-oxid hexafluorophosphate; DBU=1,8-diazabicyclo(5.4.0)undec-7-ene; $LiAlH_4$=lithium aluminium hydride; $NH_3$=ammonia; $H_2SO_4$=sulfuric acid; $H_2O_2$=hydrogen peroxide; EDCI=N-(3-dimethylaminopropyl)-N'-ethylcarbodiimide hydrochloride; HOBT=1-hydroxybenzotriazole hydrate; DHP=dihydropyran; TsOH=p-Toluenesulfonic acid; FA=formic acid; TCFH=N,N,N,N'-tetramethylchloroformamidinium hexafluorophosphate; NMI=N-methylimidazole; $Pd(dppf)Cl_2$=(1,1'-Bis(diphenylphosphino)ferrocene)dichloropalladium(II); $Pd(dppf)Cl_2$-DCM=(1,1'-Bis(diphenylphosphino)ferrocene)dichloropalladium(II), complex with dichloromethane.

Certain compounds of the present disclosure possess asymmetric carbon atoms. When the absolute stereochemistry of exemplified compounds has not yet been determined, it is noted in the text, and each isolated isomer is assigned a name. Further work may reveal that an isomer with an assigned name may have a different absolute stereochemistry.

SYNTHETIC EXAMPLES

Intermediate A 5-((4-chlorobenzyl)oxy)-1,3,4-thiadiazol-2-amine

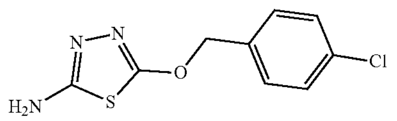 [SMILES: Nc1nnc(OCc2ccc(Cl)cc2)s1]

To a solution of NaH (42.0 g, 1.05 mol, 60.0% purity) in THF (750 mL) was added a solution of (4-chlorophenyl)methanol (100 g, 701 mmol) in THF (250 mL) dropwise at 5° C. The mixture was stirred at 5° C. for 4 h. Then 2-amino-5-bromo-1,3,4-thiadiazole (152 g, 842 mmol) was added to the mixture at 5° C. The mixture was stirred at 5° C. for 3 h. The mixture was poured into $H_2O$ and extracted with EtOAc (3×). The combined organic layers were dried over $Na_2SO_4$, filtered and concentrated under reduce pressure. The crude was purified by silica gel column chromatography, eluted with 9%-66% EtOAc in PE to afford a residue. The residue was diluted with MeOH and the slurry was stirred at 25° C. for 0.5 h. The solids were collected and diluted with MeOH. The slurry was stirred at 80° C. for 16 h. The solids were collected to afford 5-((4-chlorobenzyl)oxy)-1,3,4-thiadiazol-2-amine (61.0 g, 18% yield) as a grey solid.

Intermediate B 3-(2-methoxyphenyl) pyridine-4-carboxylic acid

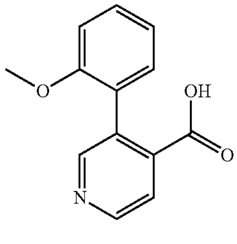 [SMILES: COc1ccccc1-c1cnccc1C(=O)O]

To a solution of 3-bromopyridine-4-carboxylic acid (2.0 g, 9.9 mmol) in dioxane (10 mL) and water (10 mL) was added 2-methoxyphenylboronic acid (2.3 g, 14.9 mmol), $Na_2CO_3$ (1.1 g, 9.9 mmol) and $Pd(PPh_3)_4$ (1.1 g, 0.99 mmol) at room temperature under nitrogen. The mixture was stirred at 100° C. overnight. The mixture was cooled to room temperature and diluted with water. The mixture was extracted with EtOAc (2×). The aqueous layer was acidified to pH 6 with HCl (1 M). A solid formed and mixture was filtered to afford 3-(2-methoxyphenyl) pyridine-4-carboxylic acid as a white solid, which was used to next step without further purification.

Intermediate C 5-((5-chloropyridin-2-yl)methoxy)-1,3,4-thiadiazol-2-amine

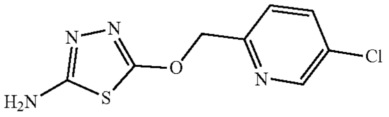 [SMILES: Nc1nnc(OCc2ccc(Cl)cn2)s1]

Step 1. Preparation of (5-chloropyridin-2-yl)methanol

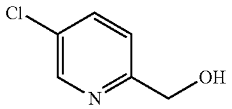

To a solution of methyl 5-chloropicolinate (95 g, 554 mmol) in MeOH (950 mL) was added $NaBH_4$ (42.0 g, 1.11 mol) in portions at 0° C. Then the mixture was stirred at rt for 2 h. The mixture was poured into $H_2O$. Mixture was cooled to 0° C. and 6 N HCl was added until pH of solution was 1~2. The temperature of the solution was 0-10° C. Then the mixture was concentrated under reduce pressure to remove MeOH. 6 N NaOH was added until the pH of the solution was 8~10. The mixture was extracted with EtOAc (3×). The combined organic layers were dried over $Na_2SO_4$, filtered and concentrated under reduce pressure to afford the title compound (158 g) as a yellow oil, which was used in the next step without further purification.

Step 2. Preparation of 5-((5-chloropyridin-2-yl)methoxy)-1,3,4-thiadiazol-2-amine

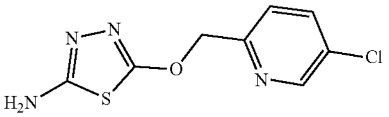 [SMILES: Nc1nnc(OCc2ccc(Cl)cn2)s1]

To a solution of NaH (65.7 g, 1.64 mol, 60.0% purity) in THF (1.20 L) was added a solution of (5-chloropyridin-2-yl)methanol (158 g, 1.10 mol) in THF (400 mL) at 5° C. dropwise. The mixture was stirred at 5° C. for 1 h. Then 2-amino-5-bromo-1,3,4-thiadiazole (237 g, 1.31 mol) was added in portions at 5° C. The mixture was stirred at 5° C. for 4 h. The mixture was poured into $H_2O$ and extracted with EtOAc (4×). The combined organic layer was dried over $Na_2SO_4$, filtered and concentrated under reduce pressure. The residue was diluted with MeOH and slurry was stirred at 25° C. for 0.5 h. The solids were collected and diluted with MeOH. The slurry was stirred at 80° C. for 2 h. The solids were collected to afford 5-((5-chloropyridin-2-yl)methoxy)-1,3,4-thiadiazol-2-amine (57.6 g, 21% yield) as a grey solid.

Intermediate D 4-(2-methoxyphenyl)-6-methylnicotinic acid

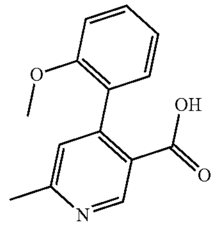 [SMILES: COc1ccccc1-c1cc(C)ncc1C(=O)O]

Step 1: Preparation of methyl 4-(2-methoxyphenyl)-6-methylnicotinate

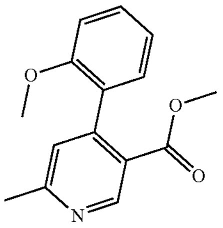

To a solution of methyl 4-chloro-6-methylpyridine-3-carboxylate (300 mg, 1.61 mmol) in 1,4-dioxane (4 mL) and water (0.5 mL), was added 2-methoxyphenylboronic acid (491 mg, 3.23 mmol), $K_2CO_3$ (446 mg, 3.23 mmol), $Pd(dtbpf)Cl_2$ (105 mg, 0.162 mmol). The mixture was stirred for 2 h at 80° C. The mixture was diluted with water and extracted with EtOAc (3×). The combined organic extracts were concentrated under reduced pressure. The residue was purified by Prep-TLC (eluent: 10% MeOH in DCM) to afford the title compound (330 mg, 72% yield) as a brown oil.

Step 2: Preparation of 4-(2-methoxyphenyl)-6-methylnicotinic acid

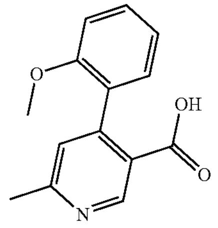 [SMILES: COc1ccccc1-c1cc(C)ncc1C(=O)O]

The title compound was prepared according to General Procedure F employing methyl 4-chloro-6-methylpyridine-3-carboxylate. The mixture was diluted with water and MeOH was removed under reduced pressure. The mixture was acidified to pH 5 with HCl (1 M). The precipitated solids were collected by filtration and washed with water (2×) to afford 4-(2-methoxyphenyl)-6-methylnicotinic acid (140 mg, 41% yield) as a white solid.

Intermediate E 4-(2-(difluoromethoxy)-6-fluorophenyl)-6-methylnicotinic acid

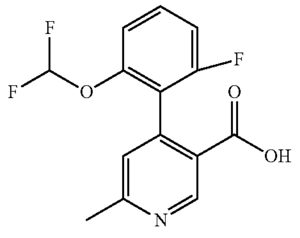 [SMILES: Cc1cc(-c2c(F)cccc2OC(F)F)c(C(=O)O)cn1]

The title compound was prepared following the procedures for Intermediate D to afford 4-(2-(difluoromethoxy)-6-fluorophenyl)-6-methylnicotinic acid as a white solid which was used without further purification.

Intermediate F 4-(2-fluoro-6-methoxyphenyl)-6-methylnicotinic acid

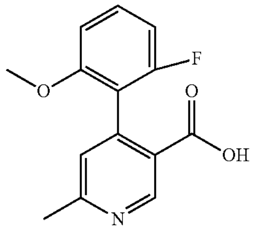 [SMILES: COc1cccc(F)c1-c1cc(C)ncc1C(=O)O]

The title compound was prepared following the procedures for Intermediate D employing methyl 3-bromoisonicotinate and 2-fluoro-6-methoxyphenylboronic acid to afford 4-(2-fluoro-6-methoxyphenyl)-6-methylnicotinic acid as a white solid which was used without further purification.

Intermediate G

5'-methoxy-2',6-dimethyl-(4,4'-bipyridine)-3-carboxylic acid

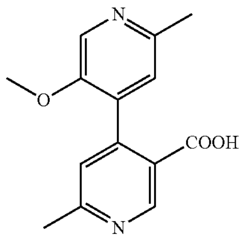 [SMILES: COc1cnc(C)cc1-c1cc(C)ncc1C(=O)O]

Step 1 benzyl 4-chloro-6-methylnicotinate

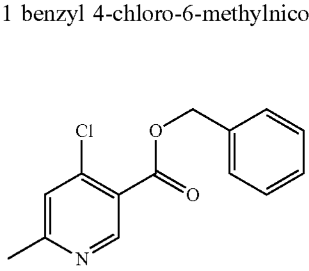

A mixture of 4-chloro-6-methylpyridine-3-carboxylic acid (10.00 g, 58.3 mmol) and $Cs_2CO_3$ (37.98 g, 116.6 mmol) in DMF (100 mL) was added benzyl bromide (14.95 g, 87.45 mmol). The resulting mixture was stirred at room temperature for 16 h. The reaction mixture was quenched with water and extracted with ethyl acetate. The combined organic layers were washed with brine, dried over anhydrous sodium sulfate, filtered, and concentrated under vacuum. The residue was purified by flash chromatography on silica gel with 0~30% ethyl acetate in petroleum ether to afford benzyl 4-chloro-6-methylnicotinate (12.94 g, 84.8%) as a yellow oil. MS (ESI) calc'd for ($C_{14}H_{12}ClNO_2$) $(M+1)^+$, 262.0, found 262.1.

Step 2 benzyl 2'-chloro-5'-methoxy-6-methyl-(4,4'-bipyridine)-3-carboxylate

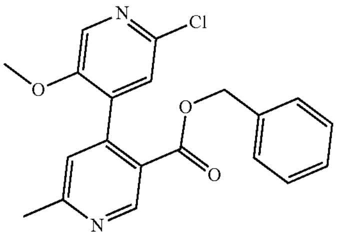 [SMILES: COc1cnc(Cl)cc1-c1cc(C)ncc1C(=O)OCc1ccccc1]

To a degassed mixture of methyl benzyl 4-chloro-6-methylpyridine-3-carboxylate (6.00 g, 22.926 mmol) and 2-chloro-5-methoxypyridin-4-ylboronic acid (4.30 g, 22.926 mmol) in 1,4-dioxane (50 mL) and $H_2O$ (5 mL) were added $K_2CO_3$ (9.51 g, 0.069 mmol) and $Pd(DtBPF)Cl_2$ (1.49 g, 2.29 mmol). The resulting mixture was stirred at 80° C. for 2 h under nitrogen atmosphere. The reaction mixture was quenched with water and extracted with ethyl acetate. The combined organic layers were washed with brine, dried over anhydrous sodium sulfate, filtered, and concentrated under vacuum. The residue was purified by flash chromatography on silica gel with 0~50% ethyl acetate in petroleum ether to afford benzyl 2'-chloro-5'-methoxy-6-methyl-(4,4'-bipyridine)-3-carboxylate (4 g, 47.3%) as a yellow oil. MS (ESI) calc'd for ($C_{20}H_{17}ClN_2O_3$) $(M+1)^+$, 369.1, found 369.0.

Step 3 benzyl 5'-methoxy-2',6-dimethyl-(4,4'-bipyridine)-3-carboxylate

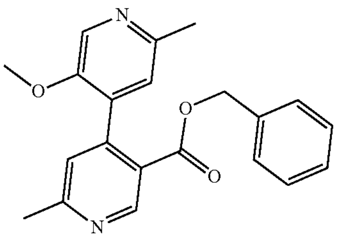 [SMILES: COc1cnc(C)cc1-c1cc(C)ncc1C(=O)OCc1ccccc1]

To a degassed mixture of benzyl 2-chloro-5-methoxy-6-methyl-(4,4-bipyridine)-3-carboxylate (4.00 g, 10.845 mmol) and $K_2CO_3$ (4.50 g, 33.0 mmol) in DME (30 mL) were added Pd(dppf)$Cl_2$ (0.79 g, 1.0 mmol) and trimethyl-1,3,5,2,4,6-trioxatriborinane (1.50 g, 12.0 mmol). The resulting mixture was stirred at 120° C. for 2 h under nitrogen atmosphere. The reaction mixture was quenched with water and extracted with ethyl acetate. The combined organic layers were washed with brine, dried over anhydrous sodium sulfate, filtered, and concentrated under vacuum. The residue was purified by reverse phase flash chromatography with 5~70% acetonitrile in water to afford benzyl 5'-methoxy-2',6-dimethyl-(4,4'-bipyridine)-3-carboxylate (2.8 g, 74.1%) as a yellow oil. MS (ESI) calc'd for ($C_{21}H_{20}N_2O_3$) $(M+1)^+$, 349.1, found 349.0.

Step 4 5'-methoxy-2',6-dimethyl-(4,4'-bipyridine)-3-carboxylic acid

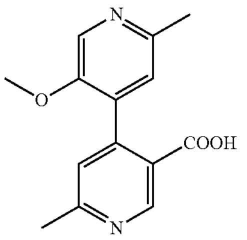 [SMILES: COc1cnc(C)cc1-c1cc(C)ncc1C(=O)O]

To a mixture of benzyl 5-methoxy-2,6-dimethyl-(4,4-bipyridine)-3-carboxylate (2.80 g, 8.037 mmol) in THF (20.00 mL) were added Pd/C (2.80 g, 10%). The resulting mixture was stirred at room temperature for 1 h under hydrogen atmosphere. The resulting mixture was filtered. The filtrate was concentrated vacuum to afford 5'-methoxy-2',6-dimethyl-(4,4'-bipyridine)-3-carboxylic acid (2.5 g, curde) as a yellow solid, which was used for the next step directly without further purification. MS (ESI) calc'd for ($C_{14}H_{14}N_2O_3$) (M+1)+, 259.1, found 259.0.

Intermediate H

2'-chloro-5'-methoxy-6-methyl-(4,4'-bipyridine)-3-carboxylic acid

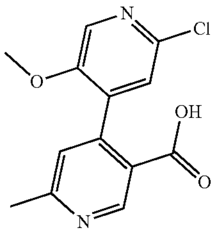 [SMILES: COc1cnc(Cl)cc1-c1cc(C)ncc1C(=O)O]

Step-7: 2-chloro-5-methoxypyridin-4-ylboronic acid

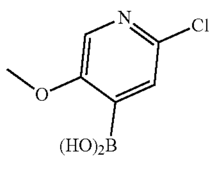

A stirred solution of 2-chloro-5-methoxypyridine (10.0 g, 69.65 mmol) in THF (500 mL) was added LDA (14.9 g, 139.30 mmol) dropwise at −78° C. under $N_2$ atmosphere. The resulting mixture was stirred at −78° C. for 2 h. Then Triisopropyl borate (26.2 g, 139.30 mmol) was added to the above mixture at −78° C. The resulting mixture was stirred at −78° C. for 2 h. Then the resulting mixture was stirred at room temperature for 16 h. The resulting mixture was quenched with HCl (2 N) and stirred at room temperature for 30 min. The resulting mixture was extracted with ethyl acetate. The reaction mixture was diluted with water and extracted with ethyl acetate. The combined organic layers were washed with brine, dried over anhydrous sodium sulfate, filtered, and concentrated under vacuum. 2-chloro-5-methoxypyridin-4-ylboronic acid (9 g, 68.9%) as a brown solid. MS (ESI) calc'd for ($C_6H_7BClNO_3$) $(M+1)^+$, 188.0; found 188.0.

Step-8: methyl 2'-chloro-5'-methoxy-6-methyl-[4,4'-bipyridine]-3-carboxylate

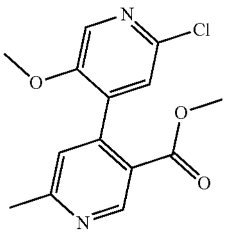

To a degassed solution of methyl 4-chloro-6-methylpyridine-3-carboxylate (700 mg, 3.77 mmol) and 2-chloro-5-methoxypyridin-4-ylboronic acid (918 mg, 4.90 mmol) in dioxane (6 mL) and $H_2O$ (2 mL) were added Pd(dppf)$Cl_2$ (275 mg, 0.37 mmol) and $K_2CO_3$ (1563 mg, 11.31 mmol) under nitrogen atmosphere. The resulting mixture was stirred at 80° C. for 16 h under nitrogen atmosphere. The resulting mixture was filtered and the filtrate was concentrated under reduced pressure. The residue was purified by flash column chromatography with 0~60% ethyl acetate in petroleum ether to afford methyl 2'-chloro-5'-methoxy-6-methyl-[4,4'-bipyridine]-3-carboxylate (220 mg, 19.9%) as a white solid. MS (ESI) calc'd for ($C_{14}H_{13}ClN_2O_3$) (M+1)+, 293.1; found 293.1.

Step-9: 2'-chloro-5'-methoxy-6-methyl-(4,4'-bipyridine)-3-carboxylic acid

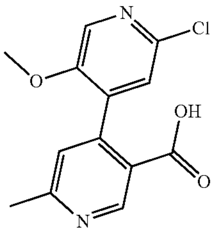 [SMILES: COc1cnc(Cl)cc1-c1cc(C)ncc1C(=O)O]

To a stirred solution of methyl 2'-chloro-5'-methoxy-6-methyl-[4,4'-bipyridine]-3-carboxylate (220 mg, 0.75 mmol) in THF (2 mL) and water (2 mL) were added LiOH·$H_2O$ (126 mg, 3.01 mmol). The resulting mixture was stirred at room temperature for 2 h. The mixture was acidified to pH 3 with citric acid. The resulting mixture was extracted with ethyl acetate. The combined organic layers were washed with brine, dried over anhydrous sodium sulfate, filtered, and concentrated under vacuum to afford 2'-chloro-5'-methoxy-6-methyl-(4,4'-bipyridine)-3-carboxylic acid (160 mg, 76.3%) as a white solid. MS (ESI) calc'd for ($C_{13}H_{11}ClN_2O_3$) $(M+1)^+$, 279.0; found, 279.0.

Example 1

3-(2-methoxyphenyl)-N-(5-((tetrahydro-2H-pyran-4-yl)methoxy)-1,3,4-thiadiazol-2-yl)isonicotinamide

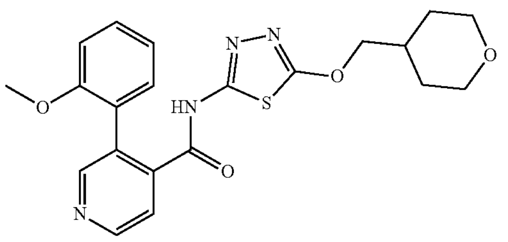 [SMILES: COc1ccccc1-c1cnccc1C(=O)Nc1nnc(OCC2CCOCC2)s1]

Step 1
(methylsulfanyl)((oxan-4-yl)methoxy)methanethione

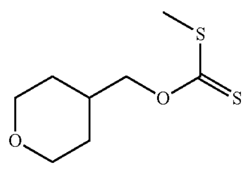

To a stirred solution of (oxan-4-yl)methanol (3.00 g, 25.826 mmol, 1.00 equiv) in THF (30 mL) in a 100 mL 3-necked round-bottom flask, was added NaH (1.24 g, 51.713 mmol, 2.00 equiv) dropwise at 0° C. under nitrogen atmosphere. $CS_2$ (2.95 g, 38.744 mmol, 1.50 equiv) was added to the above mixture at 0° C. And the mixture was stirred for 10 min, MeI (4.39 g, 30.985 mmol, 1.20 equiv) was added at 0° C. The mixture was stirred for 3 h at room temperature under nitrogen atmosphere. The reaction was monitored by TLC. The reaction was quenched by the addition of saturated $NH_4Cl$ (aq.) (50 mL) at room temperature. The aqueous layer was extracted with EtOAc (4×50 mL). The resulting mixture was concentrated under vacuum. The residue was purified by silica gel column (PE:EtOAc=5:1) to afford (methylsulfanyl)((oxan-4-yl)methoxy)methanethione (1.4 g) as light yellow oil.

Step 2 O-((tetrahydro-2H-pyran-4-yl)methyl) hydrazinecarbothioate

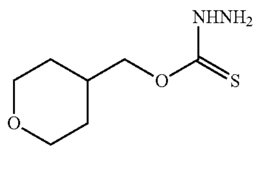 [SMILES: NNC(=S)OCC1CCOCC1]

Into a 50 mL 3-necked round-bottom flask were added (methylsulfanyl)((oxan-4-yl)methoxy)methanethione (1.40 g, 6.785 mmol, 1.00 equiv) and hydrazine (326.00 mg, 10.178 mmol, 1.50 equiv) in MeOH (14 mL) at room temperature. The mixture was evaporated and the residue was re-dissolved in 4 mL of MeOH and the solution was evaporated again. The crude 0-((tetrahydro-2H-pyran-4-yl) methyl) hydrazinecarbothioate was used in the next step directly without further purification.

Step 3 5-((tetrahydro-2H-pyran-4-yl)methoxy)-1,3,4-thiadiazol-2-amine

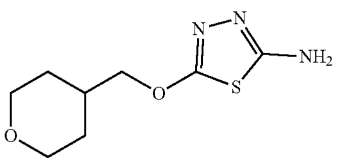 [SMILES: Nc1nnc(OCC2CCOCC2)s1]

To a stirred solution of ((((oxan-4-yl)methoxy)methanethioyl)amino)amine (1.29 g, 6.780 mmol, 1.00 equiv) and BrCN (865.80 mg, 8.140 mmol, 1.20 equiv) in MeOH (13 mL) in a 50 mL 3-necked round-bottom flask, was added $Et_3N$ (1.37 g, 13.560 mmol, 2.00 equiv). The mixture was stirred for 1 h at room temperature under nitrogen atmosphere. The reaction was monitored by TLC. The solution was evaporated and precipitated by the addition of MeOH. This resulted in 5-((tetrahydro-2H-pyran-4-yl)methoxy)-1,3,4-thiadiazol-2-amine (560 mg) as a white solid.

Step 4 3-(2-methoxyphenyl)-N-(5-((tetrahydro-2H-pyran-4-yl)methoxy)-1,3,4-thiadiazol-2-yl)isonicotinamide

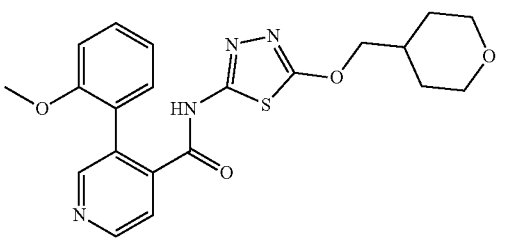 [SMILES: COc1ccccc1-c1cnccc1C(=O)Nc1nnc(OCC2CCOCC2)s1]

To a stirred solution of 5-(oxan-4-ylmethoxy)-1,3,4-thiadiazol-2-amine (34.00 mg, 0.158 mmol, 1.00 equiv) and 3-(2-methoxyphenyl)pyridine-4-carboxylic acid (36.21 mg, 0.158 mmol, 1.00 equiv) in DMF (400.00 uL) was added DIEA (40.83 mg, 0.316 mmol, 2.00 equiv) and HATU (72.06 mg, 0.190 mmol, 1.20 equiv) at room temperature. The resulting mixture was stirred for 1 h at rt. The reaction was diluted with EA (20 mL). The resulting mixture was washed with 2×10 mL of water. The organic layer was concentrated under vacuum. The residue was purified by Prep-TLC ($CH_2Cl_2$/MeOH 15:1) to afford 3-(2-methoxyphenyl)-N-(5-((tetrahydro-2H-pyran-4-yl)methoxy)-1,3,4-thiadiazol-2-yl)isonicotinamide (68.2 mg, 101.15%) as a white solid. MS (ESI) $(M+1)^+$, 427. $^1H$ NMR (300 MHz, DMSO): δ 12.83 (s, 1H), 8.72-8.70 (d, 1H), 8.61 (s, 1H), 7.63-7.60 (d, 1H), 7.40-7.35 (m, 2H), 7.12-6.95 (m, 2H), 4.29-4.27 (d, 2H), 3.89-3.84 (m, 2H), 3.51 (s, 3H), 3.31-3.31 (m, 2H), 2.06-1.98 (m, 1H), 1.65-1.60 (d, 2H), 1.37-1.24 (m, 2H) ppm.

Example 2

3-(2-methoxyphenyl)-N-(5-((tetrahydro-2H-pyran-2-yl)methoxy)-1,3,4-thiadiazol-2-yl)isonicotinamide

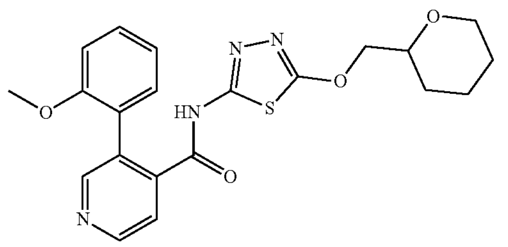 [SMILES: COc1ccccc1-c1cnccc1C(=O)Nc1nnc(OCC2CCCCO2)s1]

Step 1. S-methyl O-((tetrahydro-2H-pyran-2-yl)methyl) carbonodithioate

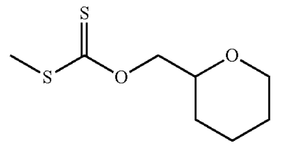

A solution of tetrahydropyran-2-methanol (5.00 g, 43.044 mmol, 1.00 equiv) and NaH (2.06 g, 51.653 mmol, 1.2 equiv, 60%) in THF (50 mL) was stirred for 30 min at 0 degrees C. under nitrogen atmosphere. To the above mixture was added $CS_2$ (3.93 g, 51.653 mmol, 1.2 equiv) at 0 degrees C. The resulting mixture was stirred for additional 20 min at 0 degrees C. To the above mixture was added $CH_3I$ (7.33 g, 51.653 mmol, 1.2 equiv) at 0 degrees C. The resulting mixture was stirred 20 min at 0 degrees C. under nitrogen atmosphere. The reaction was quenched with (100 mL) $NH_4Cl$ (aq.) at room temperature. The aqueous layer was extracted with EtOAc (3×30 mL). The resulting mixture was concentrated under vacuum. The residue was purified by silica gel column chromatography, eluted with $CH_2Cl_2$/MeOH (90:1) to afford S-methyl 0-((tetrahydro-2H-pyran-2-yl)methyl) carbonodithioate (6 g, yield 67.56%).

Step 2. O-((tetrahydro-2H-pyran-2-yl)methyl) 2-methylhydrazine-1-carbothioate

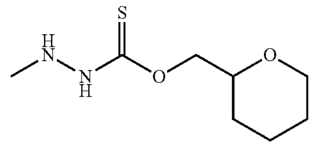

To a stirred solution of S-methyl O-((tetrahydro-2H-pyran-2-yl)methyl) carbonodithioate (6.00 g, 29.081 mmol, 1.00 equiv) and hydrazine hydrate (1.53 g, 30.535 mmol, 1.05 equiv) in MeOH (70 mL) at 0 degrees C. under nitrogen atmosphere. The resulting mixture was stirred for 2 h at 0 degrees C. under nitrogen atmosphere. The resulting mixture was concentrated under vacuum. The residue was purified by trituration with EtOAc (20 mL). This resulted in S-methyl O-((tetrahydro-2H-pyran-2-yl)methyl) carbonodithioate (5 g, yield 90.37%) as a white solid.

Step 3. 5-((tetrahydro-2H-pyran-2-yl)methoxy)-1,3,4-thiadiazol-2-amine

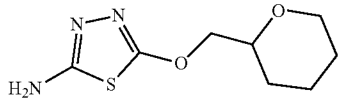

To a stirred solution of S-methyl O-((tetrahydro-2H-pyran-2-yl)methyl) carbonodithioate (5.80 g, 30.485 mmol, 1.00 equiv) and $Et_3N$ (6.17 g, 60.969 mmol, 2.00 equiv) in MeOH (60 mL) was added cyanogen bromide (3.87 g, 36.582 mmol, 1.20 equiv) at 0 degrees C. under air atmosphere. The resulting mixture was stirred for 2 h. The resulting mixture was concentrated under vacuum. The residue was purified by trituration with MeOH (20 mL). This resulted in 5-((tetrahydro-2H-pyran-2-yl)methoxy)-1,3,4-thiadiazol-2-amine (2.5 g, yield 38.10%) as a pink solid.

Step 4. 3-(2-methoxyphenyl)-N-(5-((tetrahydro-2H-pyran-2-yl)methoxy)-1,3,4-thiadiazol-2-yl)isonicotinamide

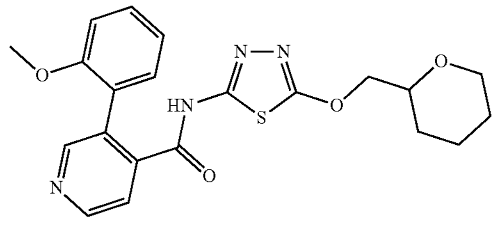 [SMILES: COc1ccccc1-c1cnccc1C(=O)Nc1nnc(OCC2CCCCO2)s1]

To a stirred solution of 5-((tetrahydro-2H-pyran-2-yl)methoxy)-1,3,4-thiadiazol-2-amine (100.00 mg, 0.465 mmol, 1.00 equiv), 3-(2-methoxyphenyl)pyridine-4-carboxylic acid (127.78 mg, 0.557 mmol, 1.20 equiv), DIEA (120.08 mg, 0.929 mmol, 2.00 equiv) and HATU (264.94 mg, 0.697 mmol, 1.50 equiv) in DMF (2 mL) at room temperature under air atmosphere. The resulting mixture was stirred overnight at room temperature under air atmosphere. The resulting mixture was diluted with brine (50 mL). The aqueous layer was extracted with EtOAc (2×20 ml). The resulting mixture was concentrated under vacuum. The residue was purified by Prep-TLC ($CH_2Cl_2$/MeOH 12:1) to afford 3-(2-methoxyphenyl)-N-(5-((tetrahydro-2H-pyran-2-yl)methoxy)-1,3,4-thiadiazol-2-yl)isonicotinamide (100.2 mg, yield 50.58%) as a white solid. MS (ESI) $(M+1)^+$, 427. $^1H$ NMR (400 MHz, DMSO) δ12.82 (s, 1H), 8.71-8.70 (d, 1H), 8.60 (s, 1H), 7.63-7.61 (d, 1H), 7.37-7.35 (m, 2H), 7.07-7.06 (t, 1H), 6.99-6.97 (d, 1H), 4.36-4.30 (m, 2H), 3.89-3.86 (m, 1H), 3.68-3.63 (t, 1H), 3.51 (s, 3H), 3.37-3.30 (m, 1H), 1.82-1.79 (m, 1H), 1.60-1.51 (m, 1H), 1.41-1.43 (m, 3H), 1.33-1.23 (m, 1H) ppm.

Example 3

3-(2-methoxyphenyl)-N-(5-(4,5,6,7-tetrahydro-1H-indazol-4-ylmethoxy)-1,3,4-thiadiazol-2-yl)pyridine-4-carboxamide

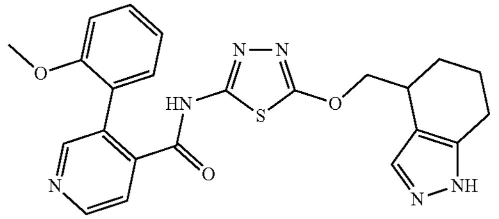 [SMILES: COc1ccccc1-c1cnccc1C(=O)Nc1nnc(OCC2CCCc3[nH]ncc32)s1]

Step 1. 1-((2-(trimethylsilyl)ethoxy)methyl)-6,7-dihydro-5H-indazol-4-one

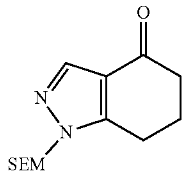 [SMILES: C[Si](C)(C)CCOCn1ncc2c1CCCC2=O]

To a stirred solution of 1,5,6,7-tetrahydroindazol-4-one (5.00 g, 36.723 mmol, 1.00 equiv) in DMF (50 mL) were added NaH (1.76 g, 0.073 mmol, 2 equiv) in portions at 0 degrees C. under nitrogen atmosphere. The resulting mixture was stirred for 2 h at 0 degrees C. To the above mixture was added SEMCl (7.35 g, 0.044 mmol, 1.20 equiv) dropwise at 0 degrees C. The resulting mixture was stirred for additional overnight at room temperature. The reaction was quenched with 200 mL of $NH_4Cl$ (aq.) at room temperature. The aqueous layer was extracted with EtOAc (2×200 mL). The resulting mixture was concentrated under reduced pressure. The residue was purified by silica gel column chromatography, eluted with hexane/EtOAc (10:1) to afford 1-((2-(trimethylsilyl)ethoxy)methyl)-6,7-dihydro-5H-indazol-4-one (8.3 g, 83.14%) as a light brown oil.

Step 2. 4-methylidene-1-((2-(trimethylsilyl)ethoxy)methyl)-6,7-dihydro-5H-indazole

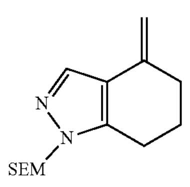 [SMILES: C=C1CCCc2c1cnn2COCC[Si](C)(C)C]

To a stirred solution of methyltriphenylphosphanium bromide (16.49 g, 0.046 mmol, 1.5 equiv) in DMSO (200 mL) was added NaH (2.48 g, 0.062 mmol, 2 equiv, 60% in oil) in portions at room temperature under nitrogen atmosphere. The resulting mixture was stirred for 2 h at room temperature. To the above mixture was added 1-((2-(trimethylsilyl)ethoxy)methyl)-6,7-dihydro-5H-indazol-4-one (8.20 g, 0.031 mmol, 1.00 equiv) dropwise at room temperature. The resulting mixture was stirred for additional 4 h at room temperature. The reaction was quenched with $NH_4Cl$ (aq.) at room temperature. The aqueous layer was extracted with EtOAc (2×100 mL). The resulting mixture was concentrated under reduced pressure. The residue was purified by silica gel column chromatography, eluted with hexane/EtOAc (100:1~15:1) to afford 4-methylidene-1-((2-(trimethylsilyl)ethoxy)methyl)-6,7-dihydro-5H-indazole (6.1 g, 73.45%) as a colorless oil.

Step 3. (1-((2-(trimethylsilyl)ethoxy)methyl)-4,5,6,7-tetrahydroindazol-4-yl)methanol

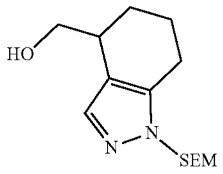 [SMILES: C[Si](C)(C)CCOCn1ncc2c1CCCC2CO]

To a stirred solution of 4-methylidene-1-((2-(trimethylsilyl)ethoxy)methyl)-6,7-dihydro-5H-indazole (3.10 g, 11.723 mmol, 1.00 equiv) in THF (30 mL) was added 1M $BH_3$-THF (100.00 mL, 46.892 mmol, 4 equiv) dropwise at 0 degrees C. under nitrogen atmosphere. The resulting mixture was stirred for 3 h at 55 degrees C. under nitrogen atmosphere. To the above mixture was added 1M $K_2CO_3$ (5.67 g, 0.041 mmol, 3.50 equiv) in $H_2O$ dropwise at 0 degrees C. followed by $H_2O_2$ (3.67 g, 41.000 mmol, 3.50 equiv, 38%). The resulting mixture was stirred for additional 3 h at room temperature. The aqueous layer was extracted with EtOAc (2×100 mL). The resulting mixture was concentrated under reduced pressure. The residue was purified by silica gel column chromatography, eluted with hexane/EtOAc (50:1~1:1) to afford (1-((2-(trimethylsilyl)ethoxy)methyl)-4,5,6,7-tetrahydroindazol-4-yl)methanol (2 g, 59.19%) as a colorless oil.

Step 4. (methylsulfanyl)((1-((2-(trimethylsilyl)ethoxy)methyl)-4,5,6,7-tetrahydroindazol-4-yl)methoxy)methanethione

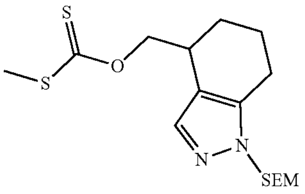 [SMILES: CSC(=S)OCC1CCCc2c1cnn2COCC[Si](C)(C)C]

To a stirred solution/mixture of (1-((2-(trimethylsilyl)ethoxy)methyl)-4,5,6,7-tetrahydroindazol-4-yl)methanol (3.10 g, 10.975 mmol, 1.00 equiv) in THF (30 mL) were added NaH (0.88 g, 21.950 mmol, 2.00 equiv, 60% in oil) in portions at 0 degrees C. under nitrogen atmosphere. The resulting mixture was stirred for 2 h at 0 degrees C. To the above mixture was added $CS_2$ (1.00 g, 13.170 mmol, 1.20 equiv) dropwise at 0 degrees C. After 10 min, MeI (1.87 g, 0.013 mmol, 1.2 equiv) was added to the above mixture. The resulting mixture was stirred for additional 5 min at 0 degrees C. The reaction was quenched by the addition of $NH_4Cl$ (aq.) (20 mL) at room temperature. The aqueous layer was extracted with EtOAc (1×20 mL). The resulting mixture was concentrated under reduced pressure. The residue was purified by silica gel column chromatography, eluted with hexane/EtOAc (100:1~10:1) to afford (methylsulfanyl)((1-((2-(trimethylsilyl)ethoxy)methyl)-4,5,6,7-tetrahydroindazol-4-yl)methoxy)methanethione (2 g, 47.93%) as a colorless oil.

Step 5. O-((1-((2-(trimethylsilyl)ethoxy)methyl)-4,5,6,7-tetrahydro-1H-indazol-4-yl)methyl) hydrazinecarbothioate

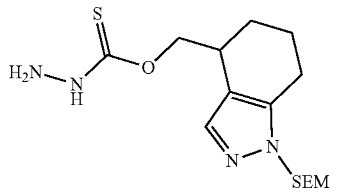 [SMILES: C[Si](C)(C)CCOCn1ncc2c1CCCC2COC(=S)NN]

Into a 50-mL 3-necked round-bottom flask purged and maintained with an inert atmosphere of nitrogen, was placed MeOH (20.00 mL), (methylsulfanyl)((1-((2-(trimethylsilyl)ethoxy)methyl)-4,5,6,7-tetrahydroindazol-4-yl)methoxy)methanethione (2.00 g, 5.367 mmol, 1.00 equiv), hydrazine hydrate (98%)(0.54 g, 10.787 mmol, 2.01 equiv). The resulting solution was stirred for 20 min at room temperature. The resulting mixture was diluted with water (50 mL). The aqueous layer was extracted with EtOAc (2×20 mL). The resulting mixture was concentrated under reduced pressure. This resulted in 0-((1-((2-(trimethylsilyl)ethoxy)methyl)-4,5,6,7-tetrahydro-1H-indazol-4-yl)methyl) hydrazinecarbothioate (1.7 g, 88.83%) as an off-white solid.

Step 6. 5-((1-((2-(trimethylsilyl)ethoxy)methyl)-4,5,6,7-tetrahydroindazol-4-yl)methoxy)-1,3,4-thiadiazol-2-amine

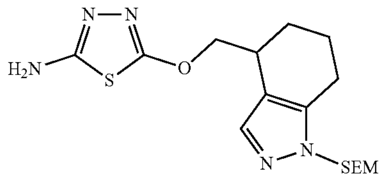 [SMILES: C[Si](C)(C)CCOCn1ncc2c1CCCC2COc1nnc(N)s1]

To a stirred solution of ((((1-((2-(trimethylsilyl)ethoxy)methyl)-4,5,6,7-tetrahydroindazol-4-yl)methoxy)methanethioyl)amino)amine (1.70 g, 4.768 mmol, 1.00 equiv) and TEA (0.96 g, 9.536 mmol, 2 equiv) in MeOH (20 mL) were added BrCN (1.01 g, 9.535 mmol, 2.00 equiv) in portions at room temperature under nitrogen atmosphere. The resulting mixture was stirred for 1 h at room temperature. The reaction was quenched with water at room temperature. The aqueous layer was extracted with EtOAc (2×50 mL). The resulting mixture was concentrated under reduced pressure. The residue was purified by silica gel column chromatography, eluted with $CH_2Cl_2$/MeOH (20:1) to afford 5-((1-((2-(trimethylsilyl)ethoxy)methyl)-4,5,6,7-tetrahydroindazol-4-yl)methoxy)-1,3,4-thiadiazol-2-amine (1.5 g, 79.15%) as an off-white solid.

Step 7. 3-(2-methoxyphenyl)-N-(5-((1-((2-(trimethylsilyl)ethoxy)methyl)-4,5,6,7-tetrahydroindazol-4-yl)methoxy)-1,3,4-thiadiazol-2-yl)pyridine-4-carboxamide

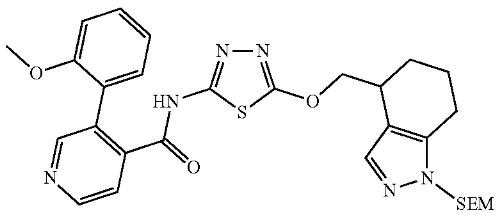 [SMILES: COc1ccccc1-c1cnccc1C(=O)Nc1nnc(OCC2CCCc3c2cnn3COCC[Si](C)(C)C)s1]

To a stirred solution of 3-(2-methoxyphenyl)pyridine-4-carboxylic acid (300.38 mg, 1.310 mmol, 1.00 equiv) and DIEA (338.71 mg, 2.621 mmol, 2 equiv) in DMF (5 mL) were added HATU (597.89 mg, 1.572 mmol, 1.20 equiv) at room temperature under nitrogen atmosphere. The resulting mixture was stirred for 2 h at room temperature. To the above mixture was added 5-((1-((2-(trimethylsilyl)ethoxy)methyl)-4,5,6,7-tetrahydroindazol-4-yl)methoxy)-1,3,4-thiadiazol-2-amine (500.00 mg, 1.310 mmol, 1.00 equiv) at room temperature. The resulting mixture was stirred for additional 3 h at room temperature. The resulting mixture was diluted with water (50 mL). The aqueous layer was extracted with EtOAc (2×20 mL). The resulting mixture was concentrated under reduced pressure. The residue was purified by Prep-TLC ($CH_2Cl_2$/MeOH 30:1) to afford 3-(2-methoxyphenyl)-N-(5-((1-((2-(trimethylsilyl)ethoxy)methyl)-4,5,6,7-tetrahydroindazol-4-yl)methoxy)-1,3,4-thiadiazol-2-yl)pyridine-4-carboxamide (440 mg, 56.64%) as a white solid.

Step 8. 3-(2-methoxyphenyl)-N-(5-(4,5,6,7-tetrahydro-1H-indazol-4-ylmethoxy)-1,3,4-thiadiazol-2-yl)pyridine-4-carboxamide

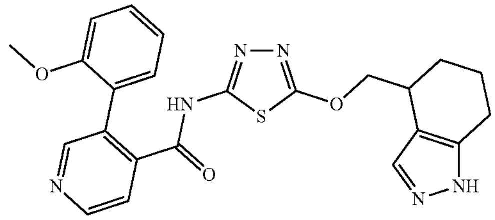 [SMILES: COc1ccccc1-c1cnccc1C(=O)Nc1nnc(OCC2CCCc3[nH]ncc32)s1]

Into a 20-mL sealed tube purged and maintained with an inert atmosphere of nitrogen, was placed THF (10.00 mL), 3-(2-methoxyphenyl)-N-(5-((1-((2-(trimethylsilyl)ethoxy)methyl)-4,5,6,7-tetrahydroindazol-4-yl)methoxy)-1,3,4-thiadiazol-2-yl)pyridine-4-carboxamide (220.00 mg, 0.371 mmol, 1.00 equiv), CsF (1127.51 mg, 7.423 mmol, 20.00 equiv), TBAF (970.35 mg, 3.711 mmol, 10 equiv). The resulting solution was stirred for 1 hr at 70 degrees C. The resulting mixture was diluted with water (30 mL). The aqueous layer was extracted with EtOAc (1×20 mL). The resulting mixture was concentrated under reduced pressure. The residue was purified by Prep-TLC ($CH_2Cl_2$/MeOH 20:1) to afford 3-(2-methoxyphenyl)-N-(5-(4,5,6,7-tetrahydro-1H-indazol-4-ylmethoxy)-1,3,4-thiadiazol-2-yl)pyridine-4-carboxamide (49.6 mg, 28.72%) as a white solid. MS (ESI) $(M+1)^+$, 463. $^1H$ NMR (300 MHz, DMSO-d6) δ12.80 (s, 1H), 12.31 (s, 1H), 8.71-8.70 (d, 1H), 8.60 (s, 1H), 7.63-7.62 (d, 1H), 7.44-7.35 (m, 3H), 7.09-7.07 (m, 1H), 7.00-6.98 (d, 1H), 4.51-4.45 (m, 1H), 4.39-4.33 (m, 1H), 3.52 (s, 3H), 3.15-3.08 (m, 1H), 2.95-2.57 (m, 2H), 1.93-1.83 (m, 2H), 1.75-1.63 (m, 1H), 1.54-1.41 (m, 1H) ppm.

Example 4

1-(6-(((5-(4-(2-methoxyphenyl)-6-methylnicotinamido)-1,3,4-thiadiazol-2-yl)oxy)methyl)pyridin-3-yl)cyclopropane-1-carboxylic acid

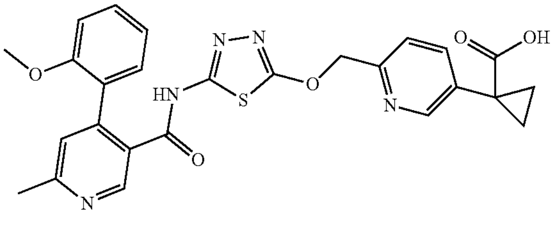 [SMILES: COc1ccccc1-c1cc(C)ncc1C(=O)Nc1nnc(OCc2ccc(C3(C(=O)O)CC3)cn2)s1]

Step-1:1-(6-chloropyridin-3-yl)cyclopropane-1-carbonitrile

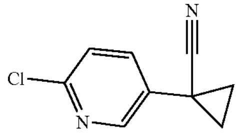 [SMILES: N#CC1(c2ccc(Cl)nc2)CC1]

To a solution of NaOH (100 g) in $H_2O$ (100 mL) were added 2-(6-chloropyridin-3-yl)acetonitrile (20 g, 131.079 mmol) and dibromoethane (27 g, 142.658 mmol). The mixture was stirred at 50° C. for 16 hours. The resulting mixture was extracted with ethyl acetate. The combined organic layers was dried over anhydrous sodium sulfate, filtered, and concentrated under vacuum. The residue was purified by flash chromatography on silica gel with 0-50% ethyl acetate in petroleum ether to afford 1-(6-chloropyridin-3-yl)cyclopropane-1-carbonitrile (18 g, 77%) as a yellow solid. MS (ESI) calc'd for $(C_9H_7ClN_2)$ $(M+1)^+$, 179.0, found 179.2.

Step-2:
1-(6-vinylpyridin-3-yl)cyclopropane-1-carbonitrile

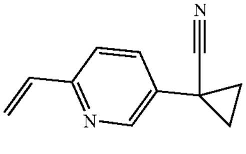

To a solution of ethenyltrifluoro-lambda4-borane potassium (11.5 g, 0.084 mmol) in dioxane (100 mL) and $H_2O$ (20 mL) were added 1-(6-chloropyridin-3-yl)cyclopropane-1-carbonitrile (10 g, 55.985 mmol), $K_2CO_3$ (23.2 g, 0.168 mmol) and Pd(dppf)$Cl_2$ (4.1 g, 0.006 mmol). The resulting mixture was stirred at 80° C. for 12 hours under nitrogen. The resulting mixture was extracted with ethyl acetate. The combined organic layers was dried over anhydrous sodium sulfate, filtered, and concentrated under vacuum. The residue was purified by flash chromatography on silica gel with 0-50% ethyl acetate in petroleum ether to afford 1-(6-ethenylpyridin-3-yl)cyclopropane-1-carbonitrile (6.84 g, 72%) as a yellow solid. MS (ESI) calc'd for $(C_{11}H_{10}N_2)$ $(M+1)^+$, 171.0, found 171.0.

Step-3: 1-(6-formylpyridin-3-yl)cyclopropane-1-carbonitrile

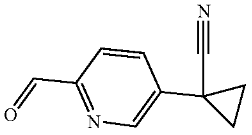 [SMILES: N#CC1(c2ccc(C=O)nc2)CC1]

To a solution of 1-(6-ethenylpyridin-3-yl)cyclopropane-1-carbonitrile (6.84 g, 40.184 mmol) in THF (120 mL) and $H_2O$ (40 mL) were added $OsO_4$ (1.02 g, 4.018 mmol) and $NaIO_4$ (34.5 g, 160.73 mmol). The resulting mixture was stirred at room temperature for 16 h. The resulting mixture was extracted with ethyl acetate. The combined organic layers were washed with brine, dried over anhydrous sodium sulfate, filtered, and concentrated under vacuum. The residue was purified by flash chromatography on silica gel with 0-50% ethyl acetate in petroleum ether to afford 1-(6-formylpyridin-3-yl)cyclopropane-1-carbonitrile (2.11 g, 40%) as a yellow solid. MS (ESI) calc'd for $(C_{10}H_8N_2O)$ $(M+1)^+$, 173.0, found 173.0.

Step-4: 1-(6-(hydroxymethyl)pyridin-3-yl)cyclopropane-1-carbonitrile

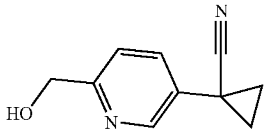 [SMILES: N#CC1(c2ccc(CO)nc2)CC1]

To a solution of 1-(6-formylpyridin-3-yl)cyclopropane-1-carbonitrile (2.12 g, 12.254 mmol) in MeOH (20 mL) was added $NaBH_4$ (0.46 g, 12.254 mmol) at 0° C. The mixture was stirred at room temperature for 1 h. The reaction was then quenched by the addition of water and extracted with ethyl acetate. The combined organic layers were washed with brine, dried over anhydrous sodium sulfate, filtered, and concentrated under vacuum to afford 1-(6-(hydroxymethyl)pyridin-3-yl)cyclopropane-1-carbonitrile (1.11 g, 70%) as a yellow solid. MS (ESI) calc'd for $(C_{10}H_{10}N_2O)$ $(M+1)^+$, 175.1, found 175.0.

Step-5: 1-(6-(((5-amino-1,3,4-thiadiazol-2-yl)oxy)methyl)pyridin-3-yl)cyclopropane-1-carbonitrile

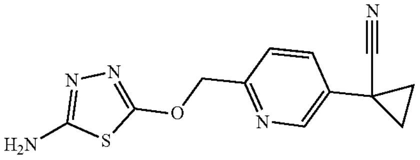 [SMILES: N#CC1(c2ccc(COc3nnc(N)s3)nc2)CC1]

To a solution of NaH (0.73 g, 17.502 mmol, 60%) in THF (10 mL) was added 1-(6-(hydroxymethyl)pyridin-3-yl)cyclopropane-1-carbonitrile (2.11 g, 12.112 mmol) in portions at 0~5° C. and stirred at 5° C. for 1 h. Then 5-bromo-1,3,4-thiadiazol-2-amine (2.62 g, 14.534 mmol,) was added to the mixture in small portions at 5° C. and stirred at 5° C. for 5 h. The reaction mixture was then quenched by the addition of water and extracted with ethyl acetate. The combined organic layers were washed with brine, dried over anhydrous sodium sulfate, filtered, and concentrated under vacuum. The residue was purified by flash chromatography on silica gel with 0~10% methanol in dichloromethane to afford 1-(6-(((5-amino-1,3,4-thiadiazol-2-yl)oxy)methyl)pyridin-3-yl)cyclopropane-1-carbonitrile (1.11 g, 33%) as a white solid. MS (ESI) calc'd for ($C_{12}H_{11}N_5OS$) $(M+1)^+$, 274.1, found 274.0.

Step-6: methyl 1-(6-(((5-amino-1,3,4-thiadiazol-2-yl)oxy)methyl)pyridin-3-yl)cyclopropane-1-carboxylate

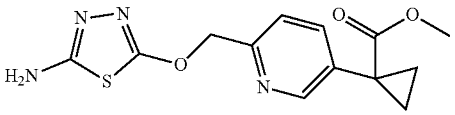 [SMILES: COC(=O)C1(c2ccc(COc3nnc(N)s3)nc2)CC1]

To a solution of sulfuric acid (8 mL, 98%) in $H_2O$ (8 mL) was added 1-(6-(((5-amino-1,3,4-thiadiazol-2-yl)oxy)methyl)pyridin-3-yl)cyclopropane-1-carbonitrile (362 mg, 1.325 mmol) in portions at 0~5° C. and stirred at 80° C. for 12 hours. Then MeOH (32 mL) was added to the above mixture in small portions at room temperature and stirred at 80° C. for 3 h. The mixture was concentrated under vacuum. Then the aqueous solution was neutralized with saturated $NaHCO_3$ aqueous solution and extracted with ethyl acetate. The combined organic layers were washed with brine, dried over anhydrous sodium sulfate, filtered, and concentrated under vacuum to afford methyl 1-(6-(((5-amino-1,3,4-thiadiazol-2-yl)oxy)methyl)pyridin-3-yl)cyclopropane-1-carboxylate (280 mg, 77.3%) as a light yellow solid. MS (ESI) calc'd for ($C_{13}H_{14}N_4O_3S$) $(M+1)^+$, 307.1; found, 307.0.

Step-7: methyl 1-(6-(((5-(4-(2-methoxyphenyl)-6-methylnicotinamido)-1,3,4-thiadiazol-2-yl)oxy)methyl)pyridin-3-yl)cyclopropane-1-carboxylate

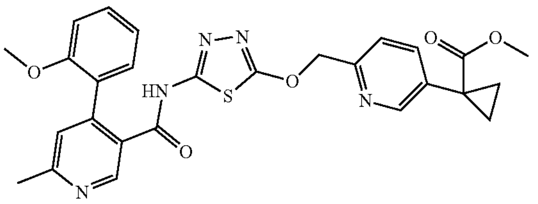

To a mixture of methyl 1-(6-(((5-amino-1,3,4-thiadiazol-2-yl)oxy)methyl)pyridin-3-yl)cyclopropane-1-carboxylate (450 mg, 1.466 mmol) in DMF (20 mL) were added DIEA (379 mg, 2.938 mmol), HATU (557 mg, 1.466 mmol) and 4-(2-methoxyphenyl)-6-methylpyridine-3-carboxylic acid (238 mg, 0.979 mmol, Intermediate D). The resulting mixture was stirred at room temperature for 2 h. The mixture was diluted with water and extracted with ethyl acetate. The combined organic layers were washed with brine, dried over anhydrous sodium sulfate, filtered, and concentrated under vacuum. The residue was purified by flash chromatography on silica gel with 0~10% methanol in dichloromethane and further purified by prep-HPLC with the following conditions: (Column: Sunfire prep C18 column, 30*150, 5 um; Mobile Phase A: Water (0.10% FA), Mobile Phase B: ACN; Flow rate: 60 mL/min; Gradient: 25 B to 55 B in 8 min; 220 nm; RT1: 7.23 min) to afford methyl 1-(6-(((5-(4-(2-methoxyphenyl)-6-methylnicotinamido)-1,3,4-thiadiazol-2-yl)oxy)methyl)pyridin-3-yl)cyclopropane-1-carboxylate (340 mg, 76%) as a yellow solid. MS (ESI) calc'd for ($C_{27}H_{25}FN_5O_5S$) $(M+1)^+$, 532.2; found 532.2.

Step-8: 1-(6-(((5-(4-(2-methoxyphenyl)-6-methylnicotinamido)-1,3,4-thiadiazol-2-yl)oxy)methyl)pyridin-3-yl)cyclopropane-1-carboxylic acid

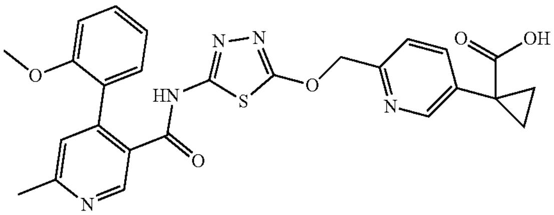 [SMILES: COc1ccccc1-c1cc(C)ncc1C(=O)Nc1nnc(OCc2ccc(C3(C(=O)O)CC3)cn2)s1]

To a solution of methyl 1-(6-(((5-(4-(2-methoxyphenyl)-6-methylpyridine-3-amido)-1,3,4-thiadiazol-2-yl)oxy)methyl)pyridin-3-yl)cyclopropane-1-carboxylate (25 mg, 0.047 mmol) in MeOH (0.5 mL) and $H_2O$ (0.5 mL) was added NaOH (5 mg, 0.094 mmol). The resulting mixture was stirred at room temperature for 8 hours. The mixture was acidified to pH ~4 by HCl (1 N) and then purified by prep-HPLC with the following conditions: (Column: Xselect CSH OBD Column 30*150 mm 5 um; Mobile Phase A: Water (0.1% FA), Mobile Phase B: ACN; Flow rate: 60 mL/min; Gradient: 15 B to 40 B in 8 min; 220/254 nm; RT: 6.99 min) to afford 1-(6-(((5-(4-(2-methoxyphenyl)-6-methylpyridine-3-amido)-1,3,4-thiadiazol-2-yl)oxy)methyl)pyridin-3-yl)cyclopropane-1-carboxylic acid (8.1 mg, 25%) as a white solid. MS (ESI) calc'd for ($C_{26}H_{23}N_5O_5S$) $(M+1)^+$, 518.1; found, 518.2. $^1H$ NMR (400 MHz, $CD_3OD$) δ 8.66 (s, 1H), 8.58 (s, 1H), 7.89-7.87 (m, 1H), 7.58-7.56 (m, 1H), 7.44-7.38 (m, 3H), 7.13-7.11 (m, 1H), 6.99-6.97 (m, 1H), 5.56 (s, 2H), 3.61 (s, 3H), 2.65 (s, 3H), 1.68-1.65 (m, 2H), 1.33-1.25 (m, 2H).

Example 5

N-(5-((5-(hydroxymethyl)pyridin-2-yl)methoxy)-1,3,4-thiadiazol-2-yl)-4-(2-methoxyphenyl)-6-methylnicotinamide

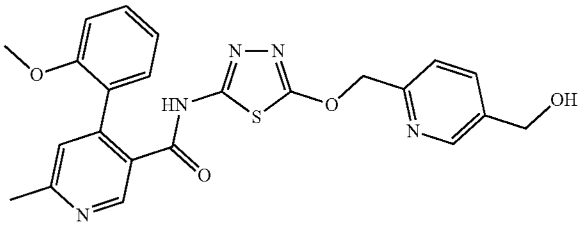 [SMILES: COc1ccccc1-c1cc(C)ncc1C(=O)Nc1nnc(OCc2ccc(CO)cn2)s1]

Step-1: methyl 6-(((5-amino-1,3,4-thiadiazol-2-yl)oxy)methyl)nicotinate

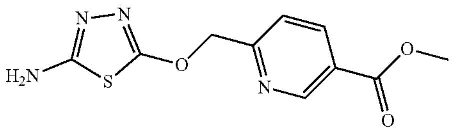 [SMILES: COC(=O)c1ccc(COc2nnc(N)s2)nc1]

To a solution of NaH (358.9 mg, 25.92 mmol, 60%) in THF (15.00 mL) were added methyl 6-(hydroxymethyl)nicotinate (1 g, 6.0 mmol) in portions at 0° C. under nitrogen. The resulting mixture was stirred at 0° C. for 1 h. To the above mixture was added 5-bromo-1,3,4-thiadiazol-2-amine (1.3 g, 7.2 mmol) dropwise at 0° C. The resulting mixture was stirred at 0~5° C. for 5 h. The resulting mixture was quenched with water and extracted with ethyl acetate. The organic layers were combined, washed with brine, dried over anhydrous sodium sulfate and filtered. The filtrate was concentrated under vacuum. The residue was purified by reverse phase flash column chromatography with 5-50% acetonitrile in water to afford methyl 6-(((5-amino-1,3,4-thiadiazol-2-yl)oxy)methyl)nicotinate (320 mg, 20%) as a yellow solid. MS (ESI) calc'd for ($C_{10}H_{10}N_4O_3S$) $(M+1)^+$, 267.0; found 267.0.

Step-2: methyl 6-(((5-(4-(2-methoxyphenyl)-6-methylpyridine-3-amido)-1,3,4-thiadiazol-2-yl)oxy)methyl)pyridine-3-carboxylate

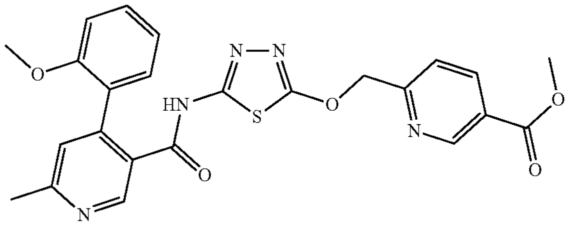 [SMILES: COC(=O)c1ccc(COc2nnc(NC(=O)c3cnc(C)cc3-c3ccccc3OC)s2)nc1]

To a mixture of 4-(2-methoxyphenyl)-6-methylpyridine-3-carboxylic acid (274.0 mg, 1.126 mmol, Intermediate D).) and HATU (642.0 mg, 1.688 mmol) in DMF (5 mL) was added DIEA (436.0 mg, 3.373 mmol). The resulting mixture was stirred at room temperature for 30 min. To the above mixture was added methyl 6-(((5-amino-1,3,4-thiadiazol-2-yl)oxy)methyl)pyridine-3-carboxylate (300.0 mg, 1.127 mmol). The mixture was stirred at 50° C. for 16 hours under nitrogen atmosphere. The resulting mixture was quenched with water. The aqueous layer was extracted with ethyl acetate. The organic layers were combined, washed with brine, dried over anhydrous sodium sulfate and filtered. The filtrate was concentrated under vacuum. The residue was purified by reverse phase flash column chromatography with 5~50% acetonitrile in water to afford methyl 6-(((5-(4-(2-methoxyphenyl)-6-methylpyridine-3-amido)-1,3,4-thiadiazol-2-yl)oxy)methyl)pyridine-3-carboxylate (60 mg, 11%) as a white solid. MS (ESI) calc'd for ($C_{24}H_{21}N_5O_5S$) $(M+1)^+$, 492.1; found 492.0.

Step-3: N-(5-((5-(hydroxymethyl)pyridin-2-yl)methoxy)-1,3,4-thiadiazol-2-yl)-4-(2-methoxyphenyl)-6-methylpyridine-3-carboxamide

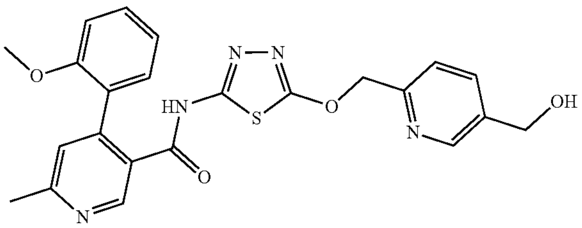 [SMILES: COc1ccccc1-c1cc(C)ncc1C(=O)Nc1nnc(OCc2ccc(CO)cn2)s1]

To a mixture of methyl 6-(((5-(4-(2-methoxyphenyl)-6-methylpyridine-3-amido)-1,3,4-thiadiazol-2-yl)oxy)methyl)pyridine-3-carboxylate (160.0 mg, 0.326 mmol) in THF (5 mL) was added $LiAlH_4$ (12.3 mg, 0.326 mmol) in portions at 0° C. The mixture was stirred at 0° C. for 1 hour under nitrogen. The resulting mixture was quenched with water. The suspension was filtered. The filtrate was collected and concentrated under vacuum. The residue was purified by reverse phase flash column chromatography with 5~50% acetonitrile in water and further purified by prep-HPLC with the following conditions: (Column: XBridge Shield RP18 OBD Column, 30*150 mm, 5 um; Mobile Phase A: Water (10 MMOL/L $NH_4HCO_3$+0.1% $NH_3 \cdot H_2O$), Mobile Phase B: ACN; Flow rate: 60 mL/min; Gradient: 9 B to 28 B in 8 min; 254/220 nm; RT1: 8.52 min) to afford N-(5-((5-(hydroxymethyl)pyridin-2-yl)methoxy)-1,3,4-thiadiazol-2-yl)-4-(2-methoxyphenyl)-6-methylpyridine-3-carboxamide (7.9 mg, 5%) as a white solid. MS (ESI) calc'd for ($C_{23}H_{21}N_5O_4S$) $(M+1)^+$, 464.1; found, 464.1. $^1$H NMR (400 MHz, DMSO-$d_6$) δ 12.75 (s, 1H), 8.66 (s, 1H), 8.53 (d, J=2.4 Hz, 1H), 7.82-7.75 (m, 1H), 7.52 (d, J=8.0 Hz, 1H), 7.44-7.32 (m, 2H), 7.30 (s, 1H), 7.12-7.03 (m, 1H), 6.98 (d, J=8.4 Hz, 1H), 5.52 (s, 2H), 5.39-5.32 (m, 1H), 4.55 (d, J=5.6 Hz, 2H), 3.51 (s, 3H), 2.56 (s, 3H).

Example 6

N-(5-((6-(hydroxymethyl)pyridin-2-yl)methoxy)-1,3,4-thiadiazol-2-yl)-4-(2-methoxyphenyl)-6-methylpyridine-3-carboxamide

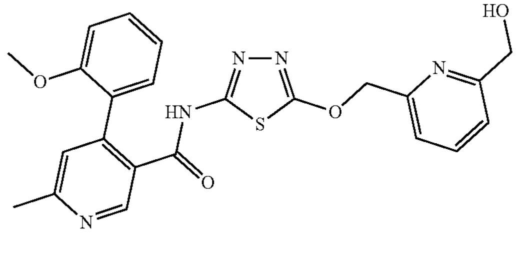 [SMILES: COc1ccccc1-c1cc(C)ncc1C(=O)Nc1nnc(OCc2cccc(CO)n2)s1]

Step-1: methyl 6-((((methylsulfanyl)methanethioyl) oxy)methyl)pyridine-2-carboxylate

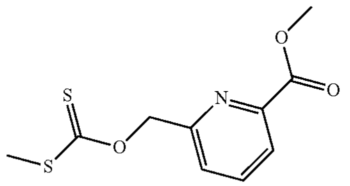 [SMILES: COC(=O)c1cccc(COC(=S)SC)n1]

To a solution of methyl 6-(hydroxymethyl)pyridine-2-carboxylate (500.00 mg, 2.991 mmol) in THF (5 mL) was added NaH (238.3 mg, 5.982 mmol, 60%) at 0° C. and stirred at ° C. under nitrogen. then $CS_2$ (341.62 mg, 4.487 mmol) and MeI (636.83 mg, 4.487 mmol) were sequentially added to the above mixture at 0° C. The resulting solution was stirred at 0° C. for 1 hours under nitrogen atmosphere. The reaction mixture was quenched with the addition of water and extracted with ethyl acetate. The combined organic layers were washed with brine, dried over anhydrous sodium sulfate, filtered, and concentrated under vacuum. The residue was purified by flash column chromatography with 0~10% ethyl acetate in petroleum ether to afford methyl 6-((((methylsulfanyl)methanethioyl)oxy)methyl)pyridine-2-carboxylate (290 mg, 35%) as a yellow solid. MS (ESI) calc'd for ($C_{10}H_{11}NO_3S_2$) $(M+1)^+$, 258.0; found, 258.0.

Step-2: methyl 6-(((aminocarbamothioyl)oxy) methyl)pyridine-2-carboxylate

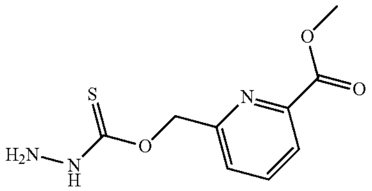 [SMILES: COC(=O)c1cccc(COC(=S)NN)n1]

To a solution of methyl 6-((((methylsulfanyl)methanethioyl)oxy)methyl)pyridine-2-carboxylate (290.00 mg, 1.127 mmol) in MeOH (5 mL) was added $NH_2NH_2 \cdot H_2O$ (62.06 mg, 1.240 mmol) at 0° C. The resulting solution was stirred at 0° C. for 0.5 h under nitrogen. The resulting mixture was quenched with water and extracted with ethyl acetate. The combined organic layers were washed with $H_2O$, dried over anhydrous $Na_2SO_4$. After filtration, the filtrate was concentrated under vacuum to afford methyl 6-(((aminocarbamothioyl)oxy)methyl)pyridine-2-carboxylate (254 mg, crude) as a yellow solid. MS (ESI) calc'd for ($C_9H_{11}N_3O_3S$) $(M+1)^+$, 242.0; found 242.0.

Step-3: methyl 6-(((5-amino-1,3,4-thiadiazol-2-yl) oxy)methyl)pyridine-2-carboxylate

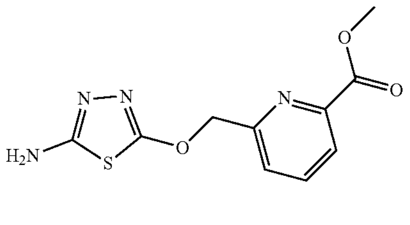 [SMILES: COC(=O)c1cccc(COc2nnc(N)s2)n1]

To a solution of methyl 6-(((aminocarbamothioyl)oxy) methyl)pyridine-2-carboxylate (254.00 mg, 1.053 mmol) in MeOH (10 mL) were added and BrCN (122.66 mg, 1.158 mmol) and $Et_3N$ (213.06 mg, 2.108 mmol) at 0° C. The resulting mixture was stirred for 30 min at 0° C. The resulting mixture was quenched with water and extracted with ethyl acetate. The combined organic layers were washed with $H_2O$, dried over anhydrous $Na_2SO_4$. After filtration, the filtrate was concentrated under vacuum to afford methyl 6-(((5-amino-1,3,4-thiadiazol-2-yl)oxy) methyl)pyridine-2-carboxylate (248 mg, 82%) as a light brown solid. MS (ESI) calc'd for ($C_{10}H_{10}N_4O_3S$) $(M+1)^+$, 267.0; found 267.0.

Step-4: methyl 6-(((5-(4-(2-methoxyphenyl)-6-methylpyridine-3-amido)-1,3,4-thiadiazol-2-yl)oxy) methyl)pyridine-2-carboxylate

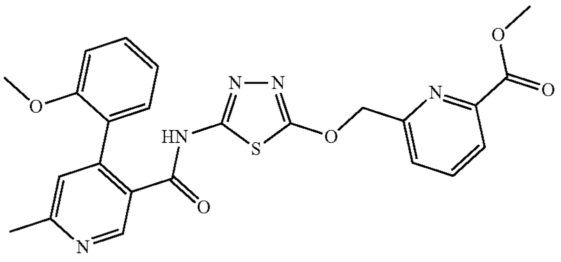 [SMILES: COC(=O)c1cccc(COc2nnc(NC(=O)c3cnc(C)cc3-c3ccccc3OC)s2)n1]

To a solution of 4-(2-methoxyphenyl)-6-methylpyridine-3-carboxylic acid (139.77 mg, 0.575 mmol, Intermediate D).) in DMF (2 mL) were added HATU (327.71 mg, 0.862 mmol), DIEA (222.78 mg, 1.724 mmol) and methyl 6-(((5-amino-1,3,4-thiadiazol-2-yl)oxy)methyl)pyridine-2-carboxylate (153.00 mg, 0.575 mmol). The resulting mixture was stirred at 50° C. for 2 h under nitrogen atmosphere. The residue was purified by reverse phase flash column chromatography with 5~40% acetonitrile in water to afford methyl 6-(((5-(4-(2-methoxyphenyl)-6-methylpyridine-3-amido)-1,3,4-thiadiazol-2-yl)oxy)methyl)pyridine-2-carboxylate (155 mg, 38%) as a yellow oil. MS (ESI) calc'd for ($C_{24}H_{21}N_5O_5S$) $(M+1)^+$, 492.1; found 492.1.

Step-5: N-(5-((6-(hydroxymethyl)pyridin-2-yl) methoxy)-1,3,4-thiadiazol-2-yl)-4-(2-methoxyphenyl)-6-methylpyridine-3-carboxamide

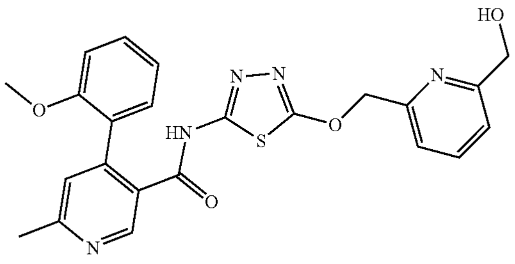 [SMILES: COc1ccccc1-c1cc(C)ncc1C(=O)Nc1nnc(OCc2cccc(CO)n2)s1]

To a solution of 6-(((5-(4-(2-methoxyphenyl)-6-methylpyridine-3-amido)-1,3,4-thiadiazol-2-yl)oxy)methyl)pyridine-2-carboxylic acid (189.00 mg, 0.396 mmol) in THF (8.00 mL) was added $LiAlH_4$ (30.05 mg, 0.792 mmol) in portions at 0° C. under nitrogen atmosphere. The resulting mixture was stirred for 0.5 h at 0° C. under nitrogen atmosphere. The resulting mixture was quenched by the addition of water and extracted with ethyl acetate. The combined organic layers were washed with brine, dried over anhydrous $Na_2SO_4$. After filtration, the filtrate was concentrated under reduced pressure. The residue was purified by reverse phase flash column chromatography with 5-40% acetonitrile in water to afford methyl N-(5-((6-(hydroxymethyl)pyridin-2-yl)methoxy)-1,3,4-thiadiazol-2-yl)-4-(2-methoxyphenyl)-6-methylpyridine-3-carboxamide (27.1 mg, 14%) as a white solid. MS (ESI) calc'd for ($C_{23}H_{21}N_5O_4S$) $(M+1)^+$, 464.1; found 464.1. $^1H$ NMR (400 MHz, DMSO-d6) δ 12.76 (s, 1H), 8.67 (s, 1H), 7.86 (t, J=7.6 Hz, 1H), 7.47 (d, J=7.6 Hz, 1H), 7.44-7.32 (m, 3H), 7.30 (s, 1H), 7.12-7.03 (m, 1H), 6.98 (d, J=8.4 Hz, 1H), 5.52-5.43 (m, 3H), 4.57 (d, J=6.0 Hz, 2H), 3.51 (s, 3H), 2.57 (s, 3H).

Example 7

N-(5-((5-(1-(hydroxymethyl)cyclopropyl)pyridin-2-yl)methoxy)-1,3,4-thiadiazol-2-yl)-4-(2-methoxyphenyl)-6-methylnicotinamide

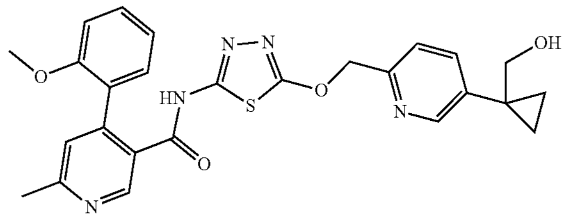 [SMILES: COc1ccccc1-c1cc(C)ncc1C(=O)Nc1nnc(OCc2ccc(C3(CO)CC3)cn2)s1]

Step-1: methyl 1-(6-(((5-amino-1,3,4-thiadiazol-2-yl)oxy)methyl)pyridin-3-yl)cyclopropane-1-carboxylate

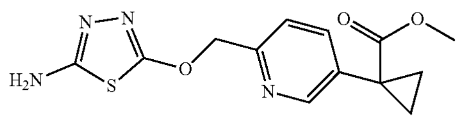 [SMILES: COC(=O)C1(c2ccc(COc3nnc(N)s3)nc2)CC1]

To a solution of sulfuric acid (8 mL, 98%) in $H_2O$ (8 mL) was added 1-(6-(((5-amino-1,3,4-thiadiazol-2-yl)oxy)methyl)pyridin-3-yl)cyclopropane-1-carbonitrile (362 mg, 1.325 mmol) in portions at 0~5° C. and stirred at 80° C. for 12 hours. Then MeOH (32 mL) was added to the above mixture in small portions at room temperature and stirred at 80° C. for 3 h. The mixture was concentrated under vacuum. Then the aqueous solution was neutralized with saturated $NaHCO_3$ aqueous solution and extracted with ethyl acetate. The combined organic layers were washed with brine, dried over anhydrous sodium sulfate, filtered, and concentrated under vacuum to afford methyl 1-(6-(((5-amino-1,3,4-thiadiazol-2-yl)oxy)methyl)pyridin-3-yl)cyclopropane-1-carboxylate (280 mg, 77.3%) as a light yellow solid. MS (ESI) calc'd for ($C_{13}H_{14}N_4O_3S$) $(M+1)^+$, 307.1; found, 307.0.

Step-2: methyl 1-(6-(((5-(4-(2-methoxyphenyl)-6-methylnicotinamido)-1,3,4-thiadiazol-2-yl)oxy)methyl)pyridin-3-yl)cyclopropane-1-carboxylate

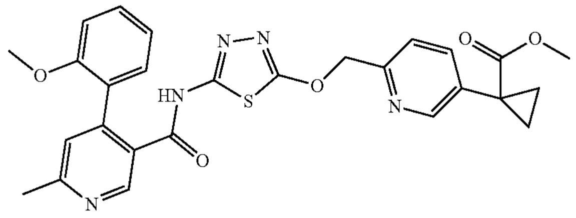

To a mixture of methyl 1-(6-(((5-amino-1,3,4-thiadiazol-2-yl)oxy)methyl)pyridin-3-yl)cyclopropane-1-carboxylate (450 mg, 1.466 mmol) in DMF (20 mL) were added DIEA (379 mg, 2.938 mmol), HATU (557 mg, 1.466 mmol) and 4-(2-methoxyphenyl)-6-methylpyridine-3-carboxylic acid (238 mg, 0.979 mmol, Intermediate D).). The resulting mixture was stirred at room temperature for 2 h. The mixture was diluted with water and extracted with ethyl acetate. The combined organic layers were washed with brine, dried over anhydrous sodium sulfate, filtered, and concentrated under vacuum. The residue was purified by flash chromatography on silica gel with 0~10% methanol in dichloromethane and further purified by prep-HPLC with the following conditions: (Column: Sunfire prep C18 column, 30*150, 5 um; Mobile Phase A: Water (0.1% FA), Mobile Phase B: ACN; Flow rate: 60 mL/min; Gradient: 25 B to 55 B in 8 min; 220 nm; RT1: 7.23 min) to afford methyl 1-(6-(((5-(4-(2-methoxyphenyl)-6-methylnicotinamido)-1,3,4-thiadiazol-2-yl)oxy)methyl)pyridin-3-yl)cyclopropane-1-carboxylate (340 mg, 76%) as a yellow solid. MS (ESI) calc'd for ($C_{27}H_{25}FN_5O_5S$) $(M+1)^+$, 532.2; found 532.2.

Step-3: N-(5-((5-(1-(hydroxymethyl)cyclopropyl)pyridin-2-yl)methoxy)-1,3,4-thiadiazol-2-yl)-4-(2-methoxyphenyl)-6-methylnicotinamide

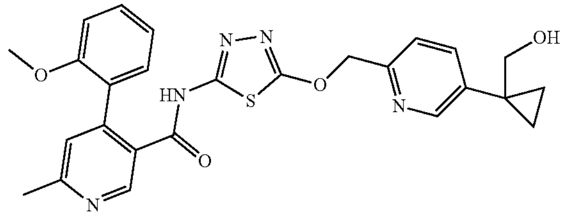 [SMILES: COc1ccccc1-c1cc(C)ncc1C(=O)Nc1nnc(OCc2ccc(C3(CO)CC3)cn2)s1]

To a solution of methyl 1-(6-(((5-(4-(2-methoxyphenyl)-6-methylpyridine-3-amido)-1,3,4-thiadiazol-2-yl)oxy)methyl)pyridin-3-yl)cyclopropane-1-carboxylate (140 mg, 0.263 mmol) in THF (5 mL) was added $LiAlH_4$ (10 mg, 0.263 mmol) in portions at 0~5° C. and then stirred at room temperature for 1 h. The reaction mixture was then quenched by the addition of water and extracted with ethyl acetate. The combined organic layers were washed with brine, dried over anhydrous sodium sulfate, filtered, and concentrated under vacuum. The residue was purified by flash chromatography on silica gel with 0~10% methanol in dichloromethane to afford N-(5-((5-(1-(hydroxymethyl)cyclopropyl)pyridin-2-yl)methoxy)-1,3,4-thiadiazol-2-yl)-4-(2-methoxyphenyl)-6-methylnicotinamide (25.2 mg, 18%) as a white solid. MS (ESI) calc'd for ($C_{26}H_{25}N_5O_4S$) $(M+1)^+$, 504.2; found, 504.2. $^1$H NMR (400 MHz, DMSO-$d_6$) δ 12.74 (s, 1H), 8.66 (s, 1H), 8.54 (s, 1H), 7.74-7.73 (m, 1H), 7.46-7.44 (m, 1H), 7.40 (s, 1H), 7.35-7.34 (m, 1H), 7.30-7.28 (m, 1H), 7.08-7.05 (m, 1H), 7.02-6.95 (m, 1H), 5.49 (s, 2H), 4.80 (s, 1H), 3.52-3.51 (m, 5H), 2.33 (s, 3H), 0.91-0.85 (m, 2H), 0.85-0.78 (m, 2H).

Example 8

2'-chloro-N-(5-((5-chloropyridin-2-yl)methoxy)-1,3,4-thiadiazol-2-yl)-5'-methoxy-6-methyl-[4,4'-bipyridine]-3-carboxamide

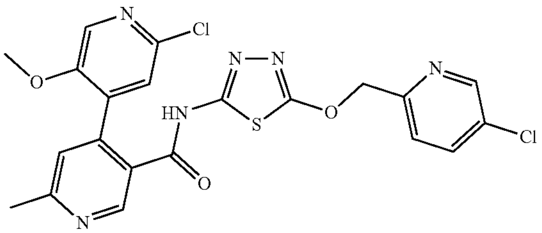

Step-1: methyl 2'-chloro-5'-methoxy-6-methyl-(4,4'-bipyridine)-3-carboxylate

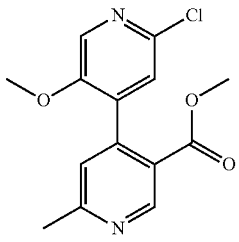 [SMILES: COC(=O)c1cnc(C)cc1-c1cc(Cl)ncc1OC]

To a solution of 4-chloro-6-methylnicotinic acid (244 mg, 1.31 mmol) in dioxane (5 mL) and water (1 mL) were added (2-chloro-5-methoxypyridin-4-yl)boronic acid (320 mg, 1.70 mmol), $K_2CO_3$ (363 mg, 2.62 mmol) and $PdCl_2$ (DTBPF) (171 mg, 0.26 mmol). The mixture was stirred at 90° C. for 2 h under nitrogen atmosphere. The resulting mixture was diluted with water. The aqueous layer was extracted with EtOAc. The combined organic phase was washed with brine, dried over sodium sulfate and filtered. The filtration was concentrated under vacuum. The residue was purified by reverse phase flash chromatography with 5~45% ACN in water to afford methyl 2'-chloro-5'-methoxy-6-methyl-(4,4'-bipyridine)-3-carboxylate (94 mg, 18%) as a yellow solid. MS (ESI) calc'd for ($C_{14}H_{13}ClN_2O_3$) $(M+1)^+$, 293.0, found 292.9.

Step-2: 2'-chloro-5'-methoxy-6-methyl-(4,4'-bipyridine)-3-carboxylic acid

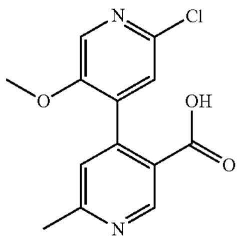

A solution of methyl 2'-chloro-5'-methoxy-6-methyl-[4,4'-bipyridine]-3-carboxylate (50.0 mg, 0.17 mmol) and LiOH (5.3 mg, 0.22 mmol) in THF (1 mL) and water (0.3 mL) was stirred at room temperature for 16 h. The aqueous solution was acidified with citric acid to pH 5-6. The aqueous layer was extracted with EtOAc. The combined organic solution was dried over sodium sulfate, filtered, and concentrated under vacuum to afford 2'-chloro-5'-methoxy-6-methyl-(4,4'-bipyridine)-3-carboxylic acid (40.0 mg, crude) as a yellow solid. MS (ESI) calc'd for ($C_{13}H_{11}ClN_2O_3$) $(M+1)^+$, 279.0, found 279.0.

Step-3: 2'-chloro-N-(5-((5-chloropyridin-2-yl)methoxy)-1,3,4-thiadiazol-2-yl)-5'-methoxy-6-methyl-[4,4'-bipyridine]-3-carboxamide

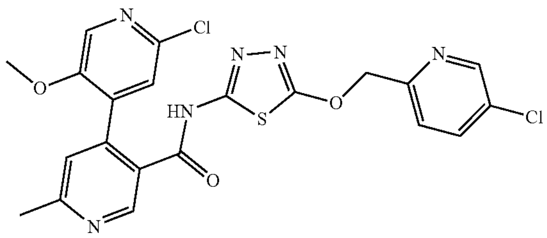 [SMILES: COc1cnc(Cl)cc1-c1cc(C)ncc1C(=O)Nc1nnc(OCc2ccc(Cl)cn2)s1]

A solution of 2'-chloro-5'-methoxy-6-methyl-(4,4'-bipyridine)-3-carboxylic acid (25.0 mg, 0.09 mmol), 5-((5-chloropyridin-2-yl) methoxy)-1,3,4-thiadiazol-2-amine (23.9 mg, 0.09 mmol), HOBt (15.7 mg, 0.11 mmol), EDCI (22.3 mg, 0.11 mmol) and DIEA (23.1 mg, 0.17 mmol) in DMF (1 mL) was stirred at room temperature for 16 h. The solution was purified by reverse flash chromatography with 5-62% ACN in water to afford crude product (19.0 mg). The crude product (19.0 mg) was further purified by Prep-HPLC with the following conditions: (Column: X Bridge Prep OBD C18 Column, 30×150 mm 5 um; Mobile Phase A: Water (10 MMOL/L $NH_4HCO_3$+0.1% $NH_3 \cdot H_2O$), Mobile Phase B: ACN; Flow rate: 60 mL/min; Gradient: 20% B to 45% B in 8 min; 220 nm; RT1: 7.23 min) to afford 2'-chloro-N-(5-((5-chloropyridin-2-yl)methoxy)-1,3,4-thiadiazol-2-yl)-5'-methoxy-6-methyl-[4,4'-bipyridine]-3-carboxamide (6.3 mg, 13%) as a white solid. MS (ESI) calc'd for ($C_{21}H_{16}Cl_2N_6O_3S$) $(M+1)^+$, 503.0, found 502.9. $^1$H NMR (400 MHz, DMSO-$d_6$) δ 12.95 (s, 1H), 8.81 (s, 1H), 8.66 (d, J=2.4 Hz, 1H), 8.17 (s, 1H), 8.05-7.97 (m, 1H), 7.61 (d, J=8.4 Hz, 1H), 7.55 (s, 1H), 7.44 (s, 1H), 5.55 (s, 2H), 3.63 (s, 3H), 2.59 (s, 3H).

Example 9

N-(5-((5-chloropyridin-2-yl)methoxy)-1,3,4-thiadiazol-2-yl)-2-(2-methoxyphenyl)-1,5-naphthyridine-3-carboxamide

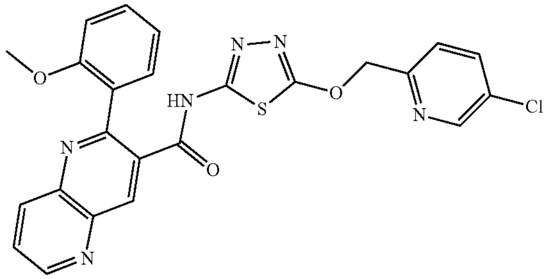 [SMILES: COc1ccccc1-c1nc2cccnc2cc1C(=O)Nc1nnc(OCc2ccc(Cl)cn2)s1]

Step-1: methyl 3-(3-ethoxy-3-oxopropanamido)picolinate

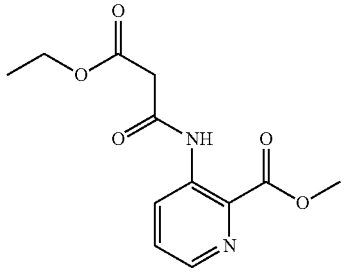 [SMILES: CCOC(=O)CC(=O)Nc1cccnc1C(=O)OC]

To a stirred solution of methyl 3-aminopicolinate (5000.0 mg, 32.86 mmol) in dichloromethane (40.0 mL) was added ethyl 3-chloro-3-oxopropanoate (4947.6 mg, 32.86 mmol) at room temperature. The resulting mixture was stirred at 80° C. for 2 h under $N_2$. The resulting mixture was quenched by saturated $NaHCO_3$ aqueous solution and extracted with dichloromethane. The combined organic layers were washed with brine, dried over anhydrous sodium sulfate and filtered. The filtrate was concentrated under reduced pressure to afford methyl 3-(3-ethoxy-3-oxopropanamido)picolinate (7750 mg, crude) as a yellow solid. MS (ESI) calc'd for ($C_{12}H_{14}N_2O_5$) $(M+1)^+$, 267.1, found 267.0.

Step-2: ethyl 4-hydroxy-2-oxo-1,2-dihydro-1,5-naphthyridine-3-carboxylate

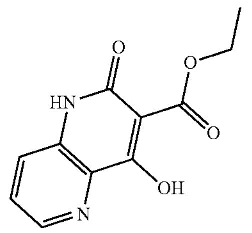 [SMILES: CCOC(=O)c1c(O)c2ncccc2[nH]c1=O]

To a stirred solution of methyl 3-(3-ethoxy-3-oxopropanamido)picolinate (7750.0 mg, 29.10 mmol) in EtOH (50.0 mL) were added EtONa (2376.9 mg, 34.92 mmol). The resulting mixture was stirred at 50° C. for 1 h under $N_2$. The resulting mixture was concentrated under vacuum and washed with ethyl acetate to afford ethyl 4-hydroxy-2-oxo-1,2-dihydro-1,5-naphthyridine-3-carboxylate (6500 mg crude) as a yellow solid. MS (ESI) calc'd for ($C_{11}H_{10}N_2O_4$) $(M+1)^+$, 235.1, found 235.0.

Step-3: ethyl 2,4-dichloro-1,5-naphthyridine-3-carboxylate

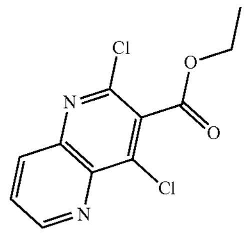 [SMILES: CCOC(=O)c1c(Cl)nc2cccnc2c1Cl]

To a stirred mixture of ethyl 4-hydroxy-2-oxo-1,2-dihydro-1,5-naphthyridine-3-carboxylate (5000.0 mg, 21.34 mmol) was added $POCl_3$ (250 mL) in portions at room temperature. The resulting mixture was stirred at 130° C. for 48 h under $N_2$. The mixture was allowed to cool down to room temperature and concentrated under vacuum. The residue was poured into ice water and basified to pH 10 with saturated $Na_2CO_3$ (aq.). The resulting mixture was extracted with ethyl acetate. The combined organic layers were washed with brine, dried over anhydrous $Na_2SO_4$. After filtration, the filtrate was concentrated under reduced pressure. The residue was purified by flash chromatography with 0~27% ethyl acetate in petroleum ether to afford ethyl 2,4-dichloro-1,5-naphthyridine-3-carboxylate (1120 mg, 20%) as a dark yellow solid. MS (ESI) calc'd for ($C_{11}H_8Cl_2N_2O_2$) $(M+1)^+$, 271.0, found 270.0.

Step-4: ethyl 4-chloro-2-(2-methoxyphenyl)-1,5-naphthyridine-3-carboxylate

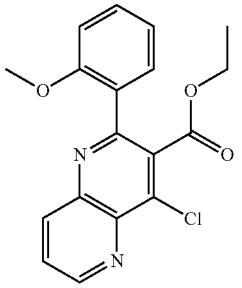 [SMILES: CCOC(=O)c1c(-c2ccccc2OC)nc2cccnc2c1Cl]

To a stirred mixture of ethyl 2,4-dichloro-1,5-naphthyridine-3-carboxylate (135.0 mg, 0.49 mmol) in 1,4-dioxane (5 mL) and $H_2O$ (1 mL) were added (2-methoxyphenyl)boronic acid (75.6 mg, 0.49 mmol), $K_2CO_3$ (206.4 mg, 1.49 mmol) and Pd(dppf)$Cl_2$ (36.4 mg, 0.05 mmol). The resulting mixture was stirred at 80° C. for 2 h under $N_2$. The resulting mixture was quenched with water and extracted with ethyl acetate. The combined organic layers were washed with brine, dried over anhydrous $Na_2SO_4$. After filtration, the filtrate was concentrated under reduced pressure. The residue was purified by flash chromatography with 0~32% ethyl acetate in petroleum ether to afford a mixture of ethyl 4-chloro-2-(2-methoxyphenyl)-1,5-naphthyridine-3-carboxylate and ethyl 2-chloro-4-(2-methoxyphenyl)-1,5-naphthyridine-3-carboxylate (510 mg, 66%) as off-white solid. MS (ESI) calc'd for ($C_{17}H_{17}ClN_2O_3$) $(M+1)^+$, 333.1, found 333.0.

Step-5: ethyl 2-(2-methoxyphenyl)-1,5-naphthyridine-3-carboxylate

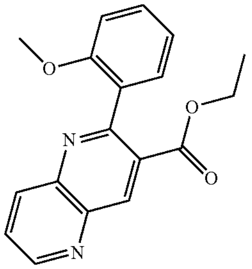 [SMILES: CCOC(=O)c1cc2ncccc2nc1-c1ccccc1OC]

To a stirred solution of the mixture of ethyl 4-chloro-2-(2-methoxyphenyl)-1,5-naphthyridine-3-carboxylate and ethyl 2-chloro-4-(2-methoxyphenyl)-1,5-naphthyridine-3-carboxylate (240.0 mg, 0.70 mmol) in DMF (3.0 mL) were added TEA (212.5 mg, 2.10 mmol), CHOOH (161.0 mg, 3.50 mmol) and Pd(dppf)$Cl_2$ (51.2 mg, 0.07 mmol). The resulting mixture was stirred at 60° C. for 3 h under $N_2$. The resulting mixture was quenched with water and extracted with ethyl acetate. The combined organic layers were washed with brine, dried over anhydrous $Na_2SO_4$. After filtration, the filtrate was concentrated under reduced pressure. The residue was purified by flash column chromatography with 0~37% ethyl acetate in petroleum ether to afford a mixture of ethyl 2-(2-methoxyphenyl)-1,5-naphthyridine-3-carboxylate and ethyl 4-(2-methoxyphenyl)-1,5-naphthyridine-3-carboxylate (210 mg, 97%) as a yellow oil. MS (ESI) calc'd for ($C_{18}H_{16}N_2O_3$) (M+1)$^+$, 309.1, found 309.0.

Step-6: 2-(2-methoxyphenyl)-1,5-naphthyridine-3-carboxylic acid

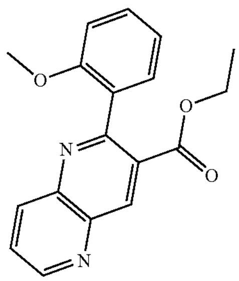 [SMILES: CCOC(=O)c1cc2ncccc2nc1-c1ccccc1OC]

To a stirred solution of the mixture of ethyl 2-(2-methoxyphenyl)-1,5-naphthyridine-3-carboxylate and ethyl 4-(2-methoxyphenyl)-1,5-naphthyridine-3-carboxylate (230.0 mg, 0.74 mmol) in EtOH (4 mL) and $H_2O$ (4.0 mL) was added NaOH (149.1 mg, 3.73 mmol). The resulting mixture was stirred at room temperature for 1.5 h. The residue was acidified to pH 7 with HCl (1 N). The resulting mixture was extracted with ethyl acetate, dried over anhydrous $Na_2SO_4$. After filtration, the filtrate was concentrated under reduced pressure to afford a mixture of 2-(2-methoxyphenyl)-1,5-naphthyridine-3-carboxylic acid and 4-(2-methoxyphenyl)-1,5-naphthyridine-3-carboxylic acid and ethyl 4-(2-methoxyphenyl)-1,5-naphthyridine-3-carboxylate (100 mg, 48%) as an off-white solid. MS (ESI) calc'd for ($C_{16}H_{12}N_2O_3$) (M+1)$^+$, 281.1, found 281.0.

Step-7: N-(5-((5-chloropyridin-2-yl)methoxy)-1,3,4-thiadiazol-2-yl)-2-(2-methoxyphenyl)-1,5-naphthyridine-3-carboxamide

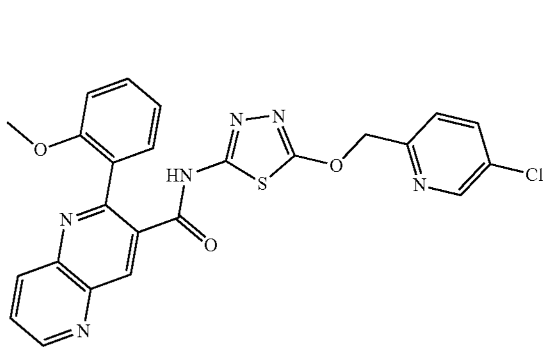 [SMILES: COc1ccccc1-c1nc2cccnc2cc1C(=O)Nc1nnc(OCc2ccc(Cl)cn2)s1]

To a stirred solution of the mixture of 2-(2-methoxyphenyl)-1,5-naphthyridine-3-carboxylic acid and 4-(2-methoxyphenyl)-1,5-naphthyridine-3-carboxylic acid and ethyl 4-(2-methoxyphenyl)-1,5-naphthyridine-3-carboxylate (80.0 mg, 0.28 mmol) in acetonitrile (3.0 mL) were added TCFH (88.0 mg, 0.31 mmol), 5-((5-chloropyridin-2-yl)methoxy)-1,3,4-thiadiazol-2-amine (83.1 mg, 0.34 mmol, Intermediate C) and NMI (49.2 mg, 0.59 mmol). The resulting mixture was stirred at room temperature for 1.5 h. The resulting mixture was concentrated under vacuum. The crude product was purified and separated by Prep-HPLC with the following conditions: (Column: XBridge Prep OBD C18 Column, 30×150 mm 5 um; Mobile Phase A: Water (10 MMOL/L $NH_4HCO_3$+0.1% $NH_3 \cdot H_2O$), Mobile Phase B:ACN; Flow rate: 60 mL/min; Gradient: 20 B to 45 B in 7 min; 220 nm; RT1: 5.87 min) to afford N-(5-((5-chloropyridin-2-yl)methoxy)-1,3,4-thiadiazol-2-yl)-2-(2-methoxyphenyl)-1,5-naphthyridine-3-carboxamide (8.0 mg). MS (ESI) calc'd for ($C_{24}H_{17}ClN_6O_3S$) (M+1)$^+$, 505.1, found 505.1. $^1H$ NMR (400 MHz, DMSO-$d_6$) δ 13.09 (s, 1H), 9.11-9.10 (m, 1H), 8.70-8.66 (m, 2H), 8.51 (d, J=8.0 Hz, 1H), 8.03-8.01 (m, 1H), 7.92-7.89 (m, 1H), 7.67-7.62 (m, 2H), 7.48-7.43 (m, 1H), 7.15-7.11 (m, 1H), 7.01 (d, J=8.4 Hz, 1H), 5.57 (s, 2H), 3.53 (s, 3H).

Example 10

N-(5-((1H-pyrazolo(4,3-c)pyridin-4-yl)methoxy)-1,3,4-thiadiazol-2-yl)-4-(2-methoxyphenyl)-6-methylnicotinamide

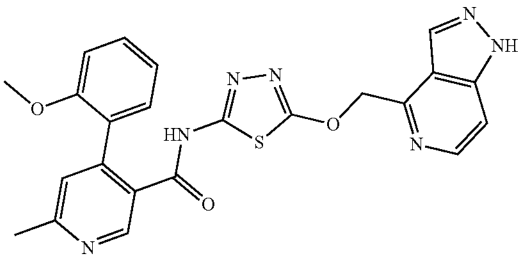 [SMILES: COc1ccccc1-c1cc(C)ncc1C(=O)Nc1nnc(OCc2nccc3[nH]ncc23)s1]

Step-1: 4-chloro-1-((2-(trimethylsilyl)ethoxy)methyl)-1H-pyrazolo(4,3-c)pyridine

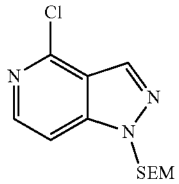 [SMILES: C[Si](C)(C)CCOCn1ncc2c(Cl)nccc21]

To a solution of NaH (392 mg, 9.802 mmol, 60%) in THF (10 mL) was added 4-chloro-1H-pyrazolo(4,3-c)pyridine (1 g, 6.535 mmol) at 0° C. and stirred at 5° C. for 0.5 h, then SEM-Cl (1.3 g, 7.842 mmol) was added to the mixture dropwise at 5° C. and stirred at 5° C. for 5 h. The reaction mixture was then quenched by the addition of water and extracted with ethyl acetate. The combined organic layers were washed with brine, dried over anhydrous sodium sulfate, filtered, and concentrated under vacuum. The residue was purified by flash chromatography on silica gel with 0~10% methanol in dichloromethane to afford 4-chloro-1-((2-(trimethylsilyl)ethoxy)methyl)-1H-pyrazolo(4,3-c)pyridine (900 mg, 50%) as a white solid. MS (ESI) calc'd for ($Cl_2H_{18}ClN_3OSi$) $(M+1)^+$, 284.1; found, 284.1.

Step-2: methyl 1-((2-(trimethylsilyl)ethoxy)methyl)-1H-pyrazolo(4,3-c)pyridine-4-carboxylate

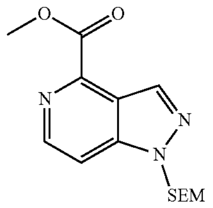 [SMILES: COC(=O)c1nccc2c1cnn2COCC[Si](C)(C)C]

To a degassed solution of 4-chloro-1-((2-(trimethylsilyl)ethoxy)methyl)pyrazolo(4,3-c)pyridine (1 g, 3.523 mmol) in MeOH (10 mL) was added TEA (2 mL) and $Pd(PPh_3)_2Cl_2$ (0.25 g, 0.352 mmol). The resulting solution was stirred at 80° C. for 24 h under CO (10 atm). The resulting mixture was concentrated. The residue was purified by flash chromatography on silica gel with 0~50% ethyl acetate in petroleum ether to afford methyl 1-((2-(trimethylsilyl)ethoxy)methyl)pyrazolo(4,3-c)pyridine-4-carboxylate (1 g, 83.1%) as a yellow oil. MS (ESI) calc'd for ($C_{14}H_{21}N_3O_3Si$) $(M+1)^+$, 308.1; found 308.1.

Step-3: (1-((2-(trimethylsilyl)ethoxy)methyl)-1H-pyrazolo(4,3-c)pyridin-4-yl)methanol

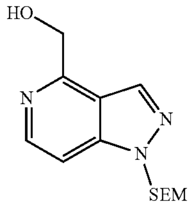 [SMILES: C[Si](C)(C)CCOCn1ncc2c(CO)nccc21]

To a solution of methyl 1-((2-(trimethylsilyl)ethoxy)methyl)pyrazolo(4,3-c)pyridine-4-carboxylate (1 g, 3.257 mmol) in THF (20 mL) was added $LiAlH_4$ (248 mg, 6.514 mmol) in portions at 0° C. The resulting solution was stirred at 0° C. for 1 h. The reaction mixture was diluted with water and extracted with ethyl acetate. The combined organic layers were washed with brine, dried over anhydrous sodium sulfate, filtered, and concentrated under vacuum to afford (1-((2-(trimethylsilyl)ethoxy)methyl)-1H-pyrazolo(4,3-c)pyridin-4-yl)methanol (800 mg, 80%) as a yellow solid. MS (ESI) calc'd for ($C_{13}H_{21}N_3O_2Si$) $(M+1)^+$, 280.1; found, 280.1.

Step-4: 5-((1-((2-(trimethylsilyl)ethoxy)methyl)-1H-pyrazolo(4,3-c)pyridin-4-yl)methoxy)-1,3,4-thiadiazol-2-amine

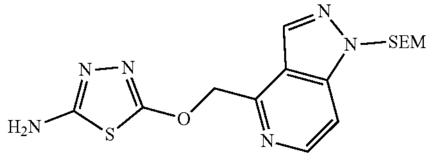 [SMILES: C[Si](C)(C)CCOCn1ncc2c(COc3nnc(N)s3)nccc21]

To a solution of NaH (108 mg, 2.684 mmol, 60%) in THF (8 mL) was added (1-((2-(trimethylsilyl)ethoxy)methyl)pyrazolo(4,3-c)pyridin-4-yl)methanol (500 mg, 1.789 mmol) at 0° C. and stirred at 0~5° C. for 1 h, then 5-bromo-1,3,4-thiadiazol-2-amine (387 mg, 2.147 mmol) was added to the mixture in small portions at 5° C. and stirred at 5° C. for 5 h. The reaction mixture was then quenched by the addition of water and extracted with ethyl acetate. The combined organic layers were washed with brine, dried over anhydrous sodium sulfate, filtered, and concentrated under vacuum. The residue was purified by flash chromatography on silica gel with 0~10% methanol in dichloromethane to afford 5-((1-((2-(trimethylsilyl)ethoxy)methyl)pyrazolo(4,3-c)pyridin-4-yl)methoxy)-1,3,4-thiadiazol-2-amine (200 mg, 29.5%) as a yellow solid. MS (ESI) calc'd for ($C_{13}H_{21}N_3O_2Si$) $(M+1)^+$, 379.1; found, 379.1.

Step-5: 4-(2-methoxyphenyl)-6-methyl-N-(5-((1-((2-(trimethylsilyl)ethoxy)methyl)-1H-pyrazolo(4,3-c)pyridin-4-yl)methoxy)-1,3,4-thiadiazol-2-yl)nicotinamide

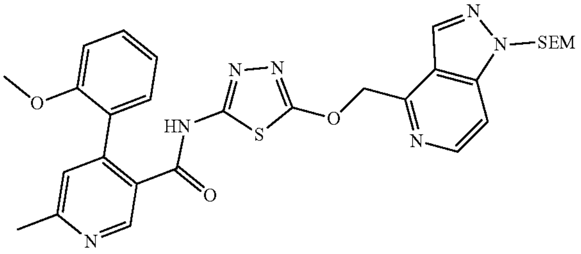 [SMILES: COc1ccccc1-c1cc(C)ncc1C(=O)Nc1nnc(OCc2nccc3c2cnn3COCC[Si](C)(C)C)s1]

To a solution of 5-((1-((2-(trimethylsilyl)ethoxy)methyl)pyrazolo(4,3-c)pyridin-4-yl)methoxy)-1,3,4-thiadiazol-2-amine (180 mg, 0.476 mmol) in DMF (10 mL) were added HATU (361 mg, 0.951 mmol), DIEA (185 mg, 1.427 mmol) and 4-(2-methoxyphenyl)-6-methylpyridine-3-carboxylic acid (174 mg, 0.713 mmol, Intermediate D). The resulting solution was stirred at room temperature for 2 h. The mixture was diluted with water and extracted with ethyl acetate. The combined organic layers were washed with brine, dried over anhydrous sodium sulfate, filtered, and concentrated under vacuum. The residue was purified by flash chromatography on silica gel with 0~10% methanol in dichloromethane to afford 4-(2-methoxyphenyl)-6-methyl-N-(5-((1-((2-(trimethylsilyl)ethoxy)methyl)-1H-pyrazolo(4,3-c)pyridin-4-yl)methoxy)-1,3,4-thiadiazol-2-yl)nicotinamide (150 mg, 25%) as a yellow solid. MS (ESI) calc'd for ($C_{15}H_{22}N_6O_2SSi$) $(M+1)^+$, 604.2; found, 604.2.

Step-6: N-(5-((1H-pyrazolo(4,3-c)pyridin-4-yl) methoxy)-1,3,4-thiadiazol-2-yl)-4-(2-methoxyphenyl)-6-methylnicotinamide

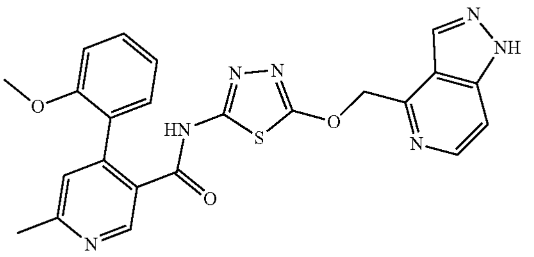 [SMILES: COc1ccccc1-c1cc(C)ncc1C(=O)Nc1nnc(OCc2nccc3[nH]ncc23)s1]

To a solution of 4-(2-methoxyphenyl)-6-methyl-N-(5-((1-((2-(trimethylsilyl)ethoxy)methyl)pyrazolo(4,3-c)pyridin-4-yl)methoxy)-1,3,4-thiadiazol-2-yl)pyridine-3-carboxamide (100 mg, 0.166 mmol) in THF (3 mL) was added TBAF (260 mg, 0.994 mmol) and CsF (252 mg, 1.656 mmol). The resulting solution was stirred at 60° C. for 12 h before concentrated under vacuum. The residue was purified by flash column chromatography with 0~10% methanol in dichloromethane and further purification with following condition: (Column: XBridge Prep OBD C18 Column, 30×150 mm 5 um; Mobile Phase A: Water (10 MMOL/L $NH_4HCO_3$+0.1% $NH_3 \cdot H_2O$), Mobile Phase B: ACN; Flow rate: 60 mL/min; Gradient: 15 B to 40 B in 8 min; 220 nm; RT1: 6.23 min) to afford 4-(2-methoxyphenyl)-6-methyl-N-(5-(1H-pyrazolo(4,3-c)pyridin-4-ylmethoxy)-1,3,4-thiadiazol-2-yl)pyridine-3-carboxamide (4 mg, 10.7%) as a white solid. MS (ESI) calc'd for ($C_{23}H_{19}N_7O_3S$) $(M+1)^+$, 474.1; found, 474.1. $^1$H NMR (400 MHz, DMSO-$d_6$) δ 13.80 (s, 1H), 12.87 (s, 1H), 8.66 (s, 1H), 8.47 (s, 1H), 8.39 (s, 1H), 7.55 (s, 1H), 7.41-7.33 (m, 2H), 7.11-7.05 (m, 3H), 5.85 (s, 2H), 3.50 (s, 3H), 2.51 (s, 3H).

Example 11 and 12

(S)—N-(5-(1-(5-chloropyridin-2-yl)ethoxy)-1,3,4-thiadiazol-2-yl)-4-(2-methoxyphenyl)-6-methylnicotinamide (Example 11) and (R)—N-(5-(1-(5-chloropyridin-2-yl)ethoxy)-1,3,4-thiadiazol-2-yl)-4-(2-methoxyphenyl)-6-methylnicotinamide (Example 12)

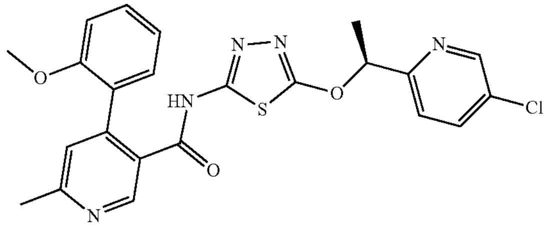

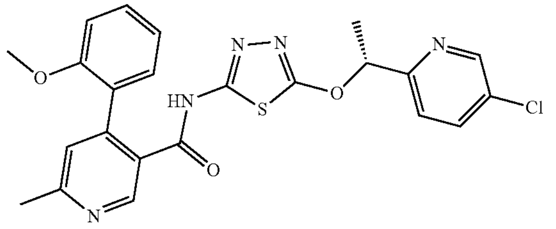

Step-1: 1-(5-chloropyridin-2-yl)ethan-1-ol

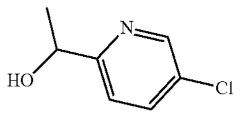

To a solution of 1-(5-chloropyridin-2-yl)ethanone (3.0 g, 9.3 mmol) in MeOH (30 mL) was added $NaBH_4$ (763 mg, 20.2 mmol) in portions at 0° C. The mixture was stirred at room temperature for 2 h. The reaction mixture was quenched by the addition of water and extracted with ethyl acetate. The combined organic layers were washed with brine, dried over anhydrous sodium sulfate, filtered, and concentrated under vacuum to afford 1-(5-chloropyridin-2-yl)ethan-1-ol (2.5 g, 82.2%) as a yellow oil. MS (ESI) calc'd for ($C_7H_8ClNO$) $(M+1)^+$, 158.0, found 158.0.

Step-2: 5-(2-(5-chloropyridin-2-yl)ethoxy)-1,3,4-thiadiazol-2-amine

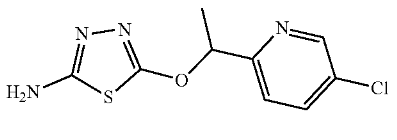 [SMILES: CC(Oc1nnc(N)s1)c1ccc(Cl)cn1]

To a solution of NaH (77 mg, 1.9 mmol, 60%) in THF (5 mL) was added a solution of 1-(5-chloropyridin-2-yl)ethan-1-ol (200 mg, 1.2 mmol) in THF (1 mL) at 0° C. and stirred at 0° C. for 30 min under nitrogen. To the above solution was added 5-bromo-1,3,4-thiadiazol-2-amine (455 mg, 2.5 mmol) at 0° C. under nitrogen. The mixture was stirred at room temperature for 4 h. The reaction mixture was quenched by the addition of water and extracted with ethyl acetate. The combined organic layers were washed with brine, dried over anhydrous sodium sulfate, filtered, and concentrated under vacuum. The residue was purified by flash chromatography on silica gel with 0~50% ethyl acetate in petroleum ether to afford 5-(1-(5-chloropyridin-2-yl)ethoxy)-1,3,4-thiadiazol-2-amine (60 mg, 18.4%) as a yellow solid. MS (ESI) calc'd for ($C_9H_9ClN_4OS$) $(M+1)^+$, 257.0, found 257.0.

Step-3 & Step-4: (S)—N-(5-(1-(5-chloropyridin-2-yl)ethoxy)-1,3,4-thiadiazol-2-yl)-4-(2-methoxyphenyl)-6-methylnicotinamide and (R)—N-(5-(1-(5-chloropyridin-2-yl)ethoxy)-1,3,4-thiadiazol-2-yl)-4-(2-methoxyphenyl)-6-methylnicotinamide

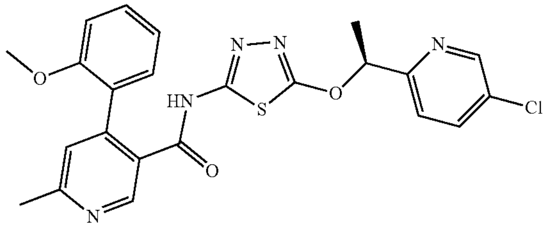

-continued

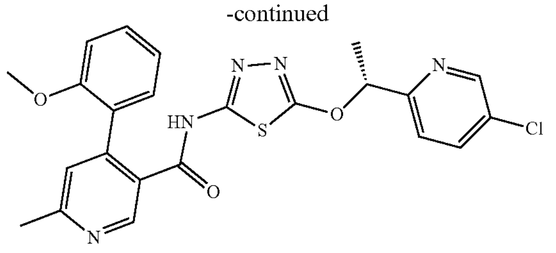

To a solution of 5-(1-(5-chloropyridin-2-yl)ethoxy)-1,3,4-thiadiazol-2-amine (52 mg, 0.2 mmol) in DMF (2 mL) were added DIEA (78 mg, 0.6 mmol), HATU (116 mg, 0.3 mmol) and 4-(2-methoxyphenyl)-6-methylnicotinic acid (50 mg, 0.2 mmol, Intermediate D). The mixture was stirred at room temperature for 16 h. The mixture was quenched with water and extracted with ethyl acetate. The combined organic layers were washed with brine, dried over anhydrous sodium sulfate, filtered, and concentrated under vacuum. The residue was purified by flash chromatography on silica gel with 0~10% methanol in dichloromethane to afford the racemic product, which was further separated by prep-HPLC with the following conditions: (Column: CHIRALPAK ID, 2*25 cm, 5 um; Mobile Phase A: Hex (0.2% DEA)-HPLC, Mobile Phase B: EtOH:DCM=1:1-HPLC; Flow rate: 20 mL/min; Gradient: 45 B to 45 B in 13 min; 220/254 nm) to afford (S)—N-(5-(1-(5-chloropyridin-2-yl)ethoxy)-1,3,4-thiadiazol-2-yl)-4-(2-methoxyphenyl)-6-methylnicotinamide (7.8 mg, 8%) as a white solid with shorter retention time on chiral-HPLC and (R)—N-(5-(1-(5-chloropyridin-2-yl)ethoxy)-1,3,4-thiadiazol-2-yl)-4-(2-methoxyphenyl)-6-methylnicotinamide (5.7 mg, 7%) as a white solid with longer retention time on chiral-HPLC.

(S)—N-(5-(1-(5-chloropyridin-2-yl)ethoxy)-1,3,4-thiadiazol-2-yl)-4-(2-methoxyphenyl)-6-methylnicotinamide: MS (ESI) calc'd for ($C_{23}H_{20}ClN_5O_3S$) $(M+1)^+$, 482.1; found 482.2. $^1H$ NMR (400 MHz, DMSO-$d_6$) δ 12.71 (s, 1H), 8.64 (s, 2H), 7.98-7.96 (m, 1H), 7.58-7.55 (m, 1H), 7.41-6.96 (m, 5H), 6.04-5.99 (m, 1H), 3.49 (s, 3H), 2.52 (s, 3H), 1.66 (d, J=6.4 Hz, 3H).

(R)—N-(5-(1-(5-chloropyridin-2-yl)ethoxy)-1,3,4-thiadiazol-2-yl)-4-(2-methoxyphenyl)-6-methylnicotinamide: MS (ESI) calc'd for ($C_{23}H_{20}ClN_5O_3S$) $(M+1)^+$, 482.1; found 482.2. $^1H$ NMR (400 MHz, DMSO-$d_6$) δ 12.71 (s, 1H), 8.64 (s, 2H), 7.98-7.96 (m, 1H), 7.58-7.55 (m, 1H), 7.41-7.30 (m, 3H), 7.09-6.96 (m, 2H), 6.04-5.99 (m, 1H), 3.49 (s, 3H), 2.52 (s, 3H), 1.66 (d, J=6.4 Hz, 3H).

Example 13

N-(5-((5-chloropyridin-2-yl)methoxy)-1,3,4-thiadiazol-2-yl)-4-(5-fluoro-2-methoxyphenyl)-6-methylnicotinamide

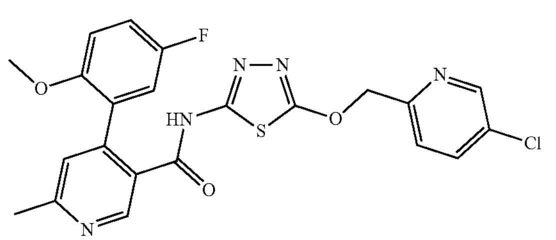 [SMILES: COc1ccc(F)cc1-c1cc(C)ncc1C(=O)Nc1nnc(OCc2ccc(Cl)cn2)s1]

Step-1: 4-chloro-N-(5-((5-chloropyridin-2-yl)methoxy)-1,3,4-thiadiazol-2-yl)-6-methylnicotinamide

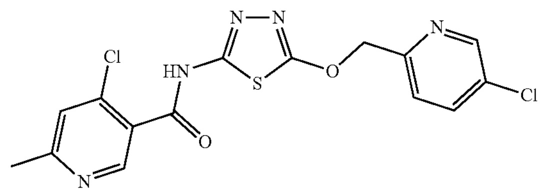 [SMILES: Cc1cc(Cl)c(C(=O)Nc2nnc(OCc3ccc(Cl)cn3)s2)cn1]

To a mixture of 4-chloro-6-methylnicotinic acid (5.0 g, 29.23 mmol) in DCM (50 mL) were added oxalyl chloride (4.42 g, 35.08 mmol) and DMF (1 mL). The mixture was stirred at room temperature for 2 h. The solvents were removed under vacuum to afford 4-chloro-6-methylnicotinoyl chloride.

To a mixture of 5-((5-chloropyridin-2-yl)methoxy)-1,3,4-thiadiazol-2-amine (5.11 g, 21.050 mmol, Intermediate C) and DIEA (8.16 g, 63.151 mmol) in DCM (100 mL) was added the above solution of 4-chloro-6-methylnicotinoyl chloride in DCM (50 mL) dropwise at 0° C. The reaction mixture was diluted with water and extracted with ethyl acetate. The combined organic layers were washed with brine, dried over anhydrous sodium sulfate, filtered, and concentrated under vacuum. The residue was purified by flash column chromatography with 0~10% methanol in dichloromethane to afford 4-chloro-N-(5-((5-chloropyridin-2-yl)methoxy)-1,3,4-thiadiazol-2-yl)-6-methylpyridine-3-carboxamide (1.8 g, 21.58%) as a yellow solid. MS (ESI) calc'd for ($C_{15}H_{11}Cl_2N_5O_2S$) $(M+1)^+$, 396.0; found, 396.0.

Step-2: N-(5-((5-chloropyridin-2-yl)methoxy)-1,3,4-thiadiazol-2-yl)-4-(5-fluoro-2-methoxyphenyl)-6-methylnicotinamide

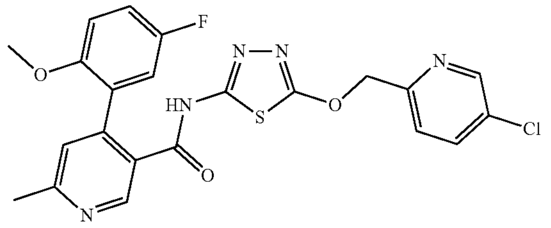 [SMILES: COc1ccc(F)cc1-c1cc(C)ncc1C(=O)Nc1nnc(OCc2ccc(Cl)cn2)s1]

To a degassed solution of 4-chloro-N-(5-((5-chloropyridin-2-yl)methoxy)-1,3,4-thiadiazol-2-yl)-6-methylnicotinamide (156 mg, 0.394 mmol) in dioxane (7 mL) and $H_2O$ (1.4 mL) were added (5-fluoro-2-methoxyphenyl)boronic acid (201 mg, 1.182 mmol), $K_3PO_4$ (418 mg, 1.972 mmol) and Pd(dtbpf)$Cl_2$ (30 mg, 0.046 mmol). The resulting solution was stirred at 100° C. for 8 h. The aqueous solution was concentrated under vacuum. The residue was purified by flash chromatography on silica gel with 0~10% methanol in dichloromethane and further purified by prep-HPLC with the following conditions: (Column: Sunfire prep C18 column, 30*150, 5 um; Mobile Phase A: Water (0.1% FA), Mobile Phase B: ACN; Flow rate: 40 mL/min; Gradient: 25 B to 55 B in 8 min; 220 nm; RT1: 7.23 min) to afford N-(5-((5-chloropyridin-2-yl)methoxy)-1,3,4-thiadiazol-2-yl)-4-(5-fluoro-2-methoxyphenyl)-6-methylnicotinamide (13 mg, 8.3%) as a white solid. MS (ESI) calc'd for ($C_{22}H_{17}ClFN_5O_3S$) $(M+1)^+$, 486.1; found, 486.1. $^1H$ NMR (400 MHz, DMSO-$d_6$) δ 12.70 (s, 1H), 8.70-8.65 (m, 2H), 8.01-7.99 (m, 1H), 7.62-7.60 (m, 1H), 7.34-7.20 (m, 3H), 7.00-6.97 (m, 1H), 5.54 (s, 2H), 3.53 (s, 3H), 2.57 (s, 3H).

Example 14

4-(2-fluoro-6-methoxyphenyl)-N-(5-((5-(hydroxymethyl)pyridin-2-yl)methoxy)-1,3,4-thiadiazol-2-yl)-6-methylpyridine-3-carboxamide

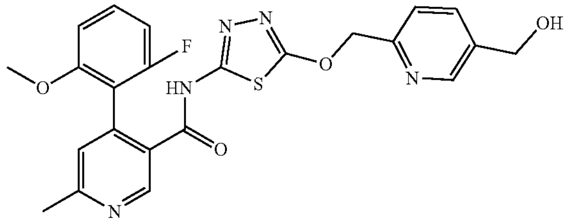 [SMILES: COc1cccc(F)c1-c1cc(C)ncc1C(=O)Nc1nnc(OCc2ccc(CO)cn2)s1]

Step-1: methyl 6-(((5-(4-(2-fluoro-6-methoxyphenyl)-6-methylpyridine-3-amido)-1,3,4-thiadiazol-2-yl)oxy)methyl)pyridine-3-carboxylate

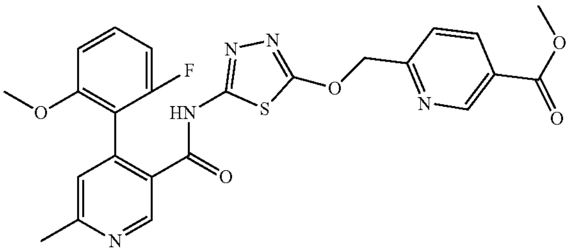 [SMILES: COC(=O)c1ccc(COc2nnc(NC(=O)c3cnc(C)cc3-c3c(F)cccc3OC)s2)nc1]

To a mixture of methyl 6-(((5-amino-1,3,4-thiadiazol-2-yl)oxy)methyl)pyridine-3-carboxylate (150 mg, 0.563 mmol, Example 5, Step 1) and 4-(2-fluoro-6-methoxyphenyl)-6-methylpyridine-3-carboxylic acid (191 mg, 0.732 mmol, Intermediate F) in MeCN (4 mL) were added NMI (162 mg, 1.972 mmol) and TCFH (205 mg, 0.732 mmol). The resulting mixture was stirred at room temperature for 1 h under nitrogen atmosphere. The resulting mixture was diluted with water. The precipitated solids were collected by filtration and washed with CAN to afford 6-(((5-(4-(2-fluoro-6-methoxyphenyl)-6-methylpyridine-3-amido)-1,3,4-thiadiazol-2-yl)oxy)methyl)pyridine-3-carboxylate (220 mg, 76.6%) as a white solid. MS (ESI) calc'd for ($C_{24}H_{20}FN_5O_5S$) $(M+1)^+$, 509.5; found, 509.5.

Step-2: 4-(2-fluoro-6-methoxyphenyl)-N-(5-((5-(hydroxymethyl)pyridin-2-yl)methoxy)-1,3,4-thiadiazol-2-yl)-6-methylpyridine-3-carboxamide

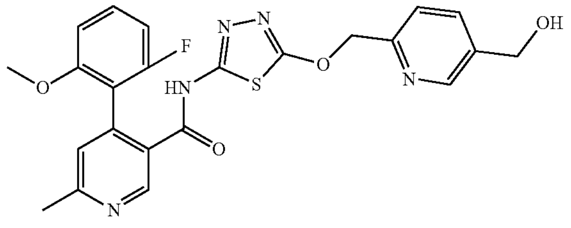 [SMILES: COc1cccc(F)c1-c1cc(C)ncc1C(=O)Nc1nnc(OCc2ccc(CO)cn2)s1]

To a mixture of methyl 6-(((5-(4-(2-fluoro-6-methoxyphenyl)-6-methylpyridine-3-amido)-1,3,4-thiadiazol-2-yl)oxy)methyl)pyridine-3-carboxylate (150 mg, 0.294 mmol) in THF (3 mL) was added $LiAlH_4$ (22 mg, 0.588 mmol) in portions at 0° C. under nitrogen atmosphere. The resulting mixture was stirred for 1 h at 0° C. under nitrogen atmosphere. The reaction mixture was diluted with water and extracted with ethyl acetate. The combined organic layers were washed with brine, dried over anhydrous sodium sulfate, filtered, and concentrated under vacuum. The residue was purified by prep-HPLC with the following conditions: (Column: XBridge Shield RP18 OBD Column, 30*150 mm, 5 um; Mobile Phase A: Water (10 mmol/L $NH_4HCO_3$+0.1% $NH_3 \cdot H_2O$), Mobile Phase B: ACN; Flow rate: 60 mL/min; Gradient: 17 B to 30 B in 8 min; 254/220 nm) to afford 4-(2-fluoro-6-methoxyphenyl)-N-(5-((5-(hydroxymethyl)pyridin-2-yl)methoxy)-1,3,4-thiadiazol-2-yl)-6-methylpyridine-3-carboxamide (52.8 mg, 37.2%) as a yellow solid. MS (ESI) calc'd for ($C_{23}H_{20}FN_5O_4S$) $(M+1)^+$, 482.0; found 482.0. $^1H$ NMR (400 MHz, DMSO-$d_6$) δ 12.89 (s, 1H), 8.81 (s, 1H), 8.53 (d, J=2.0 Hz, 1H), 7.82-7.75 (m, 1H), 7.51 (d, J=8.0 Hz, 1H), 7.46-7.36 (m, 1H), 7.33 (d, J=1.6 Hz, 1H), 6.97-6.86 (m, 2H), 5.52 (s, 2H), 5.39-5.32 (m, 1H), 4.55 (d, J=5.6 Hz, 2H), 3.59 (s, 3H), 2.57 (s, 3H).

Example 15

4-(2-fluoro-6-methoxyphenyl)-6-methyl-N-(5-((1-methylpyrazol-3-yl)methoxy)-1,3,4-thiadiazol-2-yl)pyridine-3-carboxamide

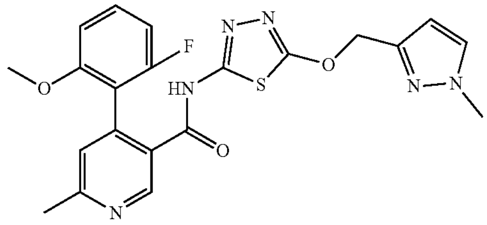

Step-1: 5-((1-methylpyrazol-3-yl)methoxy)-1,3,4-thiadiazol-2-amine

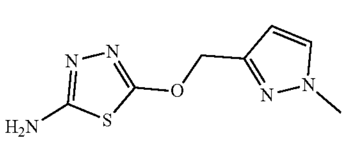

To a stirred solution of NaH (214 mg, 8.92 mmol) in THF (6 mL) was added a solution of (1-methylpyrazol-3-yl)methanol (500 mg, 4.46 mmol) in THF (2 mL) dropwise at 0° C. and stirred at 0° C. for 40 min under nitrogen atmosphere. 5-bromo-1,3,4-thiadiazol-2-amine (959 mg, 5.33 mmol) was added to the above mixture in portions at 0° C. The resulting mixture was stirred at 0° C. for 4 h under nitrogen atmosphere. The reaction mixture was quenched with water and extracted with ethyl acetate. The combined organic layers were washed with brine, dried over anhydrous sodium sulfate, filtered, and concentrated under vacuum. The residue was purified by reverse phase flash column chromatography with 5~80% ACN in water to afford 5-((1-methylpyrazol-3-yl)methoxy)-1,3,4-thiadiazol-2-amine (280 mg, 29.73%) as a white solid. MS (ESI) calc'd for ($C_7H_9N_5OS$) $(M+1)^+$, 212.1, found 211.9.

Step-2: 4-(2-fluoro-6-methoxyphenyl)-6-methyl-N-(5-((1-methylpyrazol-3-yl)methoxy)-1,3,4-thiadiazol-2-yl)pyridine-3-carboxamide

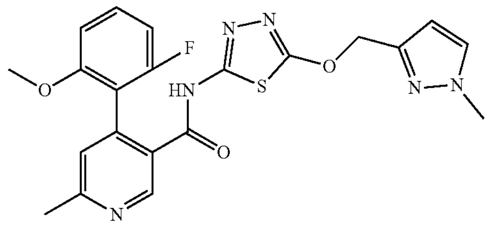

To a stirred solution 5-((1-methylpyrazol-3-yl)methoxy)-1,3,4-thiadiazol-2-amine (250 mg, 1.18 mmol) and 4-(2-fluoro-6-methoxyphenyl)-6-methylpyridine-3-carboxylic acid (206 mg, 0.79 mmol, Intermediate F) in MeCN (4.00 mL) were added NMI (259 mg, 3.15 mmol) and TCFH (288 mg, 1.03 mmol). The residue was purified by reverse phase flash column chromatography with 5~80% ACN in water and further purified by Prep-HPLC with the following conditions: (Column: XBridge Prep OBD C18 Column, 30×150 mm 5 um; Mobile Phase A: Water (10 MMOL/L $NH_4HCO_3$+0.1% $NH_3 \cdot H_2O$), Mobile Phase B: ACN; Flow rate: 60 mL/min; Gradient: 10 B to 45 B in 7 min; 220 nm; RT1:6.6 min) to afford 4-(2-fluoro-6-methoxyphenyl)-6-methyl-N-(5-((1-methylpyrazol-3-yl)methoxy)-1,3,4-thiadiazol-2-yl)pyridine-3-carboxamide (30 mg, 8.3%) as a white solid. MS (ESI) calc'd for ($C_{21}H_{19}FN_6O_3S$) $(M-1)^-$, 453.1, found 453.1. $^1H$ NMR (400 MHz, DMSO-$d_6$) δ 8.88 (s, 1H), 7.68 (d, J=2.0 Hz, 1H), 7.42-7.32 (m, 1H), 7.23 (s, 1H), 6.90-6.85 (m, 2H), 6.35 (d, J=2.4 Hz, 1H), 5.32 (s, 2H), 3.84 (s, 3H), 3.59 (s, 3H), 2.55 (s, 3H).

Example 16

N-(5-((5-chloropyridin-2-yl)methoxy)-1,3,4-thiadiazol-2-yl)-4-(3-fluoro-2-methoxyphenyl)-6-methylnicotinamide

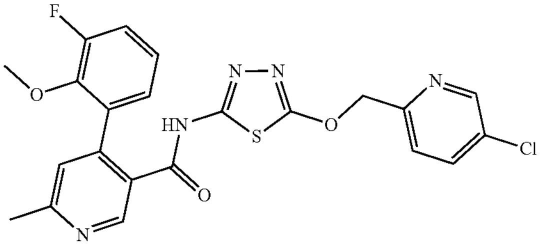 [SMILES: COc1c(F)cccc1-c1cc(C)ncc1C(=O)Nc1nnc(OCc2ccc(Cl)cn2)s1]

To a degassed solution of 4-chloro-N-(5-((5-chloropyridin-2-yl)methoxy)-1,3,4-thiadiazol-2-yl)-6-methylnicotinamide (150 mg, 0.379 mmol, Example 13, Step 1) in dioxane (3 mL) and $H_2O$ (0.6 mL) was added (3-fluoro-2-methoxyphenyl)boronic acid (194 mg, 1.141 mmol), $K_3PO_4$ (301 mg, 1.419 mmol) and Pd(dtbpf)$Cl_2$ (50 mg, 0.077 mmol) under nitrogen. The resulting solution was stirred at 100° C. for 8 h under nitrogen. The aqueous solution was concentrated under vacuum. The residue was purified by flash chromatography on silica gel with 0~10% methanol in dichloromethane and further purified by prep-HPLC with the following conditions: (Column: Sunfire prep C18 column, 30*150, 5 um; Mobile Phase A: Water (0.1% FA), Mobile Phase B: ACN; Flow rate: 40 mL/min; Gradient: 25 B to 55 B in 8 min; 220 nm; RT1: 7.23 min) to afford N-(5-((5-chloropyridin-2-yl)methoxy)-1,3,4-thiadiazol-2-yl)-4-(3-fluoro-2-methoxyphenyl)-6-methylnicotinamide (22.6 mg, 15.1%) as a white solid. MS (ESI) calc'd for ($C_{22}H_{17}ClFN_5O_3S$) $(M+1)^+$, 486.1; found, 486.1. $^1H$ NMR (400 MHz, DMSO-d6) δ 12.94 (s, 1H), 8.78 (s, 1H), 8.65 (s, 1H), 8.01-7.99 (m, 1H), 7.61-7.59 (m, 1H), 7.35-7.30 (m, 2H), 7.21-7.13 (m, 2H), 5.54 (s, 2H), 3.56 (s, 3H), 2.68 (s, 3H).

Example 17

4-(2-(difluoromethoxy)phenyl)-N-(5-((5-(hydroxymethyl)pyridin-2-yl)methoxy)-1,3,4-thiadiazol-2-yl)-6-methylpyridine-3-carboxamide

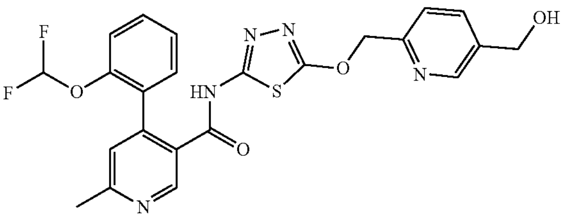 [SMILES: Cc1cc(-c2ccccc2OC(F)F)c(C(=O)Nc2nnc(OCc3ccc(CO)cn3)s2)cn1]

Step-1: 5-(methoxycarbonyl)-2-methylpyridin-4-ylboronic acid

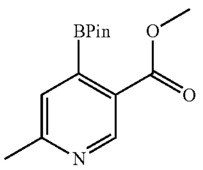

To a solution of methyl 4-chloro-6-methylpyridine-3-carboxylate (1.00 g, 5.388 mmo) and Pd(dppf)$Cl_2$ (1.18 g, 1.616 mmol) in dioxane (10.00 mL) were added AcOK (1.59 g, 16.163 mmol) and $B_2Pin$ (2.73 g, 10.775 mmol). The resulting solution was stirred at 80° C. for 3 hours under nitrogen atmosphere in sealed tube. The resulting mixture was used in the next step directly without further purification. MS (ESI) calc'd for ($C_8H_{10}BNO_4$) $(M+1)^+$, 196.0; found, 196.0.

Step-2: methyl 4-(2-(difluoromethoxy)phenyl)-6-methylpyridine-3-carboxylate

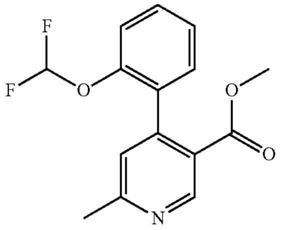 [SMILES: COC(=O)c1cnc(C)cc1-c1ccccc1OC(F)F]

To a solution of 5-(methoxycarbonyl)-2-methylpyridin-4-ylboronic acid (347.00 mg, 1.780 mmol) and 1-bromo-2-(difluoromethoxy)benzene (396.90 mg, 1.780 mmol) in dioxane (10.00 mL) and $H_2O$ (2 mL) were added Pd(dppf)$Cl_2$ (130.22 mg, 0.178 mmol) and $K_2CO_3$ (737.88 mg, 5.339 mmol). The resulting solution was stirred at 80° C. for 16 hours under nitrogen atmosphere in sealed tube. The resulting mixture was concentrated under vacuum. The residue was purified by flash column chromatography with 0~10% MeOH in DCM to afford methyl 4-(2-(difluoromethoxy) phenyl)-6-methylpyridine-3-carboxylate (551 mg, 68.62%) as a yellow oil. MS (ESI) calc'd for ($C_{15}H_{13}F_2NO_3$) $(M+1)^+$, 294.0; found, 294.0.

Step-3: 4-(2-(difluoromethoxy)phenyl)-6-methylpyridine-3-carboxylic acid

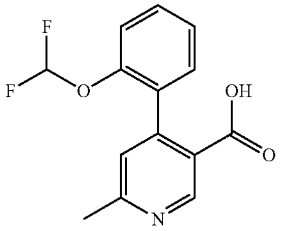 [SMILES: Cc1cc(-c2ccccc2OC(F)F)c(C(=O)O)cn1]

To a solution of methyl 4-(2-(difluoromethoxy)phenyl)-6-methylpyridine-3-carboxylate (350.00 mg, 1.193 mmol, 1 equiv) in THF (5.00 mL) and $H_2O$ (1.00 mL) were added NaOH (190.94 mg, 4.772 mmol, 4 equiv). The resulting mixture was stirred for 4 h at 50° C. under nitrogen atmosphere. The mixture was acidified to pH 2 with citric acid. The residue was purified by flash column chromatography with 5~50% water in acetonitrile to afford 4-(2-(difluoromethoxy)phenyl)-6-methylpyridine-3-carboxylic acid (129 mg, 37.55%) as a light yellow solid. MS (ESI) calc'd for ($C_{14}H_{11}F_2NO_3$) $(M+1)^+$, 280.0; found 280.0.

Step-4: 6-(((5-(4-(2-(difluoromethoxy)phenyl)-6-methylpyridine-3-amido)-1,3,4-thiadiazol-2-yl)oxy) methyl)pyridine-3-carboxylate

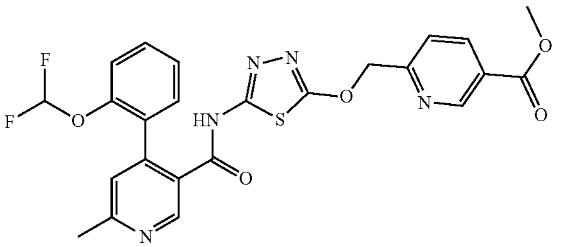 [SMILES: COC(=O)c1ccc(COc2nnc(NC(=O)c3cnc(C)cc3-c3ccccc3OC(F)F)s2)nc1]

To a mixture of 4-(2-(difluoromethoxy)phenyl)-6-methylpyridine-3-carboxylic acid (180.00 mg, 0.643 mmol,) and methyl 6-(((5-amino-1,3,4-thiadiazol-2-yl)oxy)methyl)pyridine-3-carboxylate (171.6 mg, 0.643 mmol, 1.00 equiv) in DMF (2.00 mL) were added HOBt (104.5 mg, 0.771 mmol) and EDCI (148.3 mg, 0.771 mmol,). The resulting mixture was stirred at room temperature for 16 hours. The residue was purified by flash column chromatography with 5-50% water in acetonitrile to afford 6-(((5-(4-(2-(difluoromethoxy)phenyl)-6-methylpyridine-3-amido)-1,3,4-thiadiazol-2-yl)oxy)methyl)pyridine-3-carboxylate (90 mg, 26.47%) as a yellow solid. MS (ESI) calc'd for ($C_{24}H_{19}F_2N_5O_5S$) $(M+1)^+$, 527.1; found 527.1.

Step-5: 4-(2-(difluoromethoxy)phenyl)-N-(5-((5-(hydroxymethyl)pyridin-2-yl)methoxy)-1,3,4-thiadiazol-2-yl)-6-methylpyridine-3-carboxamide

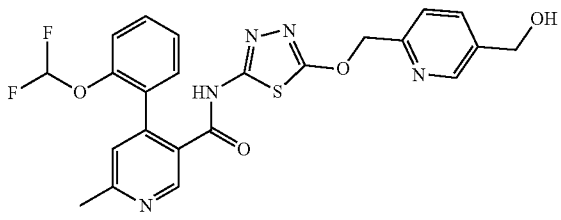 [SMILES: Cc1cc(-c2ccccc2OC(F)F)c(C(=O)Nc2nnc(OCc3ccc(CO)cn3)s2)cn1]

To a mixture of 6-(((5-(4-(2-(difluoromethoxy)phenyl)-6-methylpyridine-3-amido)-1,3,4-thiadiazol-2-yl)oxy)methyl) pyridine-3-carboxylate (90.00 mg, 0.171 mmol) in THF (3.00 mL) were added LiAlH4 (19.4 mg, 0.171 mmol) in portions at 0° C. The mixture was stirred at 0° C. for 1 hour. The resulting mixture was quenched with water. The suspension was filtered. The filtration was purified by prep-HPLC/prep-chiral-HPLC with the following conditions: Column: YMC-Actus Triart C18, 20*250 MM, 5 um, 12 nm; Mobile Phase A:undefined, Mobile Phase B:undefined; Flow rate: 60 mL/min; Gradient: 20 B to 50 B in 8 min; 220/254 nm to afford 4-(2-(difluoromethoxy)phenyl)-N-(5-((5-(hydroxymethyl)pyridin-2-yl)methoxy)-1,3,4-thiadiazol-2-yl)-6-methylpyridine-3-carboxamide (11.3 mg, 13.26%) as a white solid. MS (ESI) calc'd for (C23H19F2N5O4S) $(M+1)^+$, 499.1; found, 499.1. $^1H$ NMR (400 MHz, DMSO-$d_6$) δ 12.91 (s, 1H), 8.82 (s, 1H), 8.53 (s, 1H), 7.81-7.75 (m, 1H), 7.49 (dd, J=14.4, 8.0 Hz, 2H), 7.40 (d, J=7.6 Hz, 1H), 7.37-7.29 (m, 2H), 7.25-7.15 (m, 1H), 7.04 (s, 1H), 5.51 (s, 2H), 5.38-5.31 (m, J=5.6 Hz, 1H), 4.55 (d, J=5.2 Hz, 2H), 2.58 (s, 3H).

Example 18

N-(5-((5-chloropyridin-2-yl)methoxy)-1,3,4-thiadiazol-2-yl)-6-methyl-4-(tetrahydro-2H-pyran-4-yl) nicotinamide

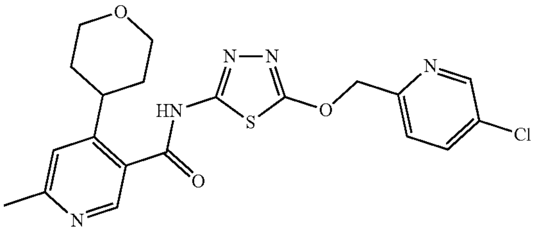 [SMILES: Cc1cc(C2CCOCC2)c(C(=O)Nc2nnc(OCc3ccc(Cl)cn3)s2)cn1]

Step-1: methyl 4-(3,6-dihydro-2H-pyran-4-yl)-6-methylpyridine-3-carboxylate

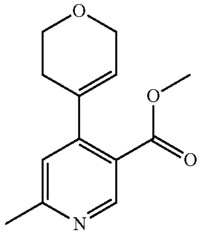

To a mixture of methyl 4-chloro-6-methylpyridine-3-carboxylate (500.0 mg, 2.694 mmol) and 2-(3,6-dihydro-2H-pyran-4-yl)-4,4,5,5-tetramethyl-1,3,2-dioxaborolane (848.8 mg, 4.041 mmol) in dioxane (5 mL) and water (1 mL) were added $K_2CO_3$ (1116.9 mg, 8.082 mmol) and Pd(dppf)$Cl_2$ (197.1 mg, 0.269 mmol). The resulting mixture was stirred at 80° C. for 16 hours under nitrogen atmosphere. The resulting mixture was quenched with water and the aqueous phase was extracted with ethyl acetate. The combined organic solution was dried over sodium sulfate, filtered, and concentrated under vacuum. The residue was purified by reverse phase flash column chromatography with 5-50% acetonitrile in water to afford methyl 4-(3,6-dihydro-2H-pyran-4-yl)-6-methylpyridine-3-carboxylate (404 mg, 64.2%) as a yellow solid. MS (ESI) calc'd for ($C_{13}H_{15}NO_3$) $(M+1)^+$, 234.0, found 234.0.

Step-2: methyl 6-methyl-4-(oxan-4-yl)pyridine-3-carboxylate

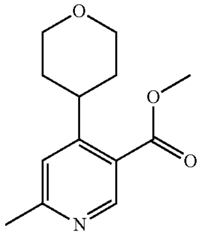

To a solution of methyl 4-(3,6-dihydro-2H-pyran-4-yl)-6-methylpyridine-3-carboxylate (200.0 mg, 0.857 mmol) in MeOH was added Pd/C (60.0 mg, 10%). The resulting mixture was stirred at room temperature for 2 hours under hydrogen atmosphere. The solids were filtered and the filtrate was concentrated under vacuum to afford methyl 6-methyl-4-(oxan-4-yl)pyridine-3-carboxylate (164 mg, crude) as a white solid. MS (ESI) calc'd for ($C_{13}H_{17}NO_3$) $(M+1)^+$, 233.1, found 233.1.

Step-3: 6-methyl-4-(oxan-4-yl)pyridine-3-carboxylic acid

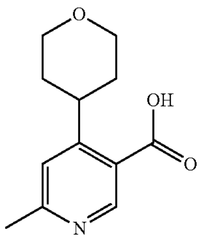 [SMILES: Cc1cc(C2CCOCC2)c(C(=O)O)cn1]

To a solution of methyl 6-methyl-4-(oxan-4-yl)pyridine-3-carboxylate (164.0 mg, 0.697 mmol) in THF (2.0 mL, 0.028 mmol) were added NaOH (83.6 mg, 2.091 mmol) and $H_2O$ (2.0 mL). The resulting mixture was stirred at room temperature for 16 h. The aqueous solution was acidified with citric acid to pH ~2. The residue was purified by reverse phase flash column chromatography with 5-55% acetonitrile in water to afford 6-methyl-4-(oxan-4-yl)pyridine-3-carboxylic acid (73 mg, 47.3%) as a white solid. MS (ESI) calc'd for ($C_{12}H_{15}NO_3$) $(M+1)^+$, 222.1, found 222.1.

Step-4: N-(5-((5-chloropyridin-2-yl)methoxy)-1,3,4-thiadiazol-2-yl)-6-methyl-4-(tetrahydro-2H-pyran-4-yl)nicotinamide

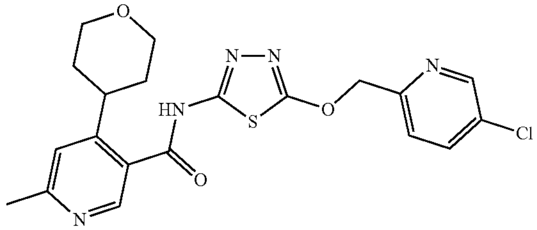 [SMILES: Cc1cc(C2CCOCC2)c(C(=O)Nc2nnc(OCc3ccc(Cl)cn3)s2)cn1]

To a stirred mixture of 6-methyl-4-(oxan-4-yl)pyridine-3-carboxylic acid (50.00 mg, 0.226 mmol, 1.00 equiv) in MeCN (1.50 mL) and DMF (0.50 mL) were added 5-((5-chloropyridin-2-yl)methoxy)-1,3,4-thiadiazol-2-amine (60.33 mg, 0.249 mmol, Intermediate C) and TCFH (82.43 mg, 0.294 mmol) and NMI (92.77 mg, 1.130 mmol). The resulting mixture was stirred at room temperature for 16 h. The residue was purified by reverse phase flash column chromatography with 5-30% acetonitrile in water and further purified by prep-HPLC with the following conditions: (Column: XBridge Prep OBD C18 Column, 30×150 mm 5 um; Mobile Phase A: Water (10 MMOL/L $NH_4HCO_3$+0.1% $NH_3 \cdot H_2O$), Mobile Phase B: ACN; Flow rate: 60 mL/min; Gradient: 5 B to 40 B in 7 min; 220 nm; RT1: 6.5 min) to afford N-(5-((5-chloropyridin-2-yl)methoxy)-1,3,4-thiadiazol-2-yl)-6-methyl-4-(oxan-4-yl)pyridine-3-carboxamide (23.6 mg, 23.4%) as a white solid. MS (ESI) calc'd for ($C_{20}H_{20}ClN_5O_3S$) $(M+1)^+$, 446.1, found 446.1. $^1H$ NMR (400 MHz, Chloroform-d) δ 12.38 (s, 1H), 8.81 (s, 1H), 8.61 (d, J=2.4 Hz, 1H), 7.76-7.69 (m, 1H), 7.47 (d, J=8.4 Hz, 1H), 7.24 (s, 1H), 5.51 (s, 2H), 4.11-4.04 (m, 2H), 3.61-3.50 (m, 2H), 3.48-3.36 (m, 1H), 2.63 (s, 3H), 1.91-1.77 (m, 4H).

Example 19

N-(5-((5-chloropyridin-2-yl)methoxy)-1,3,4-thiadiazol-2-yl)-3-(2-fluoro-6-methoxyphenyl)picolinamide

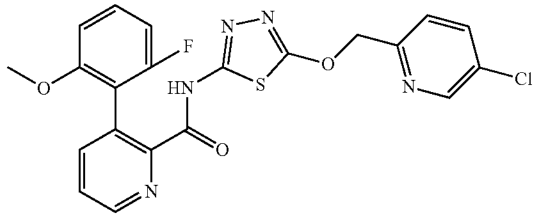 [SMILES: COc1cccc(F)c1-c1cccnc1C(=O)Nc1nnc(OCc2ccc(Cl)cn2)s1]

Step-1: methyl 3-(2-fluoro-6-methoxyphenyl)pyridine-2-carboxylate

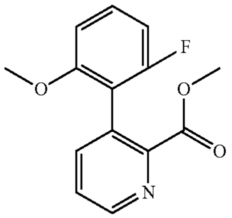

To a degassed mixture of methyl 3-bromopyridine-2-carboxylate (1.0 g, 4.629 mmol) and 2-fluoro-6-methoxyphenylboronic acid (1.2 g, 6.943 mmol) in dioxane (15 mL) and $H_2O$ (2 mL) were added $K_2CO_3$ (1.9 g, 13.887 mmol) and Pd(dppf)$Cl_2$ (338.7 mg, 0.463 mmol). The resulting mixture was stirred at 80° C. for 16 hours under nitrogen atmosphere. The resulting mixture was quenched with water and the aqueous phase was extracted with ethyl acetate. The combined organic solution was dried over sodium sulfate, filtered, and concentrated under vacuum. The residue was purified by silica gel column chromatography, eluted with 0~50% acetate ethyl in petroleum ether to afford methyl 3-(2-fluoro-6-methoxyphenyl)pyridine-2-carboxylate (698 mg, 57.7%) as a yellow solid. MS (ESI) calc'd for ($C_{14}H_{12}FNO_3$) $(M+1)^+$, 262.0, found 262.0.

Step-2: 3-(2-fluoro-6-methoxyphenyl)picolinic acid

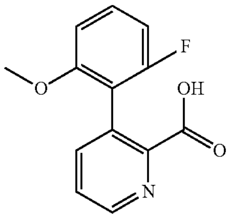 [SMILES: COc1cccc(F)c1-c1cccnc1C(=O)O]

To a solution of methyl 3-(2-fluoro-6-methoxyphenyl) pyridine-2-carboxylate (200.0 mg, 0.766 mmol) in THF (2 mL) was added a solution of NaOH (91.8 mg, 2.297 mmol) in water (2 mL). The resulting mixture was stirred at 50° C. for 16 hours. The resulting mixture was diluted with water and acidified to pH 2 with HCl (2 N). The aqueous layer was extracted with ethyl acetate. The combined organic solution was dried over sodium sulfate, filtered, and concentrated under vacuum. The residue was purified by reverse phase flash column chromatography with 5~45% acetonitrile in water to afford 3-(2-fluoro-6-methoxyphenyl)pyridine-2-carboxylic acid (182 mg, 96.1%) as a white solid. MS (ESI) calc'd for ($C_{13}H_{10}FNO_3$) $(M+1)^+$, 248.0, found 248.0.

Step-3: N-(5-((5-chloropyridin-2-yl)methoxy)-1,3,4-thiadiazol-2-yl)-3-(2-fluoro-6-methoxyphenyl)pyridine-2-carboxamide

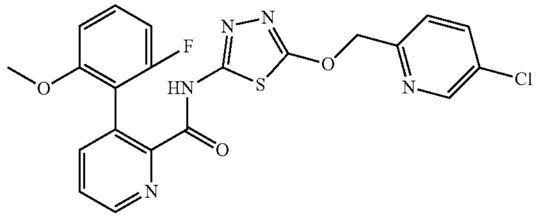 [SMILES: COc1cccc(F)c1-c1cccnc1C(=O)Nc1nnc(OCc2ccc(Cl)cn2)s1]

To a solution of 3-(2-fluoro-6-methoxyphenyl)pyridine-2-carboxylic acid (100.0 mg, 0.404 mmol) in MeCN (3.0 mL, 0.073 mmol) were added NMI (166.05 mg, 2.022 mmol), 5-((5-chloropyridin-2-yl)methoxy)-1,3,4-thiadiazol-2-amine (107.9 mg, 0.444 mmol, Intermediate C) and TCFH (147.5 mg, 0.525 mmol). The resulting mixture was stirred at room temperature for 16 h under nitrogen atmosphere. The precipitated solids were collected by filtration and washed with water and methanol to afford N-(5-((5-chloropyridin-2-yl)methoxy)-1,3,4-thiadiazol-2-yl)-3-(2-fluoro-6-methoxyphenyl)pyridine-2-carboxamide (90.3 mg, 47.3%) as a white solid. MS (ESI) calc'd for ($C_{21}H_{15}ClFN_5O_3S$) $(M+1)^+$, 472.0, found 472.1. $^1H$ NMR (400 MHz, DMSO-$d_6$) δ 12.62 (s, 1H), 8.76-8.70 (m, 1H), 8.65 (d, J=2.4 Hz, 1H), 8.04-7.97 (m, 1H), 7.96-7.89 (m, 1H), 7.74 (dd, J=8.0, 4.4 Hz, 1H), 7.61 (d, J=8.4 Hz, 1H), 7.46-7.36 (m, 1H), 6.97-6.88 (m, 2H), 5.55 (s, 2H), 3.62 (s, 3H).

Example 20

4-(2-fluoro-6-methoxyphenyl)-N-(5-((5-methoxypyridin-2-yl)methoxy)-1,3,4-thiadiazol-2-yl)-6-methylpyridine-3-carboxamide

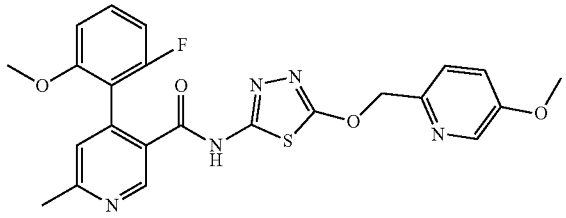

Step-1: 5-((5-methoxypyridin-2-yl)methoxy)-1,3,4-thiadiazol-2-amine

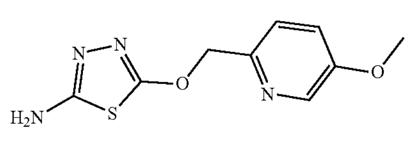 [SMILES: COc1ccc(COc2nnc(N)s2)nc1]

To a solution of NaH (66.6 mg, 1.66 mmol) in THF (5.00 mL) was added a solution of (5-methoxypyridin-2-yl)methanol (185.5 mg, 1.33 mmol) in THF (1 mL) at 0° C. and stirred at 0° C. for 1 hour. To the above mixture was added 5-bromo-1,3,4-thiadiazol-2-amine (200.00 mg, 1.11 mmol) at 0° C. The resulting mixture was stirred at room temperature for 5 hours. The resulting mixture was quenched with water. The aqueous layer was extracted with ethyl acetate. The organic layers were combined, washed with brine, dried over anhydrous sodium sulfate and filtered. The filtrate was concentrated under vacuum. The residue was purified by flash column chromatography with 5-50% acetonitrile in water to afford 5-((5-methoxypyridin-2-yl)methoxy)-1,3,4-thiadiazol-2-amine (60 mg, 22.6%) as a yellow solid. MS (ESI) calc'd for ($C_9H_{10}N_4O_2S$) $(M+1)^+$, 238.1; found 238.1.

Step-2: 4-(2-fluoro-6-methoxyphenyl)-N-(5-((5-methoxypyridin-2-yl)methoxy)-1,3,4-thiadiazol-2-yl)-6-methylpyridine-3-carboxamide

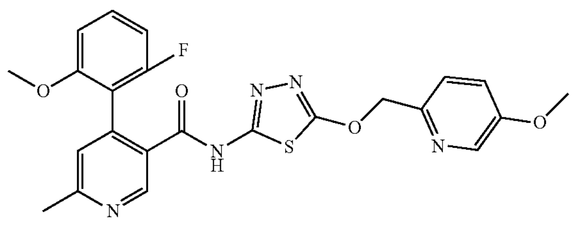

To a mixture of 5-((5-methoxypyridin-2-yl)methoxy)-1,3,4-thiadiazol-2-amine (60.00 mg, 0.252 mmol) and 4-(2-fluoro-6-methoxyphenyl)-6-methylpyridine-3-carboxylic acid (55 mg, 0.21 mmol, Intermediate F) in MeCN (1.00 mL) were added TCFH (65.00 mg, 0.231 mmol) and NMI (52.00 mg, 0.63 mmol). The mixture was stirred at room temperature for 16 hours under nitrogen atmosphere. The mixture was purified by reverse phase flash column chromatography with 5-50% acetonitrile in water to afford 4-(2-fluoro-6-methoxyphenyl)-N-(5-((5-methoxypyridin-2-yl)methoxy)-1,3,4-thiadiazol-2-yl)-6-methylpyridine-3-carboxamide (17.2 mg, 14.1%) as a light yellow solid. MS (ESI) calc'd for ($C_{23}H_{20}FN_5O_4S$) $(M+1)^+$, 481.1; found 481.1. $^1H$ NMR (400 MHz, DMSO-$d_6$) δ 12.88 (s, 1H), 8.81 (s, 1H), 8.30 (d, J=3.2 Hz, 1H), 7.53 (d, J=8.8 Hz, 1H), 7.48-7.35 (m, 2H), 7.33 (s, 1H), 6.97-6.86 (m, 2H), 5.46 (s, 2H), 3.85 (s, 3H), 3.33 (s, 3H), 2.57 (s, 3H).

Example 21

N-(5-((5-chloropyridin-2-yl)methoxy)-1,3,4-thiadiazol-2-yl)-4-(3-cyano-2-methoxyphenyl)-6-methylnicotinamide

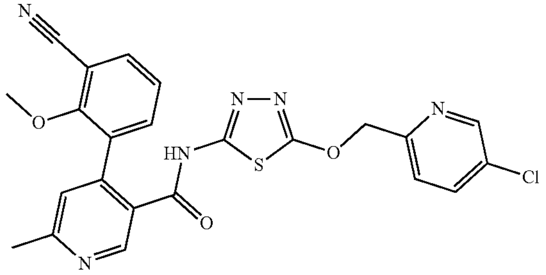 [SMILES: COc1c(C#N)cccc1-c1cc(C)ncc1C(=O)Nc1nnc(OCc2ccc(Cl)cn2)s1]

Step-1: methyl 4-(3-cyano-2-methoxyphenyl)-6-methylnicotinate

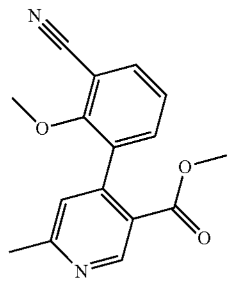

To a degassed solution of methyl 4-chloro-6-methylnicotinate (200 mg, 1.081 mmol) in dioxane (10 mL) and $H_2O$ (2 mL) was added 2-methoxy-3-(4,4,5,5-tetramethyl-1,3,2-dioxaborolan-2-yl)benzonitrile (432 mg, 1.662 mmol), $K_2CO_3$ (459 mg, 3.326 mmol) and $Pd(PPh_3)_4$ (129 mg, 0.112 mmol) under nitrogen. The resulting solution was stirred at 80° C. for 8 h under nitrogen. T The reaction mixture was diluted with water and extracted with ethyl acetate. The combined organic layers were washed with brine, dried over anhydrous sodium sulfate, filtered, and concentrated under vacuum. The residue was purified by flash chromatography on silica gel with 0~50% ethyl acetate in petroleum ether to afford methyl 4-(3-cyano-2-methoxyphenyl)-6-methylnicotinate (212 mg, 80%) as a white solid. MS (ESI) calc'd for ($C_{16}H_{14}N_2O_3$) $(M+1)^+$, 283.1; found, 283.0.

Step-2: 4-(3-cyano-2-methoxyphenyl)-6-methylnicotinic acid

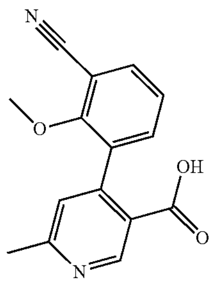 [SMILES: COc1c(C#N)cccc1-c1cc(C)ncc1C(=O)O]

To a solution of methyl 4-(3-cyano-2-methoxyphenyl)-6-methylnicotinate (250 mg, 0.883 mmol) in MeOH (10 mL) and $H_2O$ (5 mL) was added LiOH (45 mg, 1.875 mmol). The mixture was stirred at 50° C. for 2 hours. The aqueous solution was acidified with HCl to pH 5~6. The aqueous solution was extracted with ethyl acetate. The organic layers were combined, washed with brine, dried over anhydrous sodium sulfate and filtered. The filtrate was concentrated under vacuum to afford 4-(3-cyano-2-methoxyphenyl)-6-methylnicotinic acid (213 mg, 85%) as a white solid. MS (ESI) calc'd for ($C_{15}H_{12}N_2O_3$) $(M+1)^+$, 269.1; found 269.0.

Step-3: N-(5-((5-chloropyridin-2-yl)methoxy)-1,3,4-thiadiazol-2-yl)-4-(3-cyano-2-methoxyphenyl)-6-methylnicotinamide

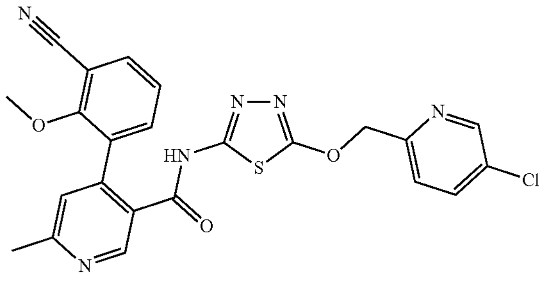 [SMILES: COc1c(C#N)cccc1-c1cc(C)ncc1C(=O)Nc1nnc(OCc2ccc(Cl)cn2)s1]

To a solution of 4-(3-cyano-2-methoxyphenyl)-6-methylnicotinic acid (213 mg, 0.792 mmol) in ACN (10 mL) were added NMI (195 mg, 2.378 mmol), 5-((5-chloropyridin-2-yl)methoxy)-1,3,4-thiadiazol-2-amine (200 mg, 0.823 mmol, Intermediate C) and TCFH (268 mg, 0.954 mmol). The mixture was stirred at room temperature for 2 h. The mixture was concentrated under vacuum. The residue was purified by flash chromatography on silica gel with 0~10% methanol in dichloromethane and further purified by prep-HPLC with the following conditions: (Column: Sunfire prep C18 column, 30*150, 5 um; Mobile Phase A: Water (0.1% FA), Mobile Phase B: ACN; Flow rate: 40 mL/min; Gradient: 25 B to 55 B in 8 min; 220 nm; RT1: 7.23 min) to afford N-(5-((5-chloropyridin-2-yl)methoxy)-1,3,4-thiadiazol-2-yl)-4-(3-cyano-2-methoxyphenyl)-6-methylnicotinamide (23.2 mg, 10.9%) as a white solid. MS (ESI) calc'd for ($C_{23}H_{17}ClN_6O_3S$) $(M+1)^+$, 493.1; found, 493.1. $^1H$ NMR (400 MHz, DMSO-$d_6$) δ 13.02 (s, 1H), 8.85 (s, 1H), 8.66 (s, 1H), 8.02-7.99 (m, 1H), 7.98-7.85 (m, 1H), 7.69-7.60 (m, 2H), 7.43-7.38 (m, 2H), 5.55 (s, 2H), 3.56 (s, 3H), 2.61 (s, 3H).

Example 22, 40 and 41

4-(2-fluoro-6-methoxyphenyl)-N-(5-((5-(1-hydroxyethyl)pyridin-2-yl)methoxy)-1,3,4-thiadiazol-2-yl)-6-methylnicotinamide (Example 22)

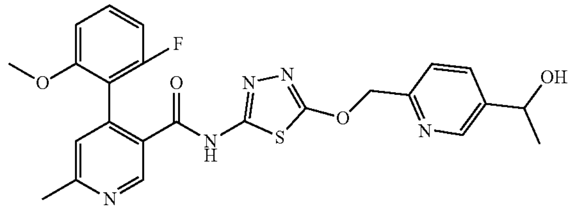 [SMILES: COc1cccc(F)c1-c1cc(C)ncc1C(=O)Nc1nnc(OCc2ccc(C(C)O)cn2)s1]

4-(2-fluoro-6-methoxyphenyl)-N-(5-((5-((S)-1-hydroxyethyl)pyridin-2-yl)methoxy)-1,3,4-thiadiazol-2-yl)-6-methylnicotinamide (Example 40) and 4-(2-fluoro-6-methoxyphenyl)-N-(5-((5-((R)-1-hydroxyethyl)pyridin-2-yl)methoxy)-1,3,4-thiadiazol-2-yl)-6-methylnicotinamide Example 41

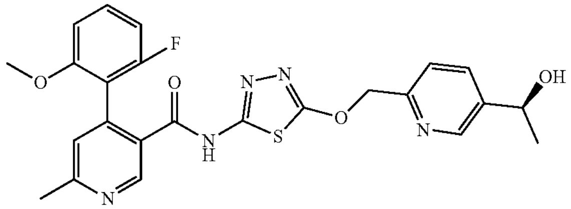

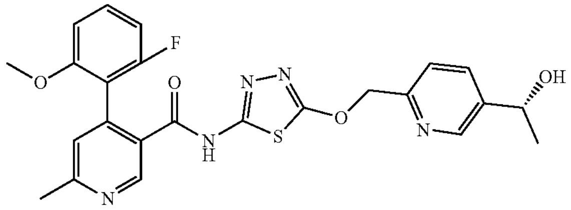

Step-1: (5-(1-ethoxyvinyl)pyridin-2-yl)methanol

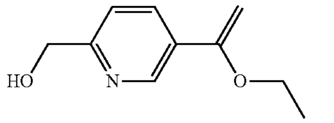

To a degassed mixture of (5-bromopyridin-2-yl)methanol (10.0 g, 53.18 mmol) in toluene (50.00 mL) were added tributyl(1-ethoxyethenyl)stannane (38.42 g, 0.11 mmol) and $Pd(PPh_3)_2Cl_2$ (3.73 g, 5.31 mmol). The resulting solution was stirred at 100° C. for 2 h under nitrogen atmosphere before concentrated under vacuum. The residue was purified by flash column chromatography with 0~50% ethyl acetate in petroleum ether to afford (5-(1-ethoxyvinyl)pyridin-2-yl) methanol (5.0 g, 52.4%) as a yellow solid. MS (ESI) calc'd for ($C_{10}H_{13}NO_2$) $(M+1)^+$, 180.1; found 180.0.

Step-2: (5-(1-ethoxyethenyl)pyridin-2-yl)methanol

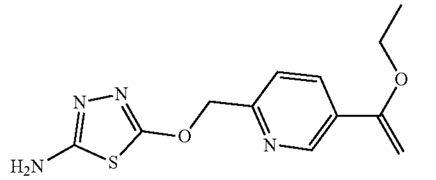 [SMILES: C=C(OCC)c1ccc(COc2nnc(N)s2)nc1]

To a solution of NaH (1.61 g, 67.09 mmol, 1.50 equiv, 60% purity) in THF (60.00 mL) was added a solution of (5-(1-ethoxyethenyl)pyridin-2-yl)methanol (8.00 g, 44.63 mmol) in THE (15 mL) dropwise at 0~5° C. and stirred at 0~5° C. for 1 hour under nitrogen atmosphere. To the above solution was added 5-bromo-1,3,4-thiadiazol-2-amine (9.64 g, 53.56 mmol) at 0° C. The resulting mixture was stirred at room temperature for 12 h under nitrogen. The reaction mixture was quenched by the addition of ice/water and extracted with ethyl acetate. The combined organic layers were washed with brine, dried over anhydrous sodium sulfate, filtered, and concentrated under vacuum. The residue was purified by flash chromatography on silica gel with 0~10% methanol in dichloromethane to afford 5-((5-(1-ethoxyethenyl)pyridin-2-yl)methoxy)-1,3,4-thiadiazol-2-amine (4.0 g, 32.2%) as a yellow solid. MS (ESI) calc'd for ($C_{12}H_{14}N_4O_2S$) $(M+1)^+$, 279.1, found 279.0.

Step-3: 1-(6-(((5-amino-1,3,4-thiadiazol-2-yl)oxy)methyl)pyridin-3-yl)ethenone

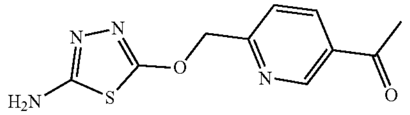

A mixture of 5-((5-(1-ethoxyethenyl)pyridin-2-yl)methoxy)-1,3,4-thiadiazol-2-amine (5.03 g, 18.07 mmol) in HCl (50 mL, 4M in dioxane) was stirred at room temperature for 2 h. The solvent was removed under vacuum. The residue was neutralized with saturated $NaHCO_3$ (aq.) and extracted with ethyl acetate. The combined organic layers were washed with brine, dried over anhydrous sodium sulfate, filtered, and concentrated under vacuum. The residue was purified by flash chromatography on silica gel with 0~10% methanol in dichloromethane to afford 1-(6-(((5-amino-1,3,4-thiadiazol-2-yl)oxy)methyl)pyridin-3-yl)ethanone (3.46 g, 68.8%) as a yellow solid. MS (ESI) calc'd for ($C_{10}H_{10}N_4O_2S$) $(M+1)^+$, 251.0, found 251.0.

Step-4: N-(5-((5-acetylpyridin-2-yl)methoxy)-1,3,4-thiadiazol-2-yl)-4-(2-fluoro-6-methoxyphenyl)-6-methylpyridine-3-carboxamide

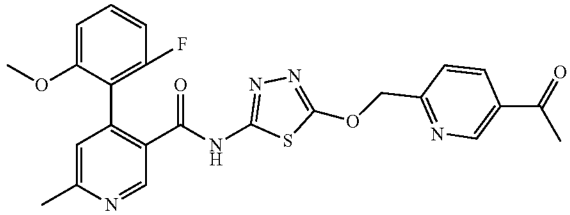 [SMILES: COc1cccc(F)c1-c1cc(C)ncc1C(=O)Nc1nnc(OCc2ccc(C(C)=O)cn2)s1]

To a stirred solution of 1-(6-(((5-amino-1,3,4-thiadiazol-2-yl)oxy)methyl)pyridin-3-yl)ethanone (300 mg, 1.19 mmol) and 4-(2-fluoro-6-methoxyphenyl)-6-methylpyridine-3-carboxylic acid (313.1 mg, 1.19 mmol, Intermediate F) in acetonitrile (5 mL) were added TCFH (504 mg, 1.79 mmol) and N-methyl imidazole (393 mg, 4.79 mmol) at room temperature under nitrogen atmosphere. The mixture resulting was stirred at room temperature for 2 h under nitrogen atmosphere. The reaction mixture was quenched with water and extracted with ethyl acetate. The combined organic layers were washed with brine, dried over anhydrous sodium sulfate, filtered, and concentrated under vacuum. The residue was purified by reverse phase flash column chromatography with 5~70% acetonitrile in water to afford N-(5-((5-acetylpyridin-2-yl)methoxy)-1,3,4-thiadiazol-2-yl)-4-(2-fluoro-6-methoxyphenyl)-6-methylpyridine-3-carboxamide (350 mg, 59.1%) as a yellow oil. MS (ESI) calc'd for ($C_{24}H_{20}FN_5O_4S$) $(M+1)^+$, 494.1; found, 494.1.

Step-5: 4-(2-fluoro-6-methoxyphenyl)-N-(5-((5-((1S)-1-hydroxyethyl)pyridin-2-yl)methoxy)-1,3,4-thiadiazol-2-yl)-6-methylpyridine-3-carboxamide

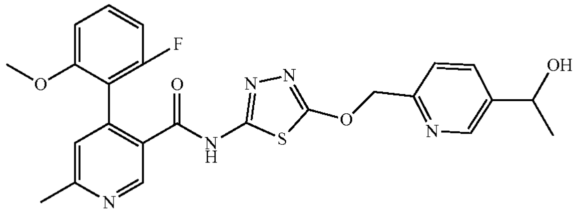

To a stirred solution of N-(5-((5-acetylpyridin-2-yl)methoxy)-1,3,4-thiadiazol-2-yl)-4-(2-fluoro-6-methoxyphenyl)-6-methylpyridine-3-carboxamide (234 mg, 0.47 mmol) in MeOH (3 mL) was added $NaBH_4$ (35 mg, 0.94 mmol). The mixture resulting was stirred at room temperature for 2 h. The reaction mixture was quenched with water and extracted with ethyl acetate. The combined organic layers were washed with brine, dried over anhydrous sodium sulfate, filtered, and concentrated under vacuum. The residue was purified by Prep-HPLC with the following conditions: (Column: XBridge Prep OBD C18 Column, 30×150 mm 5 um; Mobile Phase A: Water (10 mmol/L $NH_4HCO_3$), Mobile Phase B: ACN; Flow rate: 60 mL/min; Gradient: 25 B to B in 7 min; 220 nm) to afford 4-(2-fluoro-6-methoxyphenyl)-N-(5-((5-(1-hydroxyethyl)pyridin-2-yl)methoxy)-1,3,4-thiadiazol-2-yl)-6-methylnicotinamide (22.2 mg, 10.2%) as a white solid. MS (ESI) calc'd for ($C_{24}H_{22}FN_5O_4S$) $(M+1)^+$, 496.1; found, 496.0. $^1$H NMR (400 MHz, DMSO-$d_6$) δ 12.89 (s, 1H), 8.82 (s, 1H), 8.56 (s, 1H), 7.85-7.75 (m, 1H), 7.50 (d, J=8.0 Hz, 1H), 7.45-7.35 (m, 1H), 7.32 (d, J=1.6 Hz, 1H), 6.97-6.86 (m, 2H), 5.51 (s, 2H), 5.36 (s, 1H), 4.83-4.78 (m, 1H), 3.59 (s, 3H), 2.56 (s, 3H), 1.37 (d, J=6.4 Hz, 3H).

Step-6: 4-(2-fluoro-6-methoxyphenyl)-N-(5-((5-((S)-1-hydroxyethyl)pyridin-2-yl)methoxy)-1,3,4-thiadiazol-2-yl)-6-methylnicotinamide and 4-(2-fluoro-6-methoxyphenyl)-N-(5-((5-((R)-1-hydroxyethyl)pyridin-2-yl)methoxy)-1,3,4-thiadiazol-2-yl)-6-methylnicotinamide

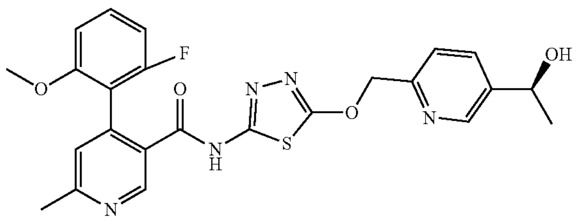

-continued

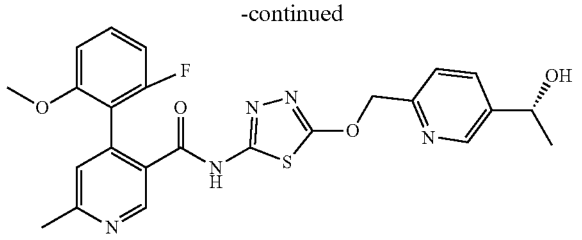

A racemic of 4-(2-fluoro-6-methoxyphenyl)-N-(5-((5-((1S)-1-hydroxyethyl)pyridin-2-yl)methoxy)-1,3,4-thiadiazol-2-yl)-6-methylpyridine-3-carboxamide (160 mg) was separated by prep-chiral-HPLC with the following conditions: (Column: DZ-CHIRALPAK IG-3, 2*25 cm, 5 um; Mobile Phase A:Hex (0.2% FA):(EtOH:DCM=1:1)=50:50, Mobile Phase B: Flow rate: 20 mL/min; Gradient: 30 B to 30 B in 25 min; 220/254 nm; RT1 8.16 min; RT2 14.12 min; Injection Volume: 2.567 ml; Number Of Runs: 3) to afford 4-(2-fluoro-6-methoxyphenyl)-N-(5-((5-((S)-1-hydroxyethyl)pyridin-2-yl)methoxy)-1,3,4-thiadiazol-2-yl)-6-methylnicotinamide (47.4 mg, 29.6%) as a white solid with shorter retention time on chiral HPLC and 4-(2-fluoro-6-methoxyphenyl)-N-(5-((5-((R)-1-hydroxyethyl)pyridin-2-yl)methoxy)-1,3,4-thiadiazol-2-yl)-6-methylnicotinamide (46.2 mg, 28.9%) as a white solid with longer retention time on chiral HPLC.

4-(2-fluoro-6-methoxyphenyl)-N-(5-((5-((S)-1-hydroxyethyl)pyridin-2-yl)methoxy)-1,3,4-thiadiazol-2-yl)-6-methylnicotinamide: MS (ESI) calc'd for ($C_{24}H_{22}FN_5O_4S$) $(M+1)^+$, 496.1; found, 496.1. $^1H$ NMR (400 MHz, DMSO-$d_6$) δ 12.99 (s, 1H), 8.82 (s, 1H), 8.56 (s, 1H), 7.85-7.75 (m, 1H), 7.50 (d, J=8.0 Hz, 1H), 7.45-7.35 (m, 1H), 7.32 (d, J=1.6 Hz, 1H), 6.97-6.86 (m, 2H), 5.51 (s, 2H), 5.36 (s, 1H), 4.83-4.78 (m, 1H), 3.59 (s, 3H), 2.56 (s, 3H), 1.37 (d, J=6.4 Hz, 3H).

4-(2-fluoro-6-methoxyphenyl)-N-(5-((5-((R)-1-hydroxyethyl)pyridin-2-yl)methoxy)-1,3,4-thiadiazol-2-yl)-6-methylnicotinamide: MS (ESI) calc'd for ($C_{24}H_{22}FN_5O_4S$) $(M+1)^+$, 496.1; found, 496.1. $^1H$ NMR (400 MHz, DMSO-d6) δ 12.89 (s, 1H), 8.82 (s, 1H), 8.56 (s, 1H), 7.85-7.75 (m, 1H), 7.50 (d, J=8.0 Hz, 1H), 7.45-7.35 (m, 1H), 7.32 (d, J=1.6 Hz, 1H), 6.97-6.86 (m, 2H), 5.51 (s, 2H), 5.36 (s, 1H), 4.83-4.78 (m, 1H), 3.59 (s, 3H), 2.56 (s, 3H), 1.37 (d, J=6.4 Hz, 3H).

Example 23

N-(5-((5-chloropyridin-2-yl)methoxy)-1,3,4-thiadiazol-2-yl)-4-(2-fluoro-5-(hydroxymethyl)phenyl)-6-methylnicotinamide

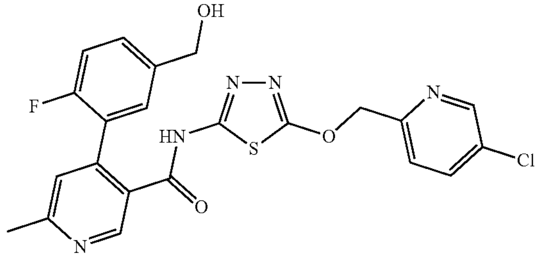 [SMILES: Cc1cc(-c2cc(CO)ccc2F)c(C(=O)Nc2nnc(OCc3ccc(Cl)cn3)s2)cn1]

Step-1: methyl 4-(2-fluoro-5-(hydroxymethyl)phenyl)-6-methylnicotinate

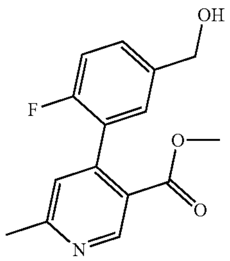

A degassed solution of methyl 4-chloro-6-methylpyridine-3-carboxylate (500.0 mg, 2.694 mmol), 2-fluoro-5-(hydroxymethyl)phenylboronic acid (457.8 mg, 2.694 mmol), $K_2CO_3$ (1116.9 mg, 8.082 mmol) and Pd(dppf)$Cl_2$ (197.11 mg, 0.269 mmol) in dioxane (10 mL) and $H_2O$ (1 mL) was stirred at 80° C. for 2 h. The solvent was removed under vacuum. The residue was purified by flash column chromatography with 0~10% methanol in dichloromethane to afford methyl 4-(2-fluoro-5-(hydroxymethyl)phenyl)-6-methylnicotinate (480 mg, 65%) as a yellow oil. MS (ESI) calc'd for ($C_{15}H_{14}FNO_3$) $(M+1)^+$, 276.1; found, 276.0.

Step-2: methyl 4-(2-fluoro-5-(((tetrahydro-2H-pyran-2-yl)oxy)methyl)phenyl)-6-methylnicotinate

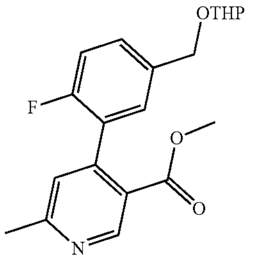

To a solution of methyl 4-(2-fluoro-5-(hydroxymethyl)phenyl)-6-methylnicotinate (380.00 mg, 1.38 mmol) in DCM (5 mL) were added DHP (233 mg, 2.76 mmol) and pTsOH (119 mg, 0.69 mmol). The resulting mixture was stirred at room temperature for 16 h. The reaction mixture was neutralized with $NaHCO_3$ (aq.). The aqueous solution was extracted with ethyl acetate. The organic layers were combined, washed with brine, dried over anhydrous sodium sulfate and filtered. The filtrate was concentrated under vacuum to afford methyl 4-(2-fluoro-5-(((tetrahydro-2H-pyran-2-yl)oxy)methyl)phenyl)-6-methylnicotinate (370 mg, 74.6%) as an off-yellow solid. MS (ESI) calc'd for ($C_{20}H_{22}FNO_4$) $(M+1)^+$, 360.1; found, 360.0.

Step-3: 4-(2-fluoro-5-(((tetrahydro-2H-pyran-2-yl)oxy)methyl)phenyl)-6-methylnicotinic acid

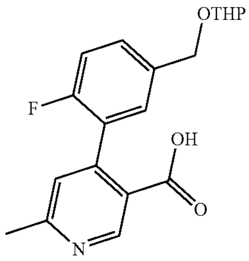

To a solution of methyl 4-(2-fluoro-5-(((tetrahydro-2H-pyran-2-yl)oxy)methyl)phenyl)-6-methylnicotinate (370 mg, 1.03 mmol) in MeOH (10 mL) and $H_2O$ (5 mL) was added NaOH (82 mg, 2.06 mmol). The mixture was stirred at 50° C. for 2 h. The aqueous solution was acidified with HCl (1 N) to pH ~6. The aqueous solution was extracted with ethyl acetate. The organic layers were combined, washed with brine, dried over anhydrous sodium sulfate and filtered. The filtrate was concentrated under vacuum to afford 4-(2-fluoro-5-(((tetrahydro-2H-pyran-2-yl)oxy)methyl)phenyl)-6-methylnicotinic acid (280 mg, 78%) as a white solid. MS (ESI) calc'd for ($C_{19}H_{20}FNO_4$) $(M+1)^+$, 346.1; found 346.0.

Step-4: N-(5-((5-chloropyridin-2-yl)methoxy)-1,3,4-thiadiazol-2-yl)-4-(2-fluoro-5-(((tetrahydro-2H-pyran-2-yl)oxy)methyl)phenyl)-6-methylnicotinamide

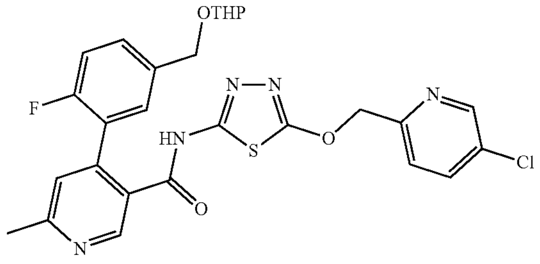

To a solution of 4-(2-fluoro-5-(((tetrahydro-2H-pyran-2-yl)oxy)methyl)phenyl)-6-methylnicotinic acid (250 mg, 0.72 mmol) in ACN (5 mL) were added 5-((5-chloropyridin-2-yl)methoxy)-1,3,4-thiadiazol-2-anine (223 mg, 0.72 mmol, Intermediate C), NMI (177 mg, 2.16 mmol) and TCFH (302 mg, 1.08 mmol). The mixture was stirred at room temperature for 2 h. The mixture was diluted with water and extracted with ethyl acetate. The combined organic layers were washed with brine, dried over anhydrous sodium sulfate, filtered, and concentrated under vacuum. The residue was purified by flash chromatography on silica gel with 0~10% methanol in dichloromethane to afford N-(5-((5-chloropyridin-2-yl)methoxy)-1,3,4-thiadiazol-2-yl)-4-(2-fluoro-5-(((tetrahydro-2H-pyran-2-yl)oxy)methyl)phenyl)-6-methylnicotinamide (170 mg, 38%) as a yellow solid. MS (ESI) calc'd for ($C_{27}H_2ClFN_5O_4S$) $(M+1)^+$, 570.1; found 570.0.

Step-5: N-(5-((5-chloropyridin-2-yl)methoxy)-1,3,4-thiadiazol-2-yl)-4-(2-fluoro-5-(hydroxymethyl)phenyl)-6-methylnicotinamide

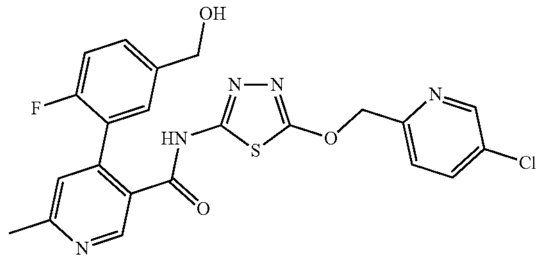 [SMILES: Cc1cc(-c2cc(CO)ccc2F)c(C(=O)Nc2nnc(OCc3ccc(Cl)cn3)s2)cn1]

To a mixture of N-(5-((5-chloropyridin-2-yl)methoxy)-1,3,4-thiadiazol-2-yl)-4-(2-fluoro-5-(((tetrahydro-2H-pyran-2-yl)oxy)methyl)phenyl)-6-methylnicotinamide (170 mg, 0.29 mmol) in $CH_2Cl_2$ (6 mL) was added TFA (2 mL). The resulting mixture was stirred at room temperature for 3 h before concentrated under vacuum. The residue was purified by prep-HPLC with the following conditions: (Column: XBridge Prep OBD C18 Column, 30×150 mm 5 um; Mobile Phase A: Water (10 mmol/L $NH_4HCO_3$), Mobile Phase B: ACN; Flow rate: 60 mL/min; Gradient: 23 B to 36 B in 8 min; 254/220 nm) to afford N-(5-((5-chloropyridin-2-yl)methoxy)-1,3,4-thiadiazol-2-yl)-4-(2-fluoro-5-(hydroxymethyl)phenyl)-6-methylnicotinamide (48 mg, 33%) as a white solid. MS (ESI) calc'd for ($C_{22}H_{17}FClN_5O_3S$) $(M+1)^+$, 486.1; found 486.1. $^1H$ NMR (400 MHz, Methanol-$d_4$) δ 8.77 (s, 1H), 8.59-8.58 (s, 1H), 7.94-7.91 (m, 1H), 7.62-7.60 (m, 1H), 7.48-7.45 (m, 3H), 7.13-7.10 (m, 1H), 5.57 (s, 2H), 4.89-4.61 (m, 2H), 2.68 (s, 3H).

Example 24

4-(2-fluoro-6-methoxyphenyl)-6-methyl-N-(5-((5-(methylsulfonyl)pyridin-2-yl)methoxy)-1,3,4-thiadiazol-2-yl)nicotinamide

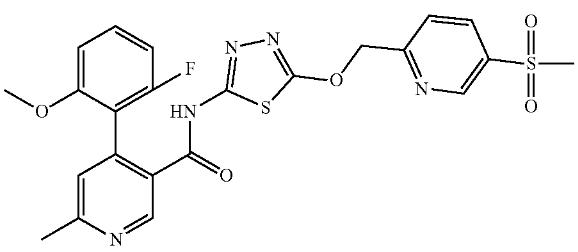

Step-1: (5-(methylsulfonyl)pyridin-2-yl)methanol

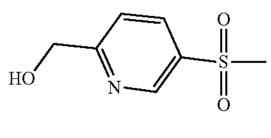

To a stirred solution of methyl 5-methanesulfonylpyridine-2-carboxylate (500 mg, 2.32 mmol) and NaOMe (1 mg, 0.02 mmol) in MeOH (15 mL) was added $NaBH_4$ (175 mg, 4.64 mmol) in portions at room temperature under $N_2$ atmosphere. The resulting mixture was stirred at room temperature for 3 h under $N_2$ atmosphere. The reaction mixture was quenched with water and extracted with ethyl acetate/THF. The combined organic layers were washed with saturate salt water, dried over anhydrous sodium sulfate. After filtration, the filtrate was concentrated under reduced pressure to afford (5-(methylsulfonyl)pyridin-2-yl) methanol (165 mg, 37.9%) as a yellow oil. MS (ESI) calculated for ($C_7H_9NO_3S$) $(M+1)^+$, 188.0; found, 188.1.

Step-2: S-methyl 0-((5-(methylsulfonyl)pyridin-2-yl)methyl) carbonodithioate

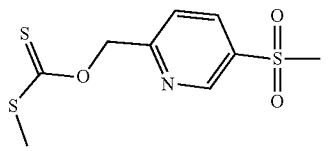 [SMILES: CSC(=S)OCc1ccc(S(C)(=O)=O)cn1]

To a solution of NaH (90 mg, 3.75 mmol, 60%) in THF (10 mL) was added a solution of (5-(methylsulfonyl)pyridin-2-yl)methanol (200 mg, 1.08 mmol) in THF (3 mL) at 0° C. The resulting mixture was stirred at 0° C. for 30 min. To the above mixture was added $CS_2$ (122 mg, 1.60 mmol) dropwise at 0° C. and stirred at 0° C. for 20 min. Then MeI (227 mg, 1.60 mmol) was added to the above mixture dropwise at 0° C. The resulting mixture was stirred at room temperature for 1 hour. The resulting mixture was quenched with water. The aqueous layer was extracted with ethyl acetate. The organic layers were combined, washed with brine, dried over anhydrous sodium sulfate and filtered. The filtrate was concentrated under vacuum. The residue was purified by reverse phase flash column chromatography with 5-70% acetonitrile in water to afford S-methyl 0-((5-(methylsulfonyl)pyridin-2-yl)methyl) carbonodithioate (140 mg, 47.2%) as a brown solid. MS (ESI) calculated for ($C_9H_{11}NO_3S_3$) $(M+1)^+$, 277.1; found, 277.1.

Step-3: O-((5-(methylsulfonyl)pyridin-2-yl)methyl) hydrazinecarbothioate

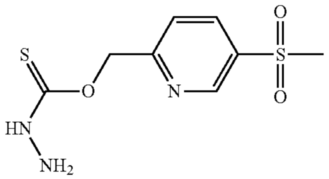 [SMILES: CS(=O)(=O)c1ccc(COC(=S)NN)nc1]

To a mixture of S-methyl 0-((5-(methylsulfonyl)pyridin-2-yl)methyl) carbonodithioate (120 mg, 0.43 mmol) in MeOH (5 mL) was added Hydrazine (14 mg, 0.43 mmol). The mixture was stirred at 0° C. for 1 hour. The resulting mixture was concentrated under vacuum and diluted with water. The resulting mixture was extracted with ethyl acetate. The combined organic layers were washed with saturated sodium chloride, dried over anhydrous sodium sulfate. After filtration, the filtrate was concentrated under vacuum to afford O-((5-(methylsulfonyl)pyridin-2-yl) methyl) hydrazinecarbothioate (120 mg, crude) as a brown solid. MS (ESI) calculated for ($C_8H_{11}N_3O_3S_2$) $(M+1)^+$, 262.0; found, 262.0.

Step-4: O-((5-(methylsulfonyl)pyridin-2-yl)methyl) hydrazinecarbothioate

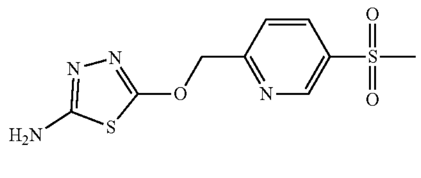 [SMILES: CS(=O)(=O)c1ccc(COc2nnc(N)s2)nc1]

To a mixture of O-((5-(methylsulfonyl)pyridin-2-yl) methyl) hydrazinecarbothioate (110 mg, 0.42 mmol) and TEA (85 mg, 0.84 mmol) in MeOH (5 mL) was added BrCN (49 mg, 0.46 mmol). The mixture was stirred at room temperature for 1 h. The resulting mixture was quenched with water. The aqueous layer was extracted with ethyl acetate. The organic layers were combined, washed with brine, dried over anhydrous sodium sulfate and filtered. The filtrate was concentrated under vacuum to afford 5-((5-methanesulfonylpyridin-2-yl)methoxy)-1,3,4-thiadiazol-2-amine (40 mg, 33.1%) as a brown solid. MS (ESI) calculated for ($C_9H_{10}N_4O_3S_2$) $(M+1)^+$, 287.0; found, 287.0.

Step-5: 4-(2-fluoro-6-methoxyphenyl)-6-methyl-N-(5-((5-(methylsulfonyl)pyridin-2-yl)methoxy)-1,3,4-thiadiazol-2-yl)nicotinamide

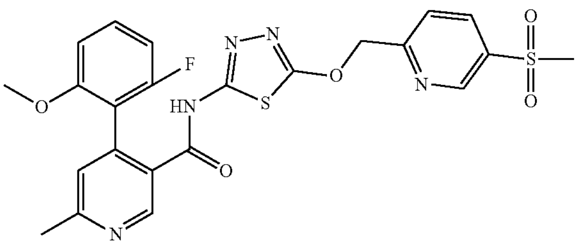

To a stirred solution of 5-((5-methanesulfonylpyridin-2-yl)methoxy)-1,3,4-thiadiazol-2-amine (40 mg, 0.14 mmol) and 4-(2-fluoro-6-methoxyphenyl)-6-methylpyridine-3-carboxylic acid (36 mg, 0.14 mmol, Intermediate F) in DMF (2 mL) were added TCFH (58 mg, 0.21 mmol) and NMI (45 mg, 0.56 mmol) under $N_2$ atmosphere. The resulting mixture was stirred at room temperature for 1 h. The residue was purified by prep-HPLC with the following conditions: (Column: YMC-Pack Diol-120-NP, 20*150 mm 5 um; Mobile Phase A: water (10 mmol/L $NH_4HCO_3$), Mobile Phase B: ACN; Flow rate: 60 mL/min; Gradient: 39 B to 52 B in 8 min; 220/254 nm; RT1: 4.2 min) to afford 4-(2-fluoro-6-methoxyphenyl)-6-methyl-N-(5-((5-(methylsulfonyl)pyridin-2-yl)methoxy)-1,3,4-thiadiazol-2-yl)nicotinamide (20 mg, 27.0%) as a white solid. MS (ESI) calculated for ($C_{23}H_{20}FN_5O_5S_2$) $(M+1)^+$, 530.0; found, 530.0. $^1H$ NMR (400 MHz, DMSO-$d_6$) δ 12.95 (s, 1H), 9.09 (d, J=2.4 Hz, 1H), 8.82 (s, 1H), 8.47-8.33 (m, 1H), 7.81 (d, J=8.4 Hz, 1H), 7.47-7.38 (m, 1H), 7.34 (s, 1H), 6.99-6.86 (m, 2H), 5.69 (s, 2H), 3.60 (s, 3H), 3.30 (s, 3H), 2.58 (s, 3H).

Example 25

4-(2-(difluoromethoxy)-6-fluorophenyl)-N-(5-((5-(hydroxymethyl)pyridin-2-yl)methoxy)-1,3,4-thiadiazol-2-yl)-6-methylnicotinamide

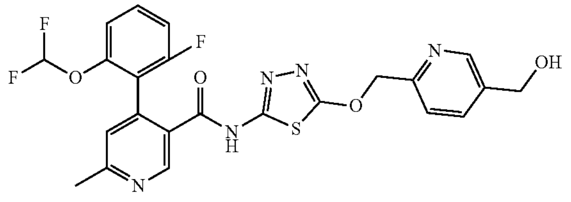 [SMILES: Cc1cc(-c2c(F)cccc2OC(F)F)c(C(=O)Nc2nnc(OCc3ccc(CO)cn3)s2)cn1]

Step-1: methyl 6-(((5-amino-1,3,4-thiadiazol-2-yl)oxy)methyl)pyridine-3-carboxylate

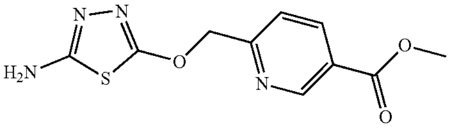 [SMILES: COC(=O)c1ccc(COc2nnc(N)s2)nc1]

To a stirred solution of NaH (575.0 mg, 14.37 mmol, 60% purity) in THF (20.00 mL) were added a solution of methyl 6-(hydroxymethyl)pyridine-3-carboxylate (2.00 g, 11.96 mmol) in THF (10 mL) drop wise at 0° C. and stirred at 0~5° C. for 1 h. Then a solution of 5-bromo-1,3,4-thiadiazol-2-amine (2.57 g, 14.27 mmol) in THF (10 mL) was added to the above mixture. The resulting mixture was stirred at room temperature overnight under nitrogen atmosphere. The reaction mixture was quenched with saturated $NH_4Cl$ aqueous solution and extracted with ethyl acetate. The combined organic layers were washed with brine, dried over anhydrous sodium sulfate, filtered, and concentrated under vacuum. The residue was purified by reverse phase flash column chromatography with 5~50% MeCN in water to afford methyl 6-(((5-amino-1,3,4-thiadiazol-2-yl)oxy)methyl)pyridine-3-carboxylate (800 mg, 21.85%) as a brown solid. MS (ESI) calc'd for ($C_{10}H_{10}N_4O_3S$) $(M+1)^+$, 267.1; found 267.0.

Step-2: methyl 6-(((5-(4-(2-(difluoromethoxy)-6-fluorophenyl)-6-methylpyridine-3-amido)-1,3,4-thiadiazol-2-yl)oxy)methyl)pyridine-3-carboxylate

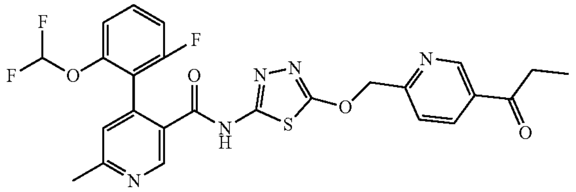 [SMILES: CCC(=O)c1ccc(COc2nnc(NC(=O)c3cnc(C)cc3-c3c(F)cccc3OC(F)F)s2)nc1]

To a stirred mixture of 4-(2-(difluoromethoxy)-6-fluorophenyl)-6-methylpyridine-3-carboxylic acid (320.00 mg, 1.07 mmol) and methyl 6-(((5-amino-1,3,4-thiadiazol-2-yl)oxy)methyl)pyridine-3-carboxylate (286.68 mg, 1.07 mmol, Example 5, Step 1) in DMF (2 mL) and MeCN (2 mL) were added TCFH (332.28 mg, 1.184 mmol) and NMI (265.18 mg, 3.230 mmol). The resulting mixture was stirred at room temperature for 2 h under nitrogen atmosphere. The reaction mixture was quenched with water and extracted with ethyl acetate. The combined organic layers were washed with brine, dried over anhydrous sodium sulfate, filtered, and concentrated under vacuum. The residue was purified by reverse phase flash column chromatography with 5~95% acetonitrile in water to afford methyl 6-(((5-(4-(2-(difluoromethoxy)-6-fluorophenyl)-6-methylpyridine-3-amido)-1,3,4-thiadiazol-2-yl)oxy)methyl)pyridine-3-carboxylate (300 mg, 47.51%) as a white solid. MS (ESI) calc'd for ($C_{24}H_{18}F_3N_5O_5S$) $(M+1)^+$, 546.1; found 546.0.

Step-3: 4-(2-(difluoromethoxy)-6-fluorophenyl)-N-(5-((5-(hydroxymethyl)pyridin-2-yl)methoxy)-1,3,4-thiadiazol-2-yl)-6-methylnicotinamide

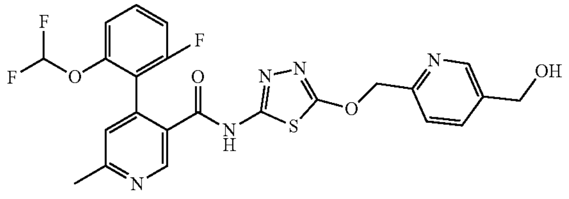 [SMILES: Cc1cc(-c2c(F)cccc2OC(F)F)c(C(=O)Nc2nnc(OCc3ccc(CO)cn3)s2)cn1]

To a stirred solution of methyl 6-(((5-(4-(2-(difluoromethoxy)-6-fluorophenyl)-6-methylpyridine-3-amido)-1,3,4-thiadiazol-2-yl)oxy)methyl)pyridine-3-carboxylate (180.00 mg, 0.330 mmol) in THF (8 mL) was added LiAlH4 (25.05 mg, 0.660 mmol) at 0° C. The resulting mixture was stirred at room temperature for 1 h. The reaction mixture was diluted with water and extracted with ethyl acetate. The combined organic layers were washed with brine, dried over anhydrous sodium sulfate, filtered, and concentrated under vacuum. The residue was purified by prep-HPLC with the following conditions: (Column: XBridge Prep OBD C18 Column, 30×150 mm 5 um; Mobile Phase A: Water (10 mmol/L $NH_4HCO_3$+0.1% $NH_3 \cdot H_2O$), Mobile Phase B: ACN; Flow rate: 60 mL/min; Gradient: 10 B to 42 B in 7 min; 220 nm; RT1: 6.02) to afford 4-(2-(difluoromethoxy)-6-fluorophenyl)-N-(5-((5-(hydroxymethyl)pyridin-2-yl)methoxy)-1,3,4-thiadiazol-2-yl)-6-methylnicotinamide (23 mg, 13.3%) as a white solid. MS (ESI) calc'd for ($C_{23}H_{18}F_3N_5O_4S$) $(M+1)^+$, 518.1; found, 518.3. $^1H$ NMR (400 MHz, DMSO-$d_6$) δ 13.03 (s, 1H), 9.35 (s, 1H), 8.94 (s, 1H), 7.79-7.76 (m, 1H), 7.56-7.37 (m, 2H), 7.31-7.11 (m, 4H), 5.51 (s, 2H), 5.37-5.34 (m, 1H), 4.55 (d, J=6.4 Hz, 2H), 2.68 (s, 3H).

Example 26

N-(5-((6-(methoxymethyl)pyridin-2-yl)methoxy)-1,3,4-thiadiazol-2-yl)-4-(2-methoxyphenyl)-6-methylnicotinamide

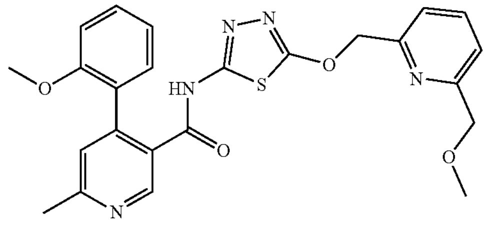 [SMILES: COCc1cccc(COc2nnc(NC(=O)c3cnc(C)cc3-c3ccccc3OC)s2)n1]

Step-1: (6-(methoxymethyl)pyridin-2-yl)methanol

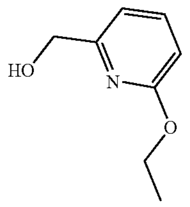

To a solution of 6-(methoxymethyl)pyridine-2-carbaldehyde (450.00 mg, 2.977 mmol) in MeOH (10.00 mL) was added $NaBH_4$ (112.6 mg, 2.977 mmol) in portions at 0° C. The resulting mixture was stirred at room temperature for 2 h. The reaction mixture was then quenched by the addition of water and extracted with ethyl acetate. The combined organic layers were washed with brine, dried over anhydrous sodium sulfate, filtered, and concentrated under vacuum to afford (6-(methoxymethyl)pyridin-2-yl)methanol (338 mg, 70.4%) as a yellow oil. MS (ESI) calc'd for ($C_7H_8ClNO$) $(M+1)^+$, 154.1, found 154.1.

Step-2: 5-((6-(methoxymethyl)pyridin-2-yl)methoxy)-1,3,4-thiadiazol-2-amine

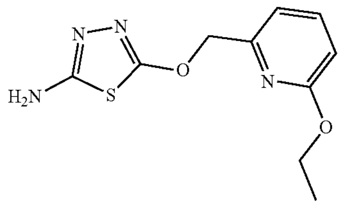 [SMILES: CCOc1cccc(COc2nnc(N)s2)n1]

To a solution of NaH (75.90 mg, 3.163 mmol, 60%) in THF (10.00 mL) was added a solution of (6-(methoxymethyl)pyridin-2-yl)methanol (323.0 mg, 2.109 mmol) in THF (2 mL) at 0° C. under nitrogen and stirred at 0° C. for 1 hour. To the above solution was added 5-bromo-1,3,4-thiadiazol-2-amine (455.51 mg, 2.531 mmol) in portions at 0° C. under nitrogen. The resulting mixture was stirred at room temperature for 4 h. The reaction mixture was quenched by the addition of water and extracted with ethyl acetate. The combined organic layers were washed with brine, dried over anhydrous sodium sulfate, filtered, and concentrated under vacuum. The residue was purified by flash chromatography on silica gel with 0~50% ethyl acetate in petroleum ether to afford 5-((6-(methoxymethyl)pyridin-2-yl)methoxy)-1,3,4-thiadiazol-2-amine (110 mg, 21.3%) as a yellow solid. MS (ESI) calc'd for ($C_{10}H_{12}N_4O_2S$) $(M+1)^+$, 253.1, found 253.1.

Step-3: N-(5-((6-(methoxymethyl)pyridin-2-yl)methoxy)-1,3,4-thiadiazol-2-yl)-4-(2-methoxyphenyl)-6-methylnicotinamide

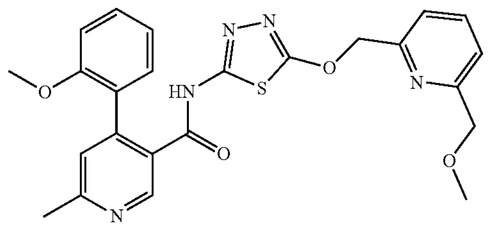 [SMILES: COCc1cccc(COc2nnc(NC(=O)c3cnc(C)cc3-c3ccccc3OC)s2)n1]

To a solution of 5-((6-(methoxymethyl)pyridin-2-yl)methoxy)-1,3,4-thiadiazol-2-amine (110 mg, 0.44 mmol) in ACN (5 mL) were added 4-(2-methoxyphenyl)-6-methylnicotinic acid (281.00 mg, 0.52 mmol, Intermediate D), NMI (263 mg, 3.21 mmol) and TCFH (449 mg, 1.61 mmol). The mixture was stirred at room temperature for 2 h. The mixture was quenched with water and extracted with ethyl acetate. The combined organic layers were washed with brine, dried over anhydrous sodium sulfate, filtered, and concentrated under vacuum. The residue was purified by flash chromatography on silica gel with 0~10% methanol in dichloromethane and further purified by prep-HPLC with the following conditions: (Column: XBridge Prep OBD C18 Column, 30×150 mm 5 um; Mobile Phase A: Water (10 MMOL/L $NH_4HCO_3$+0.1% $NH_3 \cdot H_2O$), Mobile Phase B: ACN; Flow rate: 60 mL/min; Gradient: 7 B to 40 B in 8 min; 220 nm) to afford N-(5-((6-(methoxymethyl)pyridin-2-yl)methoxy)-1,3,4-thiadiazol-2-yl)-4-(2-methoxyphenyl)-6-methylnicotinamide (61 mg, 29.3%) as a yellow solid. MS (ESI) calc'd for ($C_{25}H_{23}N_5O_4S$) $(M+1)^+$, 478.2; found 478.2. $^1H$ NMR (400 MHz, DMSO-$d_6$) δ 12.77 (s, 1H), 8.70 (s, 1H), 7.89-7.88 (m, 1H), 7.46-7.30 (m, 5H), 7.06-7.55 (m, 1H), 6.99-6.97 (m, 1H), 5.56 (s, 2H), 4.72 (s, 2H), 3.69 (s, 3H), 3.37 (s, 3H), 2.62 (s, 3H).

Example 27, 28, 29 and 30

(R)—N-(5-(2-(5-chloropyridin-2-yl)-2-hydroxyethoxy)-1,3,4-thiadiazol-2-yl)-4-(2-methoxyphenyl)-6-methylnicotinamide (Example 27), (S)—N-(5-(2-(5-chloropyridin-2-yl)-2-hydroxyethoxy)-1,3,4-thiadiazol-2-yl)-4-(2-methoxyphenyl)-6-methylnicotinamide (Example 28), (R)—N-(5-(1-(5-chloropyridin-2-yl)-2-hydroxyethoxy)-1,3,4-thiadiazol-2-yl)-4-(2-methoxyphenyl)-6-methylnicotinamide (Example 29), (S)—N-(5-(1-(5-chloropyridin-2-yl)-2-hydroxyethoxy)-1,3,4-thiadiazol-2-yl)-4-(2-methoxyphenyl)-6-methylnicotinamide (Example

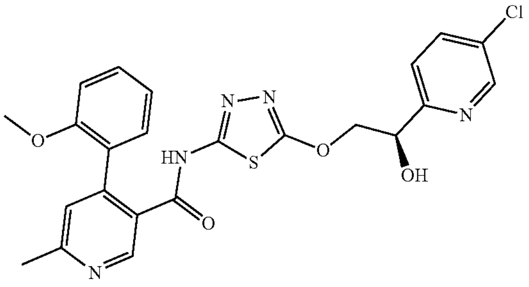

-continued

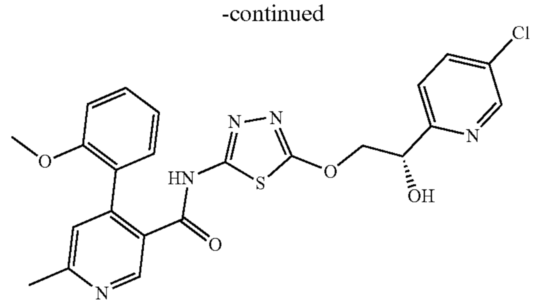

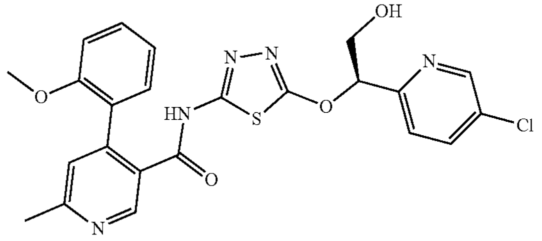

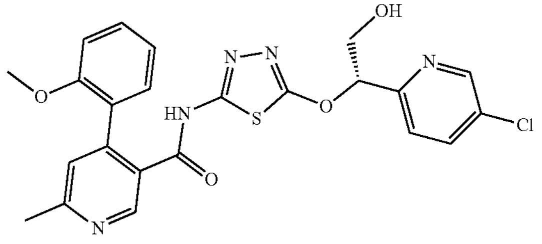

Step-1: 5-chloro-2-vinylpyridine

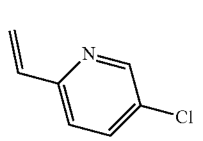

To a stirred mixture of 2,5-dichloropyridine (10.0 g, 51.96 mmol) in 1,4-dioxane (100.0 mL) and $H_2O$ (10 mL) were added $K_2CO_3$ (21.5 g, 155.89 mmol), trifluoro(vinyl)-14-borane potassium salt (13.9 g, 103.92 mmol) and Pd(dppf) $Cl_2$ (3.8 g, 5.19 mmol). The resulting mixture was stirred for 2 h at 80° C. under $N_2$ atmosphere. The reaction mixture was diluted with water and extracted with ethyl acetate. The combined organic layers were washed with brine, dried over anhydrous sodium sulfate, filtered, and concentrated under vacuum. The residue was purified by flash column chromatography with 0~13% ethyl acetate in petroleum ether to afford 5-chloro-2-vinylpyridine (2.5 g, 34.3%) as an orange oil. MS (ESI) calc'd for ($C_7H_6ClN$) $(M+1)^+$, 140.0, found 140.0.

Step-2: (R)-1-(5-chloropyridin-2-yl)ethane-1,2-diol

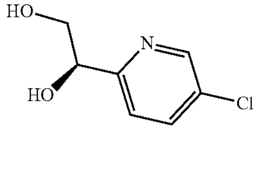 [SMILES: OC[C@H](O)c1ccc(Cl)cn1]

To a stirred solution of 5-chloro-2-vinylpyridine (2.8 g, 20.06 mmol) and methane sulfonamide (1.9 g, 20.06 mmol) in tert-butanol/$H_2O$ (28.0 mL, v/v=1/1) was added and AD-mix-0 (27.9 g, 35.91 mmol) in portions at room temperature under nitrogen atmosphere. The resulting mixture was stirred at room temperature for 24 h under $N_2$ atmosphere. The reaction mixture was quenched with $Na_2SO_3$ and stirred at room temperature for 1 h. The resulting mixture was extracted with isopropanol and ethyl acetate. The combined organic layers were washed with brine, dried over anhydrous sodium sulfate, filtered, and concentrated under vacuum to afford (R)-1-(5-chloropyridin-2-yl)ethane-1,2-diol (3100 mg, 98%) as an off-white solid. MS (ESI) calc'd for ($C_7H_8ClNO_2$) $(M+1)^+$, 174.0, found 174.0.

Step-3: (R)-2-((tert-butyldimethylsilyl)oxy)-1-(5-chloropyridin-2-yl)ethan-1-ol and (R)-2-((tert-butyldimethylsilyl)oxy)-2-(5-chloropyridin-2-yl)ethan-1-ol

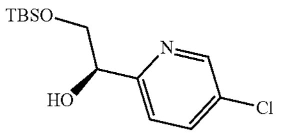

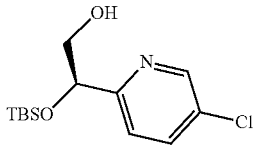

To a stirred solution of (R)-1-(5-chloropyridin-2-yl)ethane-1,2-diol (2.18 g, 7.57 mmol) and imidazole (2.57 g, 37.79 mmol) in dichloromethane (30.0 mL) was added TBS-Cl (1.14 g, 7.57 mmol) in portions at 0° C. The resulting mixture was stirred at 0° C. for 1 h. The resulting mixture was concentrated under vacuum. The residue was purified by flash column chromatography with 0~15% ethyl acetate in petroleum ether to afford a mixture of (R)-2-((tert-butyldimethylsilyl)oxy)-1-(5-chloropyridin-2-yl)ethan-1-ol and (R)-2-((tert-butyldimethylsilyl)oxy)-2-(5-chloropyridin-2-yl)ethan-1-ol (1.0 g, 45%) as yellow green oil. MS (ESI) calc'd for ($C_{13}H_{22}ClNO_2Si$) $(M+1)^+$, 288.1, found 288.0.

Step-4: (S)-1-(5-chloropyridin-2-yl)ethane-1,2-diol

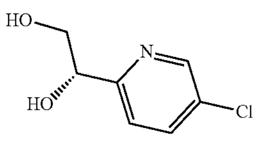 [SMILES: OC[C@@H](O)c1ccc(Cl)cn1]

To a stirred solution of 5-chloro-2-vinylpyridine (3.0 g, 21.49 mmol) and methane sulfonamide (2.04 g, 21.49 mmol) in tert-butanol/$H_2O$ (51.0 mL, v/v=2/1) was added AD-mix-α (30.0 g, 38.46 mmol) in portions at room temperature under nitrogen atmosphere. The resulting mixture was stirred at room temperature for 24 h under $N_2$ atmosphere. The reaction mixture was quenched with $Na_2SO_3$ and stirred at room temperature for 1 h. The resulting mixture was extracted with isopropanol and ethyl acetate.

The combined organic layers were washed with brine, dried over anhydrous sodium sulfate, filtered, and concentrated under vacuum. The residue was purified by flash column chromatography with 0~10% methyl alcohol in dichloromethane to afford (S)-1-(5-chloropyridin-2-yl)ethane-1,2-diol (2.8 g, 75%) as an off-white solid. MS (ESI) calc'd for ($C_7H_8ClNO_2$) $(M+1)^+$, 174.0, found 174.0.

Step-5: (S)-2-((tert-butyldimethylsilyl)oxy)-1-(5-chloropyridin-2-yl)ethan-1-ol and (S)-2-((tert-butyldimethylsilyl)oxy)-2-(5-chloropyridin-2-yl)ethan-1-ol

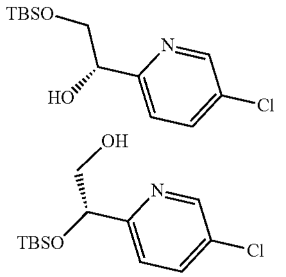

To a stirred solution of (S)-1-(5-chloropyridin-2-yl)ethane-1,2-diol (3.0 g, 17.28 mmol) and imidazole (3.53 g, 52.01 mmol) in dichloromethane (30.0 mL) was added TBS-Cl (2.60 g, 17.28 mmol) in portions at 0° C. The resulting mixture was stirred at 0° C. for 1 h. The resulting mixture was concentrated under vacuum. The residue was purified by flash column chromatography with 0~20% ethyl acetate in petroleum to afford a mixture of (S)-2-((tert-butyldimethylsilyl)oxy)-1-(5-chloropyridin-2-yl)ethan-1-ol and (S)-2-((tert-butyldimethylsilyl)oxy)-2-(5-chloropyridin-2-yl)ethan-1-ol (1.45 g, 25%) as colorless oil. MS (ESI) calc'd for ($C_{13}H_{22}ClNO_2Si$) $(M+1)^+$, 288.1, found 288.0.

Step-6: (R)-5-(2-((tert-butyldimethylsilyl)oxy)-1-(5-chloropyridin-2-yl)ethoxy)-1,3,4-thiadiazol-2-amine and (R)-5-(2-((tert-butyldimethylsilyl)oxy)-2-(5-chloropyridin-2-yl)ethoxy)-1,3,4-thiadiazol-2-amine

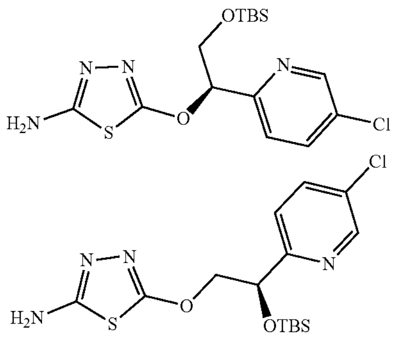

To a stirred mixture of (R)-2-((tert-butyldimethylsilyl)oxy)-1-(5-chloropyridin-2-yl)ethan-1-ol and (R)-2-((tert-butyldimethylsilyl)oxy)-2-(5-chloropyridin-2-yl)ethan-1-ol (800.0 mg, 2.77 mmol) in THF (10.0 mL) was added NaH (133.3 mg, 5.55 mmol, 60%) in portions at 0° C. and stirred at 0° C. for 30 min under nitrogen. To the above mixture was added 5-bromo-1,3,4-thiadiazol-2-amine (550.3 mg, 3.05 mmol) at 0° C. The resulting mixture was stirred at 0° C. for additional 4 h. The reaction mixture was diluted with water and extracted with ethyl acetate. The combined organic layers were washed with brine, dried over anhydrous sodium sulfate, filtered, and concentrated under vacuum. The residue was purified by flash column chromatography with 0~60% ethyl acetate in petroleum ether to afford a mixture of (R)-5-(2-((tert-butyldimethylsilyl)oxy)-1-(5-chloropyridin-2-yl)ethoxy)-1,3,4-thiadiazol-2-amine and (R)-5-(2-((tert-butyldimethylsilyl)oxy)-2-(5-chloropyridin-2-yl)ethoxy)-1,3,4-thiadiazol-2-amine (210 mg, 19%) as brown solid. MS (ESI) calc'd for ($C_{15}H_{23}ClN_4O_2SSi$) $(M+1)^+$, 387.1, found 387.0.

Step-7: (R)—N-(5-(2-((tert-butyldimethylsilyl)oxy)-1-(5-chloropyridin-2-yl)ethoxy)-1,3,4-thiadiazol-2-yl)-4-(2-methoxyphenyl)-6-methylnicotinamide and (R)—N-(5-(2-((tert-butyldimethylsilyl)oxy)-2-(5-chloropyridin-2-yl)ethoxy)-1,3,4-thiadiazol-2-yl)-4-(2-methoxyphenyl)-6-methylnicotinamide

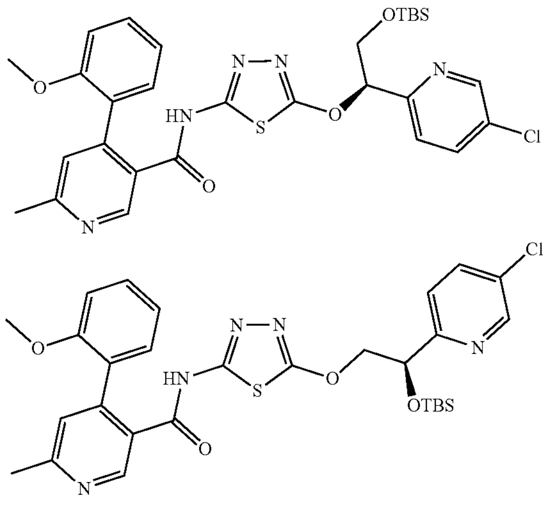

To a stirred mixture of (R)-5-(2-((tert-butyldimethylsilyl)oxy)-1-(5-chloropyridin-2-yl)ethoxy)-1,3,4-thiadiazol-2-amine and (R)-5-(2-((tert-butyldimethylsilyl)oxy)-2-(5-chloropyridin-2-yl)ethoxy)-1,3,4-thiadiazol-2-amine (210.0 mg, 0.54 mmol) in MeCN (3.0 mL) were added TCFH (167.4 mg, 0.59 mmol), 4-(2-methoxyphenyl)-6-methylnicotinic acid (145.2 mg, 0.59 mmol, Intermediate D) and NMI (133.6 mg, 1.62 mmol). The resulting mixture was stirred at room temperature for 1.5 h. The resulting mixture was concentrated under vacuum. The residue was purified by reverse phase flash chromatography with 5~85% acetonitrile in water to afford a mixture of (R)—N-(5-(2-((tert-butyldimethylsilyl)oxy)-1-(5-chloropyridin-2-yl)ethoxy)-1,3,4-thiadiazol-2-yl)-4-(2-methoxyphenyl)-6-methylnicotinamide and (R)—N-(5-(2-((tert-butyldimethylsilyl)oxy)-2-(5-chloropyridin-2-yl)ethoxy)-1,3,4-thiadiazol-2-yl)-4-(2-methoxyphenyl)-6-methylnicotinamide (146 mg, 46%) as brown oil. MS (ESI) calc'd for ($C_{29}H_{34}ClN_5O_4SSi$) $(M+1)^+$, 612.2, found 612.0.

Step-8: (R)—N-(5-(1-(5-chloropyridin-2-yl)-2-hydroxyethoxy)-1,3,4-thiadiazol-2-yl)-4-(2-methoxyphenyl)-6-methylnicotinamide and (R)—N-(5-(2-(5-chloropyridin-2-yl)-2-hydroxyethoxy)-1,3,4-thiadiazol-2-yl)-4-(2-methoxyphenyl)-6-methylnicotinamide

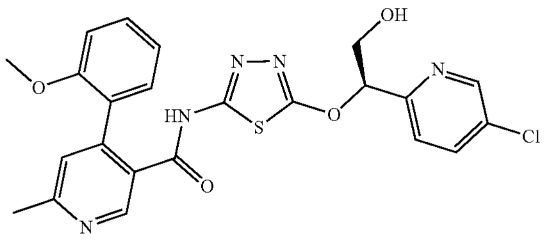

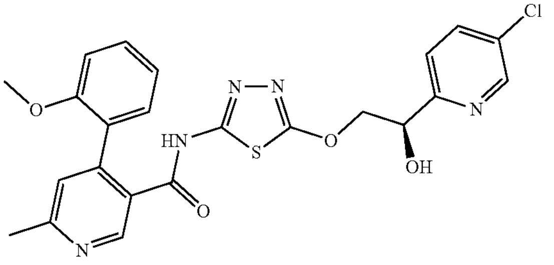

A mixture of (R)—N-(5-(2-((tert-butyldimethylsilyl)oxy)-1-(5-chloropyridin-2-yl)ethoxy)-1,3,4-thiadiazol-2-yl)-4-(2-methoxyphenyl)-6-methylnicotinamide and (R)—N-(5-(2-((tert-butyldimethylsilyl)oxy)-2-(5-chloropyridin-2-yl)ethoxy)-1,3,4-thiadiazol-2-yl)-4-(2-methoxyphenyl)-6-methylnicotinamide (146 mg, 0.23 mmol) in THF (3.0 mL) and HCl (6 N) (3.0 mL) was stirred at room temperature for 1 h. The residue was basified to pH 7 with saturated $NaHCO_3$ (aq.). The resulting mixture was extracted with ethyl acetate. The combined organic layers were washed with brine, dried over anhydrous $Na_2SO_4$. After filtration, the filtrate was concentrated under vacuum. The crude product was purified by Prep-HPLC with the following conditions: (Column: XBridge Shield RP18 OBD Column, 30*150 mm, 5 um; Mobile Phase A: water (10 mmol/L $NH_4HCO_3$), Mobile Phase B: ACN; Flow rate: 60 mL/min; Gradient: 20 B to 50 B in 7 min; 254 nm) to afford (R)—N-(5-(1-(5-chloropyridin-2-yl)-2-hydroxyethoxy)-1,3,4-thiadiazol-2-yl)-4-(2-methoxyphenyl)-6-methylnicotinamide (6.4 mg, 93% purity) as white solid and (R)—N-(5-(2-(5-chloropyridin-2-yl)-2-hydroxyethoxy)-1,3,4-thiadiazol-2-yl)-4-(2-methoxyphenyl)-6-methylnicotinamide (18.0 mg, 98% purity) as white solid.

(R)—N-(5-(1-(5-chloropyridin-2-yl)-2-hydroxyethoxy)-1,3,4-thiadiazol-2-yl)-4-(2-methoxyphenyl)-6-methylnicotinamide: MS (ESI) calc'd for ($C_{23}H_{20}ClN_5O_4S$) $(M+1)^+$, 498.1, found 498.0. $^1H$ NMR (400 MHz, DMSO-$d_6$) δ 12.72 (s, 1H), 8.66 (s, 1H), 8.59 (s, 1H), 7.96-7.93 (m, 1H), 7.51 (d, J=8.4 Hz, 1H), 7.40-7.36 (m, 2H), 7.34-7.28 (m, 1H), 7.08-7.05 (m, 1H), 6.98 (d, J=8.0 Hz, 1H), 5.88-5.85 (m, 1H), 5.30-5.27 (m, 1H), 3.88-3.85 (s, 2H), 3.49 (ds, 3H), 2.55 (s, 3H).

(R)—N-(5-(2-(5-chloropyridin-2-yl)-2-hydroxyethoxy)-1,3,4-thiadiazol-2-yl)-4-(2-methoxyphenyl)-6-methylnicotinamide: MS (ESI) calc'd for ($C_{23}H_{20}ClN_5O_4S$) $(M+1)^+$, 498.1, found 498.1. $^1H$ NMR (400 MHz, $CD_3OD$) δ 8.65 (s, 1H), 8.54 (d, J=2.4 Hz, 1H), 7.91-7.88 (m, 1H), 7.66 (d, J=8.4 Hz, 1H), 7.45-7.37 (m, 3H), 7.12-7.08 (m, 1H), 6.98 (d, J=8.0 Hz, 1H), 5.15-5.12 (m, 1H), 4.80-4.76 (m, 1H), 4.66-4.62 (m, 1H), 3.60 (s, 3H), 2.67 (s, 3H).

Step-9: (S)-5-(2-((tert-butyldimethylsilyl)oxy)-1-(5-chloropyridin-2-yl)ethoxy)-1,3,4-thiadiazol-2-amine and (S)-5-(2-((tert-butyldimethylsilyl)oxy)-2-(5-chloropyridin-2-yl)ethoxy)-1,3,4-thiadiazol-2-amine

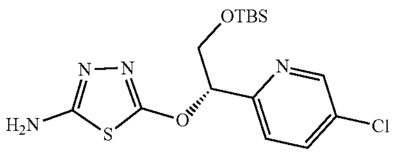

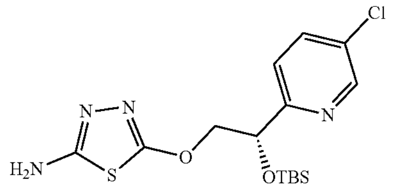

To a stirred mixture of (S)-2-((tert-butyldimethylsilyl)oxy)-1-(5-chloropyridin-2-yl)ethan-1-ol and (S)-2-((tert-butyldimethylsilyl)oxy)-2-(5-chloropyridin-2-yl)ethan-1-ol (900.0 mg, 3.12 mmol) in THF (10.0 mL) was added NaH (150.0 mg, 6.25 mmol, 60%) in portions at 0° C. and stirred at 0° C. for 30 min under nitrogen. To the above mixture was added 5-bromo-1,3,4-thiadiazol-2-amine (550.3 mg, 3.05 mmol) at 0° C. The resulting mixture was stirred at 0° C. for additional 4 h. The reaction mixture was diluted with water and extracted with ethyl acetate. The combined organic layers were washed with brine, dried over anhydrous sodium sulfate, filtered, and concentrated under vacuum. The residue was purified by flash column chromatography with 0~60% ethyl acetate in petroleum ether to afford a mixture of (S)-5-(2-((tert-butyldimethylsilyl)oxy)-1-(5-chloropyridin-2-yl)ethoxy)-1,3,4-thiadiazol-2-amine and (R)-5-(2-((tert-butyldimethylsilyl)oxy)-2-(5-chloropyridin-2-yl)ethoxy)-1,3,4-thiadiazol-2-amine (230 mg, 28%) as brown solid. MS (ESI) calc'd for ($C_{15}H_{23}ClN_4O_2SSi$) $(M+1)^+$, 387.1, found 387.0.

Step-10: (S)—N-(5-(2-((tert-butyldimethylsilyl)oxy)-1-(5-chloropyridin-2-yl)ethoxy)-1,3,4-thiadiazol-2-yl)-4-(2-methoxyphenyl)-6-methylnicotinamide and (S)—N-(5-(2-((tert-butyldimethylsilyl)oxy)-2-(5-chloropyridin-2-yl)ethoxy)-1,3,4-thiadiazol-2-yl)-4-(2-methoxyphenyl)-6-methylnicotinamide

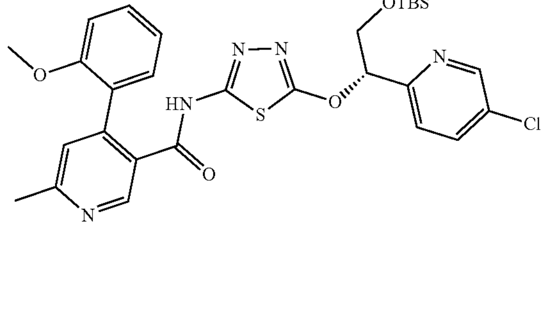

-continued

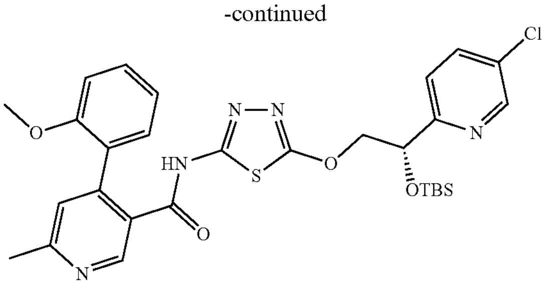

To a stirred mixture of (S)-5-(2-((tert-butyldimethylsilyl)oxy)-1-(5-chloropyridin-2-yl)ethoxy)-1,3,4-thiadiazol-2-amine and (S)-5-(2-((tert-butyldimethylsilyl)oxy)-2-(5-chloropyridin-2-yl)ethoxy)-1,3,4-thiadiazol-2-amine (230.0 mg, 0.59 mmol) in MeCN (3.0 mL) were added TCFH (277.6 mg, 0.98 mmol), 4-(2-methoxyphenyl)-6-methylnicotinic acid (262.5 mg, 1.07 mmol, Intermediate D) and NMI (221.5 mg, 2.69 mmol). The resulting mixture was stirred at room temperature for 3 h. The resulting mixture was concentrated under vacuum. The residue was purified by reverse phase flash chromatography with 5~85% acetonitrile in water to afford a mixture of (S)—N-(5-(2-((tert-butyldimethylsilyl)oxy)-1-(5-chloropyridin-2-yl)ethoxy)-1,3,4-thiadiazol-2-yl)-4-(2-methoxyphenyl)-6-methylnicotinamide and (S)—N-(5-(2-((tert-butyldimethylsilyl)oxy)-2-(5-chloropyridin-2-yl)ethoxy)-1,3,4-thiadiazol-2-yl)-4-(2-methoxyphenyl)-6-methylnicotinamide (130 mg, 23%) as brown oil. MS (ESI) calc'd for ($C_{29}H_{34}ClN_5O_4SSi$) $(M+1)^+$, 612.2, found 612.0.

Step-11: (S)—N-(5-(1-(5-chloropyridin-2-yl)-2-hydroxyethoxy)-1,3,4-thiadiazol-2-yl)-4-(2-methoxyphenyl)-6-methylnicotinamide and (S)—N-(5-(2-(5-chloropyridin-2-yl)-2-hydroxyethoxy)-1,3,4-thiadiazol-2-yl)-4-(2-methoxyphenyl)-6-methylnicotinamide

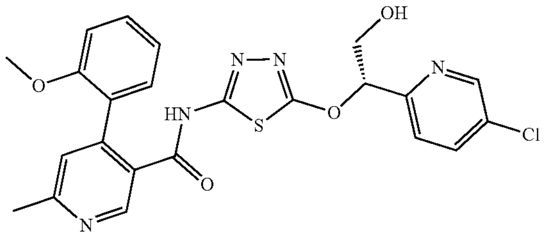

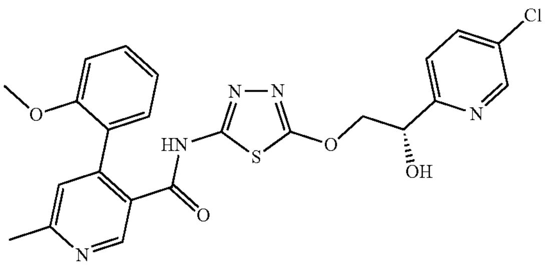

A mixture of (S)—N-(5-(2-((tert-butyldimethylsilyl)oxy)-1-(5-chloropyridin-2-yl)ethoxy)-1,3,4-thiadiazol-2-yl)-4-(2-methoxyphenyl)-6-methylnicotinamide and (S)—N-(5-(2-((tert-butyldimethylsilyl)oxy)-2-(5-chloropyridin-2-yl)ethoxy)-1,3,4-thiadiazol-2-yl)-4-(2-methoxyphenyl)-6-methylnicotinamide (130 mg, 0.21 mmol) in THF (3.0 mL) and HCl (6 N) (3.0 mL) was stirred at room temperature for 1 h. The residue was basified to pH 7 with saturated $NaHCO_3$ (aq.). The resulting mixture was extracted with ethyl acetate. The combined organic layers were washed with brine, dried over anhydrous $Na_2SO_4$. After filtration, the filtrate was concentrated under vacuum. The crude product was purified by Prep-HPLC with the following conditions: (Column: XBridge Shield RP18 OBD Column, 30*150 mm, 5 um; Mobile Phase A: water (10 mmol/L $NH_4HCO_3$), Mobile Phase B: ACN; Flow rate: 60 mL/min; Gradient: 20 B to B in 7 min; 254 nm) to afford (S)—N-(5-(1-(5-chloropyridin-2-yl)-2-hydroxyethoxy)-1,3,4-thiadiazol-2-yl)-4-(2-methoxyphenyl)-6-methylnicotinamide (10.4 mg, 93% purity) as white solid and (S)—N-(5-(2-(5-chloropyridin-2-yl)-2-hydroxyethoxy)-1,3,4-thiadiazol-2-yl)-4-(2-methoxyphenyl)-6-methylnicotinamide (15.8 mg, 98% purity) as white solid.

(S)—N-(5-(1-(5-chloropyridin-2-yl)-2-hydroxyethoxy)-1,3,4-thiadiazol-2-yl)-4-(2-methoxyphenyl)-6-methylnicotinamide: MS (ESI) calc'd for ($C_{23}H_{20}ClN_5O_4S$) $(M+1)^+$, 498.1, found 498.0. $^1H$ NMR (400 MHz, DMSO-$d_6$) δ 12.72 (s, 1H), 8.66 (s, 1H), 8.59 (s, 1H), 7.96-7.93 (m, 1H), 7.51 (d, J=8.4 Hz, 1H), 7.40-7.36 (m, 2H), 7.34-7.28 (m, 1H), 7.08-7.05 (m, 1H), 6.98 (d, J=8.0 Hz, 1H), 5.88-5.85 (m, 1H), 5.30-5.27 (m, 1H), 3.88-3.85 (s, 2H), 3.49 (ds, 3H), 2.55 (s, 3H).

(S)—N-(5-(2-(5-chloropyridin-2-yl)-2-hydroxyethoxy)-1,3,4-thiadiazol-2-yl)-4-(2-methoxyphenyl)-6-methylnicotinamide: MS (ESI) calc'd for ($C_{23}H_{20}ClN_5O_4S$) $(M+1)^+$, 498.1, found 498.1. $^1H$ NMR (400 MHz, $CD_3OD$) δ 8.64 (d, J=4.0 Hz, 1H), 8.57 (d, J=2.0 Hz, 1H), 7.89-7.86 (m, 1H), 7.55 (d, J=8.4 Hz, 1H), 7.44-7.36 (m, 3H), 7.12-7.08 (m, 1H), 6.97 (d, J=8.0 Hz, 1H), 5.98-5.95 (m, 1H), 4.08-4.00 (m, 2H), 3.60 (s, 3H), 2.66 (s, 3H).

Example 31

N-(5-((5-chloropyridin-2-yl)methoxy)-1,3,4-thiadiazol-2-yl)-4-(4-(hydroxymethyl)-2-methoxyphenyl)-6-methylnicotinamide

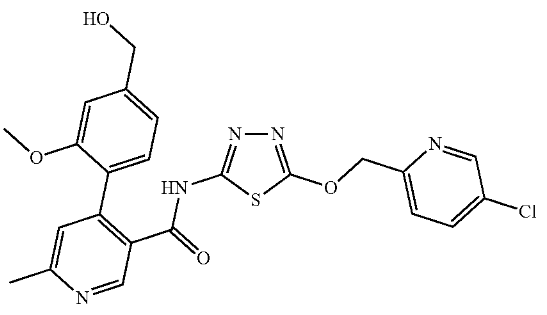 [SMILES: COc1cc(CO)ccc1-c1cc(C)ncc1C(=O)Nc1nnc(OCc2ccc(Cl)cn2)s1]

Step-1: methyl 4-(5-((5-((5-chloropyridin-2-yl)methoxy)-1,3,4-thiadiazol-2-yl)carbamoyl)-2-methylpyridin-4-yl)-3-methoxybenzoate

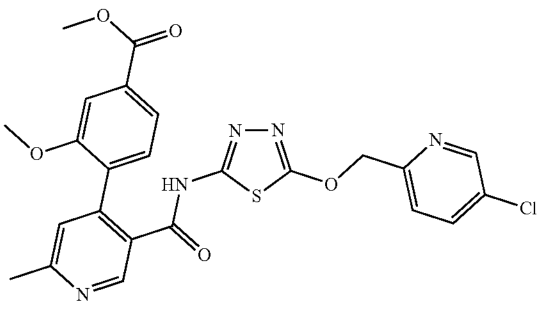 [SMILES: COC(=O)c1ccc(-c2cc(C)ncc2C(=O)Nc2nnc(OCc3ccc(Cl)cn3)s2)c(OC)c1]

To a degassed solution of 4-chloro-N-(5-((5-chloropyridin-2-yl)methoxy)-1,3,4-thiadiazol-2-yl)-6-methylnicotinamide (83 mg, 0.210 mmol) in dioxane (5 mL) and $H_2O$ (1 mL) were added (2-methoxy-4-(methoxycarbonyl)phenyl)boronic acid (130 mg, 0.619 mmol), $K_3PO_4$ (223 mg, 1.052 mmol) and Pd(dtbpf)$Cl_2$ (28 mg, 0.043 mmol) under nitrogen. The resulting solution was stirred at 100° C. for 8 h under nitrogen. The mixture was concentrated under vacuum. The residue was purified by flash chromatography on silica gel with 0~50% ethyl acetate in petroleum ether to afford methyl 4-(5-((5-((5-chloropyridin-2-yl)methoxy)-1,3,4-thiadiazol-2-yl)carbamoyl)-2-methylpyridin-4-yl)-3-methoxybenzoate (70 mg, 84.3%) as a white solid. MS (ESI) calc'd for ($C_{24}H_{20}ClN_5O_3S$) $(M+1)^+$, 526.1; found, 526.1.

Step-2: N-(5-((5-chloropyridin-2-yl)methoxy)-1,3,4-thiadiazol-2-yl)-4-(4-(hydroxymethyl)-2-methoxyphenyl)-6-methylnicotinamide

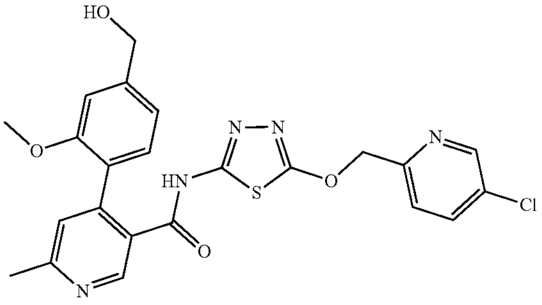 [SMILES: COc1cc(CO)ccc1-c1cc(C)ncc1C(=O)Nc1nnc(OCc2ccc(Cl)cn2)s1]

To a solution of methyl 4-(5-((5-((5-chloropyridin-2-yl)methoxy)-1,3,4-thiadiazol-2-yl)carbamoyl)-2-methylpyridin-4-yl)-3-methoxybenzoate (70 mg, 0.133 mmol) in THF (5 mL) was added $LiAlH_4$ (25 mg, 0.665 mmol) in portions at 0~5° C. and stirred at room temperature for 1 h. The reaction mixture was then quenched by the addition of water and extracted with ethyl acetate. The combined organic layers were washed with brine, dried over anhydrous sodium sulfate, filtered, and concentrated under vacuum. The residue was purified by flash chromatography on silica gel with 0~10% methanol in dichloromethane to afford N-(5-((5-chloropyridin-2-yl)methoxy)-1,3,4-thiadiazol-2-yl)-4-(4-(hydroxymethyl)-2-methoxyphenyl)-6-methylnicotinamide (2.8 mg, 4%) as a white solid. MS (ESI) calc'd for ($C_{23}H_{20}ClN_5O_4S$) $(M+1)^+$, 498.1; found, 498.1. $^1H$ NMR (400 MHz, DMSO-$d_6$) δ 12.76 (s, 1H), 8.65 (s, 2H), 8.02-7.99 (m, 1H), 7.61-7.59 (m, 1H), 7.30-7.27 (m, 2H), 7.02-7.00 (m, 1H), 6.93 (s, 1H), 5.54 (s, 2H), 5.31-5.28 (m, 1H), 4.54-4.53 (m, 2H), 3.50 (s, 3H), 2.56 (s, 3H).

Example 32

4-(5-cyano-2-methoxyphenyl)-N-(5-((5-(hydroxymethyl)pyridin-2-yl)methoxy)-1,3,4-thiadiazol-2-yl)-6-methylpyridine-3-carboxamide

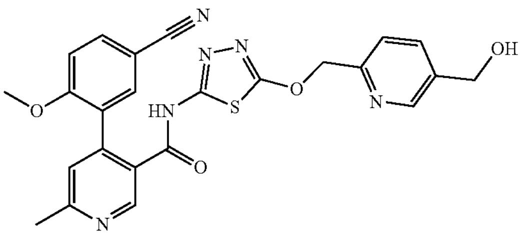 [SMILES: COc1ccc(C#N)cc1-c1cc(C)ncc1C(=O)Nc1nnc(OCc2ccc(CO)cn2)s1]

Step-1: tert-butyl 4-chloro-6-methylpyridine-3-carboxylate

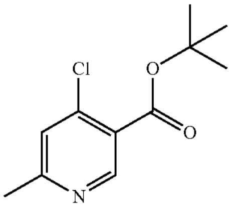

To a stirred solution of 4-chloro-6-methylpyridine-3-carboxylic acid (1.0 g, 5.82 mmol) and $BoC_2O$ (2.9 g, 13.28 mmol) in N-Methyl pyrrolidone (4 mL) was added dimethylaminopyridine (143 mg, 1.17 mmol). The resulting mixture was stirred at 30° C. for 16 h. The reaction mixture was quenched with water and extracted with ethyl acetate. The combined organic layers were washed with brine, dried over anhydrous sodium sulfate, filtered, and concentrated under vacuum. The residue was purified by flash column chromatography with 0~10% ethyl acetate in petroleum ether to afford tert-butyl 4-chloro-6-methylpyridine-3-carboxylate (900 mg, 67.8%) as a yellow oil. MS (ESI) calc'd for ($C_{11}H_{14}ClNO_2$) $(M+1)^+$, 228.1; found 228.1.

Step-2: tert-butyl 4-(5-cyano-2-methoxyphenyl)-6-methylpyridine-3-carboxylate

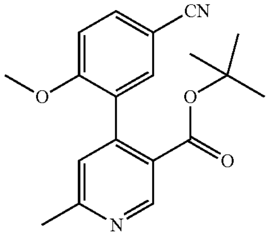 [SMILES: COc1ccc(C#N)cc1-c1cc(C)ncc1C(=O)OC(C)(C)C]

To a degassed solution of tert-butyl 4-chloro-6-methylpyridine-3-carboxylate (800 mg, 3.51 mmol) and 5-cyano-2-methoxyphenylboronic acid (619 mg, 3.49 mmol) in dioxane (6 mL) and water (2 mL) were added $Pd(PPh_3)_4$ (407 mg, 0.35 mmol) and $K_2CO_3$ (1.5 g, 10.56 mmol). The resulting mixture was stirred at 80° C. for 16 h under nitrogen atmosphere. The reaction mixture was quenched with water and extracted with ethyl acetate. The combined organic layers were washed with brine, dried over anhydrous sodium sulfate, filtered, and concentrated under vacuum. The residue was purified by flash column chromatography with 0~30% ethyl acetate in petroleum ether to afford tert-butyl 4-(5-cyano-2-methoxyphenyl)-6-methylpyridine-3-carboxylate (550 mg, 43.4%) as a yellow solid. MS (ESI) calc'd for $(C_{19}H_{20}N_2O_3)$ $(M+1)^+$, 325.1; found 325.1.

Step-3: 4-(5-cyano-2-methoxyphenyl)-6-methylnicotinic acid

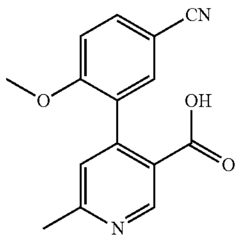 [SMILES: COc1ccc(C#N)cc1-c1cc(C)ncc1C(=O)O]

To a stirred solution of tert-butyl 4-(5-cyano-2-methoxyphenyl)-6-methylpyridine-3-carboxylate (250 mg, 0.77 mmol) in dichloromethane (4 mL) was added trifluoroacetaldehyde (2 mL). The resulting mixture was stirred at room temperature for 16 h. The residue was purified by reverse flash chromatography with 5~50% acetonitrile in water to afford 4-(5-cyano-2-methoxyphenyl)-6-methylpyridine-3-carboxylic acid (189 mg, 91.4%) as a white solid. MS (ESI) calc'd for $(C_{15}H_{12}N_2O_3)$ $(M+1)^+$, 269.1; found, 269.1.

Step-4: methyl 6-(((5-amino-1,3,4-thiadiazol-2-yl)oxy)methyl)nicotinate

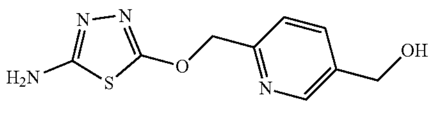 [SMILES: Nc1nnc(OCc2ccc(CO)cn2)s1]

To a stirred solution of methyl 6-(((5-amino-1,3,4-thiadiazol-2-yl)oxy)methyl)pyridine-3-carboxylate (500 mg, 1.87 mmol, Example 5, Step 1) in tetrahydrofuran (3 mL) was added $LiAlH_4$ (142 mg, 3.75 mmol) in portions at 0° C. under nitrogen atmosphere. The resulting mixture was stirred at room temperature for 2 h under nitrogen atmosphere. The reaction mixture was quenched with water and the residue was purified by reverse flash chromatography with 5~35% acetonitrile in water to afford methyl 6-(((5-amino-1,3,4-thiadiazol-2-yl)oxy)methyl)nicotinate (150 mg, 33.5%) as a green oil. MS (ESI) calc'd for $(C_9H_{10}N_4O_2S)$ $(M+1)^+$, 239.1; found, 239.1.

Step-5: 4-(5-cyano-2-methoxyphenyl)-N-(5-((5-(hydroxymethyl)pyridin-2-yl)methoxy)-1,3,4-thiadiazol-2-yl)-6-methylpyridine-3-carboxamide

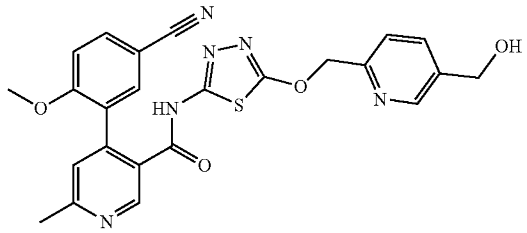 [SMILES: COc1ccc(C#N)cc1-c1cc(C)ncc1C(=O)Nc1nnc(OCc2ccc(CO)cn2)s1]

To a stirred solution of (6-(((5-amino-1,3,4-thiadiazol-2-yl)oxy)methyl)pyridin-3-yl)methanol (50 mg, 0.21 mmol) and 4-(5-cyano-2-methoxyphenyl)-6-methylpyridine-3-carboxylic acid (56 mg, 0.21 mmol) in DMF (2 mL) and MeCN (2 mL) were added TCFH (88 mg, 0.31 mmol) and N-methyl imidazole (68 mg, 0.83 mmol). The resulting mixture was stirred at room temperature for 2 h before concentrated under vacuum. The residue was purified by prep-HPLC with the following conditions: (Column: XBridge Prep OBD C18 Column, 30×150 mm 5 um; Mobile Phase A: Water (10 MMOL/L $NH_4HCO_3$+0.1% $NH_3 \cdot H_2O$), Mobile Phase B: ACN; Flow rate: 60 mL/min; Gradient: 10 B to 45 B in 8 min; 220 nm) to afford 4-(5-cyano-2-methoxyphenyl)-N-(5-((5-(hydroxymethyl)pyridin-2-yl)methoxy)-1,3,4-thiadiazol-2-yl)-6-methylpyridine-3-carboxamide (11.7 mg, 11.4%) as a white solid. MS (ESI) calc'd for $(C_{24}H_{20}N_6O_4S)$ $(M+1)^+$, 489.1; found 489.1. $^1H$ NMR (400 MHz, DMSO-$d_6$) δ 12.83 (s, 1H), 8.75 (s, 1H), 8.53 (d, J=2.0 Hz, 1H), 7.91-7.85 (m, 1H), 7.85 (d, J=2.0 Hz, 1H), 7.79-7.77 (m, 1H), 7.53 (d, J=8.0 Hz, 1H), 7.39 (s, 1H), 7.18 (d, J=8.8 Hz, 1H), 5.52 (s, 2H), 5.37 (s, 1H), 4.55 (d, J=5.2 Hz, 2H), 3.39 (s, 3H), 2.58 (s, 3H).

Example 33

4-(2-fluoro-6-methoxyphenyl)-N-(5-((5-(2-hydroxypropan-2-yl)pyridin-2-yl)methoxy)-1,3,4-thiadiazol-2-yl)-6-methylnicotinamide

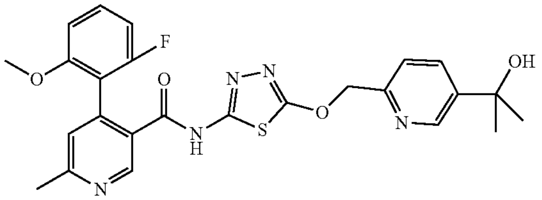 [SMILES: COc1cccc(F)c1-c1cc(C)ncc1C(=O)Nc1nnc(OCc2ccc(C(C)(C)O)cn2)s1]

Step-1: 2-(6-(((5-amino-1,3,4-thiadiazol-2-yl)oxy)methyl)pyridin-3-yl)propan-2-ol

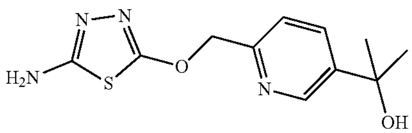 [SMILES: CC(C)(O)c1ccc(COc2nnc(N)s2)nc1]

To a solution of 1-(6-(((5-amino-1,3,4-thiadiazol-2-yl)oxy)methyl)pyridin-3-yl)ethenone (1.5 g, 5.993 mmol, Example 22 Step 3) in THF (40 mL) was added MeMgBr (24 mL, 23.973 mmol, 1 M in THF) dropwise at 0° C. The resulting mixture was stirred at room temperature for 2 h. the reaction mixture was quenched by the addition of methanol before concentrated under vacuum. The residue was purified by flash column chromatography with 0~10% methanol in dichloromethane to afford 2-(6-(((5-amino-1,3,4-thiadiazol-2-yl)oxy)methyl)pyridin-3-yl)propan-2-ol (400 mg, 13.3%) as a colorless oil. MS (ESI) calc'd for ($C_{11}H_{14}N_4O_2S$) $(M+1)^+$, 267.0; found 267.0.

Step-2: 4-(2-fluoro-6-methoxyphenyl)-N-(5-((5-(2-hydroxypropan-2-yl)pyridin-2-yl)methoxy)-1,3,4-thiadiazol-2-yl)-6-methylnicotinamide

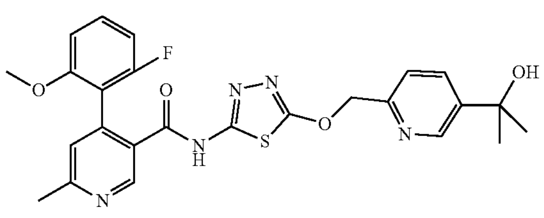 [SMILES: COc1cccc(F)c1-c1cc(C)ncc1C(=O)Nc1nnc(OCc2ccc(C(C)(C)O)cn2)s1]

To a mixture of 2-(6-(((5-amino-1,3,4-thiadiazol-2-yl)oxy)methyl)pyridin-3-yl)propan-2-ol (856.3 mg, 3.215 mmol) and 4-(2-fluoro-6-methoxyphenyl)-6-methylpyridine-3-carboxylic acid (700.0 mg, 2.679 mmol, Intermediate F) in DMF (5 mL) and MeCN (5 mL) were added NMI (659.9 mg, 8.038 mmol) and TCFH (826.9 mg, 2.947 mmol). The resulting mixture was stirred at room temperature for 2 h before concentrated under vacuum.

The residue was purified by reverse flash chromatography with 10-50% acetonitrile in water to afford 4-(2-fluoro-6-methoxyphenyl)-N-(5-((5-(2-hydroxypropan-2-yl)pyridin-2-yl)methoxy)-1,3,4-thiadiazol-2-yl)-6-methylnicotinamide (500 mg, 36.6%) as a white solid. MS (ESI) calc'd for ($C_{25}H_{24}FN_5O_4S$) $(M+1)^+$, 510.2; found 510.2. $^1H$ NMR (400 MHz, DMSO-$d_6$) δ12.89 (s, 1H), 8.81 (s, 1H), 8.69 (s, 1H), 7.90-7.88 (m, 1H), 7.48-7.32 (m, 3H), 6.94-6.88 (m, 2H), 5.50 (s, 2H), 5.24 (s, 1H), 3.59 (s, 3H), 2.57 (s, 3H), 1.46 (s, 6H).

Example 34

4-(2-fluoro-6-methoxyphenyl)-N-(5-((5-(methoxymethyl)pyridin-2-yl)methoxy)-1,3,4-thiadiazol-2-yl)-6-methylnicotinamide

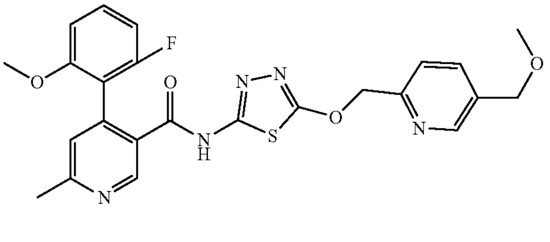 [SMILES: COCc1ccc(COc2nnc(NC(=O)c3cnc(C)cc3-c3c(F)cccc3OC)s2)nc1]

Step-1: methyl 6-(((5-(4-(2-fluoro-6-methoxyphenyl)-6-methylnicotinamido)-1,3,4-thiadiazol-2-yl)oxy)methyl)nicotinate

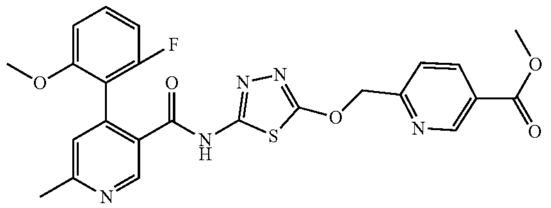 [SMILES: COC(=O)c1ccc(COc2nnc(NC(=O)c3cnc(C)cc3-c3c(F)cccc3OC)s2)nc1]

To a mixture of methyl 6-(((5-amino-1,3,4-thiadiazol-2-yl)oxy)methyl)nicotinate (2.9 g, 0.011 mol) in ACN (50 mL) were added NMI (1.8 g, 0.022 mol), 4-(2-fluoro-6-methoxyphenyl)-6-methylnicotinic acid (1.9 g, 0.007 mol, Intermediate F) and TCFH (2.5 g, 0.009 mol). The mixture was stirred at room temperature for 2 h. The mixture was concentrated under vacuum. The residue was purified by flash chromatography on silica gel with 0~10% methanol in dichloromethane to afford methyl 6-(((5-(4-(2-fluoro-6-methoxyphenyl)-6-methylnicotinamido)-1,3,4-thiadiazol-2-yl)oxy)methyl)nicotinate (2.0 g, 69%) as a white solid. MS (ESI) calc'd for ($C_{24}H_{20}FN_5O_5S$) $(M+1)^+$, 510.1; found, 510.1.

Step-2: 4-(2-fluoro-6-methoxyphenyl)-N-(5-((5-(hydroxymethyl)pyridin-2-yl)methoxy)-1,3,4-thiadiazol-2-yl)-6-methylnicotinamide

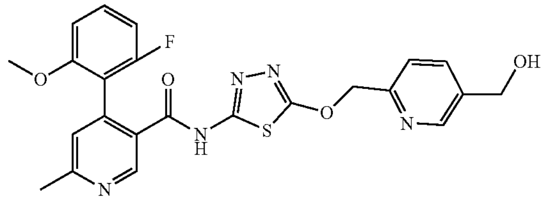 [SMILES: COc1cccc(F)c1-c1cc(C)ncc1C(=O)Nc1nnc(OCc2ccc(CO)cn2)s1]

To a solution of 6-(((5-(4-(2-fluoro-6-methoxyphenyl)-6-methylnicotinamido)-1,3,4-thiadiazol-2-yl)oxy)methyl)nicotinate (2.0 g, 0.004 mol) in THF (50 mL) was added $LiAlH_4$ (300.0 mg, 7.895 mmol) in portions at 0~5° C. and stirred at 5° C. for 30 minutes. The resulting mixture was stirred at room temperature for 1 h. The reaction mixture was then quenched by the addition of water and extracted with ethyl acetate. The combined organic layers were washed with brine, dried over anhydrous sodium sulfate, filtered, and concentrated under vacuum. The residue was purified by flash chromatography on silica gel with 0~10% methanol in dichloromethane to afford 4-(2-fluoro-6-methoxyphenyl)-N-(5-((5-(hydroxymethyl)pyridin-2-yl)methoxy)-1,3,4-thiadiazol-2-yl)-6-methylnicotinamide (300.0 mg, 15%) as a white solid. MS (ESI) calc'd for ($C_{23}H_{20}FN_5O_4S$) $(M+1)^+$, 482.0; found, 482.2.

Step-3: (6-(((5-(4-(2-fluoro-6-methoxyphenyl)-6-methylnicotinamido)-1,3,4-thiadiazol-2-yl)oxy)methyl)pyridin-3-yl)methyl methanesulfonate

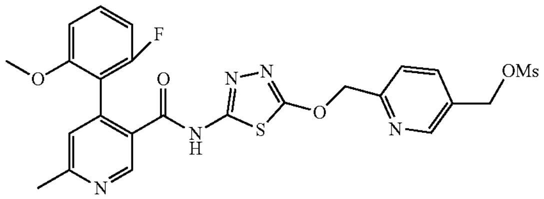 [SMILES: COc1cccc(F)c1-c1cc(C)ncc1C(=O)Nc1nnc(OCc2ccc(COS(C)(=O)=O)cn2)s1]

To a solution of 4-(2-fluoro-6-methoxyphenyl)-N-(5-((5-(hydroxymethyl)pyridin-2-yl)methoxy)-1,3,4-thiadiazol-2-yl)-6-methylnicotinamide (250 mg, 0.519 mmol) and TEA (158 mg, 1.564 mmol) in DCM (30 mL) was added MsCl (88.7 mg, 0.778 mmol) at 0° C. The resulting mixture was stirred at room temperature for 1 h. The reaction mixture was then quenched by the addition of water and extracted with ethyl acetate. The organic layers were combined, washed with brine, dried over anhydrous sodium sulfate and filtered. The filtrate was concentrated under vacuum to afford (6-(((5-(4-(2-fluoro-6-methoxyphenyl)-6-methylnicotinamido)-1,3,4-thiadiazol-2-yl)oxy)methyl)pyridin-3-yl) methyl methanesulfonate (120 mg, crude) as a white solid. MS (ESI) calc'd for ($C_{24}H_{22}FN_5O_6S_2$) $(M+1)^+$, 560.1; found 560.0.

Step-4: 4-(2-fluoro-6-methoxyphenyl)-N-(5-((5-(methoxymethyl)pyridin-2-yl)methoxy)-1,3,4-thiadiazol-2-yl)-6-methylnicotinamide

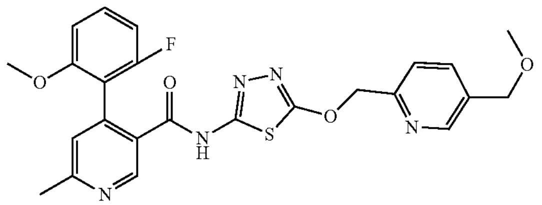 [SMILES: COCc1ccc(COc2nnc(NC(=O)c3cnc(C)cc3-c3c(F)cccc3OC)s2)nc1]

A mixture of (6-(((5-(4-(2-fluoro-6-methoxyphenyl)-6-methylnicotinamido)-1,3,4-thiadiazol-2-yl)oxy)methyl) pyridin-3-yl)methyl methanesulfonate (80 mg, 0.143 mmol) in $CH_3OH$ (5 mL) was stirred at 50° C. for 3 h. The mixture was concentrated under vacuum. The residue was purified by flash chromatography on silica gel with 0~10% methanol in dichloromethane and further purified by prep-HPLC with the following conditions: (Column: Sunfire prep C18 column, 30*150 um, 5 um; Mobile Phase A: Water (0.1% FA), Mobile Phase B: ACN; Flow rate: 60 mL/min; Gradient: 25 B to 55 B in 8 min; 220 nm; RT1: 7.23 min) to afford N-(5-((5-chloropyridin-2-yl)methoxy)-1,3,4-thiadiazol-2-yl)-4-(3,5-dimethyl-1H-pyrazol-4-yl)-6methylnicotinamide (33.1 mg, 41.3%) as a white solid. MS (ESI) calc'd for ($C_{24}H_{22}FN_5O_4S$) $(M+1)^+$, 495.1; found 495.2. $^1H$ NMR (400 MHz, Methanol-$d_4$) δ 8.94 (s, 1H), 8.67-8.63 (m, 1H), 8.09-8.07 (m, 1H), 7.79-7.71 (m, 2H), 7.50-7.44 (m, 1H), 6.93-6.89 (m, 2H), 5.66 (s, 2H), 4.89 (s, 2H), 3.86 (s, 3H), 3.46 (s, 3H). 2.76 (s, 3H).

Example 35

N-(5-(2H,3H-(1,4)dioxino(2,3-b)pyridin-6-ylmethoxy)-1,3,4-thiadiazol-2-yl)-4-(2-fluoro-6-methoxyphenyl)-6-methylpyridine-3-carboxamide

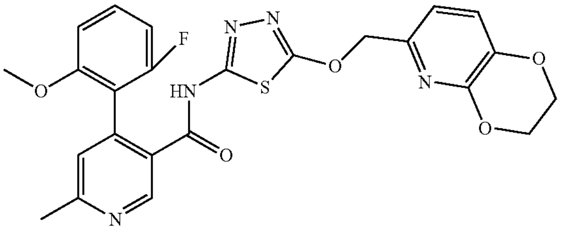 [SMILES: COc1cccc(F)c1-c1cc(C)ncc1C(=O)Nc1nnc(OCc2ccc3c(n2)OCCO3)s1]

Step-1: 5-(2H,3H-(1,4)dioxino(2,3-b)pyridin-6-ylmethoxy)-1,3,4-thiadiazol-2-amine

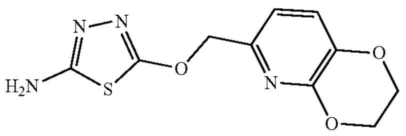 [SMILES: Nc1nnc(OCc2ccc3c(n2)OCCO3)s1]

To a solution of NaH (215.3 mg, 8.973 mmol, 60% purity) in THF (5 mL) was added a solution of 2H,3H-(1,4)dioxino(2,3-b)pyridin-6-ylmethanol (500.0 mg, 2.991 mmol) in THF (3 mL) drop wise at 0~5° C. and stirred at 0~5° C. for 30 min under nitrogen atmosphere. The a solution of 5-bromo-1,3,4-thiadiazol-2-amine (646.1 mg, 3.589 mmol) in THF (2 mL) was added to the above mixture at 0° C. The resulting mixture was stirred at room temperature for 16 h under nitrogen atmosphere. The resulting mixture was quenched with water and the aqueous phase was extracted with ethyl acetate. The combined organic solution was dried over sodium sulfate, filtered, and concentrated under vacuum. The residue was purified by flash column chromatography with 0-20% ethyl acetate in petroleum ether to afford 5-(2H,3H-(1,4)dioxino(2,3-b)pyridin-6-ylmethoxy)-1,3,4-thiadiazol-2-amine (187 mg, 23.48%) as a pink solid. MS (ESI) calc'd for ($C_{10}H_{10}N_4O_3S$) $(M+1)^+$, 267.0, found 267.0.

Step-2: N-(5-(2H,3H-(1,4)dioxino(2,3-b)pyridin-6-ylmethoxy)-1,3,4-thiadiazol-2-yl)-4-(2-fluoro-6-methoxyphenyl)-6-methylpyridine-3-carboxamide

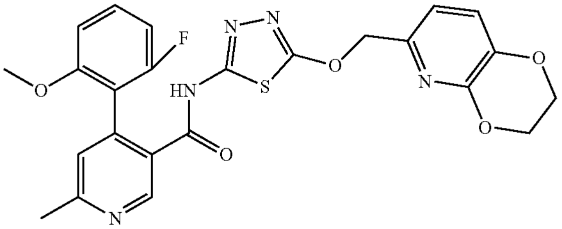 [SMILES: COc1cccc(F)c1-c1cc(C)ncc1C(=O)Nc1nnc(OCc2ccc3c(n2)OCCO3)s1]

To a stirred solution of 5-(2H,3H-(1,4)dioxino(2,3-b)pyridin-6-ylmethoxy)-1,3,4-thiadiazol-2-amine (20.0 mg, 0.075 mmol) and 4-(2-fluoro-6-methoxyphenyl)-6-methylpyridine-3-carboxylic acid (16.0 mg, 0.075 mmol, Intermediate F) in MeCN (0.5 mL) and DMF (0.5 mL) were added NMI (13.5 mg, 0.165 mmol) and TCFH (17.0 mg, 0.090 mmol). The resulting mixture was stirred at room temperature for 2 h. The reaction mixture was quenched with water and extracted with ethyl acetate. The combined organic layers were washed with brine, dried over anhydrous sodium sulfate, filtered, and concentrated under vacuum. The residue was purified by prep-HPLC with the following conditions: (Column: XBridge Prep OBD C18 Column, 30×150 mm um; Mobile Phase A:Water (10 mM ammonium formate), Mobile Phase B:ACN; Flow rate: 60 mL/min; Gradient: 28 B to 47 B in 8 min; 254/220 nm; RT1:7.53 min) to afford N-(5-(2H,3H-(1,4)dioxino(2,3-b)pyridin-6-ylmethoxy)-1,3,4-thiadiazol-2-yl)-4-(2-fluoro-6-methoxyphenyl)-6-methylpyridine-3-carboxamide (27.1 mg, 71%) as a white solid. MS (ESI) calc'd for ($C_{24}H_{20}FN_5O_5S$) $(M+1)^+$, 510.1, found 510.1. $^1H$ NMR (400 MHz, DMSO-$d_6$) δ 12.88 (s, 1H), 8.81 (s, 1H), 7.46-7.36 (m, 1H), 7.36-7.29 (m, 2H), 7.11 (d, J=8.0 Hz, 1H), 6.97-6.86 (m, 2H), 5.33 (s, 2H), 4.45-4.39 (m, 2H), 4.30-4.24 (m, 2H), 3.59 (s, 3H), 2.57 (s, 3H).

Example 36

N-(5-((5-chloropyridin-2-yl)methoxy)-1,3,4-thiadiazol-2-yl)-5'-methoxy-2',6-dimethyl-(4,4'-bipyridine)-3-carboxamide

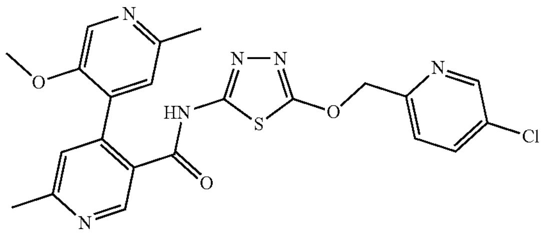 [SMILES: COc1cnc(C)cc1-c1cc(C)ncc1C(=O)Nc1nnc(OCc2ccc(Cl)cn2)s1]

Step-1: benzyl 4-chloro-6-methylnicotinate

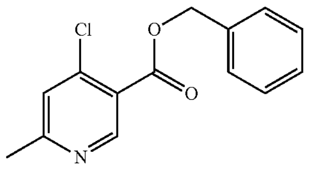 [SMILES: Cc1cc(Cl)c(C(=O)OCc2ccccc2)cn1]

A mixture of 4-chloro-6-methylpyridine-3-carboxylic acid (10.00 g, 58.3 mmol) and $Cs_2CO_3$ (37.98 g, 116.6 mmol) in DMF (100 mL) was added benzyl bromide (14.95 g, 87.45 mmol). The resulting mixture was stirred at room temperature for 16 h. The reaction mixture was quenched with water and extracted with ethyl acetate. The combined organic layers were washed with brine, dried over anhydrous sodium sulfate, filtered, and concentrated under vacuum. The residue was purified by flash chromatography on silica gel with 0~30% ethyl acetate in petroleum ether to afford benzyl 4-chloro-6-methylnicotinate (12.94 g, 84.8%) as a yellow oil. MS (ESI) calc'd for ($C_{14}H_{12}ClNO_2$) $(M+1)^+$, 262.0, found 262.1.

Step-2: benzyl 2'-chloro-5'-methoxy-6-methyl-(4,4'-bipyridine)-3-carboxylate

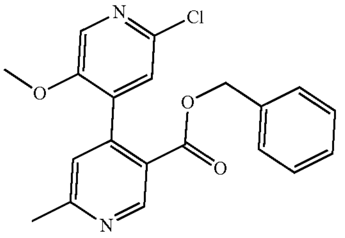 [SMILES: COc1cnc(Cl)cc1-c1cc(C)ncc1C(=O)OCc1ccccc1]

To a degassed mixture of methyl benzyl 4-chloro-6-methylpyridine-3-carboxylate (6.00 g, 22.926 mmol) and 2-chloro-5-methoxypyridin-4-ylboronic acid (4.30 g, 22.926 mmol) in 1,4-dioxane (50 mL) and $H_2O$ (5 mL) were added $K_2CO_3$ (9.51 g, 0.069 mmol) and Pd(DtBPF)$Cl_2$ (1.49 g, 2.29 mmol). The resulting mixture was stirred at 80° C. for 2 h under nitrogen atmosphere. The reaction mixture was quenched with water and extracted with ethyl acetate. The combined organic layers were washed with brine, dried over anhydrous sodium sulfate, filtered, and concentrated under vacuum. The residue was purified by flash chromatography on silica gel with 0-50% ethyl acetate in petroleum ether to afford benzyl 2'-chloro-5'-methoxy-6-methyl-(4,4'-bipyridine)-3-carboxylate (4 g, 47.3%) as a yellow oil. MS (ESI) calc'd for ($C_{20}H_{17}ClN_2O_3$) $(M+1)^+$, 369.1, found 369.0.

Step-3: benzyl 5'-methoxy-2',6-dimethyl-(4,4'-bipyridine)-3-carboxylate

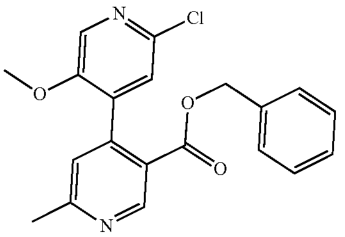 [SMILES: COc1cnc(Cl)cc1-c1cc(C)ncc1C(=O)OCc1ccccc1]

To a degassed mixture of benzyl 2-chloro-5-methoxy-6-methyl-(4,4-bipyridine)-3-carboxylate (4.00 g, 10.845 mmol) and $K_2CO_3$ (4.50 g, 33.0 mmol) in DME (30 mL) were added Pd(dppf)$Cl_2$ (0.79 g, 1.0 mmol) and trimethyl-1,3,5,2,4,6-trioxatriborinane (1.50 g, 12.0 mmol). The resulting mixture was stirred at 120° C. for 2 h under nitrogen atmosphere. The reaction mixture was quenched with water and extracted with ethyl acetate. The combined organic layers were washed with brine, dried over anhydrous sodium sulfate, filtered, and concentrated under vacuum. The residue was purified by reverse phase flash chromatography with 5~70% acetonitrile in water to afford benzyl 5'-methoxy-2',6-dimethyl-(4,4'-bipyridine)-3-carboxylate (2.8 g, 74.1%) as a yellow oil. MS (ESI) calc'd for ($C_{21}H_{20}N_2O_3$) $(M+1)^+$, 349.1, found 349.0.

Step-4: 5'-methoxy-2',6-dimethyl-(4,4'-bipyridine)-3-carboxylic acid

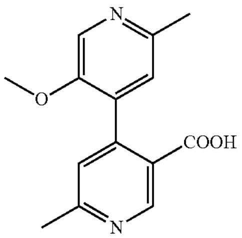 [SMILES: COc1cnc(C)cc1-c1cc(C)ncc1C(=O)O]

To a mixture of benzyl 5-methoxy-2,6-dimethyl-(4,4-bipyridine)-3-carboxylate (2.80 g, 8.037 mmol) in THF (20.00 mL) were added Pd/C (2.80 g, 10%). The resulting mixture was stirred at room temperature for 1 h under hydrogen atmosphere. The resulting mixture was filtered. The filtrate was concentrated vacuum to afford 5'-methoxy-2',6-dimethyl-(4,4'-bipyridine)-3-carboxylic acid (2.5 g, curde) as a yellow solid, which was used for the next step directly without further purification. MS (ESI) calc'd for $(C_{14}H_{14}N_2O_3)$ $(M+1)^+$, 259.1, found 259.0.

Step-5: N-(5-((5-chloropyridin-2-yl)methoxy)-1,3,4-thiadiazol-2-yl)-5'-methoxy-2',6-dimethyl-(4,4'-bipyridine)-3-carboxamide

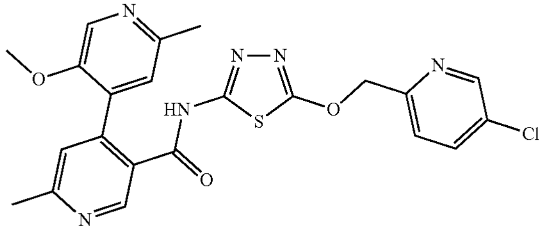 [SMILES: COc1cnc(C)cc1-c1cc(C)ncc1C(=O)Nc1nnc(OCc2ccc(Cl)cn2)s1]

To a solution of 5-methoxy-2,6-dimethyl-(4,4-bipyridine)-3-carboxylic acid (800.00 mg, 3.097 mmol) and 5-((5-chloropyridin-2-yl)methoxy)-1,3,4-thiadiazol-2-amine (751.69 mg, 3.097 mmol, Intermediate C) in DMF (5.00 mL) and ACN (5.00 mL) were added NMI (1271.56 mg, 15.485 mmol) and TCFH (955.99 mg, 3.407 mmol). The resulting mixture was stirred at room temperature for 2 h. The solvent was removed under vacuum. The residue was purified by reverse phase flash chromatography with 5~50% acetonitrile in water to afford N-(5-((5-chloropyridin-2-yl)methoxy)-1,3,4-thiadiazol-2-yl)-5-methoxy-2,6-dimethyl-(4,4-bipyridine)-3-carboxamide (1.0845 g, 72.5%) as a white solid. MS (ESI) calc'd for $(C_{22}H_{19}ClN_6O_3S)$ $(M+1)^+$, 483.1, found 483.1. $^1H$ NMR (400 MHz, DMSO-$d_6$) δ 12.93 (s, 1H), 8.75 (s, 1H), 8.66 (d, J=2.4 Hz, 1H), 8.19 (s, 1H), 8.08-7.96 (m, 1H), 7.61 (d, J=8.4 Hz, 1H), 7.37 (s, 1H), 7.26 (s, 1H), 5.55 (s, 2H), 3.58 (s, 3H), 2.58 (s, 3H), 2.47 (s, 3H).

Example 37

5-(2-fluoro-6-methoxyphenyl)-N-(5-((5-(hydroxymethyl)pyridin-2-yl)methoxy)-1,3,4-thiadiazol-2-yl)pyrimidine-4-carboxamide

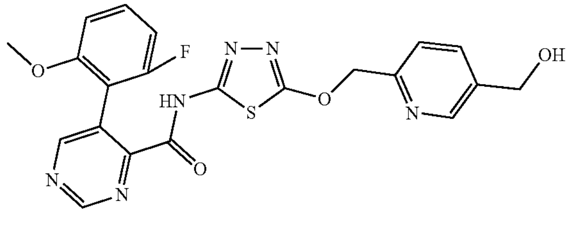 [SMILES: COc1cccc(F)c1-c1cncnc1C(=O)Nc1nnc(OCc2ccc(CO)cn2)s1]

Step-1: methyl 5-(2-fluoro-6-methoxyphenyl)pyrimidine-4-carboxylate

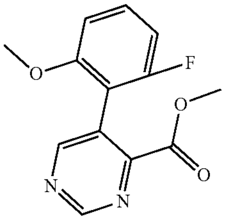

To a degassed solution of 5-bromopyrimidine-4-carboxylic acid (1 g, 4.926 mmol) in Dioxane (10 mL) and H2O (2 mL) were added 2-fluoro-6-methoxyphenylboronic acid (1004.66 mg, 5.911 mmol), $K_2CO_3$ (2042.50 mg, 14.778 mmol) and Pd(dppf)$Cl_2$ (360.45 mg, 0.493 mmol) under nitrogen. The resulting mixture was stirred at 80° C. for 5 h under nitrogen. The reaction mixture was concentrated under vacuum. The residue was purified by flash chromatography on silica gel with 0~50% ethyl acetate in petroleum ether to afford ethyl 4-chloro-5-fluoro-6-methylnicotinate (1082 mg, 88.5%) as a yellow solid. MS (ESI) calc'd for $(C_{13}HnFN_2O_3)$ $(M+1)^+$, 263.1, found 263.1.

Step-2: 5-(2-fluoro-6-methoxyphenyl)pyrimidine-4-carboxylic acid

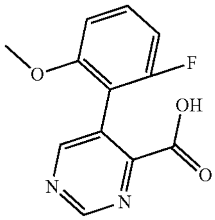 [SMILES: COc1cccc(F)c1-c1cncnc1C(=O)O]

To a solution of methyl 5-(2-fluoro-6-methoxyphenyl)pyrimidine-4-carboxylate (1082 mg, 4.13 mmol) in MeOH (20 mL) and $H_2O$ (10 mL) was added NaOH (331 mg, 8.26 mmol). The mixture was stirred 70° C. for 2 h. The reaction solution was acidified with HCl (1 N) to pH 5~6. The aqueous solution was extracted with ethyl acetate. The organic layers were combined, washed with brine, dried over anhydrous sodium sulfate and filtered. The filtrate was concentrated under vacuum to afford 5-(2-fluoro-6-methoxyphenyl)pyrimidine-4-carboxylic acid (826 mg, 80.5%) as a yellow solid. MS (ESI) calc'd for ($C_{12}H_9FN_2O_3$) $(M+1)^+$, 249.1, found 249.0.

Step-3: methyl6-(((5-(5-(2-fluoro-6-methoxyphenyl) pyrimidine-4-carboxamido)-1,3,4-thiadiazol-2-yl) oxy)methyl)nicotinate

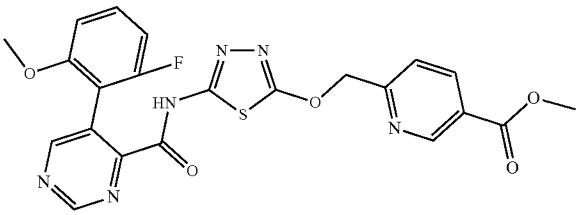

To a solution of 5-(2-fluoro-6-methoxyphenyl)pyrimidine-4-carboxylic acid (110 mg, 0.44 mmol) in ACN (5 mL) were added methyl 6-(((5-amino-1,3,4-thiadiazol-2-yl)oxy) methyl)pyridine-3-carboxylate (116.93 mg, 0.439 mmol, Example 5, Step 1), NMI (108.16 mg, 1.317 mmol) and TCFH (147.86 mg. 0.527 mmol). The mixture was stirred at room temperature for 2 h. The mixture was diluted with water and extracted with ethyl acetate. The combined organic layers were washed with brine, dried over anhydrous sodium sulfate, filtered, and concentrated under vacuum. The residue was purified by flash chromatography on silica gel with 0~10% methanol in dichloromethane to afford methyl6-(((5-(5-(2-fluoro-6-methoxyphenyl)pyrimidine-4-carboxamido)-1,3,4-thiadiazol-2-yl)oxy)methyl)nicotinate (100 mg, 45.9%) as a yellow solid. MS (ESI) calc'd for ($C_{22}H_{17}FN_6O_5S$) $(M+1)^+$, 497.1; found 497.0.

Step-4: 5-(2-fluoro-6-methoxyphenyl)-N-(5-((5-(hydroxymethyl)pyridin-2-yl)methoxy)-1,3,4-thiadiazol-2-yl)pyrimidine-4-carboxamide

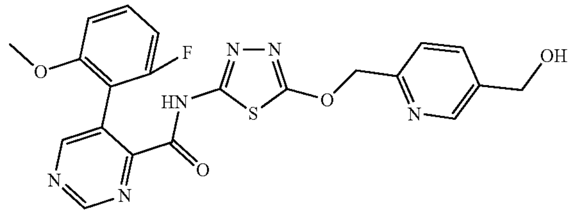 [SMILES: COc1cccc(F)c1-c1cncnc1C(=O)Nc1nnc(OCc2ccc(CO)cn2)s1]

To a solution of methyl6-(((5-(5-(2-fluoro-6-methoxyphenyl)pyrimidine-4-carboxamido)-1,3,4-thiadiazol-2-yl)oxy) methyl)nicotinate (100.00 mg, 0.201 mmol) in THF (5 mL) was added LAH (15.29 mg, 0.402 mmol) at 0° C. The mixture was stirred at room temperature for 2 h. The reaction mixture was quenched by the addition of water and extracted with ethyl acetate. The combined organic layers were washed with brine, dried over anhydrous sodium sulfate, filtered, and concentrated under vacuum. The residue was purified by flash chromatography on silica gel with 0~10% methanol in dichloromethane and further purified by prep-HPLC with the following conditions: (Column: YMC-Pack Diol-120-NP, 20*150 mm 5 um; Mobile Phase A: water (10 mmol/L $NH_4HCO_3$), Mobile Phase B: ACN; Flow rate: 60 mL/min; Gradient: 14 B to 40 B in 8 min; 220/254 nm) to afford 5-(2-fluoro-6-methoxyphenyl)-N-(5-((5-(hydroxymethyl)pyridin-2-yl)methoxy)-1,3,4-thiadiazol-2-yl)pyrimidine-4-carboxamide (13.7 mg, 14.5%) as a yellow solid. MS (ESI) calc'd for ($C_{21}H_{17}FN_6O_4S$) $(M+1)^+$, 469.1; found 469.1. $^1H$ NMR (400 MHz, DMSO-d6) δ 9.21 (s, 1H), 8.80-8.21 (m, 2H), 7.77-7.74 (m, 1H), 7.48-7.35 (m, 2H), 6.91-6.89 (m, 2H), 5.42-5.32 (m, 3H), 4.54-4.53 (m, 2H), 3.62 (s, 3H).

Example 38

4-(2-fluoro-6-methoxyphenyl)-6-methyl-N-(5-((5-(oxetan-3-yloxy)pyridin-2-yl)methoxy)-1,3,4-thiadiazol-2-yl)pyridine-3-carboxamide

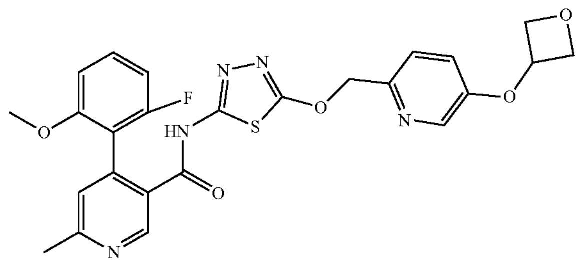 [SMILES: COc1cccc(F)c1-c1cc(C)ncc1C(=O)Nc1nnc(OCc2ccc(OC3COC3)cn2)s1]

Step-1: (5-(oxetan-3-yloxy)pyridin-2-yl)methanol

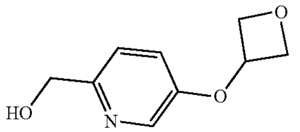 [SMILES: OCc1ccc(OC2COC2)cn1]

To a stirred solution of 6-(hydroxymethyl)pyridin-3-ol (500 mg, 3.99 mmol) and 3-iodooxetane (883 mg, 4.80 mmol) in DMF (10 mL) was added $Cs_2CO_3$ (2.6 g, 7.98 mmol). The resulting mixture was stirred at 80° C. for 2 h under nitrogen atmosphere. The reaction mixture was quenched with water and extracted with ethyl acetate. The combined organic layers were washed with brine, dried over anhydrous sodium sulfate, filtered, and concentrated under vacuum. to afford (5-(oxetan-3-yloxy)pyridin-2-yl)methanol (390 mg, 42.0%) as a brown oil. MS (ESI) calculated for ($C_9H_{11}NO_3$) $(M+1)^+$, 182.1; found, 182.0.

Step-2: 5-((5-(oxetan-3-yloxy)pyridin-2-yl) methoxy)-1,3,4-thiadiazol-2-amine

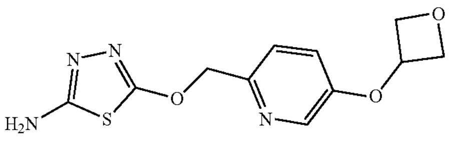 [SMILES: Nc1nnc(OCc2ccc(OC3COC3)cn2)s1]

To a stirred solution of (5-(oxetan-3-yloxy)pyridin-2-yl)methanol (100 mg, 0.55 mmol) in THF (3 mL) was added NaH (77 mg, 3.21 mmol) in portions at 0° C. and stirred at 0° C. for 40 min under nitrogen atmosphere. Then 5-bromo-1,3,4-thiadiazol-2-amine (119 mg, 0.66 mmol) was added to the above mixture at 0° C. The resulting mixture was stirred at room temperature for 2 h under nitrogen atmosphere. The reaction mixture was quenched with water and extracted with ethyl acetate. The combined organic layers were washed with brine, dried over anhydrous sodium sulfate, filtered, and concentrated under vacuum. The residue was purified by reverse phase flash column chromatography with 5~80% acetonitrile in water to afford 5-((5-(oxetan-3-yloxy)pyridin-2-yl)methoxy)-1,3,4-thiadiazol-2-amine (35 mg, 22.6%) as a yellow solid. MS (ESI) calculated for ($C_{11}H_{12}N_4O_3S$) $(M+1)^+$, 281.1; found, 281.1.

Step-3: 4-(2-fluoro-6-methoxyphenyl)-6-methyl-N-(5-((5-(oxetan-3-yloxy)pyridin-2-yl)methoxy)-1,3,4-thiadiazol-2-yl)pyridine-3-carboxamide

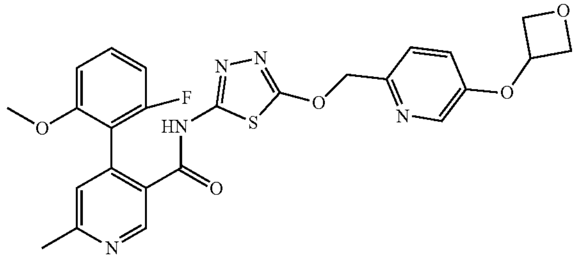 [SMILES: COc1cccc(F)c1-c1cc(C)ncc1C(=O)Nc1nnc(OCc2ccc(OC3COC3)cn2)s1]

To a stirred solution of 5-((5-(oxetan-3-yloxy)pyridin-2-yl)methoxy)-1,3,4-thiadiazol-2-amine (25 mg, 0.09 mmol) and NMI (22 mg, 0.27 mmol) in MeCN (1 mL) and DMF (1 mL) were added 4-(2-fluoro-6-methoxyphenyl)-6-methylpyridine-3-carboxylic acid (23 mg, 0.09 mmol, Intermediate F) and TCFH (28 mg, 0.10 mmol). The resulting mixture was stirred at room temperature for 2 h. The residue was purified by Prep-HPLC with the following conditions: (Column: XBridge Prep OBD C18 Column, 30×150 mm 5 um; Mobile Phase A: Water (10 mmol/L $NH_4HCO_3$), Mobile Phase B: ACN; Flow rate: 60 mL/min; Gradient: 25 B to 50 B in 7 min; 220 nm; RT1: 5.93 min) to afford 4-(2-fluoro-6-methoxyphenyl)-6-methyl-N-(5-((5-(oxetan-3-yloxy)pyridin-2-yl)methoxy)-1,3,4-thiadiazol-2-yl)pyridine-3-carboxamide (19.8 mg, 41.6%) as a white solid. MS (ESI) calculated for ($C_{25}H_{22}FN_5O_5S$) $(M+1)^+$, 524.1; found, 524.1. $^1H$ NMR (400 MHz, DMSO-$d_6$) δ 12.71 (s, 1H), 8.82 (s, 1H), 8.21 (d, J=2.8 Hz, 1H), 7.52 (d, J=8.8 Hz, 1H), 7.45-7.35 (m, 1H), 7.35-7.25 (m, 2H), 6.96-6.86 (m, 2H), 5.46 (s, 2H), 5.44-5.34 (m, 1H), 4.99-4.91 (m, 2H), 4.61-4.53 (m, 2H), 3.59 (s, 3H), 2.57 (s, 3H).

Example 39

4-(5-chloro-2-methoxyphenyl)-N-(5-((5-(hydroxymethyl)pyridin-2-yl)methoxy)-1,3,4-thiadiazol-2-yl)-6-methylpyridine-3-carboxamide

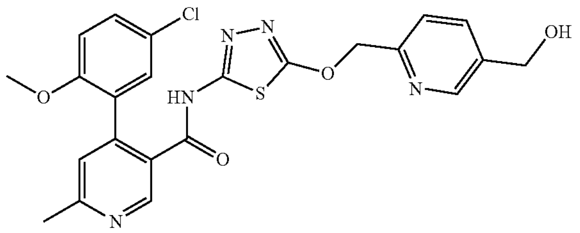 [SMILES: COc1ccc(Cl)cc1-c1cc(C)ncc1C(=O)Nc1nnc(OCc2ccc(CO)cn2)s1]

Step-1: 4-(5-chloro-2-methoxyphenyl)-6-methylpyridine-3-carboxylate

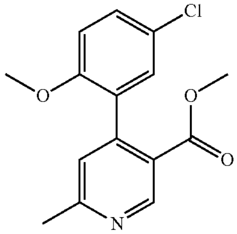 [SMILES: COC(=O)c1cnc(C)cc1-c1cc(Cl)ccc1OC]

To a degassed solution of methyl 4-chloro-6-methylpyridine-3-carboxylate (600 mg, 3.23 mmol) and 5-chloro-2-methoxyphenylboronic acid (905 mg, 4.85 mmol) in dioxane (6 mL) and water (2 mL) were added $Pd(PPh_3)_4$ (375 mg, 0.32 mmol) and $K_2CO_3$ (1343 mg, 9.72 mmol). The resulting mixture was stirred at 80° C. for 2 h under nitrogen atmosphere before concentrated under vacuum. The residue was purified by reverse phase flash column chromatography with 5~50% acetonitrile in water to afford methyl 4-(5-chloro-2-methoxyphenyl)-6-methylpyridine-3-carboxylate (730 mg, 76.6%) as a yellow oil. MS (ESI) calculated for ($C_{15}H_{14}ClNO_3$) $(M+1)^+$, 292.1; found, 292.0.

Step-2: 4-(5-chloro-2-methoxyphenyl)-6-methylpyridine-3-carboxylic acid

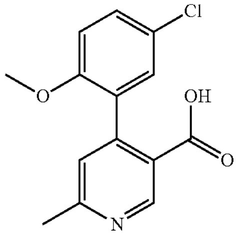 [SMILES: COc1ccc(Cl)cc1-c1cc(C)ncc1C(=O)O]

To a stirred solution of methyl 4-(5-chloro-2-methoxyphenyl)-6-methylpyridine-3-carboxylate (100 mg, 0.34 mmol) in tetrahydrofuran (1 mL) were added $LiOH·H_2O$ (58 mg, 1.38 mmol) and water (0.3 mL). The resulting mixture was stirred at room temperature for 1 h. The residue was acidified to pH 6 with citric acid. The resulting mixture was extracted with ethyl acetate. The combined organic layers were washed with brine, dried over anhydrous $Na_2SO_4$. After filtration, the filtrate was concentrated under reduced pressure to afford 4-(5-chloro-2-methoxyphenyl)-6-methylpyridine-3-carboxylic acid (93 mg, 97.70%) as a white solid. MS (ESI) calculated for ($C_{14}H_{12}ClNO_3$) $(M+1)^+$, 278.1; found, 278.0.

Step-3: methyl 6-(((5-(4-(5-chloro-2-methoxyphenyl)-6-methylpyridine-3-amido)-1,3,4-thiadiazol-2-yl)oxy)methyl)pyridine-3-carboxylate

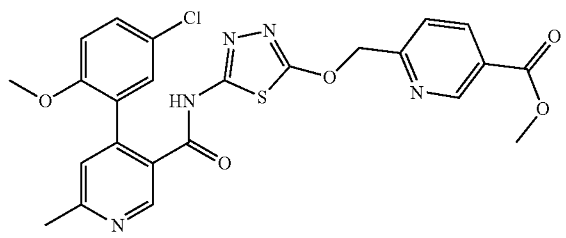 [SMILES: COC(=O)c1ccc(COc2nnc(NC(=O)c3cnc(C)cc3-c3cc(Cl)ccc3OC)s2)nc1]

To a stirred solution of 4-(5-chloro-2-methoxyphenyl)-6-methylpyridine-3-carboxylic acid (80 mg, 0.29 mmol, Example 39, Step 2) and methyl 6-(((5-amino-1,3,4-thiadiazol-2-yl)oxy)methyl)pyridine-3-carboxylate (64 mg, 0.24 mmol, Example 5, Step 1) in acetonitrile (1 mL) and DMF (1 mL) were added N,N,N',N'-Tetramethylchloroformamidinium-hexafluorophosphate (74 mg, 0.26 mmol) and 1-Methylimidazole (59 mg, 0.72 mmol). The resulting mixture was stirred at room temperature for 1 h. The mixture was purified by reverse phase flash column chromatography with 5-60% acetonitrile in water to afford methyl 6-(((5-(4-(5-chloro-2-methoxyphenyl)-6-methylpyridine-3-amido)-1,3,4-thiadiazol-2-yl)oxy)methyl)pyridine-3-carboxylate (60 mg, 34.8%) as a white solid. MS (ESI) calculated for ($C_{24}H_{20}ClN_5O_5S$) $(M+1)^+$, 526.1; found, 526.2.

Step-4: 4-(5-chloro-2-methoxyphenyl)-N-(5-((5-(hydroxymethyl)pyridin-2-yl)methoxy)-1,3,4-thiadiazol-2-yl)-6-methylpyridine-3-carboxamide

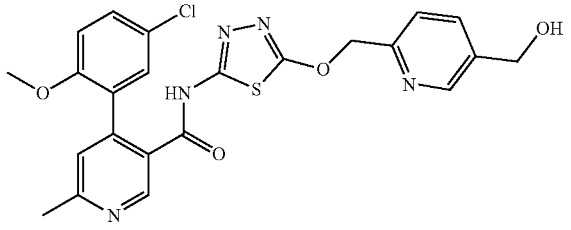

To a stirred solution of methyl 6-(((5-(4-(5-chloro-2-methoxyphenyl)-6-methylpyridine-3-amido)-1,3,4-thiadiazol-2-yl)oxy)methyl)pyridine-3-carboxylate (80 mg, 0.15 mmol) in anhydrous tetrahydrofuran (1 mL) was added $LiAlH_4$ (12 mg, 0.31 mmol) at 0° C. The resulting mixture was stirred at room temperature for 1 h under air atmosphere. The reaction mixture was quenched with water and extracted with ethyl acetate. The combined organic layers were washed with brine, dried over anhydrous sodium sulfate, filtered, and concentrated under vacuum. The residue was purified by reverse phase flash column chromatography with 5-80% acetonitrile in water to afford 4-(5-chloro-2-methoxyphenyl)-N-(5-((5-(hydroxymethyl)pyridin-2-yl)methoxy)-1,3,4-thiadiazol-2-yl)-6-methylpyridine-3-carboxamide (20 mg, 25.9%) as a white solid. MS (ESI) calculated for ($C_{23}H_{20}ClN_5O_4S$) $(M+1)^+$, 498.1; found, 498.1. $^1H$ NMR (400 MHz, DMSO-$d_6$) δ 8.80 (s, 1H), 8.52 (d, J=2.0 Hz, 1H), 7.80-7.73 (m, 1H), 7.48 (d, J=8.0 Hz, 1H), 7.41-7.33 (m, 1H), 7.26 (d, J=2.8 Hz, 1H), 7.17 (s, 1H), 6.98 (d, J=8.8 Hz, 1H), 5.43 (s, 2H), 5.38-5.30 (m, 1H), 4.54 (d, J=4.8 Hz, 2H), 3.51 (s, 3H), 2.52 (s, 3H).

Example 40 and 41

4-(2-fluoro-6-methoxyphenyl)-N-(5-((5-((S)-1-hydroxyethyl)pyridin-2-yl)methoxy)-1,3,4-thiadiazol-2-yl)-6-methylnicotinamide (Example 40) and 4-(2-fluoro-6-methoxyphenyl)-N-(5-((5-((R)-1-hydroxyethyl)pyridin-2-yl)methoxy)-1,3,4-thiadiazol-2-yl)-6-methylnicotinamide Example 41

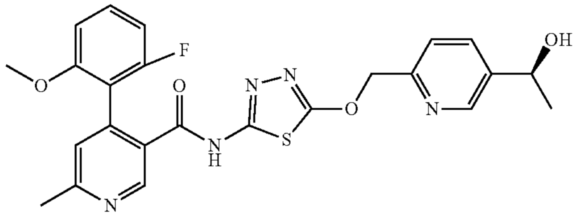

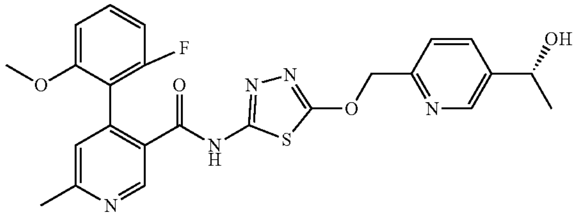

Step-1: (5-(1-ethoxyvinyl)pyridin-2-yl)methanol

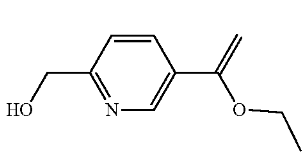

To a degassed mixture of (5-bromopyridin-2-yl)methanol (10.0 g, 53.18 mmol) in toluene (50.00 mL) were added tributyl(1-ethoxyethenyl)stannane (38.42 g, 0.11 mmol) and $Pd(PPh_3)_2Cl_2$ (3.73 g, 5.31 mmol). The resulting solution was stirred at 100° C. for 2 h under nitrogen atmosphere before concentrated under vacuum. The residue was purified by flash column chromatography with 0~50% ethyl acetate in petroleum ether to afford (5-(1-ethoxyvinyl)pyridin-2-yl)methanol (5.0 g, 52.4%) as a yellow solid. MS (ESI) calc'd for ($C_{10}H_{13}NO_2$) $(M+1)^+$, 180.1; found 180.0.

Step-2: (5-(1-ethoxyethenyl)pyridin-2-yl)methanol

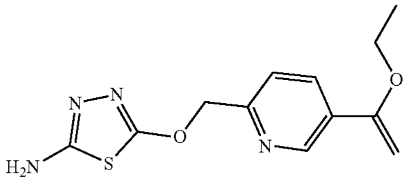 [SMILES: C=C(OCC)c1ccc(COc2nnc(N)s2)nc1]

To a solution of NaH (1.61 g, 67.09 mmol, 1.50 equiv, 60% purity) in THF (60.00 mL) was added a solution of (5-(1-ethoxyethenyl)pyridin-2-yl)methanol (8.00 g, 44.63 mmol) in THE (15 mL) dropwise at 0~5° C. and stirred at 0~5° C. for 1 hour under nitrogen atmosphere. To the above solution was added 5-bromo-1,3,4-thiadiazol-2-amine (9.64 g, 53.56 mmol) at 0° C. The resulting mixture was stirred at room temperature for 12 h under nitrogen. The reaction mixture was quenched by the addition of ice/water and extracted with ethyl acetate. The combined organic layers were washed with brine, dried over anhydrous sodium sulfate, filtered, and concentrated under vacuum. The residue was purified by flash chromatography on silica gel with 0~10% methanol in dichloromethane to afford 5-((5-(1-ethoxyethenyl)pyridin-2-yl)methoxy)-1,3,4-thiadiazol-2-amine (4.0 g, 32.2%) as a yellow solid. MS (ESI) calc'd for ($C_{12}H_{14}N_4O_2S$) $(M+1)^+$, 279.1, found 279.0.

Step-3: 1-(6-(((5-amino-1,3,4-thiadiazol-2-yl)oxy) methyl)pyridin-3-yl)ethenone

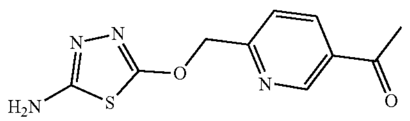

A mixture of 5-((5-(1-ethoxyethenyl)pyridin-2-yl) methoxy)-1,3,4-thiadiazol-2-amine (5.03 g, 18.07 mmol) in HCl (50 mL, 4M in dioxane) was stirred at room temperature for 2 h. The solvent was removed under vacuum. The residue was neutralized with saturated $NaHCO_3$ (aq.) and extracted with ethyl acetate. The combined organic layers were washed with brine, dried over anhydrous sodium sulfate, filtered, and concentrated under vacuum. The residue was purified by flash chromatography on silica gel with 0~10% methanol in dichloromethane to afford 1-(6-(((5-amino-1,3,4-thiadiazol-2-yl)oxy)methyl)pyridin-3-yl)ethanone (3.46 g, 68.8%) as a yellow solid. MS (ESI) calc'd for ($C_{10}H_{10}N_4O_2S$) $(M+1)^+$, 251.0, found 251.0.

Step-4: N-(5-((5-acetylpyridin-2-yl)methoxy)-1,3,4-thiadiazol-2-yl)-4-(2-fluoro-6-methoxyphenyl)-6-methylpyridine-3-carboxamide

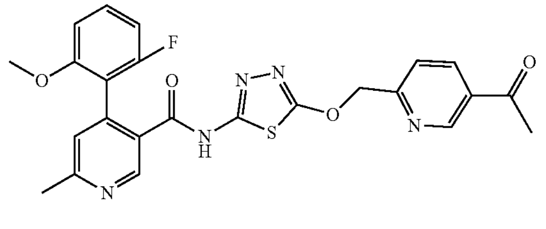 [SMILES: COc1cccc(F)c1-c1cc(C)ncc1C(=O)Nc1nnc(OCc2ccc(C(C)=O)cn2)s1]

To a stirred solution of 1-(6-(((5-amino-1,3,4-thiadiazol-2-yl)oxy)methyl)pyridin-3-yl)ethanone (300 mg, 1.19 mmol) and 4-(2-fluoro-6-methoxyphenyl)-6-methylpyridine-3-carboxylic acid (313.1 mg, 1.19 mmol, Intermediate F) in acetonitrile (5 mL) were added TCFH (504 mg, 1.79 mmol) and N-methyl imidazole (393 mg, 4.79 mmol) at room temperature under nitrogen atmosphere. The mixture resulting was stirred at room temperature for 2 h under nitrogen atmosphere. The reaction mixture was quenched with water and extracted with ethyl acetate. The combined organic layers were washed with brine, dried over anhydrous sodium sulfate, filtered, and concentrated under vacuum. The residue was purified by reverse phase flash column chromatography with 5~70% acetonitrile in water to afford N-(5-((5-acetylpyridin-2-yl)methoxy)-1,3,4-thiadiazol-2-yl)-4-(2-fluoro-6-methoxyphenyl)-6-methylpyridine-3-carboxamide (350 mg, 59.1%) as a yellow oil. MS (ESI) calc'd for ($C_{24}H_{20}FN_5O_4S$) $(M+1)^+$, 494.1; found, 494.1.

Step-5: 4-(2-fluoro-6-methoxyphenyl)-N-(5-((5-((1S)-1-hydroxyethyl)pyridin-2-yl)methoxy)-1,3,4-thiadiazol-2-yl)-6-methylpyridine-3-carboxamide

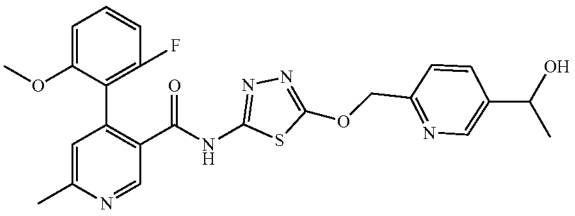

To a stirred solution of N-(5-((5-acetylpyridin-2-yl) methoxy)-1,3,4-thiadiazol-2-yl)-4-(2-fluoro-6-methoxyphenyl)-6-methylpyridine-3-carboxamide (234 mg, 0.47 mmol) in MeOH (3 mL) was added $NaBH_4$ (35 mg, 0.94 mmol). The mixture resulting was stirred at room temperature for 2 h. The reaction mixture was quenched with water and extracted with ethyl acetate. The combined organic layers were washed with brine, dried over anhydrous sodium sulfate, filtered, and concentrated under vacuum. The residue was purified by Prep-HPLC with the following conditions: (Column: XBridge Prep OBD C18 Column, 30×150 mm 5 um; Mobile Phase A: Water (10 mmol/L $NH_4HCO_3$), Mobile Phase B: ACN; Flow rate: 60 mL/min; Gradient: 25 B to B in 7 min; 220 nm) to afford 4-(2-fluoro-6-methoxyphenyl)-N-(5-((5-(1-hydroxyethyl)pyridin-2-yl)methoxy)-1,3,4-thiadiazol-2-yl)-6-methylnicotinamide (22.2 mg, 10.2%) as a white solid. MS (ESI) calc'd for ($C_{24}H_{22}FN_5O_4S$) $(M+1)^+$, 496.1; found, 496.0. $^1H$ NMR (400 MHz, DMSO-$d_6$) δ 12.89 (s, 1H), 8.82 (s, 1H), 8.56 (s, 1H), 7.85-7.75 (m, 1H), 7.50 (d, J=8.0 Hz, 1H), 7.45-7.35 (m, 1H), 7.32 (d, J=1.6 Hz, 1H), 6.97-6.86 (m, 2H), 5.51 (s, 2H), 5.36 (s, 1H), 4.83-4.78 (m, 1H), 3.59 (s, 3H), 2.56 (s, 3H), 1.37 (d, J=6.4 Hz, 3H).

Step-6: 4-(2-fluoro-6-methoxyphenyl)-N-(5-((5-((S)-1-hydroxyethyl)pyridin-2-yl)methoxy)-1,3,4-thiadiazol-2-yl)-6-methylnicotinamide and 4-(2-fluoro-6-methoxyphenyl)-N-(5-((5-((R)-1-hydroxyethyl)pyridin-2-yl)methoxy)-1,3,4-thiadiazol-2-yl)-6-methylnicotinamide

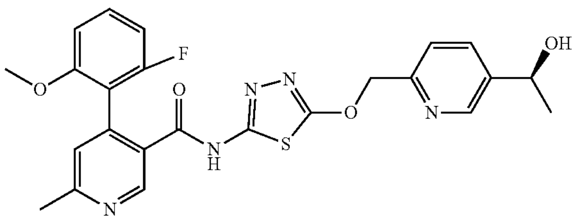

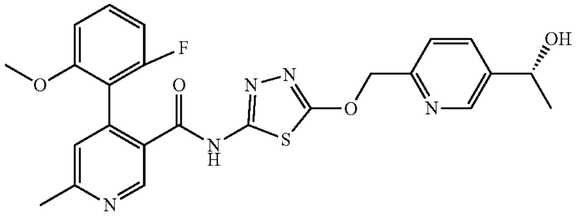

A racemic of 4-(2-fluoro-6-methoxyphenyl)-N-(5-((5-((1S)-1-hydroxyethyl)pyridin-2-yl)methoxy)-1,3,4-thiadiazol-2-yl)-6-methylpyridine-3-carboxamide (160 mg) was separated by prep-chiral-HPLC with the following conditions: (Column: DZ-CHIRALPAK IG-3, 2*25 cm, 5 um; Mobile Phase A:Hex (0.2% FA):(EtOH:DCM=1:1)=50:50, Mobile Phase B: Flow rate: 20 mL/min; Gradient: 30 B to 30 B in 25 min; 220/254 nm; RT1 8.16 min; RT2 14.12 min; Injection Volume: 2.567 ml; Number Of Runs: 3) to afford 4-(2-fluoro-6-methoxyphenyl)-N-(5-((5-((S)-1-hydroxyethyl)pyridin-2-yl)methoxy)-1,3,4-thiadiazol-2-yl)-6-methylnicotinamide (47.4 mg, 29.6%) as a white solid with shorter retention time on chiral HPLC and 4-(2-fluoro-6-methoxyphenyl)-N-(5-((5-((R)-1-hydroxyethyl)pyridin-2-yl)methoxy)-1,3,4-thiadiazol-2-yl)-6-methylnicotinamide (46.2 mg, 28.9%) as a white solid with longer retention time on chiral HPLC.

4-(2-fluoro-6-methoxyphenyl)-N-(5-((5-((S)-1-hydroxyethyl)pyridin-2-yl)methoxy)-1,3,4-thiadiazol-2-yl)-6-methylnicotinamide: MS (ESI) calc'd for ($C_{24}H_{22}FN_5O_4S$) $(M+1)^+$, 496.1; found, 496.1. $^1H$ NMR (400 MHz, DMSO-$d_6$) δ 12.99 (s, 1H), 8.82 (s, 1H), 8.56 (s, 1H), 7.85-7.75 (m, 1H), 7.50 (d, J=8.0 Hz, 1H), 7.45-7.35 (m, 1H), 7.32 (d, J=1.6 Hz, 1H), 6.97-6.86 (m, 2H), 5.51 (s, 2H), 5.36 (s, 1H), 4.83-4.78 (m, 1H), 3.59 (s, 3H), 2.56 (s, 3H), 1.37 (d, J=6.4 Hz, 3H).

4-(2-fluoro-6-methoxyphenyl)-N-(5-((5-((R)-1-hydroxyethyl)pyridin-2-yl)methoxy)-1,3,4-thiadiazol-2-yl)-6-methylnicotinamide: MS (ESI) calc'd for ($C_{24}H_{22}FN_5O_4S$) $(M+1)^+$, 496.1; found, 496.1. $^1H$ NMR (400 MHz, DMSO-$d_6$) δ 12.89 (s, 1H), 8.82 (s, 1H), 8.56 (s, 1H), 7.85-7.75 (m, 1H), 7.50 (d, J=8.0 Hz, 1H), 7.45-7.35 (m, 1H), 7.32 (d, J=1.6 Hz, 1H), 6.97-6.86 (m, 2H), 5.51 (s, 2H), 5.36 (s, 1H), 4.83-4.78 (m, 1H), 3.59 (s, 3H), 2.56 (s, 3H), 1.37 (d, J=6.4 Hz, 3H).

Example 42

N-(5-((4-(hydroxymethyl)pyridin-2-yl)methoxy)-1,3,4-thiadiazol-2-yl)-4-(2-methoxyphenyl)-6-methylpyridine-3-carboxamide

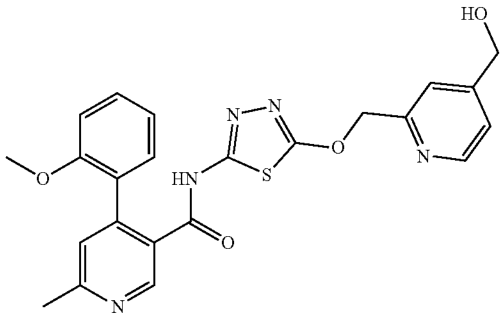 [SMILES: COc1ccccc1-c1cc(C)ncc1C(=O)Nc1nnc(OCc2cc(CO)ccn2)s1]

Step-1: methyl 2-(((5-amino-1,3,4-thiadiazol-2-yl)oxy)methyl)pyridine-4-carboxylate

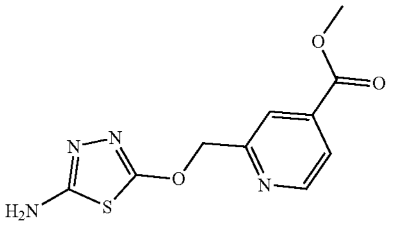 [SMILES: COC(=O)c1ccnc(COc2nnc(N)s2)c1]

To a stirred solution of NaH (287.1 mg, 11.964 mmol, 60%) and in THF (10.0 mL) was added a solution of methyl 2-(hydroxymethyl)pyridine-4-carboxylate (1000.0 mg, 5.982 mmol) in THF (5 mL) at 0° C. and stirred at 0° C. for 1 h. Then 5-bromo-1,3,4-thiadiazol-2-amine (1292.2 mg, 7.179 mmol) was added to the above mixture at 0° C. The resulting mixture was stirred at room temperature for 16 h under nitrogen atmosphere. The resulting mixture was quenched with water and the aqueous phase was extracted with ethyl acetate. The combined organic solution was dried over sodium sulfate, filtered, and concentrated under vacuum. The residue was purified by reverse phase flash column chromatography with 0-20% MeOH in DCM to afford methyl 2-(((5-amino-1,3,4-thiadiazol-2-yl)oxy)methyl)pyridine-4-carboxylate (136 mg, 8.5%) as a yellow solid. MS (ESI) calc'd for ($C_{10}H_{10}N_4O_3S$) $(M+1)^+$, 267.0, found 267.0.

Step-2: methyl 2-(((5-(4-(2-methoxyphenyl)-6-methylnicotinamido)-1,3,4-thiadiazol-2-yl)oxy) methyl)isonicotinate

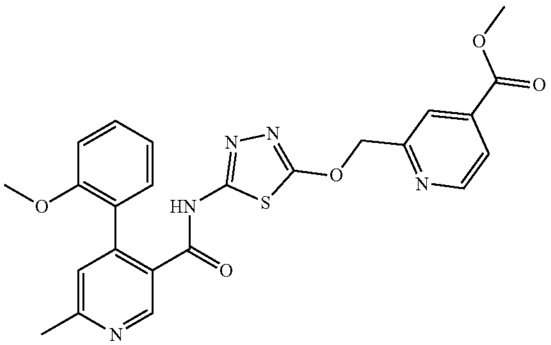 [SMILES: COC(=O)c1ccnc(COc2nnc(NC(=O)c3cnc(C)cc3-c3ccccc3OC)s2)c1]

To a stirred solution of methyl 2-(((5-amino-1,3,4-thiadiazol-2-yl)oxy)methyl)pyridine-4-carboxylate (60 mg, 0.225 mmol) and 4-(2-methoxyphenyl)-6-methylpyridine-3-carboxylic acid (49 mg, 0.201 mmol, Intermediate D) in MeCN (1.5 mL) and DMF (1.5 mL) were added NMI (46 mg, 0.561 mmol) and TCFH (84 mg, 0.301 mmol). The resulting mixture was stirred at room temperature for 2 h. The mixture was purified by reverse flash chromatography with 10~50% acetonitrile in water to afford methyl 2-(((5-(4-(2-methoxyphenyl)-6-methylnicotinamido)-1,3,4-thiadiazol-2-yl)oxy) methyl)isonicotinate (66 mg, 66.6%) as a colorless oil. MS (ESI) calc'd for ($C_{10}H_{10}N_4O_3S$) $(M+1)^+$, 492.1, found 492.1.

Step-3: N-(5-((4-(hydroxymethyl)pyridin-2-yl) methoxy)-1,3,4-thiadiazol-2-yl)-4-(2-methoxyphenyl)-6-methylpyridine-3-carboxamide

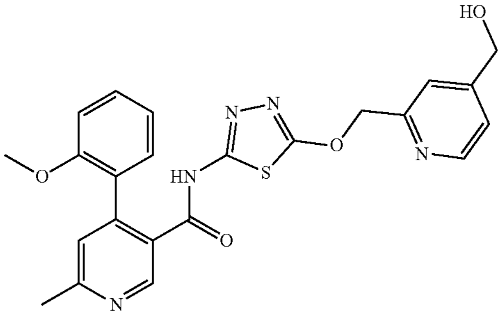 [SMILES: COc1ccccc1-c1cc(C)ncc1C(=O)Nc1nnc(OCc2cc(CO)ccn2)s1]

To a solution of methyl 2-(((5-(4-(2-methoxyphenyl)-6-methylpyridine-3-amido)-1,3,4-thiadiazol-2-yl)oxy)methyl) pyridine-4-carboxylate (96.0 mg, 0.195 mmol) in THF (5 mL) was treated with $LiAlH_4$ (14.8 mg, 0.391 mmol) at 0° C. The resulting mixture was stirred at 0° C. for 1 h under nitrogen atmosphere. The resulting mixture was quenched with water and the aqueous phase was extracted with ethyl acetate. The combined organic solution was dried over sodium sulfate, filtered, and concentrated under vacuum. The residue was purified by Prep-HPLC with the following conditions: (Column: XBridge Prep OBD C18 Column, 30*150 mm, 5 um; Mobile Phase A: Water (10 MMOL/L $NH_4HCO_3$+0.1% $NH_3 \cdot H_2O$), Mobile Phase B: ACN; Flow rate: 60 mL/min; Gradient: 35 B to 70 B in 8 min; 254/220 nm; RT: 7.4 min) to afford N-(5-((4-(hydroxymethyl)pyridin-2-yl)methoxy)-1,3,4-thiadiazol-2-yl)-4-(2-methoxyphenyl)-6-methylpyridine-3-carboxamide (12.4 mg, 13.7%) as a white solid. MS (ESI) calc'd for ($C_{23}H_{21}N_5O_4S$) $(M+1)^+$, 464.1, found 464.1. $^1H$ NMR (400 MHz, DMSO-$d_6$) δ 12.75 (s, 1H), 8.67 (s, 1H), 8.51 (d, J=5.2 Hz, 1H), 7.49 (s, 1H), 7.43-7.27 (m, 4H), 7.07 (t, J=7.6 Hz, 1H), 6.98 (d, J=8.0 Hz, 1H), 5.52 (s, 2H), 5.49 (t, J=5.6 Hz, 1H), 4.56 (d, J=5.6 Hz, 2H), 3.51 (s, 3H), 2.57 (s, 3H).

Example 43

N-(5-((5,6-dimethoxypyridin-2-yl)methoxy)-1,3,4-thiadiazol-2-yl)-4-(2-fluoro-6-methoxyphenyl)-6-methylnicotinamide

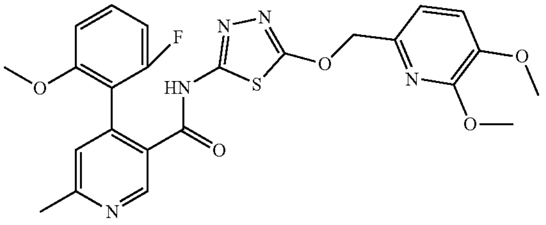

Step-1: (5,6-dimethoxypyridin-2-yl)methanol

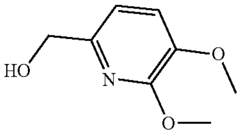

To a solution of 5,6-dimethoxypicolinaldehyde (500 mg, 2.994 mmol) in MeOH (5.00 mL) was added $NaBH_4$ (115.0 mg, 3.026 mmol) in portions at 0° C. The resulting mixture was stirred at room temperature for 2 hours. The reaction mixture was then quenched by the addition of water and extracted with ethyl acetate. The combined organic layers were washed with brine, dried over anhydrous sodium sulfate, filtered, and concentrated under vacuum to afford (5,6-dimethoxypyridin-2-yl)methanol (395 mg, 79%) as yellow oil. MS (ESI) calc'd for ($C_8H_{11}NO_3$) $(M+1)^+$, 170.0, found 170.1.

Step-2: O-((5,6-dimethoxypyridin-2-yl)methyl)S-methyl carbonodithioate

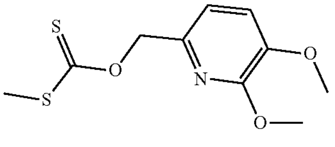

To a solution of (5,6-dimethoxypyridin-2-yl)methanol (395 mg, 2.324 mmol) in THF (10.00 mL) was added NaH (187 mg, 7.792 mmol, 60%) in portions at 0° C. and stirred at 0° C. for 30 min, then $CS_2$ (266 mg, 3.5 mmol) was added to the above mixture and stirred at 0° C. for 10 min. MeI (500 g, 3.521 mmol) was then added to the above mixture at 0° C. The resulting mixture was stirred at room temperature for 1 hour. The reaction mixture was then quenched by the addition of water and extracted with ethyl acetate. The combined organic layers were washed with brine, dried over anhydrous sodium sulfate, filtered, and concentrated under vacuum, The residue was purified by flash chromatography on silica gel with 0~50% ethyl acetate in petroleum ether to afford O-((5,6-dimethoxypyridin-2-yl)methyl)S-methyl carbonodithioate (296 mg, 74.9%) as a light yellow oil. MS (ESI) calc'd for ($C_{10}H_{13}NO_3S_2$) $(M+1)^+$, 260.0, found 260.0.

Step-3: O-((5,6-dimethoxypyridin-2-yl)methyl) hydrazinecarbothioate

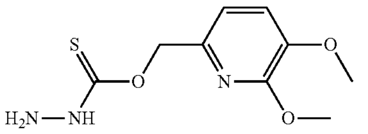 [SMILES: COc1ccc(COC(=S)NN)nc1OC]

To a solution of O-((5,6-dimethoxypyridin-2-yl)methyl) S-methyl carbonodithioate (296 mg, 1.138 mmol) in MeOH (5 mL) was added hydrazine hydrate (72 mg, 1.44 mmol, 80%). The resulting mixture was stirred at room temperature for 2 hours. The reaction mixture was quenched with water and extracted with ethyl acetate. The combined organic layers were washed with brine, dried over anhydrous sodium sulfate, filtered, and concentrated under vacuum to afford O-((5,6-dimethoxypyridin-2-yl)methyl) hydrazinecarbothioate (290 mg, crude) as a red oil. MS (ESI) calc'd for ($C_9H_{13}N_3O_3S$) $(M+1)^+$, 244.0, found 244.1.

Step-4: 5-((5,6-dimethoxypyridin-2-yl)methoxy)-1,3,4-thiadiazol-2-amine

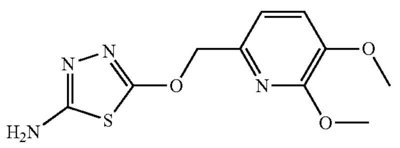 [SMILES: COc1ccc(COc2nnc(N)s2)nc1OC]

To a solution of O-((5,6-dimethoxypyridin-2-yl)methyl) hydrazinecarbothioate (290 mg, 1.189 mmol) in MeOH (5 mL) were added TEA (249 mg, 2.465 mmol) and BrCN (143 mg, 1.349 mmol). The resulting mixture was stirred at room temperature for 2 hours. The reaction mixture was quenched with water and extracted with ethyl acetate. The combined organic layers were washed with brine, dried over anhydrous sodium sulfate, filtered, and concentrated under vacuum. The residue was purified by flash chromatography on silica gel with 0-50% ethyl acetate in petroleum ether to afford 5-((5,6-dimethoxypyridin-2-yl)methoxy)-1,3,4-thiadiazol-2-amine (130 mg, 29.3%) as red solid. MS (ESI) calc'd for ($C_{10}H_{12}N_4O_3S$) $(M+1)^+$, 269.1, found 269.1.

Step-5: N-(5-((5,6-dimethoxypyridin-2-yl)methoxy)-1,3,4-thiadiazol-2-yl)-4-(2-fluoro-6-methoxyphenyl)-6-methylnicotinamide

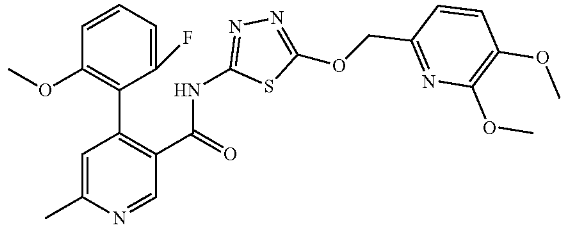

To a solution of 4-(2-fluoro-6-methoxyphenyl)-6-methylnicotinic acid (85 mg, 0.324 mmol, Intermediate F) in ACN (3 mL) were added NMI (80 mg, 0.975 mmol), 5-((5,6-dimethoxypyridin-2-yl)methoxy)-1,3,4-thiadiazol-2-amine (130 mg, 0.448 mmol) and TCFH (110 mg, 0.393 mmol). The mixture was stirred at room temperature for 2 hours. The mixture was concentrated under vacuum. The residue was purified by flash chromatography on silica gel with 0~10% methanol in dichloromethane and further purified by prep-HPLC with the following conditions: (Column: XBridge Prep OBD C18 Column, 30×150 mm 5 um; Mobile Phase A Water (10 MMOL/L $NH_4HCO_3$+0.1% $NH_3 \cdot H_2O$), Mobile Phase B: ACN; Flow rate: 60 mL/min; Gradient: 25 B to 56 B in 7 min; 220 nm) to afford N-(5-((5,6-dimethoxypyridin-2-yl)methoxy)-1,3,4-thiadiazol-2-yl)-4-(2-fluoro-6-methoxyphenyl)-6-methylnicotinamide (33.6 mg, 25.8%) as a white solid. MS (ESI) calc'd for ($C_{24}H_{22}FN_5O_5S$) $(M+1)^+$, 512.1; found 512.2. $^1H$ NMR (400 MHz, DMSO-d6) δ 12.87 (s, 1H), 8.81 (s, 1H), 7.43-7.39 (m, 1H), 7.37-7.32 (m, 2H), 7.29-7.09 (m, 1H), 6.94-6.83 (m, 2H), 5.35 (s, 2H), 3.84 (s, 3H), 3.79 (s, 3H), 3.58 (s, 3H), 2.52 (s, 3H).

Example 44

N-(5-((5-chloropyridin-2-yl)methoxy)-1,3,4-thiadiazol-2-yl)-4-(2-methoxy-5-methylphenyl)-6-methylpyridine-3-carboxamide

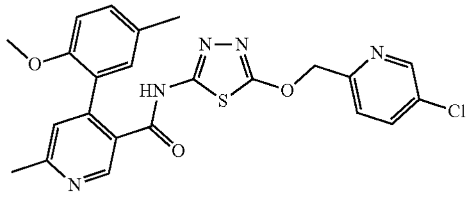 [SMILES: COc1ccc(C)cc1-c1cc(C)ncc1C(=O)Nc1nnc(OCc2ccc(Cl)cn2)s1]

Step-1: methyl 4-(2-methoxy-5-methylphenyl)-6-methylpyridine-3-carboxylate

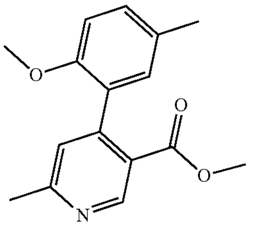

A degassed mixture of methyl 4-chloro-6-methylpyridine-3-carboxylate (500.0 mg, 2.69 mmol), 2-methoxy-5-methylphenylboronic acid (894.2 mg, 5.388 mmol), Pd(dppf)$Cl_2$ (394.21 mg, 0.53 mmol), Potassium carbonate (744.6 mg, 5.38 mmol) in dioxane (10.0 mL) and Water (1.0 mL) was stirred at 110° C. for 2 h under nitrogen. The solvent was removed under vacuum. The residue was purified by flash column chromatography with 0~44% ethyl acetate in petroleum ether to afford methyl 4-(2-methoxy-5-methylphenyl)-6-methylpyridine-3-carboxylate (800.0 mg, 57%) as a yellow oil. MS (ESI) calc'd for ($C_{16}H_{17}NO_3$) $(M+1)^+$, 272.1, found 272.1.

Step-2: 4-(2-methoxy-5-methylphenyl)-6-methylpyridine-3-carboxylic acid

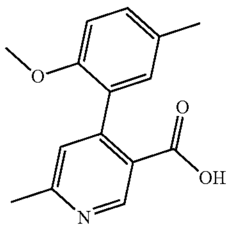 [SMILES: COc1ccc(C)cc1-c1cc(C)ncc1C(=O)O]

A mixture of methyl 4-(2-methoxy-5-methylphenyl)-6-methylpyridine-3-carboxylate (700.0 mg, 2.58 mmol), NaOH (309.5 mg, 7.74 mmol) in THF (10.0 mL) and Water (3.0 mL) was stirred at room temperature for 16 h. The reaction mixture was acidified with HCl (1 N) to pH ~4. The aqueous layer was extracted with ethyl acetate. The combined organic solution was dried over sodium sulfate, filtered, and concentrated under vacuum to afford 4-(2-methoxy-5-methylphenyl)-6-methylpyridine-3-carboxylic acid (550.0 mg, crude) as a yellow oil. MS (ESI) calc'd for ($C_{15}H_{15}NO_3$) $(M+1)^+$, 258.1, found 258.4.

Step-3: N-(5-((5-chloropyridin-2-yl)methoxy)-1,3,4-thiadiazol-2-yl)-4-(2-methoxy-5-methylphenyl)-6-methylpyridine-3-carboxamide

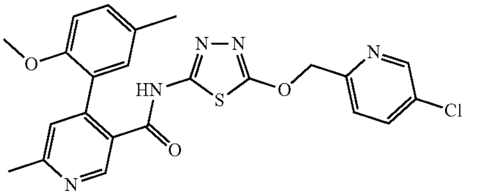 [SMILES: COc1ccc(C)cc1-c1cc(C)ncc1C(=O)Nc1nnc(OCc2ccc(Cl)cn2)s1]

To a mixture of 4-(2-methoxy-5-methylphenyl)-6-methylpyridine-3-carboxylic acid (150.0 mg, 0.58 mmol, Example 44, Step 2) and 5-((5-chloropyridin-2-yl)methoxy)-1,3,4-thiadiazol-2-amine (282.9 mg, 1.16 mmol, Intermediate C) in MeCN (3 mL) were added NMI (100.5 mg, 1.22 mmol) and TCFH (243.6 mg, 0.87 mmol). The resulting mixture was stirred at room temperature for 2 h before concentrated under vacuum. The residue was purified by flash column chromatography with 0~16% methanol in dichloromethane to afford N-(5-((5-chloropyridin-2-yl)methoxy)-1,3,4-thiadiazol-2-yl)-4-(2-methoxy-5-methylphenyl)-6-methylpyridine-3carboxamide (56.0 mg, 19%) as an off-white solid. MS (ESI) calc'd for ($C_{23}H_{20}ClN_5O_3S$) $(M+1)^+$, 482.0, found 482.0. $^1$H NMR (400 MHz, DMSO-$d_6$) δ 12.73 (s, 1H), 8.69-8.61 (m, 2H), 8.02-8.00 (m, 1H), 7.61 (d, J=8.4 Hz, 1H), 7.30 (s, 1H), 7.19 (d, J=7.6 Hz, 2H), 6.86 (d, J=8.4 Hz, 1H), 5.54 (s, 2H), 3.46 (s, 3H), 3.34 (s, 3H), 2.32 (s, 3H).

Example 45

2'-chloro-5'-methoxy-N-(5-((5-methoxypyridin-2-yl)methoxy)-1,3,4-thiadiazol-2-yl)-6-methyl-(4,4'-bipyridine)-3-carboxamide

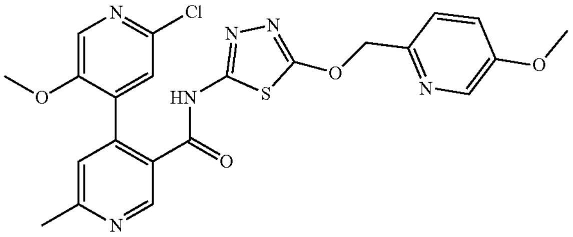

To a stirred solution of 2'-chloro-5'-methoxy-6-methyl-(4,4'-bipyridine)-3-carboxylic acid (100 mg, 0.35 mmol) and 55-((5-methoxypyridin-2-yl)methoxy)-1,3,4-thiadiazol-2-amine (85 mg, 0.35 mmol, Example 20, Step 1) in MeCN (1 mL) and DMF (1 mL) were added NMI (117 mg, 1.43 mmol) and TCFH (151 mg, 0.53 mmol). The resulting mixture was stirred at room temperature for 2 h under $N_2$ atmosphere. The resulting mixture was purified by reverse phase flash column chromatography with ACN in water (5~80%) to afford 2'-chloro-5'-methoxy-N-(5-((5-methoxypyridin-2-yl)methoxy)-1,3,4-thiadiazol-2-yl)-6-methyl-(4,4'-bipyridine)-3-carboxamide (100 mg, 55.8%) as a light yellow oil. MS (ESI) calculated for ($C_{22}H_{19}ClN_6O_4S$) $(M+1)^+$, 499.2; found, 499.2. $^1$H NMR (400 MHz, DMSO-$d_6$) δ 12.93 (s, 1H), 8.81 (s, 1H), 8.31 (d, J=3.2 Hz, 1H), 8.17 (s, 1H), 7.58-7.53 (m, 2H), 7.49-7.40 (m, 2H), 5.46 (s, 2H), 3.85 (s, 3H), 3.63 (s, 3H), 2.59 (s, 3H).

Example 46

4-(2-(difluoromethoxy)-6-fluorophenyl)-N-(5-((5-methoxypyridin-2-yl)methoxy)-1,3,4-thiadiazol-2-yl)-6-methylnicotinamide

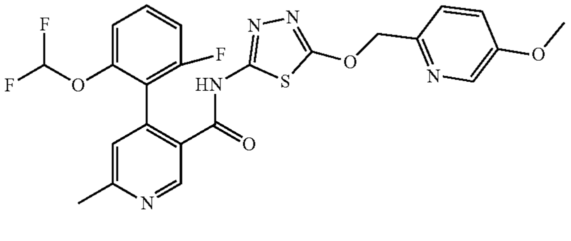 [SMILES: COc1ccc(COc2nnc(NC(=O)c3cnc(C)cc3-c3c(F)cccc3OC(F)F)s2)nc1]

Step-1: 5-((5-methoxypyridin-2-yl)methoxy)-1,3,4-thiadiazol-2-amine

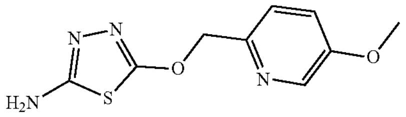 [SMILES: COc1ccc(COc2nnc(N)s2)nc1]

To a solution of NaH (216 mg, 5.4 mmol, 60% purity) in THF (5.00 mL) was added a solution of (5-methoxypyridin-2-yl)methanol (500 mg, 3.5 mmol, Example 20, Step 1)) in THF (5 mL) dropwise at 0~5° C. and stirred at 0~5° C. for 1 hour under nitrogen atmosphere. To the above solution was added 5-bromo-1,3,4-thiadiazol-2-amine (430 mg, 4.2 mmol) at 0° C. The resulting mixture was stirred at room temperature for 4 h under nitrogen. The reaction mixture was quenched by the addition of water and extracted with ethyl acetate. The combined organic layers were washed with brine, dried over anhydrous sodium sulfate, filtered, and concentrated under vacuum. The residue was purified by flash chromatography on silica gel with 0~50% ethyl acetate in petroleum ether to afford 5-((5-methoxypyridin-2-yl)methoxy)-1,3,4-thiadiazol-2-amine (280 mg, 32.9%) as a yellow solid. MS (ESI) calc'd for ($C_9H_{10}N_4O_2S$) $(M+1)^+$, 239.1, found 239.0.

Step-2: 4-(2-(difluoromethoxy)-6-fluorophenyl)-N-(5-((5-methoxypyridin-2-yl)methoxy)-1,3,4-thiadiazol-2-yl)-6-methylnicotinamide

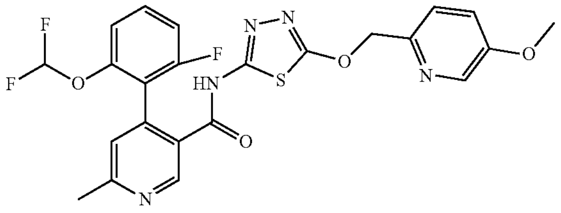 [SMILES: COc1ccc(COc2nnc(NC(=O)c3cnc(C)cc3-c3c(F)cccc3OC(F)F)s2)nc1]

To a solution of 5-((5-methoxypyridin-2-yl)methoxy)-1,3,4-thiadiazol-2-amine (280 mg, 1.178 mmol, Example 20, Step 1) in ACN (2 mL) and DMF (2 mL) was added 4-(2-(difluoromethoxy)-6-fluorophenyl)-6-methylnicotinic acid (341 mg, 1.178 mmol, Intermediate E), NMI (290 mg, 3.534 mmol) and TCFH (494 mg, 1.767 mmol). The mixture was stirred at room temperature for 2 h. The mixture was quenched with water and extracted with ethyl acetate. The combined organic layers were washed with brine, dried over anhydrous sodium sulfate, filtered, and concentrated under vacuum. The residue was purified by flash chromatography on silica gel with 0~10% in methanol in dichloromethane and further purified by prep-HPLC with the following conditions: (Column: YMC-Triart Diol Hilic, 20*150 mm um; Mobile Phase A:undefined, Mobile Phase B:undefined; Flow rate: 60 mL/min; Gradient: 27 B to 36 B in 8 min, 36 B to Bin min, B to Bin min, B to Bin min, B to Bin min; 220/254 nm) to afford 4-(2-(difluoromethoxy)-6-fluorophenyl)-N-(5-((5-methoxypyridin-2-yl)methoxy)-1,3,4-thiadiazol-2-yl)-6-methylnicotinamide (12.7 mg, 2.1%) as a white solid. MS (ESI) calc'd for ($C_{23}H_{18}F_3N_5O_4S$)$(M+1)^+$, 518.1; found 518.1. $^1$H NMR (400 MHz, DMSO-$d_6$) δ 13.11 (s, 1H), 8.93 (s, 1H), 8.30 (s, 1H), 7.53-7.42 (m, 4H), 7.37-6.94 (m, 3H), 5.45 (s, 2H), 3.84 (s, 3H), 2.51 (s, 3H).

Example 47

4-(2-(difluoromethoxy)-6-fluorophenyl)-N-(5-((2,3-dihydro-(1,4)dioxino(2,3-b)pyridin-6-yl)methoxy)-1,3,4-thiadiazol-2-yl)-6-methylnicotinamide

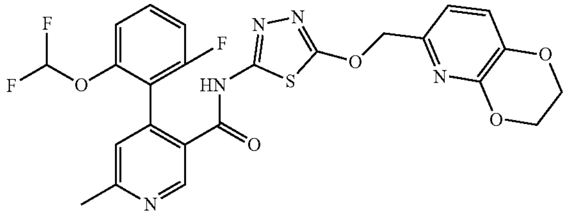 [SMILES: Cc1cc(-c2c(F)cccc2OC(F)F)c(C(=O)Nc2nnc(OCc3ccc4c(n3)OCCO4)s2)cn1]

To a solution of 4-(2-(difluoromethoxy)-6-fluorophenyl)-6-methylnicotinic acid (30 mg, 0.101 mmol, Intermediate E) in ACN (4 mL) were added NMI (25 mg, 0.304 mmol), 5-((2,3-dihydro-(1,4)dioxino(2,3-b)pyridin-6-yl)methoxy)-1,3,4-thiadiazol-2-amine (41 mg, 0.154 mmol, Example 35, Step 1) and TCFH (34 mg, 0.121 mmol). The mixture was stirred at room temperature for 2 h. The mixture was concentrated under vacuum. The residue was purified by flash chromatography on silica gel with 0~10% methanol in dichloromethane and further purified by prep-HPLC with the following conditions: (Column: XBridge Prep OBD C18 Column, 30×150 mm 5 um; Mobile Phase A: Water (10 MMOL/L $NH_4HCO_3$+0.1% $NH_3 \cdot H_2O$), Mobile Phase B: ACN; Flow rate: 60 mL/min; Gradient: 25 B to 56 B in 7 min; 220 nm) to afford 4-(2-(difluoromethoxy)-6-fluorophenyl)-N-(5-((2,3-dihydro-(1,4)dioxino(2,3-b)pyridin-6-yl)methoxy)-1,3,4-thiadiazol-2-yl)-6-methylnicotinamide (22.6 mg, 55.1%) as a white solid. MS (ESI) calc'd for ($C_{24}H_{18}F_3N_5O_5S$) $(M+1)^+$, 546.1; found 546.2. $^1$H NMR (400 MHz, DMSO-$d_6$) δ 13.03 (s, 1H), 8.94 (s, 1H), 7.57-7.47 (m, 1H), 7.36 (s, 1H), 7.32 (d, J=8.0 Hz, 1H), 7.22 (t, J=8.8 Hz, 1H), 7.14-7.08 (m, 3H), 5.32 (s, 2H), 4.51-4.34 (m, 2H), 4.34-4.20 (m, 2H), 2.59 (s, 3H).

Example 48

4-(2-fluoro-6-methoxyphenyl)-N-(5-((5-(1-hydroxycyclopropyl)pyridin-2-yl)methoxy)-1,3,4-thiadiazol-2-yl)-6-methylnicotinamide

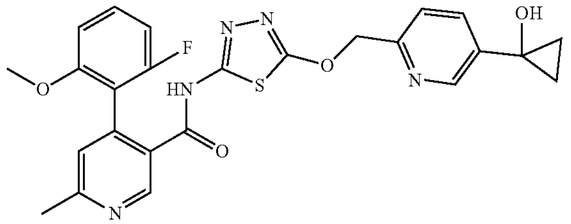 [SMILES: COc1cccc(F)c1-c1cc(C)ncc1C(=O)Nc1nnc(OCc2ccc(C3(O)CC3)cn2)s1]

Step-1: 1-(6-chloropyridin-3-yl)cyclopropan-1-ol

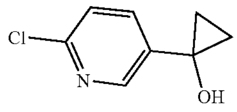

To a stirred solution of methyl 6-chloropyridine-3-carboxylate (10.0 g, 58.28 mmol) in THF (400 mL) were sequentially added Ti(Oi-Pr)$_4$ (23.2 g, 81.59 mmol) and EtMgBr (55 mL, 416.82 mmol) dropwise at 0° C. under $N_2$ atmosphere. The resulting mixture was stirred at room temperature for 16 h under nitrogen. The reaction was quenched with saturated $NH_4Cl$ aqueous solution. The resulting mixture was extracted with ethyl acetate. The combined organic layers were washed with water, dried over anhydrous sodium sulfate. After filtration, the filtrate was concentrated under vacuum. The residue was purified by flash column chromatography with 0-80% ethyl acetate in petroleum ether to afford 1-(6-chloropyridin-3-yl)cyclopropan-1-ol (2.2 g, 22.2%) as a yellow oil. MS (ESI) calculated for ($C_8H_8ClNO$) $(M+1)^+$, 170.0; found, 170.1.

Step-2: 5-(1-((tert-butyldimethylsilyl)oxy)cyclopropyl)-2-chloropyridine

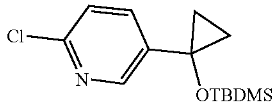 [SMILES: CC(C)(C)[Si](C)(C)OC1(c2ccc(Cl)nc2)CC1]

To a stirred solution of 1-(6-chloropyridin-3-yl)cyclopropan-1-ol (1.0 g, 5.89 mmol) and TBDMSCl (0.9 g, 6.48 mmol) in DMF (20 mL) was added Imidazole (602.0 g, 8.84 mmol). The resulting mixture was stirred at room temperature for 2 h under $N_2$ atmosphere. The reaction mixture was quenched with water and extracted with ethyl acetate. The combined organic layers were washed with brine, dried over anhydrous sodium sulfate, filtered, and concentrated under vacuum. The residue was purified by flash column chromatography with 0-20% ethyl acetate in petroleum ether to afford 5-(1-((tert-butyldimethylsilyl)oxy)cyclopropyl)-2-chloropyridine (0.9 g, 53.7%) as colorless oil. MS (ESI) calculated for ($C_{14}H_{22}ClNOSi$) $(M+1)^+$, 284.1; found, 284.1.

Step-3: methyl 5-(1-((tert-butyldimethylsilyl)oxy) cyclopropyl)picolinate

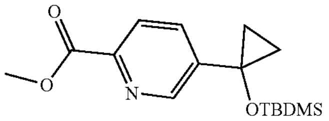 [SMILES: COC(=O)c1ccc(C2(O[Si](C)(C)C(C)(C)C)CC2)cn1]

To a degassed solution of 5-(1-((tert-butyldimethylsilyl) oxy)cyclopropyl)-2-chloropyridine (400 mg, 1.40 mmol) and TEA (285 mg, 2.81 mmol) in MeOH (5 mL) was added Pd(dppf)$Cl_2$ (206 mg, 0.28 mmol). The resulting mixture was stirred at 60° C. for 16 h under CO (2 atm). The reaction mixture was quenched with water and extracted with ethyl acetate. The combined organic layers were washed with brine, dried over anhydrous sodium sulfate, filtered, and concentrated under vacuum. The residue was purified by reverse phase flash column chromatography with 5-80% ACN in water to afford methyl 5-(1-((tert-butyldimethylsilyl)oxy)cyclopropyl)picolinate (250 mg, 57.7%) as a brown oil. MS (ESI) calculated for ($C_{16}H_{25}NO_3Si$) $(M+1)^+$, 308.1; found, 308.1.

Step-4: (5-(1-((tert-butyldimethylsilyl)oxy)cyclopropyl)pyridin-2-yl)methanol

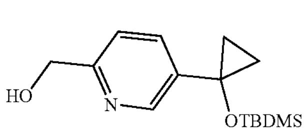 [SMILES: CC(C)(C)[Si](C)(C)OC1(c2ccc(CO)nc2)CC1]

To a stirred solution of methyl 5-(1-((tert-butyldimethylsilyl)oxy)cyclopropyl)picolinate (336 mg, 1.09 mmol) in THF (5 mL) was added LiAlH4 (82 mg, 2.18 mmol) in portions at 0° C. under $N_2$ atmosphere. The resulting mixture was stirred at 0° C. for 1 h. The reaction mixture was quenched with water and extracted with ethyl acetate. The combined organic layers were washed with brine, dried over anhydrous sodium sulfate, filtered, and concentrated under vacuum. The residue was purified by reverse phase flash column chromatography with 5~80% ACN in water to afford (5-(1-((tert-butyldimethylsilyl)oxy)cyclopropyl)pyridin-2-yl)methanol (110 mg, 36.0%) as a colorless oil. MS (ESI) calculated for ($C_{15}H_{25}NO_2Si$) $(M+1)^+$, 280.1; found, 280.1.

Step-5:5-((5-(1-((tert-butyldimethylsilyl)oxy)cyclopropyl)pyridin-2-yl)methoxy)-1,3,4-thiadiazol-2-amine

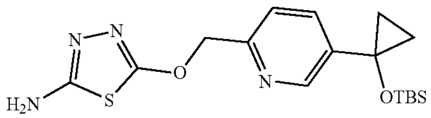 [SMILES: CC(C)(C)[Si](C)(C)OC1(c2ccc(COc3nnc(N)s3)nc2)CC1]

To a stirred solution of (5-(1-((tert-butyldimethylsilyl) oxy)cyclopropyl)pyridin-2-yl)methanol (110 mg, 0.39 mmol) in THF (5 mL) was added NaH (25 mg, 1.07 mmol) in portions at 0° C. and stirred at 0° C. for 1 h under $N_2$ atmosphere. To this was added 5-bromo-1,3,4-thiadiazol-2-amine (84 mg, 0.46 mmol) at 0° C. The resulting mixture was stirred at room temperature for 1 h. The reaction mixture was quenched with water and extracted with ethyl acetate. The combined organic layers were washed with brine, dried over anhydrous sodium sulfate, filtered, and concentrated under vacuum to afford 5-((5-(1-((tert-butyldimethylsilyl) oxy)cyclopropyl)pyridin-2-yl)methoxy)-1,3,4-thiadiazol-2-amine (180 mg, crude) as a brown oil. MS (ESI) calculated for ($C_{17}H_{26}N_4O_2SSi$) $(M+1)^+$, 379.1; found, 379.1.

Step-6: N-(5-((5-(1-((tert-butyldimethylsilyl)oxy) cyclopropyl)pyridin-2-yl)methoxy)-1,3,4-thiadiazol-2-yl)-4-(2-fluoro-6-methoxyphenyl)-6-methylnicotinamide

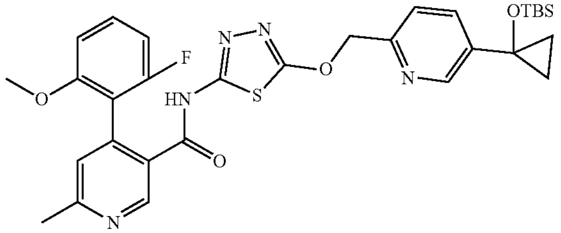 [SMILES: COc1cccc(F)c1-c1cc(C)ncc1C(=O)Nc1nnc(OCc2ccc(C3(O[Si](C)(C)C(C)(C)C)CC3)cn2)s1]

To a stirred solution of 5-((5-(1-((tert-butyldimethylsilyl) oxy)cyclopropyl)pyridin-2-yl)methoxy)-1,3,4-thiadiazol-2-amine (32 mg, 0.08 mmol) and 4-(2-fluoro-6-methoxyphenyl)-6-methylpyridine-3-carboxylic acid (22 mg, 0.08 mmol, Intermediate F) in DMF (1 mL) and MeCN (1 mL) were added NMI (28 mg, 0.34 mmol) and TCFH (36 mg, 0.13 mmol). The resulting mixture was stirred at room temperature for 1 h under nitrogen. The residue was purified by reverse phase flash column chromatography with 5~80% ACN in water to afford N-(5-((5-(1-((tert-butyldimethylsilyl)oxy)cyclopropyl)pyridin-2-yl)methoxy)-1,3,4-thiadiazol-2-yl)-4-(2-fluoro-6-methoxyphenyl)-6-methylnicotinamide (32 mg, 60.8%) as a yellow solid. MS (ESI) calculated for ($C_{31}H_{36}FN_5O_4SSi$) $(M+1)^+$, 622.2; found, 622.0.

Step-7: 4-(2-fluoro-6-methoxyphenyl)-N-(5-((5-(1-hydroxycyclopropyl)pyridin-2-yl)methoxy)-1,3,4-thiadiazol-2-yl)-6-methylnicotinamide

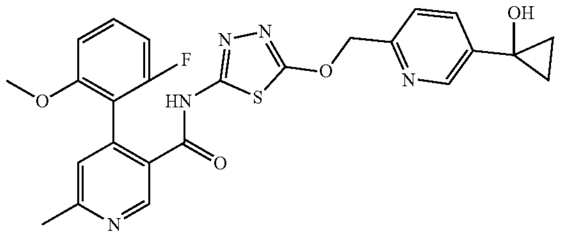 [SMILES: COc1cccc(F)c1-c1cc(C)ncc1C(=O)Nc1nnc(OCc2ccc(C3(O)CC3)cn2)s1]

A stirred solution of N-(5-((5-(1-((tert-butyldimethylsilyl) oxy)cyclopropyl)pyridin-2-yl)methoxy)-1,3,4-thiadiazol-2-yl)-4-(2-fluoro-6-methoxyphenyl)-6-methylnicotinamide (50 mg, 0.08 mmol) in THF (1 mL, 12.34 mmol) was added TBAF (21 mg, 0.08 mmol). The resulting mixture was stirred at room temperature for 2 h. The reaction mixture was diluted with water and extracted with ethyl acetate. The combined organic layers were washed with brine, dried over anhydrous sodium sulfate, filtered, and concentrated under vacuum. The residue was purified by prep-HPLC with the following conditions: (Column: XBridge Shield RP18 OBD Column, 30*150 mm, 5 um; Mobile Phase A: Water (0.1% FA), Mobile Phase B: ACN; Flow rate: 60 mL/min; Gradient: 20 B to 40 B in 7 min; 220 nm; RT1:6.55 min) to afford 4-(2-fluoro-6-methoxyphenyl)-N-(5-((5-(1-hydroxycyclopropyl)pyridin-2-yl)methoxy)-1,3,4-thiadiazol-2-yl)-6-methylnicotinamide (7.7 mg, 18.8%) as a white solid. MS (ESI) calculated for ($C_{25}H_{22}FN_5O_4S$) $(M+1)^+$, 508.1; found, 508.1. $^1$H NMR (400 MHz, DMSO-$d_6$) δ 12.89 (s, 1H), 8.81 (s, 1H), 8.48 (s, 1H), 7.65 (d, J=8.0 Hz, 1H), 7.55-7.37 (m, 2H), 7.33 (s, 1H), 7.0.3-6.81 (m, 2H), 6.15 (s, 1H), 5.50 (s, 2H), 3.59 (s, 3H), 2.57 (s, 3H), 1.16 (s, 2H), 1.03 (s, 2H).

Example 49

N-(5-((5-(difluoromethoxy)pyridin-2-yl)methoxy)-1,3,4-thiadiazol-2-yl)-4-(2-fluoro-6-methoxyphenyl)-6-methylnicotinamide

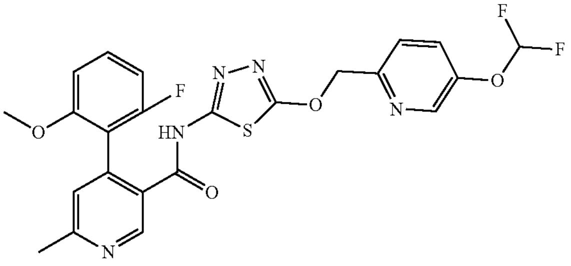 [SMILES: COc1cccc(F)c1-c1cc(C)ncc1C(=O)Nc1nnc(OCc2ccc(OC(F)F)cn2)s1]

To a solution of 5-((5-(difluoromethoxy)pyridin-2-yl) methoxy)-1,3,4-thiadiazol-2-amine (25 mg, 0.091 mmol, Example 82, Step 3) in ACN (1 mL) and DMF (1 mL) were added 4-(2-fluoro-6-methoxyphenyl)-6-methylnicotinic acid (28.5 mg, 0.109 mmol, Intermediate F), NMI (22.4 mg, 0.273 mmol) and TCFH (38.2 mg, 0.136 mmol). The resulting solution was stirred at room temperature for 2 h. The mixture was purified by prep-HPLC with the following conditions: (Column: XSelect CSH Prep C18 OBD Column, 19*250 mm, 5 um; Mobile Phase A: Water (0.1% FA), Mobile Phase B: ACN; Flow rate: 25 mL/min; Gradient: 15 B to 40 B in 11 min, 40 B to B in min; 254 nm; RT1: 8 min) to afford N-(5-((5-(difluoromethoxy)pyridin-2-yl)methoxy)-1,3,4-thiadiazol-2-yl)-4-(2-fluoro-6-methoxyphenyl)-6-methylnicotinamide (9.5 mg, 20%) as a white solid. MS (ESI) calc'd for ($C_{23}H_{18}F_3N_5O_4S$) $(M+1)^+$, 518.1; found, 518.1. $^1$H NMR (400 MHz, DMSO-$d_6$) δ 12.91 (s, 1H), 8.80 (s, 1H), 8.51 (s, 1H), 7.75-7.64 (m, 2H), 7.53-7.16 (m, 3H), 6.94-6.88 (m, 2H), 5.51 (s, 2H), 3.58 (s, 3H), 2.57 (s, 3H).

Example 50

4-(2-(difluoromethoxy)-6-fluorophenyl)-N-(5-((5-(2-hydroxypropan-2-yl)pyridin-2-yl)methoxy)-1,3,4-thiadiazol-2-yl)-6-methylnicotinamide

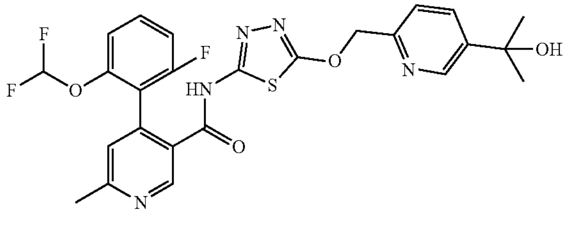 [SMILES: Cc1cc(-c2c(F)cccc2OC(F)F)c(C(=O)Nc2nnc(OCc3ccc(C(C)(C)O)cn3)s2)cn1]

Step-1: N-(5-((5-acetylpyridin-2-yl)methoxy)-1,3,4-thiadiazol-2-yl)-4-(2-(difluoromethoxy)-6-fluorophenyl)-6-methylnicotinamide

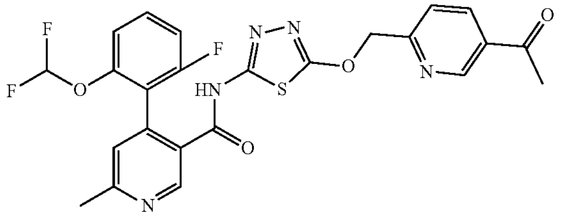 [SMILES: CC(=O)c1ccc(COc2nnc(NC(=O)c3cnc(C)cc3-c3c(F)cccc3OC(F)F)s2)nc1]

To a solution of 4-(2-(difluoromethoxy)-6-fluorophenyl)-6-methylnicotinic acid (220 mg, 0.73 mmol, Intermediate E) in MeCN (4 mL) were added NMI (182 mg, 2.21 mmol), 1-(6-(((5-amino-1,3,4-thiadiazol-2-yl)oxy)methyl)pyridin-3-yl)ethan-1-one (223 mg, 0.88 mmol, Example 22, Step 3) and TCFH (249 mg, 0.88 mmol). The mixture was stirred at room temperature for 2 h. The mixture was concentrated under vacuum. The residue was purified by flash chromatography on silica gel with 0~10% methanol in dichloromethane to afford N-(5-((5-acetylpyridin-2-yl)methoxy)-1,3,4-thiadiazol-2-yl)-4-(2-(difluoromethoxy)-6-fluorophenyl)-6-methylnicotinamide (180 mg, 81%) as a white solid. MS (ESI) calc'd for ($C_{24}$His $F_3N_5O_4S$) $(M+1)^+$, 530.1; found, 530.1.

Step-2: 4-(2-(difluoromethoxy)-6-fluorophenyl)-N-(5-((5-(2-hydroxypropan-2-yl)pyridin-2-yl)methoxy)-1,3,4-thiadiazol-2-yl)-6-methylnicotinamide

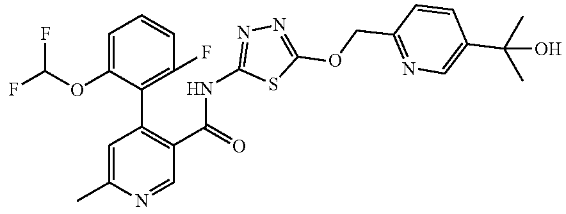 [SMILES: Cc1cc(-c2c(F)cccc2OC(F)F)c(C(=O)Nc2nnc(OCc3ccc(C(C)(C)O)cn3)s2)cn1]

To a mixture of N-(5-((5-acetylpyridin-2-yl)methoxy)-1,3,4-thiadiazol-2-yl)-4-(2-(difluoromethoxy)-6-fluorophenyl)-6-methylnicotinamide (180 mg, 0.34 mmol) in THF (5 mL) was added MeMgBr (1.0 mL, 1M in THF) at 0° C. under nitrogen. The mixture was stirred at room temperature for 3 h. The reaction mixture was then quenched by the addition of water and extracted with ethyl acetate. The combined organic layers were washed with brine, dried over anhydrous sodium sulfate, filtered, and concentrated under vacuum. The residue was purified by reverse phase flash column chromatography with 5-80% acetonitrile in water and further purified by prep-HPLC with the following conditions: (Column: Sunfire prep C18 column, 30*150, 5 um; Mobile Phase A: Water (0.1% FA), Mobile Phase B: ACN; Flow rate: 60 mL/min; Gradient: 25 B to 55 B in 8 min; 220 nm; RT1: 7.23 min) to afford 4-(2-(difluoromethoxy)-6-fluorophenyl)-N-(5-((5-(2-hydroxypropan-2-yl)pyridin-2-yl)methoxy)-1,3,4-thiadiazol-2-yl)-6-methylnicotinamide (16 mg, 8.9%) as a white solid. MS (ESI) calc'd for ($C_{25}H_{22}F_3N_5O_4S$) $(M+1)^+$, 546.1; found 546.2. $^1$H NMR (400 MHz, DMSO-$d_6$) δ 13.04 (s, 1H), 8.94 (s, 1H), 8.69 (s, 1H), 7.94-7.84 (m, 1H), 7.58-7.48 (m, 1H), 7.49-7.47 (m, 1H), 7.38-7.37 (m, 1H), 7.32-6.95 (m, 3H), 5.51 (s, 2H), 5.25 (s, 1H), 2.60 (s, 3H), 1.46 (s, 6H).

Example 51

2'-chloro-N-(5-((2,3-dihydro-[1,4]dioxino[2,3-b]pyridin-6-yl)methoxy)-1,3,4-thiadiazol-2-yl)-5'-methoxy-6-methyl-[4,4'-bipyridine]-3-carboxamide

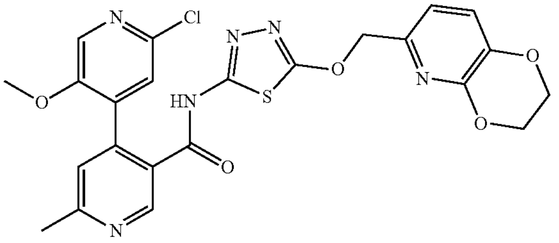 [SMILES: COc1cnc(Cl)cc1-c1cc(C)ncc1C(=O)Nc1nnc(OCc2ccc3c(n2)OCCO3)s1]

To a stirred solution of 5-(2H,3H-(1,4)dioxino(2,3-b)pyridin-6-ylmethoxy)-1,3,4-thiadiazol-2-amine (60 mg, 0.22 mmol, Example 35, Step 1) and 2'-chloro-5'-methoxy-6-methyl-(4,4'-bipyridine)-3-carboxylic acid (63 mg, 0.22 mmol, Intermediate H) in acetonitrile (1 mL) and DMF (1 mL) were added N,N,N',N'-Tetramethylchloroformamidinium-hexafluorophosphate (70 mg, 0.25 mmol) and 1-Methylimidazole (56 mg, 0.68 mmol). The resulting mixture was stirred at room temperature for 1 h. The mixture was purified by Prep-HPLC with the following conditions: (Column: XBridge Prep OBD C18 Column, 30×150 mm 5 um; Mobile Phase A: Water (10 MMOL/L $NH_4HCO_3$), Mobile Phase B: ACN; Flow rate: 60 mL/min; Gradient: 20 B to 38 B in 8 min, 254/220 nm; RT1:7.67 min) to afford 2'-chloro-N-(5-((2,3-dihydro-[1,4]dioxino[2,3-b]pyridin-6-yl)methoxy)-1,3,4-thiadiazol-2-yl)-5'-methoxy-6-methyl-[4,4'-bipyridine]-3-carboxamide (47.7 mg, 40.2%) as a white solid. MS (ESI) calculated for ($C_{23}H_{19}ClN_6O_5S$) $(M+1)^+$, 527.1; found, 527.0. $^1$H NMR (400 MHz, DMSO-$d_6$) δ 12.94 (s, 1H), 8.83 (s, 1H), 8.16 (s, 1H), 7.52 (s, 1H), 7.41 (s, 1H), 7.33 (d, J=8.0 Hz, 1H), 7.11 (d, J=8.0 Hz, 1H), 5.33 (s, 2H), 4.45-4.39 (m, 2H), 4.30-4.24 (m, 2H), 3.63 (s, 3H), 2.59 (s, 3H).

Example 52

4-(5-chloro-2-methoxyphenyl)-N-(5-((5-methoxypyridin-2-yl)methoxy)-1,3,4-thiadiazol-2-yl)-6-methylpyridine-3-carboxamide

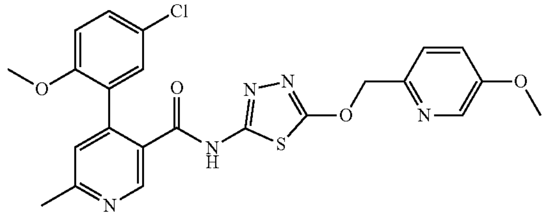

To a stirred solution of 4-(5-chloro-2-methoxyphenyl)-6-methylpyridine-3-carboxylic acid (100 mg, 0.36 mmol, Example 39, Step 2) and 5-((5-methoxypyridin-2-yl)methoxy)-1,3,4-thiadiazol-2-amine (86 mg, 0.36 mmol, Example 20, Step 1) in acetonitrile (1 mL) and DMF (1 mL) were added N,N,N',N'-Tetramethylchloroformamidinium-hexafluorophosphate (110 mg, 0.39 mmol) and 1-Methyl-imidazole (90 mg, 1.09 mmol). The resulting mixture was stirred at room temperature for 1 h. The mixture was purified by Prep-HPLC with the following conditions: (Column: XBridge Prep OBD C18 Column, 30×150 mm 5 um; Mobile Phase A:Water (10 mmol/L $NH_4HCO_3$), Mobile Phase B:ACN; Flow rate: 60 mL/min; Gradient: 35 B to 45 B in 8 min; 254/220 nm; RT1: 7.67 min) to afford 4-(5-chloro-2-methoxyphenyl)-N-(5-((5-methoxypyridin-2-yl)methoxy)-1,3,4-thiadiazol-2-yl)-6-methylpyridine-3-carboxamide (23.2 mg, 12.8%) as a white solid. MS (ESI) calculated for ($C_{23}H_{20}ClN_5O_4S$) $(M+1)^+$, 498.1; found, 498.1. $^1H$ NMR (400 MHz, DMSO-$d_6$) δ 12.78 (s, 1H), 8.70 (s, 1H), 8.30 (d, J=2.8 Hz, 1H), 7.54 (d, J=8.4 Hz, 1H), 7.47-7.38 (m, 3H), 7.35 (s, 1H), 7.01 (d, J=8.8 Hz, 1H), 5.45 (s, 2H), 3.85 (s, 3H), 3.50 (s, 3H), 2.57 (s, 3H).

Example 53

4-(2-(difluoromethoxy)phenyl)-N-(5-((5-methoxy-pyridin-2-yl)methoxy)-1,3,4-thiadiazol-2-yl)-6-methylnicotinamide

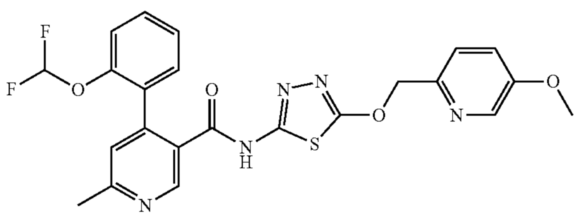 [SMILES: COc1ccc(COc2nnc(NC(=O)c3cnc(C)cc3-c3ccccc3OC(F)F)s2)nc1]

Step-1 methyl 4-(2-(difluoromethoxy)phenyl)-6-methylnicotinate

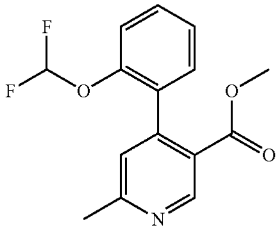 [SMILES: COC(=O)c1cnc(C)cc1-c1ccccc1OC(F)F]

To a degassed solution of methyl 4-chloro-6-methylpyridine-3-carboxylate (1 g, 5.41 mmol) in dioxane (10 mL) were added Pd(dppf)$Cl_2$ (39.5 mg, 0.054 mmol), KOAc (1.06 g, 10.82 mmol) and $B_2Pin_2$ (1.37 g, 5.41 mmol) under nitrogen. The resulting mixture was stirred at 80° C. for 2 h. To the above mixture were added a solution of Pd(dppf)$Cl_2$ (39.5 mg, 0.054 mmol), $K_2CO_3$ (1.49 g, 10.82 mmol) and 1-bromo-2-(difluoromethoxy)benzene (1.2 g, 5.41 mmol) in dioxane (5 mL) and water (2 mL). The resulting mixture was stirred at 80° C. for additional 16 h under nitrogen atmosphere. The reaction repeat three times. The reaction mixture was diluted with water and extracted with ethyl acetate. The combined organic layers were washed with brine, dried over anhydrous sodium sulfate, filtered, and concentrated under vacuum. The residue was purified by flash column chromatography with 0~30% ethyl acetate in petroleum ether to afford methyl 4-(2-(difluoromethoxy)phenyl)-6-methylnicotinate (3.0 g, 64%) as a yellow oil. MS (ESI) calculated for ($C_{15}H_{13}F_2NO_3$) $(M+1)^+$, 294.1; found, 294.0.

Step 2: 4-(2-(difluoromethoxy)phenyl)-6-methylnicotinic acid

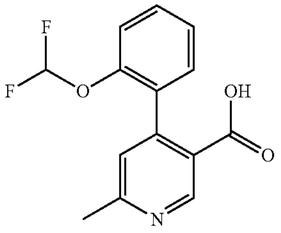 [SMILES: Cc1cc(-c2ccccc2OC(F)F)c(C(=O)O)cn1]

To a mixture of methyl 4-(2-(difluoromethoxy)phenyl)-6-methylnicotinate (3.0 g, 10.24 mmol) in MeOH (20 mL) was added a solution of NaOH (1.64 g, 40.95 mmol) in water (20 mL). The resulting mixture was stirred at room temperature for 16 h. The solvent was removed under vacuum. The residue was acidified with HCl (2 N) to pH ~5. The mixture was extracted with ethyl acetate. The combined organic layers were washed with brine, dried over anhydrous sodium sulfate, filtered, and concentrated under vacuum to afford 4-(2-(difluoromethoxy)phenyl)-6-methylnicotinic acid (2.48 g, 86.8%) as a yellow solid. MS (ESI) calculated for ($C_{14}H_{11}F_2NO_3$) $(M+1)^+$, 280.1; found, 280.0.

Step-4: 4-(2-(difluoromethoxy)phenyl)-N-(5-((5-methoxypyridin-2-yl)methoxy)-1,3,4-thiadiazol-2-yl)-6-methylnicotinamide

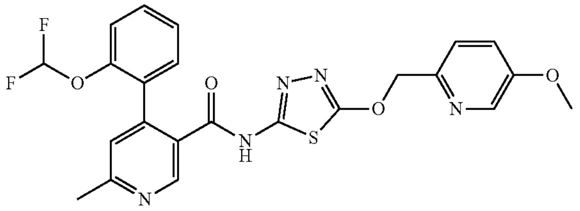 [SMILES: COc1ccc(COc2nnc(NC(=O)c3cnc(C)cc3-c3ccccc3OC(F)F)s2)nc1]

To a stirred mixture of 4-(2-(difluoromethoxy)phenyl)-6-methylpyridine-3-carboxylic acid (50.00 mg, 0.179 mmol) and 5-((5-methoxypyridin-2-yl)methoxy)-1,3,4-thiadiazol-2-amine (42.66 mg, 0.179 mmol, Example 20, Step 1) in MeCN (1.00 mL) and DMF (1.00 mL) were added TCFH (55.26 mg, 0.197 mmol) and NMI (44.10 mg, 0.537 mmol). The resulting mixture was stirred at room temperature for 2 h. The resulting mixture was concentrated under vacuum. The crude product was purified by Prep-HPLC with the following conditions: (Column: XBridge Prep OBD C18 Column, 30×150 mm 5 um; Mobile Phase A: Water (10 MMOL/L $NH_4HCO_3$), Mobile Phase B:ACN; Flow rate: 60 mL/min; Gradient: 25 B to 52 B in 8 min, 220 nm; RT1: 7.23 min) to afford 4-(2-(difluoromethoxy)phenyl)-N-(5-((5-methoxypyridin-2-yl)methoxy)-1,3,4-thiadiazol-2-yl)-6-methylnicotinamide (17.8 mg, 19.58%) as a white solid. MS (ESI) calculated for ($C_{23}H_{19}F_2N_5O_4S$) $(M+1)^+$, 500.1; found, 500.1. $^1H$ NMR (400 MHz, DMSO-$d_6$) δ 12.92 (s, 1H), 8.80 (s, 1H), 8.31 (s, 1H), 7.54-7.19 (m, 4H), 7.17-7.03 (m, 4H), 5.45 (s, 2H), 3.84 (s, 3H), 2.52 (s, 3H).

Example 54

4-(2-fluoro-6-methoxyphenyl)-6-methyl-N-(5-((5-(oxetan-3-ylmethyl)pyridin-2-yl)methoxy)-1,3,4-thiadiazol-2-yl)nicotinamide

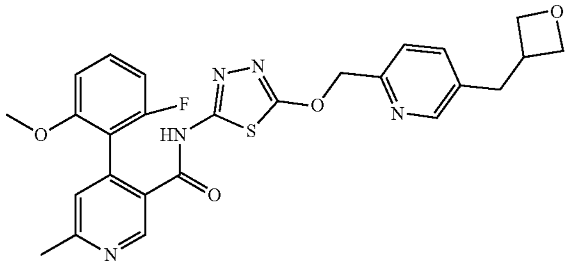 [SMILES: COc1cccc(F)c1-c1cc(C)ncc1C(=O)Nc1nnc(OCc2ccc(CC3COC3)cn2)s1]

Step-1: 2-bromo-5-(bromomethyl)pyridine

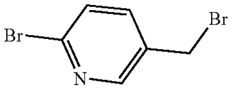

A solution of (6-bromopyridin-3-yl)methanol (5.0 g, 0.027 mol) in HBr in HOAc (50 mL) was stirred at 80° C. for 8 h. The solvents were removed by concentrated under vacuum. The residue was purified by flash chromatography on silica gel with 0-50% ethyl acetate in petroleum ether to afford 2-bromo-5-(bromomethyl)pyridine (1.5 g, 30%) as a yellow solid. MS (ESI) calc'd for ($C_6H_5Br_2N$) $(M+1)^+$, 249.8; found, 250.1.

Step-2: 2-bromo-5-((triphenyl-14-phosphaneyl) methyl)pyridine

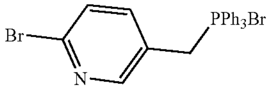

To a solution of 2-bromo-5-(bromomethyl)pyridine (1.0 g, 0.004 mol) in Toluene (30 mL) was added triphenylphosphine (1.06 g, 0.004 mol). The mixture was stirred at 120° C. for 5 h. The mixture was concentrated under vacuum to afford 2-bromo-5-((triphenyl-14-phosphaneyl)methyl)pyridine (2.0 g, crude) as a white solid. MS (ESI) calc'd for ($C_{24}H_{20}Br_2NP$) $(M+1)^+$, 512.0; found, 432.

Step-3: 2-bromo-5-(oxetan-3-ylidenemethyl)pyridine

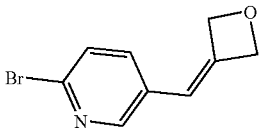 [SMILES: Brc1ccc(C=C2COC2)cn1]

To a solution of 2-bromo-5-((triphenyl-14-phosphaneyl) methyl)pyridine (2.0 g, 5.0 mmol) in THF (50 mL) was sequentially added potassium tert-butoxide (0.89 g, 10.0 mmol) and oxetan-3-one (0.5 g, 7.0 mmol) at 0° C. and the mixture was stirred at room temperature for 2 h. The reaction mixture was quenched with water and extracted with ethyl acetate. The combined organic layers were washed with brine, dried over anhydrous sodium sulfate, filtered, and concentrated under vacuum. The residue was purified by flash chromatography on silica gel with 0-50% ethyl acetate in petroleum ether to afford 2-bromo-5-(oxetan-3-ylidenemethyl)pyridine (650 mg, 33%) as a yellow solid. MS (ESI) calc'd for ($C_9H_8BrNO$) $(M+1)^+$, 225.0; found, 225.1.

Step-4: methyl 5-(oxetan-3-ylidenemethyl)picolinate

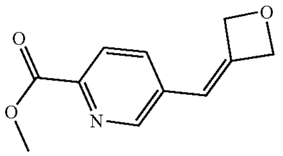

To a solution of 2-bromo-5-(oxetan-3-ylidenemethyl) pyridine (650 mg, 2.889 mmol) in MeOH (30 mL) were added TEA (876 mg, 8.673 mmol) and Pd(dppf)$Cl_2$ (472 mg, 0.578 mmol). The resulting solution was stirred at 70° C. for 8 h under carbon monoxide. The reaction mixture was concentrated under vacuum. The residue was purified by flash chromatography on silica gel with 0~50% ethyl acetate in petroleum ether to afford methyl 5-(oxetan-3-ylidenemethyl)picolinate (630 mg, 97%) as a yellow oil. MS (ESI) calc'd for ($C_{11}H_{11}NO_3$) $(M+1)^+$, 206.1; found, 206.1.

Step-5: methyl 5-(oxetan-3-ylmethyl)picolinate

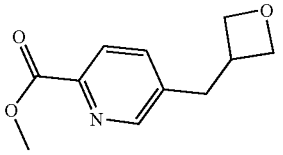

To a solution of methyl 5-(oxetan-3-ylidenemethyl)picolinate (630 mg, 3.058 mmol) in MeOH (30 mL) was added Pd/C (60 mg, 10%). The resulting mixture was stirred at room temperature for 2 h. The suspension was filtered and the filtrate was collected and concentrated under vacuum. The residue was purified by flash chromatography on silica gel with 0~50% ethyl acetate in petroleum ether to afford methyl 5-(oxetan-3-ylmethyl)picolinate (600 mg, 95%) as a yellow oil. MS (ESI) calc'd for ($C_{11}H_{13}NO_3$) $(M+1)^+$, 208.1; found 208.0.

Step-6: (5-(oxetan-3-ylmethyl)pyridin-2-yl)methanol

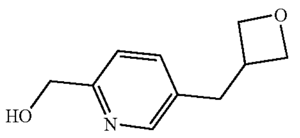 [SMILES: OCc1ccc(CC2COC2)cn1]

To a solution of methyl 5-(oxetan-3-ylmethyl)picolinate (600 mg, 2.884 mmol) in THF (50 mL) was added $LiAlH_4$ (230 mg, 6.053 mmol) in portions at 0~5° C. and stirred at 5° C. for 30 min. The resulting mixture was stirred at room temperature for 1 h. The reaction mixture was then quenched by the addition of water and extracted with ethyl acetate. The combined organic layers were washed with brine, dried over anhydrous sodium sulfate, filtered, and concentrated under vacuum. The residue was purified by flash chromatography on silica gel with 0~10% methanol in dichloromethane to afford (5-(oxetan-3-ylmethyl)pyridin-2-yl)methanol (150 mg, 25%) as a yellow oil. MS (ESI) calc'd for ($C_{10}H_{13}NO_2$) $(M+1)^+$, 180.1; found, 180.0.

Step-7: 5-((5-(oxetan-3-ylmethyl)pyridin-2-yl)methoxy)-1,3,4-thiadiazol-2-amine

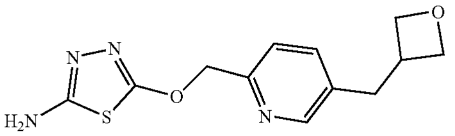

To a solution of NaH (48 mg, 2.001 mmol, 60%) in THF (20 mL) was added (5-(oxetan-3-ylmethyl)pyridin-2-yl)methanol (143 mg, 0.794 mmol) in portions at 0~5° C. and stirred at 5° C. for 1 h. Then 5-bromo-1,3,4-thiadiazol-2-amine (171 mg, 0.955 mmol) was added to the mixture in small portions at 5° C. and stirred at 5° C. for 5 h. The reaction mixture was then quenched by the addition of water and extracted with ethyl acetate. The combined organic layers were washed with brine, dried over anhydrous sodium sulfate, filtered, and concentrated under vacuum. The residue was purified by flash chromatography on silica gel with 0~50% ethyl acetate in petroleum ether to afford 5-((5-(oxetan-3-ylmethyl)pyridin-2-yl)methoxy)-1,3,4-thiadiazol-2-amine (84 mg, 30.1%) as a yellow solid. MS (ESI) calc'd for ($C_{12}H_{14}N_4O_2S$) $(M+1)^+$, 279.0; found, 279.1.

Step-8: 4-(2-fluoro-6-methoxyphenyl)-6-methyl-N-(5-((5-(oxetan-3-ylmethyl)pyridin-2-yl)methoxy)-1,3,4-thiadiazol-2-yl)nicotinamide

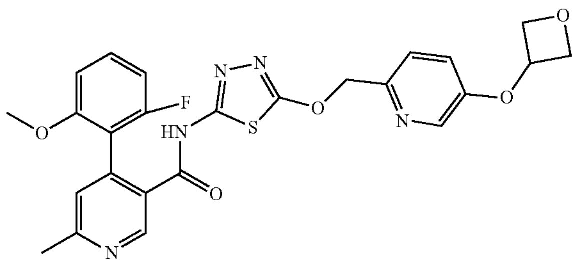 [SMILES: COc1cccc(F)c1-c1cc(C)ncc1C(=O)Nc1nnc(OCc2ccc(OC3COC3)cn2)s1]

To a solution of 4-(2-fluoro-6-methoxyphenyl)-6-methyl-nicotinic acid (53 mg, 0.202 mmol, Intermediate F) in ACN (1 mL) and DMF (1 mL) were added NMI (51 mg, 0.622 mmol), 5-((5-(oxetan-3-ylmethyl)pyridin-2-yl)methoxy)-1,3,4-thiadiazol-2-amine (84 mg, 0.301 mmol) and TCFH (69 mg, 0.246 mmol). The mixture was stirred at room temperature for 2 h. The reaction mixture was quenched with water and extracted with dichloromethane. The combined organic layers were washed with brine, dried over anhydrous sodium sulfate, filtered, and concentrated under vacuum. The residue was purified by flash chromatography on silica gel with 0~10% methanol in dichloromethane and further purified by prep-HPLC with the following conditions: (Column: Sunfire prep C18 column, 30*150, 5 um; Mobile Phase A: Water (0.1% FA), Mobile Phase B: ACN; Flow rate: 40 mL/min; Gradient: 25 B to 55 B in 8 min; 220 nm; RT1: 7.23 min) to afford 4-(2-fluoro-6-methoxyphenyl)-6-methyl-N-(5-((5-(oxetan-3-ylmethyl)pyridin-2-yl)methoxy)-1,3,4-thiadiazol-2-yl)nicotinamide (25 mg, 19.8%) as a white solid. MS (ESI) calc'd for ($C_{26}H_{24}FN_5O_4S$) $(M+1)^+$, 522.1; found, 522.1. $^1H$ NMR (400 MHz, DMSO-$d_6$) δ 12.88 (s, 1H), 8.81 (s, 1H), 8.45 (d, J=2.4 Hz, 1H), 7.73-7.63 (m, 1H), 7.45-7.35 (d, J=8.0 Hz, 1H), 7.40 (s, 1H), 7.32 (s, 1H), 6.96-6.86 (m, 2H), 5.48 (s, 2H), 4.68-4.58 (m, 2H), 4.34 (t, J=6.0 Hz, 2H), 3.59 (s, 3H), 3.26 (d, J=7.6 Hz, 1H), 2.99 (d, J=7.6 Hz, 2H), 2.57 (s, 3H).

Example 55

4-(2-fluoro-6-methoxyphenyl)-N-(5-((5-(2-hydroxy-ethyl)pyridin-2-yl)methoxy)-1,3,4-thiadiazol-2-yl)-6-methylnicotinamide

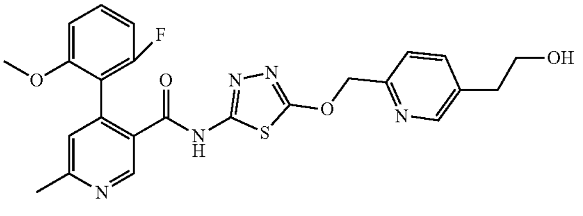 [SMILES: COc1cccc(F)c1-c1cc(C)ncc1C(=O)Nc1nnc(OCc2ccc(CCO)cn2)s1]

Step-1: methyl 2-(6-vinylpyridin-3-yl)acetate

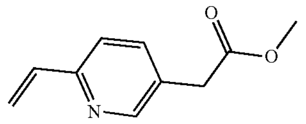

To a degassed solution of methyl 2-(6-chloropyridin-3-yl)acetate (2 g, 10.8 mmol) in Dioxane (50 mL) and $H_2O$ (5 mL) were added ethenyltrifluoro-lambda4-borane potassium (1.43 g, 10.8 mmol), $K_2CO_3$ (4.47 g, 32.4 mmol) and Pd(dppf)$Cl_2$ (703 mg, 1.08 mmol) under nitrogen. The mixture was stirred at 80° C. for 5 hours under nitrogen. The reaction mixture was concentrated under vacuum. The residue was purified by flash chromatography on silica gel with 0-50% ethyl acetate in petroleum ether to afford methyl 2-(6-vinylpyridin-3-yl)acetate (1.3 g, 68%) as a yellow solid. MS (ESI) calc'd for ($C_{10}H_{11}NO_2$) $(M+1)^+$, 177.1, found 177.1.

Step-2: methyl 2-(6-formylpyridin-3-yl)acetate

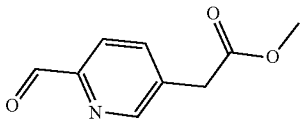

To a solution of methyl 2-(6-vinylpyridin-3-yl)acetate (1300 mg, 7.34 mmol) in THF (30 mL) and $H_2O$ (10 mL) were sequentially added $OsO_4$ (1361 mg, 0.74 mmol) and $NaOI_4$ (6284 mg, 29.36 mmol). The mixture was stirred at room temperature for 5 h. The mixture was diluted with water and extracted with ethyl acetate. The combined organic layers were washed with brine, dried over anhydrous sodium sulfate, filtered, and concentrated under vacuum. The residue was purified by flash chromatography on silica gel with 0~10% methanol in dichloromethane to afford methyl 2-(6-formylpyridin-3-yl)acetate (600 mg, 46%) as a yellow solid. MS (ESI) calc'd for ($C_9H_9NO_3$)$(M+1)^+$, 179.1; found 179.1.

Step-3: methyl 2-(6-(hydroxymethyl)pyridin-3-yl)acetate

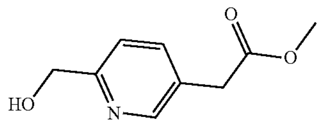

To a solution of methyl 2-(6-formylpyridin-3-yl)acetate (600 mg, 3.35 mmol) in MeOH (10 mL) was added $NaBH_4$ (127 mg, 3.35 mmol) in portions at 0° C. The mixture was stirred at 0° C. for 2 hours. The reaction mixture was then quenched by the addition of water and extracted with ethyl acetate. The combined organic layers were washed with brine, dried over anhydrous sodium sulfate, filtered, and concentrated under vacuum to afford methyl 2-(6-(hydroxymethyl)pyridin-3-yl)acetate (450 mg, 75%) as a yellow solid. MS (ESI) calc'd for ($C_9H_{11}NO_3$) $(M+1)^+$, 182.1, found 182.1.

Step-4: methyl 2-(6-(((5-amino-1,3,4-thiadiazol-2-yl)oxy)methyl)pyridin-3-yl)acetate

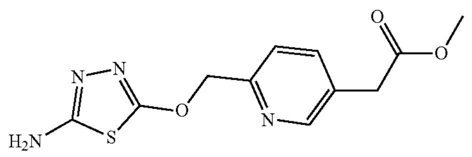 [SMILES: COC(=O)Cc1ccc(COc2nnc(N)s2)nc1]

To a solution of NaH (149 ng, 372 mmol, 60%) in THF (5.0 mL) was added a solution of 2-(6-(hydroxymethyl) pyridin-3-yl)acetate (450 mg, 35 mmol) in THF (2 mL) at 0° C. and stirred at 0° C. for 1 hour under nitrogen. To the above solution was added 5-bromo-1,3,4-thiadiazol-2-amine (532 mg. 2.98 mmol) at 0° C. under nitrogen. The mixture was stirred at room temperature for 4 h. The reaction mixture was quenched by the addition of water and extracted with ethyl acetate. The combined organic layers were washed with brine, dried over anhydrous sodium sulfate, filtered, and concentrated under vacuum. The residue was purified by flash chromatography on silica gel with 0~50% ethyl acetate in petroleum ether to afford methyl 2-(6-(((5-amino-1,3,4-thiadiazol-2-yl)oxy)methyl)pyridin-3-yl)acetate (140 mg, 17.9%) as a yellow solid. MS (ESI) calc'd for ($C_{11}H_{12}N_4O_3S$) $(M+1)^+$, 281.1, found 281.0.

Step-5: methyl 2-(6-(((5-amino-1,3,4-thiadiazol-2-yl)oxy)methyl)pyridin-3-yl)acetate

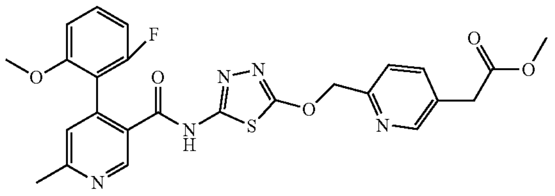

To a solution of methyl 2-(6-(((5-amino-1,3,4-thiadiazol-2-yl)oxy)methyl)pyridin-3-yl)acetate (140 mg, 0.51 mmol) in acetonitrile (5 mL) were added 4-(2-fluoro-6-methoxyphenyl)-6-methylnicotinic acid (131 mg, 0.51 mmol, Intermediate F), NMI (123 mg, 1.5 mmol) and TCFH (210 mg, 0.75 mmol). The resulting mixture was stirred at room temperature for 2 h. The mixture was quenched with water and extracted with ethyl acetate. The combined organic layers were washed with brine, dried over anhydrous sodium sulfate, filtered, and concentrated under vacuum. The residue was purified by flash chromatography on silica gel with 0~10% methanol in dichloromethane to afford methyl 2-(6-(((5-(4-(2-fluoro-6-methoxyphenyl)-6-methylnicotinamido)-1,3,4-thiadiazol-2-yl)oxy)methyl)pyridin-3-yl)acetate (70 mg, 26.8%) as a yellow solid. MS (ESI) calc'd for ($C_{25}H_{22}FN_5O_2S$) $(M+1)^+$, 524.1; found 524.1.

Step-6:4-(2-fluoro-6-methoxyphenyl)-N-(5-((5-(2-hydroxyethyl)pyridin-2-yl)methoxy)-1,3,4-thiadiazol-2-yl)-6-methylnicotinamide

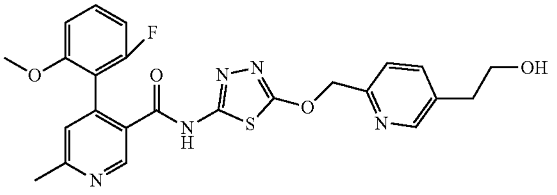 [SMILES: COc1cccc(F)c1-c1cc(C)ncc1C(=O)Nc1nnc(OCc2ccc(CCO)cn2)s1]

To a solution of methyl 4-(2-fluoro-6-methoxyphenyl)-N-(5-((5-(2-hydroxyethyl)pyridin-2-yl)methoxy)-1,3,4-thiadiazol-2-yl)-6-methylnicotinamide (70 mg, 0.14 mmol) in THF (5 mL) was added LAH (10.6 mg, 0.28 mmol) at 0° C. under nitrogen. The mixture was stirred at room temperature for 1 h. The reaction mixture was quenched by the addition of water and extracted with ethyl acetate. The combined organic layers were washed with brine, dried over anhydrous sodium sulfate, filtered, and concentrated under vacuum. The residue was purified by prep-HPLC with the following conditions: (Column: XBridge Prep OBD C18 Column, 30×150 mm 5 um; Mobile Phase A: Water (10 MMOL/L $NH_4HCO_3$), Mobile Phase B: ACN; Flow rate: 60 mL/min; Gradient: 20 B to 37 B in 8 min; 254/220 nm) to afford 4-(2-fluoro-6-methoxyphenyl)-N-(5-((5-(2-hydroxyethyl)pyridin-2-yl)methoxy)-1,3,4-thiadiazol-2-yl)-6-methylnicotinamide (8.1 mg, 2.1%) as a white solid. MS (ESI) calc'd for $(C_{24}H_{22}FN_5O_4S)(M+1)^+$, 496.1; found 496.1. $^1H$ NMR (400 MHz, DMSO-$d_6$) δ 9.02 (s, 1H), 8.42-8.42 (m, 1H), 7.68-7.66 (m, 1H), 7.40-7.35 (m, 2H), 7.04 (s, 1H), 6.85-6.78 (m, 2H), 5.36 (s, 2H), 4.71-4.69 (m, 1H), 3.62-3.59 (m, 2H), 3.35 (s, 3H), 2.75-2.67 (m, 2H), 2.52 (s, 3H).

Example 56 and 57

4-(2-(difluoromethoxy)-6-fluorophenyl)-N-(5-((5-((S)-1-hydroxyethyl)pyridin-2-yl)methoxy)-1,3,4-thiadiazol-2-yl)-6-methylnicotinamide (Example 56) and 4-(2-(difluoromethoxy)-6-fluorophenyl)-N-(5-((5-((R)-1-hydroxyethyl)pyridin-2-yl)methoxy)-1,3,4-thiadiazol-2-yl)-6-methylnicotinamide (Example 57)

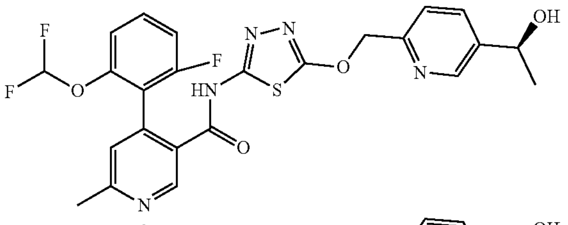

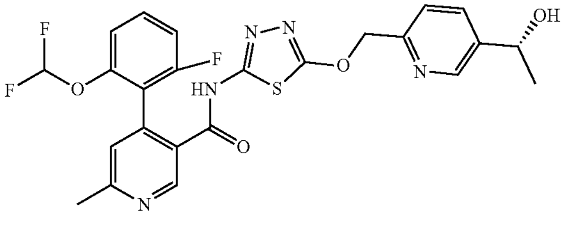

Step-1: 4-(2-(difluoromethoxy)-6-fluorophenyl)-N-(5-((5-(1-hydroxyethyl)pyridin-2-yl)methoxy)-1,3,4-thiadiazol-2-yl)-6-methylnicotinamide

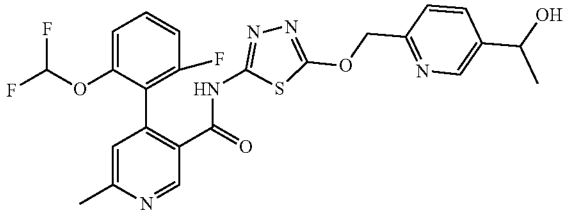 [SMILES: Cc1cc(-c2c(F)cccc2OC(F)F)c(C(=O)Nc2nnc(OCc3ccc(C(C)O)cn3)s2)cn1]

To a solution of N-(5-((5-acetylpyridin-2-yl)methoxy)-1,3,4-thiadiazol-2-yl)-4-(2-(difluoromethoxy)-6-fluorophenyl)-6-methylnicotinamide (500 mg, 0.94 mmol) in MeOH (2 mL) was added $NaBH_4$ (36 mg, 0.94 mmol) at 0° C. The mixture was stirred at room temperature for 2 h. The reaction mixture was then quenched by the addition of water and extracted with ethyl acetate. The combined organic layers were washed with brine, dried over anhydrous sodium sulfate, filtered, and concentrated under vacuum. The residue was purified by flash column chromatography with 0~10% methanol in dichloromethane to afford 4-(2-(difluoromethoxy)-6-fluorophenyl)-N-(5-((5-(1-hydroxyethyl)pyridin-2-yl)methoxy)-1,3,4-thiadiazol-2-yl)-6-methylnicotinamide (200 mg, 40%) as a white solid. MS (ESI) calc'd for $(C_{24}H_{20}F_3N_5O_4S)$ $(M+1)^+$, 531.1, found 531.1.

Step-2: 4-(2-(difluoromethoxy)-6-fluorophenyl)-N-(5-((5-((S)-1-hydroxyethyl)pyridin-2-yl)methoxy)-1,3,4-thiadiazol-2-yl)-6-methylnicotinamide and 4-(2-(difluoromethoxy)-6-fluorophenyl)-N-(5-((5-((R)-1-hydroxyethyl)pyridin-2-yl)methoxy)-1,3,4-thiadiazol-2-yl)-6-methylnicotinamide

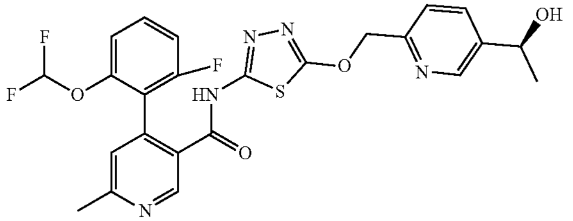

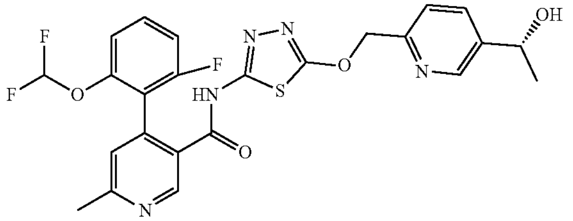

A racemic of 4-(2-(difluoromethoxy)-6-fluorophenyl)-N-(5-((5-(1-hydroxyethyl)pyridin-2-yl)methoxy)-1,3,4-thiadiazol-2-yl)-6-methylnicotinamide (200 mg) was separated by prep-chiral-HPLC with the following conditions: (Column: CHIRALPAK IG, 2*25 cm, 5 um; Mobile Phase A:Hex: DCM=3:1 (0.1% FA)-HPLC, Mobile Phase B: EtOH-HPLC; Flow rate: 20 mL/min; Gradient: 30 B to 30 B in 29.5 min; 220/254 nm; RT1:14.213; RT2:24.142; Injection Volume:2.567 ml; Number Of Runs:3) to afford 4-(2-(difluoromethoxy)-6-fluorophenyl)-N-(5-((5-((S)-1-hydroxyethyl)pyridin-2-yl)methoxy)-1,3,4-thiadiazol-2-yl)-6-methylnicotinamide (68.6 mg) as a white solid with shorter retention time on chiral HPLC and 4-(2-(difluoromethoxy)-6-fluorophenyl)-N-(5-((5-((R)-1-hydroxyethyl)pyridin-2-yl)methoxy)-1,3,4-thiadiazol-2-yl)-6-methylnicotinamide (51.5 mg) as a white solid with longer retention time on chiral HPLC.

4-(2-(difluoromethoxy)-6-fluorophenyl)-N-(5-((5-((S)-1-hydroxyethyl)pyridin-2-yl)methoxy)-1,3,4-thiadiazol-2-yl)-6-methylnicotinamide: MS (ESI) calc'd for ($C_{24}H_{20}F_3N_5O_4S$) $(M+1)^+$, 531.1, found 531.1. $^1H$ NMR (400 MHz, DMSO-$d_6$) δ 13.03 (s, 1H), 8.93 (s, 1H), 8.55 (s, 1H), 7.81-7.48 (m, 4H), 7.37-6.94 (m, 3H), 5.51 (s, 2H), 5.34 (s, 1H), 4.81-4.79 (m, 1H), 2.59-2.49 (m, 3H), 1.36 (d, J=6.4 Hz, 3H).

4-(2-(difluoromethoxy)-6-fluorophenyl)-N-(5-((5-((R)-1-hydroxyethyl)pyridin-2-yl)methoxy)-1,3,4-thiadiazol-2-yl)-6-methylnicotinamide: MS (ESI) calc'd for ($C_{24}H_{20}F_3N_5O_4S$) $(M+1)^+$, 531.1, found 531.1. $^1H$ NMR (400 MHz, DMSO-$d_6$) δ 13.05 (s, 1H), 8.94 (s, 1H), 8.55 (s, 1H), 7.91-7.48 (m, 4H), 7.37-6.94 (m, 3H), 5.51 (s, 2H), 5.34 (s, 1H), 4.81-4.79 (m, 1H), 2.59-2.49 (m, 3H), 1.36 (d, J=6.4 Hz, 3H).

Example 58

2'-chloro-N-(5-((5-(2-hydroxypropan-2-yl)pyridin-2-yl)methoxy)-1,3,4-thiadiazol-2-yl)-5'-methoxy-6-methyl-[4,4'-bipyridine]-3-carboxamide

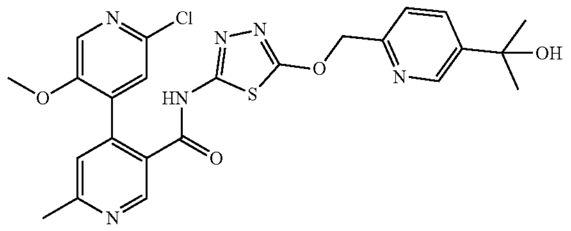 [SMILES: COc1cnc(Cl)cc1-c1cc(C)ncc1C(=O)Nc1nnc(OCc2ccc(C(C)(C)O)cn2)s1]

Step-1: N-(5-((5-acetylpyridin-2-yl)methoxy)-1,3,4-thiadiazol-2-yl)-2'-chloro-5'-methoxy-6-methyl-(4,4'-bipyridine)-3-carboxamide

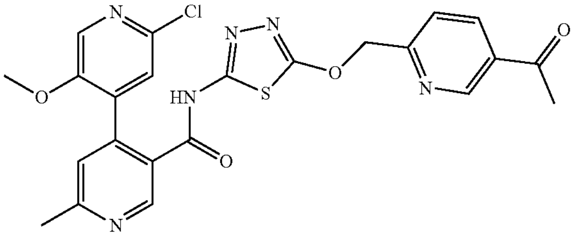 [SMILES: COc1cnc(Cl)cc1-c1cc(C)ncc1C(=O)Nc1nnc(OCc2ccc(C(C)=O)cn2)s1]

To a stirred solution of 1-(6-(((5-amino-1,3,4-thiadiazol-2-yl)oxy)methyl)pyridin-3-yl)ethanone (200 mg, 0.80 mmol) and 2'-chloro-5'-methoxy-6-methyl-(4,4'-bipyridine)-3-carboxylic acid (222 mg, 0.80 mmol, Intermediate H) in N,N-Dimethylformamide (2 mL) were added N,N,N',N'-Tetramethylchloroformamidinium-hexafluorophosphate (337 mg, 1.20 mmol) and N-methylmorpholine (323 mg, 3.19 mmol) at room temperature. The resulting mixture was stirred at room temperature for 2 h. The resulting solution was purified by reverse phase flash column chromatography with 5-50% acetonitrile in water to afford N-(5-((5-acetylpyridin-2-yl)methoxy)-1,3,4-thiadiazol-2-yl)-2'-chloro-5'-methoxy-6-methyl-(4,4'-bipyridine)-3-carboxamide (180 mg, 44.1%) as a white solid. MS (ESI) calculated for ($C_{23}H_{19}ClN_6O_4S$) $(M+1)^+$, 511.1; found, 511.1.

Step-2: 2-chloro-N-(5-((5-(2-hydroxypropan-2-yl)pyridin-2-yl)methoxy)-1,3,4-thiadiazol-2-yl)-5-methoxy-6-methyl-(4,4-bipyridine)-3-carboxamide

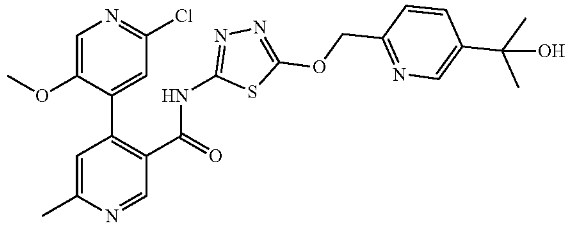 [SMILES: COc1cnc(Cl)cc1-c1cc(C)ncc1C(=O)Nc1nnc(OCc2ccc(C(C)(C)O)cn2)s1]

To a stirred solution of N-(5-((5-acetylpyridin-2-yl)methoxy)-1,3,4-thiadiazol-2-yl)-2-chloro-5-methoxy-6-methyl-(4,4-bipyridine)-3-carboxamide (90 mg, 0.17 mmol) in tetrahydrofuran (2 mL) was added $CH_3MgBr$ (0.3 mL, 2.60 mmol) dropwise at 0° C. The resulting mixture was stirred at room temperature for 1 h under nitrogen atmosphere. The reaction mixture was quenched with water and extracted with ethyl acetate. The combined organic layers were washed with brine, dried over anhydrous sodium sulfate, filtered, and concentrated under vacuum. The residue was purified by reverse phase flash column chromatography with 5~75% acetonitrile in water to afford 2'-chloro-N-(5-((5-(2-hydroxypropan-2-yl)pyridin-2-yl)methoxy)-1,3,4-thiadiazol-2-yl)-5'-methoxy-6-methyl-[4,4'-bipyridine]-3-carboxamide (26.7 mg, 27.6%) as a white solid. MS (ESI) calculated for ($C_{24}H_{23}ClN_6O_4S$) $(M+1)^+$, 527.1; found, 527.1. $^1H$ NMR (400 MHz, DMSO-$d_6$) δ 12.97 (s, 1H), 8.81 (s, 1H), 8.72-8.67 (m, 1H), 8.17 (s, 1H), 7.94-7.86 (m, 1H), 7.55 (s, 1H), 7.52-7.36 (m, 2H), 5.51 (s, 2H), 5.27 (s, 1H), 3.63 (s, 3H), 2.59 (s, 3H), 1.46 (s, 6H).

Example 59

4-(2-(difluoromethoxy)phenyl)-N-(5-((5-(2-hydroxypropan-2-yl)pyridin-2-yl)methoxy)-1,3,4-thiadiazol-2-yl)-6-methylnicotinamide

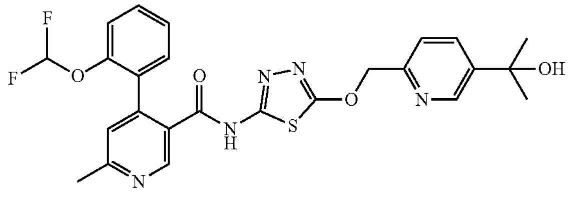 [SMILES: Cc1cc(-c2ccccc2OC(F)F)c(C(=O)Nc2nnc(OCc3ccc(C(C)(C)O)cn3)s2)cn1]

Step-1: N-(5-((5-acetylpyridin-2-yl)methoxy)-1,3,4-thiadiazol-2-yl)-4-(2-(difluoromethoxy)phenyl)-6-methylpyridine-3-carboxamide

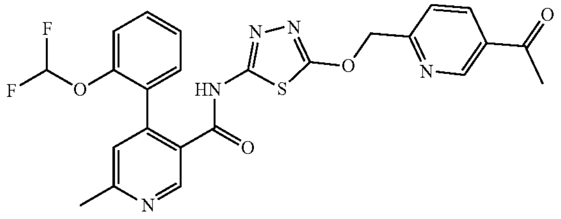 [SMILES: CC(=O)c1ccc(COc2nnc(NC(=O)c3cnc(C)cc3-c3ccccc3OC(F)F)s2)nc1]

To a stirred mixture of 4-(2-(difluoromethoxy)phenyl)-6-methylpyridine-3-carboxylic acid (200.00 mg, 0.716 mmol) and 1-(6-(((5-amino-1,3,4-thiadiazol-2-yl)oxy)methyl)pyridin-3-yl)ethanone (215.11 mg, 0.859 mmol) in MeCN (2.00 mL) and DMF (2.00 mL) were added NMI (176.41 mg, 2.149 mmol) and TCFH (221.05 mg, 0.788 mmol). The resulting mixture was stirred at room temperature for 2 h under nitrogen atmosphere. The reaction mixture was quenched with water and extracted with ethyl acetate. The combined organic layers were washed with brine, dried over anhydrous sodium sulfate, filtered, and concentrated under vacuum. The residue was purified by flash column chromatography with 0~50% ethyl acetate in petroleum ether to afford N-(5-((5-acetylpyridin-2-yl)methoxy)-1,3,4-thiadiazol-2-yl)-4-(2-(difluoromethoxy)phenyl)-6-methylpyridine-3-carboxamide (180 mg, 49.1%) as a white solid. MS (ESI) calculated for $(C_{24}H_{19}F_2N_5O_4S)$ $(M+1)^+$, 512.1; found, 512.0.

Step-2: 4-(2-(difluoromethoxy)phenyl)-N-(5-((5-(2-hydroxypropan-2-yl)pyridin-2-yl)methoxy)-1,3,4-thiadiazol-2-yl)-6-methylnicotinamide

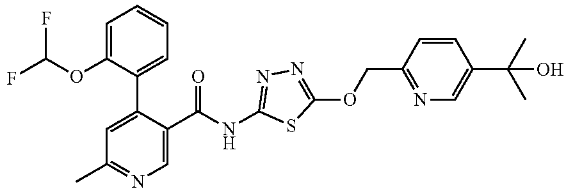 [SMILES: Cc1cc(-c2ccccc2OC(F)F)c(C(=O)Nc2nnc(OCc3ccc(C(C)(C)O)cn3)s2)cn1]

To a stirred solution of N-(5-((5-acetylpyridin-2-yl)methoxy)-1,3,4-thiadiazol-2-yl)-4-(2-(difluoromethoxy)phenyl)-6-methylpyridine-3-carboxamide (160.00 mg, 0.313 mmol) in THF (10.00 mL) were added MeMgBr (186.50 mg, 1.564 mmol) dropwise at 0° C. The resulting mixture was stirred at room temperature for 2 h under nitrogen atmosphere. The reaction mixture was diluted with water and extracted with ethyl acetate. The combined organic layers were washed with brine, dried over anhydrous sodium sulfate, filtered, and concentrated under vacuum. The residue was purified by flash column chromatography with 0~10% methanol in dichloromethane and further purified by Prep-HPLC with the following conditions: (Column: YMC-Actus Triart C18, 30 mm×150 mm, 5 um; Mobile Phase A: Water (10 MMOL/L $NH_4HCO_3$), Mobile Phase B: ACN; Flow rate: 60 mL/min; Gradient: 30 B to 50 B in 8 min, 220 nm; RT1:7.23 min) to afford 4-(2-(difluoromethoxy)phenyl)-N-(5-((5-methoxypyridin-2-yl)methoxy)-1,3,4-thiadiazol-2-yl)-6-methylnicotinamide (17.8 mg, 19.6%) as a white solid. MS (ESI) calculated for $(C_{25}H_{23}F_2N_5O_4S)$ $(M+1)^+$, 528.1; found, 528.1. $^1H$ NMR (400 MHz, DMSO-$d_6$) δ 12.92 (s, 1H), 8.81 (s, 1H), 8.69 (s, 1H), 7.90-7.88 (m, 1H), 7.50-7.40 (m, 3H), 7.22-6.86 (m, 4H), 5.49 (s, 2H), 5.27 (s, 1H), 2.52 (s, 3H), 1.46 (s, 6H).

Example 60

2'-chloro-N-(5-((5-(hydroxymethyl)pyridin-2-yl)methoxy)-1,3,4-thiadiazol-2-yl)-5'-methoxy-6-methyl-[4,4'-bipyridine]-3-carboxamide

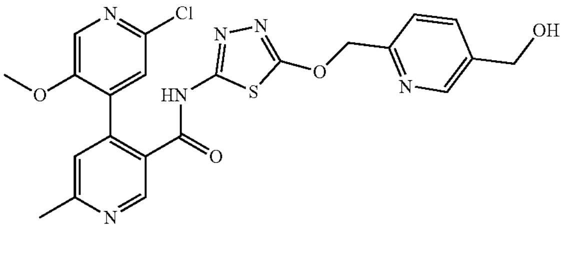 [SMILES: COc1cnc(Cl)cc1-c1cc(C)ncc1C(=O)Nc1nnc(OCc2ccc(CO)cn2)s1]

Step-1: 2-chloro-5-methoxypyridin-4-ylboronic acid

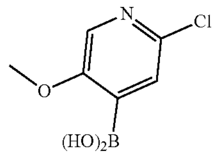

A stirred solution of 2-chloro-5-methoxypyridine (10.0 g, 69.65 mmol) in THF (500 mL) was added LDA (14.9 g, 139.30 mmol) dropwise at −78° C. under $N_2$ atmosphere. The resulting mixture was stirred at −78° C. for 2 h. Then Triisopropyl borate (26.2 g, 139.30 mmol) was added to the above mixture at −78° C. The resulting mixture was stirred at −78° C. for 2 h. Then the resulting mixture was stirred at room temperature for 16 h. The resulting mixture was quenched with HCl (2 N) and stirred at room temperature for 30 min. The resulting mixture was extracted with ethyl acetate. The reaction mixture was diluted with water and extracted with ethyl acetate. The combined organic layers were washed with brine, dried over anhydrous sodium sulfate, filtered, and concentrated under vacuum. 2-chloro-5-methoxypyridin-4-ylboronic acid (9 g, 68.9%) as a brown solid. MS (ESI) calc'd for $(C_6H_7BClNO_3)$ $(M+1)^+$, 188.0; found 188.0.

Step-2: methyl 2-chloro-5-methoxy-6-methyl-(4,4-bipyridine)-3-carboxylate

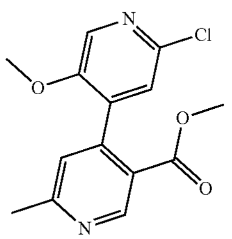

To a degassed solution of methyl 4-chloro-6-methylpyridine-3-carboxylate (700 mg, 3.77 mmol) and 2-chloro-5-methoxypyridin-4-ylboronic acid (918 mg, 4.90 mmol) in dioxane (6 mL) and $H_2O$ (2 mL) were added $Pd(dppf)Cl_2$ (275 mg, 0.37 mmol) and $K_2CO_3$ (1563 mg, 11.31 mmol) under nitrogen atmosphere. The resulting mixture was stirred at 80° C. for 16 h under nitrogen atmosphere. The resulting mixture was filtered and the filtrate was concentrated under reduced pressure. The residue was purified by flash column chromatography with 0-60% ethyl acetate in petroleum ether to afford methyl 2-chloro-5-methoxy-6-methyl-(4,4-bipyridine)-3-carboxylate (220 mg, 19.9%) as a white solid. MS (ESI) calc'd for ($C_{14}H_{13}ClN_2O_3$) $(M+1)^+$, 293.1; found 293.1.

Step-3 2'-chloro-5'-methoxy-6-methyl-(4,4'-bipyridine)-3-carboxylic acid

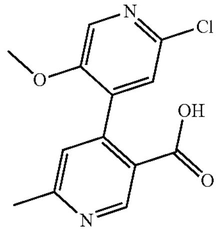 [SMILES: COc1cnc(Cl)cc1-c1cc(C)ncc1C(=O)O]

To a stirred solution of methyl 2'-chloro-5'-methoxy-6-methyl-[4,4'-bipyridine]-3-carboxylate (220 mg, 0.75 mmol) in THF (2 mL) and water (2 mL) were added $LiOH \cdot H_2O$ (126 mg, 3.01 mmol). The resulting mixture was stirred at room temperature for 2 h. The mixture was acidified to pH 3 with citric acid. The resulting mixture was extracted with ethyl acetate. The combined organic layers were washed with brine, dried over anhydrous sodium sulfate, filtered, and concentrated under vacuum to afford 2'-chloro-5'-methoxy-6-methyl-(4,4'-bipyridine)-3-carboxylic acid (160 mg, 76.3%) as a white solid. MS (ESI) calc'd for ($C_{13}H_{11}ClN_2O_3$) $(M+1)^+$, 279.0; found, 279.0.

Step-4: methyl 6-(((5-(2-chloro-5-methoxy-6-methyl-(4,4-bipyridine)-3-amido)-1,3,4-thiadiazol-2-yl)oxy)methyl)pyridine-3-carboxylate

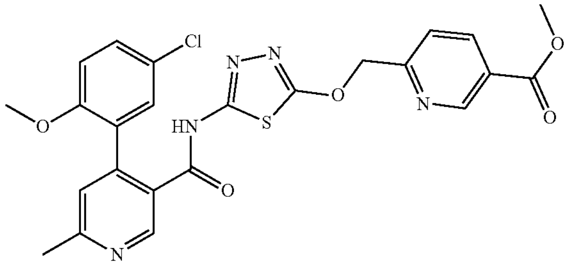 [SMILES: COC(=O)c1ccc(COc2nnc(NC(=O)c3cnc(C)cc3-c3cc(Cl)ccc3OC)s2)nc1]

To a stirred solution of 2'-chloro-5'-methoxy-6-methyl-(4,4'-bipyridine)-3-carboxylic acid (100 mg, 0.35 mmol, Intermediate H) and methyl 6-(((5-amino-1,3,4-thiadiazol-2-yl)oxy)methyl)pyridine-3-carboxylate (95 mg, 0.35 mmol, Example 5, Step 1) in DMF (2 mL) and MeCN (2 mL) were added TCFH (151 mg, 0.53 mmol) and NMI (117 mg, 1.43 mmol). The resulting mixture was stirred at room temperature for 2 h under nitrogen atmosphere. The resulting mixture was purified by reverse phase flash column chromatography with X~X % acetonitrile in water to afford methyl 6-(((5-(2-chloro-5-methoxy-6-methyl-(4,4-bipyridine)-3-amido)-1,3,4-thiadiazol-2-yl)oxy)methyl)pyridine-3-carboxylate (100 mg, 52.8%) as a yellow solid. MS (ESI) calc'd for ($C_{23}H_{19}ClN_6O_5$) $(M+1)^+$, 527.1; found, 527.1.

Step-5:2'-chloro-N-(5-((5-(hydroxymethyl)pyridin-2-yl)methoxy)-1,3,4-thiadiazol-2-yl)-5'-methoxy-6-methyl-[4,4'-bipyridine]-3-carboxamide

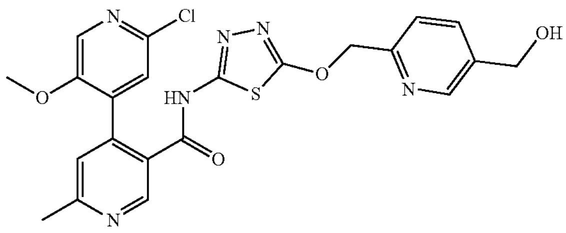 [SMILES: COc1cnc(Cl)cc1-c1cc(C)ncc1C(=O)Nc1nnc(OCc2ccc(CO)cn2)s1]

To a solution of methyl 6-(((5-(2-chloro-5-methoxy-6-methyl-(4,4-bipyridine)-3-amido)-1,3,4-thiadiazol-2-yl) oxy)methyl)pyridine-3-carboxylate (80 mg, 0.15 mmol) in THF (1 mL) was added $LiAlH_4$ (11 mg, 0.30 mmol) at 0° C. under nitrogen atmosphere. The resulting mixture was stirred at room temperature for 2 h under nitrogen atmosphere. The reaction mixture was quenched with water and extracted with ethyl acetate. The combined organic layers were washed with brine, dried over anhydrous sodium sulfate, filtered, and concentrated under vacuum. The residue was purified by prep-HPLC with the following conditions: (Column: XBridge Prep OBD C18 Column, 30×150 mm 5 um; Mobile Phase A: Water (10 MMOL/L $NH_4HCO_3$), Mobile Phase B: ACN; Flow rate: 60 mL/min; Gradient: 15 B to 32 B in 8 min; 254/220 nm; RT1:6.6 min) to afford 2'-chloro-N-(5-((5-(hydroxymethyl)pyridin-2-yl) methoxy)-1,3,4-thiadiazol-2-yl)-5'-methoxy-6-methyl-[4,4'-bipyridine]-3-carboxamide (8.8 mg, 11.5%) as a white solid. MS (ESI) calc'd for ($C_{22}H_{19}ClN_6O_4S$) $(M+1)^+$, 499.1; found 499.0. $^1H$ NMR (400 MHz, DMSO-$d_6$) δ 12.96 (s, 1H), 8.82 (s, 1H), 8.53 (d, J=2.4 Hz, 1H), 8.17 (s, 1H), 7.84-7.74 (m, 1H), 7.52 (d, J=8.4 Hz, 2H), 7.42 (s, 1H), 5.52 (s, 2H), 5.36 (t, J=5.6 Hz, 1H), 4.55 (d, J=5.6 Hz, 2H), 3.63 (s, 3H), 2.59 (s, 3H).

Example 61

4-(2-fluoro-6-methoxyphenyl)-N-(5-((3-hydroxybicyclo(1.1.1)pentan-1-yl)methoxy)-1,3,4-thiadiazol-2-yl)-6-methylnicotinamide

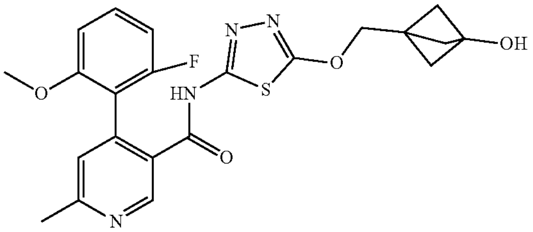

Step-1: methyl 3-((tert-butyldimethylsilyl)oxy)bicyclo(1.1.1)pentane-1-carboxylate

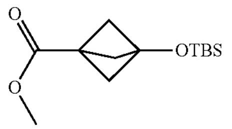 [SMILES: COC(=O)C12CC(O[Si](C)(C)C(C)(C)C)(C1)C2]

To a solution of methyl 3-hydroxybicyclo(1.1.1)pentane-1-carboxylate (500 mg, 3.517 mmol) in DCM (10 mL) was added Imidazole (718 mg, 10.552 mmol), TBSCl (795 mg, 5.276 mmol) and DMAP (43 mg, 0.352 mmol). The resulting solution was stirred at room temperature for 12 hours. The reaction was monitored by TLC. The residue was purified by flash chromatography on silica gel with 0~50% ethyl acetate in petroleum ether to afford methyl 3-((tert-butyldimethylsilyl)oxy)bicyclo(1.1.1)pentane-1-carboxylate (800 mg, 88.70%) as a colorless solid.

Step-2: (3-((tert-butyldimethylsilyl)oxy)bicyclo(1.1.1)pentan-1-yl)methanol

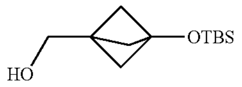 [SMILES: CC(C)(C)[Si](C)(C)OC12CC(CO)(C1)C2]

To a solution of methyl 3-((tert-butyldimethylsilyl)oxy)bicyclo(1.1.1)pentane-1-carboxylate (450 mg, 1.755 mmol) in THF (5 mL) was added LAH (133 mg, 3.510 mmol) in portions at 0° C. The resulting solution was stirred at room temperature for 2 hours. The reaction was monitored by TLC. The reaction was then quenched by the addition of water. The resulting solution was extracted with of ethyl acetate. The combined organic layers were washed with brine, dried over anhydrous sodium sulfate, filtered, and concentrated under vacuum to afford (3-((tert-butyldimethylsilyl)oxy)bicyclo(1.1.1)pentan-1-yl)methanol (300 mg, crude) as yellow oil.

Step-3: O-((3-((tert-butyldimethylsilyl)oxy)bicyclo(1.1.1)pentan-1-yl)methyl)S-methyl carbonodithioate

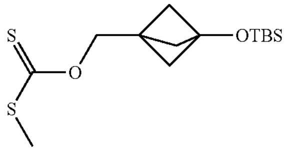 [SMILES: CSC(=S)OCC12CC(O[Si](C)(C)C(C)(C)C)(C1)C2]

To a solution of NaH (79 mg, 1.973 mmol, 60%) in THF (10 mL) was added a solution of methyl 6-(hydroxymethyl) nicotinate (300 mg, 1.315 mmol) in THF (2 mL) dropwise at 0~5° C. and stirred at 5° C. for 1 h, Then $CS_2$ (150 mg, 1.973 mmol) was added to the mixture at 0° C. and stirred for 30 min, then MeI (282 mg, 1.973 mmol) was added to the above mixture. The resulting mixture was stirred at room temperature for 1 h. The reaction mixture was quenched by the addition of water and extracted with ethyl acetate. The combined organic layers were washed with brine, dried over anhydrous sodium sulfate, filtered, and concentrated under vacuum. The residue was purified by flash chromatography on silica gel with 0-50% ethyl acetate in petroleum ether to afford O-((3-((tert-butyldimethylsilyl)oxy)bicyclo(1.1.1)pentan-1-yl)methyl) S-methyl carbonodithioate (200 mg, 71%) as a yellow solid.

Step-4: O-((3-((tert-butyldimethylsilyl)oxy)bicyclo(1.1.1)pentan-1-yl)methyl) hydrazinecarbothioate

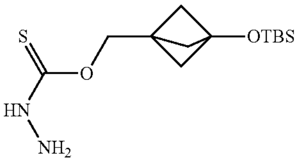

To a solution of ((3-((tert-butyldimethylsilyl)oxy)bicyclo(1.1.1)pentan-1-yl)methoxy)(methylsulfanyl)methanethione (200 mg, 0.628 mmol) in EtOH (5 mL) was added Hydrazine (20.12 mg, 0.628 mmol). The resulting solution was stirred at room temperature for 2 hours. The reaction mixture was quenched with water and extracted with ethyl acetate. The combined organic layers were washed with brine, dried over anhydrous sodium sulfate, filtered, and concentrated under vacuum to afford O-((3-((tert-butyldimethylsilyl)oxy)bicyclo(1.1.1)pentan-1-yl)methyl) hydrazinecarbothioate (200 mg, crude) as a yellow solid. MS (ESI) calc'd for ($C_{13}H_{26}N_2O_2SSi$) $(M+1)^+$, 303.1; found, 303.1.

Step-5: 5-((3-((tert-butyldimethylsilyl)oxy)bicyclo(1.1.1)pentan-1-yl)methoxy)-1,3,4-thiadiazol-2-amine

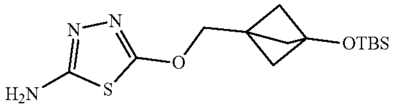

To a solution of ((((3-((tert-butyldimethylsilyl)oxy)bicyclo(1.1.1)pentan-1-yl)methoxy)methanethioyl)amino)amine (200 mg, 0.661 mmol) in MeOH (5 mL) were added TEA (135 mg, 1.322 mmol) and BrCN (77 mg, 0.727 mmol). The resulting solution was stirred at room temperature for 40 min. The reaction mixture was quenched with water and extracted with ethyl acetate. The combined organic layers were washed with brine, dried over anhydrous sodium sulfate, filtered, and concentrated under vacuum to afford 5-((3-((tert-butyldimethylsilyl)oxy)bicyclo(1.1.1)pentan-1-yl)methoxy)-1,3,4-thiadiazol-2-amine (210 mg, crude) as a yellow solid. MS (ESI) calc'd for ($C_{14}H_{25}N_3O_2SSi$) $(M+1)^+$, 328.0; found, 328.0.

Step-6: 5-((3-((tert-butyldimethylsilyl)oxy)bicyclo (1.1.1)pentan-1-yl)methoxy)-1,3,4-thiadiazol-2-amine

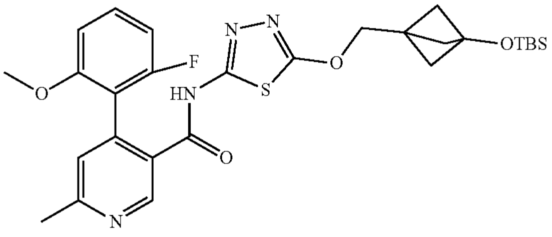 [SMILES: COc1cccc(F)c1-c1cc(C)ncc1C(=O)Nc1nnc(OCC23CC(O[Si](C)(C)C(C)(C)C)(C2)C3)s1]

To a solution of 5-((3-((tert-butyldimethylsilyl)oxy)bicyclo(1.1.1)pentan-1-yl)methoxy)-1,3,4-thiadiazol-2-amine (95 mg, 0.290 mmol) in DMF (2 mL) and MeCN (2 mL) were added 4-(2-fluoro-6-methoxyphenyl)-6-methylpyridine-3-carboxylic acid (75 mg, 0.290 mmol, Intermediate F), NMI (72 mg, 0.870 mmol) and TCFH (98 mg, 0.348 mmol). The resulting solution was stirred at room temperature for 2 hours. The reaction mixture was quenched with water and extracted with ethyl acetate. The combined organic layers were washed with brine, dried over anhydrous sodium sulfate, filtered, and concentrated under vacuum. The residue was purified by flash chromatography on silica gel with 0~10% methanol in dichloromethane to afford N-(5-((3-((tert-butyldimethylsilyl)oxy)bicyclo(1.1.1)pentan-1-yl)methoxy)-1,3,4-thiadiazol-2-yl)-4-(2-fluoro-6-methoxyphenyl)-6-methylpyridine-3-carboxamide (50 mg, 30.2%) as a yellow solid. MS (ESI) calc'd for ($C_{28}H_{35}FN_4O_4SSi$) $(M+1)^+$, 571.2; found, 571.2.

Step-7: 5-((3-((tert-butyldimethylsilyl)oxy)bicyclo (1.1.1)pentan-1-yl)methoxy)-1,3,4-thiadiazol-2-amine

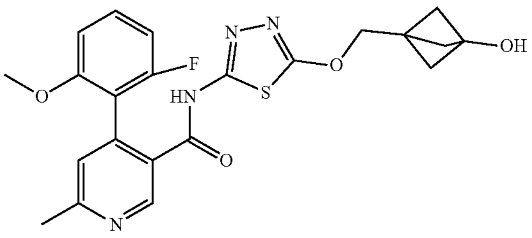

To a solution of N-(5-((3-((tert-butyldimethylsilyl)oxy) bicyclo(1.1.1)pentan-1-yl)methoxy)-1,3,4-thiadiazol-2-yl)-4-(2-fluoro-6-methoxyphenyl)-6-methylpyridine-3-carboxamide (50 mg, 0.087 mmol) in THF (10 mL) was added TBAF (27 mg, 0.104 mmol). The resulting solution was stirred at room temperature for 2 hours. The resulting mixture was concentrated. The residue was purified by flash chromatography on silica gel with 0~10% methanol in dichloromethane and further purified by prep-HPLC with the following conditions: (Column: XBridge Prep OBD C18 Column, 30×150 mm 5 um; Mobile Phase A: Water (10 MMOL/L $NH_4HCO_3$), Mobile Phase B: ACN; Flow rate: 60 mL/min; Gradient: 25 B to 40 B in 8 min; 254/220 nm; RT1: 7.38 min) to afford 4-(2-fluoro-6-methoxyphenyl)-N-(5-((3-hydroxybicyclo(1.1.1)pentan-1-yl)methoxy)-1,3,4-thiadiazol-2-yl)-6-methylpyridine-3-carboxamide (20 mg, 12.5%) as a white solid. MS (ESI) calc'd for ($C_{22}H_{21}FN_4O_4S$) $(M+1)^+$, 457.1; found, 457.1. $^1H$ NMR (400 MHz, DMSO-$d_6$) δ 12.84 (s, 1H), 8.80 (s, 1H), 7.41-7.39 (m, 2H), 6.92-6.87 (m, 2H), 6.27 (s, 1H), 4.54 (s, 2H), 3.57 (s, 3H), 2.51 (s, 3H), 1.78 (s, 6H).

Example 62

N-(5-((3-(hydroxymethyl)pyridin-2-yl)methoxy)-1,3,4-thiadiazol-2-yl)-4-(2-methoxyphenyl)-6-methylpyridine-3-carboxamide

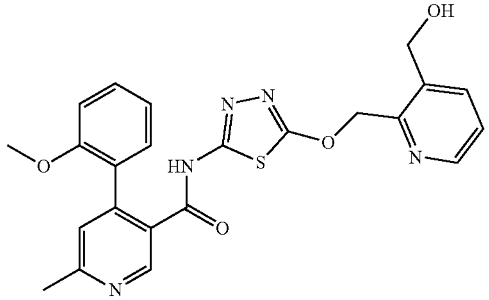 [SMILES: COc1ccccc1-c1cc(C)ncc1C(=O)Nc1nnc(OCc2ncccc2CO)s1]

Step-1: (3-ethenylpyridin-2-yl)methanol

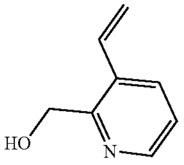

To a stirred solution of (3-bromopyridin-2-yl)methanol (2.0 g, 10.64 mmol) and ethenyl trifluoro-lambda4-borane potassium (2.2 g, 16.05 mmol) in dioxane (12 mL) and water (4 mL) were added Pd(dppf)$Cl_2$ (781 mg, 1.07 mmol) and $K_2CO_3$ (4.4 g, 32.05 mmol). The resulting mixture was stirred at 80° C. for overnight under nitrogen atmosphere. The reaction mixture was quenched with water and extracted with ethyl acetate. The combined organic layers were washed with brine, dried over anhydrous sodium sulfate, filtered, and concentrated under vacuum. The residue was purified by flash column chromatography with 0-50% ethyl acetate in petroleum ether to afford (3-ethenylpyridin-2-yl) methanol (800 mg, 55.6%) as a brown oil. MS (ESI) calculated for ($C_8H_9NO$) $(M+1)^+$, 136.1; found, 136.0.

Step-2: 5-((3-ethenylpyridin-2-yl)methoxy)-1,3,4-thiadiazol-2-amine

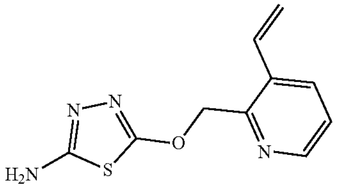 [SMILES: C=Cc1cccnc1COc1nnc(N)s1]

To a stirred solution of (3-ethenylpyridin-2-yl)methanol (770 mg, 5.69 mmol) in THF (20 mL) was added NaH (297 mg, 7.42 mmol, 60%) in portions at 0° C. and was stirred at 0° C. for 40 min under nitrogen atmosphere. 5-bromo-1,3,4-thiadiazol-2-amine (1.2 g, 6.83 mmol) was added to the above mixture at 0° C. The resulting mixture was stirred at room temperature for 2 h under nitrogen atmosphere. The reaction was quenched by the addition of water at room temperature. The resulting mixture was extracted with ethyl acetate. The combined organic layers were washed with brine, dried over anhydrous $Na_2SO_4$. After filtration, the filtrate was concentrated under reduced pressure. The residue was purified by reverse phase flash column chromatography with 5~50% acetonitrile in water to afford 5-((3-ethenylpyridin-2-yl)methoxy)-1,3,4-thiadiazol-2-amine (140 mg, 10.5%) as a yellow solid. MS (ESI) calculated for $(C_{10}H_{10}N_4OS)$ $(M+1)^+$, 235.1; found, 235.1.

Step-3: N-(5-((3-ethenylpyridin-2-yl)methoxy)-1,3,4-thiadiazol-2-yl)-4-(2-methoxyphenyl)-6-methylpyridine-3-carboxamide

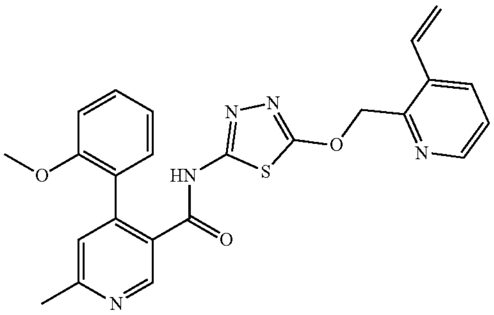 [SMILES: C=Cc1cccnc1COc1nnc(NC(=O)c2cnc(C)cc2-c2ccccc2OC)s1]

To a stirred solution of 5-((3-ethenylpyridin-2-yl)methoxy)-1,3,4-thiadiazol-2-amine (130 mg, 0.55 mmol) and 4-(2-methoxyphenyl)-6-methylpyridine-3-carboxylic acid (135 mg, 0.55 mmol, Intermediate D) in acetonitrile (2 mL) were added TCFH (172 mg, 0.61 mmol) and NMI (137 mg, 1.67 mmol). The resulting mixture was stirred at room temperature for 1 h. The residue was purified by reverse phase flash column chromatography with 5-50% acetonitrile in water to afford N-(5-((3-ethenylpyridin-2-yl)methoxy)-1,3,4-thiadiazol-2-yl)-4-(2-methoxyphenyl)-6-methylpyridine-3-carboxamide (135 mg, 52.4%) as a yellow solid. MS (ESI) calculated for $(C_{24}H_{21}N_5O_3S)$ $(M+1)^+$, 460.1; found, 460.1.

Step-4: N-(5-((3-formylpyridin-2-yl)methoxy)-1,3,4-thiadiazol-2-yl)-4-(2-methoxyphenyl)-6-methylpyridine-3-carboxamide

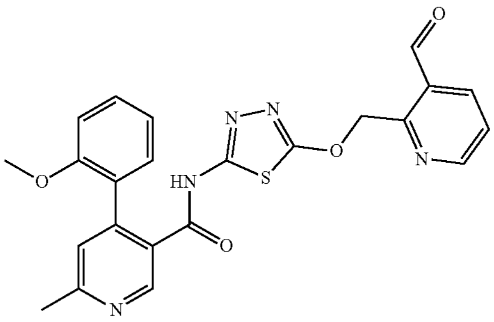 [SMILES: COc1ccccc1-c1cc(C)ncc1C(=O)Nc1nnc(OCc2ncccc2C=O)s1]

To a stirred solution of N-(5-((3-ethenylpyridin-2-yl)methoxy)-1,3,4-thiadiazol-2-yl)-4-(2-methoxyphenyl)-6-methylpyridine-3-carboxamide (118 mg, 0.25 mmol) and water (1.5 mL) in THF (1.5 mL) were added $OsO_4$ (7 mg, 0.03 mmol) and $NaIO_4$ (220 mg, 1.03 mmol) in portions at room temperature under nitrogen atmosphere. The resulting mixture was stirred at room temperature for 1 h. The resulting mixture was extracted with ethyl acetate. The combined organic layers were washed with brine, dried over anhydrous $Na_2SO_4$. After filtration, the filtrate was concentrated under reduced pressure to afford N-(5-((3-formylpyridin-2-yl)methoxy)-1,3,4-thiadiazol-2-yl)-4-(2-methoxyphenyl)-6-methylpyridine-3-carboxamide (65 mg, 43.8%) as a yellow solid. MS (ESI) calculated for $(C_{23}H_{19}N_5O_4S)$ $(M+1)^+$, 462.1; found, 462.1.

Step-5: N-(5-((3-(hydroxymethyl)pyridin-2-yl)methoxy)-1,3,4-thiadiazol-2-yl)-4-(2-methoxyphenyl)-6-methylpyridine-3-carboxamide

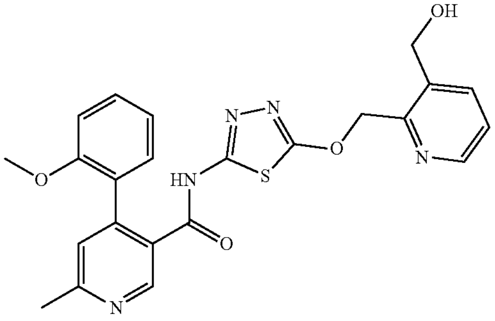 [SMILES: COc1ccccc1-c1cc(C)ncc1C(=O)Nc1nnc(OCc2ncccc2CO)s1]

A stirred solution of N-(5-((3-formylpyridin-2-yl)methoxy)-1,3,4-thiadiazol-2-yl)-4-(2-methoxyphenyl)-6-methylpyridine-3-carboxamide (60 mg, 0.13 mmol) in $CH_3OH$ (1 mL) was added $NaBH_4$ (5 mg, 0.13 mmol) in portions at 0° C. under $N_2$ atmosphere. The resulting mixture was stirred at room temperature for 1 h before quenched with water. The residue was purified by reverse phase flash column chromatography with 5-50% acetonitrile in water to afford N-(5-((3-(hydroxymethyl)pyridin-2-yl)methoxy)-1,3,4-thiadiazol-2-yl)-4-(2-methoxyphenyl)-6-methylpyridine-3-carboxamide (10.7 mg, 17.2%) as a white solid. MS (ESI) calculated for $(C_{23}H_{21}N_5O_4S)$ $(M+1)^+$, 464.1; found, 464.1. $^1H$ NMR (400 MHz, DMSO-$d_6$) δ 8.81 (s, 1H), 8.48-8.42 (m, 1H), 7.90-7.83 (m, 1H), 7.43-7.36 (m, 1H), 7.27 (d, J=8.4 Hz, 1H), 7.17-7.10 (m, 1H), 7.02 (s, 1H), 6.99-6.89 (m, 2H), 5.40 (s, 3H), 4.65 (s, 2H), 3.64 (s, 3H), 2.48 (s, 3H).

Example 63

4-(5-fluoro-2-methoxyphenyl)-N-(5-((5-(2-hydroxypropan-2-yl)pyridin-2-yl)methoxy)-1,3,4-thiadiazol-2-yl)-6-methylnicotinamide

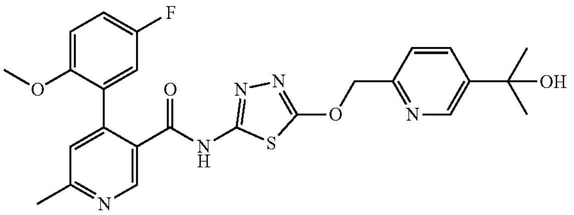 [SMILES: COc1ccc(F)cc1-c1cc(C)ncc1C(=O)Nc1nnc(OCc2ccc(C(C)(C)O)cn2)s1]

Step-1: 4-(5-fluoro-2-methoxyphenyl)-6-methylnicotinic acid

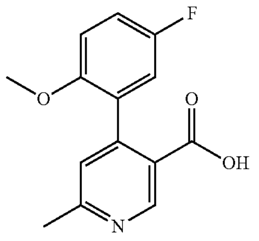 [SMILES: COc1ccc(F)cc1-c1cc(C)ncc1C(=O)O]

To a degassed solution of 4-chloro-6-methylnicotinic acid (200 mg, 1.169 mmol) in dioxane (10 mL) and $H_2O$ (2 mL) were added (5-fluoro-2-methoxyphenyl)boronic acid (300 mg, 1.754 mmol), $K_2CO_3$ (485 mg, 3.514 mmol) and $Pd(dppf)Cl_2$ (96 mg, 0.118 mmol) under nitrogen atmosphere. The resulting solution was stirred at 80° C. for 8 hour. The mixture was concentrated under vacuum. The residue was purified by flash chromatography on silica gel with 0-50% ethyl acetate in petroleum ether to afford ethyl methyl 4-(2-fluoro-6-methoxyphenyl)-6-methylnicotinate (130 mg, 65%) as a white solid. MS (ESI) calc'd for ($C_{14}H_{12}FNO_3$) $(M+1)^+$, 262.1; found, 262.1.

Step-2:4-(5-fluoro-2-methoxyphenyl)-N-(5-((5-(2-hydroxypropan-2-yl)pyridin-2-yl)methoxy)-1,3,4-thiadiazol-2-yl)-6-methylnicotinamide

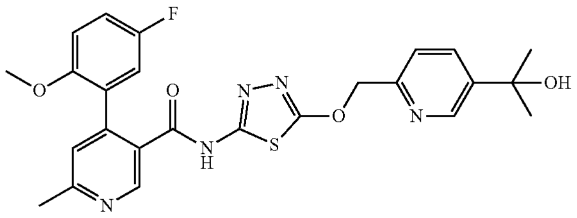 [SMILES: COc1ccc(F)cc1-c1cc(C)ncc1C(=O)Nc1nnc(OCc2ccc(C(C)(C)O)cn2)s1]

To a solution of 4-(5-fluoro-2-methoxyphenyl)-6-methylnicotinic acid (130 mg, 0.496 mmol) in ACN (10 mL) were added NMI (121 mg, 1.476 mmol), 2-(6-(((5-amino-1,3,4-thiadiazol-2-yl)oxy)methyl)pyridin-3-yl)propan-2-ol (198 mg, 0.744 mmol, Example 33, Step 1) and TCFH (162 mg, 0.577 mmol). The mixture was stirred at room temperature for 2 h. The mixture was concentrated under vacuum. The residue was purified by flash chromatography on silica gel with 0~10% dichloromethane in methanol and further purified by prep-HPLC with the following conditions: (Column: Sunfire prep C18 column, 30*150, 5 um; Mobile Phase A: Water (0.1% FA), Mobile Phase B: ACN; Flow rate: 40 mL/min; Gradient: 25 B to 55 B in 8 min; 220 nm; RT1: 7.23 min) to afford 4-(5-fluoro-2-methoxyphenyl)-N-(5-((5-(2-hydroxypropan-2-yl)pyridin-2-yl)methoxy)-1,3,4-thiadiazol-2-yl)-6-methylnicotinamide (21 mg, 16.2%) as a white solid. MS (ESI) calc'd for ($C_{25}H_{24}FN_5O_4S$) $(M+1)^+$, 510.1; found, 510.1. $^1H$ NMR (400 MHz, DMSO-$d_6$) δ 12.77 (s, 1H), 8.69 (d, J=2.4 Hz, 2H), 7.95-7.85 (m, 1H), 7.48 (d, J=8.4 Hz, 1H), 7.34 (s, 1H), 7.23 (t, J=8.8 Hz, 2H), 7.03-6.93 (m, 1H), 5.50 (s, 2H), 5.25 (s, 1H), 3.49 (s, 3H), 2.57 (s, 3H), 1.46 (s, 6H).

Example 64

N-(5-((5-chloropyridin-2-yl)methoxy)-1,3,4-thiadiazol-2-yl)-5-(2-fluoro-6-methoxyphenyl)pyridazine-4-carboxamide

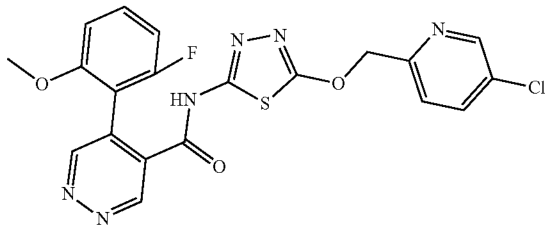 [SMILES: COc1cccc(F)c1-c1cnncc1C(=O)Nc1nnc(OCc2ccc(Cl)cn2)s1]

Step-1: 5-(2-fluoro-6-methoxyphenyl)pyridazin-4-amine

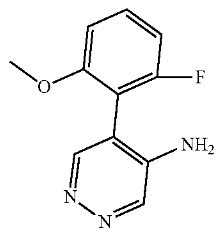 [SMILES: COc1cccc(F)c1-c1cnncc1N]

To a degassed solution of 5-bromopyridazin-4-amine (1.5 g, 8.621 mmol) in dioxane (20 mL) and $H_2O$ (4 mL), was added 2-fluoro-6-methoxyphenylboronic acid (2.2 g, 12.945 mmol), $K_2CO_3$ (3.58 g, 25.831 mmol), $Pd(dppf)Cl_2$ (0.63 g, 0.861 mmol). The resulting solution was stirred at 80° C. for 3 h under nitrogen before concentrated under vacuum. The residue was purified by flash chromatography on silica gel with 0~10% methanol in dichloromethane to afford 5-(2-fluoro-6-methoxyphenyl)pyridazin-4-amine (1.2 g, 50.8%) as a yellow solid. MS (ESI) calc'd for ($C_{11}H_{10}FN_3O$) $(M+1)^+$, 220.1; found, 220.0.

Step-2: 4-bromo-5-(2-fluoro-6-methoxyphenyl)pyridazine

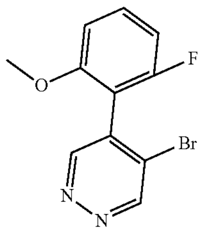 [SMILES: COc1cccc(F)c1-c1cnncc1Br]

To a solution of 5-(2-fluoro-6-methoxyphenyl)pyridazin-4-amine (900 mg, 4.105 mmol) in MeCN (10 mL) were added tBuONO (975 mg, 9.443 mmol) and $CuBr_2$ (1375 mg, 6.158 mmol) at room temperature under nitrogen. The resulting solution was stirred at 40° C. for 12 h under nitrogen. The resulting mixture was concentrated. The residue was purified by flash chromatography on silica gel with 0~10% methanol in dichloromethane to afford 4-bromo-5-(2-fluoro-6-methoxyphenyl)pyridazine (570 mg, 49.0%) as a yellow solid. MS (ESI) calc'd for ($C_{11}H_8BrFN_2O$) $(M+1)^+$, 283.0; found, 283.0.

Step-3: 5-(2-fluoro-6-methoxyphenyl)pyridazine-4-carbonitrile

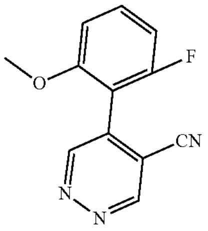 [SMILES: COc1cccc(F)c1-c1cnncc1C#N]

To a degassed solution of 4-bromo-5-(2-fluoro-6-methoxyphenyl)pyridazine (570 mg, 2.013 mmol) in DMF (5 mL) were added zinc cyanide (472 mg, 4.027 mmol) and $Pd(PPh_3)_4$ (232 mg, 0.201 mmol). The resulting solution was stirred at 130° C. for 16 h under nitrogen. The reaction mixture was diluted with water and extracted with ethyl acetate. The combined organic layers were washed with brine, dried over anhydrous sodium sulfate, filtered, and concentrated under vacuum. The residue was purified by flash chromatography on silica gel with 0~10% methanol in dichloromethane to afford 5-(2-fluoro-6-methoxyphenyl)pyridazine-4-carbonitrile (300 mg, 65.0%) as a yellow solid. MS (ESI) calc'd for ($Cl_2H_8FN_3O$) $(M+1)^+$, 230.1; found, 230.1.

Step-4: 5-(2-fluoro-6-methoxyphenyl)pyridazine-4-carboxylic acid

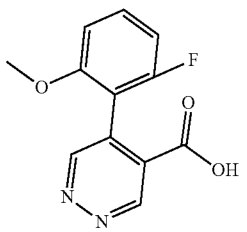 [SMILES: COc1cccc(F)c1-c1cnncc1C(=O)O]

A solution of 5-(2-fluoro-6-methoxyphenyl)pyridazine-4-carbonitrile (150 mg, 0.654 mmol) in HCl (8 mL, 6 N) was stirred at 90° C. for 16 h. The solvent was removed under vacuum to afford 5-(2-fluoro-6-methoxyphenyl)pyridazine-4-carboxylic acid (150 mg, crude) as a yellow solid, which was used for the next step without further purification. MS (ESI) calc'd for ($C_{12}H_9FN_2O_3$) $(M+1)^+$, 249.0; found, 249.0.

Step-5: N-(5-((5-chloropyridin-2-yl)methoxy)-1,3,4-thiadiazol-2-yl)-5-(2-fluoro-6-methoxyphenyl) pyridazine-4-carboxamide

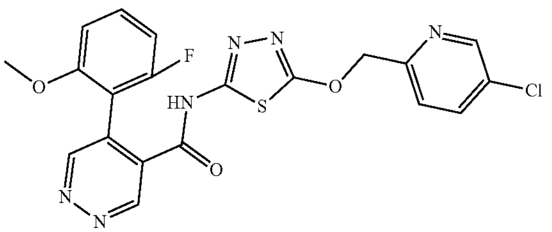 [SMILES: COc1cccc(F)c1-c1cnncc1C(=O)Nc1nnc(OCc2ccc(Cl)cn2)s1]

To a solution of 5-(2-fluoro-6-methoxyphenyl) pyridazine-4-carboxylic acid (60 mg, 0.242 mmol) in DMF (5 mL) were added HATU (110 mg, 0.290 mmol), DIEA (156 mg, 1.209 mmol) and 5-((5-chloropyridin-2-yl) methoxy)-1,3,4-thiadiazol-2-amine (59 mg, 0.242 mmol, Intermediate C). The resulting solution was stirred at room temperature for 2 h. The reaction mixture was quenched with water and extracted with ethyl acetate. The combined organic layers were washed with brine, dried over anhydrous sodium sulfate, filtered, and concentrated under vacuum. The residue was purified by flash chromatography on silica gel with 0~10% methanol in dichloromethane and further purified by following conditions: (Column: Xselect CSH OBD Column 30*150 mm 5 um; Mobile Phase A: Water (0.1% FA), Mobile Phase B: ACN; Flow rate: 60 mL/min; Gradient: 10 B to 40 B in 8 min, 40 B to B in min; 220 nm; RT1:7.3 min) to afford N-(5-((5-chloropyridin-2-yl) methoxy)-1,3,4-thiadiazol-2-yl)-5-(2-fluoro-6-methoxyphenyl)pyridazine-4-carboxamide (6 mg, 5.2%) as a white solid. MS (ESI) calc'd for ($C_{20}H_{14}ClFN_6O_3S$) $(M+1)^+$, 473.0; found, 473.0. $^1H$ NMR (400 MHz, DMSO-$d_6$) δ 13.33 (s, 1H), 9.55 (s, 1H), 9.33 (s, 1H), 8.66 (s, 1H), 8.00 (s, 1H), 7.61-7.50 (m, 2H), 7.00-6.98 (m, 2H), 5.54 (s, 2H), 3.63 (s, 3H).

Example 65

4-(2-fluoro-6-methoxyphenyl)-N-(5-((4-fluorobicyclo(2.2.2)octan-1-yl)methoxy)-1,3,4-thiadiazol-2-yl)-6-methylnicotinamide

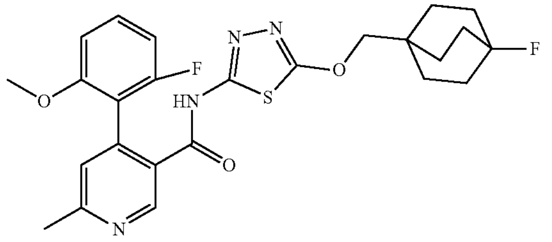 [SMILES: COc1cccc(F)c1-c1cc(C)ncc1C(=O)Nc1nnc(OCC23CCC(F)(CC2)CC3)s1]

Step-1: O-((4-fluorobicyclo(2.2.2)octan-1-yl) methyl)S-methyl carbonodithioate

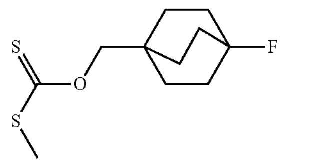

To a solution of (4-fluorobicyclo(2.2.2)octan-1-yl)methanol (500 mg, 3.167 mmol) in THF (10 mL) was added NaH (252 mg, 6.3 mmol, 60%) in portions at 0° C. and stirred at 0° C. for 30 min, then $CS_2$ (325 mg, 4.74 mmol) was added to the above mixture and stirred at 0° C. for 20 min. MeI (607 mg, 4.74 mmol) was then added to the above mixture at 0° C. The resulting mixture was stirred at room temperature for 1 h. The reaction mixture was then quenched by the addition of water and extracted with ethyl acetate. The combined organic layers were washed with brine, dried over anhydrous sodium sulfate, filtered, and concentrated under vacuum to afford 0-((4-fluorobicyclo(2.2.2)octan-1-yl) methyl)S-methyl carbonodithioate (600 mg, crude) as a yellow oil. MS (ESI) calc'd for ($C_{11}H_{17}FOS_2$) $(M+1)^+$, 249.0, found 249.0.

Step-2: O-((4-fluorobicyclo(2.2.2)octan-1-yl)methyl) hydrazinecarbothioate

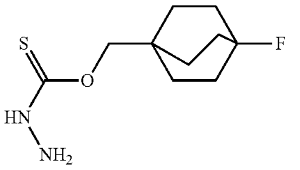 [SMILES: NNC(=S)OCC12CCC(F)(CC1)CC2]

To a solution of O-((4-fluorobicyclo(2.2.2)octan-1-yl) methyl)S-methyl carbonodithioate (600 mg, 2.59 mmol) in MeOH (10 mL) was added hydrazine (162 mg, 2.59 mmol). The mixture was stirred at room temperature for 2 hours. The mixture was quenched with water and extracted with ethyl acetate. The combined organic layers were washed with brine, dried over anhydrous sodium sulfate, filtered, and concentrated under vacuum to afford 0-((4-fluorobicyclo(2.2.2)octan-1-yl)methyl) hydrazinecarbothioate (660 mg, crude) as a red oil. MS (ESI) calc'd for ($C_{10}H_{17}FN_2OS$) $(M+1)^+$, 233.0, found 233.0.

Step-3: 5-((4-fluorobicyclo(2.2.2)octan-1-yl) methoxy)-1,3,4-thiadiazol-2-amine

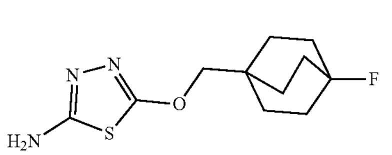 [SMILES: Nc1nnc(OCC23CCC(F)(CC2)CC3)s1]

To a solution of (((1-(5-chloropyridin-2-yl)ethoxy)methanethioyl)amino)amine (660 mg, 2.84 mmol) in MeOH (10 mL) were added BrCN (331 mg, 3.12 mmol) and TEA (573 mg, 5.68 mmol). The resulting mixture was stirred at room temperature for 1 h. The mixture was quenched with water and extracted with ethyl acetate. The combined organic layers were washed with brine, dried over anhydrous sodium sulfate, filtered, and concentrated under vacuum to afford 5-((4-fluorobicyclo(2.2.2)octan-1-yl)methoxy)-1,3,4-thiadiazol-2-amine (550 mg, crude) as a red solid. MS (ESI) calc'd for ($C_{11}H_{16}FNO_3S$) $(M+1)^+$, 258.1, found 258.0.

Step-4: 4-(2-fluoro-6-methoxyphenyl)-N-(5-((4-fluorobicyclo(2.2.2)octan-1-yl)methoxy)-1,3,4-thiadiazol-2-yl)-6-methylnicotinamide

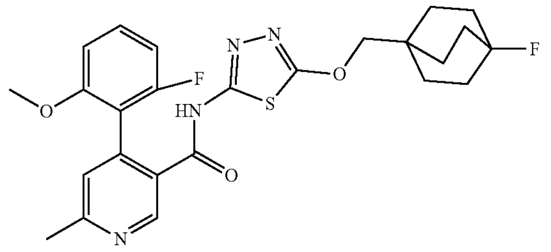 [SMILES: COc1cccc(F)c1-c1cc(C)ncc1C(=O)Nc1nnc(OCC23CCC(F)(CC2)CC3)s1]

To a solution of 5-((4-fluorobicyclo(2.2.2)octan-1-yl) methoxy)-1,3,4-thiadiazol-2-amine (550 mg, 2.37 mmol) in ACN (10 mL) was added 4-(2-fluoro-6-methoxyphenyl)-6-methylnicotinic acid (483 mg, 2.37 mmol, Intermediate F), NMI (305 mg, 7.01 mmol) and TCFH (995 mg, 3.50 mmol). The mixture was stirred at room temperature for 2 h. The mixture was quenched with water and extracted with ethyl acetate. The combined organic layers were washed with brine, dried over anhydrous sodium sulfate, filtered, and concentrated under vacuum. The residue was purified by flash chromatography on silica gel with 0~10% methanol in dichloromethane and further purified by prep-HPLC with the following conditions: (Column: Sunfire prep C18 column, 30*150 mm, 5 um; Mobile Phase A: Water (0.1% FA), Mobile Phase B: ACN; Flow rate: 60 mL/min; Gradient: 45 B to 65 B in 8 min; 220 nm) to afford 4-(2-fluoro-6-methoxyphenyl)-N-(5-((4-fluorobicyclo(2.2.2)octan-1-yl) methoxy)-1,3,4-thiadiazol-2-yl)-6-methylnicotinamide (160 mg, 13%) as a white solid. MS (ESI) calc'd for ($C_{25}H_{26}F_2N_4O_3S$) $(M+1)^+$, 501.2; found 501.2. $^1H$ NMR (400 MHz, DMSO-$d_6$) δ 12.83 (s, 1H), 8.80 (s, 1H), 7.43-7.35 (m, 2H), 6.94-6.88 (m, 2H), 4.12-4.06 (in, 2H), 3.38 (s, 3H), 2.67 (s, 3H), 1.77-1.24 (m, 12H).

Example 66

4-(2-fluoro-6-methoxyphenyl)-N-(5-((4-hydroxybicyclo(2.2.2)octan-1-yl)methoxy)-1,3,4-thiadiazol-2-yl)-6-methylnicotinamide

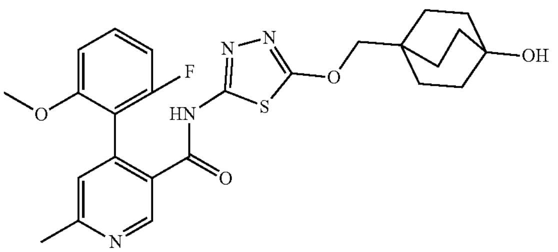 [SMILES: COc1cccc(F)c1-c1cc(C)ncc1C(=O)Nc1nnc(OCC23CCC(O)(CC2)CC3)s1]

Step-1: methyl 4-((tert-butyldimethylsilyl)oxy)bicyclo(2.2.2)octane-1-carboxylate

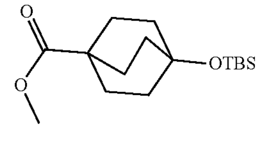 [SMILES: COC(=O)C12CCC(O[Si](C)(C)C(C)(C)C)(CC1)CC2]

To a stirred solution of methyl 4-hydroxybicyclo(2.2.2)octane-1-carboxylate (500 mg, 2.71 mmol) in DMF (20 mL) were added 2.6-lutidine (580 mg, 5.42 mmol) and TBSOTf (2.2 g, 8.14 mmol). The resulting mixture was stirred at room temperature for 2 h under $N_2$ atmosphere. The reaction mixture was quenched with water and extracted with ethyl acetate. The combined organic layers were washed with brine, dried over anhydrous sodium sulfate, filtered, and concentrated under vacuum. The residue was purified by flash column chromatography with 0~100% ethyl acetate in petroleum ether to afford methyl 4-((tert-butyldimethylsilyl)oxy)bicyclo(2.2.2)octane-1-carboxylate (600 mg, 74.1%) as a colorless oil. MS (ESI) calculated for ($C_{16}H_{30}O_3Si$) $(M+1)^+$, 299.2; found, 299.0.

Step-2: (4-((tert-butyldimethylsilyl)oxy)bicyclo(2.2.2)octan-1-)methanol

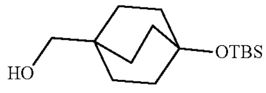 [SMILES: CC(C)(C)[Si](C)(C)OC12CCC(CO)(CC1)CC2]

To a stirred solution of methyl 4-((tert-butyldimethylsilyl)oxy)bicyclo(2.2.2)octane-1-carboxylate (600 mg, 2.01 mmol) in THF (5 mL) was added $LiAlH_4$ (153 mg, 4.02 mmol) in portions at 0° C. The resulting mixture was stirred at room temperature for 1 h under $N_2$ atmosphere. The reaction mixture was quenched with water and extracted with ethyl acetate. The combined organic layers were washed with brine, dried over anhydrous sodium sulfate, filtered, and concentrated under vacuum to afford (4-((tert-butyldimethylsilyl)oxy)bicyclo(2.2.2)octan-1-yl)methanol (520 mg, crude) as a white solid. MS (ESI) calculated for ($C_{15}H_{30}O_2Si$) $(M+1)^+$, 271.2; found, 271.2.

Step-3: O-((4-((tert-butyldimethylsilyl)oxy)bicyclo(2.2.2)octan-1-yl)methyl)S-methyl carbonodithioate

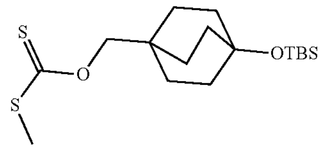 [SMILES: CSC(=S)OCC12CCC(O[Si](C)(C)C(C)(C)C)(CC1)CC2]

To a solution of (4-((tert-butyldimethylsilyl)oxy)bicyclo(2.2.2)octan-1-yl)methanol (412 mg, 1.52 mmol) in THF (5 mL) was added NaH (73 mg, 3.04 mmol, 60%) in portions at 0° C. and stirred at 0° C. for 30 min. To the above mixture was added $CS_2$ (173 mg, 2.28 mmol) at 0° C. and stirred at 0° C. for 20 min. Then MeI (324 mg, 2.28 mmol) was added to the above mixture at 0° C. The resulting mixture was stirred at room temperature for 1 h. The reaction mixture was quenched with water and extracted with ethyl acetate. The combined organic layers were washed with brine, dried over anhydrous sodium sulfate, filtered, and concentrated under vacuum. The residue was purified by flash column chromatography with 0~50% ethyl acetate in petroleum ether to afford O-((4-((tert-butyldimethylsilyl)oxy)bicyclo(2.2.2)octan-1-yl)methyl)S-methyl carbonodithioate (260 mg, 47.3%) as a green oil. MS (ESI) calculated for ($C_{17}H_{32}O_2S_2Si$) $(M+1)^+$, 361.1; found, 361.1.

Step-4: O-((4-((tert-butyldimethylsilyl)oxy)bicyclo(2.2.2)octan-1-yl)methyl) hydrazinecarbothioate

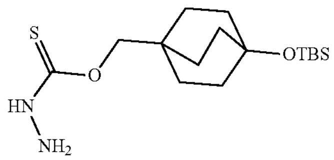 [SMILES: CC(C)(C)[Si](C)(C)OC12CCC(COC(=S)NN)(CC1)CC2]

To a stirred solution of O-((4-((tert-butyldimethylsilyl)oxy)bicyclo(2.2.2)octan-1-yl)methyl)S-methyl carbonodithioate (260 mg, 0.72 mmol) in MeOH (5 mL) was added hydrazine (23 mg, 0.72 mmol). The resulting mixture was stirred at 0° C. for 1 h. The reaction mixture was quenched with water and extracted with ethyl acetate. The combined organic layers were washed with brine, dried over anhydrous sodium sulfate, filtered, and concentrated under vacuum to afford O-((4-((tert-butyldimethylsilyl)oxy)bicyclo(2.2.2)octan-1-yl)methyl) hydrazinecarbothioate (250 mg, crude) as a pink oil. MS (ESI) calculated for ($C_{16}H_{32}N_2O_2SSi$) $(M+1)^+$, 345.2; found, 345.0.

Step-5: 5-((4-((tert-butyldimethylsilyl)oxy)bicyclo(2.2.2)octan-1-yl)methoxy)-1,3,4-thiadiazol-2-amine

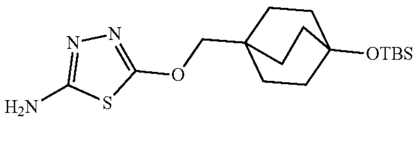

To a stirred solution of O-((4-((tert-butyldimethylsilyl)oxy)bicyclo(2.2.2)octan-1-yl)methyl) hydrazinecarbothioate (270 mg, 0.78 mmol) and TEA (158 mg, 1.56 mmol) in MeOH (5 mL) was added BrCN (91 mg, 0.86 mmol). The resulting mixture was stirred at 0° C. for 1 h. The reaction mixture was quenched with water and extracted with ethyl acetate. The combined organic layers were washed with brine, dried over anhydrous sodium sulfate, filtered, and concentrated under vacuum to afford 5-((4-((tert-butyldimethylsilyl)oxy)bicyclo(2.2.2)octan-1-yl)methoxy)-1,3,4-thiadiazol-2-amine (250 mg, crude) as a pink solid. MS (ESI) calculated for ($C_{17}H_{31}N_{302}SSi$) $(M+1)^+$, 370.2; found, 370.0.

Step-6: N-(5-((4-((tert-butyldimethylsilyl)oxy)bicyclo(2.2.2)octan-1-yl)methoxy)-1,3,4-thiadiazol-2-yl)-4-(2-fluoro-6-methoxyphenyl)-6-methylnicotinamide

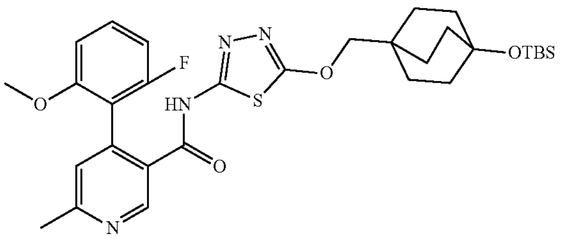 [SMILES: COc1cccc(F)c1-c1cc(C)ncc1C(=O)Nc1nnc(OCC23CCC(O[Si](C)(C)C(C)(C)C)(CC2)CC3)s1]

To a stirred solution of 5-((4-((tert-butyldimethylsilyl)oxy)bicyclo(2.2.2)octan-1-yl)methoxy)-1,3,4-thiadiazol-2-amine (150 mg, 0.41 mmol) and 4-(2-fluoro-6-methoxyphenyl)-6-methylpyridine-3-carboxylic acid (106 mg, 0.41 mmol, Intermediate F) in DMF (3 mL) were added TCFH (171 mg, 0.61 mmol) and NMI (133 mg, 1.62 mmol). The resulting mixture was stirred at room temperature for 1 h. The residue was purified by reverse phase flash column chromatography with 5~100% acetonitrile in water to afford N-(5-((4-((tert-butyldimethylsilyl)oxy)bicyclo(2.2.2)octan-1-yl)methoxy)-1,3,4-thiadiazol-2-yl)-4-(2-fluoro-6-methoxyphenyl)-6-methylnicotinamide (100 mg, 40.2%) as a white solid. MS (ESI) calculated for ($C_{31}H_{41}FN_4O_4SSi$) $(M+1)^+$, 613.3; found, 613.0.

Step-7: 4-(2-fluoro-6-methoxyphenyl)-N-(5-((4-hydroxybicyclo(2.2.2)octan-1-yl)methoxy)-1,3,4-thiadiazol-2-yl)-6-methylnicotinamide

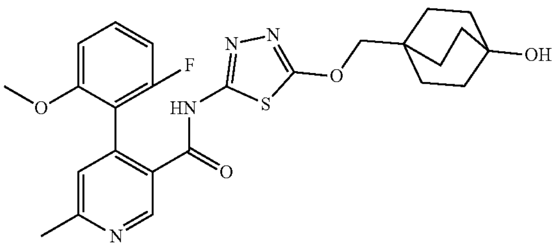 [SMILES: COc1cccc(F)c1-c1cc(C)ncc1C(=O)Nc1nnc(OCC23CCC(O)(CC2)CC3)s1]

To a stirred solution of N-(5-((4-((tert-butyldimethylsilyl)oxy)bicyclo(2.2.2)octan-1-yl)methoxy)-1,3,4-thiadiazol-2-yl)-4-(2-fluoro-6-methoxyphenyl)-6-methylnicotinamide (80 mg, 0.13 mmol) in ACN (1 mL) was added $BF_3 \cdot Et_2O$ (27 mg, 0.19 mmol). The resulting mixture was stirred at 0° C. for 1 h. The residue was purified by prep-HPLC with the following conditions: (Column: Xselect CSH OBD Column 30*150 mm, 5 um; Mobile Phase A: Water (0.1% FA), Mobile Phase B: ACN; Flow rate: 60 mL/min; Gradient: 25 B to 55 B in 8 min; 220 nm; RT1: 7.15 min) to afford 4-(2-fluoro-6-methoxyphenyl)-N-(5-((4-hydroxybicyclo(2.2.2)octan-1-yl)methoxy)-1,3,4-thiadiazol-2-yl)-6-methylnicotinamide (42 mg, 64.5%) as a white solid. MS (ESI) calculated for ($C_{25}H_{27}FN_4O_4S$) $(M+1)^+$, 499.2; found, 499.1. $^1H$ NMR (400 MHz, DMSO-$d_6$) δ 12.82 (s, 1H), 8.79 (s, 1H), 7.47-7.30 (m, 2H), 6.98-6.84 (m, 2H), 4.28 (s, 1H), 4.09 (s, 2H), 3.58 (s, 3H), 2.57 (s, 3H), 1.65-1.42 (m, 12H).

Example 67

4-(2-fluoro-6-methoxyphenyl)-N-(5-((4-methoxypyridin-2-yl)methoxy)-1,3,4-thiadiazol-2-yl)-6-methylnicotinamide

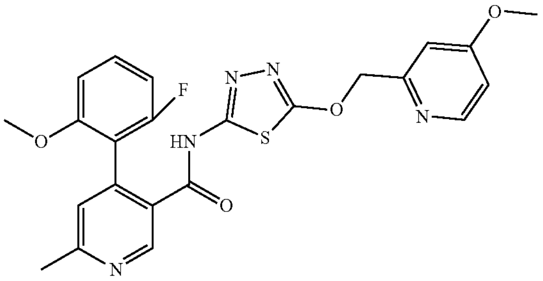

Step-1: 5-((4-methoxypyridin-2-yl)methoxy)-1,3,4-thiadiazol-2-amine

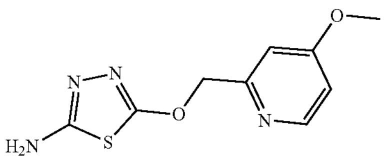 [SMILES: COc1ccnc(COc2nnc(N)s2)c1]

To a solution of NaH (149 mg, 3.72 mmol, 60%) in THF (10.00 mL was added a solution of (4-methoxypyridin-2-yl)methanol (347 mg, 3.5 mmol) in THF (1 mL) at 0° C. and stirred at 0° C. for 1 h under nitrogen. To the above solution was added 5-bromo-1,3,4-thiadiazol-2-amine (532 mg, 2.98 mmol) at 0° C. under nitrogen. The mixture was stirred at room temperature for 4 h. The reaction mixture was quenched by the addition of water. The mixture was extracted with ethyl acetate. The combined organic layers were washed with brine, dried over anhydrous sodium sulfate, filtered, and concentrated under vacuum. The residue was purified by flash chromatography on silica gel with 0-50% ethyl acetate in petroleum ether to afford 5-((4-methoxypyridin-2-yl)methoxy)-1,3,4-thiadiazol-2-amine (340 mg, 49.9%) as a yellow solid. MS (ESI) calc'd for ($C_9H_{10}N_4O_2S$) $(M+1)^+$, 238.1, found 238.1.

Step-2: 4-(2-fluoro-6-methoxyphenyl)-N-(5-((4-methoxypyridin-2-yl)methoxy)-1,3,4-thiadiazol-2-yl)-6-methylnicotinamide

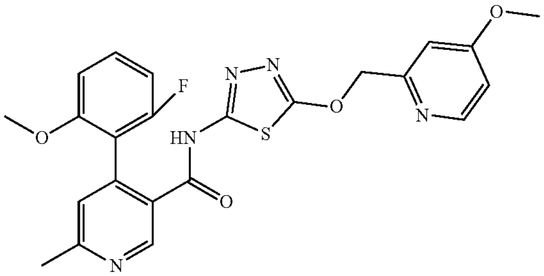

To a solution of 5-((4-methoxypyridin-2-yl)methoxy)-1,3,4-thiadiazol-2-amine (340 mg, 1.42 mmol) in ACN (5 mL) were added 4-(2-fluoro-6-methoxyphenyl)-6-methylnicotinic acid (370 mg, 1.42 mmol, Intermediate F), NMI (305 mg, 1.26 mmol) and TCFH (594 mg, 2.13 mmol). The mixture was stirred at room temperature for 2 h. The mixture was diluted with water and extracted with ethyl acetate. The combined organic layers were washed with brine, dried over anhydrous sodium sulfate, filtered, and concentrated under vacuum. The residue was purified by flash chromatography on silica gel with 0~10% methanol in dichloromethane and further purified by prep-HPLC with the following conditions: (Column: XBridge Prep OBD C18 Column, 30×150 mm 5 um; Mobile Phase A: Water (10 MMOL/L $NH_4HCO_3$), Mobile Phase B: ACN; Flow rate: 60 mL/min; Gradient: 25 B to 50 B in 8 min; 220 nm) to afford 4-(2-fluoro-6-methoxyphenyl)-N-(5-((4-methoxypyridin-2-yl)methoxy)-1,3,4-thiadiazol-2-yl)-6-methylnicotinamide (47 mg, 15.9%) as a white solid. MS (ESI) calc'd for ($C_{23}H_{20}FN_5O_4S$) $(M+1)^+$, 481.1; found 481.1. $^1H$ NMR (400 MHz, DMSO-$d_6$) δ 12.91 (s, 1H), 8.81 (s, 1H), 8.40-8.39 (m, 1H), 7.43-7.33 (m, 2H), 7.11 (s, 1H), 6.95-6.88 (m, 3H), 5.48 (s, 2H), 3.84 (s, 3H), 3.58 (s, 3H), 2.57 (s, 3H).

Example 68 and 69

(S)-2'-chloro-N-(5-((5-(1-hydroxyethyl)pyridin-2-yl)methoxy)-1,3,4-thiadiazol-2-yl)-5'-methoxy-6-methyl-(4,4'-bipyridine)-3-carboxamide (Example 68) and (R)-2'-chloro-N-(5-((5-(1-hydroxyethyl)pyridin-2-yl)methoxy)-1,3,4-thiadiazol-2-yl)-5'-methoxy-6-methyl-(4,4'-bipyridine)-3-carboxamide (Example 69)

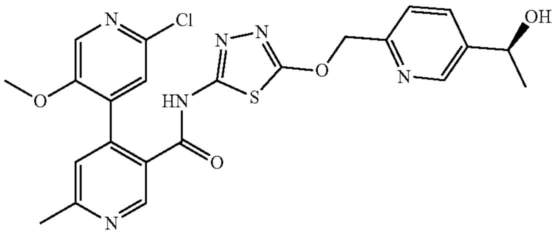

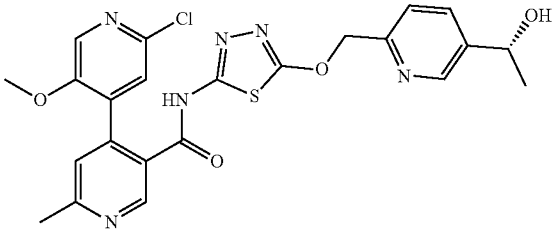

Step-1: N-(5-((5-acetylpyridin-2-yl)methoxy)-1,3,4-thiadiazol-2-yl)-2'-chloro-5'-methoxy-6-methyl-(4,4'-bipyridine)-3-carboxamide

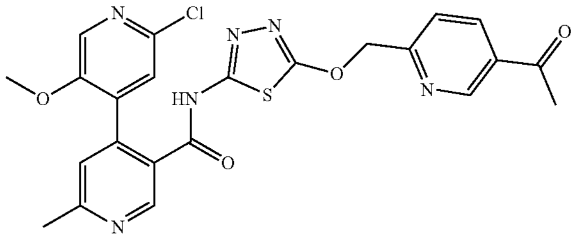 [SMILES: COc1cnc(Cl)cc1-c1cc(C)ncc1C(=O)Nc1nnc(OCc2ccc(C(C)=O)cn2)s1]

To a solution of 2'-chloro-5'-methoxy-6-methyl-(4,4'-bipyridine)-3-carboxylic acid (350 mg, 1.26 mmol) in ACN (5 mL) were added 1-(6-(((5-amino-1,3,4-thiadiazol-2-yl)oxy)methyl)pyridin-3-yl)ethan-1-one (370 mg, 1.42 mmol), NMI (305 mg, 1.26 mmol) and TCFH (594 mg, 2.13 mmol). The mixture was stirred at room temperature for 2 h. The mixture was diluted with water and extracted with ethyl acetate. The combined organic layers were washed with brine, dried over anhydrous sodium sulfate, filtered, and concentrated under vacuum. The residue was purified by flash chromatography on silica gel with 0~10% methanol in dichloromethane to afford N-(5-((5-acetylpyridin-2-yl)methoxy)-1,3,4-thiadiazol-2-yl)-2'-chloro-5'-methoxy-6-methyl-(4,4'-bipyridine)-3-carboxamide (400 mg, 62.5%) as a yellow solid. MS (ESI) calc'd for ($C_{23}H_{19}ClN_6O_4S$) $(M+1)^+$, 511.1, round 511.1.

Step-2 & Step-3: (S)-2'-chloro-N-(5-((5-(1-hydroxyethyl)pyridin-2-yl)methoxy)-1,3,4-thiadiazol-2-yl)-5'-methoxy-6-methyl-(4,4'-bipyridine)-3-carboxamide and (R)-2'-chloro-N-(5-((5-(1-hydroxyethyl)pyridin-2-yl)methoxy)-1,3,4-thiadiazol-2-yl)-5'-methoxy-6-methyl-(4,4'-bipyridine)-3-carboxamide

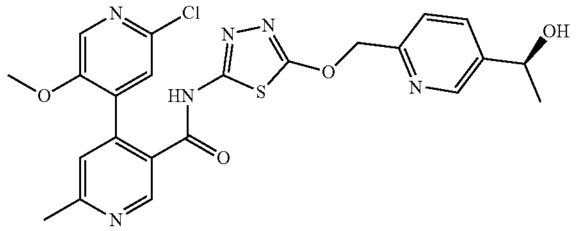

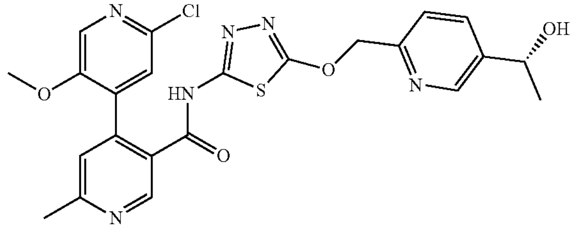

To a solution of N-(5-((5-acetylpyridin-2-yl)methoxy)-1,3,4-thiadiazol-2-yl)-2'-chloro-5'-methoxy-6-methyl-(4,4'-bipyridine)-3-carboxamide (400 mg, 0.78 mmol) in MeOH (2 mL) was added $NaBH_4$ (30 mg, 0.78 mmol) in portions at 0° C. The mixture was stirred at room temperature for 2 h. The reaction mixture was quenched by the addition of water and extracted with ethyl acetate. The combined organic layers were washed with brine, dried over anhydrous sodium sulfate, filtered, and concentrated under vacuum. The residue was purified by flash chromatography on silica gel with 0~10% methanol in dichloromethane to afford the racemic product, which was further separated by prep-chiral-HPLC with the following conditions: (Column: CHIRALPAK IC, 2*25 cm, 5 um; Mobile Phase A: Hex (0.2% FA)-HPLC, Mobile Phase B: EtOH:DCM=1:1-HPLC; Flow rate: 20 mL/min; Gradient: 55 B to 55 B in 16 min; 220/254 nm; RT1: 8.48; RT2: 12.232; Injection Volume: 1.25 ml; Number Of Runs: 6.) to afford (S)-2'-chloro-N-(5-((5-(1-hydroxyethyl)pyridin-2-yl)methoxy)-1,3,4-thiadiazol-2-yl)-5'-methoxy-6-methyl-(4,4'-bipyridine)-3-carboxamide (50 mg, 12.5%) as a white solid with shorter retention time on chiral-HPLC and (R)-2'-chloro-N-(5-((5-(1-hydroxyethyl)pyridin-2-yl)methoxy)-1,3,4-thiadiazol-2-yl)-5'-methoxy-6-methyl-(4,4'-bipyridine)-3-carboxamide (50 mg, 12.5%) as a white solid with longer retention time on chiral-HPLC.

(S)-2'-chloro-N-(5-((5-(1-hydroxyethyl)pyridin-2-yl)methoxy)-1,3,4-thiadiazol-2-yl)-5'-methoxy-6-methyl-(4,4'-bipyridine)-3-carboxamide: MS (ESI) calc'd for ($C_{23}H_{21}ClN_6O_4S$) $(M+1)^+$, 513.1; found 513.1. $^1H$ NMR (400 MHz, DMSO-$d_6$) δ 12.93 (s, 1H), 8.82 (s, 1H), 8.55-8.55 (m, 1H), 8.16-8.14 (m, 1H), 7.81-7.79 (m, 1H), 7.51-7.49 (m, 2H), 7.40 (s, 1H), 5.50 (s, 2H), 5.35 (d, J=6.4 Hz, 1H), 4.83-4.77 (m, 1H), 3.63 (s, 3H), 2.51 (s, 3H), 1.36 (d, J=6.4 Hz, 3H).

(R)-2'-chloro-N-(5-((5-(1-hydroxyethyl)pyridin-2-yl)methoxy)-1,3,4-thiadiazol-2-yl)-5'-methoxy-6-methyl-(4,4'-bipyridine)-3-carboxamide: MS (ESI) calc'd for ($C_{23}H_{21}ClN_6O_4S$) $(M+1)^+$, 513.1; found 513.1. $^1H$ NMR (400 MHz, DMSO-$d_6$) δ 12.94 (s, 1H), 8.82 (s, 1H), 8.55-8.55 (m, 1H), 8.16-8.14 (m, 1H), 7.81-7.79 (m, 1H), 7.51-7.49 (m, 2H), 7.40 (s, 1H), 5.50 (s, 2H), 5.35 (d, J=6.4 Hz, 1H), 4.83-4.77 (m, 1H), 3.63 (s, 3H), 2.51 (s, 3H), 1.36 (d, J=6.4 Hz, 3H).

Example 70

4-(2-(difluoromethoxy)-6-fluorophenyl)-N-(5-((5-(hydroxymethyl)pyrazin-2-yl)methoxy)-1,3,4-thiadiazol-2-yl)-6-methylnicotinamide

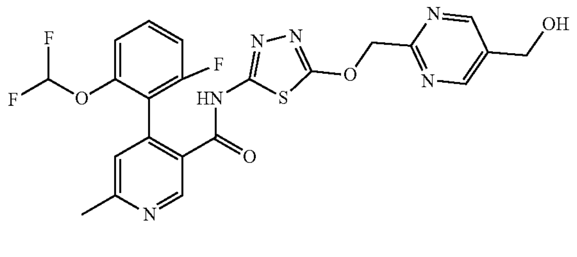 [SMILES: Cc1cc(-c2c(F)cccc2OC(F)F)c(C(=O)Nc2nnc(OCc3ncc(CO)cn3)s2)cn1]

Step-1: (5-ethenylpyrazin-2-yl)methanol

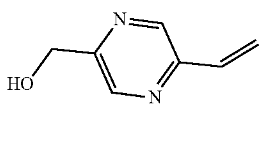

To a stirred solution of (5-chloropyrazin-2-yl)methanol (2.0 g, 13.83 mmol) in dioxane (18 mL) and water (6 mL) were added ethenyltrifluoro-lambda4-borane potassium (2.8 g, 20.90 mmol), Pd(dppf)$Cl_2$ (1.0 g, 1.36 mmol) and $K_2CO_3$ (5.7 g, 41.60 mmol) at room temperature. The mixture was stirred at 80° C. for 16 h under nitrogen. The resulting mixture was diluted with water and extracted with ethyl acetate. The combined organic layers were washed with brine, dried over anhydrous $Na_2SO_4$. After filtration, the filtrate was concentrated under vacuum. The residue was purified by flash column chromatography with 0-20% ethyl acetate in petroleum ether to afford (5-ethenylpyrazin-2-yl)methanol (1.0 g, 47%) as a brown oil. MS (ESI) calc'd for ($C_7H_8N_2O$) $(M+1)^+$, 137.1; found 137.1.

Step-2: 5-((5-ethenylpyrazin-2-yl)methoxy)-1,3,4-thiadiazol-2-amine

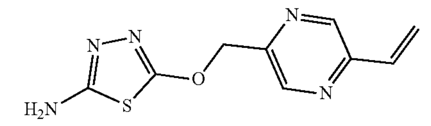 [SMILES: C=Cc1cnc(COc2nnc(N)s2)cn1]

To a stirred solution of (5-ethenylpyrazin-2-yl)methanol (1.0 g, 7.34 mmol) in THF (15 mL) was added NaH (264 mg, 11.01 mmol, 60%) in portions at 0° C. The mixture was stirred at 0° C. for 0.5 h. 5-bromo-1,3,4-thiadiazol-2-amine (1.6 g, 8.81 mmol) were added thereto at 0° C. The resulting mixture was stirred at 0° C. to room temperature for 4 h. The reaction was quenched with water. The resulting mixture was extracted with ethyl acetate. The combined organic layers were washed with brine, dried over anhydrous $Na_2SO_4$. After filtration, the filtrate was concentrated under reduced pressure. The residue was purified by reverse phase flash column chromatography with 15-50% acetonitrile in water to afford 5-((5-ethenylpyrazin-2-yl)methoxy)-1,3,4-thiadiazol-2-amine (600 mg, 34%) as a yellow solid. MS (ESI) calc'd for ($C_9H_9N_5OS$) $(M+1)^+$, 236.1; found, 236.1.

Step-3: 4-(2-(difluoromethoxy)-6-fluorophenyl)-N-(5-((5-ethenylpyrazin-2-yl)methoxy)-1,3,4-thiadiazol-2-yl)-6-methylpyridine-3-carboxamide

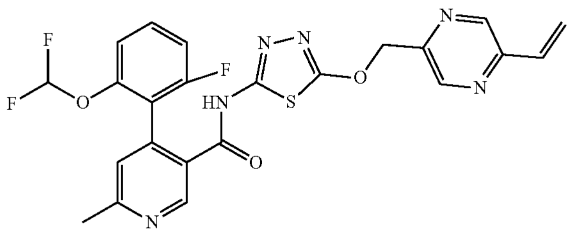 [SMILES: Cc1cc(-c2c(F)cccc2OC(F)F)c(C(=O)Nc2nnc(OCc3cnc(C=O)cn3)s2)cn1]

To a stirred solution of 5-((5-ethenylpyrazin-2-yl)methoxy)-1,3,4-thiadiazol-2-amine (150 mg, 0.63 mmol) in acetonitrile (3 mL) were added 4-(2-(difluoromethoxy)-6-fluorophenyl)-6-methylpyridine-3-carboxylic acid (88 mg, 0.29 mmol), NMI (209 mg, 2.55 mmol) and TCFH (268 mg, 0.95 mmol). The mixture was stirred at room temperature for 2 h. The resulting mixture was purified by reverse phase flash column chromatography with 5~50% acetonitrile in water to afford 4-(2-(difluoromethoxy)-6-fluorophenyl)-N-

(5-((5-ethenylpyrazin-2-yl)methoxy)-1,3,4-thiadiazol-2-yl)-6-methylpyridine-3-carboxamide (140 mg, 42%) as a white solid. MS (ESI) calc'd for ($C_{23}H_{17}F_3N_6O_3S$) $(M+1)^+$, 515.1; found, 515.1.

Step-4: 4-(2-(difluoromethoxy)-6-fluorophenyl)-N-(5-((5-formylpyrazin-2-yl)methoxy)-1,3,4-thiadiazol-2-yl)-6-methylpyridine-3-carboxamide

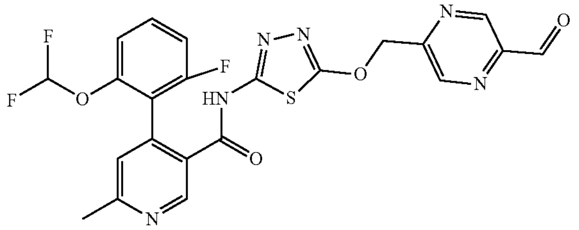

To a stirred solution of 4-(2-(difluoromethoxy)-6-fluorophenyl)-N-(5-((5-ethenylpyrazin-2-yl)methoxy)-1,3,4-thiadiazol-2-yl)-6-methylpyridine-3-carboxamide (140 mg, 0.27 mmol) in THF (1 mL) was added a solution of $NaIO_4$ (232 mg, 1.08 mmol) in water (1 mL) dropwise at room temperature under nitrogen atmosphere. And then $OsO_4$ (6 mg, 0.03 mmol) was added to the above mixture. The resulting mixture was stirred at room temperature for 2 h. The reaction was quenched with water. The aqueous layer was extracted with ethyl acetate. The combined organic layers were washed with brine, dried over anhydrous $Na_2SO_4$. After filtration, the filtrate was concentrated under reduced pressure to afford 4-(2-(difluoromethoxy)-6-fluorophenyl)-N-(5-((5-formylpyrazin-2-yl)methoxy)-1,3,4-thiadiazol-2-yl)-6-methylpyridine-3-carboxamide (140 mg, crude) as a yellow solid. MS (ESI) calc'd for ($C_{22}H_{15}F_3N_6O_4S$) $(M+1)^+$, 517.1; found, 517.1.

Step-5: 4-(2-(difluoromethoxy)-6-fluorophenyl)-N-(5-((5-(hydroxymethyl)pyrazin-2-yl)methoxy)-1,3,4-thiadiazol-2-yl)-6-methylnicotinamide

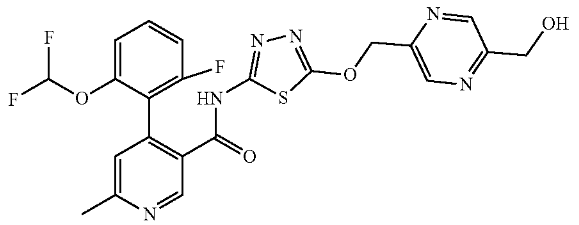 [SMILES: Cc1cc(-c2c(F)cccc2OC(F)F)c(C(=O)Nc2nnc(OCc3cnc(CO)cn3)s2)cn1]

To a stirred solution of 4-(2-(difluoromethoxy)-6-fluorophenyl)-N-(5-((5-formylpyrazin-2-yl)methoxy)-1,3,4-thiadiazol-2-yl)-6-methylpyridine-3-carboxamide (140 mg, 0.27 mmol) in MeOH (3 mL) was added $NaBH_4$ (21 mg, 0.54 mmol) in portions at 0° C. The mixture was stirred at 0° C. for 2 h. The reaction was quenched with water. The aqueous layer was extracted with ethyl acetate. The combined organic layers were washed with brine, dried over anhydrous $Na_2SO_4$. After filtration, the filtrate was concentrated under reduced pressure. The residue was purified by prep-HPLC with the following conditions: (Column: XBridge Prep OBD C18 Column, 30×150 mm 5 um; Mobile Phase A: Water (10 MMOL/L $NH_4HCO_3$), Mobile Phase B: ACN; Flow rate: 60 mL/min; Gradient: 15 B to 55 B in 8 min, 220 nm; RT1: 7.23 min) to afford 4-(2-(difluoromethoxy)-6-fluorophenyl)-N-(5-((5-(hydroxymethyl)pyrazin-2-yl)methoxy)-1,3,4-thiadiazol-2-yl)-6-methylnicotinamide (45.9 mg, 32%) as a white solid. MS (ESI) calc'd for ($C_{22}H_{17}F_3N_6O_4S$) $(M+1)^+$, 519.1; found 519.1. $^1H$ NMR (400 MHz, DMSO-$d_6$) δ 13.07 (br, 1H), 8.96 (s, 1H), 8.70-8.81 (m, 2H), 7.47-7.57 (m, 1H), 7.28-7.33 (m, 1H), 7.21-7.23 (m, 1H), 7.10-7.12 (m, 2H), 5.57-5.65 (m, 3H), 4.66 (d, J=5.2 Hz, 2H), 2.59 (s, 3H).

Example 71

4-(2-methoxyphenyl)-6-methyl-N-(5-(5,6,7,8-tetrahydro-1,6-naphthyridin-2-ylmethoxy)-1,3,4-thiadiazol-2-yl)pyridine-3-carboxamide

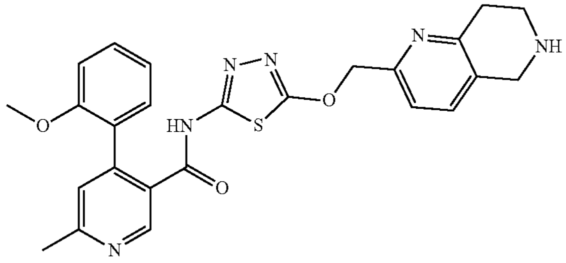 [SMILES: COc1ccccc1-c1cc(C)ncc1C(=O)Nc1nnc(OCc2ccc3c(n2)CCNC3)s1]

Step-1: tert-butyl 2-(hydroxymethyl)-7,8-dihydro-5H-1,6-naphthyridine-6-carboxylate

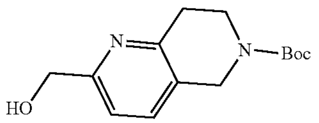 [SMILES: CC(C)(C)OC(=O)N1CCc2nc(CO)ccc2C1]

To a stirred solution of 6-tert-butyl 2-methyl 7,8-dihydro-5H-1,6-naphthyridine-2,6-dicarboxylate (1.0 g, 3.42 mmol) in THF (10 mL) was added $LiAlH_4$ (260 mg, 6.85 mmol) in portions at 0° C. The resulting mixture was stirred at room temperature for 1 h. The reaction was quenched by the addition of water. The residue was purified by reverse phase flash column chromatography with 5-50% acetonitrile in water to afford tert-butyl 2-(hydroxymethyl)-7,8-dihydro-5H-1,6-naphthyridine-6-carboxylate (315 mg, 34%) as a brown oil. MS (ESI) calc'd for ($C_{14}H_{20}N_2O_3$) $(M+1)^+$, 265.1; found 265.1.

Step-2: tert-butyl 2-((((methylsulfanyl)methanethioyl)oxy)methyl)-7,8-dihydro-5H-1,6-naphthyridine-6-carboxylate

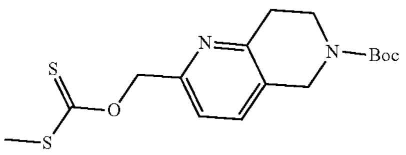 [SMILES: CSC(=S)OCc1ccc2c(n1)CCN(C(=O)OC(C)(C)C)C2]

To a stirred solution of tert-butyl 2-(hydroxymethyl)-7,8-dihydro-5H-1,6-naphthyridine-6-carboxylate (270 mg, 1.02 mmol) in THF (5 mL) was added NaH (81 mg, 2.02 mmol, 60%) in portions at 0° C. and stirred at 0° C. for 30 min under nitrogen atmosphere. To the above solution was added $CS_2$ (117 mg, 1.53 mmol) at 0° C. and stirred at 0° C. for 20 min. Then MeI (218 mg, 1.53 mmol) was added to the above mixture at 0° C. under nitrogen atmosphere. The resulting mixture was stirred at room temperature for 1 h. The reaction mixture was diluted with water and extracted with ethyl acetate. The combined organic layers were washed with brine, dried over anhydrous sodium sulfate, filtered, and concentrated under vacuum. The residue was purified by flash column chromatography with 0~50% ethyl acetate in petroleum ether to afford tert-butyl 2-((((methylsulfanyl)methanethioyl)oxy)methyl)-7,8-dihydro-5H-1,6-naphthyridine-6-carboxylate (200 mg, 55%) as a yellow oil. MS (ESI) calc'd for ($C_{16}H_{22}N_2O_3S_2$) $(M+1)^+$, 355.1; found 355.1.

Step-3: tert-butyl 2-(((aminocarbamothioyl)oxy)methyl)-7,8-dihydro-5H-1,6-naphthyridine-6-carboxylate

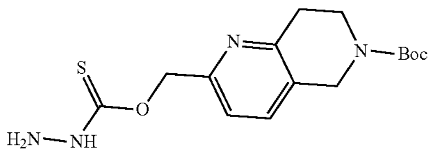 [SMILES: CC(C)(C)OC(=O)N1CCc2nc(COC(=S)NN)ccc2C1]

To a stirred solution of tert-butyl 2-((((methylsulfanyl)methanethioyl)oxy)methyl)-7,8-dihydro-5H-1,6-naphthyridine-6-carboxylate (200 mg, 0.56 mmol) in MeOH (2 mL) was added $NH_2NH_2 \cdot H_2O$ (28 mg, 0.56 mmol). The mixture resulting was stirred at 0° C. for 1 h under nitrogen atmosphere. The reaction mixture was quenched with water and extracted with ethyl acetate. The combined organic layers were washed with brine, dried over anhydrous sodium sulfate, filtered, and concentrated under vacuum to afford tert-butyl 2-(((aminocarbamothioyl)oxy)methyl)-7,8-dihydro-5H-1,6-naphthyridine-6-carboxylate (190 mg, crude) as a yellow oil. MS (ESI) calc'd for ($C_{15}H_{22}N_2O_3S$) $(M+1)^+$, 339.1; found, 339.1.

Step-4: 4-(2-(difluoromethoxy)-6-fluorophenyl)-N-(5-((5-formylpyrazin-2-yl)methoxy)-1,3,4-thiadiazol-2-yl)-6-methylpyridine-3-carboxamide

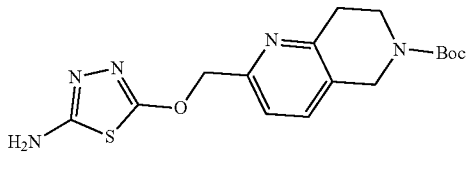 [SMILES: CC(C)(C)OC(=O)N1CCc2nc(COc3nnc(N)s3)ccc2C1]

To a stirred solution of tert-butyl 2-(((aminocarbamothioyl)oxy)methyl)-7,8-dihydro-5H-1,6-naphthyridine-6-carboxylate (190 mg, 0.56 mmol) and TEA (113 mg, 1.12 mmol) in MeOH (2 mL) was added BrCN (65 mg, 0.61 mmol). The mixture resulting was stirred at 0° C. for 1 h under nitrogen atmosphere. The reaction mixture was quenched with water and extracted with ethyl acetate. The combined organic layers were washed with brine, dried over anhydrous sodium sulfate, filtered, and concentrated under vacuum to afford tert-butyl 2-(((5-amino-1,3,4-thiadiazol-2-yl)oxy)methyl)-7,8-dihydro-5H-1,6-naphthyridine-6-carboxylate (190 mg, crude) as a pink solid. MS (ESI) calc'd for ($C_{16}H_{21}N_5O_3S$) $(M+1)^+$, 364.1; found, 364.1.

Step-5: 4-(2-(difluoromethoxy)-6-fluorophenyl)-N-(5-((5-(hydroxymethyl)pyrazin-2-yl)methoxy)-1,3,4-thiadiazol-2-yl)-6-methylpyridine-3-carboxamide

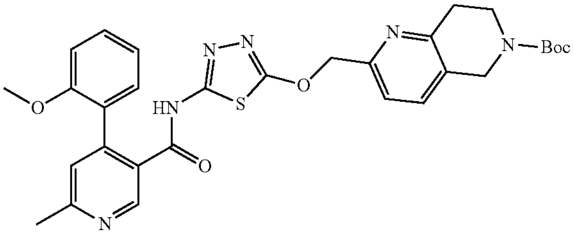 [SMILES: COc1ccccc1-c1cc(C)ncc1C(=O)Nc1nnc(OCc2ccc3c(n2)CCN(C(=O)OC(C)(C)C)C3)s1]

To a stirred solution of tert-butyl 2-(((5-amino-1,3,4-thiadiazol-2-yl)oxy)methyl)-7,8-dihydro-5H-1,6-naphthyridine-6-carboxylate (150 mg, 0.41 mmol) and 4-(2-methoxyphenyl)-6-methylpyridine-3-carboxylic acid (100 mg, 0.41 mmol, Intermediate D) in Acetonitrile (2 mL) were added TCFH (173 mg, 0.62 mmol) and NMI (135 mg, 1.65 mmol). The mixture resulting was stirred at room temperature for 2 h under nitrogen atmosphere. The residue was purified by reverse phase flash column chromatography with 5-50% acetonitrile in water to afford tert-butyl 2-(((5-(4-(2-methoxyphenyl)-6-methylpyridine-3-amido)-1,3,4-thiadiazol-2-yl)oxy)methyl)-7,8-dihydro-5H-1,6-naphthyridine-6-carboxylate (100 mg, 41%) as a white solid. MS (ESI) calc'd for ($C_{30}H_{32}N_6O_5S$) $(M+1)^+$, 589.2; found 589.2.

Step-6: 4-(2-methoxyphenyl)-6-methyl-N-(5-(5,6,7,8-tetrahydro-1,6-naphthyridin-2-ylmethoxy)-1,3,4-thiadiazol-2-yl)pyridine-3-carboxamide

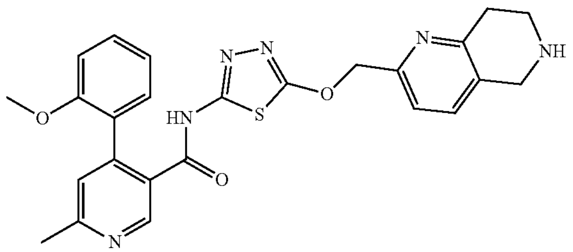 [SMILES: COc1ccccc1-c1cc(C)ncc1C(=O)Nc1nnc(OCc2ccc3c(n2)CCNC3)s1]

To a stirred solution of tert-butyl 2-(((5-(4-(2-methoxyphenyl)-6-methylpyridine-3-amido)-1,3,4-thiadiazol-2-yl)oxy)methyl)-7,8-dihydro-5H-1,6-naphthyridine-6-carboxylate (70 mg, 0.11 mmol) in DCM (2 mL) was added TFA (0.5 mL). The resulting mixture was stirred at room temperature for 2 h under nitrogen atmosphere before concentrated under vacuum. The residue was purified by prep-HPLC with the following conditions: (Column: XBridge Prep OBD C18 Column, 30×150 mm 5 um; Mobile Phase A: Water (10 MMOL/L $NH_4HCO_3$), Mobile Phase B: ACN; Flow rate: 60 mL/min; Gradient: 10 B to 40 B in 8 min; 220 nm; RT1:7.23 min) to afford 4-(2-methoxyphenyl)-6-methyl-N-(5-(5,6,7,8-tetrahydro-1,6-naphthyridin-2-ylmethoxy)-1,3,4-thiadiazol-2-yl)pyridine-3-carboxamide (25.4 mg, 43%) as a white solid. MS (ESI) calc'd for ($C_{25}H_{24}N_6O_3S$) $(M+1)^+$, 489.2; found 489.2. $^1H$ NMR (400 MHz, DMSO-$d_6$) δ 8.68 (s, 1H), 7.50 (d, J=7.6 Hz, 1H), 7.41-7.35 (m, 1H), 7.34-7.26 (m, 3H), 7.07-7.04 (m, J=7.6 Hz, 1H), 7.01-6.95 (m, 1H), 5.43 (s, 2H), 3.90 (s, 2H), 3.52 (s, 3H), 3.10-3.07 (m, J=5.6 Hz, 2H), 2.80-2.78 (m, J=6.0 Hz, 2H), 2.56 (s, 3H).

Example 72

4-(2-fluoro-6-methoxyphenyl)-N-(5-((4-(hydroxymethyl)pyridin-2-yl)methoxy)-1,3,4-thiadiazol-2-yl)-6-methylnicotinamide

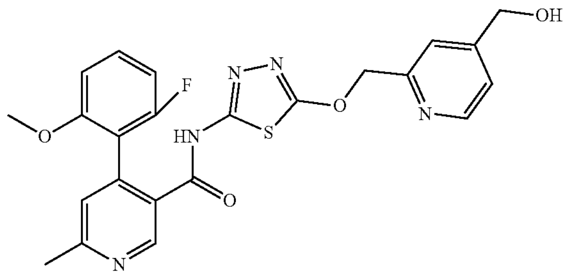 [SMILES: COc1cccc(F)c1-c1cc(C)ncc1C(=O)Nc1nnc(OCc2cc(CO)ccn2)s1]

Step-1: methyl 2-(((5-(4-(2-fluoro-6-methoxyphenyl)-6-methylnicotinamido)-1,3,4-thiadiazol-2-yl)oxy)methyl)isonicotinate

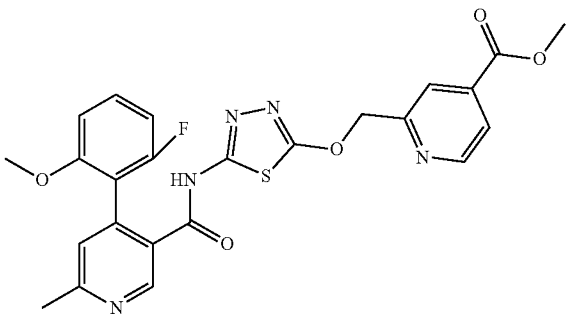

To a solution of methyl 2-(((5-amino-1,3,4-thiadiazol-2-yl)oxy)methyl)isonicotinate (125 mg, 0.47 mmol) in ACN (5 mL) were added 4-(2-fluoro-6-methoxyphenyl)-6-methylnicotinic acid (122 mg, 0.47 mmol, Intermediate F), NMI (116 mg, 1.41 mmol) and TCFH (197 mg, 0.7 mmol). The mixture was stirred at room temperature for 2 h. The mixture was quenched with water and extracted with ethyl acetate. The combined organic layers were washed with brine, dried over anhydrous sodium sulfate, filtered, and concentrated under vacuum. The residue was purified by flash chromatography on silica gel with 0~10% methanol in dichloromethane to afford methyl 2-(((5-(4-(2-fluoro-6-methoxyphenyl)-6-methylnicotinamido)-1,3,4-thiadiazol-2-yl)oxy)methyl)isonicotinate (110 mg, 46%) as a yellow solid. MS (ESI) calc'd for ($C_{24}H_{20}FN_5O_5S$) $(M+1)^+$, 510.1; found 510.1.

Step-2:4-(2-fluoro-6-methoxyphenyl)-N-(5-((4-(hydroxymethyl)pyridin-2-yl)methoxy)-1,3,4-thiadiazol-2-yl)-6-methylnicotinamide

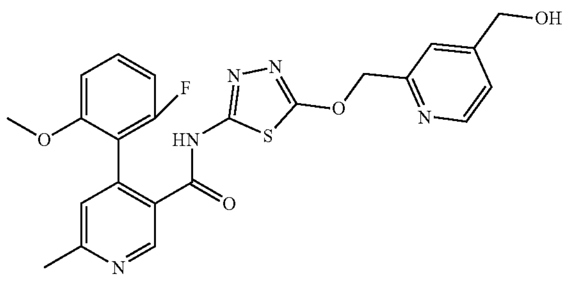 [SMILES: COc1cccc(F)c1-c1cc(C)ncc1C(=O)Nc1nnc(OCc2cc(CO)ccn2)s1]

To a solution of methyl 2-(((5-(4-(2-fluoro-6-methoxyphenyl)-6-methylnicotinamido)-1,3,4-thiadiazol-2-yl)oxy)methyl)isonicotinate (110 mg, 0.21 mmol) in THF (5 mL) was added LAH (8 mg, 0.21 mmol) at 0° C. The mixture was stirred at room temperature for 2 hours. The reaction mixture was quenched by the addition of water at room temperature. The mixture was diluted with water and extracted with ethyl acetate. The combined organic layers were washed with brine, dried over anhydrous sodium sulfate, filtered, and concentrated under vacuum. The residue was purified by flash chromatography on silica gel with 0~10% methanol in dichloromethane and further purified by prep-HPLC with the following conditions: (Column: XBridge Prep OBD C18 Column, 30×150 mm 5 um; Mobile Phase A: Water (10 MMOL/L $NH_4HCO_3$), Mobile Phase B: ACN; Flow rate: 60 mL/min; Gradient: 20 B to 45 B in 8 min; 220 nm) to afford 4-(2-fluoro-6-methoxyphenyl)-N-(5-((4-(hydroxymethyl)pyridin-2-yl)methoxy)-1,3,4-thiadiazol-2-yl)-6-methylnicotinamide (12 mg, 11%) as a white solid. MS (ESI) calc'd for ($C_{23}H_{20}FN_5O_3S$) $(M+1)^+$, 482.1; found 482.1. $^1H$ NMR (400 MHz, DMSO-$d_6$) δ 12.90 (s, 1H), 8.81 (s, 1H), 8.51-8.50 (m, 1H), 7.48 (s, 1H), 7.43-7.37 (m, 1H), 7.31-7.30 (m, 2H), 6.94-6.87 (m, 2H), 5.52-5.46 (m, 3H), 4.56-4.55 (m, 2H), 3.58 (s, 3H), 2.56 (s, 3H).

Example 73

2'-chloro-N-(5-((5-(2-hydroxypropan-2-yl)pyridin-2-yl)methoxy)-1,3,4-thiadiazol-2-yl)-6-methyl-(4,4'-bipyridine)-3-carboxamide

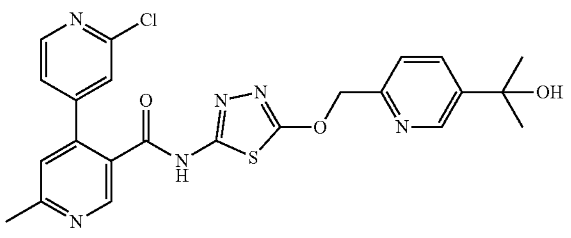 [SMILES: Cc1cc(-c2ccnc(Cl)c2)c(C(=O)Nc2nnc(OCc3ccc(C(C)(C)O)cn3)s2)cn1]

Step-1: methyl 2'-chloro-6-methyl-(4,4'-bipyridine)-3-carboxylate

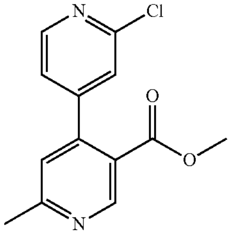

To a degassed solution of methyl 4-chloro-6-methylnicotinate (300 mg, 1.6 mmol) in Dioxane (5 mL) and water (1 mL) were added (2-chloropyridin-4-yl)boronic acid (252 mg, 1.6 mmol), $K_2CO_3$ (662 mg, 4.8 mmol) and Pd(dppf)$Cl_2$ (130 mg, 0.16 mmol). The resulting mixture was stirred at 80° C. for 5 hours under nitrogen before concentrated under vacuum. The residue was purified by flash chromatography on silica gel with 0-50% ethyl acetate in petroleum ether to afford methyl 2'-chloro-6-methyl-(4,4'-bipyridine)-3-carboxylate (228 mg, 54%) as a yellow solid. MS (ESI) calc'd for ($C_{13}H_{11}ClN_2O_2$) $(M+1)^+$, 263.1, found 263.1.

Step-2: 2'-chloro-6-methyl-(4,4'-bipyridine)-3-carboxylic acid

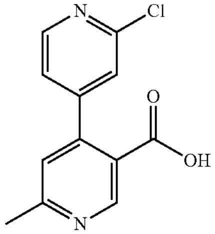 [SMILES: Cc1cc(-c2ccnc(Cl)c2)c(C(=O)O)cn1]

To a solution of ethyl methyl 2'-chloro-6-methyl-(4,4'-bipyridine)-3-carboxylate (228 mg, 0.87 mmol) in MeOH (2 mL) and $H_2O$ (1 mL) was added NaOH (70 mg, 1.74 mmol). The mixture was stirred 70° C. for 2 hours. The resulting mixture was acidified with HCl (2 N) to pH 5-6. The aqueous solution was extracted with ethyl acetate. The organic layers were combined, washed with brine, dried over anhydrous sodium sulfate and filtered. The filtrate was concentrated under vacuum to afford 2'-chloro-6-methyl-(4,4'-bipyridine)-3-carboxylic acid (130 mg, 60%) as a yellow solid. MS (ESI) calc'd for ($C_{12}H_9ClN_2O_2$) $(M+1)^+$, 249.0, found 249.0.

Step-3: 2'-chloro-N-(5-((5-(2-hydroxypropan-2-yl)pyridin-2-yl)methoxy)-1,3,4-thiadiazol-2-yl)-6-methyl-(4,4'-bipyridine)-3-carboxamide

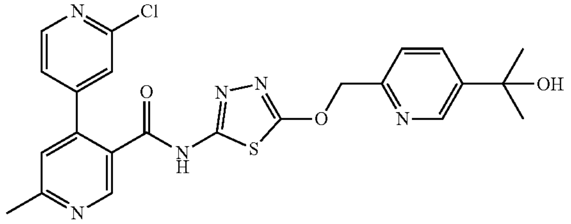

To a solution of 2'-chloro-6-methyl-(4,4'-bipyridine)-3-carboxylic acid (130 mg, 0.52 mmol) in ACN (5 mL) were added 2-(6-(((5-amino-1,3,4-thiadiazol-2-yl)oxy)methyl)pyridin-3-yl)propan-2-ol (139 mg, 0.52 mmol, Example 33, Step 1), NMI (128 mg, 1.56 mmol) and TCFH (220 mg, 0.78 mmol). The mixture was stirred at room temperature for 2 h. The resulting mixture was quenched with water and extracted with ethyl acetate. The combined organic layers were washed with brine, dried over anhydrous sodium sulfate, filtered, and concentrated under vacuum. The residue was purified by flash column chromatography with 0~10% methanol in dichloromethane and further purified by prep-HPLC with the following conditions: (Column: XBridge Prep OBD C18 Column, 30×150 mm 5 um; Mobile Phase A: Water (10 MMOL/L $NH_4HCO_3$), Mobile Phase B: ACN; Flow rate: 60 mL/min; Gradient: 5 B to 40 B in 8 min; 254/220 nm) to afford 2'-chloro-N-(5-((5-(2-hydroxypropan-2-yl)pyridin-2-yl)methoxy)-1,3,4-thiadiazol-2-yl)-6-methyl-(4,4'-bipyridine)-3-carboxamide (57 mg, 22.8%) as a white solid. MS (ESI) calc'd for ($C_{23}H_{21}ClN_6O_3S$)(M+1)$^+$, 497.1; found 497.1. $^1$H NMR (400 MHz, DMSO-$d_6$) δ 8.84 (s, 1H), 8.67-8.67 (m, 1H), 8.40-8.39 (m, 1H), 7.89-7.86 (m, 1H), 7.50-7.50 (m, 1H), 7.44-7.42 (m, 1H), 7.35-7.33 (m, 2H), 5.42 (s, 2H), 5.24 (s, 1H), 2.53 (s, 3H), 1.45 (s, 6H).

Example 74

N-(5-((5-isopropoxypyridin-2-yl)methoxy)-1,3,4-thiadiazol-2-yl)-5'-methoxy-2',6-dimethyl-(4,4'-bipyridine)-3-carboxamide

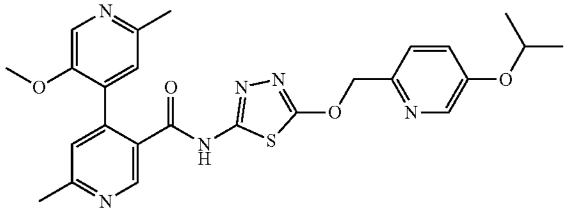 [SMILES: COc1cnc(C)cc1-c1cc(C)ncc1C(=O)Nc1nnc(OCc2ccc(OC(C)C)cn2)s1]

A mixture of 5-methoxy-2,6-dimethyl-(4,4-bipyridine)-3-carboxylic acid (20.00 mg, 0.077 mmol), 5-((5-isopropoxypyridin-2-yl)methoxy)-1,3,4-thiadiazol-2-amine (24.75 mg, 0.093 mmol), TCFH (23.90 mg, 0.085 mmol) and NMI (13.35 mg, 0.16 mmol) in MeCN (2.0 mL, 48.71 mmol) was stirred at room temperature for 1.5 h. The resulting mixture was concentrated under vacuum. The crude residue was purified by Prep-HPLC with the following conditions: (Column: XBridge Prep OBD C18 Column, 30×150 mm 5 um; Mobile Phase A: Water (10 MMOL/L $NH_4HCO_3$), Mobile Phase B: ACN; Flow rate: 60 mL/min; Gradient: 25 B to 40 B in 8 min; 254/220 nm; RT 1: 7.12 min) to afford N-(5-((5-isopropoxypyridin-2-yl)methoxy)-1,3,4-thiadiazol-2-yl)-5-methoxy-2,6-dimethyl-(4,4-bipyridine)-3-carboxamide (11.9 mg, 60%) as a white solid. MS (ESI) calc'd for ($C_{25}H_{26}N_6O_4S$) $(M+1)^+$, 507.2, found 507.3. $^1$H NMR (400 MHz, DMSO-d6) δ 12.90 (s, 1H), 8.77 (s, 1H), 8.26 (d, J=2.8 Hz, 1H), 8.19 (s, 1H), 7.52 (s, 1H), 7.47-7.40 (m, J=6.0 Hz, 1H), 7.35 (s, 1H), 7.25 (s, 1H), 5.44 (s, 2H), 4.78-4.64 (m, J=6.0 Hz, 1H), 3.59 (s, 3H), 2.58 (s, 3H), 2.47 (s, 3H), 1.30 (d, J=6.0 Hz, 6H).

Example 75

4-(2-fluoro-6-methoxyphenyl)-N-(5-((5-isopropoxy-pyridin-2-yl)methoxy)-1,3,4-thiadiazol-2-yl)-6-methylnicotinamide

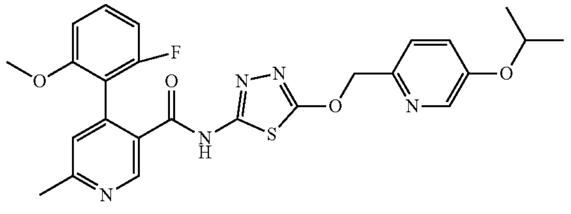 [SMILES: COc1cccc(F)c1-c1cc(C)ncc1C(=O)Nc1nnc(OCc2ccc(OC(C)C)cn2)s1]

Step-1: methyl 5-isopropoxypicolinate

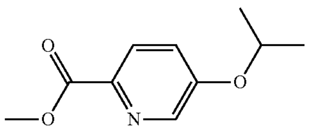

To a solution of methyl 5-hydroxypicolinate (1 g, 6.5 mmol) in NMP (20 mL) were added $CsCO_3$ (2.2 g, 13 mmol) and 2-iodopropane (1.33 g, 7.8 mmol). The resulting mixture was stirred at 80° C. for 2 h. The reaction mixture was quenched with water and extracted with ethyl acetate. The combined organic layers were washed with brine, dried over anhydrous sodium sulfate, filtered, and concentrated under vacuum. The residue was purified by flash chromatography on silica gel with 0~50% ethyl acetate in petroleum ether to afford methyl 5-isopropoxypicolinate (700 mg, 58%) as a yellow solid. MS (ESI) calc'd for ($C_{10}H_{13}NO_3$) $(M+1)^+$, 196.1, found 196.0.

Step-2: (5-isopropoxypyridin-2-yl)methanol

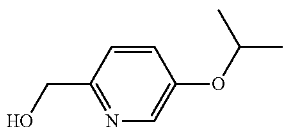

To a solution of methyl 2-(((5-(4-(2-fluoro-6-methoxy-phenyl)-6-methylnicotinamido)-1,3,4-thiadiazol-2-yl)oxy)methyl)isonicotinate (700 mg, 3.6 mmol) in THF (10 mL) was added LAH (273 mg, 7.2 mmol) in portions at 0° C. The mixture was stirred at room temperature for 2 h. The reaction mixture was quenched by the addition of water and extracted with ethyl acetate. The combined organic layers were washed with brine, dried over anhydrous sodium sulfate, filtered, and concentrated under vacuum. The residue was purified by flash chromatography on silica gel with 0-50% ethyl acetate in petroleum ether to afford (5-isopropoxypyridin-2-yl)methanol (260 mg, 44%) as a yellow solid. MS (ESI) calc'd for ($C_9H_{13}NO_2$) $(M+1)^+$168.1, found 168.0.

Step-3: 5-((5-isopropoxypyridin-2-yl)methoxy)-1,3,4-thiadiazol-2-amine

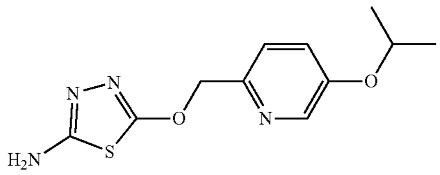

To a solution of NaH (90 mg, 2.25 mmol, 60%) in THF (5 mL) was added a solution of (5-isopropoxypyridin-2-yl)methanol (260 mg, 1.5 mmol) in THF (1 mL) dropwise at 0° C. and stirred at 0° C. for 1 h under nitrogen. To the above solution was added 5-bromo-1,3,4-thiadiazol-2-amine (270 mg, 1.5 mmol) at 0° C. under nitrogen. The mixture was stirred at room temperature for 2 h. The reaction mixture was quenched by the addition of water and extracted with ethyl acetate. The combined organic layers were washed with brine, dried over anhydrous sodium sulfate, filtered, and concentrated under vacuum. The residue was purified by flash chromatography on silica gel with 0-50% ethyl acetate in petroleum ether to afford 5-((5-isopropoxypyridin-2-yl)methoxy)-1,3,4-thiadiazol-2-amine (170 mg, 40.8%) as a yellow solid. MS (ESI) calc'd for ($C_{11}H_{14}N_4O_2S$) $(M+1)^+$, 267.1, found 267.0.

Step-4: 4-(2-fluoro-6-methoxyphenyl)-N-(5-((5-isopropoxypyridin-2-yl)methoxy)-1,3,4-thiadiazol-2-yl)-6-methylnicotinamide

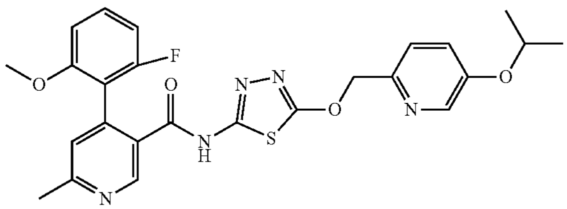 [SMILES: COc1cccc(F)c1-c1cc(C)ncc1C(=O)Nc1nnc(OCc2ccc(OC(C)C)cn2)s1]

To a solution of 5-((5-isopropoxypyridin-2-yl)methoxy)-1,3,4-thiadiazol-2-amine (170 mg, 0.63 mmol) in ACN (2 mL) were added 4-(2-fluoro-6-methoxyphenyl)-6-methylnicotinic acid (165 mg, 0.63 mmol, Intermediate F),NMI (156 mg, 1.9 mmol) and TCFH (264 mg, 0.95 mmol). The resulting mixture was stirred at room temperature for 2 h. The mixture was quenched with water and extracted with ethyl acetate. The combined organic layers were washed with brine, dried over anhydrous sodium sulfate, filtered, and concentrated under vacuum. The residue was purified by flash chromatography on silica gel with 0~10% methanol in dichloromethane and further purified by prep-HPLC with the following conditions: (Column: YMC-Actus Triart C18, 30 mm×150 mm, 5 um; Mobile Phase A: Water (10 MMOL/L $NH_4HCO_3$), Mobile Phase B: ACN; Flow rate: 60 mL/min; Gradient: 35 B to 65 B in 8 min, 220 nm) to afford 4-(2-fluoro-6-methoxyphenyl)-N-(5-((5-isopropoxypyridin-2-yl)methoxy)-1,3,4-thiadiazol-2-yl)-6-methylnicotinamide (45 mg, 13.2%) as a white solid. MS (ESI) calc'd for ($C_{25}H_{24}FN_5O_4S$) $(M+1)^+$, 510.2; found 510.2. $^1H$ NMR (400 MHz, DMSO-$d_6$) δ 12.88 (s, 1H), 8.80 (s, 1H), 8.25-8.24 (m, 1H), 7.51-7.33 (m, 4H), 6.94-6.87 (m, 2H), 5.43 (s, 2H), 4.75-4.68 (m, 1H), 3.58 (s, 3H), 2.56 (s, 3H), 1.29-1.24 (d, J=6.0 Hz, 6H).

Example 76

N-(5-((5-(2-hydroxypropan-2-yl)pyridin-2-yl)methoxy)-1,3,4-thiadiazol-2-yl)-5'-methoxy-2',6-dimethyl-(4,4'-bipyridine)-3-carboxamide

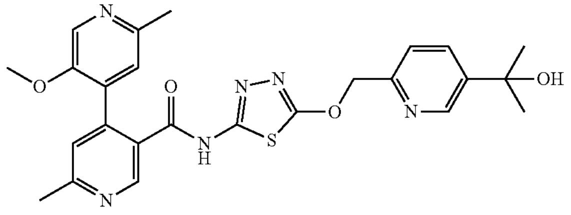 [SMILES: COc1cnc(C)cc1-c1cc(C)ncc1C(=O)Nc1nnc(OCc2ccc(C(C)(C)O)cn2)s1]

To a solution of 5'-methoxy-2',6-dimethyl-(4,4'-bipyridine)-3-carboxylic acid (80 mg, 0.310 mmol, Intermediate G) in ACN (2 mL) and DMF (2 mL) were added 2-(6-(((5-amino-1,3,4-thiadiazol-2-yl)oxy)methyl)pyridin-3-yl)propan-2-ol (83 mg, 0.310 mmol, Example 33, Step 1), NMI (77 mg, 0.929 mmol) and TCFH (105 mg, 0.372 mmol). The resulting solution was stirred at room temperature for 2 hours. The reaction mixture was quenched with water and extracted with dichloromethane. The combined organic layers were washed with brine, dried over anhydrous sodium sulfate, filtered, and concentrated under vacuum. The residue was purified by flash chromatography on silica gel with 0~10% methanol in dichloromethane and further purified by prep-HPLC with the following condition: (Column: XBridge Prep OBD C18 Column, 30×150 mm 5 um; Mobile Phase A: Water (10 MMOL/L $NH_4HCO_3$), Mobile Phase B: ACN; Flow rate: 60 mL/min; Gradient: 5 B to 30 B in 9 min; 220 nm; RT1: 8.88 min) to afford N-(5-((5-(2-hydroxypropan-2-yl)pyridin-2-yl)methoxy)-1,3,4-thiadiazol-2-yl)-5'-methoxy-2',6-dimethyl-(4,4'-bipyridine)-3-carboxamide (20.3 mg, 12.9%) as a white solid. MS (ESI) calc'd for ($C_{25}H_{26}N_6O_4S$) $(M+1)^+$, 507.2; found, 507.2. $^1H$ NMR (400 MHz, DMSO) δ 12.90 (s, 1H), 8.76 (s, 1H), 8.69 (s, 1H), 8.18 (s, 1H), 7.90 (s, 1H), 7.49-7.47 (m, 1H), 7.35-7.32 (m, 1H), 7.27-7.25 (m, 1H), 5.50 (s, 2H), 5.26 (s, 1H), 3.58 (s, 3H), 2.67 (s, 3H), 2.33 (s, 3H), 1.46 (s, 6H).

Example 77

2'-chloro-N-(5-((5-chloropyridin-2-yl)methoxy)-1,3,4-thiadiazol-2-yl)-3'-methoxy-6-methyl-(4,4'-bipyridine)-3-carboxamide

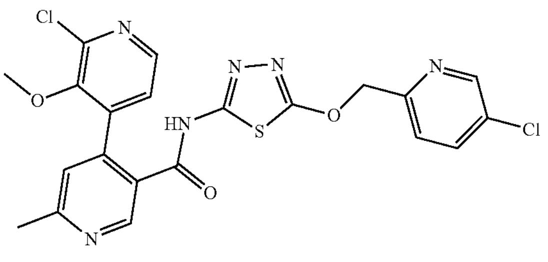 [SMILES: COc1c(-c2cc(C)ncc2C(=O)Nc2nnc(OCc3ccc(Cl)cn3)s2)ccnc1Cl]

Step-1: (2-chloro-3-methoxypyridin-4-yl)boronic acid

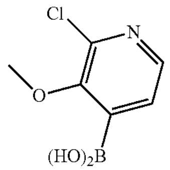

To a stirred solution of 2-chloro-3-methoxypyridine (5 g, 34.82 mmol) in THF (100 mL) was added lithium diisopropylamide (35 mL, 258.11 mmol) dropwise at −78° C. under nitrogen atmosphere. The resulting mixture was stirred at −78° C. for 2 h. To this was added $B(OiPr)_3$ (13 g, 69.12 mmol) dropwise at −78° C. under nitrogen atmosphere. The resulting mixture was stirred at −78° C. for 2 h, then stirred at room temperature for 16 under nitrogen. The resulting mixture was quenched by diluted HCl (2 N) to pH 5-6. The resulting mixture was stirred at room temperature for 30 min. The resulting mixture was extracted with ethyl acetate. The combined organic layers were washed with saturated sodium chloride, dried over anhydrous sodium sulfate. After filtration, the filtrate was concentrated under reduced pressure to afford (2-chloro-3-methoxypyridin-4-yl)boronic acid (5 g, 41.3%) as a brown solid. MS (ESI) calculated for ($C_6H_7BClNO_3$) $(M+1)^+$, 188.0; found, 188.0.

Step-2: methyl 2-chloro-3-methoxy-6-methyl-(4,4-bipyridine)-3-carboxylate

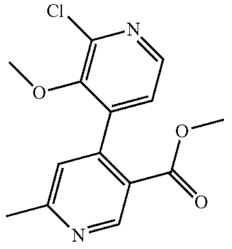

To a degassed solution of methyl 4-chloro-6-methylpyridine-3-carboxylate (412 mg, 2.22 mmol) and (2-chloro-3-methoxypyridin-4-yl)boronic acid (500 mg, 2.67 mmol) in dioxane (9 mL) and water (3 mL) were added Pd(dtbpf)$Cl_2$ (145 mg, 0.22 mmol) and $K_2CO_3$ (922 mg, 6.67 mmol). The resulting mixture was stirred at 80° C. for 2 h. The resulting mixture was filtered and the filtrate was concentrated under reduced pressure. The resulting mixture was diluted with water and extracted with ethyl acetate. The combined organic layers were washed with brine, dried over anhydrous $Na_2SO_4$. After filtration, the filtrate was concentrated under reduced pressure. The residue was purified by silica gel column chromatography, eluted with 0-70% ethyl acetate in petroleum ether to afford methyl 2-chloro-3-methoxy-6-methyl-(4,4-bipyridine)-3-carboxylate (220 mg, 33.1%) as a brown oil. MS (ESI) calculated for ($C_{14}H_{13}ClN_2O_3$) $(M+1)^+$, 293.1; found, 293.1.

Step-3: 2-chloro-3-methoxy-6-methyl-(4,4-bipyridine)-3-carboxylic acid

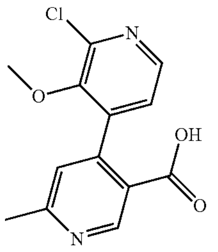 [SMILES: COc1c(-c2cc(C)ncc2C(=O)O)ccnc1Cl]

To a stirred solution of methyl 2-chloro-3-methoxy-6-methyl-(4,4-bipyridine)-3-carboxylate (100 mg, 0.34 mmol) in THF (2 mL) was added a solution of LiOH (33 mg, 1.38 mmol) in water (1 mL). The resulting mixture was stirred at 80° C. for 4 h. The residue was acidified to pH 5-6 with citric acid. The resulting mixture was extracted with ethyl acetate. The combined organic layers were washed with brine, dried over anhydrous $Na_2SO_4$. After filtration, the filtrate was concentrated under reduced pressure to afford 2-chloro-3-methoxy-6-methyl-(4,4-bipyridine)-3-carboxylic acid (98 mg, crude) as a white solid. MS (ESI) calculated for ($C_{13}H_{11}ClN_2O_3$) $(M+1)^+$, 279.0; found, 279.0.

Step-4: 2'-chloro-N-(5-((5-chloropyridin-2-yl)methoxy)-1,3,4-thiadiazol-2-yl)-3'-methoxy-6-methyl-(4,4'-bipyridine)-3-carboxamide

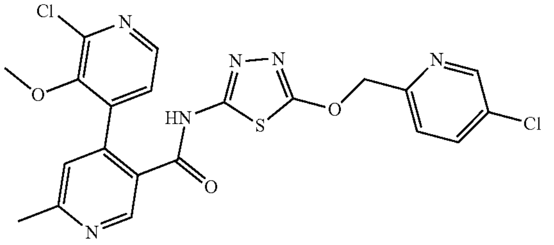 [SMILES: COc1c(-c2cc(C)ncc2C(=O)Nc2nnc(OCc3ccc(Cl)cn3)s2)ccnc1Cl]

To a stirred solution of 2-chloro-3-methoxy-6-methyl-(4,4-bipyridine)-3-carboxylic acid (70 mg, 0.25 mmol) and 5-((5-chloropyridin-2-yl)methoxy)-1,3,4-thiadiazol-2-amine (61 mg, 0.25 mmol, Intermediate C) in acetonitrile (1 mL) were added TCFH (78 mg, 0.28 mmol) and NMI (62 mg, 0.75 mmol). The resulting mixture was stirred at room temperature for 2 h. The residue was purified by Prep-HPLC with the following conditions: (Column: XBridge Prep OBD C18 Column, 30×150 mm 5 um; Mobile Phase A: Water (10 MMOL/L $NH_4HCO_3$), Mobile Phase B: ACN; Flow rate: 60 mL/min; Gradient: 25 B to 55 B in 8 min; 220 nm; RT1: 7.23 min) to afford 2'-chloro-N-(5-((5-chloropyridin-2-yl)methoxy)-1,3,4-thiadiazol-2-yl)-3'-methoxy-6-methyl-(4,4'-bipyridine)-3-carboxamide (77.1 mg, 59.5%) as a white solid. MS (ESI) calculated for ($C_{21}H_{16}Cl_2N_6O_3S$) $(M+1)^+$, 503.0; found, 503.2. $^1H$ NMR (400 MHz, DMSO-$d_6$) δ 13.11 (s, 1H), 8.92 (s, 1H), 8.78-8.73 (m, 1H), 8.28 (d, J=4.8 Hz, 1H), 8.04-7.97 (m, 1H), 7.64-7.57 (m, 1H), 7.46-7.40 (m, 2H), 5.55 (s, 2H), 3.44 (s, 3H), 2.61 (s, 3H).

Example 78

2'-chloro-N-(5-((3-fluorobicyclo(1.1.1)pentan-1-yl)methoxy)-1,3,4-thiadiazol-2-yl)-5'-methoxy-6-methyl-(4,4'-bipyridine)-3-carboxamide

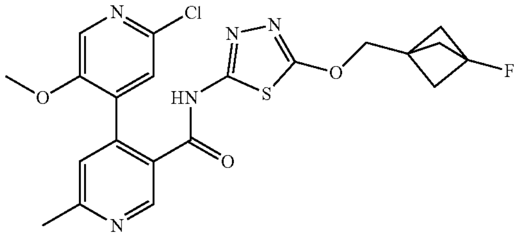 [SMILES: COc1cnc(Cl)cc1-c1cc(C)ncc1C(=O)Nc1nnc(OCC23CC(F)(C2)C3)s1]

Step 1: (3-fluorobicyclo(1.1.1)pentan-1-yl)methanol

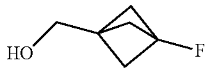

To a solution of 3-fluorobicyclo(1.1.1)pentane-1-carboxylic acid (600.0 mg, 4.61 mmol) and NMM (466.4 mg, 4.61 mmol) in THF (10.0 mL) was added 2-methylpropyl carbonochloridate (629.8 mg, 4.61 mmol) dropwise at 0° C. under nitrogen atmosphere. The resulting solution was stirred at 0° C. for 2 h. To the above mixture was added $NaBH_4$ (523.3 mg, 13.83 mmol) in MeOH (20.0 mL) in portions 0° C. under nitrogen atmosphere. The resulting solution was stirred at 0° C. to room temperature for 2 h. The reaction was quenched by the addition of saturated $NH_4Cl$ aqueous solution at 0° C. The aqueous solution was extracted with ethyl acetate. The combined organic layers were washed with brine, dried over anhydrous sodium sulfate, filtered, and concentrated under vacuum to afford the crude. The crude was purified by silica gel column chromatography and eluted with 0-50% ethyl acetate in petroleum ether to afford (3-fluorobicyclo(1.1.1)pentan-1-yl)methanol (200.0 mg, crude) as a yellow oil.

Step-2: ((3-fluorobicyclo(1.1.1)pentan-1-yl)methoxy)(methylsulfanyl)methanethione

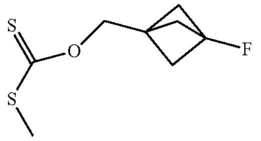

To a solution of (3-fluorobicyclo(1.1.1)pentan-1-yl)methanol (200.0 mg, 1.72 mmol) in THF (20.0 mL) was added NaH (82.6 mg, 3.44 mmol) at 0° C. under nitrogen atmosphere. The solution was stirred at 0° C. for 30 min. To the above mixture was added $CS_2$ (196.6 mg, 2.58 mmol) dropwise at 0° C. under nitrogen. The solution was stirred at 0° C. for 30 min. To the above mixture was added MeI (366.6 mg, 2.58 mmol) dropwise at 0° C. under nitrogen. The solution was stirred at 0° C. for 30 min. The reaction was then quenched by the addition of water. The aqueous layer was extracted with ethyl acetate. The combined organic solution was dried over sodium sulfate, filtered, and concentrated under vacuum to afford ((3-fluorobicyclo(1.1.1)pentan-1-yl)methoxy)(methylsulfanyl)methanethione (190.0 mg, crude) as a yellow oil, which was used in the next step without further purification.

Step-3: ((((3-fluorobicyclo(1.1.1)pentan-1-yl)methoxy)methanethioyl)amino)amine

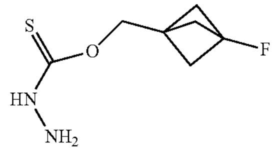 [SMILES: NNC(=S)OCC12CC(F)(C1)C2]

A mixture of ((3-fluorobicyclo(1.1.1)pentan-1-yl)methoxy)(methylsulfanyl)methanethione (190.0 mg, 0.92 mmol) and hydrazine hydrate (80%) (29.5 mg, 0.92 mmol) and MeOH (10.0 mL). The resulting solution was stirred for 2 h at 25° C. The aqueous layer was extracted with ethyl acetate. The combined organic solution was dried over sodium sulfate, filtered, and concentrated under vacuum to afford ((((3-fluorobicyclo(1.1.1)pentan-1-yl)methoxy)methanethioyl)amino)amine (220.0 mg, crude) as a yellow oil. MS (ESI) calc'd for ($C_7H_{11}FN_2O$ S) $(M+1)^+$, 191.0, found 191.0.

Step-4: 5-((3-fluorobicyclo(1.1.1)pentan-1-yl)methoxy)-1,3,4-thiadiazol-2-amine

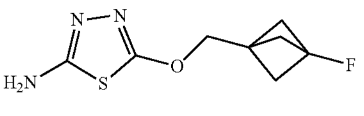 [SMILES: Nc1nnc(OCC23CC(F)(C2)C3)s1]

To a mixture of (((3-fluorobicyclo(1.1.1)pentan-1-yl)methoxy)methanethioyl)amino)amine (220.0 mg, 1.15 mmol) in MeOH (10.0 mL) were added TEA (234.0 mg, 2.31 mmol) and BrCN (134.7 mg, 1.27 mmol) at 25° C. The resulting solution was stirred for 30 min at 25° C. The aqueous layer was extracted with ethyl acetate. The combined organic solution was dried over sodium sulfate, filtered, and concentrated under vacuum. The crude residue was purified by silica gel column chromatography and eluted with 0~80% ethyl acetate in petroleum ether to afford 5-((3-fluorobicyclo(1.1.1)pentan-1-yl)methoxy)-1,3,4-thiadiazol-2-amine (60.0 mg, 19% over four steps) as a white solid. MS (ESI) calc'd for ($C_8H_{10}FN_3OS$) $(M+1)^+$, 216.2, found 216.0.

Step-5: 2'-chloro-N-(5-((3-fluorobicyclo(1.1.1)pentan-1-yl)methoxy)-1,3,4-thiadiazol-2-yl)-5'-methoxy-6-methyl-(4,4'-bipyridine)-3-carboxamide

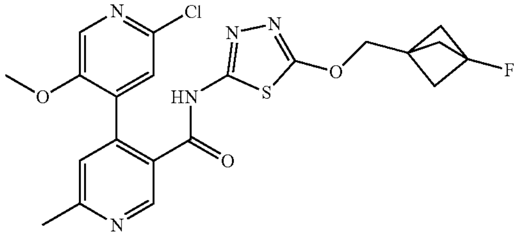 [SMILES: COc1cnc(Cl)cc1-c1cc(C)ncc1C(=O)Nc1nnc(OCC23CC(F)(C2)C3)s1]

A mixture of 2'-chloro-5'-methoxy-6-methyl-(4,4'-bipyridine)-3-carboxylic acid (20.0 mg, 0.07 mmol, Intermediate H), 5-((3-fluorobicyclo(1.1.1)pentan-1-yl)methoxy)-1,3,4-thiadiazol-2-amine (23.1 mg, 0.10 mmol), HATU (40.9 mg, 0.10 mmol), DIEA (27.8 mg, 0.21 mmol) in DMF (2.0 mL) was stirred at 25° C. for 2 h. The crude mixture was purified by Prep-HPLC with the following conditions: (Column: XSelect CSH Prep C18 OBD Column, 19*250 mm, 5 um; Mobile Phase A: Water (10 mmol/L $NH_4HCO_3$), Mobile Phase B: ACN; Flow rate: 25 mL/min; Gradient: 55 B to 65 B in 13 min; 254 nm) to afford 2'-chloro-N-(5-((3-fluorobicyclo(1.1.1)pentan-1-yl)methoxy)-1,3,4-thiadiazol-2-yl)-5'-methoxy-6-methyl-(4,4'-bipyridine)-3-carboxamide (4.1 mg, 11%) as a yellow solid. MS (ESI) calc'd for ($C_{21}H_{19}ClFN_5O_3S$) $(M+1)^+$, 476.0, found 476.0. $^1H$ NMR (400 MHz, Methanol-$d_4$) δ 8.81 (s, 1H), 8.09 (s, 1H), 7.49 (s, 1H), 7.42 (s, 1H), 4.70 (s, 2H), 3.73 (s, 3H), 2.68 (s, 3H), 2.12 (d, J=2.4 Hz, 6H).

Example 80

4-(2-fluoro-6-methoxyphenyl)-N-(5-((5-(2-methoxypropan-2-yl)pyridin-2-yl)methoxy)-1,3,4-thiadiazol-2-yl)-6-methylnicotinamide

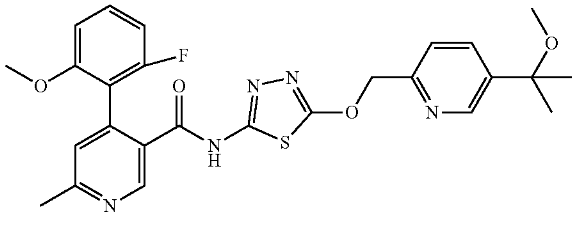 [SMILES: COc1cccc(F)c1-c1cc(C)ncc1C(=O)Nc1nnc(OCc2ccc(C(C)(C)OC)cn2)s1]

Step-1: 2-bromo-5-(2-methoxypropan-2-yl)pyridine

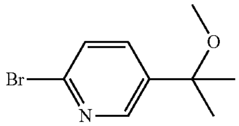

To a solution of 2-(6-bromopyridin-3-yl)propan-2-ol (970 mg, 4.491 mmol) in THF (10.00 mL) was added NaH (450 mg, 18.750 mmol, 60%) in portions at 0° C. and stirred at 0°

C. for 30 min, then MeI (1.01 g, 7.634 mmol) was added to the above mixture at 0° C. and stirred at room temperature for 1 hour. The reaction mixture was then quenched by the addition of water and extracted with ethyl acetate. The combined organic layers were washed with brine, dried over anhydrous sodium sulfate, filtered, and concentrated under vacuum. The residue was purified by flash chromatography on silica gel with 0-50% ethyl acetate in petroleum ether to afford 2-bromo-5-(2-methoxypropan-2-yl)pyridine (900 mg, 92.78%) as a white syrup. MS (ESI) calc'd for ($C_9H_{12}BrNO$) $(M+1)^+$, 230.0, found 230.0.

Step-2: methyl 5-(2-methoxypropan-2-yl)picolinate

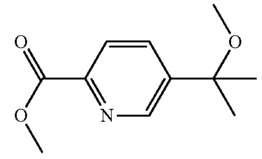

To a solution of 2-bromo-5-(2-methoxypropan-2-yl)pyridine (900 mg, 3.913 mmol) in MeOH (20 mL) were added TEA (1.2 g, 11.881 mmol) and Pd(dppf)$Cl_2$ (639 mg, 0.783 mmol). The resulting solution was stirred at 80° C. for 8 hours under carbon monoxide. The aqueous solution was concentrated under vacuum. The residue was purified by flash chromatography on silica gel with 0-50% ethyl acetate in petroleum ether to afford 5-(2-methoxypropan-2-yl)picolinate (615 mg, 68.3%) as a yellow oil. MS (ESI) calc'd for ($C_{11}H_{15}NO_3$) $(M+1)^+$, 210.1; found, 210.0.

Step-3: (5-(2-methoxypropan-2-yl)pyridin-2-yl)methanol

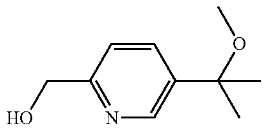

To a solution of 5-(2-methoxypropan-2-yl)picolinate (615 mg, 0.003 mol) in THF (10 mL) and MeOH (10 mL) was sequentially added $NaBH_4$ (112 mg, 0.003 mol) and $CaCl_2$) (323 mg, 0.003 mol) in portions at 0~5° C. The resulting mixture was stirred at room temperature for 2 h. The reaction mixture was then quenched by the addition of water and extracted with ethyl acetate. The combined organic layers were washed with brine, dried over anhydrous sodium sulfate, filtered, and concentrated under vacuum. The residue was purified by flash chromatography on silica gel with 0~10% methanol in dichloromethane to afford (5-(2-methoxypropan-2-yl)pyridin-2-yl)methanol (340 mg, 55%) as a yellow oil. MS (ESI) calc'd for ($C_{10}H_{15}NO_2$) $(M+1)^+$, 182.1; found, 182.2.

Step-4: 5-((5-(2-methoxypropan-2-yl)pyridin-2-yl)methoxy)-1,3,4-thiadiazol-2-amine

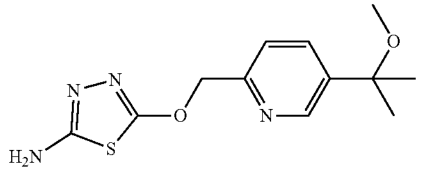 [SMILES: COC(C)(C)c1ccc(COc2nnc(N)s2)nc1]

To a solution of NaH (112 mg, 4.666 mmol, 60%) in THF (10 mL) was a solution of added (5-(2-methoxypropan-2-yl)pyridin-2-yl)methanol (340 mg, 1.868 mmol) in THF (2 mL) dropwise at 0~5° C. and stirred at 5° C. for 1 h. Then 5-bromo-1,3,4-thiadiazol-2-amine (401 mg, 2.240 mmol) was added to the mixture in small portions at 5° C. and stirred at 5° C. for 5 h. The reaction mixture was then quenched by the addition of water and extracted with ethyl acetate. The combined organic layers were washed with brine, dried over anhydrous sodium sulfate, filtered, and concentrated under vacuum. The residue was purified by flash chromatography on silica gel with 0~50% ethyl acetate in petroleum ether to afford 5-((5-(2-methoxypropan-2-yl)pyridin-2-yl)methoxy)-1,3,4-thiadiazol-2-amine (150 mg, 44.1%) as a yellow solid. MS (ESI) calc'd for ($C_{12}H_{16}N_4O_2S$) $(M+1)^+$, 281.1; found, 281.0.

Step-5: 4-(2-fluoro-6-methoxyphenyl)-N-(5-((5-(2-methoxypropan-2-yl)pyridin-2-yl)methoxy)-1,3,4-thiadiazol-2-yl)-6-methylnicotinamide

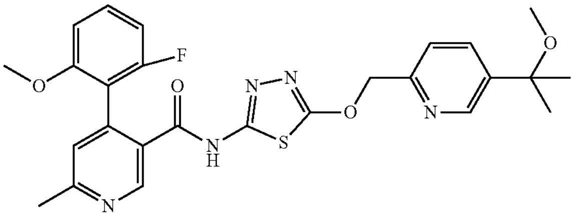 [SMILES: COc1cccc(F)c1-c1cc(C)ncc1C(=O)Nc1nnc(OCc2ccc(C(C)(C)OC)cn2)s1]

To a solution of 4-(2-fluoro-6-methoxyphenyl)-6-methylnicotinic acid (94 mg, 0.359 mmol, Intermediate F) in ACN (3 mL) and DMF (3 mL) were added NMI (89 mg, 1.085 mmol), 5-((5-(2-methoxypropan-2-yl)pyridin-2-yl)methoxy)-1,3,4-thiadiazol-2-amine (150 mg, 0.534 mmol) and TCFH (121 mg, 0.431 mmol). The mixture was stirred at room temperature for 2 h before concentrated under vacuum. The residue was purified by flash chromatography on silica gel with 0~10% methanol in dichloromethane and further purified by prep-HPLC with the following conditions: (Column: Sunfire prep C18 column, 30*150 mm, 5 um; Mobile Phase A: Water (0.1% FA), Mobile Phase B: ACN; Flow rate: 40 mL/min; Gradient: 25 B to 55 B in 8 min; 220 nm; RT1: 7.23 min) to afford 4-(2-fluoro-6-methoxyphenyl)-N-(5-((5-(2-methoxypropan-2-yl)pyridin-2-yl)methoxy)-1,3,4-thiadiazol-2-yl)-6-methylnicotinamide (18.7 mg, 12.8%) as a white solid. MS (ESI) calc'd for ($C_{26}H_{26}FN_5O_4S$) $(M+1)^+$, 524.2; found, 524.2. $^1H$ NMR (400 MHz, DMSO-$d_6$) δ 12.92 (s, 1H), 8.84 (s, 1H), 8.61-8.60 (m, 1H), 7.85-7.82 (m, 1H), 7.53-7.51 (m, 1H), 7.40-7.38 (m, 1H), 7.29 (s, 1H), 6.90-6.87 (m, 2H), 5.51 (s, 2H), 3.59 (s, 3H), 3.01 (s, 3H), 2.53 (s, 3H), 1.48 (s, 6H).

Example 81

5-(2-fluoro-6-methoxyphenyl)-N-(5-((5-(2-hydroxypropan-2-yl)pyridin-2-yl)methoxy)-1,3,4-thiadiazol-2-yl)pyridazine-4-carboxamide

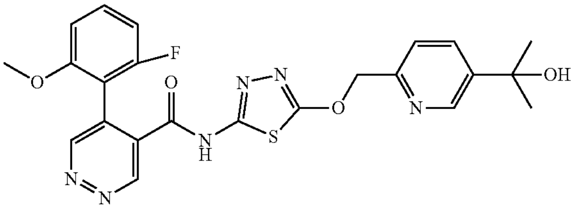 [SMILES: COc1cccc(F)c1-c1cnncc1C(=O)Nc1nnc(OCc2ccc(C(C)(C)O)cn2)s1]

To a solution of 5-(2-fluoro-6-methoxyphenyl)pyridazine-4-carboxylic acid (15 mg, 0.060 mmol, Example 64, Step 4) in DMF (1 mL) and MeCN (1 mL) were added 2-(6-(((5-amino-1,3,4-thiadiazol-2-yl)oxy)methyl)pyridin-3-yl)propan-2-ol (16 mg, 0.060 mmol, Example 33, Step 1), NMI (15 mg, 0.181 mmol) and TCFH (20 mg, 0.073 mmol). The mixture was purified by flash chromatography on silica gel with 0~10% methanol in dichloromethane and further purified by prep-HPLC with the following condition: (Column: XBridge Prep OBD C18 Column, 30×150 mm 5 um; Mobile Phase A: Water (10 MMOL/L $NH_4HCO_3$), Mobile Phase B: ACN; Flow rate: 60 mL/min; Gradient: 5 B to 30 B in 9 min; 220 nm; RT1: 8.88 min) to afford 5-(2-fluoro-6-methoxyphenyl)-N-(5-((5-(2-hydroxypropan-2-yl)pyridin-2-yl)methoxy)-1,3,4-thiadiazol-2-yl)pyridazine-4-carboxamide (2.5 mg, 8.1%) as a yellow solid. MS (ESI) calc'd for ($C_{23}H_{21}FN_6O_4S$) $(M+1)^+$, 497.2; found, 497.0. $^1H$ NMR (400 MHz, $CD_3OD$) δ 9.52 (s, 1H), 9.26 (s, 1H), 8.71 (s, 1H), 8.01-8.00 (m, 1H), 7.59-7.57 (m, 1H), 7.48-7.45 (m, 1H), 6.93-6.88 (m, 2H), 5.54 (s, 2H), 3.70 (s, 3H), 1.58 (s, 6H).

Example 82

N-(5-((5-(difluoromethoxy)pyridin-2-yl)methoxy)-1,3,4-thiadiazol-2-yl)-5'-methoxy-2',6-dimethyl-(4,4'-bipyridine)-3-carboxamide

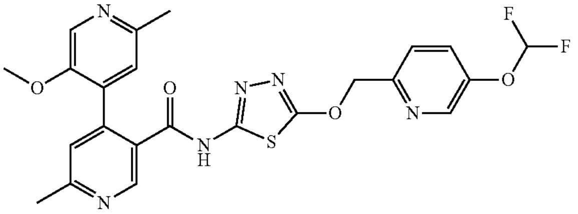 [SMILES: COc1cnc(C)cc1-c1cc(C)ncc1C(=O)Nc1nnc(OCc2ccc(OC(F)F)cn2)s1]

Step-1: methyl 5-(difluoromethoxy)picolinate

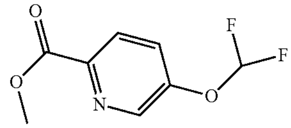

To a solution of methyl 5-hydroxypyridine-2-carboxylate (5 g, 32.651 mmol) in DMF (100 mL) were added $K_2CO_3$ (13.5 g, 97.970 mmol) and sodium 2-chloro-2,2-difluoroacetate (5 g, 32.795 mmol). The resulting solution was stirred at 80° C. for 4 h. The reaction mixture was quenched with water and extracted with ethyl acetate. The combined organic layers were washed with brine, dried over anhydrous sodium sulfate, filtered, and concentrated under vacuum. The residue was purified by flash chromatography on silica gel with 0-50% ethyl acetate in petroleum ether to afford methyl 5-(difluoromethoxy)picolinate (1.8 g, 45.6%) as a yellow oil. MS (ESI) calc'd for ($C_8H_7F_2NO_3$) $(M+1)^+$, 204.0; found, 204.0.

Step-2: (5-(difluoromethoxy)pyridin-2-yl)methanol

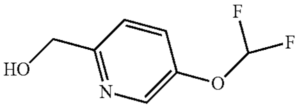 [SMILES: OCc1ccc(OC(F)F)cn1]

To a solution of methyl 5-(difluoromethoxy)pyridine-2-carboxylate (3.5 g, 17.229 mmol) in THF (10 mL) and EtOH (10 mL) were added $NaBH_4$ (0.65 g, 17.229 mmol) and $CaCl_2$) (1.91 g, 17.210 mmol) at 0° C. The resulting solution was stirred at room temperature for 4 h under nitrogen. The reaction mixture was quenched with water and extracted with ethyl acetate. The combined organic layers were washed with brine, dried over anhydrous sodium sulfate, filtered, and concentrated under vacuum to afford (5-(difluoromethoxy)pyridin-2-yl)methanol (3.1 g, 72.6%) as a yellow solid. MS (ESI) calc'd for ($C_7H_7F_2NO_2$) $(M+1)^+$, 176.0; found, 176.0.

Step-3: 5-((5-(difluoromethoxy)pyridin-2-yl)methoxy)-1,3,4-thiadiazol-2-amine

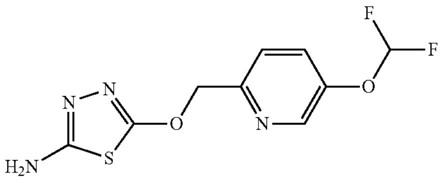 [SMILES: Nc1nnc(OCc2ccc(OC(F)F)cn2)s1]

To a solution of NaH (0.76 g, 31.670 mmol, 60%) in THF (10 mL) was added (5-(difluoromethoxy)pyridin-2-yl)methanol (3.1 g, 17.701 mmol) in portions at 0~5° C. and stirred at 5° C. for 1 h, then 5-bromo-1,3,4-thiadiazol-2-amine (3.82 g, 21.241 mmol) was added to the above mixture in small portions at 0° C., the mixture was stirred at room temperature for 12 h under nitrogen. The reaction mixture was quenched with water and extracted with ethyl acetate. The combined organic layers were washed with brine, dried over anhydrous sodium sulfate, filtered, and concentrated under vacuum. The residue was purified by flash chromatography on silica gel with 0~10% methanol in dichloromethane to afford 5-((5-(difluoromethoxy)pyridin-2-yl)methoxy)-1,3,4-thiadiazol-2-amine (1.8 g, 45.2%) as a yellow solid. MS (ESI) calc'd for ($C_9H_8F_2N_4O_2S$) $(M+1)^+$, 275.0; found, 275.0.

Step-4: N-(5-((5-(difluoromethoxy)pyridin-2-yl)methoxy)-1,3,4-thiadiazol-2-yl)-5'-methoxy-2',6-dimethyl-(4,4'-bipyridine-3-carboxamide

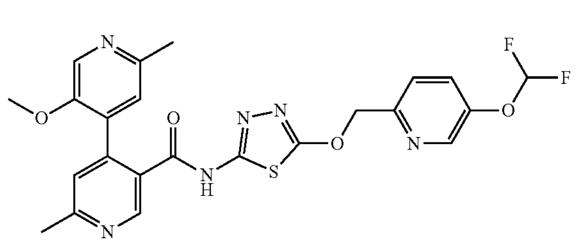 [SMILES: COc1cnc(C)cc1-c1cc(C)ncc1C(=O)Nc1nnc(OCc2ccc(OC(F)F)cn2)s1]

To a solution of 5-((5-(difluoromethoxy)pyridin-2-yl)methoxy)-1,3,4-thiadiazol-2-amine (300 mg, 1.094 mmol) in ACN (5 mL) and DMF (5 mL) were added 5'-methoxy-2',6-dimethyl-(4,4'-bipyridine)-3-carboxylic acid (282 mg, 1.094 mmol, Intermediate G), NMI (270 mg, 3.282 mmol) and TCFH (368 mg, 1.313 mmol). The resulting solution was stirred at room temperature for 2 h. The reaction mixture was quenched with water and extracted with ethyl acetate. The combined organic layers were washed with brine, dried over anhydrous sodium sulfate, filtered, and concentrated under vacuum. The residue was purified by flash chromatography on silica gel with 0~10% methanol in dichloromethane and further purification by following conditions: (Column: XSelect CSH Prep C18 OBD Column, 19*250 mm, 5 um; Mobile Phase A: Water (0.1% FA), Mobile Phase B: ACN; Flow rate: 25 mL/min; Gradient: 15 B to 40 B in 11 min, 40 B to B in min; 254 nm; RT1: 8 min) to afford N-(5-((5-(difluoromethoxy)pyridin-2-yl)methoxy)-1,3,4-thiadiazol-2-yl)-5'-methoxy-2',6-dimethyl-(4,4'-bipyridine)-3-carboxamide (22.8%, 10%) as a white solid. MS (ESI) calc'd for ($C_{23}H_{20}F_2N_6O_4S$) $(M+1)^+$, 515.1; found, 515.1. $^1H$ NMR (400 MHz, DMSO-$d_6$) δ 12.95 (s, 1H), 8.76 (s, 1H), 8.51 (s, 1H), 8.18 (s, 1H), 7.75 (s, 1H), 7.66 (s, 1H), 7.53 (s, 1H), 7.35 (s, 1H), 7.24 (s, 1H), 5.53 (s, 2H), 3.58 (s, 3H), 2.67 (s, 3H), 2.47 (s, 3H).

Example 83

N-(5-((5-(2-cyanopropan-2-yl)pyridin-2-yl)methoxy)-1,3,4-thiadiazol-2-yl)-5'-methoxy-2',6-dimethyl-(4,4'-bipyridine)-3-carboxamide

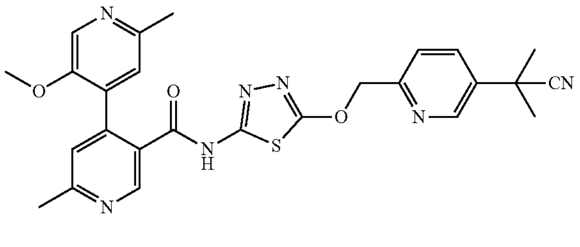

To a solution of 2-(6-(((5-amino-1,3,4-thiadiazol-2-yl)oxy)methyl)pyridin-3-yl)-2-methylpropanenitrile (10 mg, 0.036 mmol, Example 84, Step 1) in ACN (2 mL) and DMF (2 mL) were added 5'-methoxy-2',6-dimethyl-(4,4'-bipyridine)-3-carboxylic acid (10 mg, 0.036 mmol, Intermediate G), NMI (10 mg, 0.1 mmol) and TCFH (15 mg, 0.054 mmol). The mixture was stirred at room temperature for 2 h. The mixture was quenched with water and extracted with ethyl acetate. The combined organic layers were washed with brine, dried over anhydrous sodium sulfate, filtered, and concentrated under vacuum. The residue was purified by prep-HPLC with the following conditions: (Column: XBridge Prep OBD C18 Column, 30×150 mm 5 um; Mobile Phase A: Water (10 MMOL/L $NH_4HCO_3$), Mobile Phase B: ACN; Flow rate: 60 mL/min; Gradient: 20 B to 40 B in 7 min; 220 nm) to afford N-(5-((5-(2-cyanopropan-2-yl)pyridin-2-yl)methoxy)-1,3,4-thiadiazol-2-yl)-5'-methoxy-2',6-dimethyl-(4,4'-bipyridine)-3-carboxamide (6.5 mg, 36.3%) as a white solid. MS (ESI) calc'd for ($C_{26}H_{25}N_7O_3S$) $(M+1)^+$, 516.2; found 516.2. $^1H$ NMR (400 MHz, DMSO-$d_6$) δ 12.92 (s, 1H), 8.77 (s, 2H), 8.18 (s, 1H), 8.02-8.00 (m, 1H), 7.62-7.59 (m, 1H), 7.33 (s, 1H), 7.23 (s, 1H), 5.55 (s, 2H), 3.58 (s, 3H), 2.51 (s, 3H), 2.46 (s, 3H), 1.74 (s, 6H).

Example 84

2'-chloro-N-(5-((5-(2-cyanopropan-2-yl)pyridin-2-yl)methoxy)-1,3,4-thiadiazol-2-yl)-5'-methoxy-6-methyl-(4,4'-bipyridine)-3-carboxamide

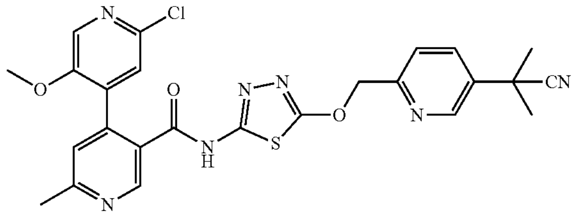 [SMILES: COc1cnc(Cl)cc1-c1cc(C)ncc1C(=O)Nc1nnc(OCc2ccc(C(C)(C)C#N)cn2)s1]

Step-1: 2-(6-chloropyridin-3-yl)-2-methylpropanenitrile

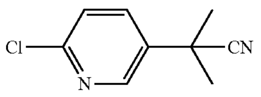

To a solution of NaOH (10 g) in $H_2O$ (10.00 mL) were added TEBAC (227.00 mg, 0.98 mmol), 2-(6-chloropyridin-3-yl)acetonitrile (5 g, 32.8 mmol) and MeI (6.7 g, 36 mmol). The resulting mixture was stirred at 50° C. for 5 h. The mixture was diluted with water and extracted with ethyl acetate. The combined organic layers were washed with brine, dried over anhydrous sodium sulfate, filtered, and concentrated under vacuum. The residue was purified by flash chromatography on silica gel with 0-50% ethyl acetate in petroleum ether to afford 2-(6-chloropyridin-3-yl)-2-methylpropanenitrile (2.6 g, 44%) as a yellow solid. MS (ESI) calc'd for ($C_9H_9ClN_2$) $(M+1)^+$, 181.0, found 181.0.

Step-2: 2-methyl-2-(6-vinylpyridin-3-yl)propanenitrile

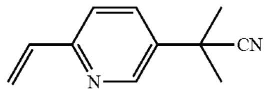

To a solution of 2-(6-chloropyridin-3-yl)-2-methylpropanenitrile (2.6 g, 14.4 mmol) in Dioxane (10 mL) and water (1 mL) were added Potassium Vinyl trifluoroborate (2873 mg, 21.6 mmol), $K_2CO_3$ (5.98 g, 43.3 mmol) and Pd(dppf) $Cl_2$ (1.14 g, 1.4 mmol) under nitrogen. The mixture was stirred at 80° C. for 5 h under nitrogen. The reaction mixture was concentrated under vacuum. The residue was purified by flash chromatography on silica gel with 0-50% ethyl acetate in petroleum ether to afford 2-methyl-2-(6-vinylpyridin-3-yl)propanenitrile (1.5 g, 60%) as a yellow solid. MS (ESI) calc'd for ($C_{11}H_{12}N_2$) $(M+1)^+$, 173.1, found 173.1.

Step-3: 2-(6-formylpyridin-3-yl)-2-methylpropanenitrile

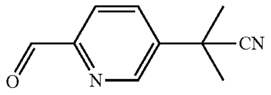

To a solution of 2-methyl-2-(6-vinylpyridin-3-yl)propanenitrile (1.5 g, 8.62 mmol) in THF (30 mL) and $H_2O$ (10 mL) were added $OsO_4$ (219 mg, 0.86 mmol) and $NaOI_4$ (7.4 g, 34.4 mmol). The mixture was stirred at room temperature for 5 h. The mixture was diluted with water and extracted with ethyl acetate. The combined organic layers were washed with brine, dried over anhydrous sodium sulfate, filtered, and concentrated under vacuum. The residue was purified by flash chromatography on silica gel with 0~10% methanol in dichloromethane to afford 2-(6-formylpyridin-3-yl)-2-methylpropanenitrile (680 mg, 66.6%) as a red solid. MS (ESI) calc'd for ($C_{10}H_{10}N_{20}$) $(M+1)^+$, 175.1 found 175.1.

Step-4: 2-(6-(hydroxymethyl)pyridin-3-yl)-2-methylpropanenitrile

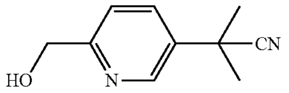

To a solution of 2-(6-formylpyridin-3-yl)-2-methylpropanenitrile (680 mg, 3.84 mmol) in MeOH (10 mL) was added $NaBH_4$ (146 mg, 3.84 mmol) slowly at 0° C. The mixture was stirred at room temperature for 2 h. The reaction mixture was quenched by the addition of water and extracted with ethyl acetate. The combined organic layers were washed with brine, dried over anhydrous sodium sulfate, filtered, and concentrated under vacuum to afford 2-(6-(hydroxymethyl)pyridin-3-yl)-2-methylpropanenitrile (620 mg, 91%) as a yellow oil. MS (ESI) calc'd for ($C_{10}H_{12}1N_2O$) $(M+1)^+$, 177.7, found 177.1.

Step-5: 2-(6-(((5-amino-1,3,4-thiadiazol-2-yl)oxy)methyl)pyridin-3-yl)-2-methylpropanenitrile

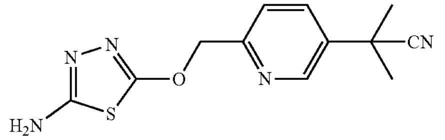 [SMILES: CC(C)(C#N)c1ccc(COc2nnc(N)s2)nc1]

To a solution of NaH (210 mg, 5.2 mmol, 60% purity) in THF (10.00 mL) was added a solution of 2-(6-(hydroxymethyl)pyridin-3-yl)-2-methylpropanenitrile (619 mg, 3.5 mmol) in THF (2 mL) dropwise at 0° C. and stirred at 0° C. for 1 h under nitrogen. To the above solution was added 5-bromo-1,3,4-thiadiazol-2-amine (623 mg, 3.5 mmol) at 0° C. under nitrogen. The mixture was stirred at room temperature for 4 h. The reaction mixture was quenched by the addition of water and extracted with ethyl acetate. The combined organic layers were washed with brine, dried over anhydrous sodium sulfate, filtered, and concentrated under vacuum. The residue was purified by flash chromatography on silica gel with 0-50% ethyl acetate in petroleum ether to afford 2-(6-(((5-amino-1,3,4-thiadiazol-2-yl)oxy)methyl)pyridin-3-yl)-2-methylpropanenitrile (420 mg, 43%) as a yellow solid. MS (ESI) calc'd for ($Cl_2H_{13}N_5OS$) $(M+1)^+$, 276.1, found 276.0.

Step-6: 2'-chloro-N-(5-((5-(2-cyanopropan-2-yl)pyridin-2-yl)methoxy)-1,3,4-thiadiazol-2-yl)-5'-methoxy-6-methyl-(4,4'-bipyridine)-3-carboxamide

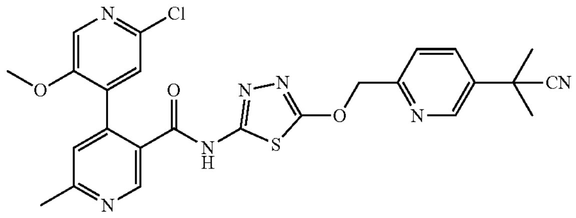

To a solution of 2-(6-(((5-amino-1,3,4-thiadiazol-2-yl)oxy)methyl)pyridin-3-yl)-2-methylpropanenitrile (50 mg, 0.18 mmol) in ACN (5.0 mL) were added 2'-chloro-5'-methoxy-6-methyl-(4,4'-bipyridine)-3-carboxylic acid (51 mg, 0.18 mmol), NMI (44 mg, 0.54 mmol) and TCFH (76 mg, 0.27 mmol). The resulting mixture was stirred at room temperature for 2 h. The mixture was diluted with water and extracted with ethyl acetate. The combined organic layers were washed with brine, dried over anhydrous sodium sulfate, filtered, and concentrated under vacuum. The residue was purified by flash chromatography on silica gel with 0~10% methanol in dichloromethane and further purified by prep-HPLC with the following conditions: (Column: XBridge Prep OBD C18 Column, 30×150 mm 5 um; Mobile Phase A: Water (10 MMOL/L $NH_4HCO_3$), Mobile Phase B: ACN; Flow rate: 60 mL/min; Gradient: 20 B to 45 B in 8 min; 220 nm) to afford 2'-chloro-N-(5-((5-(2-cyanopropan-2-yl)pyridin-2-yl)methoxy)-1,3,4-thiadiazol-2-yl)-5'-methoxy-6-methyl-(4,4'-bipyridine)-3-carboxamide (23 mg, 23.7%) as a white solid. MS (ESI) calc'd for ($C_{25}H_{22}ClN_7O_3S$) $(M+1)^+$, 536.1; found 536.1. $^1H$ NMR (400 MHz, DMSO-$d_6$) δ 12.96 (s, 1H), 8.81-8.77 (s, 2H), 8.17 (s, 1H), 8.03-8.00 (m, 1H), 7.62-7.60 (m, 1H), 7.53 (s, 1H), 7.42 (s, 1H), 5.56 (s, 2H), 3.63 (s, 3H), 2.67 (s, 3H), 1.74 (s, 6H).

Example 85

N-(5-((5-chloropyridin-2-yl)methoxy)-1,3,4-thiadiazol-2-yl)-2'-cyano-3'-methoxy-6-methyl-[4,4'-bipyridine]-3-carboxamide

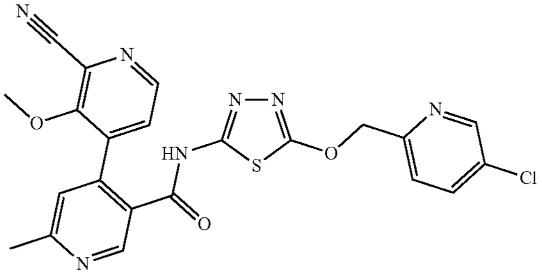 [SMILES: COc1c(-c2cc(C)ncc2C(=O)Nc2nnc(OCc3ccc(Cl)cn3)s2)ccnc1C#N]

Step-1: methyl 2-cyano-3-methoxy-6-methyl-(4,4-bipyridine)-3-carboxylate

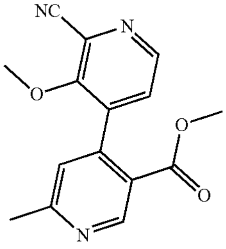

To a degassed solution of methyl 2-chloro-3-methoxy-6-methyl-(4,4-bipyridine)-3-carboxylate (170 mg, 0.58 mmol) and $Zn(CN)_2$ (136 mg, 1.16 mmol) in N-Methyl pyrrolidone (1 mL) were added Zn (17 mg, 0.26 mmol), $Pd_2(dba)_3$ (53 mg, 0.06 mmol) and dppf (4 mg, 0.01 mmol). The resulting mixture was stirred at 120° C. for overnight. The resulting mixture was quenched with water and extracted with ethyl acetate. The combined organic layers were washed with brine, dried over anhydrous $Na_2SO_4$. After filtration, the filtrate was concentrated under reduced pressure. The residue was purified by silica gel column chromatography, eluted with 0-60% ethyl acetate in ethyl acetate to afford methyl 2-cyano-3-methoxy-6-methyl-(4,4-bipyridine)-3-carboxylate (90 mg, 49.2%) as a yellow solid. MS (ESI) calculated for ($C_{15}H_{13}N_3O_3$) $(M+1)^+$, 284.1; found, 284.1.

Step-2: 2-cyano-3-methoxy-6-methyl-(4,4-bipyridine)-3-carboxylic acid

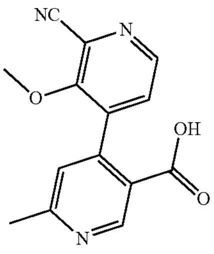 [SMILES: COc1c(-c2cc(C)ncc2C(=O)O)ccnc1C#N]

To a stirred solution of methyl 2-cyano-3-methoxy-6-methyl-(4,4-bipyridine)-3-carboxylate (85 mg, 0.30 mmol) in tetrahydrofuran (1 mL) were added LiOH (14 mg, 0.60 mmol) and water (1 mL). The resulting mixture was stirred at 80° C. for 1 h. The residue was acidified to pH 5-6 with citric acid. The resulting mixture was extracted with ethyl acetate. The combined organic layers were washed with brine, dried over anhydrous $Na_2SO_4$. After filtration, the filtrate was concentrated under reduced pressure to afford 2-cyano-3-methoxy-6-methyl-(4,4-bipyridine)-3-carboxylic acid (60 mg, crude) as a white solid. MS (ESI) calculated for ($C_{14}HnN_3O_3$) $(M+1)^+$, 293.1; found, 293.1.

Step-3: N-(5-((5-chloropyridin-2-yl)methoxy)-1,3,4-thiadiazol-2-yl)-2'-cyano-3'-methoxy-6-methyl-[4,4'-bipyridine]-3-carboxamide

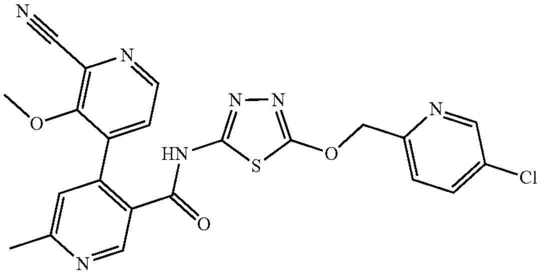 [SMILES: COc1c(-c2cc(C)ncc2C(=O)Nc2nnc(OCc3ccc(Cl)cn3)s2)ccnc1C#N]

To a stirred solution of 2-cyano-3-methoxy-6-methyl-(4,4-bipyridine)-3-carboxylic acid (66 mg, 0.24 mmol) and 5-((5-chloropyridin-2-yl)methoxy)-1,3,4-thiadiazol-2-amine (59 mg, 0.24 mmol, Intermediate C) in acetonitrile (1 mL) were added TCFH (76 mg, 0.27 mmol) and NMI (60 mg, 0.73 mmol). The resulting mixture was stirred at room temperature for 2 h. The residue was purified by Prep-HPLC with the following conditions: (Column: XBridge Prep OBD C18 Column, 30×150 mm 5 um; Mobile Phase A: Water (10 MMOL/L $NH_4HCO_3$), Mobile Phase B: acetonitrile; Flow rate: 607 mL/min; Gradient: 15 B to 40 B in 7 min; 220 nm; RT1:7.38 min) to afford N-(5-((5-chloropyridin-2-yl)methoxy)-1,3,4-thiadiazol-2-yl)-2'-cyano-3'-methoxy-6-methyl-[4,4'-bipyridine]-3-carboxamide (44.5 mg, 35.5%) as a white solid. MS (ESI) calculated for ($C_{22}H_{16}ClN_7O_3S$) $(M+1)^+$, 494.1; found, 494.2. $^1H$ NMR (400 MHz, DMSO-$d_6$) δ 13.18 (s, 1H), 8.96 (s, 1H), 8.68-8.63 (m, 1H), 8.58 (d, J=4.8 Hz, 1H), 8.04-7.97 (m, 1H), 7.75 (d, J=4.8 Hz, 1H), 7.61 (d, J=8.4 Hz, 1H), 7.46 (s, 1H), 5.55 (s, 2H), 3.64 (s, 3H), 2.62 (s, 3H).

Example 86

2'-chloro-5'-methoxy-6-methyl-N-(5-((5-(3-methyloxetan-3-yl)pyridin-2-yl)methoxy)-1,3,4-thiadiazol-2-yl)-[4,4'-bipyridine]-3-carboxamide

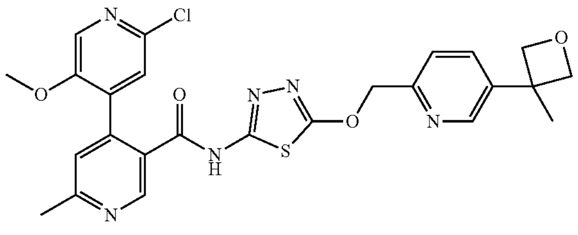 [SMILES: COc1cnc(Cl)cc1-c1cc(C)ncc1C(=O)Nc1nnc(OCc2ccc(C3(C)COC3)cn2)s1]

To a stirred solution of 5-((5-(3-methyloxetan-3-yl)pyridin-2-yl)methoxy)-1,3,4-thiadiazol-2-amine (40 mg, 0.14 mmol, Example 140, Step7) and 2'-chloro-5'-methoxy-6-methyl-(4,4'-bipyridine)-3-carboxylic acid (40 mg, 0.14 mmol, Intermediate H) in MeCN (1 mL) were added NMI (47 mg, 0.57 mmol) and TCFH (60 mg, 0.22 mmol). The resulting mixture was stirred at room temperature for 1 h. The resulting mixture was purified by prep-HPLC with the following conditions: (Column: Xselect CSH F-Phenyl OBD column, 19*250 mm, 5 um; Mobile Phase A: Water (0.1% FA), Mobile Phase B: ACN; Flow rate: 25 mL/min; Gradient: 3% B to 30% B in 7 min, 30% B; Wave Length: 254 nm; RT1 (min)) to afford 2'-chloro-5'-methoxy-6-methyl-N-(5-((5-(3-methyloxetan-3-yl)pyridin-2-yl)methoxy)-1,3,4-thiadiazol-2-yl)-[4,4'-bipyridine]-3-carboxamide (16.7 mg, 21%) as a white solid. MS (ESI) calc'd for ($C_{25}H_{23}ClN_6O_4S$) $(M+1)^+$, 539.0; found 539.0. $^1H$ NMR (400 MHz, DMSO-$d_6$) δ 12.93 (s, 1H), 8.81 (s, 1H), 8.59-8.49 (m, 1H), 8.16 (s, 1H), 7.84-7.74 (m, 1H), 7.58-7.50 (m, 2H), 7.44 (s, 1H), 5.54 (s, 2H), 4.84 (d, J=5.6 Hz, 2H), 4.58 (d, J=5.6 Hz, 2H), 3.64 (s, 3H), 2.59 (s, 3H), 2.08 (s, 1H), 1.67 (s, 3H).

Example 87

N-(5-((3-fluoro-5-(2-hydroxypropan-2-yl)pyridin-2-yl)methoxy)-1,3,4-thiadiazol-2-yl)-4-(2-fluoro-6-methoxyphenyl)-6-methylpyridine-3-carboxamide

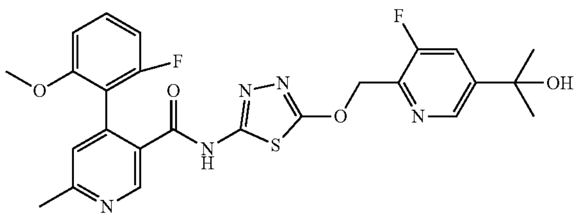 [SMILES: COc1cccc(F)c1-c1cc(C)ncc1C(=O)Nc1nnc(OCc2ncc(C(C)(C)O)cc2F)s1]

Step-1: (5-bromo-3-fluoropyridin-2-yl)methanol

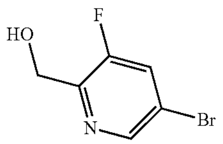

To a stirred solution of 5-bromo-3-fluoropyridine-2-carboxylic acid (3 g, 13.63 mmol) in THF (30 mL) was added $BH_3$·THF (68 mL, 67.99 mmol) dropwise at 0° C. The resulting mixture was stirred at room temperature for 5 h. The reaction was quenched by the addition of water at room temperature and extracted with ethyl acetate. The combined organic layers were washed with brine, dried over anhydrous sodium sulfate, filtered, and concentrated under vacuum. The residue was purified by flash column chromatography with 0-80% ethyl acetate in petroleum ether to afford (5-bromo-3-fluoropyridin-2-yl)methanol (1.5 g, 52%) as a colorless oil. MS (ESI) calc'd for ($C_6H_5BrFNO$) $(M+1)^+$, 206.0; found 206.0.

Step-2: (5-(1-ethoxyethenyl)-3-fluoropyridin-2-yl) methanol

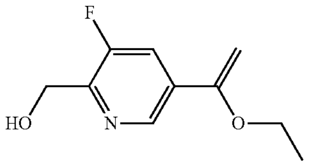

To a stirred solution of (5-bromo-3-fluoropyridin-2-yl) methanol (1.0 g, 4.85 mmol) and tributyl(1-ethoxyethenyl) stannane (1.75 g, 4.85 mmol) in Toluene (10 mL) were added tributyl(1-ethoxyethenyl)stannane(3.51 g, 0.01 mmol) and $Pd(PPh_3)_2Cl_2$ (0.34 g, 0.48 mmol). The resulting mixture was stirred at 100° C. for 2 h under nitrogen atmosphere. The resulting mixture was filtered, the filtrate was concentrated under reduced pressure. The residue was purified by flash column chromatography with 0-50% ethyl acetate in petroleum ether to afford (5-(1-ethoxyethenyl)-3-fluoropyridin-2-yl)methanol (470 mg, 49%) as a green oil. MS (ESI) calc'd for ($C_{10}H_{12}FNO_2$) $(M+1)^+$, 198.1; found 198.1.

Step-3: ((5-(1-ethoxyethenyl)-3-fluoropyridin-2-yl) methoxy)(methylsulfanyl)methanethione

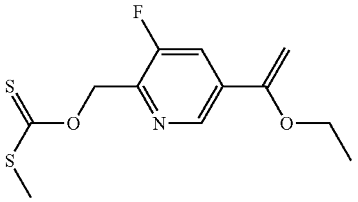 [SMILES: C=C(OCC)c1cnc(COC(=S)SC)c(F)c1]

To a stirred solution of NaH (112 mg, 4.66 mmol, 60%) in THF (3 mL) was added a solution of (5-(1-ethoxyethenyl)-3-fluoropyridin-2-yl)methanol (460 mg, 2.33 mmol) in THF (1 mL) and stirred at 0° C. for 30 min under nitrogen atmosphere. To the above mixture was added $CS_2$ (266 mg, 3.50 mmol) at 0° C. and stirred for 20 min. Then MeI (496 mg, 3.50 mmol) was added to the above mixture at 0° C. The resulting mixture was stirred at room temperature for 1 h under nitrogen atmosphere. The reaction mixture was quenched with water and extracted with ethyl acetate. The combined organic layers were washed with brine, dried over anhydrous sodium sulfate, filtered, and concentrated under vacuum. The residue was purified by reverse phase flash column chromatography with 50~100% acetonitrile in water to afford ((5-(1-ethoxyethenyl)-3-fluoropyridin-2-yl) methoxy)(methylsulfanyl)methanethione (150 mg, 22%) as a yellow solid. MS (ESI) calc'd for ($C_{12}H_{14}FNO_2S_2$) $(M+1)^+$, 288.0; found 288.0.

Step-4: ((((5-(1-ethoxyethenyl)-3-fluoropyridin-2-yl) methoxy)methanethioyl)amino)amine

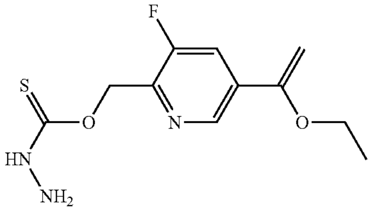 [SMILES: C=C(OCC)c1cnc(COC(=S)NN)c(F)c1]

To a stirred solution of ((5-(1-ethoxyethenyl)-3-fluoropyridin-2-yl)methoxy)(methylsulfanyl)methanethione (150 mg, 0.52 mmol) in MeOH (3 mL) was added $NH_2NH_2 \cdot H_2O$ (26 mg, 0.52 mmol) at 0° C. under nitrogen atmosphere. The mixture resulting was stirred at 0° C. for 1 h under nitrogen atmosphere. The reaction mixture was diluted with water and extracted with ethyl acetate. The combined organic layers were washed with brine, dried over anhydrous sodium sulfate, filtered, and concentrated under vacuum to afford ((((5-(1-ethoxyethenyl)-3-fluoropyridin-2-yl)methoxy) methanethioyl)amino)amine (100 mg, crude) as a yellow oil. MS (ESI) calc'd for ($C_{11}H_{14}FN_3O_2S$) $(M+1)^+$, 272.1; found, 272.1.

Step-5: 5-((5-(1-ethoxyethenyl)-3-fluoropyridin-2-yl)methoxy)-1,3,4-thiadiazol-2-amine

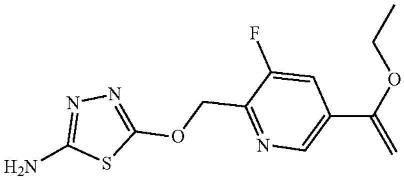 [SMILES: C=C(OCC)c1cnc(COc2nnc(N)s2)c(F)c1]

To a stirred solution of ((((5-(1-ethoxyethenyl)-3-fluoropyridin-2-yl)methoxy)methanethioyl)amino)amine (100 mg, 0.37 mmol) and TEA (74 mg, 0.74 mmol) in MeOH (2 mL) was added BrCN (42 mg, 0.41 mmol) at 0° C. under nitrogen atmosphere. The mixture resulting was stirred at 0° C. for 1 h under nitrogen atmosphere. The reaction mixture was quenched with water and extracted with ethyl acetate. The combined organic layers were washed with brine, dried over anhydrous sodium sulfate, filtered, and concentrated under vacuum to afford 5-((5-(1-ethoxyethenyl)-3-fluoropyridin-2-yl)methoxy)-1,3,4-thiadiazol-2-amine (90 mg, crude) as a yellow solid. MS (ESI) calc'd for ($C_{12}H_{13}FN_4O_2S$) $(M+1)^+$, 297.1; found, 297.1.

Step-6: 1-(6-(((5-amino-1,3,4-thiadiazol-2-yl)oxy) methyl)-5-fluoropyridin-3-yl)ethenone

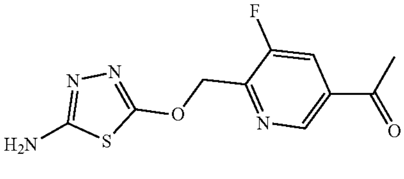 [SMILES: CC(=O)c1cnc(COc2nnc(N)s2)c(F)c1]

A solution of 5-((5-(1-ethoxyethenyl)-3-fluoropyridin-2-yl)methoxy)-1,3,4-thiadiazol-2-amine (90 mg, 0.31 mmol) in HCl (4 M in dioxane, 3 mL) and $CH_3OH$ (2 mL) was stirred at room temperature for 30 min under nitrogen atmosphere. The reaction mixture was quenched with water and extracted with ethyl acetate. The combined organic layers were washed with brine, dried over anhydrous sodium sulfate, filtered, and concentrated under vacuum to afford 1-(6-(((5-amino-1,3,4-thiadiazol-2-yl)oxy)methyl)-5-fluoropyridin-3-yl)ethanone (90 mg, crude) as a yellow solid. MS (ESI) calc'd for ($C_{10}H_9FN_4O_2S$) $(M+1)^+$, 269.0; found 269.0.

Step-7: N-(5-((5-acetyl-3-fluoropyridin-2-yl) methoxy)-1,3,4-thiadiazol-2-yl)-4-(2-fluoro-6-methoxyphenyl)-6-methylpyridine-3-carboxamide

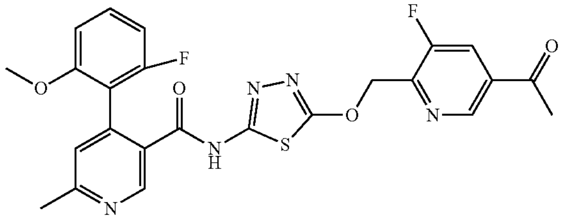 [SMILES: COc1cccc(F)c1-c1cc(C)ncc1C(=O)Nc1nnc(OCc2ncc(C(C)=O)cc2F)s1]

To a stirred solution of 1-(6-(((5-amino-1,3,4-thiadiazol-2-yl)oxy)methyl)-5-fluoropyridin-3-yl)ethanone (80 mg, 0.29 mmol) and 4-(2-fluoro-6-methoxyphenyl)-6-methylnicotinic acid (75 mg, 0.29 mmol, Intermediate F) in ACN (2 mL) were added NMI (97 mg, 1.19 mmol) and TCFH (125 mg, 0.45 mmol). The residue was purified by reverse phase flash chromatography with the 5~50% acetonitrile in water to afford N-(5-((5-acetyl-3-fluoropyridin-2-yl)methoxy)-1,3,4-thiadiazol-2-yl)-4-(2-fluoro-6-methoxyphenyl)-6-methylpyridine-3-carboxamide (50 mg, 32%) as a yellow solid. MS (ESI) calc'd for ($C_{24}H_{19}F_2N_5O_4S$) $(M+1)^+$, 512.1; found 512.1.

Step-8: N-(5-((3-fluoro-5-(2-hydroxypropan-2-yl) pyridin-2-yl)methoxy)-1,3,4-thiadiazol-2-yl)-4-(2-fluoro-6-methoxyphenyl)-6-methylpyridine-3-carboxamide

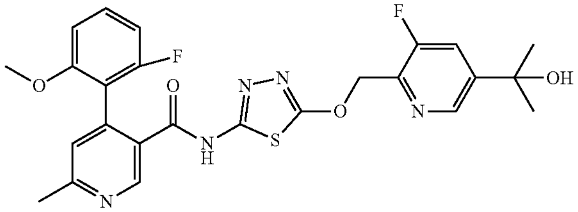 [SMILES: COc1cccc(F)c1-c1cc(C)ncc1C(=O)Nc1nnc(OCc2ncc(C(C)(C)O)cc2F)s1]

To a stirred solution of N-(5-((5-acetyl-3-fluoropyridin-2-yl)methoxy)-1,3,4-thiadiazol-2-yl)-4-(2-fluoro-6-methoxyphenyl)-6-methylpyridine-3-carboxamide (32 mg, 0.06 mmol) in THF (2 mL) was added MeMgBr (0.3 mL, 0.30 mmol, 1M in THF) dropwise at 0° C. under nitrogen atmosphere. The resulting mixture was stirred at 0° C. for 2 h under nitrogen atmosphere. The reaction mixture was quenched with water and extracted with ethyl acetate. The combined organic layers were washed with brine, dried over anhydrous sodium sulfate, filtered, and concentrated under vacuum. The crude product was purified by prep-HPLC with the following conditions: (Column: XBridge Prep OBD C18 Column, 30×150 mm 5 um; Mobile Phase A: Water (10 MMOL/L $NH_4HCO_3$), Mobile Phase B: ACN; Flow rate: 60 mL/min; Gradient: 25 B to 40 B in 8 min; 254/220 nm; RT1: 7.95 min) to afford N-(5-((3-fluoro-5-(2-hydroxypropan-2-yl)pyridin-2-yl)methoxy)-1,3,4-thiadiazol-2-yl)-4-(2-fluoro-6-methoxyphenyl)-6-methylpyridine-3-carboxamide (2.0 mg, 7%) as a white solid. MS (ESI) calc'd for ($C_{25}H_{23}F_2N_5O_4S$) $(M+1)^+$, 528.1; found 528.4. $^1H$ NMR (400 MHz, DMSO-$d_6$) δ 12.91 (s, 1H), 8.82 (s, 1H), 8.57-8.56 (m, J=1.6 Hz, 1H), 7.84-7.74 (m, 1H), 7.43-7.36 (m, 1H), 7.32 (s, 1H), 6.96-6.86 (m, 2H), 5.57 (s, 2H), 5.42 (s, 1H), 3.59 (s, 3H), 2.57 (s, 3H), 1.47 (s, 6H).

Example 88

N-(5-((5-(2-cyanopropan-2-yl)pyridin-2-yl)methoxy)-1,3,4-thiadiazol-2-yl)-4-(2-fluoro-6-methoxyphenyl)-6-methylnicotinamide

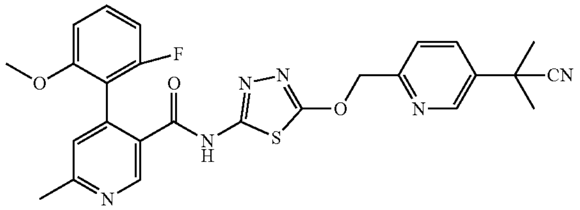 [SMILES: COc1cccc(F)c1-c1cc(C)ncc1C(=O)Nc1nnc(OCc2ccc(C(C)(C)C#N)cn2)s1]

To a solution of 2-(6-(((5-amino-1,3,4-thiadiazol-2-yl)oxy)methyl)pyridin-3-yl)-2-methylpropanenitrile (50 mg, 0.18 mmol, Example 84, Step 5) in ACN (5.0 mL) were added 4-(2-fluoro-6-methoxyphenyl)-6-methylpyridine-3-carboxylic acid (50.00 mg, 0.191 mmol, Intermediate F), NMI (44 mg, 0.54 mmol) and TCFH (76 mg, 0.27 mmol). The resulting mixture was stirred at room temperature for 2 h. The mixture was diluted with water and extracted with ethyl acetate. The combined organic layers were washed with brine, dried over anhydrous sodium sulfate, filtered, and concentrated under vacuum. The residue was purified by reverse phase flash chromatography with 5-60% acetonitrile in water to afford N-(5-((5-(2-cyanopropan-2-yl)pyridin-2-yl)methoxy)-1,3,4-thiadiazol-2-yl)-4-(2-fluoro-6-methoxyphenyl)-6-methylnicotinamide (30 mg, 30%) as a white solid. MS (ESI) calc'd for ($C_{26}H_{23}FN_6O_3S$) $(M+1)^+$, 519.2; found 519.2. $^1H$ NMR (400 MHz, DMSO-$d_6$) δ 12.92 (s, 1H), 8.82 (s, 1H), 8.77-8.76 (m, 1H), 8.02-7.99 (m, 1H), 7.61-7.59 (m, 1H), 7.43-7.37 (m, 1H), 7.31 (s, 1H), 6.93-6.88 (m, 2H), 5.55 (s, 2H), 3.59 (s, 3H), 2.56 (s, 3H), 1.74 (s, 6H).

Example 89

N-(5-((5-(2-hydroxypropan-2-yl)pyridin-2-yl)methoxy)-1,3,4-thiadiazol-2-yl)-2',6-dimethyl-(4,4'-bipyridine)-3-carboxamide

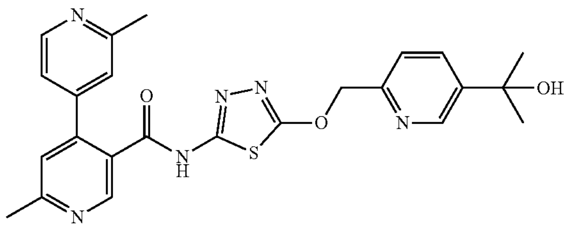 [SMILES: Cc1cc(-c2cc(C)ncc2C(=O)Nc2nnc(OCc3ccc(C(C)(C)O)cn3)s2)ccn1]

Step-1: methyl 2',6-dimethyl-(4,4'-bipyridine)-3-carboxylate

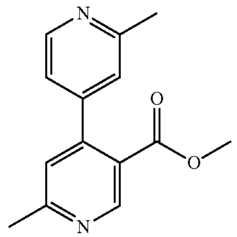

To a degassed solution of methyl 4-chloro-6-methylnicotinate (300 mg, 1.6 mmol) in Dioxane (5 mL) and water (1 mL) were added (2-methylpyridin-4-yl)boronic acid (219 mg, 1.6 mmol), $K_2CO_3$ (662 mg, 4.8 mmol) and Pd(dppf)$Cl_2$ (130 mg, 0.16 mmol). The resulting mixture was stirred at 80° C. for 5 hours under nitrogen. The reaction mixture was concentrated under vacuum. The residue was purified by flash chromatography on silica gel with 0~50% ethyl acetate in petroleum ether to afford methyl 2',6-dimethyl-(4,4'-bipyridine)-3-carboxylate (305 mg, 78%) as a yellow solid. MS (ESI) calc'd for ($C_{14}H_{14}N_2O_2$) $(M+1)^+$, 243.1, found 243.1.

Step-2: 2',6-dimethyl-(4,4'-bipyridine)-3-carboxylic acid

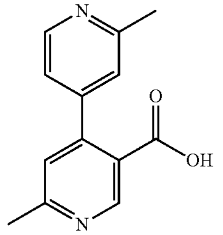 [SMILES: Cc1cc(-c2cc(C)ncc2C(=O)O)ccn1]

To a solution of methyl 2',6-dimethyl-(4,4'-bipyridine)-3-carboxylate (305 mg, 1.26 mmol) in MeOH (5 mL) and $H_2O$ (1 mL) was added NaOH (70 mg, 1.26 mmol). The mixture was stirred 70° C. for 2 hours. The aqueous solution was acidified with HCl (2 N) to pH 5-6. The aqueous solution was extracted with ethyl acetate. The organic layers were combined, washed with brine, dried over anhydrous sodium sulfate and filtered. The filtrate was concentrated under vacuum to afford 2',6-dimethyl-(4,4'-bipyridine)-3-carboxylic acid (170 mg, 60%) as a yellow solid. MS (ESI) calc'd for ($C_{13}H_{12}N_2O_2$) $(M+1)^+$, 229.1, found 229.1.

Step-3: N-(5-((5-(2-hydroxypropan-2-yl)pyridin-2-yl)methoxy)-1,3,4-thiadiazol-2-yl)-2',6-dimethyl-(4,4'-bipyridine)-3-carboxamide

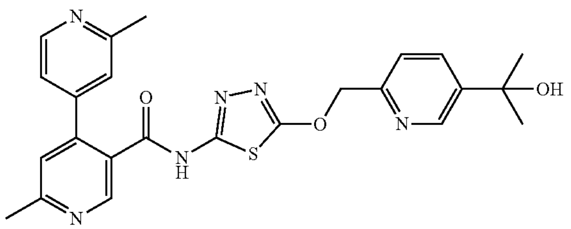

To a solution of 2',6-dimethyl-(4,4'-bipyridine)-3-carboxylic acid (170 mg, 0.75 mmol) in ACN (5 mL) were added N-(5-((5-(2-hydroxypropan-2-yl)pyridin-2-yl)methoxy)-1,3,4-thiadiazol-2-yl)-2',6-dimethyl-(4,4'-bipyridine)-3-carboxamide (199 mg, 0.75 mmol), NMI (184 mg, 2.25 mmol) and TCFH (315 mg, 1.125 mmol). The mixture was stirred at room temperature for 2 h. The mixture was quenched with water and extracted with ethyl acetate. The combined organic layers were washed with brine, dried over anhydrous sodium sulfate, filtered, and concentrated under vacuum. The residue was purified by flash chromatography on silica gel with 0~10% methanol in dichloromethane and further purified by prep-HPLC with the following conditions: (Column: XBridge Prep OBD C18 Column, 30×150 mm 5 um; Mobile Phase A: Water (10 MMOL/L $NH_4HCO_3$), Mobile Phase B: ACN; Flow rate: 60 mL/min; Gradient: 5 B to 40 B in 8 min; 254/220 nm) to afford N-(5-((5-(2-hydroxypropan-2-yl)pyridin-2-yl)methoxy)-1,3,4-thiadiazol-2-yl)-2',6-dimethyl-(4,4'-bipyridine)-3-carboxamide (59 mg, 17.3%) as a white solid. MS (ESI) calc'd for ($C_{24}H_{24}N_6O_3S$) $(M+1)^+$, 477.2; found 477.2. $^1H$ NMR (400 MHz, DMSO-$d_6$) δ 13.06 (s, 1H), 8.81 (s, 1H), 8.69-8.69 (m, 1H), 8.53-8.51 (m, 1H), 7.91-7.89 (m, 1H), 7.49-4.47 (m, 2H), 7.381 (s, 1H), 7.22-7.21 (m, 1H), 5.52 (s, 2H), 5.23 (s, 1H), 2.57 (s, 3H), 2.36 (s, 3H), 1.46 (s, 6H).

Example 90

6-(((5-(5'-methoxy-2',6-dimethyl-(4,4'-bipyridine)-3-amido)-1,3,4-thiadiazol-2-yl)oxy)methyl)pyridine-3-carboxylic acid

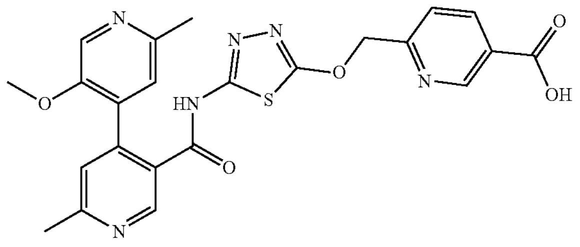 [SMILES: COc1cnc(C)cc1-c1cc(C)ncc1C(=O)Nc1nnc(OCc2ccc(C(=O)O)cn2)s1]

Step-1: methyl 6-(((5-(5'-methoxy-2',6-dimethyl-(4,4'-bipyridine)-3-amido)-1,3,4-thiadiazol-2-yl)oxy)methyl)pyridine 3-carboxylate

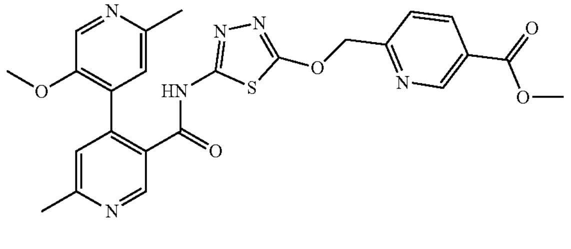

A mixture of 5-methoxy-2,6-dimethyl-(4,4-bipyridine)-3-carboxylic acid (50.0 mg, 0.20 mmol), methyl 6-(((5-amino-1,3,4-thiadiazol-2-yl)oxy)methyl)pyridine-3-carboxylate (61.9 mg, 0.23 mmol, Example 5, Step 1), TCFH (59.8 mg, 0.21 mmol) and NMI (33.4 mg, 0.41 mmol) in MeCN (1.5 mL) was stirred at room temperature for 2 h. The mixture was purified by reverse phase flash column chromatography with 5-80% acetonitrile in water to afford methyl 6-(((5-(5-methoxy-2,6-dimethyl-(4,4-bipyridine)-3-amido)-1,3,4-thiadiazol-2-yl)oxy)methyl)pyridine-3-carboxylate (50.0 mg, 48%) as a yellow solid. MS (ESI) calc'd for ($C_{24}H_{22}N_6O_5S$) $(M+1)^+$, 507.1, found 507.1.

Step-2: 6-(((5-(5'-methoxy-2',6-dimethyl-(4,4'-bipyridine)-3-amido)-1,3,4-thiadiazol-2-yl)oxy)methyl)pyridine-3-carboxylic acid

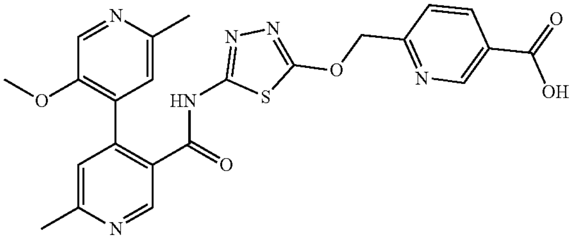 [SMILES: COc1cnc(C)cc1-c1cc(C)ncc1C(=O)Nc1nnc(OCc2ccc(C(=O)O)cn2)s1]

A mixture of methyl 6-(((5-(5-methoxy-2,6-dimethyl-(4,4-bipyridine)-3-amido)-1,3,4-thiadiazol-2-yl)oxy)methyl)pyridine-3-carboxylate (50.0 mg, 0.10 mmol) and lithium hydroxide (4.7 mg, 0.20 mmol) in THF (1.0 mL) and water (0.5 mL) was stirred at room temperature for 1 h. The resulting mixture was acidified to pH ~2 with HCl (2 N). The mixture was purified by Prep-HPLC with the following conditions: (Column: Sunfire prep C18 column, 30*150 mm, 5 um; Mobile Phase A: Water (0.1% FA), Mobile Phase B: ACN; Flow rate: 60 mL/min; Gradient: 1 B to 10 B in 8 min; 220 nm; RT 1: 6.58 min) to afford 6-(((5-(5-methoxy-2,6-dimethyl-(4,4-bipyridine)-3-amido)-1,3,4-thiadiazol-2-yl)oxy)methyl)pyridine-3-carboxylic acid (10.8 mg, 22%) as a white solid. MS (ESI) calc'd for ($C_{23}H_{20}N_6O_5S$) $(M+1)^+$, 493.1, found 493.1. $^1H$ NMR (400 MHz, DMSO-$d_6$) δ 9.03 (d, J=2.0 Hz, 1H), 8.77 (s, 1H), 8.30-8.25 (m, 1H), 8.18 (s, 1H), 7.60 (d, J=8.4 Hz, 1H), 7.34 (s, 1H), 7.24 (s, 1H), 5.60 (s, 2H), 3.58 (s, 3H), 2.58 (s, 3H), 2.47 (s, 3H).

Example 91

4-(2-fluoro-6-methoxyphenyl)-N-(5-((6-methoxypyridin-2-yl)methoxy)-1,3,4-thiadiazol-2-yl)-6-methylpyridine-3-carboxamide

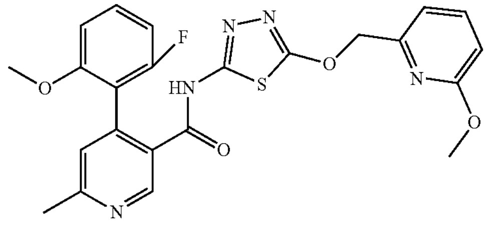 [SMILES: COc1cccc(COc2nnc(NC(=O)c3cnc(C)cc3-c3c(F)cccc3OC)s2)n1]

Step-1: 5-((6-methoxypyridin-2-yl)methoxy)-1,3,4-thiadiazol-2-amine

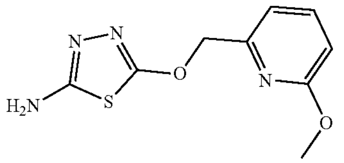 [SMILES: COc1cccc(COc2nnc(N)s2)n1]

To a mixture of NaH (103.4 mg, 4.31 mmol, 60%) in THF (5.0 mL) was added a solution of (6-methoxypyridin-2-yl) methanol (300.0 mg, 2.15 mmol) in THF (2 mL) at 0° C. and stirred at 0° C. for 30 min under nitrogen atmosphere. To the above mixture was added 5-bromo-1,3,4-thiadiazol-2-amine (698.5 mg, 3.88 mmol) in THF (5.0 mL) at 0° C. The resulting mixture was stirred at room temperature for 2 h. The mixture was quenched by the addition of saturated $NH_4Cl$ aqueous solution at 0° C. The aqueous solution was extracted with ethyl acetate. The combined organic layers were washed with brine, dried over anhydrous sodium sulfate, filtered, and concentrated under vacuum. The residue was purified by flash column chromatography with 5~40% acetonitrile in water to afford 5-((6-methoxypyridin-2-yl)methoxy)-1,3,4-thiadiazol-2-amine (65.0 mg, 12%) as a white solid. MS (ESI) calc'd for ($C_9H_{10}N_4O_2S$) $(M+1)^+$, 239.1, found 239.1.

Step-2: 4-(2-fluoro-6-methoxyphenyl)-N-(5-((6-methoxypyridin-2-yl)methoxy)-1,3,4-thiadiazol-2-yl)-6-methylpyridine-3-carboxamide

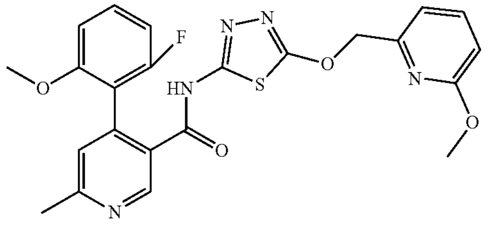 [SMILES: COc1cccc(COc2nnc(NC(=O)c3cnc(C)cc3-c3c(F)cccc3OC)s2)n1]

A mixture of 4-(2-fluoro-6-methoxyphenyl)-6-methylpyridine-3-carboxylic acid (28.0 mg, 0.11 mmol, Intermediate F), 5-((6-methoxypyridin-2-yl)methoxy)-1,3,4-thiadiazol-2-amine (30.6 mg, 0.13 mmol), TCFH (33.1 mg, 0.12 mmol) and NMI (18.5 mg, 0.23 mmol) in acetonitrile (1.0 mL) and DMF (1.0 mL) was stirred at room temperature for 1.5 h. The resulting mixture was concentrated under vacuum. The crude residue was purified by flash column chromatography with 5~54% acetonitrile in water to afford 4-(2-fluoro-6-methoxyphenyl)-N-(5-((6-methoxypyridin-2-yl)methoxy)-1,3,4-thiadiazol-2-yl)-6-methylpyridine-3-carboxamide (32.5 mg, 62%) as a white solid. MS (ESI) calc'd for ($C_{23}H_{20}FN_5O_4S$) $(M+1)^+$, 482.1, found 482.1. $^1H$ NMR (400 MHz, DMSO-$d_6$) δ 12.91 (s, 1H), 8.81 (s, 1H), 7.79-7.69 (m, 1H), 7.47-7.36 (m, 1H), 7.33 (d, J=1.6 Hz, 1H), 7.11 (d, J=7.2 Hz, 1H), 6.98-6.85 (m, 2H), 6.80 (d, J=8.4 Hz, 1H), 5.45 (s, 2H), 3.83 (s, 3H), 3.58 (s, 3H), 2.57 (s, 3H).

Example 93 and 94

4-(2-fluoro-6-methoxyphenyl)-N-(5-((5-((S)-1-methoxyethyl)pyridin-2-yl)methoxy)-1,3,4-thiadiazol-2-yl)-6-methylnicotinamide and 4-(2-fluoro-6-methoxyphenyl)-N-(5-((5-((R)-1-methoxyethyl) pyridin-2-yl)methoxy)-1,3,4-thiadiazol-2-yl)-6-methylnicotinamide

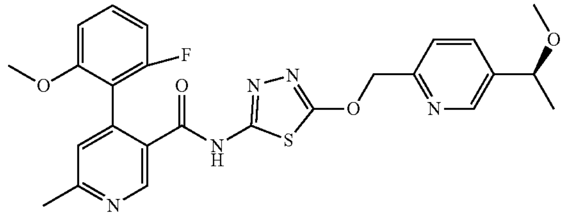

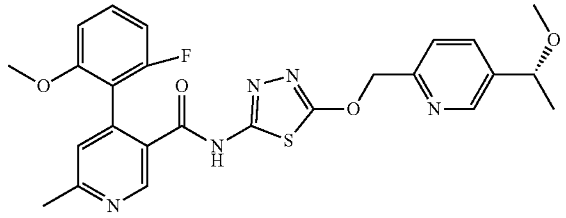

Step-1: 1-(6-bromopyridin-3-yl)ethan-1-ol

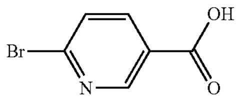

To a solution of 1-(6-bromopyridin-3-yl)ethan-1-one (3.9 g, 0.02 mol) in MeOH (50.00 mL) was added $NaBH_4$ (817 mg, 0.022 mol) in portions at 0° C. and stirred at 0° C. for 2 hours. The reaction mixture was then quenched by the addition of water and extracted with ethyl acetate. The combined organic layers were washed with brine, dried over anhydrous sodium sulfate, filtered, and concentrated under vacuum to afford 1-(6-bromopyridin-3-yl)ethan-1-ol (3.64 g, 93%) as yellow oil. MS (ESI) calc'd for ($C_7H_8BrNO$) $(M+1)^+$, 202.0, found 202.0.

Step-2: 2-bromo-5-(1-methoxyethyl pyridine

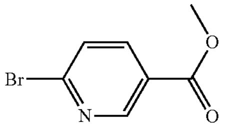

To a solution of 1-(6-bromopyridin-3-yl)ethan-1-ol (3.64 g, 0.018 mmol) in THF (50.00 mL) was added NaH (1.45 g, 0.061 mol, 60%) in portions at 0° C. and stirred for 30 min, and then MeI (3.09 g, 0.022 mmol) was added to the above mixture dropwise at) ° C. The resulting mixture was stirred at room temperature for 1 hour. The reaction mixture was then quenched by the addition of water and extracted with ethyl acetate. The combined organic layers were washed with brine, dried over anhydrous sodium sulfate, filtered, and concentrated under vacuum, The residue was purified by flash chromatography on silica gel with 0~50% ethyl acetate in petroleum ether to afford 2-bromo-5-(1-methoxyethyl) pyridine (2.07 g, 56.9%) as a white syrup. MS (ESI) calc'd for ($C_8H_{10}BrNO$) $(M+1)^+$, 216.0, found 216.0.

Step-3: methyl 5-(1-methoxyethyl)picolinate

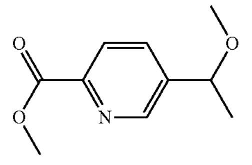

To a solution of 2-bromo-5-(1-methoxyethyl)pyridine (2.07 g, 0.01 mol) in MeOH (50 mL) were added TEA (2.9 g, 0.029 mol) and Pd(dppf)$Cl_2$ (1.56 g, 0.002 mol). The resulting solution was stirred at 80° C. for 8 hours under carbon monoxide. The resulting mixture was concentrated under vacuum. The residue was purified by flash chromatography on silica gel with 0~50% ethyl acetate in petroleum ether to afford methyl 5-(1-methoxyethyl)picolinate (1.59 g, 76.8%) as a yellow oil. MS (ESI) calc'd for ($C_{10}H_{13}NO_3$) $(M+1)^+$, 196.1; found, 196.0

Step-4: (5-(1-methoxyethyl)pyridin-2-yl)methanol

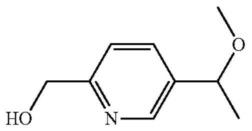

To a solution of methyl 5-(1-methoxyethyl)picolinate (1.59 g, 0.008 mol) in THF (30 mL) and MeOH (30 mL) was sequentially added $NaBH_4$ (617 mg, 0.016 mol) and $CaCl_2$) (1.78 g, 0.016 mol) in portions at 0~5° C. stirred at 5° C. for 10 minutes. The resulting mixture was then stirred at room temperature for 2 h. The reaction mixture was quenched by the addition of water and extracted with ethyl acetate. The combined organic layers were washed with brine, dried over anhydrous sodium sulfate, filtered, and concentrated under vacuum. The residue was purified by flash chromatography on silica gel with 0~10% methanol in dichloromethane to afford (5-(1-methoxyethyl)pyridin-2-yl)methanol (980 mg, 62%) as a yellow oil. MS (ESI) calc'd for ($C_9H_{13}NO_2$) $(M+1)^+$, 168.1; found, 168.2.

Step-5: 5-((5-(1-methoxyethyl)pyridin-2-yl) methoxy)-1,3,4-thiadiazol-2-amine

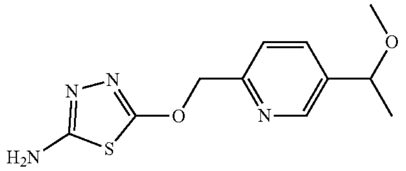

To a solution of NaH (350 mg, 0.015 mol, 60%) in THF (10 mL) was added a solution of (5-(1-methoxyethyl)pyridin-2-yl)methanol (980 mg, 0.006 mol) in THF (5 mL) dropwise at 0~5° C. and stirred at 5° C. for 1 h. Then 5-bromo-1,3,4-thiadiazol-2-amine (1.25 g, 0.007 mol) was added to the mixture in small portions at 5° C. and stirred at 5° C. for 5 h. The reaction mixture was then quenched by the addition of water and extracted with ethyl acetate. The combined organic layers were washed with brine, dried over anhydrous sodium sulfate, filtered, and concentrated under vacuum. The residue was purified by flash chromatography on silica gel with 0~50% ethyl acetate in petroleum ether to afford 5-((5-(1-methoxyethyl)pyridin-2-yl)methoxy)-1,3,4-thiadiazol-2-amine (306 mg, 32%) as a yellow solid. MS (ESI) calc'd for ($C_{11}H_{14}N_4O_2S$) $(M+1)^+$, 267.0; found, 267.0.

Step-6: 4-(2-fluoro-6-methoxyphenyl)-N-(5-((5-((S)-1-methoxyethyl)pyridin-2-yl)methoxy)-1,3,4-thiadiazol-2-yl)-6-methylnicotinamide and 4-(2-fluoro-6-methoxyphenyl)-N-(5-((5-((R)-1-methoxyethyl) pyridin-2-yl)methoxy)-1,3,4-thiadiazol-2-yl)-6-methylnicotinamide

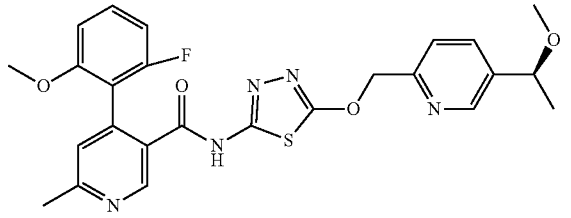

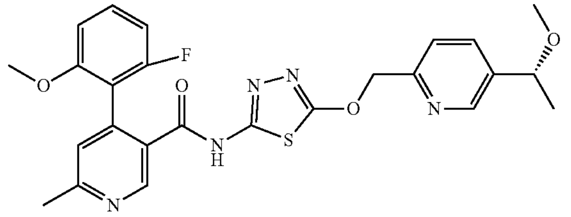

To a solution of 4-(2-fluoro-6-methoxyphenyl)-6-methylnicotinic acid (200 mg, 0.763 mmol, Intermediate F) in ACN (5 mL) and DMF (5 mL) were added NMI (188 mg, 2.293 mmol), 5-((5-(1-methoxyethyl)pyridin-2-yl)methoxy)-1,3,4-thiadiazol-2-amine (306 mg, 1.146 mmol) and TCFH (258 mg, 0.918 mmol). The resulting mixture was stirred at room temperature for 2 h. The reaction mixture was diluted with water and extracted with ethyl acetate. The combined organic layers were washed with brine, dried over anhydrous sodium sulfate, filtered, and concentrated under vacuum. The residue was purified by flash chromatography on silica gel with 0~10% methanol in dichloromethane to afford the racemic product, which was separated by prep-chiral HPLC with the following conditions: (Column: CHIRALPAK IG, 2*25 cm, 5 um; Mobile Phase A: Hex (0.2% DEA)-HPLC, Mobile Phase B:EtOH:DCM=1: 1-HPLC; Flow rate: 20 mL/min; Gradient: 50 B to 50 B in 24 min; 220/254 nm; RT1:16.254; RT2:22.66; Injection Volumn:0.3 ml; Number Of Runs:10) to afford 4-(2-fluoro-6-methoxyphenyl)-N-(5-((5-((S)-1-methoxyethyl)pyridin-2-yl)methoxy)-1,3,4-thiadiazol-2-yl)-6-methylnicotinamide (40 mg, 11%) as a white solid with shorter retention time on chiral-HPLC and 4-(2-fluoro-6-methoxyphenyl)-N-(5-((5-((R)-1-methoxyethyl)

pyridin-2-yl)methoxy)-1,3,4-thiadiazol-2-yl)-6-methylnicotinamide (40 mg, 11%) as a white solid with longer retention time on chiral-HPLC.

4-(2-fluoro-6-methoxyphenyl)-N-(5-((5-((S)-1-methoxyethyl)pyridin-2-yl)methoxy)-1,3,4-thiadiazol-2-yl)-6-methylnicotinamide: MS (ESI) calc'd for ($C_{25}H_{24}FN_5O_4S$) $(M+1)^+$, 510.2; found, 510.2. $^1H$ NMR (400 MHz, DMSO-$d_6$) δ 12.88 (s, 1H), 8.80 (s, 1H), 8.53 (s, 1H), 7.80-7.77 (m, 1H), 7.55-7.53 (m, 1H), 7.41-7.39 (m, 1H), 7.33 (s, 1H), 6.94-6.87 (m, 2H), 5.52 (s, 2H), 5.43-4.41 (m, 1H), 3.58 (s, 3H), 3.14 (s, 3H), 2.53 (s, 3H), 1.37-1.36 (m, 3H).

4-(2-fluoro-6-methoxyphenyl)-N-(5-((5-((R)-1-methoxyethyl)pyridin-2-yl)methoxy)-1,3,4-thiadiazol-2-yl)-6-methylnicotinamide: MS (ESI) calc'd for ($C_{25}H_{24}FN_5O_4S$) $(M+1)^+$, 510.2; found, 510.2. $^1H$ NMR (400 MHz, DMSO-$d_6$) δ 12.92 (s, 1H), 8.80 (s, 1H), 8.53 (s, 1H), 7.78-7.77 (m, 1H), 7.55-7.53 (m, 1H), 7.41-7.37 (m, 1H), 7.32 (s, 1H), 6.94-6.87 (m, 2H), 5.52 (s, 2H), 4.43-4.41 (m, 1H), 3.58 (s, 3H), 3.14 (s, 3H), 2.53 (s, 3H), 1.37-1.36 (m, 3H).

Example 95

N-(5-((3-cyanobicyclo(1.1.1)pentan-1-yl)methoxy)-1,3,4-thiadiazol-2-yl)-4-(2-fluoro-6-methoxyphenyl)-6-methylpyridine-3-carboxamide

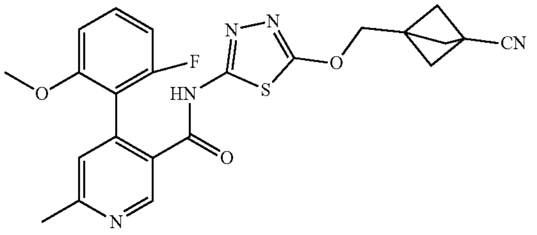

Step-1:3-(((5-amino-1,3,4-thiadiazol-2-yl)oxy)methyl)bicyclo(1.1.1)pentane-1-carbonitrile

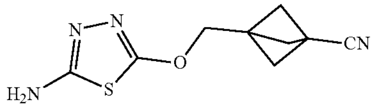 [SMILES: N#CC12CC(COc3nnc(N)s3)(C1)C2]

To a stirred solution of NaH (58 mg, 2.43 mmol, 60%) in THF (4 mL) was added a solution of 3-(hydroxymethyl)bicyclo(1.1.1)pentane-1-carbonitrile (200 mg, 1.62 mmol) dropwise at 0° C. and stirred at 0° C. for 1 h under nitrogen atmosphere. Then to the mixture was added 5-bromo-1,3,4-thiadiazol-2-amine (350 mg, 1.95 mmol) at 0° C. for and stirred at room temperature for 3 h under nitrogen atmosphere. The reaction mixture was quenched with water and extracted with ethyl acetate. The combined organic layers were washed with brine, dried over anhydrous sodium sulfate, filtered, and concentrated under vacuum. The residue was purified by reverse phase flash chromatography with 5-50% acetonitrile in water to afford 3-(((5-amino-1,3,4-thiadiazol-2-yl)oxy)methyl)bicyclo(1.1.1)pentane-1-carbonitrile (90 mg, 24%) as a yellow solid. MS (ESI) calc'd for ($C_9H_{10}N_4OS$) $(M+1)^+$, 223.1; found 223.1.

Step-2: N-(5-((3-cyanobicyclo(1.1.1)pentan-1-yl)methoxy)-1,3,4-thiadiazol-2-yl)-4-(2-fluoro-6-methoxyphenyl)-6-methylpyridine-3-carboxamide

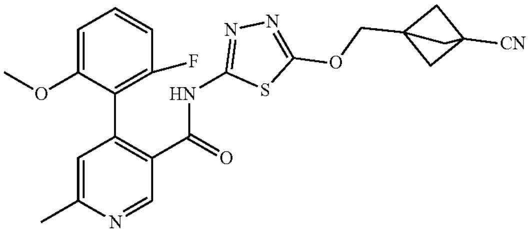 [SMILES: COc1cccc(F)c1-c1cc(C)ncc1C(=O)Nc1nnc(OCC23CC(C#N)(C2)C3)s1]

To a stirred solution of 3-(((5-amino-1,3,4-thiadiazol-2-yl)oxy)methyl)bicyclo(1.1.1)pentane-1-carbonitrile (50 mg, 0.22 mmol) and 4-(2-fluoro-6-methoxyphenyl)-6-methylpyridine-3-carboxylic acid (58 mg, 0.22 mmol, Intermediate F) in acetonitrile (1 mL) were added NMI (73 mg, 0.90 mmol) and TCFH (94.6 mg, 0.33 mmol). The resulting mixture was stirred at room temperature for 2 h under nitrogen atmosphere. The mixture was purified by prep-HPLC with the following conditions: (Column: XBridge Shield RP18 OBD Column, 5 um, 19*150 mm; Mobile Phase A:undefined, Mobile Phase B:undefined; Flow rate: 60 mL/min; Gradient: 35 B to 55 B in 8 min; 220/254 nm; RT1: 6.22 min) to afford N-(5-((3-cyanobicyclo(1.1.1)pentan-1-yl)methoxy)-1,3,4-thiadiazol-2-yl)-4-(2-fluoro-6-methoxyphenyl)-6-methylpyridine-3-carboxamide (35.2 mg, 33%) as a white solid. MS (ESI) calc'd for ($C_{23}H_2OFN_5O_3S$) $(M+1)^+$, 466.1; found 466.3. $^1H$ NMR (400 MHz, DMSO-$d_6$) δ 12.88 (s, 1H), 8.81 (s, 1H), 7.43-7.31 (m, 2H), 6.94-6.87 (m, 2H), 4.44 (s, 2H), 3.58 (s, 3H), 2.53 (s, 3H), 2.27 (s, 6H).

Example 96

4-(5-chloro-2-methoxyphenyl)-N-(5-((5-(2-hydroxypropan-2-yl)pyridin-2-yl)methoxy)-1,3,4-thiadiazol-2-yl)-6-methylnicotinamide

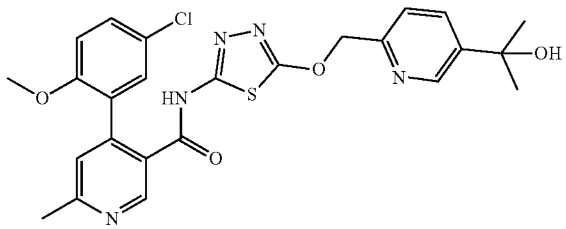 [SMILES: COc1ccc(Cl)cc1-c1cc(C)ncc1C(=O)Nc1nnc(OCc2ccc(C(C)(C)O)cn2)s1]

To a mixture of 2-(6-(((5-amino-1,3,4-thiadiazol-2-yl)oxy)methyl)pyridin-3-yl)propan-2-ol (19 mg, 0.072 mmol, Example 33, Step 1) in MeCN (1 mL) and DMF (1 mL) were added NMI (17 mg, 0.216 mmol), 4-(5-chloro-2-methoxyphenyl)-6-methylpyridine-3-carboxylic acid (20 mg, 0.072 mmol, Example 39, Step 2) and TCFH (22 mg, 0.079 mmol). The resulting mixture was stirred at room temperature for 16 h under nitrogen atmosphere. The residue was purified by prep-HPLC with the following conditions: (Column: XBridge Prep OBD C18 Column, 30×150 mm 5 um; Mobile Phase A: Water (10 mmol/L $NH_4HCO_3$), Mobile Phase B: ACN; Flow rate: 60 mL/min; Gradient: 20 B to 50

B in 8 min; 220 nm) to afford 4-(5-chloro-2-methoxyphenyl)-N-(5-((5-(2-hydroxypropan-2-yl)pyridin-2-yl)methoxy)-1,3,4-thiadiazol-2-yl)-6-methylnicotinamide (6.7 mg, 17.7%) as a white solid. MS (ESI) calc'd for ($C_{25}H_{24}ClN_5O_4S$) $(M+1)^+$, 526.1; found 526.3. $^1H$ NMR (400 MHz, DMSO-$d_6$) δ 12.78 (s, 1H), 8.69 (d, J=2.4 Hz, 2H), 7.93-7.86 (m, 1H), 7.52-7.39 (m, 4H), 7.36 (s, 1H), 5.51 (s, 2H), 5.26 (s, 1H), 3.51 (s, 3H), 2.57 (s, 3H), 1.46 (s, 6H).

Example 97

4-(2-fluoro-6-methoxyphenyl)-N-(5-((5-(hydroxymethyl)pyrazin-2-yl)methoxy)-1,3,4-thiadiazol-2-yl)-6-methylnicotinamide

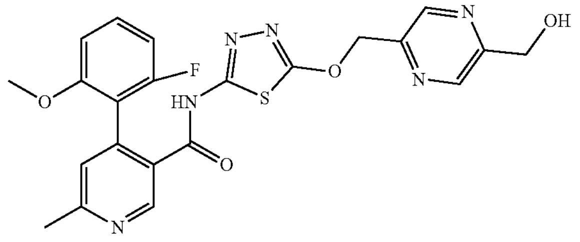 [SMILES: COc1cccc(F)c1-c1cc(C)ncc1C(=O)Nc1nnc(OCc2cnc(CO)cn2)s1]

Step-1: 4-(2-fluoro-6-methoxyphenyl)-6-methyl-N-(5-((5-vinylpyrazin-2-yl)methoxy)-1,3,4-thiadiazol-2-yl)nicotinamide

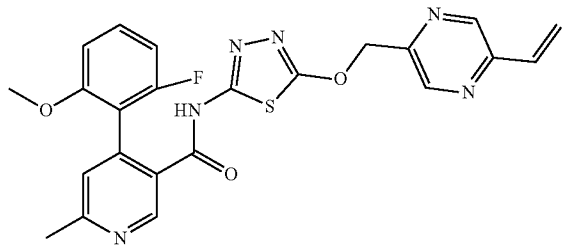 [SMILES: C=Cc1cnc(COc2nnc(NC(=O)c3cnc(C)cc3-c3c(F)cccc3OC)s2)cn1]

To a stirred solution of 5-((5-ethenylpyrazin-2-yl)methoxy)-1,3,4-thiadiazol-2-amine (250 mg, 1.06 mmol) in acetonitrile (5 mL) were added 4-(2-fluoro-6-methoxyphenyl)-6-methylnicotinic acid (333 mg, 1.27 mmol, Intermediate F), NMI (220 mg, 2.65 mmol) and TCFH (358 mg, 1.27 mmol). The mixture was stirred at room temperature for 2 h. The resulting mixture was purified by reverse phase flash column chromatography with 5-50% acetonitrile in water to afford 4-(2-fluoro-6-methoxyphenyl)-6-methyl-N-(5-((5-vinylpyrazin-2-yl)methoxy)-1,3,4-thiadiazol-2-yl)nicotinamide (160 mg, 31.5%) as a white solid. MS (ESI) calc'd for ($C_{23}H_{19}FN_6O_3S$) $(M+1)^+$, 479.1; found, 479.0.

Step-2: 4-(2-fluoro-6-methoxyphenyl)-N-(5-((5-formylpyrazin-2-yl)methoxy)-1,3,4-thiadiazol-2-yl)-6-methylnicotinamide

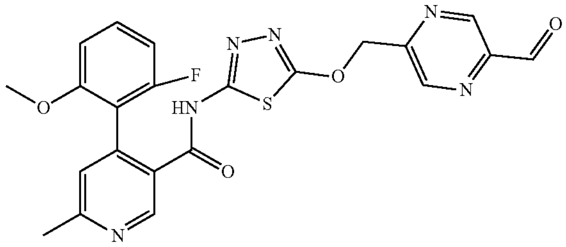 [SMILES: COc1cccc(F)c1-c1cc(C)ncc1C(=O)Nc1nnc(OCc2cnc(C=O)cn2)s1]

To a stirred solution of 4-(2-fluoro-6-methoxyphenyl)-6-methyl-N-(5-((5-vinylpyrazin-2-yl)methoxy)-1,3,4-thiadiazol-2-yl)nicotinamide (160 mg, 0.33 mmol) in THF (1 mL) was added a solution of $NaIO_4$ (232 mg, 1.08 mmol) in water (1 mL) dropwise at room temperature under nitrogen atmosphere. And then $OSO_4$ (10 mg, 0.03 mmol) was added to the above mixture. The resulting mixture was stirred at room temperature for 2 h. The reaction was quenched with water. The aqueous layer was extracted with ethyl acetate. The combined organic layers were washed with brine, dried over anhydrous $Na_2SO_4$. After filtration, the filtrate was concentrated under reduced pressure to afford 4-(2-fluoro-6-methoxyphenyl)-N-(5-((5-formylpyrazin-2-yl)methoxy)-1,3,4-thiadiazol-2-yl)-6-methylnicotinamide (70 mg, crude) as a yellow solid. MS (ESI) calc'd for ($C_{22}H_{17}FN_6O_4S$) $(M+1)^+$, 481.1; found, 481.0.

Step-3: 4-(2-fluoro-6-methoxyphenyl)-N-(5-((5-(hydroxymethyl)pyrazin-2-yl)methoxy)-1,3,4-thiadiazol-2-yl)-6-methylnicotinamide

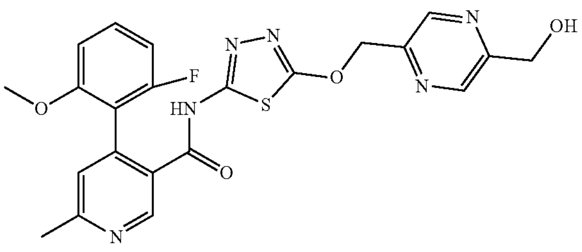 [SMILES: COc1cccc(F)c1-c1cc(C)ncc1C(=O)Nc1nnc(OCc2cnc(CO)cn2)s1]

To a solution of 4-(2-fluoro-6-methoxyphenyl)-N-(5-((5-formylpyrazin-2-yl)methoxy)-1,3,4-thiadiazol-2-yl)-6-methylnicotinamide (70 mg, 0.14 mmol) in methanol (3 mL) was added $NaBH_4$ (11 mg, 0.28 mmol) at 0° C. The resulting mixture was stirred at 0° C. for 2 h. The reaction mixture was quenched with water and extracted with ethyl acetate. The combined organic layers were washed with brine, dried over anhydrous sodium sulfate, filtered, and concentrated under vacuum. The residue was purified by prep-HPLC with the following conditions: (Column: XBridge Prep OBD C18 Column, 30×150 mm 5 um; Mobile Phase A: Water (10 MMOL/L $NH_4HCO_3$), Mobile Phase B: ACN; Flow rate: 60 mL/min; Gradient: 25 B to 40 B in 8 min; 220 nm; RT1:5.45 min) to afford 4-(2-fluoro-6-methoxyphenyl)-N-(5-((5-(hydroxymethyl)pyrazin-2-yl)methoxy)-1,3,4-thiadiazol-2-yl)-6-methylnicotinamide (16.0 mg, 24%) as a white solid. MS (ESI) calculated for ($C_{22}H_{19}FN_6O_4S$) $(M+1)^+$, 483.1; found, 483.0. $^{1}$H NMR (400 MHz, DMSO-$d_6$) δ 12.90 (s, 1H), 8.81 (s, 1H), 8.73 (d, J=7.2 Hz, 2H), 7.46-7.36 (m, 1H), 7.33 (s, 1H), 6.97-6.84 (m, 2H), 5.65-5.60 (m, 3H), 4.66 (d, J=5.8 Hz, 2H), 3.59 (s, 3H), 2.57 (s, 3H).

Example 98

N-(5-((3-hydroxybicyclo(1.1.1)pentan-1-yl) methoxy)-1,3,4-thiadiazol-2-yl)-5'-methoxy-2',6-dimethyl-(4,4'-bipyridine)-3-carboxamide

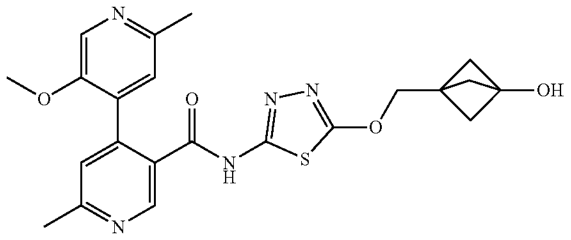 [SMILES: COc1cnc(C)cc1-c1cc(C)ncc1C(=O)Nc1nnc(OCC23CC(O)(C2)C3)s1]

Step-1: N-(5-((3-((tert-butyldimethylsilyl)oxy)bicyclo(1.1.1)pentan-1-yl)methoxy)-1,3,4-thiadiazol-2-yl)-5'-methoxy-2',6-dimethyl-(4,4'-bipyridine)-3-carboxamide

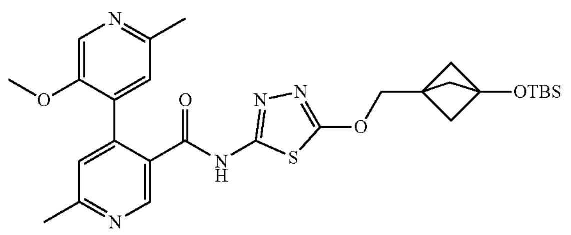

To a solution of 5-((3-((tert-butyldimethylsilyl)oxy)bicyclo(1.1.1)pentan-1-yl)methoxy)-1,3,4-thiadiazol-2-amine (22.8 mg, 0.070 mmol) in DMF (1 mL) and MeCN (1 mL) were added 5'-methoxy-2',6-dimethyl-(4,4'-bipyridine)-3-carboxylic acid (15 mg, 0.058 mmol, Intermediate G), NMI (15 mg, 0.174 mmol) and TCFH (32.6 mg, 0.116 mmol). The resulting solution was stirred at room temperature for 2 hours. The solvent was removed under vacuum to afford N-(5-((3-((tert-butyldimethylsilyl)oxy)bicyclo(1.1.1)pentan-1-yl)methoxy)-1,3,4-thiadiazol-2-yl)-5'-methoxy-2',6-dimethyl-(4,4'-bipyridine)-3-carboxamide (60 mg, crude) as a yellow solid. MS (ESI) calc'd for ($C_{28}H_{37}N_5O_4SSi$) $(M+1)^+$, 568.2; found, 568.0.

Step-2: N-(5-((3-hydroxybicyclo(1.1.1)pentan-1-yl) methoxy)-1,3,4-thiadiazol-2-yl)-5'-methoxy-2',6-dimethyl-(4,4'-bipyridine)-3-carboxamide

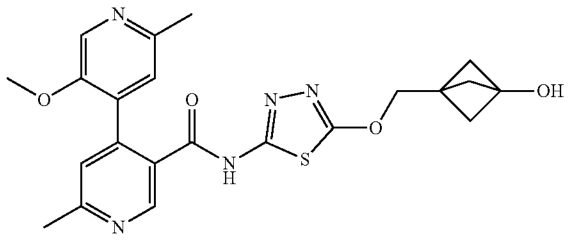 [SMILES: COc1cnc(C)cc1-c1cc(C)ncc1C(=O)Nc1nnc(OCC23CC(O)(C2)C3)s1]

To a solution of N-(5-((3-((tert-butyldimethylsilyl)oxy) bicyclo(1.1.1)pentan-1-yl)methoxy)-1,3,4-thiadiazol-2-yl)-5'-methoxy-2',6-dimethyl-(4,4'-bipyridine)-3-carboxamide (60 mg, crude) in DCM (1 mL) was added TFA (0.3 mL). The resulting solution was stirred at room temperature for 2 hours before concentrated under vacuum. The residue was purified by prep-HPLC with the following conditions: (Column: YMC-Actus Triart C18 ExRS, 30 mm×150 mm, 5 um; Mobile Phase A: Water (10 MMOL/L $NH_4HCO_3$), Mobile Phase B: ACN; Flow rate: 60 mL/min; Gradient: 25 B to 35 B in 8 min; 254 nm; RT1: 8.13 min) to afford N-(5-((3-hydroxybicyclo(1.1.1)pentan-1-yl)methoxy)-1,3,4-thiadiazol-2-yl)-5'-methoxy-2',6-dimethyl-(4,4'-bipyridine)-3-carboxamide (3.1 mg, 11.7%) as a white solid. MS (ESI) calc'd for ($C_{22}H_{23}N_5O_4S$) $(M+1)^+$, 454.1; found, 454.1. $^{1}$H NMR (400 MHz, DMSO-$d_6$) δ 12.84 (s, 1H), 8.75 (s, 1H), 8.18 (s, 1H), 7.35 (s, 1H), 7.25 (s, 1H), 6.27 (s, 1H), 4.54 (s, 2H), 3.57 (s, 3H), 2.53 (s, 3H), 2.42 (s, 3H), 1.78 (s, 6H).

Example 99

2'-chloro-N-(5-((3-hydroxybicyclo(1.1.1)pentan-1-yl)methoxy)-1,3,4-thiadiazol-2-yl)-5'-methoxy-6-methyl-(4,4'-bipyridine)-3-carboxamide

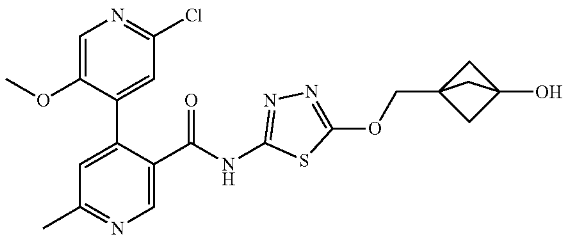 [SMILES: COc1cnc(Cl)cc1-c1cc(C)ncc1C(=O)Nc1nnc(OCC23CC(O)(C2)C3)s1]

Step-1: N-(5-((3-((tert-butyldimethylsilyl)oxy)bicyclo(1.1.1)pentan-1-yl)methoxy)-1,3,4-thiadiazol-2-yl)-2'-chloro-5'-methoxy-6-methyl-(4,4'-bipyridine)-3-carboxamide

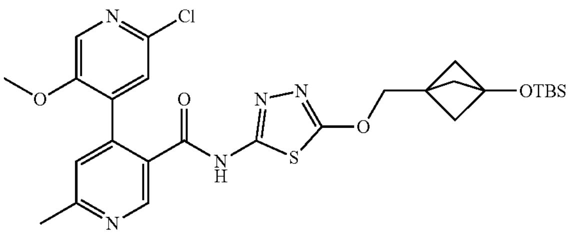 [SMILES: COc1cnc(Cl)cc1-c1cc(C)ncc1C(=O)Nc1nnc(OCC23CC(O[Si](C)(C)C(C)(C)C)(C2)C3)s1]

To a solution of 5-((3-((tert-butyldimethylsilyl)oxy)bicyclo(1.1.1)pentan-1-yl)methoxy)-1,3,4-thiadiazol-2-amine (38 mg, 0.12 mmol) in DMF (1 mL) and MeCN (1 mL) were added 2'-chloro-5'-methoxy-6-methyl-(4,4'-bipyridine)-3-carboxylic acid (28 mg, 0.10 mmol), NMI (29 mg, 0.30 mmol) and TCFH (28 mg, 0.20 mmol). The resulting solution was stirred at room temperature for 2 hours. The solvent was removed under vacuum to afford N-(5-((3-((tert-butyldimethylsilyl)oxy)bicyclo(1.1.1)pentan-1-yl) methoxy)-1,3,4-thiadiazol-2-yl)-2'-chloro-5'-methoxy-6-methyl-(4,4'-bipyridine)-3-carboxamide (74 mg, crude) as a yellow solid. MS (ESI) calc'd for ($C_{27}H_{34}ClN_5O_4SSi$) $(M+1)^+$, 588.2; found, 588.0.

Step-2: 2'-chloro-N-(5-((3-hydroxybicyclo(1.1.1)pentan-1-yl)methoxy)-1,3,4-thiadiazol-2-yl)-5'-methoxy-6-methyl-(4,4'-bipyridine)-3-carboxamide

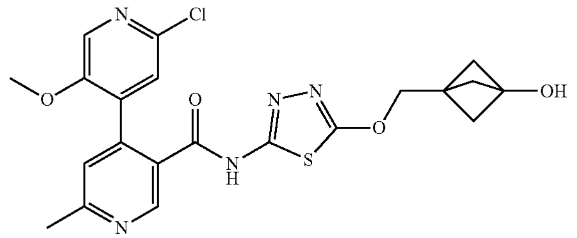 [SMILES: COc1cnc(Cl)cc1-c1cc(C)ncc1C(=O)Nc1nnc(OCC23CC(O)(C2)C3)s1]

To a solution of N-(5-((3-((tert-butyldimethylsilyl)oxy)bicyclo(1.1.1)pentan-1-yl)methoxy)-1,3,4-thiadiazol-2-yl)-2'-chloro-5'-methoxy-6-methyl-(4,4'-bipyridine)-3-carboxamide (74 mg, crude) in THF (1 mL) was added TBAF (20 mg). The resulting solution was stirred at room temperature for 2 hours before concentrated under vacuum. The residue was purified by prep-HPLC with the following conditions: (Column: YMC-Actus Triart C18 ExRS, 30 mm×150 mm, 5 um; Mobile Phase A: Water (10 MMOL/L $NH_4HCO_3$), Mobile Phase B: ACN; Flow rate: 60 mL/min; Gradient: 23 B to 32 B in 8 min) to afford 2'-chloro-N-(5-((3-hydroxybicyclo(1.1.1)pentan-1-yl)methoxy)-1,3,4-thiadiazol-2-yl)-5'-methoxy-6-methyl-(4,4'-bipyridine)-3-carboxamide (3.1 mg, 6.3%) as a white solid. MS (ESI) calc'd for ($C_{21}H_{20}ClN_5O_4S$) $(M+1)^+$, 474.1; found, 474.1. $^1H$ NMR (400 MHz, DMSO-$d_6$) δ 12.89 (s, 1H), 8.82 (s, 1H), 8.16 (s, 1H), 7.52 (s, 1H), 7.41 (s, 1H), 6.27 (s, 1H), 4.87 (s, 2H), 3.62 (s, 3H), 2.67 (s, 3H), 1.78 (s, 6H).

Example 100

N-(5-(((1r,4r)-4-hydroxycyclohexyl)methoxy)-1,3,4-thiadiazol-2-yl)-5'-methoxy-2',6-dimethyl-[4,4'-bipyridine]-3-carboxamide

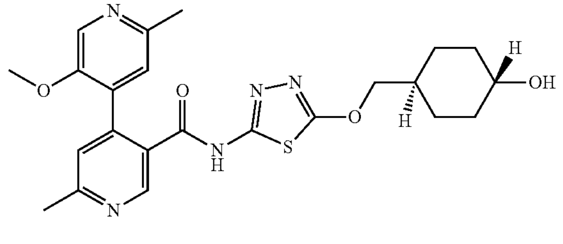 [SMILES: COc1cnc(C)cc1-c1cc(C)ncc1C(=O)Nc1nnc(OC[C@H]2CC[C@H](O)CC2)s1]

Step-1: methyl (1r,4r)-4-((tert-butyldimethylsilyl)oxy)cyclohexane-1-carboxylate

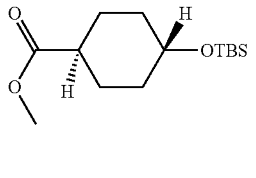 [SMILES: COC(=O)[C@H]1CC[C@H](O[Si](C)(C)C(C)(C)C)CC1]

To a solution of methyl (1r,4r)-4-hydroxycyclohexane-1-carboxylate (500 mg, 3.145 mmol) and imidazole (642 mg, 9.441 mmol) in DCM (10 mL) was added TBS-Cl (712 mg, 4.715 mmol) at 0° C. The resulting mixture was stirred at room temperature for 8 h. The reaction mixture was then quenched by the addition of water and extracted with ethyl acetate. The organic layers were combined, washed with brine, dried over anhydrous sodium sulfate and filtered. The filtrate was concentrated under vacuum. The residue was purified by flash chromatography on silica gel with 0~50% ethyl acetate in petroleum ether to afford methyl (1r,4r)-4-((tert-butyldimethylsilyl)oxy)cyclohexane-1-carboxylate (900 mg, 88%) as a white solid. MS (ESI) calc'd for ($C_{14}H_{28}O_3Si$) $(M+1)^+$, 273.2; found 272.0.

Step-2: ((1r,4r)-4-((tert-butyldimethylsilyl)oxy)cyclohexyl)methanol

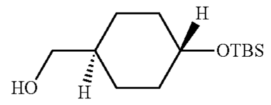 [SMILES: CC(C)(C)[Si](C)(C)O[C@H]1CC[C@H](CO)CC1]

To a solution of methyl (1r,4r)-4-((tert-butyldimethylsilyl)oxy)cyclohexane-1-carboxylate (900 mg, 3.297 mmol) in THF (30 mL) was added $LiAlH_4$ (250 mg, 6.579 mmol) in portions at 0~5° C. The resulting mixture was stirred at room temperature for 1 h. The reaction mixture was then quenched by the addition of water and extracted with ethyl acetate. The combined organic layers were washed with brine, dried over anhydrous sodium sulfate, filtered, and concentrated under vacuum. The residue was purified by flash chromatography on silica gel with 0~10% methanol in dichloromethane to afford ((1r,4r)-4-((tert-butyldimethylsilyl)oxy)cyclohexyl)methanol (690 mg, 77%) as a white solid. MS (ESI) calc'd for ($C_{13}H_{28}O_2Si$) $(M+1)^+$, 245.0; found, 245.0.

Step-3: O-(((1r,4r)-4-((tert-butyldimethylsilyl)oxy)cyclohexyl)methyl)S-methyl carbonodithioate

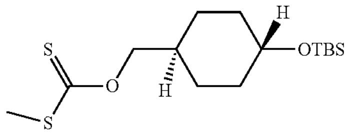 [SMILES: CSC(=S)OC[C@H]1CC[C@H](O[Si](C)(C)C(C)(C)C)CC1]

To a solution of ((1r,4r)-4-((tert-butyldimethylsilyl)oxy)cyclohexyl)methanol (690 mg, 2.816 mmol) in THF (20 mL) was added NaH (225 mg, 9.375 mmol, 60%) in portions at 0° C. and stirred at 0° C. for 30 min. Then $CS_2$ (321 mg, 4.224 mmol) was added to the above mixture and stirred at 0° C. for 10 min, Then MeI (600 mg, 4.225 mmol) was added to the above mixture at 5° C. The resulting mixture was stirred at room temperature for 1 hour. The reaction mixture was quenched by the addition of water and extracted with ethyl acetate. The combined organic layers were washed with brine, dried over anhydrous sodium sulfate, filtered, and concentrated under vacuum, The residue was purified by flash chromatography on silica gel with 0-50% ethyl acetate in petroleum ether to afford O-(((1r,4r)-4-((tert-butyldimethylsilyl)oxy)cyclohexyl)methyl)S-methyl carbonodithioate (700 mg, 78%) as a colorless oil. MS (ESI) calc'd for ($C_{15}H_{30}O_2S_2Si$) $(M+1)^+$, 335.0, found 335.0.

Step-4: 0-(((1r,4r)-4-((tert-butyldimethylsilyl)oxy) cyclohexyl)methyl) hydrazinecarbothioate

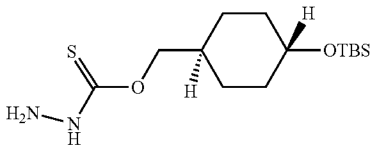 [SMILES: CC(C)(C)[Si](C)(C)O[C@H]1CC[C@H](COC(=S)NN)CC1]

To a solution of O-(((1r,4r)-4-((tert-butyldimethylsilyl) oxy)cyclohexyl)methyl)S-methyl carbonodithioate (700 mg, 2.089 mmol) in MeOH (10 mL) was added hydrazine (130 mg, 4.062 mmol, 80%). The resulting mixture was stirred at room temperature for 2 hours. The reaction mixture was quenched with water and extracted with ethyl acetate. The combined organic layers were washed with brine, dried over anhydrous sodium sulfate, filtered, and concentrated under vacuum to afford O-(((1r,4r)-4-((tert-butyldimethylsilyl)oxy)cyclohexyl)methyl) hydrazinecarbothioate (630 mg, 90%) as red oil. MS (ESI) calc'd for ($C_{14}H_{30}N_2O_2SSi$) $(M+1)^+$, 319.0, found 319.1.

Step-5: 5-(((1r,4r)-4-((tert-butyldimethylsilyl)oxy) cyclohexyl)methoxy)-1,3,4-thiadiazol-2-amine

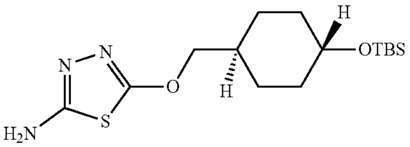 [SMILES: CC(C)(C)[Si](C)(C)O[C@H]1CC[C@H](COc2nnc(N)s2)CC1]

To a solution of O-(((1r,4r)-4-((tert-butyldimethylsilyl) oxy)cyclohexyl)methyl) hydrazinecarbothioate (630 mg, 1.975 mmol) in MeOH (10.00 mL) were added TEA (402 mg, 3.981 mmol) and BrCN (232 mg, 2.189 mmol). The resulting mixture was stirred at room temperature for 30 min. The reaction mixture was quenched with water and extracted with ethyl acetate. The combined organic layers were washed with brine, dried over anhydrous sodium sulfate, filtered, and concentrated under vacuum. The residue was purified by flash chromatography on silica gel with 0~50% ethyl acetate in petroleum ether to afford 5-(((1r,4r)-4-((tert-butyldimethylsilyl)oxy)cyclohexyl)methoxy)-1,3,4-thiadiazol-2-amine (300 mg, 48%) as a red solid. MS (ESI) calc'd for ($C_{15}H_{29}N_3O_2SSi$) $(M+1)^+$, 344.1, found 344.0.

Step-6: N-(5-(((1r,4r)-4-((tert-butyldimethylsilyl) oxy)cyclohexyl)methoxy)-1,3,4-thiadiazol-2-yl)-5'-methoxy-2',6-dimethyl-(4,4'-bipyridine)-3-carboxamide

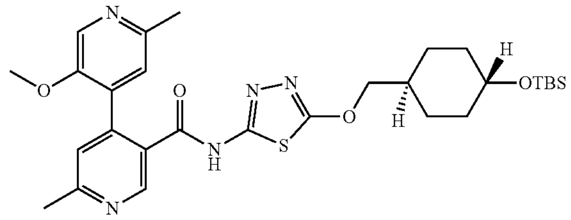 [SMILES: COc1cnc(C)cc1-c1cc(C)ncc1C(=O)Nc1nnc(OC[C@H]2CC[C@H](O[Si](C)(C)C(C)(C)C)CC2)s1]

To a solution of 5'-methoxy-2',6-dimethyl-(4,4'-bipyridine)-3-carboxylic acid (15 mg, 0.058 mmol, Intermediate G) in ACN (3 mL) and DMF (3 mL) were added NMI (15 mg, 0.183 mmol), 5-(((1r,4r)-4-((tert-butyldimethylsilyl) oxy)cyclohexyl)methoxy)-1,3,4-thiadiazol-2-amine (30 mg, 0.087 mmol) and TCFH (20 mg, 0.071 mmol). The mixture was stirred at room temperature for 2 h. The reaction mixture was quenched with water and extracted with ethyl acetate. The combined organic layers were washed with brine, dried over anhydrous sodium sulfate, filtered, and concentrated under vacuum. The residue was purified by flash chromatography on silica gel with 0~10% methanol in dichloromethane to afford N-(5-(((1r,4r)-4-((tert-butyldimethylsilyl)oxy)cyclohexyl)methoxy)-1,3,4-thiadiazol-2-yl)-5'-methoxy-2',6-dimethyl-(4,4'-bipyridine)-3-carboxamide (30 mg, 65%) as a white solid. MS (ESI) calc'd for ($C_{29}H_{41}N_5O_4SSi$) $(M+1)^+$, 584.1; found 584.2.

Step-7: N-(5-(((1r,4r)-4-hydroxycyclohexyl) methoxy)-1,3,4-thiadiazol-2-yl)-5'-methoxy-2',6-dimethyl-[4,4'-bipyridine]-3-carboxamide

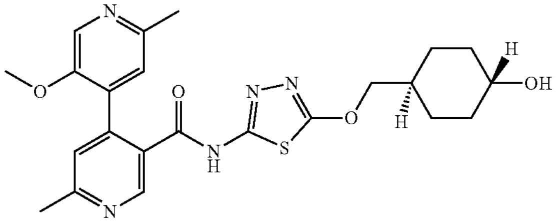 [SMILES: COc1cnc(C)cc1-c1cc(C)ncc1C(=O)Nc1nnc(OC[C@H]2CC[C@H](O)CC2)s1]

To a mixture of N-(5-(((1r,4r)-4-((tert-butyldimethylsilyl) oxy)cyclohexyl)methoxy)-1,3,4-thiadiazol-2-yl)-5'-methoxy-2',6-dimethyl-(4,4'-bipyridine)-3-carboxamide (30 mg, 0.087 mmol) in $CH_2Cl_2$ (5 mL) were added TFA (1 mL), The mixture was stirred at room temperature for 3 h before concentrated under vacuum. The residue was purified by prep-HPLC with the following conditions: (Column: Sunfire prep C18 column, 30*150, 5 um; Mobile Phase A: Water (0.1% FA), Mobile Phase B: ACN; Flow rate: 40 mL/min; Gradient: 25 B to 55 B in 8 min; 220 nm; RT1: 7.23 min) to afford N-(5-(((1r,4r)-4-hydroxycyclohexyl)methoxy)-1,3,4-thiadiazol-2-yl)-5'-methoxy-2',6-dimethyl-[4,4'-bipyridine]-3-carboxamide (13.6 mg, 45%) as a white solid. MS (ESI) calc'd for ($C_{23}H_{27}N_5O_3S$) $(M+1)^+$, 470.2; found 470.2. $^1$H NMR (400 MHz, DMSO-$d_6$) δ 12.85 (s, 1H), 8.75 (s, 1H), 8.18 (s, 1H), 7.34 (s, 1H), 7.24 (s, 1H), 4.54 (d, J=4.4 Hz, 1H), 4.21 (d, J=6.0 Hz, 2H), 3.58 (s, 3H), 3.33-3.35 (m, 1H), 2.57 (s, 3H), 2.43 (s, 3H), 1.85-1.82 (m, 2H), 1.76-1.73 (m, 3H), 1.16-1.02 (m, 4H).

Example 101

4-(2-fluoro-6-methoxyphenyl)-N-(5-(((1s,4s)-4-hydroxycyclohexyl)methoxy)-1,3,4-thiadiazol-2-yl)-6-methylnicotinamide

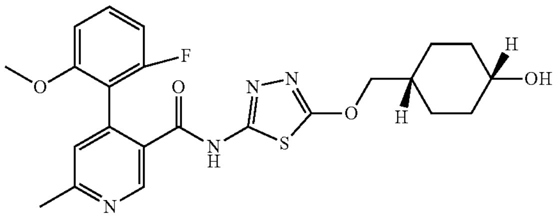 [SMILES: COc1cccc(F)c1-c1cc(C)ncc1C(=O)Nc1nnc(OC[C@H]2CC[C@@H](O)CC2)s1]

Step-1: methyl (1s,4s)-4-((tert-butyldimethylsilyl) oxy)cyclohexane-1-carboxylate

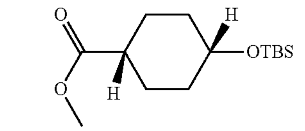 [SMILES: COC(=O)[C@H]1CC[C@@H](O[Si](C)(C)C(C)(C)C)CC1]

To a solution of methyl (1s,4s)-4-hydroxycyclohexane-1-carboxylate (750 mg, 4.741 mmol) in DCM (10 mL) were added imidazole (968 mg, 14.223 mmol) and TBSCl (1072 mg, 7.111 mmol). The resulting solution was stirred at room temperature for 12 hours. The resulting mixture was concentrated under vacuum. The residue was purified by flash chromatography on silica gel with 0~30% ethyl acetate in petroleum ether to afford methyl (1s,4s)-4-((tert-butyldimethylsilyl)oxy)cyclohexane-1-carboxylate (1.2 g, 83.6%) as a yellow oil.

Step-2: ((1s,4s)-4-((tert-butyldimethylsilyl)oxy)cyclohexyl)methanol

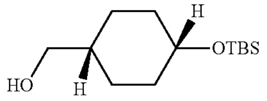 [SMILES: CC(C)(C)[Si](C)(C)O[C@H]1CC[C@@H](CO)CC1]

To a solution of methyl (1s,4s)-4-((tert-butyldimethylsilyl)oxy)cyclohexane-1-carboxylate (1.2 g, 4.404 mmol) in THF (10 mL) was added $LiAlH_4$ (335 mg, 8.809 mmol) in portions at 0° C. The resulting solution was stirred at room temperature for 4 hours. The reaction mixture was quenched with water and extracted with ethyl acetate. The combined organic layers were washed with brine, dried over anhydrous sodium sulfate, filtered, and concentrated under vacuum to afford ((1s,4s)-4-((tert-butyldimethylsilyl)oxy)cyclohexyl) methanol (870 mg, 72.7%) as yellow oil.

Step-3: (methylsulfanyl)((((1s,4s)-4-((tert-butyldimethylsilyl)oxy)cyclohexyl)methoxy))methanethione

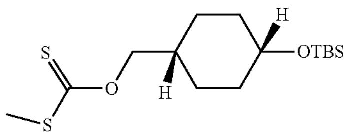 [SMILES: CSC(=S)OC[C@H]1CC[C@@H](O[Si](C)(C)C(C)(C)C)CC1]

To a solution of NaH (108 mg, 2.684 mmol, 60%) in THF (8 mL) was added ((1s,4s)-4-((tert-butyldimethylsilyl)oxy) cyclohexyl)methanol (870 mg, 3.559 mmol) at 0° C. and stirred at 5° C. for 1 h, then $CS_2$ (406 mg, 5.339 mmol) was added to the mixture at 0° C. and stirred at 0° C. for 0.5 h, then to the above mixture was added MeI (757 mg, 5.338 mmol). The resulting mixture was stirred at room temperature for 10 min. The reaction mixture was then quenched by the addition of water and extracted with ethyl acetate. The combined organic layers were washed with brine, dried over anhydrous sodium sulfate, filtered, and concentrated under vacuum. The residue was purified by flash chromatography on silica gel 0~30% ethyl acetate in petroleum ether to afford (methylsulfanyl)((((1s,4s)-4-((tert-butyldimethylsilyl)oxy) cyclohexyl)methoxy))methanethione (1.0 g, 29.5%) as a yellow oil.

Step-4: (((((1s,4s)-4-((tert-butyldimethylsilyl)oxy) cyclohexyl)methoxy)methanethioyl)amino)amine

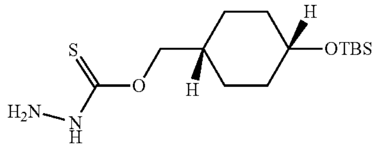 [SMILES: CC(C)(C)[Si](C)(C)O[C@H]1CC[C@@H](COC(=S)NN)CC1]

To a solution of (methylsulfanyl)((((1s,4s)-4-((tert-butyldimethylsilyl)oxy)cyclohexyl)methoxy))methanethione (1 g, 2.989 mmol) in MeOH was added hydrazine (0.17 g, 3.287 mmol, 80%). The resulting solution was stirred at room temperature for 2 hours. The resulting solution was diluted with of $H_2O$ and extracted with ethyl acetate. The combined organic layers were washed with brine, dried over anhydrous sodium sulfate, filtered, and concentrated under vacuum to afford (((((1s,4s)-4-((tert-butyldimethylsilyl)oxy)cyclohexyl)methoxy)methanethioyl)amino)amine (1.2 g, 75.6%) as a yellow solid. MS (ESI) calc'd for ($C_{14}H_{30}N_2O_2SSi$) $(M+1)^+$, 319.1; found, 319.0.

Step-5: 5-(((1s,4s)-4-((tert-butyldimethylsilyl)oxy) cyclohexyl)methoxy)-1,3,4-thiadiazol-2-amine

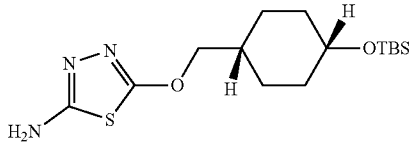 [SMILES: CC(C)(C)[Si](C)(C)O[C@H]1CC[C@@H](COc2nnc(N)s2)CC1]

To a solution of (((((1s,4s)-4-((tert-butyldimethylsilyl) oxy)cyclohexyl)methoxy)methanethioyl)amino)amine (1.2 g, 3.767 mmol) in MeOH (10 mL) were added TEA (1143 mg, 11.301 mmol) and BrCN (439 mg, 4.144 mmol). The resulting solution was stirred at room temperature for 1 hour. The resulting solution was quenched with $H_2O$ and extracted with ethyl acetate. The combined organic layers were washed with brine, dried over anhydrous sodium sulfate, filtered, and concentrated under vacuum. The residue was purified by flash chromatography on silica gel with 0~10% methanol in dichloromethane to afford 5-(((1s,4s)-4-((tert-butyldimethylsilyl)oxy)cyclohexyl)methoxy)-1,3,4-thiadiazol-2-amine (500 mg, 39.5%) as a yellow solid. MS (ESI) calc'd for ($C_{15}H_{29}N_3O_2SSi$) $(M+1)^+$, 344.2; found, 344.0.

Step-6: 4-(2-fluoro-6-methoxyphenyl)-6-methyl-N-(5-(((1s,4s)-4-((tertbutyldimethylsilyl)oxy)cyclohexyl)methoxy)-1,3,4-thiadiazol-2-yl)pyridine-3-carboxamide

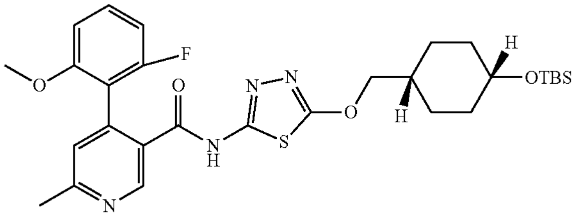 [SMILES: COc1cccc(F)c1-c1cc(C)ncc1C(=O)Nc1nnc(OC[C@H]2CC[C@@H](O[Si](C)(C)C(C)(C)C)CC2)s1]

To a solution of 5-(((1s,4s)-4-((tert-butyldimethylsilyl)oxy)cyclohexyl)methoxy)-1,3,4-thiadiazol-2-amine (200 mg, 0.582 mmol) in DMF (2 mL) and MeCN (2 mL) were added 4-(2-fluoro-6-methoxyphenyl)-6-methylpyridine-3-carboxylic acid (152 mg, 0.582 mmol, Intermediate F), NMI (143.39 mg, 1.746 mmol) and TCFH (196 mg, 0.698 mmol). The resulting solution was stirred at room temperature for 2 hours. The mixture was diluted with water and extracted with ethyl acetate. The combined organic layers were washed with brine, dried over anhydrous sodium sulfate, filtered, and concentrated under vacuum. The residue was purified by flash chromatography on silica gel with 0~10% methanol in dichloromethane to afford 4-(2-fluoro-6-methoxyphenyl)-6-methyl-N-(5-(((1s,4s)-4-((tertbutyldimethylsilyl)oxy)cyclohexyl)methoxy)-1,3,4-thiadiazol-2-yl)pyridine-3-carboxamide (130 mg, 38.0%) as a yellow solid. MS (ESI) calc'd for ($C_{29}H_{39}FN_4O_4SSi$) $(M+1)^+$, 587.2; found, 587.2.

Step-7: 4-(2-fluoro-6-methoxyphenyl)-6-methyl-N-(5-(((1s,4s)-4-hydroxycyclohexyl)methoxy)-1,3,4-thiadiazol-2-yl)pyridine-3-carboxamide

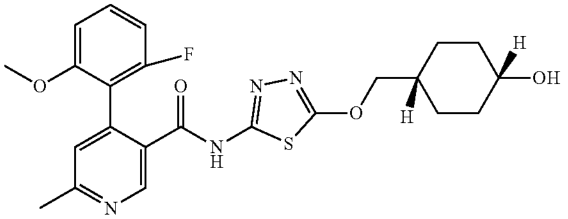 [SMILES: COc1cccc(F)c1-c1cc(C)ncc1C(=O)Nc1nnc(OC[C@H]2CC[C@@H](O)CC2)s1]

To a solution of 4-(2-fluoro-6-methoxyphenyl)-6-methyl-N-(5-(((1s,4s)-4-((tert-butyldimethylsilyl)oxy)cyclohexyl)methoxy)-1,3,4-thiadiazol-2-yl)pyridine-3-carboxamide (130 mg, 0.222 mmol) in DCM (5 mL) was added TFA (1 mL). The resulting solution was stirred at room temperature for 2 hours. The pH value of the solution was basified to 7-8 with the saturated $NaHCO_3$ aqueous. The resulting solution was extracted with ethyl acetate. The combined organic layers were washed with brine, dried over anhydrous sodium sulfate, filtered, and concentrated under vacuum. The residue was purified by flash chromatography on silica gel with 0~10% methanol in dichloromethane and further purified by prep-HPLC with the following conditions: (Column: XBridge Shield RP18 OBD Column, 19*250 mm, 10 um; Mobile Phase A: water (10 mmol/L $NH_4HCO_3$), Mobile Phase B: ACN; Flow rate: 60 mL/min; Gradient: 27 B to 43 B in 8 min; 220/254 nm; RT1: 7.62 min) to afford 4-(2-fluoro-6-methoxyphenyl)-6-methyl-N-(5-(((1s,4s)-4-hydroxycyclohexyl)methoxy)-1,3,4-thiadiazol-2-yl)pyridine-3-carboxamide (27.8 mg, 46.81%) as a white solid. MS (ESI) calc'd for ($C_{23}H_{25}FN_4O_4S$) $(M+1)^+$, 473.2; found, 473.2. H NMR (400 MHz, DMSO-$d_6$) δ 12.84 (s, 1H), 8.79 (s, 1H), 7.40-7.32 (m, 2H), 6.94-6.87 (m, 2H), 4.33 (s, 1H), 4.32 (s, 2H), 3.58-5.57 (m, 1H), 3.33 (s, 3H), 2.51 (s, 3H), 1.87-1.85 (m, 2H), 1.46-1.44 (m, 7H).

Example 102

4-(2-fluoro-6-methoxyphenyl)-6-methyl-N-(5-(5H,7H,8H-pyrano(4,3-b)pyridin-2-ylmethoxy)-1,3,4-thiadiazol-2-yl)pyridine-3-carboxamide

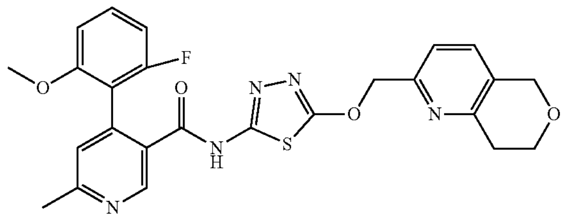 [SMILES: COc1cccc(F)c1-c1cc(C)ncc1C(=O)Nc1nnc(OCc2ccc3c(n2)CCOC3)s1]

Step-1: methyl 5H,7H,8H-pyrano(4,3-b)pyridine-2-carboxylate

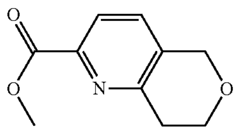

A mixture of 2-chloro-5H,7H,8H-pyrano(4,3-b)pyridine (350.0 mg, 2.06 mmol), Pd(dppf)$Cl_2$ (150.9 mg, 0.20 mmol) and TEA (626.4 mg, 6.19 mmol) in methanol (5.0 mL) was stirred at 80° C. for 16 h under CO (5 atm). The reaction mixture was quenched with water and extracted with ethyl acetate. The combined organic layers were washed with brine, dried over anhydrous sodium sulfate, filtered, and concentrated under vacuum. The crude residue was purified by flash column chromatography with 0-40% ethyl acetate in petroleum ether to afford methyl 5H,7H,8H-pyrano(4,3-b)pyridine-2-carboxylate (350.0 mg, 87%) as a yellow oil. MS (ESI) calc'd for ($C_{10}HnNO_3$) $(M+1)^+$, 194.0, found 194.0.

Step-2: 5H,7H,8H-pyrano(4,3-b)pyridin-2-ylmethanol

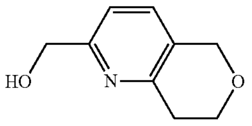 [SMILES: OCc1ccc2c(n1)CCOC2]

To a mixture of methyl 5H,7H,8H-pyrano(4,3-b)pyridine-2-carboxylate (150.0 mg, 0.77 mmol) in tetrahydrofuran (2.0 mL) and methanol (2.0 mL) were added $NaBH_4$ (29.3 mg, 0.77 mmol) and $CaCl_2$) (86.1 mg, 0.77 mmol). The resulting solution was stirred at 0° C. for 5 h. The reaction mixture was quenched with water and extracted with ethyl acetate. The combined organic layers were washed with brine, dried over anhydrous sodium sulfate, filtered, and concentrated under vacuum to afford 5H,7H,8H-pyrano(4,3-b)pyridin-2-ylmethanol (120.0 mg, crude) as a yellow oil. MS (ESI) calc'd for ($C_9H_{11}NO_2$) $(M+1)^+$, 166.0, found 166.0.

Step-3: 5-(5H,7H,8H-pyrano(4,3-b)pyridin-2-ylmethoxy)-1,3,4-thiadiazol-2-amine

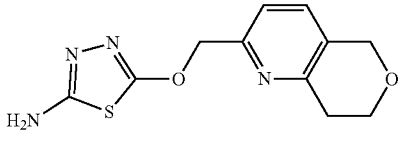 [SMILES: Nc1nnc(OCc2ccc3c(n2)CCOC3)s1]

To a mixture of NaH (8.7 mg, 0.36 mmol, 60%) in tetrahydrofuran (2.0 mL) was added 5H,7H,8H-pyrano(4,3-b)pyridin-2-ylmethanol (30.0 mg, 0.18 mmol) in THF (2.0 mL) at 0° C. and stirred at 0° C. for 0.5 h. To the above mixture was added 5-bromo-1,3,4-thiadiazol-2-amine (58.8 mg, 0.32 mmol) in THF (1.0 mL), the mixture was stirred at 0° C. for 2 h. The mixture was quenched by the addition of $NH_4Cl$ at 0° C. The aqueous solution was extracted with ethyl acetate. The combined organic layers were washed with brine, dried over anhydrous sodium sulfate, filtered, and concentrated under vacuum. The crude residue was purified by reverse phase flash column chromatography with 5-30% acetonitrile in water to afford 5-(5H,7H,8H-pyrano(4,3-b)pyridin-2-ylmethoxy)-1,3,4-thiadiazol-2-amine (30.0 mg, 14%) as a yellow solid. MS (ESI) calc'd for ($C_{11}H_{12}N_4O_2S$) $(M+1)^+$, 265.0, found 264.9.

Step-4: 4-(2-fluoro-6-methoxyphenyl)-6-methyl-N-(5-(5H,7H,8H-pyrano(4,3-b)pyridin-2-ylmethoxy)-1,3,4-thiadiazol-2-yl)pyridine-3-carboxamide

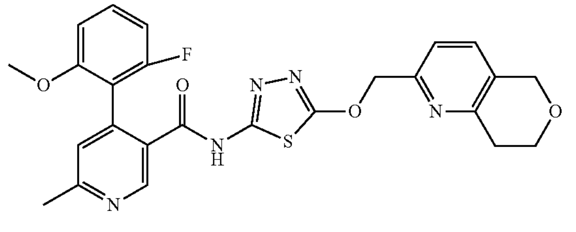 [SMILES: COc1cccc(F)c1-c1cc(C)ncc1C(=O)Nc1nnc(OCc2ccc3c(n2)CCOC3)s1]

A mixture of 4-(2-fluoro-6-methoxyphenyl)-6-methylpyridine-3-carboxylic acid (36.0 mg, 0.13 mmol, Intermediate F), 5-(5H,7H,8H-pyrano(4,3-b)pyridin-2-ylmethoxy)-1,3,4-thiadiazol-2-amine (43.7 mg, 0.16 mmol), TCFH (42.5 mg, 0.15 mmol) and NMI (23.7 mg, 0.28 mmol) in DMF (0.2 mL) and MeCN (3.0 mL) was stirred at room temperature for 2 h. The resulting solution was purified by reverse phase flash column chromatography with 5~50% acetonitrile in water to afford 4-(2-fluoro-6-methoxyphenyl)-6-methyl-N-(5-(5H,7H,8H-pyrano(4,3-b)pyridin-2-ylmethoxy)-1,3,4-thiadiazol-2-yl)pyridine-3-carboxamide (38.9 mg, 55%) as a white solid. MS (ESI) calc'd for ($C_{25}H_{22}FN_5O_4S$) $(M+1)^+$, 508.1, found 508.1. $^1H$ NMR (400 MHz, DMSO-$d_6$) δ 12.90 (s, 1H), 8.80 (s, 1H), 7.53 (d, J=8.0 Hz, 1H), 7.45-7.27 (m, 3H), 7.01-6.83 (m, 2H), 5.47 (s, 2H), 4.72 (s, 2H), 3.98 (t, J=6.0 Hz, 2H), 3.58 (s, 3H), 2.88 (t, J=6.0 Hz, 2H), 2.57 (s, 3H).

Example 103

4-(2-fluoro-6-methoxyphenyl)-N-(5-((3-(2-hydroxypropan-2-yl)bicyclo(1.1.1)pentan-1-yl)methoxy)-1,3,4-thiadiazol-2-yl)-6-methylpyridine-3-carboxamide

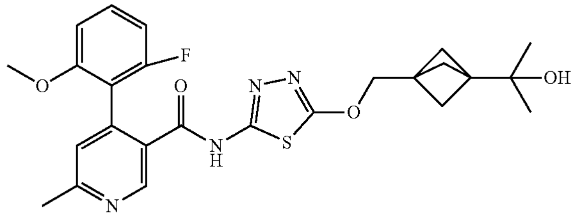 [SMILES: COc1cccc(F)c1-c1cc(C)ncc1C(=O)Nc1nnc(OCC23CC(C(C)(C)O)(C2)C3)s1]

Step-1: methyl 3-(hydroxymethyl)bicyclo(1.1.1)pentane-1-carboxylate

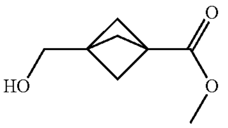

To a mixture of 3-(methoxycarbonyl)bicyclo(1.1.1)pentane-1-carboxylic acid (2.00 g, 11.75 mmol) and NMM (1.19 g, 11.75 mmol) in THF (20.0 mL) was added Isobutyl chloroformate (1.61 g, 11.78 mmol) at 0° C. The resulting solution was stirred at 0° C. for 2 h. To the above mixture was added $NaBH_4$ (1.33 g, 35.15 mmol) and MeOH (20.0 mL) slowly at 0° C. The resulting solution was stirred at 0° C. for 2 h. The resulting mixture was quenched with water and the organic solvents was removed under vacuum. The aqueous layer was extracted with ethyl acetate. The combined organic solution was dried over sodium sulfate, filtered, and concentrated under vacuum to afford methyl 3-(hydroxymethyl)bicyclo(1.1.1)pentane-1-carboxylate (1.2 g, 65%) as a yellow oil.

Step-2: methyl 3-((((methylsulfanyl)methanethioyl)oxy)methyl)bicyclo(1.1.1)pentane-1-carboxylate

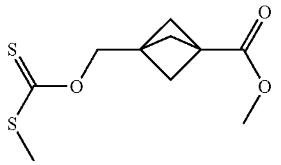

To a mixture of methyl 3-(hydroxymethyl)bicyclo(1.1.1)pentane-1-carboxylate (1.00 g, 6.40 mmol) in THF (10.0 mL, 493.72 mmol) was added NaH (0.31 g, 12.91 mmol) in portions at 0° C. and stirred at 0° C. for 30 min. To the above mixture was added $CS_2$ (0.73 g, 9.60 mmol) dropwise at 0°

C. and stirred at 0° C. for 10 min. Then MeI (1.36 g, 9.60 mmol) was added to the above mixture dropwise at 0° C. The resulting solution was stirred at 0° C. for 30 min. The reaction mixture was quenched with water and extracted with ethyl acetate. The combined organic layers were washed with brine, dried over anhydrous sodium sulfate, filtered, and concentrated under vacuum to afford methyl 3-((((methylsulfanyl)methanethioyl)oxy)methyl)bicyclo(1.1.1)pentane-1-carboxylate (360.0 mg, 23%) as a yellow oil.

Step-3: methyl 3-(((aminocarbamothioyl)oxy)methyl)bicyclo(1.1.1)pentane-1-carboxylate

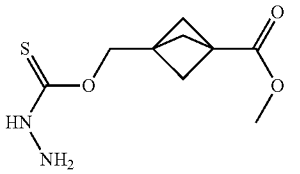

A mixture of methyl 3-((((methylsulfanyl)methanethioyl)oxy)methyl)bicyclo(1.1.1)pentane-1-carboxylate (360.0 mg, 1.46 mmol) and hydrazine (46.83 mg, 1.46 mmol) in MeOH (6 mL) was stirred at room temperature for 2 h. The reaction mixture was diluted with water and extracted with ethyl acetate. The combined organic layers were washed with brine, dried over anhydrous sodium sulfate, filtered, and concentrated under vacuum to afford methyl 3-(((aminocarbamothioyl)oxy)methyl)bicyclo(1.1.1)pentane-1-carboxylate (300.0 mg, 89%) as a yellow oil. MS (ESI) calc'd for ($C_9H_{14}N_2O_3S$) $(M+1)^+$, 231.1, found 231.0.

Step-4: methyl 3-(((5-amino-1,3,4-thiadiazol-2-yl)oxy)methyl)bicyclo(1.1.1)pentane-1-carboxylate

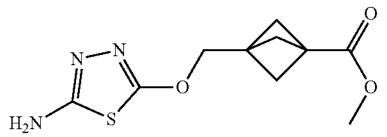 [SMILES: COC(=O)C12CC(COc3nnc(N)s3)(C1)C2]

To a mixture of methyl 3-(((aminocarbamothioyl)oxy)methyl)bicyclo(1.1.1)pentane-1-carboxylate (300.0 mg, 1.30 mmol) in MeOH (8 mL) were added TEA (263.6 mg, 2.60 mmol) and BrCN (70.83 mg, 0.66 mmol) at room temperature. The resulting solution was stirred at room temperature for 30 min. The reaction mixture was diluted with water and extracted with ethyl acetate. The combined organic layers were washed with brine, dried over anhydrous sodium sulfate, filtered, and concentrated under vacuum. The crude was purified by silica gel column chromatography, eluted with 0-80% acetate ethyl in petroleum ether to afford methyl 3-(((5-amino-1,3,4-thiadiazol-2-yl)oxy)methyl)bicyclo(1.1.1)pentane-1-carboxylate (60.0 mg, 18%) as a white solid. MS (ESI) calc'd for ($C_{10}H_{13}N_3O_3S$) $(M+1)^+$, 256.1, found 256.2.

Step-5: 2-(3-(((5-amino-1,3,4-thiadiazol-2-yl)oxy)methyl)bicyclo(1.1.1)pentan-1-yl)propan-2-ol

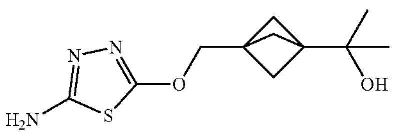 [SMILES: CC(C)(O)C12CC(COc3nnc(N)s3)(C1)C2]

To a mixture of methyl 3-(((5-amino-1,3,4-thiadiazol-2-yl)oxy)methyl)bicyclo(1.1.1)pentane-1-carboxylate (50.00 mg, 0.19 mmol) in THF (10.0 mL) was added bromo(methyl)magnesium (0.78 mL, 0.78 mmol, 1 M in THF) dropwise at 0° C. under nitrogen. The resulting mixture was stirred at 0° C. for 2 h under nitrogen. The reaction mixture was diluted with water and extracted with ethyl acetate. The combined organic layers were washed with brine, dried over anhydrous sodium sulfate, filtered, and concentrated under vacuum. The residue was purified by reverse phase flash column chromatography with 5~100% acetonitrile in water to afford 2-(3-(((5-amino-1,3,4-thiadiazol-2-yl)oxy)methyl)bicyclo(1.1.1)pentan-1-yl)propan-2-ol (50.0 mg, 99%) as a white solid. MS (ESI) calc'd for ($C_{11}H_{17}N_3O_2S$) $(M+1)^+$, 255.1, found 255.9.

Step-6: 4-(2-fluoro-6-methoxyphenyl)-N-(5-((3-(2-hydroxypropan-2-yl)bicyclo(1.1.1)pentan-1-yl)methoxy)-1,3,4-thiadiazol-2-yl)-6-methylpyridine-3-carboxamide

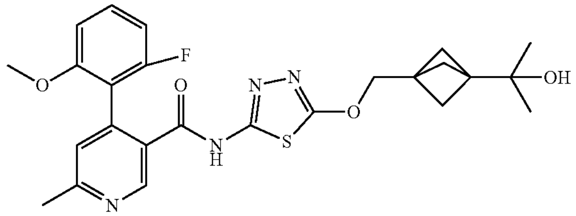 [SMILES: COc1cccc(F)c1-c1cc(C)ncc1C(=O)Nc1nnc(OCC23CC(C(C)(C)O)(C2)C3)s1]

A mixture of 4-(2-fluoro-6-methoxyphenyl)-6-methylpyridine-3-carboxylic acid (30.00 mg, 0.11 mmol, Intermediate F), 2-(3-(((5-amino-1,3,4-thiadiazol-2-yl)oxy)methyl)bicyclo(1.1.1)pentan-1-yl)propan-2-ol (35.19 mg, 0.13 mmol), TCFH (38.66 mg, 0.13 mmol), NMI (19.80 mg, 0.24 mmol) in MeCN (2.0 mL) and DMF (0.5 mL) was stirred at room temperature for 1.5 h. The resulting mixture was concentrated under vacuum. The residue was purified by reverse phase flash column chromatography with 5~55% acetonitrile in water to afford 4-(2-fluoro-6-methoxyphenyl)-N-(5-((3-(2-hydroxypropan-2-yl)bicyclo(1.1.1)pentan-1-yl)methoxy)-1,3,4-thiadiazol-2-yl)-6-methylpyridine-3-carboxamide (28.4 mg, 49%) as a white solid. MS (ESI) calc'd for ($C_{25}H_{27}FN_4O_4S$) $(M+1)^+$, 499.2, found 499.2. $^1H$ NMR (400 MHz, DMSO-$d_6$) δ 12.85 (s, 1H), 8.80 (s, 1H), 7.41-7.37 (m, 1H), 7.33 (s, 1H), 6.96-6.86 (m, 2H), 4.43 (d, J=1.6 Hz, 2H), 4.12 (s, 1H), 3.58 (s, 3H), 2.57 (s, 3H), 1.57 (s, 6H), 1.01 (s, 6H).

Example 104

4-(2-fluoro-6-methoxyphenyl)-N-(5-(((1r,4r)-4-hydroxycyclohexyl)methoxy)-1,3,4-thiadiazol-2-yl)-6-methylnicotinamide

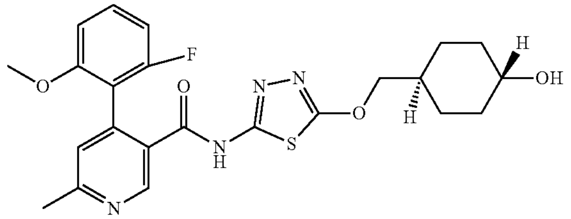 [SMILES: COc1cccc(F)c1-c1cc(C)ncc1C(=O)Nc1nnc(OC[C@H]2CC[C@H](O)CC2)s1]

Step-1: N-(5-(((1r,4r)-4-((tert-butyldimethylsilyl)oxy)cyclohexyl)methoxy)-1,3,4-thiadiazol-2-yl)-4-(2-fluoro-6-methoxyphenyl)-6-methylnicotinamide

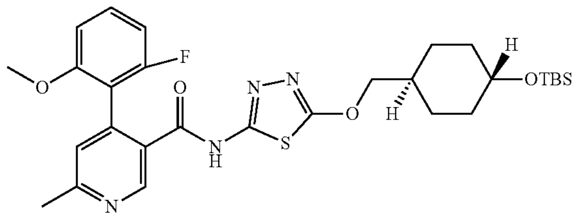 [SMILES: COc1cccc(F)c1-c1cc(C)ncc1C(=O)Nc1nnc(OC[C@H]2CC[C@H](O[Si](C)(C)C(C)(C)C)CC2)s1]

To a solution of 4-(2-fluoro-6-methoxyphenyl)-6-methylnicotinic acid (25 mg, 0.058 mmol, Intermediate F) in ACN (3 mL) and DMF (3 mL) were added NMI (24 mg, 0.183 mmol), 5-(((1r,4r)-4-((tert-butyldimethylsilyl)oxy)cyclohexyl)methoxy)-1,3,4-thiadiazol-2-amine (50 mg, 0.087 mmol, Example 100, Step 5) and TCFH (20 mg, 0.071 mmol). The resulting mixture was stirred at room temperature for 2 h. The reaction mixture was diluted with water and extracted with ethyl acetate. The combined organic layers were washed with brine, dried over anhydrous sodium sulfate, filtered, and concentrated under vacuum. The residue was purified by flash chromatography on silica gel with 0~10% methanol in dichloromethane to afford N-(5-(((1r,4r)-4-((tert-butyldimethylsilyl)oxy)cyclohexyl)methoxy)-1,3,4-thiadiazol-2-yl)-4-(2-fluoro-6-methoxyphenyl)-6-methylnicotinamide (50 mg, 65%) as a white solid. MS (ESI) calc'd for ($C_{29}H_{39}FN_4O_4SSi$) $(M+1)^+$, 586.1; found 586.2.

Step-2: 4-(2-fluoro-6-methoxyphenyl)-N-(5-(((1r,4r)-4-hydroxycyclohexyl)methoxy)-1,3,4-thiadiazol-2-yl)-6-methylnicotinamide

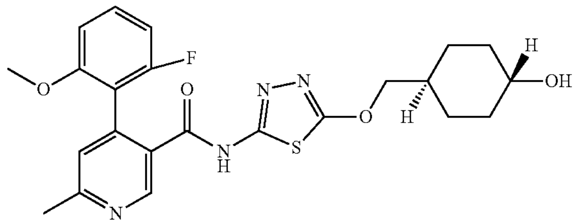 [SMILES: COc1cccc(F)c1-c1cc(C)ncc1C(=O)Nc1nnc(OC[C@H]2CC[C@H](O)CC2)s1]

To a mixture of N-(5-(((1r,4r)-4-((tert-butyldimethylsilyl)oxy)cyclohexyl)methoxy)-1,3,4-thiadiazol-2-yl)-4-(2-fluoro-6-methoxyphenyl)-6-methylnicotinamide (50 mg, 0.087 mmol) in $CH_2Cl_2$ (5 mL) was added TFA (1 mL). The mixture was stirred at room temperature for 3 h. And concentrated under vacuum. The residue was purified by prep-HPLC with the following conditions: (Column: Sunfire prep C18 column, 30*150, 5 um; Mobile Phase A: Water (0.1% FA), Mobile Phase B: ACN; Flow rate: 40 mL/min; Gradient: 25 B to 55 B in 8 min; 220 nm; RT1: 7.23 min) to afford 4-(2-fluoro-6-methoxyphenyl)-N-(5-(((1r,4r)-4-hydroxycyclohexyl)methoxy)-1,3,4-thiadiazol-2-yl)-6-methylnicotinamide (15 mg, 50%) as a white solid. MS (ESI) calc'd for ($C_{23}H_{25}FN_4O_4S$) $(M+1)^+$, 473.1; found 473.1. $^1H$ NMR (400 MHz, Methanol-$d_4$) δ 8.77 (s, 1H), 7.46-7.36 (m, 2H), 6.89-6.84 (m, 2H), 4.26 (d, J=6.4 Hz, 2H), 3.67 (s, 3H), 3.59-3.49 (m, 1H), 2.65 (s, 3H), 2.03-2.01 (m, 2H), 1.91-1.81 (m, 3H), 1.35-1.250 (m, 2H), 1.24-1.14 (m, 2H).

Example 105

2'-cyclopropyl-N-(5-((5-(2-hydroxypropan-2-yl)pyridin-2-yl)methoxy)-1,3,4-thiadiazol-2-yl)-5'-methoxy-6-methyl-[4,4'-bipyridine]-3-carboxamide

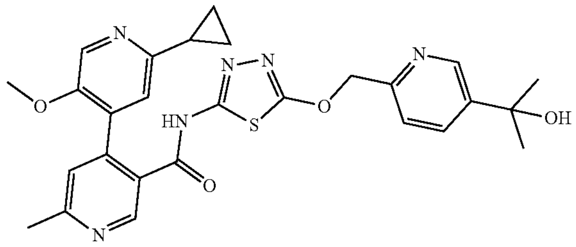 [SMILES: COc1cnc(C2CC2)cc1-c1cc(C)ncc1C(=O)Nc1nnc(OCc2ccc(C(C)(C)O)cn2)s1]

Step-1: benzyl 2-cyclopropyl-5-methoxy-6-methyl-(4,4-bipyridine)-3-carboxylate

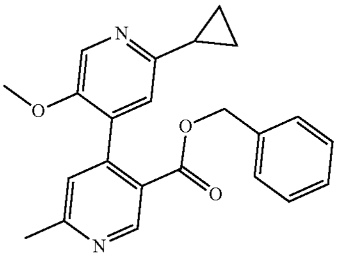 [SMILES: COc1cnc(C2CC2)cc1-c1cc(C)ncc1C(=O)OCc1ccccc1]

To a degassed solution of benzyl 2-chloro-5-methoxy-6-methyl-(4,4-bipyridine)-3-carboxylate (200 mg, 0.542 mmol) and cyclopropylboronic acid (139 mg, 1.63 mmol) in 1,4-dioxane (10 mL) and water (1 mL) were added $K_3PO_4$ (345 mg, 1.627 mmol) and PdAMPhos (19 mg, 0.03 mmol). The resulting mixture was stirred at 110° C. for 16 h under nitrogen atmosphere. The mixture was concentrated under reduced pressure. The residue was purified by reverse flash chromatography with the following conditions 10~50% Acetonitrile in water to afford benzyl 2-cyclopropyl-5-methoxy-6-methyl-(4,4-bipyridine)-3-carboxylate (60 mg, 29%) as a white solid. MS (ESI) calc'd for ($C_{23}H_{22}N_2O_3$) $(M+1)^+$, 375.2; found 375.2.

Step-2: 2-cyclopropyl-5-methoxy-6-methyl-(4,4-bipyridine)-3-carboxylic acid

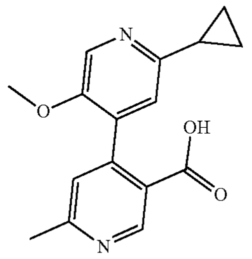 [SMILES: COc1cnc(C2CC2)cc1-c1cc(C)ncc1C(=O)O]

To a stirred solution of benzyl 2-cyclopropyl-5-methoxy-6-methyl-(4,4-bipyridine)-3-carboxylate (60 mg, 0.16 mmol) in THF (0.90 mL) and $H_2O$ (0.3 mL) was added $LiOH{\cdot}H_2O$ (26.9 mg, 0.64 mmol). The resulting mixture was stirred at room temperature for 3 h. The resulting mixture was acidified to pH ~5 with HCl (1 N). The residue was purified by prep-HPLC with the following conditions: (Column: Sunfire prep C18 column, 30*150 um, 5 um; Mobile Phase A: Water (0.1% FA), Mobile Phase B: ACN; Flow rate: 60 mL/min; Gradient: 2 B to 10 B in 8 min; 254 nm) to afford 2-cyclopropyl-5-methoxy-6-methyl-(4,4-bipyridine)-3-carboxylic acid (20 mg, 65%) as a white solid. MS (ESI) calc'd for ($C_{16}H_{16}N_2O_3$) $(M+1)^+$, 285.1; found 285.1.

Step-3: 2'-cyclopropyl-N-(5-((5-(2-hydroxypropan-2-yl)pyridin-2-yl)methoxy)-1,3,4-thiadiazol-2-yl)-5'-methoxy-6-methyl-[4,4'-bipyridine]-3-carboxamide

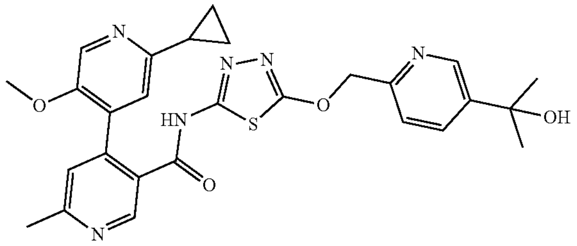 [SMILES: COc1cnc(C2CC2)cc1-c1cc(C)ncc1C(=O)Nc1nnc(OCc2ccc(C(C)(C)O)cn2)s1]

To a stirred solution of 2-cyclopropyl-5-methoxy-6-methyl-(4,4-bipyridine)-3-carboxylic acid (16 mg, 0.06 mmol) and 2-(6-(((5-amino-1,3,4-thiadiazol-2-yl)oxy)methyl)pyridin-3-yl)propan-2-ol (15 mg, 0.06 mmol) in DMF (1 mL) and MeCN (1 mL) were added NMI (18 mg, 0.26 mmol) and TCFH (24 mg, 0.09 mmol). The resulting mixture was stirred at room temperature for 1 h. The mixture was purified by prep-HPLC with the following conditions: (Column: XBridge Shield RP18 OBD Column, 30*150 mm, 5 um; Mobile Phase A: water (10 mmol/L $NH_4HCO_3$), Mobile Phase B: ACN; Flow rate: 60 mL/min; Gradient: 20 B to 40 B in 8 min; 220/254 nm) to afford 2'-cyclopropyl-N-(5-((5-(2-hydroxypropan-2-yl)pyridin-2-yl)methoxy)-1,3,4-thiadiazol-2-yl)-5'-methoxy-6-methyl-[4,4'-bipyridine]-3-carboxamide (12.0 mg, 40%) as a white solid. MS (ESI) calc'd for ($C_{27}H_{28}N_6O_4S$) $(M+1)^+$, 533.2; found 533.2. $^1H$ NMR (400 MHz, DMSO-$d_6$) δ 12.88 (s, 1H), 8.77 (s, 1H), 8.69 (d, J=2.0 Hz, 1H), 8.14 (s, 1H), 7.94-7.84 (m, 1H), 7.47 (d, J=8.0 Hz, 1H), 7.36 (s, 1H), 7.27 (s, 1H), 5.49 (s, 2H), 5.26 (s, 1H), 3.56 (s, 3H), 2.58 (s, 3H), 2.17-2.06 (m, 1H), 1.46 (s, 6H), 0.95-0.85 (m, 4H).

Example 106

2'-ethyl-N-(5-((5-(2-hydroxypropan-2-yl)pyridin-2-yl)methoxy)-1,3,4-thiadiazol-2-yl)-5'-methoxy-6-methyl-[4,4'-bipyridine]-3-carboxamide

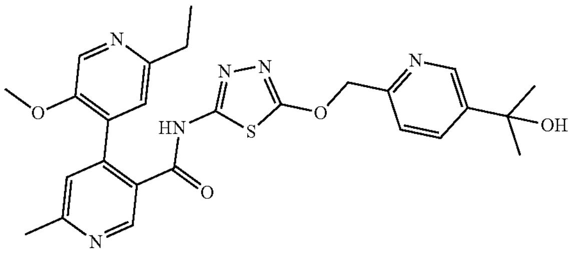 [SMILES: CCc1cc(-c2cc(C)ncc2C(=O)Nc2nnc(OCc3ccc(C(C)(C)O)cn3)s2)c(OC)cn1]

Step-1: benzyl 2-ethenyl-5-methoxy-6-methyl-(4,4-bipyridine)-3-carboxylate

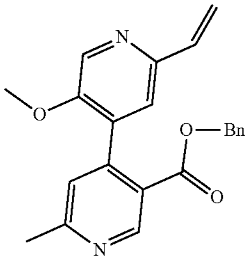 [SMILES: C=Cc1cc(-c2cc(C)ncc2C(=O)OCc2ccccc2)c(OC)cn1]

To a degassed solution of benzyl 2-chloro-5-methoxy-6-methyl-(4,4-bipyridine)-3-carboxylate (200 mg, 0.54 mmol) and ethenyltrifluoro-lambda4-borane potassium (108 mg, 0.81 mmol) in dioxane (5.00 mL) and $H_2O$ (1 mL) were added $K_2CO_3$ (225 mg, 1.63 mmol) and Pd(dppf)$Cl_2$ (40 mg, 0.05 mmol). The resulting mixture was stirred at 80° C. for 4 h under nitrogen atmosphere. The residue was purified by reverse phase flash chromatography with 10~50% acetonitrile in water to afford benzyl 2-ethenyl-5-methoxy-6-methyl-(4,4-bipyridine)-3-carboxylate (190 mg, 97%) as a yellow solid. MS (ESI) calc'd for ($C_{22}H_{20}N_2O_3$) $(M+1)^+$, 361.2; found 361.2.

Step-2: (((3,3,3-trifluoro-2,2-dimethylpropoxy)methanethioyl)amino)amine

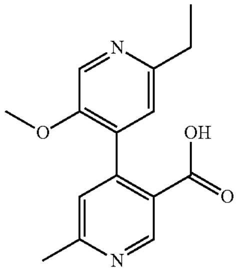 [SMILES: CCc1cc(-c2cc(C)ncc2C(=O)O)c(OC)cn1]

To a stirred solution of benzyl 2-ethenyl-5-methoxy-6-methyl-(4,4-bipyridine)-3-carboxylate (180 mg, 0.5 mmol) in MeOH (2 mL) was added Pd/C (20 mg, 10%). The resulting mixture was stirred at room temperature under hydrogen atmosphere. The resulting mixture was filtered and the filtrate was concentrated under reduced pressure to afford 2-ethyl-5-methoxy-6-methyl-(4,4-bipyridine)-3-carboxylic acid (60 mg, crude) as a white solid. MS (ESI) calc'd for ($C_{15}H_{16}N_2O_3$) $(M+1)^+$, 273.1; found 273.1.

Step-3: 2'-ethyl-N-(5-((5-(2-hydroxypropan-2-yl)pyridin-2-yl)methoxy)-1,3,4-thiadiazol-2-yl)-5'-methoxy-6-methyl-[4,4'-bipyridine]-3-carboxamide

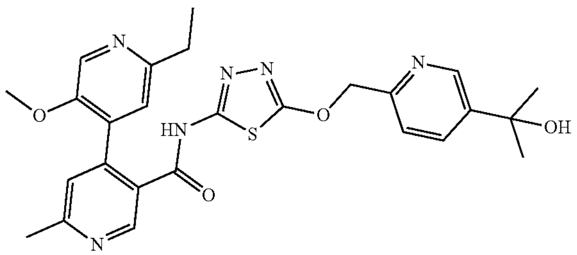 [SMILES: CCc1cc(-c2cc(C)ncc2C(=O)Nc2nnc(OCc3ccc(C(C)(C)O)cn3)s2)c(OC)cn1]

To a stirred solution of 2-ethyl-5-methoxy-6-methyl-(4,4-bipyridine)-3-carboxylic acid (20 mg, 0.07 mmol) and 2-(6-(((5-amino-1,3,4-thiadiazol-2-yl)oxy)methyl)pyridin-3-yl)propan-2-ol (20 mg, 0.07 mmol, Example 33, Step 1) in DMF (1 mL) and MeCN (1 mL) were added NMI (25 mg, 0.31 mmol) and TCFH (31.68 mg, 0.11 mmol). The resulting mixture was stirred at room temperature for 1 h. The mixture was purified by Prep-HPLC with the following conditions: (Column: XBridge Prep OBD C18 Column, 30×150 mm 5 um; Mobile Phase A: Water (10 MMOL/L $NH_4HCO_3$), Mobile Phase B: ACN; Flow rate: 60 mL/min; Gradient: 15 B to 40 B in 8 min; 254/220 nm) to afford 2'-ethyl-N-(5-((5-(2-hydroxypropan-2-yl)pyridin-2-yl)methoxy)-1,3,4-thiadiazol-2-yl)-5'-methoxy-6-methyl-[4,4'-bipyridine]-3-carboxamide (10.6 mg, 27%) as a white solid. MS (ESI) calc'd for ($C_{26}H_{28}N_6O_4S$) $(M+1)^+$, 521.1; found 521.4. $^1H$ NMR (400 MHz, DMSO-$d_6$) δ 12.92 (s, 1H), 8.76 (s, 1H), 8.67 (s, 1H), 8.22 (s, 1H), 7.95-7.85 (m, 1H), 7.48 (d, J=8.0 Hz, 1H), 7.36 (s, 1H), 7.24 (s, 1H), 5.50 (s, 2H), 5.26 (s, 1H), 3.60 (s, 3H), 2.81-2.71 (m, 2H), 2.58 (s, 3H), 1.46 (s, 6H), 1.24-1.26 (m, J=7.6 Hz, 3H).

Example 107

N-(5-(((1r,3r)-3-hydroxycyclobutyl)methoxy)-1,3,4-thiadiazol-2-yl)-5'-methoxy-2',6-dimethyl-[4,4'-bipyridine]-3-carboxamide

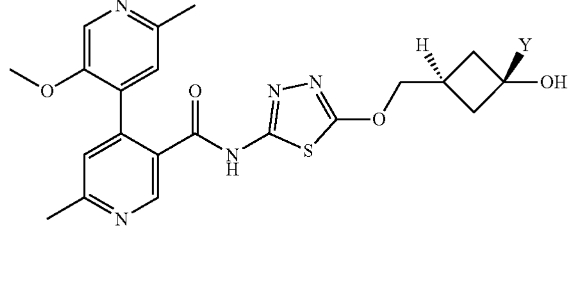

Step-1: methyl (1r,3r)-3-((tert-butyldimethylsilyl)oxy)cyclobutane-1-carboxylate

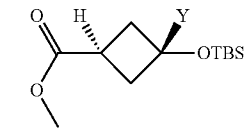

To a mixture of methyl (1r,3r)-3-hydroxycyclobutane-1-carboxylate (3 g, 23.052 mmol) and Imidazole (2.3 g, 34.520 mmol) in DCM (30 mL) were added TBS-Cl (5.2 g, 34.578 mmol) and DMAP (281 mg, 2.305 mmol) at 0° C. The resulting mixture was stirred at 0° C. for 1 hour. The reaction mixture was then quenched by the addition of water and extracted with ethyl acetate. The organic layers were combined, washed with brine, dried over anhydrous sodium sulfate and filtered. The filtrate was concentrated under vacuum. The residue was purified by flash chromatography on silica gel with 0~30% ethyl acetate in petroleum ether to afford methyl (1r,3r)-3-((tert-butyldimethylsilyl)oxy)cyclobutane-1-carboxylate (4.9 g, 86%) as a colorless oil. MS (ESI) calc'd for ($C_{12}H_{24}O_3Si$) $(M+1)^+$, 245.1.

Step-2: ((1r,3r)-3-((tert-butyldimethylsilyl)oxy)cyclobutyl)methanol

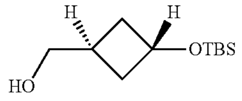 [SMILES: CC(C)(C)[Si](C)(C)O[C@H]1C[C@H](CO)C1]

To a solution of methyl (1r,3r)-3-((tert-butyldimethylsilyl)oxy)cyclobutane-1-carboxylate (4.9 g, 21.400 mmol) in THF (30 mL) was added $LiAlH_4$ (1.6 g, 42.683 mmol) in portions at 0~5° C. The resulting mixture was stirred at 0° C. for 1 hour. The reaction mixture was then quenched by the addition of water and extracted with ethyl acetate. The combined organic layers were washed with brine, dried over anhydrous sodium sulfate, filtered, and concentrated under vacuum. The residue was purified by flash chromatography on silica gel with 0~40% ethyl acetate in petroleum ether to afford ((1r,3r)-3-((tert-butyldimethylsilyl)oxy)cyclobutyl)methanol (3.9 g, 84%) as a colorless oil. MS (ESI) calc'd for ($C_{11}H_{24}O_2Si$) $(M+1)^+$, 217.1.

Step-3: 0-(((1r,3r)-3-((tert-butyldimethylsilyl)oxy)cyclobutyl)methyl)S-methyl carbonodithioate

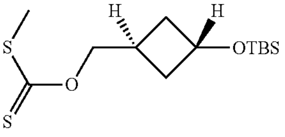 [SMILES: CSC(=S)OC[C@H]1C[C@H](O[Si](C)(C)C(C)(C)C)C1]

To a solution of (((1r,3r)-3-((tert-butyldimethylsilyl)oxy)cyclobutyl)methanol (3.90 g, 18.023 mmol) in THF (20 mL) was added NaH (0.4 g, 18.023 mmol, 60%) in portions at 0° C. and stirred at 0° C. for 30 min. Then $CS_2$ (2.0 g, 27.035 mmol) was added to the above mixture and stirred at 0° C.

for 10 min, and then MeI (3.8 g, 27.035 mmol) was added to the above mixture at 5° C. The resulting mixture was stirred at room temperature for 1 hour. The reaction mixture was quenched by the addition of water and extracted with ethyl acetate. The combined organic layers were washed with brine, dried over anhydrous sodium sulfate, filtered, and concentrated under vacuum, The residue was purified by flash chromatography on silica gel with 0-50% ethyl acetate in petroleum ether to afford O-(((1r,3r)-3-((tert-butyldimethylsilyl)oxy)cyclobutyl)methyl)S-methyl carbonodithioate (4.2 g, 76%) as a colorless oil. MS (ESI) calc'd for ($C_{13}H_{26}O_2S_2Si$) $(M+1)^+$, 307.1.

Step-4: 0-(((1r,3r)-3-((tert-butyldimethylsilyl)oxy)cyclobutyl)methyl) hydrazinecarbothioate

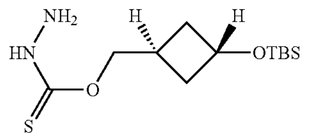 [SMILES: CC(C)(C)[Si](C)(C)O[C@H]1C[C@H](COC(=S)NN)C1]

To a solution of O-(((1r,3r)-3-((tert-butyldimethylsilyl)oxy)cyclobutyl)methyl)S-methyl carbonodithioate (4.2 g, 13.701 mmol) in MeOH (20 mL) was added hydrazine (0.6 g, 20.552 mmol, 80%) at 0° C. The resulting mixture was stirred at room temperature for 1 hour. The reaction mixture was quenched with water and extracted with ethyl acetate. The combined organic layers were washed with brine, dried over anhydrous sodium sulfate, filtered, and concentrated under vacuum to afford O-(((1r,3r)-3-((tert-butyldimethylsilyl)oxy)cyclobutyl)methyl) hydrazinecarbothioate (3.9 g, 97%) as red oil. MS (ESI) calc'd for ($C_{12}H_{26}N_2O_2SSi$) $(M+1)^+$, 291.1.

Step-5: 5-(((1r,3r)-3-((tert-butyldimethylsilyl)oxy)cyclobutyl)methoxy)-1,3,4-thiadiazol-2-amine

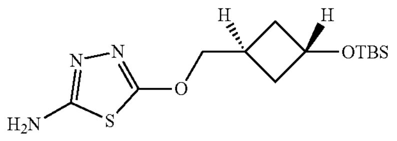 [SMILES: CC(C)(C)[Si](C)(C)O[C@H]1C[C@H](COc2nnc(N)s2)C1]

To a solution of O-(((1r,3r)-3-((tert-butyldimethylsilyl)oxy)cyclobutyl)methyl) hydrazinecarbothioate (3.9 g, 13.425 mmol) in MeOH (20.00 mL) were added TEA (4.0 g, 40.275 mmol) and BrCN (2.2 g, 21.480 mmol). The resulting mixture was stirred at 0° C. for 2 hours. The reaction mixture was quenched with water and extracted with ethyl acetate. The combined organic layers were washed with brine, dried over anhydrous sodium sulfate, filtered, and concentrated under vacuum. The residue was purified by flash chromatography on silica gel with 0~60% ethyl acetate in petroleum ether to afford 5-(((1r,3r)-3-((tert-butyldimethylsilyl)oxy)cyclobutyl)methoxy)-1,3,4-thiadiazol-2-amine (2 g, 47%) as a yellow solid. MS (ESI) calc'd for ($C_{13}H_{25}N_3O_2SSi$) $(M+1)^+$, 316.1; found 316.1.

Step-6: N-(5-(((1r,3r)-3-((tert-butyldimethylsilyl)oxy)cyclobutyl)methoxy)-1,3,4-thiadiazol-2-yl)-5'-methoxy-2',6-dimethyl-[4,4'-bipyridine]-3-carboxamide

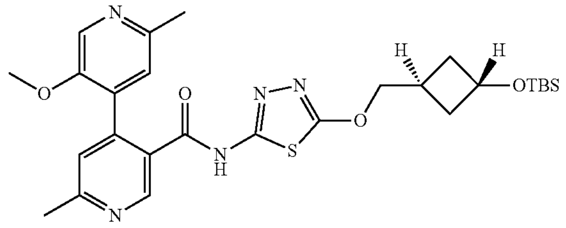 [SMILES: COc1cnc(C)cc1-c1cc(C)ncc1C(=O)Nc1nnc(OC[C@H]2C[C@H](O[Si](C)(C)C(C)(C)C)C2)s1]

To a solution of 5-methoxy-2,6-dimethyl-(4,4-bipyridine)-3-carboxylic acid (99 mg, 0.387 mmol, Intermediate G) in ACN (0.5 mL) and DMF (0.5 mL) were added NMI (95 mg, 1.160 mmol), 5-(((1r,3r)-3-((tert-butyldimethylsilyl)oxy)cyclobutyl)methoxy)-1,3,4-thiadiazol-2-amine (122 mg, 0.387 mmol) and TCFH (119 mg, 0.425 mmol). The mixture was stirred at room temperature for 2 hours. The resulting mixture was filtered. The filter cake was collected and dried under vacuum to afford N-(5-(((1r,3r)-3-((tert-butyldimethylsilyl)oxy)cyclobutyl)methoxy)-1,3,4-thiadiazol-2-yl)-5'-methoxy-2',6-dimethyl-[4,4'-bipyridine]-3-carboxamide (100 mg, 46%) as a white solid. MS (ESI) calc'd for ($C_{27}H_{37}N_5O_4SSi$) $(M+1)^+$, 556.2; found 556.0.

Step-7: N-(5-(((1r,3r)-3-hydroxycyclobutyl)methoxy)-1,3,4-thiadiazol-2-yl)-5'-methoxy-2',6-dimethyl-[4,4'-bipyridine]-3-carboxamide

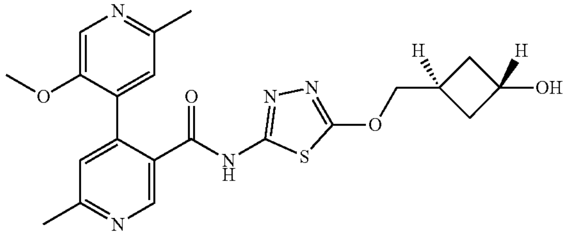 [SMILES: COc1cnc(C)cc1-c1cc(C)ncc1C(=O)Nc1nnc(OC[C@H]2C[C@H](O)C2)s1]

To a mixture of N-(5-(((1r,3r)-3-((tert-butyldimethylsilyl)oxy)cyclobutyl)methoxy)-1,3,4-thiadiazol-2-yl)-5'-methoxy-2',6-dimethyl-[4,4'-bipyridine]-3-carboxamide (90 mg, 0.162 mmol) in THF (1 mL) were added TBAF (105 mg, 0.405 mmol). The mixture was stirred at room temperature for 24 hours before concentrated under vacuum. The resulting mixture was purified by reverse phase flash chromatography with 10-70% acetonitrile in water to afford to afford N-(5-(((1r,3r)-3-hydroxycyclobutyl)methoxy)-1,3,4-thiadiazol-2-yl)-5'-methoxy-2',6-dimethyl-[4,4'-bipyridine]-3-carboxamide (38 mg, 53%) as a white solid. MS (ESI) calc'd for ($C_{21}H_{23}N_5O_4S$) $(M+1)^+$, 442.1; found 442.0. $^1H$ NMR (400 MHz, DMSO-$d_6$) δ 12.83 (s, 1H), 8.75 (s, 1H), 8.18 (s, 1H), 7.35 (s, 1H), 7.25 (s, 1H), 5.04 (d, J=6.4 Hz, 1H), 4.41 (d, J=7.6 Hz, 2H), 4.30-4.15 (m, 1H), 3.59 (s, 3H), 2.61-2.55 (m, 4H), 2.47 (s, 3H), 2.15-2.05 (m, 2H), 2.03-1.94 (m, 2H).

Example 108

2'-chloro-N-(5-(((1r,3r)-3-hydroxycyclobutyl) methoxy)-1,3,4-thiadiazol-2-yl)-5'-methoxy-6-methyl-[4,4'-bipyridine]-3-carboxamide

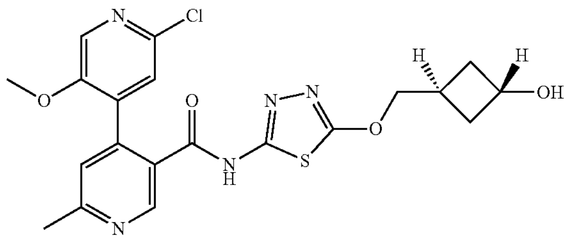

Step-1: N-(5-(((1r,3r)-3-((tert-butyldimethylsilyl) oxy)cyclobutyl)methoxy)-1,3,4-thiadiazol-2-yl)-2'-chloro-5'-methoxy-6-methyl-[4,4'-bipyridine]-3-carboxamide

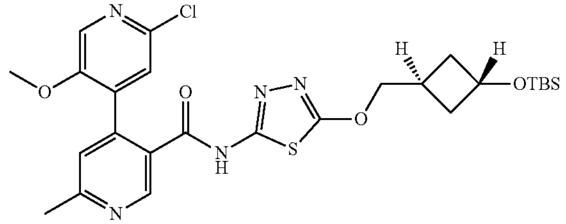 [SMILES: COc1cnc(Cl)cc1-c1cc(C)ncc1C(=O)Nc1nnc(OC[C@H]2C[C@H](O[Si](C)(C)C(C)(C)C)C2)s1]

To a solution of 2'-chloro-5'-methoxy-6-methyl-(4,4'-bipyridine)-3-carboxylic acid (100 mg, 0.358 mmol, Intermediate H) in ACN (2 mL) and DMF (2 mL) were added NMI (88 mg, 1.074 mmol), 5-(((1r,3r)-3-((tert-butyldimethylsilyl)oxy)cyclobutyl)methoxy)-1,3,4-thiadiazol-2-amine (113 mg, 0.358 mmol, Example 107, Step 5) and TCFH (110 mg, 0.394 mmol). The mixture was stirred at room temperature for 1 hour. The resulting mixture was filtered. The filter cake was collected and dried under vacuum to afford N-(5-(((1r, 3r)-3-((tert-butyldimethylsilyl)oxy)cyclobutyl)methoxy)-1, 3,4-thiadiazol-2-yl)-2'-chloro-5'-methoxy-6-methyl-[4,4'-bipyridine]-3-carboxamide (110 mg, 53%) as a white solid. MS (ESI) calc'd for ($C_{26}H_{34}ClN_5O_4SSi$) $(M+1)^+$, 576.1; found 576.1.

Step-2: 2'-chloro-N-(5-(((1r,3r)-3-hydroxycyclobutyl)methoxy)-1,3,4-thiadiazol-2-yl)-5'-methoxy-6-methyl-[4,4'-bipyridine]-3-carboxamide

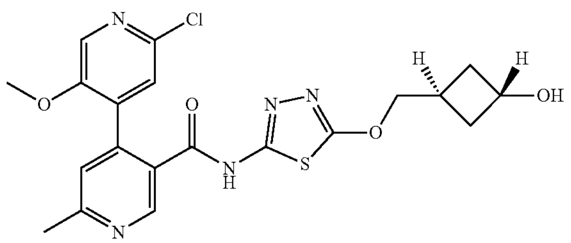 [SMILES: COc1cnc(Cl)cc1-c1cc(C)ncc1C(=O)Nc1nnc(OC[C@H]2C[C@H](O)C2)s1]

To a mixture of N-(5-(((1r,3r)-3-((tert-butyldimethylsilyl) oxy)cyclobutyl)methoxy)-1,3,4-thiadiazol-2-yl)-2'-chloro-5'-methoxy-6-methyl-[4,4'-bipyridine]-3-carboxamide (110 mg, 0.191 mmol) in THF (2 mL) was added TBAF (124 mg, 0.478 mmol). The resulting mixture was stirred at room temperature for 48 hours before concentrated under vacuum. The resulting mixture was purified by reverse phase flash chromatography with 20-80% acetonitrile in water to afford 2'-chloro-N-(5-(((1r,3r)-3-hydroxycyclobutyl)methoxy)-1, 3,4-thiadiazol-2-yl)-5'-methoxy-6-methyl-[4,4'-bipyridine]-3-carboxamide (51.8 mg, 58%) as a white solid. MS (ESI) calc'd for ($C_{20}H_{20}ClN_5O_4S$) $(M+1)^+$, 462.1; found 462.0. $^1$H NMR (400 MHz, DMSO-6) δ 12.88 (s, 1H), 8.81 (s, 1H), 8.17 (s, 1H), 7.54 (s, 1H), 7.43 (s, 1H), 5.04 (d, J=6.4 Hz, 1H), 4.41 (d, J=7.6 Hz, 2H), 4.31-4.20 (m, 1H), 3.63 (s, 3H), 2.62-2.55 (m, 4H), 2.17-2.04 (m, 2H), 2.05-1.91 (m, 2H).

Example 109

4-(2-fluoro-6-methoxyphenyl)-N-(5-((6-(2-hydroxypropan-2-yl)pyridin-3-yl)methoxy)-1,3,4-thiadiazol-2-yl)-6-methylpyridine-3-carboxamide

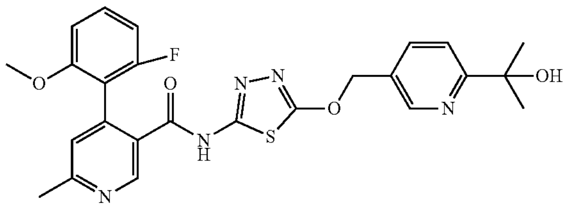 [SMILES: COc1cccc(F)c1-c1cc(C)ncc1C(=O)Nc1nnc(OCc2ccc(C(C)(C)O)nc2)s1]

Step-1: 2-(5-bromopyridin-2-yl)propan-2-ol

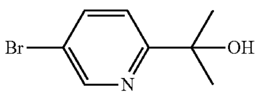

To a stirred solution of 1-(5-bromopyridin-2-yl)ethanone (5.0 g, 25 mmol) in THF (50 mL) was added MeMgBr in THF (6.0 g, 0.05 mmol) dropwise at 0° C. under nitrogen atmosphere. The mixture resulting was stirred at room temperature for 2 h under nitrogen atmosphere. The resulting mixture was quenched with saturated $NH_4Cl$ aqueous solution and extracted with ethyl acetate. The combined organic layers were washed with brine, dried over anhydrous $Na_2SO_4$. After filtration, the filtrate was concentrated under reduced pressure. The residue was purified by silica gel column chromatography, eluted with 0-50% ethyl acetate in petroleum ether to afford 2-(5-bromopyridin-2-yl)propan-2-ol (3.3 g, 61%) as a yellow oil. MS (ESI) calc'd for ($C_8H_{10}BrNO$) $(M+1)^+$, 216.0; found 216.0.

Step-2: 5-bromo-2-(2-((tert-butyldimethylsilyl)oxy) propan-2-yl)pyridine

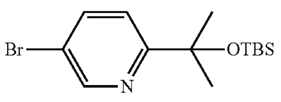 [SMILES: CC(C)(O[Si](C)(C)C(C)(C)C)c1ccc(Br)cn1]

To a stirred solution of 2-(5-bromopyridin-2-yl)propan-2-ol (3.3 g, 15.27 mmol) and 2,6-lutidine (3.3 g, 30.54 mmol) in DCM (30 mL) was added TBSOTf (6.1 g, 22.9 mmol) in portions at room temperature under nitrogen atmosphere. The mixture resulting was stirred at room temperature for 2 h under nitrogen atmosphere. The resulting mixture was quenched with water and extracted with DCM. The combined organic layers were washed with brine, dried over anhydrous $Na_2SO_4$. After filtration, the filtrate was concentrated under reduced pressure. The residue was purified by silica gel column chromatography, eluted with 0~50% ethyl acetate in petroleum ether to afford 5-bromo-2-(2-((tert-butyldimethylsilyl)oxy)propan-2-yl)pyridine (3.3 g, 67%) as a yellow oil. MS (ESI) calc'd for ($C_{14}H_{24}BrNOSi$) $(M+1)^+$, 330.1; found 330.0.

Step-3: 2-(2-((tert-butyldimethylsilyl)oxy)propan-2-yl)-5-ethenylpyridine

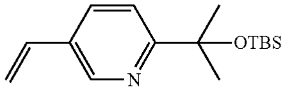 [SMILES: C=Cc1ccc(C(C)(C)O[Si](C)(C)C(C)(C)C)nc1]

To a degassed solution of 5-bromo-2-(2-((tert-butyldimethylsilyl)oxy)propan-2-yl)pyridine (2.4 g, 7.26 mmol) and boron trifluoride ethenyl potassium (1.5 g, 0.01 mol) in dioxane (10 mL) and water (1 mL) were added Pd(dppf)$Cl_2$ (0.5 g, 0.001 mol) and $K_2CO_3$ (3.0 g, 0.02 mol) under nitrogen atmosphere. The resulting mixture was stirred at 80° C. for 2 h under nitrogen atmosphere. The resulting mixture was filtered, the filtrate was concentrated under reduced pressure. The residue was purified by silica gel column chromatography, eluted with 0-50% ethyl acetate in petroleum ether to afford 2-(2-((tert-butyldimethylsilyl)oxy)propan-2-yl)-5-ethenylpyridine (1 g, 49%) as an off-white oil. MS (ESI) calc'd for ($C_{16}H_{27}NO_2Si$) (M+1)+, 278.0; found 278.0.

Step-4: 6-(2-((tert-butyldimethylsily)oxy)propan-2-yl)pyridine-3-carbaldehyde

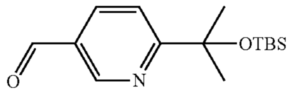 [SMILES: CC(C)(O[Si](C)(C)C(C)(C)C)c1ccc(C=O)cn1]

To a stirred solution of 2-(2-((tert-butyldimethylsilyl)oxy)propan-2-yl)-5-ethenylpyridine (1.0 g, 3.60 mmol) in THF (9 mL) was added $NaIO_4$ (3.1 g, 0.01 mol) in water (1 mL) dropwise at room temperature under nitrogen atmosphere. Then to the above mixture was added $OSO_4$ (0.09 g, 0.001 mol) at room temperature for 5 h under nitrogen atmosphere. The resulting mixture was extracted with ethyl acetate. The combined organic layers were washed with brine, dried over anhydrous $Na_2SO_4$. After filtration, the filtrate was concentrated under reduced pressure to afford 6-(2-((tert-butyldimethylsilyl)oxy)propan-2-yl)pyridine-3-carbaldehyde (950 mg, crude) as a yellow oil. MS (ESI) calc'd for ($C_{15}H_{25}NO_2Si$) $(M+1)^+$, 280.2; found, 280.0.

Step-5: 6-(2-((tert-butyldimethylsilyl)oxy)propan-2-yl)pyridin-3-yl)methanol

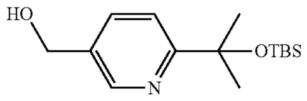

To a stirred solution of 6-(2-((tert-butyldimethylsilyl)oxy)propan-2-yl)pyridine-3-carbaldehyde (950 mg, 3.4 mmol) in MeOH (1 mL) was added $NaBH_4$ (257 mg, 6.8 mmol) in portions at room temperature under nitrogen atmosphere. The mixture resulting was stirred at room temperature for 1 h. The resulting mixture was quenched with water and extracted with ethyl acetate. The combined organic layers were washed with brine, dried over anhydrous $Na_2SO_4$. After filtration, the filtrate was concentrated under reduced pressure. The residue was purified by reverse flash chromatography with 5-70% acetonitrile in water to afford (6-(2-((tert-butyldimethylsilyl)oxy)propan-2-yl)pyridin-3-yl)methanol (500 mg, 52%) as a green oil. MS (ESI) calc'd for ($C_{15}H_{27}NO_2Si$) $(M+1)^+$, 282.2; found, 282.0.

Step-6: ((6-(2-((tert-butyldimethylsilyl)oxy)propan-2-yl)pyridin-3-yl)methoxy)(methylsulfanyl)methanethione

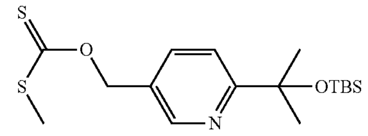 [SMILES: CSC(=S)OCc1ccc(C(C)(C)O[Si](C)(C)C(C)(C)C)nc1]

To a stirred solution of (6-(2-((tert-butyldimethylsilyl)oxy)propan-2-yl)pyridin-3-yl)methanol (390 mg, 1.38 mmol) THF (4 mL) was added NaH (61 mg, 1.52 mmol, 60%) in portions at 0° C. and stirred at 0° C. for 30 min. And then to the above mixture was sequentially added $CS_2$ (158 mg, 2.08 mmol) and MeI (295 mg, 2.08 mmol) at 0° C. under nitrogen. The resulting mixture was stirred at room temperature for 1 h under nitrogen atmosphere. The resulting mixture was quenched with water and extracted with ethyl acetate. The combined organic layers were washed with brine, dried over anhydrous $Na_2SO_4$. After filtration, the filtrate was concentrated under reduced pressure. The residue was purified by flash column chromatography with 0~15% ethyl acetate in petroleum ether to afford ((6-(2-((tert-butyldimethylsilyl)oxy)propan-2-yl)pyridin-3-yl)methoxy)(methylsulfanyl)methanethione (300 mg, 68%) as a yellow oil. MS (ESI) calc'd for ($C_{10}H_9FN_4O_2S$) $(M+1)^+$, 372.1; found 372.1.

Step-7: ((((6-(2-((tert-butyldimethylsilyl)oxy)propan-2-yl)pyridin-3-yl)methoxy)methanethioyl)amino)amine

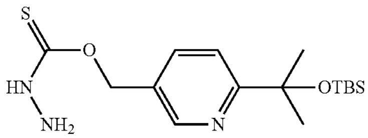

To a stirred solution of ((6-(2-((tert-butyldimethylsilyl)oxy)propan-2-yl)pyridin-3-yl)methoxy)(methylsulfanyl)methanethione (270 mg, 0.72 mmol) in MeOH (3 mL) was added Hydrazine (23 mg, 0.72 mmol). The mixture resulting was stirred at 0° C. for 1 h. The reaction mixture was quenched with water and extracted with ethyl acetate. The combined organic layers were washed with brine, dried over anhydrous sodium sulfate, filtered, and concentrated under vacuum to afford ((((6-(2-((tert-butyldimethylsilyl)oxy)propan-2-yl)pyridin-3-yl)methoxy)methanethioyl)amino)amine (260 mg, crude) as an colorless oil. MS (ESI) calc'd for $(C_{24}H_{19}F_2N_5O_4S)$ $(M+1)^+$, 356.2; found 356.0.

Step-8: 5-((6-(2-((tert-butyldimethylsilyl)oxy)propan-2-yl)pyridin-3-yl)methoxy)-1,3,4-thiadiazol-2-amine

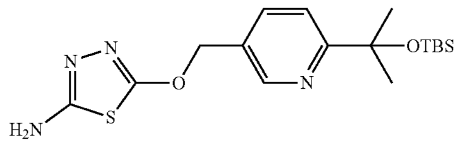 [SMILES: CC(C)(O[Si](C)(C)C(C)(C)C)c1ccc(COc2nnc(N)s2)cn1]

To a stirred solution of ((((6-(2-((tert-butyldimethylsilyl)oxy)propan-2-yl)pyridin-3-yl)methoxy)methanethioyl)amino)amine (260 mg, 0.73 mmol) and TEA (148 mg, 1.46 mmol) in MeOH (3 mL) was added BrCN (85.2 mg, 0.80 mmol). The resulting mixture was stirred at room temperature for 2 h. The reaction mixture was quenched with water and extracted with ethyl acetate. The combined organic layers were washed with brine, dried over anhydrous sodium sulfate, filtered, and concentrated under vacuum to afford 5-((6-(2-((tert-butyldimethylsilyl)oxy)propan-2-yl)pyridin-3-yl)methoxy)-1,3,4-thiadiazol-2-amine (250 mg, crude) as a pink solid. MS (ESI) calc'd for $(C_{17}H_{28}N_4O_2SSi)$ $(M+1)^+$, 381.2; found 381.0.

Step-9: N-(5-((6-(2-((tert-butyldimethylsilyl)oxy)propan-2-yl)pyridin-3-yl)methoxy)-1,3,4-thiadiazol-2-yl)-4-(2-fluoro-6-methoxyphenyl)-6-methylpyridine-3-carboxamide

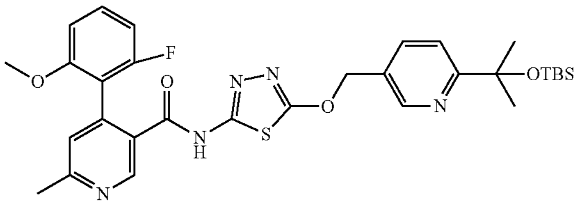 [SMILES: COc1cccc(F)c1-c1cc(C)ncc1C(=O)Nc1nnc(OCc2ccc(C(C)(C)O[Si](C)(C)C(C)(C)C)nc2)s1]

To a stirred solution of 5-((6-(2-((tert-butyldimethylsilyl)oxy)propan-2-yl)pyridin-3-yl)methoxy)-1,3,4-thiadiazol-2-amine (70 mg, 0.18 mmol) and 4-(2-fluoro-6-methoxyphenyl)-6-methylpyridine-3-carboxylic acid (48 mg, 0.18 mmol, Intermediate F) in MeCN/DMF (2/2 mL) were added NMI (60 mg, 0.73 mmol) and TCFH (77 mg, 0.27 mmol). The mixture resulting was stirred at room temperature for 1 h under nitrogen atmosphere before concentrated under vacuum. The residue was purified by reverse flash column chromatography with 5-95% acetonitrile in water to afford N-(5-((6-(2-((tert-butyldimethylsilyl)oxy)propan-2-yl)pyridin-3-yl)methoxy)-1,3,4-thiadiazol-2-yl)-4-(2-fluoro-6-methoxyphenyl)-6-methylpyridine-3-carboxamide (70 mg, 61%) as a white solid. MS (ESI) calc'd for $(C_{31}H_{38}FN_5O_4SSi)$ $(M+1)^+$, 624.2; found 624.0.

Step-10: 4-(2-fluoro-6-methoxyphenyl)-N-(5-((6-(2-hydroxypropan-2-yl)pyridin-3-yl)methoxy)-1,3,4-thiadiazol-2-yl)-6-methylpyridine-3-carboxamide

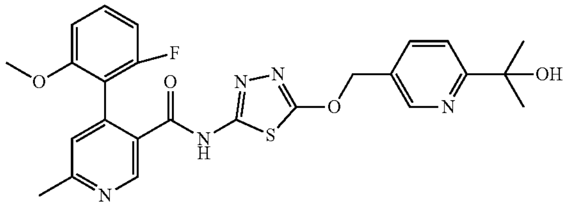

To a stirred solution of N-(5-((6-(2-((tert-butyldimethylsilyl)oxy)propan-2-yl)pyridin-3-yl)methoxy)-1,3,4-thiadiazol-2-yl)-4-(2-fluoro-6-methoxyphenyl)-6-methylpyridine-3-carboxamide (50 mg, 0.08 mmol) in THF (2 mL) was added TBAF in THF (0.5 mL, 0.50 mmol). The resulting mixture was stirred at 60° C. for 2 h under nitrogen atmosphere. The resulting mixture was purified by reverse phase flash column chromatography with 5-95% MeCN in water and further purified by prep-HPLC with the following conditions: (Column: XBridge Prep Phenyl OBD Column, 19*100 mm 5 um 13 nm; Mobile Phase A: Water (10MMOL/L $NH_4HCO_3$), Mobile Phase B:ACN; Flow rate: 60 mL/min; Gradient: 15 B to 35 B in 8 min; 254/220 nm) to afford 4-(2-fluoro-6-methoxyphenyl)-N-(5-((6-(2-hydroxypropan-2-yl)pyridin-3-yl)methoxy)-1,3,4-thiadiazol-2-yl)-6-methylpyridine-3-carboxamide (8.6 mg, 20%) as a white solid. MS (ESI) calc'd for $(C_{25}H_{24}FN_5O_4S)$ $(M+1)^+$, 510.2; found 510.4. $^1H$ NMR (400 MHz, DMSO-$d_6$) δ 12.88 (s, 1H), 8.81 (s, 1H), 8.61 (s, 1H), 7.90 (d, J=8.4 Hz, 1H), 7.69 (d, J=8.0 Hz, 1H), 7.40 (d, J=7.6 Hz, 1H), 7.32 (s, 1H), 6.89 (t, J=8.0 Hz, 2H), 5.49 (s, 2H), 5.25 (s, 1H), 3.58 (s, 3H), 2.57 (s, 3H), 1.44 (s, 6H).

Example 110 and 111

4-(2-fluoro-6-methoxyphenyl)-N-(5-((5-((S)-1-hydroxyethyl)pyrazin-2-yl)methoxy)-1,3,4-thiadiazol-2-yl)-6-methylnicotinamide (Example 110) and 4-(2-fluoro-6-methoxyphenyl)-N-(5-((5-((R)-1-hydroxyethyl)pyrazin-2-yl)methoxy)-1,3,4-thiadiazol-2-yl)-6-methylnicotinamide Example 111

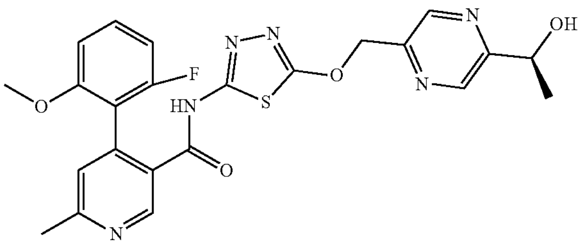

-continued

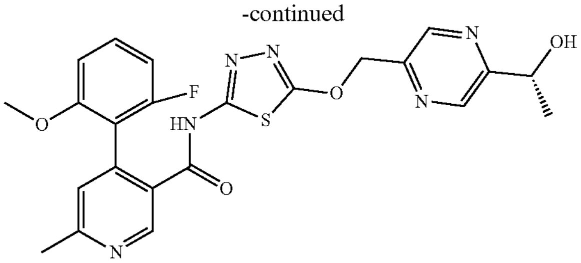

To a solution of 4-(2-fluoro-6-methoxyphenyl)-N-(5-((5-formylpyrazin-2-yl)methoxy)-1,3,4-thiadiazol-2-yl)-6-methylnicotinamide (520 mg, 1.1 mmol, Example 97, Step 2) in THF (5 mL) was added methylmagnesium bromide (13.3 mL, 3.3 mmol, 1M in THF) dropwise at 0° C. The mixture was stirred at room temperature for 2 h under nitrogen. The reaction mixture was quenched by the addition of saturated $NH_4Cl$ aqueous solution and extracted with ethyl acetate. The combined organic layers were washed with brine, dried over anhydrous sodium sulfate, filtered, and concentrated under vacuum. The residue was purified by flash chromatography on silica gel with 0~10% methanol in dichloromethane to afford racemic product, which was further separated by prep chiral-HPLC with the following conditions: (Column: CHIRAL ART Amylose-SA, 2*25 cm, 5 um; Mobile Phase A: Hex (0.2% FA)-HPLC, Mobile Phase B: EtOH-HPLC; Flow rate: 20 mL/min; Gradient: 20 B to 20 B in 13.5 min; 220/254 nm; RT1: 10.618; RT2: 11.716) to afford 4-(2-fluoro-6-methoxyphenyl)-N-(5-((5-((S)-1-hydroxyethyl)pyrazin-2-yl)methoxy)-1,3,4-thiadiazol-2-yl)-6-methylnicotinamide (14.2 mg, 2.4%) as a white solid with shorter retention time on chiral-HPLC and afford 4-(2-fluoro-6-methoxyphenyl)-N-(5-((5-((R)-1-hydroxyethyl)pyrazin-2-yl)methoxy)-1,3,4-thiadiazol-2-yl)-6-methylnicotinamide (13 mg, 2.4%) as a white solid with longer retention time on chiral-HPLC.

4-(2-fluoro-6-methoxyphenyl)-N-(5-((5-((S)-1-hydroxyethyl)pyrazin-2-yl)methoxy)-1,3,4-thiadiazol-2-yl)-6-methylnicotinamide: MS (ESI) calc'd for $(C_{23}H_{21}FN_6O_4S)$ $(M+1)^+$, 497.1; found 497.1. $^1H$ NMR (400 MHz, DMSO-$d_6$) δ 12.88 (s, 1H), 8.83-8.72 (m, 3H), 7.42-7.29 (m, 2H), 6.93-6.87 (m, 2H), 5.64-5.58 (m, 3H), 4.85-4.82 (m, 1H), 3.58 (s, 3H), 2.57 (s, 3H), 1.41 (d, J=6.4 Hz, 3H).

4-(2-fluoro-6-methoxyphenyl)-N-(5-((5-((R)-1-hydroxyethyl)pyrazin-2-yl)methoxy)-1,3,4-thiadiazol-2-yl)-6-methylnicotinamide: MS (ESI) calc'd for $(C_{23}H_{21}FN_6O_4S)$ $(M+1)^+$, 497.1; found 497.1. $^1H$ NMR (400 MHz, DMSO-$d_6$) δ 12.88 (s, 1H), 8.83-8.72 (m, 3H), 7.42-7.29 (m, 2H), 6.93-6.87 (m, 2H), 5.64 (s, 2H), 5.58 (s, 1H), 4.85-4.82 (m, 1H), 3.58 (s, 3H), 2.57 (s, 3H), 1.41 (d, J=6.4 Hz, 3H).

Example 112

4-(2-fluoro-6-methoxyphenyl)-N-(5-((4-hydroxybicyclo(2.2.1)heptan-1-yl)methoxy)-1,3,4-thiadiazol-2-yl)-6-methylpyridine-3-carboxamide

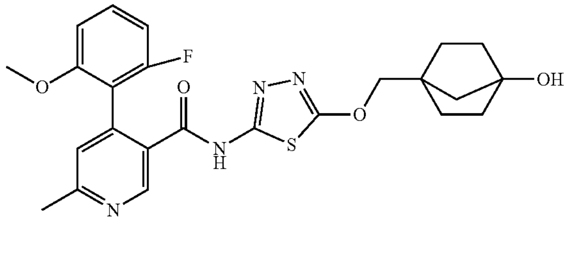 [SMILES: COc1cccc(F)c1-c1cc(C)ncc1C(=O)Nc1nnc(OCC23CCC(O)(CC2)C3)s1]

Step-1: methyl 4-((tert-butyldimethylsilyl)oxy)bicyclo(2.2.1)heptane-1-carboxylate

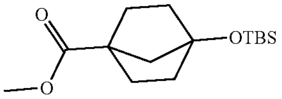 [SMILES: COC(=O)C12CCC(O[Si](C)(C)C(C)(C)C)(CC1)C2]

To a mixture of methyl 4-hydroxybicyclo(2.2.1)heptane-1-carboxylate (300.0 mg, 1.76 mmol) in THF (12 mL) were added imidazole (299.9 mg, 4.40 mmol) and TBSCl (318.7 mg, 2.11 mmol). The resulting solution was stirred at room temperature for 16 h. The reaction was monitored by TLC. The reaction mixture was quenched with water and extracted with ethyl acetate. The combined organic layers were washed with brine, dried over anhydrous sodium sulfate, filtered, and concentrated under vacuum. The residue was purified by silica gel column chromatography, eluted with 0~50% ethyl acetate in petroleum ether to afford methyl 4-((tert-butyldimethylsilyl)oxy)bicyclo(2.2.1)heptane-1-carboxylate (280.0 mg, 47%) as a colorless oil.

Step-2: (4-((tert-butyldimethylsilyl)oxy)bicyclo(2.2.1)heptan-1-yl)methanol

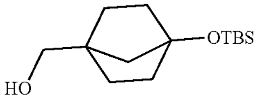 [SMILES: CC(C)(C)[Si](C)(C)OC12CCC(CO)(CC1)C2]

To a mixture of methyl 4-((tert-butyldimethylsilyl)oxy)bicyclo(2.2.1)heptane-1-carboxylate (280.0 mg, 0.98 mmol) in THF (10 mL) was added LiAlH4 (37.36 mg, 0.98 mmol) in portions at 0° C. The resulting solution was stirred at 0° C. for 2 h. The reaction was monitored by TLC. The reaction mixture was quenched with water and extracted with ethyl acetate. The combined organic layers were washed with brine, dried over anhydrous sodium sulfate, filtered, and concentrated under vacuum to afford (4-((tert-butyldimethylsilyl)oxy)bicyclo(2.2.1)heptan-1-yl)methanol (260.0 mg, crude) as a colorless oil.

Step-3: ((4-((tert-butyldimethylsilyl)oxy)bicyclo(2.2.1)heptan-1-yl)methoxy)(methylsulfanyl)methanethione

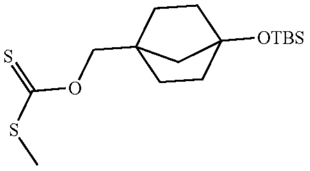 [SMILES: CSC(=S)OCC12CCC(O[Si](C)(C)C(C)(C)C)(CC1)C2]

To a mixture of (4-((tert-butyldimethylsilyl)oxy)bicyclo(2.2.1)heptan-1-yl)methanol (260.00 mg, 1.01 mmol) in THF (13.0 mL, 180.28 mmol) was added NaH (48.66 mg, 2.02 mmol, 60%) in portions at 0° C. and stirred at 0° C. for 30 min. To the above mixture was added $CS_2$ (115.79 mg, 1.52 mmol) at 0° C. and stirred at 0° C. for 10 min. To the above mixture was added MeI (215.85 mg, 1.521 mmol) at 0° C. The resulting solution was stirred at 0° C. for 30 min. The reaction mixture was quenched with water and extracted with ethyl acetate. The combined organic layers were washed with brine, dried over anhydrous sodium sulfate, filtered, and concentrated under vacuum to afford ((4-((tert-butyldimethylsilyl)oxy)bicyclo(2.2.1)heptan-1-yl)methoxy)(methylsulfanyl)methanethione (300.0 mg, 85%) as a yellow oil. MS (ESI) calc'd for ($C_{16}H_{30}O_2S_2Si$) $(M+1)^+$, 347.1, found 347.2.

Step-4: ((((4-((tert-butyldimethylsilyl)oxy)bicyclo(2.2.1)heptan-1-yl)methoxy)methanethioyl)amino amine

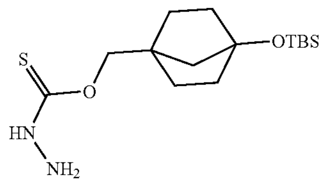 [SMILES: CC(C)(C)[Si](C)(C)OC12CCC(COC(=S)NN)(CC1)C2]

To a mixture of ((4-((tert-butyldimethylsilyl)oxy)bicyclo(2.2.1)heptan-1-yl)methoxy)(methylsulfanyl)methanethione (300.0 mg, 0.86 mmol) in MeOH (6.5 mL, 203.53 mmol) was added hydrazine (27.74 mg, 0.86 mmol) at room temperature. The resulting solution was stirred at room temperature for 2 h. The reaction mixture was quenched with water and extracted with ethyl acetate. The combined organic layers were washed with brine, dried over anhydrous sodium sulfate, filtered, and concentrated under vacuum to afford ((((4-((tert-butyldimethylsilyl)oxy)bicyclo(2.2.1)heptan-1-yl)methoxy)methanethioyl)amino)amine (230 mg, crude) as a white solid. MS (ESI) calc'd for ($C_{15}H_{30}N_2O_2SSi$) $(M+1)^+$, 330.2, found 330.1.

Step-5: 5-((4-((tert-butyldimethylsilyl)oxy)bicyclo(2.2.1)heptan-1-yl)methoxy)-1,3,4-thiadiazol-2-amine

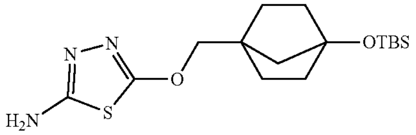 [SMILES: CC(C)(C)[Si](C)(C)OC12CCC(COc3nnc(N)s3)(CC1)C2]

To a mixture of ((((4-((tert-butyldimethylsilyl)oxy)bicyclo(2.2.1)heptan-1-yl)methoxy)methanethioyl)amino)amine (230.0 mg, 0.69 mmol) in MeOH (6.0 mL, 148.19 mmol) were added TEA (140.81 mg, 1.39 mmol) and BrCN (81.07 mg, 0.76 mmol) at room temperature. The resulting solution was stirred at room temperature for 30 min. The reaction mixture was quenched with water and extracted with ethyl acetate. The combined organic layers were washed with brine, dried over anhydrous sodium sulfate, filtered, and concentrated under vacuum. The crude residue was purified by silica gel column chromatography, eluted with 0~60% ethyl acetate in petroleum ether to afford 5-((4-((tert-butyldimethylsilyl)oxy)bicyclo(2.2.1)heptan-1-yl)methoxy)-1,3,4-thiadiazol-2-amine (100.0 mg, 40%) as a yellow oil. MS (ESI) calc'd for ($C_{16}H_{29}N_3O_2SSi$) $(M+1)^+$, 356.0, found 356.0.

Step-6: N-(5-((4-((tert-butyldimethylsilyl)oxy)bicyclo(2.2.1)heptan-1-yl)methoxy)-1,3,4-thiadiazol-2-yl)-4-(2-fluoro-6-methoxyphenyl)-6-methylpyridine-3-carboxamide

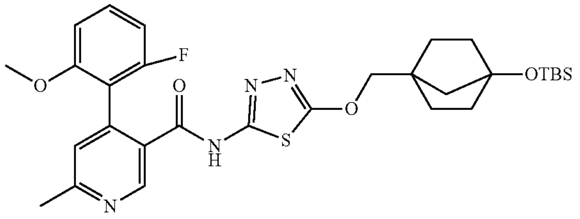 [SMILES: COc1cccc(F)c1-c1cc(C)ncc1C(=O)Nc1nnc(OCC23CCC(O[Si](C)(C)C(C)(C)C)(CC2)C3)s1]

To a mixture of 4-(2-fluoro-6-methoxyphenyl)-6-methylpyridine-3-carboxylic acid (100.0 mg, 0.38 mmol, Intermediate F) in MeCN (1 mL) and DMF (1.0 mL) were added 5-((4-((tert-butyldimethylsilyl)oxy)bicyclo(2.2.1)heptan-1-yl)methoxy)-1,3,4-thiadiazol-2-amine (163.3 mg, 0.45 mmol), TCFH (118.1 mg, 0.42 mmol) and NMI (66.00 mg, 0.80 mmol). The reaction mixture was quenched with water and extracted with ethyl acetate. The combined organic layers were washed with brine, dried over anhydrous sodium sulfate, filtered, and concentrated under vacuum. The crude residue was purified by flash column chromatography with 5~100% acetonitrile in water to afford N-(5-((4-((tert-butyldimethylsilyl)oxy)bicyclo(2.2.1)heptan-1-yl)methoxy)-1,3,4-thiadiazol-2-yl)-4-(2-fluoro-6-methoxyPhenyl)-6-methylpyridine-3-carboxamide (90.0 mg, 39%) as a white solid. MS (ESI) calc'd for ($C_{30}H_{39}FN_4O_4SSi$) $(M+1)^+$, 599.2, found 599.2.

Step-7: 4-(2-fluoro-6-methoxyphenyl)-N-(5-((4-hydroxybicyclo(2.2.1)heptan-1-yl)methoxy)-1,3,4-thiadiazol-2-yl)-6-methylpyridine-3-carboxamide

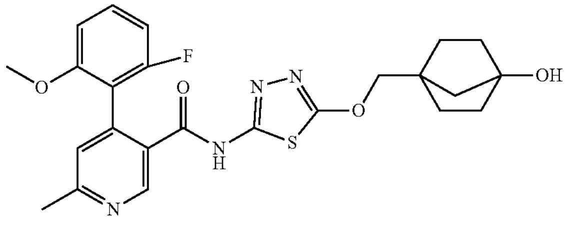 [SMILES: COc1cccc(F)c1-c1cc(C)ncc1C(=O)Nc1nnc(OCC23CCC(O)(CC2)C3)s1]

To a mixture of N-(5-((4-((tert-butyldimethylsilyl)oxy)bicyclo(2.2.1)heptan-1-yl)methoxy)-1,3,4-thiadiazol-2-yl)-4-(2-fluoro-6-methoxyphenyl)-6-methylpyridine-3-carboxamide (85.00 mg, 0.14 mmol) in DCM (5 mL) was added TFA (1.0 mL). The resulting mixture was stirred at room temperature for 2 h. The resulting mixture was concentrated under vacuum. The crude residue was purified by Prep-HPLC with the following conditions: (Column: XBridge Prep OBD C18 Column, 30×150 mm 5 um; Mobile Phase A: Water (10 MMOL/L $NH_4HCO_3$), Mobile Phase B: ACN; Flow rate: 60 mL/min; Gradient: 15 B to 28 B in 8 min; 254/220 nm; RT1: 7.25 min) to afford 4-(2-fluoro-6-methoxyphenyl)-N-(5-((4-hydroxybicyclo(2.2.1)heptan-1-yl)methoxy)-1,3,4-thiadiazol-2-yl)-6-methylpyridine-3-carboxamide (44.6 mg, 64%) as a white solid. MS (ESI) calc'd for ($C_{24}H_{25}FN_4O_4S$) $(M+1)^+$, 485.2, found 485.2. $^1H$ NMR (400 MHz, DMSO-$d_6$) δ 12.83 (s, 1H), 8.81 (s, 1H), 7.45-7.35 (m, 1H), 7.32 (d, J=1.6 Hz, 1H), 6.99-6.83 (m, 2H), 4.90 (s, 1H), 4.38 (s, 2H), 3.58 (s, 3H), 2.57 (s, 3H), 1.74-1.56 (m, 4H), 1.55-1.47 (m, 2H), 1.46-1.31 (m, 4H).

Example 113

2'-chloro-N-(5-((5-(difluoromethoxy)pyridin-2-yl)methoxy)-1,3,4-thiadiazol-2-yl)-5'-methoxy-6-methyl-(4,4'-bipyridine)-3-carboxamide

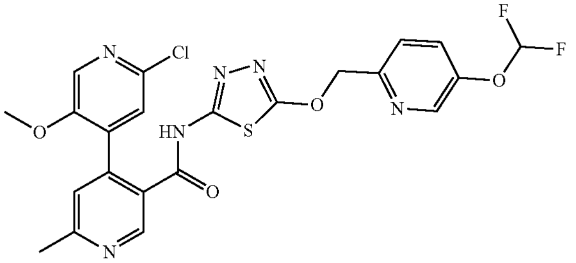 [SMILES: COc1cnc(Cl)cc1-c1cc(C)ncc1C(=O)Nc1nnc(OCc2ccc(OC(F)F)cn2)s1]

To a solution of 2'-chloro-5'-methoxy-6-methyl-(4,4'-bipyridine)-3-carboxylic acid (67 mg, 0.242 mmol) in DMF (5 mL) were added HATU (110 mg, 0.290 mmol), DIEA (156 mg, 1.209 mmol) and 5-((5-(difluoromethoxy)pyridin-2-yl)methoxy)-1,3,4-thiadiazol-2-amine (60 mg, 0.242 mmol, Example 82, Step 3). The resulting solution was stirred at room temperature for 2 h. The reaction mixture was quenched with water and extracted with ethyl acetate. The combined organic layers were washed with brine, dried over anhydrous sodium sulfate, filtered, and concentrated under vacuum. The residue was purified by flash chromatography on silica gel with 0~10% methanol in dichloromethane and further purified by following conditions: (Column: XBridge Prep OBD C18 Column, 30×150 mm 5 um; Mobile Phase A: Water (10 MMOL/L $NH_4HCO_3$), Mobile Phase B:ACN; Flow rate: 60 mL/min; Gradient: 30 B to 50 B in 8 min; 220 nm; RT1: 7.23 min) to afford N-(5-((5-chloropyridin-2-yl)methoxy)-1,3,4-thiadiazol-2-yl)-5-(2-fluoro-6-methoxyphenyl)pyridazine-4-carboxamide (25.0 mg, 19%) as a white solid. MS (ESI) calc'd for $(C_{22}H_{17}ClF_2N_6O_4S)$ $(M+1)^+$, 535.1; found, 535.0. $^1H$ NMR (400 MHz, DMSO-$d_6$) δ 13.01 (s, 1H), 8.84 (s, 1H), 8.51 (s, 1H), 8.16 (s, 1H), 7.75-7.74 (m, 1H), 7.53-7.49 (m, 1H), 7.37-7.16 (m, 3H), 5.52 (s, 2H), 3.63 (s, 3H), 2.57 (s, 3H).

Example 79, 114, 115

4-(2-fluoro-6-methoxyphenyl)-6-methyl-N-(5-((4-(S-methylsulfonimidoyl)benzyl)oxy)-1,3,4-thiadiazol-2-yl)nicotinamide (Example 79), 4-(2-fluoro-6-methoxyphenyl)-6-methyl-N-(5-((4-((R)—S-methylsulfonimidoyl)benzyl)oxy)-1,3,4-thiadiazol-2-yl)nicotinamide (Example 114) and 4-(2-fluoro-6-methoxyphenyl)-6-methyl-N-(5-((4-((S)—S-methylsulfonimidoyl)benzyl)oxy)-1,3,4-thiadiazol-2-yl)nicotinamide (Example 115)

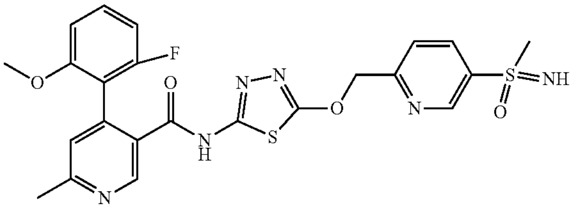

-continued

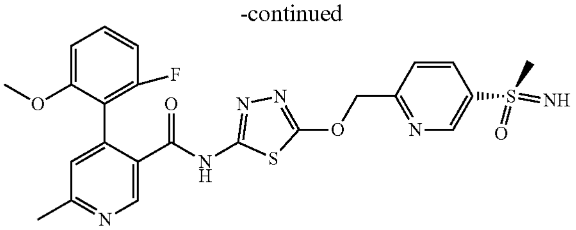

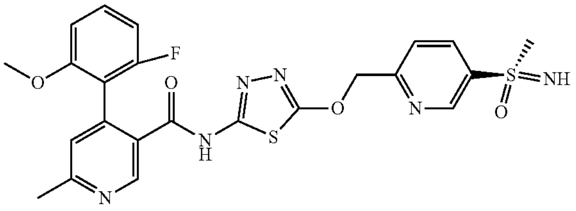

Step-1: S-methyl O-(4-(methylthio)benzyl) carbonodithioate

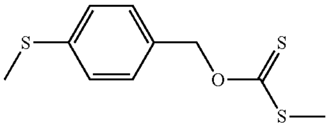

To a solution of NaH (933.58 mg, 38.903 mmol, 60%) in THF (20.0 mL) was a solution of added (4-(methylsulfanyl)phenyl)methanol (3.00 g, 19.451 mmol) in THF (5 mL) dropwise at 0° C. and stirred at 0° C. for 30 min. To the above mixture was added $CS_2$ (2.22 g, 29.177 mmol) dropwise at 0° C. and stirred at 0° C. for 20 min. And then MeI (4.14 g, 29.177 mmol) was added to the above mixture dropwise at 0° C. The resulting mixture was stirred at room temperature for 1 hour. The resulting mixture was quenched with water. The aqueous layer was extracted with ethyl acetate. The organic layers were combined, washed with brine, dried over anhydrous sodium sulfate and filtered. The filtrate was concentrated under vacuum. The residue was purified by flash chromatography on silica gel with 0~30% ethyl acetate in petroleum ether to afford S-methyl O-(4-(methylthio)benzyl) carbonodithioate (3.9 g, 82.0%) as a light yellow solid. MS (ESI) calc'd for $(C_{10}H_{12}OS_3)$ $(M+1)^+$, 245.0, found 245.0.

Step-2: O-(4-(methylthio)benzyl) hydrazinecarbothioate

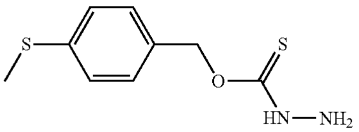

To a mixture of (methylsulfanyl)(((4-(methylsulfanyl)phenyl)methoxy))methanethione (3.90 g, 15.958 mmol) in MeOH (15.00 mL) was added Hydrazine (767.1 mg, 23.937 mmol, 80%). The mixture was stirred at 0° C. for 1 hour. The resulting mixture was concentrated under vacuum The reaction mixture was diluted with water and extracted with ethyl acetate. The combined organic layers were washed with brine, dried over anhydrous sodium sulfate, filtered, and concentrated under vacuum to afford O-(4-(methylthio)benzyl) hydrazinecarbothioate (2.0 g, 54.8%) as a colorless oil. MS (ESI) calc'd for ($C_9H_{12}N_2OS_2$) $(M+1)^+$, 229.0, found 229.0.

Step-3: 5-((4-(methylthio)benzyl)oxy)-1,3,4-thiadiazol-2-amine

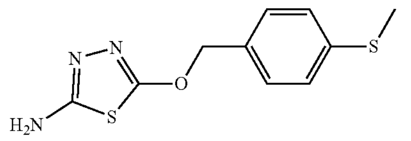

To a mixture of ((((4-(methylsulfanyl)phenyl)methoxy) methanethioyl)amino)amine (2.00 g, 8.76 mmol) and $Et_3N$ ((1.77 g, 17.52 mmol) in MeOH (10 mL) was added BrCN (1.39 g, 13.14 mmol) at 0° C. The mixture was stirred at 0° C. for 1 hour. The resulting mixture was quenched with water. The aqueous layer was extracted with ethyl acetate. The organic layers were combined, washed with brine, dried over anhydrous sodium sulfate and filtered. The residue was purified by flash chromatography on silica gel with 0-5% methanol in dichloromethane to afford 5-((4-(methylsulfanyl)phenyl)methoxy)-1,3,4-thiadiazol-2-amine (380 mg, 17.1%) as a yellow solid. MS (ESI) calc'd for ($C_{10}H_{11}N_3OS_2$) $(M+1)^+$, 254.0, found 254.0.

Step-4: 4-(2-fluoro-6-methoxyphenyl)-6-methyl-N-(5-((4-(methylsulfanyl)phenyl)methoxy)-1,3,4-thiadiazol-2-yl)pyridine-3-carboxamide

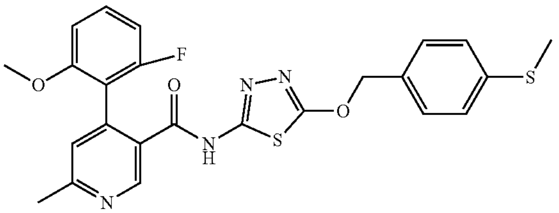

To a stirred solution of 5-((4-(methylsulfanyl)phenyl) methoxy)-1,3,4-thiadiazol-2-amine (200.00 mg, 0.789 mmol) and 4-(2-fluoro-6-methoxyphenyl)-6-methylpyridine-3-carboxylic acid (247.50 mg, 0.947 mmol, Intermediate F) in MeCN (1.00 mL) and DMF (1.00 mL) were added NMI (324.09 mg, 3.947 mmol) and TCFH (243.65 mg, 0.868 mmol). The resulting solution was stirred at room temperature for 2 hours. The mixture was purified by reverse phase flash chromatography with 5~50% acetonitrile in water to afford 4-(2-fluoro-6-methoxyphenyl)-6-methyl-N-(5-((4-(methylsulfanyl)phenyl)methoxy)-1,3,4-thiadiazol-2-yl)pyridine-3-carboxamide (160 mg, 40.8%) as a light yellow solid MS (ESI) calc'd for ($C_{24}H_{21}FN_4O_3S_2$) $(M+1)^+$, 497.1, found 497.1.

Step-5: 4-(2-fluoro-6-methoxyphenyl)-6-methyl-N-(5-((4-(S-methylsulfonimidoyl)benzyl)oxy)-1,3,4-thiadiazol-2-yl)nicotinamide

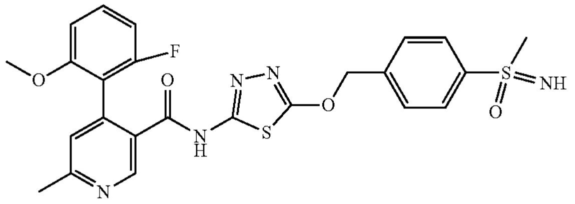 [SMILES: COc1cccc(F)c1-c1cc(C)ncc1C(=O)Nc1nnc(OCc2ccc(S(C)(=N)=O)cc2)s1]

To a stirred mixture of 4-(2-fluoro-6-methoxyphenyl)-6-methyl-N-(5-((4-(methylsulfanyl)phenyl)methoxy)-1,3,4-thiadiazol-2-yl)pyridine-3-carboxamide (150.00 mg, 0.302 mmol) in MeOH (5 mL) were added $NH_2COONH_4$ (47.1 mg, 0.604 mmol) and $PhI(OAc)_2$ (243.16 mg, 0.755 mmol). The resulting mixture was stirred at room temperature for 2 hours. The residue was purified by reverse phase flash chromatography with 5-70% acetonitrile in water to afford 4-(2-fluoro-6-methoxyphenyl)-6-methyl-N-(5-((4-(S-methylsulfonimidoyl)benzyl)oxy)-1,3,4-thiadiazol-2-yl)nicotinamide (63.0 mg, 39.5%) as a white solid. MS (ESI) calc'd for ($C_{24}H_{22}FN_5O_4S_2$) $(M+1)^+$, 528.1, found 528.0. $^1H$ NMR (400 MHz, DMSO-$d_6$) δ 12.92 (s, 1H), 8.81 (s, 1H), 7.96 (d, J=8.4 Hz, 2H), 7.70 (d, J=8.0 Hz, 2H), 7.46-7.35 (m, 1H), 7.33 (s, 1H), 6.97-6.86 (m, 2H), 5.59 (s, 2H), 4.26 (s, 1H), 3.59 (s, 3H), 3.07 (s, 3H), 2.57 (s, 3H).

Step-6: 4-(2-fluoro-6-methoxyphenyl)-6-methyl-N-(5-((4-((R)—S-methylsulfonimidoyl)benzyl)oxy)-1,3,4-thiadiazol-2-yl)nicotinamide and 4-(2-fluoro-6-methoxyphenyl)-6-methyl-N-(5-((4-((S)—S-methylsulfonimidoyl)benzyl)oxy)-1,3,4-thiadiazol-2-yl)nicotinamide

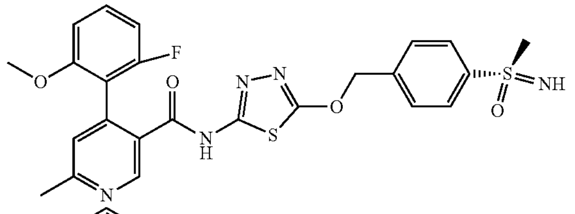

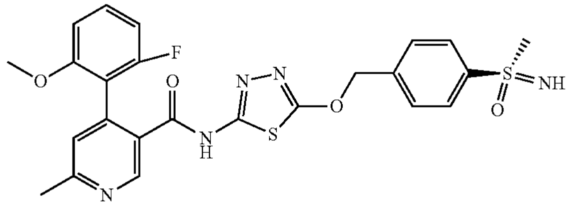

The racemic compound of 4-(2-fluoro-6-methoxyphenyl)-6-methyl-N-(5-((4-(S-methylsulfonimidoyl)benzyl) oxy)-1,3,4-thiadiazol-2-yl)nicotinamide (45.8 mg) was separated by prep-chiral-HPLC with the following conditions: (Column: CHIRALPAK IC, 2*25 cm, 5 um; Mobile Phase A: Hex (0.2% FA)-HPLC, Mobile Phase B: EtOH: DCM=1:1-HPLC; Flow rate: 20 mL/min; Gradient: 50 B to 50 B in 21 min; 220/254 nm; RT1:14.125; RT2:18.092; Injection Volume:0.82 ml; Number Of Runs:4;) to afford 4-(2-fluoro-6-methoxyphenyl)-6-methyl-N-(5-((4-((R)—S-methylsulfonimidoyl)benzyl)oxy)-1,3,4-thiadiazol-2-yl) nicotinamide (13.3 mg, 29.03%) as a white solid with shorter retention time on chiral-HPLC and 4-(2-fluoro-6-methoxyphenyl)-6-methyl-N-(5-((4-((S)—S-methylsulfonimidoyl)benzyl)oxy)-1,3,4-thiadiazol-2-yl)nicotinamide (14.1 mg, 30.78%) as a white solid with longer retention time on chiral-HPLC.

4-(2-fluoro-6-methoxyphenyl)-6-methyl-N-(5-((4-((R)—S-methylsulfonimidoyl)benzyl)oxy)-1,3,4-thiadiazol-2-yl) nicotinamide: MS (ESI) calc'd for ($C_{24}H_{22}FN_5O_4S_2$) $(M+1)^+$, 528.1, found 528.1. $^1$H NMR (400 MHz, DMSO-$d_6$) δ 12.90 (s, 1H), 8.82 (s, 1H), 7.99-7.93 (m, 2H), 7.73-7.66 (m, 2H), 7.45-7.35 (m, 1H), 7.31 (s, 1H), 6.96-6.86 (m, 2H), 5.58 (s, 2H), 4.26 (s, 1H), 3.58 (s, 3H), 3.07 (s, 3H), 2.56 (s, 3H).

4-(2-fluoro-6-methoxyphenyl)-6-methyl-N-(5-((4-((S)—S-methylsulfonimidoyl)benzyl)oxy)-1,3,4-thiadiazol-2-yl) nicotinamide: MS (ESI) calc'd for ($C_{24}H_{22}FN_5O_4S_2$) $(M+1)^+$, 528.1, found 528.1. $^1$H NMR (400 MHz, DMSO-$d_6$) δ 12.90 (s, 1H), 8.83 (s, 1H), 7.99-7.92 (m, 2H), 7.73-7.66 (m, 2H), 7.45-7.34 (m, 1H), 7.30 (s, 1H), 6.95-6.85 (m, 2H), 5.58 (s, 2H), 4.25 (s, 1H), 3.59 (s, 3H), 3.07 (s, 3H), 2.56 (s, 3H).

Example 92, 116 and 117

4-(2-fluoro-6-methoxyphenyl)-N-(5-((5-hydroxy-5,6,7,8-tetrahydroquinolin-2-yl)methoxy)-1,3,4-thiadiazol-2-yl)-6-methylnicotinamide (Example 92), 4-(2-fluoro-6-methoxyphenyl)-N-(5-(((S)-5-hydroxy-5,6,7,8-tetrahydroquinolin-2-yl)methoxy)-1,3,4-thiadiazol-2-yl)-6-methylnicotinamide (Example 116) and 4-(2-fluoro-6-methoxyphenyl)-N-(5-(((R)-5-hydroxy-5,6,7,8-tetrahydroquinolin-2-yl)methoxy)-1,3,4-thiadiazol-2-yl)-6-methylnicotinamide (Example 117)

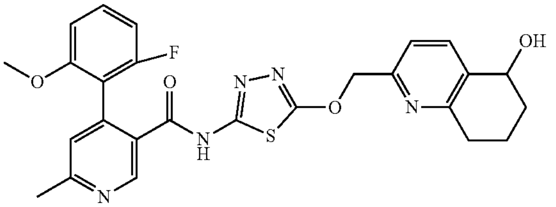

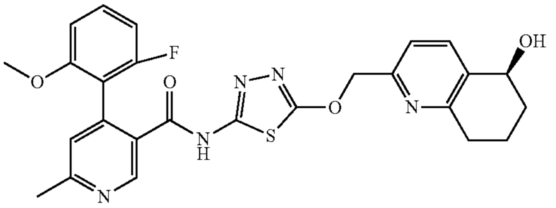

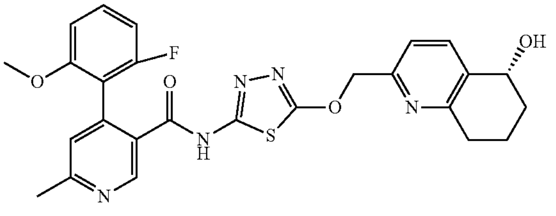

Step-1: methyl 5-oxo-7,8-dihydro-6H-quinoline-2-carboxylate

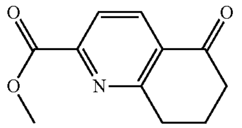

To a solution of 2-chloro-7,8-dihydro-6H-quinolin-5-one (1 g, 5.506 mmol) in MeOH (10 mL) and TEA (2 mL) was added Pd(dppf)$Cl_2$ (402 mg, 0.551 mmol). The resulting solution was stirred at 80° C. for 12 hours under CO (2 atm). The resulting mixture was concentrated under vacuum. The residue was purified by flash chromatography on silica gel with 0-50% ethyl acetate in petroleum ether to afford methyl 5-oxo-7,8-dihydro-6H-quinoline-2-carboxylate (850 mg, 75.2%) as a white solid. MS (ESI) calc'd for ($C_{11}H_{11}NO_3$) $(M+1)^+$, 206.1; found, 206.1.

Step-2: methyl 5-hydroxy-5,6,7,8-tetrahydroquinoline-2-carboxylate

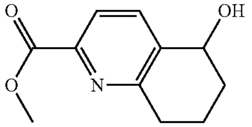

To a solution of methyl 5-oxo-7,8-dihydro-6H-quinoline-2-carboxylate (780 mg, 3.801 mmol) in MeOH (10 mL) was added $NaBH_4$ (144 mg, 3.801 mmol) in portions at 0° C. The resulting solution was stirred at room temperature for 1 hour. The reaction was then quenched by the addition of water and extracted with ethyl acetate. The combined organic layers were washed with brine, dried over anhydrous sodium sulfate, filtered, and concentrated under vacuum to afford methyl 5-hydroxy-5,6,7,8-tetrahydroquinoline-2-carboxylate (780 mg, crude) as a white solid. MS (ESI) calc'd for ($C_{11}H_{13}NO_3$) $(M+1)^+$, 208.1; found, 208.1.

Step-3: methyl 5-((tert-butyldimethylsilyl)oxy)-5,6,7,8-tetrahydroquinoline-2-carboxylate

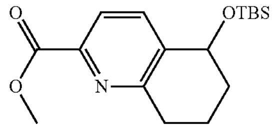 [SMILES: COC(=O)c1ccc2c(n1)CCCC2O[Si](C)(C)C(C)(C)C]

To a solution of methyl 5-hydroxy-5,6,7,8-tetrahydroquinoline-2-carboxylate (730 mg, 3.523 mmol) in DCM (5 mL) was added Imidazole (720 mg, 10.568 mmol) and t-butyldimethylchlorosilane (797 mg, 5.284 mmol). The resulting solution was stirred at room temperature for 4 hours. The resulting mixture was concentrated under vacuum. The residue was purified by flash chromatography on silica gel with 0-50% ethyl acetate in petroleum ether to afford methyl 5-((tert-butyldimethylsilyl)oxy)-5,6,7,8-tetrahydroquinoline-2-carboxylate (650 mg, 51.6%) as a yellow solid. MS (ESI) calc'd for ($C_{17}H_{27}NO_3Si$) $(M+1)^+$, 322.2; found, 322.2.

Step-4: (5-((tert-butyldimethylsilyl)oxy)-5,6,7,8-tetrahydroquinolin-2-yl)methanol

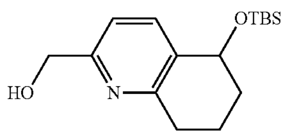

To a solution of 5-((tert-butyldimethylsilyl)oxy)-5,6,7,8-tetrahydroquinoline-2-carboxylate (600 mg, 1.866 mmol) and $CaCl_2$ (208 mg, 1.866 mmol) in THF (5 mL) and MeOH (5 mL) was added $NaBH_4$ (71 mg, 1.866 mmol) in portions at 0° C. The resulting solution was stirred at room temperature for 12 hours. The reaction mixture was quenched with water and extracted with ethyl acetate. The combined organic layers were washed with brine, dried over anhydrous sodium sulfate, filtered, and concentrated under vacuum to afford (5-((tert-butyldimethylsilyl)oxy)-5,6,7,8-tetrahydroquinolin-2-yl)methanol (600 mg, crude) as a white solid. MS (ESI) calc'd for ($C_{16}H_{27}NO_2Si$) $(M+1)^+$, 294.2; found, 294.0.

Step-5: 5-((5-((tert-butyldimethylsilyl)oxy)-5,6,7,8-tetrahydroquinolin-2-yl)methoxy)-1,3,4-thiadiazol-2-amine

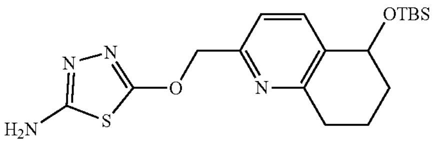 [SMILES: CC(C)(C)[Si](C)(C)OC1CCCc2nc(COc3nnc(N)s3)ccc21]

To a solution of NaH (43 mg, 1.789 mmol, 60%) in THF (8 mL) was a solution of added (5-((tert-butyldimethylsilyl)oxy)-5,6,7,8-tetrahydroquinolin-2-yl)methanol (350 mg, 1.193 mmol) in THF (2 mL) dropwise at 0° C. and stirred at 5° C. for 1 h, then 5-bromo-1,3,4-thiadiazol-2-amine (258 mg, 1.431 mmol) was added to the mixture in small portions at 5° C. and stirred at 5° C. for 5 h. The reaction mixture was then quenched by the addition of water and extracted with ethyl acetate. The combined organic layers were washed with brine, dried over anhydrous sodium sulfate, filtered, and concentrated under vacuum. The residue was purified by flash chromatography on silica gel with 0~10% methanol in dichloromethane to afford 5-((5-((tert-butyldimethylsilyl)oxy)-5,6,7,8-tetrahydroquinolin-2-yl)methoxy)-1,3,4-thiadiazol-2-amine (230 mg, 49.1%) as a yellow solid. MS (ESI) calc'd for ($C_{18}H_{28}N_4O_2SSi$) $(M+1)^+$, 393.1; found, 393.1.

Step-6: N-(5-((5-((tert-butyldimethylsilyl)oxy)-5,6,7,8-tetrahydroquinolin-2-yl)methoxy)-1,3,4-thiadiazol-2-yl)-4-(2-fluoro-6-methoxyphenyl)-6-methylpyridine-3-carboxamide

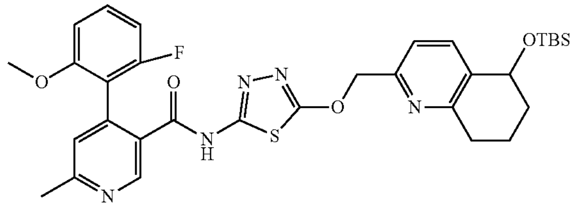 [SMILES: COc1cccc(F)c1-c1cc(C)ncc1C(=O)Nc1nnc(OCc2ccc3c(n2)CCCC3O[Si](C)(C)C(C)(C)C)s1]

To a solution of 5-((5-((tert-butyldimethylsilyl)oxy)-5,6,7,8-tetrahydroquinolin-2-yl)methoxy)-1,3,4-thiadiazol-2-amine (210 mg, 0.535 mmol) in MeCN (5 mL) were added 4-(2-fluoro-6-methoxyphenyl)-6-methylpyridine-3-carboxylic acid (140 mg, 0.535 mmol, Intermediate F), NMI (132 mg, 1.605 mmol) and TCFH (180 mg, 0.642 mmol). The resulting solution was stirred at room temperature for 2 hours. The resulting mixture was concentrated under vacuum. The residue was purified by flash chromatography on silica gel with 0~10% methanol in dichloromethane to afford N-(5-((5-((tert-butyldimethylsilyl)oxy)-5,6,7,8-tetrahydroquinolin-2-yl)methoxy)-1,3,4-thiadiazol-2-yl)-4-(2-fluoro-6-methoxyphenyl)-6-methylpyridine-3-carboxamide (150 mg, 39.6%) as a yellow solid. MS (ESI) calc'd for ($C_{32}H_{38}FN_5O_4SSi$) $(M+1)^+$, 636.2; found, 636.2.

Step-7: 4-(2-fluoro-6-methoxyphenyl)-N-(5-((5-hydroxy-5,6,7,8-tetrahydroquinolin-2-yl)methoxy)-1,3,4-thiadiazol-2-yl)-6-methylpyridine-3-carboxamide

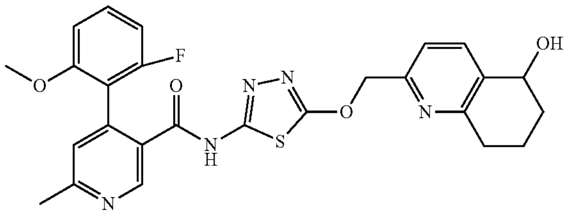

To a solution of N-(5-((5-((tert-butyldimethylsilyl)oxy)-5,6,7,8-tetrahydroquinolin-2-yl)methoxy)-1,3,4-thiadiazol-2-yl)-4-(2-fluoro-6-methoxyphenyl)-6-methylpyridine-3-carboxamide (120 mg, 0.189 mmol) in DCM (5 mL) was added TFA (1 mL). The resulting solution was stirred at room temperature for 12 hours. The resulting mixture was concentrated under vacuum. The residue was purified by prep-HPLC with the following conditions: (Column: XBridge Prep OBD C18 Column, 30×150 mm 5 um; Mobile Phase A: Water (10 MMOL/L $NH_4HCO_3$+0.1% $NH_3 \cdot H_2O$), Mobile Phase B: ACN; Flow rate: 60 mL/min; Gradient: 15 B to 37 B in 7 min; 220 nm; RT1: 6.87 min) to afford 4-(2-fluoro-6-methoxyphenyl)-N-(5-((5-hydroxy-5,6,7,8-tetrahydroquinolin-2-yl)methoxy)-1,3,4-thiadiazol-2-yl)-6-methylpyridine-3-carboxamide (35 mg, 34.8%) as a white solid. MS (ESI) calc'd for ($C_{26}H_{24}FN_5O_4S$) $(M+1)^+$, 522.2; found, 522.3. $^1H$ NMR (400 MHz, $CD_3OD$) δ 8.77 (s, 1H), 7.91 (s, 1H), 7.45-7.40 (m, 3H), 6.89-6.85 (m, 2H), 5.51 (s, 2H), 4.79-4.77 (m, 1H), 3.77 (s, 3H), 2.99-2.85 (m, 2H), 2.65 (s, 3H), 2.11-2.09 (m, 2H), 1.91-1.86 (m, 2H).

Step-8:4-(2-fluoro-6-methoxyphenyl)-N-(5-(((S)-5-hydroxy-5,6,7,8-tetrahydroquinolin-2-yl)methoxy)-1,3,4-thiadiazol-2-yl)-6-methylnicotinamide and 4-(2-fluoro-6-methoxyphenyl)-N-(5-(((R)-5-hydroxy-5,6,7,8-tetrahydroquinolin-2-yl)methoxy)-1,3,4-thiadiazol-2-yl)-6-methylnicotinamide

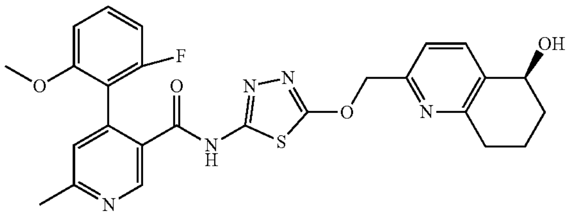

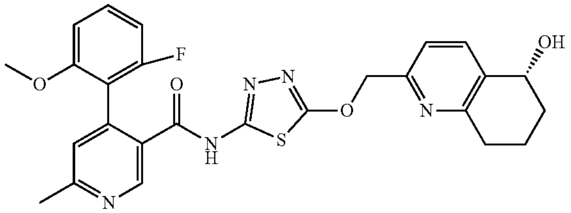 [SMILES: COc1cccc(F)c1-c1cc(C)ncc1C(=O)Nc1nnc(OCc2ccc3c(n2)CCCC3O)s1]

The racemic compound of 4-(2-fluoro-6-methoxyphenyl)-N-(5-((5-hydroxy-5,6,7,8-tetrahydroquinolin-2-yl)methoxy)-1,3,4-thiadiazol-2-yl)-6-methylpyridine-3-carboxamide (45 mg) was separated by prep-chiral-HPLC with the following conditions: (Column: CHIRAL ART Amylose-SA, 2*25 cm, 5 um; Mobile Phase A: Hex (0.2% FA)-HPLC, Mobile Phase B: EtOH-HPLC; Flow rate: 20 mL/min; Gradient: 20 B to 20 B in 13.5 min; 220/254 nm; RT1:10.618; RT2:11.716; Injection Volumn: 0.3 ml; Number Of Runs:5) to afford 4-(2-fluoro-6-methoxyphenyl)-N-(5-(((S)-5-hydroxy-5,6,7,8-tetrahydroquinolin-2-yl)methoxy)-1,3,4-thiadiazol-2-yl)-6-methylnicotinamide (9.0 mg) as a white solid with shorter retention time on chiral HPLC and 4-(2-fluoro-6-methoxyphenyl)-N-(5-(((R)-5-hydroxy-5,6,7,8-tetrahydroquinolin-2-yl)methoxy)-1,3,4-thiadiazol-2-yl)-6-methylnicotinamide (5.8 mg) as a white solid with longer retention time on chiral HPLC.

4-(2-fluoro-6-methoxyphenyl)-N-(5-(((S)-5-hydroxy-5,6,7,8-tetrahydroquinolin-2-yl)methoxy)-1,3,4-thiadiazol-2-yl)-6-methylnicotinamide MS (ESI) calc'd for ($C_{26}H_{24}FN_5O_4S$) $(M+1)^+$, 522.2; found, 522.2. $^1H$ NMR (400 MHz, DMSO-$d_6$) δ 12.89 (s, 1H), 8.82 (s, 1H), 7.79 (s, 1H), 7.41-7.32 (m, 3H), 6.94-6.88 (m, 2H), 5.44 (s, 2H), 5.32 (s, 1H), 4.64-4.62 (m, 1H), 3.58 (s, 3H), 2.68-2.56 (m, 2H), 2.37 (s, 3H), 1.99-1.91 (m, 2H), 1.76-1.67 (m, 2H).

4-(2-fluoro-6-methoxyphenyl)-N-(5-(((R)-5-hydroxy-5,6,7,8-tetrahydroquinolin-2-yl)methoxy)-1,3,4-thiadiazol-2-yl)-6-methylnicotinamide MS (ESI) calc'd for ($C_{26}H_{24}FN_5O_4S$) $(M+1)^+$, 522.2; found, 522.2. $^1H$ NMR (400 MHz, DMSO-$d_6$) δ 12.89 (s, 1H), 8.82 (s, 1H), 7.79 (s, 1H), 7.41-7.32 (m, 3H), 6.94-6.88 (m, 2H), 5.44 (s, 2H), 5.32 (s, 1H), 4.64-4.62 (m, 1H), 3.58 (s, 3H), 2.68-2.56 (m, 2H), 2.37 (s, 3H), 1.99-1.91 (m, 2H), 1.76-1.67 (m, 2H).

Example 118

N-(5-(((1s,3s)-3-hydroxycyclobutyl)methoxy)-1,3,4-thiadiazol-2-yl)-5'-methoxy-2',6-dimethyl-[4,4'-bipyridine]-3-carboxamide

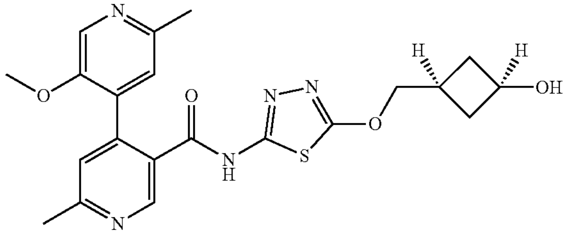 [SMILES: COc1cnc(C)cc1-c1cc(C)ncc1C(=O)Nc1nnc(OC[C@H]2C[C@@H](O)C2)s1]

Step-1: methyl (1s,3s)-3-((tert-butyldimethylsilyl)oxy)cyclobutane-1-carboxylatemethyl

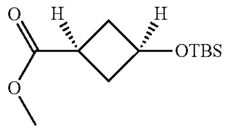 [SMILES: COC(=O)[C@H]1C[C@@H](O[Si](C)(C)C(C)(C)C)C1]

To a mixture of methyl (1s,3s)-3-hydroxycyclobutane-1-carboxylate (2.0 g, 15.368 mmol) and Imidazole (1.5 g, 23.013 mmol) in DCM (30 mL) were added TBS-Cl (3.5 g, 23.013 mmol) and DMAP (187 mg, 1.537 mmol) at 0° C. The resulting mixture was stirred at 0° C. for 1 hour. The reaction mixture was then quenched by the addition of water and extracted with ethyl acetate. The organic layers were combined, washed with brine, dried over anhydrous sodium sulfate and filtered. The filtrate was concentrated under vacuum. The residue was purified by flash chromatography on silica gel with 0~30% ethyl acetate in petroleum ether to afford methyl (1s,3s)-3-((tert-butyldimethylsilyl)oxy)cyclobutane-1-carboxylate (3.3 g, 88%) as a colorless oil. MS (ESI) calc'd for ($C_{12}H_{24}O_3Si$) $(M+1)^+$, 245.1.

Step-2: ((1s,3s)-3-((tert-butyldimethylsilyl)oxy)cyclobutyl)methanol

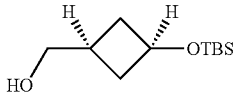 [SMILES: CC(C)(C)[Si](C)(C)O[C@H]1C[C@@H](CO)C1]

To a solution of methyl (1s,3s)-3-((tert-butyldimethylsilyl)oxy)cyclobutane-1-carboxylate (2.3 g, 9.43 mmol) in THF (20 mL) was added $LiAlH_4$ (537 mg, 14.14 mmol) in portions at 0~5° C. The resulting mixture was stirred at 0° C. for 1 hour. The reaction mixture was then quenched by the addition of water and extracted with ethyl acetate. The combined organic layers were washed with brine, dried over anhydrous sodium sulfate, filtered, and concentrated under vacuum. The residue was purified by flash chromatography on silica gel with 0~40% ethyl acetate in petroleum ether to afford ((1s,3s)-3-((tert-butyldimethylsilyl)oxy)cyclobutyl) methanol (1.0 g, 49%) as a colorless oil. MS (ESI) calc'd for ($C_{11}H_{24}O_2Si$) $(M+1)^+$, 217.1.

Step-3: O-(((1s,3s)-3-((tert-butyldimethylsilyl)oxy) cyclobutyl)methyl)S-methyl carbonodithioate

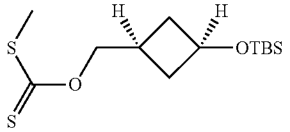 [SMILES: CSC(=S)OC[C@H]1C[C@@H](O[Si](C)(C)C(C)(C)C)C1]

To a solution of (((1s,3s)-3-((tert-butyldimethylsilyl)oxy) cyclobutyl)methanol (1.0 g, 4.63 mmol) in THF (10 mL) was added NaH (278 mg, 6.94 mmol, 60%) in portions at 0° C. and stirred at 0° C. for 30 min. Then $CS_2$ (527 mg, 6.94 mmol) was added to the above mixture and stirred at 0° C. for 10 min, and then MeI (985 mg, 6.94 mmol) was added to the above mixture at 5° C. The resulting mixture was stirred at room temperature for 1 hour. The reaction mixture was quenched by the addition of water and extracted with ethyl acetate. The combined organic layers were washed with brine, dried over anhydrous sodium sulfate, filtered, and concentrated under vacuum to afford O-(((1s,3s)-3-((tert-butyldimethylsilyl)oxy)cyclobutyl)methyl)S-methyl carbonodithioate (1.3 g, crude) as a colorless oil, which was used in the next step without further purification. MS (ESI) calc'd for ($C_{13}H_{26}O_2S_2Si$) $(M+1)^+$, 307.1.

Step-4: O-(((1s,3s)-3-((tert-butyldimethylsilyl)oxy) cyclobutyl)methyl) hydrazinecarbothioate

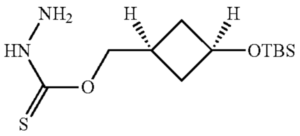 [SMILES: CC(C)(C)[Si](C)(C)O[C@H]1C[C@@H](COC(=S)NN)C1]

To a solution of O-(((1s,3s)-3-((tert-butyldimethylsilyl) oxy)cyclobutyl)methyl)S-methyl carbonodithioate (1.3 g, 4.25 mmol) in MeOH (10 mL) was added hydrazine (265 mg, 4.25 mmol, 80%) at 0° C. The resulting mixture was stirred at room temperature for 1 hour. The reaction mixture was quenched with water and extracted with ethyl acetate. The combined organic layers were washed with brine, dried over anhydrous sodium sulfate, filtered, and concentrated under vacuum to afford O-(((1s,3s)-3-((tert-butyldimethylsilyl)oxy)cyclobutyl)methyl) hydrazinecarbothioate (1.0 g, crude) as yellow oil. MS (ESI) calc'd for ($C_{12}H_{26}N_2O_2SSi$) $(M+1)^+$, 291.1.

Step-5: 5-(((1s,3s)-3-((tert-butyldimethylsilyl)oxy) cyclobut 1 methoxy)-1,3,4-thiadiazol-2-amine

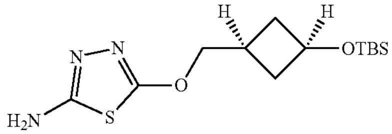 [SMILES: CC(C)(C)[Si](C)(C)O[C@H]1C[C@@H](COc2nnc(N)s2)C1]

To a solution of O-(((1s,3s)-3-((tert-butyldimethylsilyl) oxy)cyclobutyl)methyl) hydrazinecarbothioate (1.0 g, 3.45 mmol) in MeOH (10 mL) were added TEA (522 mg, 5.17 mmol) and BrCN (543 mg, 5.17 mmol). The resulting mixture was stirred at 0° C. for 2 hours. The reaction mixture was quenched with water and extracted with ethyl acetate. The combined organic layers were washed with brine, dried over anhydrous sodium sulfate, filtered, and concentrated under vacuum. The residue was purified by flash chromatography on silica gel with 0~60% ethyl acetate in petroleum ether to afford 5-(((1s,3s)-3-((tert-butyldimethylsilyl)oxy) cyclobutyl)methoxy)-1,3,4-thiadiazol-2-amine (780 mg, 76%) as a white solid. MS (ESI) calc'd for ($C_{13}H_{25}N_3O_2SSi$) $(M+1)^+$, 316.1; found 316.1.

Step-6: N-(5-(((1s,3s)-3-((tert-butyldimethylsilyl) oxy)cyclobutyl)methoxy)-1,3,4-thiadiazol-2-yl)-5'-methoxy-2',6-dimethyl-(4,4'-bipyridine)-3-carboxamide

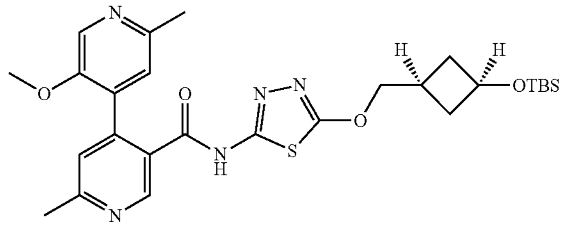 [SMILES: COc1cnc(C)cc1-c1cc(C)ncc1C(=O)Nc1nnc(OC[C@H]2C[C@@H](O[Si](C)(C)C(C)(C)C)C2)s1]

To a solution of 5-methoxy-2,6-dimethyl-(4,4-bipyridine)-3-carboxylic acid (100 mg, 0.387 mmol, Intermediate G) in ACN (0.5 mL) and DMF (0.5 mL) were added NMI (95 mg, 1.160 mmol), 5-(((1s,3s)-3-((tert-butyldimethylsilyl)oxy)cyclobutyl)methoxy)-1,3,4-thiadiazol-2-amine (122 mg, 0.387 mmol) and TCFH (119 mg, 0.425 mmol). The mixture was stirred at room temperature for 2 hours. The resulting mixture was purified by reverse phase flash column chromatography with 5~60% acetonitrile in water to afford N-(5-(((1s,3s)-3-((tert-butyldimethylsilyl)oxy)cyclobutyl) methoxy)-1,3,4-thiadiazol-2-yl)-5'-methoxy-2',6-dimethyl-(4,4'-bipyridine)-3-carboxamide (95 mg, 47%) as a white solid. MS (ESI) calc'd for ($C_{27}H_{37}N_5O_4SSi$) $(M+1)^+$, 556.2; found 556.0.

Step-7: N-(5-(((1s,3s)-3-hydroxycyclobutyl) methoxy)-1,3,4-thiadiazol-2-yl)-5'-methoxy-2',6-dimethyl-(4,4'-bipyridine)-3-carboxamide

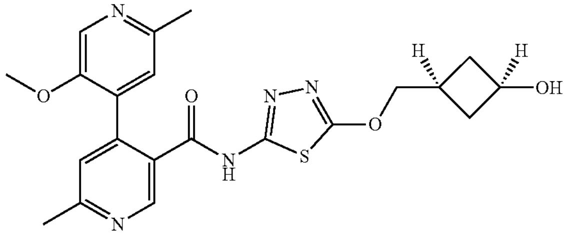 [SMILES: COc1cnc(C)cc1-c1cc(C)ncc1C(=O)Nc1nnc(OC[C@H]2C[C@@H](O)C2)s1]

To a mixture of N-(5-(((1s,3s)-3-((tert-butyldimethylsilyl) oxy)cyclobutyl)methoxy)-1,3,4-thiadiazol-2-yl)-5'-methoxy-2',6-dimethyl-(4,4'-bipyridine)-3-carboxamide (90 mg, 0.162 mmol) in THF (1 mL) were added TBAF (105 mg, 0.405 mmol). The mixture was stirred at room temperature for 24 hours before concentrated under vacuum. The resulting mixture was purified by reverse phase flash chromatography with 10-70% acetonitrile in water to afford to afford N-(5-(((1s,3s)-3-hydroxycyclobutyl)methoxy)-1,3,4-thiadiazol-2-yl)-5'-methoxy-2',6-dimethyl-(4,4'-bipyridine)-3-carboxamide (28.8 mg, 40%) as a white solid. MS (ESI) calc'd for ($C_{21}H_{23}N_5O_4S$) $(M+1)^+$, 442.2; found 442.2. $^1H$ NMR (400 MHz, DMSO-$d_6$) δ 12.82 (s, 1H), 8.75 (s, 1H), 8.18 (s, 1H), 7.35 (s, 1H), 7.24 (s, 1H), 5.04 (d, J=6.4 Hz, 1H), 4.35 (d, J=6.4 Hz, 2H), 4.00-3.95 (m, 1H), 3.59 (s, 3H), 2.66 (s, 3H), 2.47 (s, 3H), 2.34-2.15 (m, 3H), 1.72-1.65 (m, 2H).

Example 119

4-(2-fluoro-6-methoxyphenyl)-N-(5-((5-(2-hydroxypropan-2-yl)pyrazin-2-yl)methoxy)-1,3,4-thiadiazol-2-yl)-6-methylnicotinamide

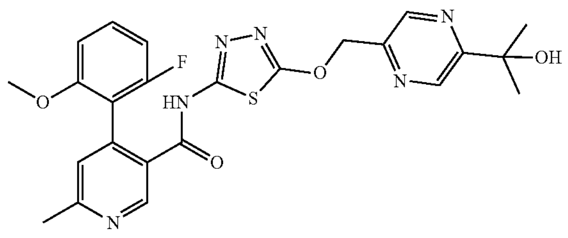 [SMILES: COc1cccc(F)c1-c1cc(C)ncc1C(=O)Nc1nnc(OCc2cnc(C(C)(C)O)cn2)s1]

Step-1: N-(5-((5-acetylpyrazin-2-yl)methoxy)-1,3,4-thiadiazol-2-yl)-4-(2-fluoro-6-methoxyphenyl)-6-methylnicotinamide

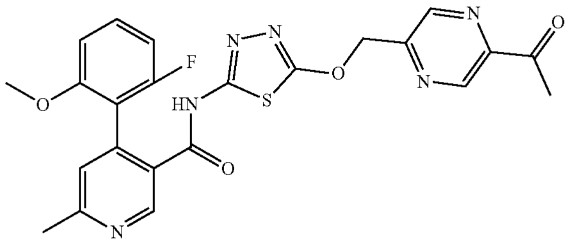 [SMILES: COc1cccc(F)c1-c1cc(C)ncc1C(=O)Nc1nnc(OCc2cnc(C(C)=O)cn2)s1]

To a stirred solution of 4-(2-fluoro-6-methoxyphenyl)-N-(5-((5-(1-hydroxyethyl)pyrazin-2-yl)methoxy)-1,3,4-thiadiazol-2-yl)-6-methylpyridine-3-carboxamide (150 mg, 0.30 mmol) in DCM (3 mL) was added Martin's reagent (256 mg, 0.60 mmol). The resulting mixture was stirred at room temperature for 1 h. The reaction was quenched with saturated sodium bicarbonate solution. The resulting mixture was extracted with ethyl acetate. The combined organic layers were washed with saturated sodium chloride, dried over anhydrous sodium sulfate. After filtration, the filtrate was concentrated under reduced pressure to afford N-(5-((5-acetylpyrazin-2-yl)methoxy)-1,3,4-thiadiazol-2-yl)-4-(2-fluoro-6-methoxyphenyl)-6-methylnicotinamide (180 mg, 84%) as a brown solid. MS (ESI) calculated for ($C_{23}H_{19}FN_6O_4S$) $(M+1)^+$, 495.1; found, 495.1.

Step-2: 4-(2-fluoro-6-methoxyphenyl)-N-(5-((5-(2-hydroxypropan-2-yl)pyrazin-2-yl)methoxy)-1,3,4-thiadiazol-2-yl)-6-methylnicotinamide

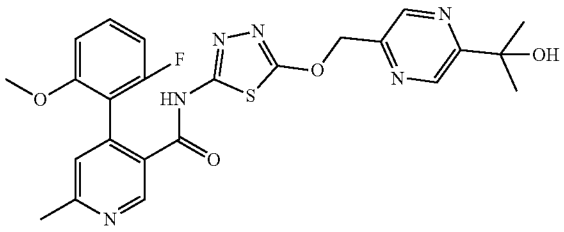 [SMILES: COc1cccc(F)c1-c1cc(C)ncc1C(=O)Nc1nnc(OCc2cnc(C(C)(C)O)cn2)s1]

To a stirred solution of N-(5-((5-acetylpyrazin-2-yl)methoxy)-1,3,4-thiadiazol-2-yl)-4-(2-fluoro-6-methoxyphenyl)-6-methylnicotinamide (10 mg, 0.02 mmol) in THF (1 mL) was added MeMgBr (0.02 mL, 0.02 mmol, 1 M in THF) dropwise at 0° C. under $N_2$ atmosphere. The resulting mixture was stirred at 0° C. for 1 h. The reaction was quenched with saturated sodium bicarbonate solution. The resulting mixture was extracted with ethyl acetate. The combined organic layers were washed with saturated sodium chloride, dried over anhydrous sodium sulfate. After filtration, the filtrate was concentrated under reduced pressure. The residue was purified by prep-HPLC with the following conditions: (Column: XBridge Prep OBD C18 Column, 30×150 mm 5 um; Mobile Phase A: Water (10 MMOL/L $NH_4HCO_3$), Mobile Phase B: ACN; Flow rate: 60 mL/min; Gradient: 20 B to 50 B in 8 min; 220 nm; RT1: 6.28 min) to afford 4-(2-fluoro-6-methoxyphenyl)-N-(5-((5-(2-hydroxypropan-2-yl)pyrazin-2-yl)methoxy)-1,3,4-thiadiazol-2-yl)-6-methylnicotinamide (10 mg, 5%) as a white solid. MS (ESI) calculated for ($C_{24}H_{23}FN_6O_4S$) $(M+1)^+$, 511.2; found, 511.2. $^1H$ NMR (400 MHz, DMSO-$d_6$) δ 12.91 (s, 1H), 8.91 (d, J=1.6 Hz, 1H), 8.85 (s, 1H), 8.71 (d, J=1.6 Hz, 1H), 7.46-7.35 (m, 1H), 7.28 (s, 1H), 6.97-6.84 (m, 2H), 5.57 (s, 2H), 5.50 (s, 1H), 3.59 (s, 3H), 2.56 (s, 3H), 1.47 (s, 6H).

Example 120

N-(5-((5-chloropyridin-2-yl)methoxy)-1,3,4-thiadiazol-2-yl)-3-methoxy-6'-methyl-(2,4'-bipyridine)-3'-carboxamide

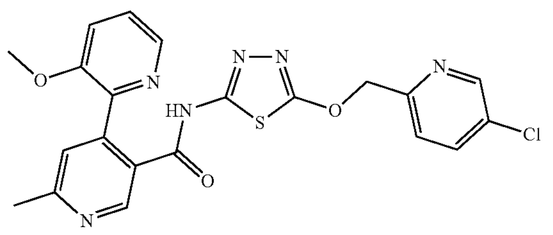 [SMILES: COc1cccnc1-c1cc(C)ncc1C(=O)Nc1nnc(OCc2ccc(Cl)cn2)s1]

Step-1: 3-methoxy-6'-methyl-(2,4'-bipyridine)-3'-carbonitrile

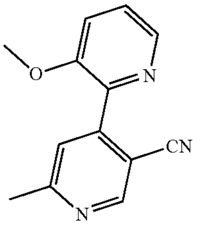 [SMILES: COc1cccnc1-c1cc(C)ncc1C#N]

A degassed mixture of 2-bromo-3-methoxypyridine (300.0 mg, 1.59 mmol), 5-cyano-2-methylpyridin-4-ylboronic acid (775.2 mg, 4.78 mmol), Pd(dtbpf)$C_{12}$ (207.9 mg, 0.31 mmol) and $K_2CO_3$ (441.0 mg, 3.19 mmol) in dioxane (6.0 mL) and $H_2O$ (2.0 mL) was stirred at 100° C. for 2 h under nitrogen atmosphere. The solvent was removed under vacuum. The residue was purified by reverse phase flash column chromatography with 5-30% acetonitrile in water to afford 3-methoxy-6'-methyl-(2,4'-bipyridine)-3'-carbonitrile (280.0 mg, 74%) as a brown yellow solid. MS (ESI) calc'd for ($C_{13}H_{11}N_3O$) $(M+1)^+$, 226.1, found 226.0.

Step-2: 3-methoxy-6'-methyl-(2,4'-bipyridine)-3'-carboxylic acid

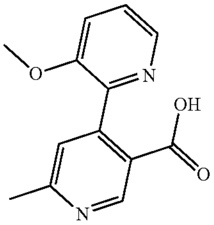 [SMILES: COc1cccnc1-c1cc(C)ncc1C(=O)O]

A mixture of 3-methoxy-6'-methyl-(2,4'-bipyridine)-3'-carbonitrile (250.0 mg, 1.11 mmol) in concentrated HCl (5.0 mL) were stirred at 100° C. for 2 h. The crude was purified by Prep-HPLC with the following conditions: (Column: XBridge Shield RP18 OBD Column, 30*150 mm, 5 um; Mobile Phase A: Water (10 MMOL/L $NH_4HCO_3$), Mobile Phase B: ACN; Flow rate: 60 mL/min; Gradient: 15 B to 45 B in 7 min, 45 B to B in min, B to B in min, B to B in min, B to B in min; 254/220 nm; RT1:7.53 min) to afford 3-methoxy-6'-methyl-(2,4'-bipyridine)-3'-carboxylic acid (210.0 mg, 73%) as a yellow solid. MS (ESI) calc'd for ($C_{13}H_{12}N_2O_3$) $(M+1)^+$, 245.1, found 245.0.

Step-3: N-(5-((5-chloropyridin-2-yl)methoxy)-1,3,4-thiadiazol-2-yl)-3-methoxy-6'-methyl-(2,4'-bipyridine)-3'-carboxamide

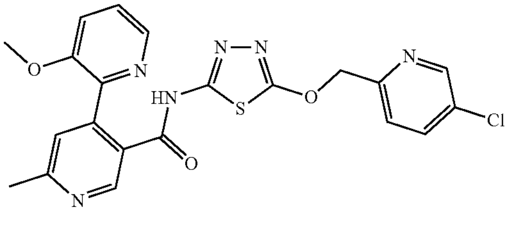 [SMILES: COc1cccnc1-c1cc(C)ncc1C(=O)Nc1nnc(OCc2ccc(Cl)cn2)s1]

To a mixture of 3-methoxy-6'-methyl-(2,4'-bipyridine)-3'-carboxylic acid (100.0 mg, 0.40 mmol) in DMF (5.0 mL) were added 5-((5-chloropyridin-2-yl)methoxy)-1,3,4-thiadiazol-2-amine (149.0 mg, 0.61 mmol, Intermediate C), DIEA (158.7 mg, 1.22 mmol) and HATU (233.5 mg, 0.61 mmol). The resulting solution was stirred at room temperature for 2 h. The combined organic layers were washed with brine, dried over anhydrous sodium sulfate, filtered, and concentrated under vacuum. The crude residue was purified by Prep-HPLC with the following conditions: (Column: XSelect CSH Prep C18 OBD Column, 19*250 mm, 5 um; Mobile Phase A: Water (10 MMOL/L $NH_4HCO_3$, Mobile Phase B: ACN; Flow rate: 25 mL/min; Gradient: 25 B to 50 B in 8 min, 254 nm; RT1: 7.1 min)) to afford N-(5-((5-chloropyridin-2-yl)methoxy)-1,3,4-thiadiazol-2-yl)-3-methoxy-6'-methyl-(2,4'-bipyridine)-3'-carboxamide (22.5 mg, 11%) as a white solid. MS (ESI) calc'd for ($C_{21}H_{17}ClN_6O_3S$) $(M+1)^+$, 469.0, found 469.0. $^1H$ NMR (400 MHz, DMSO-$d_6$) δ 12.93 (s, 1H), 8.74 (s, 1H), 8.66 (d, J=2.4 Hz, 1H), 8.23 (d, J=4.4 Hz, 1H), 8.04-7.97 (m, 1H), 7.61 (d, J=8.4 Hz, 1H), 7.49 (d, J=7.2 Hz, 2H), 7.45-7.38 (m, 1H), 5.55 (s, 2H), 3.62 (s, 3H), 2.59 (s, 3H).

Example 121

5-(5-chloro-2-methoxyphenyl)-N-(5-((4-hydroxybicyclo(2.2.2)octan-1-yl)methoxy)-1,3,4-thiadiazol-2-yl)pyridazine-4-carboxamide

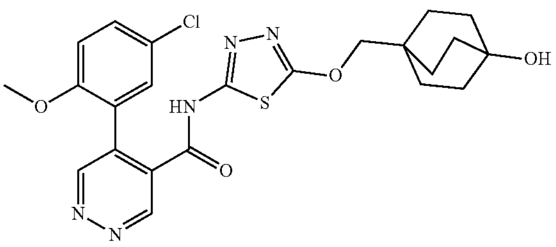 [SMILES: COc1ccc(Cl)cc1-c1cnncc1C(=O)Nc1nnc(OCC23CCC(O)(CC2)CC3)s1]

Step-1:
5-(5-chloro-2-methoxyphenyl)pyridazin-4-amine

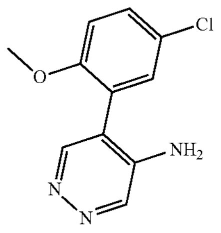 [SMILES: COc1ccc(Cl)cc1-c1cnncc1N]

To a degassed solution of 5-bromopyridazin-4-amine (1 g, 5.747 mmol) in dioxane (10 mL) and $H_2O$ (1 mL) were added 5-chloro-2-methoxyphenylboronic acid (1071 mg, 5.747 mmol), $K_2CO_3$ (2382 mg, 17.241 mmol) and Pd(dppf)$Cl_2$ (420 mg, 0.575 mmol). The resulting solution was stirred at 80° C. for 3 hours under nitrogen before concentrated under vacuum. The residue was purified by flash chromatography on silica gel with 0~10% methanol in dichloromethane to afford 5-(5-chloro-2-methoxyphenyl)

pyridazin-4-amine (1.3 g, 86.3%) as a yellow solid. MS (ESI) calc'd for ($C_{11}H_{10}ClN_3O$) $(M+1)^+$, 236.1; found, 236.1.

Step-2: 4-bromo-5-(5-chloro-2-methoxyphenyl)pyridazine

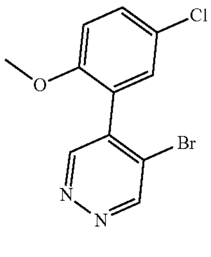 [SMILES: COc1ccc(Cl)cc1-c1cnncc1Br]

To a solution of 5-(5-chloro-2-methoxyphenyl)pyridazin-4-amine (300 mg, 1.273 mmol) in MeCN (10 mL) were added tBuONO (302 mg, 2.928 mmol) and $CuBr_2$ (427 mg, 1.909 mmol) at 0° C. The resulting solution was stirred f at room temperature or 12 hours. The resulting mixture was concentrated. The residue was purified by flash chromatography on silica gel with 0~10% methanol in dichloromethane to afford 4-bromo-5-(5-chloro-2-methoxyphenyl) pyridazine (200 mg, 47.2%) as a brown solid. MS (ESI) calc'd for ($C_{11}H_8BrClN_2O$) $(M+1)^+$, 299.0; found, 299.0.

Step-3: 5-(5-chloro-2-methoxyphenyl)pyridazine-4-carbonitrile

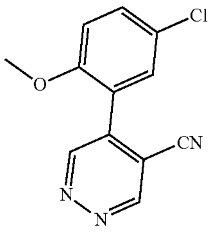 [SMILES: COc1ccc(Cl)cc1-c1cnncc1C#N]

To a solution of 4-bromo-5-(5-chloro-2-methoxyphenyl) pyridazine (170 mg, 0.568 mmol) in DMF (10 mL) were added $Zn(CN)_2$ (67 mg, 0.568 mmol) and $Pd(PPh_3)_4$ (66 mg, 0.057 mmol). The resulting solution was stirred at 130° C. for 2 hours under nitrogen. The mixture was quenched with water and extracted with ethyl acetate. The combined organic layers were washed with brine, dried over anhydrous sodium sulfate, filtered, and concentrated under vacuum. The residue was purified by flash chromatography on silica gel with 0~10% methanol in dichloromethane to afford 5-(5-chloro-2-methoxyphenyl)pyridazine-4-carbonitrile (130 mg, 85.7%) as a yellow solid. MS (ESI) calc'd for ($C_{12}H_8ClN_3O$) $(M+1)^+$, 246.0; found, 246.0.

Step-4: 5-(5-chloro-2-methoxyphenyl)pyridazine-4-carboxylic acid

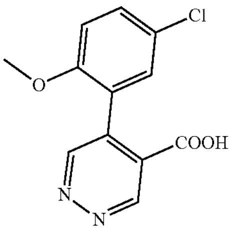 [SMILES: COc1ccc(Cl)cc1-c1cnncc1C(=O)O]

A solution of 5-(5-chloro-2-methoxyphenyl)pyridazine-4-carbonitrile (100 mg, 0.407 mmol) in concentrated hydrogen chloride (2 mL, 12 mol/L) was stirred at 90° C. for 12 hours. The resulting mixture was concentrated under vacuum to afford 5-(5-chloro-2-methoxyphenyl)pyridazine-4-carboxylic acid (100 mg, crude) as a yellow solid, which was used for the next step without further purification. MS (ESI) calc'd for ($C_{12}H_9ClN_2O_3$) $(M+1)^+$, 265.0; found, 265.0.

Step-5: N-(5-((4-((tert-butyldimethylsilyl)oxy)bicyclo(2.2.2)octan-1-yl)methoxy)-1,3,4-thiadiazol-2-yl)-5-(5-chloro-2-methoxyphenyl)pyridazine-4-carboxamide

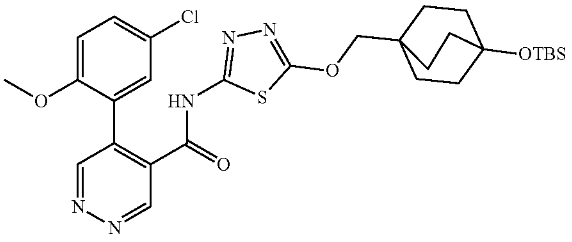 [SMILES: COc1ccc(Cl)cc1-c1cnncc1C(=O)Nc1nnc(OCC23CCC(O[Si](C)(C)C(C)(C)C)(CC2)CC3)s1]

To a solution of 5-(5-chloro-2-methoxyphenyl) pyridazine-4-carboxylic acid (60 mg, 0.227 mmol, Example 121, Step 4) in DMF (5 mL) were added DIEA (88 mg, 0.680 mmol), HATU (104 mg, 0.272 mmol) and 5-((4-((tert-butyldimethylsilyl)oxy)bicyclo(2.2.2)octan-1-yl)methoxy)-1,3,4-thiadiazol-2-amine (84 mg, 0.227 mmol). The resulting solution was stirred at room temperature for 2 hours. The mixture was quenched with water and extracted with ethyl acetate. The combined organic layers were washed with brine, dried over anhydrous sodium sulfate, filtered, and concentrated under vacuum. The residue was purified by flash chromatography on silica gel with 0~10% methanol in dichloromethane to afford N-(5-((4-((tert-butyldimethylsilyl)oxy)bicyclo(2.2.2)octan-1-yl)methoxy)-1,3,4-thiadiazol-2-yl)-5-(5-chloro-2-methoxyphenyl)pyridazine-4-carboxamide (30 mg, 21.4%) as a yellow solid. MS (ESI) calc'd for ($C_{29}H_{38}ClN_5O_4SSi$) $(M+1)^+$, 616.2; found, 616.2.

Step-6: 5-(5-chloro-2-methoxyphenyl)-N-(5-((4-hydroxybicyclo(2.2.2)octan-1-yl)methoxy)-1,3,4-thiadiazol-2-yl)pyridazine-4-carboxamide

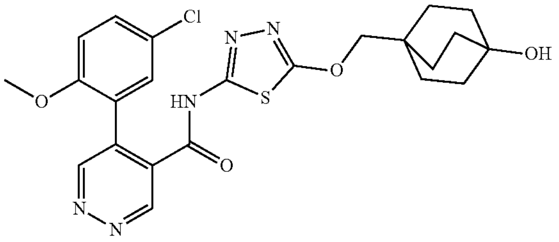 [SMILES: COc1ccc(Cl)cc1-c1cnncc1C(=O)Nc1nnc(OCC23CCC(O)(CC2)CC3)s1]

To a solution of N-(5-((4-((tert-butyldimethylsilyl)oxy) bicyclo(2.2.2)octan-1-yl)methoxy)-1,3,4-thiadiazol-2-yl)-5-(5-chloro-2-methoxyphenyl)pyridazine-4-carboxamide (20 mg, 0.032 mmol) in DCM (5 mL) was added TFA (1 mL). The resulting solution was stirred at room temperature for 2 hours. The resulting mixture was quenched with saturated $NaHCO_3$ aqueous and extracted with ethyl acetate. The combined organic layers were washed with brine, dried over anhydrous sodium sulfate, filtered, and concentrated under vacuum. The residue was purified by prep-HPLC with the following conditions: (Column: Xselect CSH OBD Column 30*150 mm 5 um; Mobile Phase A: Water (0.1% FA), Mobile Phase B: ACN; Flow rate: 60 mL/min; Gradient: 25 B to 50 B in 7 min; 220 nm; RT1:7.33 min) to afford 5-(5-chloro-2-methoxyphenyl)-N-(5-((4-hydroxybicyclo (2.2.2)octan-1-yl)methoxy)-1,3,4-thiadiazol-2-yl) pyridazine-4-carboxamide (3.7 mg, 26.5%) as a white solid. MS (ESI) calc'd for ($C_{23}H_{24}ClN_5O_4S$) $(M+1)^+$, 502.1; found, 502.1. $^1H$ NMR (400 MHz, $CD_3OD$) δ 9.42 (s, 1H), 9.41 (s, 1H), 7.67-7.64 (m, 2H), 7.07-7.05 (m, 1H), 4.10 (s, 2H), 3.68 (s, 3H), 1.70 (s, 12H).

Example 122 and 123

(R)-4-(5-chloro-2-methoxyphenyl)-6-methyl-N-(5-((4-(S-methylsulfonimidoyl)benzyl)oxy)-1,3,4-thiadiazol-2-yl)nicotinamide (Example 122) and (S)-4-(5-chloro-2-methoxyphenyl)-6-methyl-N-(5-((4-(S-methylsulfonimidoyl)benzyl)oxy)-1,3,4-thiadiazol-2-yl)nicotinamide Example 123

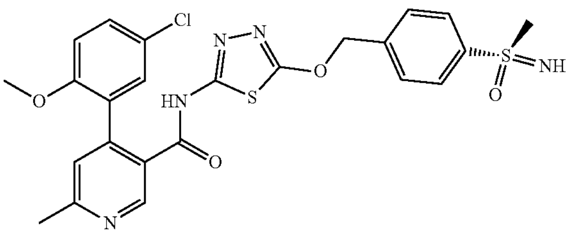

-continued

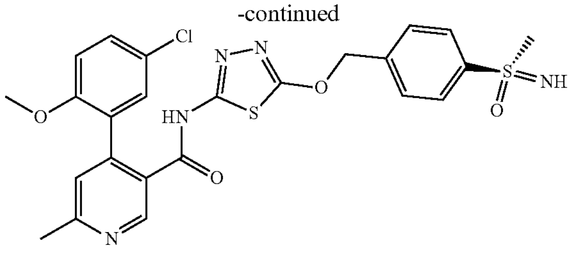

Step-1:4-(5-chloro-2-methoxyphenyl)-6-methyl-N-(5-((4-(methylthio)benzyl)oxy)-1,3,4-thiadiazol-2-yl)nicotinamide

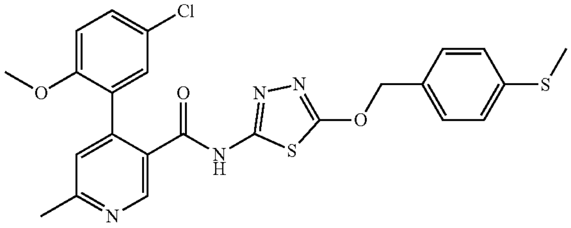

To a mixture of 5-((4-(methylsulfanyl)phenyl)methoxy)-1,3,4-thiadiazol-2-amine (120 mg, 0.47 mmol,) and 4-(5-chloro-2-methoxyphenyl)-6-methylpyridine-3-carboxylic acid (132 mg, 0.47 mmol, Example 39, Step 2) in DMF (1 mL) and MeCN (1.00 mL) were added NMI (193 mg, 2.35 mmol) and TCFH (146 mg, 0.52 mmol). The resulting mixture was stirred at room temperature for 16 hours under nitrogen atmosphere. The resulting mixture was purified by reverse phase flash chromatography with 5-65% acetonitrile in water to afford 4-(5-chloro-2-methoxyphenyl)-6-methyl-N-(5-((4-(methylthio)benzyl)oxy)-1,3,4-thiadiazol-2-yl) nicotinamide (50 mg, 21%) as a yellow solid. MS (ESI) calc'd for ($C_{24}H_{21}ClN_4O_3S_2$) $(M+1)^+$, 513.0; found 513.0.

Step-2: 4-(5-chloro-2-methoxyphenyl)-6-methyl-N-(5-((4-(S-methylsulfonimidoyl)benzyl)oxy)-1,3,4-thiadiazol-2-yl)nicotinamide

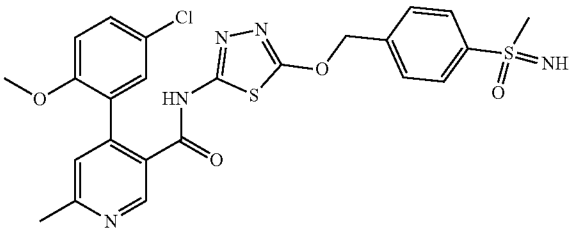 [SMILES: COc1ccc(Cl)cc1-c1cc(C)ncc1C(=O)Nc1nnc(OCc2ccc(S(C)(=N)=O)cc2)s1]

To a mixture of 4-(5-chloro-2-methoxyphenyl)-6-methyl-N-(5-((4-(methylsulfanyl)phenyl)methoxy)-1,3,4-thiadiazol-2-yl)pyridine-3-carboxamide (50 mg, 0.09 mmol) in MeOH (1 mL) were added $NH_2COONH_4$ (16.00 mg, 0.2 mmol) and $PhI(OAc)_2$ (80.00 mg, 0.25 mmol). The resulting mixture was stirred at room temperature for 3 hours under nitrogen. The reaction mixture was quenched by the addition of ice/water and extracted with ethyl acetate. The combined organic layers were washed with brine, dried over anhydrous sodium sulfate, filtered, and concentrated under vacuum. T The resulting mixture was purified by reverse phase flash chromatography with 5-50% acetonitrile in water to afford 4-(5-chloro-2-methoxyphenyl)-6-methyl-N-(5-((4-(S-methylsulfonimidoyl)benzyl)oxy)-1,3,4-thiadiazol-2-yl)nicotinamide (20 mg, 37%) as a yellow solid. MS (ESI) calc'd for ($C_{24}H_{22}ClN_5O_4S_2$) $(M+1)^+$, 544.0, found 544.0.

Step-3: (R)-4-(5-chloro-2-methoxyphenyl)-6-methyl-N-(5-((4-(S-methylsulfonimidoyl)benzyl)oxy)-1,3,4-thiadiazol-2-yl)nicotinamide and (S)-4-(5-chloro-2-methoxyphenyl)-6-methyl-N-(5-((4-(S-methylsulfonimidoyl)benzyl)oxy)-1,3,4-thiadiazol-2-yl)nicotinamide

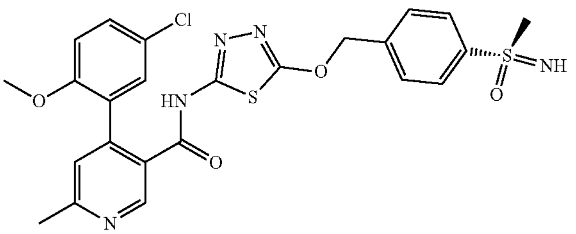

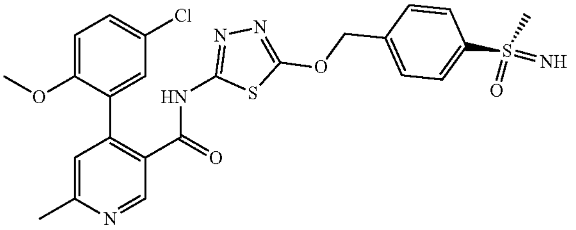

A racemic of 4-(5-chloro-2-methoxyphenyl)-6-methyl-N-(5-((4-(S-methylsulfonimidoyl)benzyl)oxy)-1,3,4-thiadiazol-2-yl)nicotinamide (20 mg) was separated by prep-chiral-HPLC with the following conditions: (Column: CHIRAL ART Cellulose-SB, 2*25 cm, 5 um; Mobile Phase A:Hex:DCM=3:1 (0.1% FA)-HPLC, Mobile Phase B:IPA-HPLC; Flow rate: 20 mL/min; Gradient: 30 B to 30 B in 16.5 min; 220/254 nm; RT1:10.247; RT2:14.215; Injection Volumn: 0.85 ml; Number Of Runs: 2) to afford (R)-4-(5-chloro-2-methoxyphenyl)-6-methyl-N-(5-((4-(S-methylsulfonimidoyl)benzyl)oxy)-1,3,4-thiadiazol-2-yl) nicotinamide (4.2 mg, 31%) as a white solid with shorter retention time on chiral HPLC and (S)-4-(5-chloro-2-methoxyphenyl)-6-methyl-N-(5-((4-(S-methylsulfonimidoyl)benzyl)oxy)-1,3,4-thiadiazol-2-yl)nicotinamide (3.3 mg, 16%) as a white solid with longer retention time on chiral HPLC.

(R)-4-(5-chloro-2-methoxyphenyl)-6-methyl-N-(5-((4-(S-methylsulfonimidoyl)benzyl)oxy)-1,3,4-thiadiazol-2-yl) nicotinamide: MS (ESI) calc'd for ($C_{24}H_{22}ClN_5O_4S_2$) $(M+1)^+$, 544.0; found, 544.1. $^1H$ NMR (400 MHz, Methanol-$d_4$) δ 8.68 (s, 1H), 8.06 (d, J=8.4 Hz, 2H), 7.74 (d, J=8.0 Hz, 2H), 7.51-7.31 (m, 3H), 6.96 (d, J=8.4 Hz, 1H), 5.60 (s, 2H), 3.60 (s, 3H), 3.18 (s, 3H), 2.66 (s, 3H).

(S)-4-(5-chloro-2-methoxyphenyl)-6-methyl-N-(5-((4-(S-methylsulfonimidoyl)benzyl)oxy)-1,3,4-thiadiazol-2-yl) nicotinamide: MS (ESI) calc'd for ($C_{24}H_{22}ClN_5O_4S_2$) $(M+1)^+$, 544.0; found, 544.1. $^1H$ NMR (400 MHz, Methanol-$d_4$) δ 8.68 (s, 1H), 8.15-7.98 (m, 2H), 7.87-7.71 (m, 2H), 7.47-7.31 (m, 3H), 7.05-6.87 (m, 1H), 5.61 (s, 2H), 3.60 (s, 3H), 3.18 (s, 3H), 2.66 (s, 3H).

Example 124

4-(2-(difluoromethoxy)-6-fluorophenyl)-N-(5-((5-(2-methoxypropan-2-yl)pyridin-2-yl)methoxy)-1,3,4-thiadiazol-2-yl)-6-methylpyridine-3-carboxamide

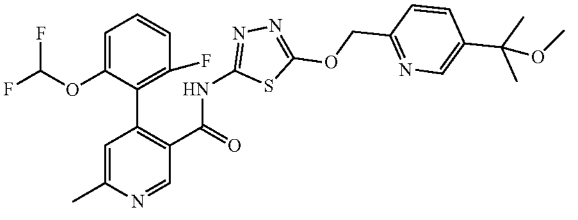 [SMILES: COC(C)(C)c1ccc(COc2nnc(NC(=O)c3cnc(C)cc3-c3c(F)cccc3OC(F)F)s2)nc1]

A mixture of 4-(2-(difluoromethoxy)-6-fluorophenyl)-6-methylpyridine-3-carboxylic acid (30.00 mg, 0.10 mmol), 5-((5-(2-methoxypropan-2-yl)pyridin-2-yl)methoxy)-1,3,4-thiadiazol-2-amine (33.96 mg, 0.12 mmol, Example 80, Step 4), TCFH (31.15 mg, 0.11 mmol) and NMI (17.40 mg, 0.21 mmol) in MeCN (2.0 mL) and DMF (0.2 mL) was stirred at room temperature for 2 h. The resulting mixture was concentrated under vacuum. The residue was purified by reverse phase flash column chromatography with 5-50% acetonitrile in water to afford 4-(2-(difluoromethoxy)-6-fluorophenyl)-N-(5-((5-(2-methoxypropan-2-yl)pyridin-2-yl)methoxy)-1,3,4-thiadiazol-2-yl)-6-methylpyridine-3-carboxamide (14.2 mg, 25%) as a white solid. MS (ESI) calc'd for ($C_{26}H_{24}F_3N_5O_4S$) $(M+1)^+$, 560.2, found 560.2. $^1H$ NMR (400 MHz, DMSO-$d_6$) δ 13.11 (s, 1H), 8.96 (s, 1H), 8.61 (d, J=2.4 Hz, 1H), 7.87-7.77 (m, 1H), 7.57-7.47 (m, 2H), 7.33 (d, J=8.4 Hz, 1H), 7.22 (t, J=8.8 Hz, 1H), 7.13 (d, J=2.4 Hz, 1H), 7.11 (s, 1H), 5.51 (s, 2H), 3.01 (s, 3H), 2.59 (s, 3H), 1.49 (s, 6H).

Example 125

2'-chloro-5'-methoxy-N-(5-((5-(2-methoxypropan-2-yl)pyridin-2-yl)methoxy)-1,3,4-thiadiazol-2-yl)-6-methyl-(4,4'-bipyridine)-3-carboxamide

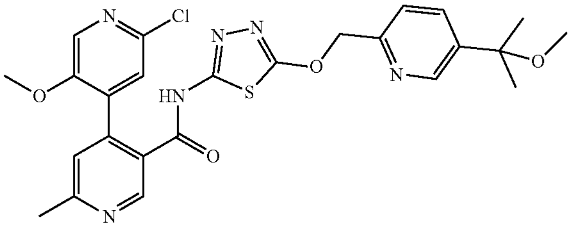

A mixture of 2'-chloro-5'-methoxy-6-methyl-(4,4'-bipyridine)-3-carboxylic acid (15.00 mg, 0.054 mmol, Intermediate H), 5-((5-(2-methoxypropan-2-yl)pyridin-2-yl) methoxy)-1,3,4-thiadiazol-2-amine (18.11 mg, 0.065 mmol, Example 80, Step 4), TCFH (16.61 mg, 0.059 mmol), NMI (9.28 mg, 0.113 mmol) in MeCN (1.0 mL) and DMF (0.2 mL) was stirred at room temperature for 2 h. The resulting mixture was concentrated under vacuum. The crude residue was purified by flash column chromatography with 5-65% acetonitrile in water to afford 2-chloro-5-methoxy-N-(5-((5-(2-methoxypropan-2-yl)pyridin-2-yl)methoxy)-1,3,4-thiadiazol-2-yl)-6-methyl-(4,4bipyridine)-3-carboxamide (8.5 mg, 29%) as a white solid. MS (ESI) calc'd for ($C_{25}H_{25}ClN_6O_4S$) $(M+1)^+$, 541.0, found 541.2. H NMR (400 MHz, DMSO-$d_6$) δ 12.96 (s, 1H), 8.81 (s, 1H), 8.61 (d, J=2.4 Hz, 1H), 8.17 (s, 1H), 7.88-7.81 (m, 1H), 7.53 (s, 2H), 7.42 (s, 1H), 5.53 (s, 2H), 3.63 (s, 3H), 3.02 (s, 3H), 2.59 (s, 3H), 1.49 (s, 6H).

Example 126

5'-methoxy-N-(5-((5-(2-methoxypropan-2-yl)pyridin-2-yl)methoxy)-1,3,4-thiadiazol-2-yl)-2',6-dimethyl-(4,4'-bipyridine)-3-carboxamide

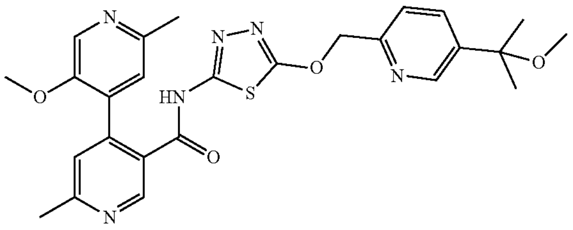

A mixture of 5-methoxy-2,6-dimethyl-(4,4-bipyridine)-3-carboxylic acid (15.00 mg, 0.058 mmol), 5-((5-(2-methoxypropan-2-yl)pyridin-2-yl)methoxy)-1,3,4-thiadiazol-2-amine (16.28 mg, 0.058 mmol, Example 80, Step 4), TCFH (17.92 mg, 0.064 mmol) and NMI (10.01 mg, 0.12 mmol) in MeCN (3.0 mL) and DMF (0.6 mL) was stirred at room temperature for 2 h. The resulting mixture was concentrated under vacuum. The crude residue was purified by reverse phase flash column chromatography with 5~50% acetonitrile in water to afford 5-methoxy-N-(5-((5-(2-methoxypropan-2-yl)pyridin-2-yl)methoxy)-1,3,4-thiadiazol-2-yl)-2,6-dimethyl-(4,4-bipyridine)-3-carboxamide (14.9 mg, 49%) as a white solid. MS (ESI) calc'd for ($C_{26}H_{28}N_6O_4S$) $(M+1)^+$, 521.2, found 521.2. $^1$H NMR (400 MHz, DMSO-$d_6$) δ 12.91 (s, 1H), 8.76 (s, 1H), 8.61 (d, J=2.4 Hz, 1H), 8.18 (s, 1H), 7.87-7.80 (m, 1H), 7.53 (d, J=8.4 Hz, 1H), 7.35 (s, 1H), 7.25 (s, 1H), 5.52 (s, 2H), 3.58 (s, 3H), 3.01 (s, 3H), 2.58 (s, 3H), 2.47 (s, 3H), 1.48 (s, 6H).

Example 127

N-(5-(((1s,4s)-4-hydroxycyclohexyl)methoxy)-1,3,4-thiadiazol-2-yl)-5'-methoxy-2',6-dimethyl-[4,4'-bipyridine]-3-carboxamide

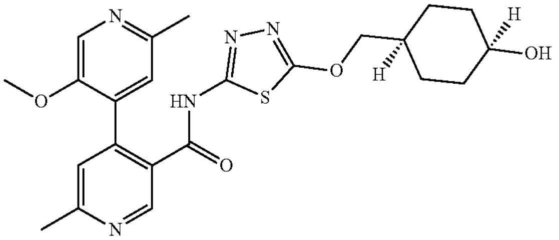

Step-1: N-(5-(((1s,4s)-4-((tert-butyldimethylsilyl)oxy)cyclohexyl)methoxy)-1,3,4-thiadiazol-2-yl)-5'-methoxy-2',6-dimethyl-[4,4'-bipyridine]-3-carboxamide

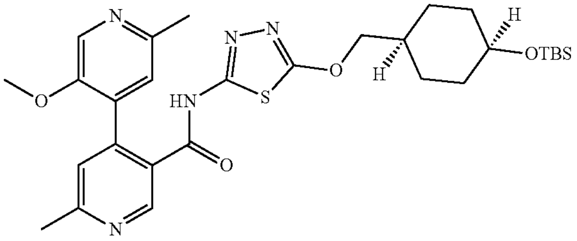 [SMILES: COc1cnc(C)cc1-c1cc(C)ncc1C(=O)Nc1nnc(OC[C@H]2CC[C@@H](O[Si](C)(C)C(C)(C)C)CC2)s1]

To a stirred mixture of 5-(((1s,4s)-4-((tert-butyldimethylsilyl)oxy)cyclohexyl)methoxy)-1,3,4-thiadiazol-2-amine (70 mg, 0.20 mmol) and 5'-methoxy-2',6-dimethyl-(4,4'-bipyridine)-3-carboxylic acid (52 mg, 0.20 mmol, Intermediate G) in ACN (0.5 mL) and DMF (0.5 mL) were added NMI (50 mg, 0.61 mmol) and TCFH (63 mg, 0.22 mmol). The resulting mixture was stirred at room temperature for 16 hours under nitrogen atmosphere. The mixture was purified by reverse phase flash chromatography with 25~80% acetonitrile in water to afford N-(5-(((1s,4s)-4-((tert-butyldimethylsilyl)oxy)cyclohexyl)methoxy)-1,3,4-thiadiazol-2-yl)-5'-methoxy-2',6-dimethyl-[4,4'-bipyridine]-3-carboxamide (80 mg, 67%) as a yellow solid. MS (ESI) calc'd for ($C_{29}H_{41}N_5O_4SSi$) $(M+1)^+$, 584.2; found 584.2.

Step-2: N-(5-(((1s,4s)-4-hydroxycyclohexyl)methoxy)-1,3,4-thiadiazol-2-yl)-5'-methoxy-2',6-dimethyl-[4,4'-bipyridine]-3-carboxamide

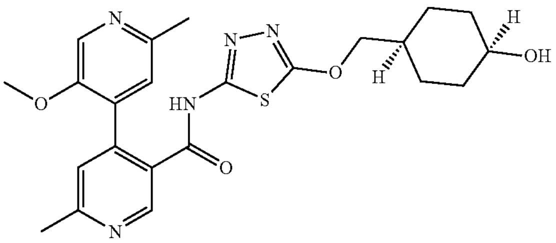

To a stirred mixture of N-(5-(((1s,4s)-4-((tert-butyldimethylsilyl)oxy)cyclohexyl)methoxy)-1,3,4-thiadiazol-2-yl)-5'-methoxy-2',6-dimethyl-[4,4'-bipyridine]-3-carboxamide (40 mg, 0.07 mmol) in DCM (0.7 mL) was added TFA (0.3 mL). The resulting mixture was stirred at room temperature for 1 hour before concentrated under vacuum. The residue was purified by reverse phase flash chromatography with 5-60% acetonitrile in water to afford N-(5-(((1s,4s)-4-hydroxycyclohexyl)methoxy)-1,3,4-thiadiazol-2-yl)-5'-methoxy-2',6-dimethyl-[4,4'-bipyridine]-3-carboxamide (7 mg, 21%) as a white solid. MS (ESI) calc'd for ($C_{23}H_{27}N_5O_4S$) $(M+1)^+$, 470.2; found 470.2. $^1$H NMR (400 MHz, DMSO-$d_6$) δ 12.99 (s, 1H), 8.85 (s, 1H), 8.33 (s, 1H), 7.61 (s, 1H), 7.42 (s, 1H), 4.26 (d, J=6.8 Hz, 2H), 3.79-3.65 (m, 2H), 3.66 (s, 3H), 2.61 (s, 6H), 1.85-1.83 (m, 1H), 1.61-1.59 (m, 2H), 1.50-1.43 (m, 6H).

Example 128

2'-chloro-N-(5-(((1s,4s)-4-hydroxycyclohexyl)methoxy)-1,3,4-thiadiazol-2-yl)-5'-methoxy-6-methyl-[4,4'-bipyridine]-3-carboxamide

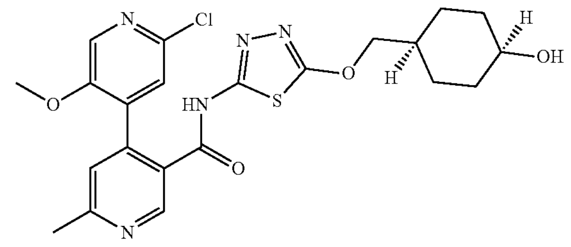 [SMILES: COc1cnc(Cl)cc1-c1cc(C)ncc1C(=O)Nc1nnc(OC[C@H]2CC[C@@H](O)CC2)s1]

Step-1: N-(5-(((1s,4s)-4-((tert-butyldimethylsilyl)oxy)cyclohexyl)methoxy)-1,3,4-thiadiazol-2-yl)-2'-chloro-5'-methoxy-6-methyl-[4,4'-bipyridine]-3-carboxamide

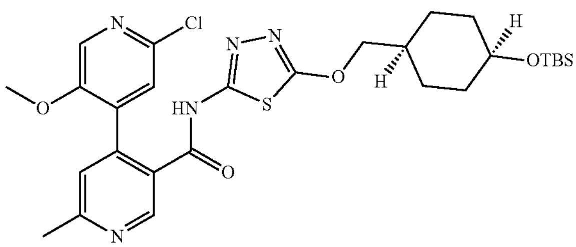 [SMILES: COc1cnc(Cl)cc1-c1cc(C)ncc1C(=O)Nc1nnc(OC[C@H]2CC[C@@H](O[Si](C)(C)C(C)(C)C)CC2)s1]

To a stirred mixture of 5-(((1s,4s)-4-((tert-butyldimethylsilyl)oxy)cyclohexyl)methoxy)-1,3,4-thiadiazol-2-amine (34 mg, 0.1 mmol) and 2'-chloro-5'-methoxy-6-methyl-(4,4'-bipyridine)-3-carboxylic acid (20 mg, 0.07 mmol, Intermediate H) in ACN (0.5 mL) and DMF (0.5 mL) were added NMI (30 mg, 0.35 mmol) and TCFH (22 mg, 0.08 mmol). The resulting mixture was stirred at room temperature for 2 hours under nitrogen atmosphere. The mixture was purified by reverse phase flash column chromatography with 25-80% acetonitrile in water to afford N-(5-(((1s,4s)-4-((tert-butyldimethylsilyl)oxy)cyclohexyl)methoxy)-1,3,4-thiadiazol-2-yl)-2'-chloro-5'-methoxy-6-methyl-[4,4'-bipyridine]-3-carboxamide (50 mg, 84%) as a yellow solid. MS (ESI) calc'd for ($C_{28}H_{38}ClN_5O_4SSi$) $(M+1)^+$, 604.2; found 604.2.

Step-2: 2'-chloro-N-(5-(((1s,4s)-4-hydroxycyclohexyl)methoxy)-1,3,4-thiadiazol-2-yl)-5'-methoxy-6-methyl-[4,4'-bipyridine]-3-carboxamide

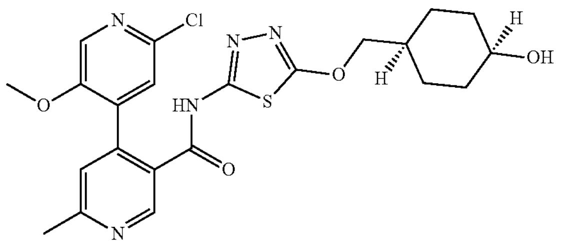 [SMILES: COc1cnc(Cl)cc1-c1cc(C)ncc1C(=O)Nc1nnc(OC[C@H]2CC[C@@H](O)CC2)s1]

To a stirred mixture of N-(5-(((1s,4s)-4-((tert-butyldimethylsilyl)oxy)cyclohexyl)methoxy)-1,3,4-thiadiazol-2-yl)-2'-chloro-5'-methoxy-6-methyl-[4,4'-bipyridine]-3-carboxamide (40 mg, 0.06 mmol) in DCM (0.6 mL) was added TFA (0.2 mL). The resulting mixture was stirred at room temperature for 1 hour before concentrated under vacuum. The residue was purified by reverse phase flash column chromatography with 5-65% acetonitrile in water to afford 2'-chloro-N-(5-(((1s,4s)-4-hydroxycyclohexyl)methoxy)-1,3,4-thiadiazol-2-yl)-5'-methoxy-6-methyl-[4,4'-bipyridine]-3-carboxamide (22.1 mg, 68%) as a white solid. MS (ESI) calc'd for ($C_{22}H_{24}ClN_5O_4S$) $(M+1)^+$, 490.1; found 490.1. $^1$H NMR (400 MHz, Methanol-$d_4$) δ 8.83 (s, 1H), 8.57 (s, 1H), 8.08 (s, 1H), 7.47 (s, 1H), 7.39 (s, 1H), 4.29 (d, J=6.8 Hz, 2H), 3.94-3.90 (m, 1H), 3.74 (s, 3H), 2.67 (s, 3H), 1.93-1.90 (m, 1H), 1.78-1.76 (m, 2H), 1.67-1.56 (m, 6H).

Example 129

2'-chloro-N-(5-(((1r,4r)-4-hydroxycyclohexyl)methoxy)-1,3,4-thiadiazol-2-yl)-5'-methoxy-6-methyl-[4,4'-bipyridine]-3-carboxamide

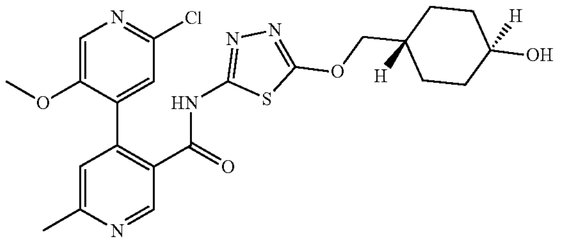 [SMILES: COc1cnc(Cl)cc1-c1cc(C)ncc1C(=O)Nc1nnc(OC[C@H]2CC[C@H](O)CC2)s1]

Step-1: N-(5-(((1r,4r)-4-((tert-butyldimethylsilyl)oxy)cyclohexyl)methoxy)-1,3,4-thiadiazol-2-yl)-2'-chloro-5'-methoxy-6-methyl-[4,4'-bipyridine]-3-carboxamide

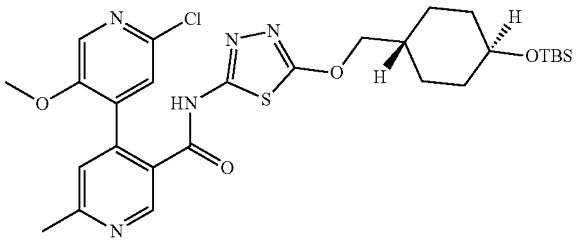 [SMILES: COc1cnc(Cl)cc1-c1cc(C)ncc1C(=O)Nc1nnc(OC[C@H]2CC[C@H](O[Si](C)(C)C(C)(C)C)CC2)s1]

To a solution of 5-(((1r,4r)-4-((tert-butyldimethylsilyl)oxy)cyclohexyl)methoxy)-1,3,4-thiadiazol-2-amine (300 mg, 0.873 mmol) in DMF (4 mL) and ACN (4 mL) were added 2'-chloro-5'-methoxy-6-methyl-(4,4'-bipyridine)-3-carboxylic acid (244 mg, 0.873 mmol), TCFH (368 mg, 1.310 mmol) and NMI (287 mg, 3.493 mmol). The resulting solution was stirred at room temperature for 2 hours. The mixture was quenched with water and extracted with ethyl acetate. The combined organic layers were washed with brine, dried over anhydrous sodium sulfate, filtered, and concentrated under vacuum. The residue was purified by flash chromatography on silica gel with 0~10% methanol in dichloromethane to afford N-(5-(((1r,4r)-4-((tert-butyldimethylsilyl)oxy)cyclohexyl)methoxy)-1,3,4-thiadiazol-2-yl)-2'-chloro-5'-methoxy-6-methyl-[4,4'-bipyridine]-3-carboxamide (200 mg, 55.4%) as a white solid. MS (ESI) calc'd for ($C_{28}H_{38}ClN_5O_4SSi$) $(M+1)^+$, 604.1; found, 604.1.

Step-2: 2'-chloro-N-(5-(((1r,4r)-4-hydroxycyclohexyl)methoxy)-1,3,4-thiadiazol-2-yl)-5'-methoxy-6-methyl-[4,4'-bipyridine]-3-carboxamide

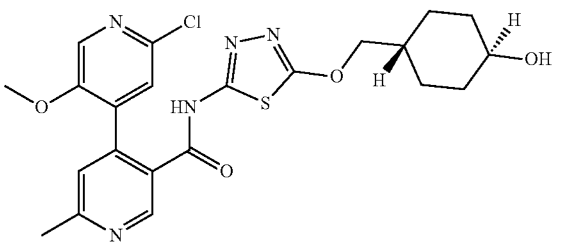 [SMILES: COc1cnc(Cl)cc1-c1cc(C)ncc1C(=O)Nc1nnc(OC[C@H]2CC[C@H](O)CC2)s1]

To a solution of N-(5-(((1r,4r)-4-((tert-butyldimethylsilyl)oxy)cyclohexyl)methoxy)-1,3,4-thiadiazol-2-yl)-2'-chloro-5'-methoxy-6-methyl-[4,4'-bipyridine]-3-carboxamide (80.00 mg, 0.132 mmol) in DCM (5 mL) was added TFA (1 mL). The resulting solution was stirred at room temperature for 2 hours before concentrated under vacuum. The resulting mixture was diluted with the saturated $NaHCO_3$ aqueous solution and extracted with ethyl acetate. The combined organic layers were washed with brine, dried over anhydrous sodium sulfate, filtered, and concentrated under vacuum. The residue was purified by flash chromatography on silica gel with 0~10% methanol in dichloromethane and further purified by the following conditions: (Column: XBridge Prep OBD C18 Column, 30×150 mm, 5 um; Mobile Phase A: Water (10 MMOL/L $NH_4HCO_3$), Mobile Phase B: ACN; Flow rate: 60 mL/min; Gradient: 20 B to 39 B in 8 min; 254/220 nm; RT1: 6.27 min) to afford 2'-chloro-N-(5-(((1r,4r)-4-hydroxycyclohexyl)methoxy)-1,3,4-thiadiazol-2-yl)-5'-methoxy-6-methyl-[4,4'-bipyridine]-3-carboxamide (6.6 mg, 9.9%) as a white solid. MS (ESI) calc'd for ($C_{22}H_{24}ClN_5O_4S$) $(M+1)^+$, 490.1; found, 490.1. $^1H$ NMR (400 MHz, DMSO-$d_6$) δ 12.88 (s, 1H), 8.82 (s, 1H), 8.16 (s, 1H), 7.56 (s, 1H), 7.38 (s, 1H), 4.52 (s, 1H), 4.21 (s, 2H), 3.87 (s, 3H), 3.36-3.33 (m, 1H), 2.51 (s, 3H), 1.86-1.55 (m, 5H), 1.41-1.15 (m, 4H).

Example 130

4-(2-fluoro-6-methoxyphenyl)-6-methyl-N-(5-((5-(oxetan-2-yl)pyridin-2-yl)methoxy)-1,3,4-thiadiazol-2-yl)nicotinamide

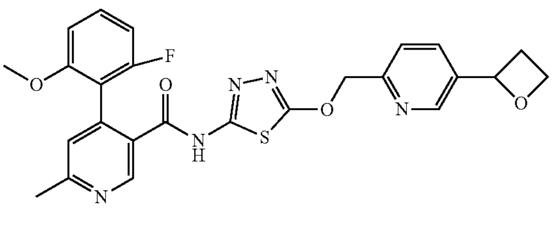 [SMILES: COc1cccc(F)c1-c1cc(C)ncc1C(=O)Nc1nnc(OCc2ccc(C3CCO3)cn2)s1]

Step-1:2-chloro-5-(oxiran-2-yl)pyridine

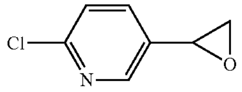

To a solution of $Me_3SOI$ (3.11 g, 0.014 mol) in DMSO (50 mL) was added NaH (508 mg, 21.167 mol, 60%) in portions at 0° C. and stirred for 15 minutes, then added 6-chloronicotinaldehyde (1 g, 0.007 mol) was added to the above mixture at 0° C. and stirred for 30 minutes. The resulting mixture was stirred at room temperature for 1 h. The reaction mixture was then quenched by the addition of water and extracted with diethyl ether. The combined organic layers were washed with brine, dried over anhydrous sodium sulfate, filtered, and concentrated under vacuum. The residue was purified by flash chromatography on silica gel with 0~10% ethyl acetate in petroleum ether to afford 2-chloro-5-(oxiran-2-yl)pyridine (420 mg, 42%) as yellow oil. MS (ESI) calc'd for ($C_7H_6ClNO$) $(M+1)^+$, 156.0, found 156.0.

Step-2: 2-chloro-5-(oxetan-2-yl)pyridine

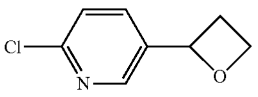 [SMILES: Clc1ccc(C2CCO2)cn1]

To a solution of $Me_3SOI$ (1.16 g, 0.005 mmol) in tBuOH (20.00 mL) were added tBuOK (590 mg, 5.268 mmol) and 2-chloro-5-(oxiran-2-yl)pyridine (410 mg, 2.645 mmol) at 0~5° C. The resulting mixture was stirred at room temperature for overnight. The reaction mixture was then quenched by the addition of water and extracted with diethyl ether. The combined organic layers were washed with brine, dried over anhydrous sodium sulfate, filtered, and concentrated under vacuum. The residue was purified by flash chromatography on silica gel with 0~10% ethyl acetate in petroleum ether to afford 2-chloro-5-(oxetan-2-yl)pyridine (300 mg, 73%) as yellow oil. MS (ESI) calc'd for ($C_8H_8ClNO$) $(M+1)^+$, 170.0, found 170.0.

Step-3: methyl 5-(oxetan-2-yl)picolinate

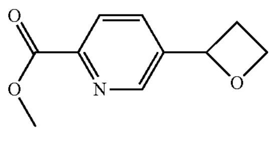

To a solution of 2-chloro-5-(oxetan-2-yl)pyridine (300 mg, 1.775 mmol) in MeOH (10 mL) were added TEA (538 mg, 5.325 mmol) and Pd(dppf)$Cl_2$ (263 mg, 0.322 mmol). The resulting solution was stirred at 70° C. for 8 hours under carbon monoxide. The mixture was concentrated under vacuum. The residue was purified by flash chromatography on silica gel with 0-50% ethyl acetate in petroleum ether to afford methyl 5-(oxetan-2-yl)picolinate (130 mg, 43.3%) as yellow oil. MS (ESI) calc'd for ($C_{10}H_{11}NO_3$) $(M+1)^+$, 194.1; found, 194.0.

Step-4: (5-(oxetan-2-yl)pyridin-2-yl)methanol

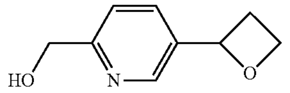 [SMILES: OCc1ccc(C2CCO2)cn1]

To a solution of methyl 5-(oxetan-2-yl)picolinate (130 mg, 0.674 mmol) in THF (2 mL) and MeOH (2 mL) was sequentially added $NaBH_4$ (26 mg, 0.684 mmol) and $CaCl_2$) (74 mg, 0.673 mmol) at 0° C. The resulting mixture was stirred at room temperature for 2 h. The reaction mixture was then quenched by the addition of water and extracted with ethyl acetate. The combined organic layers were washed with brine, dried over anhydrous sodium sulfate, filtered, and concentrated under vacuum. The residue was purified by flash chromatography on silica gel with 0~10% methanol in dichloromethane to afford (5-(oxetan-2-yl)pyridin-2-yl) methanol (72 mg, 55%) as a yellow oil. MS (ESI) calc'd for ($C_9H_{11}NO_2$) $(M+1)^+$, 166.1; found, 166.0.

Step-5: 5-((5-(oxetan-2-yl)pyridin-2-yl)methoxy)-1,3,4-thiadiazol-2-amine

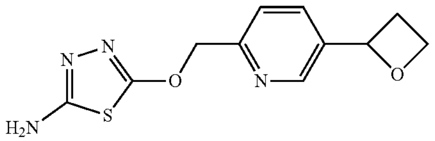

To a solution of NaH (16 mg, 0.666 mmol, 60%) in THF (3 mL) was added a solution of (5-(oxetan-2-yl)pyridin-2-yl)methanol (72 mg, 0.436 mmol) in THF (1 mL) dropwise at 0~5° C. and stirred at 5° C. for 1 h. Then 5-bromo-1,3,4-thiadiazol-2-amine (93 mg, 0.519 mmol) was added to the mixture in small portions at 5° C. and stirred at 5° C. for 5 h. The reaction mixture was then quenched by the addition of water and extracted with ethyl acetate. The combined organic layers were washed with brine, dried over anhydrous sodium sulfate, filtered, and concentrated under vacuum. The residue was purified by flash chromatography on silica gel with 0~50% ethyl acetate in petroleum ether to afford 5-((5-(oxetan-2-yl)pyridin-2-yl)methoxy)-1,3,4-thiadiazol-2-amine (38 mg, 47%) as a yellow solid. MS (ESI) calc'd for ($C_{11}H_{12}N_4O_2S$) $(M+1)^+$, 265.0; found, 265.1.

Step-6:4-(2-fluoro-6-methoxyphenyl)-6-methyl-N-(5-((5-(oxetan-2-yl)pyridin-2-yl)methoxy)-1,3,4-thiadiazol-2-yl)nicotinamide

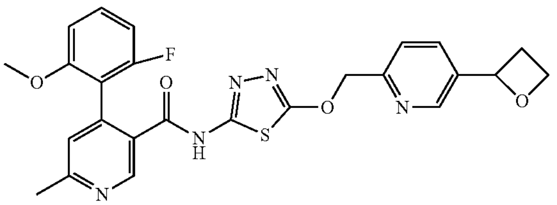 [SMILES: COc1cccc(F)c1-c1cc(C)ncc1C(=O)Nc1nnc(OCc2ccc(C3CCO3)cn2)s1]

To a solution of 4-(2-fluoro-6-methoxyphenyl)-6-methylnicotinic acid (25 mg, 0.095 mmol, Intermediate F) in ACN (2 mL) and DMF (2 mL) were added NMI (24 mg, 0.293 mmol), 5-((5-(oxetan-2-yl)pyridin-2-yl)methoxy)-1,3,4-thiadiazol-2-amine (38 mg, 0.145 mmol) and TCFH (33 mg, 0.117 mmol). The mixture was stirred at room temperature for 2 h. The mixture was purified by flash chromatography on silica gel with 0~10% methanol in dichloromethane and further purified by prep-HPLC with the following conditions: (Column: Sunfire prep C18 column, 30*150 mm, 5 um; Mobile Phase A: Water (0.1% FA), Mobile Phase B: ACN; Flow rate: 40 mL/min; Gradient: 25 B to 55 B in 8 min; 220 nm; RT1: 7.23 min) to afford 4-(2-fluoro-6-methoxyphenyl)-N-(5-((5-(2-methoxypropan-2-yl)pyridin-2-yl)methoxy)-1,3,4-thiadiazol-2-yl)-6-methylnicotinamide (18.7 mg, 12.8%) as a white solid. MS (ESI) calc'd for ($C_{25}H_{22}FN_5O_4S$) $(M+1)^+$, 508.1; found, 508.1. $^1H$ NMR (400 MHz, DMSO-$d_6$) δ 12.90 (s, 1H), 8.81 (s, 1H), 8.63 (s, 1H), 7.97-7.95 (m, 1H), 7.59-7.57 (m, 1H), 7.43-7.39 (m, 1H), 7.37-7.32 (m, 1H), 6.94-6.88 (m, 2H), 5.83-5.79 (m, 1H), 5.54 (s, 2H), 4.73-4.68 (m, 1H), 4.63-4.57 (m, 1H), 3.58 (s, 3H), 3.06-2.89 (m, 1H), 2.69-2.67 (m, 1H), 2.63 (s, 3H).

Example 131

2'-chloro-5'-methoxy-6-methyl-N-(5-((3-methyloxolan-3-yl)methoxy)-1,3,4-thiadiazol-2-yl)-(4,4'-bipyridine)-3-carboxamide

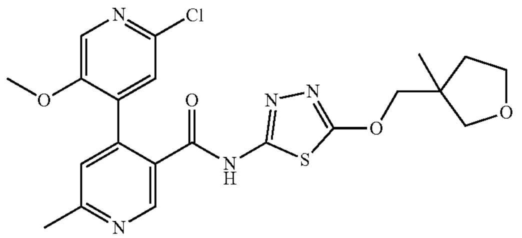 [SMILES: COc1cnc(Cl)cc1-c1cc(C)ncc1C(=O)Nc1nnc(OCC2(C)CCOC2)s1]

Step-1: ((3-methyloxolan-3-yl)methoxy)(methylsulfanyl)methanethione

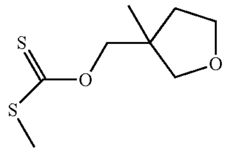

To a mixture of (3-methyloxolan-3-yl)methanol (100.0 mg, 0.86 mmol) in THF (8.0 mL) was added NaH (41.32 mg, 1.72 mmol) in portions at 0° C. and stirred at 0° C. for 30 min. To the above mixture was added $CS_2$ (380.2 mg, 4.99 mmol) dropwise at 0° C. and stirred at 0° C. for 10 min. Then MeI (183.2 mg, 1.29 mmol) was added to the above mixture dropwise at 0° C. The resulting solution was stirred at 0° C. for 30 min. The reaction mixture was quenched with water and extracted with ethyl acetate. The combined organic layers were washed with brine, dried over anhydrous sodium sulfate, filtered, and concentrated under vacuum to afford ((3-methyloxolan-3-yl)methoxy)(methylsulfanyl)

methanethione (224.0 mg, crude) as a yellow oil. MS (ESI) calc'd for ($C_8H_{14}O_2S_2$) $(M+1)^+$, 207.0, found 207.1.

Step-2: ((((3-methyloxolan-3-yl)methoxy)methanethioyl)amino)amine

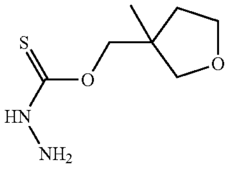

A solution of ((3-methyloxolan-3-yl)methoxy)(methylsulfanyl)methanethione (180.0 mg, 0.87 mmol) and Hydrazine (27.96 mg, 0.87 mmol) in MeOH (2.0 mL) was stirred at 25° C. for 2 h. The reaction mixture was quenched with water and extracted with ethyl acetate. The combined organic solution was dried over sodium sulfate, filtered, and concentrated under vacuum to afford ((((3-methyloxolan-3-yl)methoxy)methanethioyl)amino)amine (120.0 mg, 72%) as a yellow oil. MS (ESI) calc'd for ($C_7H_{14}N_2O_2S$) $(M+1)^+$, 191.1, found 191.1.

Step-3: 5-((3-methyloxolan-3-yl)methoxy)-1,3,4-thiadiazol-2-amine

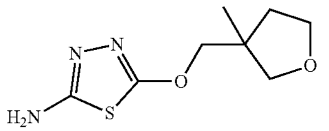

To a mixture of ((((3-methyloxolan-3-yl)methoxy)methanethioyl)amino)amine (221.0 mg, 1.16 mmol) in MeOH (8.0 mL) were added TEA (235.0 mg, 2.32 mmol) and BrCN (135.3 mg, 1.27 mmol) at 25° C. The resulting solution was stirred at 25° C. for 30 min. The reaction mixture was quenched with water and extracted with ethyl acetate. The combined organic layers were washed with brine, dried over anhydrous sodium sulfate, filtered, and concentrated under vacuum. The crude residue was purified by silica gel column chromatography, eluted with 0~100% acetate ethyl in petroleum ether to afford 5-((3-methyloxolan-3-yl)methoxy)-1,3,4-thiadiazol-2-amine (97.0 mg, 38%) as a yellow solid. MS (ESI) calc'd for ($C_8H_{13}N_3O_2S$) $(M+1)^+$, 216.1, found 216.1.

Step-4: 2'-chloro-5'-methoxy-6-methyl-N-(5-((3-methyloxolan-3-yl)methoxy)-1,3,4-thiadiazol-2-yl)-(4,4'-bipyridine)-3-carboxamide

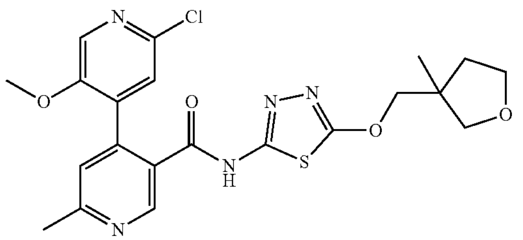 [SMILES: COc1cnc(Cl)cc1-c1cc(C)ncc1C(=O)Nc1nnc(OCC2(C)CCOC2)s1]

A mixture of 2'-chloro-5'-methoxy-6-methyl-(4,4'-bipyridine)-3-carboxylic acid (50.0 mg, 0.17 mmol, Intermediate H), 5-((3-methyloxolan-3-yl)methoxy)-1,3,4-thiadiazol-2-amine (46.3 mg, 0.21 mmol), TCFH (55.3 mg, 0.19 mmol), NMI (30.9 mg, 0.37 mmol) in MeCN (3.0 mL) and DMF (0.2 mL) was stirred at 25° C. for 2 h. The resulting mixture was concentrated under vacuum. The crude residue was purified by flash column chromatography with 5-50% acetonitrile in water and further purified by Prep-HPLC with the following conditions: (Column: XBridge Shield RP18 OBD Column, 30*150 mm, 5 um; Mobile Phase A: Water (10 mmol/L $NH_4HCO_3$), Mobile Phase B: ACN; Flow rate: 60 mL/min; Gradient: 20 B to 40 B in 8 min; 254 nm; RT1:7.5 min) to afford 2-chloro-5-methoxy-6-methyl-N-(5-((3-methyloxolan-3-yl)methoxy)-1,3,4-thiadiazol-2-yl)-(4,4-bipyridine)-3-carboxamide (8.8 mg, 98%) as a white solid. MS (ESI) calc'd for ($C_{21}H_{22}ClN_5O_4S$) $(M+1)^+$, 476.1, found 476.2. $^1H$ NMR (400 MHz, DMSO-$d_6$) δ 8.84 (s, 1H), 8.16 (s, 1H), 7.49 (d, J=3.6 Hz, 1H), 7.36 (d, J=4.4 Hz, 1H), 4.27 (s, 2H), 3.85-3.71 (m, 2H), 3.68-3.61 (m, 4H), 3.36-3.34 (m, 1H), 2.57 (s, 3H), 1.94-1.81 (m, 1H), 1.70-1.60 (m, 1H), 1.16 (s, 3H).

Example 132

4-(2-fluoro-6-methoxyphenyl)-N-(5-((3-(hydroxymethyl)bicyclo(1.1.1)pentan-1-yl)methoxy)-1,3,4-thiadiazol-2-yl)-6-methylpyridine-3-carboxamide

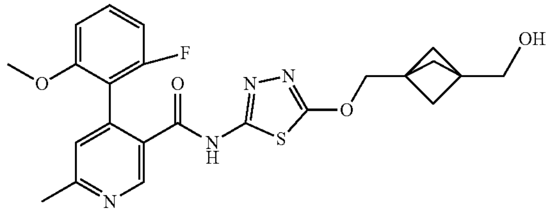 [SMILES: COc1cccc(F)c1-c1cc(C)ncc1C(=O)Nc1nnc(OCC23CC(CO)(C2)C3)s1]

Step-1: methyl 3-(((5-(4-(2-fluoro-6-methoxyphenyl)-6-methylpyridine-3-amido)-1,3,4-thiadiazol-2-yl)oxy)methyl)bicyclo(1.1.1)pentane-1-carboxylate

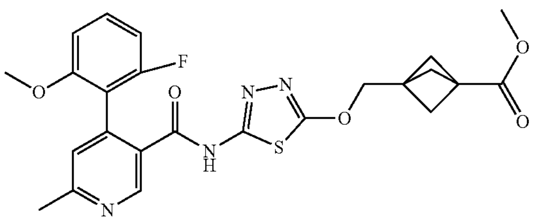 [SMILES: COC(=O)C12CC(COc3nnc(NC(=O)c4cnc(C)cc4-c4c(F)cccc4OC)s3)(C1)C2]

To a mixture of 4-(2-fluoro-6-methoxyphenyl)-6-methylpyridine-3-carboxylic acid (110.0 mg, 0.42 mmol, Intermediate F) in MeCN (2.0 mL) and DMF (0.5 mL) were added methyl 3-(((5-amino-1,3,4-thiadiazol-2-yl)oxy)methyl)bicyclo(1.1.1)pentane-1-carboxylate (128.9 mg, 0.50 mmol, Example 103, Step 4), TCFH (129.9 mg, 0.46 mmol) and NMI (72.6 mg, 0.88 mmol). The resulting solution was stirred at room temperature for 2 h. The resulting solution was purified by reverse phase flash column chromatography with 5-50% acetonitrile in water to afford methyl 3-(((5-(4-(2-fluoro-6-methoxyphenyl)-6-methylpyridine-3-amido)-1,3,4-thiadiazol-2-yl)oxy)methyl) bicyclo(1.1.1)pentane-1-carboxylate (200.0 mg, 90%) as a white solid. MS (ESI) calc'd for ($C_{24}H_{23}FN_4O_5S$) $(M+1)^+$, 499.1, found 499.2.

Step-2: 4-(2-fluoro-6-methoxyphenyl)-N-(5-((3-(hydroxymethyl)bicyclo(1.1.1)pentan-1-yl) methoxy)-1,3,4-thiadiazol-2-yl)-6-methylpyridine-3-carboxamide

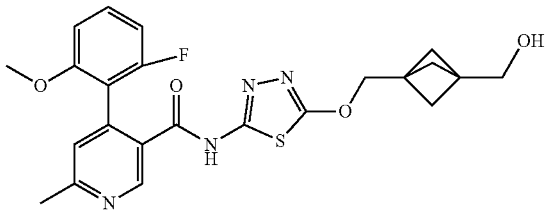 [SMILES: COc1cccc(F)c1-c1cc(C)ncc1C(=O)Nc1nnc(OCC23CC(CO)(C2)C3)s1]

To a solution of methyl 3-(((5-(4-(2-fluoro-6-methoxyphenyl)-6-methylpyridine-3-amido)-1,3,4-thiadiazol-2-yl) oxy)methyl)bicyclo(1.1.1)pentane-1-carboxylate (80.0 mg, 0.16 mmol) in THF (5.0 mL) was added LAH (6.0 mg, 0.16 mmol) dropwise at 0° C. under nitrogen. The resulting solution was stirred at 0° C. for 2 h. The reaction mixture was quenched with water and extracted with ethyl acetate. The combined organic layers were washed with brine, dried over anhydrous sodium sulfate, filtered, and concentrated under vacuum. The resulting mixture was purified by reverse phase flash column chromatography with 5-40% acetonitrile in water to afford 4-(2-fluoro-6-methoxyphenyl)-N-(5-((3-(hydroxymethyl)bicyclo(1.1.1)pentan-1-yl)methoxy)-1,3,4-thiadiazol-2-yl)-6-methylpyridine-3-carboxamide (52.0 mg, 65%) as a white solid. MS (ESI) calc'd for ($C_{23}H_{23}FN_4O_4S$) $(M+1)^+$, 471.1, found 471.2. $^1H$ NMR (400 MHz, DMSO-$d_6$) δ 12.83 (s, 1H), 8.81 (s, 1H), 7.50-7.34 (m, 1H), 7.32 (d, J=1.6 Hz, 1H), 7.00-6.75 (m, 2H), 4.55-4.35 (m, 3H), 3.58 (s, 3H), 3.37 (d, J=5.6 Hz, 2H), 2.57 (s, 3H), 1.62 (s, 6H).

Example 133

4-(5-chloro-2-methoxyphenyl)-N-(5-((5-(hydroxymethyl)pyrazin-2-yl)methoxy)-1,3,4-thiadiazol-2-yl)-6-methylpyridine-3-carboxamide

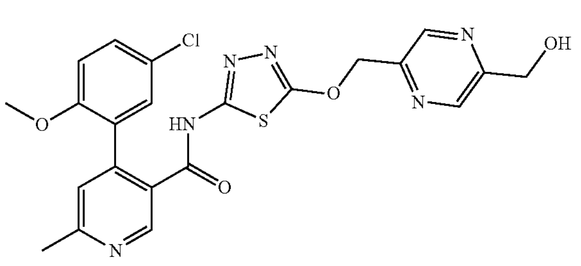 [SMILES: COc1ccc(Cl)cc1-c1cc(C)ncc1C(=O)Nc1nnc(OCc2cnc(CO)cn2)s1]

Step-1: tert-butyl N-(5-((5-ethenylpyrazin-2-yl) methoxy)-1,3,4-thiadiazol-2-yl)carbamate

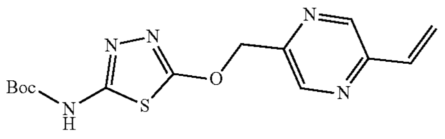 [SMILES: C=Cc1cnc(COc2nnc(NC(=O)OC(C)(C)C)s2)cn1]

To a stirred solution of 5-((5-ethenylpyrazin-2-yl) methoxy)-1,3,4-thiadiazol-2-amine (2.7 g, 11.47 mmol) and $Boc_2O$ (2.7 g, 12.62 mmol) in DCM (30 mL) was added DMAP (0.14 g, 1.14 mmol). The resulting mixture was stirred at room temperature for 16 h. The reaction mixture was quenched with water and extracted with ethyl acetate. The combined organic layers were washed with brine, dried over anhydrous sodium sulfate, filtered, and concentrated under vacuum. The residue was purified by reverse flash chromatography with the following conditions: (column, C18 silica gel; mobile phase, acetonitrile in water, 5% to 26%) to afford tert-butyl N-(5-((5-ethenylpyrazin-2-yl) methoxy)-1,3,4-thiadiazol-2-yl)carbamate (2.2 g, 57%) as a white solid. MS (ESI) calc'd for ($C_9H_9N_5OS$) $(M+1)^+$, 336.1; found 336.0.

Step-2: tert-butyl N-(5-((5-formylpyrazin-2-yl) methoxy)-1,3,4-thiadiazol-2-yl)carbamate

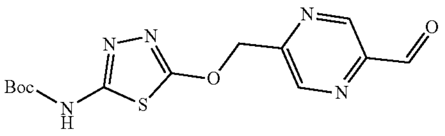 [SMILES: CC(C)(C)OC(=O)Nc1nnc(OCc2cnc(C=O)cn2)s1]

To a stirred solution of tert-butyl N-(5-((5-ethenylpyrazin-2-yl)methoxy)-1,3,4-thiadiazol-2-yl)carbamate (2.2 g, 6.56 mmol) in THF (30 mL) was added $NaIO_4$ (5.6 g, 7.22 mmol) in water (30 mL) dropwise at ° C. under nitrogen atmosphere and stirred for 30 min. $OsO_4$ (1.7 g, 6.68 mmol) was added to the above mixture. The mixture resulting mixture was stirred at room temperature for 1 h. The reaction mixture was quenched with water and extracted with ethyl acetate. The combined organic layers were washed with brine, dried over anhydrous sodium sulfate, filtered, and concentrated under vacuum to afford tert-butyl N-(5-((5-formylpyrazin-2-yl)methoxy)-1,3,4-thiadiazol-2-yl)carbamate (2.1 g, crude) as a yellow solid. MS (ESI) calc'd for ($C_{14}H_{17}N_5O_3S$) $(M+1)^+$, 338.1; found, 338.0.

Step-3: tert-butyl N-(5-((5-(hydroxymethyl)pyrazin-2-yl)methoxy)-1,3,4-thiadiazol-2-yl)carbamate

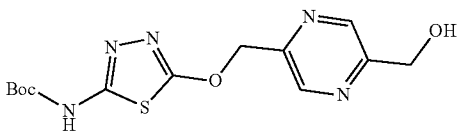 [SMILES: CC(C)(C)OC(=O)Nc1nnc(OCc2cnc(CO)cn2)s1]

To a stirred solution of tert-butyl N-(5-((5-formylpyrazin-2-yl)methoxy)-1,3,4-thiadiazol-2-yl)carbamate (2.1 g, 6.22 mmol) in MeOH (1 mL) was added $NaBH_4$ (0.5 g, 12.44 mmol) in portions at 0° C. The resulting mixture was stirred at 0° C. for 1 h. The reaction mixture was quenched with water and extracted with ethyl acetate. The combined organic layers were washed with brine, dried over anhydrous sodium sulfate, filtered, and concentrated under vacuum. The residue was purified by silica gel column chromatography, eluted with 0~100% ethyl acetate in petroleum ether to afford tert-butyl N-(5-((5-(hydroxymethyl)pyrazin-2-yl)methoxy)-1,3,4-thiadiazol-2-yl)carbamate (1.4 g, 66%) as a brown solid. MS (ESI) calc'd for ($C_{13}H_{15}N_5O_4S$) $(M+1)^+$, 340.0; found, 340.0.

Step-4: (5-(((5-amino-1,3,4-thiadiazol-2-yl)oxy)methyl)pyrazin-2-yl)methanol

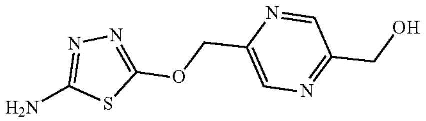

To a stirred solution of tert-butyl N-(5-((5-(hydroxymethyl)pyrazin-2-yl)methoxy)-1,3,4-thiadiazol-2-yl)carbamate (1.4 g, 4.12 mmol) in DCM (12 mL) was added TFA (4 mL, 53.85 mmol) dropwise at room temperature. The mixture resulting was stirred at room temperature for 2 h before concentrated under vacuum. The residue was purified by reverse phase flash chromatography with the following conditions: (column, C18 silica gel; mobile phase, acetonitrile in water, 5% to 35% gradient in 30 min; detector, UV 254 nm) to afford (5-(((5-amino-1,3,4-thiadiazol-2-yl)oxy)methyl)pyrazin-2-yl)methanol (300 mg, 30%) as a yellow solid. MS (ESI) calc'd for ($C_{13}H_{17}N_5O_4S$) $(M+1)^+$, 240.0; found, 240.0.

Step-5: 4-(5-chloro-2-methoxyphenyl)-N-(5-((5-(hydroxymethyl)pyrazin-2-yl)methoxy)-1,3,4-thiadiazol-2-yl)-6-methylpyridine-3-carboxamide

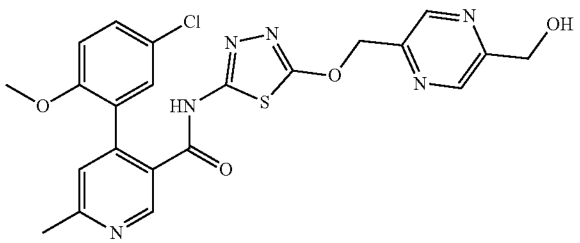 [SMILES: COc1ccc(Cl)cc1-c1cc(C)ncc1C(=O)Nc1nnc(OCc2cnc(CO)cn2)s1]

To a stirred solution of (5-(((5-amino-1,3,4-thiadiazol-2-yl)oxy)methyl)pyrazin-2-yl)methanol (50 mg, 0.21 mmol) and 4-(5-chloro-2-methoxyphenyl)-6-methylpyridine-3-carboxylic acid (58 mg, 0.21 mmol, Example 39, Step 2) in DMF (1 mL) and MeCN (1 mL) were added NMI (68 mg, 0.87 mmol) and TCFH (88 mg, 0.33 mmol). The resulting mixture was stirred at room temperature for 1 h. The mixture was purified by prep-HPLC with the following conditions: (Column: XBridge Prep OBD C18 Column, 30×150 mm 5 um; Mobile Phase A: Water (10 MMOL/L $NH_4HCO_3$), Mobile Phase B: ACN; Flow rate: 60 mL/min; Gradient: 20 B to 40 B in 8 min; 254/220 nm) to afford 4-(5-chloro-2-methoxyphenyl)-N-(5-((5-(hydroxymethyl)pyrazin-2-yl)methoxy)-1,3,4-thiadiazol-2-yl)-6-methylpyridine-3-carboxamide (26.1 mg, 25%) as a white solid. MS (ESI) calc'd for ($C_{22}H_{19}ClN_6O_4S$) $(M+1)^+$, 499.1; found 499.1. $^1$H NMR (400 MHz, DMSO-$d_6$) δ 12.80 (s, 1H), 8.74-8.70 (m, 3H), 7.44-7.34 (m, 3H), 7.01 (d, J=8.8 Hz, 1H), 5.63 (s, 1H), 5.62 (s, 2H), 4.66 (d, J=5.6 Hz, 2H), 3.50 (s, 3H), 2.57 (s, 3H).

Example 134

N-(5-((5-(hydroxymethyl)pyrazin-2-yl)methoxy)-1,3,4-thiadiazol-2-yl)-4-(2-methoxy-5-methylphenyl)-6-methylpyridine-3-carboxamide

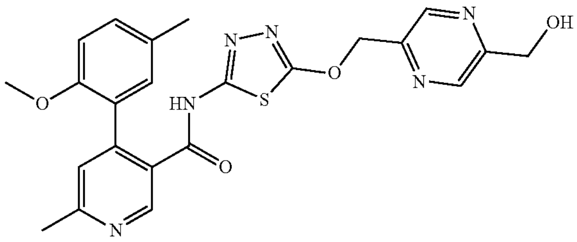 [SMILES: COc1ccc(C)cc1-c1cc(C)ncc1C(=O)Nc1nnc(OCc2cnc(CO)cn2)s1]

To a stirred solution of (5-(((5-amino-1,3,4-thiadiazol-2-yl)oxy)methyl)pyrazin-2-yl)methanol (50 mg, 0.21 mmol, Example 133, Step 4) and 4-(2-methoxy-5-methylphenyl)-6-methylpyridine-3-carboxylic acid (54 mg, 0.21 mmol, Example 44, Step 2) in DMF (1 mL) and MeCN (1 mL) were added NMI (69 mg, 0.84 mmol) and TCFH (88 mg, 0.31 mmol). The resulting mixture was stirred at room temperature for 1 h. The mixture was purified by prep-HPLC with the following conditions: (Column: XBridge Prep OBD C18 Column, 30×150 mm 5 um; Mobile Phase A: Water (10 MMOL/L $NH_4HCO_3$), Mobile Phase B:ACN; Flow rate: 60 mL/min; Gradient: 24 B to 36 B in 8 min; 254/220 nm; RT1: 7.98 min) to afford N-(5-((5-(hydroxymethyl)pyrazin-2-yl)methoxy)-1,3,4-thiadiazol-2-yl)-4-(2-methoxy-5-methylphenyl)-6-methylpyridine-3-carboxamide (47.0 mg, 46%) as a white solid. MS (ESI) calc'd for ($C_{23}H_{22}N_6O_4S$) $(M+1)^+$, 479.1; found 479.1. $^1$H NMR (400 MHz, DMSO-$d_6$) δ 12.71 (s, 1H), 8.73-8.64 (m, 3H), 7.37-7.16 (m, 3H), 6.86 (d, J=8.4 Hz, 1H), 5.63 (t, J=5.6 Hz, 1H), 5.60 (s, 2H), 4.66 (d, J=5.6 Hz, 2H), 3.46 (s, 3H), 2.56 (s, 3H), 2.30 (s, 3H).

Example 135

4-(2-fluoro-6-methoxyphenyl)-6-methyl-N-(5-(4H,5H,6H,7H-pyrazolo(1,5-a)pyridin-4-ylmethoxy)-1,3,4-thiadiazol-2-yl)pyridine-3-carboxamide

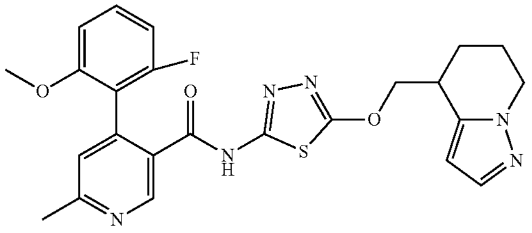 [SMILES: COc1cccc(F)c1-c1cc(C)ncc1C(=O)Nc1nnc(OCC2CCCn3nccc32)s1]

Step-1: 4H,5H,6H,7H-pyrazolo(1,5-a)pyridin-4-ylmethanol

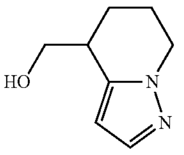 [SMILES: OCC1CCCn2nccc21]

To a mixture of 4H,5H,6H,7H-pyrazolo(1,5-a)pyridine-4-carboxylic acid (300.0 mg, 1.80 mmol) and NMM (182.6 mg, 1.80 mmol) in THF (20.0 mL) was added 2-methylpropyl carbonochloridate (246.5 mg, 1.80 mmol) at 0° C. and stirred at 0° C. for 2 h. To the above mixture was added sequentially $NaBH_4$ (204.9 mg, 5.41 mmol) in portions and MeOH (40.0 mL) at 0° C. The resulting solution was stirred at 0° C. for 2 h. The reaction was monitored by TLC. The reaction was quenched by the addition of $NH_4Cl$ aqueous solution at 0° C. The aqueous solution was extracted with ethyl acetate. The combined organic layers were washed with brine, dried over anhydrous sodium sulfate, filtered, and concentrated under vacuum to afford 4H,5H,6H,7H-pyrazolo(1,5-a)pyridin-4-ylmethanol (170.0 mg, 61%) as a yellow oil.

Step-2: (methylsulfanyl)((4H,5H,6H,7H-pyrazolo(1,5-a)pyridin-4-ylmethoxy))methanethione

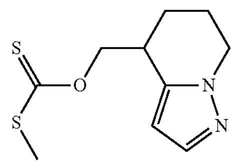

To a mixture of 4H,5H,6H,7H-pyrazolo(1,5-a)pyridin-4-ylmethanol (150.0 mg, 0.98 mmol) in THF (5.0 mL) was added NaH (47.30 mg, 1.97 mmol, 60%) in portions at 0° C. and stirred at 0° C. for 30 min. To the above mixture was added $CS_2$ (112.5 mg, 1.47 mmol) at 0° C. and stirred at 0° C. for 10 min. The MeI (209.8 mg, 1.47 mmol) was added to the above mixture dropwise at 0° C. the resulting solution was stirred at 0° C. for 30 min. The reaction was monitored by TLC The reaction was quenched by the addition of water and extracted with ethyl acetate. The combined organic solution was dried over sodium sulfate, filtered, and concentrated under vacuum to afford (methylsulfanyl)((4H,5H,6H,7H-pyrazolo(1,5-a)pyridin-4-ylmethoxy))methanethione (140.0 mg, 58%) as a yellow oil.

Step-3: (((4H,5H,6H,7H-pyrazolo(1,5-a)pyridin-4-ylmethoxy)methanethioyl)amino)amine

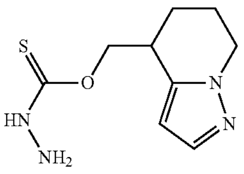

A mixture of (methylsulfanyl)((4H,5H,6H,7H-pyrazolo(1,5-a)pyridin-4-ylmethoxy))methanethione (140.0 mg, 0.57 mmol) and Hydrazine (27.77 mg, 0.86 mmol, 80%) in MeOH (3.0 mL) was stirred at room temperature for 2 h. The reaction mixture was quenched with water and extracted with ethyl acetate. The combined organic solution was dried over sodium sulfate, filtered, and concentrated under vacuum to afford (((4H,5H,6H,7H-pyrazolo(1,5-a)pyridin-4-ylmethoxy)methanethioyl)amino)amine (130.0 mg, 99%) as a yellow oil. MS (ESI) calc'd for ($C_9H_{14}N_4OS$) $(M+1)^+$, 227.1, found 227.1.

Step-4:5-(4H,5H,6H,7H-pyrazolo(1,5-a)pyridin-4-ylmethoxy)-1,3,4-thiadiazol-2-amine

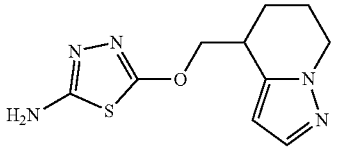 [SMILES: Nc1nnc(OCC2CCCn3nccc32)s1]

To a mixture of (((4H,5H,6H,7H-pyrazolo(1,5-a)pyridin-4-ylmethoxy)methanethioyl)amino)amine (140.0 mg, 0.61 mmol) in MeOH (5.0 mL) were added TEA (125.2 mg, 1.23 mmol) and BrCN (72.08 mg, 0.68 mmol). The resulting solution was stirred at room temperature for 30 min. The reaction mixture was diluted with water and extracted with ethyl acetate. The aqueous layer was extracted with ethyl acetate. The combined organic solution was dried over sodium sulfate, filtered, and concentrated under vacuum to afford 5-(4H,5H,6H,7H-pyrazolo(1,5-a)pyridin-4-ylmethoxy)-1,3,4-thiadiazol-2-amine (160.0 mg, crude) as a red oil. MS (ESI) calc'd for ($C_{10}H_{13}N_5OS$) $(M+1)^+$, 252.1, found 252.0.

Step-5:4-(2-fluoro-6-methoxyphenyl)-6-methyl-N-(5-(4H,5H,6H,7H-pyrazolo(1,5-a)pyridin-4-ylmethoxy)-1,3,4-thiadiazol-2-pyridine-3-carboxamide

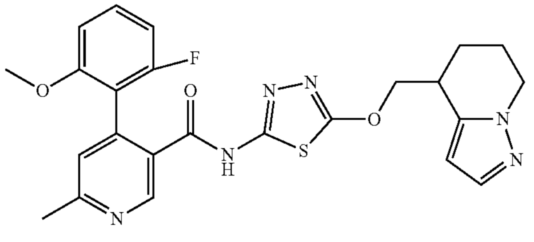 [SMILES: COc1cccc(F)c1-c1cc(C)ncc1C(=O)Nc1nnc(OCC2CCCn3nccc32)s1]

To a mixture of 4-(2-fluoro-6-methoxyphenyl)-6-methylpyridine-3-carboxylic acid (60.00 mg, 0.23 mmol, Intermediate F) in MeCN (2.0 mL) and DMF (0.1 mL) were added 5-(4H,5H,6H,7H-pyrazolo(1,5-a)pyridin-4-ylmethoxy)-1,3,4-thiadiazol-2-amine (69.26 mg, 0.27 mmol), TCFH (70.88 mg, 0.25 mmol) and NMI (39.60 mg, 0.48 mmol). The resulting solution was stirred at room temperature for 2 h. The resulting mixture was concentrated under vacuum. The crude residue was purified by reverse phase flash column chromatography with 5-56% acetonitrile in water to afford 4-(2-fluoro-6-methoxyphenyl)-6-methyl-N-(5-(4H,5H,6H,7H-pyrazolo(1,5-a)pyridin-4-ylmethoxy)-1,3,4-thiadiazol-2yl)pyridine-3-carboxamide (18.9 mg, 16%)

as a white solid. MS (ESI) calc'd for ($C_{24}H_{23}FN_6O_3S$) $(M+1)^+$, 495.1, found 495.1. $^1H$ NMR (400 MHz, DMSO-$d_6$) δ 12.89 (s, 1H), 8.82 (s, 1H), 7.46-7.21 (m, 3H), 6.91 (m, 2H), 6.20 (s, 1H), 4.56 (m, 2H), 4.21-3.90 (m, 2H), 3.59 (s, 3H), 3.40 (d, J=7.0 Hz, 1H), 2.57 (s, 3H), 2.16-2.01 (m, 2H), 1.99-1.85 (m, 1H), 1.71-1.60 (m, 1H).

Example 136

2'-chloro-N-(5-((4-hydroxybicyclo(2.2.2)octan-1-yl) methoxy)-1,3,4-thiadiazol-2-yl)-5'-methoxy-6-methyl-(4,4'-bipyridine)-3-carboxamide

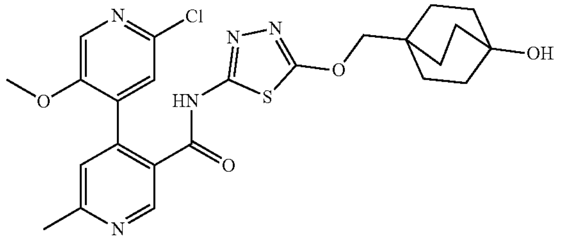 [SMILES: COc1cnc(Cl)cc1-c1cc(C)ncc1C(=O)Nc1nnc(OCC23CCC(O)(CC2)CC3)s1]

Step-1: N-(5-((4-((tert-butyldimethylsilyl)oxy)bicyclo(2.2.2)octan-1-yl)methoxy)-1,3,4-thiadiazol-2-yl)-2'-chloro-5'-methoxy-6-methyl-(4,4'-bipyridine)-3-carboxamide

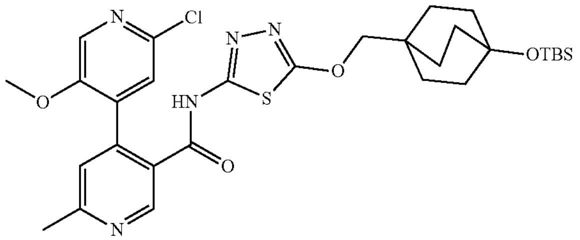 [SMILES: COc1cnc(Cl)cc1-c1cc(C)ncc1C(=O)Nc1nnc(OCC23CCC(O[Si](C)(C)C(C)(C)C)(CC2)CC3)s1]

To a mixture of 2'-chloro-5'-methoxy-6-methyl-(4,4'-bipyridine)-3-carboxylic acid (90.0 mg, 0.32 mmol) in MeCN (2.0 mL) and DMF (0.5 mL) were added 5-((4-((tert-butyldimethylsilyl)oxy)bicyclo(2.2.2)octan-1-yl)methoxy)-1,3,4-thiadiazol-2-amine (143.2 mg, 0.38 mmol), TCFH (99.6 mg, 0.35 mmol) and NMI (55.6 mg, 0.68 mmol). The resulting solution was stirred at room temperature for 2 h. The resulting solution was purified by reverse phase flash column chromatography with 5-50% acetonitrile in water to afford N-(5-((4-((tert-butyldimethylsilyl)oxy)bicyclo(2.2.2)octan-1-yl)methoxy)-1,3,4-thiadiazol-2-yl)-2'-chloro-5'-methoxy-6-methyl-(4,4'-bipyridine)-3-carboxamide (60.0 mg, 23%) as a white solid. MS (ESI) calc'd for ($C_{30}H_{40}ClN_5O_4SSi$) $(M+1)^+$, 630.2, found 630.2.

Step-2: 2'-chloro-N-(5-((4-hydroxybicyclo(2.2.2)octan-1-yl)methoxy)-1,3,4-thiadiazol-2-yl)-5'-methoxy-6-methyl-(4,4'-bipyridine)-3-carboxamide

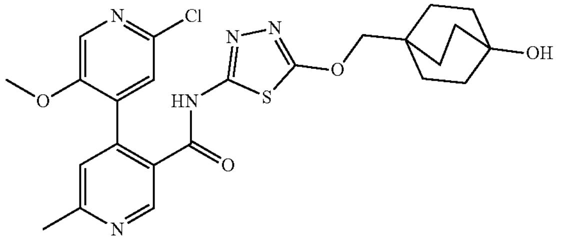 [SMILES: COc1cnc(Cl)cc1-c1cc(C)ncc1C(=O)Nc1nnc(OCC23CCC(O)(CC2)CC3)s1]

To a mixture of N-(5-((4-((tert-butyldimethylsilyl)oxy)bicyclo(2.2.2)octan-1-yl)methoxy)-1,3,4-thiadiazol-2-yl)-2-chloro-5-methoxy-6-methyl-(4,4-bipyridine)-3-carboxamide (60.0 mg, 0.09 mmol) in DCM (2.0 mL) was added TFA (0.4 mL). The resulting mixture was stirred at room temperature for 2 h before concentrated under vacuum. The residue was purified by reverse phase flash column chromatography with 5~49% acetonitrile in water to afford 2-chloro-N-(5-((4-hydroxybicyclo(2.2.2)octan-1-yl) methoxy)-1,3,4-thiadiazol-2-yl)-5-methoxy-6-methyl-(4,4-bipyridine)-3-carboxamide (13.6 mg, 27%) as a white solid. MS (ESI) calc'd for ($C_{24}H_{26}ClN_5O_4S$) $(M+1)^+$, 516.1, found 516.1. $^1H$ NMR (400 MHz, DMSO-$d_6$) δ 12.90 (s, 1H), 8.80 (s, 1H), 8.17 (s, 1H), 7.56 (s, 1H), 7.44 (s, 1H), 4.31 (s, 1H), 4.06 (s, 2H), 3.63 (s, 3H), 2.59 (s, 3H), 1.54 (s, 12H).

Example 137

2'-chloro-5'-methoxy-N-(5-(((1r,4r)-4-methoxycyclohexyl)methoxy)-1,3,4-thiadiazol-2-yl)-6-methyl-[4,4'-bipyridine]-3-carboxamide

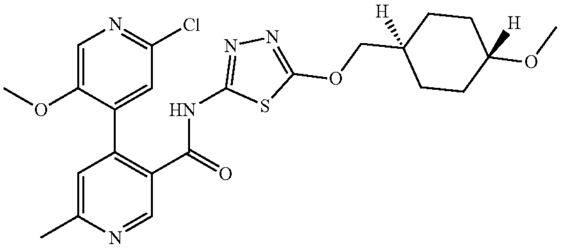

Step-1: (1r,4r)-methyl 4-methoxycyclohexanecarboxylate

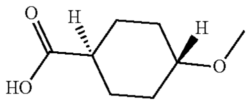

To a mixture of methyl (1r,4r)-4-hydroxycyclohexane-1-carboxylate (3.00 g, 18.96 mmol) in THF (20.0 mL) was added NaH (910.0 mg, 37.92 mmol, 60%) at 0° C. and stirred at 0° C. for 30 min. To the above mixture was added MeI (3.50 g, 24.65 mmol). The resulting solution was stirred at 0° C. for 3 h. The reaction mixture was quenched with water and extracted with ethyl acetate. The combined organic layers were washed with brine, dried over anhydrous sodium sulfate, filtered, and concentrated under vacuum. The crude residue was purified by silica gel column chromatography, eluted with 0~60% acetate ethyl in petroleum ether to afford (1r,4r)-methyl 4-methoxycyclohexanecarboxylate (2.00 g, 61%) as a yellow oil.

Step-2: ((1r,4r)-4-methoxycyclohexyl)methanol

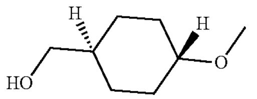

To a solution of (1r,4r)-4-methoxycyclohexane-1-carboxylic acid (1.50 g, 9.48 mmol) in THF (10.0 mL) was added $BH_3$-$Me_2S$ (2.16 g, 28.43 mmol) at 0° C. The resulting solution was stirred at 25° C. for 1 h. The reaction mixture was quenched with methanol and then removed the solvents under vacuum. The crude residue was purified by silica gel column chromatography, eluted with 10~80% acetate ethyl in petroleum ether to afford ((1r,4r)-4-methoxycyclohexyl) methanol (700.0 mg, 41%) as a yellow oil.

Step-3: (methylsulfanyl)((((1r,4r)-4-methoxycyclohexyl)methoxy))methanethione

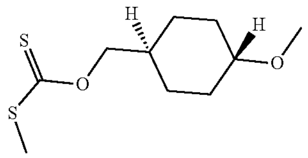

To a mixture of ((1r,4r)-4-methoxycyclohexyl)methanol (400.0 mg, 2.77 mmol) in THF (40.0 mL) was added NaH (133.1 mg, 5.54 mmol, 60%) at 0° C. and stirred at 0° C. for 30 min. To the above mixture was added $CS_2$ (316.7 mg, 4.16 mmol) at 0° C. and stirred at 0° C. for 10 min. Then MeI (590.5 mg, 4.16 mmol) was added to the above mixture at 0° C. The resulting solution was stirred at 0° C. for 30 min. The reaction mixture was quenched with water and extracted with ethyl acetate. The combined organic layers were washed with brine, dried over anhydrous sodium sulfate, filtered, and concentrated under vacuum to afford (methylsulfanyl)((((1r,4r)-4-methoxycyclohexyl)methoxy))methanethione (400.0 mg, crude) as a yellow oil, which was used in the next step without further purification.

Step-4: (((((1r,4r)-4-methoxycyclohexyl)methoxy) methanethioyl)amino)amine

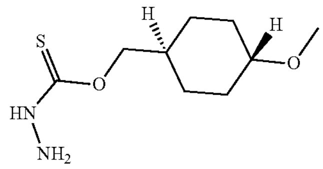

A mixture of (methylsulfanyl)((((1r,4r)-4-methoxycyclohexyl)methoxy))methanethione (400.0 mg, 1.70 mmol) and Hydrazine (54.69 mg, 1.70 mmol) in MeOH (20.0 mL) was stirred at 25° C. for 2 h. The reaction mixture was quenched with water and extracted with ethyl acetate. The combined organic solution was dried over sodium sulfate, filtered, and concentrated under vacuum to afford (((((1r,4r)-4-methoxycyclohexyl)methoxy)methanethioyl)amino)amine (380.0 mg, crude) as a yellow oil. MS (ESI) calc'd for ($C_9H_{18}N_2O_2S$) $(M+1)^+$, 219.1, found 219.1.

Step-5: 5-(((1r,4r)-4-methoxycyclohexyl)methoxy)-1,3,4-thiadiazol-2-amine

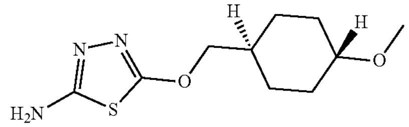 [SMILES: CO[C@H]1CC[C@H](COc2nnc(N)s2)CC1]

To a mixture of (((((1r,4r)-4-methoxycyclohexyl) methoxy)methanethioyl)amino)amine (300.0 mg, 1.37 mmol) in MeOH (10.0 mL) were added TEA (278.0 mg, 2.75 mmol) and BrCN (160.1 mg, 1.51 mmol) at 25° C. The resulting solution was stirred at 25° C. for 30 min. The reaction mixture was diluted with water and extracted with ethyl acetate. The combined organic layers were washed with brine, dried over anhydrous sodium sulfate, filtered, and concentrated under vacuum to afford the crude. The crude was purified by silica gel column chromatography, eluted with 0%-80% acetate ethyl in petroleum ether to afford 5-(((1r,4r)-4-methoxycyclohexyl)methoxy)-1,3,4-thiadiazol-2-amine (100.0 mg, 15% over three steps) as a white solid. MS (ESI) calc'd for ($C_{10}H_{17}N_3O_2S$) $(M+1)^+$, 244.1, found 244.0.

Step-6: 2'-chloro-5'-methoxy-N-(5-(((1r,4r)-4-methoxycyclohexyl)methoxy)-1,3,4-thiadiazol-2-yl)-6-methyl-[4,4'-bipyridine]-3-carboxamide

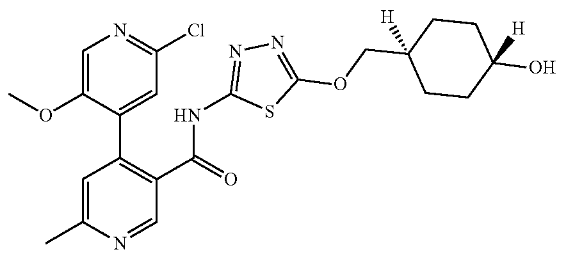 [SMILES: COc1cnc(Cl)cc1-c1cc(C)ncc1C(=O)Nc1nnc(OC[C@H]2CC[C@H](O)CC2)s1]

To a mixture of 2'-chloro-5'-methoxy-6-methyl-(4,4'-bipyridine)-3-carboxylic acid (100.0 mg, 0.35 mmol, Intermediate H) in MeCN (3.0 mL) and DMF (3.0 mL) were added TCFH (110.7 mg, 0.39 mmol), NMI (88.38 mg, 1.07 mmol) and 5-(((1r,4r)-4-methoxycyclohexyl)methoxy)-1,3,4-thiadiazol-2-amine (104.7 mg, 0.43 mmol). The resulting solution was stirred at 25° C. for 2 h before concentrated under vacuum. The crude residue was purified by reverse phase flash column chromatography with 5-55% acetonitrile in water to afford 2'-chloro-5'-methoxy-N-(5-(((1r,4r)-4-methoxycyclohexyl)methoxy)-1,3,4-thiadiazol-2-yl)-6-methyl-[4,4'-bipyridine]-3-carboxamide (46.90 mg, 25%) as a white solid. MS (ESI) calc'd for ($C_{23}H_{26}ClN_5O_4S$) $(M+1)^+$, 504.1, found 504.2. $^1H$ NMR (400 MHz, DMSO-$d_6$) δ 12.89 (s, 1H), 8.81 (s, 1H), 8.17 (s, 1H), 7.53 (s, 1H), 7.42 (s, 1H), 4.24 (d, J=6.0 Hz, 2H), 3.63 (s, 3H), 3.24 (s, 3H), 3.13-3.00 (m, 1H), 2.59 (s, 3H), 2.08-1.98 (m, 2H), 1.81 (d, J=10.6 Hz, 3H), 1.19-0.98 (m, 4H).

Example 138

2'-chloro-N-(5-((6-hydroxyspiro[3.3]heptan-2-yl)methoxy)-1,3,4-thiadiazol-2-yl)-5'-methoxy-6-methyl-[4,4'-bipyridine]-3-carboxamide

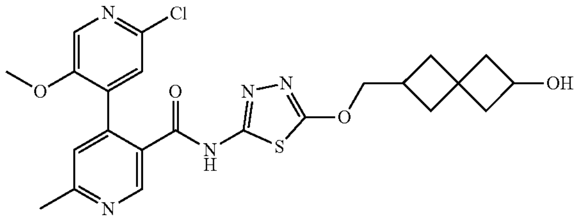 [SMILES: COc1cnc(Cl)cc1-c1cc(C)ncc1C(=O)Nc1nnc(OCC2CC3(CC(O)C3)C2)s1]

Step-1: N-(5-((6-((tert-butyldimethylsilyl)oxy)spiro(3.3)heptan-2-yl)methoxy)-1,3,4-thiadiazol-2-yl)-2'-chloro-5'-methoxy-6-methyl-(4,4'-bipyridine)-3-carboxamide

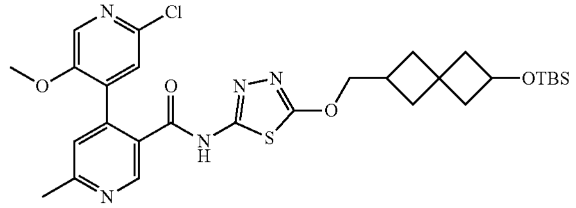 [SMILES: COc1cnc(Cl)cc1-c1cc(C)ncc1C(=O)Nc1nnc(OCC2CC3(C2)CC(O[Si](C)(C)C(C)(C)C)C3)s1]

To a mixture of 2'-chloro-5'-methoxy-6-methyl-(4,4'-bipyridine)-3-carboxylic acid (100.0 mg, 0.35 mmol, Intermediate H) in MeCN (1.0 mL) and DMF (1.0 mL) were added TCFH (110.7 mg, 0.39 mmol), NMI (61.8 mg, 0.75 mmol) and 5-((6-((tert-butyldimethylsilyl)oxy)spiro(3.3)heptan-2-yl)methoxy)-1,3,4-thiadiazol-2-amine (127.5 mg, 0.35 mmol, Example 141, Step 6). The resulting solution was stirred at 25° C. for 2 h. The reaction mixture was quenched with water and extracted with ethyl acetate. The combined organic solution was dried over sodium sulfate, filtered, and concentrated under vacuum to afford N-(5-((6-((tert-butyldimethylsilyl)oxy)spiro(3.3)heptan-2-yl)methoxy)-1,3,4-thiadiazol-2-yl)-2'-chloro-5'-methoxy-6-methyl-(4,4'-bipyridine)-3-carboxamide (260.0 mg, crude) as a red solid. MS (ESI) calc'd for ($C_{29}H_{38}ClN_5O_4SSi$) $(M+1)^+$, 616.2, found 616.1.

Step-2: 2'-chloro-N-(5-((6-hydroxyspiro(3.3)heptan-2-yl)methoxy)-1,3,4-thiadiazol-2-yl)-5'-methoxy-6-methyl-(4,4'-bipyridine)-3-carboxamide

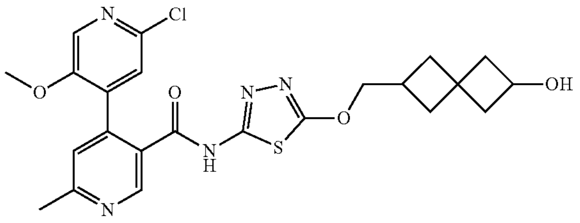 [SMILES: COc1cnc(Cl)cc1-c1cc(C)ncc1C(=O)Nc1nnc(OCC2CC3(CC(O)C3)C2)s1]

A mixture of N-(5-((6-((tert-butyldimethylsilyl)oxy)spiro(3.3)heptan-2-yl)methoxy)-1,3,4-thiadiazol-2-yl)-2'-chloro-5'-methoxy-6-methyl-(4,4'-bipyridine)-3-carboxamide (240.0 mg, 0.38 mmol) in TFA (0.6 mL) and DCM (3.0 mL) was stirred at 0° C. for 2 h. The organic solvent was removed under vacuum. The resulting residue was dissolved in DMF (2.0 mL) and was purified by reverse phase flash chromatography on 40 g C18 column with 5-30% acetonitrile in water to afford 2'-chloro-N-(5-((6-hydroxyspiro(3.3)heptan-2-yl)methoxy)-1,3,4-thiadiazol-2-yl)-5'-methoxy-6-methyl-(4,4'-bipyridine)-3-carboxamide (78.7 mg, 39%) as a white solid. MS (ESI) calc'd for ($C_{23}H_{24}ClN_5O_4S$) $(M+1)^+$, 502.1, found 502.1. $^1H$ NMR (400 MHz, DMSO-$d_6$) δ 12.89 (s, 1H), 8.82 (s, 1H), 8.17 (s, 1H), 7.53 (s, 1H), 7.42 (s, 1H), 4.86 (d, J=6.4 Hz, 1H), 4.34 (d, J=6.8 Hz, 2H), 3.98-3.86 (m, 1H), 3.63 (s, 3H), 2.69-2.59 (m, 1H), 2.59 (s, 3H), 2.39-2.28 (m, 1H), 2.20-2.14 (m, 1H), 2.13-1.98 (m, 2H), 1.87-1.71 (m, 4H).

Example 139

N-(5-((6-hydroxyspiro[3.3]heptan-2-yl)methoxy)-1,3,4-thiadiazol-2-yl)-5'-methoxy-2',6-dimethyl-[4,4'-bipyridine]-3-carboxamide

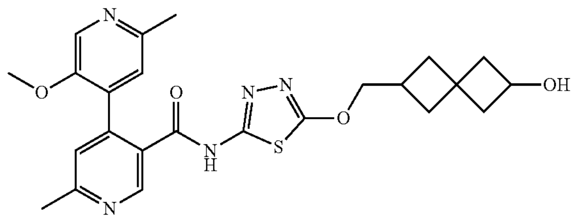 [SMILES: COc1cnc(C)cc1-c1cc(C)ncc1C(=O)Nc1nnc(OCC2CC3(CC(O)C3)C2)s1]

Step-1: N-(5-((6-((tert-butyldimethylsilyl)oxy)spiro(3.3)heptan-2-yl)methoxy)-1,3,4-thiadiazol-2-yl)-5'-methoxy-2',6-dimethyl-(4,4'-bipyridine)-3-carboxamide

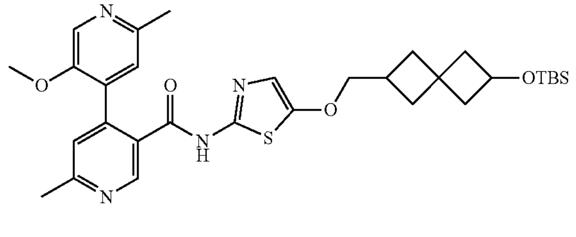 [SMILES: COc1cnc(C)cc1-c1cc(C)ncc1C(=O)Nc1ncc(OCC2CC3(C2)CC(O[Si](C)(C)C(C)(C)C)C3)s1]

To a mixture of 5'-methoxy-2',6-dimethyl-(4,4'-bipyridine)-3-carboxylic acid (91.00 mg, 0.35 mmol, Intermediate G) in MeCN (5.0 mL) and DMF (5.0 mL) was added TCFH (108.7 mg, 0.38 mmol), NMI (60.7 mg, 0.74 mmol) and 5-((6-((tert-butyldimethylsilyl)oxy)spiro(3.3)heptan-2-yl)methoxy)-1,3,4-thiadiazol-2-amine (125.2 mg, 0.35 mmol, Example 141, Step 6). The resulting solution was stirred at 25° C. for 2 h. The reaction mixture was quenched with water and extracted with ethyl acetate. The combined organic solution was dried over sodium sulfate, filtered, and concentrated under vacuum to afford N-(5-((6-((tert-butyldimethylsilyl)oxy)spiro(3.3)heptan-2-yl)methoxy)-1,3,4-thiadiazol-2-yl)-5'-methoxy-2',6-dimethyl-(4,4'-bipyridine)-3-carboxamide (270.0 mg, crude) as a yellow solid. MS (ESI) calc'd for ($C_{30}H_{41}N_5O_4SSi$) $(M+1)^+$, 596.2, found 596.1.

Step-2: N-(5-((6-hydroxyspiro(3.3)heptan-2-yl)methoxy)-1,3,4-thiadiazol-2-yl)-5'-methoxy-2',6-dimethyl-(4,4'-bipyridine)-3-carboxamide

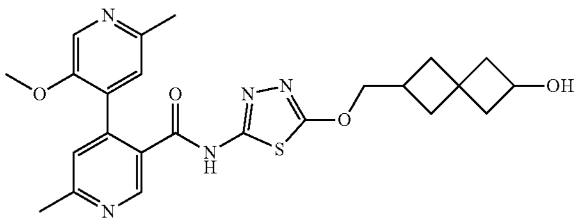 [SMILES: COc1cnc(C)cc1-c1cc(C)ncc1C(=O)Nc1nnc(OCC2CC3(CC(O)C3)C2)s1]

A mixture of N-(5-((6-((tert-butyldimethylsilyl)oxy)spiro(3.3)heptan-2-yl)methoxy)-1,3,4-thiadiazol-2-yl)-5'-methoxy-2',6-dimethyl-(4,4'-bipyridine)-3-carboxamide (240.0 mg, 0.40 mmol) in TFA (0.6 mL) and DCM (3.0 mL) was stirred at 0° C. for 2 h. The organic solvent was removed under vacuum. The resulting mixture was dissolved in DMF (2.0 mL) and was purified by reverse phase flash chromatography on 40 g C18 column with 5%-30% acetonitrile in water to afford N-(5-((6-hydroxyspiro(3.3)heptan-2-yl)methoxy)-1,3,4-thiadiazol-2-yl)-5'-methoxy-2',6-dimethyl-(4,4'-bipyridine)-3-carboxamide (83.7 mg, 43%) as a white solid. MS (ESI) calc'd for ($C_{24}H_{27}N_5O_4S$) $(M+1)^+$, 482.1, found 482.1. $^1H$ NMR (400 MHz, DMSO-$d_6$) δ 12.82 (s, 1H), 8.75 (s, 1H), 8.18 (s, 1H), 7.35 (s, 1H), 7.24 (s, 1H), 4.85 (d, J=6.4 Hz, 1H), 4.34 (d, J=6.8 Hz, 2H), 3.98-3.87 (m, 1H), 3.58 (s, 3H), 2.65-2.60 (m, 1H), 2.58 (s, 3H), 2.47 (s, 3H), 2.43-2.28 (m, 1H), 2.23-2.15 (m, 1H), 2.13-1.98 (m, 2H), 1.83-1.76 (m, 4H).

Example 140

4-(2-fluoro-6-methoxyphenyl)-6-methyl-N-(5-((5-(3-methyloxetan-3-yl)pyridin-2-yl)methoxy)-1,3,4-thiadiazol-2-yl)nicotinamide

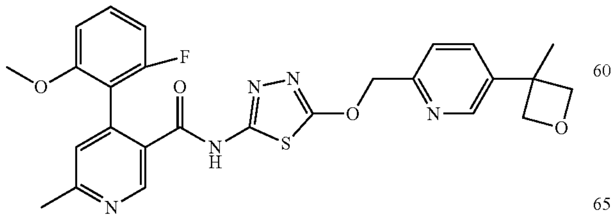

Step-1: 5-bromo-2-(((tert-butyldimethylsilyl)oxy)methyl)pyridine

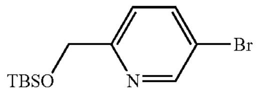

To a stirred solution of (5-bromopyridin-2-yl)methanol (10.0 g, 53.18 mmol) and 1H-Imidazole (7.9 g, 117.00 mmol) in DMF (250 mL) was added t-butyldimethylchlorosilane (8.8 g, 58.50 mmol) in portions at 0° C. under $N_2$ atmosphere. The resulting mixture was stirred at room temperature for 16 h. The reaction was quenched with water and extracted with ethyl acetate. The combined organic layers were washed with water and brine, dried over anhydrous sodium sulfate. After filtration, the filtrate was concentrated under reduced pressure. The residue was purified by flash column chromatography with ethyl acetate in petroleum ether (0~50%) to afford 5-bromo-2-(((tert-butyldimethylsilyl)oxy)methyl)pyridine (13 g, 73%) as a colorless oil. MS (ESI) calculated for ($C_{12}H_{20}BrNOSi$) $(M+1)^+$, 302.0; found, 302.0.

Step-2: diethyl 2-(6-(((tert-butyldimethylsilyl)oxy)methyl)pyridin-3-yl)malonate

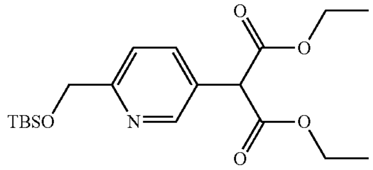 [SMILES: CCOC(=O)C(C(=O)OCC)c1ccc(CO[Si](C)(C)C(C)(C)C)nc1]

To a degassed mixture of 5-bromo-2-(((tert-butyldimethylsilyl)oxy)methyl)pyridine (6.5 g, 21.50 mmol), diethyl malonate (3.4 g, 21.50 mmol) and benzo(d)oxazole (0.5 g, 4.30 mmol) in DMSO (60 mL) were added CuI (409 mg, 2.15 mmol) and $K_3PO_4$ (13.7 g, 64.51 mmol). The resulting mixture was stirred at 50° C. for 16 h under $N_2$ atmosphere. The reaction was quenched with water and extracted with ethyl acetate. The combined organic layers were washed with saturated sodium chloride, dried over anhydrous sodium sulfate. After filtration, the filtrate was concentrated under reduced pressure. The residue was purified by flash column chromatography with ethyl acetate in petroleum ether (0~60%) to afford diethyl 2-(6-(((tert-butyldimethylsilyl)oxy)methyl)pyridin-3-yl)malonate (1.7 g, 21%) as a yellow oil. MS (ESI) calculated for ($C_{12}H_{20}BrNOSi$) $(M+1)^+$, 382.2; found, 382.2.

Step-3: diethyl 2-(6-(((tert-butyldimethylsilyl)oxy)methyl)pyridin-3-yl)-2-methylmalonate

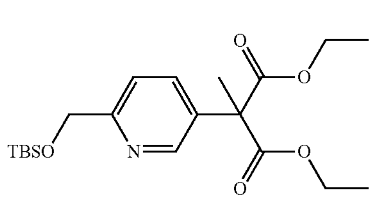 [SMILES: CCOC(=O)C(C)(C(=O)OCC)c1ccc(CO[Si](C)(C)C(C)(C)C)nc1]

To a stirred mixture of diethyl 2-(6-(((tert-butyldimethylsilyl)oxy)methyl)pyridin-3-yl)malonate (700 mg, 1.83 mmol) in DMF (4 mL) was added NaH (110 mg, 4.58 mmol, 60%) in portions at 0° C. under $N_2$ atmosphere and stirred at 0° C. for 45 min. MeI (781 mg, 5.51 mmol) was then added to the above mixture. The resulting mixture was stirred at room temperature for 16 h. The reaction mixture was quenched with saturated ammonium chloride aqueous solution. The resulting mixture was extracted with ethyl acetate. The combined organic layers were washed with saturated sodium chloride, dried over anhydrous sodium sulfate. After filtration, the filtrate was concentrated under reduced pressure. The residue was purified by flash column chromatography with ethyl acetate in petroleum ether (0~60%) to afford diethyl 2-(6-(((tert-butyldimethylsilyl)oxy)methyl)pyridin-3-yl)-2-methylmalonate (280 mg, 38%) as a yellow oil. MS (ESI) calculated for ($C_{20}H_{33}NO_5Si$) $(M+1)^+$, 396.2; found, 396.2.

Step-4: 2-(6-(((tert-butyldimethylsilyl)oxy)methyl)pyridin-3-yl)-2-methylpropane-1,3-diol

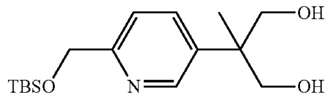 [SMILES: CC(CO)(CO)c1ccc(CO[Si](C)(C)C(C)(C)C)nc1]

To a stirred solution of diethyl 2-(6-(((tert-butyldimethylsilyl)oxy)methyl)pyridin-3-yl)-2-methylmalonate (4.0 g, 10.11 mmol) in THF (30 mL) were added LAH (767 mg, 20.22 mmol) in portions at 0° C. The resulting mixture was stirred at room temperature for 2 h. The reaction mixture was quenched by the addition of water at 0° C. The resulting mixture was extracted with ethyl acetate. The combined organic layers were washed with saturated sodium chloride, dried over anhydrous sodium sulfate. After filtration, the filtrate was concentrated under reduced pressure. The residue was purified by reverse phase flash column chromatography with acetonitrile in water (5~60%) to afford 2-(6-(((tert-butyldimethylsilyl)oxy)methyl)pyridin-3-yl)-2-methylpropane-1,3-diol (1.6 g, 49%) as a white solid. MS (ESI) calculated for ($C_{16}H_{29}NO_3Si$) $(M+1)^+$, 312.2; found, 312.0.

Step-5: 2-(((tert-butyldimethylsilyl)oxy)methyl)-5-(3-methyloxetan-3-yl)pyridine

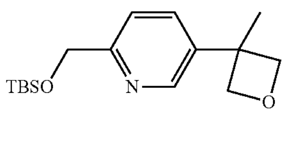 [SMILES: CC1(c2ccc(CO[Si](C)(C)C(C)(C)C)nc2)COC1]

To a solution of 2-(6-(((tert-butyldimethylsilyl)oxy)methyl)pyridin-3-yl)-2-methylpropane-1,3-diol (1.0 g, 3.21 mmol) in Toluene (20 mL) was added $PPh_3$ (1.7 g, 6.42 mmol) and stirred for 10 min at room temperature. Then to this was added ziram (1.5 g, 4.82 mmol) and a solution of DEAD (1.1 g, 6.42 mmol) in Toluene (20 mL). The resulting mixture was stirred at room temperature for 16 h under nitrogen. After filtration over celite, the filtrate was evaporation under vacuum. The residue was purified by flash column chromatography with 5~25% of ethyl acetate in petroleum ether to afford 2-(((tert-butyldimethylsilyl)oxy)methyl)-5-(3-methyloxetan-3-yl)pyridine (880 mg, 93%) as a yellow oil. MS (ESI) calculated for ($C_{16}H_{27}NO_2Si$) $(M+1)^+$, 294.2; found, 294.2.

Step-6: (5-(3-methyloxetan-3-yl)pyridin-2-yl)methanol

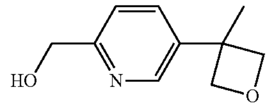

To a stirred solution of 2-(((tert-butyldimethylsilyl)oxy)methyl)-5-(3-methyloxetan-3-yl)pyridine (860 mg, 2.93 mmol) in THF (10 mL) was added TBAF (766 mg, 2.93 mmol). The resulting mixture was stirred at room temperature for 1 h before concentrated under vacuum. The residue was purified by reverse phase flash column chromatography with acetonitrile in water (5~30%) to afford (5-(3-methyloxetan-3-yl)pyridin-2-yl)methanol (650 mg, 95%) as a colorless oil. MS (ESI) calculated for ($C_{10}H_{13}NO_2$) $(M+1)^+$, 180.1; found, 180.1.

Step-7: 5-((5-(3-methyloxetan-3-yl)pyridin-2-yl)methoxy)-1,3,4-thiadiazol-2-amine

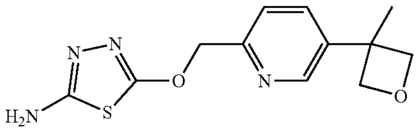 [SMILES: CC1(c2ccc(COc3nnc(N)s3)nc2)COC1]

To a stirred solution of (5-(3-methyloxetan-3-yl)pyridin-2-yl)methanol (500 mg, 2.79 mmol) in THF (10 mL) was added NaH (170 mg, 7.08 mmol, 60%) in portions at 0° C. The resulting mixture was stirred at 0° C. for 1 h under $N_2$ atmosphere. To this was added 5-bromo-1,3,4-thiadiazol-2-amine (502 mg, 2.79 mmol). The resulting mixture was stirred at room temperature for 16 h. The reaction mixture was quenched with water and extracted with ethyl acetate. The combined organic layers were washed with brine, dried over anhydrous sodium sulfate, filtered, and concentrated under vacuum. The residue was purified by reverse phase flash column chromatography with acetonitrile in water (5~60%) to afford 5-((5-(3-methyloxetan-3-yl)pyridin-2-yl)methoxy)-1,3,4-thiadiazol-2-amine (45 mg, 6%) as a brown oil. MS (ESI) calculated for ($C_{12}H_{14}N_4O_2S$) $(M+1)^+$, 279.1; found, 279.1.

Step-8: 4-(2-fluoro-6-methoxyphenyl)-6-methyl-N-(5-((5-(3-methyloxetan-3-yl)pyridin-2-yl)methoxy)-1,3,4-thiadiazol-2-yl)nicotinamide

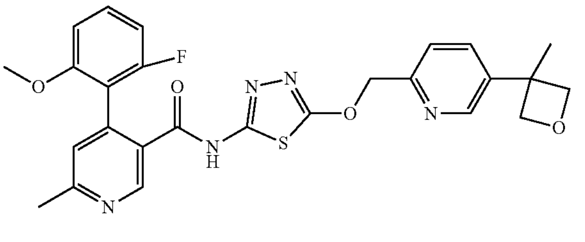 [SMILES: COc1cccc(F)c1-c1cc(C)ncc1C(=O)Nc1nnc(OCc2ccc(C3(C)COC3)cn2)s1]

To a stirred solution of 5-((5-(3-methyloxetan-3-yl)pyridin-2-yl)methoxy)-1,3,4-thiadiazol-2-amine (20 mg, 0.07 mmol) and 4-(2-fluoro-6-methoxyphenyl)-6-methylpyridine-3-carboxylic acid (18 mg, 0.07 mmol, Intermediate F) in MeCN (1 mL) were added NMI (23 mg, 0.28 mmol) and TCFH (30 mg, 0.11 mmol). The resulting mixture was stirred at room temperature for 1 h. The mixture was purified by prep-HPLC with the following conditions: (Column: XBridge Prep OBD C18 Column, 30×150 mm 5 um; Mobile Phase A: Water (10 MMOL/L $NH_4HCO_3$), Mobile Phase B:ACN; Flow rate: 60 mL/min; Gradient: 20 B to 50 B in 8 min; 220 nm; RT1: 7.18 min) to afford 4-(2-fluoro-6-methoxyphenyl)-6-methyl-N-(5-((5-(3-methyloxetan-3-yl) pyridin-2-yl)methoxy)-1,3,4-thiadiazol-2-yl)nicotinamide (8.8 mg, 23%) as a white solid. MS (ESI) calculated for ($C_{26}H_{24}FN_5O_4S$) $(M+1)^+$, 522.1; found, 522.1. $^1$H NMR (400 MHz, DMSO-$d_6$) δ 12.91 (s, 1H), 8.82 (s, 1H), 8.53 (d, J=2.4 Hz, 1H), 7.82-7.73 (m, 1H), 7.54 (d, J=8.0 Hz, 1H), 7.46-7.36 (m, 1H), 7.32 (s, 1H), 6.97-6.81 (m, 2H), 5.52 (s, 2H), 4.84 (d, J=5.6 Hz, 2H), 4.58 (d, J=5.6 Hz, 2H), 3.59 (s, 3H), 2.57 (s, 3H), 1.66 (s, 3H).

Example 141

4-(2-fluoro-6-methoxyphenyl)-N-(5-((6-hydroxyspiro(3.3)heptan-2-yl)methoxy)-1,3,4-thiadiazol-2-yl)-6-methylpyridine-3-carboxamide

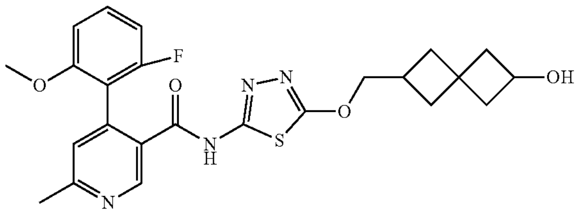 [SMILES: COc1cccc(F)c1-c1cc(C)ncc1C(=O)Nc1nnc(OCC2CC3(CC(O)C3)C2)s1]

Step-1: methyl 6-hydroxyspiro(3.3)heptane-2-carboxylate

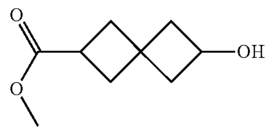

To a solution of methyl 6-oxospiro(3.3)heptane-2-carboxylate (1.00 g, 5.94 mmol) in MeOH (20.0 mL) was added $NaBH_4$ (0.67 g, 17.70 mmol) in portions at 0° C. under nitrogen. The resulting solution was stirred at 0° C. for 2 h. The reaction was monitored by TLC. The reaction mixture was quenched with water and extracted with ethyl acetate. The combined organic layers were washed with brine, dried over anhydrous sodium sulfate, filtered, and concentrated under vacuum to afford methyl 6-hydroxyspiro(3.3)heptane-2-carboxylate (800.0 mg, crude) as a yellow oil, which was used for the next step without further purification.

Step-2: methyl 6-((tert-butyldimethylsilyl)oxy)spiro (3.3)heptane-2-carboxylate

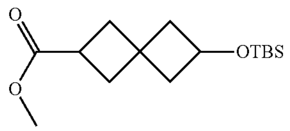 [SMILES: COC(=O)C1CC2(CC(O[Si](C)(C)C(C)(C)C)C2)C1]

To a mixture of methyl 6-hydroxyspiro(3.3)heptane-2-carboxylate (800.0 mg, 4.70 mmol) and imidazole (479.9 mg, 7.05 mmol) in DMF (8.0 mL) was added TBSCl (850.1 mg, 5.64 mmol). The resulting mixture was stirred at room temperature for 24 h. The reaction was monitored by TLC. The reaction mixture was quenched with water and extracted with ethyl acetate. The combined organic layers were washed with brine, dried over anhydrous sodium sulfate, filtered, and concentrated under vacuum. The residue was purified by flash column chromatography with 0-20% methanol in dichloromethane to afford methyl 6-((tert-butyldimethylsilyl)oxy)spiro(3.3)heptane-2-carboxylate (1.0 g, crude) as a yellow oil.

Step-3: (6-((tert-butyldimethylsilyl)oxy)spiro(3.3) heptan-2-yl) methanol

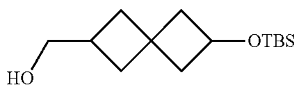 [SMILES: CC(C)(C)[Si](C)(C)OC1CC2(CC(CO)C2)C1]

To a solution of methyl 6-((tert-butyldimethylsilyl)oxy) spiro(3.3)heptane-2-carboxylate (1.0 g, 3.51 mmol) in THF (20.0 mL) was added LAH (133.4 mg, 3.51 mmol) in portions at 0° C. under nitrogen. The resulting solution was stirred at 0° C. for 2 h. The reaction was monitored by TLC. The reaction mixture was quenched by the addition of water at 0° C. The aqueous solution was extracted with ethyl acetate. The combined organic layers were washed with brine, dried over anhydrous sodium sulfate, filtered, and concentrated under vacuum to afford (6-((tert-butyldimethylsilyl)oxy)spiro(3.3)heptan-2-yl)methanol (860.0 mg, crude) as a yellow oil.

Step-4: methyl 6-((tert-butyldimethylsilyl)oxy)spiro (3.3)heptane-2-carbodithioate

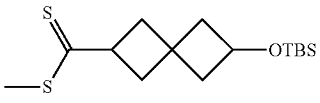 [SMILES: CSC(=S)C1CC2(CC(O[Si](C)(C)C(C)(C)C)C2)C1]

To a solution of (6-((tert-butyldimethylsilyl)oxy)spiro (3.3)heptan-2-yl)methanol (860.0 mg, 3.35 mmol) in THF (30.0 mL) was added NaH (160.9 mg, 6.70 mmol) in portions at 0° C. and stirred at 0° C. for 30 min. To the above mixture was added $CS_2$ (382.9 mg, 5.03 mmol) at 0° C. and stirred at 0° C. for 30 min. To the above mixture was then added MeI (141.9 mg, 5.03 mmol) at 0° C. under nitrogen. The reaction mixture was quenched with water and extracted with ethyl acetate. The combined organic layers were washed with brine, dried over anhydrous sodium sulfate, filtered, and concentrated under vacuum to afford methyl 6-((tert-butyldimethylsilyl)oxy)spiro(3.3)heptane-2-carbodithioate (1.05 g, crude) as a yellow oil. MS (ESI) calc'd for ($C_{15}H_{28}OS_2Si$) $(M+1)^+$, 316.1, found 316.2.

Step-5: N-amino-6-((tert-butyldimethylsilyl)oxy) spiro(3.3)heptane-2-carbothioamide

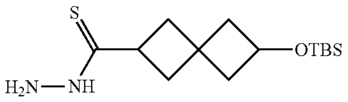

A mixture of methyl 6-((tert-butyldimethylsilyl)oxy)spiro (3.3)heptane-2-carbodithioate (1.05 g, 3.31 mmol) and hydrazine hydrate (80%) (166.0 mg, 3.31 mmol) in MeOH (30.0 mL) was stirred at room temperature for 2 h. The reaction mixture was quenched with water and extracted with ethyl acetate. The combined organic solution was dried over sodium sulfate, filtered, and concentrated under vacuum to afford N-amino-6-((tert-butyldimethylsilyl)oxy) spiro(3.3)heptane-2-carbothioamide (955.4 mg, crude) as a yellow oil. MS (ESI) calc'd for ($C_{14}H_{28}N_2OSSi$) $(M+1)^+$, 301.1, found 301.0.

Step-6:5-((6-((tert-butyldimethylsilyl)oxy)spiro(3.3) heptan-2-yl)methoxy)-1,3,4-thiadiazol-2-amine

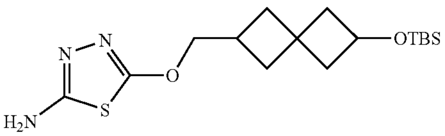 [SMILES: CC(C)(C)[Si](C)(C)OC1CC2(CC(COc3nnc(N)s3)C2)C1]

To a mixture of N-amino-6-((tert-butyldimethylsilyl)oxy) spiro(3.3)heptane-2-carbothioamide (955.4 mg, 3.18 mmol) and TEA (643.3 mg, 6.35 mmol) in MeOH (30.0 mL) was added BrCN (404.0 mg, 3.81 mmol). The resulting mixture was stirred at room temperature for 30 min. The reaction mixture was quenched with water and extracted with ethyl acetate. The combined organic solution was dried over sodium sulfate, filtered, and concentrated under vacuum. The residue was purified by flash column chromatography on silica gel with 0-60% ethyl acetate in petroleum ether to afford 5-((6-((tert-butyldimethylsilyl)oxy)spiro(3.3)heptan-2-yl)methoxy)-1,3,4-thiadiazol-2-amine (200.0 mg, 16%) as a white solid. MS (ESI) calc'd for ($C_{16}H_{29}N_3O_2SSi$) $(M+1)^+$, 356.1, found 356.1.

Step-7: N-(5-((6-((tert-butyldimethylsilyl)oxy)spiro (3.3)heptan-2-yl)methoxy)-1,3,4-thiadiazol-2-yl)-4-(2-fluoro-6-methoxyphenyl)-6-methylpyridine-3-carboxamide

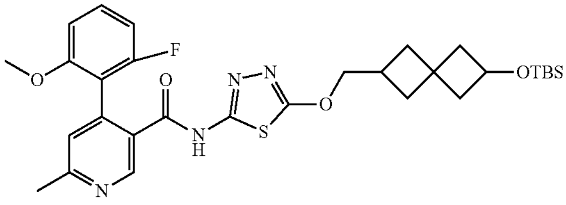 [SMILES: COc1cccc(F)c1-c1cc(C)ncc1C(=O)Nc1nnc(OCC2CC3(C2)CC(O[Si](C)(C)C(C)(C)C)C3)s1]

To a mixture of 4-(2-fluoro-6-methoxyphenyl)-6-methylpyridine-3-carboxylic acid (60.0 mg, 0.23 mmol, Intermediate F) in MeCN (2.0 mL) and DMF (0.5 mL) were added 5-((6-((tert-butyldimethylsilyl)oxy)spiro(3.3)heptan-2-yl) methoxy)-1,3,4-thiadiazol-2-amine (97.9 mg, 0.27 mmol), TCFH (70.8 mg, 0.25 mmol) and NMI (39.6 mg, 0.48 mmol). The resulting solution was stirred at room temperature for 2 h. The resulting solution was purified by reverse phase flash column chromatography with 5-50% acetonitrile in water to afford N-(5-((6-((tert-butyldimethylsilyl)oxy) spiro(3.3)heptan-2-yl)methoxy)-1,3,4-thiadiazol-2-yl)-4-(2-fluoro-6-methoxyPhenyl)-6-methylpyridine-3-carboxamide (90.0 mg, 62%) as a white solid. MS (ESI) calc'd for ($C_{30}H_{39}FN_4O_4SSi$) $(M+1)^+$, 599.2, found 599.2.

Step-8: 4-(2-fluoro-6-methoxyphenyl)-N-(5-((6-hydroxyspiro(3.3)heptan-2-yl)methoxy)-1,3,4-thiadiazol-2-yl)-6-methylpyridine-3-carboxamide

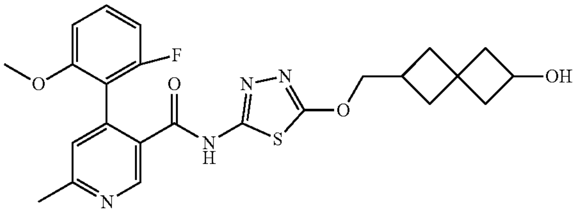 [SMILES: COc1cccc(F)c1-c1cc(C)ncc1C(=O)Nc1nnc(OCC2CC3(CC(O)C3)C2)s1]

A mixture of N-(5-((6-((tert-butyldimethylsilyl)oxy)spiro (3.3)heptan-2-yl)methoxy)-1,3,4-thiadiazol-2-yl)-4-(2-fluoro-6-methoxyphenyl)-6-methylpyridine-3-carboxamide (90.0 mg, 0.15 mmol) in TFA (0.2 mL) and DCM (1.0 mL) was stirred at room temperature for 2 h. The solvent was removed under vacuum and the residue was purified by reverse phase flash column chromatography with 5~45% acetonitrile in water to afford 4-(2-fluoro-6-methoxyphenyl)-N-(5-((6-hydroxyspiro(3.3)heptan-2-yl)methoxy)-1,3,4-thiadiazol-2-yl)-6-methylpyridine-3-carboxamide (10.5 mg, 14%) as a white solid. MS (ESI) calc'd for ($C_{24}H_{25}FN_4O_4S$) $(M+1)^+$, 485.2, found 485.2. $^1H$ NMR (400 MHz, DMSO-$d_6$) δ 12.83 (s, 1H), 8.80 (s, 1H), 7.41-7.39 (m, 1H), 7.33 (s, 1H), 6.97-6.80 (m, 2H), 4.87 (d, J=6.4 Hz, 1H), 4.34 (d, J=6.8 Hz, 2H), 3.96-3.90 (m, 1H), 3.59 (s, 3H), 2.73-2.58 (m, 1H), 2.57 (s, 3H), 2.39-2.27 (m, 2H), 2.19-2.16 (m, 1H), 2.15-1.93 (m, 2H), 1.86-1.70 (m, 4H).

Example 142

5-(5-chloro-2-methoxyphenyl)-N-(5-((4-fluorobicyclo(2.2.2)octan-1-yl)methoxy)-1,3,4-thiadiazol-2-yl) pyridazine-4-carboxamide

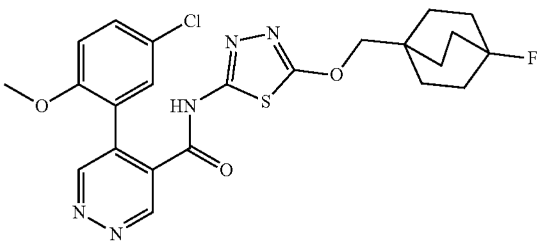 [SMILES: COc1ccc(Cl)cc1-c1cnncc1C(=O)Nc1nnc(OCC23CCC(F)(CC2)CC3)s1]

To a solution of 5-(5-chloro-2-methoxyphenyl) pyridazine-4-carboxylic acid (50 mg, 0.189 mmol, Example 121, Step 4) in ACN (2 mL) and DMF (2 mL) were added 5-((4-fluorobicyclo(2.2.2)octan-1-yl)methoxy)-1,3,4-thiadiazol-2-amine (48.61 mg, 0.189 mmol, Example 65, Step 3), NMI (46.53 mg, 0.567 mmol) and TCFH (63.61 mg, 0.227 mmol). The resulting solution was stirred at room temperature for 2 hours. The mixture was quenched with water and extracted with ethyl acetate. The combined organic layers were washed with brine, dried over anhydrous sodium sulfate, filtered, and concentrated under vacuum. The residue was purified by reverse phase flash chromatography on silica gel with 0~10% methanol in dichloromethane and further purified by prep-HPLC with the following conditions: (Column: Xselect CSH OBD Column 30*150 mm 5 um; Mobile Phase A: Water (0.1% FA), Mobile Phase B: ACN; Flow rate: 60 mL/min; Gradient: 40 B to 85 B in 7 min; 220 nm; RT1: 6.42 min) to afford 5-(5-chloro-2-methoxyphenyl)-N-(5-((4-fluorobicyclo(2.2.2)octan-1-yl) methoxy)-1,3,4-thiadiazol-2-yl)pyridazine-4-carboxamide (4.5 mg, 5.0%) as a yellow solid. MS (ESI) calc'd for ($C_{23}H_{23}ClFN_5O_3S$) $(M+1)^+$, 504.2; found, 504.2. $^1H$ NMR (400 MHz, $CD_3OD$) δ 9.41-9.38 (m, 2H), 7.54-7.50 (m, 2H), 7.07-7.05 (m, 1H), 4.12 (s, 2H), 3.65 (s, 3H), 1.83-1.80 (m, 12H).

Example 143

2'-chloro-N-(5-((3-(2-hydroxypropan-2-yl)bicyclo (1.1.1)pentan-1-yl)methoxy)-1,3,4-thiadiazol-2-yl)-5'-methoxy-6-methyl-(4,4'-bipyridine)-3-carboxamide

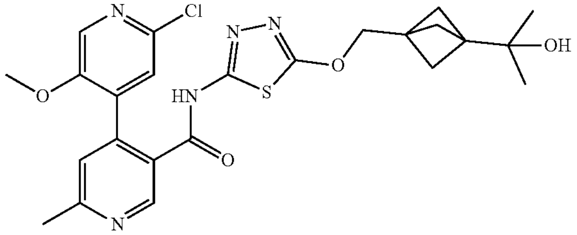 [SMILES: COc1cnc(Cl)cc1-c1cc(C)ncc1C(=O)Nc1nnc(OCC23CC(C(C)(C)O)(C2)C3)s1]

A mixture of 2'-chloro-5'-methoxy-6-methyl-(4,4'-bipyridine)-3-carboxylic acid (25.00 mg, 0.090 mmol, Intermediate H), 2-(3-(((5-amino-1,3,4-thiadiazol-2-yl)oxy)methyl) bicyclo(1.1.1)pentan-1-yl)propan-2-ol (27.49 mg, 0.10 mmol, Example 103, Step 5), TCFH (27.69 mg, 0.099 mmol) and NMI (15.47 mg, 0.18 mmol) in MeCN (1.0 mL) and DMF (0.1 mL) was stirred at room temperature for 2 h. The resulting mixture was concentrated under vacuum. The residue was purified by reverse phase flash column chromatography with 5~40% acetonitrile in water to afford 2-chloro-N-(5-((3-(2-hydroxypropan-2-yl)bicyclo(1.1.1) pentan-1-yl)methoxy)-1,3,4-thiadiazol-2-yl)-5-methoxy-6-methyl-(4,4-bipyridine)-3-carboxamide (8.5 mg, 18%) as a white solid. MS (ESI) calc'd for ($C_{24}H_{26}ClN_5O_4S$) $(M+1)^+$, 516.2, found 516.2. $^1H$ NMR (400 MHz, DMSO-$d_6$) δ 12.89 (s, 1H), 8.83 (s, 1H), 8.16 (s, 1H), 7.50 (s, 1H), 7.38 (s, 1H), 4.42 (s, 2H), 4.11 (s, 1H), 3.63 (s, 3H), 2.58 (s, 3H), 1.58 (s, 6H), 1.02 (s, 6H).

Example 144 and Example 152

(R)-4-(5-chloro-2-methoxyphenyl)-N-(5-((5-(N,S-dimethylsulfonimidoyl)pyridin-2-yl)methoxy)-1,3,4-thiadiazol-2-yl)-6-methylnicotinamide (Example 144) and (S)-4-(5-chloro-2-methoxyphenyl)-N-(5-((5-(N,S-dimethylsulfonimidoyl)pyridin-2-yl) methoxy)-1,3,4-thiadiazol-2-yl)-6-methylnicotinamide (Example 152)

(Example 144)

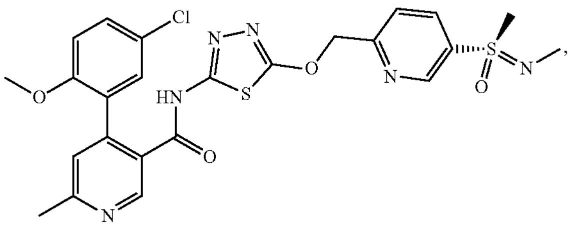

(Example 152)

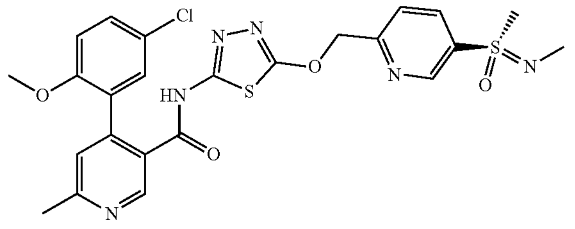

Step-1: tert-butyl N-(5-((5-(methylsulfanyl)pyridin-2-yl)methoxy)-1,3,4-thiadiazol-2-yl)carbamate

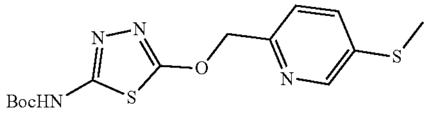 [SMILES: CSc1ccc(COc2nnc(NC(=O)OC(C)(C)C)s2)nc1]

To a stirred solution of 5-((5-(methylsulfanyl)pyridin-2-yl)methoxy)-1,3,4-thiadiazol-2-amine (700 mg, 2.75 mmol) in DCM (5 mL) were added $(Boc)_2O$ (901 mg, 4.12 mmol) and DMAP (33 mg, 0.275 mmol). The resulting solution was stirred at 25° C. for 2 h. The resulting residue was dissolved in DCM (10 mL) and was applied to a 40 g silica gel column that was eluted with 0~45% ethyl acetate in petroleum ether within 45 min to afford tert-butyl N-(5-((5-(methylsulfanyl) pyridin-2-yl)methoxy)-1,3,4-thiadiazol-2-yl)carbamate (238 mg, 24%) as a yellow solid. MS (ESI) calc'd for ($C_{14}H_{18}N_4O_3S_2$) $(M+1)^+$, 355.1; found 355.1.

Step-2: tert-butyl N-(5-((5-(imino(methyl)oxo-lambda6-sulfanyl)pyridin-2-yl)methoxy)-1,3,4-thiadiazol-2-yl)carbamate

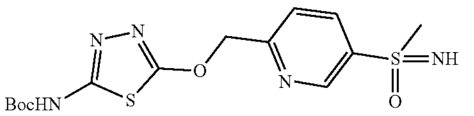 [SMILES: CC(C)(C)OC(=O)Nc1nnc(OCc2ccc(S(C)(=N)=O)cn2)s1]

To a stirred solution of tert-butyl N-(5-((5-(methylsulfanyl)pyridin-2-yl) tert-butyl N-(5-((5-(imino(methyl)oxo-lambda6-sulfanyl)pyridin-2-yl)methoxy)-1,3,4-thiadiazol-2-yl)carbamate (200 mg, 0.56 mmol) in MeOH (2 mL) were added $NH_2COONH_4$ (176 mg, 2.25 mmol) and $PhI(OAc)_2$ (817 mg, 2.53 mmol). The resulting mixture was stirred at 25° C. for 1 h. The reaction mixture was purified by silica gel column chromatography, eluted with acetonitrile in water (0-55%) to afford tert-butyl N-(5-((5-(imino(methyl) oxo-lambda6-sulfanyl)pyridin-2-yl)methoxy)-1,3,4-thiadiazol-2-yl)carbamate (202 mg, 92%) as a white solid. MS (ESI) calc'd for ($C_{14}H_{19}N_5O_4S_2$) $(M+1)^+$, 386.1; found 386.1.

Step-3: tert-butyl N-(5-((5-(methyl(methylimino) oxo-lambda6-sulfanyl)pyridin-2-yl)methoxy)-1,3,4-thiadiazol-2-yl)carbamate

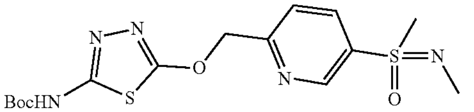 [SMILES: CN=S(C)(=O)c1ccc(COc2nnc(NC(=O)OC(C)(C)C)s2)nc1]

To a stirred solution of tert-butyl N-(5-((5-(imino(methyl) oxo-lambda6-sulfanyl)pyridin-2-yl)methoxy)-1,3,4-thiadiazol-2-yl)carbamate (150 mg, 0.38 mmol) in 1,4-dioxane (2 mL) were added $Cu(AcO)_2$ (106 mg, 0.58 mmol) and Methylboronic acid (70 mg, 1.16 mmol). The resulting mixture was stirred at 100° C. for 2 h under oxygen atmosphere. The reaction mixture was purified by flash column chromatography with 0~30% ethyl acetate in petroleum ether to afford tert-butyl N-(5-((5-(methyl(methylimino)oxo-lambda6-sulfanyl)pyridin-2-yl)methoxy)-1,3,4-thiadiazol-2-yl)carbamate (111 mg, 71%) as a yellow solid. MS (ESI) calc'd for ($C_{15}H_{21}N_5O_4S_2$) $(M+1)^+$, 400.1; found 400.1.

Step-4:5-((5-(methyl(methylimino)oxo-lambda6-sulfanyl)pyridin-2-yl)methoxy)-1,3,4-thiadiazol-2-amine

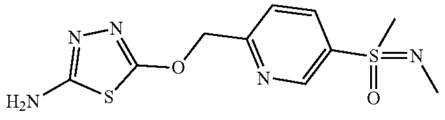

To a stirred solution of tert-butyl N-(5-((5-(methyl(methylimino)oxo-lambda6-sulfanyl)pyridin-2-yl)methoxy)-1,3,4-thiadiazol-2-yl)carbamate (100 mg, 0.20 mmol) in DCM (1.8 mL) was added TFA (0.6 mL). The resulting mixture was stirred at 25° C. for 4 h. The resulting mixture was concentrated under reduced pressure. The residue was neutralized to pH ~8 with saturated $NaHCO_3$ (aq.). The residue was purified by reverse phase flash chromatography with 5~65% acetonitrile in water to afford 5-((5-(methyl(methylimino)oxo-lambda6-sulfanyl)pyridin-2-yl)methoxy)-1,3,4-thiadiazol-2-amine (50 mg, 53%) as a white solid. MS (ESI) calc'd for ($C_{10}H_{13}N_5O_2S_2$) $(M+1)^+$, 300.1; found, 300.1.

Step-5: (R)-4-(5-chloro-2-methoxyphenyl)-N-(5-((5-(N,S-dimethylsulfonimidoyl)pyridin-2-yl)methoxy)-1,3,4-thiadiazol-2-yl)-6-methylnicotinamide (Example 144) and (S)-4-(5-chloro-2-methoxyphenyl)-N-(5-((5-(N,S-dimethylsulfonimidoyl)pyridin-2-yl)methoxy)-1,3,4-thiadiazol-2-yl)-6-methylnicotinamide (Example 152)

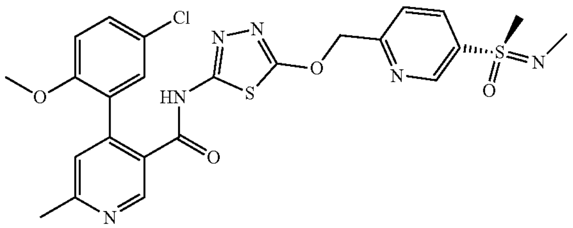

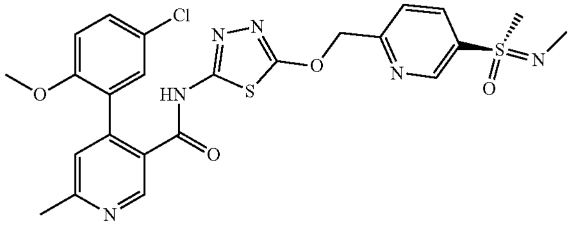

To a stirred solution of 5-((5-(methyl(methylimino)oxo-lambda6-sulfanyl)pyridin-2-yl)methoxy)-1,3,4-thiadiazol-2-amine (45 mg, 0.15 mmol) and 4-(5-chloro-2-methoxyphenyl)-6-methylpyridine-3-carboxylic acid (41 mg, 0.15 mmol, Example 39, Step 2) in DMF (1 mL) were added NMI (49 mg, 0.60 mmol) and TCFH (63 mg, 0.22 mmol). The resulting mixture was stirred at 25° C. for 2 h. The residue was purified by reverse phase flash chromatography with acetonitrile in water (5~45%) to afford racemic product. The racemic compound (28 mg) was separated by prep-chiral HPLC with the following conditions: (Column: CHIRAL ART Cellulose-SC, 2*25 cm, 5 μm; Mobile Phase A: Hex: DCM=1: 1-HPLC, Mobile Phase B: MeOH-HPLC; Flow rate: 20 mL/min; Gradient: 50% B to 50% B in 14 min; Wave Length: 220/254 nm; RT1 (min): 11.15; RT2 (min): 13.09; Sample Solvent: EtOH:DCM=1: 1-HPLC; Injection Volume: 0.5 mL; Number Of Runs: 5) to afford (R)-4-(5-chloro-2-methoxyphenyl)-N-(5-((5-(N,S-dimethylsulfonimidoyl)pyridin-2-yl)methoxy)-1,3,4-thiadiazol-2-yl)-6-methylnicotinamide (1.1 mg, 1.6%) as a white solid with shorter retention time on chiral-HPLC and (S)-4-(5-chloro-2-methoxyphenyl)-N-(5-((5-(N,S-dimethylsulfonimidoyl) pyridin-2-yl)methoxy)-1,3,4-thiadiazol-2-yl)-6-methylnicotinamide (1.1 mg, 1.6%) as a white solid with longer retention time on chiral-HPLC.

(R)-4-(5-chloro-2-methoxyphenyl)-N-(5-((5-(N,S-dimethylsulfonimidoyl)pyridin-2-yl)methoxy)-1,3,4-thiadiazol-2-yl)-6-methylnicotinamide: MS (ESI) calc'd for ($C_{24}H_{23}ClN_6O_4S_2$) $(M+1)^+$, 559.2; found, 559.2. $^1H$ NMR (400 MHz, Methanol-$d_4$) δ 9.02 (d, J=2.4 Hz, 1H), 8.69 (s, 1H), 8.38-8.28 (m, 1H), 7.84 (d, J=8.0 Hz, 1H), 7.44-7.36 (m, 3H), 7.01-6.95 (m, 1H), 5.71 (s, 2H), 3.62 (s, 3H), 3.25 (s, 3H), 2.66 (s, 3H), 2.63 (s, 3H).

(S)-4-(5-chloro-2-methoxyphenyl)-N-(5-((5-(N,S-dimethylsulfonimidoyl)pyridin-2-yl)methoxy)-1,3,4-thiadiazol-2-yl)-6-methylnicotinamide: MS (ESI) calc'd for ($C_{24}H_{23}ClN_6O_4S_2$) $(M+1)^+$, 559.2; found, 559.2. $^1H$ NMR (400 MHz, Methanol-$d_4$) δ 9.02 (d, J=2.4 Hz, 1H), 8.69 (s, 1H), 8.37-8.27 (m, 1H), 7.84 (d, J=8.4 Hz, 1H), 7.44-7.36 (m, 3H), 7.01-6.95 (m, 1H), 5.71 (s, 2H), 3.62 (s, 3H), 3.25 (s, 3H), 2.66 (s, 3H), 2.63 (s, 3H).

Example 145

2'-chloro-N-(5-((5-(hydroxymethyl)pyrazin-2-yl)methoxy)-1,3,4-thiadiazol-2-yl)-5'-methoxy-6-methyl-(4,4'-bipyridine)-3-carboxamide

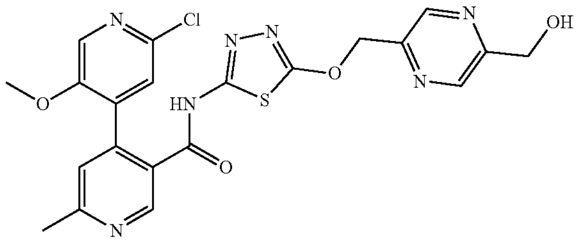

To a stirred solution of (5-(((5-amino-1,3,4-thiadiazol-2-yl)oxy)methyl)pyrazin-2-yl)methanol (30 mg, 0.13 mmol, Example 133, Step 4)) and 2'-chloro-5'-methoxy-6-methyl-(4,4'-bipyridine)-3-carboxylic acid (35 mg, 0.13 mmol, Intermediate H) in DMF (1 mL) and MeCN (1 mL) were added NMI (41 mg, 0.50 mmol) and TCFH (35 mg, 0.13 mmol). The resulting mixture was stirred at room temperature for 1 h. The mixture was purified by prep-HPLC with the following conditions: (Column: Xcelect CSH F-pheny OBD Column, 19*250 mm, 5 um; Mobile Phase A: Water (0.1% FA), Mobile Phase B: ACN; Flow rate: 25 mL/min; Gradient: 20 B to 50 B in 8 min; 254 nm; RT1: 7 min) to afford 2'-chloro-N-(5-((5-(hydroxymethyl)pyrazin-2-yl)methoxy)-1,3,4-thiadiazol-2-yl)-5'-methoxy-6-methyl-(4,4'-bipyridine)-3-carboxamide (4.0 mg, 6%) as a white solid. MS (ESI) calc'd for ($C_{21}H_{18}ClN_7O_4S$) $(M+1)^+$, 500.1; found 500.1. $^1H$ NMR (400 MHz, DMSO-$d_6$) δ 12.98 (s, 1H), 8.84 (s, 1H), 8.73-8.72 (m, 2H), 8.16 (s, 1H), 7.50 (s, 1H), 7.38 (s, 1H), 5.60 (s, 1H), 5.59 (s, 2H), 4.66 (s, 2H), 3.63 (s, 3H), 2.58 (s, 3H).

Example 146

N-(5-((5-(hydroxymethyl)pyrazin-2-yl)methoxy)-1,3,4-thiadiazol-2-yl)-5'-methoxy-2',6-dimethyl-[4,4'-bipyridine]-3-carboxamide

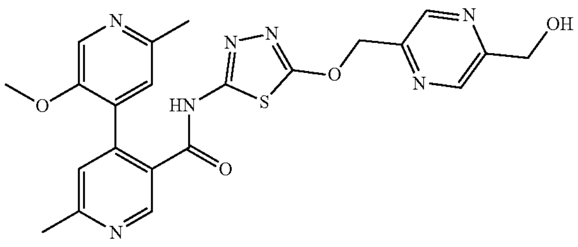

To a stirred solution of (5-(((5-amino-1,3,4-thiadiazol-2-yl)oxy)methyl)pyrazin-2-yl)methanol (30 mg, 0.13 mmol, Example 133, Step 4) and 5-methoxy-2,6-dimethyl-(4,4-bipyridine)-3-carboxylic acid (32 mg, 0.13 mmol) in DMF (1 mL) and MeCN (1 mL) were added NMI (41 mg, 0.50 mmol) and TCFH (35 mg, 0.13 mmol). The resulting mixture was stirred at room temperature for 1 h. The mixture was purified by prep-HPLC with the following conditions: (Column: Xcelect CSH F-pheny OBD Column, 19*250 mm, 5 um; Mobile Phase A: Water (0.1% FA), Mobile Phase B: ACN; Flow rate: 25 mL/min; Gradient: 5 B to 30 B in 7 min; 254 nm; RT1: 6.5 min) to afford N-(5-((5-(hydroxymethyl)pyrazin-2-yl)methoxy)-1,3,4-thiadiazol-2-yl)-5'-methoxy-2',6-dimethyl-[4,4'-bipyridine]-3-carboxamide (2.2 mg, 4%) as a white solid. MS (ESI) calc'd for ($C_{22}H_{21}N_7O_4S$) $(M+1)^+$, 480.1; found 480.1. $^1H$ NMR (400 MHz, DMSO-$d_6$) δ 12.90 (s, 1H), 8.83-8.65 (m, 3H), 8.18 (s, 1H), 7.34 (s, 1H), 7.24 (s, 1H), 5.60 (s, 3H), 4.66 (d, J=3.2 Hz, 2H), 3.58 (s, 3H), 2.58 (s, 3H), 2.47 (s, 3H).

Example 147 and 148

(R)-4-(5-chloro-2-methoxyphenyl)-6-methyl-N-(5-((5-(S-methylsulfonimidoyl)pyridin-2-yl)methoxy)-1,3,4-thiadiazol-2-yl)nicotinamide (Example 147) and (S)-4-(5-chloro-2-methoxyphenyl)-6-methyl-N-(5-((5-(S-methylsulfonimidoyl)pyridin-2-yl)methoxy)-1,3,4-thiadiazol-2-yl)nicotinamide (Example 148)

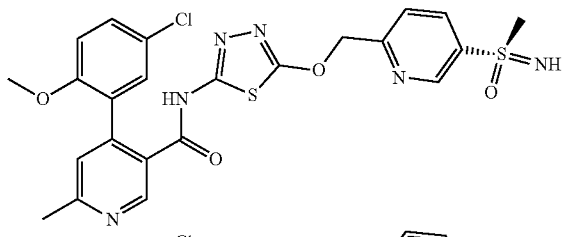

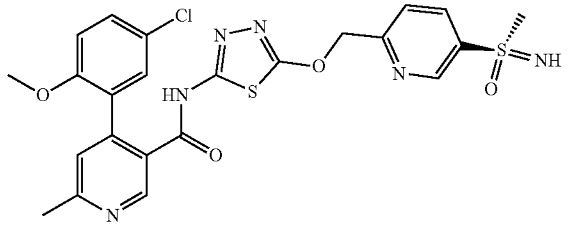

Step-1: 4-(5-chloro-2-methoxyphenyl)-6-methyl-N-(5-((5-(methylthio)pyridin-2-yl)methoxy)-1,3,4-thiadiazol-2-yl)nicotinamide

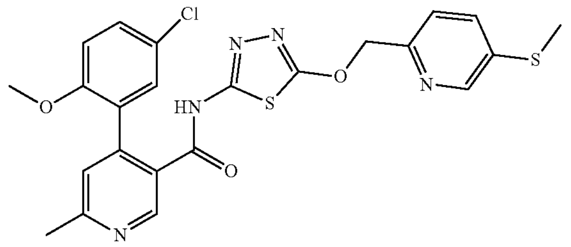

To a solution of 5-((5-(methylthio)pyridin-2-yl)methoxy)-1,3,4-thiadiazol-2-amine (200 mg, 0.79 mmol, Example 149, Step 4) in ACN (5 mL) were added 4-(5-chloro-2-methoxyphenyl)-6-methylnicotinic acid (219 mg, 0.79 mmol, Example 39, Step 2), NMI (190 mg, 2.37 mmol) and TCFH (332 mg, 1.18 mmol). The resulting mixture was stirred at room temperature for 2 hours. The mixture was diluted with water and extracted with ethyl acetate. The combined organic layers were washed with brine, dried over anhydrous sodium sulfate, filtered, and concentrated under vacuum. The residue was purified by flash column chromatography with 0~10% methanol in dichoromathane to afford 4-(5-chloro-2-methoxyphenyl)-6-methyl-N-(5-((5-(methylthio)pyridin-2-yl)methoxy)-1,3,4-thiadiazol-2-yl)nicotinamide (230 mg, 57%) as a white solid. MS (ESI) calc'd for ($C_{23}H_{20}ClN_5O_3S_2$) $(M+1)^+$, 514.1; found 514.1.

Step-2: (R)-4-(5-chloro-2-methoxyphenyl)-6-methyl-N-(5-((5-(S-methylsulfonimidoyl)pyridin-2-yl)methoxy)-1,3,4-thiadiazol-2-yl)nicotinamide

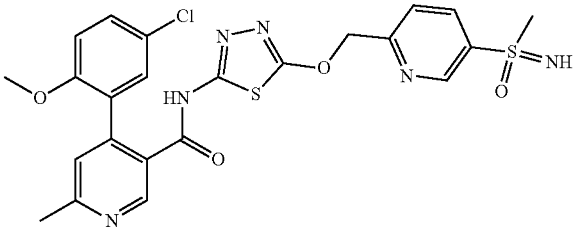

To a solution of 4-(5-chloro-2-methoxyphenyl)-6-methyl-N-(5-((5-(methylthio)pyridin-2-yl)methoxy)-1,3,4-thiadiazol-2-yl)nicotinamide (230 mg, 0.45 mmol) in methanol (5 mL) were added ammonium carbamate (140 mg, 1.8 mmol) and (diacetoxyiodo)benzene (580 mg, 1.8 mmol). The resulting mixture was stirred at room temperature for 2 hours. The mixture was diluted with water and extracted with ethyl acetate. The combined organic layers were washed with brine, dried over anhydrous sodium sulfate, filtered, and concentrated under vacuum. The residue was purified by flash column chromatography with 0~10% methanol to afford 4-(5-chloro-2-methoxyphenyl)-6-methyl-N-(5-((5-(S-methylsulfonimidoyl)pyridin-2-yl)methoxy)-1,3,4-thiadiazol-2-yl)nicotinamide (70 mg, 28%) as a white solid. MS (ESI) calc'd for ($C_{23}H_{21}ClN_6O_4S_2$) $(M+1)^+$, 545.1; found 545.1.

Step-3: (R)-4-(5-chloro-2-methoxyphenyl)-6-methyl-N-(5-((5-(S-methylsulfonimidoyl)pyridin-2-yl)methoxy)-1,3,4-thiadiazol-2-yl)nicotinamideand (S)-4-(5-chloro-2-methoxyphenyl)-6-methyl-N-(5-((5-(S-methylsulfonimidoyl)pyridin-2-yl)methoxy)-1,3,4-thiadiazol-2-yl)nicotinamide

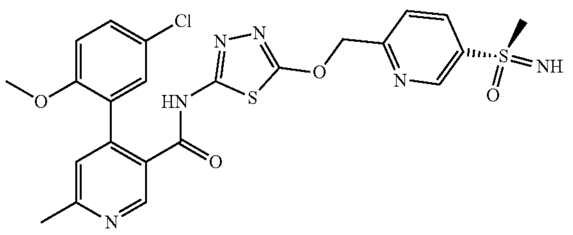

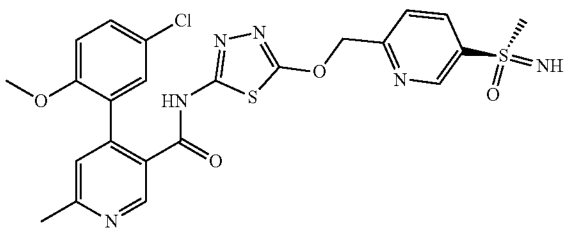

A racemic of 4-(5-chloro-2-methoxyphenyl)-6-methyl-N-(5-((5-(S-methylsulfonimidoyl)pyridin-2-yl)methoxy)-1,3,4-thiadiazol-2-yl)nicotinamide (70 mg) was separated by prep-chiral-HPLC with the following conditions: (Column: CHIRAL ART Cellulose-SB, 2*25 cm, 5 um; Mobile Phase A: Hex:DCM=1:1-HPLC, Mobile Phase B: EtOH-HPLC; Flow rate: 20 mL/min; Gradient: 50 B to 50 B in 10 min; 220/254 nm; RT1: 5.7; RT2: 8.576; Injection Volumn: 2 ml; Number Of Runs: 6) to afford (R)-4-(5-chloro-2-methoxyphenyl)-6-methyl-N-(5-((5-(S-methylsulfonimidoyl)pyridin-2-yl)methoxy)-1,3,4-thiadiazol-2-yl)nicotinamide (23.9 mg, 10%) as a white solid with shorter retention time on chiral HPLC and (S)-4-(5-chloro-2-methoxyphenyl)-6-methyl-N-(5-((5-(S-methylsulfonimidoyl)pyridin-2-yl)methoxy)-1,3,4-thiadiazol-2-yl)nicotinamide (29 mg, 12%) as a white solid with longer retention time on chiral HPLC.

(R)-4-(5-chloro-2-methoxyphenyl)-6-methyl-N-(5-((5-(S-methylsulfonimidoyl)pyridin-2-yl)methoxy)-1,3,4-thiadiazol-2-yl)nicotinamide: MS (ESI) calc'd for ($C_{23}H_{21}ClN_6O_4S_2$) $(M+1)^+$, 545.1; found 545.1. $^1H$ NMR (400 MHz, DMSO-$d_6$) δ 12.80 (s, 1H), 9.06-9.05 (m, 1H), 8.70 (s, 1H), 8.35-8.32 (m, 1H), 7.77-7.75 (m, 1H), 7.46-7.36 (m, 3H), 7.03-7.01 (m, 1H), 5.66 (s, 2H), 4.65-4.34 (m, 1H), 3.51 (s, 3H), 3.17-3.17 (m, 3H), 2.51 (s, 3H).

(S)-4-(5-chloro-2-methoxyphenyl)-6-methyl-N-(5-((5-(S-methylsulfonimidoyl)pyridin-2-yl)methoxy)-1,3,4-thiadiazol-2-yl)nicotinamide: MS (ESI) calc'd for ($C_{23}H_{21}ClN_6O_4S_2$) $(M+1)^+$, 545.1; found 545.1. $^1H$ NMR (400 MHz, DMSO-$d_6$) δ 12.80 (s, 1H), 9.06-9.05 (m, 1H), 8.70 (s, 1H), 8.35-8.32 (m, 1H), 7.77-7.75 (m, 1H), 7.46-7.36 (m, 3H), 7.03-7.01 (m, 1H), 5.66 (s, 2H), 4.55-4.34 (m, 1H), 3.51 (s, 3H), 3.17 (s, 3H), 2.66 (s, 3H).

Example 149 and 150

4-(2-fluoro-6-methoxyphenyl)-6-methyl-N-(5-((5-((R)—S-methylsulfonimidoyl)pyridin-2-yl)methoxy)-1,3,4-thiadiazol-2-yl)nicotinamide (Example 149) and 4-(2-fluoro-6-methoxyphenyl)-6-methyl-N-(5-((5-((S)—S-methylsulfonimidoyl)pyridin-2-yl)methoxy)-1,3,4-thiadiazol-2-yl)nicotinamide (Example 150)

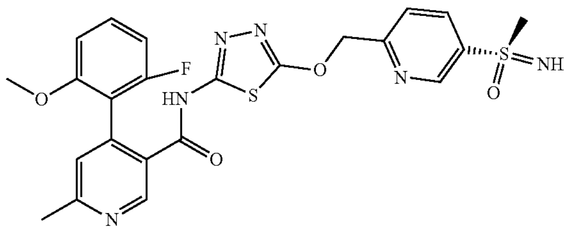

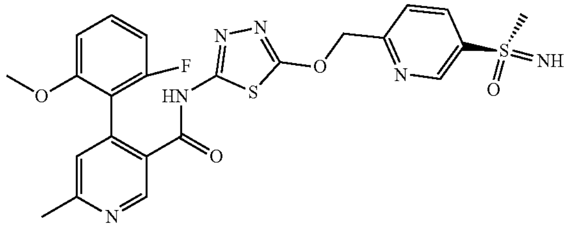

Step-1: methyl 5-(methylthio)picolinate

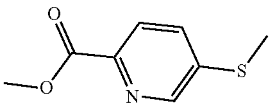

To a solution of 2-bromo-5-(methylthio)pyridine (1 g, 4.95 mmol) in MeOH (10 mL) were added TEA (2 mL) and Pd(dppf)$Cl_2$ (403 mg, 0.49 mmol). The mixture was stirred at 80° C. for 8 hours under CO (10 atm) before concentrated under vacuum. The mixture was diluted with water and extracted with ethyl acetate. The combined organic layers were washed with brine, dried over anhydrous sodium sulfate, filtered, and concentrated under vacuum. The residue was purified by flash column chromatography with 0-50% ethyl acetate in petroleum ether to afford methyl 5-(methylthio)picolinate (800 mg, 88.9%) as yellow solid. MS (ESI) calc'd for ($C_8H_9NO_2S$) $(M+1)^+$, 184.0, found 184.0.

Step-2: (5-(methylthio)pyridin-2-yl)methanol

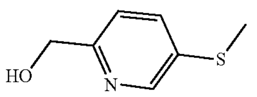

To a solution of methyl 5-(methylthio)picolinate (800 mg, 4.37 mmol) in MeOH (5 mL) was added $NaBH_4$ (166 mg, 4.37 mmol) and $CaCl_2$) (485 mg, 4.37 mmol) in portions at 0° C. The mixture was stirred at room temperature for 2 hours. The reaction mixture was quenched by the addition of water and extracted with ethyl acetate. The combined organic layers were washed with brine, dried over anhydrous sodium sulfate, filtered, and concentrated under vacuum to afford (5-(methylthio)pyridin-2-yl)methanol (500 mg, crude) as a yellow solid. MS (ESI) calc'd for ($C_7H_9NOS$) $(M+1)^+$, 156.0, found 156.0.

Step-3: 5-((5-(methylthio)pyridin-2-yl)methoxy)-1,3,4-thiadiazol-2-amine

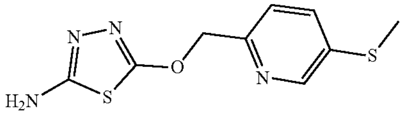

To a solution of NaH (114 mg, 2.85 mmol, 60%) in THF (5 mL) was added a solution of (5-(methylthio)pyridin-2-yl)methanol (300 mg, 1.9 mmol) in THF (2 mL) dropwise at 0° C. and stirred at 0° C. for 1 hour under nitrogen. To the above solution was added 5-bromo-1,3,4-thiadiazol-2-amine (517 mg, 2.85 mmol) at 0° C. under nitrogen. The mixture was stirred at room temperature for 4 hours. The reaction mixture was quenched by the addition of water and extracted with ethyl acetate. The combined organic layers were washed with brine, dried over anhydrous sodium sulfate, filtered, and concentrated under vacuum. The residue was purified by flash chromatography on silica gel with 0-50% ethyl acetate in petroleum ether to afford 5-((5-(methylthio)pyridin-2-yl)methoxy)-1,3,4-thiadiazol-2-amine (260 mg, 32%) as a yellow solid. MS (ESI) calc'd for ($C_9H_{10}N_4OS_2$) $(M+1)^+$, 255.0, found 255.0. $^1H$ NMR (400 MHz, DMSO-$d_6$) δ 8.48-8.47 (m, 1H), 7.77-7.74 (m, 1H), 7.47-7.45 (m, 1H), 6.79 (s, 2H), 5.35 (s, 2H), 2.54-2.50 (m, 3H).

Step-4: 4-(2-fluoro-6-methoxyphenyl)-6-methyl-N-(5-((5-(methylthio)pyridin-2-yl)methoxy)-1,3,4-thiadiazol-2-yl)nicotinamide

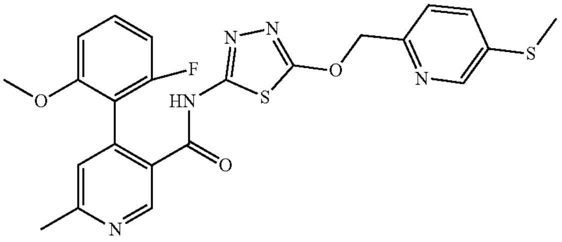

To a solution of 5-((5-(methylsulfanyl)pyridin-2-yl)methoxy)-1,3,4-thiadiazol-2-amine (300 mg, 1.180 mmol) in ACN (2 mL) and DMF (2 mL) was added 4-(2-fluoro-6-methoxyphenyl)-6-methylpyridine-3-carboxylic acid (308 mg, 1.180 mmol, Intermediate F), NMI (290 mg, 3.539 mmol) and TCFH (397 mg, 1.416 mmol). The resulting solution was stirred at room temperature for 2 hours. The mixture was quenched with water and extracted with ethyl acetate. The combined organic layers were washed with brine, dried over anhydrous sodium sulfate, filtered, and concentrated under vacuum. The residue was purified by flash chromatography on silica gel with 0~10% methanol in dichloromethane to afford 4-(2-fluoro-6-methoxyphenyl)-6-methyl-N-(5-((5-(methylthio)pyridin-2-yl)methoxy)-1,3,4-thiadiazol-2-yl)nicotinamide (226 mg, 70.2%) as a yellow solid. MS (ESI) calc'd for ($C_{23}H_{20}FN_5O_3S_2$) $(M+1)^+$, 498.1; found, 498.0.

Step-5: 4-(2-fluoro-6-methoxyphenyl)-6-methyl-N-(5-((5-((R)—S-methylsulfonimidoyl)pyridin-2-yl)methoxy)-1,3,4-thiadiazol-2-yl)nicotinamide and 4-(2-fluoro-6-methoxyphenyl)-6-methyl-N-(5-((5-((S)—S-methylsulfonimidoyl)pyridin-2-yl)methoxy)-1,3,4-thiadiazol-2-yl)nicotinamide

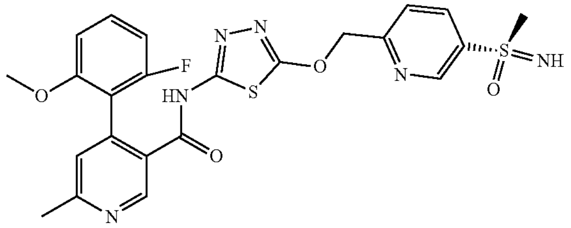

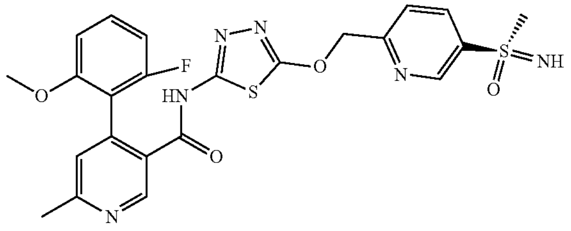

To a solution of 4-(2-fluoro-6-methoxyphenyl)-6-methyl-N-(5-((5-(methylsulfanyl)pyridin-2-yl)methoxy)-1,3,4-thiadiazol-2-yl)pyridine-3-carboxamide (226 mg, 0.454 mmol) in MeOH (5 mL) were added $PhI(OAc)_2$ (655 mg, 0.908 mmol) and $NH_2COONH_4$ (142 mg, 1.816 mmol). The resulting solution was stirred at room temperature for 3 hours. The reaction mixture was quenched with water and extracted with ethyl acetate. The combined organic layers were washed with brine, dried over anhydrous sodium sulfate, filtered, and concentrated under vacuum. The residue was purified by flash chromatography on silica gel 0~10% methanol in dichloromethane to afford racemic 4-(2-fluoro-6-methoxyphenyl)-6-methyl-N-(5-((5-(S-methylsulfonimidoyl)pyridin-2-yl)methoxy)-1,3,4-thiadiazol-2-yl)nicotinamide (184 mg, 67.2%) as a yellow solid, which was separated by prep chiral-HPLC with the following conditions: (Column: CHIRAL ART Cellulose-SB, 2*25 cm, 5 um; Mobile Phase A: Hex:DCM=1:1-HPLC, Mobile Phase B:EtOH-HPLC; Flow rate: 20 mL/min; Gradient: 50 B to 50 B in 10 min; 220/254 nm; RT1: 5.405 min, RT2: 8.15 min) to afford 4-(2-fluoro-6-methoxyphenyl)-6-methyl-N-(5-((5-((R)—S-methylsulfonimidoyl)pyridin-2-yl)methoxy)-1,3,4-thiadiazol-2-yl)nicotinamide (22.5 mg) as a white solid with shorter retention time on chiral HPLC and 4-(2-fluoro-6-methoxyphenyl)-6-methyl-N-(5-((5-((S)—S-methylsulfonimidoyl)pyridin-2-yl)methoxy)-1,3,4-thiadiazol-2-yl)nicotinamide (11.5 mg) as a white solid with longer retention time on chiral HPLC.

4-(2-fluoro-6-methoxyphenyl)-6-methyl-N-(5-((5-((R)—S-methylsulfonimidoyl)pyridin-2-yl)methoxy)-1,3,4-thiadiazol-2-yl)nicotinamide: MS (ESI) calc'd for ($C_{23}H_{21}FN_6O_4S_2$) $(M+1)^+$, 529.1; found, 529.1. $^1H$ NMR (400 MHz, DMSO-$d_6$) δ 12.93 (s, 1H), 9.05 (s, 1H), 8.80 (s, 1H), 8.34-8.31 (m, 1H), 7.75-7.73 (m, 1H), 7.41-7.40 (m, 1H), 7.33-7.31 (m, 1H), 6.94-6.88 (m, 2H), 5.65 (s, 2H), 4.55 (s, 1H), 3.59 (s, 3H), 3.33 (s, 3H), 2.52 (s, 3H).

4-(2-fluoro-6-methoxyphenyl)-6-methyl-N-(5-((5-((S)—S-methylsulfonimidoyl)pyridin-2-yl)methoxy)-1,3,4-thiadiazol-2-yl)nicotinamide: MS (ESI) calc'd for ($C_{23}H_{21}FN_6O_4S_2$) $(M+1)^+$, 529.1; found, 529.1. $^1H$ NMR (400 MHz, DMSO-$d_6$) δ 12.94 (s, 1H), 9.05 (s, 1H), 8.80 (s, 1H), 8.34-8.31 (m, 1H), 7.75-7.73 (m, 1H), 7.41-7.40 (m, 1H), 7.33-7.31 (m, 1H), 6.94-6.88 (m, 2H), 5.65 (s, 2H), 4.55 (s, 1H), 3.59 (s, 3H), 3.33 (s, 3H), 2.52 (s, 3H).

Example 151

2'-chloro-5'-methoxy-6-methyl-N-(5-(5H,7H,8H-pyrano(4,3-b)pyridin-2-ylmethoxy)-1,3,4-thiadiazol-2-yl)-(4,4'-bipyridine)-3-carboxamide

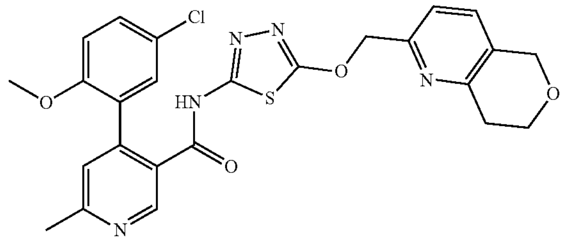 [SMILES: COc1ccc(Cl)cc1-c1cc(C)ncc1C(=O)Nc1nnc(OCc2ccc3c(n2)CCOC3)s1]

To a mixture of 2'-chloro-5'-methoxy-6-methyl-(4,4'-bipyridine)-3-carboxylic acid (5.00 mg, 0.018 mmol, Intermediate H) in MeCN (1.0 mL) and DMF (0.2 mL) were added 5-(5H,7H,8H-pyrano(4,3-b)pyridin-2-ylmethoxy)-1,3,4-thiadiazol-2-amine (5.69 mg, 0.022 mmol, Example 102, Step 3), TCFH (5.54 mg, 0.020 mmol) and NMI (3.09 mg, 0.038 mmol). The resulting solution was stirred at room temperature for 2 h. The solution was concentrated under vacuum. The crude residue was purified by Prep-HPLC with the following conditions: (Column: XBridge Prep OBD C18 Column, 30×150 mm 5 um; Mobile Phase A: Water (10 MMOL/L $NH_4HCO_3$), Mobile Phase B: ACN; Flow rate: 60 mL/min; Gradient: B to 7 B in 40 min; 254/220 nm; RT 1: 6.0 min) to afford 2'-chloro-5'-methoxy-6-methyl-N-(5-(5H,7H,8H-pyrano(4,3-b)pyridin-2-ylmethoxy)-1,3,4-thiadiazol-2-yl)-(4,4'-bipyridine)-3-carboxamide (1.3 mg, 13%) as a white solid. MS (ESI) calc'd for ($C_{24}H_{21}ClN_6O_4S$) $(M+1)^+$, 525.0, found 525.0. $^1H$ NMR (400 MHz, Methanol-$d_4$) δ 8.83 (s, 1H), 8.08 (d, J=4.4 Hz, 1H), 7.57 (d, J=7.6 Hz, 1H), 7.52-7.37 (m, 3H), 5.51 (s, 2H), 4.80 (s, 2H), 4.09 (t, J=5.6 Hz, 2H), 3.73 (s, 3H), 2.99 (t, J=5.6 Hz, 2H), 2.67 (s, 3H).

Example 153

2'-chloro-N-(5-((4,4-difluorocyclohexyl)methoxy)-1,3,4-thiadiazol-2-yl)-5'-methoxy-6-methyl-(4,4'-bipyridine)-3-carboxamide

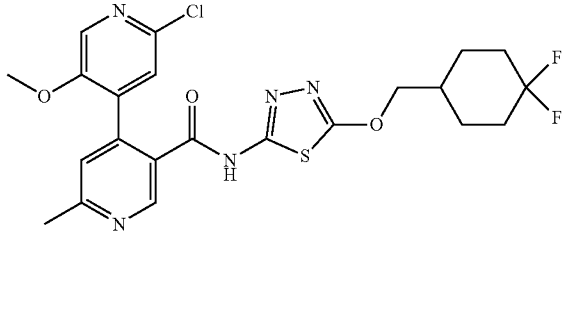 [SMILES: COc1cnc(Cl)cc1-c1cc(C)ncc1C(=O)Nc1nnc(OCC2CCC(F)(F)CC2)s1]

Step-1: ((4,4-difluorocyclohexyl)methoxy)(methylsulfanyl)methanethione

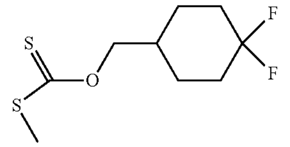

To a mixture of (4,4-difluorocyclohexyl)methanol (500.0 mg, 3.33 mmol) in THF (10.0 mL) was added NaH (159.80 mg, 6.65 mmol) in portions at 0° C. and stirred at 0° C. for 30 min. To the above mixture was added $CS_2$ (380.28 mg, 4.99 mmol) dropwise at 0° C. and stirred at 0° C. for 10 min. Then MeI (708.9 mg, 4.99 mmol) was added to the above mixture dropwise at 0° C. The resulting solution was stirred at 0° C. for 30 min. The reaction mixture was quenched with water and extracted with ethyl acetate. The combined organic solution was dried over sodium sulfate, filtered, and concentrated under vacuum to afford ((4,4-difluorocyclohexyl)methoxy)(methylsulfanyl)methanethione (889.0 mg, crude) as a yellow oil.

Step-2: ((((4,4-difluorocyclohexyl)methoxy)methanethioyl)amino)amine

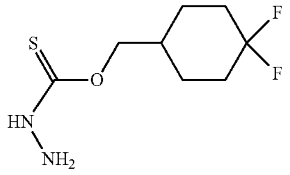 [SMILES: NNC(=S)OCC1CCC(F)(F)CC1]

To a mixture of ((4,4-difluorocyclohexyl)methoxy)(methylsulfanyl)methanethione (787.0 mg, 3.27 mmol) in MeOH (10.0 mL) was added Hydrazine (125.9 mg, 3.93 mmol, 80%). The mixture was stirred at room temperature for 2 h. The reaction mixture was quenched with water and extracted with ethyl acetate. The combined organic layers were washed with brine, dried over anhydrous sodium sulfate, filtered, and concentrated under vacuum to afford ((((4,4-difluorocyclohexyl)methoxy)methanethioyl)amino)amine (720 mg, crude) as a yellow oil. MS (ESI) calc'd for $(C_8H_{14}F_2N_2OS)$ $(M-1)^+$, 223.0, found 223.0.

Step-3: 5-((4,4-difluorocyclohexyl)methoxy)-1,3,4-thiadiazol-2-amine

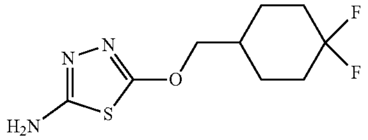 [SMILES: Nc1nnc(OCC2CCC(F)(F)CC2)s1]

To a mixture of ((((4,4-difluorocyclohexyl)methoxy)methanethioyl)amino)amine (711.0 mg, 3.17 mmol) and TEA (641.6 mg, 6.34 mmol) in MeOH (10.0 mL) was added BrCN (369.38 mg, 3.487 mmol). The resulting solution was stirred at room temperature for 30 min. The reaction mixture was quenched with water and extracted with ethyl acetate. The combined organic layers were washed with brine, dried over anhydrous sodium sulfate, filtered, and concentrated under vacuum. The crude residue was purified by reverse phase flash column chromatography with 5~87% acetonitrile in water to afford 5-((4,4-difluorocyclohexyl)methoxy)-1,3,4-thiadiazol-2-amine (245.0 mg, 31%) as a yellow solid. MS (ESI) calc'd for $(C_9H_{13}F_2N_3OS)$ $(M+1)^+$, 250.0, found 250.1.

Step-4: 2'-chloro-N-(5-((4,4-difluorocyclohexyl)methoxy)-1,3,4-thiadiazol-2-yl)-5'-methoxy-6-methyl-(4,4'-bipyridine)-3-carboxamide

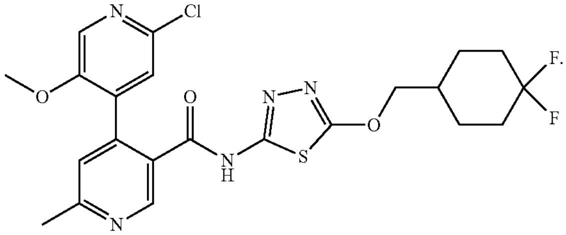 [SMILES: COc1cnc(Cl)cc1-c1cc(C)ncc1C(=O)Nc1nnc(OCC2CCC(F)(F)CC2)s1]

To a mixture of 2'-chloro-5'-methoxy-6-methyl-(4,4'-bipyridine)-3-carboxylic acid (50.00 mg, 0.17 mmol, Intermediate H) in MeCN (2.0 mL) and DMF (0.1 mL) were added 5-((4,4-difluorocyclohexyl)methoxy)-1,3,4-thiadiazol-2-amine (58.14 mg, 0.23 mmol), TCFH (55.37 mg, 0.19 mmol) and NMI (30.93 mg, 0.37 mmol). The resulting solution was stirred at room temperature for 2 h. The resulting mixture was concentrated under vacuum. The crude residue was purified by flash column chromatography with 5~49% acetonitrile in water to afford 2-chloro-N-(5-((4,4-difluorocyclohexyl)methoxy)-1,3,4-thiadiazol-2-yl)-5-methoxy-6-methyl-(4,4-bipyridine)-3-carboxamide (21.9 mg, 23%) as a white solid. MS (ESI) calc'd for $(C_{22}H_{22}ClF_2N_5O_3S)$ $(M+1)^+$, 510.1, found 510.2. $^1H$ NMR (400 MHz, DMSO-$d_6$) δ 12.92 (s, 1H), 8.81 (s, 1H), 8.17 (s, 1H), 7.48 (d, J=4.4 Hz, 2H), 4.31 (d, J=6.4 Hz, 2H), 3.63 (s, 3H), 2.59 (s, 3H), 2.02-1.98 (m, 3H), 1.91-1.68 (m, 3H), 1.41-1.21 (m, 3H).

Example 154 and Example 155

N-(5-((4-((R)—N,S-dimethylsulfonimidoyl)benzyl)oxy)-1,3,4-thiadiazol-2-yl)-4-(2-fluoro-6-methoxyphenyl)-6-methylnicotinamide (Example 154) and N-(5-((4-((S)—N,S-dimethylsulfonimidoyl)benzyl)oxy)-1,3,4-thiadiazol-2-yl)-4-(2-fluoro-6-methoxyphenyl)-6-methylnicotinamide (Example 155)

(Example 154)

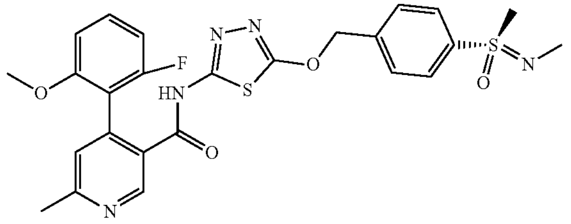

-continued (Example 155)

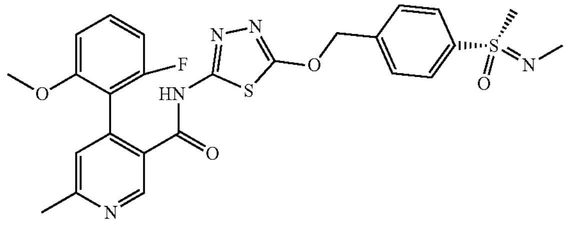

Step-1: tert-butyl N-(5-((4-(methylsulfanyl)phenyl) methoxy)-1,3,4-thiadiazol-2-yl)carbamate

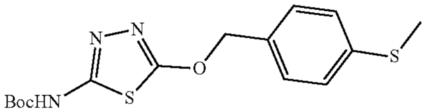 [SMILES: CSc1ccc(COc2nnc(NC(=O)OC(C)(C)C)s2)cc1]

To a stirred solution of 5-((4-(methylsulfanyl)phenyl) methoxy)-1,3,4-thiadiazol-2-amine(4.6 g, 18.15 mmol) and $Boc_2O$ (4.4 g, 19.97 mmol) in DCM (50 mL) was added DMAP (221 mg, 1.81 mmol). The resulting mixture was stirred at 25° C. for 16 h before concentrated under vacuum. The residue was purified by flash column chromatography with ethyl acetate in petroleum ether (0~60%) to afford tert-butyl N-(5-((4-(methylsulfanyl)phenyl)methoxy)-1,3,4-thiadiazol-2-yl)carbamate (3.5 g, 70%) as a yellow solid. MS (ESI) calc'd for ($C_{15}H_{19}N_3O_3S_2$) $(M+1)^+$, 354.1; found 354.1.

Step-2: tert-butyl N-(5-((4-(imino(methyl)oxo-lambda6-sulfanyl)phenyl)methoxy)-1,3,4-thiadiazol-2-yl)carbamate

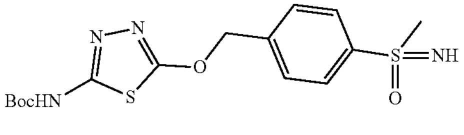 [SMILES: CC(C)(C)OC(=O)Nc1nnc(OCc2ccc(S(C)(=N)=O)cc2)s1]

To a stirred solution of tert-butyl N-(5-((4-(methylsulfanyl)phenyl)methoxy)-1,3,4-thiadiazol-2-yl)carbamate (3.1 g, 8.77 mmol) and ammonium carbamate (2.7 g, 35.08 mmol) in MeOH (100 mL) was added Iodobenzene diacetate (12.6 g, 39.46 mmol) under nitrogen atmosphere. The resulting mixture was stirred at 25° C. for 16 h before concentrated under vacuum. The residue was purified by reverse phase flash column chromatography with acetonitrile in water (5~80%) to afford tert-butyl N-(5-((4-(imino(methyl) oxo-lambda6-sulfanyl)phenyl)methoxy)-1,3,4-thiadiazol-2-yl)carbamate (2.0 g, 59%) as a yellow solid. MS (ESI) calc'd for ($C_{15}H_{20}N_4O_4S_2$) $(M+1)^+$, 385.1; found 385.1.

Step-3: tert-butyl (5-((4-(N,S-dimethylsulfonimidoyl)benzyl)oxy)-1,3,4-thiadiazol-2-yl)carbamate

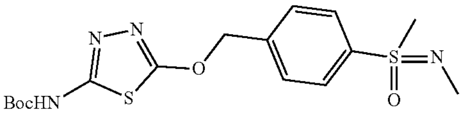 [SMILES: CN=S(C)(=O)c1ccc(COc2nnc(NC(=O)OC(C)(C)C)s2)cc1]

To a stirred solution of tert-butyl N-(5-((4-(imino(methyl) oxo-lambda6-sulfanyl)phenyl)methoxy)-1,3,4-thiadiazol-2-yl)carbamate (1.0 g, 2.60 mmol) in dioxane (20 mL) were added $MeB(OH)_2$ (311 mg, 5.20 mmol), $Cu(OAc)_2$ (708 mg, 3.90 mmol) and Pyridine (493 mg, 6.24 mmol). The resulting mixture was stirred at 100° C. for 2 h under oxygen atmosphere. The solvent was removed under vacuum. The residue was purified by reverse phase FC with acetonitrile in water (5~55%) to afford tert-butyl (5-((4-(N,S-dimethylsulfonimidoyl)benzyl)oxy)-1,3,4-thiadiazol-2-yl)carbamate (550 mg, 53%) as a yellow solid. MS (ESI) calc'd for ($C_{16}H_{22}N_4O_4S_2$) $(M+1)^+$, 399.1; found 399.1.

Step-4: 5-((4-(methyl(methylimino)oxo-lambda6-sulfanyl)phenyl)methoxy)-1,3,4-thiadiazol-2-amine

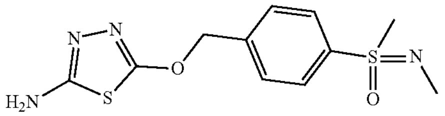 [SMILES: CN=S(C)(=O)c1ccc(COc2nnc(N)s2)cc1]

To a stirred solution of tert-butyl (5-((4-(N,S-dimethylsulfonimidoyl)benzyl)oxy)-1,3,4-thiadiazol-2-yl)carbamate (550 mg, 1.38 mmol) in DCM (4.5 mL) was added TFA (1.5 mL). The resulting mixture was stirred at 25° C. for 2 h under nitrogen atmosphere. The resulting mixture was concentrated under reduced pressure. The residue was basified to pH ~8 with saturated $NaHCO_3$ (aq.). The residue was purified by reverse phase flash column chromatography with acetonitrile in water (5~70%) to afford 5-((4-(methyl(methylimino)oxo-lambda6-sulfanyl)phenyl)methoxy)-1,3,4-thiadiazol-2-amine (200 mg, 46%) as a white solid. MS (ESI) calc'd for ($C_{11}H_{14}N_4O_2S_2$) $(M+1)^+$, 299.1; found, 299.1.

Step-5: N-(5-((4-((R)—N,S-dimethylsulfonimidoyl) benzyl)oxy)-1,3,4-thiadiazol-2-yl)-4-(2-fluoro-6-methoxyphenyl)-6-methylnicotinamide (Example 154) and N-(5-((4-((S)—N,S-dimethylsulfonimidoyl)benzyl)oxy)-1,3,4-thiadiazol-2-yl)-4-(2-fluoro-6-methoxyphenyl)-6-methylnicotinamide (Example 155)

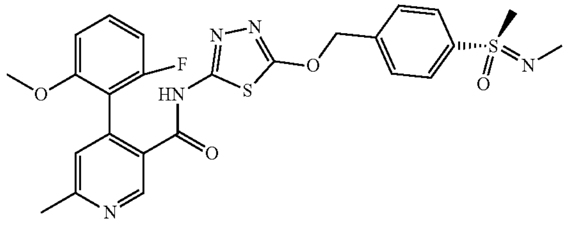

-continued

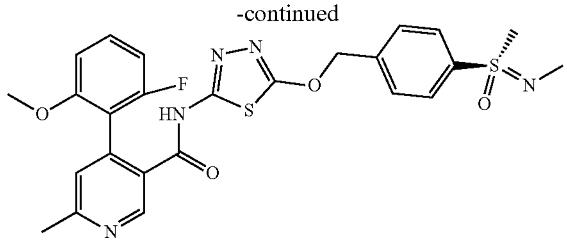

To a stirred solution of 5-((4-(methyl(methylimino)oxo-lambda6-sulfanyl)phenyl)methoxy)-1,3,4-thiadiazol-2-amine (180 mg, 0.60 mmol) and 4-(2-fluoro-6-methoxyphenyl)-6-methylpyridine-3-carboxylic acid (157 mg, 0.60 mmol, Intermediate F) in DMF (2 mL) were added NMI (198 mg, 2.41 mmol) and TCFH (253 mg, 0.90 mmol). The mixture resulting was stirred at 25° C. for 1 h under nitrogen atmosphere. The residue was purified by reverse phase flash column chromatography with acetonitrile in water (5~45%) to afford the racemic product. The racemic compound (200 mg) was separated by prep-chiral HPLC with the following conditions: (Column: CHIRAL ART Cellulose-SC, 2*25 cm, 5 μm; Mobile Phase A: Hex:DCM=3:1-HPLC, Mobile Phase B: EtOH-HPLC; Flow rate: 18 mL/min; Gradient: 50% B to 50% B in 14 min; Wave Length: 220/254 nm; RT1 (min): 8.994; RT2 (min): 11.639; Sample Solvent: EtOH: DCM=1: 1-HPLC; Injection Volume: 1 mL; Number Of Runs: 4) to afford N-(5-((4-((R)—N,S-dimethylsulfonimidoyl)benzyl)oxy)-1,3,4-thiadiazol-2-yl)-4-(2-fluoro-6-methoxyphenyl)-6-methylnicotinamide (51.1 mg, 15%) as a white solid with shorter retention time on chiral HPLC and N-(5-((4-((S)—N,S-dimethylsulfonimidoyl)benzyl)oxy)-1,3,4-thiadiazol-2-yl)-4-(2-fluoro-6-methoxyphenyl)-6-methylnicotinamide (23.1 mg, 11%) as a white solid with longer retention time on chiral HPLC.

N-(5-((4-((R)—N,S-dimethylsulfonimidoyl)benzyl)oxy)-1,3,4-thiadiazol-2-yl)-4-(2-fluoro-6-methoxyphenyl)-6-methylnicotinamide MS (ESI) calc'd for ($C_{25}H_{24}FN_5O_4S_2$) $(M+1)^+$, 542.2; found, 542.2. $^1$H NMR (400 MHz, DMSO-$d_6$) δ 12.90 (s, 1H), 8.81 (s, 1H), 7.90-7.83 (m, 2H), 7.76-7.70 (m, 2H), 7.46-7.36 (m, 1H), 7.33 (d, J=1.6 Hz, 1H), 6.97-6.86 (m, 2H), 5.60 (s, 2H), 3.59 (s, 3H), 3.12 (s, 3H), 2.57 (s, 3H), 2.47 (s, 3H).

N-(5-((4-((S)—N,S-dimethylsulfonimidoyl)benzyl)oxy)-1,3,4-thiadiazol-2-yl)-4-(2-fluoro-6-methoxyphenyl)-6-methylnicotinamide MS (ESI) calc'd for ($C_{25}H_{24}FN_5O_4S_2$) $(M+1)^+$, 542.2; found, 542.3. $^1$H NMR (400 MHz, DMSO-$d_6$) δ 12.87 (s, 1H), 8.83 (d, J=2.4 Hz, 1H), 7.90-7.83 (m, 2H), 7.73 (d, J=8.0 Hz, 2H), 7.45-7.350 (m, 1H), 7.31 (d, J=2.4 Hz, 1H), 6.96-6.86 (m, 2H), 5.59 (s, 2H), 3.59 (s, 3H), 3.12 (s, 3H), 2.57 (s, 3H), 2.52 (s, 3H).

Example 156

2'-chloro-N-(5-((2-isobutyryl-2-azabicyclo[2.2.1]heptan-5-yl)methoxy)-1,3,4-thiadiazol-2-yl)-5'-methoxy-6-methyl-[4,4'-bipyridine]-3-carboxamide

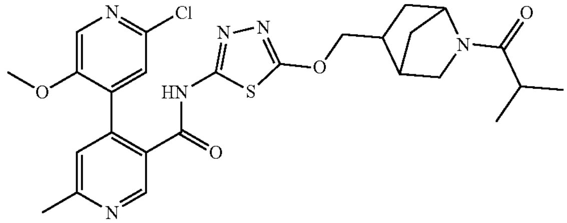 [SMILES: COc1cnc(Cl)cc1-c1cc(C)ncc1C(=O)Nc1nnc(OCC2CC3CC2CN3C(=O)C(C)C)s1]

Step-1: tert-butyl 5-(hydroxymethyl)-2-azabicyclo(2.2.1)heptane-2-carboxylate

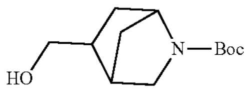

To a stirred solution of 2-(tert-butoxycarbonyl)-2-azabicyclo(2.2.1)heptane-5-carboxylic acid (480 mg, 1.98 mmol) in THF (4 mL, 49 mmol) was added $LiAlH_4$ (151 mg, 3.97 mmol) in portions at 0° C. under nitrogen atmosphere. The resulting mixture was stirred at 0° C. for 2 h. The reaction mixture was quenched by water and the residue was purified by reverse flash chromatography with the following conditions: (column, C18 silica gel; mobile phase, acetonitrile in water, 5% to 35% gradient in 10 min; detector, UV 254 nm) to afford tert-butyl 5-(hydroxymethyl)-2-azabicyclo(2.2.1)heptane-2-carboxylate (300 mg, 66%) as an off-white oil. MS (ESI) calc'd for ($C_{12}H_{21}NO_3$) $(M+1)^+$, 228.2; found 228.2.

Step-2: tert-butyl 5-((((methylthio)carbonothioyl)oxy)methyl)-2-azabicyclo(2.2.1)heptane-2-carboxylate

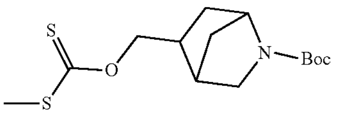 [SMILES: CSC(=S)OCC1CC2CC1CN2C(=O)OC(C)(C)C]

To a stirred solution of tert-butyl 5-(hydroxymethyl)-2-azabicyclo(2.2.1)heptane-2-carboxylate (300 mg, 1.32 mmol) in THF (2 mL) was added NaH (63 mg, 2.64 mmol, 60%) in portions at 0° C. under nitrogen atmosphere. The resulting mixture was stirred at 0° C. for 30 min. Then to the mixture was added $CS_2$ (150 mg, 1.98 mmol) and stirred at 0° C. for 20 min. To the above mixture was added MeI (281 mg, 1.98 mmol). The resulting mixture was stirred at room temperature for 2 h. The reaction was quenched with water and was extracted with ethyl acetate. The combined organic layers were washed with brine, dried over anhydrous $Na_2SO_4$. After filtration, the filtrate was concentrated under reduced pressure. The residue was purified by silica gel column chromatography, eluted with 0-35% ethyl acetate in petroleum ether to afford tert-butyl 5-((((methylthio)carbonothioyl)oxy)methyl)-2-azabicyclo(2.2.1)heptane-2-carboxylate (280 mg, 66%) as a yellow oil. MS (ESI) calc'd for ($C_{14}H_{23}NO_3S_2$) $(M+1)^+$, 318.1; found 318.1.

Step-3: tert-butyl 5-(((aminocarbamothioyl)oxy)methyl)-2-azabicyclo(2.2.1)heptane-2-carboxylate

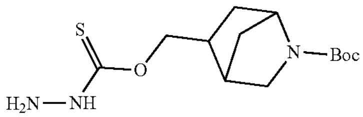

To a stirred solution of tert-butyl tert-butyl 5-((((methylthio)carbonothioyl)oxy)methyl)-2-azabicyclo(2.2.1)heptane-2-carboxylate (280 mg, 0.88 mmol) in MeOH (3 mL) was added Hydrazine (28 mg, 0.88 mmol) dropwise at 0° C. The resulting mixture was stirred at 0° C. for 1 h. The solvent was removed by concentrated under vacuum to afford tert-butyl 5-(((aminocarbamothioyl)oxy)methyl)-2-azabicyclo(2.2.1)heptane-2-carboxylate (242 mg, 86%) as a white solid. MS (ESI) calc'd for ($C_{13}H_{23}NO_3S_2$) $(M+1)^+$, 302.1; found, 302.1.

Step-4: tert-butyl 5-(((5-amino-1,3,4-thiadiazol-2-yl)oxy)methyl)-2-azabicyclo(2.2.1)heptane-2-carboxylate

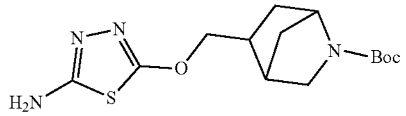

To a stirred solution of tert-butyl 5-(((aminocarbamothioyl)oxy)methyl)-2-azabicyclo(2.2.1)heptane-2-carboxylate (242 mg, 0.80 mmol) in MeOH (3 mL) were added BrCN (93 mg, 0.88 mmol) and TEA (162 mg, 1.61 mmol). The resulting mixture was stirred for 1 h at 0° C. The reaction was quenched with water and was extracted with ethyl acetate. The combined organic layers were washed with saturated sodium chloride, dried over anhydrous $Na_2SO_4$. The residue was purified by silica gel column chromatography, eluted with 0~65% ethyl acetate in petroleum ether to afford tert-butyl 5-(((5-amino-1,3,4-thiadiazol-2-yl)oxy)methyl)-2-azabicyclo(2.2.1)heptane-2-carboxylate (230 mg, 87%) as a pink oil. MS (ESI) calc'd for ($C_{14}H_{22}N_4O_3S$) $(M+1)^+$, 327.1; found, 327.1.

Step-5: tert-butyl 5-(((5-(2'-chloro-5'-methoxy-6-methyl-[4,4'-bipyridine]-3-carboxamido)-1,3,4-thiadiazol-2-yl)oxy)methyl)-2-azabicyclo[2.2.1]heptane-2-carboxylate

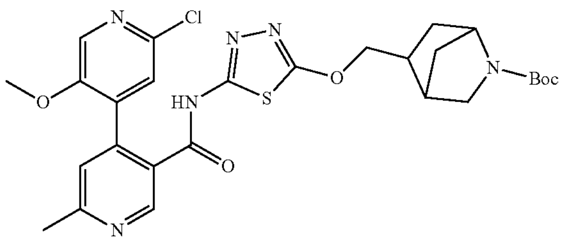 [SMILES: COc1cnc(Cl)cc1-c1cc(C)ncc1C(=O)Nc1nnc(OCC2CC3CC2CN3C(=O)OC(C)(C)C)s1]

To a stirred solution of tert-butyl 5-(((5-amino-1,3,4-thiadiazol-2-yl)oxy)methyl)-2-azabicyclo(2.2.1)heptane-2-carboxylate (100 mg, 0.36 mmol) and 2'-chloro-5'-methoxy-6-methyl-(4,4'-bipyridine)-3-carboxylic acid (100 mg, 0.36 mmol, Intermediate H) in DMF (2 mL) were added TCFH (151 mg, 0.55 mmol) and NMI (118 mg, 1.47 mmol). The resulting mixture was stirred at 25° C. for 1 h. The resulting mixture was purified reverse phase column chromatography, eluted with 0~55% acetonitrile in water to afford tert-butyl 5-(((5-(2'-chloro-5'-methoxy-6-methyl-[4,4'-bipyridine]-3-carboxamido)-1,3,4-thiadiazol-2-yl)oxy)methyl)-2-azabicyclo[2.2.1]heptane-2-carboxylate (120 mg, 55%) as a red solid. MS (ESI) calc'd for ($C_{27}H_3ClN_6O_5S$) $(M+1)^+$, 587.2; found 587.2.

Step-6: N-(5-((2-azabicyclo[2.2.1]heptan-5-yl)methoxy)-1,3,4-thiadiazol-2-yl)-2'-chloro-5'-methoxy-6-methyl-[4,4'-bipyridine]-3-carboxamide

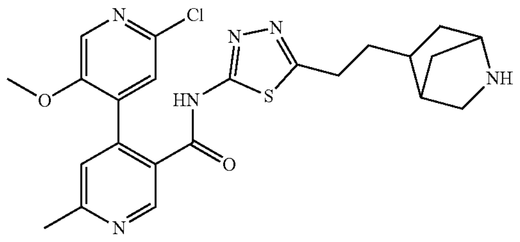 [SMILES: COc1cnc(Cl)cc1-c1cc(C)ncc1C(=O)Nc1nnc(CCC2CC3CC2CN3)s1]

To a stirred solution of tert-butyl 5-(((5-(2'-chloro-5'-methoxy-6-methyl-[4,4'-bipyridine]-3-carboxamido)-1,3,4-thiadiazol-2-yl)oxy)methyl)-2-azabicyclo[2.2.1]heptane-2-carboxylate (120 mg, 0.20 mmol) in DCM (3 mL) was added TFA (1 mL, 0.009 mmol). The mixture resulting was stirred at 25° C. for 2 h. The resulting mixture was concentrated under reduced pressure to afford N-(5-((2-azabicyclo[2.2.1]heptan-5-yl)methoxy)-1,3,4-thiadiazol-2-yl)-2'-chloro-5'-methoxy-6-methyl-[4,4'-bipyridine]-3-carboxamide (170 mg, crude) as a yellow oil. MS (ESI) calc'd for ($C_{22}H_{23}ClN_6O_3S$) $(M+1)^+$, 487.1; found 487.1.

Step-7: 2'-chloro-N-(5-((2-isobutyryl-2-azabicyclo[2.2.1]heptan-5-yl)methoxy)-1,3,4-thiadiazol-2-yl)-5'-methoxy-6-methyl-[4,4'-bipyridine]-3-carboxamide

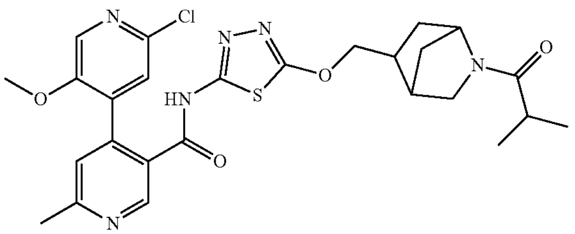 [SMILES: COc1cnc(Cl)cc1-c1cc(C)ncc1C(=O)Nc1nnc(OCC2CC3CC2CN3C(=O)C(C)C)s1]

To a stirred solution of N-(5-((2-azabicyclo[2.2.1]heptan-5-yl)methoxy)-1,3,4-thiadiazol-2-yl)-2'-chloro-5'-methoxy-6-methyl-[4,4'-bipyridine]-3-carboxamide (170 mg, 0.57 mmol) and isobutyric acid (30.7 mg, 0.575 mmol) in DMF (3 mL) were added NMI (188 mg, 2.30 mmol) and TCFH (151 mg, 0.86 mmol). The mixture resulting was stirred at 25° C. for 1 h. The residue was purified by reverse phase flash column chromatography with 5~45% acetonitrile in water to afford 2'-chloro-N-(5-((2-isobutyryl-2-azabicyclo[2.2.1]heptan-5-yl)methoxy)-1,3,4-thiadiazol-2-yl)-5'-methoxy-6-methyl-[4,4'-bipyridine]-3-carboxamide (53.1 mg, 16%) as a white solid. MS (ESI) calc'd for ($C_{26}H_{29}ClN_6O_4S$) $(M+1)^+$, 557.2; found 557.3. $^1H$ NMR (400 MHz, DMSO-$d_6$) δ 12.89 (s, 1H), 8.81 (s, 1H), 8.17 (s, 1H), 7.54 (s, 1H), 7.43 (s, 1H), 4.43-4.24 (m, 3H), 3.64 (s, 3H), 3.48-3.38 (m, 1H), 3.22-3.16 (m, 2H), 2.59 (s, 3H), 2.29-2.22 (m, 2H), 1.78-1.33 (m, 4H), 1.34-0.88 (m, 6H).

Example 157

2-morpholino-N-(5-((tetrahydro-2H-pyran-4-yl)methoxy)-1,3,4-thiadiazol-2-yl)nicotinamide

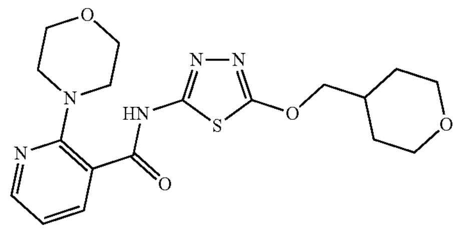 [SMILES: O=C(Nc1nnc(OCC2CCOCC2)s1)c1cccnc1N1CCOCC1]

Step 1 S-methyl O-((tetrahydro-2H-pyran-4-yl)methyl) carbonodithioate

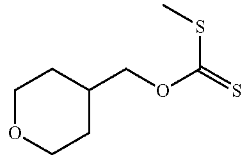

To a stirred solution of (oxan-4-yl)methanol (3.00 g, 25.826 mmol, 1.00 equiv) in THF (30 mL) in a 100 mL 3-necked round-bottom flask, was added NaH (1.24 g, 51.713 mmol, 2.00 equiv) dropwise at 0° C. under nitrogen atmosphere. $CS_2$ (2.95 g, 38.744 mmol, 1.50 equiv) was added to the above mixture at 0° C. And the mixture was stirred for 10 min, MeI (4.39 g, 30.985 mmol, 1.20 equiv) was added at 0° C. The mixture was stirred for 3 h at room temperature under nitrogen atmosphere. The reaction was monitored by TLC. The reaction was quenched by the addition of saturated $NH_4Cl$ (aq.) (50 mL) at room temperature. The aqueous layer was extracted with EtOAc (4×50 mL). The resulting mixture was concentrated under vacuum. The residue was purified by silica gel column (PE:EtOAc=5:1) to afford (methylsulfanyl)((oxan-4-yl)methoxy)methanethione (1.4 g) as light yellow oil.

Step 2 O-((tetrahydro-2H-pyran-4-yl)methyl) hydrazinecarbothioate

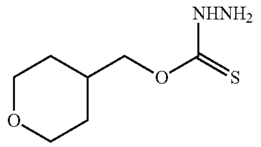 [SMILES: NNC(=S)OCC1CCOCC1]

Into a 50 mL 3-necked round-bottom flask were added (methylsulfanyl)((oxan-4-yl)methoxy)methanethione (1.40 g, 6.785 mmol, 1.00 equiv) and hydrazine (326.00 mg, 10.178 mmol, 1.50 equiv) in MeOH (14 mL) at room temperature. The mixture was evaporated and the residue was re-dissolved in 4 mL of MeOH and the solution was evaporated again. The crude product was used in the next step directly without further purification.

Step 3 5-((tetrahydro-2H-pyran-4-yl)methoxy)-1,3,4-thiadiazol-2-amine

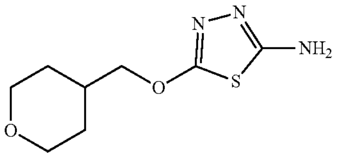 [SMILES: Nc1nnc(OCC2CCOCC2)s1]

To a stirred solution of ((((oxan-4-yl)methoxy)methanethioyl)amino)amine (1.29 g, 6.780 mmol, 1.00 equiv) and BrCN (865.80 mg, 8.140 mmol, 1.20 equiv) in MeOH (13 mL) in a 50 mL 3-necked round-bottom flask, was added $Et_3N$ (1.37 g, 13.560 mmol, 2.00 equiv). The mixture was stirred for 1 h at room temperature under nitrogen atmosphere. The reaction was monitored by TLC. The solution was evaporated and precipitated by the addition of MeOH. This resulted in 5-((tetrahydro-2H-pyran-4-yl)methoxy)-1,3,4-thiadiazol-2-amine (560 mg) as a white solid.

Step 4 2-morpholino-N-(5-((tetrahydro-2H-pyran-4-yl)methoxy)-1,3,4-thiadiazol-2-yl)nicotinamide

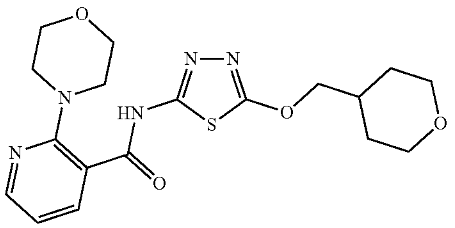 [SMILES: O=C(Nc1nnc(OCC2CCOCC2)s1)c1cccnc1N1CCOCC1]

To a stirred solution 5-((oxan-4-yl)methoxy)-1,3,4-thiadiazol-2-amine (100.00 mg, 0.465 mmol, 1.00 equiv) and triethylamine (94.01 mg, 0.929 mmol, 2.00 equiv) in DCM (1 mL) in an 8 mL vial, was added 2-(morpholin-4-yl)pyridine-3-carbonyl chloride (105.29 mg, 0.465 mmol, 1.00 equiv) dropwise at room temperature under nitrogen atmosphere. The reaction was quenched with 1 mL water at room temperature. The aqueous layer was extracted with EtOAc (3×1 mL). The resulting mixture was concentrated under vacuum. The residue was purified by Prep-TLC ($CH_2Cl_2$:MeOH=40:1). The crude product was precipitated by 1 mL MeOH to afford 2-(morpholin-4-yl)-N-(5-((oxan-4-yl)methoxy)-1,3,4-thiadiazol-2-yl)pyridine-3-carboxamide (67.0 mg) as a white solid. LC-MS m z $(M+H)^+$406, $^1H$ NMR (300 MHz, DMSO, ppm): 612.84-12.88 (d, 1H), 8.34-8.36 (m, 1H), 7.89-7.92 (m, 1H), 6.97-7.01 (m, 1H), 4.29-4.32 (d, 2H), 3.85-3.90 (m, 2H), 3.65-3.68 (t, 4H), 3.28-3.29 (d, 2H), 3.17-3.24 (m, 4H), 2.06-2.15 (m, 1H), 1.58-1.69 (m, 2H), 1.23-1.40 (m, 2H).

Example 158

N-(5-((1,1-dioxidotetrahydro-2H-thiopyran-4-yl)methoxy)-1,3,4-thiadiazol-2-yl)-4-(2-fluoro-6-methoxyphenyl)-6-methylnicotinamide

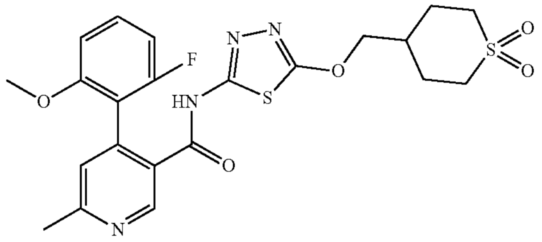 [SMILES: COc1cccc(F)c1-c1cc(C)ncc1C(=O)Nc1nnc(OCC2CCS(=O)(=O)CC2)s1]

Step-1: O-((1,1-dioxidotetrahydro-2H-thiopyran-4-yl)methyl)S-methyl carbonodithioate

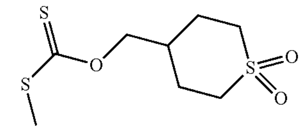

To a stirred solution of 4-(hydroxymethyl)tetrahydro-2H-thiopyran 1,1-dioxide (260.0 mg, 1.58 mmol) in THF (3 mL) was added NaH (127.0 mg, 3.20 mmol, 60%) in portions at 0° C. and stirred at 0° C. for 30 min under nitrogen atmosphere. Then $CS_2$ (179.0 mg, 2.36 mmol) was added to the above mixture and stirred at 0° C. for 10 min. and then MeI (335.0 mg, 2.36 mmol) was added to the above mixture at 0° C. The resulting mixture was stirred at 23° C. for 2 hr. The resulting mixture was stirred at room temperature for 1 hour. The reaction mixture was quenched by the addition of water and extracted with ethyl acetate. The combined organic layers were washed with brine, dried over anhydrous sodium sulfate, filtered, and concentrated under vacuum to afford O-((1,1-dioxidotetrahydro-2H-thiopyran-4-yl)methyl)S-methyl carbonodithioate (286.0 mg, 64%) as a white solid. MS (ESI) calculated for ($C_8H_{14}O_3S_3$) $(M+1)^+$, 255.0; found, 255.0.

Step-2: O-((1,1-dioxidotetrahydro-2H-thiopyran-4-yl)methyl hydrazinecarbothioate

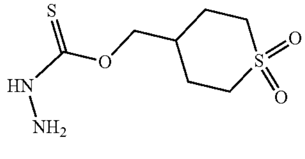

To a stirred solution of O-((1,1-dioxidotetrahydro-2H-thiopyran-4-yl)methyl)S-methyl carbonodithioate (282.0 mg, 0.37 mmol) in MeOH (1 mL) was added Hydrazine (45.0 mg, 0.37 mmol) dropwise at 0° C. The resulting mixture was stirred at room temperature for 2 hr. The resulting mixture was concentrated under vacuum. The reaction mixture was diluted with water and extracted with ethyl acetate. The combined organic layers were washed with brine, dried over anhydrous sodium sulfate, filtered, and concentrated under vacuum to afford O-((1,1-dioxidotetrahydro-2H-thiopyran-4-yl)methyl) hydrazinecarbothioate (240.0 mg, crude) as a white solid. MS (ESI) calculated for ($C_7H_{14}N_2O_3S_2$) $(M+1)^+$, 239.0; found, 239.0.

Step-3: 4-(((5-amino-1,3,4-thiadiazol-2-yl)oxy)methyl)tetrahydro-2H-thiopyran 1,1-dioxide

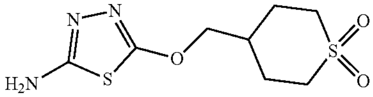

To a stirred solution of O-((1,1-dioxidotetrahydro-2H-thiopyran-4-yl)methyl) hydrazinecarbothioate (234.0 mg, 0.98 mmol) and TEA (199.0 mg, 1.96 mmol) in MeOH (3 mL) was added BrCN (114.0 mg, 1.08 mmol) in portions at 0° C. under nitrogen atmosphere. The resulting mixture was stirred at 25° C. for 1 hr. The resulting residue was dissolved in DMF (1 mL) which was applied to a 20 g C18 column and purified by Combi Flash (Biotage Isolera Prime), eluted with 5~30% acetonitrile in water to afford 4-(((5-amino-1,3,4-thiadiazol-2-yl)oxy)methyl)tetrahydro-2H-thiopyran 1,1-dioxide (90.0 mg, 33%) as a white solid. MS (ESI) calculated for ($C_8H_{13}N_3O_3S_2$) $(M+1)^+$, 264.0; found, 264.0.

Step-4: N-(5-((1,1-dioxidotetrahydro-2H-thiopyran-4-yl)methoxy)-1,3,4-thiadiazol-2-yl)-4-(2-fluoro-6-methoxyphenyl)-6-methylnicotinamide

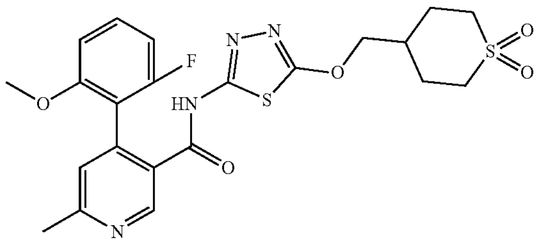 [SMILES: COc1cccc(F)c1-c1cc(C)ncc1C(=O)Nc1nnc(OCC2CCS(=O)(=O)CC2)s1]

To a degassed solution of 4-(((5-amino-1,3,4-thiadiazol-2-yl)oxy)methyl)tetrahydro-2H-thiopyran 1,1-dioxide (80.0 mg, 0.30 mmol) and Intermediate F (79.0 mg, 0.30 mmol) in N,N-Dimethylformamide (0.6 mL) and Acetonitrile (0.6 mL) were added N,N,N',N'-Tetramethylchloroformamidinium hexafluorophosphate (94.0 mg, 0.33 mmol) and 1-methylimidazole (75.0 mg, 0.91 mmol). The resulting solution was stirred at 20° C. for 2 hr under nitrogen atmosphere. The resulting residue was dissolved in DMF (1 mL) which was applied to a 40 g C18 column and purified by Combi Flash (Biotage Isolera Prime) eluted with 5-45% acetonitrile in water within 30 min to afford N-(5-((1,1-dioxidotetrahydro-2H-thiopyran-4-yl)methoxy)-1,3,4-thiadiazol-2-yl)-4-(2-fluoro-6-methoxyphenyl)-6-methylnicotinamide (34.7 mg, 21%) as a white solid. MS (ESI) calculated for ($C_{22}H_{23}FN_4O_5S_2$) $(M+1)^+$, 507.1; found, 507.1. $^1H$ NMR (400 MHz, DMSO-$d_6$) δ 12.85 (s, 1H), 8.80 (s, 1H), 7.46-7.35 (m, 1H), 7.35-7.30 (m, 1H), 6.97-6.86 (m, 2H), 4.40-4.28 (m, 2H), 3.59 (s, 3H), 3.25-3.13 (m, 2H), 3.12-3.02 (m, 2H), 2.57 (s, 3H), 2.22-2.12 (m, 1H), 2.12-2.06 (m, 2H), 1.79-1.72 (m, 2H).

Example 159

2'-chloro-N-(5-(((1r,4r)-4-(difluoromethoxy)cyclohexyl)methoxy)-1,3,4-thiadiazol-2-yl)-5'-methoxy-6-methyl-(4,4'-bipyridine)-3-carboxamide

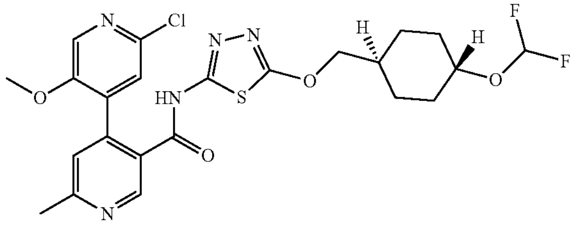 [SMILES: COc1cnc(Cl)cc1-c1cc(C)ncc1C(=O)Nc1nnc(OC[C@H]2CC[C@H](OC(F)F)CC2)s1]

Step-1: methyl (1r,4r)-4-(difluoromethoxy)cyclohexane-1-carboxylate

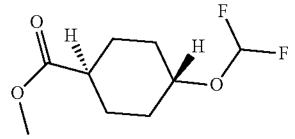

To a stirred solution of methyl (1r,4r)-4-hydroxycyclohexane-1-carboxylate (500.0 mg, 3.16 mmol) and difluoro (sulfo)acetic acid (1.1 g, 6.32 mmol) in MeCN (5 mL) was added CuI (120.0 mg, 0.63 mmol) at room temperature under nitrogen atmosphere. The resulting mixture was stirred at 50° C. for 3 hr under nitrogen atmosphere before concentrated under vacuum. The resulting residue purified by Combi Flash (Biotage Isolera Prime) which applied to an 80 g silica gel column that was eluted with 0~30% ethyl acetate in petroleum ether within 40 min to afford methyl (1r,4r)-4-(difluoromethoxy)cyclohexane-1-carboxylate (300.0 mg, 45%) as a yellow oil. MS (ESI) calc'd for ($C_9H_{14}F_2O_3$) $(M+1)^+$, 209.1; found 209.1.

Step-2: ((1r,4r)-4-(difluoromethoxy)cyclohexyl)methanol

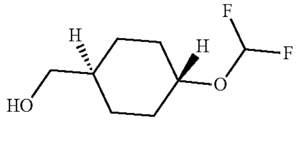 [SMILES: OC[C@H]1CC[C@H](OC(F)F)CC1]

To a stirred solution of methyl (1r,4r)-4-(difluoromethoxy)cyclohexane-1-carboxylate (3.8 g, 18.25 mmol,) in THF (60 mL) were added LAH (1.4 g, 0.04 mmol) in portions at 0° C. The resulting mixture was stirred at 0° C. for 2 hr. The reaction was quenched with water at 0° C. The precipitated solids were collected by filtration and washed with ethyl acetate to afford ((1r,4r)-4-(difluoromethoxy) cyclohexyl)methanol (1.7 g, 51%) as a yellow oil. MS (ESI) calc'd for ($C_8H_{14}F_2O_2$) $(M+1)^+$, 181.1; found, 181.1.

Step-3: O-(((1r,4r)-4-(difluoromethoxy)cyclohexyl) methyl)S-methyl carbonodithioate

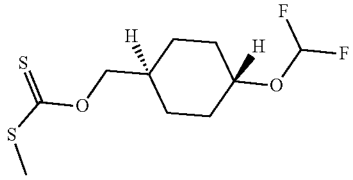 [SMILES: CSC(=S)OC[C@H]1CC[C@H](OC(F)F)CC1]

To a stirred solution of ((1r,4r)-4-(difluoromethoxy)cyclohexyl)methanol (1.7 g, 9.43 mmol) in THF (30 mL) was added NaH (0.5 g, 0.02 mmol, 60%) in portions at 0° C. and stirred at 0° C. for 30 min under nitrogen atmosphere. Then $CS_2$ (1.1 g, 0.01 mmol) was added to the above mixture and stirred at 0° C. for 10 min, and then MeI (2.0 g, 0.01 mmol) was added to the above mixture at 0° C. The resulting mixture was stirred at room temperature for 1 hour. The reaction mixture was quenched by the addition of water and extracted with ethyl acetate. The combined organic layers were washed with brine, dried over anhydrous sodium sulfate, filtered, and concentrated under vacuum. The resulting residue was dissolved in DCM (8 mL) and purified by Combi Flash (Biotage Isolera Prime) which applied to a 80 g silica gel column that was eluted with 0~30% ethyl acetate in petroleum ether within 40 min afford O-(((1r,4r)-4-(difluoromethoxy)cyclohexyl)methyl)S-methyl carbonodithioate (1.3 g, 50%) as an off-white syrup. MS (ESI) calc'd for ($C_{10}H_{16}F_2O_2S_2$) $(M+1)^+$, 271.1, found, 271.1.

Step-4: O-(((1r,4r)-4-(difluoromethoxy)cyclohexyl) methyl) hydrazinecarbothioate

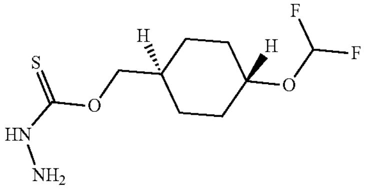 [SMILES: NNC(=S)OC[C@H]1CC[C@H](OC(F)F)CC1]

To a stirred solution of O-(((1r,4r)-4-(difluoromethoxy) cyclohexyl)methyl)S-methyl carbonodithioate (1.3 g, 4.85 mmol) in MeOH (20 mL) was added Hydrazine (160.0 mg, 5.00 mmol) dropwise at 0° C. The resulting mixture was stirred for 1 hr at 0° C. The organic solvent was removed under vacuum to afford O-(((1r,4r)-4-(difluoromethoxy)cyclohexyl)methyl) hydrazinecarbothioate (1.2 g, crude) as a white solid. MS (ESI) calc'd for ($C_9H_{16}F_2N_2O_2S$) $(M+1)^+$, 255.1, found 255.0.

Step-5:5-(((1r,4r)-4-(difluoromethoxy)cyclohexyl) methoxy)-1,3,4-thiadiazol-2-amine

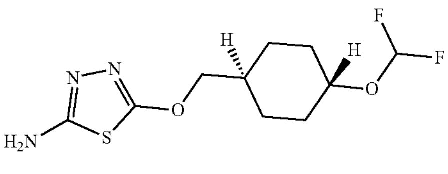 [SMILES: Nc1nnc(OC[C@H]2CC[C@H](OC(F)F)CC2)s1]

To a stirred solution of O-(((1r,4r)-4-(difluoromethoxy)cyclohexyl)methyl) hydrazinecarbothioate (1.2 g, 4.88 mmol) in MeOH (10 mL) were added TEA (568.0 mg, 5.36 mmol) and BrCN (986.0 mg, 9.75 mmol,) in portions at 0° C. The resulting mixture was stirred for at 0° C. for 1 hr. The reaction mixture was quenched by the addition of water and extracted with ethyl acetate. The combined organic layers were washed with brine, dried over anhydrous sodium sulfate, filtered, and concentrated under vacuum. The resulting residue was purified by Combi Flash (Biotage Isolera Prime) which applied to 40 g silica gel column and eluted with 0~15% methanol in dichloromethane within 30 min to afford 5-(((1r,4r)-4-(difluoromethoxy)cyclohexyl)methoxy)-1,3,4-thiadiazol-2-amine (310.0 mg, 61%) as a yellow solid. MS (ESI) calc'd for ($C_{10}H_{15}F_2N_3O_2S$) $(M+1)^+$, 280.1, found 280.1.

Step-6: 2'-chloro-N-(5-(((1r,4r)-4-(difluoromethoxy)cyclohexyl)methoxy)-1,3,4-thiadiazol-2-yl)-5'-methoxy-6-methyl-(4,4'-bipyridine)-3-carboxamide

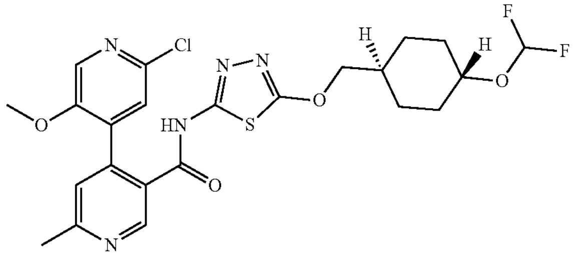 [SMILES: COc1cnc(Cl)cc1-c1cc(C)ncc1C(=O)Nc1nnc(OC[C@H]2CC[C@H](OC(F)F)CC2)s1]

To a stirred solution of 5-(((1r,4r)-4-(difluoromethoxy)cyclohexyl)methoxy)-1,3,4-thiadiazol-2-amine (200.0 mg, 0.72 mmol) and Intermediate H (200.0 mg, 0.72 mmol) in DMF (2 mL) were added, N,N,N',N'-Tetramethylchloroformamidinium hexafluorophosphate (301.0 mg, 1.1 mmol) and 1-methylimidazole (0.2 mL, 2.9 mmol) at 23° C. The resulting solution was stirred at 23° C. for 1 hr under nitrogen. The resulting residue was dissolved in DMF (5 mL) and was purified by prep-HPLC with the following conditions: (Column: Xselect CSH OBD Column 30*150 mm um, n; Mobile Phase A: Water (10 mmol/L $NH_4HCO_3$), Mobile Phase B: ACN; Flow rate: 60 mL/min; Gradient: 45% B to 50% B in 8 min, 50% B to 95% B in 8.2 min, 95% B to 95% B in 9.7 min, 95% B to 5% B in 11 min, 5% B; Wave Length: 220 nm; RT1 (min): 5.68; Injection Volume: 1.2 mL; Number Of Runs: 7) to afford 2'-chloro-N-(5-(((1r,4r)-4-(difluoromethoxy)cyclohexyl)methoxy)-1,3,4-thiadiazol-2-yl)-5'-methoxy-6-methyl-(4,4'-bipyridine)-3-carboxamide (31.0 mg, 8%) as a white solid. MS (ESI) calc'd for ($C_{23}H_{24}ClF_2N_5O_4S$) $(M+1)^+$, 540.1; found 540.1. $^1H$ NMR (400 MHz, DMSO-$d_6$) δ 12.88 (s, 1H), 8.82 (s, 1H), 8.17 (s, 1H), 7.51 (s, 1H), 7.40 (s, 1H), 6.95-6.51 (m, 1H), 4.24 (d, J=6.0 Hz, 2H), 4.00 (d, J=5.2 Hz, 1H), 3.63 (s, 3H), 2.59 (s, 3H), 2.03-1.90 (m, 2H), 1.87-1.75 (m, 3H), 1.40-1.38 (m, 2H), 1.26-1.07 (m, 2H).

Example 160 and 161

(R)-2'-chloro-5'-methoxy-6-methyl-N-(5-((3-methyltetrahydrofuran-3-yl)methoxy)-1,3,4-thiadiazol-2-yl)-(4,4'-bipyridine)-3-carboxamide and (S)-2'-chloro-5'-methoxy-6-methyl-N-(5-((3-methyltetrahydrofuran-3-yl)methoxy)-1,3,4-thiadiazol-2-yl)-(4,4'-bipyridine)-3-carboxamide

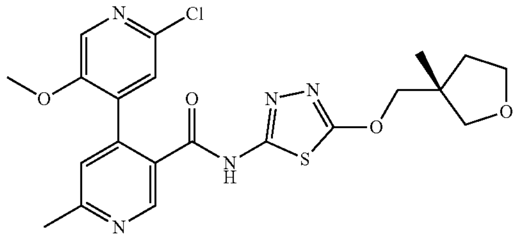

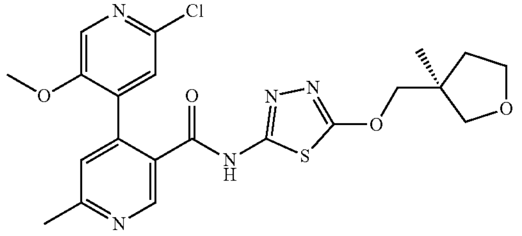

Step-1: S-methyl O-((3-methyltetrahydrofuran-3-yl)methyl) carbonodithioate

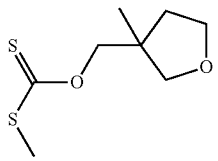

To a solution of (3-methyltetrahydrofuran-3-yl)methanol (650.0 mg, 5.60 mmol) in THF (15 mL) was added NaH (448.0 mg, 11.19 mmol, 60%) in portions at 0° C. and stirred at 0° C. for 30 min under nitrogen. To the above solution was added $CS_2$ (0.50 mL, 8.39 mmol) at 0° C. under nitrogen. The resulting solution was stirred at 0° C. for 15 min under nitrogen. To the above solution was added MeI (0.52 mL, 8.39 mmol) at 0° C. under nitrogen. The resulting solution was stirred at 0° C. for 1 hr. The reaction mixture was quenched by the addition of water and extracted with ethyl acetate. The combined organic layers were washed with brine, dried over anhydrous sodium sulfate, filtered, and concentrated under vacuum. The residue was dissolved in DCM (5 mL) and was applied to a 80 g silica gel column that was eluted with 0~19% ethyl acetate in petroleum ether within 46 min to afford S-methyl O-((3-methyltetrahydrofuran-3-yl)methyl) carbonodithioate (942.0 mg, 76%) as a yellow oil. MS (ESI) calc'd for ($C_8H_{14}O_2S_2$) $(M+1)^+$, 207.1, found 207.0.

Step-2: O-((3-methyltetrahydrofuran-3-yl)methyl) hydrazinecarbothioate

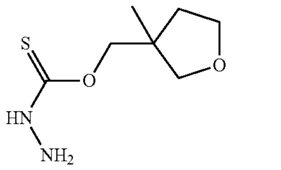

To a solution of S-methyl O-((3-methyltetrahydrofuran-3-yl)methyl) carbonodithioate (900.0 mg, 4.06 mmol) in Methanol (2 mL) was added hydrazine (229.6 mg, 5.74 mmol, 80%) at 18° C. The resulting solution was stirred at 18° C. for 2 hr. The reaction mixture was quenched by the addition of water and extracted with ethyl acetate. The combined organic layers were washed with brine, dried over anhydrous sodium sulfate, filtered, and concentrated under vacuum to afford O-((3-methyltetrahydrofuran-3-yl)methyl) hydrazinecarbothioate (829.0 mg, crude) as a yellow oil. MS (ESI) calc'd for ($C_7H_{14}N_2O_2S$) $(M+1)^+$, 191.1, found 191.0.

Step-3: 5-((3-methyltetrahydrofuran-3-yl)methoxy)-1,3,4-thiadiazol-2-amine

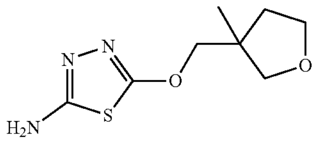

To a solution of O-((3-methyltetrahydrofuran-3-yl) methyl) hydrazinecarbothioate (800.0 mg, 3.87 mmol) in Methanol (4 mL) was added TEA (732.2 mg, 7.25 mmol) and cyanic bromide (451.0 mg, 4.26 mmol) at 20° C. The resulting solution was stirred at 20° C. for 30 min. The reaction mixture was diluted with water and extracted with ethyl acetate. The combined organic layers were washed with brine, dried over anhydrous sodium sulfate, filtered, and concentrated under vacuum. The residue was dissolved in DMF (4.0 mL) which was applied to a 40 g C18 column and purified by Combi Flash (Biotage Isolera Prime), eluted with 5~21% acetonitrile in water within 43 min to afford 5-((3-methyltetrahydrofuran-3-yl)methoxy)-1,3,4-thiadiazol-2-amine (413.0 mg, 46%) as a yellow solid. MS (ESI) calc'd for ($C_8H_{13}N_3O_2S$) $(M+1)^+$, 216.0; found, 216.0.

Step-4: 2'-chloro-5'-methoxy-6-methyl-N-(5-((3-methyltetrahydrofuran-3-yl)methoxy)-1,3,4-thiadiazol-2-yl)-(4,4'-bipyridine)-3-carboxamide

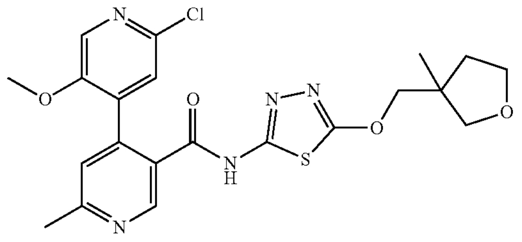 [SMILES: COc1cnc(Cl)cc1-c1cc(C)ncc1C(=O)Nc1nnc(OCC2(C)CCOC2)s1]

To a solution of 5-((3-methyltetrahydrofuran-3-yl) methoxy)-1,3,4-thiadiazol-2-amine (101.0 mg, 0.40 mmol) in DMF (0.5 mL) and Acetonitrile (0.5 mL) were added 1-methyl-1H-imidazole (84.0 mg, 1.02 mmol) and Intermediate H (100 mg, 0.34 mmol) at 18° C. under nitrogen. To the above was added a solution of TCFH (143 mg, 0.51 mmol) in Acetonitrile (1 mL) at 23° C. under nitrogen. The resulting solution was stirred at 20° C. under nitrogen for 2 hr. The reaction mixture was concentrated under vacuum. The resulting residue was dissolved in DMF (3 mL) which was applied to a 40 g C18 column that was eluted with 5-35% acetonitrile in water within 42 min to afford 2'-chloro-5'-methoxy-6-methyl-N-(5-((3-methyltetrahydrofuran-3-yl)methoxy)-1,3,4-thiadiazol-2-yl)-(4,4'-bipyridine)-3-carboxamide (130.0 mg, 79%) as a white solid. MS (ESI) calc'd for ($C_{21}H_{22}ClN_5O_4S$) $(M+1)^+$, 476.1; found, 476.0.

Step-5: (R)-2'-chloro-5'-methoxy-6-methyl-N-(5-((3-methyltetrahydrofuran-3-yl)methoxy)-1,3,4-thiadiazol-2-yl)-(4,4'-bipyridine)-3-carboxamide and (S)-2'-chloro-5'-methoxy-6-methyl-N-(5-((3-methyltetrahydrofuran-3-yl)methoxy)-1,3,4-thiadiazol-2-yl)-(4,4'-bipyridine)-3-carboxamide

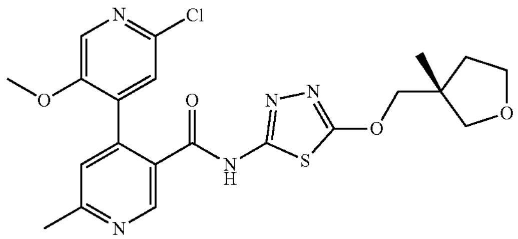

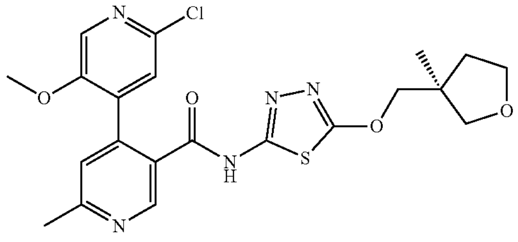

The racemic compound 2'-chloro-5'-methoxy-6-methyl-N-(5-((3-methyltetrahydrofuran-3-yl)methoxy)-1,3,4-thiadiazol-2-yl)-(4,4'-bipyridine)-3-carboxamide (130.0 mg, 0.26 mmol) was separated by prep-chiral HPLC with the following conditions: (Column: CHIRALPAK IF, 2*25 cm, 5 μm; Mobile Phase A: HEX:DCM=3: 1-HPLC, Mobile Phase B: MeOH-HPLC; Flow rate: 20 mL/min; Gradient: 30% B to 30% B in 14 min; Wave Length: 220/254 nm; RT1 (min): 10.32; RT2 (min): 12.38; Sample Solvent: MeOH: DCM=1: 1; Injection Volume: 0.3 mL; Number Of Runs: 8) to afford 2'-chloro-5'-methoxy-6-methyl-N-(5-((3-methyltetrahydrofuran-3-yl)methoxy)-1,3,4-thiadiazol-2-yl)-(4,4'-bipyridine)-3-carboxamide, isomer 1 (49.3 mg, 38%) as a white solid with shorter retention time on chiral-HPLC and 2'-chloro-5'-methoxy-6-methyl-N-(5-((3-methyltetrahydrofuran-3-yl)methoxy)-1,3,4-thiadiazol-2-yl)-(4,4'-bipyridine)-3-carboxamide, isomer 2 (49.5 mg, 38%) as a white solid with longer retention time on chiral-HPLC. The absolute stereochemistry was not determined.

Isomer 1: 2'-chloro-5'-methoxy-6-methyl-N-(5-((3-methyltetrahydrofuran-3-yl)methoxy)-1,3,4-thiadiazol-2-yl)-(4, 4'-bipyridine)-3-carboxamide: MS (ESI) calc'd for ($C_{21}H_{22}ClN_5O_4S$) $(M+1)^+$, 476.1; found, 476.0. $^1H$ NMR (400 MHz, DMSO-$d_6$) δ 12.88 (s, 1H), 8.81 (s, 1H), 8.17 (s, 1H), 7.53 (s, 1H), 7.43 (s, 1H), 4.31 (s, 2H), 3.85-3.72 (m, 2H), 3.69-3.64 (m, 1H), 3.64 (s, 3H), 3.42-3.34 (m, 1H), 2.59 (s, 3H), 1.94-1.83 (m, 1H), 1.71-1.60 (m, 1H), 1.17 (s, 3H).

Isomer 2: 2'-chloro-5'-methoxy-6-methyl-N-(5-((3-methyltetrahydrofuran-3-yl)methoxy)-1,3,4-thiadiazol-2-yl)-(4,4'-bipyridine)-3-carboxamide: MS (ESI) calc'd for ($C_{21}H_{22}ClN_5O_4S$) $(M+1)^+$, 476.1; found, 476.0. $^1H$ NMR (400 MHz, DMSO-$d_6$) δ 12.89 (s, 1H), 8.82 (s, 1H), 8.17 (s, 1H), 7.53 (s, 1H), 7.42 (s, 1H), 4.30 (s, 2H), 3.85-3.77 (m, 2H), 3.71-3.65 (m, 1H), 3.64 (s, 3H), 3.44-3.34 (m, 1H), 2.59 (s, 3H), 1.94-1.82 (m, 1H), 1.70-1.61 (m, 1H), 1.17 (s, 3H).

Example 162

2'-chloro-5'-methoxy-6-methyl-N-(5-((3-methyloxetan-3-yl)methoxy)-1,3,4-thiadiazol-2-yl)-(4,4'-bipyridine)-3-carboxamide

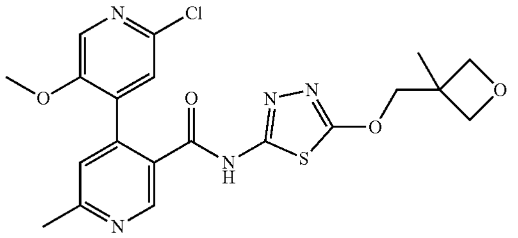 [SMILES: COc1cnc(Cl)cc1-c1cc(C)ncc1C(=O)Nc1nnc(OCC2(C)COC2)s1]

Step-1: 5-((3-methyloxetan-3-yl)methoxy)-1,3,4-thiadiazol-2-amine

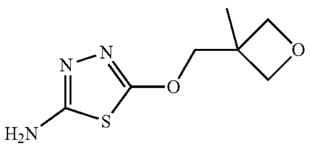

To a stirred solution of (3-methyloxetan-3-yl)methanol (500.0 mg, 4.90 mmol) in THF (30 mL) was added NaH (392.0 mg, 9.79 mmol, 60%) in portions at 0° C. The resulting solution was stirred at 0° C. for 1 hr under nitrogen. To the above solution was added 5-bromo-1,3,4-thiadiazol-2-amine (1.0 g, 5.87 mmol) at 0° C. under nitrogen. The resulting mixture was stirred at room temperature for 2 hr. The reaction mixture was quenched by the addition of water and extracted with ethyl acetate. The combined organic layers were washed with brine, dried over anhydrous sodium sulfate, filtered, and concentrated under vacuum to afford 5-((3-methyloxetan-3-yl)methoxy)-1,3,4-thiadiazol-2-amine (500.0 mg, crude) as a yellow solid. MS (ESI) calc'd for ($C_7H_{11}N_3O_2S$) $(M+1)^+$, 202.0, found 202.0.

Step-2: 2'-chloro-5'-methoxy-6-methyl-N-(5-((3-methyloxetan-3-yl)methoxy)-1,3,4-thiadiazol-2-yl)-(4,4'-bipyridine)-3-carboxamide

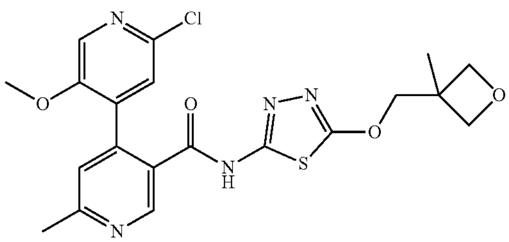 [SMILES: COc1cnc(Cl)cc1-c1cc(C)ncc1C(=O)Nc1nnc(OCC2(C)COC2)s1]

To a mixture of 5-((3-methyloxetan-3-yl)methoxy)-1,3,4-thiadiazol-2-amine (156.0 mg, 0.38 mmol) in acetonitrile (2 mL) were added Intermediate H (100.0 mg, 0.32 mmol) and NMI (132.0 mg, 1.61 mmol). A solution of TCFH (90.0 mg, 0.32 mmol) in acetonitrile (1 mL) was added thereto dropwise under nitrogen. The mixture was stirred at 20° C. for 2 hr under nitrogen. The reaction mixture was applied to a 40 g C18 column and purified by Combi Flash (Biotage Isolera Prime), eluted with 5~40% acetonitrile in water within 45 min to afford a yellow oil. The residue was further purified by prep-HPLC with the following conditions: (Column: XBridge Shield RP18 OBD Column, 30*150 mm, 5 μm; Mobile Phase A: Water (10 mmol/L $NH_4HCO_3$), Mobile Phase B: ACN; Flow rate: 60 mL/min; Gradient: 20% B to 33% B in 8 min, 33% B to 95% B in 8.2 min, 95% B to 95% B in 9.5 min, 95% B to 5% B in 11 min, 5% B; Wave Length: 254 nm; RT 1 (min): 7.7; Injection Volume: 0.3 mL; Number Of Runs: 3) to afford racemic 2'-chloro-5'-methoxy-6-methyl-N-(5-((3-methyloxetan-3-yl)methoxy)-1,3,4-thiadiazol-2-yl)-(4,4'-bipyridine)-3-carboxamide (37.6 mg, 24%) as a white solid. MS (ESI) calc'd for ($C_{20}H_{20}ClN_5O_4S$) $(M+1)^+$, 462.0, found 462.0. $^1H$ NMR (400 MHz, DMSO-$d_6$) δ 12.91 (s, 1H), 8.83 (s, 1H), 8.17 (s, 1H), 7.52 (s, 1H), 7.41 (s, 1H), 4.60-4.40 (m, 4H), 4.30 (d, J=8.0 Hz, 2H), 3.64 (s, 3H), 2.59 (s, 3H), 1.35 (s, 3H).

Example 163

2'-chloro-N-(5-((3-(2-fluoropropan-2-yl)bicyclo(1.1.1)pentan-1-yl)methoxy)-1,3,4-thiadiazol-2-yl)-5'-methoxy-6-methyl-(4,4'-bipyridine)-3-carboxamide

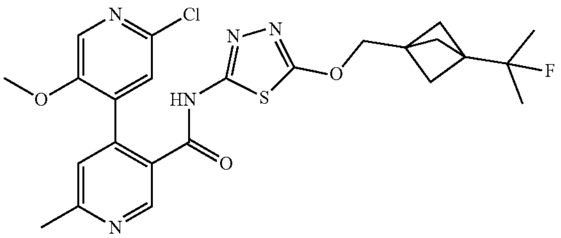 [SMILES: COc1cnc(Cl)cc1-c1cc(C)ncc1C(=O)Nc1nnc(OCC23CC(C(C)(C)F)(C2)C3)s1]

Step-1: methyl 3-(hydroxymethyl)bicyclo(1.1.1) pentane-1-carboxylate

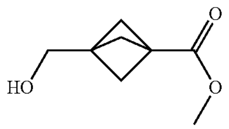

To a mixture of 3-(methoxycarbonyl)bicyclo(1.1.1)pentane-1-carboxylic acid (2.0 g, 11.75 mmol) and NMM (1.1 g, 11.75 mmol) in THF (20 mL) was added Isobutyl chloroformate (1.6 g, 11.78 mmol) at 0° C. The resulting solution was stirred at 0° C. for 2 hr. To the above mixture was added $NaBH_4$ (1.3 g, 35.15 mmol) and MeOH (20 mL) slowly at 0° C. The resulting solution was stirred at 0° C. for 2 hr. The resulting mixture was quenched with water and the organic solvents was removed under vacuum. The aqueous layer was extracted with ethyl acetate. The combined organic solution was dried over sodium sulfate, filtered, and concentrated under vacuum to afford methyl 3-(hydroxymethyl)bicyclo (1.1.1)pentane-1-carboxylate (1.2 g, crude) as a yellow oil.

Step-2: methyl 3-((((methylsulfanyl)methanethioyl) oxy)methyl)bicyclo(1.1.1)pentane-1-carboxylate

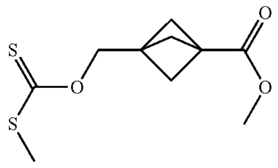

To a mixture of methyl 3-(hydroxymethyl)bicyclo(1.1.1) pentane-1-carboxylate (1.0 g, 6.40 mmol) in THF (10 mL) was added NaH (0.3 g, 12.91 mmol, 60%) in portions at 0° C. and stirred at 0° C. for 30 min. To the above mixture was added $CS_2$ (0.7 g, 9.60 mmol) dropwise at 0° C. and stirred at 0° C. for 10 min. Then MeI (1.4 g, 9.60 mmol) was added to the above mixture dropwise at 0° C. The resulting solution was stirred at 0° C. for 30 min. The reaction mixture was quenched with water and extracted with ethyl acetate. The combined organic layers were washed with brine, dried over anhydrous sodium sulfate, filtered, and concentrated under vacuum to afford methyl 3-((((methylsulfanyl)methanethioyl)oxy)methyl)bicyclo(1.1.1)pentane-1-carboxylate (360.0 mg, crude) as a yellow oil.

Step-3: methyl 3-(((aminocarbamothioyl)oxy) methyl)bicyclo(1.1.1)pentane-1-carboxylate

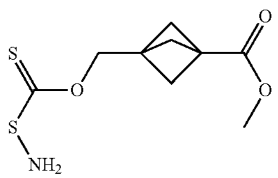

A mixture of methyl 3-((((methylsulfanyl)methanethioyl) oxy)methyl)bicyclo(1.1.1)pentane-1-carboxylate (360.0 mg, 1.46 mmol) and hydrazine (58.5 mg, 1.46 mmol, 80%) in MeOH (6 mL) was stirred at room temperature for 2 hr. The reaction mixture was diluted with water and extracted with ethyl acetate. The combined organic layers were washed with brine, dried over anhydrous sodium sulfate, filtered, and concentrated under vacuum to afford methyl 3-(((aminocarbamothioyl)oxy)methyl)bicyclo(1.1.1)pentane-1-carboxylate (300.0 mg, crude) as a yellow oil. MS (ESI) calc'd for ($C_9H_{14}N_2O_3S$) $(M+1)^+$, 231.1, found 231.0.

Step-4: methyl 3-(((5-amino-1,3,4-thiadiazol-2-yl) oxy)methyl)bicyclo(1.1.1)pentane-1-carboxylate

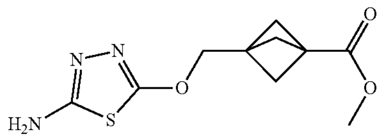 [SMILES: COC(=O)C12CC(COc3nnc(N)s3)(C1)C2]

To a mixture of methyl 3-(((aminocarbamothioyl)oxy) methyl)bicyclo(1.1.1)pentane-1-carboxylate (300.0 mg, 1.30 mmol) in MeOH (8 mL) were added TEA (263.6 mg, 2.60 mmol) and BrCN (70.8 mg, 0.66 mmol) at 20° C. The resulting solution was stirred at 20° C. for 30 min. The reaction mixture was diluted with water and extracted with ethyl acetate. The combined organic layers were washed with brine, dried over anhydrous sodium sulfate, filtered, and concentrated under vacuum. The resulting residue was purified by Combi Flash (Biotage Isolera Prime) which applied to 40 g silica gel column and eluted with 0~80% acetate ethyl in petroleum ether to afford methyl 3-(((5-amino-1,3,4-thiadiazol-2-yl)oxy)methyl)bicyclo(1.1.1)pentane-1-carboxylate (60.0 mg, 18%) as a white solid. MS (ESI) calc'd for ($C_{10}H_{13}N_3O_3S$) $(M+1)^+$, 256.1, found 256.2.

Step-5: 2-(3-(((5-amino-1,3,4-thiadiazol-2-yl)oxy) methyl)bicyclo(1.1.1)pentan-1-yl)propan-2-ol

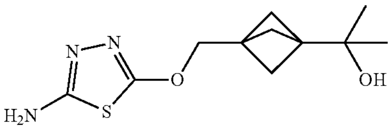 [SMILES: CC(C)(O)C12CC(COc3nnc(N)s3)(C1)C2]

To a mixture of methyl 3-(((5-amino-1,3,4-thiadiazol-2-yl)oxy)methyl)bicyclo(1.1.1)pentane-1-carboxylate (50.0 mg, 0.19 mmol) in THF (5 mL) was added bromo(methyl) magnesium (0.78 mL, 0.78 mmol, 1 M in THF) dropwise at 0° C. under nitrogen. The resulting mixture was stirred at 0° C. for 2 hr under nitrogen. The reaction mixture was diluted with water and extracted with ethyl acetate. The combined organic layers were washed with brine, dried over anhydrous sodium sulfate, filtered, and concentrated under vacuum. The resulting residue was purified by Combi Flash (Biotage Isolera Prime) which applied to 40 g silica gel column and eluted with 5~70% acetonitrile in water within 45 min to afford 2-(3-(((5-amino-1,3,4-thiadiazol-2-yl)oxy)methyl)bicyclo(1.1.1)pentan-1-yl)propan-2-ol (50.0 mg, 99%) as a white solid. MS (ESI) calc'd for ($C_{11}H_{17}N_3O_2S$) $(M+1)^+$, 256.1, found 255.9.

Step-6: 5-((3-(2-fluoropropan-2-yl)bicyclo(1.1.1)pentan-1-yl)methoxy)-1,3,4-thiadiazol-2-amine

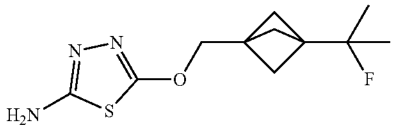 [SMILES: CC(C)(F)C12CC(COc3nnc(N)s3)(C1)C2]

To a solution of 2-(3-(((5-amino-1,3,4-thiadiazol-2-yl)oxy)methyl)bicyclo(1.1.1)pentan-1-yl)propan-2-ol (100.0 mg, 0.32 mmol) in Dichloromethane (DCM) (2 mL) was added BAST (0.097 mL, 0.52 mmol) at −70° C. under nitrogen atmosphere. The resulting solution was stirred at −70° C. for 2 hr. The reaction mixture was quenched by the addition of water and extracted with ethyl acetate. The combined organic layers were washed with brine, dried over anhydrous sodium sulfate, filtered, and concentrated under vacuum. The resulting residue was dissolved in DMF (1 mL) which was applied to a 20 g C18 column and purified by Combi Flash (Biotage Isolera Prime), eluted with 5~45% acetonitrile in water within 40 min to afford the crude yellow oil. The crude product was further purified by prep-HPLC with the following conditions: (Column: XBridge Shield RP18 OBD Column, 30*150 mm, 5 μm; Mobile Phase A: Water (10 mmol/L $NH_4HCO_3$), Mobile Phase B: ACN; Flow rate: 60 mL/min; Gradient: 35% B to 42% B in 8 min, 42% B to 95% B in 8.2 min, 95% B to 95% B in 9.5 min, 95% B to 5% B in 11 min, 5% B; Wave Length: 254 nm; RT1 (min): 7; Injection Volume: 0.5 mL; Number Of Runs: 4) to afford 5-((3-(2-fluoropropan-2-yl)bicyclo(1.1.1)pentan-1-yl)methoxy)-1,3,4-thiadiazol-2-amine (30.0 mg, 29%) as a white solid. MS (ESI) calc'd for ($C_{11}H_{17}N_3O_2S$) $(M+1)^+$, 258.1, found 258.2.

Step-7: 2'-chloro-N-(5-((3-(2-fluoropropan-2-yl)bicyclo(1.1.1)pentan-1-yl)methoxy)-1,3,4-thiadiazol-2-yl)-5'-methoxy-6-methyl-(4,4'-bipyridine)-3-carboxamide

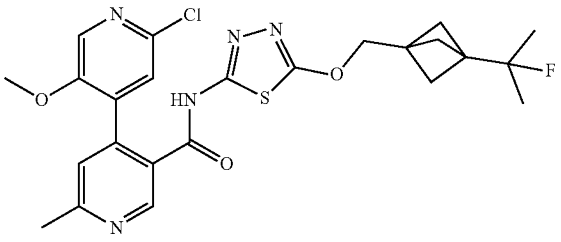 [SMILES: COc1cnc(Cl)cc1-c1cc(C)ncc1C(=O)Nc1nnc(OCC23CC(C(C)(C)F)(C2)C3)s1]

To a solution of Intermediate H (20.0 mg, 0.065 mmol) in Acetonitrile (1 mL) were added 1-methyl-1H-imidazole (26.5 mg, 0.323 mmol), 5-((3-(2-fluoropropan-2-yl)bicyclo(1.1.1)pentan-1-yl)methoxy)-1,3,4-thiadiazol-2-amine (20.3 mg, 0.071 mmol) at 20° C. To the above was added a solution of TCFH (27.1 mg, 0.097 mmol) in acetonitrile (1 mL) at 20° C. under nitrogen. The resulting solution was stirred at 20° C. under nitrogen for 2 hr. The reaction mixture was concentrated under vacuum. The resulting residue was dissolved in DMF (2 mL) which was applied to a 12 g C18 column and purified by Combi Flash (Biotage Isolera Prime), eluted with 5~65% acetonitrile in water within 45 min to afford 2'-chloro-N-(5-((3-(2-fluoropropan-2-yl)bicyclo(1.1.1)pentan-1-yl)methoxy)-1,3,4-thiadiazol-2-yl)-5'-methoxy-6-methyl-(4,4'-bipyridine)-3-carboxamide (4.4 mg, 12%) as a white solid. MS (ESI) calc'd for ($C_{24}H_{25}ClFN_5O_3S$) $(M+1)^+$, 518.1, found 518.1. $^1H$ NMR (400 MHz, Methanol-$d_4$) δ 8.80 (s, 1H), 8.10 (s, 1H), 7.50 (s, 1H), 7.44 (s, 1H), 4.49 (s, 2H), 3.74 (s, 3H), 2.69 (s, 3H), 1.78 (s, 6H), 1.32 (s, 3H), 1.27 (s, 3H).

Example 164

2'-chloro-5'-methoxy-6-methyl-N-(5-(oxetan-3-ylmethoxy)-1,3,4-thiadiazol-2-yl)-(4,4'-bipyridine)-3-carboxamide

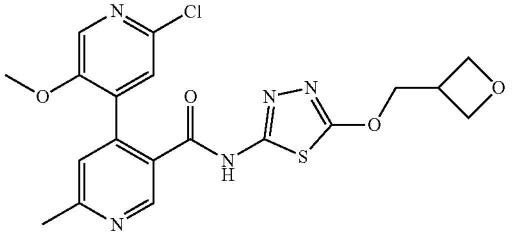 [SMILES: COc1cnc(Cl)cc1-c1cc(C)ncc1C(=O)Nc1nnc(OCC2COC2)s1]

Step-1: 5-(oxetan-3-ylmethoxy)-1,3,4-thiadiazol-2-amine

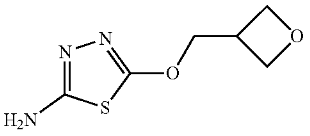 [SMILES: Nc1nnc(OCC2COC2)s1]

To a solution of oxetan-3-ylmethanol (1 g, 11.35 mmol) in THF (1 mL) was added NaH (0.7 g, 17.02 mmol, 60%) in portions at 0° C. and stirred at 0° C. for 30 min under nitrogen atmosphere. To the above solution was added 5-bromo-1,3,4-thiadiazol-2-amine (2.1 g, 11.35 mmol) at 0° C. The resulting solution was stirred at 0° C. for 1 hr. The reaction mixture was quenched by the addition of water and extracted with ethyl acetate. The combined organic layers were washed with brine, dried over anhydrous sodium sulfate, filtered, and concentrated under vacuum. The resulting residue was dissolved in DCM (2 mL) and purified by Combi Flash (Biotage Isolera Prime) which applied to a 40 g silica gel column that was eluted with 0~90% ethyl acetate in petroleum ether within 35 min to afford 5-(oxetan-3-ylmethoxy)-1,3,4-thiadiazol-2-amine (412.0 mg, 18%) as a yellow solid MS (ESI) calc'd for ($C_6H_9N_3O_2S$) $(M+1)^+$, 188.0; found, 188.0.

Step-2: 2'-chloro-5'-methoxy-6-methyl-N-(5-(oxetan-3-ylmethoxy)-1,3,4-thiadiazol-2-yl)-(4,4'-bipyridine)-3-carboxamide

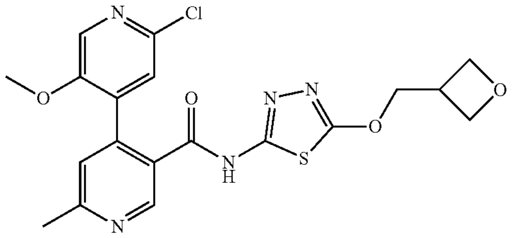 [SMILES: COc1cnc(Cl)cc1-c1cc(C)ncc1C(=O)Nc1nnc(OCC2COC2)s1]

To a solution of Intermediate H (149 mg, 0.54 mmol) in Acetonitrile (2 mL) were added 5-(oxetan-3-ylmethoxy)-1,3,4-thiadiazol-2-amine (100 mg, 0.54 mmol) and 1-methylimidazole (219 mg, 2.67 mmol) at 20° C. under nitrogen. To the above solution was added TCFH (150 mg, 0.54 mmol) in Acetonitrile (2 mL) at 20° C. under nitrogen. The resulting mixture was then stirred at 20° C. for 1 hr. The resulting residue was dissolved in DMF (1 mL) which was applied to a 20 g C18 column and purified by Combi Flash (Biotage Isolera Prime), eluted with 5~55% acetonitrile in water within 30 min to afford 2'-chloro-5'-methoxy-6-methyl-N-(5-(oxetan-3-ylmethoxy)-1,3,4-thiadiazol-2-yl)-(4,4'-bipyridine)-3-carboxamide (61.7 mg, 25%) as a white solid MS (ESI) calc'd for ($C_{19}H_{18}ClN_5O_2S$) $(M+1)^+$, 448.1; found 448.1. $^1H$ NMR (400 MHz, DMSO-$d_6$) δ 12.90 (s, 1H), 8.81 (s, 1H), 8.17 (s, 1H), 7.54 (s, 1H), 7.44 (s, 1H), 4.74-4.62 (m, 4H), 4.43 (s, 2H), 3.64 (s, 3H), 3.45-3.43 (m, 1H), 2.59 (s, 3H).

Example 165

2'-chloro-5'-methoxy-6-methyl-N-(5-(oxetan-2-ylmethoxy)-1,3,4-thiadiazol-2-yl)-(4,4'-bipyridine)-3-carboxamide

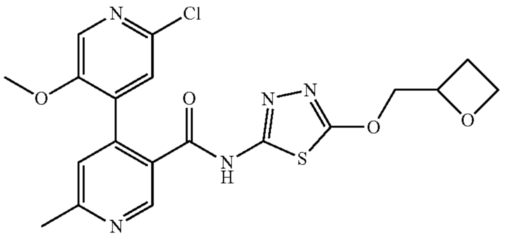 [SMILES: COc1cnc(Cl)cc1-c1cc(C)ncc1C(=O)Nc1nnc(OCC2CCO2)s1]

Step-1: 5-(oxetan-2-ylmethoxy)-1,3,4-thiadiazol-2-amine

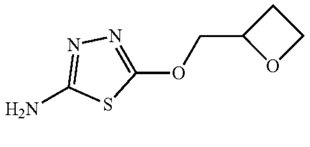 [SMILES: Nc1nnc(OCC2CCO2)s1]

To a stirred solution of oxetan-2-ylmethanol (500.0 mg, 5.67 mmol) in THF (10 mL) was added NaH (340.0 mg, 8.51 mmol, 60%) in portions at 0° C. The resulting solution was stirred at 0° C. for 1 hr under nitrogen. To the above solution was added 5-bromo-1,3,4-thiadiazol-2-amine (1.2 g, 6.81 mmol) at 0° C. under nitrogen. The resulting mixture was then stirred at 0° C. for 1 hr under nitrogen. The reaction mixture was quenched by the addition of water and extracted with ethyl acetate. The combined organic layers were washed with brine, dried over anhydrous sodium sulfate, filtered, and concentrated under vacuum. The resulting residue was dissolved in DCM (5 mL) and purified by Combi Flash (Biotage Isolera Prime) which applied to a 40 g silica gel column that was eluted with 0~60% ethyl acetate in petroleum ether within 30 min to afford 5-(oxetan-2-ylmethoxy)-1,3,4-thiadiazol-2-amine (90 mg, 7%) as a white solid. MS (ESI) calc'd for ($C_6H_9N_3O_2S$) $(M+1)^+$, 188.0; found, 188.0.

Step-2: 2'-chloro-5'-methoxy-6-methyl-N-(5-(oxetan-2-ylmethoxy)-1,3,4-thiadiazol-2-yl)-(4,4'-bipyridine)-3-carboxamide

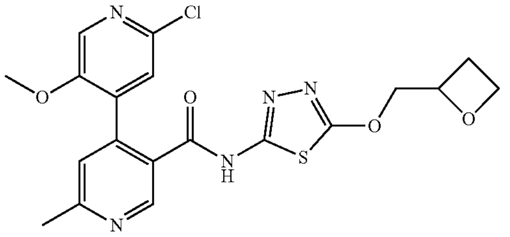 [SMILES: COc1cnc(Cl)cc1-c1cc(C)ncc1C(=O)Nc1nnc(OCC2CCO2)s1]

To a stirred solution of 5-(oxetan-2-ylmethoxy)-1,3,4-thiadiazol-2-amine (64.0 mg, 0.34 mmol), Intermediate H (95.0 mg, 0.34 mmol) and 1-methylimidazole (140.0 mg, 1.71 mmol) in Acetonitrile (0.1 mL) at 20° C. To the above solution was added a solution of TCFH (96.0 mg, 0.34 mmol) in Acetonitrile (0.1 mL) at 20° C. under nitrogen. The resulting mixture was then stirred at 20° C. for 2 hr under nitrogen. The mixture was purified by prep-HPLC with the following conditions: (Column: XBridge Prep OBD C18 Column, 30*150 mm, 5 μm; Mobile Phase A: Water (10 mmol/L $NH_4HCO_3$), Mobile Phase B: ACN; Flow rate: 60 mL/min; Gradient: 15% B to 35% B in 8 min, 35% B; Wave Length: 254 nm; RT1 (min): 7; Number Of Runs: 0) to afford racemic 2'-chloro-5'-methoxy-6-methyl-N-(5-(oxetan-2-ylmethoxy)-1,3,4-thiadiazol-2-yl)-(4,4'-bipyridine)-3-carboxamide (73.7 mg, 48%) as a white solid. MS (ESI) calc'd for ($C_{19}H_{18}N_5O_4S$) $(M+1)^+$, 448.0; found, 448.0. $^1H$ NMR (400 MHz, Methanol-$d_4$) δ 8.83 (s, 1H), 8.08 (s, 1H), 7.47 (s, 1H), 7.39 (s, 1H), 5.23-5.12 (m, 1H), 4.76-4.67 (m, 1H), 4.67-4.53 (m, 3H), 3.74 (s, 3H), 2.88-2.67 (m, 2H), 2.67 (s, 3H).

Example 166

2'-chloro-N-(5-((1,1-dioxidothietan-3-yl)methoxy)-1,3,4-thiadiazol-2-yl)-5'-methoxy-6-methyl-(4,4'-bipyridine)-3-carboxamide

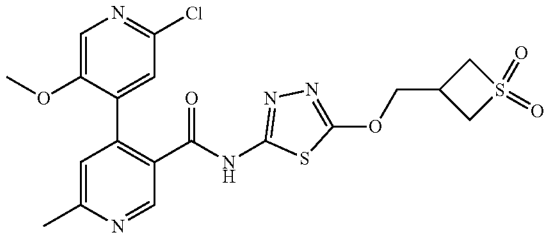 [SMILES: COc1cnc(Cl)cc1-c1cc(C)ncc1C(=O)Nc1nnc(OCC2CS(=O)(=O)C2)s1]

Step-1: 3-(((5-amino-1,3,4-thiadiazol-2-yl)oxy) methyl)thietane 1,1-dioxide

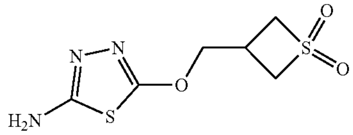 [SMILES: Nc1nnc(OCC2CS(=O)(=O)C2)s1]

To a degassed solution of 3-(hydroxymethyl)thietane 1,1-dioxide (300.0 mg, 0.85 mmol) in dry THF (10 mL) was added NaH (176.0 mg, 1.71 mmol, 60%) in portions at 0° C. The resulting solution was stirred at 0° C. for 1 hr under nitrogen. To the above solution was added 5-bromo-1,3,4-thiadiazol-2-amine (473.0 mg, 1.02 mmol) at 0° C. under nitrogen. The resulting mixture was then stirred at 0° C. for 2 hr. The reaction mixture was quenched by the addition of water and extracted with ethyl acetate. The combined organic layers were washed with brine, dried over anhydrous sodium sulfate, filtered, and concentrated under vacuum. The resulting residue was dissolved in DCM (2 mL) and purified by Combi Flash (Biotage Isolera Prime) which applied to a 40 g silica gel column that was eluted with 0-12% methanol in dichloromethane within 40 min to afford 3-(((5-amino-1,3,4-thiadiazol-2-yl)oxy)methyl)thietane 1,1-dioxide (80.0 mg, 37%) as a red solid. MS (ESI) calc'd for ($C_6H_9N_3O_3S_2$) $(M+1)^+$, 236.2, found 236.3.

Step-3: 2'-chloro-N-(5-((1,1-dioxidothietan-3-yl) methoxy)-1,3,4-thiadiazol-2-yl)-5'-methoxy-6-methyl-(4,4'-bipyridine)-3-carboxamide

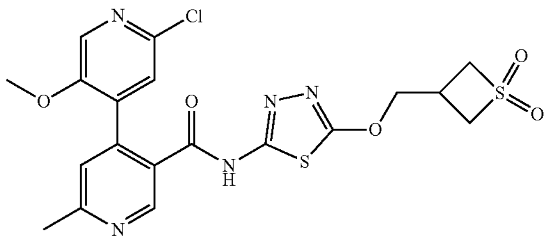 [SMILES: COc1cnc(Cl)cc1-c1cc(C)ncc1C(=O)Nc1nnc(OCC2CS(=O)(=O)C2)s1]

To a solution of Intermediate H (70.0 mg, 0.23 mmol) in acetonitrile (2 mL) were added 1-methyl-1H-imidazole (93.0 mg, 1.13 mmol) and 3-(((5-amino-1,3,4-thiadiazol-2-yl)oxy)methyl)thietane 1,1-dioxide (61.6 mg, 0.25 mmol) at 20° C. A solution of TCFH (95.0 mg, 0.34 mmol) in acetonitrile (1 mL) was added thereto dropwise under nitrogen. The mixture was stirred at 20° C. for 2 hr under nitrogen. The reaction mixture was concentrated under vacuum. The resulting residue was dissolved in DMF (2 mL) which was applied to 20 g C18 column and purified by Combi Flash (Biotage Isolera Prime), eluted with 5-15% acetonitrile in water within 45 min to afford a yellow oil. The yellow oil was further purified by prep-HPLC with the following conditions: (Column: YMC-Actus Triart C18 ExRS, 3*150 mm, 5 μm; Mobile Phase A: Water (10 mmol/L $NH_4HCO_3$), Mobile Phase B: ACN; Flow rate: 60 mL/min; Gradient: 20% B to 40% B in 8 min, 40% B to 95% B in 8.2 min, 95% B to 95% B in 10 min, 95% B to 5% B in 12 min, 5% B; Wave Length: 220 nm; RT1 (min): 6.4; Injection Volume: 400 mL; Number Of Runs: 6) to afford 2'-chloro-N-(5-((1,1-dioxidothietan-3-yl)methoxy)-1,3,4-thiadiazol-2-yl)-5'-methoxy-6-methyl-(4,4'-bipyridine)-3-carboxamide (41.2 mg, 36%) as a white solid. MS (ESI) calc'd for ($C_{19}H_{18}ClN_5O_5S_2$) $(M+1)^+$, 495.9, found 496.0. $^1H$ NMR (400 MHz, DMSO-$d_6$) δ 12.95 (s, 1H), 8.85 (s, 1H), 8.16 (s, 1H), 7.49 (s, 1H), 7.37 (s, 1H), 4.57 (d, J=7.2 Hz, 2H), 4.32-4.28 (m, 2H), 4.12-4.05 (m, 2H), 3.63 (s, 3H), 3.08-3.00 (m, 1H), 2.58 (s, 3H).

Example 167

2'-chloro-5'-methoxy-6-methyl-N-(5-((tetrahydrofuran-3-yl)methoxy)-1,3,4-thiadiazol-2-yl)-(4,4'-bipyridine)-3-carboxamide

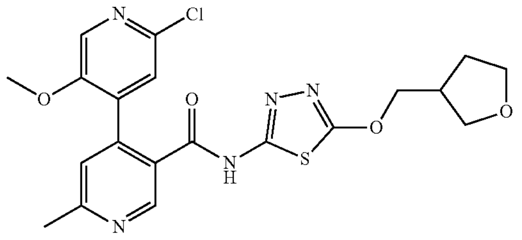

Step-1: 5-((tetrahydrofuran-3-yl)methoxy)-1,3,4-thiadiazol-2-amine

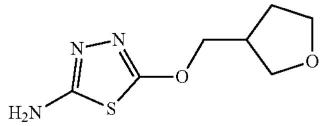

To a solution of (tetrahydrofuran-3-yl)methanol (1.0 g, 9.79 mmol) in THF (5 mL) was added NaH (0.5 g, 14.69 mmol, 60%) in portions at 0° C. and stirred at 0° C. for 30 min under nitrogen atmosphere. To the above solution was added 5-bromo-1,3,4-thiadiazol-2-amine (2.1 g, 11.75 mmol) at 0° C. under nitrogen. The resulting solution was then stirred at 0° C. for 1 hr. The reaction mixture was quenched by the addition of water and extracted with ethyl acetate. The combined organic layers were washed with brine, dried over anhydrous sodium sulfate, filtered, and concentrated under vacuum. The resulting residue was dissolved in DCM (3 mL) and was applied to a 20 g silica gel column that was eluted with 0-50% ethyl acetate in petroleum ether within 30 min to afford 5-((tetrahydrofuran-3-yl)methoxy)-1,3,4-thiadiazol-2-amine (120.0 mg, 69%) as a yellow solid, MS (ESI) calc'd for ($C_7H_{11}N_3O_2S$) $(M+1)^+$, 202.1; found, 202.1.

Step-2: Synthesis of 2'-chloro-5'-methoxy-6-methyl-N-(5-((tetrahydrofuran-3-yl)methoxy)-1,3,4-thiadiazol-2-yl)-(4,4'-bipyridine)-3-carboxamide

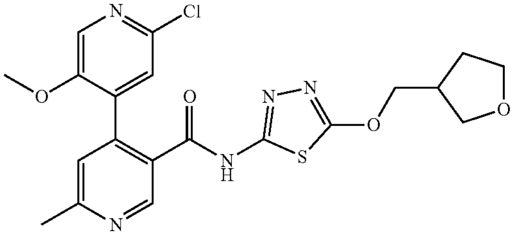

To a solution of Intermediate H (100.0 mg, 0.36 mmol) in Acetonitrile (2 mL) were added 5-((tetrahydrofuran-3-yl)methoxy)-1,3,4-thiadiazol-2-amine (72.0 mg, 0.36 mmol) and 1-methylimidazole (147.0 mg, 1.79 mmol) at 20° C. under nitrogen. To the above solution was added TCFH (100.0 mg, 0.36 mmol) in Acetonitrile (2 mL) at 20° C. under nitrogen. The resulting mixture was then stirred at 20° C. for 1 hr. The resulting residue was dissolved in DMF (1 mL) which was applied to a 20 g C18 column and purified by Combi Flash (Biotage Isolera Prime), eluted with 5~55% acetonitrile in water within 30 min to afford racemic 2'-chloro-5'-methoxy-6-methyl-N-(5-((tetrahydrofuran-3-yl)methoxy)-1,3,4-thiadiazol-2-yl)-(4,4'-bipyridine)-3-carboxamide (67.4 mg, 39%) as a yellow solid. MS (ESI) calc'd for ($C_{20}H_{20}ClN_5O_4S$) $(M+1)^+$, 462.1; found 462.1. $^1H$ NMR (400 MHz, DMSO-$d_6$) δ 12.87 (s, 1H), 8.81 (s, 1H), 8.17 (s, 1H), 7.54 (s, 1H), 7.43 (s, 1H), 4.44-4.30 (m, 2H), 3.82-3.72 (m, 2H), 3.71-3.60 (m, 1H), 3.64 (s, 3H), 3.53-3.50 (m, 1H), 2.74-2.75 (m, 1H), 2.59 (s, 3H), 2.02-1.99 (m, 1H), 1.66-1.64 (m, 1H).

Example 168 and 169

(R)-2'-chloro-5'-methoxy-6-methyl-N-(5-(oxetan-2-ylmethoxy)-1,3,4-thiadiazol-2-yl)-(4,4'-bipyridine)-3-carboxamide and (S)-2'-chloro-5'-methoxy-6-methyl-N-(5-(oxetan-2-ylmethoxy)-1,3,4-thiadiazol-2-yl)-(4,4'-bipyridine)-3-carboxamide

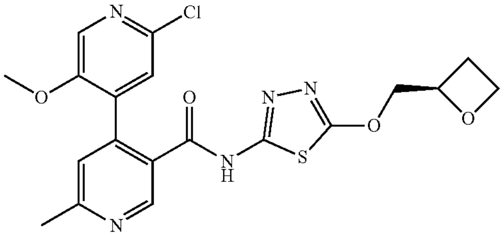

-continued

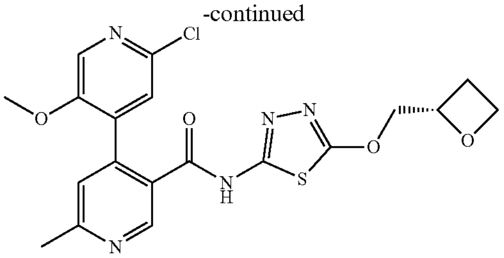

Racemic 2'-chloro-5'-methoxy-6-methyl-N-(5-(oxetan-2-ylmethoxy)-1,3,4-thiadiazol-2-yl)-(4,4'-bipyridine)-3-carboxamide (Example 165, 100 mg) was separated by prep-chiral-HPLC with the following conditions: (Column: CHIRALPAK IG, 2*25 cm, 5 μm; Mobile Phase A: HEX: DCM=3: 1-HPLC, Mobile Phase B: MeOH-HPLC; Flow rate: 20 mL/min; Gradient: 30% B to 30% B in 19 min; Wave Length: 220/254 nm; RT1 (min): 12.17; RT2 (min): 15.94; Sample Solvent: EtOH:DCM=1: 1-HPLC; Injection Volume: 0.3 mL; Number Of Runs: 11) to afford (R)-2'-chloro-5'-methoxy-6-methyl-N-(5-(oxetan-2-ylmethoxy)-1,3,4-thiadiazol-2-yl)-(4,4'-bipyridine)-3-carboxamide, isomer 1 (29.7 mg, 29%) as a white solid with shorter retention time on chiral HPLC and (S)-2'-chloro-5'-methoxy-6-methyl-N-(5-(oxetan-2-ylmethoxy)-1,3,4-thiadiazol-2-yl)-(4,4'-bipyridine)-3-carboxamide, isomer 2 (28.0 mg, 28%) as a white solid with longer retention time on chiral HPLC. The absolute stereochemistry was not determined.

Isomer 1: (R)-2'-chloro-5'-methoxy-6-methyl-N-(5-(oxetan-2-ylmethoxy)-1,3,4-thiadiazol-2-yl)-(4,4'-bipyridine)-3-carboxamide: MS (ESI) calc'd for ($C_{19}H_{18}ClN_5O_4S$) $(M+1)^+$, 448.0; found, 448.0. $^1H$ NMR (400 MHz, DMSO-$d_6$) δ 12.92 (s, 1H), 8.82 (s, 1H), 8.17 (s, 1H), 7.53 (s, 1H), 7.42 (s, 1H), 5.09-4.98 (m, 1H), 4.64-4.43 (m, 4H), 3.64 (s, 3H), 2.77-2.64 (m, 1H), 2.59 (s, 3H), 2.59-2.53 (m, 1H).

Isomer 2: (S)-2'-chloro-5'-methoxy-6-methyl-N-(5-(oxetan-2-ylmethoxy)-1,3,4-thiadiazol-2-yl)-(4,4'-bipyridine)-3-carboxamide: MS (ESI) calc'd for ($C_{19}H_{18}ClN_5O_4S$) $(M+1)^+$, 448.0; found, 448.0. $^1H$ NMR (400 MHz, DMSO-$d_6$) δ 12.92 (s, 1H), 8.82 (s, 1H), 8.17 (s, 1H), 7.54 (s, 1H), 7.43 (s, 1H), 5.09-4.98 (m, 1H), 4.64-4.43 (m, 4H), 3.64 (s, 3H), 2.77-2.64 (m, 1H), 2.59 (s, 3H), 2.59-2.53 (m, 1H).

Example 170 and 171

(R)-2'-chloro-5'-methoxy-6-methyl-N-(5-((tetrahydrofuran-3-yl)methoxy)-1,3,4-thiadiazol-2-yl)-(4,4'-bipyridine)-3-carboxamide and 2'-chloro-5'-methoxy-6-methyl-N-(5-((tetrahydrofuran-3-yl)methoxy)-1,3,4-thiadiazol-2-yl)-(4,4'-bipyridine)-3-carboxamide

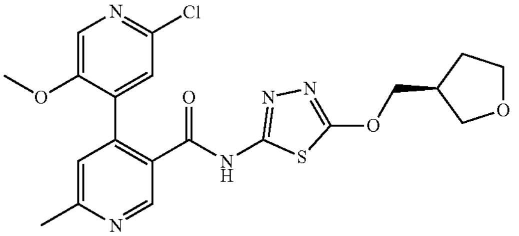

-continued

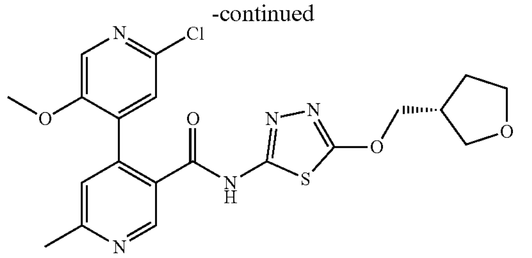

Racemic 2'-chloro-5'-methoxy-6-methyl-N-(5-((tetrahydrofuran-3-yl)methoxy)-1,3,4-thiadiazol-2-yl)-(4,4'-bipyridine)-3-carboxamide (Example 167, 67.4 mg) was separated by prep-chiral HPLC with the following conditions: (Column: CHIRALPAK IF, 2*25 cm, 5 μm; Mobile Phase A: MtBE (0.1% FA)-HPLC, Mobile Phase B: EtOH-HPLC; Flow rate: 11 mL/min; Gradient: 50% B to 50% B in 34 min; Wave Length: 220/254 nm; RT1 (min): 18.66; RT2 (min): 27.68; Sample Solvent: MeOH:DCM=1: 1; Injection Volume: 1 mL; Number Of Runs: 2) to afford (R)-2'-chloro-5'-methoxy-6-methyl-N-(5-((tetrahydrofuran-3-yl)methoxy)-1,3,4-thiadiazol-2-yl)-(4,4'-bipyridine)-3-carboxamide (25.6 mg, 38%) as a white solid with retention time on chiral-HPLC and (S)-2'-chloro-5'-methoxy-6-methyl-N-(5-((tetrahydrofuran-3-yl)methoxy)-1,3,4-thiadiazol-2-yl)-(4,4'-bipyridine)-3-carboxamide (25.3 mg, 37%) as a white solid with retention time on chiral-HPLC. The absolute stereochemistry was determined using vibrational circular dichroism spectroscopy.

(R)-2'-chloro-5'-methoxy-6-methyl-N-(5-((tetrahydrofuran-3-yl)methoxy)-1,3,4-thiadiazol-2-yl)-(4,4'-bipyridine)-3-carboxamide: MS (ESI) calc'd for $(C_{20}H_{20}ClN_5O_4S)$ $(M+1)^+$, 462.1; found, 462.1. $^1H$ NMR (400 MHz, DMSO-$d_6$) δ 12.91 (s, 1H), 8.82 (s, 1H), 8.17 (s, 1H), 7.52 (s, 1H), 7.41 (s, 1H), 4.43-4.28 (m, 2H), 3.76-3.73 (m, 2H), 3.65-3.63 (m, 4H), 3.53-3.51 (m, 1H), 2.73-2.70 (m, 1H), 2.58 (s, 3H), 2.01-2.05 (m, 1H), 1.65-1.68 (m, 1H).

(S)-2'-chloro-5'-methoxy-6-methyl-N-(5-((tetrahydrofuran-3-yl)methoxy)-1,3,4-thiadiazol-2-yl)-(4,4'-bipyridine)-3-carboxamide: MS (ESI) calc'd for $(C_{20}H_{20}ClN_5O_4S)$ $(M+1)^+$, 462.1; found, 462.1. $^1H$ NMR (400 MHz, DMSO-$d_6$) δ 12.91 (s, 1H), 8.83 (s, 1H), 8.16 (s, 1H), 7.52 (s, 1H), 7.40 (s, 1H), 4.38-4.35 (m, 2H), 3.81-3.71 (m, 2H), 3.66-3.63 (m, 4H), 3.53-3.50 (m, 1H), 2.73-2.71 (m, 1H), 2.58 (s, 3H), 2.01-2.03 (m, 1H), 1.65-1.68 (m, 1H).

Example 172

N-(5-((2-oxaspiro(3.3)heptan-6-yl)methoxy)-1,3,4-thiadiazol-2-yl)-2'-chloro-5'-methoxy-6-methyl-(4,4'-bipyridine)-3-carboxamide

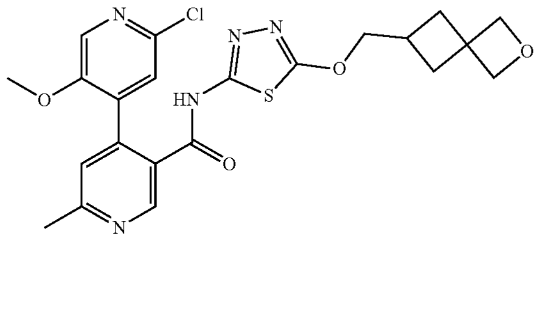 [SMILES: COc1cnc(Cl)cc1-c1cc(C)ncc1C(=O)Nc1nnc(OCC2CC3(COC3)C2)s1]

Step-1: O-((2-oxaspiro(3.3)heptan-6-yl)methyl)S-methyl carbonodithioate

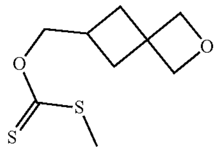

To a solution of (2-oxaspiro(3.3)heptan-6-yl)methanol (500.0 mg, 3.90 mmol) in (THF) (5 mL) was added NaH (187.0 mg, 4.68 mmol, 60%) in portions at 0° C. and stirred at 0° C. for 30 min. Then $CS_2$ (444.6 mg, 5.85 mmol) was added to the above mixture and stirred at 0° C. for 10 min. The resulting mixture was then stirred at 0° C. for 30 min. and then MeI (830.7, 5.85 mmol) was added to the above mixture at 0° C. The resulting mixture was then stirred at 0° C. for 30 min. The reaction mixture was quenched by the addition of water and extracted with ethyl acetate. The combined organic layers were washed with brine, dried over anhydrous sodium sulfate, filtered, and concentrated under vacuum. The resulting residue was purified by Combi Flash (Biotage Isolera Prime) which applied to a 40 g silica gel column that was eluted with 0~100% ethyl acetate in petroleum ether within 20 min to afford O-((2-oxaspiro(3.3)heptan-6-yl)methyl) S-methyl carbonodithioate (697.0 mg, 81%) as a colorless oil. MS (ESI) calc'd for $(C_9H_{14}O_2S_2)$ $(M+1)^+$, 219.0.

Step-2: O-((2-oxaspiro(3.3)heptan-6-yl)methyl) hydrazinecarbothioate

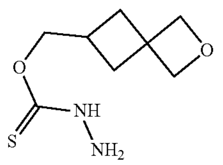 [SMILES: NNC(=S)OCC1CC2(COC2)C1]

To a stirred solution of O-((2-oxaspiro(3.3)heptan-6-yl)methyl)S-methyl carbonodithioate (690.0 mg, 3.16 mmol) in Methanol (2.5 mL) was added hydrazine (21.7, 3.48 mmol, 80%) at 20° C. The resulting solution was stirred at 20° C. for 30 min. The organic solvent was removed under vacuum to afford O-((2-oxaspiro(3.3)heptan-6-yl)methyl) hydrazinecarbothioate (600.0 mg, crude) as a colorless oil. MS (ESI) calc'd for $(C_8H_{14}N_2O_2S)$ $(M+1)^+$, 203.0.

Step-3: 5-((2-oxaspiro(3.3)heptan-6-yl)methoxy)-1,3,4-thiadiazol-2-amine

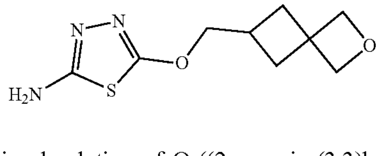

To a stirred solution of O-((2-oxaspiro(3.3)heptan-6-yl)methyl) hydrazinecarbothioate (600.0 mg, 2.97 mmol) in Methanol (2.5 mL) were added TEA (0.82 mL, 5.93 mmol)

and BrCN (343.0 mg, 3.26 mmol) at 20° C. The resulting solution was stirred at 20° C. for 1 hr. The reaction mixture was quenched by the addition of water and extracted with ethyl acetate. The combined organic layers were washed with brine, dried over anhydrous sodium sulfate, filtered, and concentrated under vacuum. The resulting residue was purified by Combi Flash (Biotage Isolera Prime) which applied to a 40 g silica gel column that was eluted with 0~20% methanol in dichloromethane within 30 min to afford 5-((2-oxaspiro(3.3)heptan-6-yl)methoxy)-1,3,4-thiadiazol-2-amine (243.0 mg, 35%) as a yellow solid. MS (ESI) calc'd for ($C_9H_{13}N_3O_2S$) $(M+1)^+$, 228.0. found: 228.1.

Step-4: N-(5-((2-oxaspiro(3.3)heptan-6-yl)methoxy)-1,3,4-thiadiazol-2-yl)-2'-chloro-5'-methoxy-6-methyl-(4,4'-bipyridine)-3-carboxamide

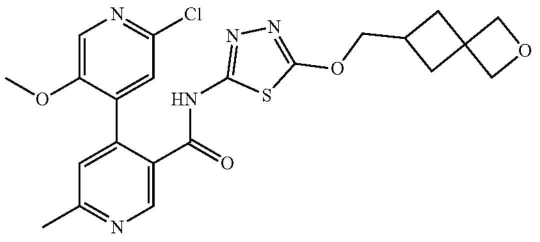 [SMILES: COc1cnc(Cl)cc1-c1cc(C)ncc1C(=O)Nc1nnc(OCC2CC3(COC3)C2)s1]

To a stirred solution of 5-((2-oxaspiro(3.3)heptan-6-yl)methoxy)-1,3,4-thiadiazol-2-amine (100.0 mg, 0.44 mmol) in Acetonitrile (1 mL) were added Intermediate H (123.0 mg, 0.44 mmol) and 1-methylimidazole (0.17 mL, 2.20 mmol) at 20° C. To the above solution was added TCFH (124.0 mg, 0.44 mmol) in Acetonitrile (0.5 mL) at 20° C. under nitrogen. The resulting mixture was then stirred at 20° C. for 2 hr. The resulting mixture was dissolved in acetonitrile (3 mL) which was applied to a 40 g C18 column and purified by Combi Flash (Biotage Isolera Prime), eluted with 5~100% acetonitrile in water within 25 min to afford N-(5-((2-oxaspiro(3.3)heptan-6-yl)methoxy)-1,3,4-thiadiazol-2-yl)-2'-chloro-5'-methoxy-6-methyl-(4,4'-bipyridine)-3-carboxamide (109.2 mg, 49%) as a white solid. MS (ESI) calc'd for ($C_{22}H_{22}ClN_5O_4S$) $(M+1)^+$, 488.1. found: 488.2. $^1H$ NMR (400 MHz, DMSO-$d_6$) δ 12.88 (s, 1H), 8.81 (s, 1H), 8.17 (s, 1H), 7.53 (s, 1H), 7.43 (s, 1H), 4.57 (s, 2H), 4.50 (s, 2H), 4.33 (d, J=6.4 Hz, 2H), 3.63 (s, 3H), 2.59 (s, 3H), 2.53-2.52 (m, 1H), 2.40-2.30 (m, 2H), 2.10-1.99 (m, 2H).

Example 173

N-(5-(azetidin-3-ylmethoxy)-1,3,4-thiadiazol-2-yl)-2'-chloro-5'-methoxy-6-methyl-(4,4'-bipyridine)-3-carboxamide

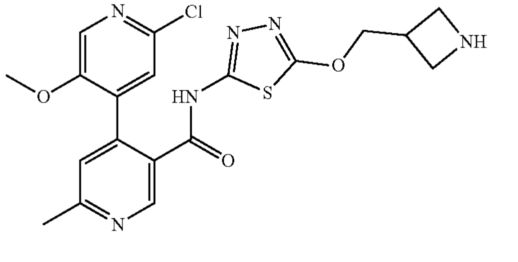 [SMILES: COc1cnc(Cl)cc1-c1cc(C)ncc1C(=O)Nc1nnc(OCC2CNC2)s1]

Step-1: tert-butyl 3-((((methylthio)carbonothioyl)oxy)methyl)azetidine-1-carboxylate

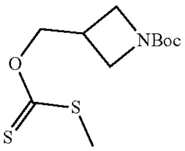

To a degassed solution of tert-butyl 3-(hydroxymethyl)azetidine-1-carboxylate (2.0 g, 10.68 mmol) in THF (10 mL) was added NaH (0.4 g, 10.68 mmol, 60%) in portions at 0° C. and stirred at 25° C. for 30 min. Then $CS_2$ (812.0 mg, 10.68 mmol) was added to the above mixture and stirred at 0° C. for 10 min. and then MeI (1.6 g, 10.68 mmol) was added to the above mixture at 0° C. The resulting mixture was stirred at room temperature for 1 hr. The reaction mixture was quenched by the addition of water and extracted with ethyl acetate. The combined organic layers were washed with brine, dried over anhydrous sodium sulfate, filtered, and concentrated under vacuum. The resulting residue was purified by Combi Flash (Biotage Isolera Prime) which applied to 120 g silica gel column and eluted with 0-50% ethyl acetate in petroleum ether within 30 min to afford tert-butyl 3-((((methylthio)carbonothioyl)oxy)methyl)azetidine-1-carboxylate (2.3 g, 68%) as a white solid. MS (ESI) calc'd for ($C_{11}H_{19}NO_3S_2$) $(M+1)^+$, 278.1, found 278.1.

Step-2: tert-butyl 3-(((hydrazinecarbonothioyl)oxy)methyl)azetidine-1-carboxylate

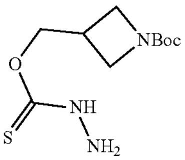

To a stirred solution of tert-butyl 3-((((methylthio)carbonothioyl)oxy)methyl)azetidine-1-carboxylate (2.3 g, 8.40 mmol) in Methanol (5 mL) was added hydrazine (580.0 mg, 9.24 mmol, 80%) at 20° C. The resulting solution was stirred at 20° C. for 0.5 hr. The reaction mixture was concentrated under vacuum to afford tert-butyl 3-(((hydrazinecarbonothioyl)oxy)methyl)azetidine-1-carboxylate (1.9 g, crude) as a yellow oil. MS (ESI) calc'd for ($C_{10}H_{19}N_3O_3S$) $(M+1)^+$, 262.2, found 262.2.

Step-3: tert-butyl 3-(((5-amino-1,3,4-thiadiazol-2-yl)oxy)methyl)azetidine-1-carboxylate

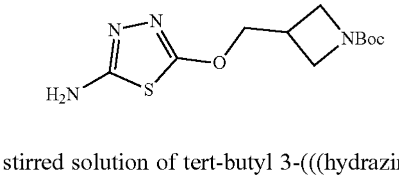

To a stirred solution of tert-butyl 3-(((hydrazinecarbonothioyl)oxy)methyl)azetidine-1-carboxylate (1.9 g, 7.42 mmol) in Methanol (5 mL) were added TEA (1.5 g, 14.85 mmol) and BrCN (0.9 g, 8.17 mmol) at 20° C. The resulting solution was stirred at 20° C. for 1 hr. The reaction mixture was quenched by the addition of water and extracted with ethyl acetate. The combined organic layers were washed with brine, dried over anhydrous sodium sulfate, filtered, and concentrated under vacuum. The resulting residue was purified by Combi Flash (Biotage Isolera Prime) which applied to 40 g silica gel column and eluted with 0-50% ethyl acetate in petroleum ether within 30 min to afford tert-butyl 3-(((5-amino-1,3,4-thiadiazol-2-yl)oxy)methyl) azetidine-1-carboxylate (1.8 g, 79%) as a white solid. MS (ESI) calc'd for ($C_{11}H_{18}N_4O_3S$) $(M+1)^+$, 287.1; found 287.1.

Step-4: tert-butyl 3-(((5-(2'-chloro-5'-methoxy-6-methyl-(4,4'-bipyridine)-3-carboxamido)-1,3,4-thiadiazol-2-yl)oxy)methyl)azetidine-1-carboxylate

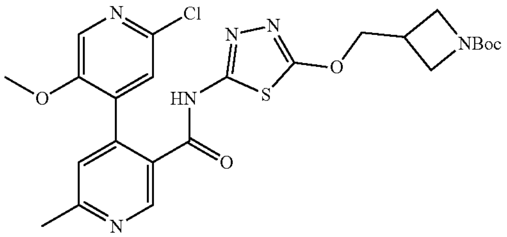 [SMILES: COc1cnc(Cl)cc1-c1cc(C)ncc1C(=O)Nc1nnc(OCC2CN(C(=O)OC(C)(C)C)C2)s1]

To a solution of Intermediate H (1.5 g, 5.33 mmol) in Acetonitrile (5 mL) were added tert-butyl 3-(((5-amino-1,3,4-thiadiazol-2-yl)oxy)methyl)azetidine-1-carboxylate (1.5 g, 5.33 mmol) and 1-methylimidazole (2.1 g, 26.7 mmol) at 20° C. under nitrogen. To the above solution was added TCFH (1.5 g, 5.33 mmol) in Acetonitrile (5 mL) at 20° C. under nitrogen. The resulting mixture was then stirred at 20° C. for 1 hr. The resulting residue was dissolved in DMF (2 mL) which was applied to a 20 g C18 column and purified by Combi Flash (Biotage Isolera Prime), eluted with 5~75% acetonitrile in water within 25 min to afford tert-butyl 3-(((5-(2'-chloro-5'-methoxy-6-methyl-(4,4'-bipyridine)-3-carboxamido)-1,3,4-thiadiazol-2-yl)oxy)methyl)azetidine-1-carboxylate (421 mg, 14%) as a white solid. MS (ESI) calc'd for ($C_{24}H_{27}ClN_4O_5S$) $(M+1)^+$, 547.1; found 547.2.

Step-5: N-(5-(azetidin-3-ylmethoxy)-1,3,4-thiadiazol-2-yl)-2'-chloro-5'-methoxy-6-methyl-(4,4'-bipyridine)-3-carboxamide

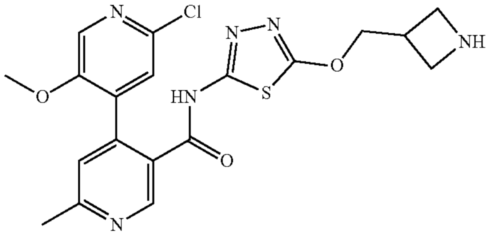 [SMILES: COc1cnc(Cl)cc1-c1cc(C)ncc1C(=O)Nc1nnc(OCC2CNC2)s1]

To a stirred solution of tert-butyl 3-(((5-(2'-chloro-5'-methoxy-6-methyl-(4,4'-bipyridine)-3-carboxamido)-1,3,4-thiadiazol-2-yl)oxy)methyl)azetidine-1-carboxylate (100.0 mg, 0.183 mmol) in DCM (1 mL) was added trifluoroacetic acid (0.2 mL) at 20° C. The resulting solution was stirred at 20° C. for 1 hr. The resulting residue was dissolved in DMF (1 mL) which was applied to a 20 g C18 column and purified by Combi Flash (Biotage Isolera Prime), eluted with 5-55% acetonitrile in water within 30 min to afford N-(5-(azetidin-3-ylmethoxy)-1,3,4-thiadiazol-2-yl)-2'-chloro-5'-methoxy-6-methyl-(4,4'-bipyridine)-3-carboxamide (36.3 mg, 44%) as a white solid with trifluoroacetic acid salt form. MS (ESI) calc'd for ($C_{19}H_{19}ClN_6O_3S$) $(M+1)^+$, 447.1; found 447.1. $^1H$ NMR (400 MHz, DMSO-$d_6$) δ 8.69 (s, 1H), 8.07 (s, 1H), 7.50 (s, 1H), 7.39 (s, 1H), 4.50 (s, 2H), 4.19-4.08 (m, 2H), 3.91-3.89 (m, 2H), 3.59 (s, 3H), 3.31-3.19 (m, 1H), 2.56 (s, 3H).

Example 174

2'-chloro-5'-methoxy-6-methyl-N-(5-(piperidin-4-ylmethoxy)-1,3,4-thiadiazol-2-yl)-(4,4'-bipyridine)-3-carboxamide

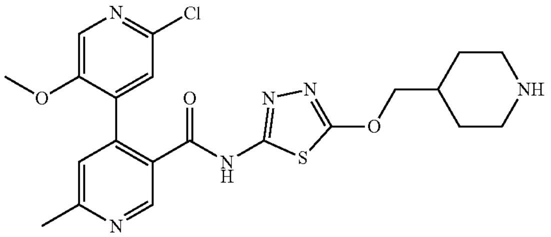 [SMILES: COc1cnc(Cl)cc1-c1cc(C)ncc1C(=O)Nc1nnc(OCC2CCNCC2)s1]

Step-1: tert-butyl 4-((((methylthio)carbonothioyl) oxy)methyl)piperidine-1-carboxylate

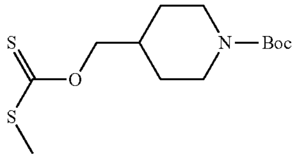 [SMILES: CSC(=S)OCC1CCN(C(=O)OC(C)(C)C)CC1]

To a solution of tert-butyl 4-(hydroxymethyl)piperidine-1-carboxylate (5.0 g, 23.22 mmol) in THF (6 mL) was added NaH (1.8 g, 46.4 mmol, 60%) in portions at 0° C. and stirred at 0° C. for 30 min under nitrogen. To the above solution was added $CS_2$ (2.1 mL, 34.8 mmol) at 0° C. under nitrogen. The resulting solution was stirred at 0° C. for 15 min under nitrogen. To the above solution was added MeI (2.2 mL, 34.8 mmol) at 0° C. under nitrogen. The resulting solution was stirred at 0° C. for 15 min under nitrogen. The reaction mixture was quenched by the addition of water and extracted with ethyl acetate. The combined organic layers were washed with brine, dried over anhydrous sodium sulfate, filtered, and concentrated under vacuum to afford tert-butyl 4-((((methylthio)carbonothioyl)oxy)methyl)piperidine-1-carboxylate (8.0 g, 90%) as a yellow solid.

Step-2: tert-butyl 4-(((hydrazinecarbonothioyl)oxy) methyl)piperidine-1-carboxylate

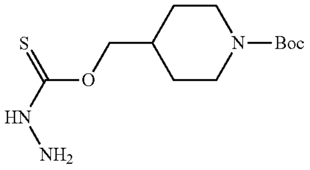

To a solution of tert-butyl 4-((((methylthio)carbonothioyl) oxy)methyl)piperidine-1-carboxylate (5.0 g, 13.10 mmol) in methanol (40 mL) was added hydrazine (0.7 mL, 15.71 mmol, 80%) at 16° C. The resulting solution was stirred at 16° C. for 2 hr. The reaction mixture was quenched by the addition of water and extracted with ethyl acetate. The combined organic layers were washed with brine, dried over anhydrous sodium sulfate, filtered, and concentrated under vacuum to afford tert-butyl 4-(((hydrazinecarbonothioyl) oxy)methyl)piperidine-1-carboxylate (5.0 g, crude) as a yellow oil. MS (ESI) calc'd for ($C_{12}H_{23}N_3O_3S$) $(M+1)^+$, 290.1; found 290.1.

Step-3: tert-butyl 4-(((5-amino-1,3,4-thiadiazol-2-yl) oxy)methyl)piperidine-1-carboxylate

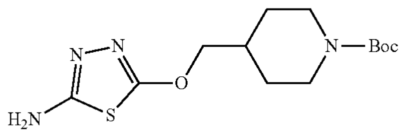 [SMILES: CC(C)(C)OC(=O)N1CCC(COc2nnc(N)s2)CC1]

To a solution of tert-butyl 4-(((hydrazinecarbonothioyl) oxy)methyl)piperidine-1-carboxylate (5.0 g, 17.28 mmol) in methanol (20 mL) were added TEA (4.8 mL, 34.6 mmol) and cyanic bromide (2.0 g, 19.01 mmol) at 18° C. The resulting solution was stirred at 18° C. for 30 min. The reaction mixture was quenched by the addition of water and extracted with ethyl acetate. The combined organic layers were washed with brine, dried over anhydrous sodium sulfate, filtered, and concentrated under vacuum. The residue was dissolved in DCM (3 mL) which was applied to a 40 g silica gel column and eluted with 0-19% ethyl acetate in petroleum ether within 35 min to afford tert-butyl 4-(((5-amino-1,3,4-thiadiazol-2-yl)oxy)methyl)piperidine-1-carboxylate (650.0 mg, 10%) as a yellow solid. MS (ESI) calc'd for ($C_{13}H_{22}N_4O_3S$) $(M+1)^+$, 315.1; found 315.1.

Step-4: tert-butyl 4-(((5-(2'-chloro-5'-methoxy-6-methyl-(4,4'-bipyridine)-3-carboxamido)-1,3,4-thiadiazol-2-yl)oxy)methyl)piperidine-1-carboxylate

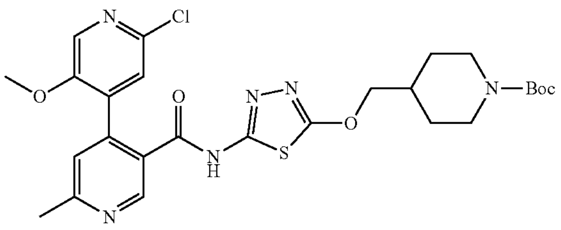 [SMILES: COc1cnc(Cl)cc1-c1cc(C)ncc1C(=O)Nc1nnc(OCC2CCN(C(=O)OC(C)(C)C)CC2)s1]

To a solution of tert-butyl 4-(((5-amino-1,3,4-thiadiazol-2-yl)oxy)methyl)piperidine-1-carboxylate (559.0 mg, 1.77 mmol) in acetonitrile (2 mL) were added Intermediate H (413.0 mg, 1.48 mmol) and NMI (365.0 mg, 4.45 mmol). A solution of TCFH (622.0 mg, 2.22 mmol) in acetonitrile (1 mL) was added thereto dropwise under nitrogen. The resulting solution was stirred at 18° C. for 2 hr. The organic solvent was removed under vacuum. The resulting residue was dissolved in DMF (4 mL) which was applied to a 40 g Cis column and purified by Combi Flash (Biotage Isolera Prime), eluted with 5~60% acetonitrile in water within 35 min to afford tert-butyl 4-(((5-(2'-chloro-5'-methoxy-6-methyl-(4,4'-bipyridine)-3-carboxamido)-1,3,4-thiadiazol-2-yl)oxy)methyl)piperidine-1-carboxylate (113.0 mg, 12%) as a brown solid. MS (ESI) calc'd for ($C_{26}H_3ClN_6O_5S$) $(M+1)^+$, 575.1; found 575.1.

Step-5: 2'-chloro-5'-methoxy-6-methyl-N-(5-(piperidin-4-ylmethoxy)-1,3,4-thiadiazol-2-yl)-(4,4'-bipyridine)-3-carboxamide

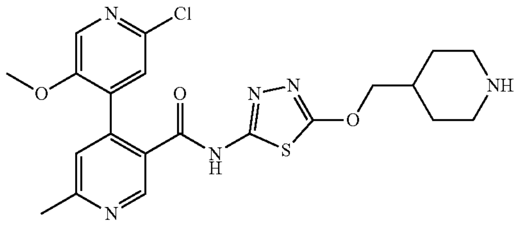 [SMILES: COc1cnc(Cl)cc1-c1cc(C)ncc1C(=O)Nc1nnc(OCC2CCNCC2)s1]

To a solution of tert-butyl 4-(((5-(2'-chloro-5'-methoxy-6-methyl-(4,4'-bipyridine)-3-carboxamido)-1,3,4-thiadiazol-2-yl)oxy)methyl)piperidine-1-carboxylate (100.0 mg, 0.15 mmol) in DCM (1.5 mL) was added TFA (0.5 mL) at 20° C. The resulting solution was stirred at 20° C. for 30 min. The organic solvent was removed under vacuum. The residue was diluted with water. The aqueous layer was basified with sodium bicarbonate to pH ~8, and concentrated under vacuum. The crude product was dissolved in DMF (4 mL) which was applied to a 40 g Cis column and purified by Combi Flash (Biotage Isolera Prime), eluted with 5-35% acetonitrile in water within 35 min to afford 2'-chloro-5'-methoxy-6-methyl-N-(5-(piperidin-4-ylmethoxy)-1,3,4-thiadiazol-2-yl)-(4,4'-bipyridine)-3-carboxamide (5.2 mg, 7%) as a white solid. MS (ESI) calc'd for ($C_{21}H_{23}ClN_6O_3S$) $(M+1)^+$, 475.1; found 475.3. $^1H$ NMR (400 MHz, DMSO-$d_6$) δ 8.97 (s, 1H), 8.11 (s, 1H), 7.30 (s, 1H), 7.14 (s, 1H), 4.19 (d, J=6.4 Hz, 2H), 3.63 (s, 3H), 3.26-3.15 (m, 2H), 2.85-2.75 (m, 2H), 2.68 (s, 3H), 2.10-1.95 (m, 1H), 1.85-1.75 (m, 2H), 1.44-1.30 (m, 2H).

Example 175

2'-chloro-5'-methoxy-6-methyl-N-(5-(pyrrolidin-3-ylmethoxy)-1,3,4-thiadiazol-2-yl)-(4,4'-bipyridine)-3-carboxamide

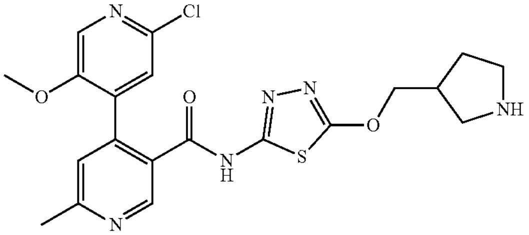 [SMILES: COc1cnc(Cl)cc1-c1cc(C)ncc1C(=O)Nc1nnc(OCC2CCNC2)s1]

Step-1: tert-butyl 3-((((methylthio)carbonothioyl) oxy)methyl)pyrrolidine-1-carboxylate

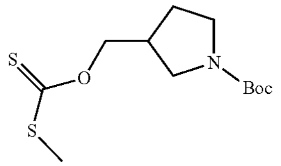 [SMILES: CSC(=S)OCC1CCN(C(=O)OC(C)(C)C)C1]

To a degassed solution of tert-butyl 3-(hydroxymethyl) pyrrolidine-1-carboxylate (2.0 g, 9.94 mmol) in THF (40 mL) was added NaH (800.1 mg, 19.99 mmol, 60%) in portions at 0° C. and stirred at 25° C. for 30 min. Then $CS_2$ (1.1 g, 14.91 mmol) was added to the above mixture and stirred at 0° C. for 10 min. and then MeI (2.1 g, 14.91 mmol) was added to the above mixture at 0° C. The resulting mixture was stirred at room temperature for 1 hr. The reaction mixture was quenched by the addition of water and extracted with ethyl acetate. The combined organic layers were washed with brine, dried over anhydrous sodium sulfate, filtered, and concentrated under vacuum. The resulting residue was purified by Combi Flash (Biotage Isolera Prime) which applied to 80 g silica gel column and eluted with 0~50% ethyl acetate in petroleum ether within 30 min to afford tert-butyl 3-((((methylthio)carbonothioyl)oxy) methyl)pyrrolidine-1-carboxylate (2.5 g, 83%) as a yellow oil.

Step-2: tert-butyl 3-((2-hydrazineyl-2-thioxoethoxy) methyl)pyrrolidine-1-carboxylate

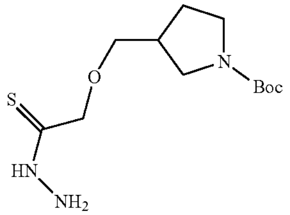 [SMILES: CC(C)(C)OC(=O)N1CCC(COCC(=S)NN)C1]

To a stirred solution of tert-butyl 3-((((methylthio)carbonothioyl)oxy)methyl)pyrrolidine-1-carboxylate (2.5 g, 8.58 mmol) in Methanol (5 mL) was added hydrazine hydrate (580.0 mg, 9.28 mmol, 80%) at 20° C. The resulting solution was stirred at 20° C. for 0.5 hr. The reaction mixture was concentrated under vacuum to afford tert-butyl 3-((2-hydrazineyl-2-thioxoethoxy)methyl)pyrrolidine-1-carboxylate (2.5 g, crude) as a yellow oil. MS (ESI) calc'd for ($C_{12}H_{23}N_3O_3S$) $(M+1)^+$, 289.1, found 289.2.

Step-3: tert-butyl 3-(((5-amino-1,3,4-thiadiazol-2-yl) oxy)methyl)pyrrolidine-1-carboxylate

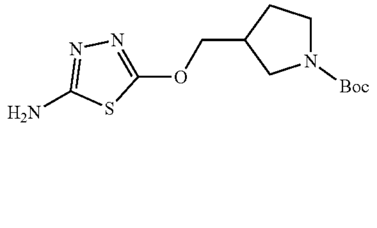

To a stirred solution of tert-butyl 3-((2-hydrazineyl-2-thioxoethoxy)methyl)pyrrolidine-1-carboxylate (2.5 g, 8.64 mmol) in Methanol (5 mL) were added TEA (1.6 g, 15.84 mmol) and BrCN (1.0 g, 9.50 mmol) at 20° C. The resulting solution was stirred at 20° C. for 1 hr. The reaction mixture was quenched by the addition of water and extracted with ethyl acetate. The combined organic layers were washed with brine, dried over anhydrous sodium sulfate, filtered, and concentrated under vacuum. The resulting residue was purified by Combi Flash (Biotage Isolera Prime) which applied to 80 g silica gel column and eluted with 0~12% ethyl acetate in petroleum ether within 30 min to afford tert-butyl 3-(((5-amino-1,3,4-thiadiazol-2-yl)oxy)methyl) pyrrolidine-1-carboxylate (2.3 g, 65%) as a brown oil. MS (ESI) calculated for ($C_{12}H_{20}N_4O_3S$) $(M+1)^+$, 301.1; found, 301.1.

Step-4: tert-butyl 3-{((5-{2'-chloro-5'-methoxy-6-methyl-(4,4'-bipyridine)-3-amido}-1,3,4-thiadiazol-2-yl)oxy)methyl}pyrrolidine-1-carboxylate

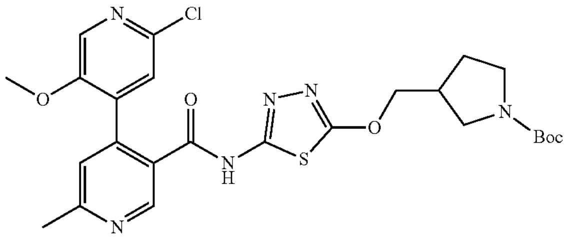 [SMILES: COc1cnc(Cl)cc1-c1cc(C)ncc1C(=O)Nc1nnc(OCC2CCN(C(=O)OC(C)(C)C)C2)s1]

To a solution of Intermediate H (300.0 mg, 1.08 mmol) in Acetonitrile (1 mL) were added tert-butyl 3-(((5-amino-1,3,4-thiadiazol-2-yl)oxy)methyl)pyrrolidine-1-carboxylate (711.0 mg, 1.18 mmol) and 1-methylimidazole (442.0 mg, 5.38 mmol) at 20° C. under nitrogen. To the above solution was added a solution of TCFH (332.0 mg, 1.18 mmol) in Acetonitrile (1 mL) at 20° C. under nitrogen. The mixture was then stirred at 20° C. for 1 hr. The resulting mixture was diluted with DMF (1 mL) which was applied to a 40 g C18 column and purified by Combi Flash (Biotage Isolera Prime), eluted with 5~50% acetonitrile in water within 35 min to afford tert-butyl 3-{((5-{2'-chloro-5'-methoxy-6-methyl-(4,4'-bipyridine)-3-amido}-1,3,4-thiadiazol-2-yl) oxy)methyl}pyrrolidine-1-carboxylate (180.0 mg, 28%) as a yellow solid. MS (ESI) calculated for ($C_{25}H_{29}ClN_6O_5S$) $(M+1)^+$, 561.2; found, 561.2.

Step-5: 2'-chloro-5'-methoxy-6-methyl-N-(5-(pyrrolidin-3-ylmethoxy)-1,3,4-thiadiazol-2-yl)-(4,4'-bipyridine)-3-carboxamide

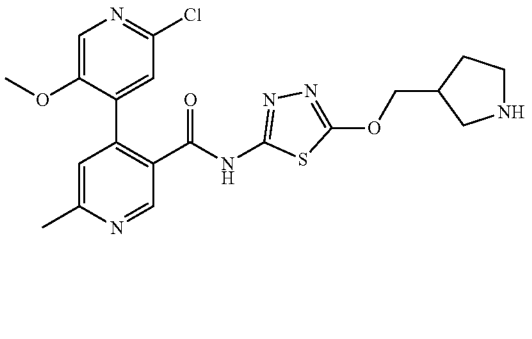 [SMILES: COc1cnc(Cl)cc1-c1cc(C)ncc1C(=O)Nc1nnc(OCC2CCNC2)s1]

To a stirred solution of tert-butyl 3-{((5-{2'-chloro-5'-methoxy-6-methyl-(4,4'-bipyridine)-3-amido}-1,3,4-thiadiazol-2-yl)oxy)methyl}pyrrolidine-1-carboxylate (180.0 mg, 0.30 mmol) in DCM (2 mL) was added trifluoroacetic acid (0.7 mL) at 20° C. The resulting solution was stirred at 20° C. for 1 hr. The mixture was then concentrated under vacuum. The resulting residue was dissolved in DMF (1 mL), adjusted to pH ~7 by sat. $NaHCO_3$ aq., applied to a 40 g C18 column and purified by Combi Flash (Biotage Isolera Prime), eluted with 5~30% acetonitrile in water within 30 min to afford racemic 2'-chloro-5'-methoxy-6-methyl-N-(5-(pyrrolidin-3-ylmethoxy)-1,3,4-thiadiazol-2-yl)-(4,4'-bipyridine)-3-carboxamide (58.4 mg, 41%) as a light yellow solid. MS (ESI) calculated for ($C_{20}H_{21}ClN_6O_3S$) $(M+1)^+$, 461.1; found, 461.2. $^1H$ NMR (400 MHz, DMSO-$d_6$), S 8.95 (s, 1H), 8.12 (s, 1H), 7.35 (s, 1H), 7.20 (s, 1H), 4.37-4.28 (m, 2H), 3.79 (s, 3H), 3.30-3.22 (m, 2H), 3.22-3.18 (m, 1H), 3.14-3.09 (m, 1H), 3.07-2.95 (m, 1H), 2.76-2.72 (m, 1H), 2.51-2.50 (m, 3H), 2.07-2.03 (m, 1H), 1.71-1.66 (m, 1H).

Example 176

2'-chloro-5'-methoxy-6-methyl-N-(5-((1-methylpyrrolidin-3-yl)methoxy)-1,3,4-thiadiazol-2-yl)-(4,4'-bipyridine)-3-carboxamide

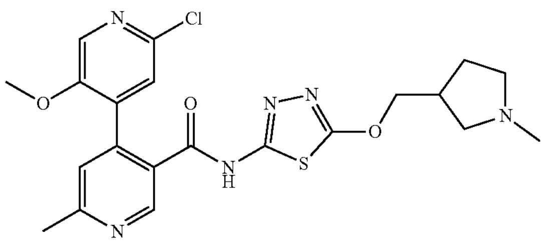

To a solution of 2'-chloro-5'-methoxy-6-methyl-N-(5-(pyrrolidin-3-ylmethoxy)-1,3,4-thiadiazol-2-yl)-(4,4'-bipyridine)-3-carboxamide (Example 175, 50.0 mg, 0.11 mmol) in Methanol (1 mL) was added formaldehyde (24.8 mg, 0.33 mmol, 40%) at 20° C. The resulting solution was stirred at 20° C. for 2 hr. To the above solution was added sodium triacetoxyborohydride (46.0 mg, 0.22 mmol) at 20° C. The resulting solution was stirred at 20° C. for 1 hr. The mixture was dissolved in DMF (1 mL) and was purified by prep-HPLC with the following conditions: (Column: XBridge Prep OBD C18 Column, 30*150 mm, 5 µm; Mobile Phase A: Water (10.0 mmol/L $NH_4HCO_3$), Mobile Phase B: ACN; Flow rate: 60 mL/min; Gradient: 13% B to 23% B in 8 min, 23% B; Wave Length: 254 nm; RT1 (min): 8; Injection Volume: 0.5 mL; Number Of Runs: 3) to afford 2'-chloro-5'-methoxy-6-methyl-N-(5-((1-methylpyrrolidin-3-yl)methoxy)-1,3,4-thiadiazol-2-yl)-(4,4'-bipyridine)-3-carboxamide (19.1 mg, 37%) as a white solid. MS (ESI) calculated for ($C_{21}H_{23}ClN_6O_3S$) $(M+1)^+$, 475.1; found, 475.3. $^1H$ NMR (400 MHz, DMSO-$d_6$), S 8.87 (s, 1H), 8.15 (s, 1H), 7.45 (s, 1H), 7.32 (s, 1H), 4.28-4.21 (m, 2H), 3.63 (s, 3H), 2.72-2.51 (m, 6H), 2.44-2.34 (m, 2H), 2.29 (s, 3H), 1.97-1.92 (m, 1H), 1.63-1.42 (m, 1H).

Example 177

2'-chloro-5'-methoxy-6-methyl-N-(5-((2-methyltetrahydrofuran-3-yl)methoxy)-1,3,4-thiadiazol-2-yl)-(4,4'-bipyridine)-3-carboxamide

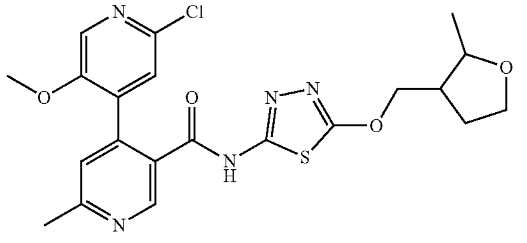 [SMILES: COc1cnc(Cl)cc1-c1cc(C)ncc1C(=O)Nc1nnc(OCC2CCOC2C)s1]

Step-1: S-methyl O-((2-methyltetrahydrofuran-3-yl)methyl) carbonodithioate

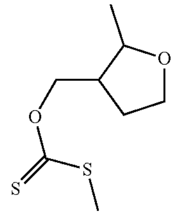

To a solution of (2-methyltetrahydrofuran-3-yl)methanol (100.0 mg, 0.86 mmol) in THF (3 mL) was added NaH (41.3 mg, 1.03 mmol, 60%) in portions at 0° C. and stirred at 0° C. for 30 min. Then $CS_2$ (98.0 mg, 1.29 mmol) was added to the above mixture and stirred at 0° C. for 10 min, and then MeI (183.1 mg, 1.29 mmol) was added to the above mixture at 5° C. The resulting mixture was stirred at room temperature for 1 hr. The reaction mixture was quenched by the addition of water and extracted with ethyl acetate. The combined organic layers were washed with brine, dried over anhydrous sodium sulfate, filtered, and concentrated under vacuum. The resulting residue was dissolved in DCM (2 mL) and purified by Combi Flash (Biotage Isolera Prime) which applied to a 20 g silica gel column that was eluted with 0~20% ethyl acetate in petroleum ether within 20 min to afford S-methyl O-((2-methyltetrahydrofuran-3-yl)methyl) carbonodithioate (140.0 mg, 76%) as a colorless oil.

Step-2: O-((2-methyltetrahydrofuran-3-yl)methyl) hydrazinecarbothioate

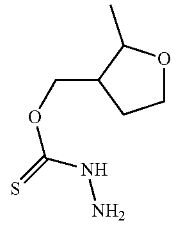

To a stirred solution of S-methyl O-((2-methyltetrahydrofuran-3-yl)methyl) carbonodithioate (140.0 mg, 0.68 mmol) in Methanol (1 mL) was added hydrazine hydrate (46.9 mg, 0.75 mmol, 80%) at 23° C. The resulting solution was stirred at 23° C. for 1 hr. The mixture was concentrated under vacuum to afford O-((2-methyltetrahydrofuran-3-yl)methyl) hydrazinecarbothioate (130.0 mg, crude) as a colorless oil. MS (ESI) calc'd for ($C_7H_{14}N_2O_2S$) $(M+1)^+$, 191.1, found 191.1.

Step-3: 5-((2-methyltetrahydrofuran-3-yl)methoxy)-1,3,4-thiadiazol-2-amine

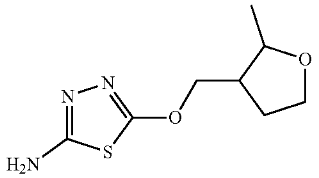

To a stirred solution of O-((2-methyltetrahydrofuran-3-yl)methyl) hydrazinecarbothioate (130.0 mg, 0.68 mmol) in Methanol (1 mL) were sequentially added TEA (138.3 mg, 1.37 mmol) and cyanic bromide (80.0 mg, 0.75 mmol) at 23° C. The resulting solution was stirred at 23° C. for 1 hr. The reaction mixture was quenched by the addition of water and extracted with ethyl acetate. The combined organic layers were washed with brine, dried over anhydrous sodium sulfate, filtered, and concentrated under vacuum. The resulting residue was dissolved in DCM (2 mL) and purified by Combi Flash (Biotage Isolera Prime) which applied to a 20 g silica gel column that was eluted with 0~10% methanol in dichloromethane within 25 min to afford 5-((2-methyltetrahydrofuran-3-yl)methoxy)-1,3,4-thiadiazol-2-amine (70.0 mg, 47%) as a yellow solid. MS (ESI) calc'd for ($C_8H_{13}N_3O_2S$) $(M+1)^+$, 216.1, found 216.1.

Step-4: 2'-chloro-5'-methoxy-6-methyl-N-(5-((2-methyltetrahydrofuran-3-yl)methoxy)-1,3,4-thiadiazol-2-yl)-(4,4'-bipyridine)-3-carboxamide

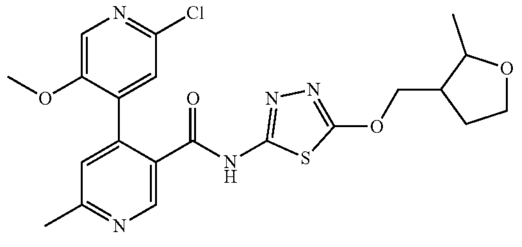 [SMILES: COc1cnc(Cl)cc1-c1cc(C)ncc1C(=O)Nc1nnc(OCC2CCOC2C)s1]

To a stirred solution of 5-((2-methyltetrahydrofuran-3-yl)methoxy)-1,3,4-thiadiazol-2-amine (60.0 mg, 0.28 mmol) in Acetonitrile (1.5 mL) were added Intermediate H (78.0 mg, 0.28 mmol) and 1-methylimidazole (114.0 mg, 1.39 mmol). To the above was added a solution of TCFH (78.0 mg, 0.28 mmol) in Acetonitrile (1.5 mL). The mixture was stirred at 23° C. for 2 hr. The resulting mixture was applied to a 40 g C18 column and purified by Combi Flash (Biotage Isolera Prime), eluted with 5~50% acetonitrile in water within 35 min to afford 2'-chloro-5'-methoxy-6-methyl-N-(5-((2-methyltetrahydrofuran-3-yl)methoxy)-1,3,4-thiadiazol-2-yl)-(4,4'-bipyridine)-3-carboxamide as a mixture of diastereomers and enantiomers (83.2 mg, 62%, white solid). MS (ESI) calc'd for ($C_{21}H_{22}ClN_5O_4S$) $(M+1)^+$, 476.1, found 476.2. $^1$H NMR (400 MHz, DMSO-$d_6$) δ 12.90 (s, 1H), 8.81 (s, 1H), 8.18 (s, 1H), 7.54 (s, 1H), 7.43 (s, 1H), 4.48-4.41 (m, 1H), 4.40-4.26 (m, 1H), 4.01-3.98 (m, 1H), 3.90-3.79 (m, 1H), 3.72-3.54 (m, 4H), 2.69-2.57 (m, 4H), 2.15-1.97 (m, 1H), 1.82-1.74 (m, 1H), 1.20 (d, J=6.4 Hz, 1H), 1.11 (d, J=6.4 Hz, 2H).

Example 178

2'-chloro-5'-methoxy-6-methyl-N-(5-((1-methylpiperidin-4-yl)methoxy)-1,3,4-thiadiazol-2-yl)-(4,4'-bipyridine)-3-carboxamide

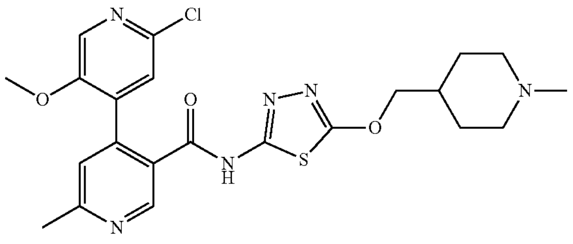

To a stirred solution of 2'-chloro-5'-methoxy-6-methyl-N-(5-(piperidin-4-ylmethoxy)-1,3,4-thiadiazol-2-yl)-(4,4'-bipyridine)-3-carboxamide (Example 174, 50.0 mg, 0.11 mmol) in formic acid (0.5 mL) was added formaldehyde (78.8 mg, 1.05 mmol, 40%) at 25° C. The resulting solution was stirred at 100° C. for 16 h. The reaction mixture was purified by prep-HPLC with the following conditions: (Column: XBridge Prep Phenyl OBD Column, 19*250 mm, 5 μm; Mobile Phase A: Water (10 mmol/L $NH_4HCO_3$), Mobile Phase B: ACN; Flow rate: 25 mL/min; Gradient: 25% B to 25% B in 10 min, 25% B to 95% B in 11.5 min, 95% B to 95% B in 12.2 min, 95% B to 5% B in 13 min, 5% B; Wave Length: 254 nm; RT1 (min): 7; Injection Volume: 05 mL; Number Of Runs: 5) to afford 2'-chloro-5'-methoxy-6-methyl-N-(5-((1-methylpiperidin-4-yl)methoxy)-1,3,4-thiadiazol-2-yl)-(4,4'-bipyridine)-3-carboxamide (19.7 mg, 38%) as a white solid. MS (ESI) calculated for ($C_{22}H_{25}ClN_6O_3S$) $(M+1)^+$, 489.1; found, 489.3. $^1$H NMR (400 MHz, DMSO-$d_6$) δ 12.43 (b, 1H), 8.86 (s, 1H), 8.15 (s, 1H), 7.45 (s, 1H), 7.33 (s, 1H), 4.23 (d, J=6.4 Hz, 2H), 3.63 (s, 3H), 2.86-2.73 (m, 2H), 2.57 (s, 3H), 2.21 (s, 3H), 2.03-1.95 (m, 2H), 1.80-1.62 (m, 3H), 1.45-1.30 (m, 2H).

Example 179, 180, 181 and 182

Synthesis of 2'-chloro-5'-methoxy-6-methyl-N-(5-(((2R,3S)-2-methyltetrahydrofuran-3-yl)methoxy)-1,3,4-thiadiazol-2-yl)-(4,4'-bipyridine)-3-carboxamide, 2'-chloro-5'-methoxy-6-methyl-N-(5-(((2S,3S)-2-methyltetrahydrofuran-3-yl)methoxy)-1,3,4-thiadiazol-2-yl)-(4,4'-bipyridine)-3-carboxamide, 2'-chloro-5'-methoxy-6-methyl-N-(5-(((2S,3R)-2-methyltetrahydrofuran-3-yl)methoxy)-1,3,4-thiadiazol-2-yl)-(4,4'-bipyridine)-3-carboxamide and 2'-chloro-5'-methoxy-6-methyl-N-(5-(((2R,3R)-2-methyltetrahydrofuran-3-yl)methoxy)-1,3,4-thiadiazol-2-yl)-(4,4'-bipyridine)-3-carboxamide

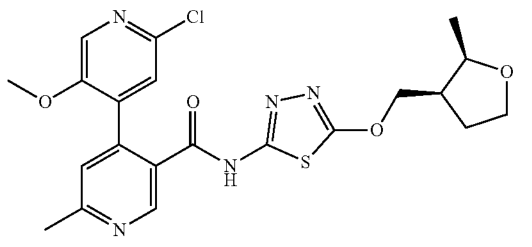

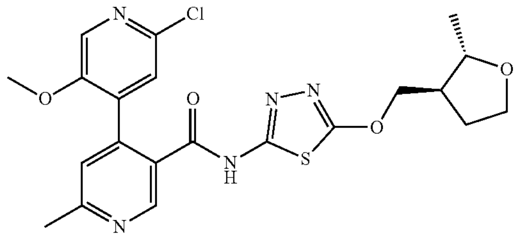

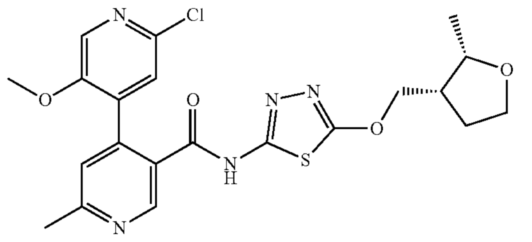

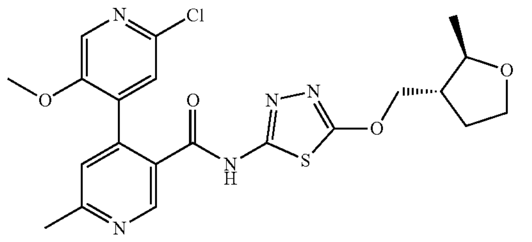

Step-1: Synthesis of S-methyl O-((2-methyltetrahydrofuran-3-yl)methyl) carbonodithioate

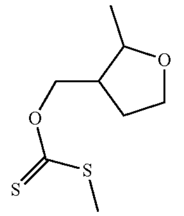

To a mixture of NaH (207.0 mg, 5.17 mmol, 60%) in THF (10 mL) was added (2-methyltetrahydrofuran-3-yl)methanol (500.0 mg, 4.30 mmol) at 0° C. and stirred at 0° C. for 0.5 hr. To the above mixture was added $CS_2$ (492.0 mg, 6.46 mmol) and stirred at 0° C. for 0.5 hr. MeI (916.0 mg, 6.46 mmol) was then added thereto. The mixture was stirred at 0° C. for 0.5 hr. The reaction mixture was quenched by the addition of water and extracted with ethyl acetate. The combined organic layers were washed with brine, dried over anhydrous sodium sulfate, filtered, and concentrated under vacuum. The resulting residue was dissolved in DCM (2 mL) and purified by Combi Flash (Biotage Isolera Prime) which applied to a 20 g silica gel column that was eluted with 0-20% ethyl acetate in petroleum ether within 20 min to afford S-methyl O-((2-methyltetrahydrofuran-3-yl)methyl) carbonodithioate (700.0 mg, 70%) as a colorless oil. MS (ESI) calc'd for ($C_8H_{14}O_2S_2$) $(M+1)^+$, 207.0.

Step-2: Synthesis of O-((2-methyltetrahydrofuran-3-yl)methyl) hydrazinecarbothioate

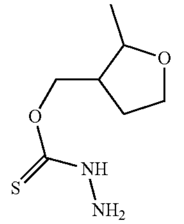

To a stirred solution of S-methyl O-((2-methyltetrahydrofuran-3-yl)methyl) carbonodithioate (700.0 mg, 3.39 mmol) in Methanol (3 mL) was added hydrazine hydrate (233.1 mg, 3.73 mmol, 80%) at 23° C. The resulting solution was stirred at 23° C. for 1 hr. The organic solvent was removed under vacuum to afford O-((2-methyltetrahydrofuran-3-yl)methyl) hydrazinecarbothioate (680.0 mg, crude) as a colorless oil. MS (ESI) calc'd for ($C_7H_{14}N_2O_2S$) $(M+1)^+$, 191.1, found 191.1.

Step-3: Synthesis of 5-((2-methyltetrahydrofuran-3-yl)methoxy)-1,3,4-thiadiazol-2-amine

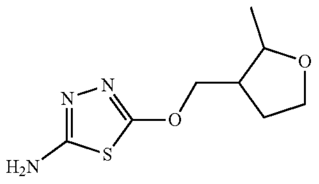

To a stirred solution of O-((2-methyltetrahydrofuran-3-yl)methyl) hydrazinecarbothioate (660.0 mg, 3.47 mmol) in Methanol (3 mL) were added TEA (700.0 mL, 6.94 mmol) and cyanic bromide (400.0 mg, 3.82 mmol) at 20° C. The resulting solution was stirred at 23° C. for 1 hr. The reaction mixture was quenched by the addition of water and extracted with ethyl acetate. The combined organic layers were washed with brine, dried over anhydrous sodium sulfate, filtered, and concentrated under vacuum. The resulting residue was dissolved in DCM (2 mL) and purified by Combi Flash (Biotage Isolera Prime) which applied to a 20 g silica gel column that was eluted with 0~10% methanol in dichloromethane within 25 min to afford 5-((2-methyltetrahydrofuran-3-yl)methoxy)-1,3,4-thiadiazol-2-amine (240.0 mg, 28%) as a yellow solid. MS (ESI) calc'd for ($C_8H_{13}N_3O_2S$) $(M+1)^+$, 216.1, found 216.1.

Step-4: Synthesis of 2'-chloro-5'-methoxy-6-methyl-N-(5-((2-methyltetrahydrofuran-3-yl)methoxy)-1,3,4-thiadiazol-2-yl)-(4,4'-bipyridine)-3-carboxamide

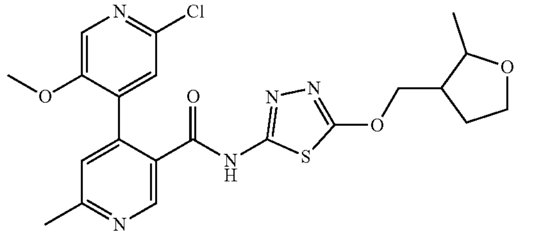 [SMILES: COc1cnc(Cl)cc1-c1cc(C)ncc1C(=O)Nc1nnc(OCC2CCOC2C)s1]

To a stirred solution of 5-((2-methyltetrahydrofuran-3-yl)methoxy)-1,3,4-thiadiazol-2-amine (240.0 mg, 1.11 mmol) in Acetonitrile (1.5 mL) were added Intermediate H (311.0 mg, 1.11 mmol) and 1-methylimidazole (458.0 mg, 5.57 mmol). To the above solution was added TCFH (313.0 mg, 1.11 mmol) in Acetonitrile (1.5 mL). The resulting mixture was stirred at 23° C. for 2 hr. The suspension was filtered. The filter cake was collected and dried under vacuum to afford 2'-chloro-5'-methoxy-6-methyl-N-(5-((2-methyltetrahydrofuran-3-yl)methoxy)-1,3,4-thiadiazol-2-yl)-(4,4'-bipyridine)-3-carboxamide (240.0 mg, 43%) as a white solid. MS (ESI) calc'd for ($C_{21}H_{22}ClN_5O_4S$) $(M+1)^+$, 476.1, found 476.1. $^1H$ NMR (400 MHz, DMSO-$d_6$) δ 12.90 (s, 1H), 8.81 (s, 1H), 8.18 (s, 1H), 7.54 (s, 1H), 7.43 (s, 1H), 4.49-4.41 (m, 1H), 4.40-4.26 (m, 1H), 4.03-3.96 (m, 1H), 3.90-3.79 (m, 1H), 3.72-3.54 (m, 4H), 2.65-2.52 (m, 4H), 2.15-1.97 (m, 1H), 1.80-1.74 (m, 1H), 1.20 (d, J=6.4 Hz, 1H), 1.11 (d, J=6.4 Hz, 2H).

Step-5: Synthesis of 2'-chloro-5'-methoxy-6-methyl-N-(5-(((2R,3S)-2-methyltetrahydrofuran-3-yl)methoxy)-1,3,4-thiadiazol-2-yl)-(4,4'-bipyridine)-3-carboxamide, 2'-chloro-5'-methoxy-6-methyl-N-(5-(((2S,3S)-2-methyltetrahydrofuran-3-yl)methoxy)-1,3,4-thiadiazol-2-yl)-(4,4'-bipyridine)-3-carboxamide, 2'-chloro-5'-methoxy-6-methyl-N-(5-(((2S,3R)-2-methyltetrahydrofuran-3-yl)methoxy)-1,3,4-thiadiazol-2-yl)-(4,4'-bipyridine)-3-carboxamide and 2'-chloro-5'-methoxy-6-methyl-N-(5-(((2R,3R)-2-methyltetrahydrofuran-3-yl)methoxy)-1,3,4-thiadiazol-2-yl)-(4,4'-bipyridine)-3-carboxamide

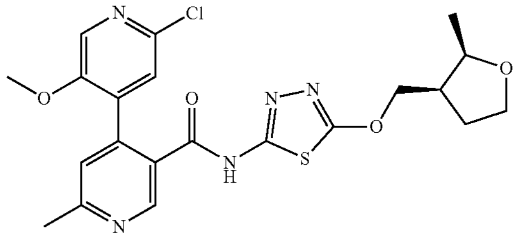

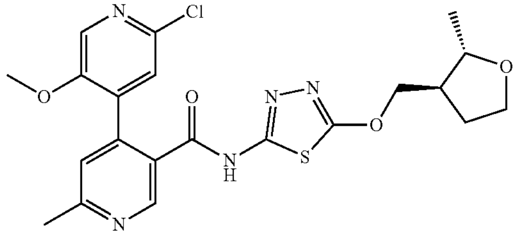

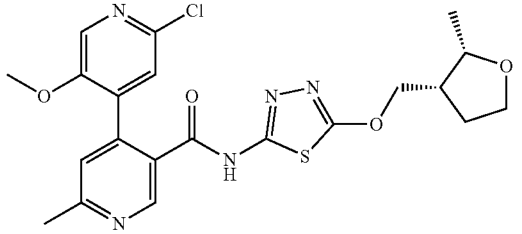

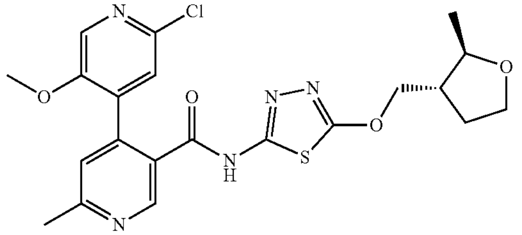

The racemic compound (240.0 mg) was separated by prep-chiral HPLC with the following conditions: (Column: CHIRALPAK IE, 2*25 cm, 5 μm; Mobile Phase A: MtBE (0.1% FA)-HPLC, Mobile Phase B: MeOH:DCM=1: 1; Flow rate: 20 mL/min; Gradient: 15% B to 15% B in 29 min; Wave Length: 220/254 nm; RT1 (min): 15.67; RT2 (min): 17.49; Sample Solvent: MeOH:DCM=1: 1; Injection Volume: 0.4 mL; Number Of Runs: 4) to afford a mixture of 2'-chloro-5'-methoxy-6-methyl-N-(5-(((2R,3S)-2-methyltetrahydrofuran-3-yl)methoxy)-1,3,4-thiadiazol-2-yl)-(4,4'-bipyridine)-3-carboxamide and 2'-chloro-5'-methoxy-6-methyl-N-(5-(((2S,3S)-2-methyltetrahydrofuran-3-yl)methoxy)-1,3,4-thiadiazol-2-yl)-(4,4'-bipyridine)-3-carboxamide (93.4 mg, 48%) as a white solid (first peak on prep-chiral HPLC) and a mixture of 2'-chloro-5'-methoxy- 6-methyl-N-(5-(((2S,3R)-2-methyltetrahydrofuran-3-yl)methoxy)-1,3,4-thiadiazol-2-yl)-(4,4'-bipyridine)-3-carboxamide and 2'-chloro-5'-methoxy-6-methyl-N-(5-(((2R,3R)-2-methyltetrahydrofuran-3-yl)methoxy)-1,3,4-thiadiazol-2-yl)-(4,4'-bipyridine)-3-carboxamide (85.8 mg, 42%) as a white solid (second peak on prep-chiral HPLC).

A mixture of 2'-chloro-5'-methoxy-6-methyl-N-(5-(((2R,3S)-2-methyltetrahydrofuran-3-yl)methoxy)-1,3,4-thiadiazol-2-yl)-(4,4'-bipyridine)-3-carboxamide (93.4 mg) was separated by prep-chiral HPLC with the following conditions: (Column: CHIRALPAK IF, 2*25 cm, 5 μm; Mobile Phase A: MtBE (0.1% FA)-HPLC, Mobile Phase B: MeOH: DCM=1: 1; Flow rate: 20 mL/min; Gradient: 20% B to 20% B in 14 min; Wave Length: 220/254 nm; RT1 (min): 9.91; RT2 (min): 12.63; Sample Solvent: MeOH:DCM=1: 1; Injection Volume: 0.6 mL; Number Of Runs: 5) to afford 2'-chloro-5'-methoxy-6-methyl-N-(5-(((2R,3S)-2-methyltetrahydrofuran-3-yl)methoxy)-1,3,4-thiadiazol-2-yl)-(4,4'-bipyridine)-3-carboxamide, isomer 1 (24.3 mg, 25%) as a white solid (first peak on chiral HPLC) and 2'-chloro-5'-methoxy-6-methyl-N-(5-(((2S,3S)-2-methyltetrahydrofuran-3-yl)methoxy)-1,3,4-thiadiazol-2-yl)-(4,4'-bipyridine)-3-carboxamide, isomer 2 (52.9 mg, 56%) as a white solid (second peak on chiral HPLC). The mixture of 2'-chloro-5'-methoxy-6-methyl-N-(5-(((2S,3R)-2-methyltetrahydrofuran-3-yl)methoxy)-1,3,4-thiadiazol-2-yl)-(4,4'-bipyridine)-3-carboxamide and 2'-chloro-5'-methoxy-6-methyl-N-(5-(((2R,3R)-2-methyltetrahydrofuran-3-yl)methoxy)-1,3,4-thiadiazol-2-yl)-(4,4'-bipyridine)-3-carboxamide was separated by prep-chiral HPLC with the following conditions: (Column: CHIRALPAK ID, 2*25 cm, 5 μm; Mobile Phase A: MtBE (0.1% FA)-HPLC, Mobile Phase B: MeOH-HPLC; Flow rate: 20 mL/min; Gradient: 20% B to 20% B in 12.6 min; Wave Length: 220/254 nm; RT1 (min): 9.77; RT2 (min): 11.74; Sample Solvent: MeOH: DCM=1: 1; Injection Volume: 0.4 mL; Number Of Runs: 8) to afford 2'-chloro-5'-methoxy-6-methyl-N-(5-(((2S,3R)-2-methyltetrahydrofuran-3-yl)methoxy)-1,3,4-thiadiazol-2-yl)-(4,4'-bipyridine)-3-carboxamide, isomer 3 (22.3 mg, 26%) as a white solid (first peak on chiral HPLC) and 2'-chloro-5'-methoxy-6-methyl-N-(5-(((2R,3R)-2-methyltetrahydrofuran-3-yl)methoxy)-1,3,4-thiadiazol-2-yl)-(4,4'-bipyridine)-3-carboxamide, isomer 4 (49.2 mg, 57%) as a white solid (second peak on chiral HPLC). The absolute stereochemistry was not determined.

Isomer 1: 2'-chloro-5'-methoxy-6-methyl-N-(5-(((2R,3S)-2-methyltetrahydrofuran-3-yl)methoxy)-1,3,4-thiadiazol-2-yl)-(4,4'-bipyridine)-3-carboxamide: MS (ESI) calc'd for ($C_{21}H_{22}ClN_5O_4S$) $(M+1)^+$, 476.1; found, 476.1. $^1$H NMR (400 MHz, DMSO-$d_6$) δ 12.90 (s, 1H), 8.81 (s, 1H), 8.17 (s, 1H), 7.54 (s, 1H), 7.43 (s, 1H), 4.50-4.36 (m, 2H), 3.85-3.75 (m, 1H), 3.75-3.63 (m, 2H), 3.63 (s, 3H), 2.59 (s, 3H), 2.28-2.15 (m, 1H), 2.14-2.01 (m, 1H), 1.77-1.64 (m, 1H), 1.20 (d, J=6.0 Hz, 3H).

Isomer 2: 2'-chloro-5'-methoxy-6-methyl-N-(5-(((2S,3S)-2-methyltetrahydrofuran-3-yl)methoxy)-1,3,4-thiadiazol-2-yl)-(4,4'-bipyridine)-3-carboxamide: MS (ESI) calc'd for ($C_{21}H_{22}ClN_5O_4S$) $(M+1)^+$, 476.1; found, 476.1. $^1$H NMR (400 MHz, DMSO-$d_6$) δ 12.90 (s, 1H), 8.81 (s, 1H), 8.18 (s, 1H), 7.54 (s, 1H), 7.43 (s, 1H), 4.51-4.42 (m, 1H), 4.36-4.28 (m, 1H), 4.06-3.95 (m, 1H), 3.90-3.80 (m, 1H), 3.63 (s, 3H), 3.62-3.53 (m, 1H), 2.69-2.59 (m, 1H), 2.59 (s, 3H), 2.12-2.00 (m, 1H), 1.81-1.68 (m, 1H), 1.11 (d, J=6.4 Hz, 3H).

Isomer 3: 2'-chloro-5'-methoxy-6-methyl-N-(5-(((2S,3R)-2-methyltetrahydrofuran-3-yl)methoxy)-1,3,4-thiadiazol-2-yl)-(4,4'-bipyridine)-3-carboxamide: MS (ESI) calc'd for ($C_{21}H_{22}ClN_5O_4S$) $(M+1)^+$, 476.1; found, 476.1. $^1$H NMR (400 MHz, DMSO-$d_6$) δ 12.90 (s, 1H), 8.81 (s, 1H), 8.17 (s, 1H), 7.54 (s, 1H), 7.43 (s, 1H), 4.50-4.36 (m, 2H), 3.85-3.75 (m, 1H), 3.75-3.63 (m, 2H), 3.63 (s, 3H), 2.59 (s, 3H), 2.28-2.15 (m, 1H), 2.14-2.01 (m, 1H), 1.77-1.64 (m, 1H), 1.20 (d, J=6.0 Hz, 3H).

Isomer 4: 2'-chloro-5'-methoxy-6-methyl-N-(5-(((2R,3R)-2-methyltetrahydrofuran-3-yl)methoxy)-1,3,4-thiadiazol-2-yl)-(4,4'-bipyridine)-3-carboxamide: MS (ESI) calc'd for ($C_{21}H_{22}ClN_5O_4S$) $(M+1)^+$, 476.1; found, 476.1. $^1$H NMR (400 MHz, DMSO-$d_6$) δ 12.90 (s, 1H), 8.81 (s, 1H), 8.18 (s, 1H), 7.54 (s, 1H), 7.43 (s, 1H), 4.51-4.42 (m, 1H), 4.36-4.28 (m, 1H), 4.06-3.95 (m, 1H), 3.90-3.80 (m, 1H), 3.63 (s, 3H), 3.62-3.53 (m, 1H), 2.69-2.59 (m, 1H), 2.59 (s, 3H), 2.12-2.00 (m, 1H), 1.81-1.68 (m, 1H), 1.11 (d, J=6.4 Hz, 3H).

Example 183 and 184

Synthesis of 2'-chloro-3'-fluoro-5'-methoxy-6-methyl-N-(5-(((R)-tetrahydrofuran-3-yl)methoxy)-1,3,4-thiadiazol-2-yl)-(4,4'-bipyridine)-3-carboxamide and 2'-chloro-3'-fluoro-5'-methoxy-6-methyl-N-(5-(((S)-tetrahydrofuran-3-yl)methoxy)-1,3,4-thiadiazol-2-yl)-(4,4'-bipyridine)-3-carboxamide

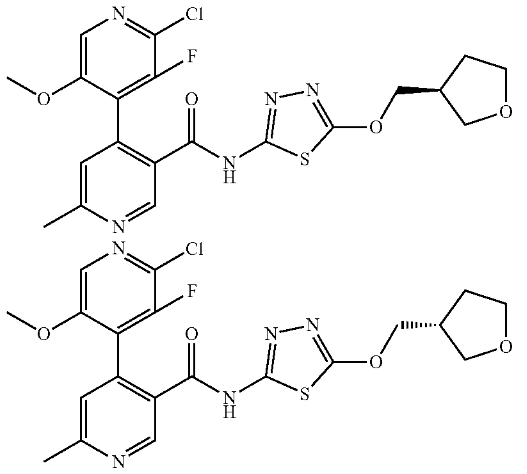

Step-1: 2-chloro-3-fluoro-5-methoxypyridine

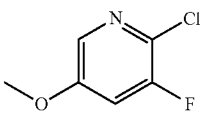

To a solution of 6-chloro-5-fluoropyridin-3-ol (20.0 g, 135.60 mmol) in Acetone (150 mL) were added MeI (17 mL, 271.00 mmol) and $K_2CO_3$ (37.5 g, 271.00 mmol) at 25° C. under nitrogen atmosphere. The resulting solution was stirred at 25° C. for 16 h under nitrogen before concentrated under vacuum. The reaction mixture was quenched with water and extracted with ethyl acetate. The combined organic layers were washed with brine, dried over anhydrous sodium sulfate, filtered, and concentrated under vacuum. The resulting residue was purified by Combi Flash (Biotage Isolera Prime) which applied to 330 g silica gel column and eluted with 0-22% ethyl acetate in petroleum ether within 45 min to afford 2-chloro-3-fluoro-5-methoxypyridine (16.0 g, 80%) as a colorless oil. MS (ESI) calc'd for ($C_6H_5ClFNO$) $(M+1)^+$, 162.0; found 162.0.

Step-2: 2-chloro-3-fluoro-4-iodo-5-methoxypyridine

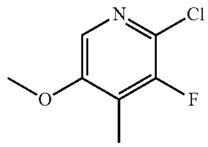

To a degassed solution of 2-chloro-3-fluoro-5-methoxypyridine (16.0 g, 99.00 mmol) in dry Tetrahydrofuran (160 mL) was added n-butyllithium (44 mL, 110.00 mmol, 2.5 N in hexane) dropwise at −60° C. and stirred at −60° C. for 1 hr under nitrogen atmosphere. Then iodine (27.6 g, 109.00 mmol) was added to the above mixture at −60° C. The resulting solution was stirred at −60~20° C. for 2 hr. The reaction mixture was quenched by the addition of saturated sodium thiosulfate aqueous solution and extracted with ethyl acetate. The combined organic layers were washed with brine, dried over anhydrous sodium sulfate, filtered, and concentrated under vacuum. The resulting residue was purified by Combi Flash (Biotage Isolera Prime) which applied to 330 g silica gel column and eluted with 0~50% ethyl acetate in petroleum ether within 40 min to afford 2-chloro-3-fluoro-4-iodo-5-methoxypyridine (22.0 g, 73%) as a white solid MS (ESI) calc'd for ($C_6H_4ClFINO$) $(M+1)^+$, 287.9; found, 287.9.

Step-3: methyl 2'-chloro-3'-fluoro-5'-methoxy-6-methyl-(4,4'-bipyridine)-3-carboxylate

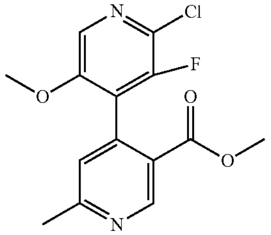

To a degassed solution of methyl 6-methyl-4-(4,4,5,5-tetramethyl-1,3,2-dioxaborolan-2-yl)nicotinate (7.2 g, 26.10 mmol) and 2-chloro-3-fluoro-4-iodo-5-methoxypyridine (5.0 g, 17.39 mmol) in dry 1,4-Dioxane (50 mL) were added Water (10 mL), (1,1'-Bis(diphenylphosphino)ferrocene)dichloropalladium(II),complex with dichloromethane (4.2 g, 5.15 mmol) and $K_2CO_3$ (7.2 g, 52.20 mmol) at 25° C. under nitrogen atmosphere. The resulting solution was stirred at 25° C. for 2 h under nitrogen atmosphere. The suspension was filtered. The filtrate was collected and concentrated under vacuum. The resulting residue was purified by Combi Flash (Biotage Isolera Prime) which applied to 120 g silica gel column and eluted with 0~46% ethyl acetate in petroleum ether within 45 min to afford methyl 2'-chloro-3'-fluoro-5'-methoxy-6-methyl-(4,4'-bipyridine)-3-carboxylate (2.8 g, 53%) as a white solid. MS (ESI) calc'd for ($C_{14}H_{12}ClFN_2O_3$) $(M+1)^+$, 311.1; found, 311.1.

Step-4: 2'-chloro-3'-fluoro-5'-methoxy-6-methyl-(4,4'-bipyridine)-3-carboxylic acid

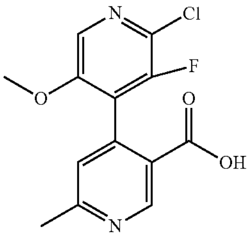 [SMILES: COc1cnc(Cl)c(F)c1-c1cc(C)ncc1C(=O)O]

To a stirred solution of methyl 2'-chloro-3'-fluoro-5'-methoxy-6-methyl-(4,4'-bipyridine)-3-carboxylate (2.8 g, 9.17 mmol) in Methanol (10 mL) were added NaOH (1.4 g, 36.70 mmol) and Water (10 mL) at 25° C. The resulting solution was stirred at 25° C. for 2 h before diluted with water. The organic solvent was removed under vacuum. The aqueous layer was acidified with Citric acid to pH ~5 and extracted with ethyl acetate. The combined organic layers were washed with brine, dried over anhydrous sodium sulfate, filtered, and concentrated under vacuum to afford 2'-chloro-3'-fluoro-5'-methoxy-6-methyl-(4,4'-bipyridine)-3-carboxylic acid (1.3 g, crude) as a yellow oil. MS (ESI) calc'd for ($C_{13}H_{10}ClFN_2O_3$) $(M+1)^+$, 297.0, found 297.0.

Step-5: Synthesis of 2'-chloro-3'-fluoro-5'-methoxy-6-methyl-N-(5-((tetrahydrofuran-3-yl)methoxy)-1,3,4-thiadiazol-2-yl)-(4,4'-bipyridine)-3-carboxamide

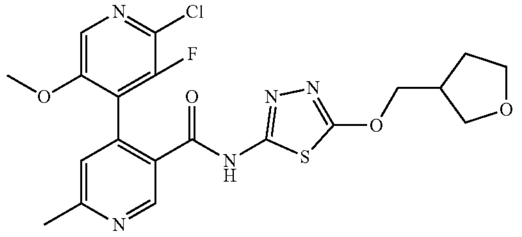

To a solution of 5-((tetrahydrofuran-3-yl)methoxy)-1,3,4-thiadiazol-2-amine (Example 167, Step 1, 200.0 mg, 0.99 mmol) in dry Acetonitrile (4 mL) were added 2'-chloro-3'-fluoro-5'-methoxy-6-methyl-(4,4'-bipyridine)-3-carboxylic acid (295.0 mg, 0.99 mmol), 1-methyl-1H-imidazole (408.0 mg, 4.97 mmol) at 25° C. Then TCFH (279.0 mg, 0.99 mmol) in acetonitrile (1 mL) was added to the above mixture at 25° C. The resulting solution was stirred at 25° C. for 1 h. The resulting mixture was applied to a 40 g C18 column and purified by Combi Flash (Biotage Isolera Prime), eluted with 5~30% acetonitrile in water within 40 min to afford 2'-chloro-3'-fluoro-5'-methoxy-6-methyl-N-(5-((tetrahydrofuran-3-yl)methoxy)-1,3,4-thiadiazol-2-yl)-(4,4'-bipyridine)-3-carboxamide (170.0 mg, 35%) as a white solid. MS (ESI) calc'd for ($C_{20}H_{19}ClFN_5O_4S$) $(M+1)^+$, 480.1; found, 480.1.

Step-6: Synthesis of 2'-chloro-3'-fluoro-5'-methoxy-6-methyl-N-(5-(((R)-tetrahydrofuran-3-yl)methoxy)-1,3,4-thiadiazol-2-yl)-(4,4'-bipyridine)-3-carboxamide and 2'-chloro-3'-fluoro-5'-methoxy-6-methyl-N-(5-(((S)-tetrahydrofuran-3-yl)methoxy)-1,3,4-thiadiazol-2-yl)-(4,4'-bipyridine)-3-carboxamide

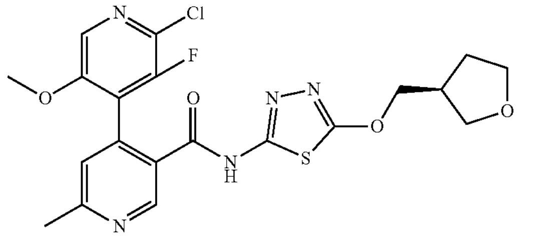

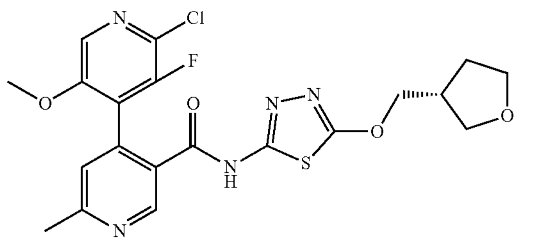

The racemic compound (170 mg) was separated by prep-chiral HPLC with the following conditions: (Column: CHIRALPAK ID, 2*25 cm, 5 μm; Mobile Phase A: Hex (0.2% FA)-HPLC, Mobile Phase B: MeOH:DCM=1: 1; Flow rate: 20 mL/min; Gradient: 25% B to 25% B in 26 min; Wave Length: 220/254 nm; RT1 (min): 19.59; RT2 (min): 20.65; Sample Solvent: MeOH:DCM=1: 1; Injection Volume: 0.5 mL; Number Of Runs: 14) to afford 2'-chloro-3'-fluoro-5'-methoxy-6-methyl-N-(5-(((R)-tetrahydrofuran-3-yl)methoxy)-1,3,4-thiadiazol-2-yl)-(4,4'-bipyridine)-3-carboxamide, isomer 1 (49.2 mg, 29%) as a white solid (first peak on chiral HPLC) and 2'-chloro-3'-fluoro-5'-methoxy-6-methyl-N-(5-(((S)-tetrahydrofuran-3-yl)methoxy)-1,3,4-thiadiazol-2-yl)-(4,4'-bipyridine)-3-carboxamide, isomer 2 (53.6 mg, 31%) as a white solid (second peak on chiral HPLC). The absolute stereochemistry was not determined.

Isomer 1: 2'-chloro-3'-fluoro-5'-methoxy-6-methyl-N-(5-(((R)-tetrahydrofuran-3-yl)methoxy)-1,3,4-thiadiazol-2-yl)-(4,4'-bipyridine)-3-carboxamide: MS (ESI) calc'd for ($C_{20}H_{19}ClFN_5O_4S$) $(M+1)^+$, 480.1; found, 480.1 $^1H$ NMR (400 MHz, DMSO-$d_6$) δ 13.03 (s, 1H), 8.97 (s, 1H), 8.18 (s, 1H), 7.47 (s, 1H), 4.43-4.33 (m, 2H), 3.78-3.72 (m, 5H), 3.71-3.56 (m, 1H), 3.54-3.51 (m, 1H), 2.74-2.62 (m, 1H), 2.61 (s, 3H), 2.08-1.98 (m, 1H), 1.72-1.58 (m, 1H).

Isomer 2: 2'-chloro-3'-fluoro-5'-methoxy-6-methyl-N-(5-(((S)-tetrahydrofuran-3-yl)methoxy)-1,3,4-thiadiazol-2-yl)-(4,4'-bipyridine)-3-carboxamide: MS (ESI) calc'd for ($C_{20}H_{19}ClFN_5O_4S$) $(M+1)^+$, 480.1; found, 480.1 $^1H$ NMR (400 MHz, DMSO-$d_6$) δ 13.03 (s, 1H), 8.97 (s, 1H), 8.18 (s, 1H), 7.48 (s, 1H), 4.43-4.31 (m, 2H), 3.78-3.72 (m, 5H), 3.71-3.55 (m, 1H), 3.54-3.51 (m, 1H), 2.74-2.62 (m, 1H), 2.60 (s, 3H), 2.05-1.98 (m, 1H), 1.72-1.58 (m, 1H).

Example 185

Synthesis of 2'-chloro-3'-fluoro-N-(5-((3-hydroxybicyclo(1.1.1)pentan-1-yl)methoxy)-1,3,4-thiadiazol-2-yl)-5'-methoxy-6-methyl-(4,4'-bipyridine)-3-carboxamide

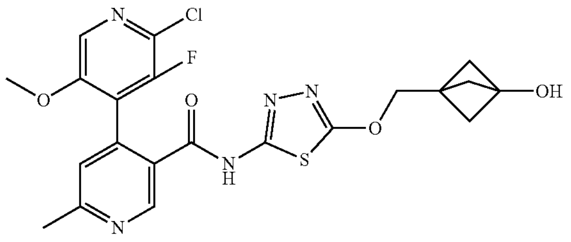 [SMILES: COc1cnc(Cl)c(F)c1-c1cc(C)ncc1C(=O)Nc1nnc(OCC23CC(O)(C2)C3)s1]

Step-1: methyl 3-((tert-butyldimethylsilyl)oxy)bicyclo(1.1.1)pentane-1-carboxylate

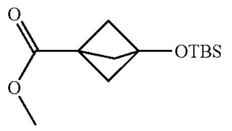 [SMILES: COC(=O)C12CC(O[Si](C)(C)C(C)(C)C)(C1)C2]

To a solution of methyl 3-hydroxybicyclo(1.1.1)pentane-1-carboxylate (500 mg, 3.517 mmol) in DCM (10 mL) was added Imidazole (718 mg, 10.552 mmol), TBSCl (795 mg, 5.276 mmol) and DMAP (43 mg, 0.352 mmol). The resulting solution was stirred at room temperature for 12 hours. The reaction was monitored by TLC. The residue was purified by flash chromatography on silica gel with 0~50% ethyl acetate in petroleum ether to afford methyl 3-((tert-butyldimethylsilyl)oxy)bicyclo(1.1.1)pentane-1-carboxylate (800 mg, 88.70%) as a colorless solid.

Step-2: (3-((tert-butyldimethylsilyl)oxy)bicyclo(1.1.1)pentan-1-yl)methanol

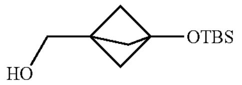 [SMILES: CC(C)(C)[Si](C)(C)OC12CC(CO)(C1)C2]

To a solution of methyl 3-((tert-butyldimethylsilyl)oxy)bicyclo(1.1.1)pentane-1-carboxylate (450 mg, 1.755 mmol) in THF (5 mL) was added LAH (133 mg, 3.510 mmol) in portions at 0° C. The resulting solution was stirred at room temperature for 2 hours. The reaction was monitored by TLC. The reaction was then quenched by the addition of water. The resulting solution was extracted with of ethyl acetate. The combined organic layers were washed with brine, dried over anhydrous sodium sulfate, filtered, and concentrated under vacuum to afford (3-((tert-butyldimethylsilyl)oxy)bicyclo(1.1.1)pentan-1-yl)methanol (300 mg, crude) as yellow oil.

Step-3: O-((3-((tert-butyldimethylsilyl)oxy)bicyclo (1.1.1)pentan-1-yl)methyl)S-methyl carbonodithioate

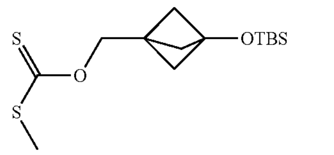 [SMILES: CSC(=S)OCC12CC(O[Si](C)(C)C(C)(C)C)(C1)C2]

To a solution of NaH (79 mg, 1.973 mmol, 60%) in THF (10 mL) was added a solution of (3-((tert-butyldimethylsilyl)oxy)bicyclo(1.1.1)pentan-1-yl)methanol (300 mg, 1.315 mmol) in THF (2 mL) dropwise at 0~5° C. and stirred at 5° C. for 1 h, Then $CS_2$ (150 mg, 1.973 mmol) was added to the mixture at 0° C. and stirred for 30 min, then MeI (282 mg, 1.973 mmol) was added to the above mixture. The resulting mixture was stirred at room temperature for 1 h. The reaction mixture was quenched by the addition of water and extracted with ethyl acetate. The combined organic layers were washed with brine, dried over anhydrous sodium sulfate, filtered, and concentrated under vacuum. The residue was purified by flash chromatography on silica gel with 0~50% ethyl acetate in petroleum ether to afford O-((3-((tert-butyldimethylsilyl)oxy)bicyclo(1.1.1)pentan-1-yl)methyl) S-methyl carbonodithioate (200 mg, 71%) as a yellow solid.

Step-4: O-((3-((tert-butyldimethylsilyl)oxy)bicyclo (1.1.1)pentan-1-yl)methyl) hydrazinecarbothioate

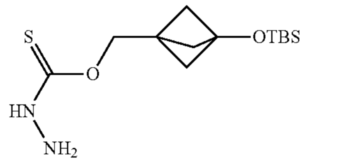

To a solution of ((3-((tert-butyldimethylsilyl)oxy)bicyclo (1.1.1)pentan-1-yl)methoxy)(methylsulfanyl)methanethione (200 mg, 0.628 mmol) in EtOH (5 mL) was added Hydrazine (20.12 mg, 0.628 mmol). The resulting solution was stirred at room temperature for 2 hours. The reaction mixture was quenched with water and extracted with ethyl acetate. The combined organic layers were washed with brine, dried over anhydrous sodium sulfate, filtered, and concentrated under vacuum to afford O-((3-((tert-butyldimethylsilyl)oxy) bicyclo(1.1.1)pentan-1-yl)methyl) hydrazinecarbothioate (200 mg, crude) as a yellow solid. MS (ESI) calc'd for $(C_{13}H_{26}N_2O_2SSi)$ $(M+1)^+$, 303.1; found, 303.1.

Step-5: 5-((3-((tert-butyldimethylsilyl)oxy)bicyclo (1.1.1)pentan-1-yl)methoxy)-1,3,4-thiadiazol-2-amine

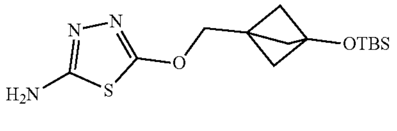

To a solution of ((((3-((tert-butyldimethylsilyl)oxy)bicyclo(1.1.1)pentan-1-yl)methoxy)methanethioyl)amino)amine (200 mg, 0.661 mmol) in MeOH (5 mL) were added TEA (135 mg, 1.322 mmol) and BrCN (77 mg, 0.727 mmol). The resulting solution was stirred at room temperature for 40 min. The reaction mixture was quenched with water and extracted with ethyl acetate. The combined organic layers were washed with brine, dried over anhydrous sodium sulfate, filtered, and concentrated under vacuum to afford 5-((3-((tert-butyldimethylsilyl)oxy)bicyclo(1.1.1)pentan-1-yl)methoxy)-1,3,4-thiadiazol-2-amine (210 mg, crude) as a yellow solid. MS (ESI) calc'd for $(C_{14}H_{25}N_3O_2SSi)$ $(M+1)^+$, 328.0; found, 328.0.

Step-6: Synthesis of N-(5-((3-((tert-butyldimethylsilyl)oxy)bicyclo(1.1.1)pentan-1-yl)methoxy)-1,3, 4thiadiazol-2-yl)-2'-chloro-3'-fluoro-5'-methoxy-6-methyl-(4,4'-bipyridine)-3-carboxamide

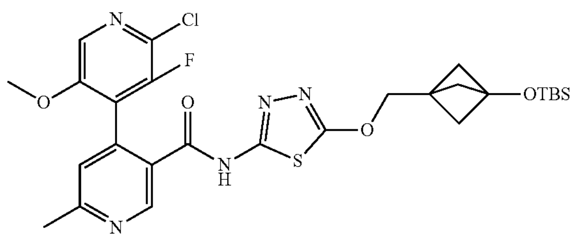 [SMILES: COc1cnc(Cl)c(F)c1-c1cc(C)ncc1C(=O)Nc1nnc(OCC23CC(O[Si](C)(C)C(C)(C)C)(C2)C3)s1]

To a stirred solution of 5-((3-((tert-butyldimethylsilyl) oxy)bicyclo(1.1.1)pentan-1-yl)methoxy)-1,3,4-thiadiazol-2-amine (165.0 mg, 0.50 mmol) in Acetonitrile (5 mL) were sequentially added 2'-chloro-3'-fluoro-5'-methoxy-6-methyl-(4,4'-bipyridine)-3-carboxylic acid (Example 184, Step 5, 149.0 mg, 0.50 mmol) and 1-methyl-1H-imidazole (207.0 mg, 2.50 mmol). To the above solution was added TCFH (141.4 mg, 0.50 mmol) in acetonitrile (1 mL) at 25° C. The resulting solution was stirred at 25° C. for 1 hr. The suspension was filtered. The filter cake was collected and dried under vacuum to afford N-(5-((3-((tert-butyldimethylsilyl)oxy)bicyclo(1.1.1)pentan-1-yl)methoxy)-1,3,4-thiadiazol-2-yl)-2'-chloro-3'-fluoro-5'-methoxy-6-methyl-(4,4'-bipyridine)-3-carboxamide (95.0 mg, 28%) as a white solid. MS (ESI) calc'd for $(C_{27}H_{33}ClFN_5O_4SSi)$ $(M+1)^+$, 606.2; found, 606.3.

Step-7: Synthesis of 2'-chloro-3'-fluoro-N-(5-((3-hydroxybicyclo(1.1.1)pentan-1-yl)methoxy)-1,3,4-thiadiazol-2-yl)-5'-methoxy-6-methyl-(4,4'-bipyridine)-3-carboxamide

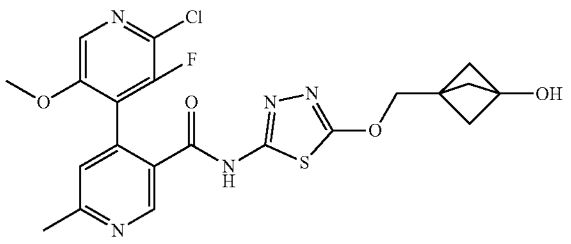 [SMILES: COc1cnc(Cl)c(F)c1-c1cc(C)ncc1C(=O)Nc1nnc(OCC23CC(O)(C2)C3)s1]

To a stirred solution of N-(5-((3-((tert-butyldimethylsilyl) oxy)bicyclo(1.1.1)pentan-1-yl)methoxy)-1,3,4-thiadiazol-2-yl)-2'-chloro-3'-fluoro-5'-methoxy-6-methyl-(4,4'-bipyridine)-3-carboxamide (80.0 mg, 0.13 mmol) in Dichloromethane (3 mL) was added Trifluoroacetic acid (0.6 mL) at 0° C. The resulting solution was stirred at 25° C. for 2 hr. The organic solvent was removed under vacuum. The residue was diluted with water. The aqueous layer was basified with $NaHCO_3$ (2 N) to pH ~7 and extracted with ethyl acetate. The combined organic layers were washed with brine, dried over anhydrous sodium sulfate, filtered, and concentrated under vacuum. The resulting residue was dissolved in DMF (1 mL) which was applied to a 20 g C18 column and purified by Combi Flash (Biotage Isolera Prime), eluted with 15~60% acetonitrile in water within 30 min to afford 2'-chloro-3'-fluoro-N-(5-((3-hydroxybicyclo(1.1.1)pentan-1-yl)methoxy)-1,3,4-thiadiazol-2-yl)-5'-methoxy-6-methyl-(4,4'-bipyridine)-3-carboxamide (16.4 mg, 25%) as a white solid. MS (ESI) calc'd for ($C_{21}H_{19}ClFN_5O_4S$) $(M+1)^+$, 492.1; found, 492.1. $^1H$ NMR (400 MHz, DMSO-$d_6$) δ 13.00 (s, 1H), 8.97 (s, 1H), 8.18 (s, 1H), 7.49 (s, 1H), 4.56 (s, 2H), 3.74 (s, 3H), 2.60 (s, 3H), 1.79 (s, 6H).

Example 186

Synthesis of (S)—N-(5-((1,4-dioxan-2-yl)methoxy)-1,3,4-thiadiazol-2-yl)-2'-chloro-5'-methoxy-6-methyl-(4,4'-bipyridine)-3-carboxamide

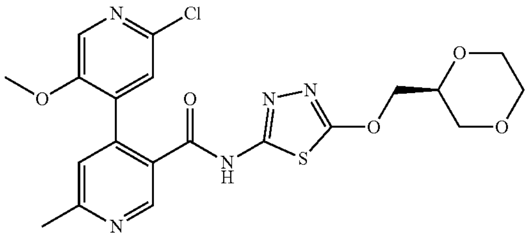

Step-1: Synthesis of (S)—O-((1,4-dioxan-2-yl)methyl)S-methyl carbonodithioate

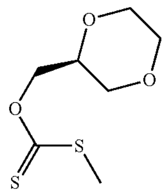

To a stirred solution of (S)-(1,4-dioxan-2-yl)methanol (200.0 mg, 1.69 mmol) in Tetrahydrofuran (5 mL) was added NaH (136.0 mg, 3.40 mmol, 60%) at 0° C. under nitrogen atmosphere. The resulting solution was stirred at 0° C. for 0.5 h. To the above solution was added $CS_2$ (193.0 mg, 2.54 mmol) at 0° C. under nitrogen atmosphere. The resulting mixture was then stirred at 0° C. for 0.5 h. To the above solution was added MeI (360.0 mg, 2.54 mmol) at 0° C. under nitrogen atmosphere. The resulting mixture was then stirred at 0° C. for 0.5 h. The reaction mixture was quenched by the addition of water and extracted with ethyl acetate. The combined organic layers were washed with brine, dried over anhydrous sodium sulfate, filtered, and concentrated under vacuum to afford (S)—O-((1,4-dioxan-2-yl)methyl)S-methyl carbonodithioate (340.0 mg, crude) as a yellow oil, which was used in the next step without further purification.

Step-2: Synthesis of (S)—O-((1,4-dioxan-2-yl)methyl) hydrazinecarbothioate

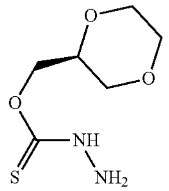 [SMILES: NNC(=S)OC[C@@H]1COCCO1]

To a stirred solution of (S)—O-((1,4-dioxan-2-yl)methyl) S-methyl carbonodithioate (340.0 mg, 1.44 mmol) in Methanol (5 mL) was added hydrazine hydrate (90.5 mg, 1.45 mmol, 80%) at 25° C. under nitrogen atmosphere. The resulting solution was stirred at 25° C. for 0.5 h. The solvents were removed under vacuum to afford (S)—O-((1,4-dioxan-2-yl)methyl) hydrazinecarbothioate (280.0 mg, crude) as a yellow oil, which was used in the next step without further purification. MS (ESI) calc'd for ($C_6H_{12}N_2O_3S$) $(M+1)^+$, 193.1, found 193.2.

Step-3: Synthesis of (S)-5-((1,4-dioxan-2-yl)methoxy)-1,3,4-thiadiazol-2-amine

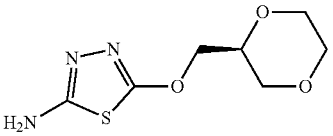 [SMILES: Nc1nnc(OC[C@@H]2COCCO2)s1]

To a stirred solution of (S)—O-((1,4-dioxan-2-yl)methyl) hydrazinecarbothioate (280.0 mg, 1.46 mmol) in Methanol (8 mL) were added TEA (342.0 mg, 2.91 mmol) and BrCN (170.0 mg, 1.60 mmol) at 25° C. under nitrogen atmosphere. The resulting solution was stirred at 25° C. for 1 h under nitrogen atmosphere. The reaction mixture was quenched by the addition of water and extracted with ethyl acetate. The combined organic layers were washed with brine, dried over anhydrous sodium sulfate, filtered, and concentrated under vacuum. The resulting residue was dissolved in DCM (1 mL) and purified by Combi Flash (Biotage Isolera Prime) which applied to a 40 g silica gel column that was eluted with 0~10% methanol in dichloromethane within 25 min to afford (S)-5-((1,4-dioxan-2-yl)methoxy)-1,3,4-thiadiazol-2-amine (150.0 mg, 46%) as a yellow solid. MS (ESI) calc'd for ($C_7H_{11}N_3O_3S$) $(M+1)^+$, 218.1, found 218.2.

Step-4: Synthesis of (S)—N-(5-((1,4-dioxan-2-yl)methoxy)-1,3,4-thiadiazol-2-yl)-2'-chloro-5'-methoxy-6-methyl-(4,4'-bipyridine)-3-carboxamide

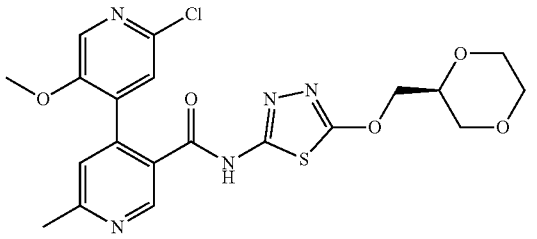

To a stirred solution of (S)-5-((1,4-dioxan-2-yl)methoxy)-1,3,4-thiadiazol-2-amine (100.0 mg, 0.46 mmol) in Acetonitrile (4 mL) was added Intermediate H (128.0 mg, 0.46 mmol) and NMI (189.0 mg, 2.30 mmol). To the above solution was added TCFH (129.0 mg, 0.46 mmol) in MeCN (0.5 mL) at 25° C. under nitrogen atmosphere. The resulting solution was stirred at 25° C. under nitrogen atmosphere for 1 h. The solvent was removed under vacuum. The resulting residue was dissolved in DMF (1 mL) which was applied to a 40 g C18 column and purified by Combi Flash (Biotage Isolera Prime), eluted with 5~80% acetonitrile in water within 35 min to afford (S)—N-(5-((1,4-dioxan-2-yl)methoxy)-1,3,4-thiadiazol-2-yl)-2'-chloro-5'-methoxy-6-methyl-(4,4'-bipyridine)-3-carboxamide (75.5 mg, 34%) as a white solid. MS (ESI) calc'd for ($C_{20}H_{20}ClN_5O_5S$) $(M+1)^+$, 478.1, found 478.2. $^1H$ NMR (400 MHz, DMSO-$d_6$) δ 12.90 (s, 1H), 8.81 (s, 1H), 8.17 (s, 1H), 7.54 (s, 1H), 7.44 (s, 1H), 4.46-4.34 (m, 2H), 3.97-3.87 (m, 1H), 3.83-3.73 (m, 2H), 3.70-3.57 (m, 5H), 3.55-3.44 (m, 1H), 3.42-3.34 (m, 1H), 2.59 (s, 3H).

Example 187

Synthesis of (R)—N-(5-((1,4-dioxan-2-yl)methoxy)-1,3,4-thiadiazol-2-yl)-2'-chloro-5'-methoxy-6-methyl-(4,4'-bipyridine)-3-carboxamide

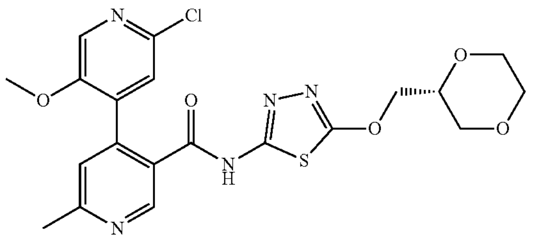 [SMILES: COc1cnc(Cl)cc1-c1cc(C)ncc1C(=O)Nc1nnc(OC[C@H]2COCCO2)s1]

Step-1: Synthesis of (R)—O-((1,4-dioxan-2-yl)methyl)S-methyl carbonodithioate

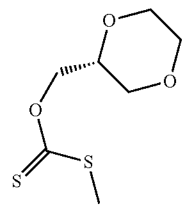

To a stirred solution of (R)-(1,4-dioxan-2-yl)methanol (200.0 mg, 1.69 mmol) in Tetrahydrofuran (5 mL) was added NaH (136.0 mg, 3.40 mmol) at 0° C. under nitrogen atmosphere. The resulting solution was stirred at 0° C. for 0.5 h. To the above solution was added $CS_2$ (193.0 mg, 2.54 mmol) at 0° C. under nitrogen atmosphere. The resulting mixture was then stirred at 0° C. for 0.5 h. To the above solution was added MeI (360.0 mg, 2.54 mmol) at 0° C. under nitrogen atmosphere. The resulting mixture was then stirred at 0° C. for 0.5 h. The reaction mixture was quenched by the addition of water and extracted with ethyl acetate. The combined organic layers were washed with brine, dried over anhydrous sodium sulfate, filtered, and concentrated under vacuum to afford (R)—O-((1,4-dioxan-2-yl)methyl)S-methyl carbonodithioate (360.0 mg, crude) as a yellow oil, the crude product was used in the next step without further purification.

Step-2: Synthesis of (R)—O-((1,4-dioxan-2-yl)methyl) hydrazinecarbothioate

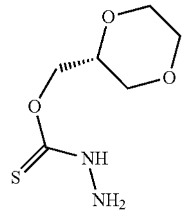 [SMILES: NNC(=S)OC[C@H]1COCCO1]

To a stirred solution of (R)—O-((1,4-dioxan-2-yl)methyl) S-methyl carbonodithioate (360.0 mg, 1.73 mmol) in Methanol (4 mL) were sequentially added hydrazine hydrate (96.0 mg, 1.90 mmol) at 25° C. The resulting solution was stirred at 25° C. for 0.5 h. The solvents were removed under vacuum to afford (R)—O-((1,4-dioxan-2-yl)methyl) hydrazinecarbothioate (400.0 mg, crude) as a yellow oil, which was used in the next step without further purification. MS (ESI) calculated for ($C_6H_{12}N_2O_3S$) $(M+1)^+$, 193.1; found, 193.2.

Step-3: Synthesis of (R)-5-((1,4-dioxan-2-yl)methoxy)-1,3,4-thiadiazol-2-amine

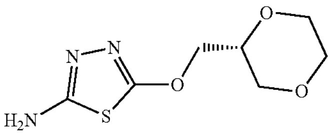 [SMILES: Nc1nnc(OC[C@H]2COCCO2)s1]

To a stirred solution of (R)—O-((1,4-dioxan-2-yl)methyl) hydrazinecarbothioate (400.0 mg, 2.08 mmol) in Methanol (4 mL) were sequentially added TEA (0.58 mL, 4.16 mmol) and cyanic bromide (242.0 mg, 2.29 mmol) at 23° C. The resulting solution was stirred at 25° C. for 1 h. The reaction mixture was quenched by the addition of water and extracted with ethyl acetate. The combined organic layers were washed with brine, dried over anhydrous sodium sulfate, filtered, and concentrated under vacuum. The resulting residue was dissolved in DCM (1 mL) and purified by Combi Flash which applied to a 20 g silica gel column that was eluted with 0~15% ethyl acetate in petroleum ether within 25 min to afford (R)-5-((1,4-dioxan-2-yl)methoxy)-1,3,4-thiadiazol-2-amine (140.0 mg, 30%) as a white solid. MS (ESI) calculated for ($C_7H_{11}N_3O_3S$) $(M+1)^+$, 218.1; found, 218.2.

Step-4: Synthesis of (R)—N-(5-((1,4-dioxan-2-yl)methoxy)-1,3,4-thiadiazol-2-yl)-2'-chloro-5'-methoxy-6-methyl-(4,4'-bipyridine)-3-carboxamide

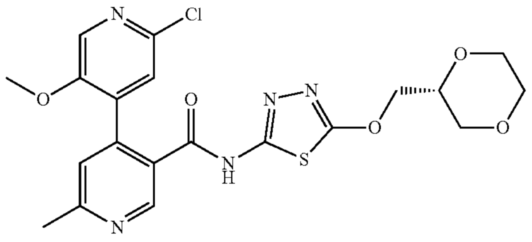 [SMILES: COc1cnc(Cl)cc1-c1cc(C)ncc1C(=O)Nc1nnc(OC[C@H]2COCCO2)s1]

To a stirred solution of (R)-5-((1,4-dioxan-2-yl)methoxy)-1,3,4-thiadiazol-2-amine (100.0 mg, 0.46 mmol) in acetonitrile (1 mL) were added Intermediate H (128.0 mg, 0.46 mmol) and NMI (189.0 mg, 2.30 mmol). To the above solution was added TCFH (129.3 mg, 0.46 mmol) in acetonitrile (1 mL). The resulting solution was stirred at 25° C. under nitrogen for 1 hr. The solvents were removed under vacuum and purified directly. The resulting residue was dissolved in DMF (1 mL) which was applied to a 25 g C18 column and purified by Combi Flash, eluted with 5~80% acetonitrile in water within 25 min to afford (R)—N-(5-((1,4-dioxan-2-yl)methoxy)-1,3,4-thiadiazol-2-yl)-2'-chloro-5'-methoxy-6-methyl-(4,4'-bipyridine)-3-carboxamide (26.6 mg, 11.9%) as a white solid. MS (ESI) calculated for ($C_{20}H_{20}ClN_5O_5S$) $(M+1)^+$, 478.1; found, 478.2. $^1H$ NMR (400 MHz, DMSO-$d_6$) δ 12.91 (s, 1H), 8.82 (s, 1H), 8.17 (s, 1H), 7.53 (s, 1H), 7.42 (s, 1H), 4.45-4.33 (m, 2H), 3.95-3.87 (m, 1H), 3.83-3.73 (m, 2H), 3.63-3.57 (m, 5H), 3.55-3.45 (m, 1H), 3.42-3.34 (m, 1H), 2.59 (s, 3H).

Example 188 and 189

Synthesis of (R)-2'-chloro-N-(5-((5,5-dimethyltetrahydrofuran-3-yl)methoxy)-1,3,4-thiadiazol-2-yl)-5'-methoxy-6-methyl-(4,4'-bipyridine)-3-carboxamide and (S)-2'-chloro-N-(5-((5,5-dimethyltetrahydrofuran-3-yl)methoxy)-1,3,4-thiadiazol-2-yl)-5'-methoxy-6-methyl-(4,4'-bipyridine)-3-carboxamide

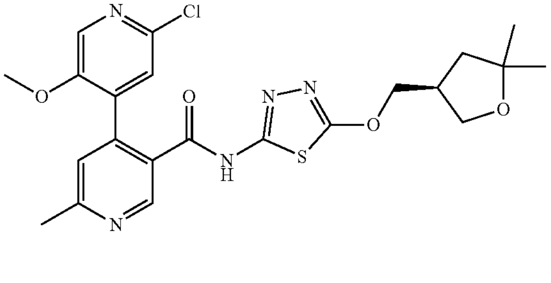

-continued

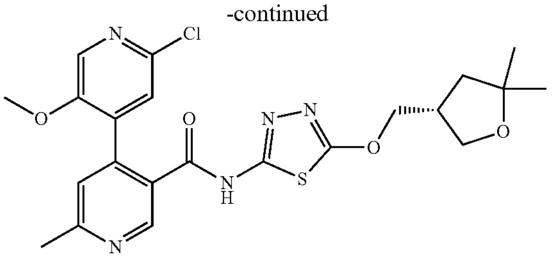

Step-1: Synthesis of O-((5,5-dimethyltetrahydrofuran-3-yl)methyl)S-methyl carbonodithioate

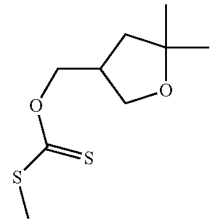

To a stirred solution of (5,5-dimethyltetrahydrofuran-3-yl)methanol (100.0 mg, 0.77 mmol) in Tetrahydrofuran (5 mL) was added NaH (61.0 mg, 1.53 mmol, 60%) at 0° C. under nitrogen atmosphere. The resulting solution was stirred at 0° C. for 0.5 hr. To the above solution was added $CS_2$ (88.0 mg, 1.16 mmol) at 0° C. under nitrogen atmosphere. The resulting mixture was then stirred at 0° C. for 0.5 hr. To the above solution was added MeI (164.0 mg, 1.16 mmol) at 0° C. under nitrogen atmosphere. The resulting mixture was then stirred at 0° C. for 0.5 hr. The reaction mixture was quenched by the addition of water (5 mL) and extracted with ethyl acetate. The combined organic layers were washed with brine, dried over anhydrous sodium sulfate, filtered, and concentrated under vacuum to afford O-((5,5-dimethyltetrahydrofuran-3-yl)methyl) S-methyl carbonodithioate (180.0 mg, crude) as a yellow oil. The crude product was used in the next step without further purification.

Step-2: Synthesis of O-((5,5-dimethyltetrahydrofuran-3-yl)methyl) hydrazinecarbothioate

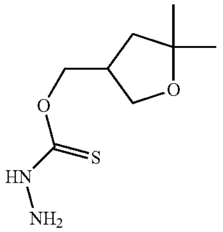

To a stirred solution of O-((5,5-dimethyltetrahydrofuran-3-yl)methyl)S-methyl carbonodithioate (180.0 mg, 0.82 mmol) in Methanol (4 mL) was added hydrazine hydrate (50.0 mg, 0.82 mmol) at 25° C. under nitrogen atmosphere. The resulting solution was stirred at 25° C. for 0.5 hr. The solvents were removed under vacuum to afford O-((5,5-dimethyltetrahydrofuran-3-yl)methyl) hydrazinecarbothioate (140.0 mg, crude) as a yellow oil, which was used in the next step without further purification. MS (ESI) calc'd for ($C_8H_{16}N_2O_2S$) $(M+1)^+$, 205.1; found, 205.1.

Step-3: Synthesis of 5-((5,5-dimethyltetrahydrofuran-3-yl)methoxy)-1,3,4-thiadiazol-2-amine

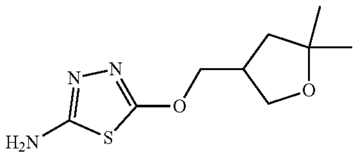

To a stirred solution of O-((5,5-dimethyltetrahydrofuran-3-yl)methyl) hydrazinecarbothioate (140.0 mg, 0.69 mmol) in Methanol (5 mL) were added TEA (0.2 mL, 1.38 mmol) and BrCN (80.0 mg, 0.75 mmol) at 25° C. under nitrogen atmosphere. The resulting solution was stirred at 25° C. for 1 hr under nitrogen atmosphere. The reaction mixture was quenched by the addition of water (5 mL) and extracted with ethyl acetate. The combined organic layers were washed with brine, dried over anhydrous sodium sulfate, filtered, and concentrated under vacuum. The resulting residue was dissolved in DCM (1 mL) and purified by Combi Flash (Biotage Isolera Prime) which applied to a 20 g silica gel column that was eluted with 0~10% methanol in dichloromethane within 25 min to afford 5-((5,5-dimethyltetrahydrofuran-3-yl)methoxy)-1,3,4-thiadiazol-2-amine (70.0 mg, 41.4%) as a yellow solid. MS (ESI) calc'd for ($C_9H_{15}N_3O_2S$) $(M+1)^+$, 230.1; found, 230.1.

Step-4: Synthesis of 2'-chloro-N-(5-((5,5-dimethyltetrahydrofuran-3-yl)methoxy)-1,3,4-thiadiazol-2-yl)-5'-methoxy-6-methyl-(4,4'-bipyridine)-3-carboxamide

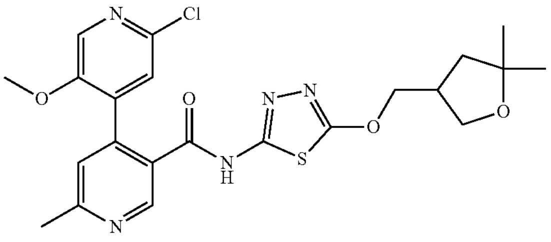

To a stirred solution of 5-((5,5-dimethyltetrahydrofuran-3-yl)methoxy)-1,3,4-thiadiazol-2-amine (60.0 mg, 0.26 mmol) in Acetonitrile (2 mL) were added Intermediate H (73.0 mg, 0.26 mmol) and NMI (107.0 mg, 1.30 mmol) at 25° C. To the above solution was added TCFH (73.0 mg, 0.26 mmol) in Acetonitrile (1 mL) at 25° C. under nitrogen atmosphere. The resulting mixture was then stirred at 25° C. for 1 hr under nitrogen. The solvents were removed under vacuum. The resulting residue was dissolved in DMF (1 mL) which was applied to a 20 g C18 column and purified by Combi Flash (Biotage Isolera Prime), eluted with 5~75% acetonitrile in water within 40 min to afford 2'-chloro-N-(5-((5,5-dimethyltetrahydrofuran-3-yl)methoxy)-1,3,4-thiadiazol-2-yl)-5'-methoxy-6-methyl-(4,4'-bipyridine)-3-carboxamide (83.0 mg, 64.1%) as a white solid. MS (ESI) calc'd for ($C_{22}H_{24}ClN_5O_4S$) $(M+1)^+$, 490.1; found, 490.2.

Step-5: Synthesis of (R)-2'-chloro-N-(5-((5,5-dimethyltetrahydrofuran-3-yl)methoxy)-1,3,4-thiadiazol-2-yl)-5'-methoxy-6-methyl-(4,4'-bipyridine)-3-carboxamide and (S)-2'-chloro-N-(5-((5,5-dimethyltetrahydrofuran-3-yl)methoxy)-1,3,4-thiadiazol-2-yl)-5'-methoxy-6-methyl-(4,4'-bipyridine)-3-carboxamide

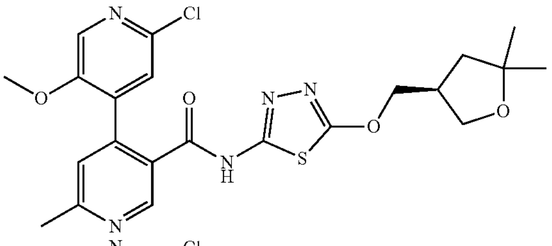

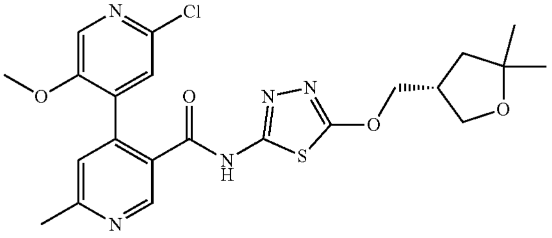

The racemic compound (83.0 mg) was separated by prep-chiral HPLC with the following conditions: (Column: CHIRALPAK IF, 2*25 cm, 5 μm; Mobile Phase A: Hex (0.2% FA)-HPLC, Mobile Phase B: MeOH:DCM=1: 1 (0.1% 2M $NH_3$-MEOH); Flow rate: 20 mL/min; Gradient: 30% B to 30% B in 22 min; Wave Length: 220/254 nm; RT1 (min): 14.68; RT2 (min): 18.52; Sample Solvent: MeOH: DCM=1: 1; Injection Volume: 0.6 mL; Number Of Runs: 3) to afford (R)-2'-chloro-N-(5-((5,5-dimethyltetrahydrofuran-3-yl)methoxy)-1,3,4-thiadiazol-2-yl)-5'-methoxy-6-methyl-(4,4'-bipyridine)-3-carboxamide, isomer 1 (31.4 mg, 37.8%) as a white solid with the first peak on chiral HPLC and (S)-2'-chloro-N-(5-((5,5-dimethyltetrahydrofuran-3-yl) methoxy)-1,3,4-thiadiazol-2-yl)-5'-methoxy-6-methyl-(4,4'-bipyridine)-3-carboxamide, isomer 2 (28.9 mg, 34.7%) as a white solid (second peak on chiral HPLC). The absolute stereochemistry was not determined.

Isomer 1: (R)-2'-chloro-N-(5-((5,5-dimethyltetrahydrofuran-3-yl)methoxy)-1,3,4-thiadiazol-2-yl)-5'-methoxy-6-methyl-(4,4'-bipyridine)-3-carboxamide: MS (ESI) calc'd for ($C_{22}H_{24}ClN_5O_4S$) $(M+1)^+$, 490.1; found, 490.2. $^1H$ NMR (400 MHz, DMSO-$d_6$) δ 12.88 (s, 1H), 8.81 (s, 1H), 8.17 (s, 1H), 7.54 (s, 1H), 7.43 (s, 1H), 4.45-4.32 (m, 2H), 3.92-3.82 (m, 1H), 3.63 (s, 3H), 3.63-3.52 (m, 1H), 2.88-2.78 (m, 1H), 2.59 (s, 3H), 1.97-1.82 (m, 1H), 1.55-1.42 (m, 1H), 1.23 (s, 3H), 1.16 (s, 3H).

Isomer 2: (S)-2'-chloro-N-(5-((5,5-dimethyltetrahydrofuran-3-yl)methoxy)-1,3,4-thiadiazol-2-yl)-5'-methoxy-6-methyl-(4,4'-bipyridine)-3-carboxamide: MS (ESI) calc'd for ($C_{22}H_{24}ClN_5O_4S$) $(M+1)^+$, 490.1; found, 490.2. $^1H$ NMR (400 MHz, DMSO-$d_6$) δ 12.89 (s, 1H), 8.81 (s, 1H), 8.17 (s, 1H), 7.54 (s, 1H), 7.43 (s, 1H), 4.45-4.31 (m, 2H), 3.92-3.82 (m, 1H), 3.63 (s, 3H), 3.63-3.52 (m, 1H), 2.88-

2.78 (m, 1H), 2.59 (s, 3H), 1.97-1.84 (m, 1H), 1.55-1.42 (m, 1H), 1.23 (s, 3H), 1.16 (s, 3H).

Example 190 and 191

Synthesis of (R)-2'-chloro-N-(5-((2,2-dimethyltetrahydrofuran-3-yl)methoxy)-1,3,4-thiadiazol-2-yl)-5'-methoxy-6-methyl-(4,4'-bipyridine)-3-carboxamide and (S)-2'-chloro-N-(5-((2,2-dimethyltetrahydrofuran-3-yl)methoxy)-1,3,4-thiadiazol-2-yl)-5'-methoxy-6-methyl-(4,4'-bipyridine)-3-carboxamide

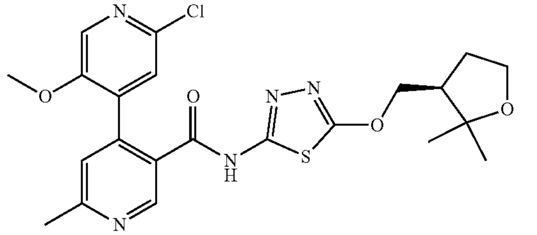

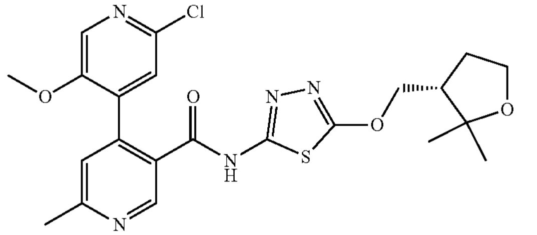

Step-1: Synthesis of O-((2,2-dimethyltetrahydrofuran-3-yl)methyl)S-methyl carbonodithioate

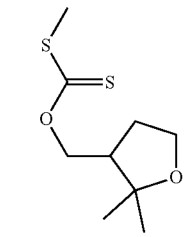

To a solution of (2,2-dimethyltetrahydrofuran-3-yl) methanol (200.0 mg, 1.53 mmol) in THF (2 mL) was added NaH (73.7 mg, 1.84 mmol, 60%) in portions at 0° C. and stirred at 0° C. for 30 min. Then $CS_2$ (174.8 mg, 2.30 mmol) was added to the above mixture and stirred at 0° C. for 10 min, and then MeI (326.6 mg, 2.30 mmol) was added to the above mixture at 5° C. The resulting mixture was stirred at room temperature for 1 hr. The reaction mixture was quenched by the addition of water and extracted with ethyl acetate. The combined organic layers were washed with brine, dried over anhydrous sodium sulfate, filtered, and concentrated under vacuum to afford O-((2,2-dimethyltetrahydrofuran-3-yl)methyl)S-methyl carbonodithioate (330.0 mg, crude) as a yellow oil. MS (ESI) calc'd for $(C_9H_{16}O_2S_2)$ $(M+1)^+$, 220.0, found 220.0.

Step-2: Synthesis of O-((2,2-dimethyltetrahydrofuran-3-yl)methyl) hydrazinecarbothioate

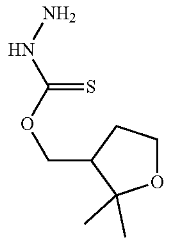

To a stirred solution of O-((2,2-dimethyltetrahydrofuran-3-yl)methyl)S-methyl carbonodithioate (340.0 mg, 1.54 mmol) in Methanol (10 mL) was added hydrazine hydrate (105.6 mg, 1.69 mmol, 80%) at 20° C. The resulting solution was stirred at 20° C. for 30 min. The organic solvent was removed under vacuum to afford O-((2,2-dimethyltetrahydrofuran-3-yl)methyl) hydrazinecarbothioate (320.0 mg, crude) as a yellow oil. MS (ESI) calc'd for $(C_8H_{16}N_2O_2S)$ $(M+1)^+$, 205.1, found 205.1.

Step-3: Synthesis of 5-((2,2-dimethyltetrahydrofuran-3-yl)methoxy)-1,3,4-thiadiazol-2-amine

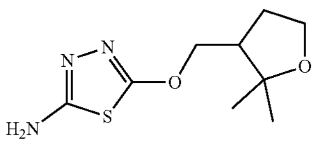

To a stirred solution of O-((2,2-dimethyltetrahydrofuran-3-yl)methyl) hydrazinecarbothioate (310.0 mg, 1.51 mmol) in Methanol (10 mL) were added TEA (306.0 mg, 3.03 mmol) and BrCN (177.0 mg, 1.66 mmol) at 20° C. The resulting solution was stirred at 20° C. for 1 hr. The reaction mixture was quenched by the addition of water and extracted with ethyl acetate. The combined organic layers were washed with brine, dried over anhydrous sodium sulfate, filtered, and concentrated under vacuum. The resulting residue was dissolved in DCM (4 mL) and purified by Combi Flash (Biotage Isolera Prime) which applied to a 80 g silica gel column that was eluted with 0~100% ethyl acetate in petroleum ether within 25 min to afford 5-((2,2-dimethyltetrahydrofuran-3-yl)methoxy)-1,3,4-thiadiazol-2-amine (170.0 mg, 47%) as a yellow solid. MS (ESI) calc'd for $(C_9H_{15}N_3O_2S)$ $(M+1)^+$, 230.1, found 230.1.

Step-4: Synthesis of 2'-chloro-N-(5-((2,2-dimethyltetrahydrofuran-3-yl)methoxy)-1,3,4-thiadiazol-2-yl)-5'-methoxy-6-methyl-(4,4'-bipyridine)-3-carboxamide

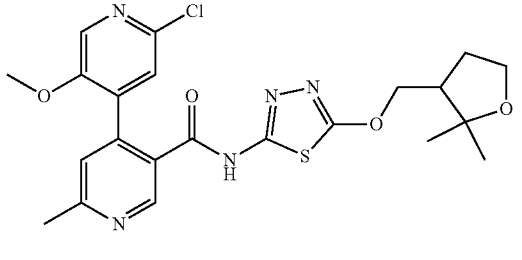 [SMILES: COc1cnc(Cl)cc1-c1cc(C)ncc1C(=O)Nc1nnc(OCC2CCOC2(C)C)s1]

To a stirred solution of 5-((2,2-dimethyltetrahydrofuran-3-yl)methoxy)-1,3,4-thiadiazol-2-amine (70.0 mg, 0.30 mmol) in Acetonitrile (1.5 mL) were added Intermediate H (85.0 mg, 0.30 mmol) and 1-methylimidazole (125.0 mg, 1.52 mmol) at 20° C. To the above solution was added TCFH (86.0 mg, 0.30 mmol) in Acetonitrile (1.5 mL) at 20° C. under nitrogen. The resulting solution was stirred at 20° C. for 1 hr under nitrogen. The solvent was removed under vacuum. The resulting residue was dissolved in DMF (2 mL) which was applied to a 25 g C18 column and purified by Combi Flash (Biotage Isolera Prime), eluted with 5~100% acetonitrile in water within 30 min to afford 2'-chloro-N-(5-((2,2-dimethyltetrahydrofuran-3-yl)methoxy)-1,3,4-thiadiazol-2-yl)-5'-methoxy-6-methyl-(4,4'-bipyridine)-3-carboxamide (104.2 mg, 69%) as a white solid. MS (ESI) calc'd for ($C_{22}H_{24}ClN_5O_4S$) $(M+1)^+$, 490.1; found, 490.1. $^1H$ NMR (400 MHz, DMSO-$d_6$) δ 12.90 (s, 1H), 8.81 (s, 1H), 8.18 (s, 1H), 7.54 (s, 1H), 7.43 (s, 1H), 4.50-4.37 (m, 2H), 3.82-3.65 (m, 2H), 3.63 (s, 3H), 2.59 (s, 3H), 2.40-2.27 (m, 1H), 2.18-2.05 (m, 1H), 1.86-1.71 (m, 1H), 1.24 (s, 3H), 1.06 (s, 3H).

Step-5: Synthesis of (R)-2'-chloro-N-(5-((2,2-dimethyltetrahydrofuran-3-yl)methoxy)-1,3,4-thiadiazol-2-yl)-5'-methoxy-6-methyl-(4,4'-bipyridine)-3-carboxamide and (S)-2'-chloro-N-(5-((2,2-dimethyltetrahydrofuran-3-yl)methoxy)-1,3,4-thiadiazol-2-yl)-5'-methoxy-6-methyl-(4,4'-bipyridine)-3-carboxamide

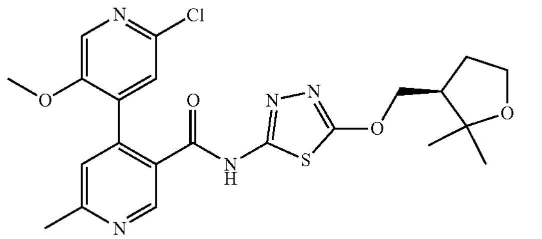

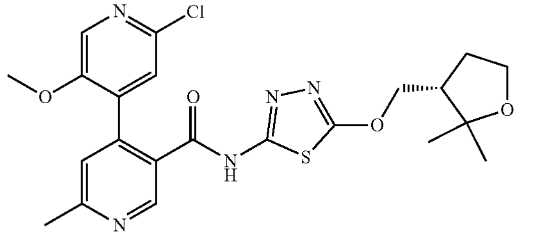

The racemic compound (104.0 mg) was separated by prep-chiral HPLC with the following conditions: (Column: CHIRALPAK IE, 2*25 cm, 5 μm; Mobile Phase A: Hex (0.2% FA)-HPLC, Mobile Phase B: EtOH:DCM=1:1-HPLC; Flow rate: 20 mL/min; Gradient: 50% B to 50% B in 17 min; Wave Length: 220/254 nm; RT1 (min): 11.87; RT2 (min): 14.04; Sample Solvent: MeOH:DCM=1:1; Injection Volume: 0.3 mL; Number Of Runs: 9) to afford (R)-2'-chloro-N-(5-((2,2-dimethyltetrahydrofuran-3-yl) methoxy)-1,3,4-thiadiazol-2-yl)-5'-methoxy-6-methyl-(4,4'-bipyridine)-3-carboxamide, isomer 1 (32.6 mg, 31%) as a white solid (first peak on chiral HPLC) and (S)-2'-chloro-N-(5-((2,2-dimethyltetrahydrofuran-3-yl)methoxy)-1,3,4-thiadiazol-2-yl)-5'-methoxy-6-methyl-(4,4'-bipyridine)-3-carboxamide, isomer 2 (33.6 mg, 32%) as a white solid (second peak on chiral HPLC). The absolute stereochemistry was not determined.

Isomer 1: (R)-2'-chloro-N-(5-((2,2-dimethyltetrahydrofuran-3-yl)methoxy)-1,3,4-thiadiazol-2-yl)-5'-methoxy-6-methyl-(4,4'-bipyridine)-3-carboxamide: MS (ESI) calc'd for ($C_{22}H_{24}ClN_5O_4S$) $(M+1)^+$, 490.1; found, 490.2. $^1H$ NMR (400 MHz, DMSO-$d_6$) δ 12.91 (s, 1H), 8.81 (s, 1H), 8.17 (s, 1H), 7.54 (s, 1H), 7.43 (s, 1H), 4.50-4.37 (m, 2H), 3.82-3.65 (m, 2H), 3.63 (s, 3H), 2.59 (s, 3H), 2.40-2.27 (m, 1H), 2.17-2.05 (m, 1H), 1.85-1.71 (m, 1H), 1.23 (s, 3H), 1.06 (s, 3H).

Isomer 2: (S)-2'-chloro-N-(5-((2,2-dimethyltetrahydrofuran-3-yl)methoxy)-1,3,4-thiadiazol-2-yl)-5'-methoxy-6-methyl-(4,4'-bipyridine)-3-carboxamide: MS (ESI) calc'd for ($C_{22}H_{24}ClN_5O_4S$) $(M+1)^+$, 490.1; found, 490.2. $^1H$ NMR (400 MHz, DMSO-$d_6$) δ 12.90 (s, 1H), 8.81 (s, 1H), 8.17 (s, 1H), 7.54 (s, 1H), 7.43 (s, 1H), 4.50-4.37 (m, 2H), 3.82-3.65 (m, 2H), 3.63 (s, 3H), 2.59 (s, 3H), 2.41-2.27 (m, 1H), 2.16-2.05 (m, 1H), 1.85-1.70 (m, 1H), 1.23 (s, 3H), 1.06 (s, 3H).

Example 192

N-(5-(2-(1-cyanocyclopropyl)ethoxy)-1,3,4-thiadiazol-2-yl)-3-(2-methoxyphenyl)pyridine-4-carboxamide

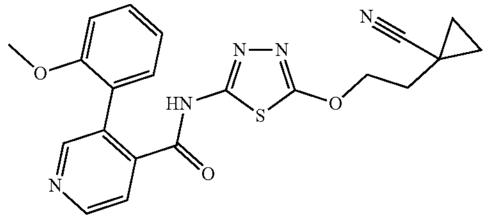 [SMILES: COc1ccccc1-c1cnccc1C(=O)Nc1nnc(OCCC2(C#N)CC2)s1]

Step 1 O-(2-(1-cyanocyclopropyl)ethyl)S-methyl carbonodithioate

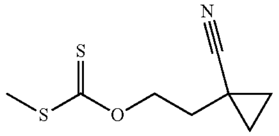

Into a 50 mL 3-necked round-bottom flask was added 1-(2-hydroxyethyl)cyclopropane-1-carbonitrile (950.00 mg, 8.547 mmol, 1.00 equiv) and THF (10.00 mL) at 0 degrees C. The resulting mixture was stirred for 20 min. NaH (410.24 mg, 10.257 mmol, 1.20 equiv, 60%) was added in several portions at the same temperature. The resulting mixture was stirred for 10 min under nitrogen atmosphere. To the above mixture was added $CS_2$ (780.98 mg, 10.257 mmol, 1.2 equiv) dropwise at 0 degrees C. The resulting mixture was stirred for additional 10 min followed by $CH_3I$ (1455.86 mg, 10.257 mmol, 1.2 equiv). The temperature of the external bath was carefully maintained between −5 and −0 degrees C. during the addition. After 10 min, the reaction was then quenched by the addition of 10 mL of ammonium chloride solution, and extracted with ethyl acetate. The solvent was evaporated in vacuum. The residue was purified by silica gel column chromatography, eluted with PE/EtOAc (50:1) to afford O-(2-(1-cyanocyclopropyl)ethyl)S-methyl carbonodithioate (1.41 g, 81.95%) as a colorless oil.

Step 2 1-(2-((aminocarbamothioyl)oxy)ethyl)cyclopropane-1-carbonitrile

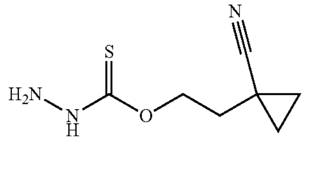 [SMILES: N#CC1(CCOC(=S)NN)CC1]

To a stirred solution of 1-(2-(((methylsulfanyl)methanethioyl)oxy)ethyl)cyclopropane-1-carbonitrile (1.40 g, 6.955 mmol, 1.00 equiv) in MeOH (20 mL) was added hydrazine hydrate (0.38 g, 7.650 mmol, 1.10 equiv) at room temperature. The resulting mixture was stirred for 20 min at room temperature. The resulting mixture was concentrated under vacuum. The crude product was used in the next step directly without further purification. This resulted in 1-(2-((aminocarbamothioyl)oxy)ethyl)cyclopropane-1-carbonitrile (1.3 g, 93.84%) as a white solid.

Step 3 1-(2-((5-amino-1,3,4-thiadiazol-2-yl)oxy)ethyl)cyclopropane-1-carbonitrile

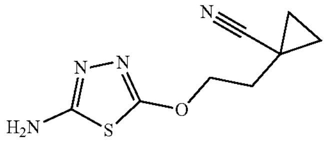 [SMILES: N#CC1(CCOc2nnc(N)s2)CC1]

To a stirred solution of 1-(2-((aminocarbamothioyl)oxy)ethyl)cyclopropane-1-carbonitrile (1.30 g, 7.018 mmol, 1.00 equiv) and $Et_3N$ (1.42 g, 0.014 mmol, 2 equiv) in MeOH (20 mL) were added BrCN (0.89 g, 0.008 mmol, 1.20 equiv) dropwise at room temperature under nitrogen atmosphere. The resulting mixture was stirred for 30 min at the same temperature. The resulting mixture was diluted with water (20 mL). The aqueous layer was extracted with EtOAc (2×20 mL). The product was precipitated by the addition of EtOAc. This resulted in 1-(2-((5-amino-1,3,4-thiadiazol-2-yl)oxy)ethyl)cyclopropane-1-carbonitrile (400 mg, 26.84%) as a pink solid.

Step 5. N-(5-(2-(1-cyanocyclopropyl)ethoxy)-1,3,4-thiadiazol-2-yl)-3-(2-methoxyphenyl)pyridine-4-carboxamide

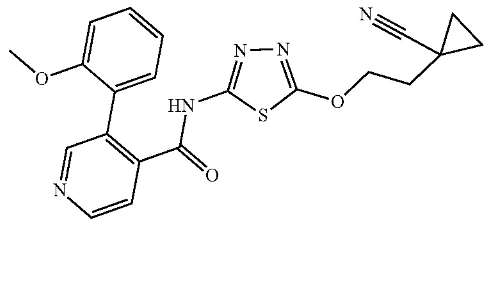 [SMILES: COc1ccccc1-c1cnccc1C(=O)Nc1nnc(OCCC2(C#N)CC2)s1]

Into a 8-mL sealed tube purged and maintained with an inert atmosphere of nitrogen, was placed DMF (2.00 mL) DIEA (147.52 mg, 1.141 mmol, 2 equiv), Intermediate A (130.83 mg, 0.571 mmol, 1.00 equiv), HATU (260.41 mg, 0.685 mmol, 1.2 equiv). The resulting solution was stirred for 1 hr at room temperature. To the above mixture was added 1-(2-((5-amino-1,3,4-thiadiazol-2-yl)oxy)ethyl)cyclopropane-1-carbonitrile (120.00 mg, 0.571 mmol, 1.00 equiv) at room temperature. The resulting mixture was stirred for additional overnight at room temperature. The resulting mixture was diluted with water (10 mL). The aqueous layer was extracted with EtOAc (2×10 mL). The residue was purified by Prep-TLC ($CH_2Cl_2$/MeOH 30:1) to afford N-(5-(2-(1-cyanocyclopropyl)ethoxy)-1,3,4-thiadiazol-2-yl)-3-(2-methoxyphenyl)pyridine-4-carboxamide (78.0 mg, 32.33%) as a white solid. LC-MS: m z 422 $(M+H)^+$. $^1H$ NMR (300 MHz, DMSO) δ12.87 (s, 1H), 8.72-8.71 (d, 1H), 8.61 (s, 1H), 7.64-7.63 (d, 1H), 7.41-7.36 (m, 2H), 7.10-7.07 (m, 1H), 7.05-6.98 (m, 1H), 4.60-4.56 (t, 2H), 3.52 (s, 3H), 2.02-1.98 (t, 2H), 1.25-1.21 (m, 2H), 1.02-0.98 (m, 2H) ppm.

Example 193

2'-chloro-N-(5-(((1s,3s)-3-hydroxycyclobutyl)methoxy)-1,3,4-thiadiazol-2-yl)-5'-methoxy-6-methyl-(4,4'-bipyridine)-3-carboxamide

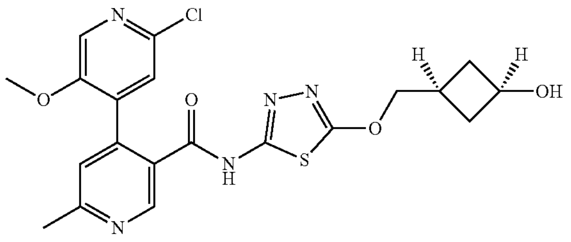 [SMILES: COc1cnc(Cl)cc1-c1cc(C)ncc1C(=O)Nc1nnc(OC[C@H]2C[C@@H](O)C2)s1]

Step-1: methyl (1s,3s)-3-((tert-butyldimethylsilyl)oxy)cyclobutane-1-carboxylate

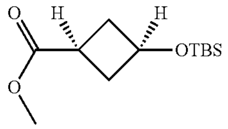 [SMILES: COC(=O)[C@H]1C[C@@H](O[Si](C)(C)C(C)(C)C)C1]

To a mixture of methyl (1s,3s)-3-hydroxycyclobutane-1-carboxylate (2.0 g, 15.368 mmol) and Imidazole (1.5 g, 23.013 mmol) in DCM (30 mL) were added TBS-Cl (3.5 g, 23.013 mmol) and DMAP (187 mg, 1.537 mmol) at 0° C. The resulting mixture was stirred at 0° C. for 1 hour. The reaction mixture was then quenched by the addition of water and extracted with ethyl acetate. The organic layers were combined, washed with brine, dried over anhydrous sodium sulfate and filtered. The filtrate was concentrated under vacuum. The residue was purified by flash chromatography on silica gel with 0~30% ethyl acetate in petroleum ether to afford methyl (1s,3s)-3-((tert-butyldimethylsilyl)oxy)cyclobutane-1-carboxylate (3.3 g, 88%) as a colorless oil. MS (ESI) calc'd for $(C_{12}H_{24}O_3Si)$ $(M+1)^+$, 245.1.

Step-2: ((1s,3s)-3-((tert-butyldimethylsilyl)oxy)cyclobutyl)methanol

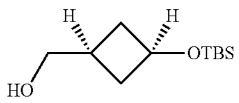

To a solution of methyl (1s,3s)-3-((tert-butyldimethylsilyl)oxy)cyclobutane-1-carboxylate (2.3 g, 9.43 mmol) in THF (20 mL) was added $LiAlH_4$ (537 mg, 14.14 mmol) in portions at 0~5° C. The resulting mixture was stirred at 0° C. for 1 hour. The reaction mixture was then quenched by the addition of water and extracted with ethyl acetate. The combined organic layers were washed with brine, dried over anhydrous sodium sulfate, filtered, and concentrated under vacuum. The residue was purified by flash chromatography on silica gel with 0-40% ethyl acetate in petroleum ether to afford ((1s,3s)-3-((tert-butyldimethylsilyl)oxy)cyclobutyl) methanol (1.0 g, 49%) as a colorless oil. MS (ESI) calc'd for ($C_{11}H_{24}O_2Si$) $(M+1)^+$, 217.1.

Step-3: O-(((1s,3s)-3-((tert-butyldimethylsilyl)oxy) cyclobutyl)methyl)S-methyl carbonodithioate

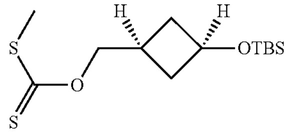 [SMILES: CSC(=S)OC[C@H]1C[C@@H](O[Si](C)(C)C(C)(C)C)C1]

To a solution of (((1s,3s)-3-((tert-butyldimethylsilyl)oxy) cyclobutyl)methanol (1.0 g, 4.63 mmol.) in THF (10 mL) was added NaH (278 mg, 6.94 mmol, 60%) in portions at 0° C. and stirred at 0° C. for 30 min. Then $CS_2$ (527 mg, 6.94 mmol) was added to the above mixture and stirred at 0° C. for 10 min, and then MeI (985 mg, 6.94 mmol) was added to the above mixture at 5° C. The resulting mixture was stirred at room temperature for 1 hour. The reaction mixture was quenched by the addition of water and extracted with ethyl acetate. The combined organic layers were washed with brine, dried over anhydrous sodium sulfate, filtered, and concentrated under vacuum to afford O-(((1s,3s)-3-((tert-butyldimethylsilyl)oxy)cyclobutyl)methyl)S-methyl carbonodithioate (1.3 g, crude) as a colorless oil, which was used in the next step without further purification. MS (ESI) calc'd for ($C_{13}H_{26}O_2S_2Si$) $(M+1)^+$, 307.1.

Step-4: O-(((1s,3s)-3-((tert-butyldimethylsilyl)oxy) cyclobutyl)methyl) hydrazinecarbothioate

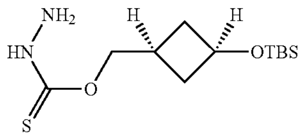 [SMILES: CC(C)(C)[Si](C)(C)O[C@H]1C[C@@H](COC(=S)NN)C1]

To a solution of O-(((1s,3s)-3-((tert-butyldimethylsilyl) oxy)cyclobutyl)methyl)S-methyl carbonodithioate (1.3 g, 4.25 mmol) in MeOH (10 mL) was added hydrazine (265 mg, 4.25 mmol, 80%) at 0° C. The resulting mixture was stirred at room temperature for 1 hour. The reaction mixture was quenched with water and extracted with ethyl acetate. The combined organic layers were washed with brine, dried over anhydrous sodium sulfate, filtered, and concentrated under vacuum to afford O-(((1s,3s)-3-((tert-butyldimethylsilyl)oxy)cyclobutyl)methyl) hydrazinecarbothioate (1.0 g, crude) as yellow oil.

MS (ESI) calc'd for ($C_{12}H_{26}N_2O_2SSi$) $(M+1)^+$, 291.1.

Step-5: 5-(((1s,3s)-3-((tert-butyldimethylsilyl)oxy) cyclobutyl)methoxy)-1,3,4-thiadiazol-2-amine

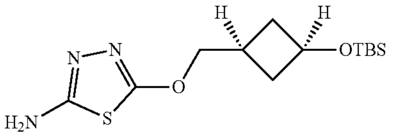

To a solution of O-(((1s,3s)-3-((tert-butyldimethylsilyl) oxy)cyclobutyl)methyl) hydrazinecarbothioate (1.0 g, 3.45 mmol) in MeOH (10 mL) were added TEA (522 mg, 5.17 mmol) and BrCN (543 mg, 5.17 mmol). The resulting mixture was stirred at 0° C. for 2 hours. The reaction mixture was quenched with water and extracted with ethyl acetate. The combined organic layers were washed with brine, dried over anhydrous sodium sulfate, filtered, and concentrated under vacuum. The residue was purified by flash chromatography on silica gel with 0~60% ethyl acetate in petroleum ether to afford 5-(((1s,3s)-3-((tert-butyldimethylsilyl)oxy) cyclobutyl)methoxy)-1,3,4-thiadiazol-2-amine (780 mg, 76%) as a white solid. MS (ESI) calc'd for ($C_{13}H_{25}N_3O_2SSi$) $(M+1)^+$, 316.1; found 316.1.

Step-6: N-(5-(((1s,3s)-3-((tert-butyldimethylsilyl) oxy)cyclobutyl)methoxy)-1,3,4-thiadiazol-2-yl)-2'-chloro-5'-methoxy-6-methyl-(4,4'-bipyridine)-3-carboxamide

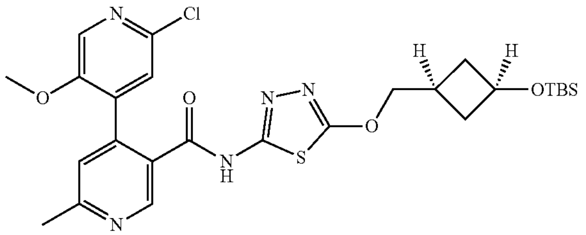 [SMILES: COc1cnc(Cl)cc1-c1cc(C)ncc1C(=O)Nc1nnc(OC[C@H]2C[C@@H](O[Si](C)(C)C(C)(C)C)C2)s1]

To a solution of Intermediate E (200 mg, 0.716 mmol) in ACN (3 mL) and DMF (3 mL) were added NMI (176 mg, 2.148 mmol), 5-(((1s,3s)-3-((tert-butyldimethylsilyl)oxy) cyclobutyl)methoxy)-1,3,4-thiadiazol-2-amine (226 mg, 0.716 mmol) and TCFH (220 mg, 0.798 mmol). The mixture was stirred at room temperature for 1 hour before concentrated under vacuum. The crude residue was purified by flash column chromatography with 0~10% methanol in dichloromethane to afford N-(5-(((1s,3s)-3-((tert-butyldimethylsilyl)oxy)cyclobutyl)methoxy)-1,3,4-thiadiazol-2-yl)-2'-chloro-5'-methoxy-6-methyl-(4,4'-bipyridine)-3-carboxamide (370 mg, 89%) as a white solid. MS (ESI) calc'd for ($C_{26}H_{34}ClN_5O_4SSi$) $(M+1)^+$, 576.1; found 576.1.

Step-7: 2'-chloro-N-(5-(((1s,3s)-3-hydroxycyclobutyl)methoxy)-1,3,4-thiadiazol-2-yl)-5'-methoxy-6-methyl-(4,4'-bipyridine)-3-carboxamide

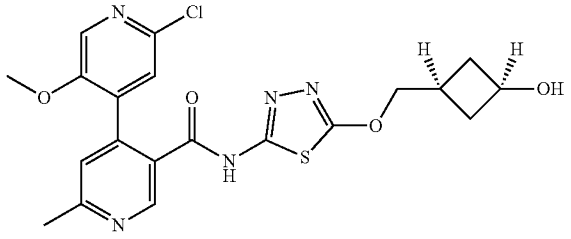 [SMILES: COc1cnc(Cl)cc1-c1cc(C)ncc1C(=O)Nc1nnc(OC[C@H]2C[C@@H](O)C2)s1]

To a mixture of N-(5-(((1s,3s)-3-((tert-butyldimethylsilyl)oxy)cyclobutyl)methoxy)-1,3,4-thiadiazol-2-yl)-2'-chloro-5'-methoxy-6-methyl-(4,4'-bipyridine)-3-carboxamide (160 mg, 0.278 mmol) in THF (3 mL) was added TBAF (168 mg, 0.695 mmol). The resulting mixture was stirred at room temperature for 48 hours before concentrated under vacuum. The resulting mixture was purified by reverse phase flash chromatography with 10~70% acetonitrile in water to afford 2'-chloro-N-(5-(((1s,3s)-3-hydroxycyclobutyl)methoxy)-1,3,4-thiadiazol-2-yl)-5'-methoxy-6-methyl-(4,4'-bipyridine)-3-carboxamide (48.7 mg, 38%) as a white solid. MS (ESI) calc'd for ($C_{20}H_{20}ClN_5O_4S$) (M−1)-, 460.1; found 460.0. $^1$H NMR (400 MHz, DMSO-$d_6$) δ 12.87 (s, 1H), 8.81 (s, 1H), 8.17 (s, 1H), 7.53 (s, 1H), 7.42 (s, 1H), 5.04 (d, J=6.4 Hz, 1H), 4.36 (d, J=6.4 Hz, 2H), 4.03-3.95 (m, 1H), 3.63 (s, 3H), 2.67 (s, 3H), 2.33-2.08 (m, 3H), 1.72-1.65 (m, 2H).

Example 194

6-(2-fluoro-6-methoxyphenyl)-N-(5-(((1r,4r)-4-hydroxycyclohexyl)methoxy)-1,3,4-thiadiazol-2-yl)-3-methylpyrazolo(1,5-a)pyridine-5-carboxamide

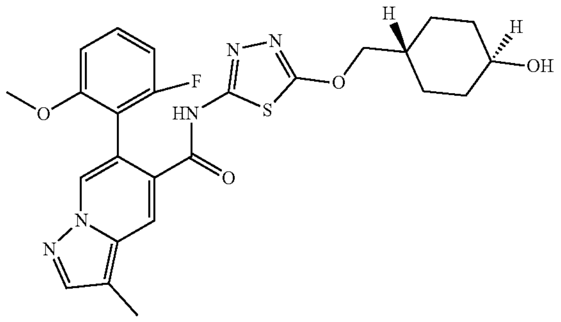 [SMILES: COc1cccc(F)c1-c1cn2ncc(C)c2cc1C(=O)Nc1nnc(OC[C@H]2CC[C@H](O)CC2)s1]

Step-1: methyl 3-(2-fluoro-6-methoxyphenyl)isonicotinate

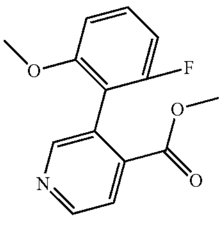

A mixture of methyl 3-bromopyridine-4-carboxylate (5.0 g, 23.14 mmol), 2-fluoro-6-methoxyphenylboronic acid (7.9 g, 46.30 mmol), Pd(dppf)$Cl_2$ (1.7 g, 2.31 mmol) and Potassium carbonate (6.4 g, 46.28 mmol) in dioxane (50 mL) and Water (10 mL) was stirred at 80° C. for 2 hr under nitrogen atmosphere. The aqueous layer was extracted with ethyl acetate. The combined organic solution was dried over sodium sulfate, filtered, and concentrated under vacuum. The resulting residue was dissolved in DCM (5 mL) and purified by Combi Flash (Biotage Isolera Prime) which applied to a 120 g silica gel column that was eluted with 0-50% ethyl acetate in petroleum ether within 35 min to afford as methyl 3-(2-fluoro-6-methoxyphenyl)isonicotinate (4.5 g, 74%) as a yellow solid. MS (ESI) calc'd for ($C_{14}H_{12}FNO_3$) $(M+1)^+$, 262.1, found 262.0.

Step-2: 1-amino-3-(2-fluoro-6-methoxyphenyl)-4-(methoxycarbonyl)pyridin-1-ium

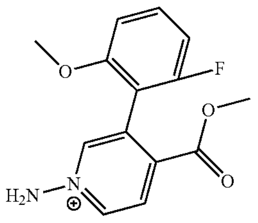 [SMILES: COC(=O)c1cc[n+](N)cc1-c1c(F)cccc1OC]

A solution of methyl 3-(2-fluoro-6-methoxyphenyl)pyridine-4-carboxylate (3.3 g, 12.63 mmol), amino 2,4,6-trimethylbenzenesulfonate (4.1 g, 18.95 mmol) in DCM (50 mL) was stirred at 0° C. to room temperature under nitrogen atmosphere for 18 hr. The organic solvent was removed under vacuum. The suspension was filtered. The filter cake was collected, washed with $Et_2O$ and dried under vacuum to afford 1-amino-3-(2-fluoro-6-methoxyphenyl)-4-(methoxycarbonyl)pyridin-1-ium (3.0 g, crude) as a yellow solid. MS (ESI) calc'd for ($C_{14}H_{14}FN_2O_3^+$) $(M+1)^+$, 278.1, found 278.1.

Step-3: dimethyl 6-(2-fluoro-6-methoxyphenyl)pyrazolo(1,5-a)pyridine-3,5-dicarboxylate

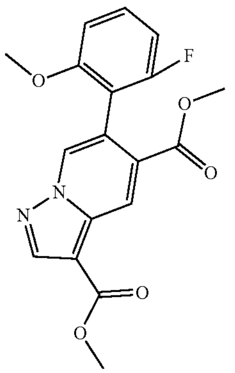

A solution of 1-amino-3-(2-fluoro-6-methoxyphenyl)-4-(methoxycarbonyl)pyridin-1-ium (3.0 g, 11.03 mmol), ethyl propiolate (2.2 g, 22.06 mmol) and Potassium carbonate (6.1 g, 44.14 mmol) in DMF (20 mL) was stirred at 20° C. for 2 hr under nitrogen atmosphere. The resulting mixture was diluted with ethyl acetate and washed by water. The combined organic solution was dried over sodium sulfate, filtered, and concentrated under vacuum. The resulting residue was dissolved in DCM (4 mL) and purified by Combi Flash (Biotage Isolera Prime) which applied to a 120 g silica gel column that was eluted with 0~50% ethyl acetate in petroleum ether within 45 min to afford dimethyl 6-(2-fluoro-6-methoxyphenyl)pyrazolo(1,5-a)pyridine-3,5-dicarboxylate (1.8 g, 34%) as a red solid. MS (ESI) calc'd for ($C_{18}H_{15}FN_2O_5$) $(M+1)^+$, 359.1, found 359.1.

Step-4: 6-(2-fluoro-6-methoxyphenyl)pyrazolo(1,5-a)pyridine-5-carboxylic acid

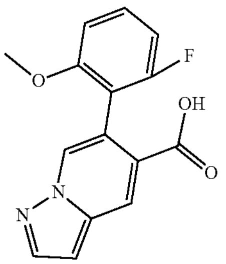 [SMILES: COc1cccc(F)c1-c1cn2nccc2cc1C(=O)O]

A mixture of dimethyl 6-(2-fluoro-6-methoxyphenyl) pyrazolo(1,5-a)pyridine-3,5-dicarboxylate (500.0 mg, 1.20 mmol) in Hydrochloric acid (3 mL, concd.) was stirred at 100° C. for 16 hr. The solvents were removed under vacuum. The resulting residue was dissolved in DMF (3 mL) and purified by Combi Flash (Biotage Isolera Prime) a 40 g C18 column that was eluted with 5~32% acetonitrile in water within 40 min to afford 6-(2-fluoro-6-methoxyphenyl)pyrazolo(1,5-a)pyridine-5-carboxylic acid (220.0 mg, 57%) as a yellow solid. MS (ESI) calc'd for ($C_{15}H_{11}FN_2O_3$) $(M+1)^+$, 287.1, found 287.1.

Step-5: 6-(2-fluoro-6-methoxyphenyl)-3-methylpyrazolo(1,5-a)pyridine-5-carboxylic acid

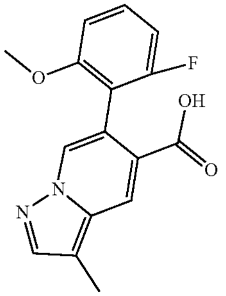 [SMILES: COc1cccc(F)c1-c1cn2ncc(C)c2cc1C(=O)O]

To a mixture of 6-(2-fluoro-6-methoxyphenyl)pyrazolo(1,5-a)pyridine-5-carboxylic acid (100.0 mg, 0.31 mmol) in Tetrahydrofuran (5 mL) was added LDA (0.5 mL, 1.10 mmol, 2M in THF) dropwise at −78° C. and stirred at −78° C. for 1 hr. To the above mixture was added MeI (133.5 mg, 0.94 mmol) at −78° C. The resulting solution was stirred at −78° C. for 30 min. The reaction mixture was quenched by the addition of water and extracted with ethyl acetate. The combined organic layers were washed with brine, dried over anhydrous sodium sulfate, filtered, and concentrated under vacuum. The residue was purified by prep-HPLC with the following conditions: (Column: Xselect CSH OBD Column 30*150 mm 5 um; Mobile Phase A: Water (0.1% FA), Mobile Phase B: ACN; Flow rate: 60 mL/min; Gradient: 35% B to 50% B in 8 min, 50% B to 95% B in 8.2 min, 95% B to 95% B in 9.7 min, 95% B to 5% B in 11 min, 5% B; Wave Length: 220 nm; RT1 (min): 5.18; Injection Volume: 0.4 mL; Number Of Runs: 7) to afford 6-(2-fluoro-6-methoxyphenyl)-3-methylpyrazolo(1,5-a)pyridine-5-carboxylic acid (40.0 mg, 40%) as a white solid. MS (ESI) calc'd for ($C_{16}H_{13}FN_2O_3$) $(M+1)^+$, 301.1, found 301.1.

Step-6: N-(5-(((1r,4r)-4-((tert-butyldimethylsilyl)oxy)cyclohexyl)methoxy)-1,3,4-thiadiazol-2-yl)-6-(2-fluoro-6-methoxyphenyl)-3-methylpyrazolo(1,5-a)pyridine-5-carboxamide

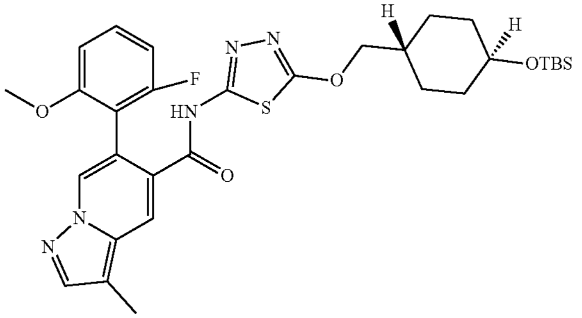 [SMILES: COc1cccc(F)c1-c1cn2ncc(C)c2cc1C(=O)Nc1nnc(OC[C@H]2CC[C@H](O[Si](C)(C)C(C)(C)C)CC2)s1]

To a solution of 6-(2-fluoro-6-methoxyphenyl)-3-methylpyrazolo(1,5-a)pyridine-5-carboxylic acid (50.0 mg, 0.16 mmol) in N,N-Dimethylformamide (DMF) (1 mL) and Acetonitrile (1 mL) were added 1-methyl-1H-imidazole (41.0 mg, 0.50 mmol), N,N,N',N'-Tetramethylchloroformamidinium hexafluorophosphate (69.9 mg, 0.25 mmol) and 5-(((1r,4r)-4-((tert-butyldimethylsilyl)oxy)cyclohexyl) methoxy)-1,3,4-thiadiazol-2-amine (Example 100, Step 68.6 mg, 0.20 mmol) at 20° C. The resulting mixture was stirred at 20° C. under nitrogen for 2 hr. The solvents were removed under vacuum. The residue was purified by Combi Flash (Biotage Isolera Prime) which applied to a 20 g C18 column that was eluted with 5~80% acetonitrile in water within 45 min to afford N-(5-(((1r,4r)-4-((tert-butyldimethylsilyl)oxy)cyclohexyl)methoxy)-1,3,4-thiadiazol-2-yl)-6-(2-fluoro-6-methoxyphenyl)-3-methylpyrazolo(1,5-a)pyridine-5-carboxamide (40.0 mg, 34%) as a white solid. MS (ESI) calc'd for ($C_{32}H_{41}FN_4O_4SSi$) $(M+1)^+$, 625.3, found 625.3.

Step-7: 6-(2-fluoro-6-methoxyphenyl)-N-(5-(((1r,4r)-4-hydroxycyclohexyl)methoxy)-1,3,4-thiadiazol-2-yl)-3-methylpyrazolo(1,5-a)pyridine-5-carboxamide

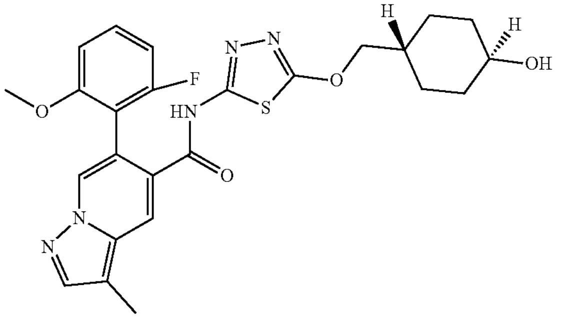 [SMILES: COc1cccc(F)c1-c1cn2ncc(C)c2cc1C(=O)Nc1nnc(OC[C@H]2CC[C@H](O)CC2)s1]

To a stirred solution of N-(5-(((1r,4r)-4-((tert-butyldimethylsilyl)oxy)cyclohexyl)methoxy)-1,3,4-thiadiazol-2-yl)-6-(2-fluoro-6-methoxyphenyl)-3-methylpyrazolo(1,5-a)pyridine-5-carboxamide (40.0 mg, 0.06 mmol) in Dichloromethane (DCM) (2 mL) was added Trifluoroacetic acid (TFA) (0.4 mL) at 0° C. The resulting solution was stirred at 0° C. for 1 hr. The organic solvent was removed under vacuum. The resulting residue was dissolved in DMF (2 mL) and purified by Combi Flash (Biotage Isolera Prime) which applied to a 20 g C18 column that was eluted with 5~25% acetonitrile in water within 40 min to afford 6-(2-fluoro-6-methoxyphenyl)-N-(5-(((1r,4r)-4-hydroxycyclohexyl)methoxy)-1,3,4-thiadiazol-2-yl)-3-methylpyrazolo(1,5-a)pyridine-5-carboxamide (17.0 mg, 57%) as a white solid. MS (ESI) calc'd for ($C_{25}H_{26}FN_5O_4S$) $(M+1)^+$, 512.2, found 512.1. $^1H$ NMR (400 MHz, DMSO-$d_6$) δ 8.22 (s, 1H), 8.04 (s, 1H), 7.36-7.26 (m, 1H), 6.85-6.72 (m, 3H), 4.49 (s, 1H), 4.02 (d, J=6.4 Hz, 2H), 3.62 (s, 3H), 2.72-2.62 (m, 1H), 2.36 (s, 3H), 1.88-1.72 (m, 2H), 1.82-1.74 (m, 2H), 1.73-1.51 (m, 1H), 1.19-1.07 (m, 2H), 1.06-0.94 (m, 2H).

Example 195

7-(2-fluoro-6-methoxyphenyl)-N-(5-(((1r,4r)-4-hydroxycyclohexyl)methoxy)-1,3,4-thiadiazol-2-yl)-3-methylimidazo(1,5-a)pyridine-6-carboxamide

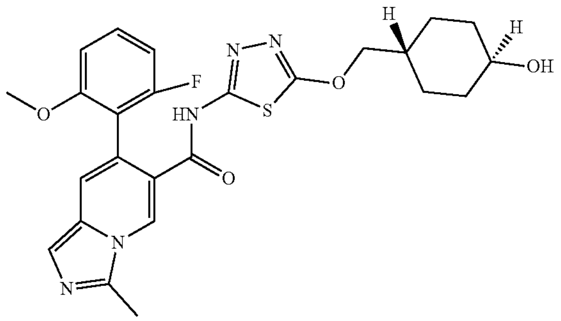 [SMILES: COc1cccc(F)c1-c1cc2cnc(C)n2cc1C(=O)Nc1nnc(OC[C@H]2CC[C@H](O)CC2)s1]

Step-1: ethyl 4-chloro-6-vinylnicotinate

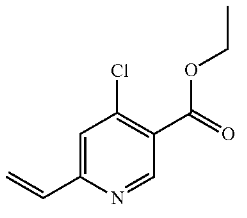

To a stirred solution of ethyl 4,6-dichloronicotinate (10.0 g, 45.40 mmol) in 1,4-Dioxane (60 mL) were added trifluoro (vinyl)-14-borane, potassium salt (6.1 g, 45.40 mmol), $K_2CO_3$ (12.5 g, 91.00 mmol), Water (6 mL) and $PdCl_2$(dppf) $\cdot CH_2Cl_2$ (3.7 g, 4.54 mmol) at 23° C. The resulting solution was stirred at 80° C. for 1.5 hr under nitrogen atmosphere. The reaction mixture was quenched by the addition of water and extracted with ethyl acetate. The combined organic layers were washed with brine, dried over anhydrous sodium sulfate, filtered, and concentrated under vacuum. The resulting residue was purified by Combi Flash (Biotage Isolera Prime) which applied to 120 g silica gel column and eluted with 0-50% ethyl acetate in petroleum ether within 35 min to afford ethyl 4-chloro-6-vinylnicotinate (9.0 g, 75%) as a yellow solid. MS (ESI) calc'd for ($C_{10}H_{10}ClNO_2$) $(M+1)^+$, 212.0; found, 212.0.

Step-2: ethyl 4-chloro-6-formylnicotinate

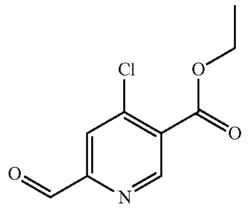

To a stirred solution of ethyl 4-chloro-6-vinylnicotinate (9.0 g, 42.50 mmol) in Tetrahydrofuran (210 mL) and Water (70 mL) were added osmium tetroxide (2.1 g, 8.50 mmol) and sodium periodate (18.2 g, 85.00 mmol) at 20° C. The resulting solution was stirred at 20° C. for 16 hr. The reaction mixture was quenched by the addition of water and extracted with ethyl acetate. The combined organic layers were washed with brine, dried over anhydrous sodium sulfate, filtered, and concentrated under vacuum. The resulting residue was dissolved in DCM (8 mL) and purified by Combi Flash (Biotage Isolera Prime) which applied to a 330 g silica gel column that was eluted with 0-50% ethyl acetate in petroleum ether within 25 min to afford ethyl 4-chloro-6-formylnicotinate (3.1 g, 310%) as a yellow solid. MS (ESI) calc'd for ($C_9H_8ClNO_3$) $(M+1)^+$, 214.0; found, 214.0.

Step-3: ethyl 4-chloro-6-(hydroxymethyl)nicotinate

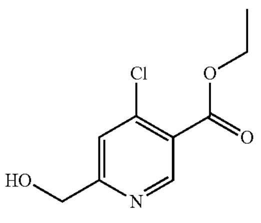

To a stirred solution of ethyl 4-chloro-6-formylnicotinate (2.0 g, 9.36 mmol) in Ethanol (20 mL) was added $NaBH_4$ (0.4 g, 9.34 mmol) at 0° C. The resulting solution was stirred at 0° C. for 30 min. The reaction mixture was quenched by the addition of water and extracted with ethyl acetate. The combined organic layers were washed with brine, dried over anhydrous sodium sulfate, filtered, and concentrated under vacuum to afford ethyl 4-chloro-6-(hydroxymethyl)nicotinate (2.0 g, crude) as a yellow oil. MS (ESI) calc'd for ($C_9H_{10}ClNO_3$) $(M+1)^+$, 216.0; found, 216.0.

Step-4: ethyl 4-(2-fluoro-6-methoxyphenyl)-6-(hydroxymethyl)nicotinate

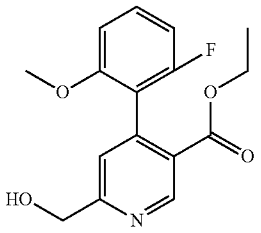 [SMILES: CCOC(=O)c1cnc(CO)cc1-c1c(F)cccc1OC]

To a stirred solution of ethyl 4-chloro-6-(hydroxymethyl) nicotinate (2.0 g, 9.28 mmol) and (2-fluoro-6-methoxyphenyl)boronic acid (1.5 g, 9.28 mmol) in 1,4-Dioxane (20 mL) and Water (4 mL) were added $K_2CO_3$ (3.7 g, 27.85 mmol) and $PdCl_2$(dppf)-$CH_2Cl_2$ (0.7 g, 0.92 mmol) at 20° C. The resulting solution was stirred at 80° C. for 2 hr under nitrogen. The reaction mixture was dilute by the addition of water and extracted with ethyl acetate. The combined organic layers were washed with brine, dried over anhydrous sodium sulfate, filtered, and concentrated under vacuum. The resulting residue was dissolved in DCM (5 mL) and purified by Combi Flash (Biotage Isolera Prime) which applied to a 80 g silica gel column that was eluted with 0~40% ethyl acetate in petroleum ether within 35 min to afford methyl 4-(2-fluoro-6-methoxyphenyl)-6-(hydroxymethyl)nicotinate (2.8 g, 85%) as a white solid. MS (ESI) calc'd for ($C_{16}H_{16}FNO_4$) $(M+1)^+$, 306.1; found, 306.1.

Step-5: ethyl 6-(azidomethyl)-4-(2-fluoro-6-methoxyphenyl)nicotinate

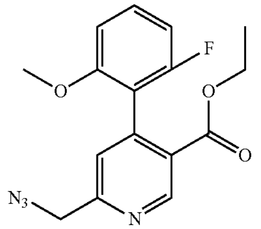 [SMILES: CCOC(=O)c1cnc(CN=[N+]=[N-])cc1-c1c(F)cccc1OC]

To a stirred solution of ethyl 4-(2-fluoro-6-methoxyphenyl)-6-(hydroxymethyl)nicotinate (1.0 g, 3.28 mmol) in Tetrahydrofuran (10 mL) were added DBU (598.0 mg, 3.93 mmol) and DPPA (1.0 g, 3.93 mmol) at 0° C. The resulting solution was stirred at 20° C. for 16 hr under nitrogen. The solvents were removed under vacuum. The resulting residue was dissolved in DCM (2 mL) and purified by Combi Flash (Biotage Isolera Prime) which applied to a 40 g silica gel column that was eluted with 0~60% ethyl acetate in petroleum ether within 30 min to afford ethyl 6-(azidomethyl)-4-(2-fluoro-6-methoxyphenyl)nicotinate (910.0 mg, 80%) as a white solid. MS (ESI) calc'd for ($C_{16}H_{15}FN_4O_3$) $(M+1)^+$, 331.1; found, 331.1.

Step-6: ethyl 6-(aminomethyl)-4-(2-fluoro-6-methoxyphenyl)nicotinate

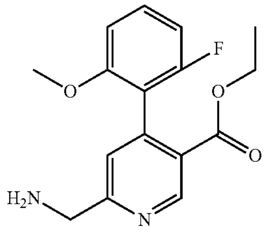 [SMILES: CCOC(=O)c1cnc(CN)cc1-c1c(F)cccc1OC]

To a stirred solution of ethyl 6-(azidomethyl)-4-(2-fluoro-6-methoxyphenyl)nicotinate (860.0 mg, 2.60 mmol) in Methanol (6 mL) was added Pd/C (277.0 mg) at 20° C. The resulting solution was stirred at 20° C. for 2 hr under hydrogen. The suspension was filtered. The filtrate was collected and concentrated under vacuum to afford ethyl 6-(aminomethyl)-4-(2-fluoro-6-methoxyphenyl)nicotinate (520.0 mg, crude) as a green oil. MS (ESI) calc'd for ($C_{16}H_{17}FN_2O_3$) $(M+1)^+$, 305.1; found, 305.1.

Step-7: ethyl 7-(2-fluoro-6-methoxyphenyl)-3-methylimidazo(1,5-a)pyridine-6-carboxylate

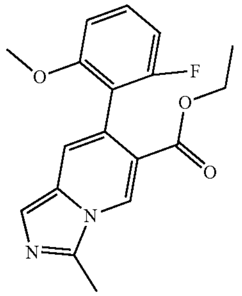 [SMILES: CCOC(=O)c1cn2c(C)ncc2cc1-c1c(F)cccc1OC]

To a stirred solution of ethyl 6-(aminomethyl)-4-(2-fluoro-6-methoxyphenyl)nicotinate (500.0 mg, 1.64 mmol) in Acetic anhydride (2 mL) was added TsOH (283.0 mg, 1.64 mmol) at 20° C. The resulting solution was stirred at 100° C. for 3 hr. The reaction mixture was quenched by the addition of saturated sodium carbonate aqueous solution and extracted with ethyl acetate. The combined organic layers were washed with brine, dried over anhydrous sodium sulfate, filtered, and concentrated under vacuum. The resulting residue was dissolved in DCM (2 mL) and purified by Combi Flash (Biotage Isolera Prime) which applied to a 40 g silica gel column that was eluted with 0-60% ethyl acetate in petroleum ether within 25 min to afford ethyl 7-(2-fluoro-6-methoxyphenyl)-3-methylimidazo(1,5-a)pyridine-6-carboxylate (320.0 mg, 56%) as a yellow solid. MS (ESI) calc'd for ($C_{18}H_{17}FN_2O_3$) $(M+1)^+$, 329.1; found, 329.1.

Step-8: 7-(2-fluoro-6-methoxyphenyl)-3-methylimidazo(1,5-a)pyridine-6-carboxylic acid

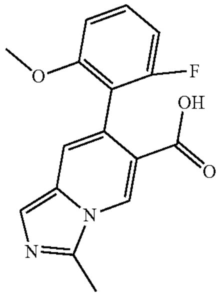 [SMILES: COc1cccc(F)c1-c1cc2cnc(C)n2cc1C(=O)O]

To a stirred solution of ethyl 7-(2-fluoro-6-methoxyphenyl)-3-methylimidazo(1,5-a)pyridine-6-carboxylate (300.0 mg, 0.91 mmol) in Tetrahydrofuran (1 mL) and Water (1 mL) was added LiOH (175.0 mg, 7.31 mmol) at 20° C. The resulting solution was stirred at 50° C. for 16 hr. The aqueous layer was acidified with citric acid to pH ~4 and extracted with ethyl acetate. The combined organic layers were washed with brine, dried over anhydrous sodium sulfate, filtered, and concentrated under vacuum to afford 7-(2-fluoro-6-methoxyphenyl)-3-methylimidazo(1,5-a)pyridine-6-carboxylic acid (70.0 mg, crude) as a yellow solid. MS (ESI) calc'd for ($C_{16}H_{13}FN_2O_3$) (M+1)$^+$, 301.0; found, 301.0.

Step-9: N-(5-(((1r,4r)-4-((tert-butyldimethylsilyl)oxy)cyclohexyl)methoxy)-1,3,4-thiadiazol-2-yl)-7-(2-fluoro-6-methoxyphenyl)-3-methylimidazo(1,5-a)pyridine-6-carboxamide

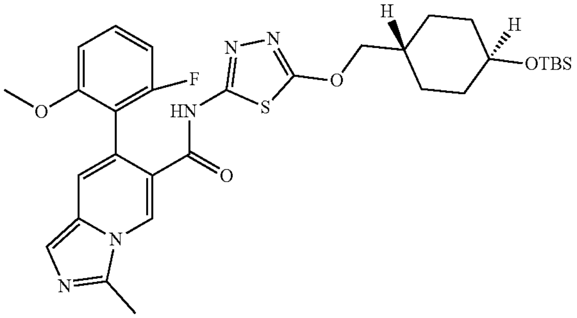 [SMILES: COc1cccc(F)c1-c1cc2cnc(C)n2cc1C(=O)Nc1nnc(OC[C@H]2CC[C@H](O[Si](C)(C)C(C)(C)C)CC2)s1]

To a stirred solution of 5-(((1r,4r)-4-((tert-butyldimethylsilyl)oxy)cyclohexyl)methoxy)-1,3,4-thiadiazol-2-amine (Example 100, Step 5, 68.0 mg, 0.20 mmol) in Acetonitrile (0.6 mL) were added 7-(2-fluoro-6-methoxyphenyl)-3-methylimidazo(1,5-a)pyridine-6-carboxylic acid (60 mg, 0.20 mmol) and 1-methylimidazole (82.0 mg, 0.99 mmol). To the above was added a solution of TCFH (56.1 mg, 0.20 mmol) in Acetonitrile (0.6 mL) at 20° C. under nitrogen. The resulting solution was stirred at 20° C. for 6 hr under nitrogen. The resulting residue was dissolved in DMF (1 mL) which was applied to a 20 g C18 column and purified by Combi Flash (Biotage Isolera Prime), eluted with 5~40% acetonitrile in water within 25 min to afford N-(5-(((1r,4r)-4-((tert-butyldimethylsilyl)oxy)cyclohexyl)methoxy)-1,3,4-thiadiazol-2-yl)-7-(2-fluoro-6-methoxyphenyl)-3-methylimidazo(1,5-a)pyridine-6-carboxamide (120.0 mg, 86%) as a yellow solid. MS (ESI) calc'd for ($C_{31}H_{40}FN_5O_4SSi$) (M+1)$^+$, 626.3; found, 626.2.

Step-10: 7-(2-fluoro-6-methoxyphenyl)-N-(5-(((1r,4r)-4-hydroxycyclohexyl)methoxy)-1,3,4-thiadiazol-2-yl)-3-methylimidazo(1,5-a)pyridine-6-carboxamide

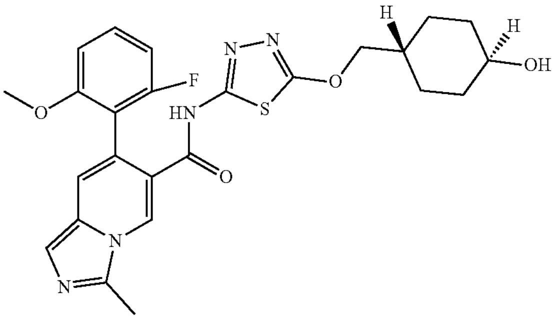 [SMILES: COc1cccc(F)c1-c1cc2cnc(C)n2cc1C(=O)Nc1nnc(OC[C@H]2CC[C@H](O)CC2)s1]

To a stirred solution of N-(5-(((1r,4r)-4-((tert-butyldimethylsilyl)oxy)cyclohexyl)methoxy)-1,3,4-thiadiazol-2-yl)-7-(2-fluoro-6-methoxyphenyl)-3-methylimidazo(1,5-a)pyridine-6-carboxamide (110.0 mg, 0.17 mmol) in Dichloromethane (1 mL) was added Trifluoroacetic acid (0.2 mL) at 20° C. The resulting solution was stirred at 20° C. for 1 hr. The organic solvent was removed under vacuum before diluted with water. The aqueous layer was basified with NaOH (2 N) to pH ~12. The resulting mixture was dissolved in DMF (2 mL) which was applied to a 20 g C18 column and purified by Combi Flash (Biotage Isolera Prime), eluted with 5-70% acetonitrile in water within 35 min to afford 7-(2-fluoro-6-methoxyphenyl)-N-(5-(((1r,4r)-4-hydroxycyclohexyl)methoxy)-1,3,4-thiadiazol-2-yl)-3-methylimidazo(1,5-a)pyridine-6-carboxamide (23.4 mg, 26%) as a white solid. MS (ESI) calc'd for ($C_{25}H_{26}FN_5O_4S$) (M+1)$^+$, 512.2; found, 512.2. $^1$H NMR (400 MHz, Methanol-$d_4$) δ 8.54 (s, 1H), 7.43 (s, 1H), 7.36-7.24 (m, 2H), 6.85-6.74 (m, 2H), 4.19 (d, J=6.4 Hz, 2H), 3.65 (s, 3H), 3.58-3.50 (m, 1H), 2.74 (s, 3H), 2.01-1.91 (m, 2H), 1.90-1.77 (m, 2H), 1.77-1.62 (m, 1H), 1.37-1.10 (m, 4H).

Example 196 and 197

2'-chloro-N-(5-(((1s,4s)-4-fluorocyclohexyl)methoxy)-1,3,4-thiadiazol-2-yl)-5'-methoxy-6-methyl-(4,4'-bipyridine)-3-carboxamide and 2'-chloro-N-(5-(((1r,4r)-4-fluorocyclohexyl)methoxy)-1,3,4-thiadiazol-2-yl)-5'-methoxy-6-methyl-(4,4'-bipyridine)-3-carboxamide

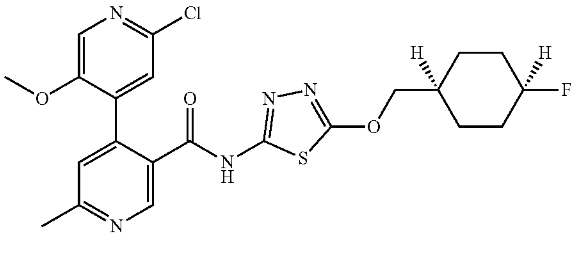

-continued

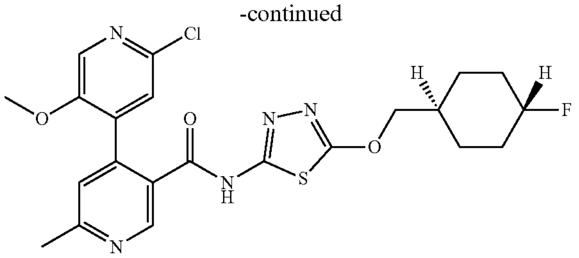

Step-1: (4-fluorocyclohexyl)methanol

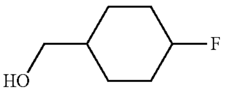

To a mixture of 4-fluorocyclohexane-1-carboxylic acid (350.0 mg, 2.39 mmol) and NMM (242.0 mg, 2.39 mmol) in THF (5 mL) was added Isobutyl chloroformate (327.0 mg, 2.39 mmol) at 0° C. The resulting solution was stirred at 0° C. for 2 hr. To the above mixture was added $NaBH_4$ (272.0 mg, 7.18 mmol) and Methanol (10 mL) at 0° C. The resulting solution was stirred at 0° C. for 2 hr. The resulting mixture was quenched with water. The aqueous layer was extracted with ethyl acetate. The combined organic layers were washed with brine, dried over anhydrous sodium sulfate, filtered, and concentrated under vacuum to afford (4-fluorocyclohexyl)methanol (300.0 mg, crude) as a yellow oil.

Step-2: O-((4-fluorocyclohexyl)methyl)S-methyl carbonodithioate

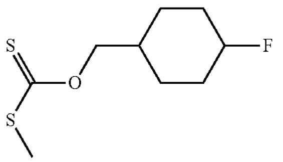

To a solution of (4-fluorocyclohexyl)methanol (180.0 mg, 1.08 mmol) in THF (2 mL) was added NaH (87.0 mg, 2.17 mmol, 60%) in portions at 0° C. and stirred at 0° C. for 30 min. Then $CS_2$ (124.0 mg, 1.63 mmol) was added to the above mixture and stirred at 0° C. for 10 min, and then MeI (229.0 mg, 1.63 mmol) was added to the above mixture at 0° C. The resulting mixture was stirred at 0° C. for 30 min under nitrogen atmosphere. The reaction mixture was quenched by the addition of water and extracted with ethyl acetate. The combined organic layers were washed with brine, dried over anhydrous sodium sulfate, filtered, and concentrated under vacuum to afford O-((4-fluorocyclohexyl)methyl)S-methyl carbonodithioate (300.0 mg, crude) as a yellow oil.

Step-3: O-((4-fluorocyclohexyl)methyl) hydrazinecarbothioate

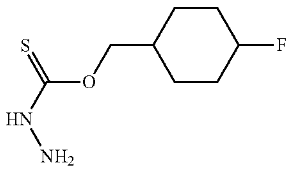 [SMILES: NNC(=S)OCC1CCC(F)CC1]

A mixture of O-((4-fluorocyclohexyl)methyl)S-methyl carbonodithioate (300.0 mg, 0.94 mmol), Hydrazine hydrate (59.10 mg, 0.94 mmol, 80%) in Methanol (5 mL) were stirred at 25° C. for 2 hr. The reaction mixture was quenched by the addition of water and extracted with ethyl acetate. The combined organic layers were washed with brine, dried over anhydrous sodium sulfate, filtered, and concentrated under vacuum to afford O-((4-fluorocyclohexyl)methyl) hydrazinecarbothioate (200.0 mg, crude) as a yellow oil. MS (ESI) calc'd for ($C_8H_{15}FN_2OS$) $(M+1)^+$, 207.1; found, 207.0.

Step-4: 5-((4-fluorocyclohexyl)methoxy)-1,3,4-thiadiazol-2-amine

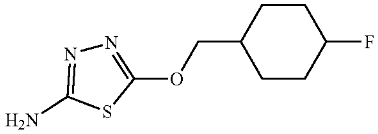 [SMILES: Nc1nnc(OCC2CCC(F)CC2)s1]

To a mixture of O-((4-fluorocyclohexyl)methyl) hydrazinecarbothioate (200.0 mg, 0.82 mmol) in Methanol (6 mL) were added TEA (0.23 mL, 1.64 mmol) and cyanic bromide (96.00 mg, 0.90 mmol) at 25° C. The resulting solution was stirred at 25° C. for 30 min. The reaction mixture was quenched by the addition of water and extracted with ethyl acetate. The combined organic layers were washed with brine, dried over anhydrous sodium sulfate, filtered, and concentrated under vacuum. The resulting residue was dissolved in DCM (2 mL) and purified by Combi Flash (Biotage Isolera Prime) which applied to a 20 g silica gel column that was eluted with 0~60% ethyl acetate in petroleum ether within 20 min to afford as a red solid 5-((4-fluorocyclohexyl)methoxy)-1,3,4-thiadiazol-2-amine (180.0 mg, crude). MS (ESI) calc'd for ($C_9H_{14}FN_3OS$) $(M+1)^+$, 232.1; found, 232.2.

Step-5: 2'-chloro-N-(5-((4-fluorocyclohexyl)methoxy)-1,3,4-thiadiazol-2-yl)-5'-methoxy-6-methyl-(4,4'-bipyridine)-3-carboxamide

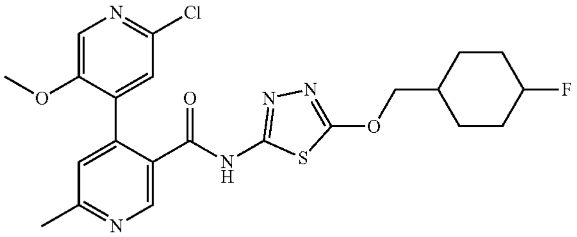 [SMILES: COc1cnc(Cl)cc1-c1cc(C)ncc1C(=O)Nc1nnc(OCC2CCC(F)CC2)s1]

To a stirred solution of Intermediate E (160.0 mg, 0.51 mmol)) in Acetonitrile (1 mL) and N,N-Dimethylformamide (DMF) (1 mL) were added TCFH (159.0 mg, 0.56 mmol), NMI (127.0 mg, 1.55 mmol) and 5-((4-fluorocyclohexyl) methoxy)-1,3,4-thiadiazol-2-amine (179.0 mg, 0.62 mmol) at 20° C. The resulting solution was stirred at 20° C. for 2 hr. The reaction mixture was purified by prep-HPLC directly with the following conditions: (Column: XBridge Shield RP18 OBD Column, 30*150 mm, 5 μm; Mobile Phase A: Water (10 mmol/L $NH_4HCO_3$), Mobile Phase B: ACN; Flow rate: 60 mL/min; Gradient: 37% B to 47% B in 8 min, 47% B to 95% B in 8.2 min, 95% B to 95% B in 9.5 min, 95% B to 5% B in 11 min, 5% B; Wave Length: 254 nm; RT 1 (min): 6.3; Injection Volume: 1 mL; Number Of Runs: 5) to afford 2'-chloro-N-(5-((4-fluorocyclohexyl)methoxy)-1,3,4-thiadiazol-2-yl)-5'-methoxy-6-methyl-(4,4'-bipyridine)-3-carboxamide (90.0 mg, 33%) as a white solid. MS (ESI) calc'd for ($C_{22}H_{23}ClFN_5O_3S$) $(M+1)^+$, 492.1; found, 492.1.

Step-5: 2'-chloro-N-(5-(((1s,4s)-4-fluorocyclohexyl) methoxy)-1,3,4-thiadiazol-2-yl)-5'-methoxy-6-methyl-(4,4'-bipyridine)-3-carboxamide and 2'-chloro-N-(5-(((1r,4r)-4-fluorocyclohexyl) methoxy)-1,3,4-thiadiazol-2-yl)-5'-methoxy-6-methyl-(4,4'-bipyridine)-3-carboxamide

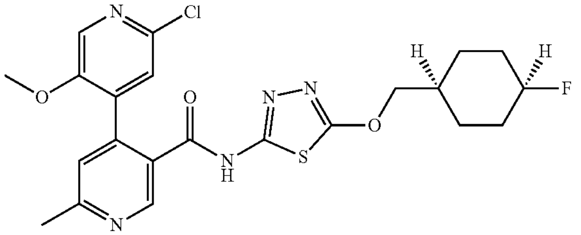

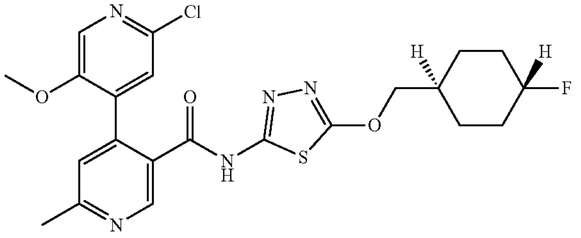

2'-Chloro-N-(5-((4-fluorocyclohexyl)methoxy)-1,3,4-thiadiazol-2-yl)-5'-methoxy-6-methyl-(4,4'-bipyridine)-3-carboxamide (90.0 mg, 0.17 mmol) was separated by prep-chiral HPLC with the following conditions: (Column: CHIRALPAK IE, 2*25 cm, 5 μm; Mobile Phase A: Hex-HPLC, Mobile Phase B: MeOH:EtOH=1: 1-HPLC; Flow rate: 15 mL/min; Gradient: 70% B to 70% B in 30 min; Wave Length: 220/254 nm; RT1 (min): 18.79; RT2 (min): 26.12; Sample Solvent: MeOH:DCM=1: 1; Injection Volume: 3 mL; Number Of Runs: 4) to afford 2'-chloro-N-(5-((4-fluorocyclohexyl)methoxy)-1,3,4-thiadiazol-2-yl)-5'-methoxy-6-methyl-(4,4'-bipyridine)-3-carboxamide, isomer 1 (12.5 mg, 14%) as a white solid with shorter retention time on chiral HPLC and 2'-chloro-N-(5-((4-fluorocyclohexyl) methoxy)-1,3,4-thiadiazol-2-yl)-5'-methoxy-6-methyl-(4,4'-bipyridine)-3-carboxamide, isomer 2 (29.2 mg, 35%) as a white solid with longer retention time on chiral-HPLC. The absolute stereochemistry was not determined.

Isomer 1: 2'-chloro-N-(5-(((1s,4s)-4-fluorocyclohexyl) methoxy)-1,3,4-thiadiazol-2-yl)-5'-methoxy-6-methyl-(4,4'-bipyridine)-3-carboxamide: MS (ESI) calc'd for ($C_{22}H_{23}ClFN_5O_3S$) $(M+1)^+$, 492.1; found, 492.1. $^1H$ NMR (400 MHz, DMSO-$d_6$) δ 12.88 (s, 1H), 8.82 (s, 1H), 8.17 (s, 1H), 7.51 (s, 1H), 7.40 (s, 1H), 4.62-4.39 (m, 1H), 4.25 (d, J=6.0 Hz, 2H), 3.63 (s, 3H), 2.59 (s, 3H), 2.10-2.00 (m, 2H), 1.94-1.69 (m, 3H), 1.52-1.36 (m, 2H), 1.22-1.08 (m, 2H).

Isomer 2: 2'-chloro-N-(5-(((1r,4r)-4-fluorocyclohexyl) methoxy)-1,3,4-thiadiazol-2-yl)-5'-methoxy-6-methyl-(4,4'-bipyridine)-3-carboxamide: MS (ESI) calc'd for $C_{22}H_{23}ClFN_5O_3S$) $(M+1)^+$, 492.1; found, 492.1. $^1H$ NMR (400 MHz, DMSO-$d_6$) 1H NMR (400 MHz, DMSO-$d_6$) δ 12.88 (s, 1H), 8.81 (s, 1H), 8.17 (s, 1H), 7.52 (s, 1H), 7.42 (s, 1H), 4.99-4.63 (m, 1H), 4.27 (d, J=6.4 Hz, 2H), 3.64 (s, 3H), 2.59 (s, 3H), 1.96-1.88 (m, 3H), 1.67-1.59 (m, 3H), 1.57-1.45 (m, 1H), 1.41-1.31 (m, 2H).

Example 198

2'-chloro-N-(5-((1-fluorocyclopropyl)methoxy)-1,3,4-thiadiazol-2-yl)-5'-methoxy-6-methyl-(4,4'-bipyridine)-3-carboxamide

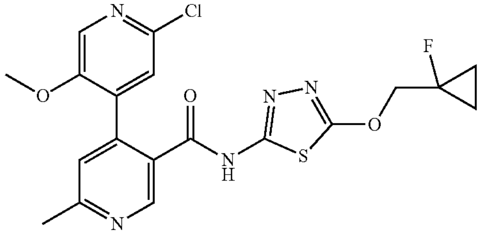 [SMILES: COc1cnc(Cl)cc1-c1cc(C)ncc1C(=O)Nc1nnc(OCC2(F)CC2)s1]

Step-1: 5-((1-fluorocyclopropyl)methoxy)-1,3,4-thiadiazol-2-amine

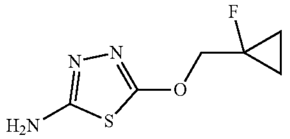 [SMILES: Nc1nnc(OCC2(F)CC2)s1]

To a degassed solution of (1-fluorocyclopropyl)methanol (200.0 mg, 2.22 mmol) in dry THF (10 mL) was added NaH (178.0 mg, 4.44 mmol, 60%) in portions at 0° C. The resulting solution was stirred at 0° C. for 1 hr under nitrogen. To the above solution was added 5-bromo-1,3,4-thiadiazol-2-amine (480.0 mg, 2.66 mmol) at 0° C. under nitrogen. The resulting mixture was then stirred at 0° C. for 2 hr. The reaction mixture was quenched by the addition of water and extracted with ethyl acetate. The combined organic layers were washed with brine, dried over anhydrous sodium sulfate, filtered, and concentrated under vacuum. The resulting residue was dissolved in DMF (2 mL) which was applied to a 40 g C18 column and purified by Combi Flash (Biotage Isolera Prime), eluted with 5~35% acetonitrile in water within 45 min to afford 5-((1-fluorocyclopropyl)methoxy)-1,3,4-thiadiazol-2-amine (50.0 mg, 11%) as a white solid. MS (ESI) calc'd for ($C_6H_8FN_3OS$) $(M+1)^+$, 190.0, found 189.9.

Step-2: 2'-chloro-N-(5-((1-fluorocyclopropyl) methoxy)-1,3,4-thiadiazol-2-yl)-5'-methoxy-6-methyl-(4,4'-bipyridine)-3-carboxamide

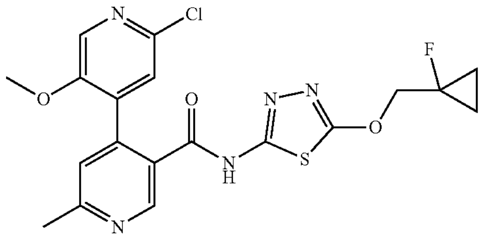 [SMILES: COc1cnc(Cl)cc1-c1cc(C)ncc1C(=O)Nc1nnc(OCC2(F)CC2)s1]

To a mixture of 5-((1-fluorocyclopropyl)methoxy)-1,3,4-thiadiazol-2-amine (33.6 mg, 0.16 mmol) in acetonitrile (2 mL) were added Intermediate E (45.0 mg, 0.14 mmol) and NMI (59.6 mg, 0.72 mmol). A solution of TCFH (44.8 mg, 0.16 mmol) in acetonitrile (1 mL) was added thereto dropwise under nitrogen. The mixture was stirred at 20° C. for 2 hr under nitrogen. The reaction mixture was applied to a 20 g C18 column and purified by Combi Flash (Biotage Isolera Prime), eluted with 5~45% acetonitrile in water within 45 min to afford 2'-chloro-N-(5-((1-fluorocyclopropyl) methoxy)-1,3,4-thiadiazol-2-yl)-5'-methoxy-6-methyl-(4,4'-bipyridine)-3-carboxamide (53.0 mg, 81%) as a white solid. MS (ESI) calc'd for ($C_{19}H_{17}ClFN_5O_3S$) $(M+1)^+$, 450.0, found 450.1. $^1H$ NMR (400 MHz, DMSO-$d_6$) δ 12.92 (s, 1H), 8.82 (s, 1H), 8.17 (s, 1H), 7.54 (s, 1H), 7.43 (s, 1H), 4.76-4.74 (m, 2H), 3.64 (s, 3H), 2.59 (s, 3H), 1.23-1.11 (m, 2H), 0.97-0.94 (m, 2H).

Example 199

5-(2-fluoro-6-methoxyphenyl)-N-(5-(((1r,4r)-4-hydroxycyclohexyl)methoxy)-1,3,4-thiadiazol-2-yl)-1H-benzo(d)imidazole-6-carboxamide

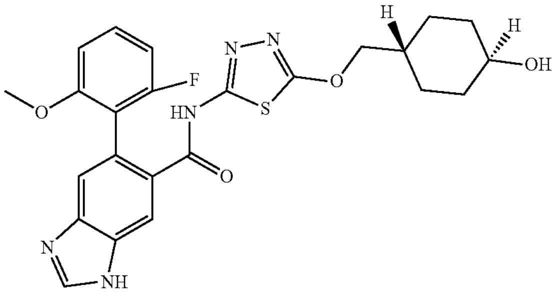 [SMILES: COc1cccc(F)c1-c1cc2nc[nH]c2cc1C(=O)Nc1nnc(OC[C@H]2CC[C@H](O)CC2)s1]

Step-1: methyl 5-bromo-1-((2-(trimethylsilyl) ethoxy)methyl)-1H-benzo(d)imidazole-6-carboxylate

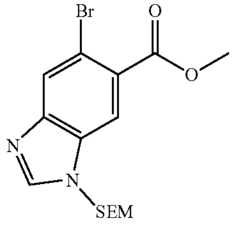 [SMILES: COC(=O)c1cc2c(cc1Br)ncn2COCC[Si](C)(C)C]

To a degassed solution of methyl 5-bromo-1H-benzo(d) imidazole-6-carboxylate (820.0 mg, 3.21 mmol) in N,N-Dimethylformamide (DMF) (12 mL) was added sodium hydride (129.0 mg, 3.21 mmol) in portions at 0° C. The resulting solution was stirred at 0° C. for 1 hr under nitrogen. To the above solution was added (2-(chloromethoxy)ethyl) trimethylsilane (590.0 mg, 3.54 mmol) at 0° C. The resulting solution was then stirred at 0° C. for 1 hr under nitrogen. The reaction mixture was quenched by the addition of water and extracted with ethyl acetate. The combined organic layers were washed with brine, dried over anhydrous sodium sulfate, filtered, and concentrated under vacuum. The resulting residue was dissolved in DCM (4 mL) and purified by Combi Flash (Biotage Isolera Prime) which applied to a 40 g silica gel column that was eluted with 0~48% ethyl acetate in petroleum ether within 30 min to afford methyl 5-bromo-1-((2-(trimethylsilyl)ethoxy)methyl)-1H-benzo(d)imidazole-6-carboxylate (825.0 mg, 66%) as a grey oil. MS (ESI) calculated for ($C_{15}H_{21}BrN_2O_3Si$) $(M+1)^+$, 385.1; found, 385.1.

Step-2: methyl 5-(2-fluoro-6-methoxyphenyl)-1-((2-(trimethylsilyl)ethoxy)methyl)-1H-benzo(d)imidazole-6-carboxylate

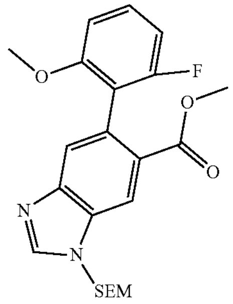

To a stirred solution of methyl 5-bromo-1-((2-(trimethylsilyl)ethoxy)methyl)-1H-benzo(d)imidazole-6-carboxylate (825.0 mg, 2.14 mmol) in 1,4-Dioxane (4 mL) were sequentially added Water (4 mL), (2-fluoro-6-methoxyphenyl)boronic acid (546.0 mg, 3.21 mmol), $K_2CO_3$ (888.0 mg, 6.42 mmol) and $PdCl_2$(dtbpf) (140.0 mg, 0.21 mmol) at 25° C. The resulting solution was stirred at 80° C. for 2 hr. The suspension was filtered. The filtrate was collected and concentrated under vacuum. The resulting residue was dissolved in DMF (4 mL) which was applied to a 40 g C18 column and purified by Combi Flash (Biotage Isolera Prime), eluted with 5~50% acetonitrile in water within 30 min to afford methyl 5-(2-fluoro-6-methoxyphenyl)-1-((2-(trimethylsilyl)ethoxy)methyl)-1H-benzo(d)imidazole-6-carboxylate (610.0 mg, 61%) as a yellow oil. MS (ESI) calculated for ($C_{22}H_{27}FN_2O_4Si$) $(M+1)^+$, 331.2; found, 331.2.

Step-3: 5-(2-fluoro-6-methoxyphenyl)-1-((2-(trimethylsilyl)ethoxy)methyl)-1H-benzo(d)imidazole-6-carboxylic acid

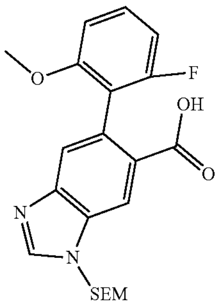 [SMILES: COc1cccc(F)c1-c1cc2ncn(COCC[Si](C)(C)C)c2cc1C(=O)O]

To a stirred solution of methyl 5-(2-fluoro-6-methoxyphenyl)-1-((2-(trimethylsilyl)ethoxy)methyl)-1H-benzo(d)imidazole-6-carboxylate (610.0 mg, 1.42 mmol) in Methanol (3 mL) were sequentially added Water (3 mL) and NaOH (227.0 mg, 5.67 mmol) at 25° C. The resulting solution was stirred at 80° C. for 1 hr before diluted with water. The organic solvent was removed under vacuum. The aqueous layer was acidified with citric acid to pH ~6 and extracted with ethyl acetate. The combined organic layers were washed with brine, dried over anhydrous sodium sulfate, filtered, and concentrated under vacuum to afford 5-(2-fluoro-6-methoxyphenyl)-1-((2-(trimethylsilyl)ethoxy)methyl)-1H-benzo(d)imidazole-6-carboxylic acid (650.0 mg, crude) as a brown solid. MS (ESI) calculated for ($C_{21}H_{25}FN_2O_4Si$) $(M+1)^+$, 417.2; found, 417.2.

Step-4: N-(5-(((1r,4r)-4-((tert-butyldimethylsilyl)oxy)cyclohexyl)methoxy)-1,3,4-thiadiazol-2-yl)-5-(2-fluoro-6-methoxyphenyl)-1-((2-(trimethylsilyl)ethoxy)methyl)-1H-benzo(d)imidazole-6-carboxamide

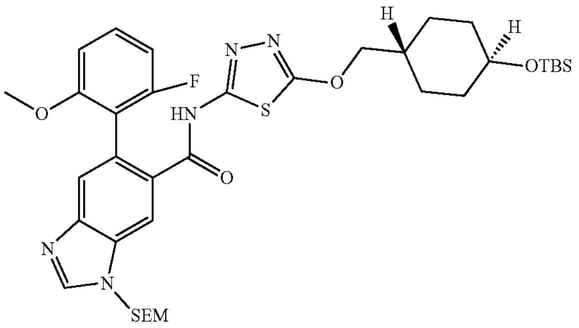 [SMILES: COc1cccc(F)c1-c1cc2ncn(COCC[Si](C)(C)C)c2cc1C(=O)Nc1nnc(OC[C@H]2CC[C@H](O[Si](C)(C)C(C)(C)C)CC2)s1]

To a stirred solution of 5-(2-fluoro-6-methoxyphenyl)-1-((2-(trimethylsilyl)ethoxy)methyl)-1H-benzo(d)imidazole-6-carboxylic acid (600.0 mg, 1.44 mmol) in Dichloromethane (DCM) (6 mL) were sequentially added N,N-dimethylformamide (105.0 mg, 1.44 mmol) and sulfurous dichloride (257.0 mg, 2.16 mmol) at 0° C. The resulting solution was stirred at 0° C. to 25° C. for 30 min. The volatiles were removed under vacuum. The residue was dissolved with DCM (2 mL). To this was added a solution of 5-(((1r,4r)-4-((tert-butyldimethylsilyl)oxy)cyclohexyl)methoxy)-1,3,4-thiadiazol-2-amine (Example 100, Step 5, 990.0 mg, 2.88 mmol) and TEA (291.0 mg, 2.88 mmol) in Dichloromethane (DCM) (3 mL). The resulting solution was stirred at 25° C. for 16 hr. The reaction mixture was quenched by the addition of water. The organic solvent was removed under vacuum. The resulting residue was dissolved in DMF (3 mL) which was applied to a 80 g C18 column and purified by Combi Flash (Biotage Isolera Prime), eluted with 5~80% acetonitrile in water within 40 min to afford N-(5-(((1r,4r)-4-((tert-butyldimethylsilyl)oxy)cyclohexyl)methoxy)-1,3,4-thiadiazol-2-yl)-5-(2-fluoro-6-methoxyphenyl)-1-((2-(trimethylsilyl)ethoxy)methyl)-1H-benzo(d)imidazole-6-carboxamide (430.0 mg, 36%) as a yellow oil. MS (ESI) calculated for ($C_{36}H_{52}FN_5O_5SSi_2$) $(M+1)^+$, 742.3; found, 742.3.

Step-5: 5-(2-fluoro-6-methoxyphenyl)-N-(5-(((1r,4r)-4-hydroxycyclohexyl)methoxy)-1,3,4-thiadiazol-2-yl)-1H-benzo(d)imidazole-6-carboxamide

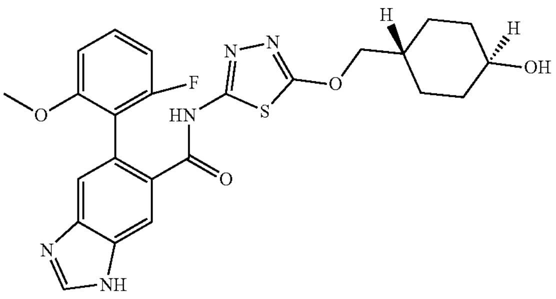 [SMILES: COc1cccc(F)c1-c1cc2nc[nH]c2cc1C(=O)Nc1nnc(OC[C@H]2CC[C@H](O)CC2)s1]

To a stirred solution of N-(5-(((1r,4r)-4-((tert-butyldimethylsilyl)oxy)cyclohexyl)methoxy)-1,3,4-thiadiazol-2-yl)-5-(2-fluoro-6-methoxyphenyl)-1-((2-(trimethylsilyl)ethoxy)methyl)-1H-benzo(d)imidazole-6-carboxamide (190.0 mg, 0.26 mmol) in dry Dichloromethane (DCM) (1 mL) was added TFA (0.2 mL) at 0° C. The resulting solution was stirred at 25° C. for 1 hr. The volatiles were removed under vacuum. The residue was diluted with water (0.5 mL). The aqueous layer was basified with NaOH (1N) to pH ~12. The resulting mixture was stirred at 25° C. for 5 min. The mixture was then dissolved in DMF (2 mL) which was applied to a 40 g C18 column and purified by Combi Flash (Biotage Isolera Prime), eluted with 5~60% acetonitrile in water within 30 min to afford 5-(2-fluoro-6-methoxyphenyl)-N-(5-(((1r,4r)-4-hydroxycyclohexyl)methoxy)-1,3,4-thiadiazol-2-yl)-1H-benzo(d)imidazole-6-carboxamide (18.0 mg, 14%) as a white solid. MS (ESI) calculated for ($C_{24}H_{24}FN_5O_4S$) $(M+1)^+$, 498.2; found, 498.2. $^1H$ NMR (400 MHz, DMSO-$d_6$+$D_2O$) δ 8.38 (s, 1H), 8.02 (s, 1H), 7.53 (s, 1H), 7.37-7.26 (m, 1H), 6.90-6.79 (m, 2H), 4.24-4.12 (m, 2H), 3.54 (s, 3H), 3.41-3.28 (m, 1H), 1.88-1.79 (m, 2H), 1.73-1.56 (m, 3H), 1.22-0.96 (m, 4H).

Example 200

5-(2-fluoro-6-methoxyphenyl)-N-(5-(((1r,4r)-4-hydroxycyclohexyl)methoxy)-1,3,4-thiadiazol-2-yl)-1-methyl-1H-benzo(d)imidazole-6-carboxamide

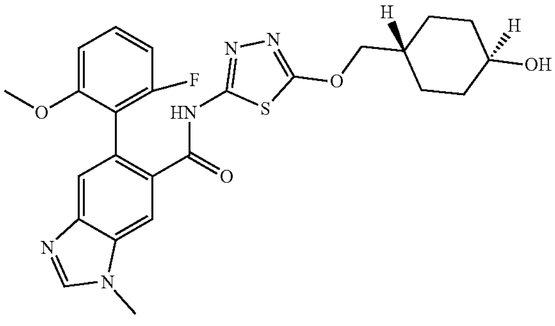 [SMILES: COc1cccc(F)c1-c1cc2ncn(C)c2cc1C(=O)Nc1nnc(OC[C@H]2CC[C@H](O)CC2)s1]

Step-1: methyl 2-bromo-5-(methylamino)-4-nitrobenzoate

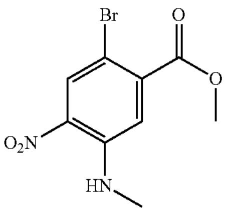 [SMILES: CNc1cc(C(=O)OC)c(Br)cc1[N+](=O)[O-]]

To a solution of methyl 2-bromo-5-fluoro-4-nitrobenzoate (1.0 g, 1.67 mmol) in THF (10 mL) was added $CH_3NH_2$ (2.5 mL, 2 N in THF, 5.00 mmol) at 0° C. The resulting solution was stirred at 0° C. for 1 hr. The resulting mixture was concentrated to afford methyl 2-bromo-5-(methylamino)-4-nitrobenzoate (990.0 mg, crude) as a yellow solid. MS (ESI) calc'd for ($C_9H_9BrN_2O_4$) $(M+1)^+$, 289.0; found 288.9.

Step-2: methyl 4-amino-2-bromo-5-(methylamino)benzoate

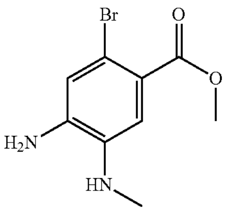

To a solution of methyl 2-bromo-5-(methylamino)-4-nitrobenzoate (990.0 mg, 3.43 mmol) in EtOH (10 mL) were added water (10 mL), Fe powder (956.0 mg, 17.13 mmol) and $NH_4C_1$ (916.0 mg, 17.13 mmol) at 25° C. The resulting mixture was stirred at 80° C. for 2 hr. The suspension was filtered. The filtrate was collected and concentrated under vacuum to afford methyl 4-amino-2-bromo-5-(methylamino)benzoate (870.0 mg, crude) as a yellow solid. MS (ESI) calc'd for ($C_9H_{11}BrN_2O_2$) $(M+1)^+$, 259.0; found, 259.1.

Step-3: methyl 5-bromo-1-methyl-1H-benzo(d)imidazole-6-carboxylate

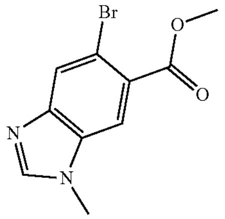

A solution of methyl 4-amino-2-bromo-5-(methylamino) benzoate (870.0 mg, 3.35 mmol) in HCOOH (2 mL) was stirred at 100° C. for 2 hr. The organic solvent was removed under vacuum. The residue was diluted with water. The aqueous layer was basified with Sodium carbonate solution to pH ~7 and extracted with ethyl acetate. The combined organic layers were washed with brine, dried over anhydrous sodium sulfate, filtered, and concentrated under vacuum to afford methyl 5-bromo-1-methyl-1H-benzo(d)imidazole-6-carboxylate (600.0 mg, crude) as a yellow solid. MS (ESI) calc'd for ($C_{10}H_9BrN_2O_2$) $(M+1)^+$, 269.0, found 269.1.

Step-4: methyl 5-(2-fluoro-6-methoxyphenyl)-1-methyl-1H-benzo(d)imidazole-6-carboxylate

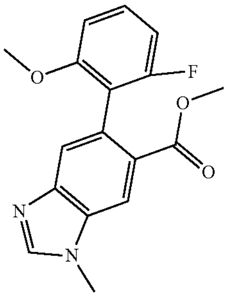

To a solution of methyl 5-bromo-1-methyl-1H-benzo(d)imidazole-6-carboxylate (300.0 mg, 1.12 mmol) and 2-fluoro-6-methoxyphenylboronic acid (227.0 mg, 1.34 mmol) in 1,4-dioxane (3 mL) were added water (1 mL), $K_2CO_3$ (462.0 mg, 3.36 mmol) and 1,1'-Bis(di-tert-butylphosphino)ferrocene (53.0 mg, 0.11 mmol). The resulting mixture was stirred at 80° C. for 2 hr. The suspension was filtered. The filtrate was collected, diluted with water and extracted with ethyl acetate. The combined organic layers were washed with brine, dried over anhydrous sodium sulfate, filtered, and concentrated under vacuum. The resulting residue was dissolved in DCM (3 mL) and purified by Combi Flash (Biotage Isolera Prime) which applied to a 40 g silica gel column that was eluted with 0~100% ethyl acetate in petroleum ether within 30 min to afford methyl 5-(2-fluoro-6-methoxyphenyl)-1-methyl-1H-benzo(d)imidazole-6-carboxylate (200.0 mg, 57%) as a yellow solid. MS (ESI) calc'd for ($C_{17}H_{15}FN_2O_3$) $(M+1)^+$, 315.1, found 315.2.

Step-5: 5-(2-fluoro-6-methoxyphenyl)-1-methyl-1H-benzo(d)imidazole-6-carboxylic acid

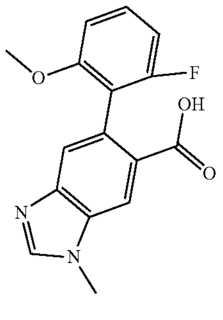 [SMILES: COc1cccc(F)c1-c1cc2ncn(C)c2cc1C(=O)O]

To a solution of methyl 5-(2-fluoro-6-methoxyphenyl)-1-methyl-1H-benzo(d)imidazole-6-carboxylate (200.0 mg, 0.64 mmol) in methanol (1.5 mL) were added water (0.5 mL) and lithium hydroxide (91.0 mg, 3.82 mmol) at 25° C. The resulting mixture was stirred at 50° C. for 2 hr. The organic solvent was removed under vacuum. The residue was diluted with water. The aqueous layer was acidified with citric acid to pH 5-6 and extracted with ethyl acetate. The combined organic layers were washed with brine, dried over anhydrous sodium sulfate, filtered, and concentrated under vacuum to afford 5-(2-fluoro-6-methoxyphenyl)-1-methyl-1H-benzo(d)imidazole-6-carboxylic acid (177.0 mg, crude) as a yellow solid. MS (ESI) calc'd for ($C_{16}H_{13}FN_2O_3$) $(M+1)^+$, 301.1, found 301.1.

Step-6: N-(5-(((1r,4r)-4-((tert-butyldimethylsilyl)oxy)cyclohexyl)methoxy)-1,3,4-thiadiazol-2-yl)-5-(2-fluoro-6-methoxyphenyl)-1-methyl-1H-benzo(d)imidazole-6-carboxamide

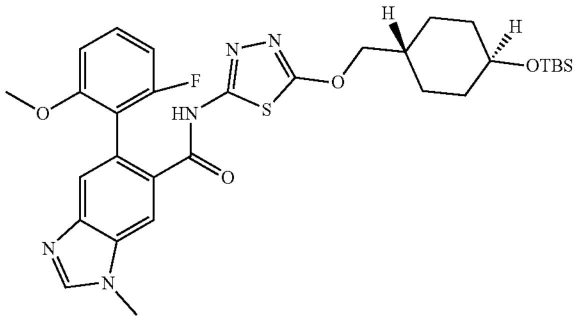 [SMILES: COc1cccc(F)c1-c1cc2ncn(C)c2cc1C(=O)Nc1nnc(OC[C@H]2CC[C@H](O[Si](C)(C)C(C)(C)C)CC2)s1]

To a stirred solution of 5-(2-fluoro-6-methoxyphenyl)-1-methyl-1H-benzo(d)imidazole-6-carboxylic acid (170.0 mg, 0.57 mmol) in DCM (5 mL) were sequentially added N,N-dimethylformamide (0.05 mL) and thionyl chloride (0.07 mL) at 25° C. The resulting solution was stirred at 25° C. for 30 min. The solvents were removed under vacuum. The residue was diluted with DCM (1 mL). To the above solution was added a solution of and 5-(((1r,4r)-4-((tert-butyldimethylsilyl)oxy)cyclohexyl)methoxy)-1,3,4-thiadiazol-2-amine (Example 100, Step 5, 389.3 mg, 1.13 mmol) in dichloromethane (5 mL) and TEA (114.5 mg, 1.13 mmol). The resulting solution was stirred at 25° C. for 16 hr. The mixture was concentrated under vacuum. The resulting residue was dissolved in DMF (1 mL) which was applied to a 20 g C18 column and purified by Combi Flash (Biotage Isolera Prime), eluted with 5~60% acetonitrile in water within 30 min to afford N-(5-(((1r,4r)-4-((tert-butyldimethylsilyl)oxy)cyclohexyl)methoxy)-1,3,4-thiadiazol-2-yl)-5-(2-fluoro-6-methoxyphenyl)-1-methyl-1H-benzo(d)imidazole-6-carboxamide (180.0 mg, 51%) as a white solid. MS (ESI) calc'd for ($C_{31}H_{40}FN_5O_4SSi$) $(M+1)^+$, 626.3; found 626.3.

Step-7: 5-(2-fluoro-6-methoxyphenyl)-N-(5-(((1r,4r)-4-hydroxycyclohexyl)methoxy)-1,3,4-thiadiazol-2-yl)-1-methyl-1H-benzo(d)imidazole-6-carboxamide

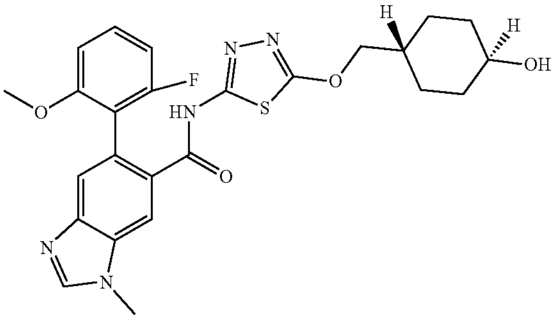 [SMILES: COc1cccc(F)c1-c1cc2ncn(C)c2cc1C(=O)Nc1nnc(OC[C@H]2CC[C@H](O)CC2)s1]

To a stirred solution of N-(5-(((1r,4r)-4-((tert-butyldimethylsilyl)oxy)cyclohexyl)methoxy)-1,3,4-thiadiazol-2-yl)-5-(2-fluoro-6-methoxyphenyl)-1-methyl-1H-benzo(d)imidazole-6-carboxamide (170.0 mg, 0.27 mmol) in dichloromethane (8 mL) was added trifluoroacetic acid (2 mL) at 0° C. The resulting solution was stirred at 0° C. for 1 hr under nitrogen. The organic solvent was removed under vacuum. The residue was purified by prep-HPLC with the following conditions: (Column: YMC-Actus Triart C18 ExRS, 30*150 mm, 5 μm; Mobile Phase A: Water (10 mmol/L $NH_4HCO_3$), Mobile Phase B: ACN; Flow rate: 60 mL/min; Gradient: 25% B to 45% B in 8 min, 45% B to 95% B in 8.2 min, 95% B to 95% B in 9.7 min, 95% B to 5% B in 11 min, 5% B; Wave Length: 220 nm; RT1 (min): 6.33; Injection Volume: 0.4 mL; Number Of Runs: 6) to afford 5-(2-fluoro-6-methoxyphenyl)-N-(5-(((1r,4r)-4-hydroxycyclohexyl)methoxy)-1,3,4-thiadiazol-2-yl)-1-methyl-1H-benzo(d)imidazole-6-carboxamide (32.0 mg, 22%) as a white solid. MS (ESI) calc'd for ($C_{25}H_{26}FN_5O_4S$) $(M+1)^+$, 512.2; found 512.2. $^1H$ NMR (400 MHz, DMSO-$d_6$) δ 12.50 (s, 1H), 8.38 (s, 1H), 8.12 (s, 1H), 7.55 (d, J=1.6 Hz, 1H), 7.31 (d, J=6.8 Hz, 1H), 6.91-6.80 (m, 2H), 4.51 (d, J=4.4 Hz, 1H), 4.26-4.16 (m, 2H), 3.94 (s, 3H), 3.57 (s, 3H), 3.39-3.33 (m, 1H), 1.90-1.81 (m, 2H), 1.80-1.65 (m, 3H), 1.22-0.99 (m, 4H).

Example 201

3-fluoro-6-(2-fluoro-6-methoxyphenyl)-N-(5-(((1r, 4r)-4-hydroxycyclohexyl)methoxy)-1,3,4-thiadiazol-2-yl)pyrazolo(1,5-a)pyridine-5-carboxamide

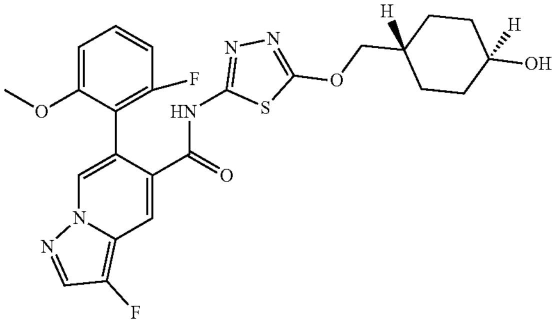 [SMILES: COc1cccc(F)c1-c1cn2ncc(F)c2cc1C(=O)Nc1nnc(OC[C@H]2CC[C@H](O)CC2)s1]

Step-1: 3-fluoro-6-(2-fluoro-6-methoxyphenyl)pyrazolo(1,5-a)pyridine-5-carboxylic acid

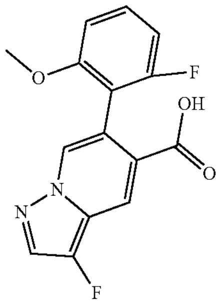 [SMILES: COc1cccc(F)c1-c1cn2ncc(F)c2cc1C(=O)O]

To a stirred solution of 6-(2-fluoro-6-methoxyphenyl) pyrazolo(1,5-a)pyridine-5-carboxylic acid (200.0 mg, 0.62 mmol) in 1,2-dichloroethane (DCE) (3 mL) and Water (1 mL) were added KF (73.1 mg, 1.25 mmol), selecflour (334.0 mg, 0.94 mmol) at 20° C. The resulting solution was stirred at 80° C. for 2 hr under nitrogen. The reaction mixture was quenched by the addition of water and extracted with ethyl acetate. The combined organic layers were washed with brine, dried over anhydrous sodium sulfate, filtered, and concentrated under vacuum. The residue was purified by prep-HPLC with the following conditions: (Column: Xselect CSH OBD Column 30*150 mm 5 um, n; Mobile Phase A: Water (0.1% FA), Mobile Phase B: ACN; Flow rate: 60 mL/min; Gradient: 35% B to 45% B in 8 min, 45% B to 95% B in 8.2 min, 95% B to 95% B in 9.7 min, 95% B to 5% B in 11 min, 5% B; Wave Length: 220 nm; RT1 (min): 7.15; Injection Volume: 1.3 mL; Number Of Runs: 3) to afford 3-fluoro-6-(2-fluoro-6-methoxyphenyl)pyrazolo(1,5-a)pyridine-5-carboxylic acid (40.0 mg, 19%) as a yellow solid. MS (ESI) calc'd for ($C_{15}H_{10}F_2N_2O_3$) $(M+1)^+$, 305.2, found 305.1.

Step-2: N-(5-(((1r,4r)-4-((tert-butyldimethylsilyl) oxy)cyclohexyl)methoxy)-1,3,4-thiadiazol-2-yl)-3-fluoro-6-(2-fluoro-6-methoxyphenyl)pyrazolo(1,5-a) pyridine-5-carboxamide

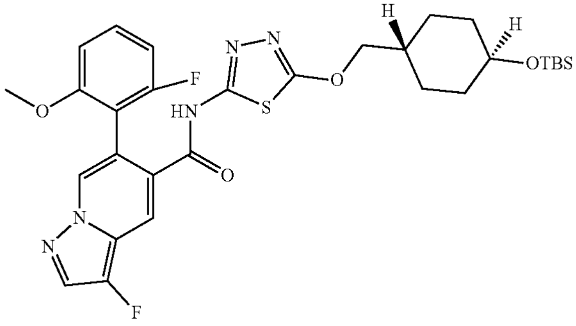 [SMILES: COc1cccc(F)c1-c1cn2ncc(F)c2cc1C(=O)Nc1nnc(OC[C@H]2CC[C@H](O[Si](C)(C)C(C)(C)C)CC2)s1]

To a solution of 3-fluoro-6-(2-fluoro-6-methoxyphenyl) pyrazolo(1,5-a)pyridine-5-carboxylic acid (40.0 mg, 0.12 mmol) in DMF (1 mL) and Acetonitrile (1 mL) were added 1-methyl-1H-imidazole (30.8 mg, 0.37 mmol), 5-(((1r,4r)-4-((tert-butyldimethylsilyl)oxy)cyclohexyl)methoxy)-1,3,4-thiadiazol-2-amine (Example 100, Step 5, 47.7 mg, 0.12 mmol) at 20° C. A solution of TCFH (52.5 mg, 0.18 mmol) in Acetonitrile (1 mL) was added thereto under nitrogen. The resulting solution was stirred at 20° C. under nitrogen for 2 hr. The reaction mixture was quenched by the addition of water and extracted with ethyl acetate. The combined organic layers were washed with brine, dried over anhydrous sodium sulfate, filtered, and concentrated under vacuum to afford N-(5-(((1r,4r)-4-((tert-butyldimethylsilyl)oxy)cyclohexyl)methoxy)-1,3,4-thiadiazol-2-yl)-3-fluoro-6-(2-fluoro-6-methoxyphenyl)pyrazolo(1,5-a)pyridine-5-carboxamide (60.0 mg, crude) as a red solid. MS (ESI) calc'd for ($C_{30}H_{37}F_2N_5O_4SSi$) $(M+1)^+$, 630.2 found 629.7.

Step-3: 3-fluoro-6-(2-fluoro-6-methoxyphenyl)-N-(5-(((1r,4r)-4-hydroxycyclohexyl) methoxy)-1,3,4-thiadiazol-2-yl)pyrazolo(1,5-a)pyridine-5-carboxamide

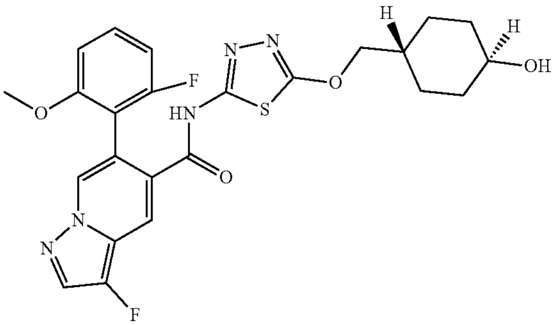 [SMILES: COc1cccc(F)c1-c1cn2ncc(F)c2cc1C(=O)Nc1nnc(OC[C@H]2CC[C@H](O)CC2)s1]

To a stirred solution of N-(5-(((1r,4r)-4-((tert-butyldimethylsilyl)oxy)cyclohexyl)methoxy)-1,3,4-thiadiazol-2-yl)-3-fluoro-6-(2-fluoro-6-methoxyphenyl)pyrazolo(1,5-a)pyridine-5-carboxamide (60.0 mg, 0.08 mmol) in DCM (1 mL) was added TFA (0.2 mL) at 0° C. The resulting solution was stirred at 0° C. for 1 hr. The organic solvent was removed under vacuum. The resulting residue was dissolved in DMF (2 mL) and purified by Combi Flash (Biotage Isolera Prime) which applied to a 20 g C18 column that was eluted with 5-19% acetonitrile in water within 40 min to afford 3-fluoro-6-(2-fluoro-6-methoxyphenyl)-N-(5-(((1r,4r)-4-hydroxycyclohexyl) methoxy)-1,3,4-thiadiazol-2-yl)pyrazolo(1,5-a) pyridine-5-carboxamide (33.9 mg, 83%) as a yellow solid. MS (ESI) calc'd for ($C_{24}H_{23}F_2N_5O_4S$) $(M+1)^+$, 516.1, found 516.3. $^1H$ NMR (400 MHz, DMSO-$d_6$) δ 8.28 (s, 1H), 8.23 (s, 1H), 8.11 (s, 1H), 7.29-7.25 (m, 1H), 6.86-6.75 (m, 2H), 4.49 (d, J=4.4 Hz, 1H), 4.04 (d, J=6.4 Hz, 2H), 3.60 (s, 3H), 3.38-3.34 (m, 1H), 1.84-1.61 (m, 5H), 1.21-0.93 (m, 4H).

Example 202

2'-chloro-N-(5-(((1S,2S)-2-fluorocyclopropyl) methoxy)-1,3,4-thiadiazol-2-yl)-5'-methoxy-6-methyl-(4,4'-bipyridine)-3-carboxamide

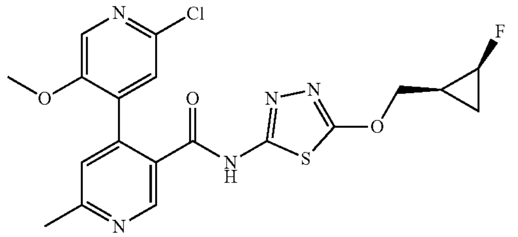 [SMILES: COc1cnc(Cl)cc1-c1cc(C)ncc1C(=O)Nc1nnc(OC[C@@H]2C[C@@H]2F)s1]

Step-1: ((1S,2S)-2-fluorocyclopropyl)methanol

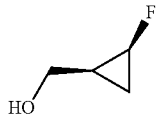

To a stirred solution of (1S,2S)-2-fluorocyclopropane-1-carboxylic acid (1.0 g, 9.61 mmol) in THF (30 mL) was added $LiAlH_4$ (365.0 mg, 9.61 mmol) in portions at 0° C. under nitrogen. The resulting solution was stirred at 20° C. for 12 hr under nitrogen. The reaction mixture was quenched by the addition of water and extracted with ethyl acetate. The combined organic layers were washed with brine, dried over anhydrous sodium sulfate, filtered, and concentrated under vacuum to afford the ((1S,2S)-2-fluorocyclopropyl)methanol (300.0 mg, crude) as a yellow oil.

Step-2: 5-(((1S,2S)-2-fluorocyclopropyl)methoxy)-1,3,4-thiadiazol-2-amine

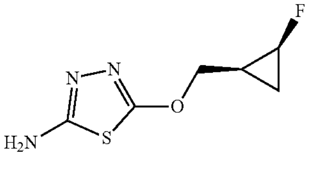 [SMILES: Nc1nnc(OC[C@@H]2C[C@@H]2F)s1]

To a degassed solution of ((1S,2S)-2-fluorocyclopropyl) methanol (250.0 mg, 2.49 mmol) in dry THF (30 mL) was added NaH (300.0 mg, 7.49 mmol, 60%) in portions at 0° C. The resulting solution was stirred at 0° C. for 1 hr under nitrogen. To the above solution was added 5-bromo-1,3,4-thiadiazol-2-amine (539.0 mg, 3.00 mmol) at 0° C. under nitrogen. The resulting mixture was then stirred at 0° C. for 2 hr. The reaction mixture was quenched by the addition of water and extracted with ethyl acetate. The combined organic layers were washed with brine, dried over anhydrous sodium sulfate, filtered, and concentrated under vacuum. The resulting residue was dissolved in DMF (2 mL) which was applied to a 40 g C18 column and purified by Combi Flash (Biotage Isolera Prime), eluted with 5~30% acetonitrile in water within 45 min to afford 5-(((1S,2S)-2-fluorocyclopropyl)methoxy)-1,3,4-thiadiazol-2-amine (50.0 mg, 9%) as a white solid. MS (ESI) calc'd for ($C_6H_8FN_3OS$) $(M+1)^+$, 190.0, found 190.0.

Step-3: 2'-chloro-N-(5-(((1S,2S)-2-fluorocyclopropyl)methoxy)-1,3,4-thiadiazol-2-yl)-5'-methoxy-6-methyl-(4,4'-bipyridine)-3-carboxamide

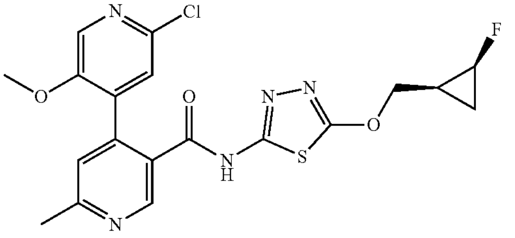 [SMILES: COc1cnc(Cl)cc1-c1cc(C)ncc1C(=O)Nc1nnc(OC[C@@H]2C[C@@H]2F)s1]

To a mixture of 5-(((1S,2S)-2-fluorocyclopropyl) methoxy)-1,3,4-thiadiazol-2-amine (41.1 mg, 0.19 mmol) in acetonitrile (2 mL) were added Intermediate E (55.0 mg, 0.17 mmol) and NMI (72.8 mg, 0.88 mmol). A solution of TCFH (54.7 mg, 0.19 mmol) in acetonitrile (1 mL) was added thereto dropwise under nitrogen. The mixture was stirred at 20° C. for 2 hr under nitrogen. The organic solvent was removed under vacuum. The resulting residue was dissolved in DMF (2 mL) which was applied to a 40 g C18 column and purified by Combi Flash (Biotage Isolera Prime), eluted with 5~50% acetonitrile in water within 40 min to afford 2'-chloro-N-(5-(((1S,2S)-2-fluorocyclopropyl) methoxy)-1,3,4-thiadiazol-2-yl)-5'-methoxy-6-methyl-(4,4'-bipyridine)-3-carboxamide (14.7 mg, 17%) as a white solid. MS (ESI) calc'd for ($C_{19}H_{17}ClFN_5O_3S$) $(M+1)^+$, 450.0, found 450.1. $^1H$ NMR (400 MHz, DMSO-$d_6$) δ 12.91 (s, 1H), 8.82 (s, 1H), 8.17 (s, 1H), 7.52 (s, 1H), 7.41 (s, 1H), 5.02-4.82 (m, 1H), 4.69-4.64 (m, 1H), 4.42-4.32 (m, 1H), 3.63 (s, 3H), 2.59 (s, 3H), 1.54-1.44 (m, 1H), 1.05-0.83 (m, 2H).

Example 203

N-(5-((1-fluorocyclopropyl)methoxy)-1,3,4-thiadiazol-2-yl)-5'-methoxy-2',6-dimethyl-(4,4'-bipyridine)-3-carboxamide

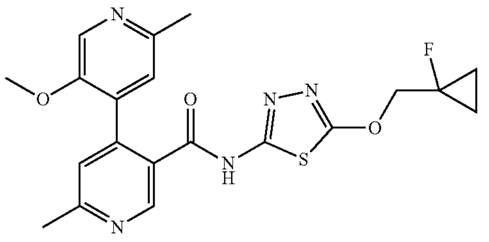 [SMILES: COc1cnc(C)cc1-c1cc(C)ncc1C(=O)Nc1nnc(OCC2(F)CC2)s1]

Step-1: 5-((1-fluorocyclopropyl)methoxy)-1,3,4-thiadiazol-2-amine

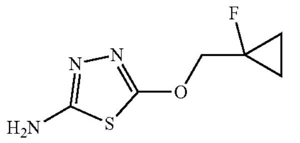 [SMILES: Nc1nnc(OCC2(F)CC2)s1]

To a solution of (1-fluorocyclopropyl)methanol (200.0 mg, 2.22 mmol) in Tetrahydrofuran (3 mL) was added NaH (89.0 mg, 2.22 mmol, 60%) in portions at 0° C. under nitrogen atmosphere and stirred at 0° C. for 1 hr. To the above solution was added 5-bromo-1,3,4-thiadiazol-2-amine (400.0 mg, 2.22 mmol) at 0° C. under nitrogen atmosphere. The resulting solution was stirred at 0° C. for 2 hr. The reaction mixture was quenched by the addition of water and extracted with ethyl acetate. The combined organic layers were washed with brine, dried over anhydrous sodium sulfate, filtered, and concentrated under vacuum. The resulting residue was dissolved in DMF (4 mL) which was applied to a 40 g C18 column and purified by Combi Flash (Biotage Isolera Prime), eluted with 5~60% acetonitrile in water within 25 min to afford 5-((1-fluorocyclopropyl) methoxy)-1,3,4-thiadiazol-2-amine (145.0 mg, 30%) as a white solid. MS (ESI) calc'd for ($C_6H_8FN_3OS$) $(M+1)^+$, 190.0; found 190.1.

Step-2: N-(5-((1-fluorocyclopropyl)methoxy)-1,3,4-thiadiazol-2-yl)-5'-methoxy-2',6-dimethyl-(4,4'-bipyridine)-3-carboxamide

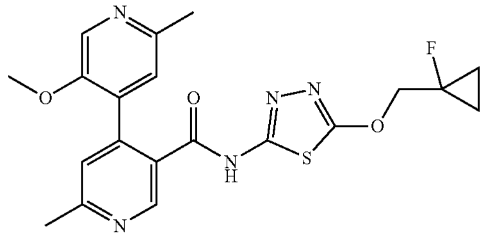 [SMILES: COc1cnc(C)cc1-c1cc(C)ncc1C(=O)Nc1nnc(OCC2(F)CC2)s1]

To a stirred solution of 5-((1-fluorocyclopropyl) methoxy)-1,3,4-thiadiazol-2-amine (120.0 mg, 0.63 mmol) in Acetonitrile (2 mL) were added Intermediate D (164.0 mg, 0.63 mmol) and 1-methylimidazole (260.0 mg, 3.17 mmol). To the above was added TCFH (178.0 mg, 0.63 mmol) in Acetonitrile (2 mL). The resulting mixture was then stirred at 23° C. for 2 hr under nitrogen atmosphere. The organic solvent was neutralized with NaOH to pH ~12. The reaction mixture (4 mL) was purified by prep-HPLC with the following conditions: (Column: XBridge Prep OBD C18 Column, 30*150 mm, 5 m; Mobile Phase A: Water (10 mmol/L $NH_4HCO_3$), Mobile Phase B: ACN; Flow rate: 60 mL/min; Gradient: 21% B to 31% B in 8 min, 31% B; Wave Length: 254 nm; RT1 (min): 8) to afford N-(5-((1-fluorocyclopropyl)methoxy)-1,3,4-thiadiazol-2-yl)-5'-methoxy-2',6-dimethyl-(4,4'-bipyridine)-3-carboxamide (91.6 mg, 33%) as a white solid. MS (ESI) calc'd for ($C_{20}H_{20}FN_5O_3S$) $(M+1)^+$, 430.1; found, 430.1. $^1H$ NMR (400 MHz, DMSO-$d_6$) δ 12.90 (s, 1H), 8.77 (s, 1H), 8.18 (s, 1H), 7.34 (s, 1H), 7.24 (s, 1H), 4.76 (s, 1H), 4.70 (s, 1H), 3.33 (s, 3H), 2.58 (s, 3H), 2.47 (s, 3H), 1.19-1.14 (m, 2H), 0.94-0.91 (m, 2H).

Example 204

2'-chloro-N-(5-((2,2-difluorocyclobutyl)methoxy)-1,3,4-thiadiazol-2-yl)-5'-methoxy-6-methyl-(4,4'-bipyridine)-3-carboxamide

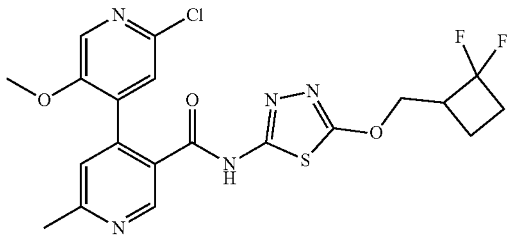 [SMILES: COc1cnc(Cl)cc1-c1cc(C)ncc1C(=O)Nc1nnc(OCC2CCC2(F)F)s1]

Step-1: 5-((2,2-difluorocyclobutyl)methoxy)-1,3,4-thiadiazol-2-amine

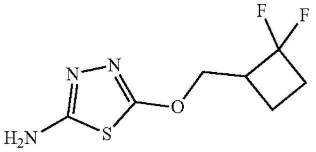 [SMILES: Nc1nnc(OCC2CCC2(F)F)s1]

To a degassed solution of (2,2-difluorocyclobutyl)methanol (200.0 mg, 1.63 mmol) in dry tetrahydrofuran (10 mL) was added NaH (131.0 mg, 3.28 mmol, 60%) in portions at 0° C. The resulting solution was stirred at 0° C. for 1 hr under nitrogen. To the above solution was added 5-bromo-1,3,4-thiadiazol-2-amine (354.0 mg, 1.96 mmol) at 0° C. under nitrogen. The resulting mixture was then stirred at 0° C. for 2 hr. The reaction mixture was quenched by the addition of water and extracted with ethyl acetate. The combined organic layers were washed with brine, dried over anhydrous sodium sulfate, filtered, and concentrated under vacuum to afford 5-((2,2-difluorocyclobutyl)methoxy)-1,3,4-thiadiazol-2-amine (180.0 mg, crude) yellow oil. MS (ESI) calc'd for ($C_7H_9F_2N_3O$ S) $(M+1)^+$, 222.0, found 222.0.

Step-2: 2'-chloro-N-(5-((2,2-difluorocyclobutyl) methoxy)-1,3,4-thiadiazol-2-yl)-5'-methoxy-6-methyl-(4,4'-bipyridine)-3-carboxamide

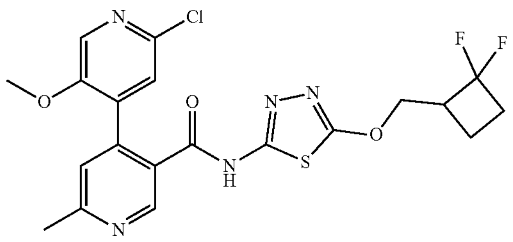 [SMILES: COc1cnc(Cl)cc1-c1cc(C)ncc1C(=O)Nc1nnc(OCC2CCC2(F)F)s1]

To a mixture of 5-((2,2-difluorocyclobutyl)methoxy)-1,3,4-thiadiazol-2-amine (175.0 mg, 0.19 mmol) in acetonitrile (2 mL) were added Intermediate E (50.0 mg, 0.17 mmol) and NMI (73.6 mg, 0.89 mmol). A solution of TCFH (55.3 mg, 0.19 mmol) in acetonitrile (1 mL) was added thereto dropwise under nitrogen. The mixture was stirred at 20° C. for 2 hr under nitrogen. The organic solvent was removed under vacuum. The residue was purified by prep-HPLC with the following conditions: (Column: XBridge Prep OBD C18 Column, 30*150 mm, 5 μm; Mobile Phase A: Water (10 mmol/L $NH_4HCO_3$), Mobile Phase B: ACN; Flow rate: 60 mL/min; Gradient: 30% B to 40% B in 8 min, 40% B to 95% B in 8.2 min, 95% B to 95% B in 9.5 min, 95% B to 5% B in 11 min, 5% B; Wave Length: 254 nm; RT1 (min): 6.73; Injection Volume: 1 mL; Number Of Runs: 2) to afford 2'-chloro-N-(5-((2,2-difluorocyclobutyl)methoxy)-1,3,4-thiadiazol-2-yl)-5'-methoxy-6-methyl-(4,4'-bipyridine)-3-carboxamide (5.0 mg, 5%) as a white solid. MS (ESI) calc'd for ($C_{20}H_{18}ClF_2N_5O_3S$) $(M+1)^+$, 482.1, found 482.0. $^1H$ NMR (400 MHz, Methanol-$d_4$) δ 8.81 (s, 1H), 8.09 (s, 1H), 7.49 (s, 1H), 7.42 (s, 1H), 4.66-4.51 (m, 2H), 3.73 (s, 3H), 2.68 (s, 3H), 2.62-2.50 (m, 2H), 2.07-1.98 (m, 1H), 1.76-1.58 (m, 1H).

Example 205

2'-chloro-N-(5-((1-cyanocyclopropyl)methoxy)-1,3,4-thiadiazol-2-yl)-5'-methoxy-6-methyl-(4,4'-bipyridine)-3-carboxamide

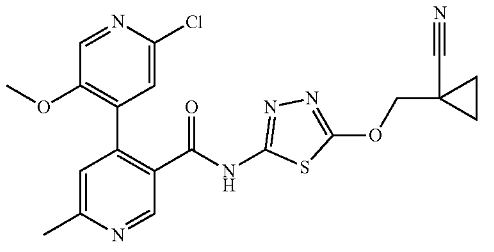 [SMILES: COc1cnc(Cl)cc1-c1cc(C)ncc1C(=O)Nc1nnc(OCC2(C#N)CC2)s1]

Step-1: 1-(((5-amino-1,3,4-thiadiazol-2-yl)oxy)methyl)cyclopropane-1-carbonitrile

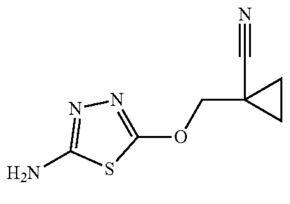 [SMILES: N#CC1(COc2nnc(N)s2)CC1]

To a degassed solution of 1-(hydroxymethyl)cyclopropane-1-carbonitrile (300.0 mg, 3.09 mmol) in dry Tetrahydrofuran (THF) (5 mL) was added NaH (185.0 mg, 4.63 mmol, 60%) in portions at 0° C. and stirred at 0° C. for 1 h under nitrogen atmosphere. Then 5-bromo-1,3,4-thiadiazol-2-amine (667.0 mg, 3.71 mmol) was added to the above mixture at 0° C. The resulting solution was stirred at 0° C. for 2 hr. The reaction mixture was quenched by the addition of water and extracted with ethyl acetate. The combined organic layers were washed with brine, dried over anhydrous sodium sulfate, filtered, and concentrated under vacuum. The resulting residue was dissolved in water (4 mL) which was applied to a 40 C18 column and purified by Combi Flash (Biotage Isolera Prime), eluted with 5~30 cetonitrile in water within 40 min to afford 1-(((5-amino-1,3,4-thiadiazol-2-yl)oxy)methyl)cyclopropane-1-carbonitrile (150.0 mg, 24%) as a yellow solid. MS (ESI) calc'd for ($C_7H_8N_4OS$) $(M+1)^+$, 197.0; found 197.1.

Step-2: 2'-chloro-N-(5-((1-cyanocyclopropyl)methoxy)-1,3,4-thiadiazol-2-yl)-5'-methoxy-6-methyl-(4,4'-bipyridine)-3-carboxamide

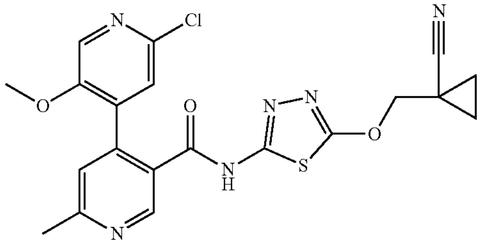 [SMILES: COc1cnc(Cl)cc1-c1cc(C)ncc1C(=O)Nc1nnc(OCC2(C#N)CC2)s1]

To a solution of 1-(((5-amino-1,3,4-thiadiazol-2-yl)oxy)methyl)cyclopropane-1-carbonitrile (130.0 mg, 0.66 mmol) in dry Acetonitrile (2 mL) was added Intermediate E (203.0 mg, 0.73 mmol) and 1-methyl-1H-imidazole (272.0 mg, 3.31 mmol) at 25° C. Then a solution of TCFH (185.0 mg, 0.66 mmol) in acetonitrile was added to the above mixture at 25° C. The resulting mixture was stirred at 25° C. for 1 hr before diluted with DMF (1 mL). The resulting solution was applied to a 40 g C18 column and purified by Combi Flash (Biotage Isolera Prime), eluted with 5~55% acetonitrile in water within 40 min to afford 2'-chloro-N-(5-((1-cyanocyclopropyl)methoxy)-1,3,4-thiadiazol-2-yl)-5'-methoxy-6-methyl-(4,4'-bipyridine)-3-carboxamide (150.5 mg, 49%) as a white solid. MS (ESI) calc'd for ($C_{20}H_{17}ClN_6O_3S$) $(M+1)^+$, 457.1; found 457.1. $^1H$ NMR (400 MHz, DMSO-$d_6$) δ 12.93 (s, 1H), 8.81 (s, 1H), 8.17 (s, 1H), 7.55 (s, 1H), 7.44 (s, 1H), 4.50 (s, 2H), 3.64 (s, 3H), 2.60 (s, 3H), 1.46-1.36 (m, 2H), 1.32-1.23 (m, 2H).

Example 206

2'-chloro-N-(5-((2,2-difluorocyclopropyl)methoxy)-1,3,4-thiadiazol-2-yl)-5'-methoxy-6-methyl-(4,4'-bipyridine)-3-carboxamide

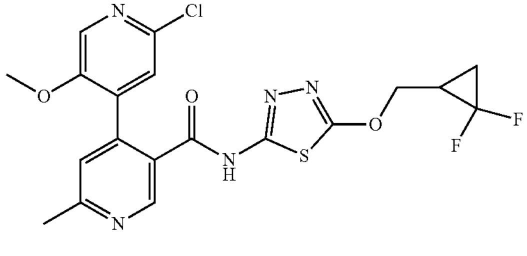 [SMILES: COc1cnc(Cl)cc1-c1cc(C)ncc1C(=O)Nc1nnc(OCC2CC2(F)F)s1]

Step-1: 5-((2,2-difluorocyclopropyl)methoxy)-1,3,4-thiadiazol-2-amine

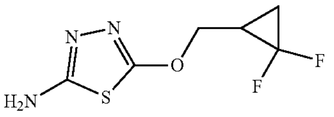

To a solution of (2,2-difluorocyclopropyl)methanol (500.0 mg, 4.63 mmol) in THF (1 mL) was added NaH (278.0 mg, 6.94 mmol, 60%) in portions at 0° C. and stirred at 0° C. for 30 min under nitrogen atmosphere. Then 5-bromo-1,3,4-thiadiazol-2-amine (999.0 mg, 5.55 mmol) was added to the above mixture at 0° C. The resulting solution was stirred at 0° C. for 1 hr. The reaction mixture was quenched by the addition of water and extracted with ethyl acetate. The combined organic layers were washed with brine, dried over anhydrous sodium sulfate, filtered, and concentrated under vacuum. The resulting residue was dissolved in DCM (2 mL) and purified by Combi Flash (Biotage Isolera Prime) which applied to a 40 g silica gel column that was eluted with 0~90% ethyl acetate in petroleum ether within 35 min to afford 5-((2,2-difluorocyclopropyl)methoxy)-1,3,4-thiadiazol-2-amine (90.0 mg, 9%) as a yellow solid. MS (ESI) calc'd for ($C_6H_7F_2N_3OS$) $(M+1)^+$, 208.0; found, 208.0.

Step-2: 2'-chloro-N-(5-((2,2-difluorocyclopropyl)methoxy)-1,3,4-thiadiazol-2-yl)-5'-methoxy-6-methyl-(4,4'-bipyridine)-3-carboxamide

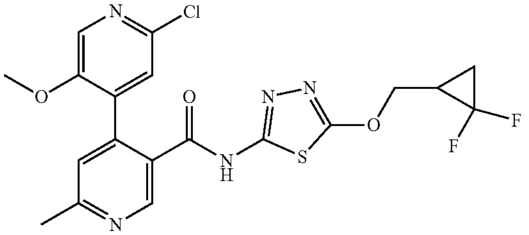 [SMILES: COc1cnc(Cl)cc1-c1cc(C)ncc1C(=O)Nc1nnc(OCC2CC2(F)F)s1]

To a solution of Intermediate E (112.0 mg, 0.40 mmol) in Acetonitrile (2 mL) were added 5-((2,2-difluorocyclopropyl)methoxy)-1,3,4-thiadiazol-2-amine (83.0 mg, 0.40 mmol) and 1-methyl-1H-imidazole (164.0 mg, 2.00 mmol) at 20° C. under nitrogen. To the above solution was added TCFH (113.0 mg, 0.40 mmol) in Acetonitrile (2 mL) at 20° C. under nitrogen. The resulting mixture was then stirred at 20° C. for 1 hr. The resulting residue was dissolved in DMF (1 mL) which was applied to a 20 g C18 column and purified by Combi Flash (Biotage Isolera Prime), eluted with 5~55% acetonitrile in water within 30 min to afford 2'-chloro-N-(5-((2,2-difluorocyclopropyl)methoxy)-1,3,4-thiadiazol-2-yl)-5'-methoxy-6-methyl-(4,4'-bipyridine)-3-carboxamide (99.9 mg, 53%) as a white solid. MS (ESI) calc'd for ($C_{19}H_{16}ClF_2N_5O_3S$) $(M+1)^+$, 468.1; found 468.1. $^1H$ NMR (400 MHz, DMSO-$d_6$) δ 12.91 (s, 1H), 8.81 (s, 1H), 8.17 (s, 1H), 7.54 (s, 1H), 7.44 (s, 1H), 4.60-4.57 (m, 1H), 4.41-4.39 (m, 1H), 3.64 (s, 3H), 2.60 (s, 3H), 2.55 (s, 1H), 1.77-1.75 (m, 1H), 1.60-1.58 (m, 1H).

Example 207

2'-chloro-N-(5-((((1R,2S)-2-fluorocyclopropyl)methoxy)-1,3,4-thiadiazol-2-yl)-5'-methoxy-6-methyl-(4,4'-bipyridine)-3-carboxamide

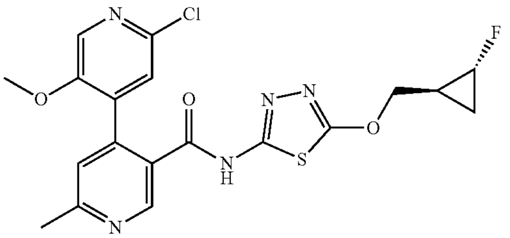 [SMILES: COc1cnc(Cl)cc1-c1cc(C)ncc1C(=O)Nc1nnc(OC[C@@H]2C[C@H]2F)s1]

Step-1: 5-(((1R,2S)-2-fluorocyclopropyl)methoxy)-1,3,4-thiadiazol-2-amine

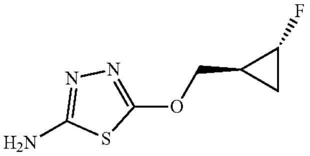

To a degassed solution of ((1R,2S)-2-fluorocyclopropyl)methanol (150.0 mg, 1.66 mmol) in dry THF (5 mL) was added NaH (133.0 mg, 3.3 mmol, 60%) in portions at 0° C. The resulting solution was stirred at 0° C. for 1 hr under nitrogen. To the above solution was added 5-bromo-1,3,4-thiadiazol-2-amine (300.0 mg, 1.66 mmol) at 0° C. under nitrogen. The resulting mixture was then stirred at 0° C. for 1 hr. The reaction was quenched with water. The aqueous layer was basified with $NaHCO_3$ to pH ~8 and extracted with ethyl acetate. The combined organic layers were washed with brine, dried over anhydrous sodium sulfate, filtered, and concentrated under vacuum to afford 5-(((1R,2S)-2-fluorocyclopropyl)methoxy)-1,3,4-thiadiazol-2-amine (120.0 mg, crude) yellow solid. MS (ESI) calc'd for ($C_6H_8FN_3OS$) $(M+1)^+$, 190.0, found 190.1.

Step-2: 2'-chloro-N-(5-(((1R,2S)-2-fluorocyclopropyl)methoxy)-1,3,4-thiadiazol-2-yl)-5'-methoxy-6-methyl-(4,4'-bipyridine)-3-carboxamide

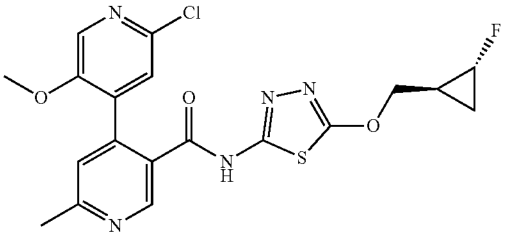 [SMILES: COc1cnc(Cl)cc1-c1cc(C)ncc1C(=O)Nc1nnc(OC[C@@H]2C[C@H]2F)s1]

To a solution of Intermediate E (15.0 mg, 0.051 mmol) in acetonitrile (1 mL) were added 1-methyl-1H-imidazole (20.9 mg, 0.25 mmol) and rac-5-(((1R,2S)-2-fluorocyclopropyl)methoxy)-1,3,4-thiadiazol-2-amine (120.0 mg, 0.31 mmol) at 20° C. A solution of TCFH (21.4 mg, 0.077 mmol) in acetonitrile (1 mL) was added thereto dropwise under nitrogen. The resulting solution was stirred at 20° C. under nitrogen for 2 hr. The solvents were removed under vacuum and purified directly. The resulting residue was dissolved in DMF (1 mL) which was applied to a 20 g C18 column and purified by Combi Flash (Biotage Isolera Prime), eluted with 5-42% acetonitrile in water within 40 min to afford 2'-chloro-N-(5-(((1R,2S)-2-fluorocyclopropyl)methoxy)-1,3,4-thiadiazol-2-yl)-5'-methoxy-6-methyl-(4,4'-bipyridine)-3-carboxamide (6.8 mg, 29%) as a white solid. MS (ESI) calc'd for ($C_{19}H_{17}ClFN_5O_3S$) $(M+1)^+$, 449.8, found 450.1 $^1H$ NMR (400 MHz, DMSO-$d_6$) δ 12.83 (s, 1H), 8.83 (s, 1H), 8.16 (s, 1H), 7.52 (s, 1H), 7.42 (s, 1H), 4.92-4.73 (m, 1H), 4.45-4.16 (m, 2H), 3.63 (s, 3H), 2.58 (s, 3H), 1.86-1.76 (m, 1H), 1.23-1.13 (m, 1H), 0.85-0.76 (m, 1H).

Example 208, 209, 210 and 211

2'-Chloro-N-(5-(((1S,3S)-3-hydroxycyclopentyl)methoxy)-1,3,4-thiadiazol-2-yl)-5'-methoxy-6-methyl-(4,4'-bipyridine)-3-carboxamide, 2'-chloro-N-(5-(((1R,3R)-3-hydroxycyclopentyl)methoxy)-1,3,4-thiadiazol-2-yl)-5'-methoxy-6-methyl-(4,4'-bipyridine)-3-carboxamide, 2'-chloro-N-(5-(((1S,3R)-3-hydroxycyclopentyl)methoxy)-1,3,4-thiadiazol-2-yl)-5'-methoxy-6-methyl-(4,4'-bipyridine)-3-carboxamide and 2'-chloro-N-(5-(((1R,3S)-3-hydroxycyclopentyl)methoxy)-1,3,4-thiadiazol-2-yl)-5'-methoxy-6-methyl-(4,4'-bipyridine)-3-carboxamide

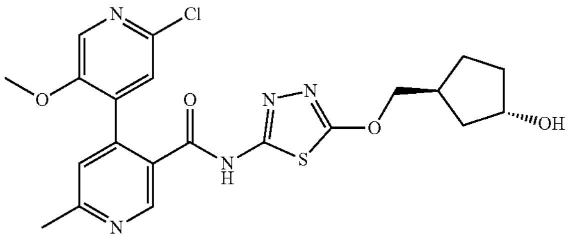

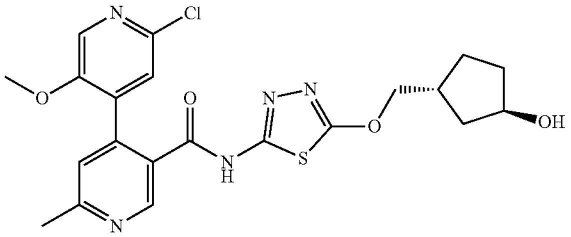

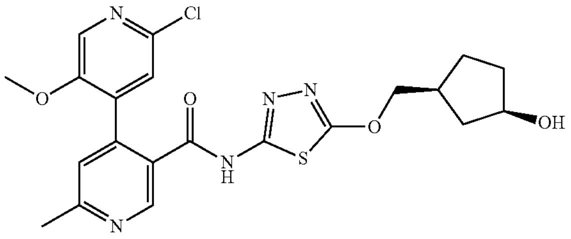

-continued

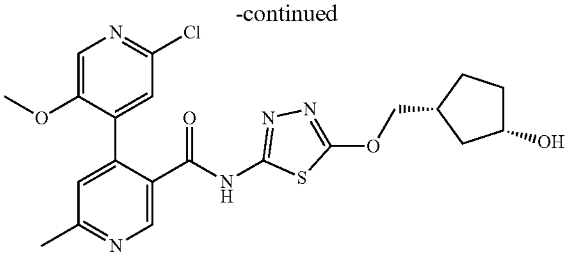

Step-1: methyl 3-((tert-butyldimethylsilyl)oxy)cyclopentane-1-carboxylate

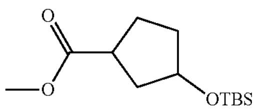 [SMILES: COC(=O)C1CCC(O[Si](C)(C)C(C)(C)C)C1]

To a stirred solution of methyl 3-hydroxycyclopentane-1-carboxylate (500.0 mg, 3.47 mmol) in N,N-Dimethylformamide (2 mL) were sequentially added imidazole (590.0 mg, 8.67 mmol) and TBS-Cl (627.0 mg, 4.16 mmol) at 23° C. The resulting solution was stirred at 23° C. for 16 h under nitrogen. The reaction mixture was quenched by the addition of water and extracted with ethyl acetate. The combined organic layer was washed with brine, dried over anhydrous sodium sulfate, filtered, and concentrated under vacuum. The resulting residue was dissolved in dichloromethane (3 mL) and purified by Combi Flash (Biotage Isolera Prime) which applied to a 40 g silica gel column that was eluted with 0~15% ethyl acetate in petroleum ether within 30 min to afford methyl 3-((tert-butyldimethylsilyl)oxy)cyclopentane-1-carboxylate (800.0 mg, 80%) as a yellow oil. MS (ESI) calculated for ($C_{13}H_{26}O_3Si$) $(M+1)^+$, 259.2.

Step-2: (3-((tert-butyldimethylsilyl)oxy)cyclopentyl)methanol

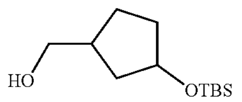 [SMILES: CC(C)(C)[Si](C)(C)OC1CCC(CO)C1]

To a stirred solution of methyl 3-((tert-butyldimethylsilyl)oxy)cyclopentane-1-carboxylate (700.0 mg, 2.71 mmol) in tetrahydrofuran (8 mL) were added methanol (174.0 mg, 5.42 mmol) and lithium borohydride (118.0 mg, 5.42 mmol) at 0° C. The resulting solution was stirred at 23° C. for 16 h. The reaction mixture was quenched by the addition of water and extracted with ethyl acetate. The combined organic layers were washed with brine, dried over anhydrous sodium sulfate, filtered, and concentrated under vacuum. The resulting residue was dissolved in dichloromethane (2 mL) and purified by Combi Flash (Biotage Isolera Prime) which applied to a 40 g silica gel column that was eluted with 0~30% ethyl acetate in petroleum ether within 30 min to afford (3-((tert-butyldimethylsilyl)oxy)cyclopentyl)methanol (360.0 mg, 52%) as a colorless oil. MS (ESI) calculated for ($C_{13}H_{26}O_2Si$) $(M+1)^+$, 231.2; found, 231.2.

Step-3: O-((3-((tert-butyldimethylsilyl)oxy)cyclopentyl)methyl)S-methyl carbonodithioate

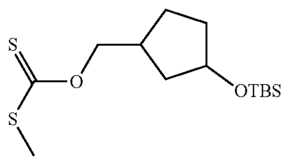 [SMILES: CSC(=S)OCC1CCC(O[Si](C)(C)C(C)(C)C)C1]

To a mixture of NaH (90.0 mg, 2.26 mmol, 60%) in tetrahydrofuran (2 mL) was added a solution of (3-((tert-butyldimethylsilyl)oxy)cyclopentyl)methanol (260.0 mg, 1.13 mmol) in tetrahydrofuran (3 mL) dropwise at 0° C. The resulting mixture was stirred at 0° C. for 30 min. To the above mixture was added $CS_2$ (129.0 mg, 1.69 mmol) dropwise at 0° C. and stirred at 0° C. for 20 min. Then MeI (240.0 mg, 1.69 mmol) was added to the above mixture dropwise at 0° C. The resulting mixture was then stirred at 0° C. for 1 h. The resulting mixture was quenched with water. The aqueous layer was extracted with ethyl acetate. The organic layers were combined, washed with brine, dried over anhydrous sodium sulfate and filtered. The filtrate was concentrated under vacuum to afford O-((3-((tert-butyldimethylsilyl)oxy)cyclopentyl)methyl)S-methyl carbonodithioate (290.0 mg, crude) as a yellow oil. MS (ESI) calculated for ($C_{14}H_{28}O_2S_2Si$) $(M+1)^+$, 321.1; found, 321.1.

Step-4: O-((3-((tert-butyldimethylsilyl)oxy)cyclopentyl)methyl) hydrazinecarbothioate

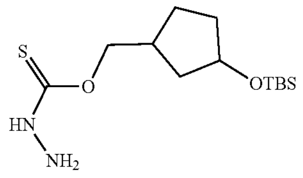

To a stirred solution of O-((3-((tert-butyldimethylsilyl)oxy)cyclopentyl)methyl)S-methyl carbonodithioate (290.0 mg, 0.91 mmol) in methanol (3 mL) was added hydrazine hydrate (56.9 mg, 0.91 mmol, 80%) at 23° C. The resulting solution was stirred at 23° C. for 1 h. The solvents were removed under vacuum to afford O-((3-((tert-butyldimethylsilyl)oxy)cyclopentyl)methyl) hydrazinecarbothioate (300.0 mg, crude) as a yellow oil. MS (ESI) calculated for ($C_{13}H_{28}N_2O_2SSi$) $(M+1)^+$, 305.2; found, 305.2.

Step-5: 5-((3-((tert-butyldimethylsilyl)oxy)cyclopentyl)methoxy)-1,3,4-thiadiazol-2-amine

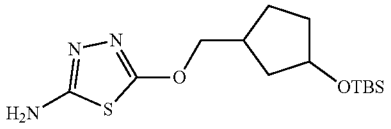

To a mixture of O-((3-((tert-butyldimethylsilyl)oxy)cyclopentyl)methyl) hydrazinecarbothioate (300.0 mg, 0.99 mmol) in methanol (3 mL) were sequentially added TEA (199.0 mg, 1.97 mmol) and BrCN (115.0 mg, 1.08 mmol). The mixture was stirred at 23° C. for 1 h. The reaction mixture was quenched by the addition of water and extracted with ethyl acetate. The combined organic layer was washed with brine, dried over anhydrous sodium sulfate, filtered, and concentrated under vacuum. The resulting residue was dissolved in acetonitrile (3 mL) which was applied to a 40 g C18 column and purified by Combi Flash (Biotage Isolera Prime), eluted with 5~79% acetonitrile in water within 30 min to afford 5-((3-((tert-butyldimethylsilyl)oxy)cyclopentyl)methoxy)-1,3,4-thiadiazol-2-amine (150.0 mg, 44%) as a white solid. MS (ESI) calculated for ($C_4H_{27}N_3O_2SSi$) $(M+1)^+$, 330.2; found, 330.2.

Step-6: N-(5-((3-((tert-butyldimethylsilyl)oxy)cyclopentyl)methoxy)-1,3,4-thiadiazol-2-yl)-2'-chloro-5'-methoxy-6-methyl-(4,4'-bipyridine)-3-carboxamide

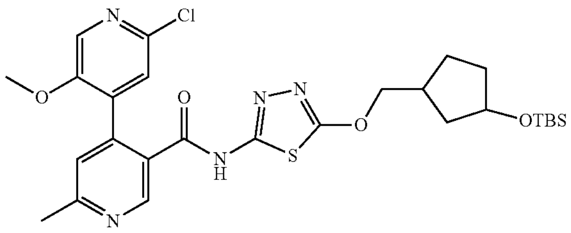 [SMILES: COc1cnc(Cl)cc1-c1cc(C)ncc1C(=O)Nc1nnc(OCC2CCC(O[Si](C)(C)C(C)(C)C)C2)s1]

To a stirred solution of 2'-chloro-5'-methoxy-6-methyl-(4,4'-bipyridine)-3-carboxylic acid (127.0 mg, 0.46 mmol) in acetonitrile (2 mL) were added 5-((3-((tert-butyldimethylsilyl)oxy)cyclopentyl)methoxy)-1,3,4-thiadiazol-2-amine (150.0 mg, 0.46 mmol) and 1-methylimidazole (0.2 mL, 2.28 mmol). Then TCFH (128.0 mg, 0.46 mmol) in acetonitrile (1 mL) was added to the above mixture at 23° C. The resulting solution was stirred at 23° C. under nitrogen for 2 h. The suspension was filtered. The filter cake was collected and dried under vacuum to afford N-(5-((3-((tert-butyldimethylsilyl)oxy)cyclopentyl)methoxy)-1,3,4-thiadiazol-2-yl)-2'-chloro-5'-methoxy-6-methyl-(4,4'-bipyridine)-3-carboxamide (185.0 mg, crude) as a white solid. MS (ESI) calculated for ($C_{27}H_{36}ClN_5O_4SSi$) $(M+1)^+$, 590.2; found, 590.2.

Step-7: 2'-chloro-N-(5-((3-hydroxycyclopentyl)methoxy)-1,3,4-thiadiazol-2-yl)-5'-methoxy-6-methyl-(4,4'-bipyridine)-3-carboxamide

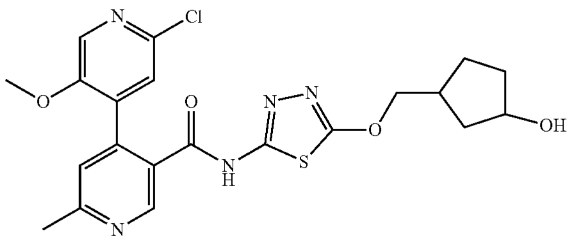 [SMILES: COc1cnc(Cl)cc1-c1cc(C)ncc1C(=O)Nc1nnc(OCC2CCC(O)C2)s1]

To a stirred solution of N-(5-((3-((tert-butyldimethylsilyl)oxy)cyclopentyl)methoxy)-1,3,4-thiadiazol-2-yl)-2'-chloro-5'-methoxy-6-methyl-(4,4'-bipyridine)-3-carboxamide (165.0 mg, 0.28 mmol) in tetrahydrofuran (2 mL) was added TBAF (219.0 mg, 0.84 mmol) at 23° C. The resulting solution was stirred at 23° C. for 16 h. The reaction mixture was quenched by the addition of water and extracted with ethyl acetate. The combined organic layer was washed with brine, dried over anhydrous sodium sulfate, filtered, and concentrated under vacuum to afford 2'-chloro-N-(5-((3-hydroxycyclopentyl)methoxy)-1,3,4-thiadiazol-2-yl)-5'-methoxy-6-methyl-(4,4'-bipyridine)-3-carboxamide (120.0 mg, crude) as a yellow solid. MS (ESI) calculated for ($C_{21}H_{22}ClN_5O_4S$) $(M+1)^+$, 476.1; found, 476.1.

Step-8: 2'-chloro-N-(5-(((1S,3S)-3-hydroxycyclopentyl)methoxy)-1,3,4-thiadiazol-2-yl)-5'-methoxy-6-methyl-(4,4'-bipyridine)-3-carboxamide, 2'-chloro-N-(5-(((1R,3R)-3-hydroxycyclopentyl)methoxy)-1,3,4-thiadiazol-2-yl)-5'-methoxy-6-methyl-(4,4'-bipyridine)-3-carboxamide, 2'-chloro-N-(5-(((1S,3R)-3-hydroxycyclopentyl)methoxy)-1,3,4-thiadiazol-2-yl)-5'-methoxy-6-methyl-(4,4'-bipyridine)-3-carboxamide and 2'-chloro-N-(5-(((1R,3S)-3-hydroxycyclopentyl)methoxy)-1,3,4-thiadiazol-2-yl)-5'-methoxy-6-methyl-(4,4'-bipyridine)-3-carboxamide

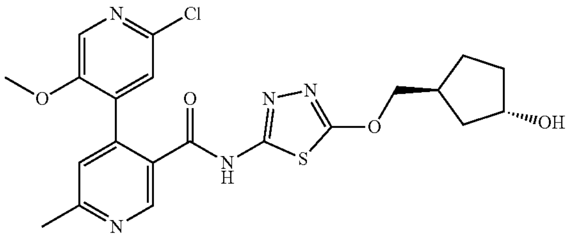

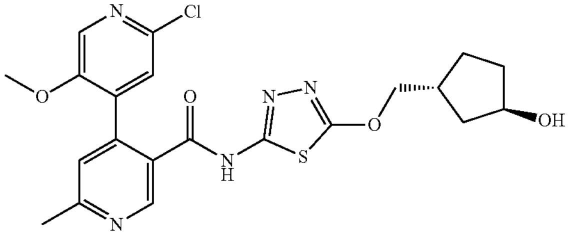

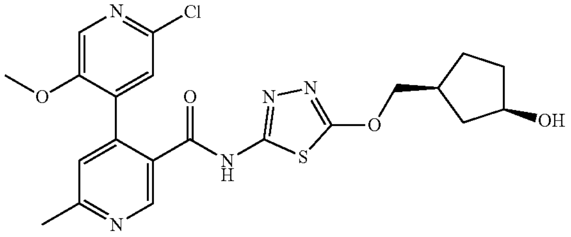

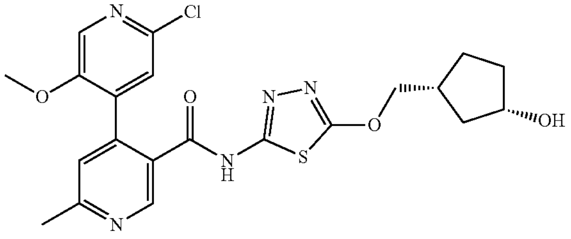

The above mixture of four diastereomers (120.0 mg) was further purified by Prep-HPLC under the following conditions (Column: XBridge Shield RP18 OBD Column, 30*150 mm, 5 μm; Mobile Phase A: Water (10 mmol/L $NH_4HCO_3$), Mobile Phase B: ACN; Flow rate: 60 mL/min; Gradient: 25% B to 25% B in 8 min, 25% B to 95% B in 8.2 min, 95% B to 95% B in 10 min, 95% B to 25% B in 11 min, 25% B; Wave Length: 254 nm; RT1 (min): 7; Injection Volume: 0.4 mL; Number Of Runs: 5) to afford mixture of enantiomers A (14.1 mg, 11%) as a white solid with the first peak on Prep-HPLC and mixture of enantiomers B (47.5 mg, 39.5%) as a white solid with the second peak on Prep-HPLC.

Enantiomeric mixture A (14.1 mg) was separated by prep-chiral HPLC with the following conditions: (Column: CHIRALPAK IF, 2*25 cm, 5 μm; Mobile Phase A: Hex (0.2% FA)-HPLC, Mobile Phase B: MeOH:DCM=1: 1; Flow rate: 20 mL/min; Gradient: 40% B to 40% B in 14 min; Wave Length: 220/254 nm; RT1 (min): 11.38; RT2 (min): 12.69; Sample Solvent: MeOH:DCM=1: 1; Injection Volume: 1 mL; Number Of Runs: 1) to afford 2'-chloro-N-(5-(((1S,3S)-3-hydroxycyclopentyl)methoxy)-1,3,4-thiadiazol-2-yl)-5'-methoxy-6-methyl-(4,4'-bipyridine)-3-carboxamide, isomer 1 (3.9 mg, 27%) as a white solid with the first peak on chiral HPLC and 2'-chloro-N-(5-(((1R,3R)-3-hydroxycyclopentyl)methoxy)-1,3,4-thiadiazol-2-yl)-5'-methoxy-6-methyl-(4,4'-bipyridine)-3-carboxamide, isomer 2 (2.8 mg, 19%) as a white solid with the second peak on chiral HPLC. Enantiomeric mixture B (47.5 mg) was separated by prep-chiral HPLC with the following conditions: (Column: CHIRALPAK IF, 2*25 cm, 5 μm; Mobile Phase A: MtBE (0.1% FA)-HPLC, Mobile Phase B: MeOH: DCM=1: 1; Flow rate: 20 mL/min; Gradient: 15% B to 15% B in 29 min; Wave Length: 220/254 nm; RT1 (min): 19.06; RT2 (min): 26.49; Sample Solvent: MeOH:DCM=1: 1; Injection Volume: 0.8 mL; Number Of Runs: 3) to afford 2'-chloro-N-(5-(((1S,3R)-3-hydroxycyclopentyl)methoxy)-1,3,4-thiadiazol-2-yl)-5'-methoxy-6-methyl-(4,4'-bipyridine)-3-carboxamide, isomer 3 (18.6 mg, 38%) as a white solid with the first peak on chiral HPLC and 2'-chloro-N-(5-(((1R,3S)-3-hydroxycyclopentyl)methoxy)-1,3,4-thiadiazol-2-yl)-5'-methoxy-6-methyl-(4,4'-bipyridine)-3-carboxamide, isomer 4 (18.4 mg, 38%) as a white solid with the second peak on chiral HPLC.

The absolute stereochemistries were not determined.

Isomer 1: 2'-Chloro-N-(5-(((1S,3S)-3-hydroxycyclopentyl)methoxy)-1,3,4-thiadiazol-2-yl)-5'-methoxy-6-methyl-(4,4'-bipyridine)-3-carboxamide: MS (ESI) calculated for ($C_{21}H_{22}ClN_5O_4S$) $(M+1)^+$, 476.1; found, 476.1. $^1H$ NMR (400 MHz, DMSO-$d_6$) δ 12.87 (s, 1H), 8.81 (s, 1H), 8.17 (s, 1H), 7.53 (s, 1H), 7.42 (s, 1H), 4.45 (d, J=3.6 Hz, 1H), 4.29 (d, J=7.2 Hz, 2H), 4.20-4.13 (m, 1H), 3.63 (s, 3H), 2.59 (s, 3H), 1.92-1.85 (m, 1H), 1.84-1.73 (m, 1H), 1.71-1.66 (m, 1H), 1.54-1.38 (m, 2H), 1.37-1.23 (m, 2H).

Isomer 2: 2'-chloro-N-(5-(((1R,3R)-3-hydroxycyclopentyl)methoxy)-1,3,4-thiadiazol-2-yl)-5'-methoxy-6-methyl-(4,4'-bipyridine)-3-carboxamide: MS (ESI) calculated for ($C_{21}H_{22}ClN_5O_4S$) $(M+1)^+$, 476.1; found, 476.1. $^1H$ NMR (400 MHz, DMSO-$d_6$) δ 12.87 (s, 1H), 8.81 (s, 1H), 8.17 (s, 1H), 7.53 (s, 1H), 7.42 (s, 1H), 4.45 (d, J=3.6 Hz, 1H), 4.29 (d, J=7.2 Hz, 2H), 4.22-4.13 (m, 1H), 3.63 (s, 3H), 2.59 (s, 3H), 1.88-1.66 (m, 3H), 1.50-1.35 (m, 2H), 1.37-1.21 (m, 2H).

Isomer 3: 2'-chloro-N-(5-(((1S,3R)-3-hydroxycyclopentyl)methoxy)-1,3,4-thiadiazol-2-yl)-5'-methoxy-6-methyl-(4,4'-bipyridine)-3-carboxamide: MS (ESI) calculated for ($C_{21}H_{22}ClN_5O_4S$) $(M+1)^+$, 476.1; found, 476.1. $^1H$ NMR (400 MHz, DMSO-$d_6$) δ 12.87 (s, 1H), 8.81 (s, 1H), 8.17 (s, 1H), 7.54 (s, 1H), 7.43 (s, 1H), 4.52 (d, J=3.6 Hz, 1H), 4.34 (d, J=7.2 Hz, 2H), 4.20-4.13 (m, 1H), 3.63 (s, 3H), 2.59 (s, 3H), 2.37-2.33 (m, 1H), 1.93-1.88 (m, 1H), 1.76-1.61 (m, 2H), 1.60-1.44 (m, 2H), 1.36-1.22 (m, 1H).

Isomer 4: 2'-chloro-N-(5-(((1R,3S)-3-hydroxycyclopentyl)methoxy)-1,3,4-thiadiazol-2-yl)-5'-methoxy-6-methyl-(4,4'-bipyridine)-3-carboxamide: MS (ESI) calculated for ($C_{21}H_{22}ClN_5O_4S$) $(M+1)^+$, 476.1; found, 476.1. $^1H$ NMR (400 MHz, DMSO-$d_6$) δ 12.88 (s, 1H), 8.81 (s, 1H), 8.17 (s, 1H), 7.53 (s, 1H), 7.42 (s, 1H), 4.52 (d, J=3.6 Hz, 1H), 4.34 (d, J=7.2 Hz, 2H), 4.20-4.13 (m, 1H), 3.63 (s, 3H), 2.59 (s, 3H), 2.39-2.29 (m, 1H), 1.96-1.92 (m, 1H), 1.77-1.60 (m, 2H), 1.59-1.44 (m, 2H), 1.32-1.23 (m, 1H).

Example 212

3'-fluoro-N-(5-(((1r,4r)-4-hydroxycyclohexyl)methoxy)-1,3,4-thiadiazol-2-yl)-5'-methoxy-2',6-dimethyl-(4,4'-bipyridine)-3-carboxamide

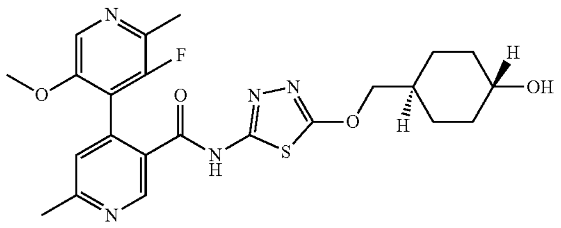 [SMILES: COc1cnc(C)c(F)c1-c1cc(C)ncc1C(=O)Nc1nnc(OC[C@H]2CC[C@H](O)CC2)s1]

Step-1: methyl 3'-fluoro-5'-methoxy-2',6-dimethyl-(4,4'-bipyridine)-3-carboxylate

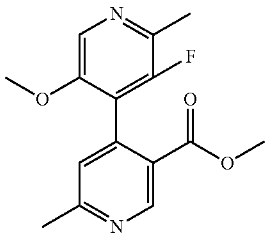

To a degassed solution of methyl 2'-chloro-3'-fluoro-5'-methoxy-6-methyl-(4,4'-bipyridine)-3-carboxylate (500.0 mg, 1.61 mmol) in DME (5 mL) were added $K_2CO_3$ (667.0 mg, 4.83 mmol), Pd(dppf)$Cl_2$ (235.0 mg, 0.32 mmol) at 25° C. under nitrogen atmosphere. Then 2,4,6-trimethyl-1,3,5,2,4,6-trioxatriborinane (222.0 mg, 1.77 mmol) was added to the above mixture at 25° C. The resulting solution was stirred at 120° C. for 1 hr under nitrogen atmosphere. The suspension was filtered. The filtrate was collected and concentrated under vacuum. The resulting residue was dissolved in DCM (4 mL) and purified by Combi Flash (Biotage Isolera Prime) which applied to a 40 g silica gel column that was eluted with 0-8% methanol in dichloromethane within 40 min to afford methyl 3'-fluoro-5'-methoxy-2',6-dimethyl-(4,4'-bipyridine)-3-carboxylate (340.0 mg, 69%) as a brown solid MS (ESI) calc'd for ($C_{15}H_{15}FN_2O_3$) $(M+1)^+$, 291.1; found, 291.1.

Step-2: 3'-fluoro-5'-methoxy-2',6-dimethyl-(4,4'-bipyridine)-3-carboxylic acid

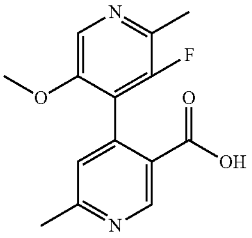 [SMILES: COc1cnc(C)c(F)c1-c1cc(C)ncc1C(=O)O]

To a stirred solution of methyl 3'-fluoro-5'-methoxy-2',6-dimethyl-(4,4'-bipyridine)-3-carboxylate (300.0 mg, 1.03 mmol) in Methanol (3 mL) were added NaOH (165.0 mg, 4.13 mmol) and Water (3 mL) at 25° C. The resulting solution was stirred at 25° C. for 2 hr. The organic solvent was removed under vacuum. The aqueous layer was acidified with Citric acid to pH ~4 and extracted with ethyl acetate. The combined organic layers were washed with brine, dried over anhydrous sodium sulfate, filtered, and concentrated under vacuum to afford 3'-fluoro-5'-methoxy-2',6-dimethyl-(4,4'-bipyridine)-3-carboxylic acid (160 mg, crude) MS (ESI) calc'd for ($C_{14}H_{13}FN_2O_3$) $(M+1)^+$, 277.1; found, 277.1.

Step-3: N-(5-(((1r,4r)-4-((tert-butyldimethylsilyl)oxy)cyclohexyl)methoxy)-1,3,4-thiadiazol-2-yl)-3'-fluoro-5'-methoxy-2',6-dimethyl-(4,4'-bipyridine)-3-carboxamide

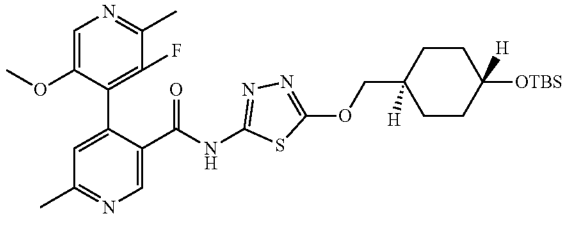 [SMILES: COc1cnc(C)c(F)c1-c1cc(C)ncc1C(=O)Nc1nnc(OC[C@H]2CC[C@H](O[Si](C)(C)C(C)(C)C)CC2)s1]

To a solution of 3'-fluoro-5'-methoxy-2',6-dimethyl-(4,4'-bipyridine)-3-carboxylic acid (160.0 mg, 0.57 mmol) in dry Acetonitrile (4 mL) were added 5-(((1r,4r)-4-((tert-butyldimethylsilyl)oxy)cyclohexyl)methoxy)-1,3,4-thiadiazol-2-amine (199.0 mg, 0.58 mmol, Example 100, Step 5), 1-methyl-1H-imidazole (238.0 mg, 2.90 mmol) at 25° C. Then TCFH (162.0 mg, 0.57 mmol) in acetonitrile (2 mL) was added to the above mixture at 25° C. The resulting solution was stirred at 25° C. for 1 hr. The resulting mixture was applied to a 40 g C18 column and purified by Combi Flash (Biotage Isolera Prime), eluted with 5~30% acetonitrile in water within 40 min to afford N-(5-(((1r,4r)-4-((tert-butyldimethylsilyl)oxy)cyclohexyl)methoxy)-1,3,4-thiadiazol-2-yl)-3'-fluoro-5'-methoxy-2',6-dimethyl-(4,4'-bipyridine)-3-carboxamide (136.0 mg, 37%) as a yellow solid. MS (ESI) calc'd for ($C_{29}H_{40}FN_5O_4SSi$) $(M+1)^+$, 602.3; found, 602.3.

Step-4: 3'-fluoro-N-(5-(((1r,4r)-4-hydroxycyclohexyl)methoxy)-1,3,4-thiadiazol-2-yl)-5'-methoxy-2',6-dimethyl-(4,4'-bipyridine)-3-carboxamide

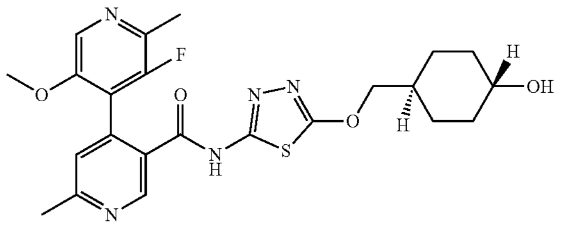 [SMILES: COc1cnc(C)c(F)c1-c1cc(C)ncc1C(=O)Nc1nnc(OC[C@H]2CC[C@H](O)CC2)s1]

To a stirred solution of N-(5-(((1r,4r)-4-((tert-butyldimethylsilyl)oxy)cyclohexyl)methoxy)-1,3,4-thiadiazol-2-yl)-3'-fluoro-5'-methoxy-2',6-dimethyl-(4,4'-bipyridine)-3-carboxamide (100.0 mg, 0.17 mmol) in THF (2 mL) was added TBAF (174.0 mg, 0.66 mmol) at 25° C. The resulting solution was stirred at 25° C. for 16 h. The reaction mixture was quenched by the addition of water and extracted with ethyl acetate. The combined organic layers were washed with brine, dried over anhydrous sodium sulfate, filtered, and concentrated under vacuum. The resulting residue was dissolved in DMF (3 mL) which was applied to a 40 g C18 column and purified by Combi Flash (Biotage Isolera Prime), eluted with 5-40% acetonitrile in water within 40 min to afford 3'-fluoro-N-(5-(((1r,4r)-4-hydroxycyclohexyl)methoxy)-1,3,4-thiadiazol-2-yl)-5'-methoxy-2',6-dimethyl-(4,4'-bipyridine)-3-carboxamide (14.0 mg, 17%) as a white solid MS (ESI) calc'd for ($C_{23}H_{26}FN_5O_4S$) $(M+1)^+$, 488.2; found, 488.2. $^1H$ NMR (400 MHz, DMSO-$d_6$) δ 12.9 (br, 1H), 8.92 (s, 1H), 8.12 (s, 1H), 7.31 (s, 1H), 4.52-4.51 (m, 1H), 4.17 (d, J=6.0 Hz, 2H), 3.66 (s, 3H), 3.38-3.28 (m, 1H), 2.56 (s, 3H), 2.40 (s, 3H), 1.88-1.80 (m, 2H), 1.79-1.71 (m, 3H), 1.16-1.06 (m, 4H).

Example 213

3'-fluoro-N-(5-(((1s,4s)-4-hydroxy-4-methylcyclohexyl)methoxy)-1,3,4-thiadiazol-2-yl)-5'-methoxy-2',6-dimethyl-(4,4'-bipyridine)-3-carboxamide

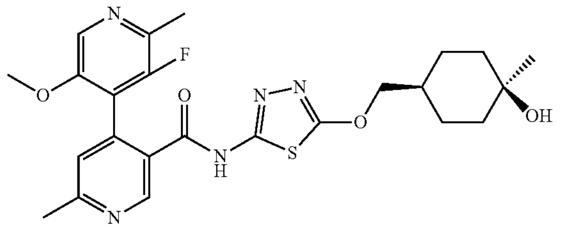

Step-1: 2-chloro-3-fluoro-5-methoxypyridine

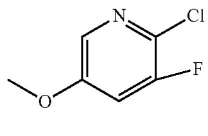

To a solution of 6-chloro-5-fluoropyridin-3-ol (10.0 g, 67.8 mmol) in acetone (100 mL) was added MeI (5.09 mL, 81 mmol) and $K_2CO_3$ (18.74 g, 136 mmol) at 0° C. under nitrogen atmosphere. The resulting solution was stirred for 12 h at room temperature under nitrogen. The reaction mixture was diluted with water and extracted with ethyl acetate (2×100 mL). The combined organic layers were washed with brine, dried over anhydrous sodium sulfate, filtered, and concentrated under vacuum to afford 2-chloro-3-fluoro-5-methoxypyridine (10.7 g, 65.5 mmol, 97% yield) as a brown oil. MS (ESI) calculated for ($C_6H_8ClFNO$) $(M+1)^+$, 162.01; found 162.0.

Step-2: 2-chloro-3-fluoro-4-iodo-5-methoxypyridine

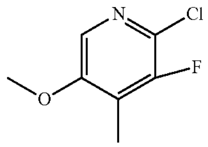

To a degassed solution of 2-chloro-3-fluoro-5-methoxypyridine (10.7 g, 66.2 mmol) in dry Tetrahydrofuran (240 mL) was added n-butyllithium (31.8 mL, 79 mmol, 2.5 M in hexane) dropwise at −78° C. and stirred at −78° C. for 30 min under nitrogen atmosphere. Then iodine (21.85 g, 86 mmol) was added to the above mixture at −78° C. The resulting solution was stirred at −78° C. for 2 h under nitrogen. The reaction mixture was quenched by the addition of saturated sodium thiosulfate aqueous solution and extracted with ethyl acetate (2×100 mL). The combined organic layers were washed with brine, dried over anhydrous sodium sulfate, filtered, and concentrated under vacuum to afford 2-chloro-3-fluoro-4-iodo-5-methoxypyridine (18 g, 62.0 mmol, 94% yield) as light yellow solid. MS (ESI) calculated for ($C_6H_4ClFINO$) $(M+1)^+$, 287.91; found, 288.0.

Step-3: methyl 2'-chloro-3'-fluoro-5'-methoxy-6-methyl-(4,4'-bipyridine)-3-carboxylate

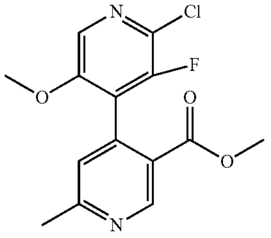

To a degassed solution of methyl 4-(5,5-dimethyl-1,3,2-dioxaborinan-2-yl)-6-methylnicotinate (17.16 g, 65.2 mmol) and 2-chloro-3-fluoro-4-iodo-5-methoxypyridine (12.5 g, 43.5 mmol) in 1,4-dioxane (250 mL) were added potassium carbonate (18.03 g, 130 mmol) and (1,1'-Bis(diphenylphosphino)ferrocene)dichloropalladium(II) (6.36 g, 8.70 mmol) at room temperature. The resulting solution was stirred at 100° C. for 16 h under nitrogen. The suspension was filtered through celite pad. The filtrate was collected and concentrated under vacuum to get crude product as a brown gum.

The crude residue was pre-absorbed on silica (using 50 mL DCM, silica (60-120 mesh), loaded onto a Biotage 350 g SNAP cartridge and eluted at 30-35% of ethyl acetate in petroleum ether for 80 mins with flow rate 25 mL/min. The two appropriate fractions were collected and concentrated under vacuum to afford methyl 2'-chloro-3'-fluoro-5'-methoxy-6-methyl-(4,4'-bipyridine)-3-carboxylate (4.83 g, 15.13 mmol, 34.8% yield) as light yellow solid. MS (ESI) calculated for ($C_{14}H_{12}ClFN_2O_3$) $(M+1)^+$, 311.11, found 311.0.

Step-4 methyl 3'-fluoro-5'-methoxy-2',6-dimethyl-(4,4'-bipyridine)-3-carboxylate

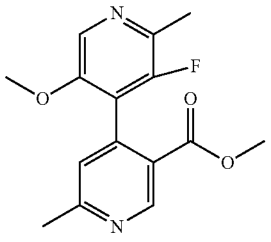

To a degassed solution of methyl 2'-chloro-3'-fluoro-5'-methoxy-6-methyl-(4,4'-bipyridine)-3-carboxylate (4 g, 12.87 mmol), and 2,4,6-trimethyl-1,3,5,2,4,6-trioxatriborinane (50% in THF) (4.85 g, 19.31 mmol) in 1,4-Dioxane (150 mL) were sequentially added water (15 mL), $Cs_2CO_3$ (8.39 g, 25.7 mmol) and $PdCl_2(dppf)$-$CH_2Cl_2$adduct (0.526 g, 0.644 mmol). The resulting solution was stirred at 100° C. for 16 h under nitrogen. After 16 h, reaction mixture was cooled to room temperature and diluted with Ethyl acetate (100 mL) and filtered through celite. The filtrate was collected and concentrated under vacuum. Then the residue was diluted with water and extracted with ethyl acetate (2×200 mL). The combine organic layer was dried over sodium sulphate, filtered and concentrated under vacuum to afford crude product as a brown gum.

The crude residue was pre-absorbed on silica (using 40 mL DCM, 20 g of silica (60-120 mesh), loaded onto a Biotage 120 g SNAP cartridge and eluted at 35-50% of ethyl acetate in petroleum ether for 60 mins with flow rate 25 mL/min. The two appropriate fractions were collected and concentrated under vacuum to afford methyl 3'-fluoro-5'-methoxy-2',6-dimethyl-(4,4'-bipyridine)-3-carboxylate (2.57 g, 8.24 mmol, 64.0% yield) as an off white solid. MS (ESI) calculated for ($C_{15}H_{15}FN_2O_5$) $(M+1)^+$, 291.12, found 291.2.

Step-5: 3'-fluoro-5'-methoxy-2',6-dimethyl-(4,4'-bipyridine)-3-carboxylic acid

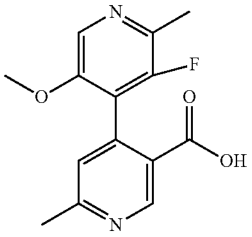 [SMILES: COc1cnc(C)c(F)c1-c1cc(C)ncc1C(=O)O]

To a stirred solution of methyl 3'-fluoro-5'-methoxy-2',6-dimethyl-(4,4'-bipyridine)-3-carboxylate (2.57 g, 8.85 mmol) in Tetrahydrofuran (THF) (25 mL) and Methanol (25 mL) was added a solution of lithium hydroxide (1.060 g, 44.3 mmol) in Water (9 mL) dropwise at 0° C. The mixture was stirred at RT for 16 h. The organic solvent was removed under vacuum. The residue was diluted with water. The aqueous layer was extracted with dichloromethane (30 mL×2). The combined organic layers were washed with brine, dried over anhydrous sodium sulfate, filtered, and concentrated under vacuum to afford 3'-fluoro-5'-methoxy-2',6-dimethyl-(4,4'-bipyridine)-3-carboxylic acid (2.15 g, 7.43 mmol, 84% yield) as an off white solid. MS (ESI) calculated for ($C_{14}H_{13}FN_2O_3$) $(M+1)^+$, 277.1, found 277.0.

Step-6: 4-(hydroxymethyl)-1-methylcyclohexan-1-ol

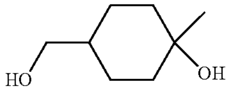

To a stirred solution of 4-(hydroxymethyl)cyclohexan-1-one (5 g, 39.0 mmol) in Tetrahydrofuran (THF) (140 mL) was added methylmagnesium chloride (26.0 mL, 78 mmol) at 0° C. The reaction mixture was warmed to rt and stirred for 2 h. After 2 h, the reaction mixture was quenched with mixture of methanol and water (110 mL 1:10) and the solvent was removed under vacuum to get off white solid material. The residue was dissolved in ethyl acetate and filtered. The filtrate was concentrated under vacuum to afford 4-(hydroxymethyl)-1-methylcyclohexan-1-ol (6 g, 17.89 mmol, 45.9% yield). GCMS m/z=126.0 (M–H2O) (43%)

Step-7: O-(((1r,4r)-4-hydroxy-4-methylcyclohexyl) methyl)S-methyl carbonodithioate and 0-(((1s,4s)-4-hydroxy-4-methylcyclohexyl)methyl)S-methyl carbonodithioate

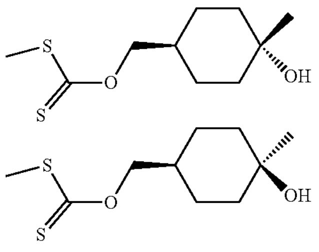

To a stirred solution of 4-(hydroxymethyl)-1-methylcyclohexan-1-ol (5 g, 34.7 mmol) in Tetrahydrofuran (THF) (150 mL) under nitrogen at 0° C. was added sodium hydride (1.664 g, 69.3 mmol) portionwise over 1 min. After addition reaction mixture was stirred at room temperature for 30 min. After 30 min to the above reaction mixture were added carbon disulfide (4.18 mL, 69.3 mmol) followed by methyl iodide (0.624 mL, 9.99 mmol) at room temperature. The reaction mixture was stirred at room temperature for additional 2 h. After 2 h the reaction was quenched with cold water and mixed with another batch of 1.2 g and combined 2 batched extracted with ethyl acetate (200 mL×3). The combine organic layer was dried over sodium sulphate, filtered and concentrated under vacuum to afford crude product as a brown gum.

The crude residue was pre-absorbed on silica (using 30 mL DCM and 5 mL MeOH, 30 g of silica (60-120 mesh), loaded onto a Biotage 120 g SNAP cartridge and eluted at 40-80% of EA/PE for 60 mins with flow rate 25 mL/min. The two appropriate fractions were collected and concentrated under vacuum to afford O-(((1r,4r)-4-hydroxy-4-methylcyclohexyl)methyl)S-methyl carbonodithioate, isomer 1 (1.2 g, 4.30 mmol, 12.40% yield) (first eluting fraction) as a yellow solid; MS (ESI) calculated for ($C_{10}H_{18}O_2S_2$) (M-$CH_3$)—, 219.05; found, 219.0 and O-(((1s,4s)-4-hydroxy-4-methylcyclohexyl)methyl)S-methyl carbonodithioate, isomer 2 (2.2 g, 6.57 mmol, 18.95% yield) (second eluting fraction) as a yellow solid; MS (ESI) calculated for ($C_{10}H_{18}O_2S_2$) (M-$CH_3$)—, 219.05; found, 219.2. The stereochemistry was not determined.

Step-8: O-(((1s,4s)-4-hydroxy-4-methylcyclohexyl) methyl) hydrazinecarbothioate

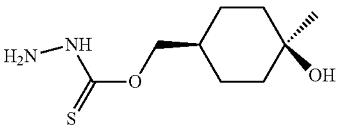

To a stirred solution of the later-eluting isomer from the previous step, O-(((1s,4s)-4-hydroxy-4-methylcyclohexyl) methyl)S-methyl carbonodithioate, isomer 2 (545 mg, 2.325 mmol) in Methanol (20 mL) was added hydrazine (0.114 mL, 2.325 mmol) at rt under nitrogen. The reaction mixture was stirred for 1 h at rt. The organic solvent was removed under vacuum. The residue was diluted with water. The aqueous layer was extracted with ethyl acetate (50 mL×3). The combined organic layers were washed with brine, dried over anhydrous sodium sulfate, filtered, and concentrated under vacuum to afford O-(((1s,4s)-4-hydroxy-4-methylcyclohexyl)methyl) hydrazinecarbothioate (485 mg, 2.088 mmol, 90% yield) as a brown solid. MS (ESI) calculated for ($C_9H_{18}N_2O_2S$) $(M+1)^+$, 219.12; found, 219.2.

Step-9: (1s,4s)-4-(((5-amino-1,3,4-thiadiazol-2-yl) oxy)methyl)-1-methylcyclohexan-1-ol

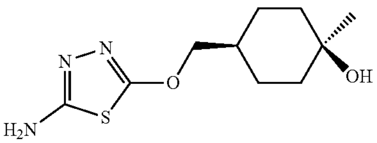 [SMILES: C[C@]1(O)CC[C@@H](COc2nnc(N)s2)CC1]

To a stirred solution of O-(((1s,4s)-4-hydroxy-4-methylcyclohexyl)methyl) hydrazinecarbothioate (485 mg, 2.222 mmol), in Ethanol (15 mL) were added TEA (0.310 mL, 2.222 mmol) followed by Cyanogen bromide (235 mg, 2.222 mmol) at room temperature. The reaction mixture was stirred at room temperature for 1 h. The organic solvent was removed under vacuum. The residue was diluted with water. The aqueous layer was extracted with ethyl acetate (100 mL×3). The combined organic layers were washed with brine, dried over anhydrous sodium sulfate, filtered, and concentrated under vacuum to get the crude product as a brown solid. The crude product was pre-absorbed on silica (using 10 mL DCM and 1 mL MeOH, 25 g of silica (60-120 mesh), loaded onto a Biotage 45 g SNAP cartridge, and eluted with 75-100% of Ethyl acetate in petroleum ether for 60 mins with flow rate 25 mL/min. The appropriate fractions were collected and concentrated under vacuum to afford (1s,4s)-4-(((5-amino-1,3,4-thiadiazol-2-yl)oxy)methyl)-1-methylcyclohexan-1-ol (330 mg, 1.329 mmol, 59.8% yield) as a yellow solid. MS (ESI) calculated for ($C_{10}H_{17}N_3O_2S$) $(M+1)^+$, 243.10; found, 244.0.

Step-10: 3'-fluoro-N-(5-(((1s,4s)-4-hydroxy-4-methylcyclohexyl)methoxy)-1,3,4-thiadiazol-2-yl)-5'-methoxy-2',6-dimethyl-(4,4'-bipyridine)-3-carboxamide

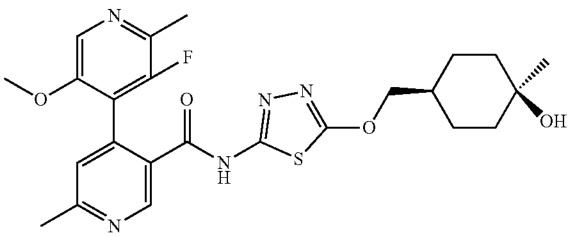

To a stirred solution of 3'-fluoro-5'-methoxy-2',6-dimethyl-(4,4'-bipyridine)-3-carboxylic acid (100 mg, 0.362 mmol) in Acetonitrile (3 mL) and N,N-Dimethylformamide (DMF) (0.5 mL) was added 1-methyl-1H-imidazole (119 mg, 1.448 mmol), Chloro-N,N,N',N'-tetramethylformamidinium hexafluorophosphate (152 mg, 0.543 mmol) and (1s,4s)-4-(((5-amino-1,3,4-thiadiazol-2-yl)oxy)methyl)-1-methylcyclohexan-1-ol (88 mg, 0.362 mmol) at rt under nitrogen. The reaction mixture was stirred for 16 h. The reaction mixture was quenched with cold water and extracted with ethyl acetate (50 mL×3). The combined organic layers were washed with brine, dried over anhydrous sodium sulfate, filtered, and concentrated under vacuum to afford the crude product as grey solid.

The crude product was purified by prep-HPLC with the following conditions: (Column: Sunfire C18 (19×150 mm) 5 m; Mobile Phase A: 0.1% FA in water 70%, Mobile Phase B: acetonitrile 30%) to afford 3'-fluoro-N-(5-(((1s,4s)-4-hydroxy-4-methylcyclohexyl)methoxy)-1,3,4-thiadiazol-2-yl)-5'-methoxy-2',6-dimethyl-(4,4'-bipyridine)-3-carboxamide (70 mg, 0.139 mmol, 38.4% yield) as light yellow solid. The stereochemistry was not determined. MS (ESI) calculated for ($C_{24}H_{28}FN_5O_4S$) $(M+1)^+$, 502.19; found, 502.2. 1H-NMR (400 MHz, DMSO-$d^6$): δ 12.97 (brs, 1H), 8.93 (s, 1H), 8.17 (s, 1H), 7.36 (s, 1H), 4.22 (d, J=5.6 Hz, 2H), 3.97 (s, 1H), 3.68 (s, 3H), 2.58 (s, 3H), 2.42 (d, J=3.2 Hz, 3H), 1.77-1.65 (m, 1H), 1.60-1.32 (m, 6H), 1.38 (td, J=12.8 Hz, 4.0 Hz, 2H), 1.10 (s, 3H).

Example 214

2'-chloro-N-(5-(((1r,4r)-4-hydroxy-4-methylcyclohexyl)methoxy)-1,3,4-thiadiazol-2-yl)-5'-methoxy-6-methyl-(4,4'-bipyridine)-3-carboxamide

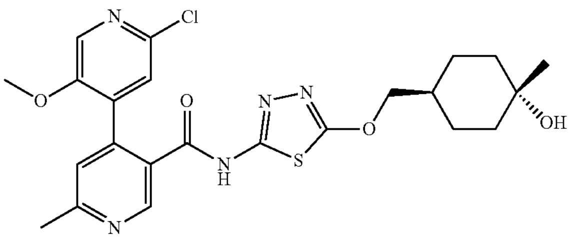

Step-1: O-(((1r,4r)-4-hydroxy-4-methylcyclohexyl) methyl) hydrazinecarbothioate

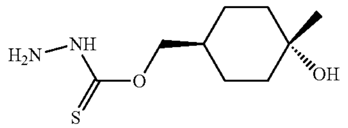

To a stirred solution of O-(((1r,4r)-4-hydroxy-4-methylcyclohexyl)methyl)S-methyl carbonodithioate (Isomer 1, Example 213, step 7) (280 mg, 1.195 mmol) in Methanol (10 mL) was added hydrazine (0.064 mL, 1.314 mmol) at rt under nitrogen. The reaction mixture was stirred for 1 h at rt. The organic solvent was removed under vacuum. The residue was diluted with water. The aqueous layer was extracted with ethyl acetate (50 mL×3). The combined organic layers were washed with brine, dried over anhydrous sodium sulfate, filtered, and concentrated under vacuum to afford O-(((1r,4r)-4-hydroxy-4-methylcyclohexyl)methyl) hydrazinecarbothioate (285 mg, 1.240 mmol, 104% yield) as a brown solid. MS (ESI) calculated for ($C_9H_{18}N_2O_2S$) $(M+1)^+$, 219.12; found, 219.2.

Step-2: (1r,4r)-4-(((5-amino-1,3,4-thiadiazol-2-yl) oxy)methyl)-1-methylcyclohexan-1-ol

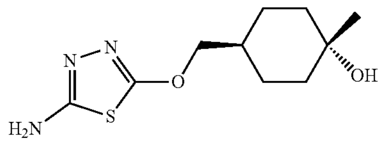 [SMILES: C[C@]1(O)CC[C@H](COc2nnc(N)s2)CC1]

To a stirred solution of O-(((1r,4r)-4-hydroxy-4-methylcyclohexyl)methyl) hydrazinecarbothioate (285 mg, 1.305 mmol), in Ethanol (8 mL) were added TEA (0.182 mL, 1.305 mmol) followed by Cyanogen bromide (138 mg, 1.305 mmol) at room temperature. The reaction mixture was stirred at room temperature for 1 h. The organic solvent was removed under vacuum. The residue was diluted with water. The aqueous layer was extracted with ethyl acetate (50 mL×3). The combined organic layers were washed with brine, dried over anhydrous sodium sulfate, filtered, and concentrated under vacuum to get the crude product as a brown solid.

The crude product was pre-absorbed on silica (using 5 mL DCM and 1 mL MeOH, 15 g of silica (60-120 mesh), loaded onto a Biotage 25 g SNAP cartridge, and eluted with 75-100% of Ethyl aetate in petroleum ether for 60 mins. The appropriate fractions were collected and concentrated under vacuum to afford (1r,4r)-4-(((5-amino-1,3,4-thiadiazol-2-yl) oxy)methyl)-1-methylcyclohexan-1-ol (90 mg, 0.333 mmol, 25.5% yield) as a yellow solid. MS (ESI) calculated for ($C_{10}H_{17}N_3O_2S$) $(M+1)^+$, 243.10; found, 244.0.

Step-3: 2'-chloro-N-(5-(((1r,4r)-4-hydroxy-4-methylcyclohexyl)methoxy)-1,3,4-thiadiazol-2-yl)-5'-methoxy-6-methyl-(4,4'-bipyridine)-3-carboxamide

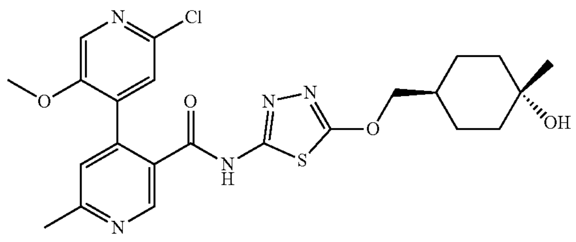

To a stirred solution of Intermediate H (100 mg, 0.359 mmol) in Acetonitrile (3 mL) and N,N-Dimethylformamide (DMF) (0.5 mL) was added 1-methyl-1H-imidazole (118 mg, 1.435 mmol), Chloro-N,N,N',N'-tetramethylformamidinium hexafluorophosphate (151 mg, 0.538 mmol) and (1r,4r)-4-(((5-amino-1,3,4-thiadiazol-2-yl)oxy)methyl)-1-methylcyclohexan-1-ol (87 mg, 0.359 mmol) at rt under nitrogen. The reaction mixture was stirred for 1 h. The reaction mixture was quenched with cold water and extracted with ethyl acetate (50 mL×3). The combined organic layers were washed with brine, dried over anhydrous sodium sulfate, filtered, and concentrated under vacuum to afford the crude product as a brown gum.

The crude product was purified by prep-HPLC with the following conditions: (Column: X-BRIDGE C8 (19*150 mm) 5 MICRON; Mobile Phase A: 10 mM ABC in MQ water 90%, Mobile Phase B: acetonitrile 10%) to afford 2'-chloro-N-(5-(((1r,4r)-4-hydroxy-4-methylcyclohexyl) methoxy)-1,3,4-thiadiazol-2-yl)-5'-methoxy-6-methyl-(4,4'-bipyridine)-3-carboxamide (37 mg, 0.072 mmol, 20.05% yield) as off-white solid. The stereochemistry was not determined. MS (ESI) calculated for ($C_{23}H_{26}ClN_5O_4S$) $(M+1)^+$, 504.15; found, 504.2. 1H-NMR (400 MHz, DMSO-$d^6$): δ 12.89 (brs, 1H), 8.81 (s, 1H), 8.17 (s, 1H), 7.53 (s, 1H), 7.42 (s, 1H), 4.31-4.24 (m, 3H), 3.63 (s, 3H), 2.59 (s, 3H), 1.82-1.77 (m, 3H), 1.85-1.67 (m, 2H), 1.60-1.50 (m, 2H), 1.36 (td, J=12.4 Hz, 3.6 Hz, 2H), 1.10 (s, 3H), Example 215

2'-chloro-N-(5-(((1s,4s)-4-hydroxy-4-methylcyclohexyl)methoxy)-1,3,4-thiadiazol-2-yl)-5'-methoxy-6-methyl-(4,4'-bipyridine)-3-carboxamide

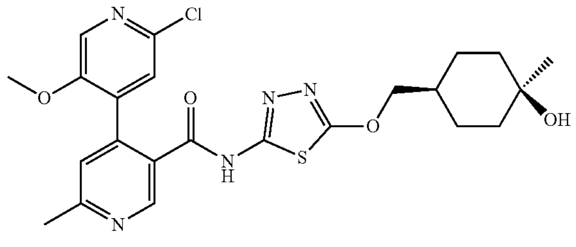

Step-1: 2'-chloro-N-(5-(((1s,4s)-4-hydroxy-4-methylcyclohexyl)methoxy)-1,3,4-thiadiazol-2-yl)-5'-methoxy-6-methyl-(4,4'-bipyridine)-3-carboxamide

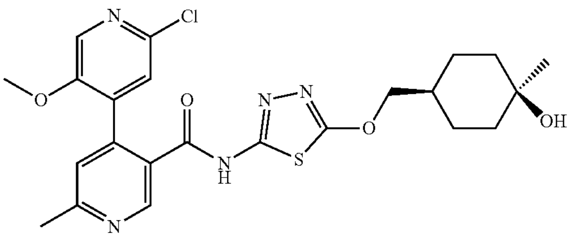

To a stirred solution of Intermediate H (100 mg, 0.359 mmol) in Acetonitrile (3 mL) and N,N-Dimethylformamide (DMF) (0.5 mL) was added 1-methyl-1H-imidazole (118 mg, 1.435 mmol), Chloro-N,N,N',N'-tetramethylformamidinium hexafluorophosphate (151 mg, 0.538 mmol) and (1s,4s)-4-(((5-amino-1,3,4-thiadiazol-2-yl)oxy)methyl)-1-methylcyclohexan-1-ol (87 mg, 0.359 mmol) at rt under nitrogen.

The reaction mixture was stirred for 1 h. The reaction mixture was quenched with cold water and extracted with ethyl acetate (50 mL×3). The combined organic layers were washed with brine, dried over anhydrous sodium sulfate, filtered, and concentrated under vacuum to afford the crude product as a brown gum.

The crude product was suspended in acetonitrile (15 mL) and stirred for 15 mins at room temperature. The solid was filtered and washed with acetonitrile (20 mL), dried under vacuum to afford 2'-chloro-N-(5-(((1s,4s)-4-hydroxy-4-methylcyclohexyl)methoxy)-1,3,4-thiadiazol-2-yl)-5'-methoxy-6-methyl-(4,4'-bipyridine)-3-carboxamide (60 mg, 0.119 mmol, 33.1% yield) was isolated as a white solid. The stereochemistry was not determined. MS (ESI) calculated for ($C_{23}H_{26}ClN_5O_4S$) $(M+1)^+$, 504.15; found, 504.0. 1H-NMR (400 MHz, DMSO-$d^6$): δ 12.90 (s, 1H), 8.80 (s, 1H), 8.17 (s, 1H), 7.55 (s, 1H), 7.44 (s, 1H), 4.24 (d, J=6.40 Hz, 2H), 3.98 (s, 1H), 3.63 (s, 3H), 2.59 (s, 3H), 1.80-1.65 (m, 1H), 1.60-1.33 (m, 6H), 1.36 (td, J=12.0 Hz, 2.4 Hz, 2H), 1.10 (s, 3H).

Example 216

(S)—N-(5-((1,4-dioxan-2-yl)methoxy)-1,3,4-thiadiazol-2-yl)-2'-chloro-5'-methoxy-6-(methoxymethyl)-(4,4'-bipyridine)-3-carboxamide

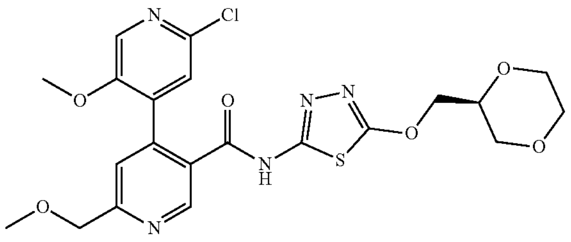 [SMILES: COCc1cc(-c2cc(Cl)ncc2OC)c(C(=O)Nc2nnc(OC[C@@H]3COCCO3)s2)cn1]

Step-1: ethyl 4-chloro-6-formylnicotinate

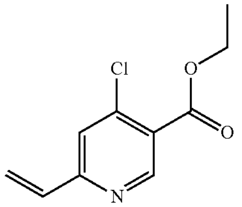

A solution of ethyl 4,6-dichloronicotinate (15 g, 68.2 mmol), 4,4,5,5-tetramethyl-2-vinyl-1,3,2-dioxaborolane (11.55 g, 75.0 mmol), K2CO3 (18.84 g, 136 mmol) in mixture of Acetonitrile (250 mL) and Ethanol (125 mL) was degassed for 15 minutes with nitrogen gas followed by addition of $PdOAc_2$ (0.765 g, 3.41 mmol), and triphenylphosphine (1.788 g, 6.82 mmol). The reaction mixture was heated to 40° C. and stirred for 16 h. After completion, the reaction mixture was filtered through celite pad and washed with ethyl acetate (300 mL), and the filtrate was concentrated to get crude product as a brown solid.

The crude residue was pre-absorbed on silica (using 35 mL DCM, 70 g of silica (60-120 mesh), loaded onto a Biotage 120 g SNAP cartridge and eluted at 2-10% of ethyl acetate in petroleum ether for 60 mins with flow rate 30 mL/min. The appropriate fractions were concentrated under reduced pressure to afford ethyl 4-chloro-6-vinylnicotinate (12 g, 54.4 mmol, 80% yield) as light brown solid. MS (ESI) calculated for ($C_{10}H_{10}ClNO_2$) $(M+1)^+$, 212.05; found, 212.2.

Step-2: ethyl 4-chloro-6-formylnicotinate

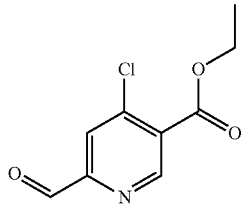

To a stirred solution of ethyl 4-chloro-6-vinylnicotinate (8.0 g, 37.8 mmol) and sodium periodate (24.25 g, 113 mmol) in Acetonitrile (210 mL) and Water (49 mL) was added osmium tetroxide (4% in Water) (8.90 mL, 1.134 mmol) dropwise under nitrogen at 0° C. The reaction mixture was warmed to rt and stirred at rt for 5 h. After completion reaction mixture was diluted with water (100 mL) and extracted with ethyl acetate (2×100 mL). The combined organics were washed with brine, dried over anhydrous Na2SO4 and concentrated under vacuo to get crude product as a Yellow oil.

The crude residue was pre-absorbed on silica (using 10 mL DCM, 21 g of silica (60-120 mesh), loaded onto a Biotage 120 g SNAP cartridge and eluted at 0-100% of ethyl acetate in petroleum ether for 60 mins. The appropriate fractions were concentrated under reduced pressure to afford ethyl 4-chloro-6-formylnicotinate (4.2 g, 19.66 mmol, 52.0% yield) as pale-yellow oil. MS (ESI) calculated for ($C_{10}H_{10}ClNO_2$) (M−1)-, 214.01 ($^{37}Cl$); found, 214.0 ($^{37}Cl$).

Step-3: ethyl 4-chloro-6-(hydroxymethyl)nicotinate

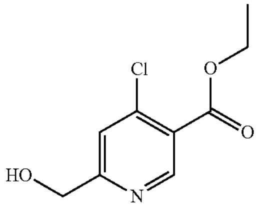

To a stirred solution of ethyl 4-chloro-6-formylnicotinate (2.0 g, 9.36 mmol) in Ethanol (30 mL) was added $NaBH_4$ (0.354 g, 9.36 mmol) at 0° C. The reaction mixture was stirred at room temperature for 2 h. Upon completion, the reaction mixture was quenched with Water (300 mL) and extracted with ethyl acetate (200 mL). The organic phase was washed with water 200 mL and separated organic phase, dried over sodium sulphate and evaporated in vacuo to afford ethyl 4-chloro-6-(hydroxymethyl)nicotinate (1.67 g, 7.31 mmol, 78% yield) as a brown liquid. MS (ESI) calculated for ($C_9H_{10}ClNO_3$) $(M+1)^+$, 216.04; found, 216.2.

Step-4: ethyl 2'-chloro-6-(hydroxymethyl)-5'-methoxy-(4,4'-bipyridine)-3-carboxylate

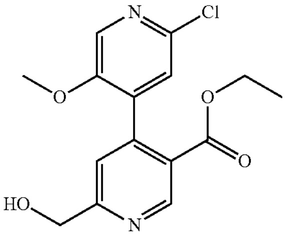 [SMILES: CCOC(=O)c1cnc(CO)cc1-c1cc(Cl)ncc1OC]

To a stirred solution of ethyl 4-chloro-6-(hydroxymethyl) nicotinate (1.5 g, 6.96 mmol) and (2-chloro-5-methoxypyridin-4-yl)boronic acid (1.304 g, 6.96 mmol) in 1,4-Dioxane (10 mL) was added a solution of $K_2CO_3$ (1.923 g, 13.91 mmol) in Water (2 mL) in one charge followed by the addition of (1,1'-Bis(di-tert-butylphosphino)ferrocene)dichloropalladium(II) (0.453 g, 0.696 mmol) at room temperature. The reaction mixture was stirred at 80° C. for 5 h. The reaction mixture was cooled to room temperature and passed through celite bed, the bed was washed with 1,4-Dioxane (100 mL). The organic phase was evaporated under vacuum to give the crude products as a brown liquid.

The crude product was pre-absorbed on silica (using 25 mL DCM, 17 g of silica (60-120 mesh), loaded onto a 125 g SNAP cartridge Orochem pre packed silica column, and eluted with 0-100% of Ethyl aetate in petroleum ether for 50 mins with flow rate 45 mL/min. The appropriate fractions were collected and concentrated under vacuum to afford ethyl 2'-chloro-6-(hydroxymethyl)-5'-methoxy-(4,4'-bipyridine)-3-carboxylate (1.3 g, 3.79 mmol, 54.4% yield) as a brown liquid. MS (ESI) calculated for ($C_{15}H_{15}ClN_2O_4$) $(M+1)^+$, 323.08; found, 323.0.

Step-5: 2'-chloro-5'-methoxy-6-(methoxymethyl)-(4,4'-bipyridine)-3-carboxylic acid

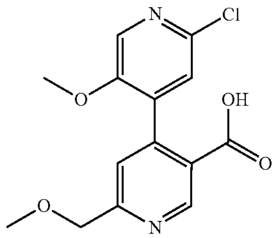 [SMILES: COCc1cc(-c2cc(Cl)ncc2OC)c(C(=O)O)cn1]

To a stirred solution of ethyl 2'-chloro-6-(hydroxymethyl)-5'-methoxy-(4,4'-bipyridine)-3-carboxylate (950 mg, 2.94 mmol) and NaH (141 mg, 3.53 mmol) in Tetrahydrofuran (THF) (20 mL) was added a solution of iodomethane (0.368 mL, 5.89 mmol) in Tetrahydrofuran (THF) (20 mL) dropwise during 5 min under nitrogen at 0° C. The reaction mixture was stirred at Room temperature for 2 h. Upon completion, the reaction mixture was quenched with water (10 mL) and ageous was washed with EA (20 mL). The aqueous layer was evaporated in vacuo to give the crude product as a yellow liquid. The crude product was purified by GRACE revelleris X2 (reverse phase) with the following conditions: (Column: 120 g Grace C18 catriage; Mobile Phase A: 0.1% FA in water, Mobile Phase B: acetonitrile) 0-100% of B in A over 0-50 min. The appropriate fractions were combined and evaporated in vacuum to afford 2'-chloro-5'-methoxy-6-(methoxymethyl)-(4,4'-bipyridine)-3-carboxylic acid (160 mg, 0.468 mmol, 15.90% yield) as off white solid. (Ester hydrolized product was obtained). MS (ESI) calculated for ($C_{14}H_{13}ClN_2O_4$) (M−1)-, 307.05; found, 307.0.

Step-6: (S)—N-(5-((1,4-dioxan-2-yl)methoxy)-1,3,4-thiadiazol-2-yl)-2'-chloro-5'-methoxy-6-(methoxymethyl)-(4,4'-bipyridine)-3-carboxamide

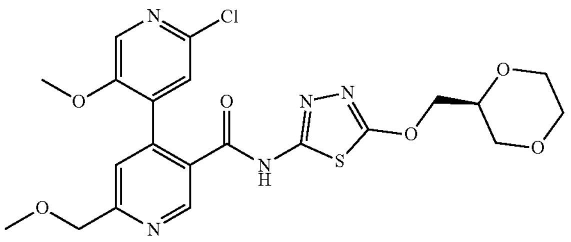 [SMILES: COCc1cc(-c2cc(Cl)ncc2OC)c(C(=O)Nc2nnc(OC[C@@H]3COCCO3)s2)cn1]

To a stirred solution of 2'-chloro-5'-methoxy-6-(methoxymethyl)-(4,4'-bipyridine)-3-carboxylic acid (70 mg, 0.227 mmol), in Acetonitrile (1 mL) were added Chloro-N,N,N',N'-tetramethylformamidinium hexafluorophosphate (95 mg, 0.340 mmol), 1-methylimidazole (0.072 mL, 0.907 mmol), N,N-Dimethylformamide (DMF) (0.2 mL) and (S)-5-((1,4-dioxan-2-yl)methoxy)-1,3,4-thiadiazol-2-amine (49.3 mg, 0.227 mmol, Example 186, Step 3) at room temperature. The reaction mixture was stirred at room temperature for 16 hr. After completion of the reaction, the reaction mixture was diluted with water (5 mL) and extracted with ethyl acetate (2×10 mL). The combined organic layer dried over anhydrous sodium sulphate (2 g), filtered concentrated under reduced pressure to afford the product as a brown gum The crude product was purified by prep-HPLC with the following conditions: (Column: x-bridge-C8 (10×150) MM 5 MICRON; Mobile Phase A: 10 mM ABC in Milli Q Water 9000, Mobile Phase B: acetonitrile 10%) to afford (S)—N-(5-((1,4-dioxan-2-yl)methoxy)-1,3,4-thiadiazol-2-yl)-2'-chloro-5'-methoxy-6-(methoxymethyl)-(4,4'-bipyridine)-3-carboxamide (17 mg, 0.033 mmol, 14.70% yield) as an off white solid. MS (ESI) calculated for $(C_{21}H_{22}ClN_5O_6S)$ $(M+1)^+$, 508.11; found, 508.0. 1H-NMR (400 MHz, DMSO-$d_6$): δ 13.01 (s, 1H), 8.90 (s, 1H), 8.18 (s, 1H), 7.57 (s, 1H), 7.48 (s, 1H), 4.62 (s, 2H), 4.45-4.35 (m, 2H), 3.95-3.86 (m, 1H), 3.84-3.73 (m, 2H), 3.70-3.57 (m, 5H), 3.55-3.45 (m, 1H), 3.42 (s, 3H), 3.41-3.36 (m, 1H), Example 217

3'-fluoro-N-(5-((4-hydroxybicyclo(2.2.1)heptan-1-yl)methoxy)-1,3,4-thiadiazol-2-yl)-5'-methoxy-2',6-dimethyl-(4,4'-bipyridine)-3-carboxamide

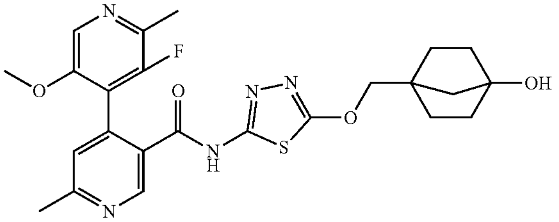 [SMILES: COc1cnc(C)c(F)c1-c1cc(C)ncc1C(=O)Nc1nnc(OCC23CCC(O)(CC2)C3)s1]

Step-1: 3'-fluoro-N-(5-((4-hydroxybicyclo(2.2.1)heptan-1-yl)methoxy)-1,3,4-thiadiazol-2-yl)-5'-methoxy-2',6-dimethyl-(4,4'-bipyridine)-3-carboxamide

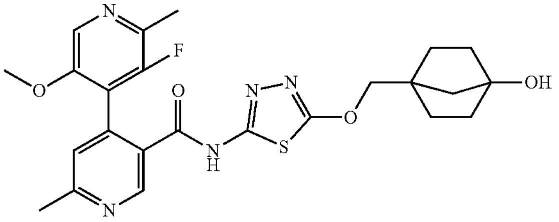 [SMILES: COc1cnc(C)c(F)c1-c1cc(C)ncc1C(=O)Nc1nnc(OCC23CCC(O)(CC2)C3)s1]

To a stirred solution of 3'-fluoro-5'-methoxy-2',6-dimethyl-(4,4'-bipyridine)-3-carboxylic acid (100 mg, 0.362 mmol, Example 213, Step 5), in Acetonitrile (2.5 mL) were added Chloro-N,N,N',N'-tetramethylformamidinium hexafluorophosphate (152 mg, 0.543 mmol), 1-methylimidazole (0.115 mL, 1.448 mmol), N,N-Dimethylformamide (DMF) (0.5 mL)) and 4-(((5-amino-1,3,4-thiadiazol-2-yl)oxy)methyl)bicyclo(2.2.1)heptan-1-ol (87 mg, 0.362 mmol, Example 218, Step 4) at room temperature. The reaction mixture was stirred at room temperature for 3 h.

After completion of the reaction, The reaction mixture was diluted with water (10 mL) and extracted with ethyl acetate (2×20 mL). The combined organic layer dried over anhydrous sodium sulphate, filtered concentrated under reduced pressure to afford the product as a brown gum.

The crude product was purified by prep-HPLC with the following conditions: (Column: X-SELECT C18(19*250) MM 5 MICRON; Mobile Phase A: 10 mM ABC in Milli Q Water 800%, Mobile Phase B: acetonitrile 20%) to afford 3'-fluoro-N-(5-((4-hydroxybicyclo(2.2.1)heptan-1-yl)methoxy)-1,3,4-thiadiazol-2-yl)-5'-methoxy-2',6-dimethyl-(4,4'-bipyridine)-3-carboxamide (45 mg, 0.090 mmol, 24.85% yield) as an off white solid. MS (ESI) calculated for $(C_{24}H_{26}FN_5O_4S)$ $(M+H)^+$, 500.18; found, 500.2 1H-NMR (400 MHz, DMSO-$d^6$): δ 12.95 (s, 1H), 8.91 (s, 1H), 8.17 (s, 1H), 7.39 (s, 1H), 4.91 (s, 1H), 4.39 (s, 2H), 3.68 (s, 3H), 2.58 (s, 3H), 2.43 (d, J=3.20 Hz, 3H), 1.75-1.56 (m, 4H), 1.55-1.46 (m, 2H), 1.45-1.33 (m, 4H).

Example 218

2'-chloro-N-(5-((4-hydroxybicyclo(2.2.1)heptan-1-yl)methoxy)-1,3,4-thiadiazol-2-yl)-5'-methoxy-6-methyl-(4,4'-bipyridine)-3-carboxamide

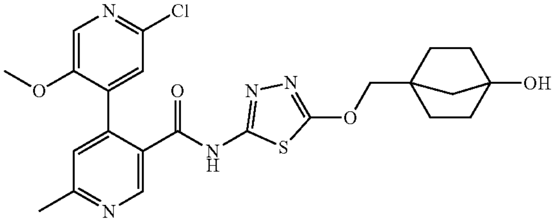

Step-1:4-(hydroxymethyl)bicyclo(2.2.1)heptan-1-ol

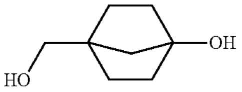

To a stirred solution of methyl 4-hydroxybicyclo(2.2.1)heptane-1-carboxylate (1 g, 5.88 mmol) in Toluene (10 mL) under nitrogen at −78° C. was added DIBAL-H (14.69 mL, 17.63 mmol) dropwise during 1 min. The reaction mixture was stirred at room temperature for 2 h. After completion of the reaction, the reaction mixture was quenched slowly with saturated aq. sodium potassium tartrate solution (20 mL) and diluted with ethyl acetate (60 mL). The resulting emulsion was filtered through celite pad and washed with ethyl acetate (50 mL). The filtrate layers were separated, the organic layer dried over sodium sulphate, filtered and concentrated under vacuum to afford 4-(hydroxymethyl)bicyclo(2.2.1)heptan-1-ol (450 mg, 2.82 mmol, 48.1% yield) as an off white solid. GCMS Calculated for $(C_8H_{14}O_2)$ $(M)^+$142.10; found; m/z, 142.0;

Step-2: O-((4-hydroxybicyclo(2.2.1)heptan-1-yl) methyl)S-methyl carbonodithioate

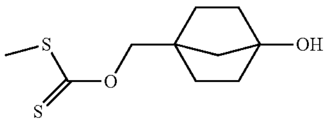

To a stirred solution of 4-(hydroxymethyl)bicyclo(2.2.1) heptan-1-ol (450 mg, 3.16 mmol) in Tetrahydrofuran (THF) (5 mL) stirred under nitrogen at 0° C. was added Sodium hydride (253 mg, 6.33 mmol) portionwise during 5 minutes. After addition the reaction mixture was stirred at room temperature for 30 minutes. After 30 minutes to the above reaction mixture were added carbon disulfide (0.382 mL, 6.33 mmol) followed by methyl iodide (0.198 mL, 3.16 mmol) at room temperature. The reaction mixture was stirred at room temperature for additional 30 minutes.

After completion of the reaction, The reaction mixture was slowly quenched with ice cold water (20 mL) and extracted with ethyl acetate (2×40 mL). The organic layer was dried over sodium sulphate (3 g), filtered and concentrated under vacuum to afford crude product as a yellow liquid.

The crude product was pre-absorbed on silica (using 2 mL DCM, 2 g of silica (60-120 mesh), loaded onto a Biotage 12 g SNAP cartridge and eluted at 5-15% of EA/PE for 60 minutes with flow rate 25 mL/min. The appropriate fractions were collected and concentrated reduced pressure to afford O-((4-hydroxybicyclo(2.2.1)heptan-1-yl)methyl)S-methyl carbonodithioate (400 mg, 1.635 mmol, 51.7% yield) as a yellow gum. MS (ESI) calculated for $C_{10}H_{16}O_2S_2$ $(M+1)^+$, 233.07; found, mass was not ionized. 1H-NMR (400 MHz, DMSO-$d^6$): δ 4.93 (s, 1H), 4.56 (s, 2H), 2.52 (s, 3H), 1.73-1.58 (m, 4H), 1.55-1.40 (m, 4H), 1.42-1.35 (m, 2H).

Step-3: O-((4-hydroxybicyclo(2.2.1)heptan-1-yl) methyl) hydrazinecarbothioate

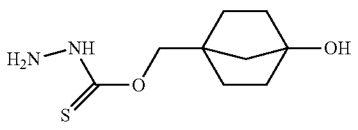 [SMILES: NNC(=S)OCC12CCC(O)(CC1)C2]

To a stirred solution of O-((4-hydroxybicyclo(2.2.1)heptan-1-yl)methyl)S-methyl carbonodithioate (400 mg, 1.721 mmol), in Methanol (5 mL) was added hydrazine hydrate (86 mg, 1.721 mmol) at room temperature. The reaction mixture was stirred at room temperature for 2 hr. After completion of the reaction, The reaction mixture was concentrated under reduced pressure to afford crude residue. The resulting residue diluted with water (10 mL) and extracted with ethyl acetate (2×30 mL). The organic layer dried over anhydrous sodium sulphate, filtered concentrated under reduced pressure to afford O-((4-hydroxybicyclo (2.2.1)heptan-1-yl)methyl) hydrazinecarbothioate (350 mg, 1.618 mmol, 94% yield) as a yellow gum. MS (ESI) calculated for $C_9H_{16}N_2O_2S$ $(M+1)^+$, 217.09; found, 217.2.

Step-4: 4-(((5-amino-1,3,4-thiadiazol-2-yl)oxy) methyl)bicyclo(2.2.1)heptan-1-ol

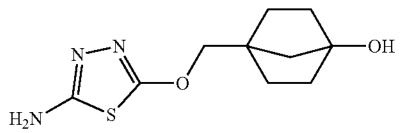 [SMILES: Nc1nnc(OCC23CCC(O)(CC2)C3)s1]

To a stirred solution of O-((4-hydroxybicyclo(2.2.1)heptan-1-yl)methyl) hydrazinecarbothioate (350 mg, 1.618 mmol), in Ethanol (5 mL) were added Cyanogen bromide (171 mg, 1.618 mmol) followed by TEA (0.226 mL, 1.618 mmol) at room temperature The reaction mixture was stirred at room temperature for 1 h.

After completion of the reaction, the reaction mixture was concentrated under reduced pressure to afford crude residue. The resulting residue diluted with water (10 mL) and extracted with ethyl acetate (2×20 mL). The organic layer dried over anhydrous sodium sulphate (2 g), filtered and concentrated under reduced pressure to afford the crude product as a brown gum The crude residue was dissolved 2 mL of DCM, loaded onto a Biotage 12 g SNAP cartridge (liquid loading), and eluted at 8-11% MeOH in DCM, for 60 minutes with flow rate 25 mL/min. the appropriate fractions were collected and concentrated under reduced pressure to afford 4-(((5-amino-1,3,4-thiadiazol-2-yl)oxy)methyl)bicyclo(2.2.1)heptan-1-ol (250 mg, 1.036 mmol, 64.0% yield) as a yellow solid. MS (ESI): Calculated for $C_{10}H_{15}N_3O_2S$ $(M+1)^+$, 242.08; found, 242.0.

Step-4: 2'-chloro-N-(5-((4-hydroxybicyclo(2.2.1) heptan-1-yl)methoxy)-1,3,4-thiadiazol-2-yl)-5'-methoxy-6-methyl-(4,4'-bipyridine)-3-carboxamide

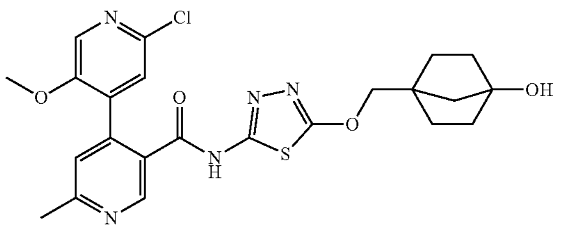 [SMILES: COc1cnc(Cl)cc1-c1cc(C)ncc1C(=O)Nc1nnc(OCC23CCC(O)(CC2)C3)s1]

To a stirred solution of Intermediate H (100 mg, 0.359 mmol), in Acetonitrile (3 mL) were added Chloro-N,N,N',N'-tetramethylformamidinium hexafluorophosphate (151 mg, 0.538 mmol), 1-methylimidazole (0.114 mL, 1.435 mmol), N,N-Dimethylformamide (DMF) (0.5 mL) and 4-(((5-amino-1,3,4-thiadiazol-2-yl)oxy)methyl)bicyclo (2.2.1)heptan-1-ol (87 mg, 0.359 mmol) at room temperature. The reaction mixture was stirred at room temperature for 3 h.

After completion of the reaction, the reaction mixture was diluted with water (10 mL) and extracted with ethyl acetate (2×20 mL). The combined organic layer dried over anhydrous sodium sulphate, filtered concentrated under reduced pressure to afford the product as a yellow gum.

The crude product was purified by prep-HPLC with the following conditions: (Column: X-SELECT C18(19*250) MM 5 MICRON; Mobile Phase A: 10 mM ABC in Milli Q Water 800%, Mobile Phase B: acetonitrile 20%) to afford 2'-chloro-N-(5-((4-hydroxybicyclo(2.2.1)heptan-1-yl)methoxy)-1,3,4-thiadiazol-2-yl)-5'-methoxy-6-methyl-(4,4'-bipyridine)-3-carboxamide (63 mg, 0.125 mmol, 34.8% yield) as an off white solid. MS (ESI): Calculated for $C_{23}H_{24}ClN_5O_4S$ $(M+1)^+$, 502.12; found, 502.0. 1H-NMR (400 MHz, DMSO-d6): δ 12.88 (s, 1H), 8.80 (s, 1H), 8.17 (s, 1H), 7.55 (s, 1H), 7.44 (s, 1H), 4.91 (s, 1H), 4.40 (s, 2H), 3.63 (s, 3H), 2.59 (s, 3H), 1.78-1.57 (m, 4H), 1.56-1.48 (m, 2H), 1.47-1.35 (m, 4H), Example 219

3'-fluoro-N-(5-((4-hydroxybicyclo(2.2.2)octan-1-yl)methoxy)-1,3,4-thiadiazol-2-yl)-5'-methoxy-2',6-dimethyl-(4,4'-bipyridine)-3-carboxamide

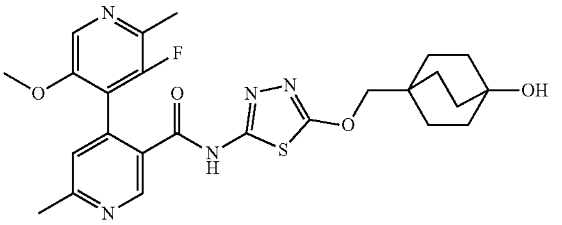 [SMILES: COc1cnc(C)c(F)c1-c1cc(C)ncc1C(=O)Nc1nnc(OCC23CCC(O)(CC2)CC3)s1]

Step-1: O-((4-hydroxybicyclo(2.2.2)octan-1-yl)methyl)S-methyl carbonodithioate

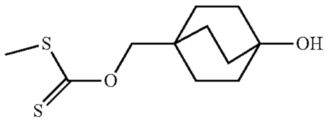

To a stirred solution of 4-(hydroxymethyl)bicyclo(2.2.2)octan-1-ol (1 g, 6.40 mmol) in Tetrahydrofuran (THF) (15 mL) stirred under nitrogen at 0° C. was added NaH (0.307 g, 12.80 mmol) portionwise during 5 min. After addition the reaction mixture was stirred at room temperature for 30 min. After 30 min to the above reaction mixture were added carbon disulfide (0.772 mL, 12.80 mmol) followed by methyl iodide (0.400 mL, 6.40 mmol) at room temperature. Then the reaction mixture was stirred at room temperature for additional 2 h. After 2 h the reaction was quenched with cold water extracted with ethyl acetate (2×25 mL). The combine organic layer was dried over sodium sulphate, filtered and concentrated under vacuum to afford O-((4-hydroxybicyclo(2.2.2)octan-1-yl)methyl)S-methyl carbonodithioate (1.65 g, 6.40 mmol, 100% yield) was isolated a white solid. MS (ESI) calculated for $(C_{11}H_{18}O_2S_2)$ $(M-CH_3)^+$, 231.05; found, 231.0.

Step-2: O-((4-hydroxybicyclo(2.2.2)octan-1-yl)methyl) hydrazinecarbothioate

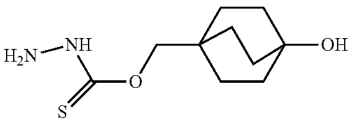 [SMILES: NNC(=S)OCC12CCC(O)(CC1)CC2]

To a stirred solution of O-((4-hydroxybicyclo(2.2.2)octan-1-yl)methyl)S-methyl carbonodithioate (1.55 g, 6.29 mmol) in Methanol (10 mL) was added hydrazine monohydrate (0.346 g, 6.92 mmol) at room temperature. The reaction mixture was stirred at room temperature for 1 h. The organic solvent was removed under vacuum. The resulting residue diluted with water (30 mL) and extracted with ethyl acetate (2×40 mL). The organic layer was dried over anhydrous sodium sulphate, filtered concentrated under vacuum to afford the product O-((4-hydroxybicyclo(2.2.2)octan-1-yl)methyl) hydrazinecarbothioate (1.1 g, 4.66 mmol, 74.0% yield) as a pale yellow solid. MS (ESI) calculated for $(C_{10}H_{18}N_2O_2S)$ $(M+1)^+$, 231.12; found, 231.2.

Step-3: 4-(((5-amino-1,3,4-thiadiazol-2-yl)oxy)methyl)bicyclo(2.2.2)octan-1-ol

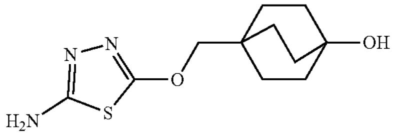 [SMILES: Nc1nnc(OCC23CCC(O)(CC2)CC3)s1]

To a stirred solution of O-((4-hydroxybicyclo(2.2.2)octan-1-yl)methyl) hydrazinecarbothioate (1.11 g, 4.67 mmol) in Ethanol (10 mL) were added TEA (0.652 mL, 4.67 mmol) followed by cyanogen bromide (0.495 g, 4.67 mmol) at room temperature. The reaction mixture was stirred at room temperature for 30 mins. The organic solvent was removed under vacuum. The resulting residue diluted with water (30 mL) and extracted with 10% MeOH in ethyl acetate (2×50 mL). The organic layer dried over anhydrous sodium sulphate, filtered concentrated under vacuum to get the crude product as an orange gum.

The crude product was dissolved in mixture of ACN (4 mL) and THF (2 mL) and loaded on 100 g C18 column, purified by GRACE revelleris X2, eluted with 0~100% acetonitrile in 0.1M formic in water over 40 min to afford 4-(((5-amino-1,3,4-thiadiazol-2-yl)oxy)methyl)bicyclo(2.2.2)octan-1-ol (500 mg, 1.950 mmol, 41.7% yield) as a white solid. MS (ESI) calculated for $(C_{11}H_{17}N_3O_2S)$ $(M+1)^+$, 256.11; found, 256.2.

Step-4: 3'-fluoro-N-(5-((4-hydroxybicyclo(2.2.2)octan-1-yl)methoxy)-1,3,4-thiadiazol-2-yl)-5'-methoxy-2',6-dimethyl-(4,4'-bipyridine)-3-carboxamide

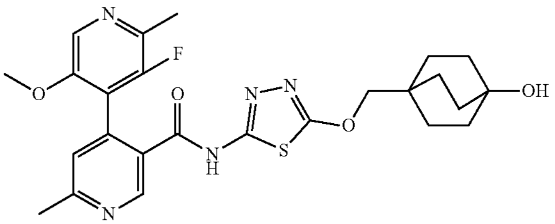 [SMILES: COc1cnc(C)c(F)c1-c1cc(C)ncc1C(=O)Nc1nnc(OCC23CCC(O)(CC2)CC3)s1]

To a stirred solution of 3'-fluoro-5'-methoxy-2',6-dimethyl-(4,4'-bipyridine)-3-carboxylic acid (70 mg, 0.253 mmol, Example 213, Step 5) in Acetonitrile (3 mL) and N,N-Dimethylformamide (DMF) (0.6 mL) were added 1-methyl-1H-imidazole (62.4 mg, 0.760 mmol), Chloro-N, N,N',N'-ttramethylformamidinium hexafluorophosphate (71.1 mg, 0.253 mmol) and 4-(((5-amino-1,3,4-thiadiazol-2-yl)oxy)methyl)bicyclo(2.2.2)octan-1-ol (64.7 mg, 0.253 mmol) at room temperature and continue to stirred at room temperature for 3 h. After 3 h reaction mixture was quenched with cold water and extracted with ethyl acetate (2×10 mL). The combined organic phase was washed with water (10 mL) and brine solution (10 mL), dried over sodium sulphate and filtered. The filtrate was concentrated under vacuum to get the crude product as a brown gum. The crude product was purified by prep-HPLC with the following conditions: (Column sunfire C18 (19*250) MM 5 MICRON; Mobile Phase A: 0.1% FA in water 70%, Mobile Phase B: acetonitrile 10%) to afford the desired product 3'-fluoro-N-(5-((4-hydroxybicyclo(2.2.2)octan-1-yl)methoxy)-1,3,4-thiadiazol-2-yl)-5'-methoxy-2',6-dimethyl-(4,4'-bipyridine)-3-carboxamide (30 mg, 0.058 mmol, 23.01% yield) as a white solid. MS (ESI) calculated for ($C_{25}H_{28}FN_5O_4S$) $(M+1)^+$, 514.19; found, 514.2. 1H-NMR (400 MHz, DMSO-$d^6$): δ 12.95 (s, 1H), 8.89 (s, 1H), 8.17 (s, 1H), 7.41 (s, 1H), 4.06 (s, 2H), 3.68 (s, 3H), 2.59 (s, 3H), 2.43 (d, J=2.80 Hz, 3H), 1.62-1.47 (m, 12H).

Example 220 and 221

(S)-2'-chloro-N-(5-((6,6-dimethyl-1,4-dioxan-2-yl)methoxy)-1,3,4-thiadiazol-2-yl)-5'-methoxy-6-methyl-(4,4'-bipyridine)-3-carboxamide and (R)-2'-chloro-N-(5-((6,6-dimethyl-1,4-dioxan-2-yl)methoxy)-1,3,4-thiadiazol-2-yl)-5'-methoxy-6-methyl-(4,4'-bipyridine)-3-carboxamide

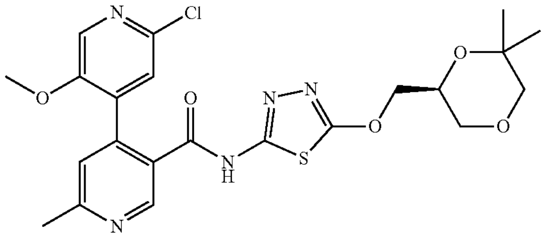

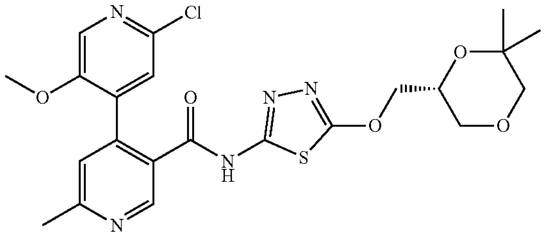

Step-1: O-((6,6-dimethyl-1,4-dioxan-2-yl)methyl)S-methyl carbonodithioate

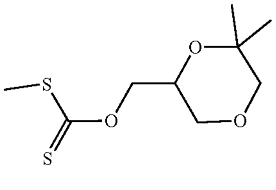

To a stirred solution of (6,6-dimethyl-1,4-dioxan-2-yl)methanol (500 mg, 3.42 mmol) in Tetrahydrofuran (THF) (10 mL) under nitrogen at 0° C. was added sodium hydride (205 mg, 5.13 mmol) portionwise over 5 min. After addition reaction mixture was stirred at room temperature for 30 min. After 30 min, to the above reaction mixture were added carbon disulfide (0.412 mL, 6.84 mmol) followed by methyl iodide (0.214 mL, 3.42 mmol) at room temperature. The reaction mixture was stirred at room temperature for additional 30 mins. After 30 mins the reaction was quenched with cold water and extracted with ethyl acetate (50 mL×2). The combined organic layer was dried over sodium sulphate, filtered and concentrated under vacuum to afford crude product as a yellow oil.

The crude residue was pre-absorbed on silica (using 5 mL DCM, 4 g of silica (60-120 mesh), loaded onto a Biotage 40 g SNAP cartridge and eluted at 5-15% of ethyl acetate in petroleum ether for 40 mins with flow rate 15 mL/min. The appropriate fractions were collected and concentrated under vacuum to afford O-((6,6-dimethyl-1,4-dioxan-2-yl)methyl) S-methyl carbonodithioate (600 mg, 2.509 mmol, 73.4% yield) was isolated as a yellow solid. MS (ESI) calculated for ($C_9H_{16}O_3S_2$) $(M+1)^+$; 237.06; found, 237.0.

Step-2: O-((6,6-dimethyl-1,4-dioxan-2-yl)methyl) hydrazinecarbothioate

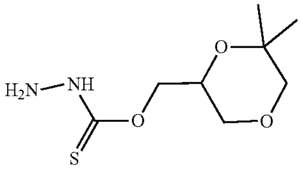

To a stirred solution of afford O-((6,6-dimethyl-1,4-dioxan-2-yl)methyl)S-methyl carbonodithioate (550 mg, 2.327 mmol) in Methanol (10 mL) was added hydrazine hydrate (116 mg, 2.327 mmol) at rt under nitrogen. The reaction mixture was stirred for 20 mins at rt. Completion of reaction was confirmed by TLC. After completion the organic solvent was removed under vacuum. The residue was diluted with water. The aqueous layer was extracted with ethyl acetate (50 mL×2). The combined organic layers were washed with saturated brine solution, dried over anhydrous sodium sulfate, filtered, and concentrated under vacuum to afford O-((6,6-dimethyl-1,4-dioxan-2-yl)methyl) hydrazinecarbothioate (300 mg, 1.294 mmol, 55.6% yield) as pink color gum. MS (ESI) calculated for ($C_8H_{16}N_2O_3S$) $(M+1)^+$; 221.10; found, 221.2.

Step-3: 5-((6,6-dimethyl-1,4-dioxan-2-yl)methoxy)-1,3,4-thiadiazol-2-amine

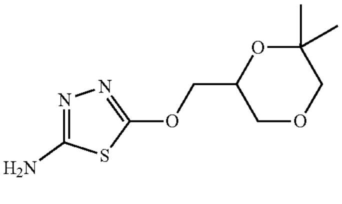 [SMILES: CC1(C)COCC(COc2nnc(N)s2)O1]

To a stirred solution of O-((6,6-dimethyl-1,4-dioxan-2-yl) methyl) hydrazinecarbothioate (300 mg, 1.362 mmol) in Ethanol (10 mL) were added TEA (0.190 mL, 1.362 mmol), followed by Cyanogen bromide (144 mg, 1.362 mmol) at room temperature. The reaction mixture was stirred at room temperature for 10 min. Completion of reaction was confirmed by TLC. After completion the organic solvent was removed under vacuum. The residue was diluted with water. The aqueous layer was extracted with ethyl acetate (30 mL×3). The combined organic layers were washed with brine, dried over anhydrous sodium sulfate, filtered, and concentrated under vacuum to afford 5-((6,6-dimethyl-1,4-dioxan-2-yl)methoxy)-1,3,4-thiadiazol-2-amine (210 mg, 0.599 mmol, 44.0% yield) as a brown gum. MS (ESI) calculated for ($C_9H_{15}N_3O_3S$) $(M+1)^+$; 246.09; found, 246.0.

Step-4: 2'-chloro-N-(5-((6,6-dimethyl-1,4-dioxan-2-yl)methoxy)-1,3,4-thiadiazol-2-yl)-5'-methoxy-6-methyl-(4,4'-bipyridine)-3-carboxamide

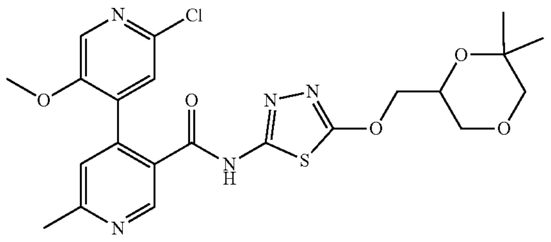

To a stirred solution of Intermediate H (180 mg, 0.646 mmol) in Acetonitrile (6 mL) and N, N-Dimethylformamide (DMF) (2.5 mL) were added 1-methylimidazole (212 mg, 2.58 mmol), Chloro-N, N,N',N'-tetramethylformamidinium hexafluorophosphate (199 mg, 0.71 mmol) and 5-((6,6-dimethyl-1,4-dioxan-2-yl)methoxy)-1,3,4-thiadiazol-2-amine (158 mg, 0.646 mmol) at rt under nitrogen. The reaction mixture was stirred for 2.5 h. The reaction mixture was quenched with cold water and extracted with ethyl acetate (50 mL×2). The combined organic layers were washed with brine, dried over anhydrous sodium sulfate, filtered, and concentrated under vacuum to afford the crude product as a brown solid.

The crude residue was pre-absorbed on silica (using 3 mL DCM, 3 g of silica (60-120 mesh), loaded onto a Biotage 25 g SNAP cartridge and eluted at 2-10% of ethyl acetate in petroleum ether for 30 mins with flow rate 15 mL/min. The appropriate fractions were collected and concentrated under vacuum to afford 2'-chloro-N-(5-((6,6-dimethyl-1,4-dioxan-2-yl)methoxy)-1,3,4-thiadiazol-2-yl)-5'-methoxy-6-methyl-(4,4'-bipyridine)-3-carboxamide (120 mg, 0.229 mmol, 35.4% yield) as a light brown solid. MS (ESI) calculated for ($C_{22}H_{24}ClN_5O_5S$) $(M+1)^+$; 506.13; found, 506.2.

Step-5: (S)-2'-chloro-N-(5-((6,6-dimethyl-1,4-dioxan-2-yl)methoxy)-1,3,4-thiadiazol-2-yl)-5'-methoxy-6-methyl-(4,4'-bipyridine)-3-carboxamide and (R)-2'-chloro-N-(5-((6,6-dimethyl-1,4-dioxan-2-yl)methoxy)-1,3,4-thiadiazol-2-yl)-5'-methoxy-6-methyl-(4,4'-bipyridine)-3-carboxamide

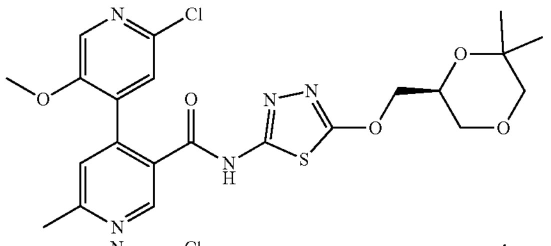

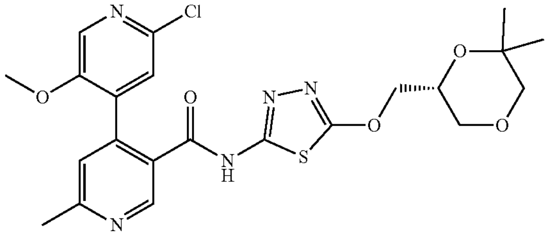

2'-chloro-N-(5-((6,6-dimethyl-1,4-dioxan-2-yl) methoxy)-1,3,4-thiadiazol-2-yl)-5'-methoxy-6-methyl-(4,4'-bipyridine)-3-carboxamide (120 mg) was purified by Chiral SFC by using following method with the following conditions:

Column: Lux Cellulose-2 (250*30)mm, 5 µm, Mobile Phase: CO2: 0.5% Isopropyl Amine in IPA (60:40)%, Total Flow: 100 g/min, Back pressure: 100 bar, Wave length: 220 nm, Cycle time: 9.0 min, 120 mg of sample was dissolved in 3.0 mL of MeOH/Acetonitrile and injected 600 µl/injection.

After SFC purification, the two appropriate fractions were collected. The absolute stereochemistry of each fraction was not determined.

Fraction-1 (first eluting fraction) was concentrated and lyophilized to afford ((S)-2'-chloro-N-(5-((6,6-dimethyl-1,4-dioxan-2-yl)methoxy)-1,3,4-thiadiazol-2-yl)-5'-methoxy-6-methyl-(4,4'-bipyridine)-3-carboxamide (50 mg) as an off-white solid.

$^1H$ NMR in DMSO-$d_6$ showed the required protons of the desired compound along with isopropyl amine.

To remove the isopropyl amine, 50 mg of ((S)-2'-chloro-N-(5-((6,6-dimethyl-1,4-dioxan-2-yl)methoxy)-1,3,4-thiadiazol-2-yl)-5'-methoxy-6-methyl-(4,4'-bipyridine)-3-carboxamide was purified by following preparative HPLC conditions: (Column: X-SELECT C18(20*250) MM 5 MICRON; Mobile Phase A: 10 mM ABC in water 60%, Mobile Phase B: acetonitrile 40%) to afford ((S)-2'-chloro-N-(5-((6,6-dimethyl-1,4-dioxan-2-yl)methoxy)-1,3,4-thiadiazol-2-yl)-5'-methoxy-6-methyl-(4,4'-bipyridine)-3-carboxamide, isomer 1 (30 mg) as an off-white solid. MS (ESI) calculated for ($C_{22}H_{24}ClN_5O_5S$) $(M+1)^+$; 506.13; found: 506.2. 1H-NMR (400 MHz, DMSO-$d_6$): δ 12.91 (s, 1H), 8.80 (s, 1H), 8.17 (s, 1H), 7.55 (s, 1H), 7.44 (s, 1H), 4.40-4.28 (m, 2H), 4.21-4.12 (m, 1H), 3.82 (dd, J=2.8 Hz, 11.2 Hz, 1H), 3.63 (s, 3H), 3.48 (d, J=11.2 Hz, 1H), 3.25-3.13 (m, 2H), 2.59 (s, 3H), 1.27 (s, 3H), 1.06 (s, 3H).

Fraction 2 (second eluting fraction) was concentrated and lyophilized to afford (R)-2'-chloro-N-(5-((6,6-dimethyl-1,4-dioxan-2-yl)methoxy)-1,3,4-thiadiazol-2-yl)-5'-methoxy-6-methyl-(4,4'-bipyridine)-3-carboxamide (50 mg) as an off-white solid.

$^1$H NMR in DMSO-$d_6$ showed the required protons of the desired compound along with isopropyl amine.

To remove the isopropyl amine, 50 mg of (R)-2'-chloro-N-(5-((6,6-dimethyl-1,4-dioxan-2-yl)methoxy)-1,3,4-thiadiazol-2-yl)-5'-methoxy-6-methyl-(4,4'-bipyridine)-3-carboxamide was purified by following preparative HPLC conditions: (Column: X-SELECT C18(20*250) MM 5 MICRON; Mobile Phase A: 10 Mm ABC in water 60%, Mobile Phase B: acetonitrile 40%) to R)-2'-chloro-N-(5-((6,6-dimethyl-1,4-dioxan-2-yl)methoxy)-1,3,4-thiadiazol-2-yl)-5'-methoxy-6-methyl-(4,4'-bipyridine)-3-carboxamide, isomer 2 (30 mg) as an off-white solid. MS (ESI) calculated for ($C_{22}H_{24}ClN_5O_5S$) $(M+1)^+$; 506.13; found; 506.2. 1H-NMR (400 MHz, DMSO-$d_6$): δ 12.91 (s, 1H), 8.81 (s, 1H), 8.17 (s, 1H), 7.54 (s, 1H), 7.42 (s, 1H), 4.39-4.27 (m, 2H), 4.20-4.12 (m, 1H), 3.82 (dd, J=2.8 Hz, 11.2 Hz, 1H), 3.63 (s, 3H), 3.48 (d, J=11.2 Hz, 1H), 3.24-3.12 (m, 2H), 2.59 (s, 3H), 1.27 (s, 3H), 1.06 (s, 3H).

Example 224

N-(5-((5-oxaspiro(3.4)octan-7-yl)methoxy)-1,3,4-thiadiazol-2-yl)-2'-chloro-5'-methoxy-6-methyl-(4,4'-bipyridine)-3-carboxamide

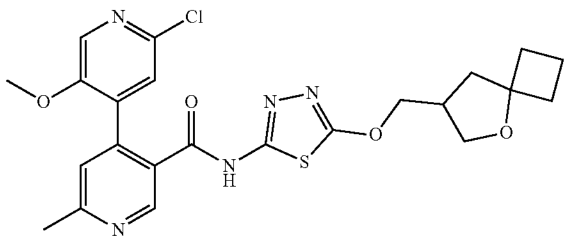 [SMILES: COc1cnc(Cl)cc1-c1cc(C)ncc1C(=O)Nc1nnc(OCC2COC3(CCC3)C2)s1]

Step-1: O-((5-oxaspiro(3.4)octan-7-yl)methyl)S-methyl carbonodithioate

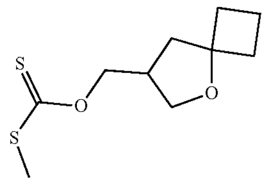

To a stirred solution of (5-oxaspiro(3.4)octan-7-yl)methanol (0.5 g, 3.52 mmol), in Tetrahydrofuran (THF) (10 mL) stirred under nitrogen at 0° C. was added sodium hydride (0.281 g, 7.03 mmol) portion wise during 5 min. After addition reaction mixture was stirred at room temperature for 30 minutes. After 30 min to the above reaction mixture were added carbon disulfide (0.424 mL, 7.03 mmol) followed by Methyl iodide (0.220 mL, 3.52 mmol) at room temperature. Then the reaction mixture was stirred at room temperature for additional 30 minutes. After completion the reaction mixture was slowly quenched with ice cold water (10 mL) and extracted with ethyl acetate (2×20 mL). The organic layer was dried over sodium sulphate, filtered and concentrated under reduced pressure to afford crude product as a yellow liquid.

The crude residue was pre-absorbed on silica (using 5 mL DCM, 3 g of silica (60-120 mesh), loaded onto a Biotage 12 g SNAP cartridge and eluted at 5-15% of Ethyl acetate in petroleum ether for 60 mins with flow rate 25 mL/min. The appropriate fractions were collected and concentrated under vacuum to afford O-((5-oxaspiro(3.4)octan-7-yl)methyl)S-methyl carbonodithioate (0.720 g, 3.04 mmol, 87% yield) as a yellow liquid. MS (ESI): Calculated for $C_{10}H_{16}O_2S_2$$(M+1)^+$, 233.07; found, 233.2.

Step-2: O-((5-oxaspiro(3.4)octan-7-yl)methyl) hydrazinecarbothioate

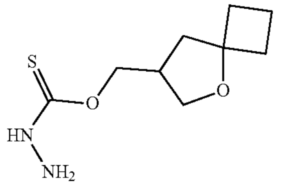 [SMILES: NNC(=S)OCC1COC2(CCC2)C1]

To a stirred solution of O-((5-oxaspiro(3.4)octan-7-yl) methyl)S-methyl carbonodithioate (710 mg, 3.06 mmol), in Methanol (10 mL) was added hydrazine hydrate (153 mg, 3.06 mmol) at room temperature. The reaction mixture was stirred at room temperature for 2 h. After completion, the reaction mixture was concentrated under reduced pressure. The resulting residue diluted with water (10 mL) and extracted with ethyl acetate (2×20 mL). The organic layer dried over anhydrous sodium sulphate, filtered concentrated under reduced pressure to afford O-((5-oxaspiro(3.4)octan-7-yl)methyl) hydrazinecarbothioate (610 mg, 2.78 mmol, 91% yield) as a yellow liquid. MS (ESI): Calculated for $C_9H_{16}N_2O_2S$ $(M+1)^+$, 217.10; found, 217.2.

Step-3: 5-((5-oxaspiro(3.4)octan-7-yl)methoxy)-1,3,4-thiadiazol-2-amine

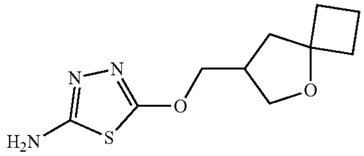 [SMILES: Nc1nnc(OCC2COC3(CCC3)C2)s1]

To a stirred solution of O-((5-oxaspiro(3.4)octan-7-yl) methyl) hydrazinecarbothioate (620 mg, 2.87 mmol), in ethanol (8 mL) were added TEA (0.400 mL, 2.87 mmol) followed by cyanogen bromide (304 mg, 2.87 mmol) at room temperature. The reaction mixture was stirred at room temperature for 3 h. After completion, the reaction mixture was concentrated under vacuum. The resulting residue diluted with water (20 mL) and extracted with ethyl acetate (2×50 mL). The organic layer dried over anhydrous sodium sulphate, filtered concentrated under reduced pressure to afford the product as a brown gum.

The crude product was triturated with MTBE (10 mL) and dried under reduced pressure to afford 5-((5-oxaspiro(3.4)octan-7-yl)methoxy)-1,3,4-thiadiazol-2-amine (270 mg, 1.119 mmol, 39.0% yield) as a yellow solid. MS (ESI): Calculated for $C_{10}H_{15}N_3O_2S$ $(M+1)^+$, 242.09; found, 242.0.

Step-4: N-(5-((5-oxaspiro(3.4)octan-7-yl)methoxy)-1,3,4-thiadiazol-2-yl)-2'-chloro-5'-methoxy-6-methyl-(4,4'-bipyridine)-3-carboxamide

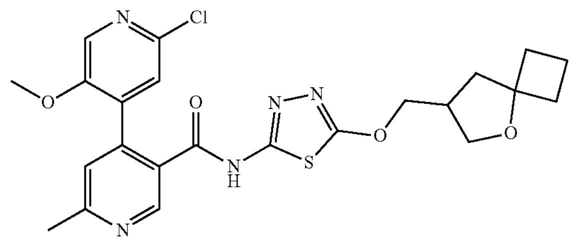 [SMILES: COc1cnc(Cl)cc1-c1cc(C)ncc1C(=O)Nc1nnc(OCC2COC3(CCC3)C2)s1]

To a stirred solution of Intermediate H (250 mg, 0.897 mmol), in Acetonitrile (2 mL) and N,N-Dimethylformamide (DMF) (1 mL) were added Chloro-N,N,N',N'-tetramethyl-formamidinium hexafluorophosphate (277 mg, 0.987 mmol), 1-methylimidazole (0.358 mL, 4.49 mmol) and 5-((5-oxaspiro(3.4)octan-7-yl)methoxy)-1,3,4-thiadiazol-2-amine (216 mg, 0.897 mmol) at room temperature. The reaction mixture was stirred at room temperature for 2.5 h. After completion, the reaction mixture was diluted with water (10 mL) and extracted with ethyl acetate (2×20 mL). The combined organic layer dried over anhydrous sodium sulphate, filtered concentrated under reduced pressure to afford the product as a yellow gum.

The Crude product was triturated with MTBE (3×10 mL) and dried under vacuum to afford N-(5-((5-oxaspiro(3.4)octan-7-yl)methoxy)-1,3,4-thiadiazol-2-yl)-2'-chloro-5'-methoxy-6-methyl-(4,4'-bipyridine)-3-carboxamide (52 mg, 0.103 mmol, 11.46% yield) as a beige solid. MS (ESI): Calculated for $C_{23}H_{24}ClN_5O_4S$ $(M+1)^+$, 502.13, Observed: 501.7. 1H-NMR (400 MHz, DMSO-$d^6$): δ 12.94 (s, 1H), 8.81 (s, 1H), 8.17 (s, 1H), 7.53 (s, 1H), 7.42 (s, 1H), 4.47-4.29 (m, 2H), 3.81 (t, J=8.40 Hz, 1H), 3.63 (s, 3H), 3.54 (t, J=8.40 Hz, 1H), 2.83-2.70 (m, 1H), 2.59 (s, 3H), 2.25-2.10 (m, 2H), 2.10-1.90 (m, 3H), 1.80-1.45 (m, 3H), Example 225

N-(5-((2,5-dioxaspiro(3.4)octan-7-yl)methoxy)-1,3,4-thiadiazol-2-yl)-2'-chloro-5'-methoxy-6-methyl-(4,4'-bipyridine)-3-carboxamide

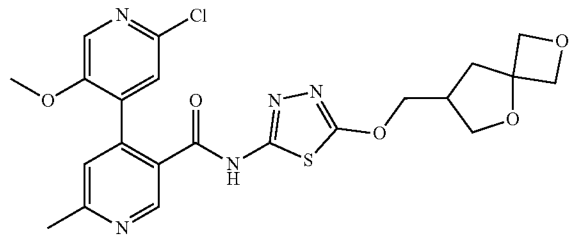 [SMILES: COc1cnc(Cl)cc1-c1cc(C)ncc1C(=O)Nc1nnc(OCC2COC3(COC3)C2)s1]

Step-1: O-((2,5-dioxaspiro(3.4)octan-7-yl)methyl)S-methyl carbonodithioate

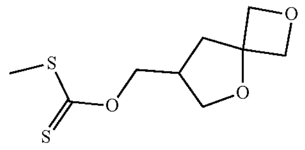

To a stirred solution of (2,5-dioxaspiro(3.4)octan-7-yl) methanol (0.5 g, 3.47 mmol) in Tetrahydrofuran (THF) (10 mL) under nitrogen at 0° C. was added NaH (0.277 g, 6.94 mmol) portions. After addition reaction mixture was stirred at room temperature for 30 min. After 30 min to the above reaction mixture were added carbon disulfide (0.418 mL, 6.94 mmol) followed by methyl iodide (0.217 mL, 3.47 mmol) at room temperature. The reaction mixture was stirred at room temperature for additional 30 mins. After 30 mins the reaction was quenched with cold water and extracted with ethyl acetate (20 mL×2). The combine organic layer was dried over sodium sulphate, filtered and concentrated under vacuum to afford O-((2,5-dioxaspiro(3.4)octan-7-yl)methyl)S-methyl carbonodithioate (810 mg, 3.15 mmol, 91% yield) as an orange oil. MS (ESI) calculated for $(C_9H_{14}O_3S_2)$ $(M+1)^+$, 235.05; found, 235.0.

Step-2: O-((2,5-dioxaspiro(3.4)octan-7-yl)methyl) hydrazinecarbothioate

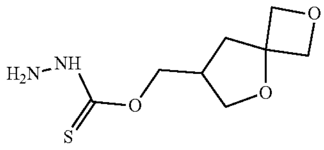 [SMILES: NNC(=S)OCC1COC2(COC2)C1]

To a stirred solution of O-((2,5-dioxaspiro(3.4)octan-7-yl)methyl)S-methyl carbonodithioate (0.81 g, 3.46 mmol) in Methanol (10 mL) was added hydrazine hydrate (0.173 g, 3.46 mmol) at rt under nitrogen. The reaction mixture was stirred for 2 h at rt. The organic solvent was removed under vacuum. The residue was diluted with water. The aqueous layer was extracted with ethyl acetate (30 mL×2). The combined organic layers were washed with brine, dried over anhydrous sodium sulfate, filtered, and concentrated under vacuum to afford O-((2,5-dioxaspiro(3.4)octan-7-yl)methyl) hydrazinecarbothioate (480 mg, 2.087 mmol, 60.4% yield) was isolated as an orange liquid. MS (ESI) calculated for $(C_8H_{14}N_2O_3S)$ $(M+1)^+$, 219.08; found, 219.2.

Step-3: 5-((2,5-dioxaspiro(3.4)octan-7-yl)methoxy)-1,3,4-thiadiazol-2-amine

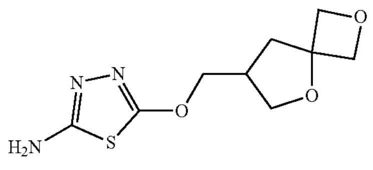

To a stirred solution of O-((2,5-dioxaspiro(3.4)octan-7-yl)methyl) hydrazinecarbothioate (480 mg, 2.199 mmol), in Ethanol (5 mL) were added TEA (0.307 mL, 2.199 mmol) followed by Cyanogen bromide (233 mg, 2.199 mmol) at room temperature. The reaction mixture was stirred at room temperature for 1 h. The organic solvent was removed under vacuum. The residue was diluted with water. The aqueous layer was extracted with ethyl acetate (15 mL×4). The combined organic layers were washed with brine, dried over anhydrous sodium sulfate, filtered, and concentrated under vacuum to get the crude product as an orange viscous liquid.

The crude product was washed with MTBE (3×10 mL) and dried under vacuum to afford pure 5-((2,5-dioxaspiro(3.4)octan-7-yl)methoxy)-1,3,4-thiadiazol-2-amine (250 mg, 0.449 mmol, 20.42% yield) as an orange viscous liquid. MS (ESI) calculated for ($C_9H_{13}N_3O_3S$) $(M+1)^+$, 244.08; found, 244.1.

Step-4: N-(5-((2,5-dioxaspiro(3.4)octan-7-yl)methoxy)-1,3,4-thiadiazol-2-yl)-2'-chloro-5'-methoxy-6-methyl-(4,4'-bipyridine)-3-carboxamide

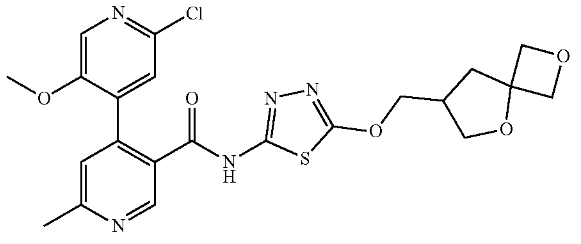 [SMILES: COc1cnc(Cl)cc1-c1cc(C)ncc1C(=O)Nc1nnc(OCC2COC3(COC3)C2)s1]

To a stirred solution of Intermediate H (115 mg, 0.413 mmol) and 5-((2,5-dioxaspiro(3.4)octan-7-yl)methoxy)-1,3,4-thiadiazol-2-amine (100 mg, 0.413 mmol) in Acetonitrile (2 mL) and N,N-Dimethylformamide (DMF) (0.2 mL) was added 1-methylimidazole (169 mg, 2.063 mmol) and Chloro-N,N,N',N'-tetramethylformamidinium hexafluorophosphate (127 mg, 0.454 mmol) at rt under nitrogen. The reaction mixture was stirred for 1 h. The organic solvent was removed under vacuum. The residue was diluted with water (10 mL) and extracted with ethyl acetate (20 mL×3). The combined organic layers were washed with brine, dried over anhydrous sodium sulfate, filtered, and concentrated under vacuum to afford the crude product as an orange gum.

The crude product was purified by prep-HPLC with the following conditions: (Column: YMC-C18(20*250) 5 MICRON; Mobile Phase A: 10 mM ABC in MQ water 90%, Mobile Phase B: acetonitrile 10%) to afford N-(5-((2,5-dioxaspiro(3.4)octan-7-yl)methoxy)-1,3,4-thiadiazol-2-yl)-2'-chloro-5'-methoxy-6-methyl-(4,4'-bipyridine)-3-carboxamide (80 mg, 0.156 mmol, 37.9% yield) as a yellow solid. MS (ESI) calculated for ($C_{22}H_{22}ClN_5O_5S$) $(M+1)^+$, 504.11; found, 504.0. 1H-NMR (400 MHz, DMSO-$d^6$): δ 13.00 (brs, 1H), 8.81 (s, 1H), 8.17 (s, 1H), 7.54 (s, 1H), 7.42 (s, 1H), 4.62-4.50 (m, 4H), 4.40-4.25 (m, 2H), 3.88 (dd, J=7.2 Hz, 8.80 Hz, 1H), 3.68-3.60 (m, 4H), 2.72-2.60 (m, 1H), 2.59 (s, 3H), 2.42-2.30 (m, 1H), 2.03 (dd, J=6.4 Hz, 13.2 Hz, 1H).

Example 226

(S)—N-(5-((5-oxaspiro(3.4)octan-7-yl)methoxy)-1,3,4-thiadiazol-2-yl)-2'-chloro-5'-methoxy-6-methyl-(4,4'-bipyridine)-3-carboxamide

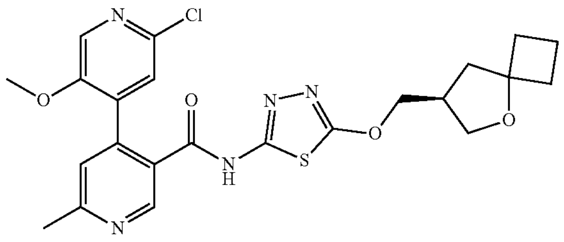 [SMILES: COc1cnc(Cl)cc1-c1cc(C)ncc1C(=O)Nc1nnc(OC[C@@H]2COC3(CCC3)C2)s1]

Step-1: Chiral SFC Separation of (S)-5-((5-oxaspiro(3.4)octan-7-yl)methoxy)-1,3,4-thiadiazol-2-amine and (R)-5-((5-oxaspiro(3.4)octan-7-yl)methoxy)-1,3,4-thiadiazol-2-amine

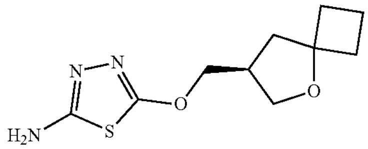

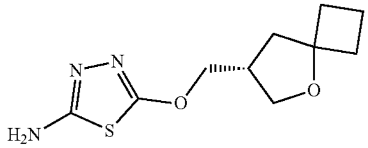

The racemic compound (280 mg, 1.160 mmol) was separated by chiral SFC with the following conditions: (Column: YMC Cellulose-SC (250*30) mm, 5 μm; Mobile Phase A: $CO_2$, Mobile Phase B: 0.1% Isopropyl amine in {(Isopropyl alcohol: Acetonitrile) (1:1)}; Flow rate: 100 g/min; Column Temperature (° C.): 35 Back Pressure (bar): 100; Wave Length: 254 nm; Sample Solvent: 3.0 mL MeOH-HPLC; Injection Volume: 350 μL; RT1 (min): 4.35; RT2 (min): 6.21; to afford (S)-5-((5-oxaspiro(3.4)octan-7-yl)methoxy)-1,3,4-thiadiazol-2-amine, isomer 1 (88 mg, 0.364 mmol, 31.4% yield) as pale brown color solid with the first peak (first eluting fraction) on chiral SFC with shorter retention time and (R)-5-((5-oxaspiro(3.4)octan-7-yl)methoxy)-1,3,4-thiadiazol-2-amine, isomer 2 (89 mg, 0.349 mmol, 30.0% yield) as pale brown color solid with the second peak (second eluting fraction) on chiral SFC with longer retention time. The absolute stereochemistry was not determined.

Isomer 1: (S)-5-((5-oxaspiro(3.4)octan-7-yl)methoxy)-1,3,4-thiadiazol-2-amine: MS (ESI) calculated for ($C_{10}H_{15}N_3O_2S$) $(M+1)^+$, 242.09; found, 242.2. 1H-NMR (400 MHz, DMSO-$d_6$): δ 6.75 (s, 2H), 4.32-4.16 (m, 2H), 3.79 (q, J=7.60 Hz, 1H), 3.50 (q, J=6.40 Hz, 1H), 2.78-2.62 (m, 1H), 2.22-2.09 (m, 2H), 2.08-1.90 (m, 3H), 1.73-1.45 (m, 3H), Isomer 2: (R)-5-((5-oxaspiro(3.4)octan-7-yl)methoxy)-1,3,4-thiadiazol-2-amine: MS (ESI) calculated for ($C_{10}H_{15}N_3O_2S$) $(M+1)^+$, 242.09; found, 242.2. 1H-NMR (400 MHz, DMSO-$d_6$): δ 6.75 (s, 2H), 4.32-4.16 (m, 2H), 3.79 (q, J=7.60 Hz, 1H), 3.50 (q, J=6.40 Hz, 1H), 2.77-2.62 (m, 1H), 2.22-2.09 (m, 2H), 2.08-1.90 (m, 3H), 1.73-1.45 (m, 3H), Step-2: (S)—N-(5-((5-oxaspiro(3.4)octan-7-yl)methoxy)-1,3,4-thiadiazol-2-yl)-2'-chloro-5'-methoxy-6-methyl-(4,4'-bipyridine)-3-carboxamide

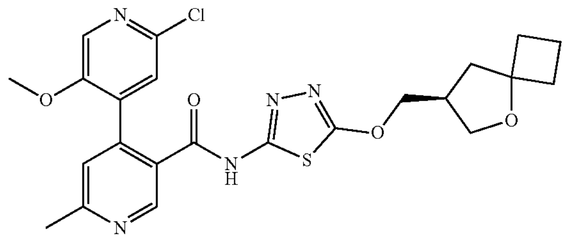 [SMILES: COc1cnc(Cl)cc1-c1cc(C)ncc1C(=O)Nc1nnc(OC[C@@H]2COC3(CCC3)C2)s1]

To a stirred solution of Intermediate H (100 mg, 0.359 mmol), in Acetonitrile (2 mL) were added Chloro-N,N,N',N'-tetramethylformamidinium hexafluorophosphate (111 mg, 0.395 mmol), 1-methylimidazole (0.143 mL, 1.794 mmol) and (S)-5-((5-oxaspiro(3.4)octan-7-yl)methoxy)-1,3,4-thiadiazol-2-amine (Isomer 1) (87 mg, 0.359 mmol) at room temperature. The reaction mixture was stirred at room temperature for 16 h. After 16 h TLC indicated both starting materials and formation of new non polar product. To the above reaction mixture were again added Chloro-N,N,N',N'-tetramethylformamidinium hexafluorophosphate (50.3 mg, 0.179 mmol), 1-methylimidazole (0.057 mL, 0.718 mmol) and N,N-Dimethylformamide (DMF) (0.5 mL) at room temperature. The reaction mixture was stirred at room temperature for additional 2 h. After 2 h the reaction mixture was diluted with water (10 mL) and extracted with ethyl acetate (2×20 mL). The combined organic layer dried over anhydrous sodium sulphate, filtered concentrated under vacuum to afford the crude product as a yellow gum.

The crude product was purified by prep-HPLC with the following conditions: (Column: X-SELECT C18(10*150) MM 5 MICRON; Mobile Phase A: 10 mM ABC in Milli Q Water 9000, Mobile Phase B: acetonitrile 10%) to afford (S)—N-(5-((5-oxaspiro(3.4)octan-7-yl)methoxy)-1,3,4-thiadiazol-2-yl)-2'-chloro-5'-methoxy-6-methyl-(4,4'-bipyridine)-3-carboxamide (55 mg, 0.110 mmol, 30.5% yield) as an off white solid. The absolute stereochemistry was not determined. MS (ESI): Calculated for $C_{23}H_{24}ClN_5O_4S$ $(M+1)^+$, 502.13; found, 502.2. 1H-NMR (400 MHz, DMSO-$d^6$): δ 12.92 (s, 1H), 8.80 (s, 1H), 8.17 (s, 1H), 7.55 (s, 1H), 7.44 (s, 1H), 4.49-4.30 (m, 2H), 3.89-3.77 (m, 1H), 3.63 (s, 3H), 3.59-3.50 (m, 1H), 2.83-2.70 (m, 1H), 2.59 (s, 3H), 2.23-2.10 (m, 2H), 2.09-1.90 (m, 3H), 1.80-1.70 (m, 1H), 1.69-1.55 (m, 1H), 1.54-1.45 (m, 1H), Example 227

(R)—N-(5-((5-oxaspiro(3.4)octan-7-yl)methoxy)-1,3,4-thiadiazol-2-yl)-2'-chloro-5'-methoxy-6-methyl-(4,4'-bipyridine)-3-carboxamide

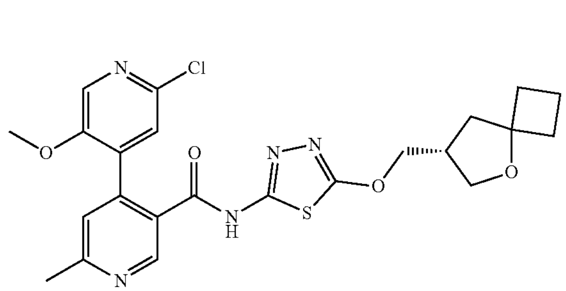 [SMILES: COc1cnc(Cl)cc1-c1cc(C)ncc1C(=O)Nc1nnc(OC[C@H]2COC3(CCC3)C2)s1]

Step-1: (R)—N-(5-((5-oxaspiro(3.4)octan-7-yl)methoxy)-1,3,4-thiadiazol-2-yl)-2'-chloro-5'-methoxy-6-methyl-(4,4'-bipyridine)-3-carboxamide

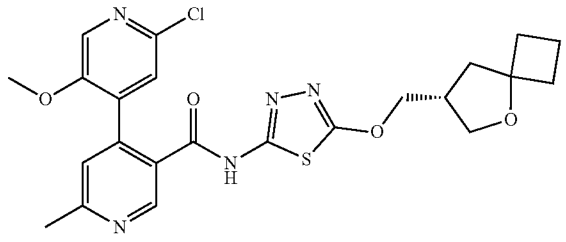 [SMILES: COc1cnc(Cl)cc1-c1cc(C)ncc1C(=O)Nc1nnc(OC[C@H]2COC3(CCC3)C2)s1]

To a stirred solution of Intermediate H (100 mg, 0.359 mmol), in Acetonitrile (2 mL) were added Chloro-N,N,N',N'-tetramethylformamidinium hexafluorophosphate (111 mg, 0.395 mmol), 1-methylimidazole (0.143 mL, 1.794 mmol) and (R)-5-((5-oxaspiro(3.4)octan-7-yl)methoxy)-1,3,4-thiadiazol-2-amine (Isomer 2, Example 226, Step 1) (87 mg, 0.359 mmol) at room temperature. The reaction mixture was stirred at room temperature for 16 h. After 16 h TLC indicated both starting materials and formation of new non polar product. To the above reaction mixture were again added Chloro-N,N,N',N'-tetramethylformamidinium hexafluorophosphate (50.3 mg, 0.179 mmol), 1-methylimidazole (0.057 mL, 0.718 mmol) and N,N-Dimethylformamide (DMF) (0.5 mL) at room temperature. The reaction mixture was stirred at room temperature for additional 2 h. After 2 h the reaction mixture was diluted with water (10 mL) and extracted with ethyl acetate (2×20 mL). The combined organic layer dried over anhydrous sodium sulphate, filtered concentrated under vacuum to afford the crude product as a yellow gum.

The crude product was purified by prep-HPLC with the following conditions: (Column: x-bridge-C8 (10×150) MM 5 MICRON; Mobile Phase A: 10 mM ABC in Milli Q Water 70%, Mobile Phase B: acetonitrile 30%) to afford (R)—N-(5-((5-oxaspiro(3.4)octan-7-yl)methoxy)-1,3,4-thiadiazol-2-yl)-2'-chloro-5'-methoxy-6-methyl-(4,4'-bipyridine)-3-carboxamide (65 mg, 0.127 mmol, 35.5% yield) as an off white solid. The absolute stereochemistry was not determined. MS (ESI): Calculated for $C_{23}H_{24}ClN_5O_4S$ $(M+1)^+$, 502.13; found, 502.2. 1H-NMR (400 MHz, DMSO-$d_6$): δ 12.92 (s, 1H), 8.82 (s, 1H), 8.17 (s, 1H), 7.52 (s, 1H), 7.40 (s, 1H), 4.50-4.30 (m, 2H), 3.87-3.77 (m, 1H), 3.63 (s, 3H), 3.59-3.49 (m, 1H), 2.85-2.70 (m, 1H), 2.58 (s, 3H), 2.23-2.10 (m, 2H), 2.09-1.90 (m, 3H), 1.80-1.69 (m, 1H), 1.68-1.55 (m, 1H), 1.54-1.45 (m, 1H).

Example 228, 222 and 223

2'-chloro-N-(5-((5,5-dimethyl-1,4-dioxan-2-yl) methoxy)-1,3,4-thiadiazol-2-yl)-5'-methoxy-6-methyl-(4,4'-bipyridine)-3-carboxamide, (S)-2'-chloro-N-(5-((5,5-dimethyl-1,4-dioxan-2-yl) methoxy)-1,3,4-thiadiazol-2-yl)-5'-methoxy-6-methyl-(4,4'-bipyridine)-3-carboxamide and (R)-2'-chloro-N-(5-((5,5-dimethyl-1,4-dioxan-2-yl) methoxy)-1,3,4-thiadiazol-2-yl)-5'-methoxy-6-methyl-(4,4'-bipyridine)-3-carboxamide

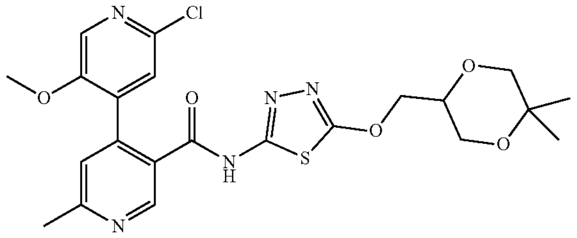

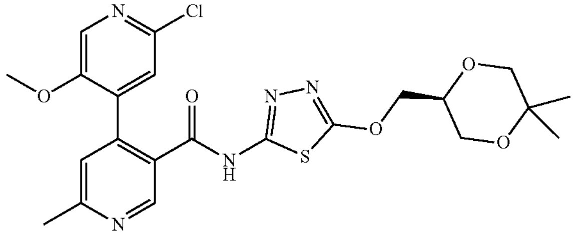

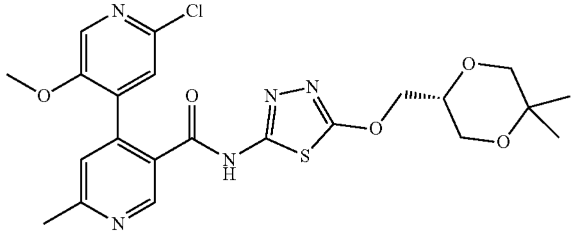

Step-1: O-((5,5-dimethyl-1,4-dioxan-2-yl) methyl)S-methyl carbonodithioate

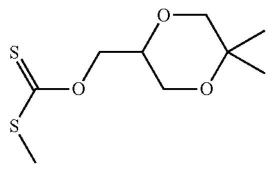

To a stirred solution of (5,5-dimethyl-1,4-dioxan-2-yl) methanol (0.5 g, 3.42 mmol) in Tetrahydrofuran (THF) (10 mL) under nitrogen at 0° C. was added sodium hydride (274 mg, 6.84 mmol) portionwise over 2 min. After addition reaction mixture was stirred at room temperature for 30 min. After 30 min, to the above reaction mixture were added carbon disulfide (0.412 mL, 6.84 mmol) followed by methyl iodide (0.214 mL, 3.42 mmol) at room temperature. The reaction mixture was stirred at room temperature for additional 30 mins. After 30 mins the reaction was quenched with cold water and extracted with ethyl acetate (20 mL×2). The combined organic layer was dried over sodium sulphate, filtered and concentrated under vacuum to afford crude product as a yellow oil.

The crude residue was pre-absorbed on silica (using 10 mL DCM, 4 g of silica (60-120 mesh), loaded onto a Biotage 25 g SNAP cartridge and eluted at 4-6% of ethyl acetate in petroleum ether for 40 mins with flow rate 25 mL/min. The appropriate fractions were collected and concentrated under vacuum to afford O-((5,5-dimethyl-1,4-dioxan-2-yl) methyl) S-methyl carbonodithioate (0.71 g, 2.88 mmol, 84% yield) as a yellow oil. MS (ESI) calculated for ($C_9H_{16}O_3S_2$) (M+1); 237.06; found, 237.0.

Step-2: O-((5,5-dimethyl-1,4-dioxan-2-yl) methyl) hydrazinecarbothioate

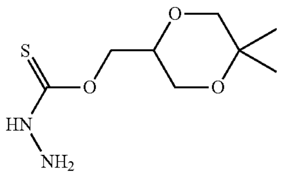

To a stirred solution of afford O-((5,5-dimethyl-1,4-dioxan-2-yl) methyl)S-methyl carbonodithioate (0.71 g, 3.00 mmol) in Methanol (10 mL) was added hydrazine hydrate (165 mg, 3.30 mmol) at rt under nitrogen. The reaction mixture was stirred for 2 h at rt. The organic solvent was removed under vacuum. The residue was diluted with water. The aqueous layer was extracted with ethyl acetate (20 mL×2). The combined organic layers were washed with saturated brine solution, dried over anhydrous sodium sulfate, filtered, and concentrated under vacuum to afford O-((5,5-dimethyl-1,4-dioxan-2-yl) methyl) hydrazinecarbothioate (0.65 g, 2.61 mmol, 87% yield) as a yellow oil. MS (ESI) calculated for ($C_8H_{16}N_2O_3S$) $(M+1)^+$; 221.10; found, 221.2.

Step-3: 5-((5,5-dimethyl-1,4-dioxan-2-yl) methoxy)-1,3,4-thiadiazol-2-amine

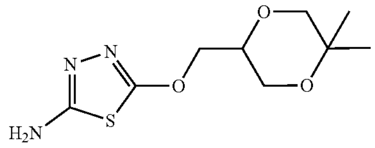 [SMILES: CC1(C)COC(COc2nnc(N)s2)CO1]

To a stirred solution of O-((5,5-dimethyl-1,4-dioxan-2-yl) methyl) hydrazinecarbothioate (650 mg, 2.95 mmol) in Ethanol (8 mL) were added TEA (0.411 mL, 2.95 mmol) followed by Cyanogen bromide (313 mg, 2.95 mmol) at room temperature. The reaction mixture was stirred at room temperature for 3 h. The organic solvent was removed under vacuum. The residue was diluted with water. The aqueous layer was extracted with ethyl acetate (50 mL×2). The combined organic layers were washed with brine, dried over anhydrous sodium sulfate, filtered, and concentrated under vacuum to get the crude product as a brown gum (510 mg). The crude product was washed with n-hexane (20 mL) and dried under reduced pressure to afford 5-((5,5-dimethyl-1,4-dioxan-2-yl) methoxy)-1,3,4-thiadiazol-2-amine (430 mg, 1.680 mmol, 56.9% yield) as a brown solid. MS (ESI) calculated for $(C_9H_{15}N_3O_3S)$ $(M+1)^+$; 246.09; found, 246.0.

Step-4: 2'-chloro-N-(5-((5,5-dimethyl-1,4-dioxan-2-yl)methoxy)-1,3,4-thiadiazol-2-yl)-5'-methoxy-6-methyl-(4,4'-bipyridine)-3-carboxamide

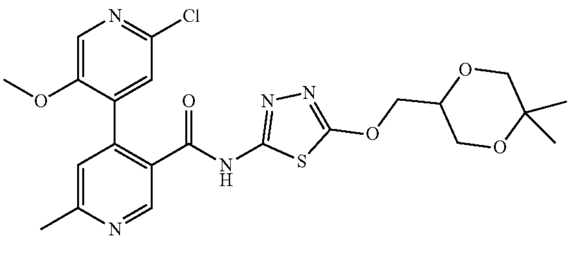

To a stirred solution of Intermediate H (250 mg, 0.897 mmol) in Acetonitrile (5 mL) and N, N-Dimethylformamide (DMF) (2.5 mL) were added 1-methylimidazole (221 mg, 2.69 mmol), Chloro-N, N,N',N'-tetramethylformamidinium hexafluorophosphate (277 mg, 0.987 mmol) and 5-((5,5-dimethyl-1,4-dioxan-2-yl) methoxy)-1,3,4-thiadiazol-2-amine (242 mg, 0.987 mmol) at rt under nitrogen. The reaction mixture was stirred for 3 h. The reaction mixture was quenched with cold water and extracted with ethyl acetate (20 mL×2). The combined organic layers were washed with brine, dried over anhydrous sodium sulfate, filtered, and concentrated under vacuum to afford the crude product as a brown gum.

The crude product was purified by prep-HPLC with the following conditions: (Column: YMC-C8(19*150) MM 5 MICRON; Mobile Phase A: 10 mM ABC in MQ WATER 70%, Mobile Phase B: acetonitrile 30%) to afford 2'-chloro-N-(5-((5,5-dimethyl-1,4-dioxan-2-yl)methoxy)-1,3,4-thiadiazol-2-yl)-5'-methoxy-6-methyl-(4,4'-bipyridine)-3-carboxamide (152 mg, 0.300 mmol, 33.5% yield) as an off-white solid. MS (ESI) calculated for $(C_{22}H_{24}ClN_5O_5S)$ $(M+1)^+$; 506.13; found, 506.2. 1H-NMR (400 MHz, DMSO-$d_6$): δ 12.93 (s, 1H), 8.81 (s, 1H), 8.17 (s, 1H), 7.55 (s, 1H), 7.44 (s, 1H), 4.42 (d, J=4.40 Hz, 2H), 3.85-3.78 (m, 1H), 3.63 (s, 3H), 3.62-3.50 (m, 2H), 3.33-3.28 (m, 2H), 2.59 (s, 3H), 1.24 (s, 3H), 1.05 (s, 3H).

Step-4: (S)-2'-chloro-N-(5-((5,5-dimethyl-1,4-dioxan-2-yl)methoxy)-1,3,4-thiadiazol-2-yl)-5'-methoxy-6-methyl-(4,4'-bipyridine)-3-carboxamide and (R)-2'-chloro-N-(5-((5,5-dimethyl-1,4-dioxan-2-yl)methoxy)-1,3,4-thiadiazol-2-yl)-5'-methoxy-6-methyl-(4,4'-bipyridine)-3-carboxamide

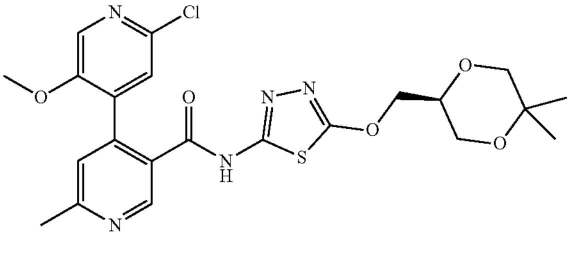

-continued

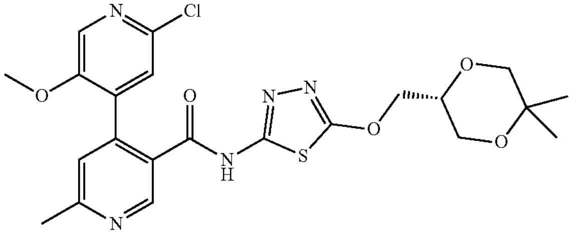

2'-chloro-N-(5-((5,5-dimethyl-1,4-dioxan-2-yl) methoxy)-1,3,4-thiadiazol-2-yl)-5'-methoxy-6-methyl-(4,4'-bipyridine)-3-carboxamide (148 mg) was purified by Chiral SFC by using following method with the following conditions:

Column: Chiralcel OX—H (250*30)mm, 5 μm Mobile Phase: CO2: 0.5% Isopropyl Amine in Methanol (60:40)%, Total Flow: 100 g/min, Back pressure: 120 bar, Wave length: 220 nm, Cycle time: 5.0 min 148 mg of sample was dissolved in 4.0 mL of MeOH/Acetonitrile and injected 500 μl/injection.

After SFC purification, the two appropriate fractions were collected. The absolute stereochemistry of each fraction was not determined.

Fraction-1 (1300 mL) (First eluting fraction) was concentrated and lyophilized to afford (S)-2'-chloro-N-(5-((5,5-dimethyl-1,4-dioxan-2-yl)methoxy)-1,3,4-thiadiazol-2-yl)-5'-methoxy-6-methyl-(4,4'-bipyridine)-3-carboxamide, isomer 1 (86 mg) as an off-white solid. MS (ESI) calculated for $(C_{22}H_{24}ClN_5O_5S)$ $(M+1)^+$; 505.12; found, 506.1 and $^1H$ NMR in DMSO-$d_6$ showed the required protons of the desired compound along with isopropyl amine.

To remove the isopropyl amine, (S)-2'-chloro-N-(5-((5,5-dimethyl-1,4-dioxan-2-yl)methoxy)-1,3,4-thiadiazol-2-yl)-5'-methoxy-6-methyl-(4,4'-bipyridine)-3-carboxamide (86 mg) was purified by following preparative HPLC conditions: (Column:X-bridge C8(10*150) MM 5 MICRON; Mobile Phase A: 0.1% ABC in water 80%, Mobile Phase B: acetonitrile 20%) to afford (S)-2'-chloro-N-(5-((5,5-dimethyl-1,4-dioxan-2-yl)methoxy)-1,3,4-thiadiazol-2-yl)-5'-methoxy-6-methyl-(4,4'-bipyridine)-3-carboxamide, isomer 1 (40 mg) as an off-white solid. MS (ESI) calculated for $(C_{22}H_{24}ClN_5O_5S)$ (M+1); 506.13; found: 506.1. 1H-NMR (400 MHz, DMSO-$d_6$): δ 12.93 (s, 1H), 8.80 (s, 1H), 8.17 (s, 1H), 7.55 (s, 1H), 7.44 (s, 1H), 4.43 (d, J=4.80 Hz, 2H), 3.83-3.78 (m, 1H), 3.65-3.53 (m, 5H), 3.34-3.29 (m, 2H), 2.59 (s, 3H), 1.24 (s, 3H), 1.05 (s, 3H).

Fraction 2 (1600 mL) (second eluting fraction) was concentrated and lyophilized to afford (R)-2'-chloro-N-(5-((5,5-dimethyl-1,4-dioxan-2-yl)methoxy)-1,3,4-thiadiazol-2-yl)-5'-methoxy-6-methyl-(4,4'-bipyridine)-3-carboxamide, isomer 2 (82 mg) as an off-white solid. MS (ESI) calculated for $(C_{22}H_{24}ClN_5O_5S)$ $(M+1)^+$; 505.12; found, 506.1. and $^1H$ NMR in DMSO-$d_6$ showed the required protons of the desired compound along with isopropyl amine.

To remove the isopropyl amine, (R)-2'-chloro-N-(5-((5,5-dimethyl-1,4-dioxan-2-yl)methoxy)-1,3,4-thiadiazol-2-yl)-5'-methoxy-6-methyl-(4,4'-bipyridine)-3-carboxamide (82 mg) was purified by following preparative HPLC conditions: (Column:X-bridge C8(10*150) MM 5 MICRON; Mobile Phase A: 0.1% ABC in water 80%, Mobile Phase B: acetonitrile 20%) to (R)-2'-chloro-N-(5-((5,5-dimethyl-1,4-dioxan-2-yl)methoxy)-1,3,4-thiadiazol-2-yl)-5'-methoxy-6-methyl-(4,4'-bipyridine)-3-carboxamide (30 mg), isomer 2 as an off-white solid. MS (ESI) calculated for ($C_{22}H_{24}ClN_5O_5S$) $(M+1)^+$; 506.13; found; 506.0. 1H-NMR (400 MHz, DMSO-$d_6$): δ 12.94 (s, 1H), 8.81 (s, 1H), 8.17 (s, 1H), 7.55 (s, 1H), 7.44 (s, 1H), 4.43 (s, 2H), 3.81 (t, J=4.00 Hz, 1H), 3.62-3.53 (m, 7H), 2.59 (s, 3H), 1.24 (s, 3H), 1.05 (s, 3H).

Example 229

N-(5-((2-oxabicyclo(2.1.1)hexan-4-yl)methoxy)-1,3,4-thiadiazol-2-yl)-2'-chloro-5'-methoxy-6-methyl-(4,4'-bipyridine)-3-carboxamide

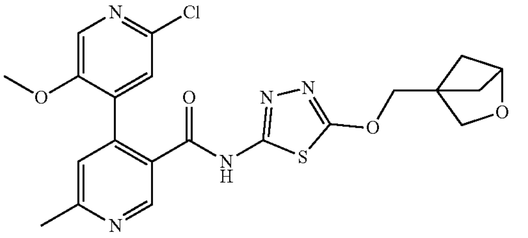 [SMILES: COc1cnc(Cl)cc1-c1cc(C)ncc1C(=O)Nc1nnc(OCC23COC(C2)C3)s1]

Step-1: O-((2-oxabicyclo(2.1.1)hexan-4-yl)methyl) S-methyl carbonodithioate

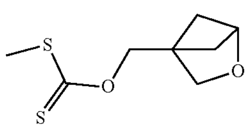

To a degassed solution of (2-oxabicyclo(2.1.1)hexan-4-yl)methanol (300 mg, 2.63 mmol) in Tetrahydrofuran (5 mL) was added NaH (210 mg, 5.26 mmol) in portions at 0° C. and stirred at room temperature for 30 min. To the above solution were sequentially added Carbon disulfide (0.317 mL, 5.26 mmol) and MeI (0.164 mL, 2.63 mmol) at room temperature. The resulting mixture was then stirred at room temperature for 30 min. The reaction was quenched with ice-water (10 mL) and diluted with ethyl acetate (15 mL). The layers were separated. The aqueous layer was extracted with ethyl acetate (15 mL×2). The combined organics were washed with brine solution (20 mL). The organic layer was dried over anhydrous sodium sulphate and filtered. The filtrate was concentrated under reduced pressure to afford O-((2-oxabicyclo(2.1.1)hexan-4-yl)methyl)S-methyl carbonodithioate (500 mg, 2.301 mmol, 88% yield) as a yellow oil. MS (ESI) calculated for $C_8H_{12}O_2S_2$ $(M+1)^+$205.04; found, Not Ionized. 1H-NMR (400 MHz, DMSO-$d^6$): δ 4.91 (s, 2H), 4.52 (s, 1H), 3.58 (s, 2H), 2.57 (s, 3H), 1.83 (d, J=4.8 Hz, 2H), 1.49 (dd, J=1.6 Hz, 4.8 Hz, 2H)

Step-2: O-((2-oxabicyclo(2.1.1)hexan-4-yl)methyl) hydrazinecarbothioate

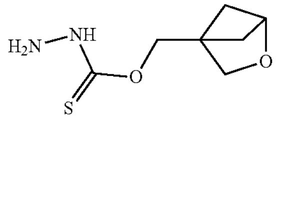 [SMILES: NNC(=S)OCC12COC(C1)C2]

To a stirred solution of O-((2-oxabicyclo(2.1.1)hexan-4-yl)methyl)S-methyl carbonodithioate (500 mg, 2.447 mmol) in Methanol (6 mL) was added hydrazine hydrate (123 mg, 2.447 mmol) at room temperature. The resulting solution was stirred at room temperature for 2 h. The reaction was diluted with water (20 mL) and extracted with ethyl acetate (30 mL×2). The organic phases were combined and washed with brine solution (20 mL). The organic layer was dried over anhydrous sodium sulphate and filtered. The filtrate was concentrated under vacuum to afford O-((2-oxabicyclo(2.1.1)hexan-4-yl)methyl) hydrazinecarbothioate (428 mg, 2.209 mmol, 90% yield) as an orange solid. MS (ESI) calculated for $C_7H_{12}N_2O_2S$, 189.07; found, 189.2.

Step-3: 5-((2-oxabicyclo(2.1.1)hexan-4-yl) methoxy)-1,3,4-thiadiazol-2-amine

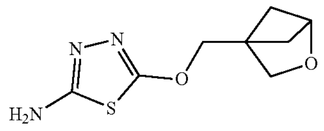

To a stirred solution of O-((2-oxabicyclo(2.1.1)hexan-4-yl)methyl) hydrazinecarbothioate (415 mg, 2.205 mmol) in Ethanol (10 mL) was added TEA (0.307 mL, 2.205 mmol) and Cyanogen bromide (234 mg, 2.205 mmol) at room temperature. The reaction mixture was stirred at room temperature for 1 h. The organic solvent was removed under vacuum. The residue was diluted with water (20 mL) and extracted with ethyl acetate (20 mL×3). The organic phases were combined and washed with brine solution (20 mL). The organic layer was dried over anhydrous sodium sulphate and filtered. The filtrate was concentrated under vacuum to afford crude product (340 mg) as an orange gum. The crude material (340 mg) was mixed with another batch of crude material (70 mg) and purified together. The combined 2 batches were adsorbed on 2.5 g silica gel (60-120 mesh), loaded on 25 g pre-packed SNAP cartridge (Oro chem) and purified by Biotage Isolera using 0% to 10% DCM in Methanol. Product was eluted in 2% DCM in Methanol. Collected fractions were combined, evaporated and dried under vacuo to afford 5-((2-oxabicyclo(2.1.1)hexan-4-yl) methoxy)-1,3,4-thiadiazol-2-amine (230 mg, 1.073 mmol, 48.7% yield) as a yellow solid. MS (ESI) calculated for $C_8H_{11}N_3O_2S$, 214.08; found, 214.2.

Step-4: N-(5-((2-oxabicyclo(2.1.1)hexan-4-yl) methoxy)-1,3,4-thiadiazol-2-yl)-2'-chloro-5'-methoxy-6-methyl-(4,4'-bipyridine)-3-carboxamide

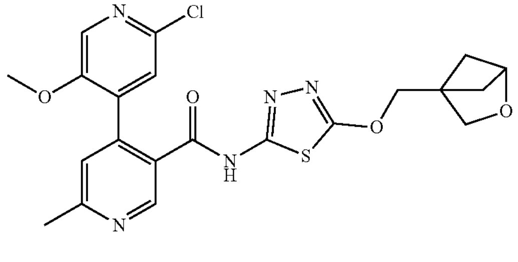 [SMILES: COc1cnc(Cl)cc1-c1cc(C)ncc1C(=O)Nc1nnc(OCC23COC(C2)C3)s1]

To a stirred solution of Intermediate H (130 mg, 0.466 mmol) and 5-((2-oxabicyclo(2.1.1)hexan-4-yl)methoxy)-1, 3,4-thiadiazol-2-amine (99 mg, 0.466 mmol) in Acetonitrile (2 mL) and N,N-Dimethylformamide (DMF) (0.2 mL) were added 1-methylimidazole (0.186 mL, 2.332 mmol) and Chloro-N,N,N',N'-tetramethylformamidinium hexafluorophosphate (144 mg, 0.513 mmol) at room temperature. The reaction mixture was stirred for 1 h.

Then the reaction mixture was concentrated under reduced pressure to get the crude. The crude was diluted with water (10 mL) and extracted with ethyl acetate (20 mL×2). The organic phases were combined and washed with water (10 mL×3) and brine solution. The organic layer was dried over anhydrous sodium sulphate and filtered. The filtrate was concentrated under reduced pressure to afford crude as a yellow solid. The crude was purified by Prep-HPLC under the following method: (Column: YMC-C18 (20×250 mm) 5 μm; Mobile Phase A: 10 mM ABC in MQ water 90%, Mobile Phase B: acetonitrile 10%;

The purified fraction was concentrated under vaccum and co-distilled with Milli-Q water (10 mL) to afford N-(5-((2-oxabicyclo(2.1.1)hexan-4-yl)methoxy)-1,3,4-thiadiazol-2-yl)-2'-chloro-5'-methoxy-6-methyl-(4,4'-bipyridine)-3-carboxamide (64 mg, 0.133 mmol, 28.4% yield) was isolated as a white solid. MS (ESI) calculated for $C_{21}H_{20}ClN_5O_4S$, 474.1; found, 474.0. 1H-NMR (400 MHz, DMSO-$d_6$): δ 12.92 (s, 1H), 8.81 (s, 1H), 8.17 (s, 1H), 7.55 (s, 1H), 7.44 (s, 1H), 4.76 (s, 2H), 4.51 (s, 1H), 3.63 (s, 3H), 3.59 (s, 2H), 2.59 (s, 3H), 1.84 (d, J=4.80 Hz, 2H), 1.49 (dd, J=1.60, 4.40 Hz, 2H).

Example 230 and 231

N-(5-(((1R,5R)-3-oxabicyclo(3.1.0)hexan-1-yl)methoxy)-1,3,4-thiadiazol-2-yl)-2'-chloro-5'-methoxy-6-methyl-(4,4'-bipyridine)-3-carboxamide and N-(5-(((1S,5S)-3-oxabicyclo(3.1.0)hexan-1-yl)methoxy)-1,3,4-thiadiazol-2-yl)-2'-chloro-5'-methoxy-6-methyl-(4,4'-bipyridine)-3-carboxamide

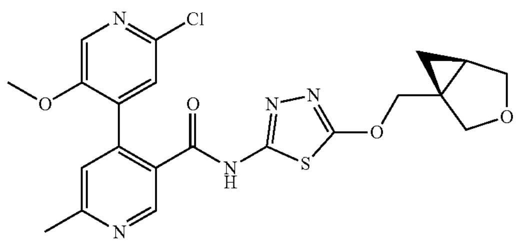

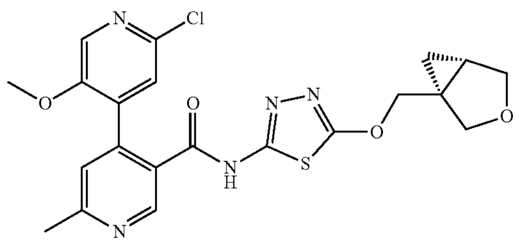

Step-1: O-((3-oxabicyclo(3.1.0)hexan-1-yl)methyl) S-methyl carbonodithioate

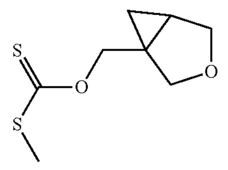

To a degassed solution of (3-oxabicyclo(3.1.0)hexan-1-yl)methanol (0.5 g, 4.38 mmol) in Tetrahydrofuran (THF) (10 mL) was added NaH (0.350 g, 8.76 mmol) in portions at 0° C. and stirred at room temperature for 30 min. To the above solution were sequentially added $CS_2$ (0.528 mL, 8.76 mmol) and MeI (0.274 mL, 4.38 mmol) at room temperature. The resulting mixture was then stirred at room temperature for 30 min. The reaction was quenched with cold water (10 mL) and extracted with ethyl acetate (20 mL×2). The combine organic layer was dried over sodium sulphate, filtered. The filtrate was concentrated under vacuum to afford O-((3-oxabicyclo(3.1.0)hexan-1-yl)methyl)S-methyl carbonodithioate (1 g) as an orange oil.

MS (ESI) calculated for $C_8H_{12}O_2S_2$ $(M+1)^+$, 205.04; found 205.0.

Step-2: O-((3-oxabicyclo(3.1.0)hexan-1-yl)methyl) hydrazinecarbothioate

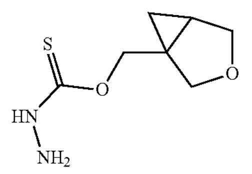

To a solution of O-((3-oxabicyclo(3.1.0)hexan-1-yl)methyl)S-methyl carbonodithioate (1 g, 4.89 mmol) in methanol (10 mL) was added hydrazine hydrate (0.245 g, 4.89 mmol) at room temperature. The resulting solution was stirred at room temperature for 2 h. The reaction was diluted with water (10 mL) and extracted with ethyl acetate (30 mL×2). The organic phases were combined and washed with brine solution. The organic layer was dried over anhydrous sodium sulphate and filtered. The filtrate was concentrated under vacuum to get the O-((3-oxabicyclo(3.1.0)hexan-1-yl)methyl) hydrazinecarbothioate (820 mg, 4.09 mmol, 84% yield) as an orange liquid. MS (ESI) calculated for $C_7H_{12}N_2O_2S$ $(M+1)^+$, 189.07; found 189.0.

Step-3: 5-((3-oxabicyclo(3.1.0)hexan-1-yl)methoxy)-1,3,4-thiadiazol-2-amine

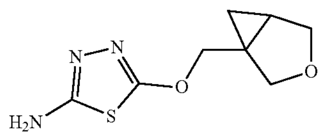

To a solution of O-((3-oxabicyclo(3.1.0)hexan-1-yl) methyl) hydrazinecarbothioate (820 mg, 4.36 mmol) in Ethanol (10 mL) was added TEA (0.607 mL, 4.36 mmol) and Cyanogen bromide (461 mg, 4.36 mmol) at room temperature. The reaction mixture was stirred at room temperature for 1 h. The organic solvent was removed under vacuum. The residue was diluted with water (10 mL). The aqueous layer was extracted with ethyl acetate (50 mL×3). The combined organic layers were washed with brine, dried over anhydrous sodium sulfate, filtered, and concentrated under vacuum to get the crude product as an orange solid.

The crude product was pre-absorbed on silica (using 10 mL DCM, 10 g of silica (60-120 mesh), loaded onto a Biotage 40 g SNAP cartridge, and was eluted at 7-9% MeOH in DCM. The appropriate fractions were collected and concentrated under vacuum to afford 5-((3-oxabicyclo (3.1.0)hexan-1-yl)methoxy)-1,3,4-thiadiazol-2-amine (420 mg, 1.885 mmol, 43.3% yield) as a yellow solid. MS (ESI) calculated for $C_8H_{11}N_3O_2S$ (M+1)$^+$, 214.07; found 214.1.

Step-4: N-(5-((3-oxabicyclo(3.1.0)hexan-1-yl) methoxy)-1,3,4-thiadiazol-2-yl)-2'-chloro-5'-methoxy-6-methyl-(4,4'-bipyridine)-3-carboxamide

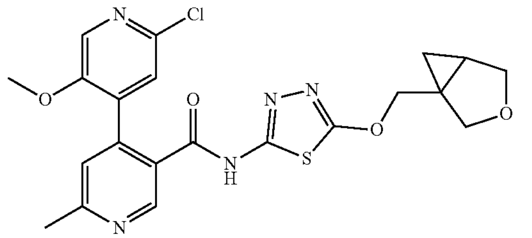 [SMILES: COc1cnc(Cl)cc1-c1cc(C)ncc1C(=O)Nc1nnc(OCC23COCC2C3)s1]

To a solution of Intermediate H (300 mg, 1.076 mmol) and 5-((3-oxabicyclo(3.1.0)hexan-1-yl)methoxy)-1,3,4-thiadiazol-2-amine (230 mg, 1.076 mmol) in Acetonitrile (2 mL) and N,N-Dimethylformamide (DMF) (1.000 mL) were added 1-methylimidazole (0.429 mL, 5.38 mmol) and Chloro-N,N,N',N'-tetramethylformamidinium hexafluorophosphate (332 mg, 1.184 mmol) at room temperature. The resulting solution was stirred at room temperature for 1 h. The solvent was removed under reduced pressure to get crude as a yellow liquid.

The crude product was purified by prep-HPLC with the following conditions: (Column: Sunfire C18 (19×150 mm) 5 m; Mobile Phase A: 0.1% FA in water 70%, Mobile Phase B: acetonitrile 30%;

The appropriate purified fraction was concentrated under reduced pressure to afford desired compound as a white solid. LCMS indicated 52.9% of the desired compound and the presence of by-product mass therefore it was further purified by Prep-HPLC under the following method: The crude product was purified by prep-HPLC with the following conditions: (Column: YMC C8 (20×250 mm) 5 m; Mobile Phase A: 0.1% FA in water 90%, Mobile Phase B: acetonitrile 10%; The purified fraction was concentrated to one-third and then lyophilized to afford N-(5-((3-oxabicyclo (3.1.0)hexan-1-yl)methoxy)-1,3,4-thiadiazol-2-yl)-2'-chloro-5'-methoxy-6-methyl-(4,4'-bipyridine)-3-carboxamide (65 mg, 0.129 mmol, 11.98% yield).

Step-5: N-(5-(((1R,5R)-3-oxabicyclo(3.1.0)hexan-1-yl)methoxy)-1,3,4-thiadiazol-2-yl)-2'-chloro-5'-methoxy-6-methyl-(4,4'-bipyridine)-3-carboxamide and N-(5-(((1S,5S)-3-oxabicyclo(3.1.0)hexan-1-yl) methoxy)-1,3,4-thiadiazol-2-yl)-2'-chloro-5'-methoxy-6-methyl-(4,4'-bipyridine)-3-carboxamide

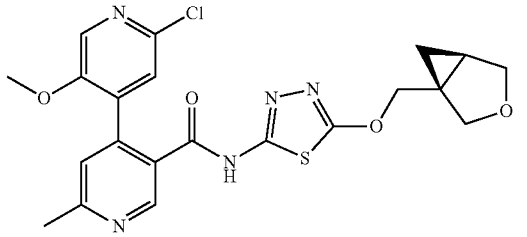

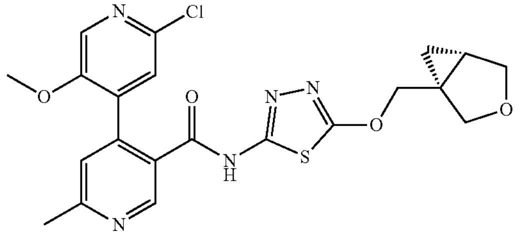

Racemic N-(5-((3-oxabicyclo(3.1.0)hexan-1-yl) methoxy)-1,3,4-thiadiazol-2-yl)-2'-chloro-5'-methoxy-6-methyl-(4,4'-bipyridine)-3-carboxamide (60 mg) was purified by Chiral SFC by using following conditions:

Column: Chiralcel OXH (250*20)mm, 5 μm, Mobile Phase: C02: 0.1% Isopropyl Amine in MeOH: ACN (1:1), Total Flow: 50 g/min, Back pressure: 100 bar, Wave length: 220 nm, Injection Volume: 400 μL/injection), Cycle time: 5.3 min, 60 mg of sample was dissolved in 3.0 mL of MeOH.

After SFC purification, the two appropriate fractions were collected. The absolute stereochemistry of each fraction was not determined.

Fraction-1 (first eluting fraction) was concentrated and lyophilized to afford N-(5-(((1R,5R)-3-oxabicyclo(3.1.0) hexan-1-yl)methoxy)-1,3,4-thiadiazol-2-yl)-2'-chloro-5'-methoxy-6-methyl-(4,4'-bipyridine)-3-carboxamide, isomer 1 (22 mg, 0.046 mmol, 4.24% yield) as a white solid. MS (ESI) calculated for $C_{21}H_{20}ClN_5O_4S$ (M+1)$^+$, 474.1; found 474.0. 1H-NMR (400 MHz, DMSO-$d^6$): δ 12.90 (s, 1H), 8.81 (s, 1H), 8.17 (s, 1H), 7.54 (s, 1H), 7.43 (s, 1H), 4.72 (d, J=11.20 Hz, 1H), 4.54 (d, J=10.80 Hz, 1H), 3.80 (d, J=8.40 Hz, 1H), 3.73-3.64 (m, 3H), 3.63 (s, 3H), 2.59 (s, 3H), 1.75-1.69 (m, 1H), 0.90 (dd, J=4.4 Hz, 8.0 Hz, 1H), 0.61 (t, J=4.40 Hz, 1H).

Fraction-2 (second eluting fraction) was concentrated and lyophilized to afford N-(5-(((1S,5S)-3-oxabicyclo(3.1.0) hexan-1-yl)methoxy)-1,3,4-thiadiazol-2-yl)-2'-chloro-5'-methoxy-6-methyl-(4,4'-bipyridine)-3-carboxamide, isomer 2 (22 mg, 0.045 mmol, 4.16% yield) as a white solid. MS (ESI) calculated for $C_{21}H_{20}ClN_5O_4S$ (M+1)$^+$, 474.1; found 474.0. 1H-NMR (400 MHz, DMSO-$d^6$): δ 12.92 (s, 1H), 8.82 (s, 1H), 8.17 (s, 1H), 7.53 (s, 1H), 7.42 (s, 1H), 4.71 (d, J=10.80 Hz, 1H), 4.53 (d, J=11.20 Hz, 1H), 3.80 (d, J=8.00 Hz, 1H), 3.73-3.64 (m, 3H), 3.63 (s, 3H), 2.59 (s, 3H), 1.75-1.69 (m, 1H), 0.90 (dd, J=4.4 Hz, 8.0 Hz, 1H), 0.61 (t, J=4.40 Hz, 1H).

Example 232

2'-chloro-6-(cyclopropoxymethyl)-N-(5-(((1r,4r)-4-hydroxycyclohexyl)methoxy)-1,3,4-thiadiazol-2-yl)-5'-methoxy-(4,4'-bipyridine)-3-carboxamide

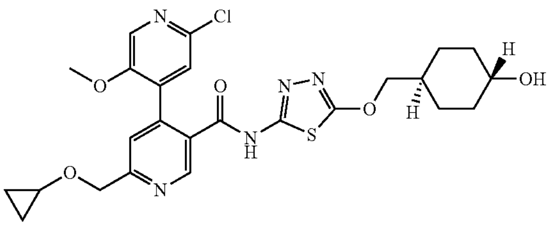 [SMILES: COc1cnc(Cl)cc1-c1cc(COC2CC2)ncc1C(=O)Nc1nnc(OC[C@H]2CC[C@H](O)CC2)s1]

Step-1: 6-(bromomethyl)-2'-chloro-5'-methoxy-(4,4'-bipyridine)-3-carboxylic acid

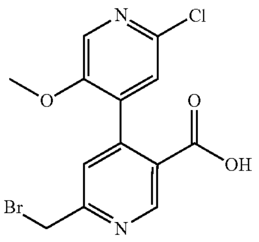 [SMILES: COc1cnc(Cl)cc1-c1cc(CBr)ncc1C(=O)O]

To a stirred solution of Intermediate H (1.2 g, 4.31 mmol) in Chloroform (10 mL) were sequentially added NBS (0.8 g, 4.31 mmol) and AIBN (0.7 g, 4.31 mmol) at 25° C. The resulting solution was stirred at 80° C. for 16 hr. The organic solvent was removed under vacuum. The resulting residue was dissolved in MeOH (6 mL) which was applied to a 80 g C18 column and purified by flash chromatography (Biotage Isolera Prime), eluted with 5~60% acetonitrile in water within 30 min to afford 6-(bromomethyl)-2'-chloro-5'-methoxy-(4,4'-bipyridine)-3-carboxylic acid (400.0 mg, 23%) as a purple solid. MS (ESI) calculated for ($C_{13}H_{10}BrClN_2O_3$) (M+1)+, 357.0, 359.0; found, 357.0, 359.0.

Step-2: 2'-chloro-6-(cyclopropoxymethyl)-5'-methoxy-(4,4'-bipyridine)-3-carboxylic acid

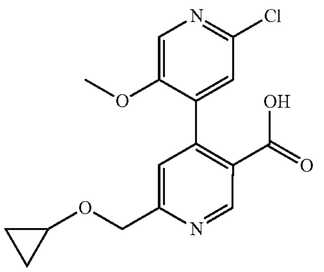 [SMILES: COc1cnc(Cl)cc1-c1cc(COC2CC2)ncc1C(=O)O]

To a stirred solution of cyclopropanol (156.0 mg, 2.68 mmol) in Tetrahydrofuran (5 mL) was added NaH (107.4 mg, 2.68 mmol, 60%) at 0° C. The reaction mixture was stirred at 0° C. for 0.5 h. Then 6-(bromomethyl)-2'-chloro-5'-methoxy-(4,4'-bipyridine)-3-carboxylic acid (400.0 mg, 1.11 mmol) in Tetrahydrofuran (5 mL) was added to the above mixture at 0° C. The resulting solution was then stirred at 25° C. for 16 h. The reaction mixture was quenched by sat. citric acid aqueous and extracted with ethyl acetate. The combined organic layers were washed with brine, dried over anhydrous sodium sulfate, filtered, and concentrated under vacuum. The resulting residue was dissolved in DMF (3 mL) which was applied to a 80 g C18 column and purified by flash chromatography (Biotage Isolera Prime), eluted with 5-50% acetonitrile in water within 35 min to afford 2'-chloro-6-(cyclopropoxymethyl)-5'-methoxy-(4,4'-bipyridine)-3-carboxylic acid (200.0 mg, 48%) as a yellow solid. MS (ESI) calculated for ($C_{16}H_{15}ClN_2O_4$) (M+1)+, 335.1; found, 335.0.

Step-3: N-(5-(((1r,4r)-4-((tert-butyldimethylsilyl)oxy)cyclohexyl)methoxy)-1,3,4-thiadiazol-2-yl)-2'-chloro-6-(cyclopropoxymethyl)-5'-methoxy-(4,4'-bipyridine)-3-carboxamide

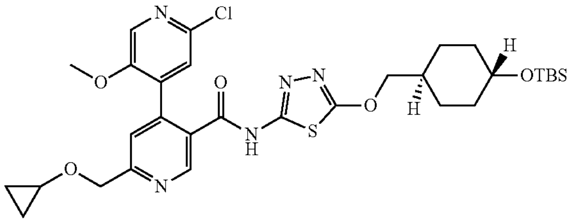 [SMILES: COc1cnc(Cl)cc1-c1cc(COC2CC2)ncc1C(=O)Nc1nnc(OC[C@H]2CC[C@H](O[Si](C)(C)C(C)(C)C)CC2)s1]

To a stirred solution of 2'-chloro-6-(cyclopropoxymethyl)-5'-methoxy-(4,4'-bipyridine)-3-carboxylic acid (130.0 mg, 0.39 mmol) in acetonitrile (2 mL) were sequentially added 5-(((1r,4r)-4-((tert-butyldimethylsilyl)oxy)cyclohexyl)methoxy)-1,3,4-thiadiazol-2-amine (133.0 mg, 0.39 mmol, Example 100, Step 5) and 1-methyl-1H-imidazole (159.0 mg, 1.94 mmol) at 25° C. Then TCFH (109.0 mg, 0.39 mmol) in acetonitrile (1 mL) was added to the above mixture at 25° C. The resulting solution was stirred at 25° C. for 2 h. The suspension was filtered. The filter cake was collected and dried under vacuum to afford N-(5-(((1r,4r)-4-((tert-butyldimethylsilyl)oxy)cyclohexyl)methoxy)-1,3,4-thiadiazol-2-yl)-2'-chloro-6-(cyclopropoxymethyl)-5'-methoxy-(4,4'-bipyridine)-3-carboxamide (190.0 mg, crude) as a yellow solid. MS (ESI) calculated for ($C_{31}H_{42}ClN_5O_5SSi$) (M+1)+, 660.2; found, 660.3.

Step-4: 2'-chloro-6-(cyclopropoxymethyl)-N-(5-(((1r,4r)-4-hydroxycyclohexyl)methoxy)-1,3,4-thiadiazol-2-yl)-5'-methoxy-(4,4'-bipyridine)-3-carboxamide

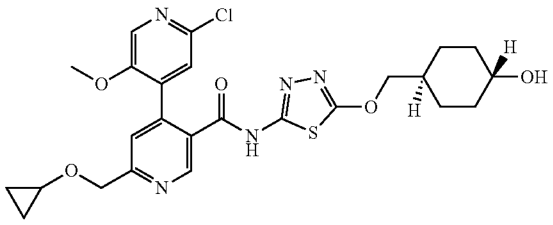 [SMILES: COc1cnc(Cl)cc1-c1cc(COC2CC2)ncc1C(=O)Nc1nnc(OC[C@H]2CC[C@H](O)CC2)s1]

To a stirred solution of N-(5-(((1r,4r)-4-((tert-butyldimethylsilyl)oxy)cyclohexyl)methoxy)-1,3,4-thiadiazol-2-yl)-2'-chloro-6-(cyclopropoxymethyl)-5'-methoxy-(4,4'-bipyridine)-3-carboxamide (170.0 mg, 0.26 mmol) in tetrahydrofuran (2.1 mL) were sequentially added water (0.9 mL) and Acetic Acid (3 mL) at 25° C. The resulting solution was stirred at 25° C. for 16 h under nitrogen. The reaction mixture was diluted with water and extracted with dichloromethane. The combined organic layers were washed with brine, dried over anhydrous sodium sulfate, filtered, and concentrated under vacuum. The resulting residue was dissolved in DMF (2 mL) which was applied to a 20 g C18 column and purified by flash chromatography (Biotage Isolera Prime), eluted with 5~50% acetonitrile in water within 25 min to afford 2'-chloro-6-(cyclopropoxymethyl)-N-(5-(((1r,4r)-4-hydroxycyclohexyl)methoxy)-1,3,4-thiadiazol-2-yl)-5'-methoxy-(4,4'-bipyridine)-3-carboxamide (93.7 mg, 64%) as a white solid. MS (ESI) calculated for ($C_{25}H_{28}ClN_5O_5S$) (M+1)+, 546.1; found, 546.2. 1H NMR (400 MHz, DMSO-$d_6$) δ 12.93 (s, 1H), 8.88 (s, 1H), 8.18 (s, 1H), 7.55 (s, 1H), 7.48 (s, 1H), 4.70 (s, 2H), 4.52 (d, J=4.4 Hz, 1H), 4.23 (d, J=6.0 Hz, 2H), 3.64 (s, 3H), 3.54-3.48 (m, 1H), 3.35-3.32 (m, 1H), 1.90-1.82 (m, 2H), 1.80-1.67 (m, 3H), 1.22-1.01 (m, 4H), 0.66-0.58 (m, 2H), 0.58-0.46 (m, 2H).

Example 233

(S)—N-(5-((1,4-dioxan-2-yl)methoxy)-1,3,4-thiadiazol-2-yl)-2'-chloro-5'-(difluoromethoxy)-6-methyl-(4,4'-bipyridine)-3-carboxamide

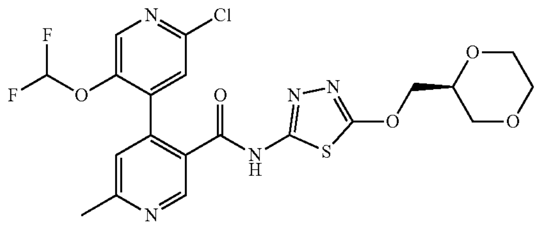 [SMILES: Cc1cc(-c2cc(Cl)ncc2OC(F)F)c(C(=O)Nc2nnc(OC[C@@H]3COCCO3)s2)cn1]

Step-1. 2-chloro-5-(difluoromethoxy)-4-iodopyridine

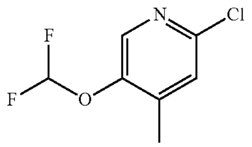

To a stirred solution of 6-chloro-4-iodopyridin-3-ol (10.0 g, 39.14 mmol) in N,N-Dimethylformamide (DMF) (50 mL) were added sodium 2-chloro-2,2-difluoroacetate (11.9 g, 78.20 mmol) and $Cs_2CO_3$ (16.6 g, 50.80 mmol) at 25° C. The reaction mixture was quenched by the addition of water and extracted with ethyl acetate. The combined organic layers were washed with brine, dried over anhydrous sodium sulfate, filtered, and concentrated under vacuum. The resulting residue was purified by flash chromatography (Biotage Isolera Prime) which applied to a 330 g silica gel column that was eluted with 0~25% ethyl acetate in petroleum ether within 40 min to afford 2-chloro-5-(difluoromethoxy)-4-iodopyridine (10.5 g, 79%) as a white solid. MS (ESI) calc'd for ($C_6H_3ClF_2INO$) $(M+1)^+$, 305.4; found 305.4.

Step-2: methyl 2'-chloro-5'-(difluoromethoxy)-6-methyl-(4,4'-bipyridine)-3-carboxylate

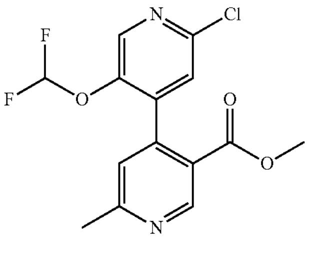 [SMILES: COC(=O)c1cnc(C)cc1-c1cc(Cl)ncc1OC(F)F]

To a degassed solution of methyl 6-methyl-4-(4,4,5,5-tetramethyl-1,3,2-dioxaborolan-2-yl)nicotinate (5.0 g, 18.04 mmol) in 1,4-Dioxane (40 mL) were added 2-chloro-5-(difluoromethoxy)-4-iodopyridine (5.5 g, 18.04 mmol), Water (8 mL), $K_2CO_3$ (7.5 g, 54.1 mmol) and (1,1'-Bis(diphenylphosphino)ferrocene)dichloropalladium(II) complex with dichloromethane (4.4 g, 5.41 mmol) at 23° C. under nitrogen atmosphere. The resulting solution was stirred at 80° C. for 2 h under nitrogen atmosphere. The suspension was filtered. The filtrate was concentrated under vacuum. The resulting residue was purified by flash chromatography (Biotage Isolera Prime) which applied to 120 g silica gel column and eluted with 0~56% ethyl acetate in petroleum ether within 40 min to afford methyl 2'-chloro-5'-(difluoromethoxy)-6-methyl-(4,4'-bipyridine)-3-carboxylate (5.7 g, 63%) as a white solid. MS (ESI) calc'd for ($C_{14}H_{11}ClF_2N_2O_3$) $(M+1)^+$, 329.0; found, 329.0.

Step-3: 2'-chloro-5'-(difluoromethoxy)-6-methyl-(4,4'-bipyridine)-3-carboxylic acid

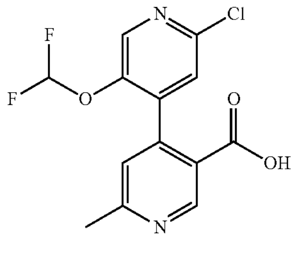 [SMILES: Cc1cc(-c2cc(Cl)ncc2OC(F)F)c(C(=O)O)cn1]

To a stirred solution of methyl 2'-chloro-5'-(difluoromethoxy)-6-methyl-(4,4'-bipyridine)-3-carboxylate (3.0 g, 9.13 mmol) in Methanol (20 mL) were added NaOH (1.4 g, 36.50 mmol) and Water (20 mL) at 25° C. The resulting solution was stirred at 25° C. for 1 h before diluted with water. The organic solvent was removed under vacuum. The aqueous layer was acidified with Citric acid to pH ~6 and extracted with ethyl acetate. The combined organic layers were washed with brine, dried over anhydrous sodium sulfate, filtered, and concentrated under vacuum to afford 2'-chloro-5'-(difluoromethoxy)-6-methyl-(4,4'-bipyridine)-3-carboxylic acid (2.5 g, crude) as a yellow oil. MS (ESI) calc'd for ($C_{13}H_9ClF_2N_2O_3$) $(M+1)^+$, 315.0, found 315.0.

Step-4: (S)—N-(5-((1,4-dioxan-2-yl)methoxy)-1,3,4-thiadiazol-2-yl)-2'-chloro-5'-(difluoromethoxy)-6-methyl-(4,4'-bipyridine)-3-carboxamide

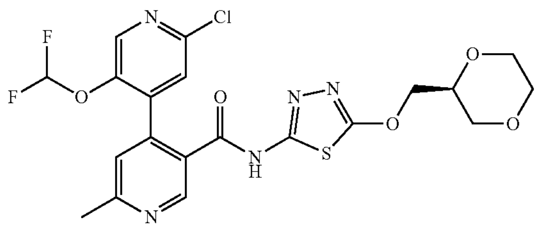 [SMILES: Cc1cc(-c2cc(Cl)ncc2OC(F)F)c(C(=O)Nc2nnc(OC[C@@H]3COCCO3)s2)cn1]

To a stirred solution of 2'-chloro-5'-(difluoromethoxy)-6-methyl-(4,4'-bipyridine)-3-carboxylic acid (155.0 mg, 0.49 mmol) in Acetonitrile (1 mL) were added (S)-5-((1,4-dioxan-2-yl)methoxy)-1,3,4-thiadiazol-2-amine (89.0 mg, 0.41 mmol, Example 186, Step 3) and 1-methylimidazole (167.3 mg, 2.04 mmol) at 20° C. To the above solution was added TCFH (115 mg, 0.410 mmol) in Acetonitrile (0.5 mL) at 20° C. The resulting solution was stirred at 20° C. for 1 hr under nitrogen. The mixture solution was basified with NaOH to pH ~11 and then extracted with ethyl acetate, the collected aqueous solution was neutralized with citric acid to pH ~7. The suspension was filtered. The filter cake was collected and triturated with Acetonitrile/$H_2O$ (1/1) to afford (S)—N-(5-((1,4-dioxan-2-yl)methoxy)-1,3,4-thiadiazol-2-yl)-2'-chloro-5'-(difluoromethoxy)-6-methyl-(4,4'-bipyridine)-3-carboxamide (102.4 mg, 47%) as a white solid. MS (ESI) calc'd for ($C_{20}H_{18}ClF_2N_5O_5S$) $(M+1)^+$, 514.1. found: 514.1. 1H NMR (400 MHz, DMSO-$d_6$) δ 9.01 (s, 1H), 8.31 (s, 1H), 7.64 (s, 1H), 7.35 (s, 1H), 7.33-6.94 (m, 1H), 4.41-4.29 (m, 2H), 3.95-3.85 (m, 1H), 3.83-3.72 (m, 2H), 3.70-3.56 (m, 2H), 3.54-3.43 (m, 1H), 3.41-3.32 (m, 1H), 2.59 (s, 3H).

Example 234

(R)—N-(5-((1,4-dioxan-2-yl)methoxy)-1,3,4-thiadiazol-2-yl)-2'-chloro-5'-(difluoromethoxy)-6-methyl-(4,4'-bipyridine)-3-carboxamide

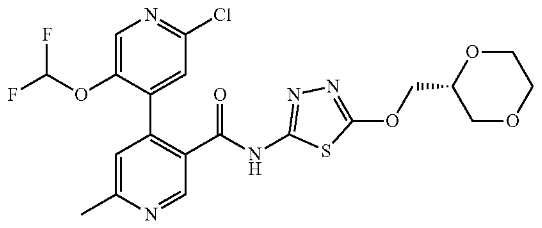 [SMILES: Cc1cc(-c2cc(Cl)ncc2OC(F)F)c(C(=O)Nc2nnc(OC[C@H]3COCCO3)s2)cn1]

To a stirred solution of 2'-chloro-5'-(difluoromethoxy)-6-methyl-(4,4'-bipyridine)-3-carboxylic acid (150.0 mg, 0.47 mmol, Example 234, Step 3) in Acetonitrile (2 mL) were added (R)-5-((1,4-dioxan-2-yl)methoxy)-1,3,4-thiadiazol-2-amine (104.0 mg, 0.47 mmol, Example 187, Step 3) and 1-methylimidazole (196.0 mg, 2.38 mmol). To the above was added TCFH (134.0 mg, 0.47 mmol) in Acetonitrile (0.5 mL) at 20° C. The resulting mixture was stirred at 20° C. for 2 hr. The mixture solution was basified with NaOH to pH ~11 and then extracted with ethyl acetate, the collected aqueous solution was neutralized with citric acid to pH ~7. The suspension was filtered. The filter cake was collected and triturated with Acetonitrile/$H_2O$ (1/1) to afford (R)—N-(5-((1,4-dioxan-2-yl)methoxy)-1,3,4-thiadiazol-2-yl)-2'-chloro-5'-(difluoromethoxy)-6-methyl-(4,4'-bipyridine)-3-carboxamide (79.1 mg, 31%) as a white solid. MS (ESI) calc'd for ($C_{20}H_{18}ClF_2N_5O_5S$) (M+1)+, 514.1; found, 514.1. 1H NMR (400 MHz, DMSO-$d_6$) δ 13.11 (s, 1H), 8.96 (s, 1H), 8.33 (s, 1H), 7.74 (s, 1H), 7.47 (s, 1H), 7.33-6.97 (m, 1H), 4.46-4.34 (m, 2H), 3.95-3.86 (m, 1H), 3.83-3.73 (m, 2H), 3.70-3.56 (m, 2H), 3.54-3.43 (m, 1H), 3.42-3.35 (m, 1H), 2.61 (s, 3H).

Example 235

(S)—N-(5-((1,4-dioxan-2-yl)methoxy)-1,3,4-thiadiazol-2-yl)-2'-bromo-5'-methoxy-6-methyl-(4,4'-bipyridine)-3-carboxamide

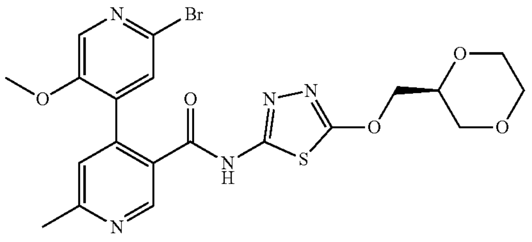

Step-1:2-bromo-4-iodo-5-methoxypyridine

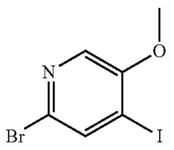

To a stirred solution of methanol (380.0 mg, 11.84 mmol) in N,N-Dimethylformamide (15 mL) was added NaH (230.0 mg, 5.68 mmol) at 0° C. The reaction mixture was stirred at 0° C. for 0.5 h. Then 2-bromo-5-fluoro-4-iodopyridine (1.4 g, 4.74 mmol) was added to the above mixture at 0° C. The resulting solution was then stirred at 25° C. for 1 h. The reaction mixture was quenched by the addition of water and extracted with ethyl acetate. The combined organic layers were washed with brine, dried over anhydrous sodium sulfate, filtered, and concentrated under vacuum. The resulting residue was dissolved in dichloromethane (5 mL) and purified by flash chromatography (Biotage Isolera Prime) which applied to a 80.0 g silica gel column that was eluted with 0-20% ethyl acetate in petroleum ether within 25 min to afford 2-bromo-4-iodo-5-methoxypyridine (1.2 g, 54% yield) as a white solid. MS (ESI) calc'd for ($C_6H_5BrINO$) $(M+1)^+$, 313.9; found 313.9.

Step-2: methyl 2'-bromo-5'-methoxy-6-methyl-(4,4'-bipyridine)-3-carboxylate

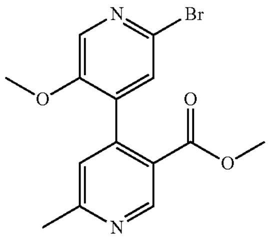

To a stirred solution of 2-bromo-4-iodo-5-methoxypyridine (200.0 mg, 0.64 mmol) and methyl 6-methyl-4-(4,4,5,5-tetramethyl-1,3,2-dioxaborolan-2-yl)nicotinate (265.0 mg, 0.96 mmol) in 1,4-dioxane (2 mL) were sequentially added water (0.4 mL), potassium carbonate (264.0 mg, 1.91 mmol) and 1,1'-bis(diphenylphosphino)ferrocene-palladium (II)dichloride dichloromethane complex (52.0 mg, 0.06 mmol) at 23° C. The resulting solution was stirred at 80° C. for 2 hr under nitrogen. The suspension was filtered. The filtrate was collected and concentrated under vacuum. The resulting residue was dissolved in acetonitrile (3 mL) which was applied to a 40.0 g C18 column and purified by flash chromatography (Biotage Isolera Prime), eluted with 5~45% acetonitrile in water within 30 min to afford methyl 2'-bromo-5'-methoxy-6-methyl-(4,4'-bipyridine)-3-carboxylate (80.0 mg, 36% yield) as a colorless oil. MS (ESI) calc'd for ($C_{14}H_{13}BrN_2O_3$) $(M+1)^+$, 337.0, found 337.0. $^1H$ NMR (400 MHz, DMSO-$d_6$) δ 8.88 (s, 1H), 8.23 (s, 1H), 7.59 (s, 1H), 7.37 (s, 1H), 3.78 (s, 3H), 3.32 (s, 3H), 2.58 (s, 3H).

Step-3: 2'-bromo-5'-methoxy-6-methyl-(4,4'-bipyridine)-3-carboxylic acid

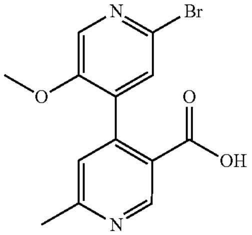 [SMILES: COc1cnc(Br)cc1-c1cc(C)ncc1C(=O)O]

To a stirred solution of methyl 2'-bromo-5'-methoxy-6-methyl-(4,4'-bipyridine)-3-carboxylate (175.0 mg, 0.52 mmol) in methanol (0.3 mL) were added water (0.3 mL) and sodium hydroxide (83.0 mg, 2.08 mmol) at 25° C. The resulting solution was stirred at 25° C. for 2 hr under nitrogen. The organic solvent was removed under vacuum. The aqueous layer was acidified with sat. citric acid solution to pH ~6 and extracted with ethyl acetate. The combined organic layers were washed with brine, dried over anhydrous sodium sulfate, filtered, and concentrated under vacuum to afford 2'-bromo-5'-methoxy-6-methyl-(4,4'-bipyridine)-3-carboxylic acid (100.0 mg, 58% yield) as a yellow solid. MS (ESI) calc'd for ($C_{13}H_{11}BrN_2O_3$) $(M+1)^+$, 323.0, found 323.1. 1H NMR (400 MHz, DMSO-$d_6$) δ 13.00 (s, 1H), 8.89 (s, 1H), 8.22 (s, 1H), 7.54 (s, 1H), 7.30 (s, 1H), 3.78 (s, 3H), 2.56 (s, 3H).

Step-4: (S)—N-(5-((1,4-dioxan-2-yl)methoxy)-1,3,4-thiadiazol-2-yl)-2'-bromo-5'-methoxy-6-methyl-(4,4'-bipyridine)-3-carboxamide

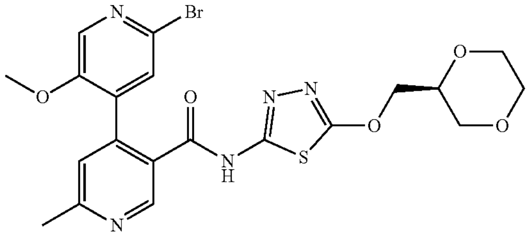

To a solution of (S)-5-((1,4-dioxan-2-yl)methoxy)-1,3,4-thiadiazol-2-amine (161.0 mg, 0.74 mmol, Example 186, Step 3) in Acetonitrile (1 mL) were added 2'-bromo-5'-methoxy-6-methyl-(4,4'-bipyridine)-3-carboxylic acid (160.0 mg, 0.50 mmol) and NMI (203.0 mg, 2.48 mmol) at 20° C. under nitrogen. To the above solution was added TCFH (166.0 mg, 0.59 mmol) in Acetonitrile (1 mL) at 25° C. under nitrogen. The resulting mixture was then stirred at 25° C. for 1 hour. The suspension was filtered. The filter cake was collected and triturated with Acetonitrile/H2O (1/1) to afford (S)—N-(5-((1,4-dioxan-2-yl) methoxy)-1,3,4-thiadiazol-2-yl)-2'-bromo-5'-methoxy-6-methyl-(4,4'-bipyridine)-3-carboxamide (90.0 mg, 34%) as a white solid. MS (ESI) calc'd for ($C_{20}H_{20}BrN_5O_5S$) (M+1)+, 522.0, 524.0; found, 522.1, 524.0. 1H NMR (400 MHz, DMSO-d6) δ 12.91 (s, 1H), 8.80 (s, 1H), 8.17 (s, 1H), 7.64 (s, 1H), 7.43 (s, 1H), 4.46-4.34 (m, 2H), 3.97-3.85 (m, 1H), 3.84-3.71 (m, 2H), 3.69-3.58 (m, 5H), 3.55-3.44 (m, 1H), 3.43-3.33 (m, 1H), 2.59 (s, 3H).

Example 236

(R)—N-(5-((1,4-dioxan-2-yl)methoxy)-1,3,4-thiadiazol-2-yl)-2'-bromo-5'-methoxy-6-methyl-(4,4'-bipyridine)-3-carboxamide

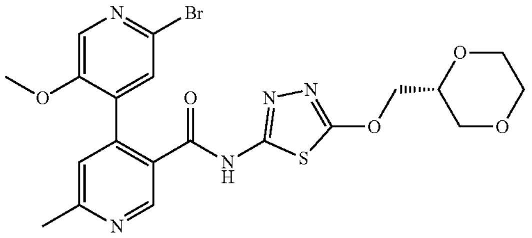

To a stirred solution of 2'-bromo-5'-methoxy-6-methyl-(4,4'-bipyridine)-3-carboxylic acid (140.0 mg, 0.43 mmol, Example 235, Step 3) in Acetonitrile (1 mL) were sequentially added (R)-5-((1,4-dioxan-2-yl)methoxy)-1,3,4-thiadiazol-2-amine (113.0 mg, 0.52 mmol, Example 187, Step 3) and 1-methyl-1H-imidazole (178.0 mg, 2.16 mmol) at 25° C. Then TCFH (122.0 mg, 0.43 mmol) in Acetonitrile (1 mL) was added to the above mixture at 25° C. The resulting solution was stirred at 25° C. for 2 h. The resulting solution (2 mL) which was applied to a 20 g C18 column and purified by flash chromatography (Biotage Isolera Prime), eluted with 5~32% acetonitrile in water within 30 min to afford (R)—N-(5-((1,4-dioxan-2-yl)methoxy)-1,3,4-thiadiazol-2-yl)-2'-bromo-5'-methoxy-6-methyl-(4,4'-bipyridine)-3-carboxamide (67.1 mg, 29%) as a white solid. MS (ESI) calc'd for ($C_{20}H_{20}BrN_5O_5S$) $(M+1)^+$, 522.0, 524.0, found 522.0, 524.0. 1H NMR (400 MHz, DMSO-$d_6$) δ 12.89 (s, 1H), 8.81 (s, 1H), 8.17 (s, 1H), 7.63 (s, 1H), 7.42 (s, 1H), 4.46-4.34 (m, 2H), 3.94-3.90 (m, 1H), 3.89-3.80 (m, 2H), 3.71-3.57 (m, 5H), 3.55-3.42 (m, 1H), 3.38-3.35 (m, 1H), 2.59 (s, 3H).

Example 239

N-(5-(((S)-1,4-dioxan-2-yl)methoxy)-1,3,4-thiadiazol-2-yl)-2'-chloro-3'-fluoro-5'-methoxy-6-methyl-(4,4'-bipyridine)-3-carboxamide

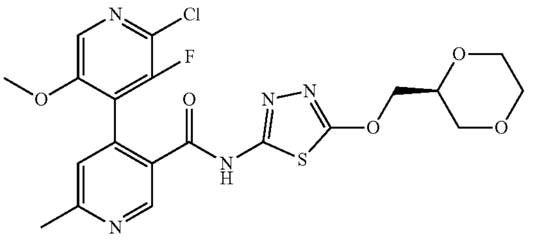 [SMILES: COc1cnc(Cl)c(F)c1-c1cc(C)ncc1C(=O)Nc1nnc(OC[C@@H]2COCCO2)s1]

To a solution of (S)-5-((1,4-dioxan-2-yl)methoxy)-1,3,4-thiadiazol-2-amine (100.0 mg, 0.46 mmol, Example 186, Step 3) in dry Acetonitrile (1.0 mL) were added 2'-chloro-3'-fluoro-5'-methoxy-6-methyl-(4,4'-bipyridine)-3-carboxylic acid (137.0 mg, 0.46 mmol, Example 184, Step 4) and 1-methyl-1H-imidazole (189.0 mg, 2.30 mmol) at 25° C. Then TCFH (194.0 mg, 0.69 mmol) in acetonitrile (1 mL) was added to the above mixture at 25° C. The resulting solution was stirred at 25° C. for 1 h. The suspension was filtered. The filter cake was collected and triturated with Acetonitrile/H2O (1/1) to afford N-(5-(((S)-1,4-dioxan-2-yl)methoxy)-1,3,4-thiadiazol-2-yl)-2'-chloro-3'-fluoro-5'-methoxy-6-methyl-(4,4'-bipyridine)-3-carboxamide (88.6 mg, 38%) as a white solid. MS (ESI) calc'd for ($C_{20}H_{19}ClN_5O_5S$) $(M+1)^+$, 496.1; found, 496.1 1H NMR (400 MHz, DMSO-$d_6$) δ 13.01 (s, 1H), 8.97 (s, 1H), 8.18 (s, 1H), 7.49 (s, 1H), 4.43-4.38 (m, 2H), 3.97-3.87 (m, 1H), 3.84-3.74 (m, 2H), 3.74 (s, 3H), 3.69-3.62 (m, 2H), 3.53-3.47 (m, 1H), 3.41-3.36 (m, 1H), 2.60 (s, 3H).

Example 240

N-(5-(((R)-1,4-dioxan-2-yl)methoxy)-1,3,4-thiadiazol-2-yl)-2'-chloro-3'-fluoro-5'-methoxy-6-methyl-(4,4'-bipyridine)-3-carboxamide

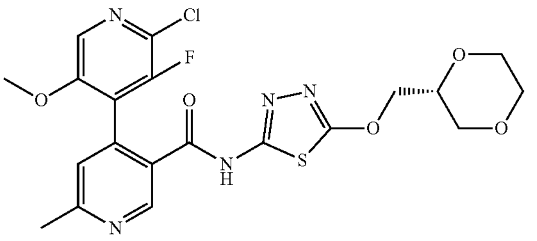

To a stirred solution of 2'-chloro-3'-fluoro-5'-methoxy-6-methyl-(4,4'-bipyridine)-3-carboxylic acid (150.0 mg, 0.51 mmol, Example 184, Step 4) in Acetonitrile (1 mL) were added (R)-5-((1,4-dioxan-2-yl)methoxy)-1,3,4-thiadiazol-2-amine (110.0 mg, 0.51 mmol, Example 187, Step 3) and 1-methylimidazole (208.0 mg, 2.53 mmol). To the above was added TCFH (142.0 mg, 0.51 mmol) in Acetonitrile (1 mL) at 30° C. The resulting mixture was stirred at 30° C. for 1 hr. The suspension was filtered. The filter cake was collected and dried under vacuum. The residue was dissolved in DMF (1 mL) and purified by prep-HPLC with the following conditions: (Column: XBridge Shield RP18 OBD Column, 30*150 mm, 5 μm; Mobile Phase A: Water (10 mmol/L $NH_4HCO_3$), Mobile Phase B: ACN; Flow rate: 60 mL/min; Gradient: 20% B to 35% B in 8 min, 35% B; Wave Length: 254 nm; RT1 (min): 7.7) to afford N-(5-(((R)-1,4-dioxan-2-yl)methoxy)-1,3,4-thiadiazol-2-yl)-2'-chloro-3'-fluoro-5'-methoxy-6-methyl-(4,4'-bipyridine)-3-carboxamide (66.0 mg, 26%) as a white solid. MS (ESI) calc'd for ($C_{20}H_{19}ClFN_5O_5S$) $(M+1)^+$, 496.1; found, 496.2. 1H NMR (400 MHz, DMSO-$d_6$) δ 13.05 (s, 1H), 8.98 (s, 1H), 8.18 (s, 1H), 7.46 (s, 1H), 4.43-4.38 (m, 2H), 3.97-3.86 (m, 1H), 3.82-3.76 (m, 2H), 3.74 (s, 3H), 3.69-3.57 (m, 2H), 3.54-3.44 (m, 1H), 3.41-3.36 (m, 1H), 2.60 (s, 3H).

Example 241

N-(5-(((S)-1,4-dioxan-2-yl)methoxy)-1,3,4-thiadiazol-2-yl)-3'-fluoro-5'-methoxy-2',6-dimethyl-(4,4'-bipyridine)-3-carboxamide

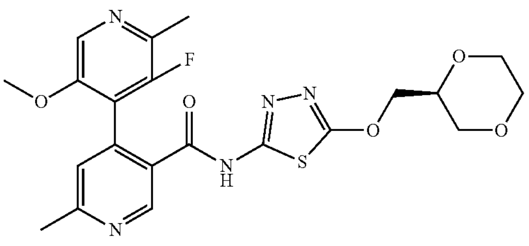 [SMILES: COc1cnc(C)c(F)c1-c1cc(C)ncc1C(=O)Nc1nnc(OC[C@@H]2COCCO2)s1]

To a stirred solution of 3'-fluoro-5'-methoxy-2',6-dimethyl-(4,4'-bipyridine)-3-carboxylic acid (150.0 mg, 0.54 mmol, Example 213, Step 5) in Acetonitrile (5 mL) were sequentially added (S)-5-((1,4-dioxan-2-yl)methoxy)-1,3,4-thiadiazol-2-amine (118.0 mg, 0.54 mmol, Example 186, Step 3) and 1-methyl-1H-imidazole (223.0 mg, 2.71 mmol) at 25° C. Then TCFH (152.0 mg, 0.54 mmol) in Acetonitrile (5 mL) was added to the above mixture at 25° C. The resulting solution was stirred at 25° C. for 2 hr. The suspension was filtered. The filter cake was triturated with Acetonitrile/$H_2O$ (1/1) to afford N-(5-(((S)-1,4-dioxan-2-yl)methoxy)-1,3,4-thiadiazol-2-yl)-3'-fluoro-5'-methoxy-2',6-dimethyl-(4,4'-bipyridine)-3-carboxamide (66.8 mg, 24%) as a white solid. MS (ESI) calc'd for ($C_{21}H_{22}FN_5O_5S$) $(M+1)^+$, 476.1, found 476.0. 1H NMR (400 MHz, DMSO-$d_6$) δ 13.07 (s, 1H), 8.91 (s, 1H), 8.18 (s, 1H), 7.40 (s, 1H), 4.46-4.34 (m, 2H), 3.95-3.86 (m, 1H), 3.83-3.75 (m, 2H), 3.71-3.65 (m, 3H), 3.64-3.60 (m, 1H), 3.50-3.45 (m, 2H), 3.44-3.33 (m, 1H), 2.59 (s, 3H), 2.43 (s, 3H).

Example 242

N-(5-(((R)-1,4-dioxan-2-yl)methoxy)-1,3,4-thiadiazol-2-yl)-3'-fluoro-5'-methoxy-2',6-dimethyl-(4,4'-bipyridine)-3-carboxamide

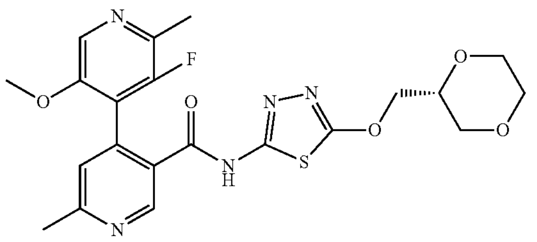 [SMILES: COc1cnc(C)c(F)c1-c1cc(C)ncc1C(=O)Nc1nnc(OC[C@H]2COCCO2)s1]

To a solution of 3'-fluoro-5'-methoxy-2',6-dimethyl-(4,4'-bipyridine)-3-carboxylic acid (150.0 mg, 0.54 mmol, Example 213, Step 5) in Acetonitrile (1 mL) were added (R)-5-((1,4-dioxan-2-yl)methoxy)-1,3,4-thiadiazol-2-amine (118.0 mg, 0.54 mmol, Example 187, Step 3) and NMI (223.0 mg, 2.71 mmol) at 20° C. under nitrogen. To the above solution was added TCFH (152.0 mg, 0.54 mmol) in Acetonitrile (1 mL) at 25° C. under nitrogen. The resulting mixture was then stirred at 25° C. for 1 hr. The suspension was filtered. The filter cake was triturated with Acetonitrile/H2O (1/1) to afford N-(5-(((R)-1,4-dioxan-2-yl)methoxy)-1,3,4-thiadiazol-2-yl)-3'-fluoro-5'-methoxy-2',6-dimethyl-(4,4'-bipyridine)-3-carboxamide (63.2 mg, 23%) as a white solid. MS (ESI) calc'd for ($C_{21}H_{22}FN_5O_5S$) $(M+1)^+$, 476.1; found 476.1. 1H NMR (400 MHz, DMSO-$d_6$) 1H NMR (400 MHz, DMSO-$d_6$) δ 13.00 (s, 1H), 8.91 (s, 1H), 8.18 (s, 1H), 7.40 (s, 1H), 4.46-4.34 (m, 2H), 3.96-3.87 (m, 1H), 3.83-3.72 (m, 2H), 3.71-3.56 (m, 5H), 3.54-3.44 (m, 1H), 3.42-3.32 (m, 1H), 2.59 (s, 3H), 1.44 (s, 3H).

Example 243

2'-chloro-5'-(difluoromethoxy)-N-(5-(((1r,4r)-4-hydroxycyclohexyl)methoxy)-1,3,4-thiadiazol-2-yl)-6-methyl-(4,4'-bipyridine)-3-carboxamide

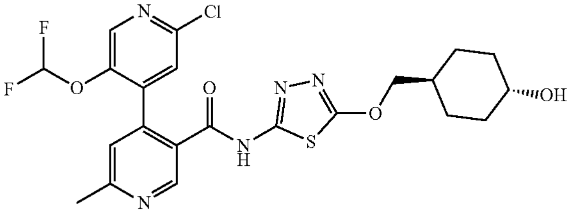 [SMILES: Cc1cc(-c2cc(Cl)ncc2OC(F)F)c(C(=O)Nc2nnc(OC[C@H]3CC[C@H](O)CC3)s2)cn1]

Step-1: N-(5-(((1r,4r)-4-((tert-butyldimethylsilyl)oxy)cyclohexyl)methoxy)-1,3,4-thiadiazol-2-yl)-2'-chloro-5'-(difluoromethoxy)-6-methyl-(4,4'-bipyridine)-3-carboxamide

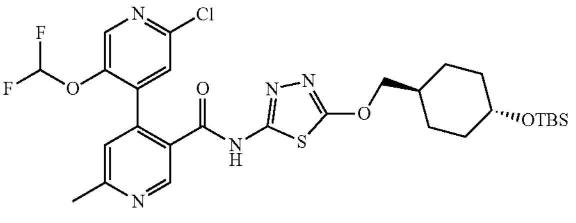 [SMILES: Cc1cc(-c2cc(Cl)ncc2OC(F)F)c(C(=O)Nc2nnc(OC[C@H]3CC[C@H](O[Si](C)(C)C(C)(C)C)CC3)s2)cn1]

To a stirred solution of 2'-chloro-5'-(difluoromethoxy)-6-methyl-(4,4'-bipyridine)-3-carboxylic acid (220.0 mg, 0.69 mmol, Example 233, Step 3) in Acetonitrile (2 mL) were added 5-(((1r,4r)-4-((tert-butyldimethylsilyl)oxy)cyclohexyl)methoxy)-1,3,4-thiadiazol-2-amine (240.0 mg, 0.69 mmol, Example 100, Step 5) and NMI (287.0 mg, 3.50 mmol). To the above mixture was added TCFH (196.0 mg, 0.69 mmol) in Acetonitrile (2 mL). The resulting mixture was stirred at 25° C. for 1 h. The solvents were removed under vacuum. The resulting residue was dissolved in DMF (3 mL) which was applied to a 40 g C18 column and purified by flash chromatography (Biotage Isolera Prime), eluted with 5~95% acetonitrile in water within 40 min to afford N-(5-(((1r,4r)-4-((tert-butyldimethylsilyl)oxy)cyclohexyl)methoxy)-1,3,4-thiadiazol-2-yl)-2'-chloro-5'-(difluoromethoxy)-6-methyl-(4,4'-bipyridine)-3-carboxamide (180.0 mg, 37%) as a yellow solid. MS (ESI) calculated for ($C_{28}H_{36}ClF_2N_5O_4SSi$) $(M+1)^+$, 640.2; found, 640.2.

Step-2: 2'-chloro-5'-(difluoromethoxy)-N-(5-(((1r,4r)-4-hydroxycyclohexyl)methoxy)-1,3,4-thiadiazol-2-yl)-6-methyl-(4,4'-bipyridine)-3-carboxamide

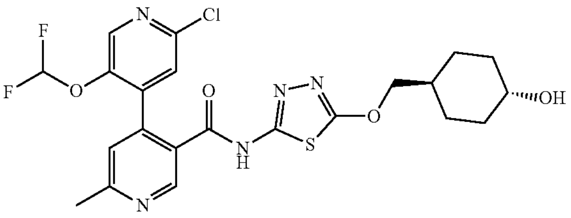 [SMILES: Cc1cc(-c2cc(Cl)ncc2OC(F)F)c(C(=O)Nc2nnc(OC[C@H]3CC[C@H](O)CC3)s2)cn1]

To a stirred solution of N-(5-(((1r,4r)-4-((tert-butyldimethylsilyl)oxy)cyclohexyl)methoxy)-1,3,4-thiadiazol-2-yl)-2'-chloro-5'-(difluoromethoxy)-6-methyl-(4,4'-bipyridine)-3-carboxamide (160.0 mg, 0.25 mmol) in Tetrahydrofuran (3 mL) was added TBAF (327.0 mg, 1.25 mmol) at 25° C. The resulting solution was stirred at 25° C. for 16 h. The reaction mixture was quenched by the addition of water and extracted with ethyl acetate. The combined organic layers were washed with brine, dried over anhydrous sodium sulfate, filtered, and concentrated under vacuum. The residue was dissolved in DMF (3 mL) and was purified by prep-HPLC with the following conditions: (Column: XBridge Prep Phenyl OBD Column, 19*250 mm, 5 μm; Mobile Phase A: Water (0.1% FA), Mobile Phase B: MeOH-HPLC; Flow rate: 25 mL/min; Gradient: 60% B to 70% B in 12 min, 70% B; Wave Length: 254 nm; RT1 (min): 11) to afford 2'-chloro- 5'-(difluoromethoxy)-N-(5-(((1r,4r)-4-hydroxycyclohexyl)methoxy)-1,3,4-thiadiazol-2-yl)-6-methyl-(4,4'-bipyridine)-3-carboxamide (63.8 mg, 48%) as a white solid. MS (ESI) calculated for ($C_{22}H_{22}ClF_2N_5O_4S$) $(M+1)^+$, 526.1; found, 526.1. 1H NMR (400 MHz, DMSO-$d_6$) δ 13.01 (s, 1H), 8.96 (s, 1H), 8.33 (s, 1H), 7.71 (s, 1H), 7.44 (s, 1H), 7.30-6.95 (m, 1H), 4.52 (d, J=4.4 Hz, 1H), 4.22 (d, J=6.4 Hz, 2H), 3.36-3.33 (m, 1H), 2.61 (s, 3H), 1.86-1.79 (m, 2H), 1.79-1.66 (m, 3H), 1.20-1.09 (m, 4H).

Example 260, 244 and 245

2'-bromo-5'-methoxy-6-methyl-N-(5-((tetrahydrofuran-3-yl)methoxy)-1,3,4-thiadiazol-2-yl)-(4,4'-bipyridine)-3-carboxamide, (S)-2'-bromo-5'-methoxy-6-methyl-N-(5-((tetrahydrofuran-3-yl)methoxy)-1,3,4-thiadiazol-2-yl)-(4,4'-bipyridine)-3-carboxamide and (R)-2'-bromo-5'-methoxy-6-methyl-N-(5-((tetrahydrofuran-3-yl)methoxy)-1,3,4-thiadiazol-2-yl)-(4,4'-bipyridine)-3-carboxamide

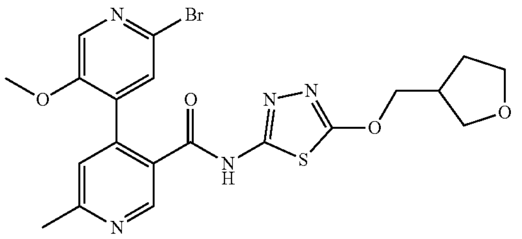

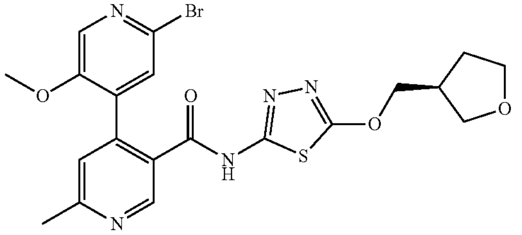

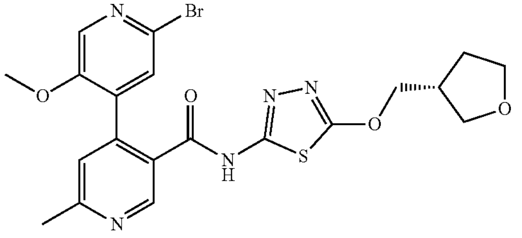

Step-1: 2'-bromo-5'-methoxy-6-methyl-N-(5-((tetrahydrofuran-3-yl)methoxy)-1,3,4-thiadiazol-2-yl)-(4,4'-bipyridine)-3-carboxamide

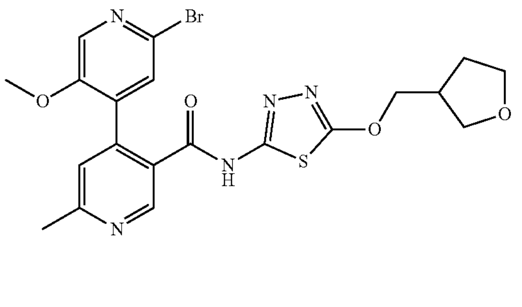

To a stirred solution of 5-((tetrahydrofuran-3-yl)methoxy)-1,3,4-thiadiazol-2-amine (155.0 mg, 0.77 mmol, Example 167, Step 1) in Acetonitrile (5 mL) was added 2'-bromo-5'-methoxy-6-methyl-(4,4'-bipyridine)-3-carboxylic acid (250.0 mg, 0.77 mmol, Example 235, Step 3) and NMI (318.0 mg, 3.87 mmol) at 25° C. To the above solution was added TCFH (217.0 mg, 0.77 mmol) in MeCN (1 mL) at 25° C. under nitrogen atmosphere. The resulting mixture was then stirred at 25° C. for 1 hr under nitrogen. The solvents were removed under vacuum. The residue was dissolved with DMF (3 mL), applied to a 20 g C18 column and purified by flash chromatography (Biotage Isolera Prime), eluted with 5-58% acetonitrile in water within 40 min to afford 2'-bromo-5'-methoxy-6-methyl-N-(5-((tetrahydrofuran-3-yl)methoxy)-1,3,4-thiadiazol-2-yl)-(4,4'-bipyridine)-3-carboxamide (150.0 mg, 37%) as a white solid. MS (ESI) calc'd for ($C_{20}H_{20}BrN_5O_4S$) $(M+1)^+$, 506.0, 508.0; found, 506.1, 508.1. $^1$H NMR (400 MHz, DMSO-$d_6$) δ 12.90 (s, 1H), 8.82 (s, 1H), 8.17 (s, 1H), 7.61 (s, 1H), 7.39 (s, 1H), 4.42-4.28 (m, 2H), 3.82-3.70 (m, 2H), 3.70-3.64 (m, 4H), 3.56-3.47 (m, 1H), 2.79-2.67 (m, 1H), 2.58 (s, 3H), 2.11-1.95 (m, 1H), 1.69-1.55 (m, 1H).

Step-2: (S)-2'-bromo-5'-methoxy-6-methyl-N-(5-((tetrahydrofuran-3-yl)methoxy)-1,3,4-thiadiazol-2-yl)-(4,4'-bipyridine)-3-carboxamide, and (R)-2'-bromo-5'-methoxy-6-methyl-N-(5-((tetrahydrofuran-3-yl)methoxy)-1,3,4-thiadiazol-2-yl)-(4,4'-bipyridine)-3-carboxamide

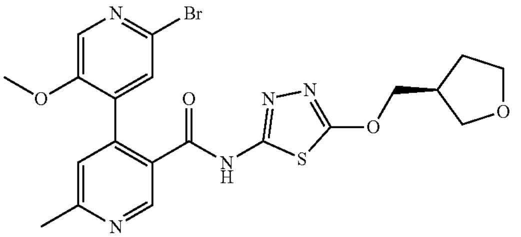

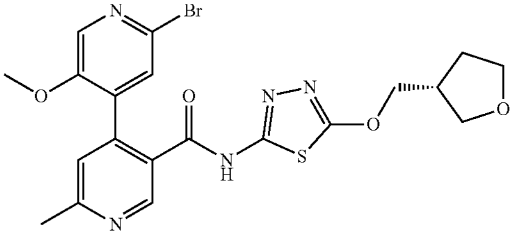

The racemic compound (150 mg) was separated by prep-chiral HPLC with the following conditions: (Column: CHIRALPAK IF, 2*25 cm, 5 μm; Mobile Phase A: Hex (0.2% FA)-HPLC, Mobile Phase B: MeOH:DCM=1: 1-HPLC; Flow rate: 20 mL/min; Gradient: 40% B to 40% B in 13 min; Wave Length: 220/254 nm; RT1 (min): 10.01; RT2 (min): 11.85; Sample Solvent: MeOH:DCM=1: 1-HPLC; Injection Volume: 0.6 mL; Number Of Runs: 12) to afford (S)-2'-bromo-5'-methoxy-6-methyl-N-(5-((tetrahydrofuran-3-yl)methoxy)-1,3,4-thiadiazol-2-yl)-(4,4'-bipyridine)-3-carboxamide, isomer 1 (62.4 mg, 41%) as a white solid with the first peak (first eluting fraction) on chiral HPLC and (R)-2'-bromo-5'-methoxy-6-methyl-N-(5-((tetrahydrofuran-3-yl)methoxy)-1,3,4-thiadiazol-2-yl)-(4,4'-bipyridine)-3-carboxamide, isomer 2 (58.7 mg, 38%) as a white solid with the second peak (second eluting raction) on chiral HPLC. The absolute stereochemistry was not determined.

Isomer 1: (S)-2'-bromo-5'-methoxy-6-methyl-N-(5-((tetrahydrofuran-3-yl)methoxy)-1,3,4-thiadiazol-2-yl)-(4,4'-bipyridine)-3-carboxamide: MS (ESI) calc'd for ($C_{20}H_{20}BrN_5O_4S$) $(M+1)^+$, 506.0; found, 506.1. $^1H$ NMR (400 MHz, DMSO-$d_6$) δ 12.85 (s, 1H), 8.85 (s, 1H), 8.15 (s, 1H), 7.56 (s, 1H), 7.34 (s, 1H), 4.41-4.25 (m, 2H), 3.82-3.71 (m, 2H), 3.71-3.63 (m, 4H), 3.56-3.48 (m, 1H), 2.76-2.66 (m, 1H), 2.57 (s, 3H), 2.09-1.93 (m, 1H), 1.69-1.57 (m, 1H).

Isomer 2: (R)-2'-bromo-5'-methoxy-6-methyl-N-(5-((tetrahydrofuran-3-yl)methoxy)-1,3,4-thiadiazol-2-yl)-(4,4'-bipyridine)-3-carboxamide: MS (ESI) calc'd for ($C_{20}H_{20}BrN_5O_4S$) $(M+1)^+$, 506.0; found, 506.1. $^1H$ NMR (400 MHz, DMSO-$d_6$) δ 12.85 (s, 1H), 8.85 (s, 1H), 8.15 (s, 1H), 7.57 (s, 1H), 7.34 (s, 1H), 4.40-4.25 (m, 2H), 3.82-3.70 (m, 2H), 3.70-3.63 (m, 4H), 3.56-3.48 (m, 1H), 2.79-2.67 (m, 1H), 2.58 (s, 3H), 2.10-1.94 (m, 1H), 1.69-1.57 (m, 1H).

Example 246, 237 and 238

2'-chloro-N-(5-((5-(hydroxymethyl)-1,4-dioxan-2-yl) methoxy)-1,3,4-thiadiazol-2-yl)-5'-methoxy-6-methyl-(4,4'-bipyridine)-3-carboxamide, rel-2'-chloro-N-(5-(((2s,5r)-5-(hydroxymethyl)-1,4-dioxan-2-yl)methoxy)-1,3,4-thiadiazol-2-yl)-5'-methoxy-6-methyl-(4,4'-bipyridine)-3-carboxamide and rel-2'-chloro-N-(5-(((2s,5s)-5-(hydroxymethyl)-1,4-dioxan-2-yl)methoxy)-1,3,4-thiadiazol-2-yl)-5'-methoxy-6-methyl-(4,4'-bipyridine)-3-carboxamide

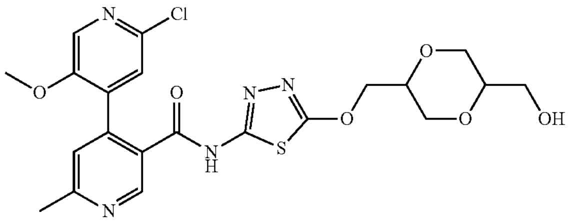

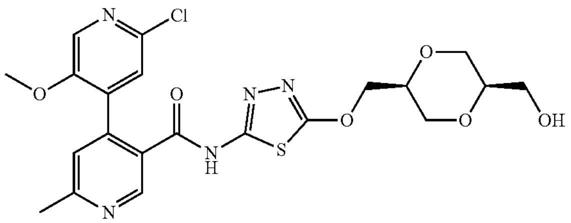

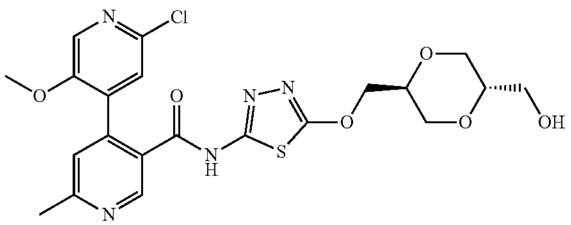

Step-1: (5-(((tert-butyldimethylsilyl)oxy)methyl)-1,4-dioxan-2-yl)methanol

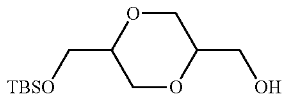 [SMILES: CC(C)(C)[Si](C)(C)OCC1COC(CO)CO1]

To a stirred solution of (1,4-dioxane-2,5-diyl)dimethanol (450.0 mg, 3.04 mmol) in Dichloromethane (2 mL) were added TBS-Cl (916.0 mg, 6.07 mmol), TEA (920.0 mg, 9.11 mmol) and DMAP (186.0 mg, 1.52 mmol) at 0° C. The resulting solution was stirred at 20° C. for 2 hr. The reaction was quenched by the addition of water and extracted with ethyl acetate. The combined organic layers were washed with brine, dried over anhydrous sodium sulfate, filtered, and concentrated under vacuum. The resulting residue was dissolved in DCM (5 mL) and purified by flash chromatography (Biotage Isolera Prime) which applied to a 20 g silica gel column that was eluted with 0-50% ethyl acetate in petroleum ether within 25 min to afford (5-(((tert-butyldimethylsilyl)oxy)methyl)-1,4-dioxan-2-yl)methanol (190.0 mg, 21%) as a colorless oil.

Step-2: O-((5-(((tert-butyldimethylsilyl)oxy) methyl)-1,4-dioxan-2-yl)methyl)S-methyl carbonodithioate

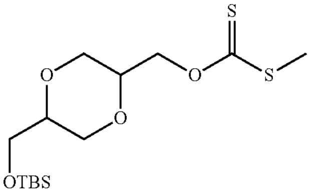 [SMILES: CSC(=S)OCC1COC(CO[Si](C)(C)C(C)(C)C)CO1]

To a degassed solution of 5-(((tert-butyldimethylsilyl) oxy)methyl)-1,4-dioxan-2-ol (190.0 mg, 0.76 mmol) in dry Tetrahydrofuran (10 mL) was added NaH (36.5 mg, 0.92 mmol, 60%) in portions at 0° C. The resulting solution was stirred at 0° C. for 30 min under nitrogen. To the above solution was added $CS_2$ (87.0 mg, 1.14 mmol) at 0° C. under nitrogen. The resulting mixture was then stirred at 0° C. for 30 min under nitrogen. And then to the above solution was added MeI (163.0 mg, 1.14 mmol) at 0° C. under nitrogen. The resulting mixture was then stirred at 0° C. for 30 min under nitrogen. The reaction was quenched by the addition of water and extracted with ethyl acetate. The combined organic layers were washed with brine, dried over anhydrous sodium sulfate, filtered, and concentrated under vacuum to afford O-(5-(((tert-butyldimethylsilyl)oxy)methyl)-1,4-dioxan-2-yl)S-methyl carbonodithioate (245.0 mg, crude) as a yellow oil.

Step-3: O-((5-(((tert-butyldimethylsilyl)oxy)methyl)-1,4-dioxan-2-yl)methyl) hydrazinecarbothioate

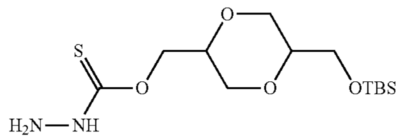 [SMILES: CC(C)(C)[Si](C)(C)OCC1COC(COC(=S)NN)CO1]

To a stirred solution of O-((5-(((tert-butyldimethylsilyl)oxy)methyl)-1,4-dioxan-2-yl)methyl)S-methyl carbonodithioate (245.0 mg, 0.70 mmol) in Methanol (10 mL) was added hydrazine hydrate (30 mg, 0.76 mmol, 80%) at 20° C. The resulting solution was stirred at 20° C. for 30 min. The organic solvent was removed under vacuum to afford O-((5-(((tert-butyldimethylsilyl)oxy)methyl)-1,4-dioxan-2-yl)methyl) hydrazinecarbothioate (227.0 mg, crude) as a colorless oil.

Step-4: 5-((5-(((tert-butyldimethylsilyl)oxy)methyl)-1,4-dioxan-2-yl)methoxy)-1,3,4-thiadiazol-2-amine

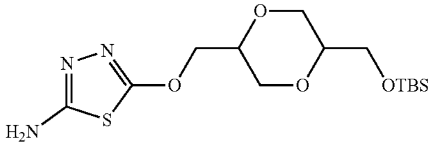

To a stirred solution of O-((5-(((tert-butyldimethylsilyl)oxy)methyl)-1,4-dioxan-2-yl)methyl) hydrazinecarbothioate (233.0 mg, 0.69 mmol) in Methanol (5 mL) were added TEA (140.0 mg, 1.38 mmol) and BrCN (80.0 mg, 0.76 mmol) at 20° C. The resulting solution was stirred at 20° C. for 1 hr. The reaction mixture was extracted with ethyl acetate. The combined organic layers were washed with brine, dried over anhydrous sodium sulfate, filtered, and concentrated under vacuum. The resulting residue was dissolved in DCM (4 mL) and purified by flash chromatography (Biotage Isolera Prime) which applied to a 40 g silica gel column that was eluted with 0~20% methanol in dichloromethane within 30 min to afford 5-((5-(((tert-butyldimethylsilyl)oxy)methyl)-1,4-dioxan-2-yl)methoxy)-1,3,4-thiadiazol-2-amine (160.0 mg, 60% over four steps) as a white solid. MS (ESI) calc'd for ($C_{14}H_{27}N_3O_4SSi$) $(M+1)^+$, 362.1, found, 362.1.

Step-5: N-(5-((5-(((tert-butyldimethylsilyl)oxy)methyl)-1,4-dioxan-2-yl)methoxy)-1,3,4-thiadiazol-2-yl)-2'-chloro-5'-methoxy-6-methyl-(4,4'-bipyridine)-3-carboxamide

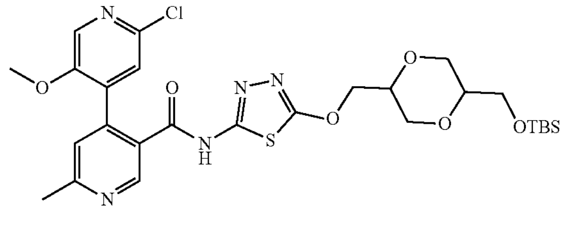 [SMILES: COc1cnc(Cl)cc1-c1cc(C)ncc1C(=O)Nc1nnc(OCC2COC(CO[Si](C)(C)C(C)(C)C)CO2)s1]

To a stirred solution of 5-((5-(((tert-butyldimethylsilyl)oxy)methyl)-1,4-dioxan-2-yl)methoxy)-1,3,4-thiadiazol-2-amine (160.0 mg, 0.44 mmol) in Acetonitrile (3 mL) were added Intermediate H (123.0 mg, 0.443 mmol) and 1-methylimidazole (182.0 mg, 2.21 mmol) at 20° C. To the above solution was added TCFH (124.0 mg, 0.44 mmol) in Acetonitrile (1 mL) at 20° C. under nitrogen. The resulting mixture was then stirred at 20° C. for 1 hr. The mixture was diluted with DMF (1 mL) which was applied to a 80 g C18 column and purified by flash chromatography (Biotage Isolera Prime), eluted with 5~70% acetonitrile in water within 30 min to afford N-(5-((5-(((tert-butyldimethylsilyl)oxy)methyl)-1,4-dioxan-2-yl)methoxy)-1,3,4-thiadiazol-2-yl)-2'-chloro-5'-methoxy-6-methyl-(4,4'-bipyridine)-3-carboxamide (210.0 mg, 76%) as a white solid. MS (ESI) calc'd for ($C_{27}H_{36}ClN_5O_6SSi$) $(M+1)^+$, 622.2; found, 622.2.

Step-6: 2'-chloro-N-(5-((5-(hydroxymethyl)-1,4-dioxan-2-yl)methoxy)-1,3,4-thiadiazol-2-yl)-5'-methoxy-6-methyl-(4,4'-bipyridine)-3-carboxamide

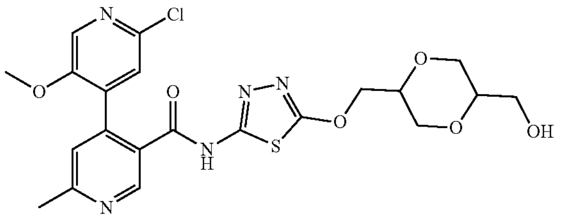 [SMILES: COc1cnc(Cl)cc1-c1cc(C)ncc1C(=O)Nc1nnc(OCC2COC(CO)CO2)s1]

To a stirred solution of N-(5-((5-(((tert-butyldimethylsilyl)oxy)methyl)-1,4-dioxan-2-yl)methoxy)-1,3,4-thiadiazol-2-yl)-2'-chloro-5'-methoxy-6-methyl-(4,4'-bipyridine)-3-carboxamide (210.0 mg, 0.33 mmol) in Dichloromethane (2 mL) was added 2,2,2-trifluoroacetaldehyde (0.5 mL) at 20° C. The resulting solution was stirred at 20° C. for 1 hr. The volatiles were removed under vacuum. The residue was dissolved in water. The aqueous layer was basified with aq. NaOH to pH ~7 and diluted with DMSO (2 mL). The mixture was applied to a 20 g C18 column and purified by flash chromatography (Biotage Isolera Prime), eluted with 5~70% acetonitrile in water within 30 min to afford 2'-chloro-N-(5-((5-(hydroxymethyl)-1,4-dioxan-2-yl)methoxy)-1,3,4-thiadiazol-2-yl)-5'-methoxy-6-methyl-(4,4'-bipyridine)-3-carboxamide (98.4 mg, 57%) as a white solid. MS (ESI) calc'd for ($C_{21}H_{22}ClN_5O_6S$) $(M+1)^+$, 508.1; found, 508.1. $^1H$ NMR (400 MHz, DMSO-$d_6$) δ 12.94 (s, 1H), 8.80 (s, 1H), 8.17 (s, 1H), 7.56 (s, 1H), 7.44 (s, 1H), 4.79-4.72 (m, 1H), 4.46-4.32 (m, 2H), 3.90-3.80 (m, 3H), 3.63 (s, 3H), 3.49-3.36 (m, 4H), 3.33-3.27 (m, 1H), 2.59 (s, 3H).

Step-7: rel-2'-chloro-N-(5-(((2s,5r)-5-(hydroxymethyl)-1,4-dioxan-2-yl)methoxy)-1,3,4-thiadiazol-2-yl)-5'-methoxy-6-methyl-(4,4'-bipyridine)-3-carboxamide and rel-2'-chloro-N-(5-(((2s,5s)-5-(hydroxymethyl)-1,4-dioxan-2-yl)methoxy)-1,3,4-thiadiazol-2-yl)-5'-methoxy-6-methyl-(4,4'-bipyridine)-3-carboxamide

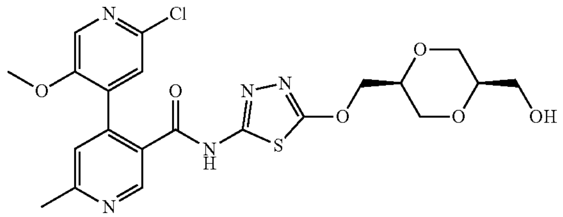

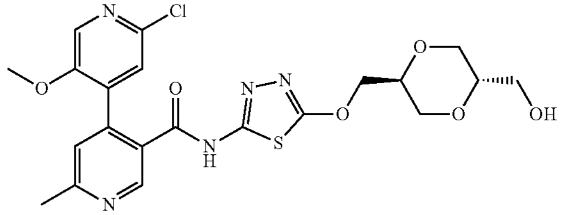

The mixture (96.4 mg) was separated by prep-chiral HPLC with the following conditions: (Column: CHIRALPAK IF, 2*25 cm, 5 μm; Mobile Phase A: Hex (0.2% FA)-HPLC, Mobile Phase B: MeOH:DCM=1: 1-HPLC; Flow rate: 20 mL/min; Gradient: 50% B to 50% B in 15 min; Wave Length: 220/254 nm; RT1 (min): 8.20; RT2 (min): 12.43; Sample Solvent: MeOH:DCM=1:1-HPLC; Injection Volume: 0.8 mL; Number Of Runs: 4) to afford rel-2'-chloro-N-(5-(((2s,5r)-5-(hydroxymethyl)-1,4-dioxan-2-yl)methoxy)-1,3,4-thiadiazol-2-yl)-5'-methoxy-6-methyl-(4,4'-bipyridine)-3-carboxamide, isomer 1 (33.3 mg, 34%) as a white solid with shorter retention time on chiral-HPLC and rel-2'-chloro-N-(5-(((2s,5s)-5-(hydroxymethyl)-1,4-dioxan-2-yl)methoxy)-1,3,4-thiadiazol-2-yl)-5'-methoxy-6-methyl-(4,4'-bipyridine)-3-carboxamide (34.3 mg, 35%), isomer 2 as a white solid with longer retention time on chiral-HPLC. Isomer 1 is a mixture of two enantiomers. Isomer 2 is a mixture of two enantiomers. The absolute stereochemistry was not determined.

Isomer 1: rel-2'-chloro-N-(5-(((2s,5r)-5-(hydroxymethyl)-1,4-dioxan-2-yl)methoxy)-1,3,4-thiadiazol-2-yl)-5'-methoxy-6-methyl-(4,4'-bipyridine)-3-carboxamide: MS (ESI) calc'd for ($C_{21}H_{22}ClN_5O_6S$) $(M+1)^+$, 508.1; found, 508.1. $^1$H NMR (400 MHz, DMSO-$d_6$) δ 12.94 (s, 1H), 8.80 (s, 1H), 8.17 (s, 1H), 7.56 (s, 1H), 7.44 (s, 1H), 4.79-4.72 (m, 1H), 4.46-4.32 (m, 2H), 3.90-3.80 (m, 3H), 3.63 (s, 3H), 3.49-3.27 (m, 5H), 2.59 (s, 3H).

Isomer 2: rel-2'-chloro-N-(5-(((2s,5s)-5-(hydroxymethyl)-1,4-dioxan-2-yl)methoxy)-1,3,4-thiadiazol-2-yl)-5'-methoxy-6-methyl-(4,4'-bipyridine)-3-carboxamide: MS (ESI) calc'd for ($C_{21}H_{22}ClN_5O_6S$) $(M+1)^+$, 508.1; found, 508.1. $^1$H NMR (400 MHz, DMSO-$d_6$) δ 12.94 (s, 1H), 8.80 (s, 1H), 8.17 (s, 1H), 7.56 (s, 1H), 7.44 (s, 1H), 4.79-4.72 (m, 1H), 4.46-4.32 (m, 2H), 3.90-3.80 (m, 3H), 3.63 (s, 3H), 3.49-3.27 (m, 5H), 2.59 (s, 3H).

Example 247

2'-bromo-N-(5-(((1r,4r)-4-hydroxycyclohexyl)methoxy)-1,3,4-thiadiazol-2-yl)-5'-methoxy-6-methyl-(4,4'-bipyridine)-3-carboxamide

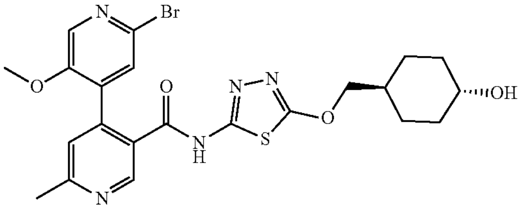 [SMILES: COc1cnc(Br)cc1-c1cc(C)ncc1C(=O)Nc1nnc(OC[C@H]2CC[C@H](O)CC2)s1]

Step-1: 2'-bromo-N-(5-(((1r,4r)-4-((tert-butyldimethylsilyl)oxy)cyclohexyl)methoxy)-1,3,4-thiadiazol-2-yl)-5'-methoxy-6-methyl-(4,4'-bipyridine)-3-carboxamide

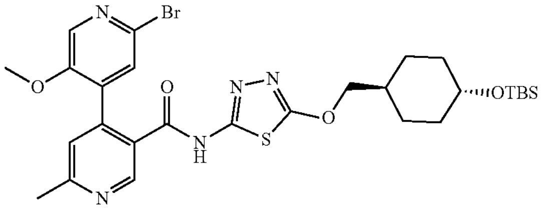 [SMILES: COc1cnc(Br)cc1-c1cc(C)ncc1C(=O)Nc1nnc(OC[C@H]2CC[C@H](O[Si](C)(C)C(C)(C)C)CC2)s1]

To a stirred solution of 2'-bromo-5'-methoxy-6-methyl-(4,4'-bipyridine)-3-carboxylic acid (150.0 mg, 0.46 mmol, Example 235, Step 3) in Acetonitrile (1 mL) were added 5-(((1r,4r)-4-((tert-butyldimethylsilyl)oxy)cyclohexyl)methoxy)-1,3,4-thiadiazol-2-amine (159.0 mg, 0.46 mmol, Example 100, Step 5) and 1-methylimidazole (191.0 mg, 2.32 mmol). To the above was added a solution of TCFH (130.0 mg, 0.46 mmol) in Acetonitrile (0.5 mL) at 25° C. The resulting mixture was stirred at 25° C. for 2 h. The suspension was filtered. The filter cake was collected and dried under vacuum to afford 2'-bromo-N-(5-(((1r,4r)-4-((tert-butyldimethylsilyl)oxy)cyclohexyl)methoxy)-1,3,4-thiadiazol-2-yl)-5'-methoxy-6-methyl-(4,4'-bipyridine)-3-carboxamide (180.0 mg, 60%) as a white solid. MS (ESI) calc'd for ($C_{28}H_{38}BrN_5O_4SSi$) $(M+1)^+$, 648.2, 650.2; found, 648.2, 650.2.

Step-2: 2'-bromo-N-(5-(((1r,4r)-4-hydroxycyclohexyl)methoxy)-1,3,4-thiadiazol-2-yl)-5'-methoxy-6-methyl-(4,4'-bipyridine)-3-carboxamide

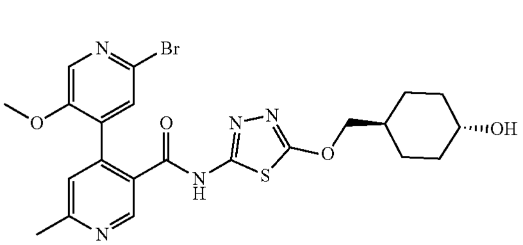 [SMILES: COc1cnc(Br)cc1-c1cc(C)ncc1C(=O)Nc1nnc(OC[C@H]2CC[C@H](O)CC2)s1]

To a stirred solution of 2'-bromo-N-(5-(((1r,4r)-4-((tert-butyldimethylsilyl)oxy)cyclohexyl)methoxy)-1,3,4-thiadiazol-2-yl)-5'-methoxy-6-methyl-(4,4'-bipyridine)-3-carboxamide (180.0 mg, 0.28 mmol) in Tetrahydrofuran (2 mL) was added TBAF (363.0 mg, 1.39 mmol) at 25° C. The resulting solution was stirred at 25° C. for 2 h. The reaction was quenched by the addition of water and extracted with ethyl acetate. The combined organic layers were washed with water, dried over anhydrous sodium sulfate, filtered, and concentrated under vacuum. The residue was dissolved in DMF (2 mL) and was purified by prep-HPLC with the following conditions: (Column: Sunfire prep C18 column, 30*150 mm, 5 m; Mobile Phase A: ACN, Mobile Phase B: Water (0.05% TFA); Flow rate: 60 mL/min; Gradient: 30% B to 38% B in 8 min, 38% B to 38% B in 10 min, 38% B; Wave Length: 254/220 nm; RT1 (min): 8.52) to afford 2'-bromo-N-(5-(((1r,4r)-4-hydroxycyclohexyl)methoxy)-1,3,4-thiadiazol-2-yl)-5'-methoxy-6-methyl-(4,4'-bipyridine)-3-carboxamide (63.0 mg, 42%) as a white solid. MS (ESI) calc'd for ($C_{22}H_{24}BrN_5O_4S$) $(M+1)^+$, 534.1, 536.1; found, 534.1, 536.1. 1H NMR (400 MHz, DMSO-$d_6$) δ 12.86 (s, 1H), 8.80 (s, 1H), 8.17 (s, 1H), 7.63 (s, 1H), 7.42 (s, 1H), 4.52 (d, J=4.4 Hz, 1H), 4.22 (d, J=6.4 Hz, 2H), 3.63 (s, 3H), 3.37-3.33 (m, 1H), 2.59 (s, 3H), 1.90-1.80 (m, 2H), 1.80-1.68 (m, 3H), 1.21-1.04 (m, 4H).

Example 248

2'-chloro-3'-fluoro-N-(5-(((1r,4r)-4-hydroxycyclohexyl)methoxy)-1,3,4-thiadiazol-2-yl)-5'-methoxy-6-methyl-(4,4'-bipyridine)-3-carboxamide

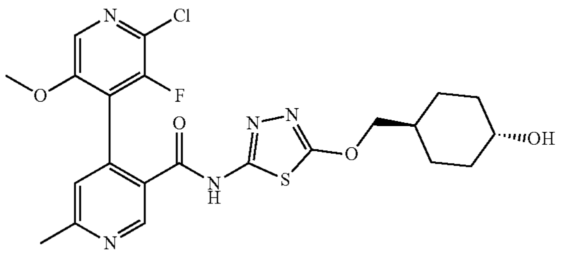 [SMILES: COc1cnc(Cl)c(F)c1-c1cc(C)ncc1C(=O)Nc1nnc(OC[C@H]2CC[C@H](O)CC2)s1]

Step-1: N-(5-(((1r,4r)-4-((tert-butyldimethylsilyl)oxy)cyclohexyl)methoxy)-1,3,4-thiadiazol-2-yl)-2'-chloro-3'-fluoro-5'-methoxy-6-methyl-(4,4'-bipyridine)-3-carboxamide

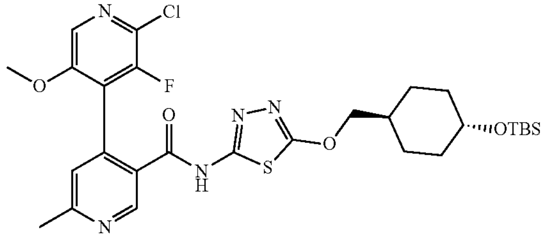 [SMILES: COc1cnc(Cl)c(F)c1-c1cc(C)ncc1C(=O)Nc1nnc(OC[C@H]2CC[C@H](O[Si](C)(C)C(C)(C)C)CC2)s1]

To a stirred solution of 5-(((1r,4r)-4-((tert-butyldimethylsilyl)oxy)cyclohexyl)methoxy)-1,3,4-thiadiazol-2-amine (164.0 mg, 0.47 mmol, Example 100, Step 5) in Acetonitrile (0.5 mL) were added 2'-chloro-3'-fluoro-5'-methoxy-6-methyl-(4,4'-bipyridine)-3-carboxylic acid (157.0 mg, 0.52 mmol, Example 184, Step 5) and 1-methylimidazole (0.21 mL, 2.65 mmol) at 20° C. To the above solution was added TCFH (149.0 mg, 0.52 mmol) in Acetonitrile (0.5 mL) at 20° C. The resulting solution was stirred at 20° C. for 1 hr under nitrogen. The suspension was filtered. The filtrate was collected and concentrated under vacuum to afford N-(5-(((1r,4r)-4-((tert-butyldimethylsilyl)oxy)cyclohexyl)methoxy)-1,3,4-thiadiazol-2-yl)-2'-chloro-3'-fluoro-5'-methoxy-6-methyl-(4,4'-bipyridine)-3-carboxamide (136.0 mg, 39%) as a white solid. MS (ESI) calc'd for ($C_{28}H_{37}ClFN_5O_4SSi$) $(M+1)^+$, 622.2. found: 622.2.

Step-2: 2'-chloro-3'-fluoro-N-(5-(((1r,4r)-4-hydroxycyclohexyl)methoxy)-1,3,4-thiadiazol-2-yl)-5'-methoxy-6-methyl-(4,4'-bipyridine)-3-carboxamide

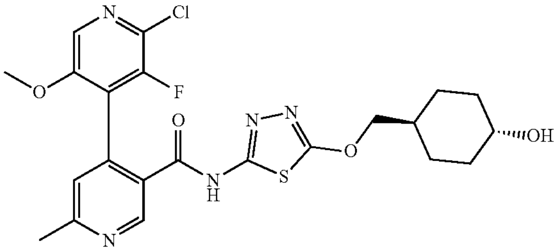 [SMILES: COc1cnc(Cl)c(F)c1-c1cc(C)ncc1C(=O)Nc1nnc(OC[C@H]2CC[C@H](O)CC2)s1]

To a stirred solution of N-(5-(((1r,4r)-4-((tert-butyldimethylsilyl)oxy)cyclohexyl)methoxy)-1,3,4-thiadiazol-2-yl)-2'-chloro-3'-fluoro-5'-methoxy-6-methyl-(4,4'-bipyridine)-3-carboxamide (130.0 mg, 0.20 mmol) in Dichloromethane (10 mL) was added TFA (0.5 mL, 6.49 mmol) at 25° C. The resulting solution was stirred at 25° C. for 1 hr. The mixture was concentrated under vacuum. The residue was dissolved with DMF, basified with aq. NaOH to pH ~7. The mixture was applied to a 40 g C18 column and purified by flash chromatography (Biotage Isolera Prime), eluted with 5-40% acetonitrile in water within 45 min to afford 2'-chloro-3'-fluoro-N-(5-(((1r,4r)-4-hydroxycyclohexyl)methoxy)-1,3,4-thiadiazol-2-yl)-5'-methoxy-6-methyl-(4,4'-bipyridine)-3-carboxamide (61.5 mg, 56%) as a white solid. MS (ESI) calc'd for ($C_{22}H_{23}ClFN_5O_4S$) $(M+1)^+$, 508.1. found: 508.1. $^1$H NMR (400 MHz, DMSO-$d_6$) δ 13.07 (s, 1H), 8.99 (s, 1H), 8.17 (s, 1H), 7.44 (s, 1H), 4.54 (d, J=4.4 Hz, 1H), 4.20 (d, J=6.4 Hz, 2H), 3.74 (s, 3H), 3.37-3.33 (m, 1H), 2.59 (s, 3H), 1.84-1.69 (m, 5H), 1.21-0.98 (m, 4H).

Example 249 and 250

3'-fluoro-5'-methoxy-2',6-dimethyl-N-(5-(((S)-tetrahydrofuran-3-yl)methoxy)-1,3,4-thiadiazol-2-yl)-(4,4'-bipyridine)-3-carboxamide and 3'-fluoro-5'-methoxy-2',6-dimethyl-N-(5-(((R)-tetrahydrofuran-3-yl)methoxy)-1,3,4-thiadiazol-2-yl)-(4,4'-bipyridine)-3-carboxamide

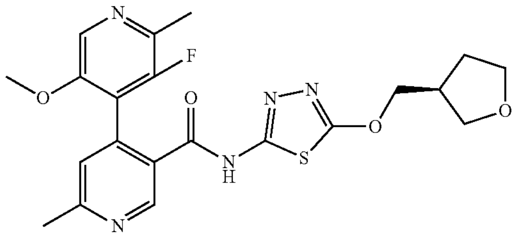

-continued

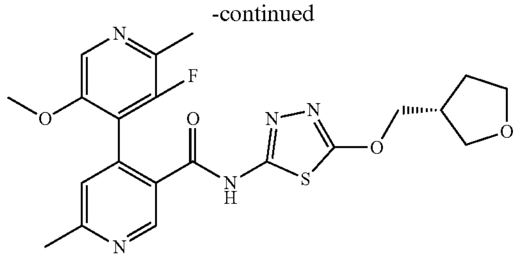

Step-1: 3'-fluoro-5'-methoxy-2',6-dimethyl-N-(5-((tetrahydrofuran-3-yl)methoxy)-1,3,4-thiadiazol-2-yl)-(4,4'-bipyridine)-3-carboxamide

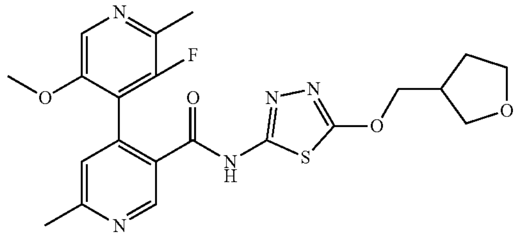 [SMILES: COc1cnc(C)c(F)c1-c1cc(C)ncc1C(=O)Nc1nnc(OCC2CCOC2)s1]

To a stirred solution of 3'-fluoro-5'-methoxy-2',6-dimethyl-(4,4'-bipyridine)-3-carboxylic acid (150.0 mg, 0.54 mmol, Example 213, Step 5) in acetonitrile (2 mL) were added 5-((tetrahydrofuran-3-yl)methoxy)-1,3,4-thiadiazol-2-amine (109.0 mg, 0.54 mmol, Example 167, Step 1) and 1-methyl-1H-imidazole (223.0 mg, 2.71 mmol). To the above solution was added TCFH (152.0 mg, 0.54 mmol) in acetonitrile (1 mL). The resulting solution was stirred at 25° C. under nitrogen for 1 hr. The reaction was quenched with water. The aqueous layer was extracted with ethyl acetate. The combined organic layers were washed with brine, dried over anhydrous sodium sulfate, filtered, and concentrated under vacuum. The resulting residue was dissolved in DMF (1 mL) which was applied to a 25 g C18 column and purified by flash chromatography (Biotage Isolera Prime), eluted with 10~80% acetonitrile in water within 30 min to afford 3'-fluoro-5'-methoxy-2',6-dimethyl-N-(5-((tetrahydrofuran-3-yl)methoxy)-1,3,4-thiadiazol-2-yl)-(4,4'-bipyridine)-3-carboxamide (90.0 mg, 35.7%) as a white solid. MS (ESI) calc'd for ($C_{21}H_{22}FN_5O_4S$) $(M+1)^+$, 460.1; found, 460.2.

Step-2:3'-fluoro-5'-methoxy-2',6-dimethyl-N-(5-(((S)-tetrahydrofuran-3-yl)methoxy)-1,3,4-thiadiazol-2-yl)-(4,4'-bipyridine)-3-carboxamide & 3'-fluoro-5'-methoxy-2',6-dimethyl-N-(5-(((R)-tetrahydrofuran-3-yl)methoxy)-1,3,4-thiadiazol-2-yl)-(4,4'-bipyridine)-3-carboxamide

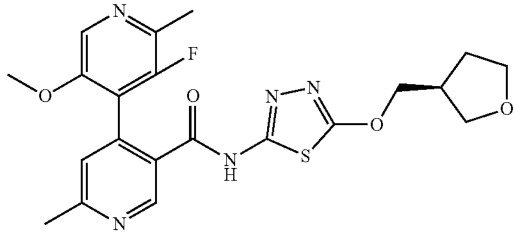

-continued

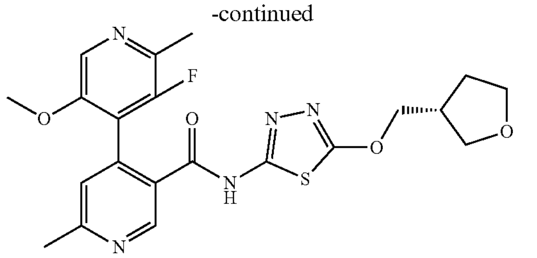

The racemic compound (220.0 mg, 0.48 mmol) was separated by prep-chiral HPLC with the following conditions: (Column: CHIRALPAK IF, 2*25 cm, 5 μm; Mobile Phase A: MtBE (0.1% FA)-HPLC, Mobile Phase B: EtOH: DCM=1: 1-HPLC; Flow rate: 17 mL/min; Gradient: 20% B to 20% B in 19 min; Wave Length: 220/254 nm; RT1 (min): 10.94; RT2 (min): 15.27; Sample Solvent: MeOH:DCM=1: 1-HPLC; Injection Volume: 0.8 mL; Number Of Runs: 4) to afford 3'-fluoro-5'-methoxy-2',6-dimethyl-N-(5-(((S)-tetrahydrofuran-3-yl)methoxy)-1,3,4-thiadiazol-2-yl)-(4,4'-bipyridine)-3-carboxamide (90.1 mg, 40.9%) as a white solid with the first peak on chiral HPLC and 3'-fluoro-5'-methoxy-2',6-dimethyl-N-(5-(((R)-tetrahydrofuran-3-yl)methoxy)-1,3,4-thiadiazol-2-yl)-(4,4'-bipyridine)-3-carboxamide (96.5 mg, 43.7%) as a white solid with the second peak on chiral HPLC. The absolute stereochemistry was determined using vibrational circular dichroism (VCD) and Ab Initio calculations.

3'-fluoro-5'-methoxy-2',6-dimethyl-N-(5-(((S)-tetrahydrofuran-3-yl)methoxy)-1,3,4-thiadiazol-2-yl)-(4,4'-bipyridine)-3-carboxamide: MS (ESI) calc'd for ($C_{21}H_{22}FN_5O_4S$) $(M+1)^+$, 460.1; found, 460.2. $^1H$ NMR (400 MHz, DMSO-$d_6$) δ 12.97 (s, 1H), 8.90 (s, 1H), 8.18 (s, 1H), 7.40 (s, 1H), 4.44-4.28 (m, 2H), 3.81-3.71 (m, 2H), 3.68 (s, 3H), 3.68-3.62 (m, 1H), 3.55-3.50 (m, 1H), 2.76-2.72 (m, 1H), 2.59 (s, 3H), 2.43 (s, 3H), 2.10-2.00 (m, 1H), 1.70-1.60 (m, 1H).

3'-fluoro-5'-methoxy-2',6-dimethyl-N-(5-(((R)-tetrahydrofuran-3-yl)methoxy)-1,3,4-thiadiazol-2-yl)-(4,4'-bipyridine)-3-carboxamide: MS (ESI) calc'd for ($C_{21}H_{22}FN_5O_4S$) $(M+1)^+$, 460.1; found, 460.2. $^1H$ NMR (400 MHz, DMSO-$d_6$) δ 12.98 (s, 1H), 8.91 (s, 1H), 8.18 (s, 1H), 7.40 (s, 1H), 4.44-4.28 (m, 2H), 3.81-3.71 (m, 2H), 3.68 (s, 3H), 3.68-3.61 (m, 1H), 3.56-3.51 (m, 1H), 2.79-2.68 (m, 1H), 2.59 (s, 3H), 2.43 (s, 3H), 2.11-2.01 (m, 1H), 1.71-1.61 (m, 1H).

Example 261, 255, 256, 272, and 273

2'-chloro-N-(5-((2-hydroxycyclopentyl)methoxy)-1,3,4-thiadiazol-2-yl)-5'-methoxy-6-methyl-(4,4'-bipyridine)-3-carboxamide

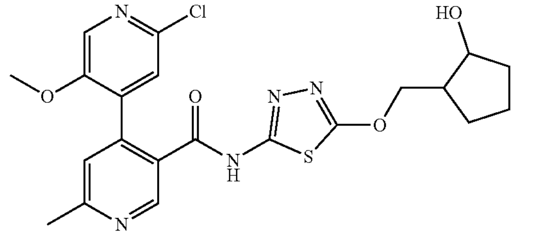

-continued

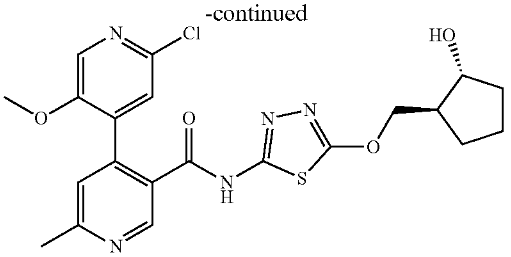

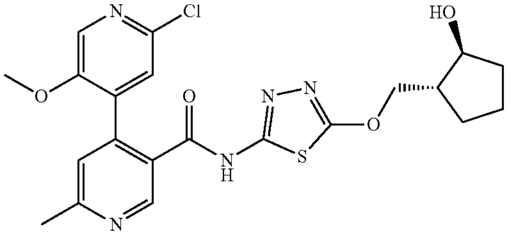

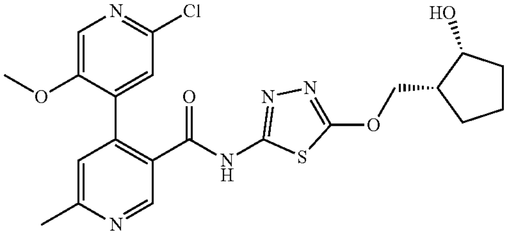

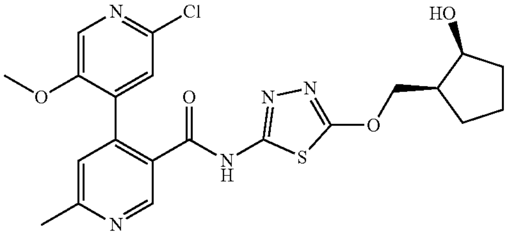

Synthesis of Example 261, 255, and 256

Step-1: ethyl 2-((tert-butyldimethylsilyl)oxy)cyclopentane-1-carboxylate

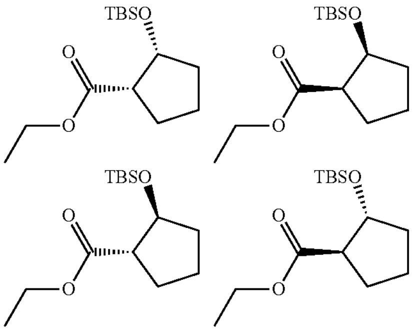

To a stirred solution of ethyl 2-hydroxycyclopentane-1-carboxylate (1.3 g, 8.22 mmol) (racemic mixture and stereochemistry not determined) (only one pair of racemic mixture was used as starting material herein) and 1H-imidazole (1.4 g, 20.54 mmol) in N,N-Dimethylformamide (DMF) (5 mL) was added TBS-Cl (1.3 g, 9.04 mmol) at 25° C. under nitrogen atmosphere. The resulting solution was stirred at 25° C. for 16 hr under nitrogen atmosphere. The reaction mixture was quenched by the addition of water and extracted with ethyl acetate. The combined organic layers were washed with brine, dried over anhydrous sodium sulfate, filtered, and concentrated under vacuum. The resulting residue was purified by flash chromatography (Biotage Isolera Prime) which applied to 40 g silica gel column and eluted with 0-25% ethyl acetate in petroleum ether within 30 min to afford ethyl 2-((tert-butyldimethylsilyl)oxy)cyclopentane-1-carboxylate (1.2 g, 49%) (racemic mixture and stereochemistry not determined) as a colorless oil.

Step-2: (2-((tert-butyldimethylsilyl)oxy)cyclopentyl) methanol

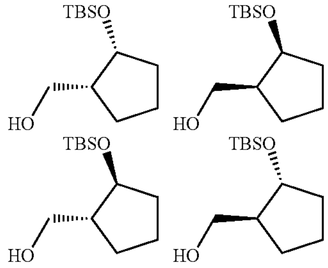

To a stirred solution of ethyl 2-((tert-butyldimethylsilyl) oxy)cyclopentane-1-carboxylate (1.2 g, 4.55 mmol) (racemic mixture and stereochemistry not determined) (only one pair of racemic mixture was used as starting material herein) in Tetrahydrofuran (20 mL) was added lithium tetrahydroborate (200 mg, 9.10 mmol) at 0° C. Then methanol (0.3 g, 9.10 mmol) was added to the above mixture at 0° C. The resulting solution was stirred at 25° C. for 2 hr. The reaction mixture was quenched by the addition of water and extracted with ethyl acetate. The combined organic layers were washed with brine, dried over anhydrous sodium sulfate, filtered, and concentrated under vacuum. The resulting residue was purified by flash chromatography (Biotage Isolera Prime) which applied to 20 g silica gel column and eluted with 0~30% ethyl acetate in petroleum ether within 20 min to afford (2-((tert-butyldimethylsilyl)oxy)cyclopentyl) methanol (620.0 mg, 59%) (racemic mixture and stereochemistry not determined) as a colorless oil.

Step-3: O-((2-((tert-butyldimethylsilyl)oxy)cyclopentyl)methyl)S-methyl carbonodithioate

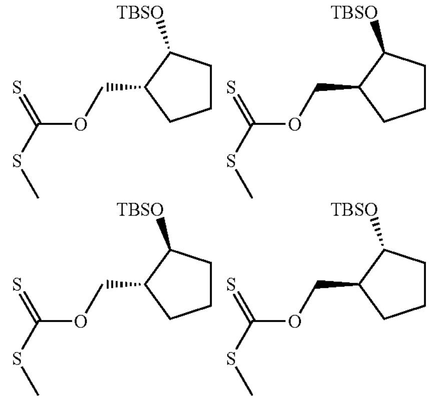

To a stirred solution of (2-((tert-butyldimethylsilyl)oxy) cyclopentyl)methanol (420.0 mg, 1.82 mmol) (racemic mixture and stereochemistry not determined) (only one pair of racemic mixture was used as starting material herein) in Tetrahydrofuran (10 mL) was added NaH (87.0 mg, 3.65 mmol, 60%) at 0° C. The resulting solution was stirred at 0° C. for 0.5 hr under nitrogen. To the above solution was added $CS_2$ (208.0 mg, 2.73 mmol) at 0° C. The resulting mixture was then stirred at 0° C. for 20 min. Then MeI (388.0 mg, 2.73 mmol) was added to the above mixture at 0° C. The resulting solution was stirred at 0° C. for 1 hr under nitrogen. The reaction mixture was quenched by the addition of water and extracted with ethyl acetate. The combined organic layers were washed with brine, dried over anhydrous sodium sulfate, filtered, and concentrated under vacuum. The resulting residue was dissolved in DMF (1 mL) which was applied to a 40 g C18 column, purified by flash chromatography (Biotage Isolera Prime) and eluted with 10~100% acetonitrile in water within 30 min to afford O-((2-((tert-butyldimethylsilyl)oxy)cyclopentyl)methyl)S-methyl carbonodithioate (500.0 mg, 80%) (racemic mixture and stereochemistry not determined) as a yellow oil.

Step-4: O-((2-((tert-butyldimethylsilyl)oxy)cyclopentyl)methyl) hydrazinecarbothioate

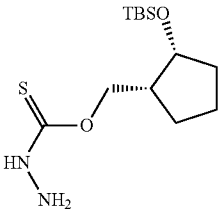
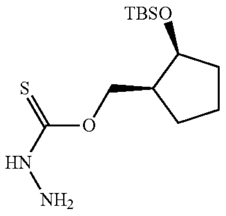
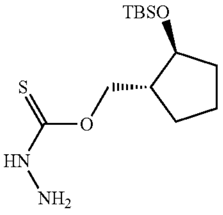
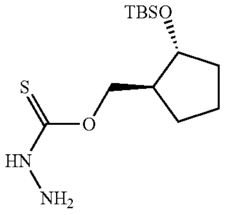

To a stirred solution of O-((2-((tert-butyldimethylsilyl) oxy)cyclopentyl)methyl)S-methyl carbonodithioate (500.0 mg, 1.56 mmol) (racemic mixture and stereochemistry not determined) (only one pair of racemic mixture was used as starting material herein) in Methanol (10 mL) was added hydrazine hydrate (97.5 mg, 1.56 mmol, 80%) at 25° C. The resulting solution was stirred at 25° C. for 0.5 hr. The organic solvent was removed under vacuum to afford O-((2-((tert-butyldimethylsilyl)oxy)cyclopentyl)methyl) hydrazinecarbothioate (660.0 mg, crude) (racemic mixture and stereochemistry not determined) as a yellow oil. The crude was used in the next step without further purification.

Step-5: 5-((2-((tert-butyldimethylsilyl)oxy)cyclopentyl)methoxy)-1,3,4-thiadiazol-2-amine

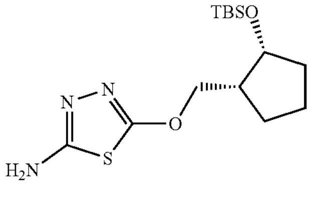
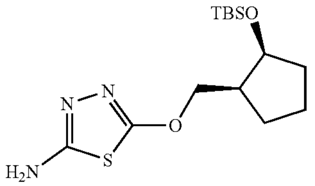
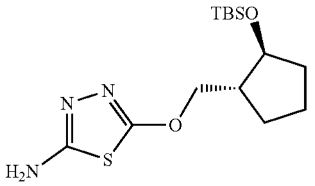
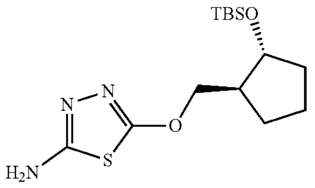

To a stirred solution of O-((2-((tert-butyldimethylsilyl) oxy)cyclopentyl)methyl) hydrazinecarbothioate (660.0 mg, 2.17 mmol) (racemic mixture and stereochemistry not determined) (only one pair of racemic mixture was used as starting material herein) in Methanol (10 mL) was added BrCN (459.0 mg, 4.33 mmol) and TEA (219.0 mg, 2.17 mmol) at 25° C. under nitrogen atmosphere. The resulting solution was stirred at 25° C. for 1 hr under nitrogen atmosphere. The reaction mixture was quenched by the addition of water and extracted with ethyl acetate. The combined organic layers were washed with brine, dried over anhydrous sodium sulfate, filtered, and concentrated under vacuum. The resulting residue was purified by flash chromatography (Biotage Isolera Prime) which applied to a 40 g silica gel column that was eluted with 0~10% methanol in dichloromethane within 25 min to afford 5-((2-((tert-butyldimethylsilyl)oxy)cyclopentyl)methoxy)-1,3,4-thiadiazol-2-amine (320.0 mg, 39%) (racemic mixture and stereochemistry not determined) as a yellow solid. MS (ESI) calc'd for $(C_{14}H_{27}N_3O_2SSi)$ $(M+1)^+$, 330.2; found, 330.2.

Step-6: N-(5-((2-((tert-butyldimethylsilyl)oxy)cyclopentyl)methoxy)-1,3,4-thiadiazol-2-yl)-2'-chloro-5'-methoxy-6-methyl-(4,4'-bipyridine)-3-carboxamide

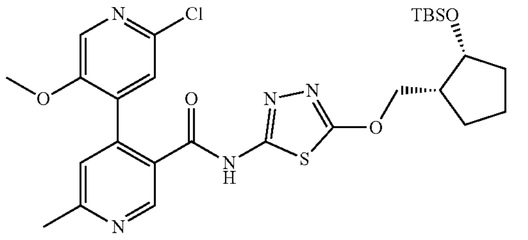

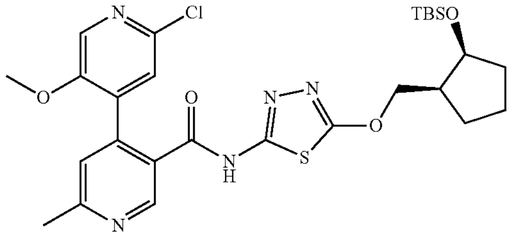

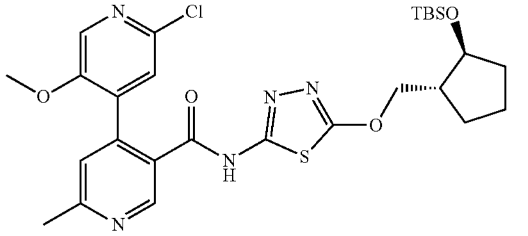

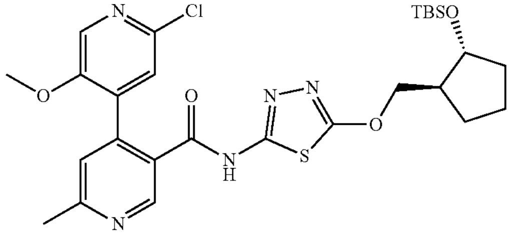

To a stirred solution of 5-((2-((tert-butyldimethylsilyl)oxy)cyclopentyl)methoxy)-1,3,4-thiadiazol-2-amine (320.0 mg, 0.97 mmol) (racemic mixture and stereochemistry not determined) (only one pair of racemic mixture was used as starting material herein) in acetonitrile (4 mL) were added Intermediate H (271.0 mg, 0.97 mmol) and 1-methyl-1H-imidazole (399.0 mg, 4.86 mmol). To the above solution was added TCFH (272.0 mg, 0.97 mmol) in acetonitrile (1 mL). The resulting solution was stirred at 25° C. under nitrogen for 1 hr. The suspension was filtered. The filter cake was collected and dried under vacuum to afford N-(5-((2-((tert-butyldimethylsilyl)oxy)cyclopentyl)methoxy)-1,3,4-thiadiazol-2-yl)-2'-chloro-5'-methoxy-6-methyl-(4,4'-bipyridine)-3-carboxamide (360.0 mg, 62%) (racemic mixture and stereochemistry not determined) as a white solid. MS (ESI) calc'd for ($C_{27}H_{36}ClN_5O_4SSi$) $(M+1)^+$, 590.2; found, 590.3.

Step-7: 2'-chloro-N-(5-((2-hydroxycyclopentyl)methoxy)-1,3,4-thiadiazol-2-yl)-5'-methoxy-6-methyl-(4,4'-bipyridine)-3-carboxamide

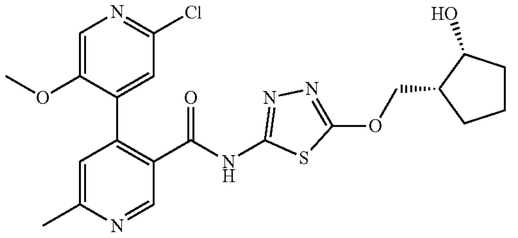

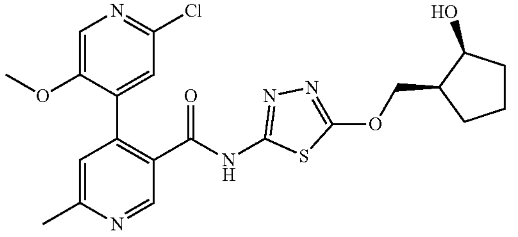

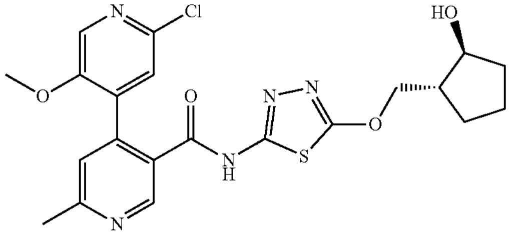

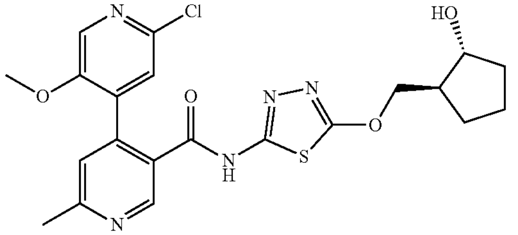

To a stirred solution of N-(5-((2-((tert-butyldimethylsilyl)oxy)cyclopentyl)methoxy)-1,3,4-thiadiazol-2-yl)-2'-chloro-5'-methoxy-6-methyl-(4,4'-bipyridine)-3-carboxamide (320 mg, 0.542 mmol) (racemic mixture and stereochemistry not determined) (only one pair of racemic mixture was used as starting material herein) in Dichloromethane (5.0 mL) was added Trifluoroacetic acid (1 mL) at 0° C. The resulting solution was stirred at 0° C. for 4 hr. The solvents were removed under vacuum. The resulting residue was dissolved in DMF (1 mL) which was applied to a 20 g C18 column and purified by flash chromatography, eluted with 5~80% acetonitrile in water within 25 min to afford 2'-chloro-N-(5-((2-hydroxycyclopentyl)methoxy)-1,3,4-thiadiazol-2-yl)-5'-methoxy-6-methyl-(4,4'-bipyridine)-3-carboxamide (150.0 mg, 57%) (racemic mixture and stereochemistry not determined) (Compound #261) as a white solid. MS (ESI) calc'd for ($C_{21}H_{22}ClN_5O_4S$) $(M+1)^+$, 476.1; found, 476.2. $^1H$ NMR (400 MHz, DMSO-$d_6$) δ 12.86 (s, 1H), 8.81 (s, 1H), 8.17 (s, 1H), 7.53 (s, 1H), 7.42 (s, 1H), 4.69 (d, J=4.4 Hz, 1H), 4.46-4.37 (m, 1H), 4.32-4.23 (m, 1H), 3.91-3.81 (m, 1H), 3.64 (s, 3H), 2.59 (s, 3H), 2.21-2.10 (m, 1H), 1.95-1.84 (m, 1H), 1.84-1.73 (m, 1H), 1.73-1.61 (m, 1H), 1.61-1.42 (m, 2H), 1.39-1.22 (m, 1H).

Step-8: 2'-chloro-N-(5-((2-hydroxycyclopentyl)methoxy)-1,3,4-thiadiazol-2-yl)-5'-methoxy-6-methyl-(4,4'-bipyridine)-3-carboxamide (Isomer A and Isomer B)

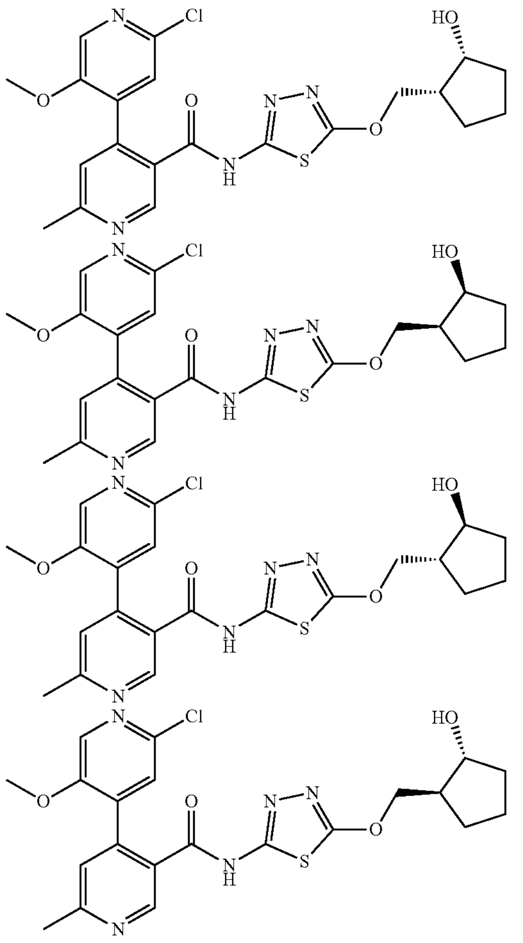

The racemic compound (220.0 mg) was separated by prep-chiral HPLC with the following conditions: (Column: CHIRALPAK IF, 2*25 cm, 5 μm; Mobile Phase A: MtBE (0.1% FA)-HPLC, Mobile Phase B: EtOH:DCM=1: 1-HPLC; Flow rate: 17 mL/min; Gradient: 20% B to 20% B in 19 min; Wave Length: 220/254 nm; RT1 (min): 10.94; RT2 (min): 15.27; Sample Solvent: MeOH:DCM=1: 1-HPLC; Injection Volume: 0.8 mL; Number Of Runs: 4) to afford isomer B as a white solid as the first peak on chiral HPLC and isomer A (40.4 mg, 26%) as a white solid as the second peak on chiral HPLC. Two racemic isomers were isolated. The absolute stereochemistry was not determined.

Isomer B (Compound #255): MS (ESI) calc'd for ($C_{21}H_{22}ClN_5O_4S$) $(M+1)^+$, 476.1; found, 476.2. $^1H$ NMR (400 MHz, DMSO-$d_6$) δ 12.86 (s, 1H), 8.80 (s, 1H), 8.17 (s, 1H), 7.54 (s, 1H), 7.43 (s, 1H), 4.70 (d, J=4.4 Hz, 1H), 4.48-4.36 (m, 1H), 4.34-4.22 (m, 1H), 3.93-3.81 (m, 1H), 3.64 (s, 3H), 2.59 (s, 3H), 2.19-2.10 (m, 1H), 1.91-1.82 (m, 1H), 1.80-1.72 (m, 1H), 1.73-1.61 (m, 1H), 1.60-1.43 (m, 2H), 1.38-1.28 (m, 1H).

Isomer A (Compound #256): MS (ESI) calc'd for ($C_{21}H_{22}ClN_5O_4S$) $(M+1)^+$, 476.1; found, 476.2. $^1H$ NMR (400 MHz, DMSO-$d_6$) δ 12.86 (s, 1H), 8.83 (s, 1H), 8.16 (s, 1H), 7.51 (s, 1H), 7.39 (s, 1H), 4.71 (d, J=4.4 Hz, 1H), 4.50-4.38 (m, 1H), 4.33-4.20 (m, 1H), 3.94-3.81 (m, 1H), 3.63 (s, 3H), 2.58 (s, 3H), 2.19-2.10 (m, 1H), 1.91-1.83 (m, 1H), 1.82-1.72 (m, 1H), 1.72-1.61 (m, 1H), 1.58-1.42 (m, 2H), 1.37-1.26 (m, 1H).

Alternative Synthesis: Examples 272, 273, 256, and 255

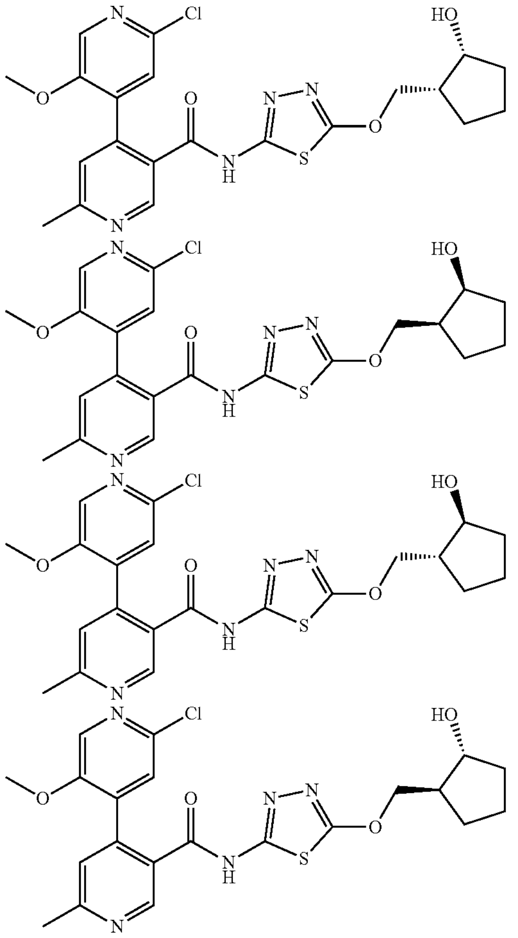

Step-1: Synthesis of ethyl 2-((tert-butyldimethylsilyl)oxy)cyclopentane-1-carboxylate

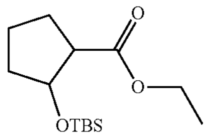 [SMILES: CCOC(=O)C1CCCC1O[Si](C)(C)C(C)(C)C]

To a stirred solution of ethyl 2-hydroxycyclopentane-1-carboxylate (4.8 g, 30.3 mmol) in N,N-Dimethylformamide (DMF) (50 mL) was added imidazole (3.10 g, 45.5 mmol), DMAP (0.185 g, 1.517 mmol) and TBDMS-Cl (5.49 g, 36.4 mmol) under nitrogen atmosphere at room temperature. The resulting reaction mixture was stirred at room temperature for 16 h. The reaction mixture was quenched with ice-water (200 mL) and extracted with methyl tertiary butyl ether (200 mL×2). The combined organic layer was washed with saturated sodium bicarbonate solution (30 mL) and the with brine (30 mL). The organic layer was dried over sodium sulphate and evaporated under vacuum to get the crude product as a colorless oil. The crude residue was pre-absorbed on silica, loaded on the biotage prepacked column (40 g) and eluted at 20% of Ethyl acetate in petroleum ether for 60 min. The appropriate fractions were collected and concentrated under vacuum to afford ethyl 2-((tert-butyldimethylsilyl)oxy)cyclopentane-1-carboxylate (7 g, 25.7 mmol, 85% yield) as a colourless oil. MS (ESI) calculated for $C_{14}H_{28}O_3Si$, $(M)^+$272.18; found, GCMS m/z=215.1 (M−57) (mixture of diastereomers). 1H-NMR (400 MHz, CDCl3): δ 4.52-4.38 (m, 1H), 4.25-4.00 (m, 2H), 2.79-2.62 (m, 1H), 2.25-2.00 (m, 1H), 1.96-1.82 (m, 1H), 1.81-1.65 (m, 3H), 1.64-1.52 (m, 1H), 1.28 (t, J=7.2 Hz, 3H), 0.88 (s, 9H), 0.05 (s, 6H).

Step-2: Synthesis of (2-((tert-butyldimethylsilyl)oxy)cyclopentyl)methanol

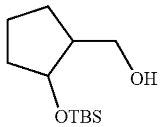 [SMILES: CC(C)(C)[Si](C)(C)OC1CCCC1CO]

To a stirred solution of ethyl 2-((tert-butyldimethylsilyl)oxy)cyclopentane-1-carboxylate (5.2 g, 19.09 mmol) in Tetrahydrofuran (100 mL) was added DIBAL-H (1M in THF) (28.6 mL, 28.6 mmol) drop wise at −78° C. under nitrogen atmosphere. The resulting reaction mixture was stirred at −78° C. for 15 min and then slowly warmed to 0° C. and stirred for 1 h. The reaction mixture was quenched using and 2M solution of sodium potassium tartrate (60 mL) at 0° C. and stirred for 20 min at room temperature. After 20 min, the reaction mixture was extracted with ethyl acetate (100 mL×2). The emulsion was formed which was passed through celite. The organic layer was separated, washed with brine (20 mL), dried over sodium sulphate and concentrated under vacuum to get crude product as a colourless gum. The crude residue was pre-absorbed on silica using 40 mL DCM, 10 g of silica (60-120 mesh), loaded on the biotage pre-pack 30 g snap and eluted at 20% of Ethyl acetate in petroleum ether for 45 min with flow rate 30 mL/min. The appropriate fractions were collected and concentrated under vacuum to afford (2-((tert-butyldimethylsilyl)oxy)cyclopentyl)methanol (1.8 g, 40.8% yield) as a colorless oil. 2.4 g of starting material was also recovered. MS (ESI) calculated for $C_{12}H_{26}O_2Si$, $(M)^+$230.17; found, GCMS m/z=173.1 (M−57) (99.56%). 1H-NMR (400 MHz, DMSO-af): S 4.45 (t, J=5.2 Hz, 1H), 3.95 (q, J=5.6 Hz, 1H), 3.38-3.30 (m, 1H), 3.28-3.19 (m, 1H), 1.95-1.56 (m, 4H), 1.55-1.39 (m, 2H), 1.32-1.17 (m, 1H), 0.85 (s, 9H), 0.03 (s, 6H)

Step-3: Synthesis of O-((2-((tert-butyldimethylsilyl)oxy)cyclopentyl)methyl)S-methyl carbonodithioate

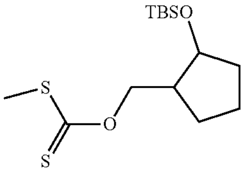 [SMILES: CSC(=S)OCC1CCCC1O[Si](C)(C)C(C)(C)C]

To a stirred solution of (2-((tert-butyldimethylsilyl)oxy)cyclopentyl)methanol (3 g, 13.02 mmol) in Tetrahydrofuran (THF) (50 mL) under nitrogen at 0° C. was added sodium hydride (1.041 g, 26.0 mmol) in portions over 3 min. After addition, the reaction mixture was stirred at room temperature for 30 min. After 30 min, to the above reaction mixture were added carbon disulfide (1.570 mL, 26.0 mmol) followed by methyl iodide (0.814 mL, 13.02 mmol) at room temperature. The reaction mixture was stirred at room temperature for an additional 30 min. The reaction was quenched with cold water and extracted with ethyl acetate (50 mL×2). The combined organic layer was washed with brine solution. The organic layer was dried over sodium sulphate, filtered, and concentrated under vacuum to afford O-((2-((tert-butyldimethylsilyl)oxy)cyclopentyl)methyl)S-methyl carbonodithioate (4.45 g) as a yellow oil. MS (ESI) calculated for $(C_{14}H_{28}O_2S_2Si)$ $(M-CH_3)$—, 305.11; found, 305.2. 1H-NMR (400 MHz, DMSO-$d^6$): δ 4.62-4.41 (m, 2H), 4.06-3.98 (m, 1H), 2.56 (s, 3H), 2.35-2.12 (m, 1H), 1.91-1.65 (m, 3H), 1.65-1.35 (m, 2H), 1.33-1.20 (m, 1H), 0.84 (s, 9H), 0.04 (s, 6H).

Step-4: Synthesis of O-((2-((tert-butyldimethylsilyl)oxy)cyclopentyl)methyl)hydrazine carbothioate

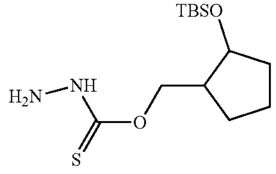 [SMILES: CC(C)(C)[Si](C)(C)OC1CCCC1COC(=S)NN]

To a stirred solution of O-((2-((tert-butyldimethylsilyl)oxy)cyclopentyl)methyl)S-methyl carbonodithioate (4.45 g, 13.88 mmol) in methanol (50 mL) was added hydrazine hydrate (1.069 g, 13.88 mmol) at room temperature. The reaction mixture was stirred for 2 h at room temperature. The organic solvent was removed under vacuum. The residue was diluted with water. The aqueous layer was extracted with ethyl acetate (100 mL×2). The combined organic layers were washed with brine, dried over anhydrous sodium sulfate, filtered, and concentrated under vacuum to afford O-((2-((tert-butyldimethylsilyl)oxy)cyclopentyl)methyl)hydrazine carbothioate (3.4 g, 77% yield) as a yellow liquid. MS (ESI) calculated for $(C_{13}H_{28}N_2O_2SSi)$ $(M+1)^+$, 305.17; found, 305.2.

Step-5: Synthesis of rac-5-(((1S,2R)-2-((tert-butyldimethylsilyl)oxy)cyclopentyl)methoxy)-1,3,4-thiadiazol-2-amine and rac-5-(((1R,2R)-2-((tert-butyldimethylsilyl)oxy)cyclopentyl) methoxy)-1,3,4-thiadiazol-2-amine

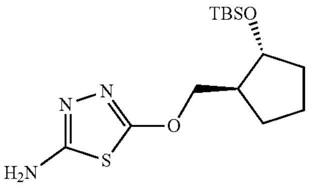

-continued

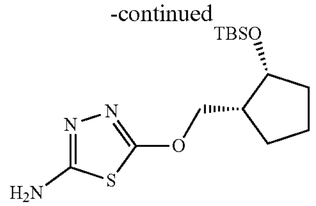

To a stirred solution of O-((2-((tert-butyldimethylsilyl)oxy)cyclopentyl)methyl) hydrazinecarbothioate (3.4 g, 11.16 mmol), in Ethanol (30 mL) were added triethylamine (1.556 mL, 11.16 mmol) followed by Cyanogen bromide (1.183 g, 11.16 mmol) at room temperature. The reaction mixture was stirred at room temperature for 3 h. The organic solvent was removed under vacuum. The residue was diluted with water. The aqueous layer was extracted with ethyl acetate (50 mL×2). The combined organic layers were washed with brine, dried over anhydrous sodium sulfate, filtered, and concentrated under vacuum to get the crude product as orange solid. The crude product was pre-absorbed on silica using 20 mL DCM 10 g of silica (60-120 mesh), loaded on the biotage pre-pack 45 g column, and eluted with 50% of Ethyl aetate in petroleum ether for 45 min with flow rate of 30 mL/min. The appropriate fractions were collected and concentrated under vacuum to afford 5-((2-((tert-butyldimethylsilyl)oxy)cyclopentyl) methoxy)-1,3,4-thiadiazol-2-amine (1.7 g, 46% yield) as orange solid. MS (ESI) calculated for ($C_{14}H_{27}N_3O_2SSi$) $(M+1)^+$, 330.54; found, 330.1.

Diastereomeric separation of 5-((2-((tert-butyldimethylsilyl)oxy)cyclopentyl) methoxy)-1,3,4-thiadiazol-2-amine:

5-((2-((tert-butyldimethylsilyl)oxy)cyclopentyl) methoxy)-1,3,4-thiadiazol-2-amine was purified by prep-HPLC for diastereomeric separation using the following conditions: (Column: YMC-C8 (19×250 mm) 5 μm; Mobile Phase A: 10 mM ABC in MQ water, Mobile Phase B: acetonitrile 50%; RT1 (min): 4.78; RT2 (min): 4.94;) to afford major isomer (Product 5A) (0.82 g, 22% yield) (mixture of enantiomers) as an off-white solid with the first peak with shorter retention time and minor isomer (Product 5B) (0.4 g, 10.8%) (mixture of enantiomers) as an off-white solid. with the second peak with longer retention time. The stereochemistry was not determined.

Product 5A: MS (ESI) calculated for ($C_{14}H_{27}N_3O_2SSi$) $(M+1)^+$, 330.17; found, 330.2. 1H-NMR (400 MHz, DMSO-$d^6$): δ 6.73 (s, 2H), 4.17 (d, J=6.8 Hz, 2H), 3.98 (q, J=5.6 Hz, 1H), 2.15-2.05 (m, 1H), 1.86-1.74 (m, 2H), 1.70-1.59 (m, 1H), 1.58-1.40 (m, 2H), 1.31-1.20 (m, 1H), 0.82 (s, 9H), 0.007 (s, 6H). The stereochemistry was not determined.

Product 5B: MS (ESI) calculated for ($C_{14}H_{27}N_3O_2SSi$) $(M+1)^+$, 330.17; found, 330.2. 1H-NMR (400 MHz, DMSO-$d^6$): δ 6.70 (s, 2H), 4.32-4.18 (m, 3H), 2.26-2.15 (m, 1H), 1.80-1.64 (m, 3H), 1.62-1.50 (m, 2H), 1.42-1.30 (m, 1H), 0.84 (s, 9H), 0.04 (s, 3H), 0.01 (s, 3H). The stereochemistry was not determined.

Step-6: Synthesis of Product 6A1 and 6A2

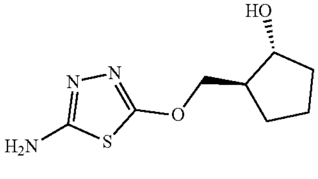

-continued

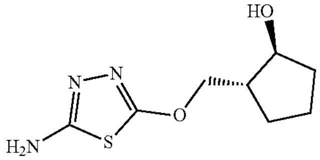

To a stirred solution of Product 5A (5.6 g, 16.99 mmol) in dichloromethane (50 mL) was added trifluoroacetic acid (19.64 mL, 255 mmol) at 0° C. The reaction mixture was stirred at room temperature for 2 h. The reaction mixture was quenched with saturated bicarbonate solution (100 mL) and extracted with ethyl acetate (100 mL×6). The combined organic layer was dried over sodium sulphate and evaporated under vacuum to get the crude product as an off-white solid. The crude product was pre-absorbed on silica using 50 mL DCM 20 g of silica (60-120 mesh), loaded on the biotage pre-pack 100 g column, and eluted with 10% of Methanol in dichloromethane for 30 min with a flow rate of 60 mL/min. The appropriate fractions were collected and concentrated under vacuum to afford Product 6A (2.5 g) as off-white solid (mixture of enantiomers).

Product 6A (2.5 g) was separated by prep-chiral SFC with the following conditions: (Column: Chiralcel OXH (30×250 mm) 5 μm; Mobile Phase A: $CO_2$, Mobile Phase B: MeOH; Flow rate: 70 mL/min; Gradient: isocratic 30% B; Column Temperature (° C.): 35; Back Pressure (bar): 110; Wave Length: 254 nm; RT1 (min): 5.74; RT2 (min): 7.31; Sample Solvent: MeOH (40 mL); Injection Volume: 0.8 mL; Number of runs: 71) to afford Product 6A1 (1 g, 26.0% yield) as a off-white solid with the first peak on chiral SFC with shorter retention time and Product 6A2 (1 g, 27.0% yield) as a off-white solid with the second peak on chiral SFC with longer retention time. The absolute stereochemistry was not determined.

Product 6A1: MS (ESI) calculated for ($C_8H_{13}N_3O_2S$) $(M+1)^+$, 216.08; found, 216.0. 1H-NMR (400 MHz, DMSO-$d^6$): δ 6.73 (s, 2H), 4.69 (d, J=4.4 Hz, 1H), 4.26 (dd, J=6.0 Hz, 10.0 Hz, 1H), 4.12 (dd, J=7.2 Hz, 10 Hz, 1H), 3.82 (quintet, J=5.6 Hz, 1H), 2.13-2.02 (m, 1H), 1.90-1.71 (m, 2H), 1.70-1.59 (m, 1H), 1.58-1.40 (m, 2H), 1.34-1.22 (m, 1H).

Product 6A2: MS (ESI) calculated for ($C_8H_{13}N_3O_2S$) $(M+1)^+$, 216.08; found, 216.0. 1H-NMR (400 MHz, DMSO-$d^6$): δ 6.73 (s, 2H), 4.69 (d, J=4.4 Hz, 1H), 4.26 (dd, J=6.0 Hz, 10.0 Hz, 1H), 4.12 (dd, J=7.6 Hz, 10.4 Hz, 1H), 3.85-3.78 (m, 1H), 212-2.02 (m, 1H), 1.90-1.70 (n 2H), 1.70-1.60 (m, 1H), 1.59-1.40 (m, 2H), 1.34-1.22 (in, 1H).

Step-7: Synthesis of 7A1 and 7A2

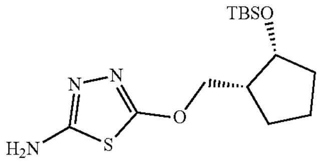

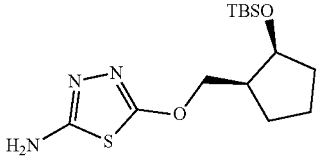

Product 5B (2.2 g, 6.79 mmol) was separated by chiral SFC with the following conditions: [Column: Lux A1 (250*30) mm, 5 μm; Mobile Phase A: CO2, Mobile Phase B: 0.5% Isopropyl amine in Methanol]; Flow rate: 70 mL/min; Gradient: isocratic 10% B; Column Temperature (° C.): Back Pressure (bar): 110; Wave Length: 254 nm; Sample Solvent: 50 mL MeOH-HPLC; Injection Volume: 800 μL; Number of runs: 76; RT1 (min): 7.90; RT2 (min): 9.58; to afford Product 7A1 (1 g, 4.62% yield) as off-white solid with the first peak on chiral SFC with shorter retention time and Product 7A2 (1 g, 3.03 mmol, 4.62% yield) as off-white solid with the second peak on chiral SFC with longer retention time. The absolute stereochemistry was not determined.

Product 7A1: MS (ESI) calculated for ($C_{14}H_{27}N_3O_2SSi$) $(M+1)^+$, 330.17; found, 330.2.

Product 7A2: MS (ESI) calculated for ($C_{14}H_{27}N_3O_2SSi$) $(M+1)^+$, 330.17; found, 330.2.

Step-8: Synthesis of 8A1

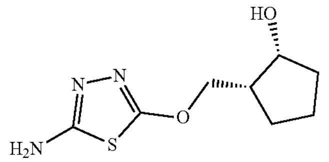 [SMILES: Nc1nnc(OC[C@H]2CCC[C@H]2O)s1]

To a stirred solution of Product 7A1 (0.9 g, 2.73 mmol) in Dichloromethane (20 mL) was added trifluoroacetic acid (4.21 mL, 54.6 mmol) at 0° C. The reaction mixture was stirred at room temperature for 4 h. The reaction mixture was quenched with saturated bicarbonate solution (10 mL) and extracted with ethyl acetate (10 mL×3). The combined organic layer was dried over sodium sulfate and evaporated under vacuum to get the crude product as an off-white solid. The crude product was pre-absorbed on silica using 10 mL DCM and 2.5 g of silica (60-120 mesh), loaded on the biotage pre-pack 25 g column, and eluted with 10% of Methanol in dichloromethane for 30 min with flow rate 25 mL/min. The appropriate fractions were collected and concentrated under vacuum to afford Product 8A1 (425 mg, 72.0% yield) as off-white solid. MS (ESI) calculated for ($C_8H_{13}N_3O_2S$) $(M+1)^+$, 216.07; found, 216.0. 1H-NMR (400 MHz, DMSO-$d^6$): δ 6.70 (s, 2H), 4.51 (brs, 1H), 4.41 (dd, J=7.6 Hz, 10.0 Hz, 1H), 4.21 (dd, J=7.2 Hz, 10 Hz, 1H), 4.14-4.06 (m, 1H), 2.20-2.08 (m, 1H), 1.80-1.62 (m, 3H), 1.61-1.47 (m, 2H), 1.46-1.35 (in, 1H).

The absolute stereochemistry was not determined.

Step-9: Synthesis of Product 9A1

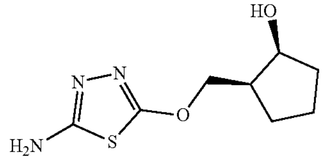 [SMILES: Nc1nnc(OC[C@@H]2CCC[C@@H]2O)s1]

To a stirred solution of Product 7A2 (0.9 g, 2.73 mmol) in Dichloromethane (20 mL was added trifluoroacetic acid (4.21 mL, 54.6 mmol) at 0° C. The reaction mixture was stirred at RT for 4 h. The reaction mixture was quenched with saturated bicarbonate solution (10 mL) and extracted with ethyl acetate (10 mL×3). The combined organic layer was dried over sodium sulphate and evaporated under vacuum to get the crude product as an off-white solid. The crude product was pre-absorbed on silica using 10 mL DCM and 2.5 g of silica (60-120 mesh), loaded on the biotage pre-pack 25 g column, and eluted with 10% of Methanol in dichloromethane for 30 min with flow rate 25 mL/min. The appropriate fractions were collected and concentrated under vacuum to afford Product 9A1 (455 mg, 77% yield) as an off-white solid. MS (ESI) calculated for ($C_8H_{13}N_3O_2S$) $(M+1)^+$, 216.07; found, 216.2. 1H-NMR (400 MHz, DMSO-$d^6$): δ 6.70 (s, 2H), 4.51 (d, J=4.0 Hz, 1H), 4.41 (dd, J=7.6 Hz, 10.0 Hz, 1H), 4.21 (dd, J=6.8 Hz, 10 Hz, 1H), 4.13-4.06 (m, 11H), 2.19-2.08 (m, 1H), 1.80-1.62 (m, 3H), 1.61-1.47 (m, 2H), 1.46-1.35 (m, 1H). The absolute stereochemistry was not determined.

Step-10: Synthesis of 2'-chloro-N-(5-((2-hydroxycyclopentyl)methoxy)-1,3,4-thiadiazol-2-yl)-5'-methoxy-6-methyl-(4,4'-bipyridine)-3-carboxamide (Isomer 1)

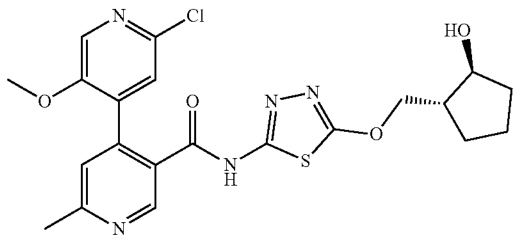 [SMILES: COc1cnc(Cl)cc1-c1cc(C)ncc1C(=O)Nc1nnc(OC[C@H]2CCC[C@@H]2O)s1]

To a stirred solution of Intermediate H (0.8 g, 2.87 mmol) in Acetonitrile (15 mL) and N,N-Dimethylformamide (DMF) (2.5 mL) was added Product 6A2 (0.618 g, 2.87 mmol), 1-methyl-1H-imidazole (0.943 mL, 11.48 mmol) and Chloro-N,N,N',N'-tetramethylformamidinium hexafluorophosphate (1.208 g, 4.31 mmol) at room temperature. The reaction mixture was stirred at room temperature for 12 h. The reaction mixture was quenched with water (100 mL) and extracted with Ethyl acetate (50 mL×2). The organic phases were combined and washed with brine solution. The organic layer was dried over anhydrous $Na_2SO_4$ and filtered. The filtrate was concentrated under reduced pressure to get the crude product as an off-white solid. The crude product was mixed with another batch of 180 mg material. The combined crude was pre-absorbed on silica using 20 mL DCM and 5 g of silica (60-120 mesh), loaded on the pre-packed biotage 45 g column and eluted at 10% of methanol in dichloromethane for 60 min with flow rate 30 mL/min. The appropriate fractions were collected and concentrated under vacuum to afford Isomer 1 (600 mg, 43.6% yield) as a white solid (Compound #256). The stereochemistry was not determined. MS (ESI) calculated for ($C_{21}H_{22}ClN_5O_4S$) $(M+1)^+$, 476.12; found, 476.0. 1H-NMR (400 MHz, DMSO-$d^6$): δ 12.88 (brs, 1H), 8.80 (s, 1H), 8.17 (s, 1H), 7.55 (s, 1H), 7.44 (s, 1H), 4.71 (d, J=4.4 Hz, 1H), 4.42 (dd, J=6.0 Hz, 10 Hz, 1H), 4.28 (dd, J=7.2 Hz, 10 Hz, 1H), 3.86 (quintet, J=5.2 Hz, 1H), 3.63 (s, 3H), 2.59 (s, 3H), 2.20-2.10 (m, 1H), 1.91-1.72 (m, 2H), 1.71-1.60 (m, 1H), 1.60-1.43 (m, 2H). 1.38-1.28 (m, 1H). The absolute stereochemistry was not determined.

Step-11: Synthesis of 2'-chloro-N-(5-((2-hydroxycyclopentyl)methoxy)-1,3,4-thiadiazol-2-yl)-5'-methoxy-6-methyl-(4,4'-bipyridine)-3-carboxamide (Isomer 2)

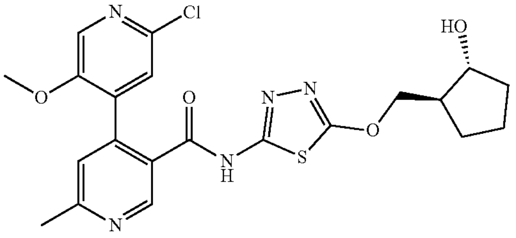 [SMILES: COc1cnc(Cl)cc1-c1cc(C)ncc1C(=O)Nc1nnc(OC[C@@H]2CCC[C@H]2O)s1]

To a stirred solution of Intermediate H (0.8 g, 2.87 mmol) in Acetonitrile (15 mL) and N,N-Dimethylformamide (2.5 mL) was added Product 6A1 (0.618 g, 2.87 mmol), 1-methyl-1H-imidazole (0.943 mL, 11.48 mmol) and Chloro-N,N,N',N'-tetramethylformamidinium hexafluorophosphate (1.208 g, 4.31 mmol) at room temperature. The reaction mixture was stirred at room temperature for 12 h. The reaction mixture was quenched with water (100 mL) and extracted with Ethyl acetate (50 mL×2). The organic phases were combined and washed with brine solution. The organic layer was dried over anhydrous $Na_2SO_4$ and filtered. The filtrate was concentrated under reduced pressure to get of the crude product as an off-white solid. The crude product was combined with another batch of 150 mg material. The combined crude was pre-absorbed on silica using 20 mL DCM and 5 g of silica (60-120 mesh), loaded on the pre-packed biotage 25 g column and eluted at 10% of methanol in dichloromethane for 60 min with flow rate 30 mL/min. The appropriate fractions were collected and concentrated under vacuum to afford Isomer 2 (620 mg, 45.3% yield) as a white solid (Compound #255). The stereochemistry was not determined. MS (ESI) calculated for $(C_{21}H_{22}ClN_5O_4S)$ $(M+1)^+$, 476.12; found, 476.0. 1H-NMR (400 MHz, DMSO-$d^6$): δ 12.88 (brs, 1H), 8.80 (s, 1H), 8.17 (s, 1H), 7.55 (s, 1H), 7.44 (s, 1H), 4.71 (d, J=4.4 Hz, 1H), 4.42 (dd, J=6.0 Hz, 10 Hz, 1H), 4.28 (dd, J=7.2 Hz, 10 Hz, 1H), 3.86 (quintet, J=5.6 Hz, 1H), 3.63 (s, 3H), 2.59 (s, 3H), 2.20-2.09 (m, 1H), 1.91-1.73 (m, 2H), 1.72-1.60 (m, 1H), 1.60-1.44 (m, 2H). 1.38-1.28 (m, 1H). The absolute stereochemistry was not determined.

Step-12: Synthesis of 2'-chloro-N-(5-((2-hydroxycyclopentyl)methoxy)-1,3,4-thiadiazol-2-yl)-5'-methoxy-6-methyl-(4,4'-bipyridine)-3-carboxamide (Isomer 3)

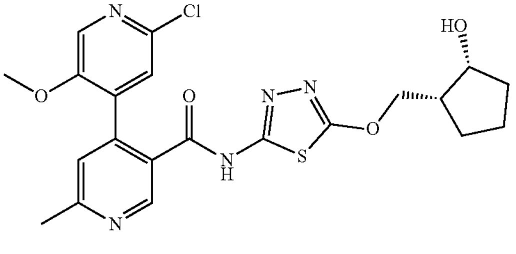 [SMILES: COc1cnc(Cl)cc1-c1cc(C)ncc1C(=O)Nc1nnc(OC[C@H]2CCC[C@H]2O)s1]

To a stirred solution of Intermediate H (500 mg, 1.794 mmol) in Acetonitrile (10 mL) and N,N-Dimethylformamide (1.5 mL) was added Product 8A1 (386 mg, 1.794 mmol), 1-methyl-1H-imidazole (0.589 mL, 7.18 mmol) and Chloro-N,N,N',N'-tetramethylformamidinium hexafluorophosphate (755 mg, 2.69 mmol) at room temperature. The resulting reaction mixture was stirred at room temperature for 16 h. The resulting reaction mixture was stirred at room temperature for 16 h. The reaction mixture was quenched with water (50 mL) and extracted with ethyl acetate (50 mL×2). The organic phases were combined and washed with brine solution. The organic layer was dried over anhydrous $Na_2SO_4$ and filtered. The filtrate was concentrated under reduced pressure to get crude product as an off-white solid. The crude was pre-absorbed on silica using 20 mL DCM and 2 g of silica (60-120 mesh), loaded on the pre-packed biotage 25 g column and eluted at 10% of methanol in dichloromethane for 60 min with flow rate 30 mL/min. The appropriate fractions were collected and concentrated under vacuum to afford Isomer 3 (330 mg, 38.6% yield) as a white solid (Compound #272). The stereochemistry was not determined. MS (ESI) calculated for $(C_{21}H_{22}ClN_5O_4S)$ $(M+1)^+$, 476.12; found, 476.0. 1H-NMR (400 MHz, DMSO-$d^6$): δ 12.86 (brs, 1H), 8.80 (s, 1H), 8.17 (s, 1H), 7.54 (s, 1H), 7.43 (s, 1H), 4.59-4.50 (m, 2H), 4.35 (dd, J=6.8 Hz, 10 Hz, 1H), 4.17-4.10 (m, 1H), 3.63 (s, 3H), 2.59 (s, 3H), 2.25-2.15 (m, 1H), 1.80-1.65 (m, 3H), 1.64-1.38 (m, 3H). The absolute stereochemistry was not determined.

Step-13: Synthesis of 2'-chloro-N-(5-((2-hydroxycyclopentyl)methoxy)-1,3,4-thiadiazol-2-yl)-5'-methoxy-6-methyl-(4,4'-bipyridine)-3-carboxamide (Isomer 4)

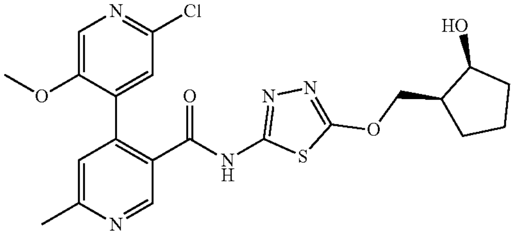 [SMILES: COc1cnc(Cl)cc1-c1cc(C)ncc1C(=O)Nc1nnc(OC[C@@H]2CCC[C@@H]2O)s1]

To a stirred solution of Intermediate H (520 mg, 1.866 mmol) in Acetonitrile (10 mL) and N,N-Dimethylformamide (1.5 mL) was added Product 9A1 (402 mg, 1.866 mmol), 1-methyl-1H-imidazole (0.613 mL, 7.46 mmol) and Chloro-N,N,N',N'-tetramethylformamidinium hexafluorophosphate (785 mg, 2.80 mmol) at room temperature. The resulting reaction mixture was stirred at room temperature for 16 h. The reaction mixture was quenched with water (50 mL) and extracted with Ethyl acetate (50 mL×2). The organic phases were combined and washed with brine solution. The organic layer was dried over anhydrous $Na_2SO_4$ and filtered. The filtrate was concentrated under reduced pressure to get the crude product as an off-white solid. The combined crude was pre-absorbed on silica using 20 mL DCM and 2 g of silica (60-120 mesh), loaded on the pre-packed biotage 25 g column and eluted at 10% of methanol in dichloromethane for 60 min with flow rate 30 mL/min. The appropriate fractions were collected and concentrated under vacuum to afford Isomer 4 (360 mg, 0.755 mmol, 40.4% yield) as a white solid (Compound #273). The stereochemistry was not determined. MS (ESI) calculated for ($C_{21}H_{22}ClN_5O_4S$) $(M+1)^+$, 476.12; found, 476.2. 1H-NMR (400 MHz, DMSO-$d^6$): δ 12.86 (brs, 1H), 8.80 (s, 1H), 8.17 (s, 1H), 7.54 (s, 1H), 7.44 (s, 1H), 4.59-4.50 (m, 2H), 4.35 (dd, J=7.2 Hz, 10 Hz, 1H), 4.17-4.10 (m, 1H), 3.63 (s, 3H), 2.59 (s, 3H), 2.25-2.14 (m, 1H), 1.81-1.65 (m, 3H), 1.64-1.39 (m, 3H). The absolute stereochemistry was not determined.

Isomer 1 and Isomer A were confirmed by Chiral HPLC to be same isomers. Isomer 2 and Isomer B were confirmed by Chiral HPLC to be same isomers.

Example 259, 257 and 258

2'-chloro-5'-(difluoromethoxy)-6-methyl-N-(5-((tetrahydrofuran-3-yl)methoxy)-1,3,4-thiadiazol-2-yl)-(4,4'-bipyridine)-3-carboxamide, (S)-2'-chloro-5'-(difluoromethoxy)-6-methyl-N-(5-((tetrahydrofuran-3-yl)methoxy)-1,3,4-thiadiazol-2-yl)-(4,4'-bipyridine)-3-carboxamide and (R)-2'-chloro-5'-(difluoromethoxy)-6-methyl-N-(5-((tetrahydrofuran-3-yl)methoxy)-1,3,4-thiadiazol-2-yl)-(4,4'-bipyridine)-3-carboxamide

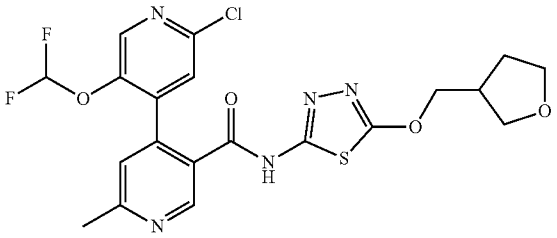 [SMILES: Cc1cc(-c2cc(Cl)ncc2OC(F)F)c(C(=O)Nc2nnc(OCC3CCOC3)s2)cn1]

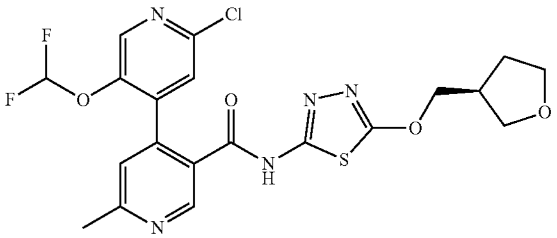

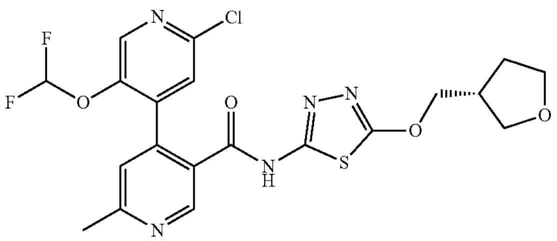

Step-1: 2'-chloro-5'-(difluoromethoxy)-6-methyl-N-(5-((tetrahydrofuran-3-yl)methoxy)-1,3,4-thiadiazol-2-yl)-(4,4'-bipyridine)-3-carboxamide

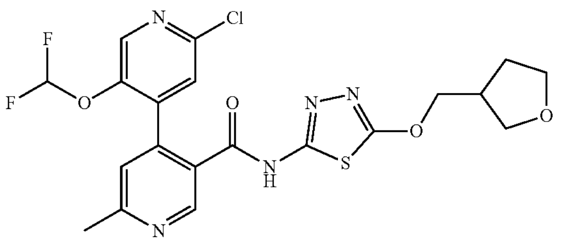

To a stirred solution of 2'-chloro-5'-(difluoromethoxy)-6-methyl-(4,4'-bipyridine)-3-carboxylic acid (120.0 mg, 0.38 mmol, Example 234, Step 3) in Acetonitrile (5 mL) was added 5-((tetrahydrofuran-3-yl)methoxy)-1,3,4-thiadiazol-2-amine (77.0 mg, 0.38 mmol, Example 167, Step 1) and NMI (157.0 mg, 1.90 mmol) at 25° C. To the above solution was added TCFH (107.0 mg, 0.38 mmol) in MeCN (0.5 mL) at 25° C. under nitrogen atmosphere. The resulting mixture was then stirred at 25° C. for 1 hr under nitrogen. The solvents were removed under vacuum. The resulting residue was dissolved in DMF (1 mL) which was applied to a 25 g C18 column and purified by flash chromatography (Biotage Isolera Prime), eluted with 5-80% acetonitrile in water within 35 min to afford 2'-chloro-5'-(difluoromethoxy)-6-methyl-N-(5-((tetrahydrofuran-3-yl)methoxy)-1,3,4-thiadiazol-2-yl)-(4,4'-bipyridine)-3-carboxamide (80.0 mg, 42%) as a white solid. MS (ESI) calc'd for ($C_{20}H_{18}ClF_2N_5O_4S$) $(M+1)^+$, 498.1; found, 498.1. $^1H$ NMR (400 MHz, DMSO-$d_6$) δ13.02 (s, 1H), 9.10 (s, 1H), 8.27 (s, 1H), 7.50 (s, 1H), 7.20 (s, 1H), 7.27-6.91 (m, 1H), 4.32-4.16 (m, 2H), 3.80-3.70 (m, 2H), 3.69-3.58 (m, 1H), 3.54-3.46 (m, 1H), 2.76-2.62 (m, 1H), 2.55 (s, 3H), 2.06-1.89 (m, 1H), 1.69-1.56 (m, 1H).

Step-2: (S)-2'-chloro-5'-(difluoromethoxy)-6-methyl-N-(5-((tetrahydrofuran-3-yl)methoxy)-1,3,4-thiadiazol-2-yl)-(4,4'-bipyridine)-3-carboxamide and (R)-2'-chloro-5'-(difluoromethoxy)-6-methyl-N-(5-((tetrahydrofuran-3-yl)methoxy)-1,3,4-thiadiazol-2-yl)-(4,4'-bipyridine)-3-carboxamide

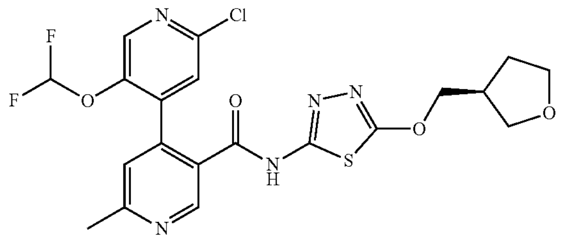

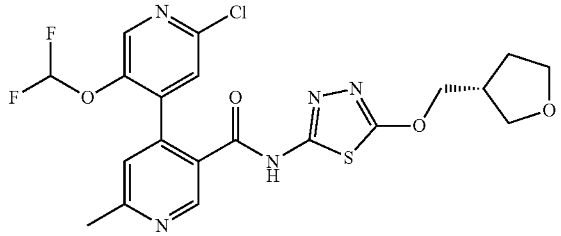

The racemic compound (75.0 mg) was separated by prep-chiral HPLC with the following conditions: (Column: CHIRAL ART Cellulose-SB, 2*25 cm, 5 μm; Mobile Phase A: Hex (0.2% FA)-HPLC, Mobile Phase B: EtOH:DCM=1: 1-HPLC; Flow rate: 20 mL/min; Gradient: 20% B to 20% B in 21 min; Wave Length: 220/254 nm; RT1 (min): 16.08; RT2 (min): 18.94; Sample Solvent: MeOH:DCM=1: 1-HPLC; Injection Volume: 0.4 mL; Number Of Runs: 6) to afford (S)-2'-chloro-5'-(difluoromethoxy)-6-methyl-N-(5-((tetrahydrofuran-3-yl)methoxy)-1,3,4-thiadiazol-2-yl)-(4,4'-bipyridine)-3-carboxamide, isomer 1 (27.2 mg, 36%) as a white solid with the first peak (first eluting fraction) on chiral HPLC and (R)-2'-chloro-5'-(difluoromethoxy)-6-methyl-N-(5-((tetrahydrofuran-3-yl)methoxy)-1,3,4-thiadiazol-2-yl)-(4,4'-bipyridine)-3-carboxamide, isomer 2 (25.8 mg, 34%) as a white solid with the second peak (second eluting fraction) on chiral HPLC. The absolute stereochemistry was not determined.

Isomer 1: (S)-2'-chloro-5'-(difluoromethoxy)-6-methyl-N-(5-((tetrahydrofuran-3-yl)methoxy)-1,3,4-thiadiazol-2-yl)-(4,4'-bipyridine)-3-carboxamide: MS (ESI) calc'd for ($C_{20}H_{18}ClF_2N_5O_4S$) $(M+1)^+$, 498.1; found, 498.1. $^1H$ NMR (400 MHz, DMSO-$d_6$) δ 12.99 (s, 1H), 9.00 (s, 1H), 8.31 (s, 1H), 7.66 (s, 1H), 7.38 (s, 1H), 7.37-6.94 (m, 1H), 4.40-4.25 (m, 2H), 3.81-3.71 (m, 2H), 3.69-3.59 (m, 1H), 3.56-3.47 (m, 1H), 2.77-2.67 (m, 1H), 2.59 (s, 3H), 2.07-1.94 (m, 1H), 1.71-1.58 (m, 1H).

Isomer 2: (R)-2'-chloro-5'-(difluoromethoxy)-6-methyl-N-(5-((tetrahydrofuran-3-yl)methoxy)-1,3,4-thiadiazol-2-yl)-(4,4'-bipyridine)-3-carboxamide: MS (ESI) calc'd for ($C_{20}H_{18}ClF_2N_5O_4S$) $(M+1)^+$, 498.1; found, 498.1. $^1H$ NMR (400 MHz, DMSO-$d_6$) δ 13.02 (s, 1H), 8.98 (s, 1H), 8.32 (s, 1H), 7.69 (s, 1H), 7.41 (s, 1H), 7.31-6.94 (m, 1H), 4.42-4.27 (m, 2H), 3.81-3.71 (m, 2H), 3.70-3.60 (m, 1H), 3.58-3.49 (m, 1H), 2.78-2.68 (m, 1H), 2.60 (s, 3H), 2.08-1.94 (m, 1H), 1.71-1.58 (m, 1H).

Example 262, 251, 252, 253 and 254

2'-chloro-5'-methoxy-6-methyl-N-(5-((5-methyltetrahydrofuran-3-yl)methoxy)-1,3,4-thiadiazol-2-yl)-(4,4'-bipyridine)-3-carboxamide, 2'-chloro-5'-methoxy-6-methyl-N-(5-(((3R,5S)-5-methyltetrahydrofuran-3-yl)methoxy)-1,3,4-thiadiazol-2-yl)-(4,4'-bipyridine)-3-carboxamide, 2'-chloro-5'-methoxy-6-methyl-N-(5-(((3R,5R)-5-methyltetrahydrofuran-3-yl)methoxy)-1,3,4-thiadiazol-2-yl)-(4,4'-bipyridine)-3-carboxamide, 2'-chloro-5'-methoxy-6-methyl-N-(5-(((3S,5R)-5-methyltetrahydrofuran-3-yl)methoxy)-1,3,4-thiadiazol-2-yl)-(4,4'-bipyridine)-3-carboxamide and 2'-chloro-5'-methoxy-6-methyl-N-(5-(((3S,5S)-5-methyltetrahydrofuran-3-yl)methoxy)-1,3,4-thiadiazol-2-yl)-(4,4'-bipyridine)-3-carboxamide

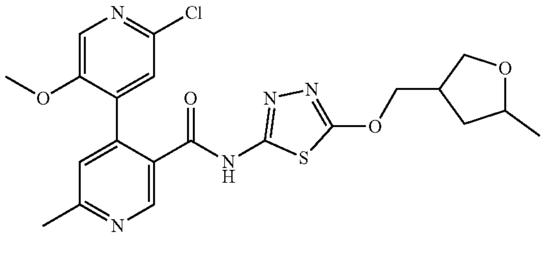

-continued

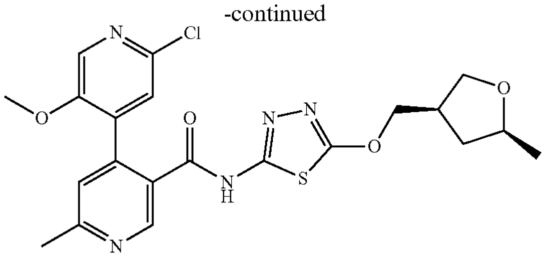

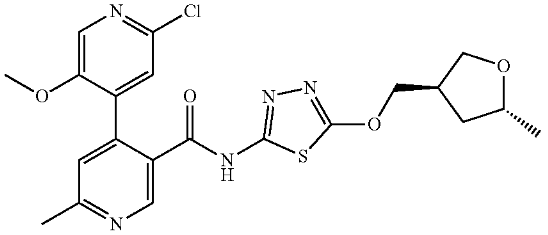

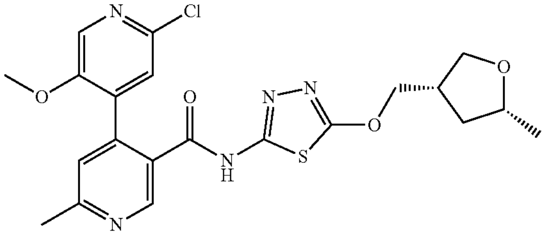

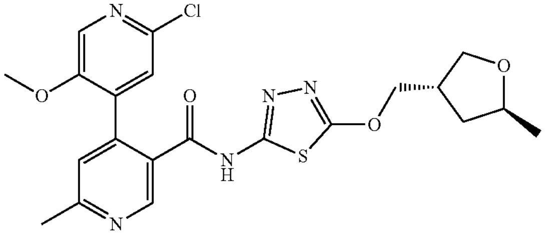

Step-1: (5-methyltetrahydrofuran-3-yl)methanol

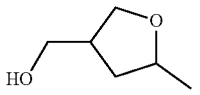

To a stirred solution of 5-methyltetrahydrofuran-3-carboxylic acid (900.0 mg, 6.92 mmol) in Tetrahydrofuran (10 mL) were sequentially added N-methylmorpholine (699.0 mg, 6.92 mmol) and isobutyl carbonochloridate (944.0 mg, 6.92 mmol) at 0° C. The resulting solution was stirred at 0° C. for 1 h. To the above solution was added $NaBH_4$ (785.3 mg, 20.75 mmol) and Methanol (20 mL) at 0° C. under nitrogen. The resulting mixture was then stirred at 0° C. for 2 hours. The reaction mixture was quenched by the addition of water and extracted with ethyl acetate. The combined organic layers were washed with brine, dried over anhydrous sodium sulfate, filtered, and concentrated under vacuum. The resulting residue was dissolved in DCM (4 mL) and purified by flash chromatography (Biotage Isolera Prime) which applied to a 40 g silica gel column that was eluted with 0-50% ethyl acetate in petroleum ether within 30 min to afford (5-methyltetrahydrofuran-3-yl)methanol (400.0 mg, 44%) as a yellow oil.

Step-2: S-methyl O-((5-methyltetrahydrofuran-3-yl)methyl) carbonodithioate

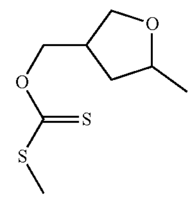

To a stirred solution of (5-methyltetrahydrofuran-3-yl) methanol (400.0 mg, 3.44 mmol) in Tetrahydrofuran (5 mL) was added NaH (165.0 mg, 4.13 mmol, 60%) at 0° C. The reaction mixture was stirred at 0° C. for 0.5 h. Then $CS_2$ (315.0 mg, 4.13 mmol) was added to the above mixture at 0° C. The resulting solution was then stirred at 0° C. for 0.5 h. Then MeI (587.0 mg, 4.13 mmol) was added to the above mixture at 0° C. The resulting solution was then stirred at 0° C. for 1 h. The reaction mixture was quenched by the addition of water and extracted with ethyl acetate. The combined organic layers were washed with brine, dried over anhydrous sodium sulfate, filtered, and concentrated under vacuum to afford S-methyl O-((5-methyltetrahydrofuran-3-yl)methyl) carbonodithioate (520.0 mg, crude) as a yellow oil.

Step-3: O-((5-methyltetrahydrofuran-3-yl)methyl) hydrazinecarbothioate

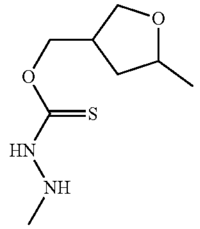

To a mixture of S-methyl O-((5-methyltetrahydrofuran-3-yl)methyl) carbonodithioate (520.0 mg, 2.17 mmol) in Methanol (6 mL) was added hydrazine hydrate (130.0 mg, 3.25 mmol, 80%). The mixture was stirred at rt for 1 hour. The resulting mixture was concentrated under vacuum and then diluted with water. The resulting mixture was extracted with ethyl acetate. The combined organic layers were washed with brine, dried over anhydrous sodium sulfate, filtered, and concentrated under vacuum to afford O-((5-methyltetrahydrofuran-3-yl)methyl) hydrazinecarbothioate (500.0 mg, crude) as a yellow oil. MS (ESI) calculated for $(C_7H_{14}ClN_2O_2S)$ $(M+1)^+$, 191.1; found, 191.1.

Step-4: 5-((5-methyltetrahydrofuran-3-yl)methoxy)-1,3,4-thiadiazol-2-amine (5)

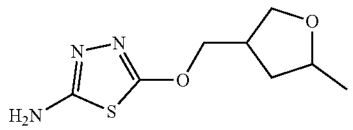

To a mixture of O-((5-methyltetrahydrofuran-3-yl) methyl) hydrazinecarbothioate (500.0 mg, 1.57 mmol)) and TEA (319.0 mg, 3.15 mmol) in Methanol (5 mL) was added BrCN (200.0 mg, 1.89 mmol). The mixture was stirred at 25° C. for 1 h. The reaction mixture was quenched by the addition of water and extracted with ethyl acetate. The combined organic layers were washed with brine, dried over anhydrous sodium sulfate, filtered, and concentrated under vacuum. The resulting residue was dissolved in DCM (4 mL) and purified by flash chromatography (Biotage Isolera Prime) which applied to a 40 g silica gel column that was eluted with 0~30% ethyl acetate in petroleum ether within 25 min to afford 5-((5-methyltetrahydrofuran-3-yl) methoxy)-1,3,4-thiadiazol-2-amine (200.0 mg, 56% over three steps) as a yellow oil. MS (ESI) calculated for $(C_8H_{13}N_3O_2S)$ $(M+1)^+$, 216.1; found, 216.0.

Step-5: 2'-chloro-5'-methoxy-6-methyl-N-(5-((5-methyltetrahydrofuran-3-yl)methoxy)-1,3,4-thiadiazol-2-yl)-(4,4'-bipyridine)-3-carboxamide

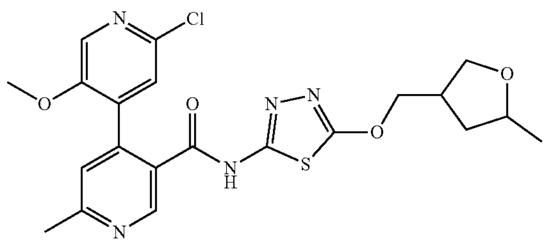

To a stirred solution of Intermediate H (259.0 mg, 0.93 mmol) in Acetonitrile (2 mL) were added 5-((5-methyltetrahydrofuran-3-yl)methoxy)-1,3,4-thiadiazol-2-amine (200.0 mg, 0.93 mmol) and NMI (381.0 mg, 4.65 mmol). To the above mixture was added TCFH (261.0 mg, 0.93 mmol) in Acetonitrile (2 mL). The resulting mixture was stirred at 25° C. for 2 hr. The solvents were removed under vacuum. The resulting residue was dissolved in DMF (3 mL) which was applied to a 40 g C18 column and purified by flash chromatography (Biotage Isolera Prime), eluted with 5~70% acetonitrile in water within 30 min to afford 2'-chloro-5'-methoxy-6-methyl-N-(5-((5-methyltetrahydrofuran-3-yl) methoxy)-1,3,4-thiadiazol-2-yl)-(4,4'-bipyridine)-3-carboxamide (160.0 mg, 35%) as a light yellow solid. MS (ESI) calculated for $(C_{21}H_{22}ClN_5O_4S)$ $(M+1)^+$, 476.1; found, 476.1. $^1H$ NMR (400 MHz, DMSO-$d_6$) δ 12.89 (s, 1H), 8.81 (s, 1H), 8.17 (s, 1H), 7.54 (s, 1H), 7.43 (s, 1H), 4.59-4.28 (m, 2H), 4.04-3.85 (m, 1H), 3.76-3.60 (m, 4H), 2.84-2.76 (m, 1H), 2.59 (s, 3H), 2.28-2.06 (m, 1H), 1.86-1.50 (m, 1H), 1.26-1.10 (m, 4H).

Step-6: 2'-chloro-5'-methoxy-6-methyl-N-(5-(((3R,5S)-5-methyltetrahydrofuran-3-yl)methoxy)-1,3,4-thiadiazol-2-yl)-(4,4'-bipyridine)-3-carboxamide, 2'-chloro-5'-methoxy-6-methyl-N-(5-(((3R,5R)-5-methyltetrahydrofuran-3-yl)methoxy)-1,3,4-thiadiazol-2-yl)-(4,4'-bipyridine)-3-carboxamide, 2'-chloro-5'-methoxy-6-methyl-N-(5-(((3S,5R)-5-methyltetrahydrofuran-3-yl)methoxy)-1,3,4-thiadiazol-2-yl)-(4,4'-bipyridine)-3-carboxamide and 2'-chloro-5'-methoxy-6-methyl-N-(5-(((3S,5S)-5-methyltetrahydrofuran-3-yl)methoxy)-1,3,4-thiadiazol-2-yl)-(4,4'-bipyridine)-3-carboxamide

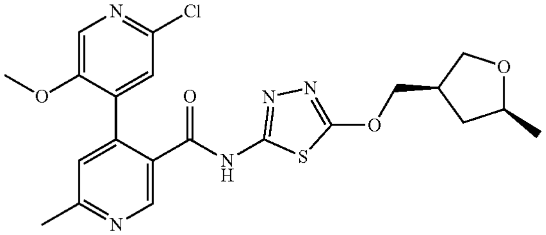

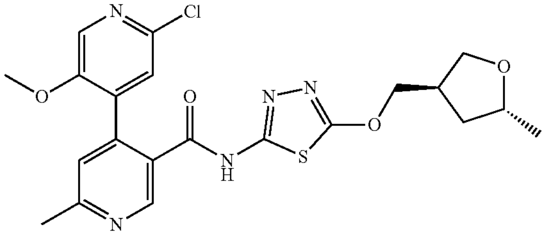

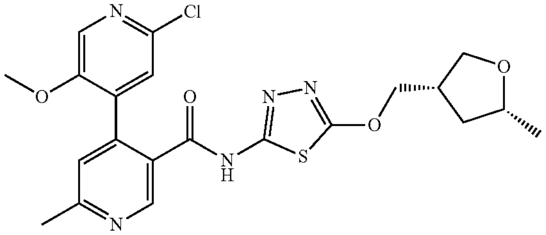

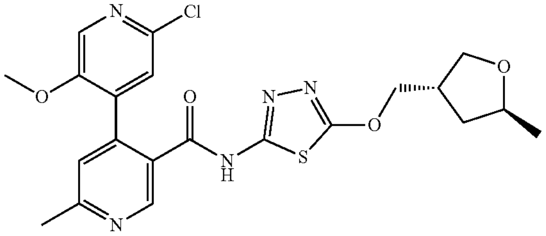

The racemic compound (150.0 mg) was separated by prep-chiral HPLC with the following conditions: (Column: CHIRALPAK IF, 2*25 cm, 5 μm; Mobile Phase A: MtBE (0.1% FA)-HPLC, Mobile Phase B: MeOH:DCM=1: 1-HPLC; Flow rate: 18 mL/min; Gradient: 15% B to 15% B in 34 min; Wave Length: 220/254 nm; RT1 (min): 14.43; RT2 (min): 18.20; Sample Solvent: MeOH:DCM=1: 1-HPLC; Injection Volume: 0.7 mL; Number Of Runs: 5) to afford 2'-chloro-5'-methoxy-6-methyl-N-(5-(((3R,5S)-5-methyltetrahydrofuran-3-yl)methoxy)-1,3,4-thiadiazol-2-yl)-(4,4'-bipyridine)-3-carboxamide, isomer 1 (33.9 mg, 22.%) as a light yellow solid with the first peak (first eluting fraction) on chiral HPLC, 2'-chloro-5'-methoxy-6-methyl-N-(5-(((3R,5R)-5-methyltetrahydrofuran-3-yl)methoxy)-1,3,4-thiadiazol-2-yl)-(4,4'-bipyridine)-3-carboxamide, isomer 2 (22.4 mg, 14%) as a white solid with the second peak (second eluting fraction) on chiral HPLC and a third peak (third eluting fraction) containing a mixture of 2'-chloro-5'-methoxy-6-methyl-N-(5-(((3S,5R)-5-methyltetrahydrofuran-3-yl)methoxy)-1,3,4-thiadiazol-2-yl)-(4,4'-bipyridine)-3-carboxamide and 2'-chloro-5'-methoxy-6-methyl-N-(5-(((3S,5S)-5-methyltetrahydrofuran-3-yl)methoxy)-1,3,4-thiadiazol-2-yl)-(4,4'-bipyridine)-3-carboxamide (60.0 mg, 39.2%) as a white solid, which was further separated by prep-chiral HPLC with the following conditions: (Column: CHIRAL ART Cellulose-SC, 2*25 cm, 5 μm; Mobile Phase A: Hex (0.2% FA)-HPLC, Mobile Phase B: MeOH: EtOH=1: 1-HPLC; Flow rate: 20 mL/min; Gradient: 35% B to 35% B in 21 min; Wave Length: 220/254 nm; RT1 (min): 16.56; RT2 (min): 18.91; Sample Solvent: MeOH:DCM=1: 1-HPLC; Injection Volume: 0.3 mL; Number Of Runs: 10) to afford 2'-chloro-5'-methoxy-6-methyl-N-(5-(((3S,5R)-5-methyltetrahydrofuran-3-yl)methoxy)-1,3,4-thiadiazol-2-yl)-(4,4'-bipyridine)-3-carboxamide, isomer 3 (20.7 mg, 34%) as a light yellow solid with the first peak (first eluting fraction) on the second chiral HPLC and 2'-chloro-5'-methoxy-6-methyl-N-(5-(((3S,5S)-5-methyltetrahydrofuran-3-yl)methoxy)-1,3,4-thiadiazol-2-yl)-(4,4'-bipyridine)-3-carboxamide, isomer 4 (19.3 mg, 32%) as a white solid with the second peak (second eluting fraction) on the second chiral HPLC. The absolute stereochemistry was not determined.

Isomer 1: 2'-chloro-5'-methoxy-6-methyl-N-(5-(((3R,5S)-5-methyltetrahydrofuran-3-yl)methoxy)-1,3,4-thiadiazol-2-yl)-(4,4'-bipyridine)-3-carboxamide: MS (ESI) calc'd for ($C_{21}H_{22}ClN_5O_4S$) $(M+1)^+$, 476.1; found, 476.1. $^1H$ NMR (400 MHz, DMSO-$d_6$) δ 12.86 (s, 1H), 8.83 (s, 1H), 8.17 (s, 1H), 7.50 (s, 1H), 7.38 (s, 1H), 4.38-4.24 (m, 2H), 3.87-3.77 (m, 1H), 3.73-3.57 (m, 5H), 2.80-2.65 (m, 1H), 2.58 (s, 3H), 2.23-2.15 (m, 1H), 1.23-1.09 (m, 4H).

Isomer 2: 2'-chloro-5'-methoxy-6-methyl-N-(5-(((3R,5R)-5-methyltetrahydrofuran-3-yl)methoxy)-1,3,4-thiadiazol-2-yl)-(4,4'-bipyridine)-3-carboxamide: MS (ESI) calc'd for ($C_{21}H_{22}ClN_5O_4S$) $(M+1)^+$, 476.1; found, 476.1. $^1H$ NMR (400 MHz, DMSO-$d_6$) δ 12.85 (s, 1H), 8.83 (s, 1H), 8.17 (s, 1H), 7.50 (s, 1H), 7.38 (s, 1H), 4.44-4.32 (m, 2H), 4.05-3.91 (m, 2H), 3.63 (s, 3H), 3.47-3.35 (m, 1H), 2.81-2.71 (m, 1H), 2.58 (s, 3H), 1.88-1.82 (m, 1H), 1.61-1.52 (m, 1H), 1.15 (d, J=6.4 Hz, 3H).

Isomer 3: 2'-chloro-5'-methoxy-6-methyl-N-(5-(((3S,5R)-5-methyltetrahydrofuran-3-yl)methoxy)-1,3,4-thiadiazol-2-yl)-(4,4'-bipyridine)-3-carboxamide: MS (ESI) calc'd for ($C_{21}H_{22}ClN_5O_4S$) $(M+1)^+$, 476.1; found, 476.1. $^1H$ NMR (400 MHz, DMSO-$d_6$) δ 12.88 (s, 1H), 8.83 (s, 1H), 8.17 (s, 1H), 7.52 (s, 1H), 7.40 (s, 1H), 4.40-4.27 (m, 2H), 3.92-3.85 (m, 1H), 3.73-3.63 (m, 5H), 2.79-2.71 (m, 1H), 2.59 (s, 3H), 2.23-2.15 (m, 1H), 1.22-1.09 (m, 4H).

Isomer 4: 2'-chloro-5'-methoxy-6-methyl-N-(5-(((3S,5S)-5-methyltetrahydrofuran-3-yl)methoxy)-1,3,4-thiadiazol-2-yl)-(4,4'-bipyridine)-3-carboxamide: MS (ESI) calc'd for ($C_{21}H_{22}ClN_5O_4S$) $(M+1)^+$, 476.1; found, 476.1. 1H NMR (400 MHz, DMSO-$d_6$) δ 12.88 (s, 1H), 8.84 (s, 1H), 8.16 (s, 1H), 7.49 (s, 1H), 7.37 (s, 1H), 4.42-4.32 (m, 2H), 4.05-3.91 (m, 2H), 3.63 (s, 3H), 3.48-3.36 (m, 1H), 2.82-2.67 (m, 1H), 2.58 (s, 3H), 1.94-1.80 (m, 1H), 1.63-1.55 (m, 1H), 1.15 (d, J=6.4 Hz, 3H).

Example 263 and 264

(R)-2'-chloro-N-(5-((3-fluorotetrahydrofuran-3-yl)methoxy)-1,3,4-thiadiazol-2-yl)-5'-methoxy-6-methyl-(4,4'-bipyridine)-3-carboxamide and (S)-2'-chloro-N-(5-((3-fluorotetrahydrofuran-3-yl)methoxy)-1,3,4-thiadiazol-2-yl)-5'-methoxy-6-methyl-(4,4'-bipyridine)-3-carboxamide

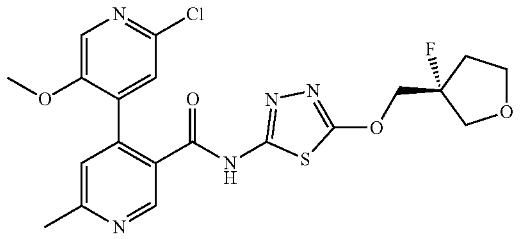

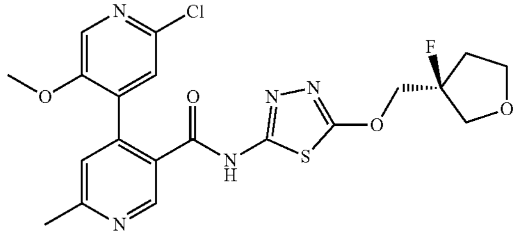

Step-1: O-((3-fluorotetrahydrofuran-3-yl)methyl)S-methyl carbonodithioate

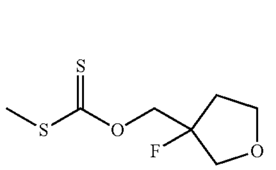

To a stirred solution of (3-fluorotetrahydrofuran-3-yl)methanol (400.0 mg, 3.33 mmol) in Tetrahydrofuran (8 mL) was added NaH (160.0 mg, 4.00 mmol, 60%) at 0° C. The reaction mixture was stirred at 0° C. for 0.5 h. Then $CS_2$ (380.0 mg, 4.99 mmol) was added to the above mixture at 0° C. The resulting solution was then stirred at 0° C. for 0.5 h. Then MeI (709.0 mg, 4.99 mmol) was added to the above mixture at 0° C. The resulting solution was then stirred at 0° C. for 1 h. The reaction mixture was quenched by the addition of water and extracted with ethyl acetate. The combined organic layers were washed with brine, dried over anhydrous sodium sulfate, filtered, and concentrated under vacuum to afford O-((3-fluorotetrahydrofuran-3-yl)methyl) S-methyl carbonodithioate (730.0 mg, crude) as a yellow oil.

Step-2: O-((3-fluorotetrahydrofuran-3-yl)methyl) hydrazinecarbothioate

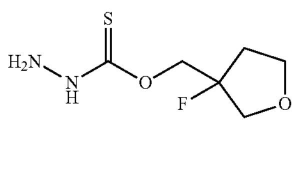 [SMILES: NNC(=S)OCC1(F)CCOC1]

To a stirred solution of O-((3-fluorotetrahydrofuran-3-yl)methyl)S-methyl carbonodithioate (730.0 mg, 3.47 mmol) in Methanol (10 mL) was added hydrazine hydrate (222.0 mg, 3.47 mmol, 80%) at 25° C. The reaction mixture was stirred at 25° C. for 1 h. The organic solvent was removed under vacuum to afford O-((3-fluorotetrahydrofuran-3-yl)methyl) hydrazinecarbothioate (710.0 mg, crude) as a yellow oil.

Step-3: 5-((3-fluorotetrahydrofuran-3-yl)methoxy)-1,3,4-thiadiazol-2-amine

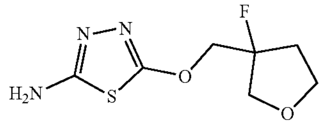 [SMILES: Nc1nnc(OCC2(F)CCOC2)s1]

To a stirred solution of O-((3-fluorotetrahydrofuran-3-yl)methyl) hydrazinecarbothioate (710.0 mg, 3.66 mmol) in Methanol (11 mL) were added cyanogen bromide (774.0 mg, 7.31 mmol) and TEA (925.0 mg, 9.14 mmol). The mixture was stirred at 25° C. for 2 h under nitrogen atmosphere. The organic solvent was removed under vacuum. The resulting residue was dissolved in MeOH (2 mL) which was applied to a 20 g C18 column and purified by flash chromatography (Biotage Isolera Prime), eluted with 5-25% acetonitrile in water within 20 min to afford 5-((3-fluorotetrahydrofuran-3-yl)methoxy)-1,3,4-thiadiazol-2-amine (360.0 mg, 35% over three steps) as a yellow oil. MS (ESI) calc'd for ($C_7H_{10}FN_3O_2S$) $(M+1)^+$, 220.0, found 220.1.

Step-4: (R)-2'-chloro-N-(5-((3-fluorotetrahydrofuran-3-yl)methoxy)-1,3,4-thiadiazol-2-yl)-5'-methoxy-6-methyl-(4,4'-bipyridine)-3-carboxamide and (S)-2'-chloro-N-(5-((3-fluorotetrahydrofuran-3-yl)methoxy)-1,3,4-thiadiazol-2-yl)-5'-methoxy-6-methyl-(4,4'-bipyridine)-3-carboxamide

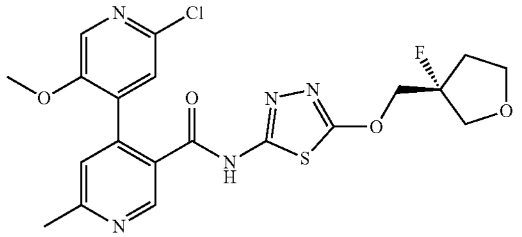

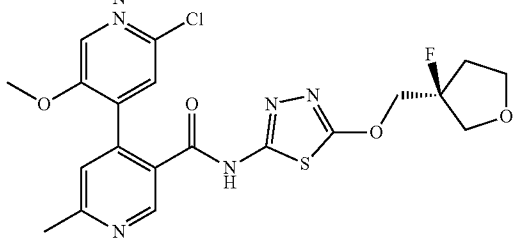

To a stirred solution of Intermediate H (465.0 mg, 1.66 mmol) in Acetonitrile (5 mL) were sequentially added 5-((3-fluorotetrahydrofuran-3-yl)methoxy)-1,3,4-thiadiazol-2-amine (360.0 mg, 1.66 mmol) and 1-methyl-1H-imidazole (685.0 mg, 8.35 mmol). To the above mixture was added TCFH (468.0 mg, 1.66 mmol) at 25° C. The resulting solution was stirred at 25° C. for 16 h. The organic solvent was removed under vacuum. The resulting residue was dissolved in DMF (4 mL), applied to a 40 g C18 column, purified by flash chromatography (Biotage Isolera Prime) and eluted with 5~45% acetonitrile in water within 30 min to afford 2'-chloro-N-(5-((3-fluorotetrahydrofuran-3-yl)methoxy)-1,3,4-thiadiazol-2-yl)-5'-methoxy-6-methyl-(4,4'-bipyridine)-3-carboxamide (300.0 mg, 33%) as a white solid. The racemic compound (150.0 mg) was separated by prep-chiral HPLC with the following conditions: (Column: CHIRALPAK IF, 2*25 cm, 5 μm; Mobile Phase A: Hex (0.2% FA)-HPLC, Mobile Phase B: MeOH:DCM=1: 1 (0.1% 2M $NH_3$-MEOH); Flow rate: 20 mL/min; Gradient: 50% B to 50% B in 14.5 min; Wave Length: 220/254 nm; RT1 (min): 9.08; RT2 (min): 13.01; Sample Solvent: MeOH: DCM=1: 1; Injection Volume: 2.5 mL; Number Of Runs: 6) to afford (R)-2'-chloro-N-(5-((3-fluorotetrahydrofuran-3-yl)methoxy)-1,3,4-thiadiazol-2-yl)-5'-methoxy-6-methyl-(4,4'-bipyridine)-3-carboxamide, isomer 1 (54.4 mg, 34%) (54.4 mg, 34%) as a white solid with the first peak (first eluting fraction) on chiral HPLC and (S)-2'-chloro-N-(5-((3-fluoro-tetrahydrofuran-3-yl)methoxy)-1,3,4-thiadiazol-2-yl)-5'-methoxy-6-methyl-(4,4'-bipyridine)-3-carboxamide, isomer 2 (49.7 mg, 33%)) as a white solid with the second peak (second eluting fraction) on chiral HPLC. The absolute stereochemistry was not determined.

Isomer 1: (R)-2'-chloro-N-(5-((3-fluorotetrahydrofuran-3-yl)methoxy)-1,3,4-thiadiazol-2-yl)-5'-methoxy-6-methyl-(4,4'-bipyridine)-3-carboxamide: MS (ESI) calc'd for ($C_{20}H_{19}ClFN_5O_4S$) $(M+1)^+$, 480.1; found, 480.2. $^1H$ NMR (400 MHz, DMSO-$d_6$) δ 12.94 (s, 1H), 8.81 (s, 1H), 8.17 (s, 1H), 7.54 (s, 1H), 7.44 (s, 1H), 4.89-4.69 (m, 2H), 3.97-3.81 (m, 4H), 3.63 (s, 3H), 2.59 (s, 3H), 2.29-2.08 (m, 2H). $^{19}F$ NMR (400 MHz, DMSO-$d_6$) δ-151.44.

Isomer 2: (S)-2'-chloro-N-(5-((3-fluorotetrahydrofuran-3-yl)methoxy)-1,3,4-thiadiazol-2-yl)-5'-methoxy-6-methyl-(4,4'-bipyridine)-3-carboxamide: MS (ESI) calc'd for ($C_{20}H_{19}ClFN_5O_4S$) $(M+1)^+$, 480.1; found, 480.1. $^1H$ NMR (400 MHz, DMSO-$d_6$) δ 12.93 (s, 1H), 8.81 (s, 1H), 8.17 (s, 1H), 7.55 (s, 1H), 7.44 (s, 1H), 4.91-4.69 (m, 2H), 4.00-3.80 (m, 4H), 3.64 (s, 3H), 2.60 (s, 3H), 2.29-2.12 (m, 2H). $^{19}F$ NMR (400 MHz, DMSO-$d_6$) δ-151.44.

Example 265, 266, 267 and 268

2'-chloro-5'-methoxy-6-methyl-N-(5-(((3S,4R)-4-methyltetrahydrofuran-3-yl)methoxy)-1,3,4-thiadiazol-2-yl)-(4,4'-bipyridine)-3-carboxamide, 2'-chloro-5'-methoxy-6-methyl-N-(5-(((3S,4S)-4-methyltetrahydrofuran-3-yl)methoxy)-1,3,4-thiadiazol-2-yl)-(4,4'-bipyridine)-3-carboxamide, 2'-chloro-5'-methoxy-6-methyl-N-(5-(((3R,4S)-4-methyltetrahydrofuran-3-yl)methoxy)-1,3,4-thiadiazol-2-yl)-(4,4'-bipyridine)-3-carboxamide and 2'-chloro-5'-methoxy-6-methyl-N-(5-(((3R,4R)-4-methyltetrahydrofuran-3-yl)methoxy)-1,3,4-thiadiazol-2-yl)-(4,4'-bipyridine)-3-carboxamide

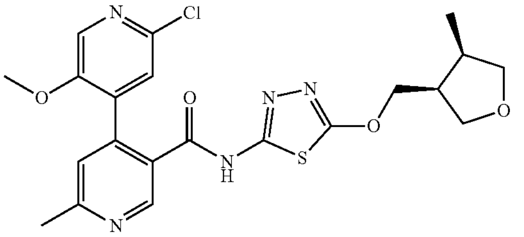

-continued

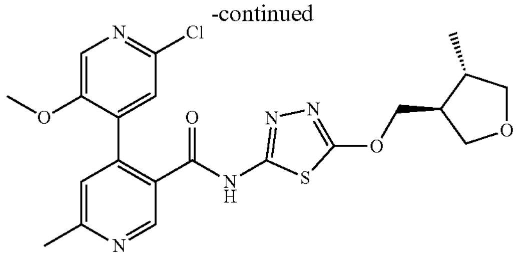

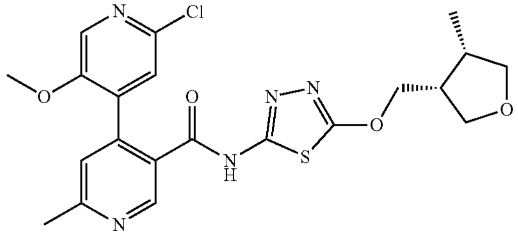

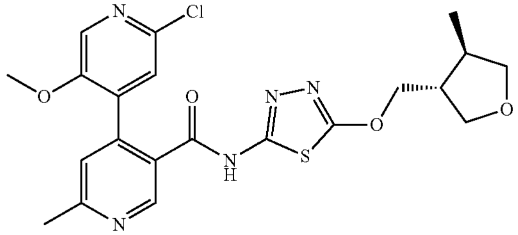

Step-1: (4-methyltetrahydrofuran-3-yl)methanol

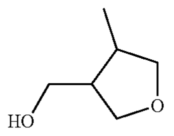

To a stirred solution of 3-(allyloxy)prop-1-ene (500.0 mg, 5.09 mmol) in Ethanol (10 mL) were added Iron phthalocyanine (289.0 mg, 0.51 mmol) and $NaBH_4$ (289.0 mg, 7.64 mmol) at 0° C. The resulting solution was stirred at 20° C. for 3 h. The reaction mixture was quenched by the addition of water and extracted with ethyl acetate. The combined organic layers were washed with brine, dried over anhydrous sodium sulfate, filtered, and concentrated under vacuum. The resulting residue was purified by flash chromatography (Biotage Isolera Prime) which applied to a 40 g silica gel column that was eluted with 0~100% ethyl acetate in petroleum ether within 25 min to afford (4-methyltetrahydrofuran-3-yl)methanol (190.0 mg, 28%) as a green oil.

Step-2: S-methyl O-((4-methyltetrahydrofuran-3-yl)methyl) carbonodithioate

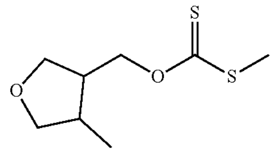

To a degassed solution of (4-methyltetrahydrofuran-3-yl) methanol (160.0 mg, 1.37 mmol) in dry Tetrahydrofuran (5 mL) was added NaH (66.1 mg, 1.65 mmol, 60%) in portions at 0° C. The resulting solution was stirred at 0° C. for 30 min. To the above solution was added $CS_2$ (157.0 mg, 2.06 mmol) at 0° C. The resulting mixture was then stirred at 0° C. for 30 min. To the above solution was added MeI (293.0 mg, 2.06 mmol) at 0° C. The resulting mixture was then stirred at 0° C. for 30 min. The reaction mixture was quenched by the addition of water and extracted with ethyl acetate. The combined organic layers were washed with brine, dried over anhydrous sodium sulfate, filtered, and concentrated under vacuum to afford S-methyl O-((4-methyltetrahydrofuran-3-yl)methyl) carbonodithioate (300.0 mg, crude) as a green oil.

Step-3: O-((4-methyltetrahydrofuran-3-yl)methyl) hydrazinecarbothioate

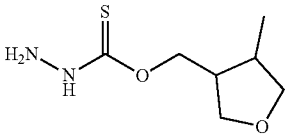

To a stirred solution of S-methyl O-((4-methyltetrahydrofuran-3-yl)methyl) carbonodithioate (30.00 mg, 1.45 mmol) in Methanol (5 mL) was added hydrazine hydrate (100.0 mg, 1.60 mmol, 80%) at 20° C. The resulting solution was stirred at 20° C. for 30 min. The organic solvent was removed under vacuum to afford O-((4-methyltetrahydrofuran-3-yl)methyl) hydrazinecarbothioate (250.0 mg, crude) as a green oil. MS (ESI) calc'd for ($C_7H_{14}N_2O_2S$) $(M+1)^+$, 191.1, found, 191.1.

Step-4: 5-((4-methyltetrahydrofuran-3-yl)methoxy)-1,3,4-thiadiazol-2-amine

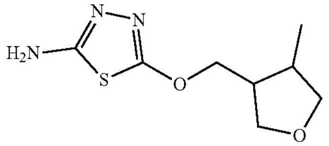

To a stirred solution of O-((4-methyltetrahydrofuran-3-yl)methyl) hydrazinecarbothioate (250.0 mg, 1.31 mmol) in Methanol (5 mL) were added triethylamine (266.0 mg, 2.63 mmol) and BrCN (152.0 mg, 1.44 mmol) at 20° C. The resulting solution was stirred at 20° C. for 0.5 hr. The reaction mixture was quenched by the addition of water and extracted with ethyl acetate. The combined organic layers were washed with brine, dried over anhydrous sodium sulfate, filtered, and concentrated under vacuum. The resulting residue was purified by flash chromatography (Biotage Isolera Prime) which applied to a 40 g silica gel column that was eluted with 0~100% ethyl acetate in petroleum ether within 25 min to afford 5-((4-methyltetrahydrofuran-3-yl)methoxy)-1,3,4-thiadiazol-2-amine (160.0 mg, 53%) as a yellow solid. MS (ESI) calc'd for ($C_8H_{13}N_3O_2S$) $(M+1)^+$, 216.1, found, 216.1.

Step-5: 2'-chloro-5'-methoxy-6-methyl-N-(5-((4-methyltetrahydrofuran-3-yl)methoxy)-1,3,4-thiadiazol-2-yl)-(4,4'-bipyridine)-3-carboxamide

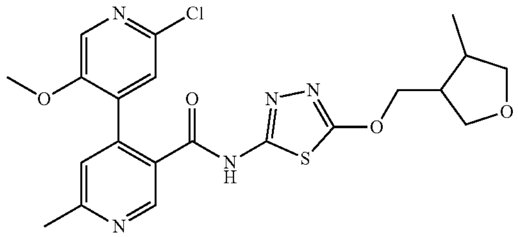 [SMILES: COc1cnc(Cl)cc1-c1cc(C)ncc1C(=O)Nc1nnc(OCC2COCC2C)s1]

To a stirred solution of 5-((4-methyltetrahydrofuran-3-yl)methoxy)-1,3,4-thiadiazol-2-amine (120.0 mg, 0.55 mmol) in Acetonitrile (1 mL) were added Intermediate H (155.0 mg, 0.56 mmol) and 1-methylimidazole (230.0 mg, 2.75 mmol) at 20° C. To the above solution was added TCFH (156.5 mg, 0.56 mmol) in Acetonitrile (1 mL) at 20° C. under nitrogen. The resulting mixture was then stirred at 20° C. for 2 hr. The resulting residue was dissolved in DMF (2 mL) which was applied to a 40 g C18 column and purified by flash chromatography (Biotage Isolera Prime), eluted with 5~80% acetonitrile in water within 35 min to afford 2'-chloro-5'-methoxy-6-methyl-N-(5-((4-methyltetrahydrofuran-3-yl)methoxy)-1,3,4-thiadiazol-2-yl)-(4,4'-bipyridine)-3-carboxamide (150.0 mg, 56%) as a white solid. MS (ESI) calc'd for ($C_{21}H_{22}ClN_5O_4S$) $(M+1)^+$, 476.1, found 476.1. $^1H$ NMR (400 MHz, DMSO-$d_6$) δ 12.91 (s, 1H), 8.81 (s, 1H), 8.17 (s, 1H), 7.54 (s, 1H), 7.43 (s, 1H), 4.57-4.48 (m, 1H), 4.42-4.33 (m, 1H), 3.90-3.80 (m, 2H), 3.63 (s, 3H), 3.62-3.55 (m, 1H), 3.39-3.33 (m, 1H), 2.75-2.62 (m, 1H), 2.59 (s, 3H), 2.49-2.34 (m, 1H), 0.96 (d, J=7.2 Hz, 3H).

Step-6: 2'-chloro-5'-methoxy-6-methyl-N-(5-(((3S,4R)-4-methyltetrahydrofuran-3-yl)methoxy)-1,3,4-thiadiazol-2-yl)-(4,4'-bipyridine)-3-carboxamide, 2'-chloro-5'-methoxy-6-methyl-N-(5-(((3S,4S)-4-methyltetrahydrofuran-3-yl)methoxy)-1,3,4-thiadiazol-2-yl)-(4,4'-bipyridine)-3-carboxamide, 2'-chloro-5'-methoxy-6-methyl-N-(5-(((3R,4S)-4-methyltetrahydrofuran-3-yl)methoxy)-1,3,4-thiadiazol-2-yl)-(4,4'-bipyridine)-3-carboxamide and 2'-chloro-5'-methoxy-6-methyl-N-(5-(((3R,4R)-4-methyltetrahydrofuran-3-yl)methoxy)-1,3,4-thiadiazol-2-yl)-(4,4'-bipyridine)-3-carboxamide

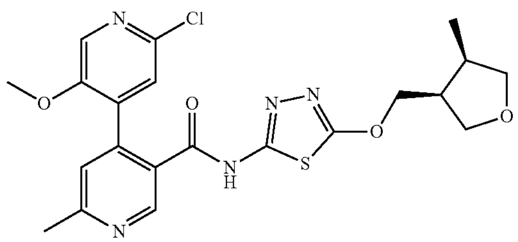

-continued

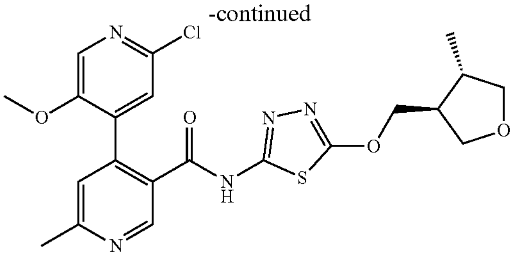

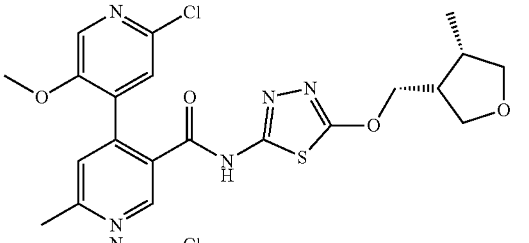

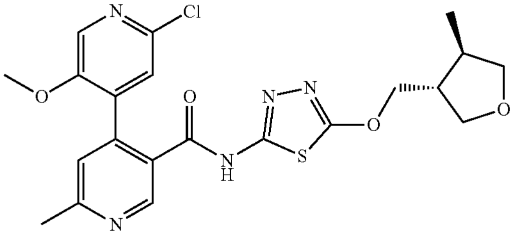

The racemic compound (140.0 mg) was separated by prep-chiral HPLC with the following conditions: (Column: CHIRALPAK IF, 2*25 cm, 5 μm; Mobile Phase A: MtBE (0.1% FA)-HPLC, Mobile Phase B: EtOH:DCM=1: 1-HPLC; Flow rate: 17 mL/min; Gradient: 40% B to 40% B in 33 min; Wave Length: 220/254 nm; RT1 (min): 10.08; RT2 (min): 11.09; Sample Solvent: MeOH:DCM=1: 1; Injection Volume: 0.8 mL; Number Of Runs: 4) to afford two single isomers: 2'-chloro-5'-methoxy-6-methyl-N-(5-(((3S,4R)-4-methyltetrahydrofuran-3-yl)methoxy)-1,3,4-thiadiazol-2-yl)-(4,4'-bipyridine)-3-carboxamide, isomer 1 (39.3 mg, 28% yield) as a white solid with the second peak (second eluting fraction) on chiral HPLC and 2'-chloro-5'-methoxy-6-methyl-N-(5-(((3S,4S)-4-methyltetrahydrofuran-3-yl)methoxy)-1,3,4-thiadiazol-2-yl)-(4,4'-bipyridine)-3-carboxamide, isomer 2 (6.5 mg, 4%) as a white solid with the third peak (third eluting fraction) on chiral HPLC and a mixture of two isomers as first peak (first eluting fraction), which was further separated by prep-chiral HPLC with the following conditions: (Column: CHIRALPAK IF, 2*25 cm, 5 μm; Mobile Phase A: MtBE (0.1% FA)-HPLC, Mobile Phase B: MeOH:DCM=1: 1; Flow rate: 20 mL/min; Gradient: 20% B to 20% B in 14 min; Wave Length: 220/254 nm; RT1 (min): 9.91; RT2 (min): 12.63; Sample Solvent: MeOH:DCM=1: 1; Injection Volume: 0.6 mL; Number Of Runs: 5) to afford 2'-chloro-5'-methoxy-6-methyl-N-(5-(((3R,4S)-4-methyltetrahydrofuran-3-yl)methoxy)-1,3,4-thiadiazol-2-yl)-(4,4'-bipyridine)-3-carboxamide, isomer 3 (29.7 mg, 57%) as a white solid with the first peak (first eluting fraction) on chiral HPLC and 2'-chloro-5'-methoxy-6-methyl-N-(5-(((3R,4R)-4-methyltetrahydrofuran-3-yl)methoxy)-1,3,4-thiadiazol-2-yl)-(4,4'-bipyridine)-3-carboxamide, isomer 4 (4.8 mg, 8%) as a white solid with the second peak (second eluting fraction) on chiral HPLC. The absolute stereochemistry was not determined.

Isomer 1: 2'-chloro-5'-methoxy-6-methyl-N-(5-(((3S,4R)-4-methyltetrahydrofuran-3-yl)methoxy)-1,3,4-thiadiazol-2-yl)-(4,4'-bipyridine)-3-carboxamide: MS (ESI) calc'd for ($C_{21}H_{22}ClN_5O_4S$) $(M+1)^+$, 476.1; found, 476.1. $^1$H NMR (400 MHz, DMSO-$d_6$) δ 12.91 (s, 1H), 8.80 (s, 1H), 8.17 (s, 1H), 7.54 (s, 1H), 7.43 (s, 1H), 4.57-4.45 (m, 1H), 4.42-4.34 (m, 1H), 3.90-3.80 (m, 2H), 3.63 (s, 3H), 3.62-3.55 (m, 1H), 3.39-3.32 (m, 1H), 2.78-2.62 (m, 1H), 2.59 (s, 3H), 2.49-2.34 (m, 1H), 0.96 (d, J=7.2 Hz, 3H).

Isomer 2: 2'-chloro-5'-methoxy-6-methyl-N-(5-(((3S,4S)-4-methyltetrahydrofuran-3-yl)methoxy)-1,3,4-thiadiazol-2-yl)-(4,4'-bipyridine)-3-carboxamide: MS (ESI) calc'd for ($C_{21}H_{22}ClN_5O_4S$) $(M+1)^+$, 476.1; found, 476.1. $^1$H NMR (400 MHz, DMSO-$d_6$) δ 12.91 (s, 1H), 8.80 (s, 1H), 8.17 (s, 1H), 7.54 (s, 1H), 7.43 (s, 1H), 4.57-4.45 (m, 1H), 4.42-4.34 (m, 1H), 3.90-3.80 (m, 2H), 3.63 (s, 3H), 3.62-3.55 (m, 1H), 3.32-3.28 (m, 1H), 2.59 (s, 3H), 2.39-2.24 (m, 1H), 2.15-2.01 (m, 1H), 1.03 (d, J=7.2 Hz, 3H).

Isomer 3: 2'-chloro-5'-methoxy-6-methyl-N-(5-(((3R,4S)-4-methyltetrahydrofuran-3-yl)methoxy)-1,3,4-thiadiazol-2-yl)-(4,4'-bipyridine)-3-carboxamide: MS (ESI) calc'd for ($C_{21}H_{22}ClN_5O_4S$) $(M+1)^+$, 476.1; found, 476.1. $^1$H NMR (400 MHz, DMSO-$d_6$) δ 12.95 (s, 1H), 8.80 (s, 1H), 8.17 (s, 1H), 7.54 (s, 1H), 7.43 (s, 1H), 4.57-4.48 (m, 1H), 4.42-4.33 (m, 1H), 3.90-3.80 (m, 2H), 3.63 (s, 3H), 3.62-3.55 (m, 1H), 3.39-3.32 (m, 1H), 2.75-2.62 (m, 1H), 2.59 (s, 3H), 2.49-2.34 (m, 1H), 0.96 (d, J=7.2 Hz, 3H).

Isomer 4: 2'-chloro-5'-methoxy-6-methyl-N-(5-(((3R,4R)-4-methyltetrahydrofuran-3-yl)methoxy)-1,3,4-thiadiazol-2-yl)-(4,4'-bipyridine)-3-carboxamide: MS (ESI) calc'd for ($C_{21}H_{22}ClN_5O_4S$) $(M+1)^+$, 476.1; found, 476.1. $^1$H NMR (400 MHz, DMSO-$d_6$) δ 12.91 (s, 1H), 8.80 (s, 1H), 8.17 (s, 1H), 7.54 (s, 1H), 7.43 (s, 1H), 4.57-4.48 (m, 1H), 4.42-4.33 (m, 1H), 3.90-3.80 (m, 2H), 3.63 (s, 3H), 3.62-3.55 (m, 1H), 3.31-3.26 (m, 1H), 2.57 (s, 3H), 2.37-2.24 (m, 1H), 2.16-1.93 (m, 1H), 1.04 (d, J=7.2 Hz, 3H).

Array Synthesis Procedure:

Step-1: (2'-chloro-5'-methoxy-6-methyl-(4,4'-bipyridin)-3-yl)(1H-imidazol-1-yl)methanone

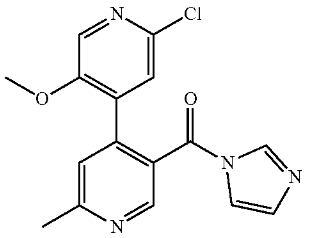 [SMILES: COc1cnc(Cl)cc1-c1cc(C)ncc1C(=O)n1ccnc1]

To a stirred solution of Intermediate H (1.0 g, 3.59 mmol) in Tetrahydrofuran (15 mL) was added CDI (0.69 g, 4.31 mmol). The mixture was stirred at room temperature for 2 hr. The reaction mixture was quenched by the addition of water and extracted with ethyl acetate. The combined organic layers were washed with brine, dried over anhydrous sodium sulfate, filtered, and concentrated under vacuum to afford (2'-chloro-5'-methoxy-6-methyl-(4,4'-bipyridin)-3-yl)(1H-imidazol-1-yl)methanone (950.0 mg, crude) as a white solid, which was used directly in next step. MS (ESI) calc'd for ($C_{16}H_{13}ClN_4O_2$) $(M+1)^+$, 329.1, found 329.1.

Step-2: N-(5-bromo-1,3,4-thiadiazol-2-yl)-2'-chloro-5'-methoxy-6-methyl-(4,4'-bipyridine)-3-carboxamide

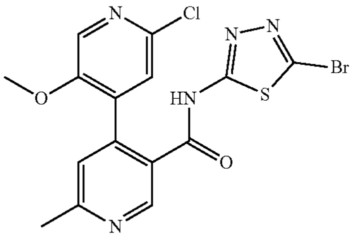 [SMILES: COc1cnc(Cl)cc1-c1cc(C)ncc1C(=O)Nc1nnc(Br)s1]

To a stirred solution of 5-bromo-1,3,4-thiadiazol-2-amine (1.0 g, 3.04 mmol) in Tetrahydrofuran (10 mL) was added NaH (300.0 mg, 7.60 mmol) at 0° C. The mixture was stirred at 0° C. to room temperature for 1 hr. (2'-chloro-5'-methoxy-6-methyl-(4,4'-bipyridin)-3-yl)(1H-imidazol-1-yl)methanone (1.3 g, 7.60 mmol) was added thereto at 0° C. The resulting mixture was stirred at room temperature for 1 h under nitrogen. The reaction mixture was quenched by the addition of sat. citric acid aq. and extracted with ethyl acetate. The combined organic layers were washed with brine, dried over anhydrous sodium sulfate, filtered, and concentrated under vacuum. The resulting residue was dissolved in DMF (10 mL) which was applied to a 330 g C18 column and purified by flash chromatography (Biotage Isolera Prime), eluted with 5~60% acetonitrile in water within 40 min to afford N-(5-bromo-1,3,4-thiadiazol-2-yl)-2'-chloro-5'-methoxy-6-methyl-(4,4'-bipyridine)-3-carboxamide (300.0 mg, 22%) as a yellow solid. MS (ESI) calc'd for ($C_{15}H_{11}BrClFN_5O_2S$) $(M+1)^+$, 439.9, 441.9; found, 439.9, 441.9. $^1H$ NMR (400 MHz, DMSO-d6) δ 13.52 (s, 1H), 8.85 (s, 1H), 8.16 (s, 1H), 7.57 (s, 1H), 7.47 (s, 1H), 3.60 (s, 3H), 2.61 (s, 3H).

Step-3: Array Synthesis

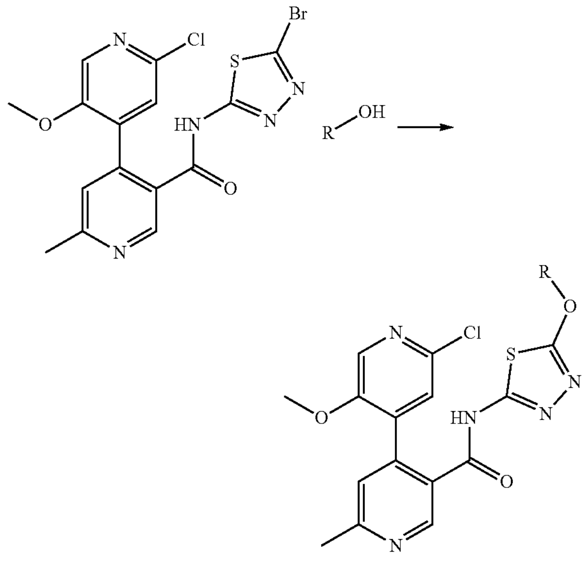

Array Synthesis Procedure (Examples 269)

N-(5-bromo-1,3,4-thiadiazol-2-yl)-2'-chloro-5'-methoxy-6-methyl-(4,4'-bipyridine)-3-carboxamide (1.1 g, 2.496 mmol) was placed in a 20 mL vial. Added to the vial was 1,4-Dioxane (15.0 mL). This slurry stirred at room temperature. In a 8 mL vial, Sodium tert-butoxide (0.96 g, 13.129 mmol) was stirred as a slurry in 1,4-Dioxane (5.0 mL). In another 8 mL vial, Copper (I) Iodide (48 mg, 0.252 mmol) and N1,N2-diphenethyloxalamide (148 mg, 0.499 mmol) were combined and stirred as a slurry in 1,4-Dioxane (5.0 mL). Twenty four vials were prepared with each containing an alcohol building block (0.2 mmol). Dispensed via pipette into each vial was N-(5-bromo-1,3,4-thiadiazol-2-yl)-2'-chloro-5'-methoxy-6-methyl-(4,4'-bipyridine)-3-carboxamide (600 mL, 0.1 mmol). Dispensed via pipette into each vial was Sodium tert-butoxide (200 mL, 0.4 mmol). Dispensed via pipette into each vial was the Copper (I) Iodide and N1,N2-diphenethyloxalamide mixture (200 mL, 0.01 and 0.02 mmol each reagent). 1 mL reaction solution total. The vials were tightly covered and the reaction plate was stirred and heated to 100° C. for 16 hours.

Array Synthesis Procedure (Examples 270 & 271)

Performed identically as above except the mixture vial contained Copper (I) Iodide (0.1 eq) and L-Proline (0.2 eq) in 1,4-Dioxane.

Array Workup Procedure (Examples 269, 270 and 271)

The reaction plate was cooled to room temperature and treated with MeOH (1 mL) then stirred at room temperature for 10 minutes. Each vessel's contents were passed through a C18 SPE, applying positive air pressure to pass the material through. Each cartridge was rinsed with MeOH (1 mL, 2×). The vials containing the filtrates (MeOH and Dioxane, ~4 mL total) were concentrated to dryness then dissolved in DMSO (1 mL) and filtered through a 45 micron filter into another filtrate collection vessel. Each filter was washed with DMSO (1 mL) and the DMSO filtrates were purified directly via reverse phase HPLC (Water and Acetonitrile, each containing 0.1% formic acid).

Example 269

2'-chloro-N-(5-((3-fluoro-1-methylazetidin-3-yl)methoxy)-1,3,4-thiadiazol-2-yl)-5'-methoxy-6-methyl-(4,4'-bipyridine)-3-carboxamide

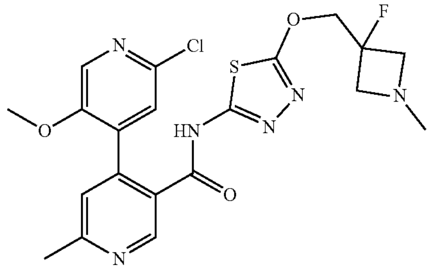

Example 269 was prepared using building block (3-fluoro-1-methylazetidin-3-yl)methanol and following the Array Synthesis Procedure and Array Workup Procedure described above to afford the title compound (10.3 mg). LCMS: M+1=479.2, Rt=0.62 min. $^1$H NMR (700 MHz, DMSO-$d_6$) δ ppm 13.51 (br s, 1H) 8.80 (s, 1H) 8.17 (s, 1H) 7.54 (s, 1H) 7.41 (s, 1H) 4.59-4.87 (m, 2H) 3.61-3.64 (m, 10H) 2.56-2.60 (s, 3H).

Example 270

(R)—N-(5-((1-acetylpyrrolidin-3-yl)methoxy)-1,3,4-thiadiazol-2-yl)-2'-chloro-5'-methoxy-6-methyl-(4,4'-bipyridine)-3-carboxamide

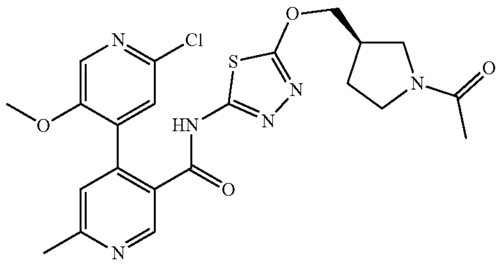 [SMILES: COc1cnc(Cl)cc1-c1cc(C)ncc1C(=O)Nc1nnc(OC[C@@H]2CCN(C(C)=O)C2)s1]

Example 270 was prepared using building block (R)-1-(3-(hydroxymethyl)pyrrolidin-1-yl)ethan-1-one and following the Array Synthesis Procedure and Array Workup Procedure described above to afford the title compound (4.9 mg). LCMS: M+1=503.2, Rt=0.77 min.

Example 271

2'-chloro-5'-methoxy-6-methyl-N-(5-(2-methyl-2-(2-oxoimidazolidin-1-yl)propoxy)-1,3,4-thiadiazol-2-yl)-(4,4'-bipyridine)-3-carboxamide

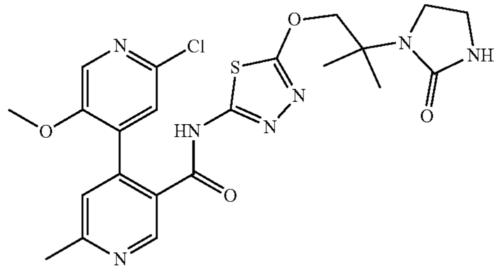 [SMILES: COc1cnc(Cl)cc1-c1cc(C)ncc1C(=O)Nc1nnc(OCC(C)(C)N2CCNC2=O)s1]

Example 271 was prepared using building 1-(1-hydroxy-2-methylpropan-2-yl)imidazolidin-2-one and following the Array Synthesis Procedure and Array Workup Procedure described above to afford the title compound (5.6 mg). LCMS: M+1=518.3, Rt=0.64 min.

Biological Assay 1

The ability of the compounds of Formula (I), (II), (III), (IV), or Table 1 (Examples 1 to Example 268) to inhibit ATPase activity of Polθ theta (1-899) was determined using the assay described below.

Polθ Theta ATPase activity was determined by measuring the rate of ATP turn over in a NADH oxidation-coupled enzymatic assay. 10-point dilution series of compounds were used in a 384 well format for the inhibition assays. Polθ theta (1-899) (10 nM) in assay buffer (20 mM Tris HCl (pH 7.80), 80 mM KCl, 10 mM $MgCl_2$, 1 mM DTT, 0.01% BSA, 0.01% Tween, 5% glycerol) was transferred to the test wells (20 μL), except the low control wells (20 μL of assay buffer was added to the low control wells). The plate was then incubated at room temperature for 15 min. An equal volume (20 μL) of 100 μM ATP, 300 nM $dT_{50}$ (single-stranded DNA (ssDNA) containing 50 thymine bases), 300 μM NADH, 6 mM PEP, 10 U/mL lactate dehydrogenase and U/mL pyruvate kinase in assay buffer was added to all the test wells. The plate was then centrifuged at 1000 rpm for 1 min. The reaction was monitored for 30 min by measuring absorbance (λ=340 nm) in a Tecan Spark multimode plate reader every minute. The high control (DMSO with enzyme) with low absorbance intensity represents no inhibition of ATPase reaction while the low control (DMSO with buffer) with high absorbance intensity represents full inhibition of ATPase activity. Slope of the reaction progress curves were used to calculate the rate of ATP hydrolysis. The rates were used to determine the percent inhibition using a four-parameter inhibition model to generate $IC_{50}$, Hill slope and max inhibition.

Biological Assay 2

The ability of the compounds (Example 269 to Example 271) of described herein to inhibit ATPase activity of Polθ theta (1-899) was determined using the assay described below.

Polθ Theta ATPase activity was determined by measuring the rate of ATP turn over in a NADH oxidation-coupled enzymatic assay. 11-point dilution series of compounds were used in a 384 well format for the inhibition assays. Polθ theta (1-899) (5 nM) in assay buffer (20 mM Tris HCl (pH 7.80), 80 mM KCl, 10 mM $MgCl_2$, 1 mM DTT, 0.01% BSA, 0.01% Tween, 5% glycerol) was transferred to the test wells (20 μL), except the low control wells (20 μL of assay buffer was added to the low control wells). The plate was then incubated at room temperature for 15 min. An equal volume (20 μL) of 100 μM ATP, 300 nM $dT_{50}$ (single-stranded DNA (ssDNA) containing 50 thymine bases), 300 μM NADH, 6 mM PEP, 10 U/mL lactate dehydrogenase and U/mL pyruvate kinase in assay buffer was added to all the test wells. The plate was then centrifuged at 1000 rpm for 1 min. The reaction was monitored for 120 min by measuring absorbance (λ=340 nm) in a PHERAstar FSX multimode plate reader every 3 minute. The high control (DMSO with enzyme) with low absorbance intensity represents no inhibition of ATPase reaction while the low control (DMSO with buffer) with high absorbance intensity represents full inhibition of ATPase activity. Slope of the reaction progress curves were used to calculate the rate of ATP hydrolysis. The rates were used to determine the percent inhibition using a four-parameter inhibition model to generate $IC_{50}$, Hill slope and max inhibition.

The $IC_{50}$ of the compounds in Table 1 above are disclosed in Table 2 below

| IC50: 10 uM ≥ (+) > 1 uM; 1 uM ≥ (++) > 500 nM; 500 nM ≥ (+++) > 200 nM; 200 nM ≥ (++++) | | | |
|---|---|---|---|
| Cpd # | ATPase NADH coupling:Standard Screening:hPolQ IC50 | Cpd # | ATPase NADH coupling:Standard Screening:hPolQ IC50 |
| 1 | +++ | 137 | ++++ |
| 2 | +++ | 138 | ++++ |
| 3 | ++++ | 139 | ++++ |
| 4 | ++++ | 140 | ++++ |
| 5 | ++++ | 141 | ++++ |
| 6 | ++++ | 142 | ++++ |
| 7 | ++++ | 143 | ++++ |
| 8 | ++++ | 144 | ++++ |
| 9 | + | 145 | ++++ |
| 10 | ++ | 146 | ++++ |
| 11 | ++++ | 147 | ++++ |
| 12 | + | 148 | ++++ |
| 13 | ++++ | 149 | ++++ |
| 14 | ++++ | 150 | ++++ |
| 15 | ++++ | 151 | ++++ |
| 16 | ++++ | 152 | ++++ |
| 17 | ++++ | 153 | ++++ |
| 18 | + | 154 | ++++ |
| 19 | + | 155 | ++++ |
| 20 | ++++ | 156 | ++++ |
| 21 | ++++ | 157 | >10 uM |
| 22 | ++++ | 158 | ++++ |
| 23 | ++++ | 159 | ++++ |
| 24 | ++++ | 160 | ++++ |
| 25 | ++++ | 161 | ++++ |
| 26 | +++ | 162 | ++++ |
| 27 | +++ | 163 | ++++ |
| 28 | ++ | 164 | ++++ |
| 29 | + | 165 | ++++ |
| 30 | ++ | 166 | ++++ |
| 31 | +++ | 167 | ++++ |
| 32 | ++++ | 168 | ++++ |
| 33 | ++++ | 169 | ++++ |
| 34 | ++++ | 170 | ++++ |
| 35 | ++++ | 171 | ++++ |
| 36 | ++++ | 172 | ++++ |
| 37 | ++++ | 173 | + |
| 38 | ++++ | 174 | ++++ |
| 39 | ++++ | 175 | ++++ |
| 40 | ++++ | 176 | +++ |
| 41 | ++++ | 177 | ++++ |
| 42 | +++ | 178 | +++ |
| 43 | ++++ | 179 | ++++ |
| 44 | ++++ | 180 | ++++ |
| 45 | ++++ | 181 | ++++ |
| 46 | ++++ | 182 | ++++ |
| 47 | ++++ | 183 | ++++ |
| 48 | ++++ | 184 | ++++ |
| 49 | ++++ | 185 | ++++ |
| 50 | ++++ | 186 | ++++ |
| 51 | ++++ | 187 | ++++ |
| 52 | ++++ | 188 | ++++ |
| 53 | ++++ | 189 | ++++ |
| 54 | ++++ | 190 | ++++ |
| 55 | ++++ | 191 | ++++ |
| 56 | ++++ | 192 | + |
| 57 | ++++ | 193 | ++++ |
| 58 | ++++ | 194 | + |
| 59 | ++++ | 195 | ++++ |
| 60 | ++++ | 196 | ++++ |
| 61 | ++++ | 197 | ++++ |
| 62 | +++ | 198 | ++++ |
| 63 | ++++ | 199 | + |
| 64 | ++++ | 200 | +++ |
| 65 | ++++ | 201 | ++++ |
| 66 | ++++ | 202 | ++++ |
| 67 | ++++ | 203 | ++++ |
| 68 | ++++ | 204 | ++++ |
| 69 | ++++ | 205 | ++++ |
| 70 | ++++ | 206 | ++++ |
| 71 | ++ | 207 | ++++ |
| 72 | ++++ | 208 | ++++ |
| 73 | ++++ | 209 | ++++ |

-continued

| IC50: 10 uM ≥ (+) > 1 uM; 1 uM ≥ (++) > 500 nM; 500 nM ≥ (+++) > 200 nM; 200 nM ≥ (++++) | | | |
|---|---|---|---|
| Cpd # | ATPase NADH coupling:Standard Screening:hPolQ IC50 | Cpd # | ATPase NADH coupling:Standard Screening:hPolQ IC50 |
| 74 | ++++ | 210 | ++++ |
| 75 | ++++ | 211 | ++++ |
| 76 | ++++ | 212 | ++++ |
| 77 | ++++ | 213 | ++++ |
| 78 | ++++ | 214 | ++++ |
| 79 | ++++ | 215 | ++++ |
| 80 | ++++ | 216 | ++++ |
| 81 | ++++ | 217 | ++++ |
| 82 | ++++ | 218 | ++++ |
| 83 | ++++ | 219 | ++++ |
| 84 | ++++ | 220 | ++++ |
| 85 | ++++ | 221 | ++++ |
| 86 | ++++ | 222 | ++++ |
| 87 | ++++ | 223 | ++++ |
| 88 | ++++ | 224 | ++++ |
| 89 | +++ | 225 | ++++ |
| 90 | ++++ | 226 | ++++ |
| 91 | ++++ | 227 | ++++ |
| 92 | ++++ | 228 | ++++ |
| 93 | ++++ | 229 | ++++ |
| 94 | ++++ | 230 | ++++ |
| 95 | ++++ | 231 | ++++ |
| 96 | ++++ | 232 | ++++ |
| 97 | ++++ | 233 | ++++ |
| 98 | ++++ | 234 | ++++ |
| 99 | ++++ | 235 | ++++ |
| 100 | ++++ | 236 | ++++ |
| 101 | ++++ | 237 | ++++ |
| 102 | ++++ | 238 | ++++ |
| 103 | ++++ | 239 | ++++ |
| 104 | ++++ | 240 | ++++ |
| 105 | ++++ | 241 | ++++ |
| 106 | ++++ | 242 | ++++ |
| 107 | ++++ | 243 | ++++ |
| 108 | ++++ | 244 | ++++ |
| 109 | ++++ | 245 | ++++ |
| 110 | ++++ | 246 | ++++ |
| 111 | ++++ | 247 | ++++ |
| 112 | ++++ | 248 | ++++ |
| 113 | ++++ | 249 | ++++ |
| 114 | ++++ | 250 | ++++ |
| 115 | ++++ | 251 | ++++ |
| 116 | ++++ | 252 | ++++ |
| 117 | ++++ | 253 | ++++ |
| 118 | ++++ | 254 | ++++ |
| 119 | +++ | 255 | ++++ |
| 120 | +++ | 256 | ++++ |
| 121 | +++ | 257 | ++++ |
| 122 | ++++ | 258 | ++++ |
| 123 | ++++ | 259 | ++++ |
| 124 | ++++ | 260 | ++++ |
| 125 | ++++ | 261 | ++++ |
| 126 | ++++ | 262 | ++++ |
| 127 | ++++ | 263 | ++++ |
| 128 | ++++ | 264 | ++++ |
| 129 | ++++ | 265 | ++++ |
| 130 | ++++ | 266 | ++++ |
| 131 | ++++ | 267 | ++++ |
| 132 | ++++ | 268 | ++++ |
| 133 | ++++ | 269 | ++++ |
| 134 | ++++ | 270 | + |
| 135 | ++++ | 271 | ++++ |
| 136 | ++++ | 272 | Not tested |
| 273 | Not tested | | |

Particular embodiments of this invention are described herein, including the best mode known to the inventors for carrying out the invention. Upon reading the foregoing, description, variations of the disclosed embodiments may become apparent to individuals working in the art, and it is expected that those skilled artisans may employ such variations as appropriate. Accordingly, it is intended that the invention be practiced otherwise than as specifically described herein, and that the invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All patent applications, patents, and printed publications cited herein are incorporated herein by reference in the entireties, except for any definitions, subject matter disclaimers or disavowals, and except to the extent that the incorporated material is inconsistent with the express disclosure herein, in which case the language in this disclosure controls.

What is claimed is:

1. A compound selected from the group consisting of:

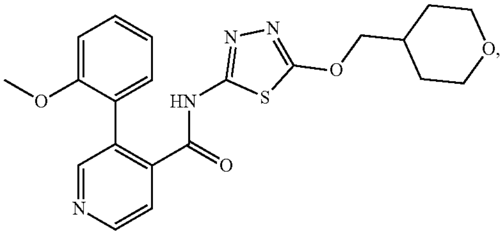
,

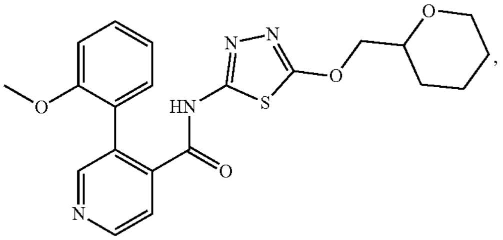
,

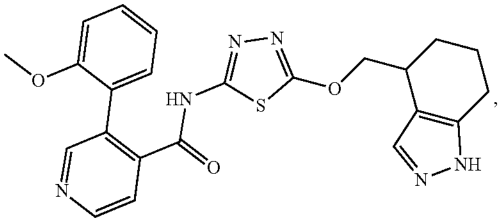
,

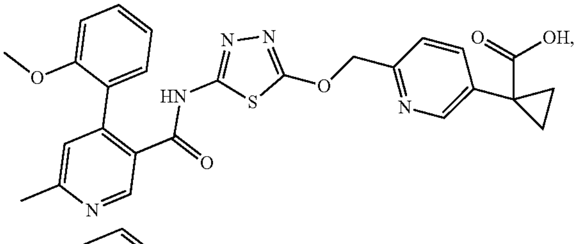
,

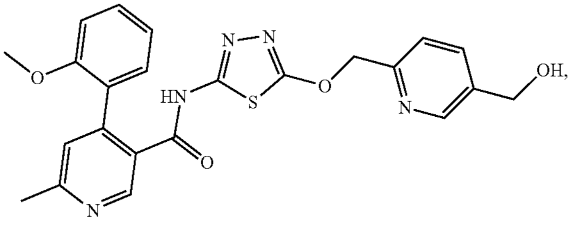
,

-continued

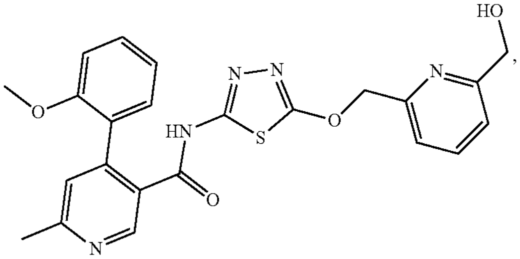
,

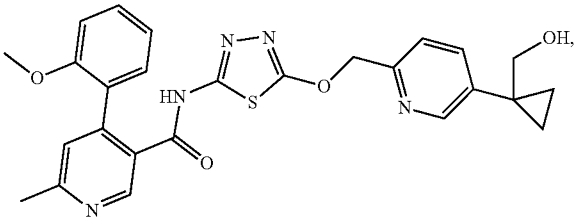
,

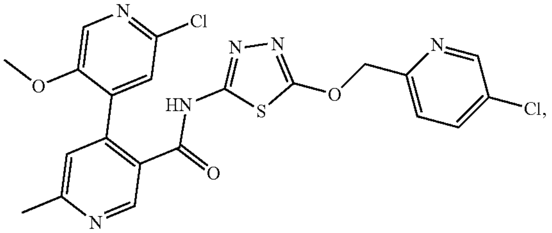
,

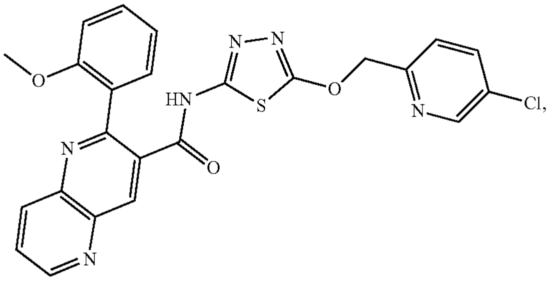
,

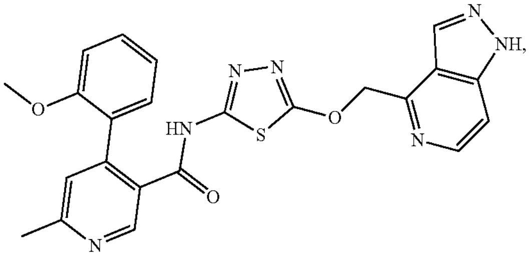
,

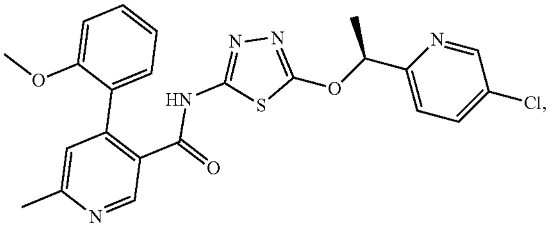
,

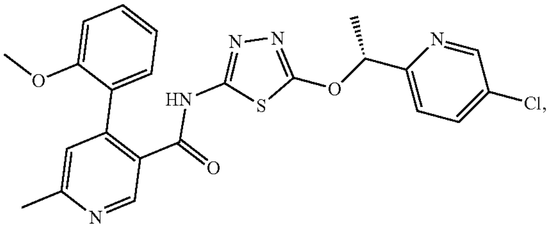
,

-continued
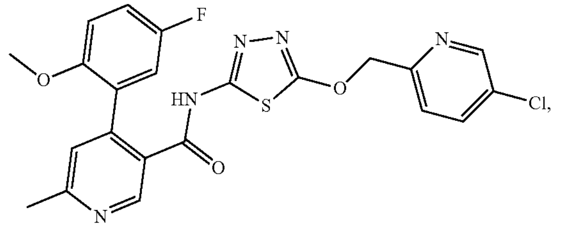
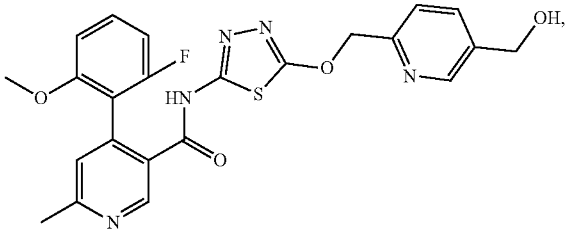
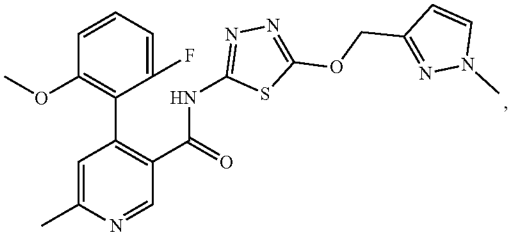
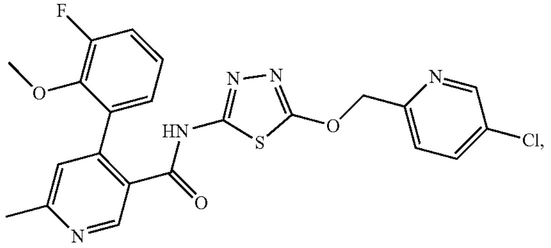
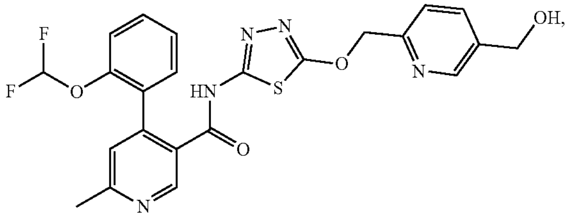
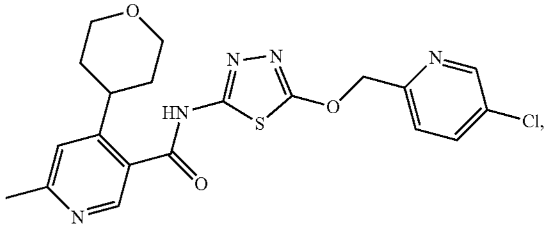
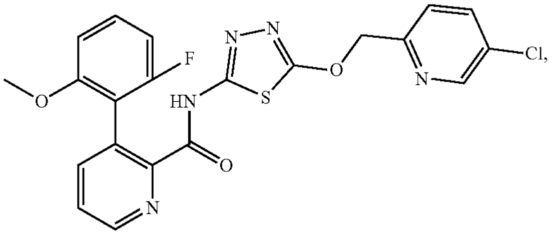
-continued
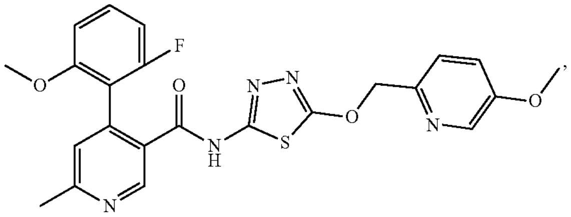
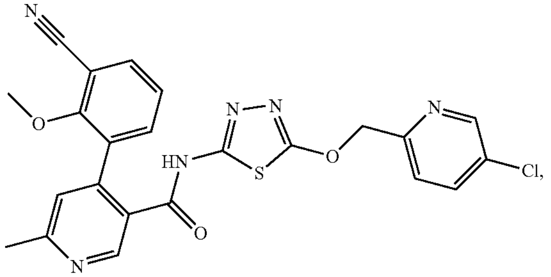
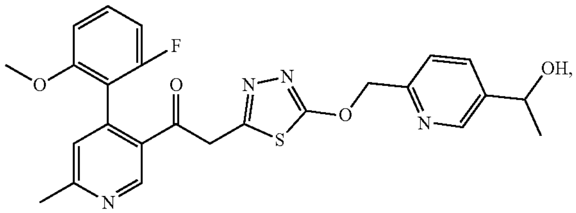
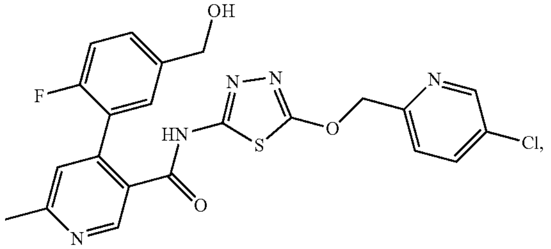
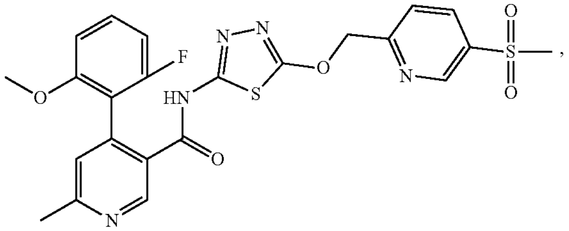
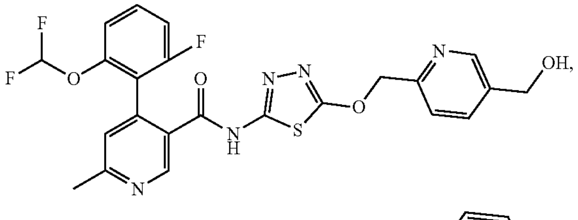
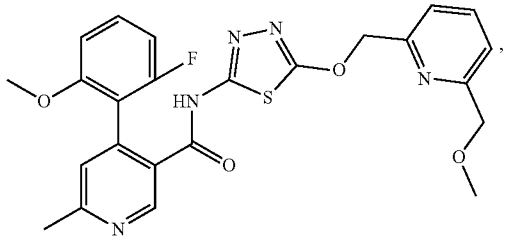

-continued
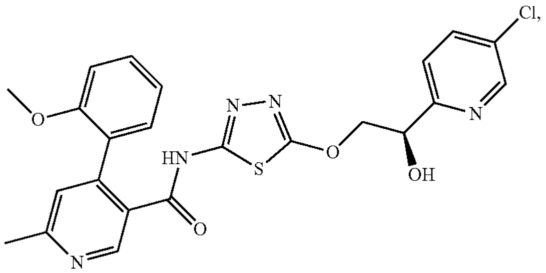
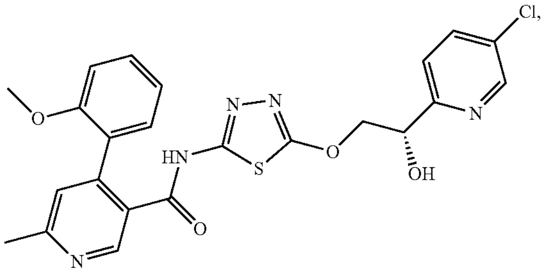
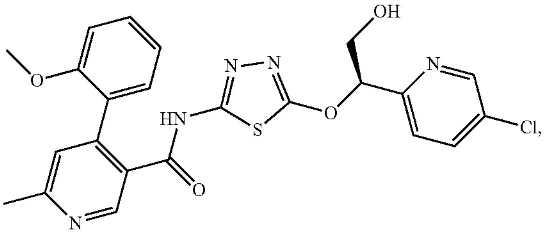
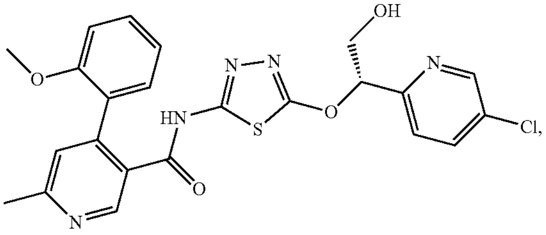
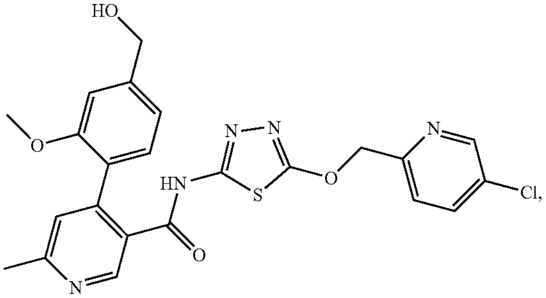
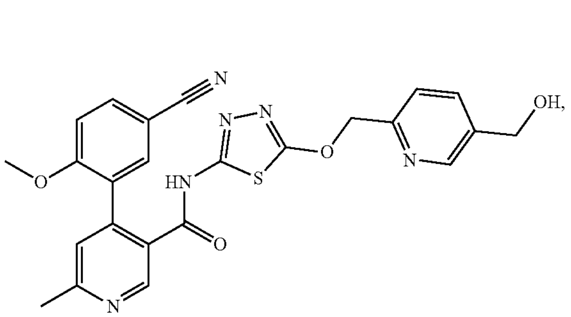
-continued
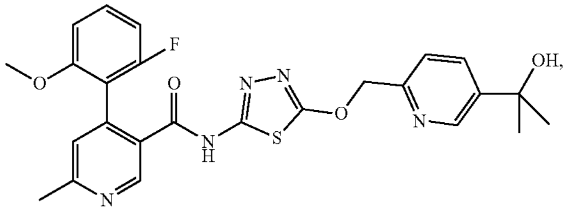
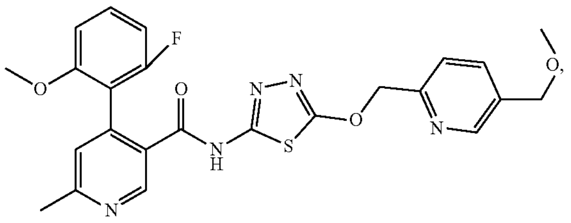
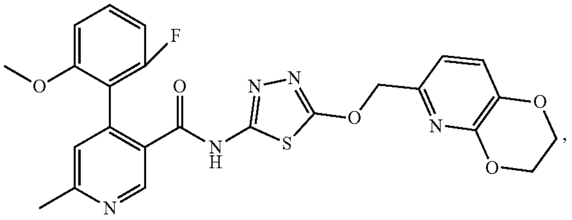
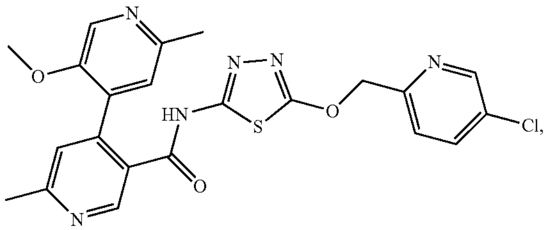
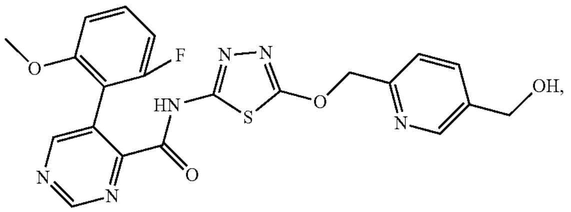
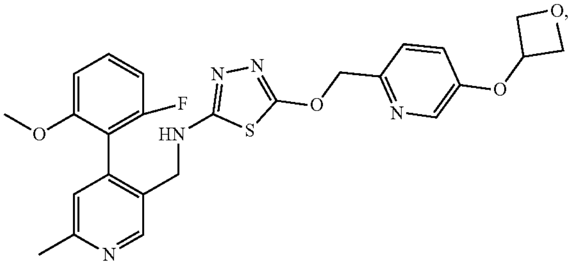
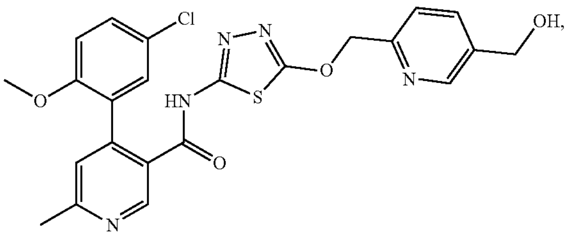

-continued
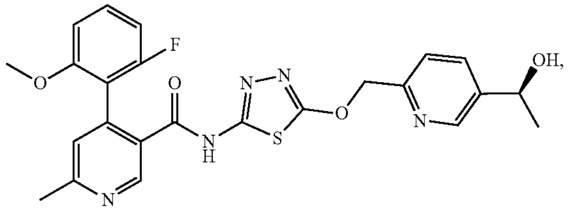
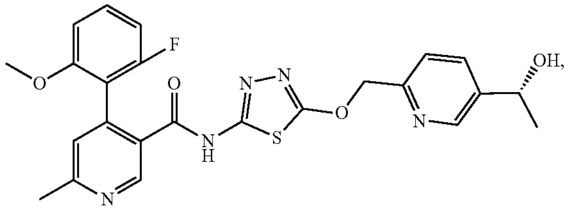
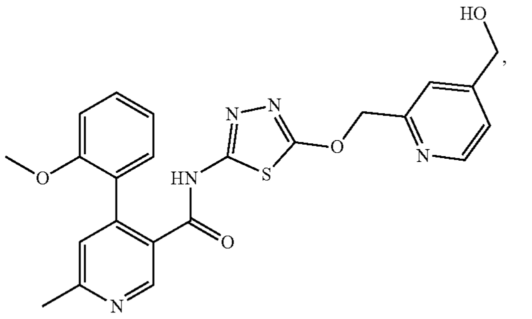
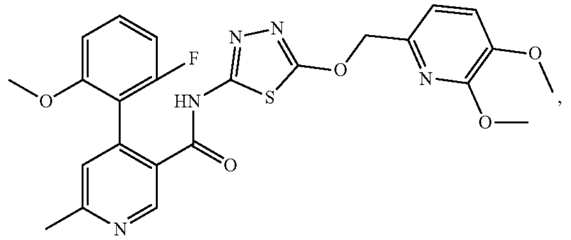
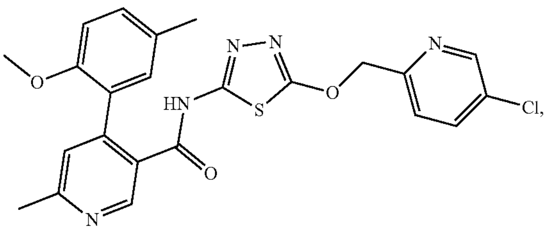
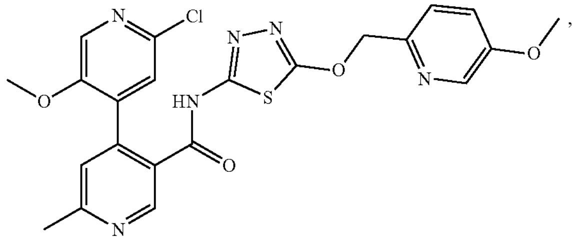
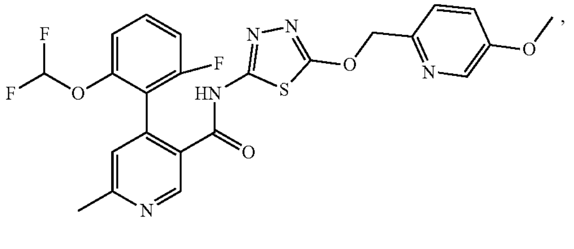
-continued
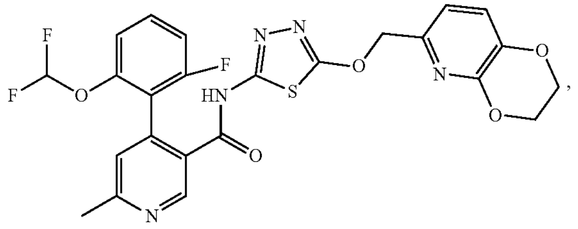
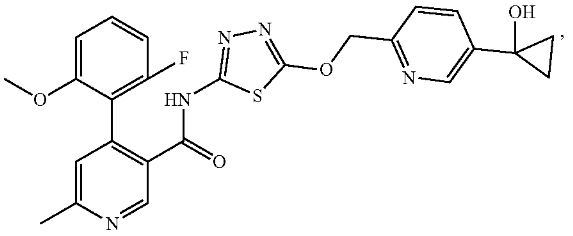
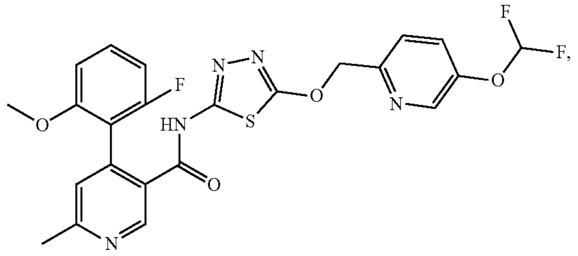
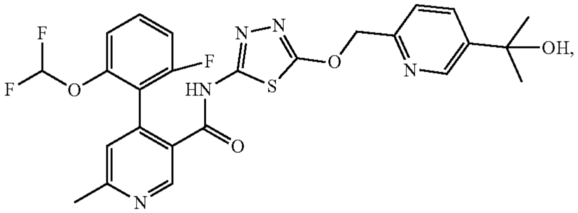
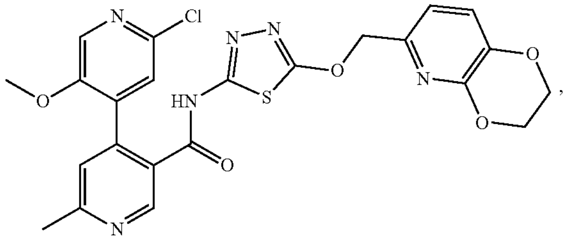
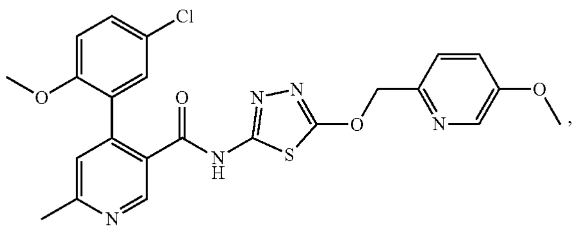
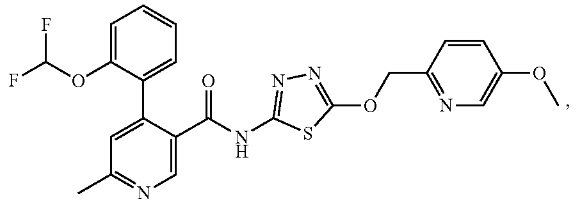

-continued
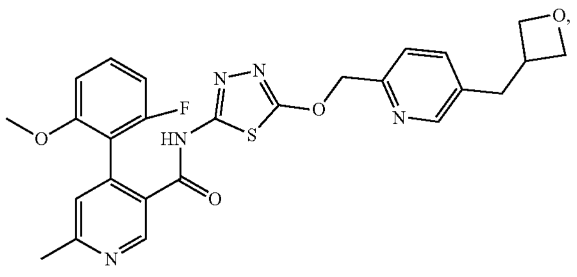
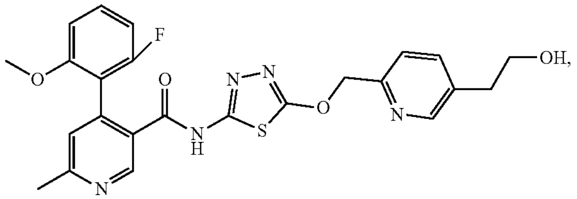
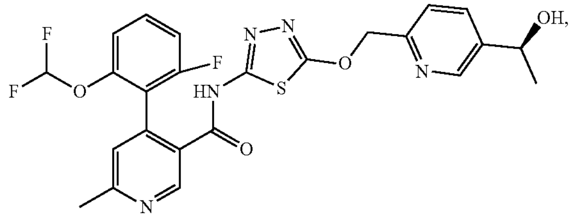
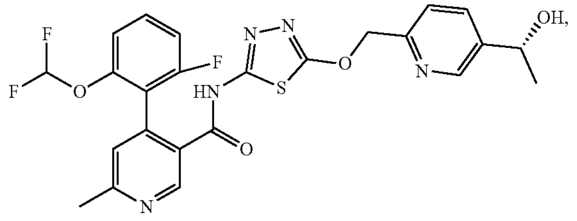
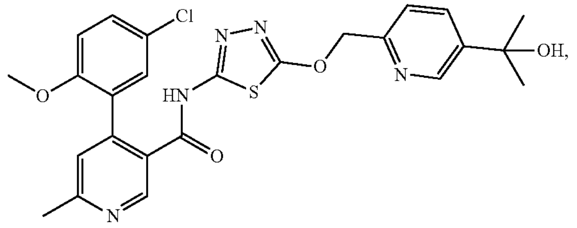
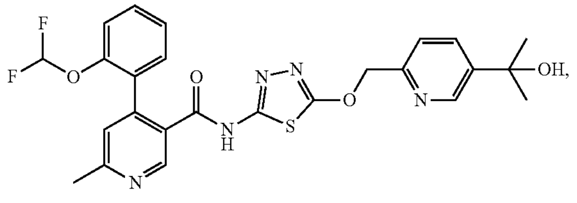
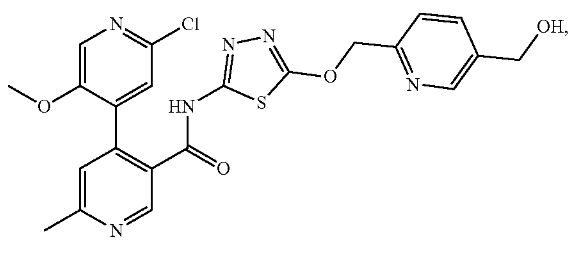
-continued
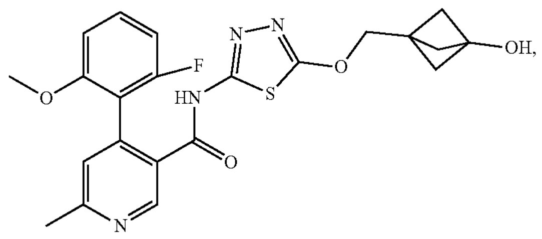
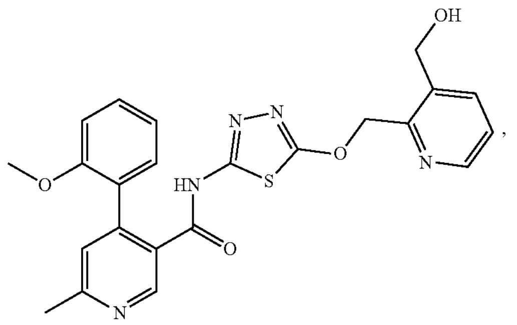
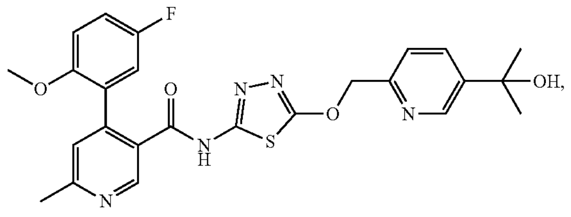
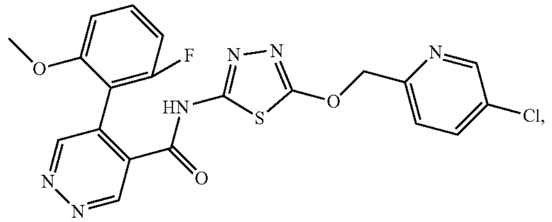
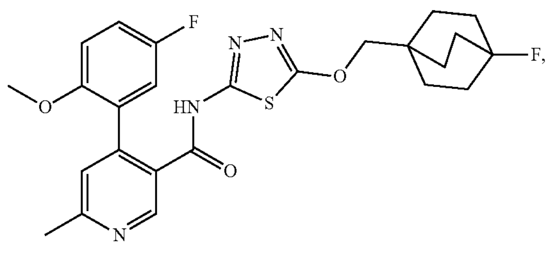
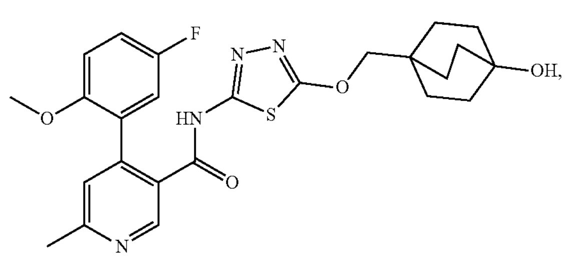

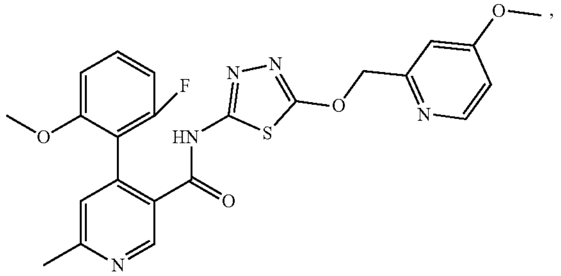
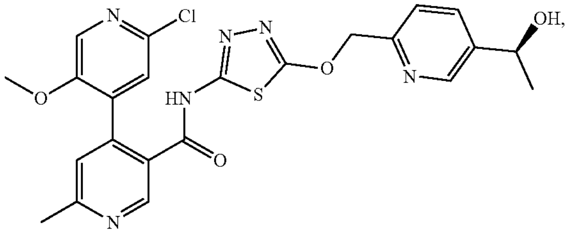
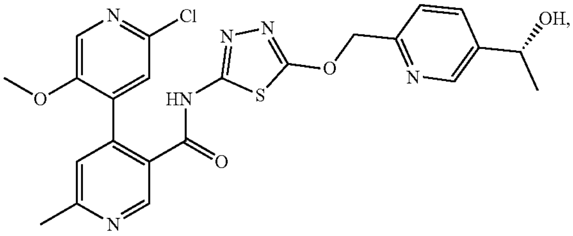
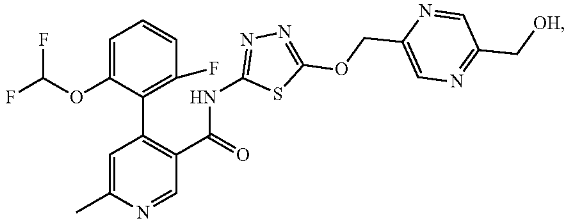
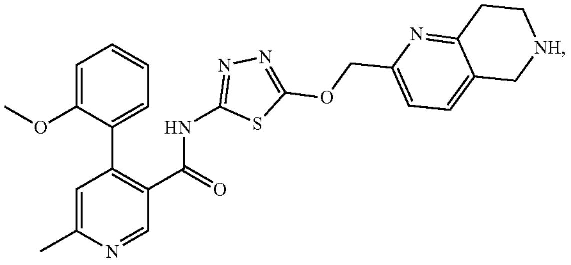
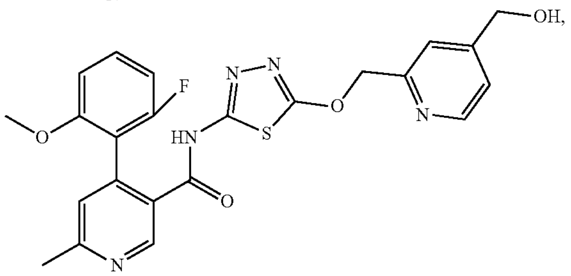
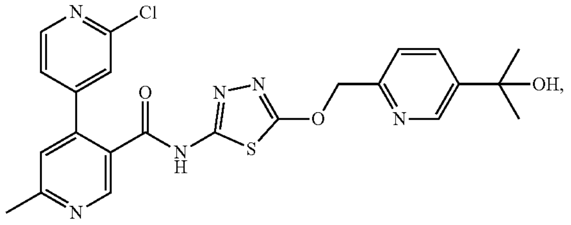
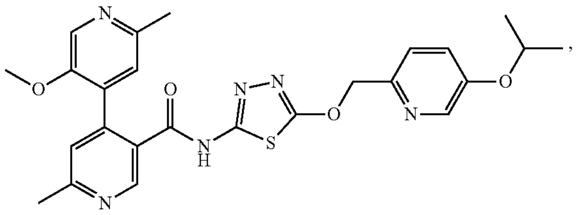
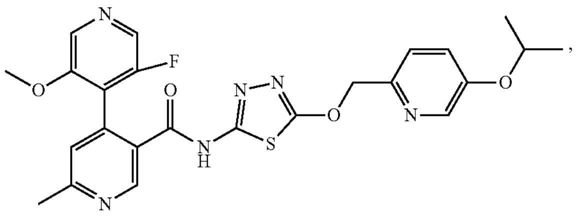
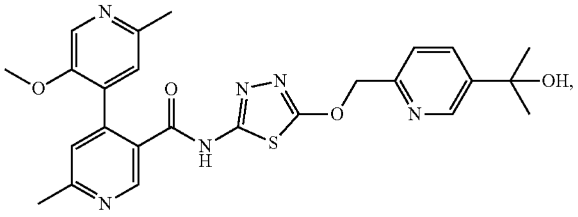
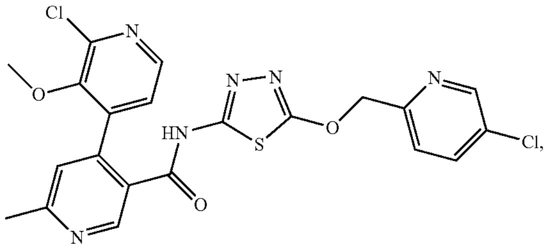
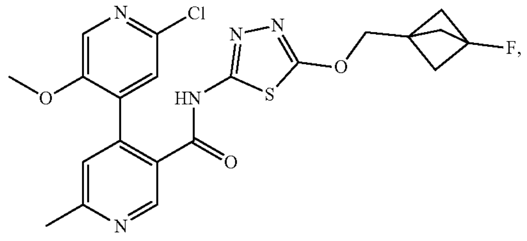
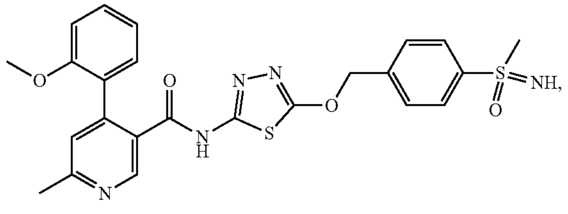
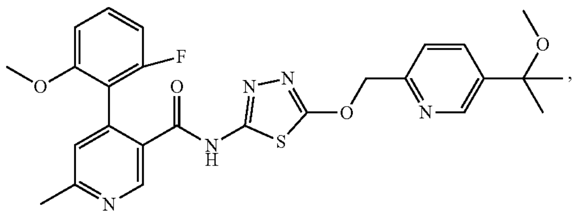

-continued
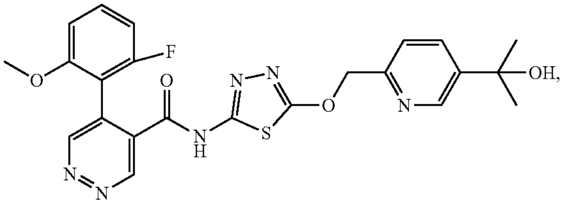
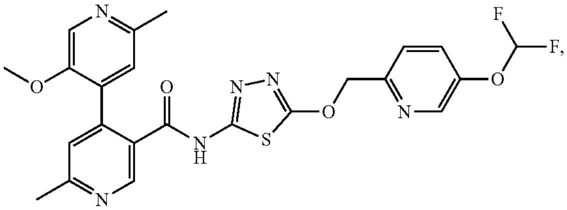
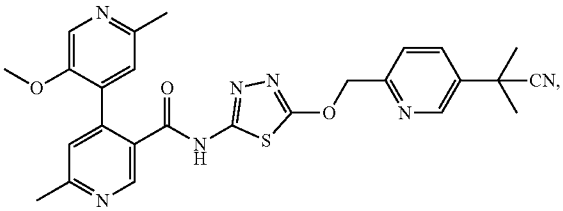
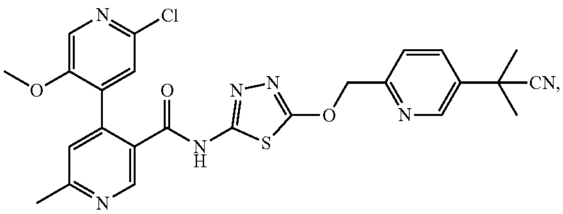
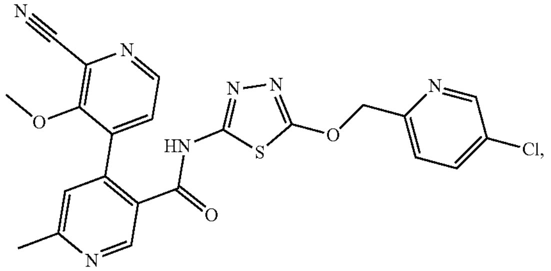
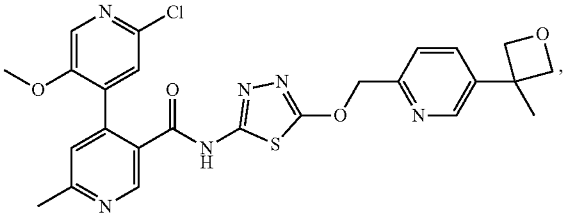
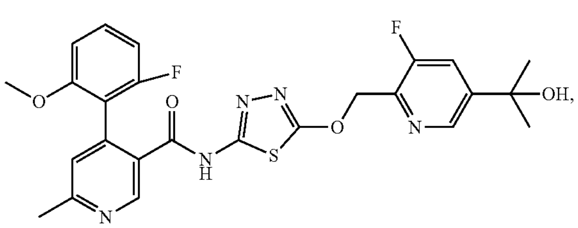
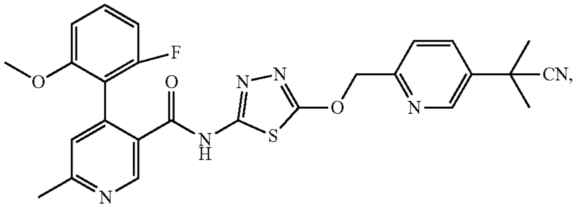
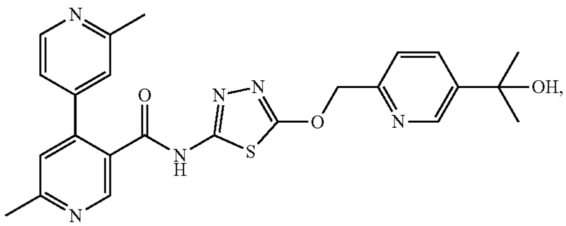
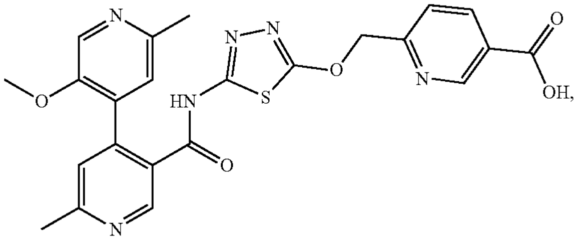
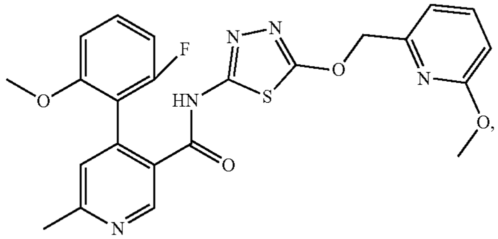
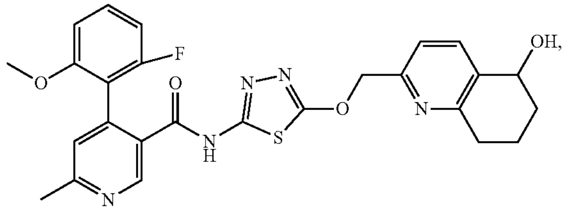
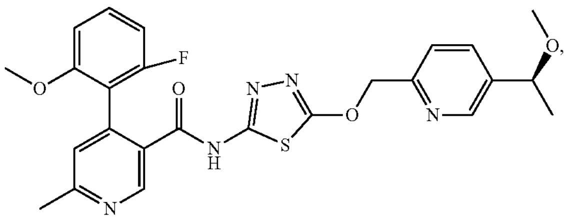
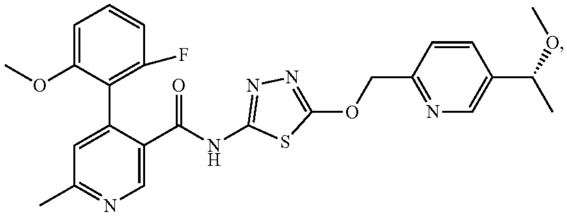

-continued
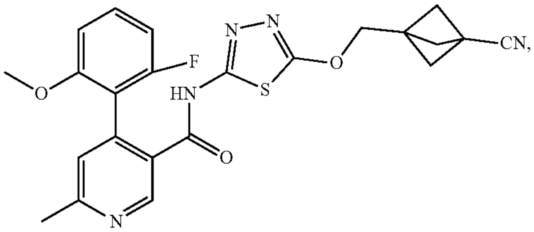
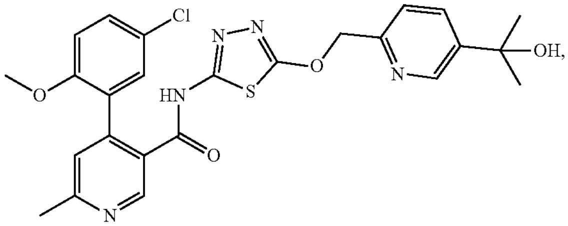
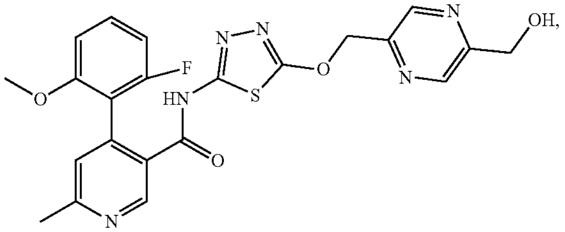
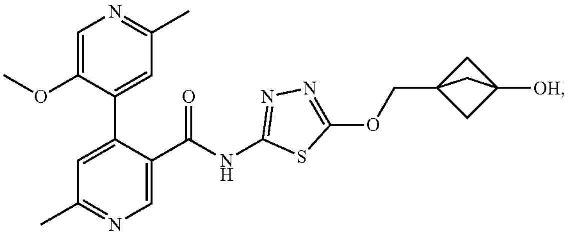
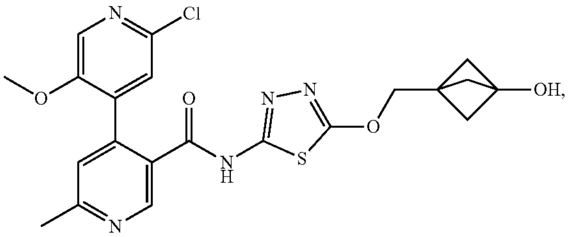
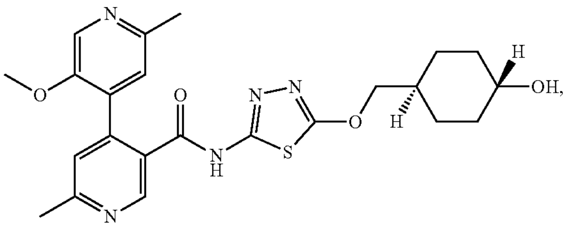
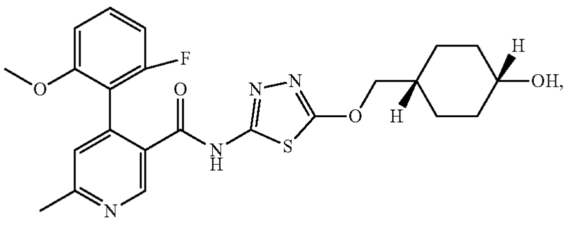
-continued
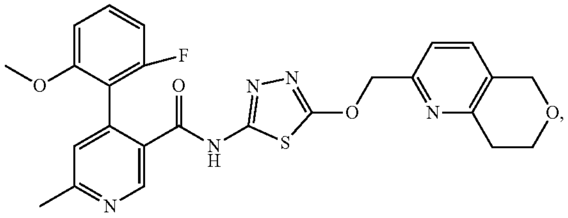
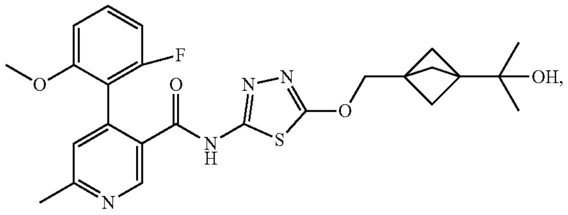
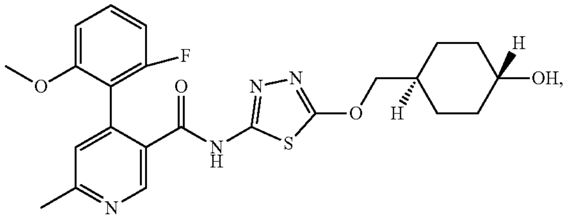
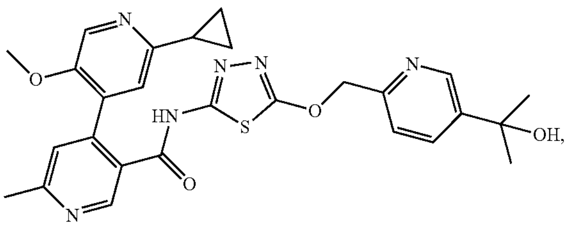
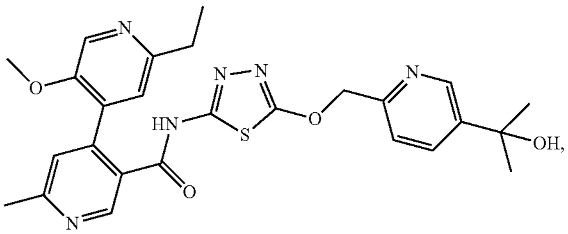
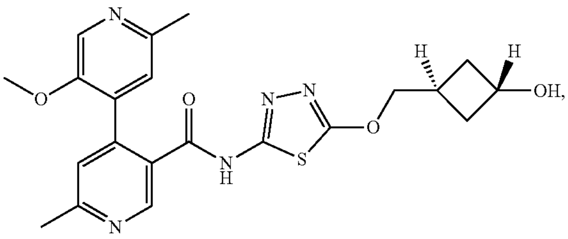
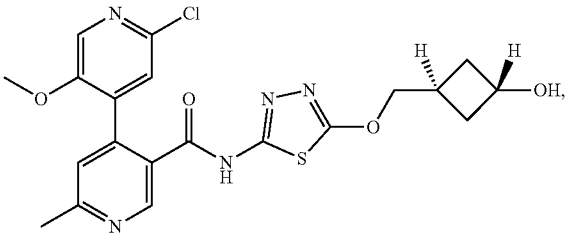

-continued
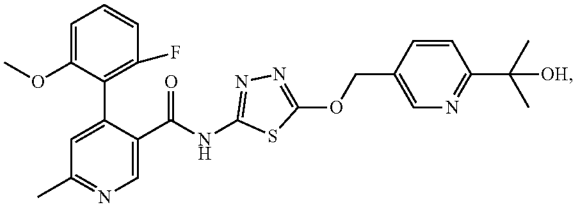
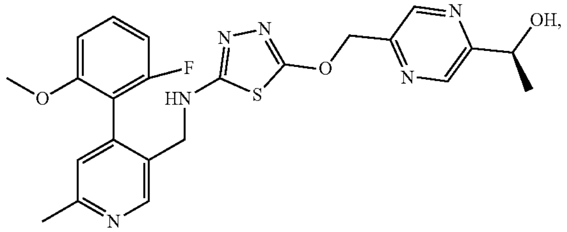
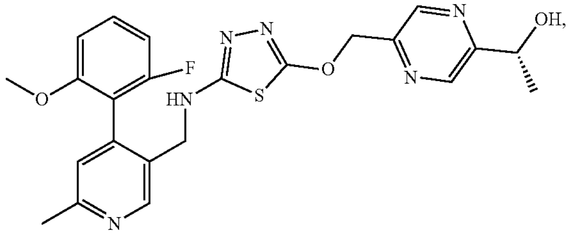
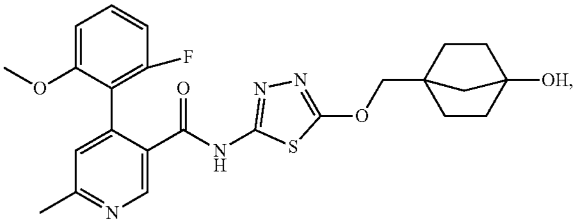
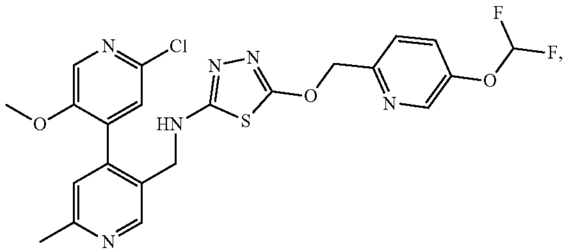
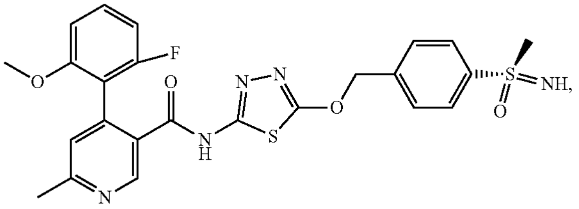
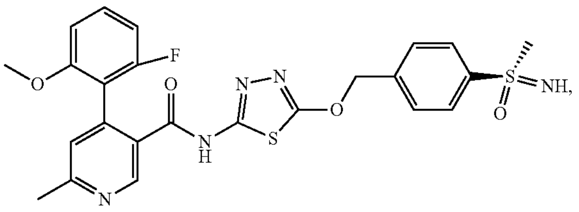
-continued
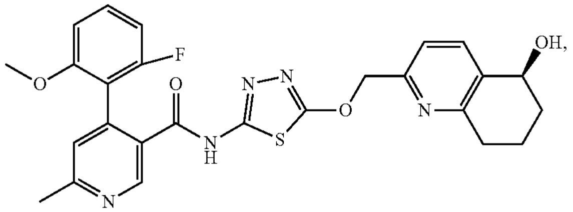
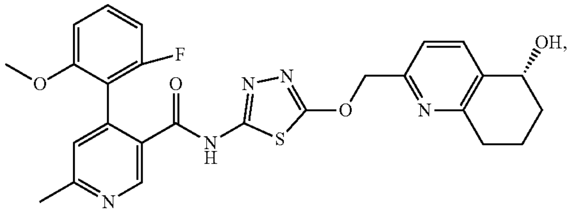
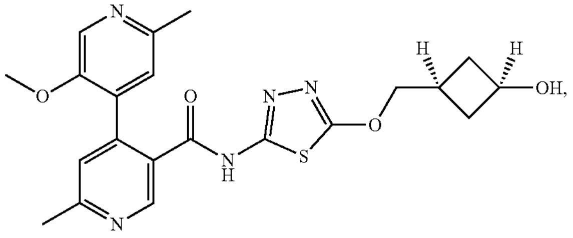
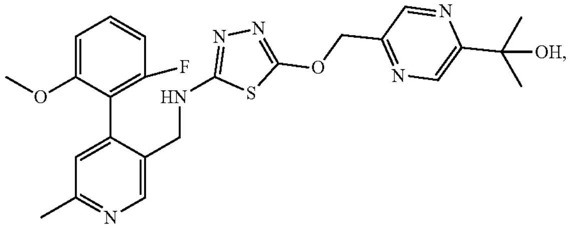
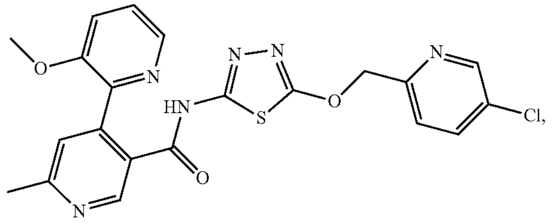
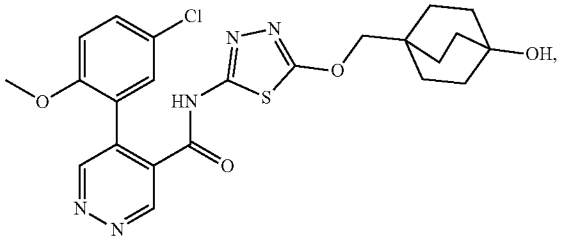
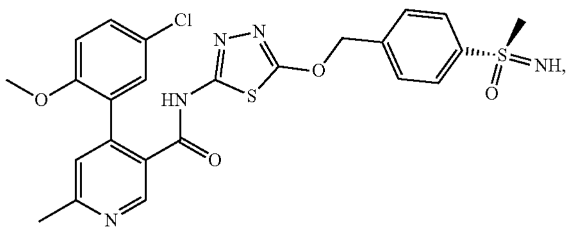

-continued
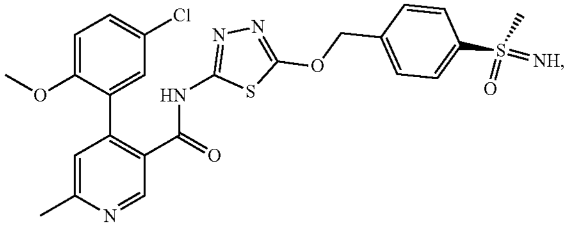
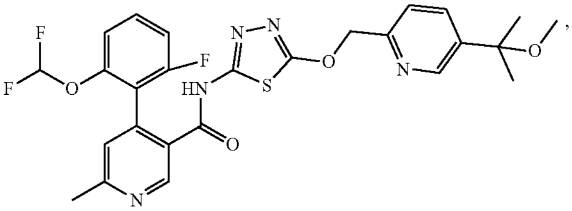
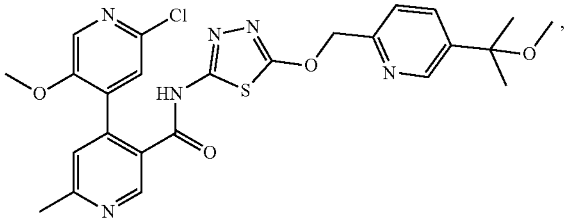
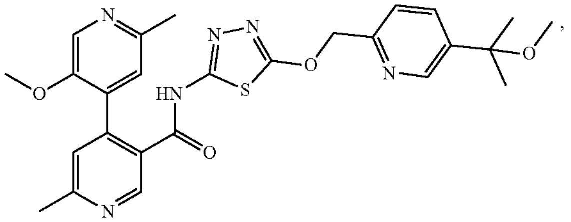
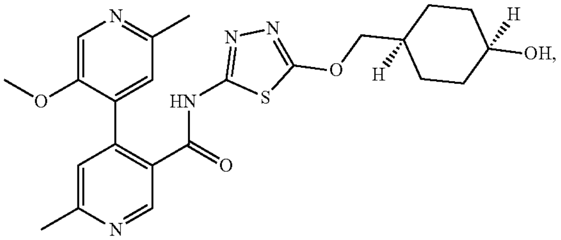
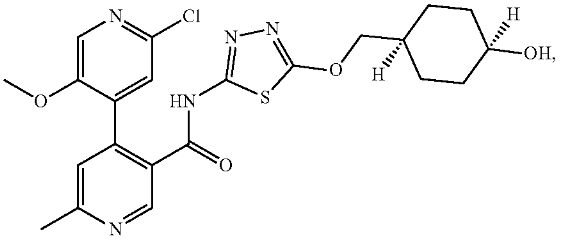
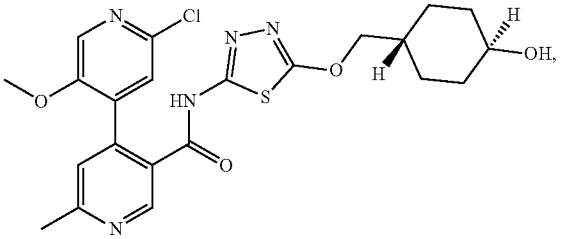
-continued
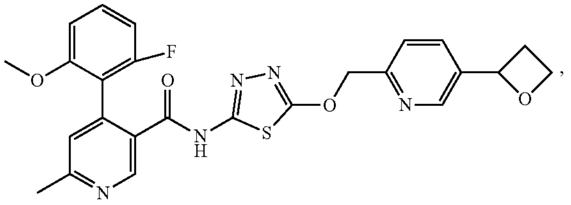
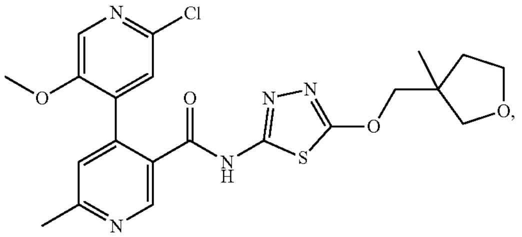
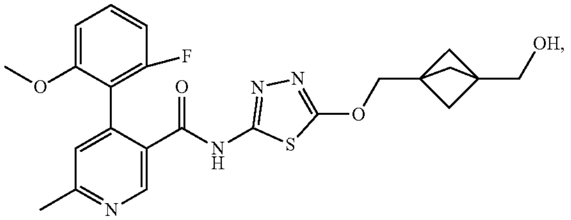
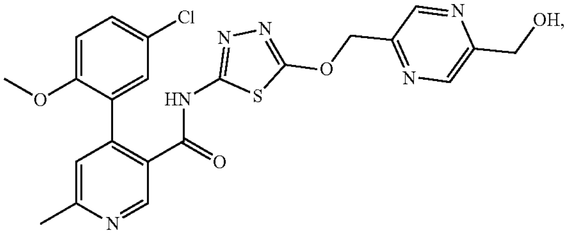
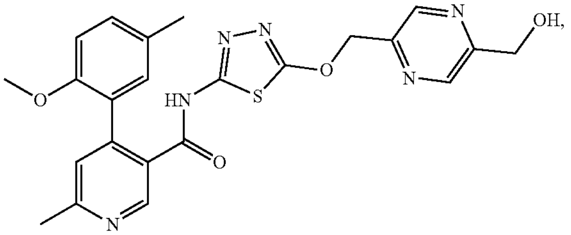
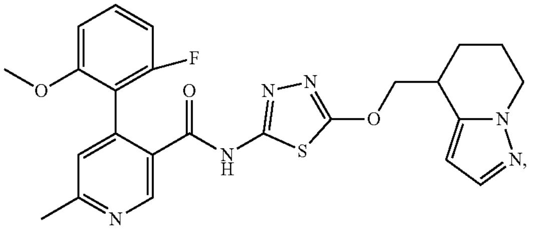
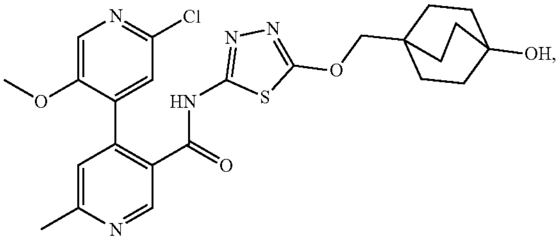

-continued
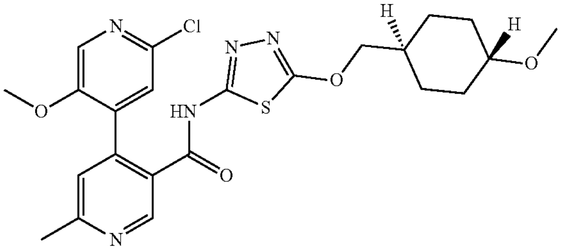
,
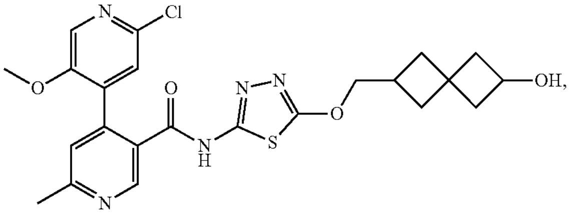
,
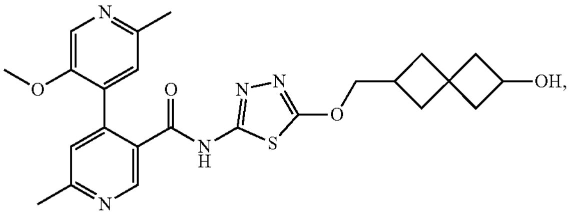
,
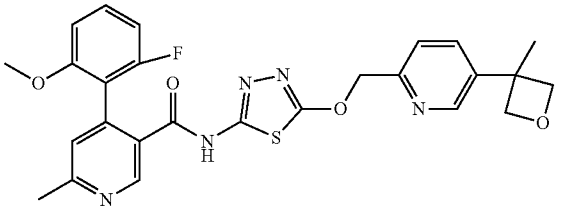
,
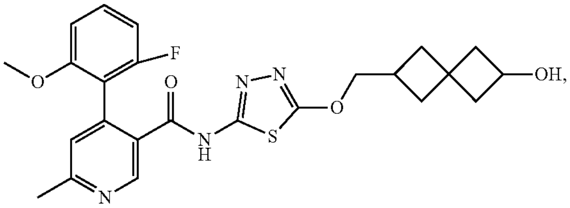
,
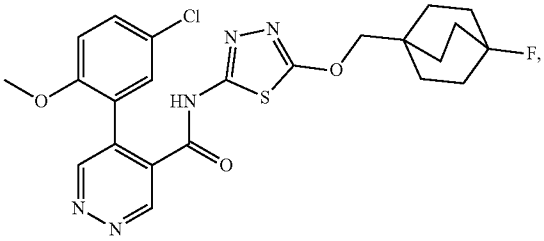
,
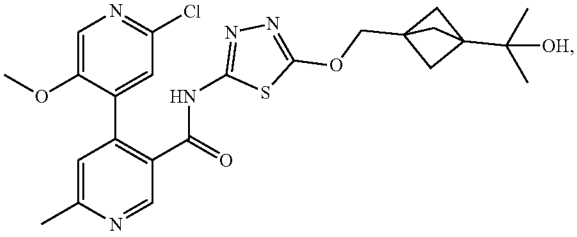
,
-continued
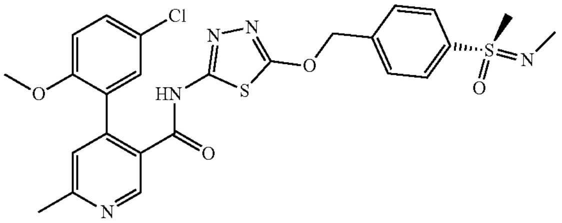
,
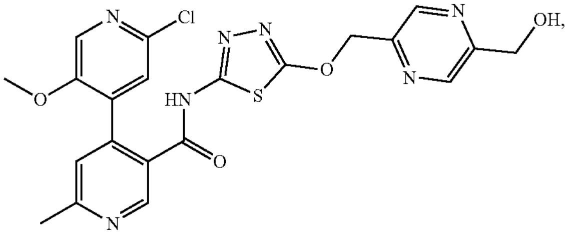
,
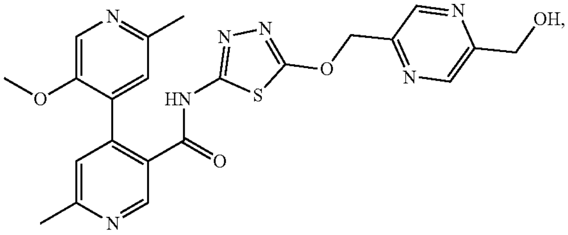
,
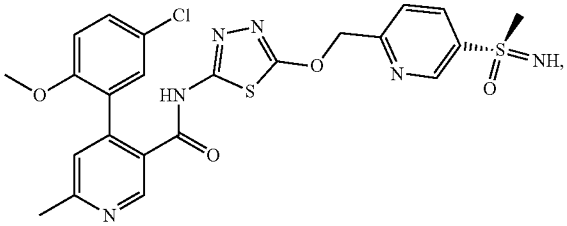
,
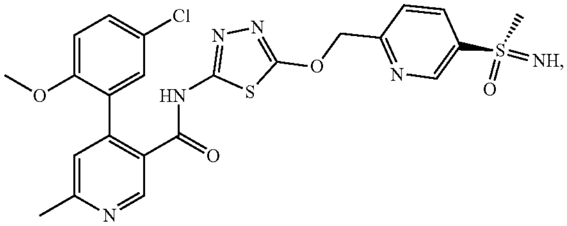
,
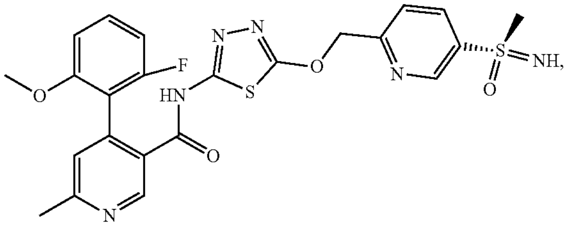
,
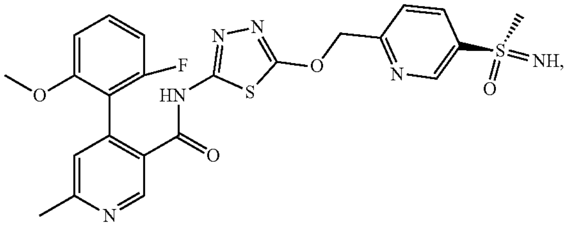
, -continued
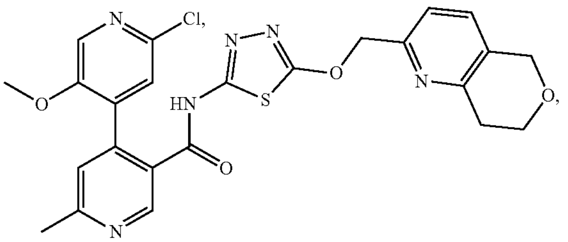
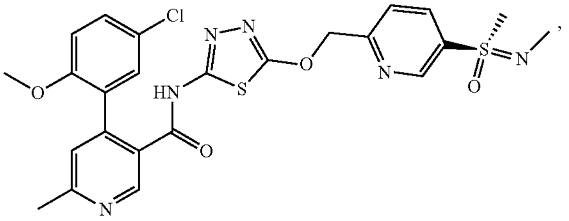
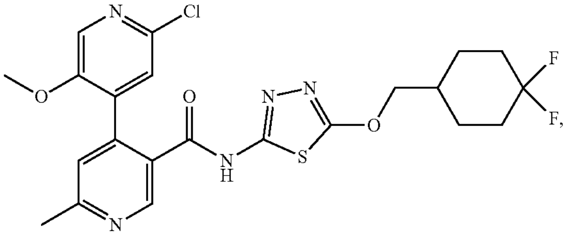
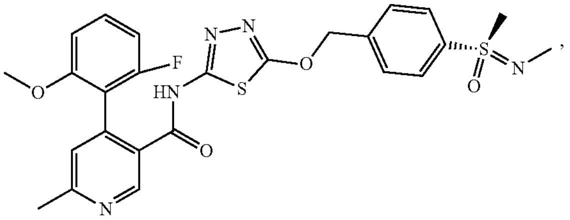
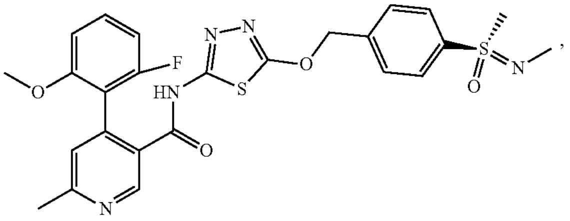
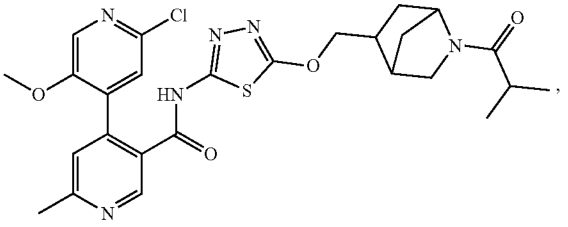
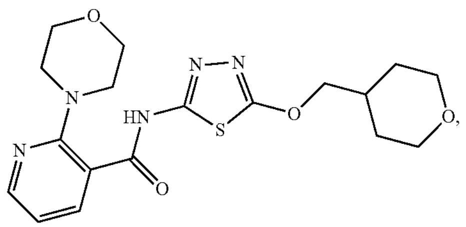
-continued
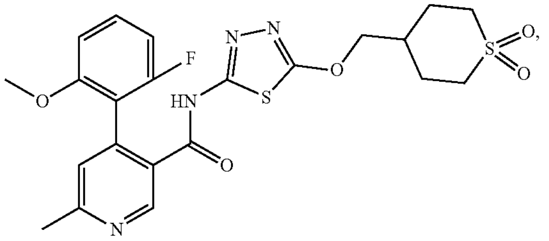
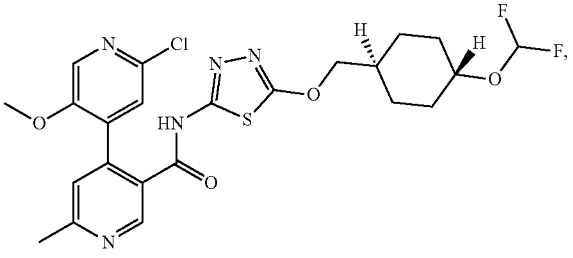
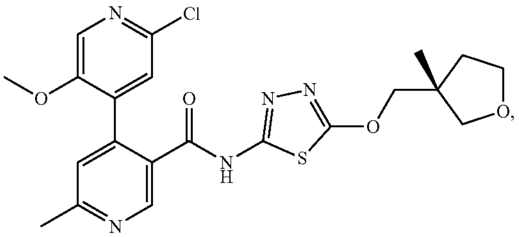
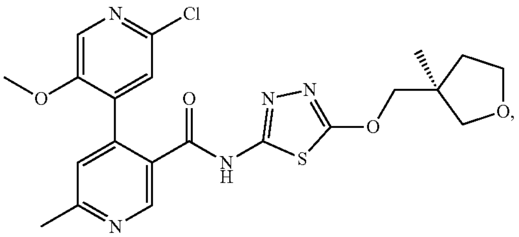
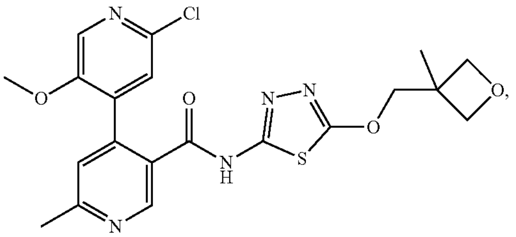
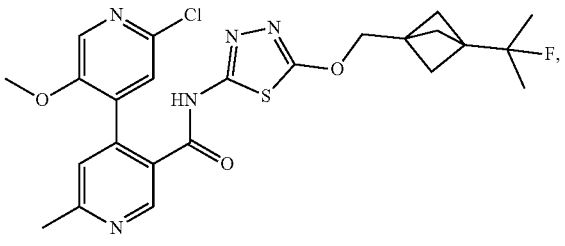
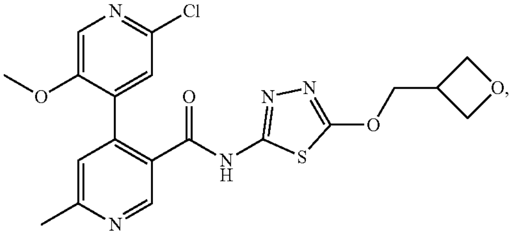

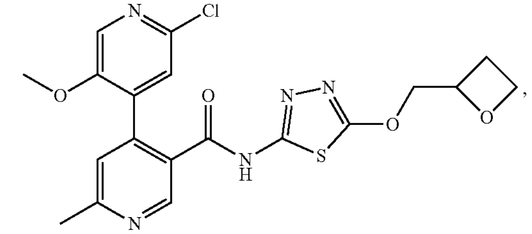,
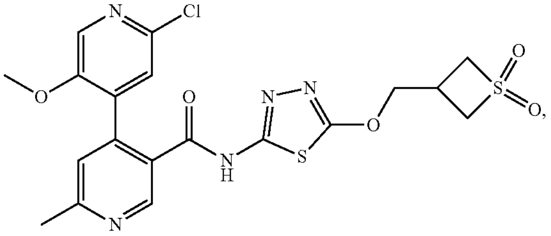,
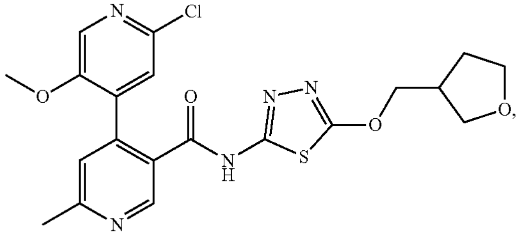,
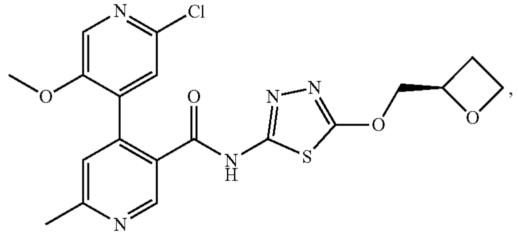,
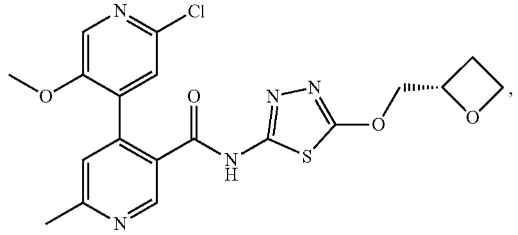,
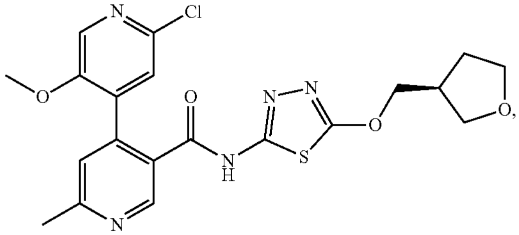,
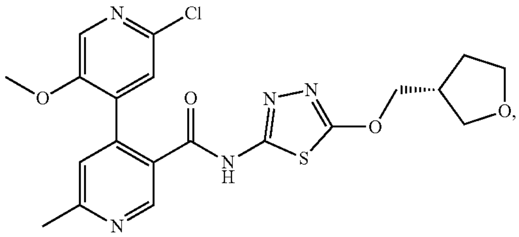,
-continued
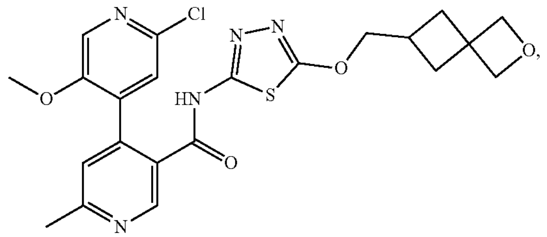,
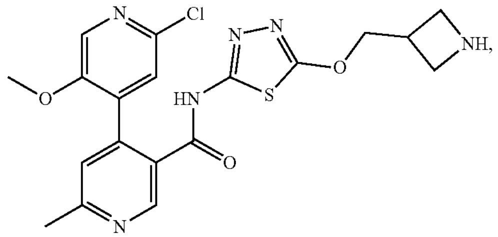,
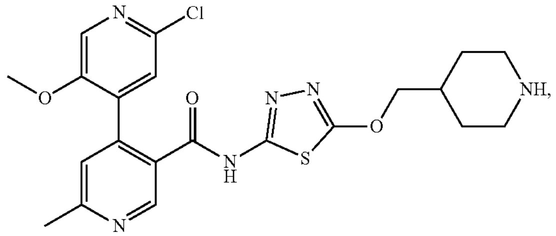,
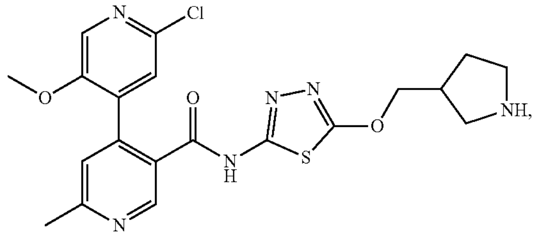,
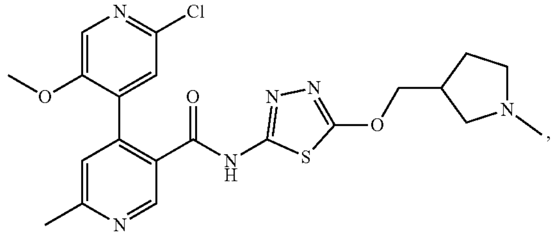,
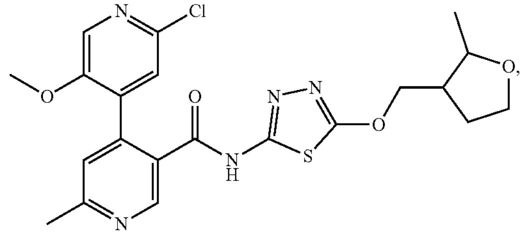,
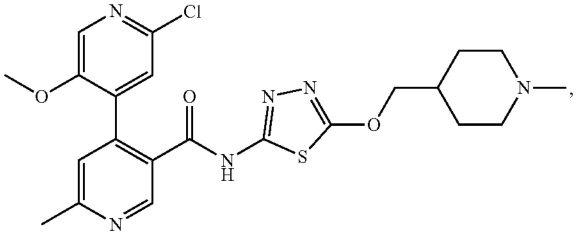, -continued
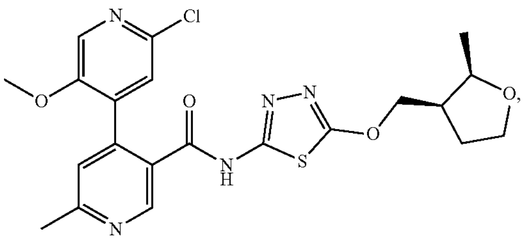,
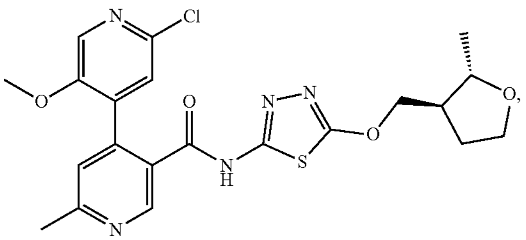,
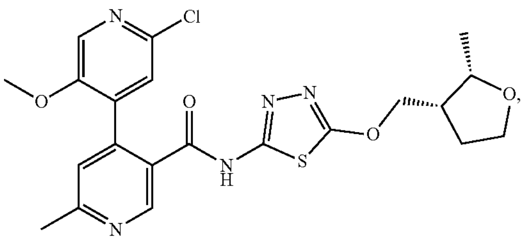,
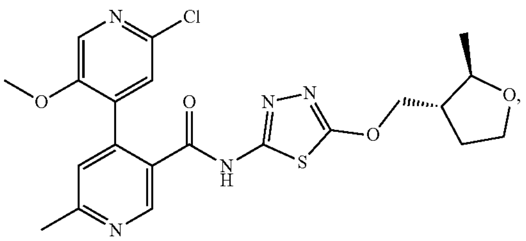,
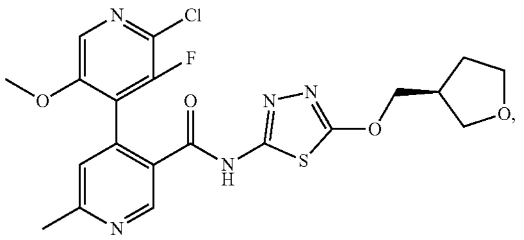,
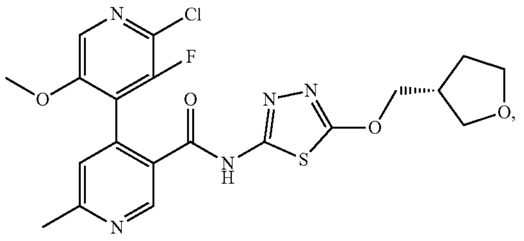,
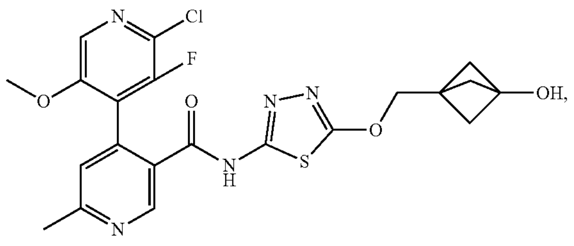,
-continued
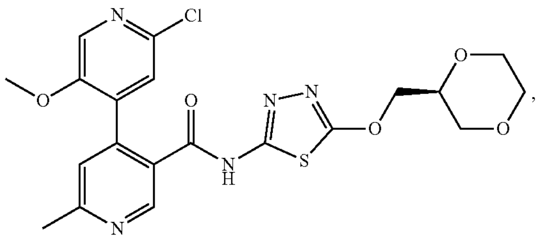,
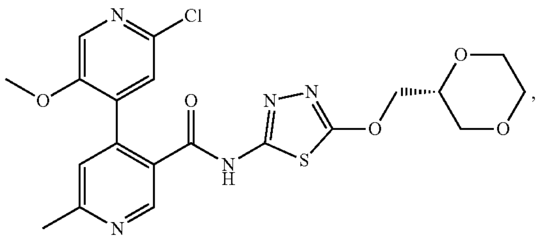,
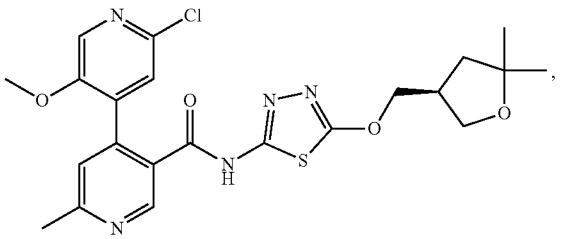,
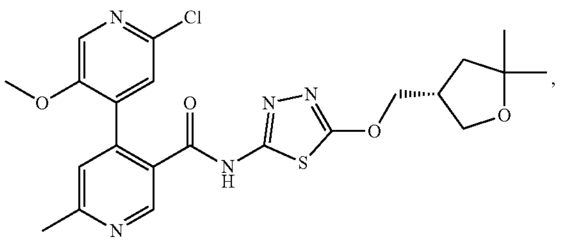,
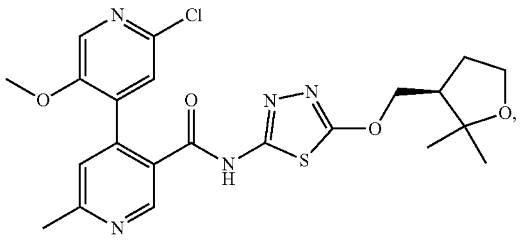,
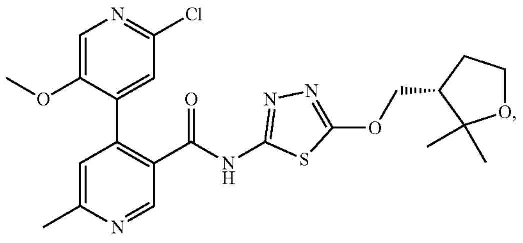,
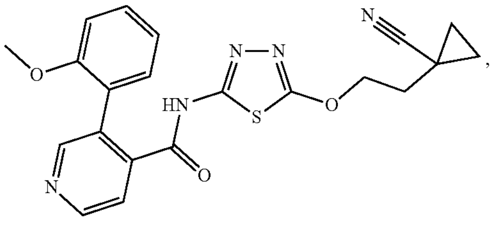, -continued
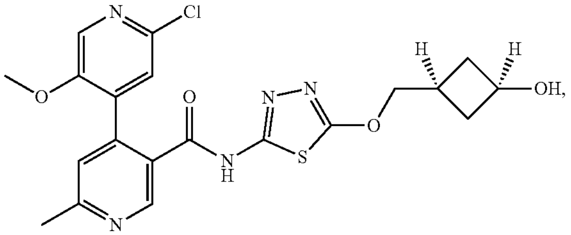
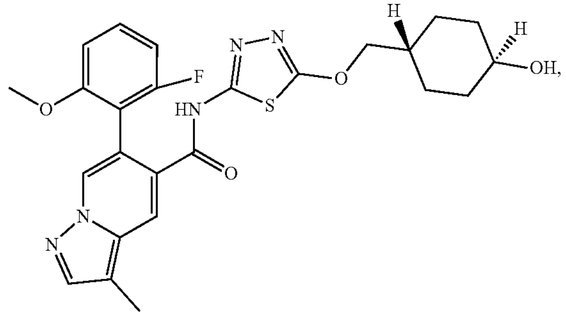
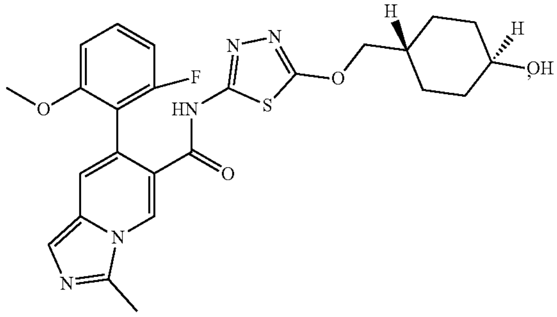
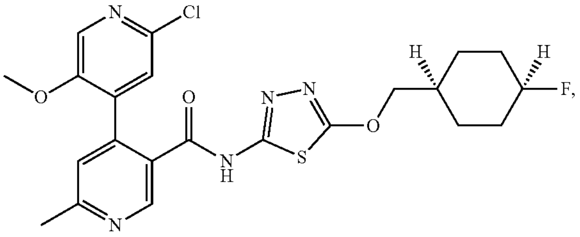
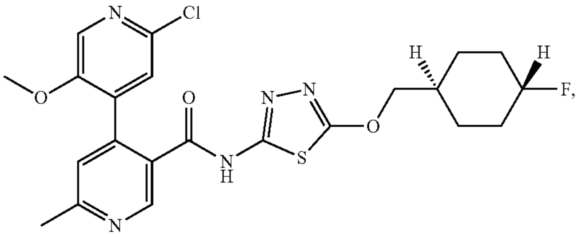
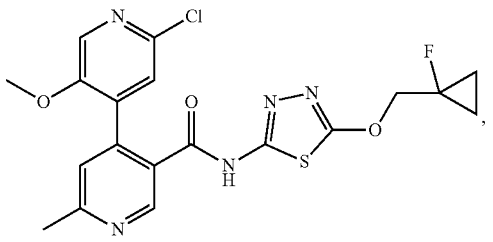
-continued
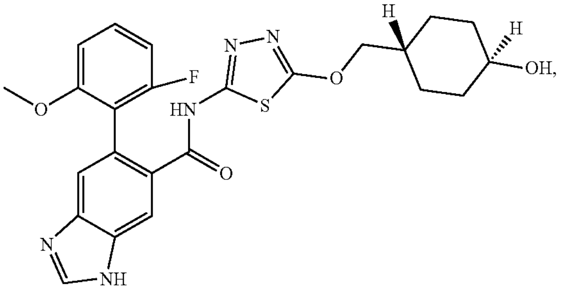
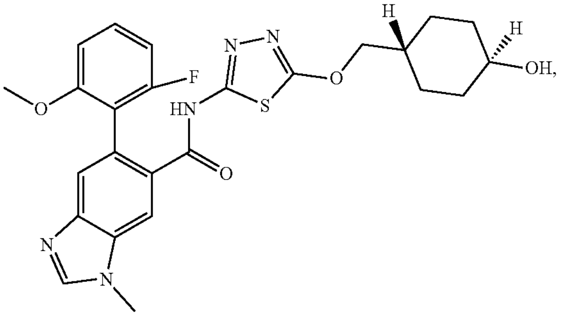
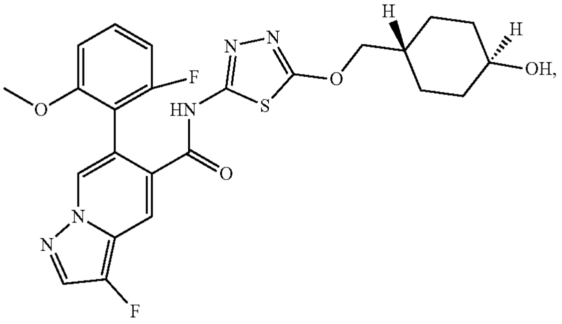
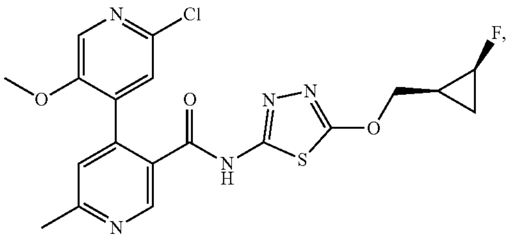
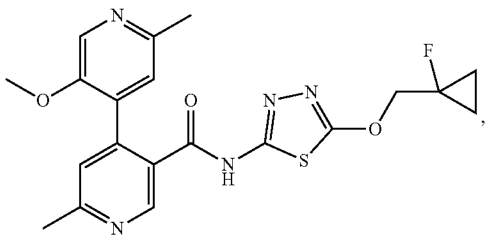
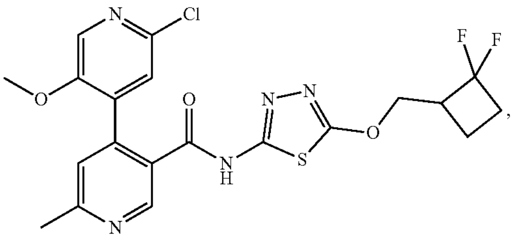

-continued
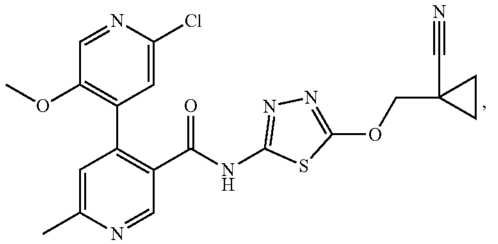
,
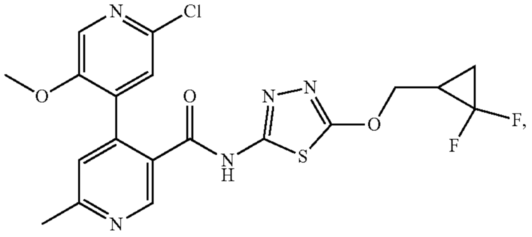
,
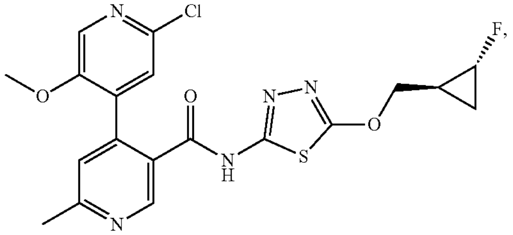
,
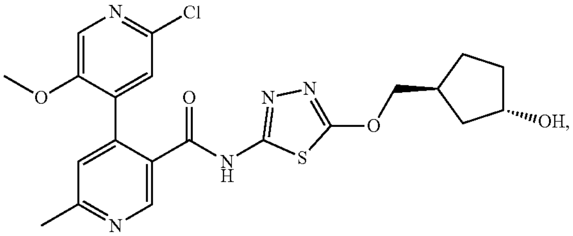
,
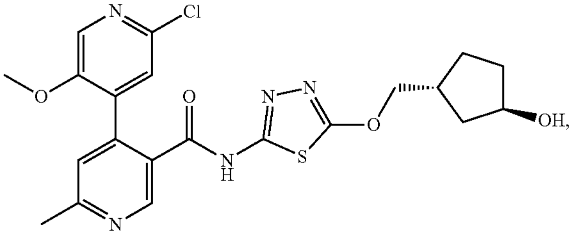
,
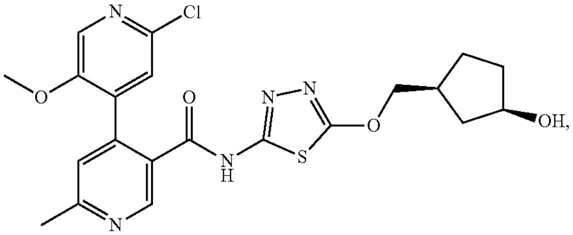
,
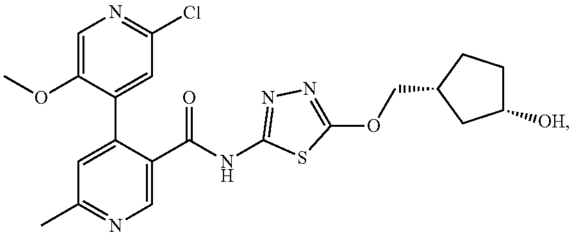
,
-continued
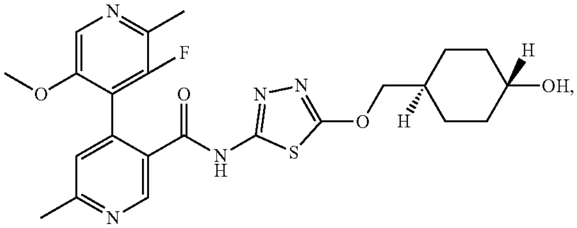
,
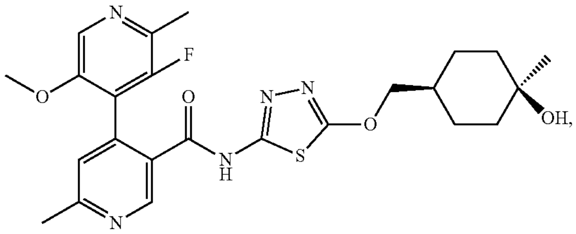
,
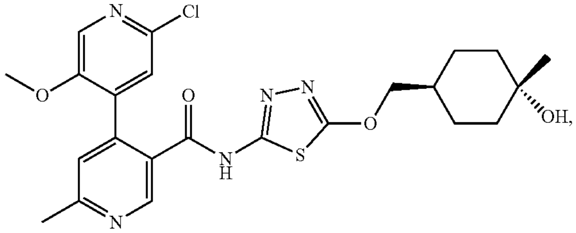
,
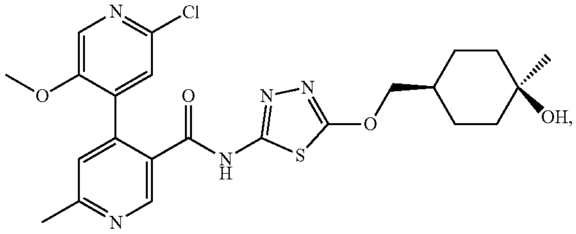
,
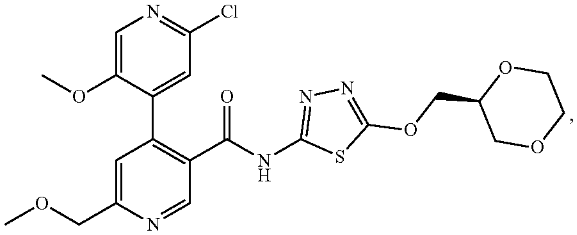
,
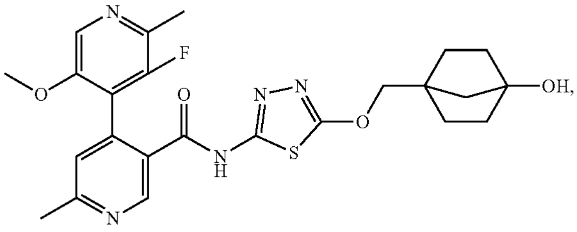
,
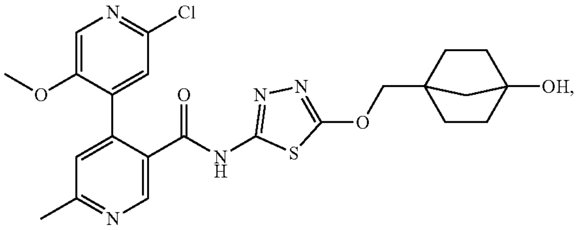
, -continued
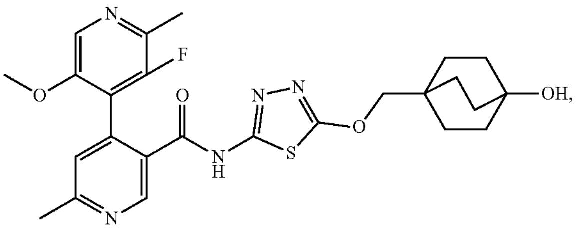
,
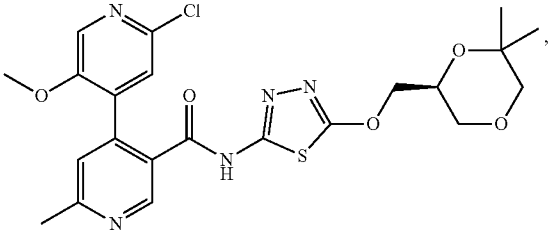
,
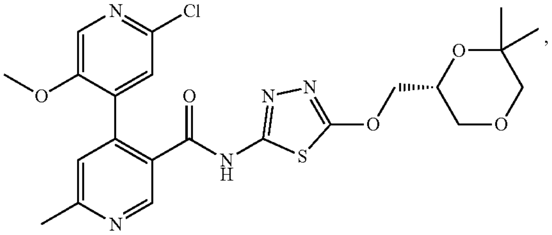
,
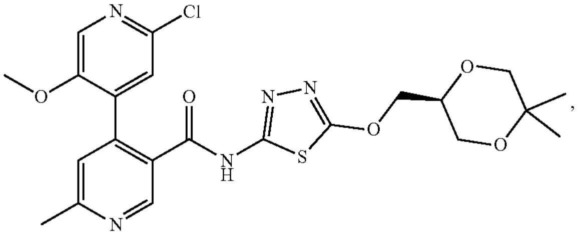
,
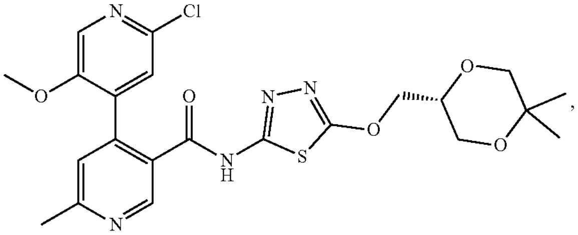
,
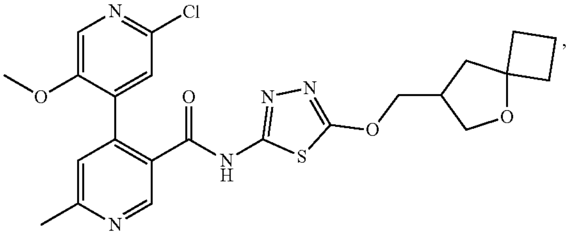
,
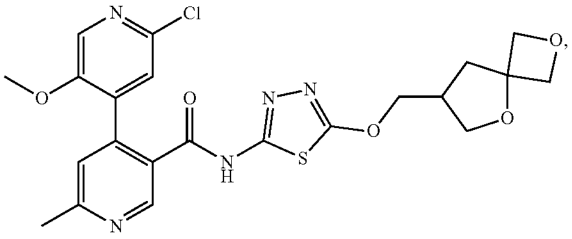
,
-continued
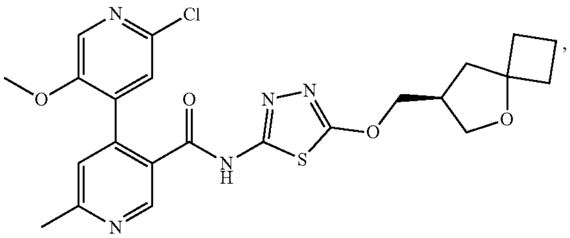
,
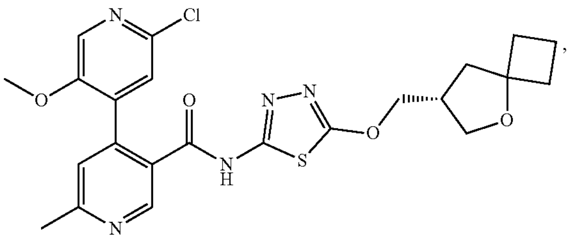
,
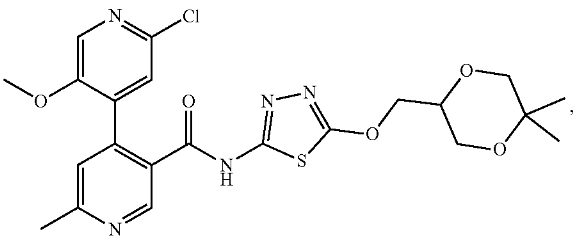
,
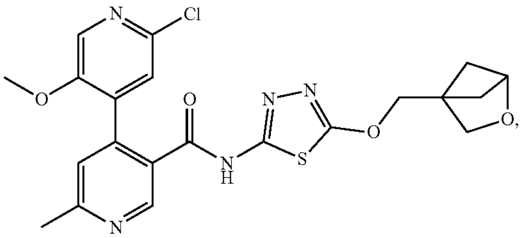
,
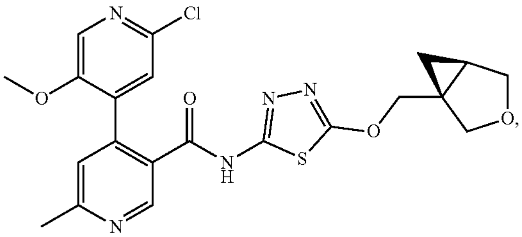
,
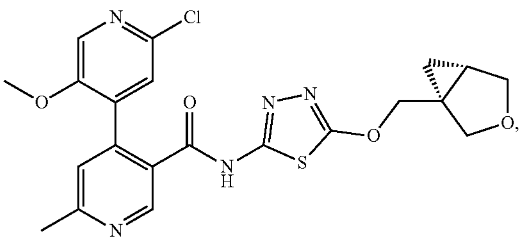
,
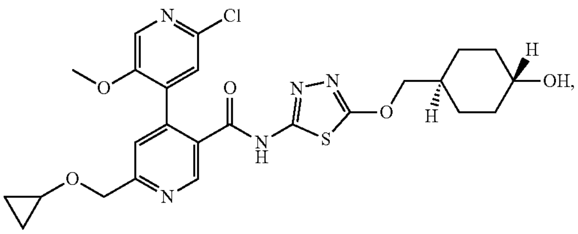
, -continued
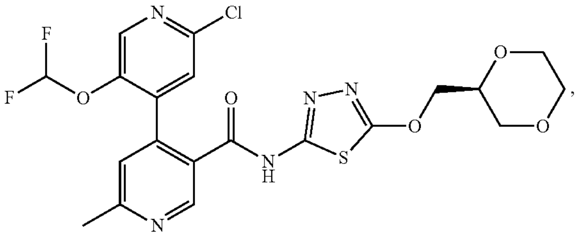
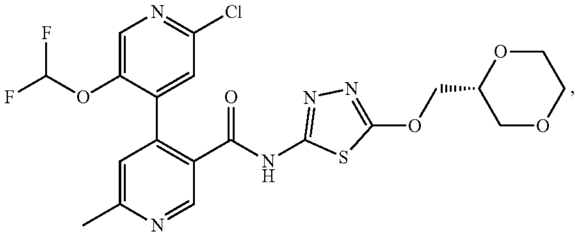
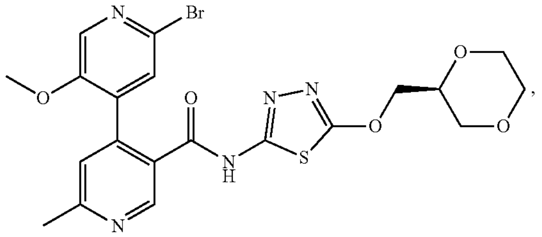
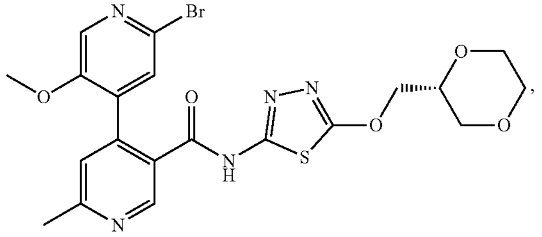
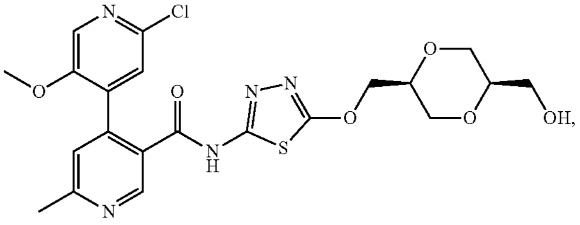
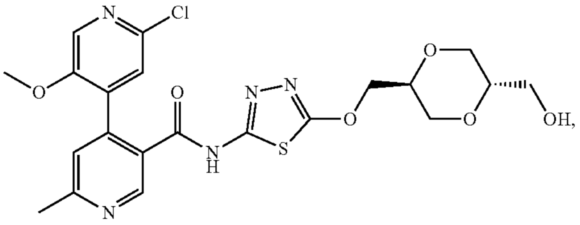
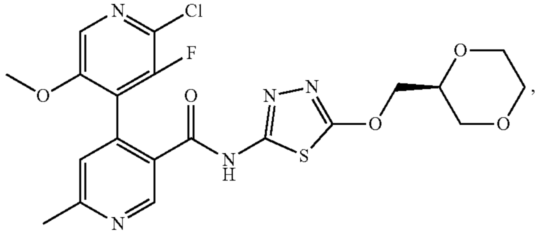
-continued
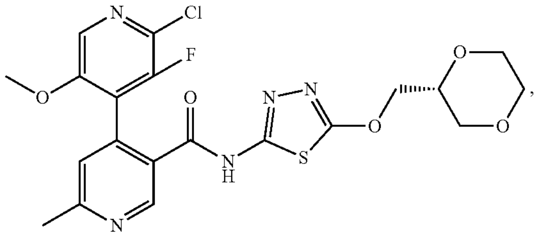
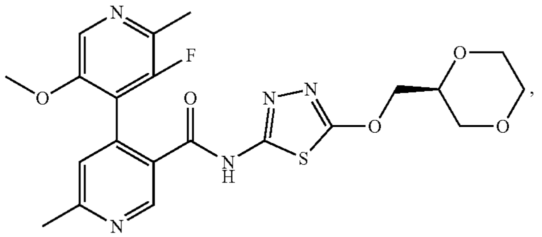
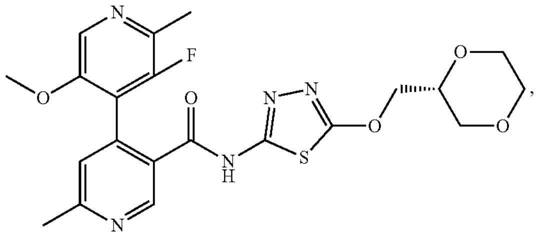
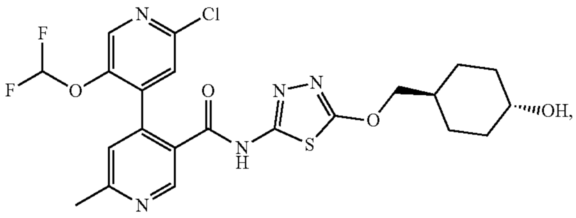
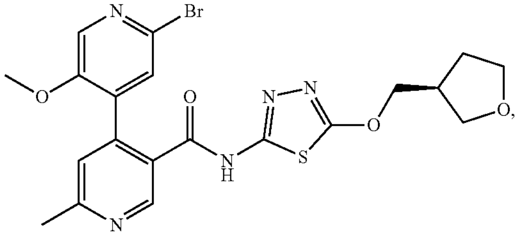
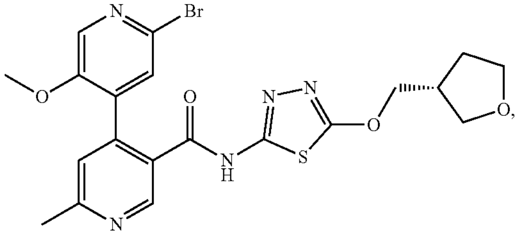
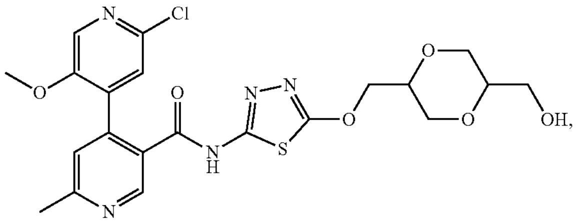

-continued
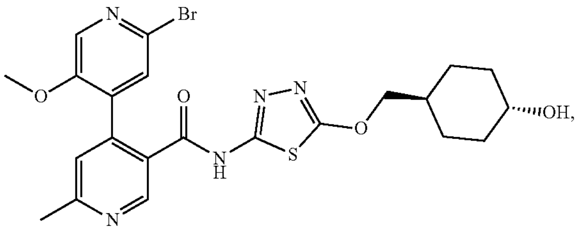,
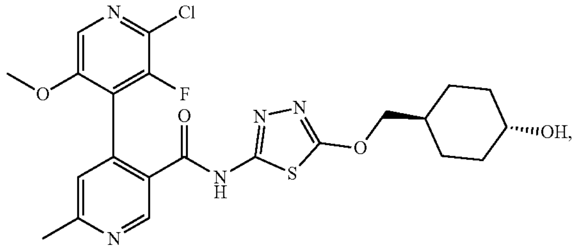,
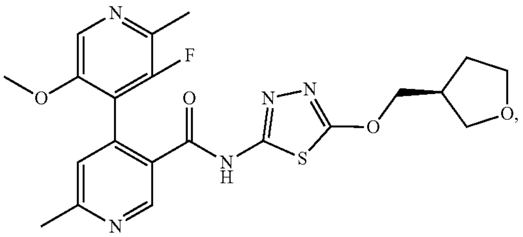,
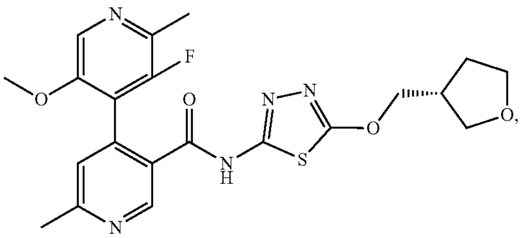,
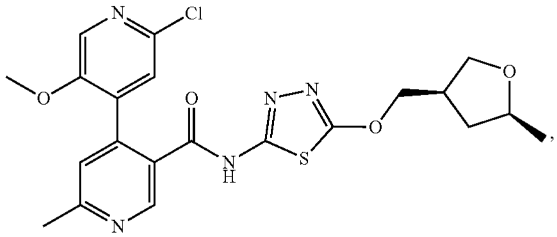,
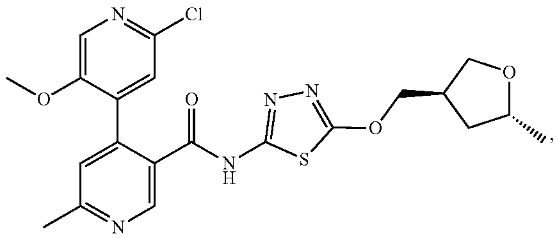,
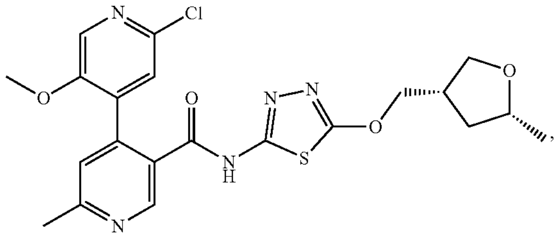,
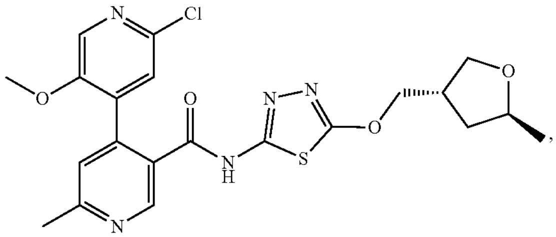,
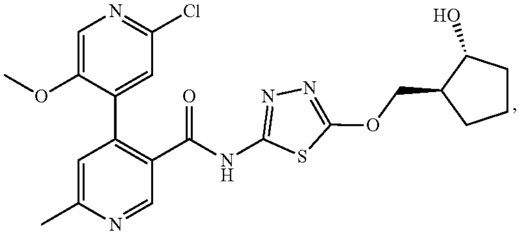,
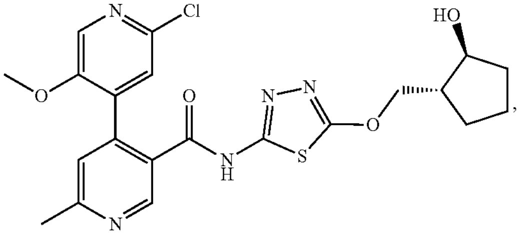,
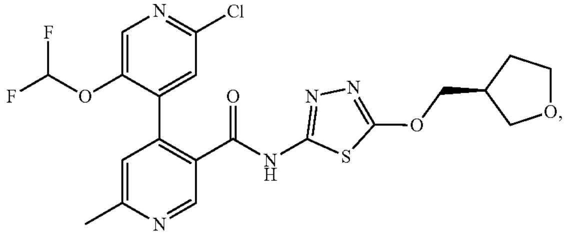,
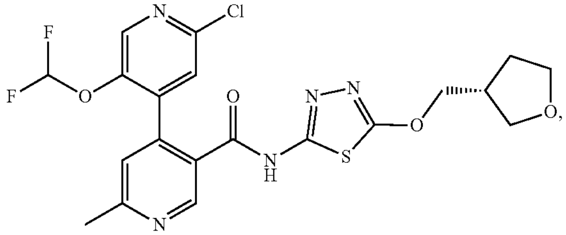,
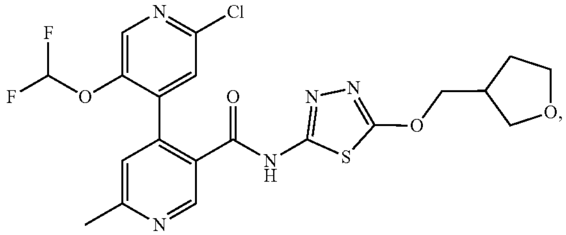,
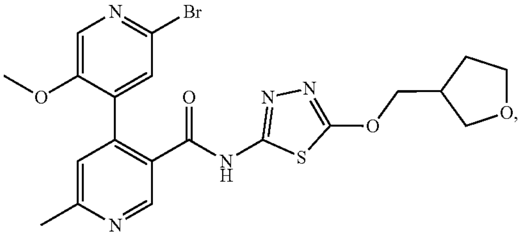, -continued
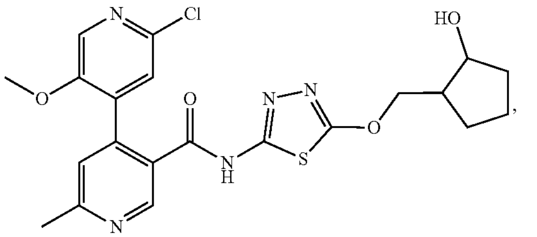
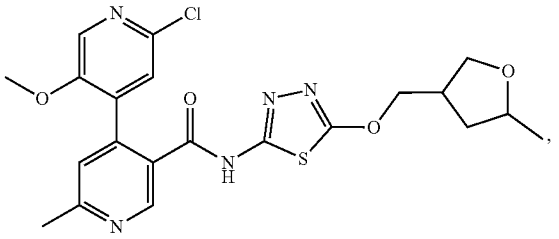
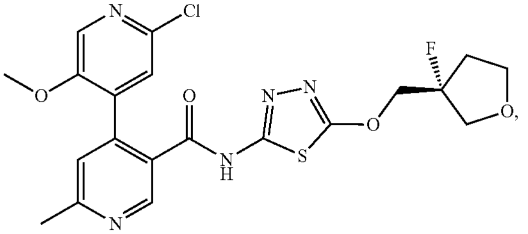
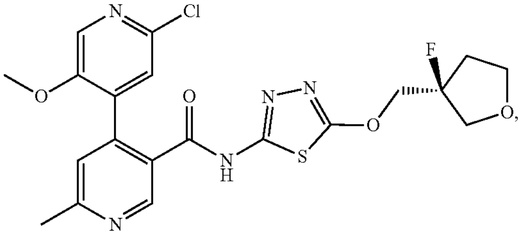
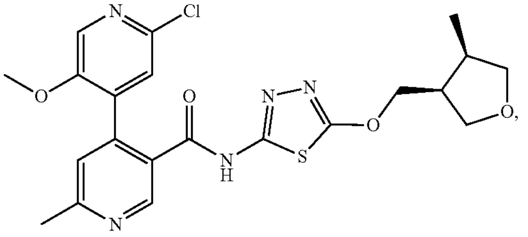
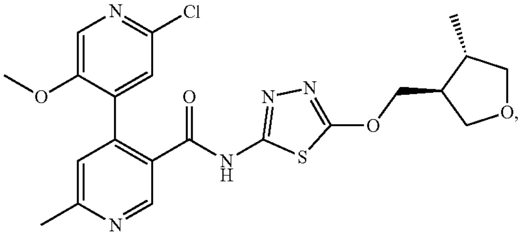
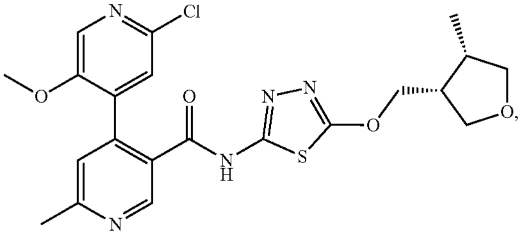
-continued
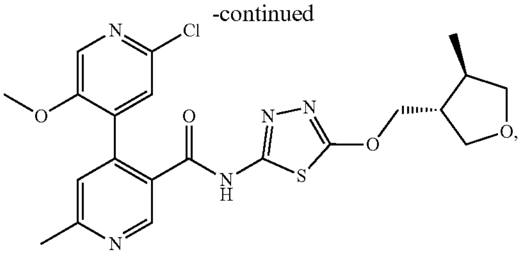
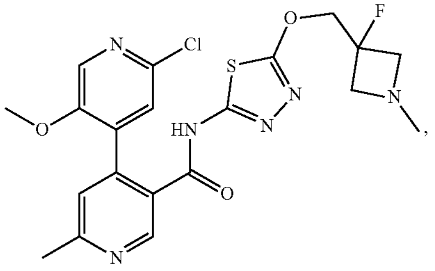
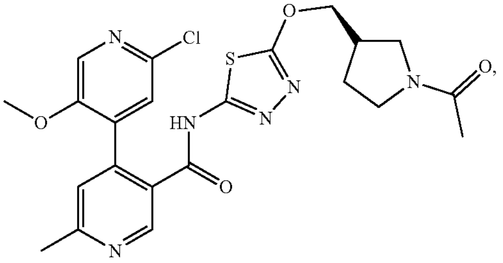
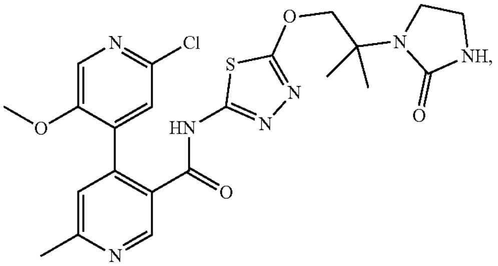
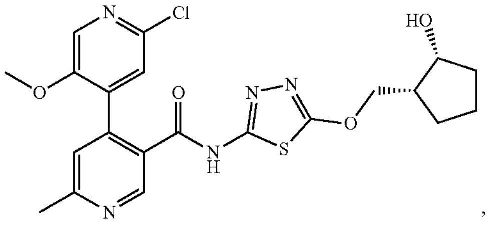
, and
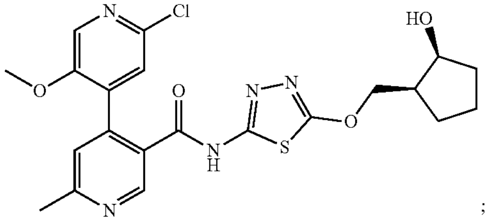
;
or a pharmaceutically acceptable salt thereof.
2. A pharmaceutical composition comprising a compound of claim 1 or pharmaceutically acceptable salt thereof, and at least one pharmaceutically acceptable excipient.

3. A compound having the structure:

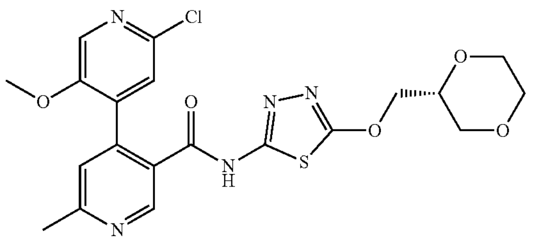 [SMILES: COc1cnc(Cl)cc1-c1cc(C)ncc1C(=O)Nc1nnc(OC[C@H]2COCCO2)s1]

or a pharmaceutically acceptable salt thereof.

4. A pharmaceutical composition comprising the compound of claim 3 or pharmaceutically acceptable salt thereof, and at least one pharmaceutically acceptable excipient.

5. A compound having the structure:

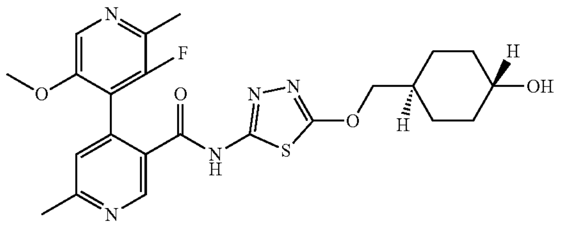 [SMILES: COc1cnc(C)c(F)c1-c1cc(C)ncc1C(=O)Nc1nnc(OC[C@H]2CC[C@H](O)CC2)s1]

or a pharmaceutically acceptable salt thereof.

6. A pharmaceutical composition comprising a compound of claim 5 or pharmaceutically acceptable salt thereof, and at least one pharmaceutically acceptable excipient.

7. The compound of claim 1 or pharmaceutically acceptable salt thereof, selected from the group consisting of:

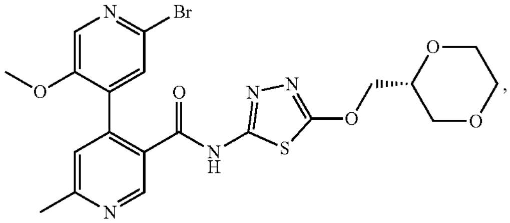,

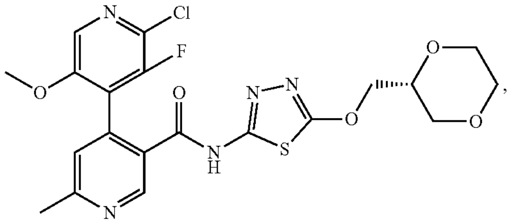,

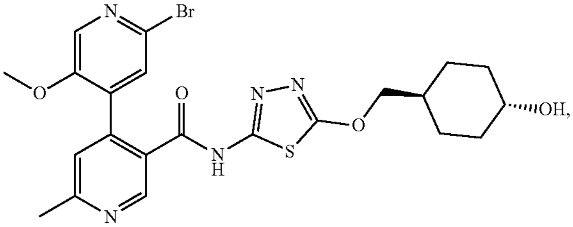,

-continued

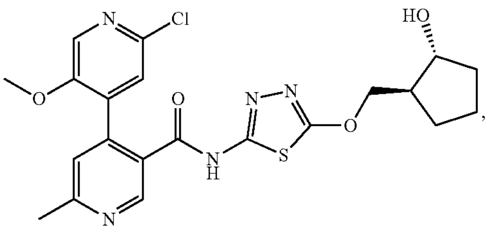, and

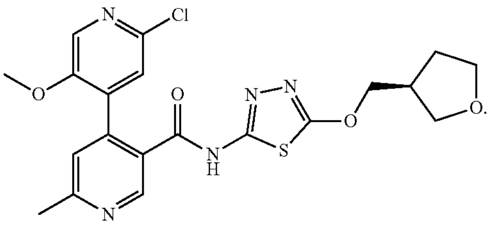.

8. A pharmaceutical composition comprising a compound of claim 7 or pharmaceutically acceptable salt thereof, and at least one pharmaceutically acceptable excipient.

9. The compound of claim 7, having the structure

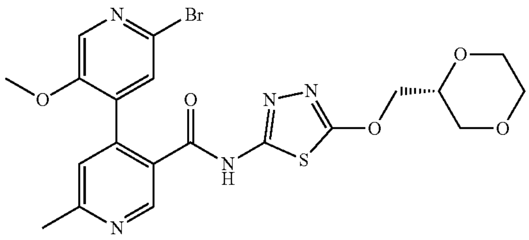

or a pharmaceutically acceptable salt thereof.

10. A pharmaceutical composition comprising a compound of claim 9 or pharmaceutically acceptable salt thereof, and at least one pharmaceutically acceptable excipient.

11. The compound of claim 7, having the structure

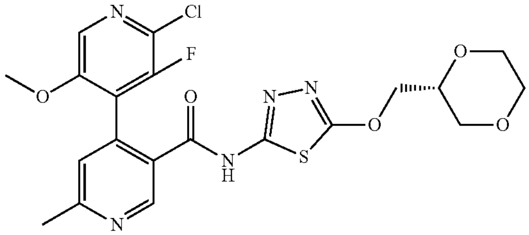 [SMILES: COc1cnc(Cl)c(F)c1-c1cc(C)ncc1C(=O)Nc1nnc(OC[C@H]2COCCO2)s1]

or a pharmaceutically acceptable salt thereof.

12. A pharmaceutical composition comprising a compound of claim 11 or pharmaceutically acceptable salt thereof, and at least one pharmaceutically acceptable excipient.

13. The compound of claim 7, having the structure

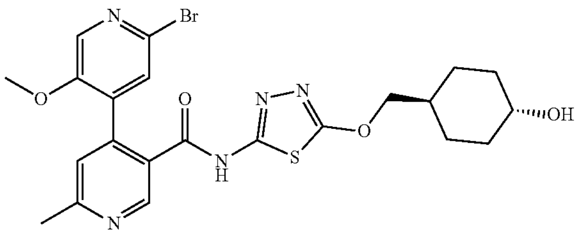 [SMILES: COc1cnc(Br)cc1-c1cc(C)ncc1C(=O)Nc1nnc(OC[C@H]2CC[C@H](O)CC2)s1]

or a pharmaceutically acceptable salt thereof.

14. A pharmaceutical composition comprising a compound of claim 13 or pharmaceutically acceptable salt thereof, and at least one pharmaceutically acceptable excipient.

15. The compound of claim 7, having the structure

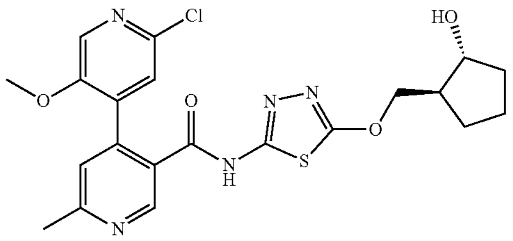 [SMILES: COc1cnc(Cl)cc1-c1cc(C)ncc1C(=O)Nc1nnc(OC[C@@H]2CCC[C@H]2O)s1]

or a pharmaceutically acceptable salt thereof.

16. A pharmaceutical composition comprising a compound of claim 15 or pharmaceutically acceptable salt thereof, and at least one pharmaceutically acceptable excipient.

17. The compound of claim 7, having the structure

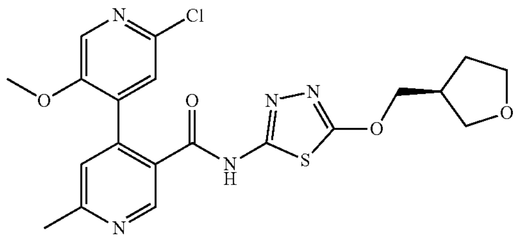

or a pharmaceutically acceptable salt thereof.

18. A pharmaceutical composition comprising a compound of claim 17 or pharmaceutically acceptable salt thereof, and at least one pharmaceutically acceptable excipient.

* * * * *